US011731953B2

(12) United States Patent
Vu et al.

(10) Patent No.: US 11,731,953 B2
(45) Date of Patent: Aug. 22, 2023

(54) METHODS AND COMPOUNDS FOR RESTORING MUTANT P53 FUNCTION

(71) Applicant: PMV Pharmaceuticals, Inc., Cranbury, NJ (US)

(72) Inventors: Binh Vu, North Caldwell, NJ (US); Romyr Dominique, East Brunswick, NJ (US); Hongju Li, Edison, NJ (US); Bruce Fahr, East Windsor, NJ (US); Yi Chen, Nutley, NJ (US)

(73) Assignee: PMV PHARMACEUTICALS, INC., Princeton, NJ (US)

( * ) Notice: Subject to any disclaimer, the term of this patent is extended or adjusted under 35 U.S.C. 154(b) by 0 days.

(21) Appl. No.: 17/354,203

(22) Filed: Jun. 22, 2021

(65) Prior Publication Data

US 2023/0056253 A1 Feb. 23, 2023

Related U.S. Application Data

(60) Provisional application No. 63/042,250, filed on Jun. 22, 2020.

(51) Int. Cl.

| | |
|---|---|
| *C07D 401/04* | (2006.01) |
| *C07D 401/12* | (2006.01) |
| *C07D 401/14* | (2006.01) |
| *C07D 403/04* | (2006.01) |
| *C07D 405/12* | (2006.01) |
| *C07D 405/14* | (2006.01) |
| *C07D 409/04* | (2006.01) |
| *C07D 409/14* | (2006.01) |
| *C07D 413/04* | (2006.01) |
| *C07D 413/14* | (2006.01) |
| *C07D 417/04* | (2006.01) |
| *C07D 417/14* | (2006.01) |
| *C07D 471/04* | (2006.01) |
| *C07D 209/46* | (2006.01) |
| *C07D 209/94* | (2006.01) |
| *C07D 209/34* | (2006.01) |

(52) U.S. Cl.
CPC ......... *C07D 401/04* (2013.01); *C07D 209/34* (2013.01); *C07D 209/46* (2013.01); *C07D 209/94* (2013.01); *C07D 401/12* (2013.01); *C07D 401/14* (2013.01); *C07D 403/04* (2013.01); *C07D 405/12* (2013.01); *C07D 405/14* (2013.01); *C07D 409/04* (2013.01); *C07D 409/14* (2013.01); *C07D 413/04* (2013.01); *C07D 413/14* (2013.01); *C07D 417/04* (2013.01); *C07D 471/04* (2013.01)

(58) Field of Classification Search
CPC ................ C07D 401/04; C07D 401/12; C07D 401/14; C07D 403/04; C07D 405/12; C07D 405/14; C07D 409/04; C07D 409/14; C07D 413/04; C07D 413/14; C07D 417/04; C07D 417/14; C07D 471/04; C07D 209/46; C07D 209/94
See application file for complete search history.

(56) References Cited

U.S. PATENT DOCUMENTS

2018/0251427 A1 9/2018 Dang et al.

FOREIGN PATENT DOCUMENTS

WO WO-2018156595 A1 8/2018
WO WO-2019079569 A1 4/2019

OTHER PUBLICATIONS

Saylik et al., Tetrahedron: Asymmetry (2001), 12(4), 657-667. (Year: 2001).*
Singh et al., European Journal of Organic Chemistry (2009), (20), 3454-3466. (Year: 2009).*
Arai et al., Cobalt-catalyzed hydrocyanation and hydroarylation of enamines, Tetrahedron Letters, Oct. 24, 2019 (Oct. 24, 2019), vol. 60, pp. 1-4; pS7.
International Search Report and Written Opinion issued in PCT/US2021/038429 dated Dec. 2, 2021.
Pubmed Compound Summary for CID 11148545, ‘2-(2'-Cyanoprop-2'-enyl)-1H-isoindole-1,3{2H)-dione’, U.S. National Library of Medicine, Dec. 6, 2019 (Dec. 6, 2019), p. 1-9; p2 (https://pubchem.ncbi.nlm.nih.gov/compound/11148545), create date Oct. 26, 2006.
Pubmed Compound Summary for CID 140118477, ‘2-[(1,3-Dioxoisoindol-2-yl)methyl]prop-2-enamide’, U.S. National Library of Medicine, Dec. 6, 2019 (Dec. 6, 2019), p. 1-8; p2 (https://pubchem.ncbi.nlm.nih.gov/compound/140118477).
Eldar et al., Structural studies of p53 inactivation by DNA-contact mutations and its rescue by suppressor mutations via alternative protein-DNA interactions. Nucleic Acids Res. Oct. 2013;41(18):8748-59.

* cited by examiner

*Primary Examiner* — Laura L Stockton
(74) *Attorney, Agent, or Firm* — Wilson Sonsini Goodrich & Rosati

(57) ABSTRACT

Mutations in oncogenes and tumor suppressors contribute to the development and progression of cancer. The present disclosure describes compounds and methods that restore DNA binding affinity of p53 mutants. The compounds of the present disclosure can bind to mutant p53 and restore the ability of the p53 mutant to bind DNA and activate downstream effectors involved in tumor suppression. The disclosed compounds can be used to reduce the progression of cancers that contain a p53 mutation.

22 Claims, No Drawings

METHODS AND COMPOUNDS FOR RESTORING MUTANT P53 FUNCTION

CROSS-REFERENCE

This application claims the benefit of U.S. Provisional application No. 63/042,250, filed Jun. 22, 2020, which is incorporated herein by reference.

BACKGROUND

Cancer, an uncontrolled proliferation of cells, is a multi-factorial disease characterized by tumor formation, growth, and in some instances, metastasis. Cells carrying an activated oncogene, damaged genome, or other cancer-promoting alterations can be prevented from replicating through an elaborate tumor suppression network. A central component of this tumor suppression network is p53, one of the most potent tumor suppressors in the cell. Both the wild type and mutant conformations of p53 are implicated in the progression of cancer.

INCORPORATION BY REFERENCE

All publications, patents, and patent applications mentioned in this specification are herein incorporated by reference to the same extent as if each individual publication, patent, or patent application was specifically and individually indicated to be incorporated by reference.

SUMMARY OF THE INVENTION

In some embodiments, described herein is a compound of the formula:

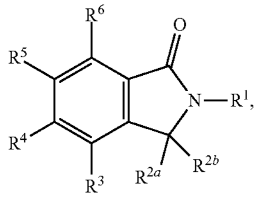

wherein:

$R^1$ is

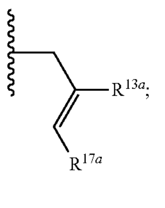

$R^{13a}$ is —C(O)NH$_2$ or —CN;

$R^{17a}$ is —CN, alkyl, aryl, heteroaryl, —NR$^7$R$^8$, —S(O)$_2$R$^7$, —SR$^7$, or OR$^7$, each which is unsubstituted or substituted, or hydrogen or halogen;

each $R^{2a}$, $R^{2b}$, $R^3$, $R^4$, $R^5$, and $R^6$ is independently alkyl, cycloalkyl, alkenyl, alkynyl, aryl, heteroaryl, heterocyclyl, —CN, —C(O)R$^9$, —C(O)OR$^9$, —C(O)NR$^9$R$^{10}$, —C(═N)NR$^9$R$^{10}$, —OR$^9$, —SR$^9$, —NR$^9$R$^{10}$, —NR$^9$C(O)R$^{10}$, —NR$^9$C(O)OR$^{10}$, —OC(O)R$^9$, —OC(O)NR$^9$R$^{10}$, —S(O)$_2$R$^9$, —NHS(O)$_2$R$^9$, —OS(O)$_2$R$^9$, each which is independently substituted or unsubstituted, or hydrogen or halogen; or $R^{2a}$ and $R^{2b}$ together with the carbon atom to which $R^{2a}$ and $R^b$ are bound is C═O or C═S; and $R^3$, $R^4$, $R^5$, and $R^6$ is independently alkyl, cycloalkyl, alkenyl, alkynyl, aryl, heteroaryl, heterocyclyl, —CN, —C(O)R$^9$, —C(O)OR$^9$, —C(O)NR$^9$R$^{10}$, —C(═N)NR$^9$R$^{10}$, —OR$^9$, —SR$^9$, —NR$^9$R$^{10}$, —NR$^9$C(O)R$^{10}$, —NR$^9$C(O)OR$^{10}$, —OC(O)R$^9$, —OC(O)NR$^9$R$^{10}$, —S(O)$_2$R$^9$, —NHS(O)$_2$R$^9$, —OS(O)$_2$R$^9$, each which is independently substituted or unsubstituted, or hydrogen or halogen; or $R^3$ and $R^4$ together with the carbon atom to which $R^3$ and $R^4$ are bound form a ring, wherein the ring is unsubstituted or substituted; and each $R^{2a}$, $R^{2b}$, $R^5$ and $R^6$ is independently alkyl, cycloalkyl, alkenyl, alkynyl, aryl, heteroaryl, heterocyclyl, —CN, —C(O)R$^9$, —C(O)OR$^9$, —C(O)NR$^9$R$^{10}$, —C(═N)NR$^9$R$^{10}$, —OR$^9$, —SR$^9$, —NR$^9$R$^{10}$, —NR$^9$C(O)R$^{10}$, —NR$^9$C(O)OR$^{10}$, —OC(O)R$^9$, —OC(O)NR$^9$R$^{10}$, —S(O)$_2$R$^9$, —NHS(O)$_2$R$^9$, —OS(O)$_2$R$^9$, each which is independently substituted or unsubstituted, or hydrogen or halogen; or $R^4$ and $R^5$ together with the carbon atom to which $R^4$ and $R^5$ are bound form a ring, wherein the ring is unsubstituted or substituted; and each $R^{2a}$, $R^{2b}$, $R^3$, and $R^6$ is independently alkyl, cycloalkyl, alkenyl, alkynyl, aryl, heteroaryl, heterocyclyl, —CN, —C(O)R$^9$, —C(O)OR$^9$, —C(O)NR$^9$R$^{10}$, —C(═N)NR$^9$R$^{10}$, —OR$^9$, —SR$^9$, —NR$^9$R$^{10}$, —NR$^9$C(O)R$^{10}$, —NR$^9$C(O)OR$^{10}$, —OC(O)R$^9$, —OC(O)NR$^9$R$^{10}$, —S(O)$_2$R$^9$, —NHS(O)$_2$R$^9$, —OS(O)$_2$R$^9$, each which is independently substituted or unsubstituted, or hydrogen or halogen; or $R^5$ and $R^6$ together with the carbon atom to which $R^5$ and $R^6$ are bound form a ring, wherein the ring is unsubstituted or substituted; and each $R^{2a}$, $R^{2b}$, $R^3$, and $R^4$ is independently alkyl, cycloalkyl, alkenyl, alkynyl, aryl, heteroaryl, heterocyclyl, —CN, —C(O)R$^9$, —C(O)OR$^9$, —C(O)NR$^9$R$^{10}$, —C(═N)NR$^9$R$^{10}$, —OR$^9$, —SR$^9$, —NR$^9$R$^{10}$, —NR$^9$C(O)R$^{10}$, —NR$^9$C(O)OR$^{10}$, —OC(O)R$^9$, —OC(O)NR$^9$R$^{10}$, —S(O)$_2$R$^9$, —NHS(O)$_2$R$^9$, —OS(O)$_2$R$^9$, each which is independently substituted or unsubstituted, or hydrogen or halogen; and each $R^7$, $R^8$, $R^9$, and $R^{10}$ is independently alkyl, cycloalkyl, alkenyl, alkynyl, aryl, heteroaryl, or heterocyclyl, each which is independently substituted or unsubstituted, or hydrogen or halogen, or a pharmaceutically-acceptable salt thereof.

In some embodiments, described herein is a compound of the formula:

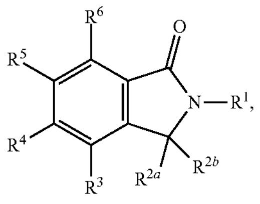

wherein:

$R^1$ is alkyl, cycloalkyl, alkenyl, alkynyl, aryl, heteroaryl, heterocyclyl, —CN, —C(O)R$^7$, —C(O)OR$^7$, —C(O)NR$^7$R$^8$, —C(═N)NR$^7$R$^8$, —OR$^7$, —SR$^7$, —NR$^7$R$^8$, —NR$^7$C(O)R$^8$, —NR$^7$C(O)OR$^8$, —OC(O)R$^7$, —OC(O)NR$^7$R$^8$, —S(O)$_2$R$^7$, —NHS(O)$_2$R$^7$, —OS(O)$_2$R$^7$, each which is independently substituted or unsubstituted, or hydrogen or halogen;

each $R^{2a}$, $R^{2b}$, $R^4$, $R^5$, and $R^6$ is independently alkyl, cycloalkyl, alkenyl, alkynyl, aryl, heteroaryl, heterocyclyl, —CN, —$C(O)R^9$, —$C(O)OR^9$, —$C(O)NR^9R^{10}$, —$C({=}N)NR^9R^{10}$, —$OR^9$, —$SR^9$, —$NR^9R^{10}$, —$NR^9C(O)R^{10}$, —$NR^9C(O)OR^{10}$, —$OC(O)R^9$, —$OC(O)NR^9R^{10}$, —$S(O)_2R^9$, —$NHS(O)_2R^9$, —$OS(O)_2R^9$, each which is independently substituted or unsubstituted, or hydrogen or halogen; or $R^{2a}$ and $R^{2b}$ together with the carbon atom to which $R^{2a}$ and $R^{2b}$ are bound is C═O or C═S; and $R^4$, $R^5$, and $R^6$ is independently alkyl, cycloalkyl, alkenyl, alkynyl, aryl, heteroaryl, heterocyclyl, —CN, —$C(O)R^9$, —$C(O)OR^9$, —$C(O)NR^9R^{10}$, —$C({=}N)NR^9R^{10}$, —$OR^9$, —$SR^9$, —$NR^9R^{10}$, —$NR^9C(O)R^{10}$, —$NR^9C(O)OR^{10}$, —$OC(O)R^9$, —$OC(O)NR^9R^{10}$, —$S(O)_2R^9$, —$NHS(O)_2R^9$, —$OS(O)_2R^9$, each which is independently substituted or unsubstituted, or hydrogen or halogen; or $R^4$ and $R^5$ together with the carbon atom to which $R^4$ and $R^5$ are bound form a ring, wherein the ring is unsubstituted or substituted; and each $R^{2a}$, $R^{2b}$, and $R^6$ is independently alkyl, cycloalkyl, alkenyl, alkynyl, aryl, heteroaryl, heterocyclyl, —CN, —$C(O)R^9$, —$C(O)OR^9$, —$C(O)NR^9R^{10}$, —$C({=}N)NR^9R^{10}$, —$OR^9$, —$SR^9$, —$NR^9R^{10}$, —$NR^9C(O)R^{10}$, —$NR^9C(O)OR^{10}$, —$OC(O)R^9$, —$OC(O)NR^9R^{10}$, —$S(O)_2R^9$, —$NHS(O)_2R^9$, —$OS(O)_2R^9$, each which is independently substituted or unsubstituted, or hydrogen or halogen; or $R^5$ and $R^6$ together with the carbon atom to which $R^5$ and $R^6$ are bound form a ring, wherein the ring is unsubstituted or substituted; and each $R^{2a}$, $R^{2b}$, and $R^4$ is independently alkyl, cycloalkyl, alkenyl, alkynyl, aryl, heteroaryl, heterocyclyl, —CN, —$C(O)R^9$, —$C(O)OR^9$, —$C(O)NR^9R^{10}$, —$C({=}N)NR^9R^{10}$, —$OR^9$, —$SR^9$, —$NR^9R^{10}$, —$NR^9C(O)R^{10}$, —$NR^9C(O)OR^{10}$, —$OC(O)R^9$, —$OC(O)NR^9R^{10}$, —$S(O)_2R^9$, —$NHS(O)_2R^9$, —$OS(O)_2R^9$, each which is independently substituted or unsubstituted, or hydrogen or halogen;

$R^3$ is

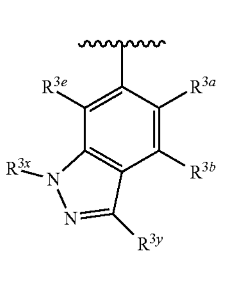
or
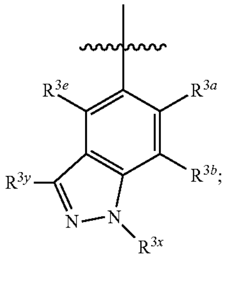
;

each $R^{3a}$, $R^{3b}$, $R^{3e}$, $R^{3x}$, and $R^{3y}$ is independently alkyl, cycloalkyl, alkenyl, alkynyl, aryl, heteroaryl, heterocyclyl, —CN, —$C(O)R^7$, —$C(O)OR^7$, —$C(O)NR^7R^8$, —$C({=}N)NR^7R^8$, —$OR^7$, —$SR^7$, —$NR^7R^8$, —$NR^7C(O)R^8$, —$NR^7C(O)OR^8$, —$OC(O)R^7$, —$OC(O)NR^7R^8$, —$S(O)_2R^7$, —$NHS(O)_2R^7$, —$OS(O)_2R^7$, each which is independently substituted or unsubstituted, or hydrogen or halogen; and each $R^7$, $R^8$, $R^9$, and $R^{10}$ is independently alkyl, cycloalkyl, alkenyl, alkynyl, aryl, heteroaryl, or heterocyclyl, each which is independently substituted or unsubstituted, or hydrogen or halogen, or a pharmaceutically-acceptable salt thereof.

In some embodiments, described herein is a compound of the formula:

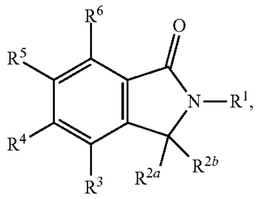

wherein:

$R^1$ is

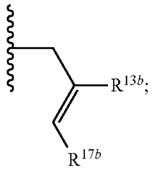

$R^{13b}$ is alkyl, cycloalkyl, alkenyl, alkynyl, aryl, heteroaryl, heterocyclyl, —CN, —$C(O)R^7$, —$C(O)OR^7$, —$C(O)NR^7R^8$, —$C({=}N)NR^7R^8$, —$OR^7$, —$SR^7$, —$NR^7R^8$, —$NR^7C(O)R^8$, —$NR^7C(O)OR^8$, —$OC(O)R^7$, —$OC(O)NR^7R^8$, —$S(O)_2R^7$, —$NHS(O)_2R^7$, —$OS(O)_2R^7$, each which is independently substituted or unsubstituted, or hydrogen or halogen;

$R^{17b}$ is —CN, alkyl, aryl, heteroaryl, —$NR^7R^8$, —$S(O)_2R^7$, —$SR^7$, or $OR^7$, each which is unsubstituted or substituted, or hydrogen or halogen;

each $R^{2a}$, $R^{2b}$, $R^3$, $R^4$, and $R^5$ is independently alkyl, cycloalkyl, alkenyl, alkynyl, aryl, heteroaryl, heterocyclyl, —CN, —$C(O)R^9$, —$C(O)OR^9$, —$C(O)NR^9R^{10}$, —$C({=}N)NR^9R^{10}$, —$OR^9$, —$SR^9$, —$NR^9R^{10}$, —$NR^9C(O)R^{10}$, —$NR^9C(O)OR^{10}$, —$OC(O)R^9$, —$OC(O)NR^9R^{10}$, —$S(O)_2R^9$, —$NHS(O)_2R^9$, —$OS(O)_2R^9$, each which is independently substituted or unsubstituted, or hydrogen or halogen; or $R^{2a}$ and $R^{2b}$ together with the carbon atom to which $R^{2a}$ and $R^{2b}$ are bound is C═O or C═S; and $R^3$, $R^4$, and $R^5$ is independently alkyl, cycloalkyl, alkenyl, alkynyl, aryl, heteroaryl, heterocyclyl, —CN, —$C(O)R^9$, —$C(O)OR^9$, —$C(O)NR^9R^{10}$, —$C({=}N)NR^9R^{10}$, —$OR^9$, —$SR^9$, —$NR^9R^{10}$, —$NR^9C(O)R^{10}$, —$NR^9C(O)OR^{10}$, —$OC(O)R^9$, —$OC(O)NR^9R^{10}$, —$S(O)_2R^9$, —$NHS(O)_2R^9$, —$OS(O)_2R^9$, each which is independently substituted or unsubstituted, or hydrogen or halogen; or $R^3$ and $R^4$ together with the carbon atom to which $R^3$ and $R^4$ are bound form a ring, wherein the ring is unsubstituted or substituted; and each $R^{2a}$, $R^{2b}$, and $R^5$ is independently alkyl, cycloalkyl, alkenyl, alkynyl, aryl, heteroaryl, heterocyclyl, —CN, —$C(O)R^9$, —$C(O)OR^9$, —$C(O)NR^9R^{10}$, —$C({=}N)NR^9R^{10}$, —$OR^9$, —$SR^9$, —$NR^9R^{10}$, —$NR^9C(O)R^{10}$, —$NR^9C(O)OR^{10}$, —$OC(O)R^9$, —$OC(O)NR^9R^{10}$, —$S(O)_2R^9$, —$NHS(O)_2R^9$, —$OS(O)_2R^9$, each which is independently substituted or unsubstituted, or hydrogen or halogen; or $R^4$ and $R^5$ together with the carbon atom to which $R^4$ and $R^5$ are bound form a ring, wherein the ring is unsubstituted or substituted; and each $R^{2a}$, $R^{2b}$, and $R^3$ is independently alkyl, cycloalkyl, alkenyl, alkynyl, aryl, heteroaryl, heterocyclyl, —CN, —C(O)$R^9$, —C(O)O$R^9$, —C(O)N$R^9R^{10}$, —C(=N)N$R^9R^{10}$, —O$R^9$, —S$R^9$, —N$R^9R^{10}$, —N$R^9$C(O)$R^{10}$, —N$R^9$C(O)O$R^{10}$, —OC(O)$R^9$, —OC(O)N$R^9R^{10}$, —S(O)$_2R^9$, —NHS(O)$_2R^9$, —OS(O)$_2R^9$, each which is independently substituted or unsubstituted, or hydrogen or halogen; or $R^6$ is $NH_2$; and each $R^7$, $R^8$, $R^9$, and $R^{10}$ is independently alkyl, cycloalkyl, alkenyl, alkynyl, aryl, heteroaryl, or heterocyclyl, each which is independently substituted or unsubstituted, or hydrogen or halogen, or a pharmaceutically-acceptable salt thereof.

In some embodiments, described herein is a pharmaceutical composition in unit dosage form comprising a pharmaceutically-acceptable excipient and a compound of the disclosure.

In some embodiments, described herein is a method of inducing apoptosis in a cell, the method comprising contacting the cell with a therapeutically-effective amount of a compound of the disclosure that binds a p53 mutant, wherein the compound increases the ability of the p53 mutant to bind DNA, wherein the cell expresses the p53 mutant. In some embodiments, described herein is a method of treating a cancer, the method comprising administering to a subject in need thereof a therapeutically-effective amount of a compound of the disclosure.

DETAILED DESCRIPTION

The present invention provides compounds and methods for restoring wild-type function to mutant p53. The compounds of the present invention can bind to mutant p53 and restore the ability of the p53 mutant to bind DNA. The restoration of activity of the p53 mutant can allow for the activation of downstream effectors of p53 leading to inhibition of cancer progression. The invention further provides methods of treatment of a cancerous lesion or a tumor harboring a p53 mutation.

Cancer is a collection of related diseases characterized by uncontrolled proliferation of cells with the potential to metastasize throughout the body. Cancer can be classified into five broad categories including, for example: carcinomas, which can arise from cells that cover internal and external parts of the body such as the lung, breast, and colon; sarcomas, which can arise from cells that are located in bone, cartilage, fat, connective tissue, muscle, and other supportive tissues; lymphomas, which can arise in the lymph nodes and immune system tissues; leukemia, which can arise in the bone marrow and accumulate in the bloodstream; and adenomas, which can arise in the thyroid, the pituitary gland, the adrenal gland, and other glandular tissues.

Although different cancers can develop in virtually any of the body's tissues, and contain unique features, the basic processes that cause cancer can be similar in all forms of the disease. Cancer begins when a cell breaks free from the normal restraints on cell division and begins to grow and divide out of control. Genetic mutations in the cell can preclude the ability of the cell to repair damaged DNA or initiate apoptosis, and can result in uncontrolled growth and division of cells.

The ability of tumor cell populations to multiply is determined not only by the rate of cell proliferation but also by the rate of cell attrition. Programmed cell death, or apoptosis, represents a major mechanism of cellular attrition. Cancer cells can evade apoptosis through a variety of strategies, for example, through the suppression of p53 function, thereby suppressing expression of pro-apoptotic proteins.

Oncogenes and tumor suppressor genes can regulate the proliferation of cells. Genetic mutations can affect oncogenes and tumor suppressors, potentially activating or suppressing activity abnormally, further facilitating uncontrolled cell division. Whereas oncogenes assist in cellular growth, tumor suppressor genes slow cell division by repairing damaged DNA and activating apoptosis. Cellular oncogenes that can be mutated in cancer include, for example, Cdk1, Cdk2, Cdk3, Cdk4, Cdk6, EGFR, PDGFR, VEGF, HER2, Raf kinase, K-Ras, and myc. Tumor suppressor genes that can be mutated in cancer include, for example, BRCA1, BRCA2, cyclin-dependent kinase inhibitor 1C, Retinoblastoma protein (pRb), PTEN, p16, p27, p53, and p73.

The tumor suppressor p53 acts as a DNA sequence-specific transcription factor regulating and activating the expression of a range of target genes in response to genotoxic stress. Activation of target genes by p53 initiates a cascade of signal transduction pathways, which leads to different cellular responses including cell-cycle arrest and apoptosis that prevent cancer development. p53 binds as a tetramer to specific response elements consisting mainly of two decametric half-sites separated by a variable number of base pairs. Mutations in the p53 gene that lead to inactivation of the protein are observed in ~50% of human cancers. The majority of tumor-related p53 mutations, particularly those defined as mutational 'hotspots', occur within the DNA-binding core domain of p53. The top hotspot mutations are located at or near the protein-DNA interface and can be divided into two major groups: DNA-contact mutations affecting residues involved directly in DNA contacts without altering p53 conformation; and structural mutations that cause a conformational change in the core domain.

R273, a DNA-contact amino acid, is one of the most frequently altered residues in human cancer (6.4% of all somatic mutations), with mutations to histidine (46.6%) and to cysteine (39.1%) being most common. Crystal structures of the p53 core-domain bound to DNA show that the positively charged guanidinium groups of R273 residues interact with the negatively charged DNA backbone at the center of each DNA half-site, supported by salt-bridge and hydrogen-bond interactions. R273 residues play a pivotal role in docking p53 to the DNA backbone at the central region of each half-site where no direct base-mediated contacts exist. Substitution of R273 by histidine (R273H) or cysteine (R273C) lead to dramatic reduction in the DNA binding affinity, even through the protein retains wild-type stability.

Tumor Suppressor p53.

The tumor suppressor protein p53 is a 393 amino acid transcription factor that can regulate cell growth in response to cellular stresses including, for example, UV radiation, hypoxia, oncogene activation, and DNA damage. p53 has various mechanisms for inhibiting the progression of cancer including, for example, initiation of apoptosis, maintenance of genomic stability, cell cycle arrest, induction of senescence, and inhibition of angiogenesis. Due to the critical role of p53 in tumor suppression, p53 is inactivated in almost all cancers either by direct mutation or through perturbation of associated signaling pathways involved in tumor suppression. Homozygous loss of the p53 gene occurs in almost all types of cancer, including carcinomas of the breast, colon, and lung. The presence of certain p53 mutations in several types of human cancer can correlate with less favorable patient prognosis.

In the absence of stress signals, p53 levels are maintained at low levels via the interaction of p53 with Mdm2, an E3 ubiquitin ligase. In an unstressed cell, Mdm2 can target p53 for degradation by the proteasome. Under stress conditions, the interaction between Mdm2 and p53 is disrupted, and p53 accumulates. The critical event leading to the activation of p53 is phosphorylation of the N-terminal domain of p53 by protein kinases, thereby transducing upstream stress signals. The phosphorylation of p53 leads to a conformational change, which can promote DNA binding by p53 and allow transcription of downstream effectors. The activation of p53 can induce, for example, the intrinsic apoptotic pathway, the extrinsic apoptotic pathway, cell cycle arrest, senescence, and DNA repair. p53 can activate proteins involved in the above pathways including, for example, Fas/Apo1, KILLER/DR5, Bax, Puma, Noxa, Bid, caspase-3, caspase-6, caspase-7, caspase-8, caspase-9, and p21 (WAF1). Additionally, p53 can repress the transcription of a variety of genes including, for example, c-MYC, Cyclin B, VEGF, RAD51, and hTERT.

Each chain of the p53 tetramer is composed of several functional domains including the transactivation domain (amino acids 1-100), the DNA-binding domain (amino acids 101-306), and the tetramerization domain (amino acids 307-355), which are highly mobile and largely unstructured. Most p53 cancer mutations are located in the DNA-binding core domain of the protein, which contains a central β-sandwich of anti-parallel pi-sheets that serves as a basic scaffold for the DNA-binding surface. The DNA-binding surface is composed of two β-turn loops, L2 and L3, which are stabilized by a zinc ion, for example, at Arg175 and Arg248, and a loop-sheet-helix motif. Altogether, these structural elements form an extended DNA-binding surface that is rich in positively-charged amino acids, and makes specific contact with various p53 response elements.

Due to the prevalence of p53 mutations in virtually every type of cancer, the reactivation of wild type p53 function in a cancerous cell can be an effective therapy. Mutations in p53 located in the DNA-binding domain of the protein or periphery of the DNA-binding surface can result in aberrant protein folding required for DNA recognition and binding or reduction in DNA binding affinity. Mutations in p53 can occur, for example, at amino acids Val143, His168, Arg175, Tyr220, Gly245, Arg248, Arg249, Phe270, Arg273, and Arg282. p53 mutations that can abrogate the activity of p53 include, for example, R175H, Y220C, G245S, R248Q, R248W, R273C, R273H, and R282H. p53 mutations can distort the structure of the DNA-binding site, thermodynamically destabilize the folded protein at body temperature, or weaken consensus DNA binding. Wild-type function of p53 mutants can be recovered by binding of the p53 mutant to a compound that can shift the folding-unfolding equilibrium towards the folded state, thereby reducing the rate of unfolding and destabilization; or by conjugating a small molecule to the DNA binding interface to restore consensus DNA binding.

Non-limiting examples of amino acids include: alanine (A, Ala); arginine (R, Arg); asparagine (N, Asn); aspartic acid (D, Asp); cysteine (C, Cys); glutamic acid (E, Glu); glutamine (Q, Gln); glycine (G, Gly); histidine (H, His); isoleucine (I, Ile); leucine (L, Leu); lysine (K, Lys); methionine (M, Met); phenylalanine (F, Phe); proline (P, Pro); serine (S, Ser); threonine (T, Thr); tryptophan (W, Trp); tyrosine (Y, Tyr); and valine (V, Val).

Mechanism of Compounds of the Disclosure.

The compounds of the present disclosure can selectively bind to a p53 mutant and can recover wild-type activity of the p53 mutant including, for example, DNA binding function and activation of downstream targets involved in tumor suppression. In some embodiments, a compound of the disclosure selectively binds to a p53R248 mutant. In some embodiments, a compound of the disclosure selectively binds to a p53 R248Q mutant. In some embodiments, a compound of the disclosure selectively binds to a p53 R248W mutant. In some embodiments, a compound of the disclosure selectively binds to a p53 R273 mutant. In some embodiments, a compound of the disclosure selectively binds to a p53 R273C mutant. In some embodiments, a compound of the disclosure selectively binds to a p53 R273H mutant.

A compound of the disclosure can bind or conjugate to an amino acid in the DNA binding interface. In some embodiments, a compound of the disclosure can conjugate to C277. In some embodiments, a compound of the disclosure can conjugate to C182.

Assays can be employed to determine the ability of a compound of the disclosure to bind to p53 and restore DNA binding affinity. Examples of assays include differential scanning fluorimetry (DSF), isothermal titration calorimetry (ITC), nuclear magnetic resonance spectrometry (NMR), X-ray crystallography, immunoprecipitation (IP), immunofluorescence (IF), or immunoblotting.

Methods used to detect the ability of the p53 mutant to bind DNA can include, for example, DNA affinity immunoblotting, modified enzyme-linked immunosorbent assay (ELISA), electrophoretic mobility shift assay (EMSA), fluorescence resonance energy transfer (FRET), homogeneous time-resolved fluorescence (HTRF), and a chromatin immunoprecipitation (ChIP) assay.

A compound of the disclosure can increase the ability of a p53 mutant to bind DNA by at least or up to about 0.1%, at least or up to about 0.2%, at least or up to about 0.3%, at least or up to about 0.4%, at least or up to about 0.5%, at least or up to about 0.6%, at least or up to about 0.7%, at least or up to about 0.8%, at least or up to about 0.9%, at least or up to about 1%, at least or up to about 2%, at least or up to about 3%, at least or up to about 4%, at least or up to about 5%, at least or up to about 6%, at least or up to about 7%, at least or up to about 8%, at least or up to about 9%, at least or up to about 10%, at least or up to about 11%, at least or up to about 12%, at least or up to about 13%, at least or up to about 14%, at least or up to about 15%, at least or up to about 16%, at least or up to about 17%, at least or up to about 18%, at least or up to about 19%, at least or up to about 20%, at least or up to about 21%, at least or up to about 22%, at least or up to about 23%, at least or up to about 24%, at least or up to about 25%, at least or up to about 26%, at least or up to about 27%, at least or up to about 28%, at least or up to about 29%, at least or up to about 30%, at least or up to about 31%, at least or up to about 32%, at least or up to about 33%, at least or up to about 34%, at least or up to about 35%, at least or up to about 36%, at least or up to about 37%, at least or up to about 38%, at least or up to about 39%, at least or up to about 40%, at least or up to about 41%, at least or up to about 42%, at least or up to about 43%, at least or up to about 44%, at least or up to about 45%, at least or up to about 46%, at least or up to about 47%, at least or up to about 48%, at least or up to about 49%, at least or up to about 50%, at least or up to about 51%, at least or up to about 52%, at least or up to about 53%, at least or up to about 54%, at least or up to about 55%, at least or up to about 56%, at least or up to about 57%, at least or up to about 58%, at least or up to about 59%, at least or up to about 60%, at least or up to about 61%, at least or up to about 62%, at least or up to about 63%, at least or up to about 64%, at least or up to about 65%, at least or up to about 66%, at least or up to about 67%, at least or up to about 68%, at least or up to about 69%, at least or up to about 70%, at least or up to about 71%, at least or up to about 72%, at least or up to about 73%, at least or up to about 74%, at least or up to about 75%, at least or up to about 76%, at least or up to about 77%, at least or up to about 78%, at least or up to about 79%, at least or up to about 80%, at least or up to about 81%, at least or up to about 82%, at least or up to about 83%, at least or up to about 84%, at least or up to about 85%, at least or up to about 86%, at least or up to about 87%, at least or up to about 88%, at least or up to about 89%, at least or up to about 90%, at least or up to about 91%, at least or up to about 92%, at least or up to about 93%, at least or up to about 94%, at least or up to about 95%, at least or up to about 96%, at least or up to about 97%, at least or up to about 98%, at least or up to about 99%, at least or up to about 100%, at least or up to about 125%, at least or up to about 150%, at least or up to about 175%, at least or up to about 200%, at least or up to about 225%, or at least or up to about 250% as compared to the ability of the p53 mutant to bind DNA in the absence of a compound of the disclosure.

A compound described herein can increase the activity of the p53 mutant that is, for example, at least or up to about 2-fold, at least or up to about 3-fold, at least or up to about 4-fold, at least or up to about 5-fold, at least or up to about 6-fold, at least or up to about 7-fold, at least or up to about 8-fold, at least or up to about 9-fold, at least or up to about 10-fold, at least or up to about 11-fold, at least or up to about 12-fold, at least or up to about 13-fold, at least or up to about 14-fold, at least or up to about 15-fold, at least or up to about 16-fold, at least or up to about 17-fold, at least or up to about 18-fold, at least or up to about 19-fold, at least or up to about 20-fold, at least or up to about 25-fold, at least or up to about 30-fold, at least or up to about 35-fold, at least or up to about 40-fold, at least or up to about 45-fold, at least or up to about 50-fold, at least or up to about 55-fold, at least or up to about 60-fold, at least or up to about 65-fold, at least or up to about 70-fold, at least or up to about 75-fold, at least or up to about 80-fold, at least or up to about 85-fold, at least or up to about 90-fold, at least or up to about 95-fold, at least or up to about 100-fold, at least or up to about 110-fold, at least or up to about 120-fold, at least or up to about 130-fold, at least or up to about 140-fold, at least or up to about 150-fold, at least or up to about 160-fold, at least or up to about 170-fold, at least or up to about 180-fold, at least or up to about 190-fold, at least or up to about 200-fold, at least or up to about 250-fold, at least or up to about 300-fold, at least or up to about 350-fold, at least or up to about 400-fold, at least or up to about 450-fold, at least or up to about 500-fold, at least or up to about 550-fold, at least or up to about 600-fold, at least or up to about 650-fold, at least or up to about 700-fold, at least or up to about 750-fold, at least or up to about 800-fold, at least or up to about 850-fold, at least or up to about 900-fold, at least or up to about 950-fold, at least or up to about 1,000-fold, at least or up to about 1,500-fold, at least or up to about 2,000-fold, at least or up to about 3,000-fold, at least or up to about 4,000-fold, at least or up to about 5,000-fold, at least or up to about 6,000-fold, at least or up to about 7,000-fold, at least or up to about 8,000-fold, at least or up to about 9,000-fold, or at least or up to about 10,000-fold greater than the activity of the p53 mutant in the absence of the compound.

A compound of the disclosure can be used, for example, to induce apoptosis, cell cycle arrest, or senescence in a cell. In some embodiments, the cell is a cancer cell. In some embodiments, the cell carries a mutation in p53.

Compounds of the Disclosure.

In some embodiments, a compound of the disclosure is a Michael acceptor. In some embodiments, a compound of the disclosure is a Michael acceptor comprising a 1-oxodihydroindole group, wherein the compound binds a mutant p53 protein and increases wild-type p53 activity of the mutant protein. In some embodiments, the compound is a Michael acceptor comprising an indazole group.

In some embodiments, described herein is a compound of the formula:

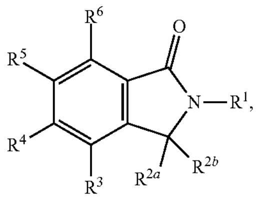

wherein:

$R^1$ is

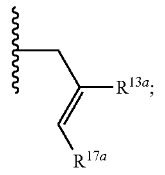

$R^{13a}$ is —C(O)$NH_2$ or —CN;

$R^{17a}$ is —CN, alkyl, aryl, heteroaryl, —$NR^7R^8$, —$S(O)_2R^7$, —$SR^7$, or $OR^7$, each which is unsubstituted or substituted, or hydrogen or halogen;

each $R^{2a}$, $R^{2b}$, $R^3$, $R^4$, $R^5$, and $R^6$ is independently alkyl, cycloalkyl, alkenyl, alkynyl, aryl, heteroaryl, heterocyclyl, —CN, —C(O)$R^9$, —C(O)$OR^9$, —C(O)$NR^9R^{10}$, —C(=N)$NR^9R^{10}$, —$OR^9$, —$SR^9$, —$NR^9R^{10}$, —$NR^9$C(O)$R^{10}$, —$NR^9$C(O)$OR^{10}$, —OC(O)$R^9$, —OC(O)$NR^9R^{10}$, —$S(O)_2R^9$, —$NHS(O)_2R^9$, —$OS(O)_2R^9$, each which is independently substituted or unsubstituted, or hydrogen or halogen;

or $R^{2a}$ and $R^{2b}$ together with the carbon atom to which $R^{2a}$ and $R^{2b}$ are bound is —C=O or —C=S;

or $R^3$ and $R^4$ together with the carbon atom to which $R^3$ and $R^4$ are bound form a ring, wherein the ring is unsubstituted or substituted;

or $R^4$ and $R^5$ together with the carbon atom to which $R^4$ and $R^5$ are bound form a ring, wherein the ring is unsubstituted or substituted;

or $R^5$ and $R^6$ together with the carbon atom to which $R^5$ and $R^6$ are bound form a ring, wherein the ring is unsubstituted or substituted;

each $R^7$, $R^8$, $R^9$, and $R^{10}$ is independently alkyl, cycloalkyl, alkenyl, alkynyl, aryl, heteroaryl, or heterocyclyl, each which is independently substituted or unsubstituted, or hydrogen or halogen;

or a pharmaceutically-acceptable salt thereof.

In some embodiments, described herein is a compound of the formula:

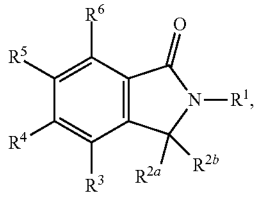

wherein:

$R^1$ is alkyl, cycloalkyl, alkenyl, alkynyl, aryl, heteroaryl, heterocyclyl, —CN, —C(O)$R^7$, —C(O)O$R^7$, —C(O)N$R^7R^8$, —C(=N)N$R^7R^8$, —O$R^7$, —S$R^7$, —N$R^7R^8$, —N$R^7$C(O)$R^8$, —N$R^7$C(O)O$R^8$, —OC(O)$R^7$, —OC(O)N$R^7R^8$, —$S(O)_2R^7$, —NH$S(O)_2R^7$, —O$S(O)_2R^7$, each which is independently substituted or unsubstituted, or hydrogen or halogen;

each $R^{2a}$, $R^{2b}$, $R^4$, $R^5$, and $R^6$ is independently alkyl, cycloalkyl, alkenyl, alkynyl, aryl, heteroaryl, heterocyclyl, —CN, —C(O)$R^9$, —C(O)O$R^9$, —C(O)N$R^9R^{10}$, —C(=N)N$R^9R^{10}$, —O$R^9$, —S$R^9$, —N$R^9R^{10}$, —N$R^9$C(O)$R^{10}$, —N$R^9$C(O)O$R^{10}$, —OC(O)$R^9$, —OC(O)N$R^9R^{10}$, —$S(O)_2R^9$, —NH$S(O)_2R^9$, —O$S(O)_2R^9$, each which is independently substituted or unsubstituted, or hydrogen or halogen;

or $R^{2a}$ and $R^{2b}$ together with the carbon atom to which $R^{2a}$ and $R^{2b}$ are bound is —C=O or —C=S;

or $R^4$ and $R^5$ together with the carbon atom to which $R^4$ and $R^5$ are bound form a ring, wherein the ring is unsubstituted or substituted;

or $R^5$ and $R^6$ together with the carbon atom to which $R^5$ and $R^6$ are bound form a ring, wherein the ring is unsubstituted or substituted;

$R^3$ is

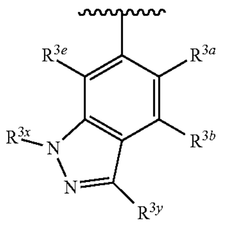 or 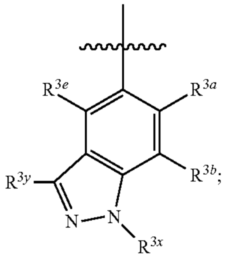

each $R^{3a}$, $R^{3b}$, $R^{3c}$, $R^{3x}$ and $R^{3y}$ is independently alkyl, cycloalkyl, alkenyl, alkynyl, aryl, heteroaryl, heterocyclyl, —CN, —C(O)$R^7$, —C(O)O$R^7$, —C(O)N$R^7R^8$, —C(=N)N$R^7R^8$, —O$R^7$, —S$R^7$, —N$R^7R^8$, —N$R^7$C(O)$R^8$, —N$R^7$C(O)O$R^8$, —OC(O)$R^7$, —OC(O)N$R^7R^8$, —$S(O)_2R^7$, —NH$S(O)_2R^7$, —O$S(O)_2R^7$, each which is independently substituted or unsubstituted, or hydrogen or halogen;

each $R^7$, $R^8$, $R^9$, and $R^{10}$ is independently alkyl, cycloalkyl, alkenyl, alkynyl, aryl, heteroaryl, or heterocyclyl, each which is independently substituted or unsubstituted, or hydrogen or halogen;

or a pharmaceutically-acceptable salt thereof.

In some embodiments, described herein is a compound of the formula:

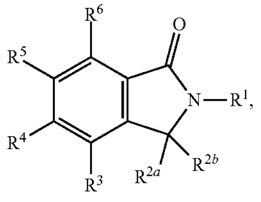

wherein:

$R^1$ is

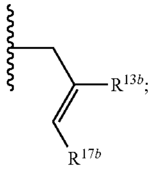

$R^{13b}$ is alkyl, cycloalkyl, alkenyl, alkynyl, aryl, heteroaryl, heterocyclyl, —CN, —C(O)$R^7$, —C(O)O$R^7$, —C(O)N$R^7R^8$, —C(=N)N$R^7R^8$, —O$R^7$, —S$R^7$, —N$R^7R^8$, —N$R^7$C(O)$R^8$, —N$R^7$C(O)O$R^8$, —OC(O)$R^7$, —OC(O)N$R^7R^8$, —$S(O)_2R^7$, —NH$S(O)_2R^7$, —O$S(O)_2R^7$, each which is independently substituted or unsubstituted, or hydrogen or halogen—

$R^{17b}$ is —CN, alkyl, aryl, heteroaryl, —N$R^7R^8$, —$S(O)_2R^7$, —S$R^7$, or O$R^7$, each which is unsubstituted or substituted, or hydrogen or halogen;

each $R^{2a}$, $R^{2b}$, $R^3$, $R^4$, and $R^5$ is independently alkyl, cycloalkyl, alkenyl, alkynyl, aryl, heteroaryl, heterocyclyl, —CN, —C(O)$R^9$, —C(O)O$R^9$, —C(O)N$R^9R^{10}$, —C(=N)N$R^9R^{10}$, —O$R^9$, —S$R^9$, —N$R^9R^{10}$, —N$R^9$C(O)$R^{10}$, —N$R^9$C(O)O$R^{10}$, —OC(O)$R^9$, —OC(O)N$R^9R^{10}$, —$S(O)_2R^9$, —NH$S(O)_2R^9$, —O$S(O)_2R^9$, each which is independently substituted or unsubstituted, or hydrogen or halogen;

or $R^{2a}$ and $R^{2b}$ together with the carbon atom to which $R^{2a}$ and $R^{2b}$ are bound is —C=O or —C=S;

or $R^3$ and $R^4$ together with the carbon atom to which $R^3$ and $R^4$ are bound form a ring, wherein the ring is unsubstituted or substituted;

or $R^4$ and $R^5$ together with the carbon atom to which $R^4$ and $R^5$ are bound form a ring, wherein the ring is unsubstituted or substituted;

$R^6$ is $NH_2$;

each $R^7$, $R^8$, $R^9$, and $R^{10}$ is independently alkyl, cycloalkyl, alkenyl, alkynyl, aryl, heteroaryl, or heterocyclyl, each which is independently substituted or unsubstituted, or hydrogen or halogen;

or a pharmaceutically-acceptable salt thereof.

In some embodiments, $R^1$ is —C(O)$R^7$. In some embodiments, $R^1$ is

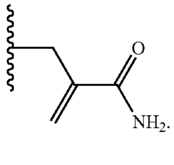 [SMILES: *CC(=C)C(N)=O]

In some embodiments, $R^1$ is

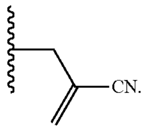 [SMILES: *CC(=C)C#N]

In some embodiments, $R^1$ is an unsubstituted or substituted alkyl or alkenyl. In some embodiments, $R^1$ is

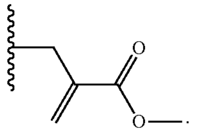 [SMILES: *CC(=C)C(=O)OC]

In some embodiments, $R^1$ is

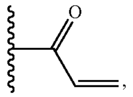 [SMILES: *C(=O)C=C]

wherein the olefin is substituted or unsubstituted. In some embodiments, $R^1$ is

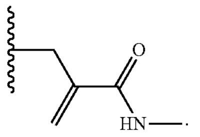 [SMILES: *CC(=C)C(=O)NC]

In some embodiments, $R^1$ is

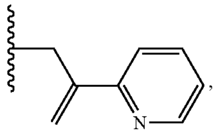 [SMILES: *CC(=C)c1ccccn1]

wherein the pyridine ring is substituted or unsubstituted. In some embodiments, $R^1$ is

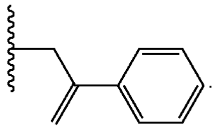 [SMILES: *CC(=C)c1ccccc1]

In some embodiments, $R^1$ is

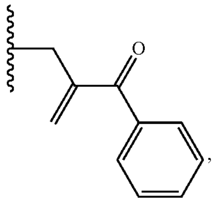 [SMILES: *CC(=C)C(=O)c1ccccc1]

wherein phenyl is substituted or unsubstituted. In some embodiments, $R^1$ is

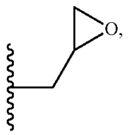 [SMILES: *CC1CO1]

wherein the epoxide is substituted or unsubstituted. In some embodiments, $R^1$ is

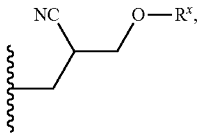

wherein $R^x$ is alkyl, halo, amino, or heterocyclyl, each of which is substituted or unsubstituted.

In some embodiments, $R^3$ is hydrogen. In some embodiments, $R^4$ is hydrogen. In some embodiments, $R^5$ is hydrogen. In some embodiments, $R^6$ is hydrogen. In some embodiments, each $R^4$ and $R^5$ is independently hydrogen. In some embodiments, each $R^3$, $R^4$, $R^5$, and $R^6$ is independently hydrogen.

In some embodiments, $R^3$ is alkyl, cycloalkyl, alkenyl, alkynyl, aryl, heteroaryl, or heterocyclyl, each which is independently substituted or unsubstituted, or hydrogen. In some embodiments, $R^3$ is substituted aryl. In some embodiments, $R^3$ is substituted phenyl. In some embodiments, $R^3$ is substituted or unsubstituted heteroaryl. In some embodiments, $R^3$ is substituted or unsubstituted pyridinyl. In some embodiments, $R^3$ is indazolyl that is substituted or unsubstituted. In some embodiments, $R^3$ is substituted or unsubstituted naphthalene.

In some embodiments, $R^5$ is H. In some embodiments, $R^5$ is $NH_2$. In some embodiments, $R^5$ is $—NR^7R^8$. In some embodiments, $R^5$ is $NHR^8$. In some embodiments, $R^5$ is $—NHC(O)R^8$.

In some embodiments, $R^6$ is hydrogen, OH, $NH_2$, $NR^7R^8$, or $NR^7C(O)R^8$, each of which is independently substituted or unsubstituted. In some embodiments, $R^6$ is hydrogen. In some embodiments, $R^6$ is $NH_2$. In some embodiments, $R^6$ is OH.

In some embodiments, the compound has the formula:

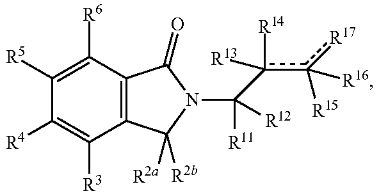

wherein:

each ------- is independently a single bond or a double bond, epoxide or cyclopropyl; wherein at least one of ------- is a single bond;

each $R^{11}$ and $R^{12}$ is independently alkyl, cycloalkyl, alkenyl, alkynyl, aryl, heteroaryl, or heterocyclyl, each which is independently substituted or unsubstituted, or hydrogen; or $R^{11}$ and $R^{12}$ together with the carbon atom to which $R^{11}$ and $R^{12}$ are bound is —C═O or —C═S;

each $R^{13}$, $R^{14}$, $R^{15}$ and $R^{16}$ is independently absent, alkyl, cycloalkyl, alkenyl, alkynyl, aryl, heteroaryl, heterocyclyl, —CN, —C(O)$R^7$, —C(O)O$R^7$, —C(O)N$R^7R^8$, —C(═N)N$R^7R^8$, —O$R^7$, —S$R^7$, —N$R^7R^8$, —N$R^7$C(O)$R^8$, —N$R^7$C(O)O$R^8$, —OC(O)$R^7$, —OC(O)N$R^7R^8$, —S$(O)_2R^7$, —NHS$(O)_2R^7$, —OS$(O)_2R^7$, each which is independently substituted or unsubstituted, or hydrogen or halogen;

$R^{17}$ is alkyl, cycloalkyl, alkenyl, alkynyl, aryl, heteroaryl, heterocyclyl, —CN, —C(O)$R^7$, —C(O)O$R^7$, —C(O)N$R^7R^8$, —C(═N)N$R^7R^8$, —O$R^7$, —S$R^7$, —N$R^7R^8$, —N$R^7$C(O)$R^8$, —N$R^7$C(O)O$R^8$, —OC(O)$R^7$, —OC(O)N$R^7R^8$, —S$(O)_2R^7$, —NHS$(O)_2R^7$, —OS$(O)_2R^7$, —C$R^{18}R^{19}$, alkyl, cycloalkyl, aryl, heteroaryl, heterocyclyl, each which is independent substituted or unsubstituted, or hydrogen or halogen; and each $R^{18}$ and $R^{19}$ is independently —CN, alkyl, cycloalkyl, alkenyl, alkynyl, aryl, heteroaryl, or heterocyclyl, each which is independently substituted or unsubstituted, or hydrogen.

In some embodiments, $R^{11}$ and $R^{12}$ are each hydrogen. In some embodiments, $R^{11}$ and $R^{12}$ together with the carbon atom to which $R^{11}$ and $R^{12}$ are bound is —C═O.

In some embodiments, one of ------- is epoxide.

In some embodiments, the compound has the formula:

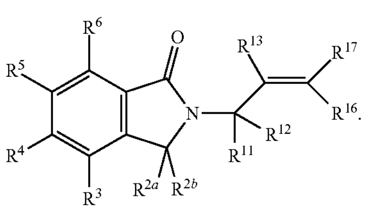

In some embodiments, the compound has the formula:

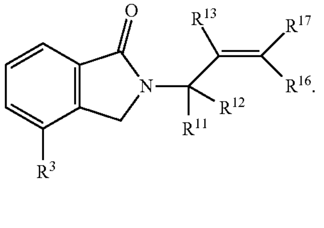

In some embodiments, $R^{16}$ and $R^{17}$ are each hydrogen. In some embodiments, one of $R^{16}$ and $R^{17}$ is hydrogen and the other is —CN.

In some embodiments, $R^{13}$ is —CN, —C(O)N$R^7R^8$, —C(O)$R^7$, C(O)O$R^7$, heteroaryl, or —O$R^7$, each which is unsubstituted or substituted. In some embodiments, $R^{13}$ is —CN. In some embodiments, $R^{13}$ is —C(O)N$R^7R^8$. In some embodiments, $R^{13}$ is —C(O)$NH_2$.

In some embodiments, the compound has the formula:

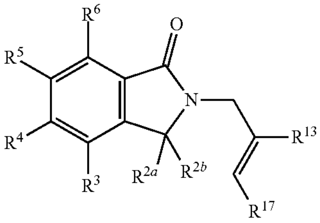

or

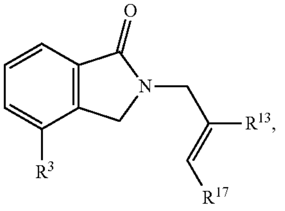

wherein $R^{17}$ is —CN, alkyl, aryl, heteroaryl, —N$R^7R^8$, —S$(O)_2R^7$, —S$R^7$, or O$R^7$, each which is unsubstituted or substituted, or hydrogen or halogen.

In some embodiments, $R^{13}$ is CN. In some embodiments, $R^{13}$ is —C(O)$NH_2$. In some embodiments, $R^{13}$ is heteroaryl which is unsubstituted or substituted. In some embodiments, $R^{13}$ is aryl which is unsubstituted or substituted.

In some embodiments, $R^{17}$ is hydrogen. In some embodiments, $R^{17}$ is methyl. In some embodiments, $R^{17}$ is heteroaryl which is unsubstituted or substituted. In some embodiments, $R^{17}$ is aryl which is unsubstituted or substituted.

In some embodiments, $R^{2a}$ and $R^{2b}$ are each hydrogen.

In some embodiments, $R^3$ is alkyl, cycloalkyl, alkenyl, alkynyl, aryl, heteroaryl, or heterocyclyl, each which is independently substituted or unsubstituted, or hydrogen. In some embodiments, $R^3$ is substituted aryl. In some embodiments, $R^3$ is substituted phenyl. In some embodiments, $R^3$ is substituted or unsubstituted heteroaryl. In some embodiments, $R^3$ is substituted or unsubstituted pyridinyl. In some embodiments, $R^3$ is indazolyl that is substituted or unsubstituted. In some embodiments, $R^3$ is substituted or unsubstituted naphthalene.

In some embodiments, $R^5$ is H. In some embodiments, $R^5$ is $NH_2$. In some embodiments, $R^5$ is —N$R^7R^8$. In some embodiments, $R^5$ is NH$R^8$. In some embodiments, $R^5$ is —NHC(O)$R^8$. In some embodiments, $R^6$ is hydrogen, OH, $NH_2$, N$R^7R^8$, or N$R^7$C(O)$R^8$, each of which is independently substituted or unsubstituted. In some embodiments, $R^6$ is hydrogen. In some embodiments, $R^6$ is $NH_2$. In some embodiments, $R^6$ is OH.

In some embodiments, $R^8$ is alkyl or heterocyclyl, each which is unsubstituted or substituted, or hydrogen. In some embodiments, $R^8$ is phenyl or heterocyclyl, each which is unsubstituted or substituted.

In some embodiments, $R^6$ is H. In some embodiments, $R^6$ is $NH_2$.

In some embodiments, the compound has the formula:
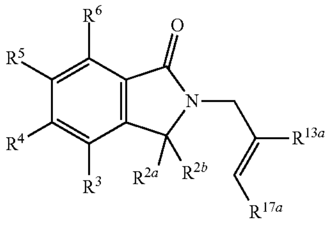
or
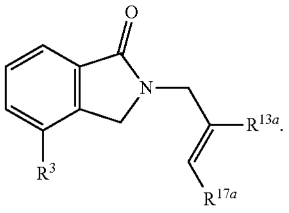
In some embodiments, the compound has the formula:
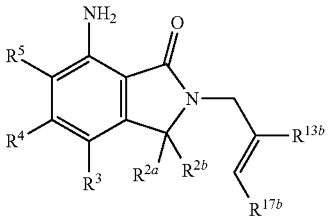
or
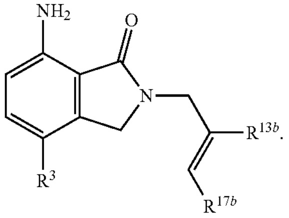
In some embodiments, the compound has the formula:
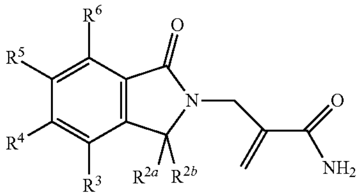
or
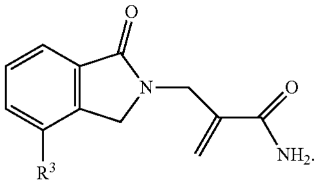
In some embodiments, the compound has the formula:
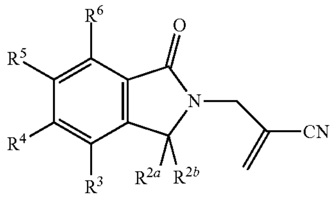
or
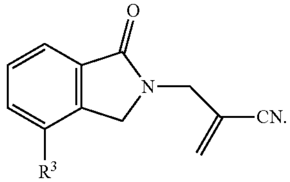
In some embodiments, the compound has the formula:
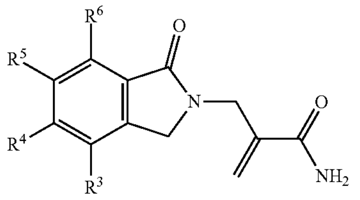
or
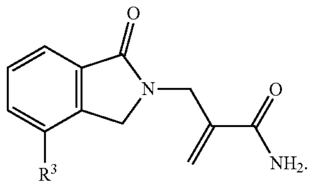
In some embodiments, the compound has the formula:
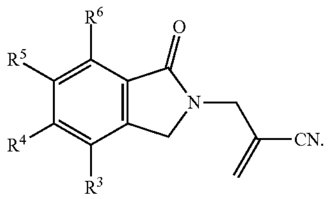
In some embodiments, the compound has the formula:
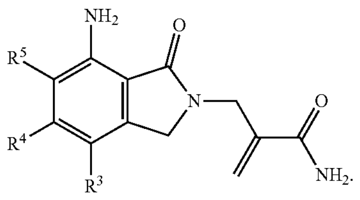

In some embodiments, the compound has the formula:

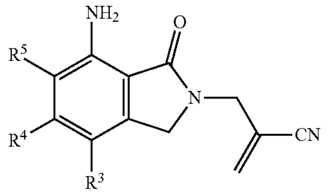 or

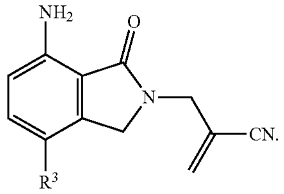

In some embodiments, $R^3$ is aryl, heterocyclyl, or heteroaryl, each which is unsubstituted or substituted. In some embodiments, $R^3$ is phenyl, naphthalenyl, pyridinyl, dihydropyridinyl, tetrahydropyridinyl, pyrazolopyridinyl, imidazopyridinyl, triazolopyridinyl, pyrimidinyl, indolyl, dihydroindolyl, pyridoindolyl, isoindolyl, indazolyl, imidazolyl, benzimidazolyl, benzodiazolyl, carbazolyl, pyrazolyl, oxazolyl, benzoxazolyl, thiazolyl, benzothiazolyl, thiophenyl, benzothiapenyl, quinolinyl, dihydroquinolinyl, isoquinolinyl, dihydroisoquinolinyl, quinoxalinyl, or dihydroquinoxalinyl, each which is unsubstituted or substituted.

In some embodiments, $R^3$ is alkyl, cycloalkyl, alkenyl, alkynyl, aryl, heteroaryl, or heterocyclyl, each which is independently substituted or unsubstituted, or hydrogen. In some embodiments, $R^3$ is substituted aryl. In some embodiments, $R^3$ is substituted phenyl. In some embodiments, $R^3$ is substituted or unsubstituted heteroaryl. In some embodiments, $R^3$ is substituted or unsubstituted pyridinyl. In some embodiments, $R^3$ is indazolyl that is substituted or unsubstituted. In some embodiments, $R^3$ is substituted or unsubstituted naphthalene.

In some embodiments, the compound has the formula:

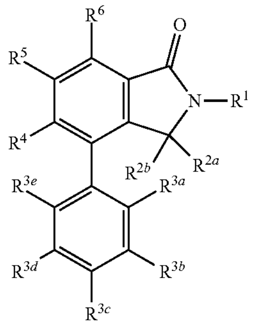

wherein each $R^{3a}$, $R^{3b}$, $R^{3c}$, $R^{3d}$ and $R^{3e}$ is independently alkyl, cycloalkyl, alkenyl, alkynyl, aryl, heteroaryl, heterocyclyl, —CN, —C(O)$R^7$, —C(O)O$R^7$, —C(O)N$R^7R^8$, —C(=N)N$R^7R^8$, —O$R^7$, —S$R^7$, —N$R^7R^8$, —N$R^7$C(O)$R^8$, —N$R^7$C(O)O$R^8$, —OC(O)$R^7$, —OC(O)N$R^7R^8$, —S(O)$_2R^7$, —NHS(O)$_2R^7$, —OS(O)$_2R^7$, each which is independently substituted or unsubstituted, or hydrogen or halogen, or $R^{3a}$ and $R^{3b}$ together with the carbon atom to which $R^{3a}$ and $R^{3b}$ are bound form a ring, wherein the ring is unsubstituted or substituted;

or $R^{3b}$ and $R^{3c}$ together with the carbon atoms to which $R^{3b}$ and $R^{3c}$ are bound form a ring, wherein the ring is unsubstituted or substituted;

or $R^{3c}$ and $R^{3d}$ together with the carbon atoms to which $R^{3c}$ and $R^{3d}$ are bound form a ring, wherein the ring is unsubstituted or substituted;

or $R^{3d}$ and $R^{3e}$ together with the carbon atoms to which $R^{3d}$ and $R^{3e}$ are bound form a ring, wherein the ring is unsubstituted or substituted.

In some embodiments, $R^{2a}$ and $R^{2b}$ are each hydrogen.

In some embodiments, $R^6$ is $NH_2$. In some embodiments, $R^4$ and $R^5$ are each hydrogen. In some embodiments, $R^4$, $R^5$, and $R^6$ are each independently hydrogen.

In some embodiments, each $R^{3a}$, $R^{3b}$, $R^{3c}$, $R^{3d}$ and $R^{3e}$ is independently C(O)$R^7$, —C(O)O$R^7$, —C(O)N$R^7R^8$, —O$R^7$, —N$R^7R^8$, —N$R^7$C(O)$R^8$, alkyl, aryl, heterocyclyl or heteroaryl, each which is independently substituted or unsubstituted, or hydrogen or halogen. In some embodiments, $R^{3b}$ and $R^{3d}$ are each halogen. In some embodiments, $R^{3c}$ is $NH_2$. In some embodiments, $R^{3a}$ and $R^{3e}$ are each hydrogen.

In some embodiments, $R^5$ is H. In some embodiments, $R^5$ is $NH_2$. In some embodiments, $R^5$ is —N$R^7R^8$. In some embodiments, $R^5$ is NH$R^8$. In some embodiments, $R^5$ is —NHC(O)$R^8$. In some embodiments, $R^6$ is hydrogen, OH, $NH_2$, N$R^7R^8$, or N$R^7$C(O)$R^8$, each of which is independently substituted or unsubstituted. In some embodiments, $R^6$ is hydrogen. In some embodiments, $R^6$ is $NH_2$. In some embodiments, $R^6$ is OH.

In some embodiments, the compound has the formula:

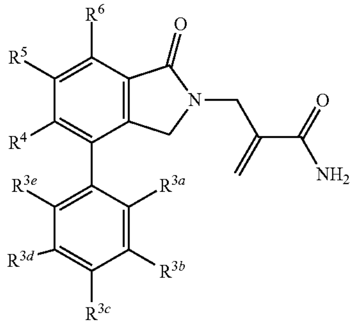 or

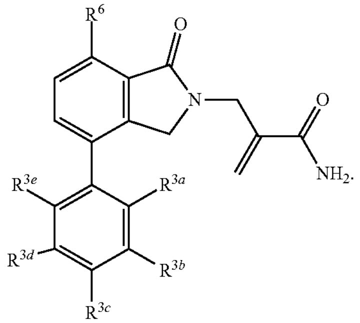

In some embodiments, the compound has the formula:

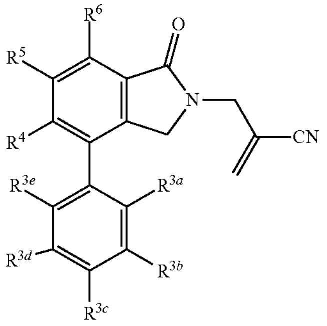

or

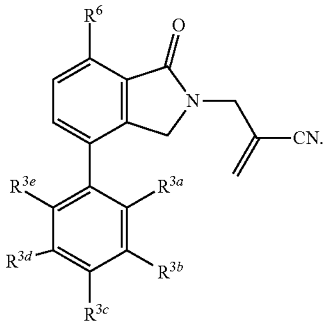

In some embodiments, $R^{3e}$ and $R^{3d}$ together with the carbon atoms to which $R^{3c}$ and $R^{3d}$ are bound form a ring, wherein the ring is unsubstituted or substituted.

In some embodiments, the compound has the formula:

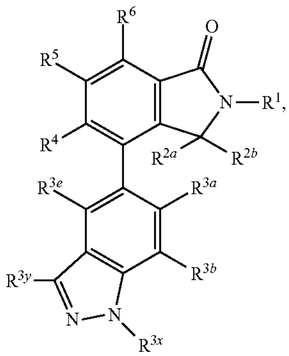

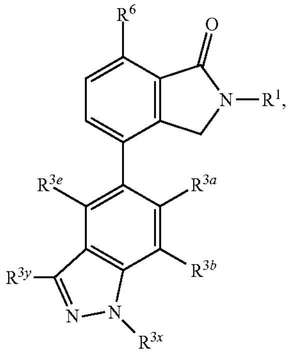

-continued

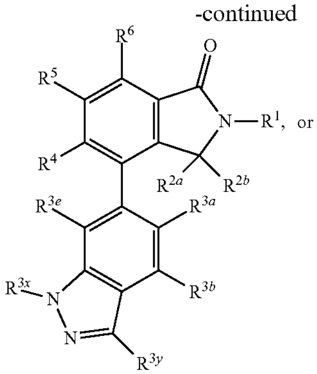

or

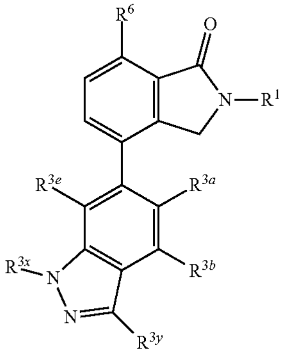

In some embodiments, $R^{2a}$ and $R^{2b}$ are each hydrogen.

In some embodiments, $R^5$ is H. In some embodiments, $R^5$ is $NH_2$. In some embodiments, $R^5$ is —$NR^7R^8$. In some embodiments, $R^5$ is $NHR^8$. In some embodiments, $R^5$ is —$NHC(O)R^8$.

In some embodiments, $R^6$ is hydrogen, OH, $NH_2$, $NR^7R^8$, or $NR^7C(O)R^8$, each of which is independently substituted or unsubstituted. In some embodiments, $R^6$ is hydrogen. In some embodiments, $R^6$ is $NH_2$. In some embodiments, $R^6$ is OH.

In some embodiments, $R^{3x}$ is hydrogen.

In some embodiments, $R^{3x}$ is methyl.

In some embodiments, $R^{3y}$ is phenyl which is unsubstituted or substituted. In some embodiments, $R^{3y}$ is heteroaryl which is unsubstituted or substituted. In some embodiments, $R^{3y}$ is heterocyclyl which is unsubstituted or substituted. In some embodiments, $R^{3y}$ is thiophenyl. In some embodiments, $R^{3y}$ is alkyl or alkoxy, each which is substituted or unsubstituted. In some embodiments, $R^{3y}$ is methyl.

In some embodiments, the compound has the formula:

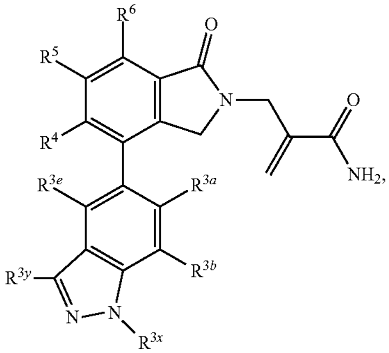

-continued

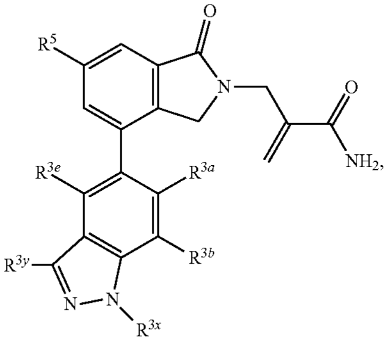

,

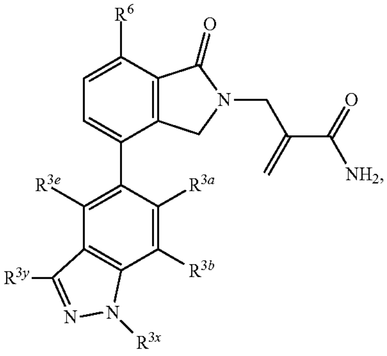

,

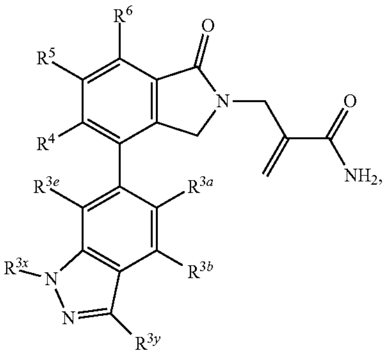

,

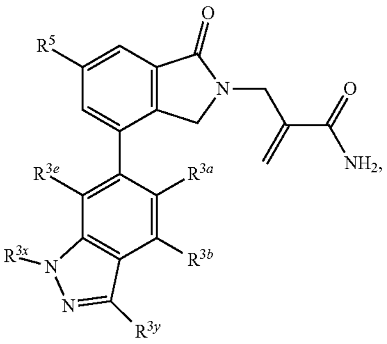

, or

-continued

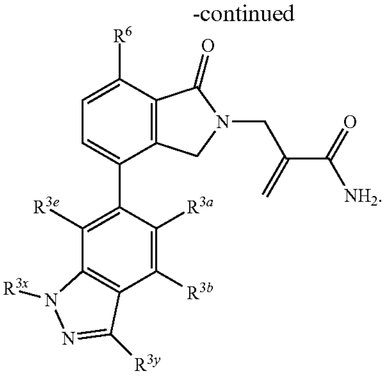

.

In some embodiments, $R^5$ is H. In some embodiments, $R^5$ is $NH_2$. In some embodiments, $R^5$ is —$NR^7R^8$. In some embodiments, $R^5$ is $NHR^8$. In some embodiments, $R^5$ is —$NHC(O)R^8$. In some embodiments, $R^6$ is hydrogen, OH, $NH_2$, $NR^7R^8$, or $NR^7C(O)R^8$, each of which is independently substituted or unsubstituted. In some embodiments, $R^6$ is hydrogen. In some embodiments, $R^6$ is $NH_2$. In some embodiments, $R^6$ is OH.

In some embodiments, the compound has the formula:

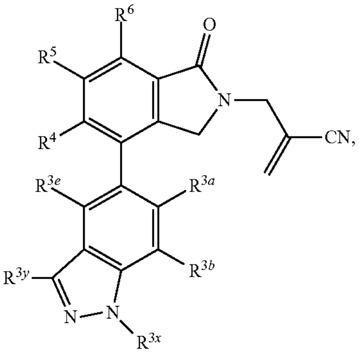

,

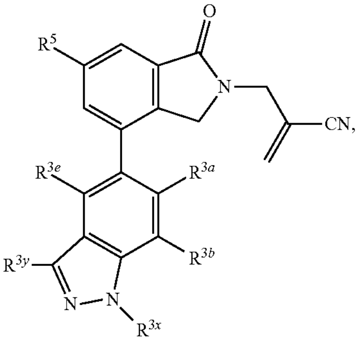

,

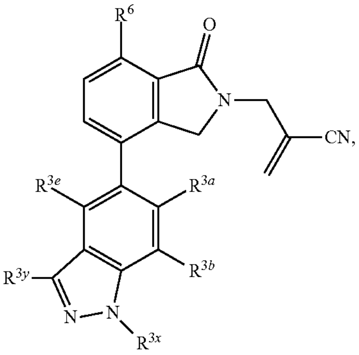

,

-continued

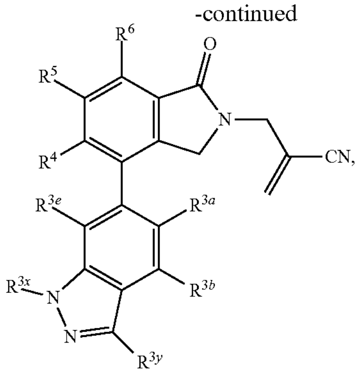

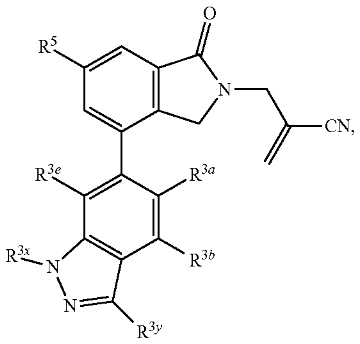

or

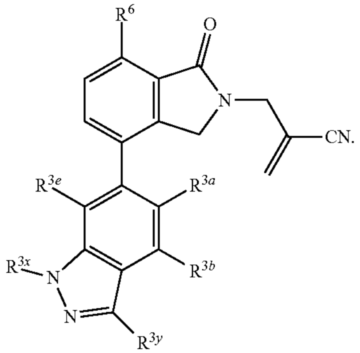

In some embodiments, $R^5$ is H. In some embodiments, $R^5$ is $NH_2$. In some embodiments, $R^5$ is —$NR^7R^8$. In some embodiments, $R^5$ is $NHR^8$. In some embodiments, $R^5$ is —$NHC(O)R^8$. In some embodiments, $R^6$ is hydrogen, OH, $NH_2$, $NR^7R^8$, or $NR^7C(O)R^8$, each of which is independently substituted or unsubstituted. In some embodiments, $R^6$ is hydrogen. In some embodiments, $R^6$ is $NH_2$. In some embodiments, $R^6$ is OH.

In some embodiments, $R^{3e}$ and $R^4$ together with the carbon atom to which $R^{3e}$ and $R^4$ are bound form a ring. In some embodiments, the ring is aryl which is unsubstituted or substituted. In some embodiments, the ring is phenyl which is unsubstituted or substituted.

In some embodiments, the compound has the formula:

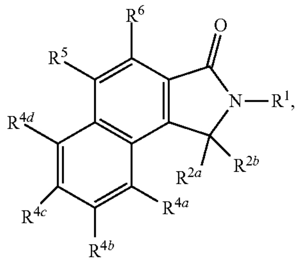

wherein each $R^{4a}$, $R^{4b}$, $R^{4c}$, and $R^{4d}$ is independently alkyl, cycloalkyl, alkenyl, alkynyl, aryl, heteroaryl, heterocyclyl, —CN, —$C(O)R^7$, —$C(O)OR^7$, —$C(O)NR^7R^8$, —$C(=N)NR^7R^8$, —$OR^7$, —$SR^7$, —$NR^7R^8$, —$NR^7C(O)R^8$, —$NR^7C(O)OR^8$, —$OC(O)R^7$, —$OC(O)NR^7R^8$, —$S(O)_2R^7$, —$NHS(O)_2R^7$, —$OS(O)_2R^7$, each which is independently substituted or unsubstituted, or hydrogen or halogen.

In some embodiments, $R^2$ and $R^{2a}$ are each hydrogen.

In some embodiments, $R^1$ is —$C(O)NH_2$.

In some embodiments, $R^6$ is $NH_2$.

In some embodiments, the compound has the formula:

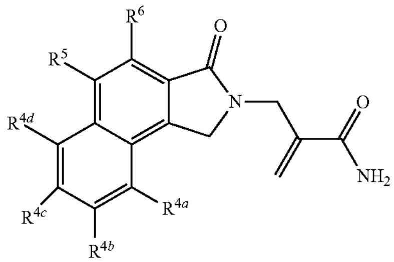

or

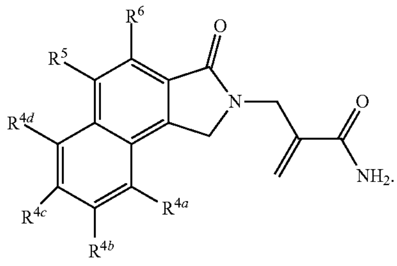

In some embodiments, $R^{4a}$, $R^{4c}$ and $R^{4d}$ are each hydrogen. In some embodiments, $R^{4b}$ is aryl, heteroaryl, or heterocyclyl, each which is unsubstituted or substituted. In some embodiments, $R^{4b}$ is substituted phenyl. In some embodiments, $R^{4b}$ is substituted heteroaryl. In some embodiments, $R^{4b}$ is substituted pyridinyl. In some embodiments, $R^{4b}$ is halogen. In some embodiments, $R^{4b}$ is —CN. In some embodiments, $R^{4b}$ is $NR^7R^8$. In some embodiments, $R^{4b}$ is —$NR^7C(O)R^8$.

In some embodiments, the compound has the formula:

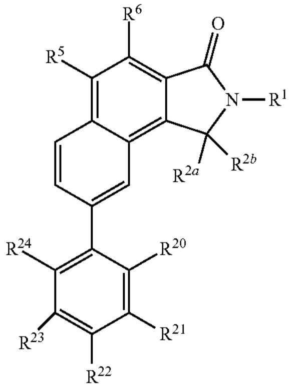

or

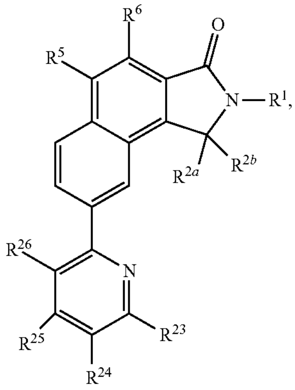

, wherein each $R^{20}$, $R^{21}$, $R^{22}$, $R^{23}$ and $R^{24}$ is alkyl, cycloalkyl, alkenyl, alkynyl, aryl, heteroaryl, heterocyclyl, —CN, —C(O)$R^7$, —C(O)O$R^7$, —C(O)N$R^7R^8$, —C(═N)N$R^7R^8$, —O$R^7$, —S$R^7$, —N$R^7R^8$, —N$R^7$C(O)$R^8$, —N$R^7$C(O)O$R^8$, —OC(O)$R^7$, —OC(O)N$R^7R^8$, —S$(O)_2R^7$, —NHS$(O)_2R^7$, —OS$(O)_2R^7$, each which is independently substituted or unsubstituted, or hydrogen or halogen.

In some embodiments, the compound has the formula:

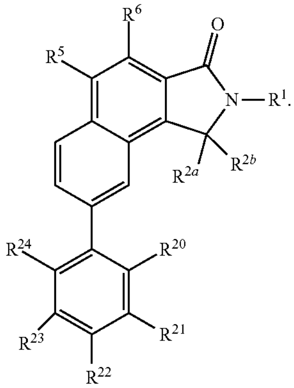

.

In some embodiments, each $R^{20}$, $R^{21}$, $R^{22}$, $R^{23}$ and $R^{24}$ is independently alkyl, heteroaryl, —CN, —C(O)$R^7$, —N$R^7$C(O)N$R^8$, —C(O)N$R^7R^8$, —C(═N)N$R^7R^8$, —O$R^7$, —N$R^7R^8$, —S$(O)_2R^7$, —NHS$(O)_2R^7$, —S$(O)_2R^7$, or each which is unsubstituted or substituted, or hydrogen or halogen. In some embodiments, $R^{20}$ is alkyl. In some embodiments, $R^{22}$ is $NH_2$. In some embodiments, $R^{22}$ is $SO_2$ Me. In some embodiments, $R^{22}$ is CN. In some embodiments, $R^{23}$ is alkoxy. In some embodiments, $R^{23}$ is halogen.

In some embodiments, the compound has the formula:

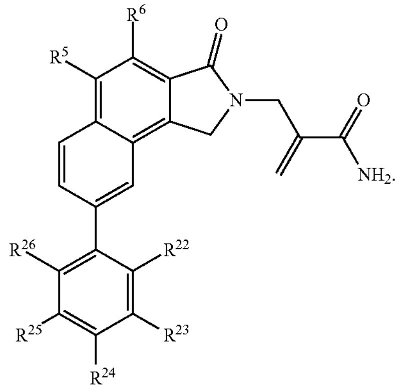

In some embodiments, $R^5$ is H. In some embodiments, $R^5$ is $NH_2$. In some embodiments, $R^5$ is —N$R^7R^8$. In some embodiments, $R^5$ is NH$R^8$. In some embodiments, $R^5$ is —NHC(O)$R^8$. In some embodiments, $R^6$ is hydrogen, OH, $NH_2$, N$R^7R^8$, or N$R^7$C(O)$R^8$, each of which is independently substituted or unsubstituted. In some embodiments, $R^6$ is hydrogen. In some embodiments, $R^6$ is $NH_2$. In some embodiments, $R^6$ is OH.

In some embodiments, each $R^{20}$, $R^{21}$, $R^{22}$, $R^{23}$ and $R^{24}$ is independently alkyl, heteroaryl, —CN, —C(O)$R^7$, —N$R^7$C(O)N$R^8$, —C(O)N$R^7R^8$, —C(═N)N$R^7R^8$, —O$R^7$, —N$R^7R^8$, —S$(O)_2R^7$, —NHS$(O)_2R^7$, —S$(O)_2R^7$, or each which is unsubstituted or substituted, or hydrogen or halogen. In some embodiments, $R^{20}$ is alkyl. In some embodiments, $R^{22}$ is $NH_2$. In some embodiments, $R^{22}$ is $SO_2$ Me. In some embodiments, $R^{22}$ is CN. In some embodiments, $R^{23}$ is alkoxy. In some embodiments, $R^{23}$ is halogen.

In some embodiments, the compound has the formula:

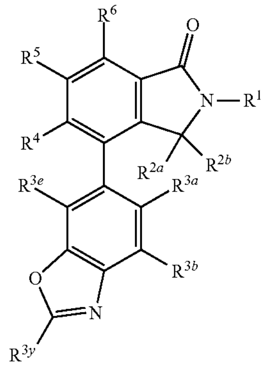

wherein each $R^{3a}$, $R^{3b}$, $R^{3e}$ and $R^{3y}$ is independently alkyl, cycloalkyl, alkenyl, alkynyl, aryl, heteroaryl, heterocyclyl, —CN, —C(O)$R^7$, —C(O)O$R^7$, —C(O)N$R^7R^8$, —C(═N)N$R^7R^8$, —O$R^7$, —S$R^7$, —N$R^7R^8$, —N$R^7$C(O)$R^8$, —N$R^7$C(O)O$R^8$, —OC(O)$R^7$, —OC(O)N$R^7R^8$, —S$(O)_2R^7$, —NHS$(O)_2R^7$, —OS$(O)_2R^7$, each which is independently substituted or unsubstituted, or hydrogen or halogen.

In some embodiments, the compound has the formula:

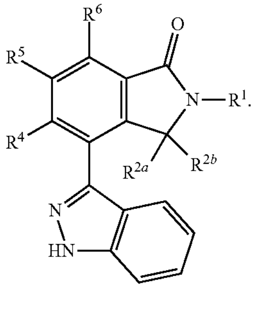

In some embodiments, the compound has the formula:

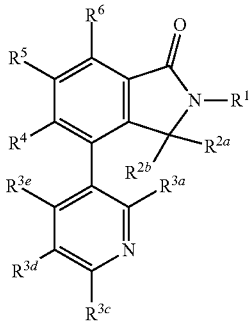

wherein each $R^{3a}$, $R^{3c}$, $R^{3d}$ and $R^{3c}$ is independently alkyl, cycloalkyl, alkenyl, alkynyl, aryl, heteroaryl, heterocyclyl, —CN, —C(O)$R^7$, —C(O)O$R^7$, —C(O)N$R^7R^8$, —C(═N)N$R^7R^8$, —O$R^7$, —S$R^7$, —N$R^7R^8$, —N$R^7$C(O)$R^8$, —N$R^7$C(O)O$R^8$, —OC(O)$R^7$, —OC(O)N$R^7R^8$, —S(O)$_2R^7$, —NHS(O)$_2R^7$, —OS(O)$_2R^7$, each which is independently substituted or unsubstituted, or hydrogen or halogen, or $R^{3c}$ and $R^{3d}$ together with the carbon atoms to which $R^{3c}$ and $R^{3d}$ are bound form a ring, wherein the ring is unsubstituted or substituted;

or $R^{3d}$ and $R^{3c}$ together with the carbon atoms to which $R^{3d}$ and $R^{3e}$ are bound form a ring, wherein the ring is unsubstituted or substituted.

In some embodiments, the compound has the formula:

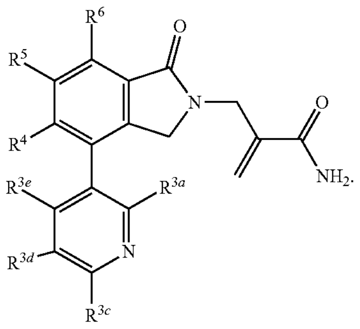

In some embodiments, the compound has the formula:

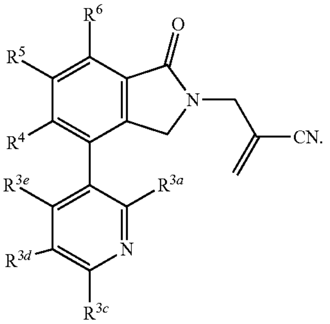

In some embodiments, the compounds is of the formula:

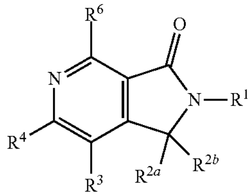

or

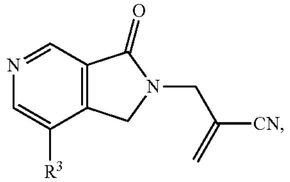

wherein:

$R^1$ is alkyl, cycloalkyl, alkenyl, alkynyl, aryl, heteroaryl, heterocyclyl, —CN, —C(O)$R^7$, —C(O)O$R^7$, —C(O)N$R^7R^8$, —C(═N)N$R^7R^8$, —O$R^7$, —S$R^7$, —N$R^7R^8$, —N$R^7$C(O)$R^8$, —N$R^7$C(O)O$R^8$, —OC(O)$R^7$, —OC(O)N$R^7R^8$, —S(O)$_2R^7$, —NHS(O)$_2R^7$, —OS(O)$_2R^7$, each which is independently substituted or unsubstituted, or hydrogen or halogen;

each $R^{2a}$, $R^{2b}$, $R^4$, and $R^6$ is independently alkyl, cycloalkyl, alkenyl, alkynyl, aryl, heteroaryl, heterocyclyl, —CN, —C(O)$R^9$, —C(O)O$R^9$, —C(O)N$R^9R^{10}$, —C(═N)N$R^9R^{10}$, —O$R^9$, —S$R^9$, —N$R^9R^{10}$, —N$R^9$C(O)$R^{10}$, —N$R^9$C(O)O$R^{10}$, —OC(O)$R^9$, —OC(O)N$R^9R^{10}$, —S(O)$_2R^9$, —NHS(O)$_2R^9$, —OS(O)$_2R^9$, each which is independently substituted or unsubstituted, or hydrogen or halogen;

$R^3$ is

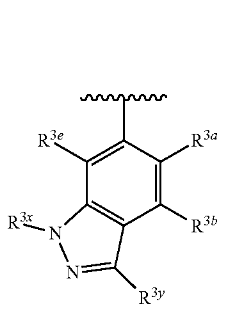

or

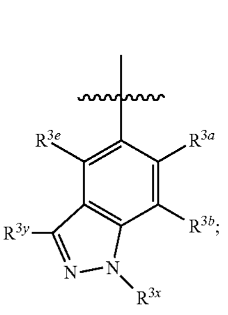

each $R^{3a}$, $R^{3b}$, $R^{3e}$, $R^{3x}$ and $R^{3y}$ is independently alkyl, cycloalkyl, alkenyl, alkynyl, aryl, heteroaryl, heterocyclyl, —CN, —C(O)$R^7$, —C(O)O$R^7$, —C(O)N$R^7R^8$, —C(═N)NR$^7$R$^8$, —OR$^7$, —SR$^7$, —NR$^7$R$^8$, —NR$^7$C(O)R$^8$, —NR$^7$C(O)OR$^8$, —OC(O)R$^7$, —OC(O)NR$^7$R$^8$, —S(O)$_2$R$^7$, —NHS(O)$_2$R$^7$, —OS(O)$_2$R$^7$, each which is independently substituted or unsubstituted, or hydrogen or halogen;

each R$^7$, R$^8$, R$^9$, and R$^{10}$ is independently alkyl, cycloalkyl, alkenyl, alkynyl, aryl, heteroaryl, or heterocyclyl, each which is independently substituted or unsubstituted, or hydrogen or halogen;

or a pharmaceutically-acceptable salt thereof.

In some embodiments, the compound is of the formula:

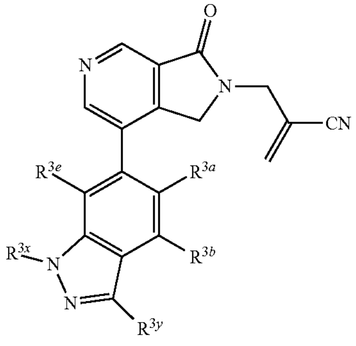

or

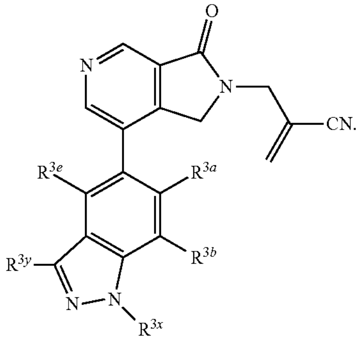

In some embodiments, each R$^{3a}$, R$^{3b}$, and R$^{3c}$ is independently hydrogen. In some embodiments, each R$^{3x}$ and R$^{3y}$ is independently alkyl that is substituted or unsubstituted. In some embodiments, each R$^{3x}$ and R$^{3y}$ is independently methyl.

In some embodiments, the compound has the formula:

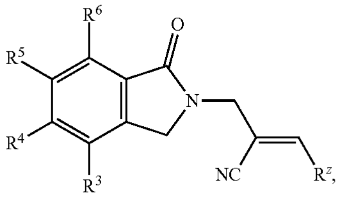

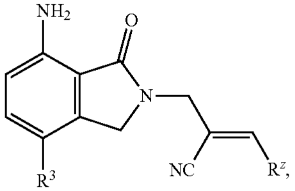

-continued

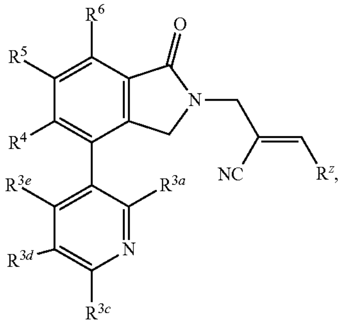

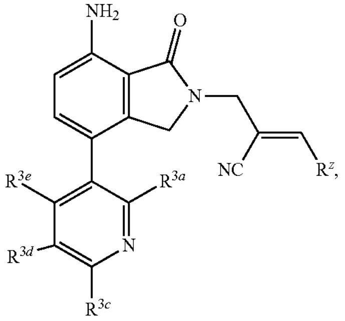

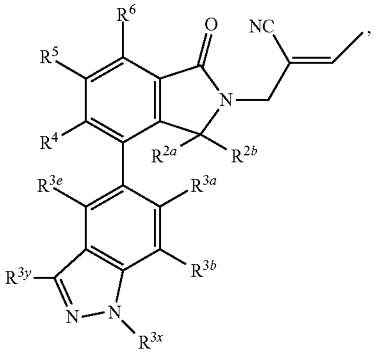

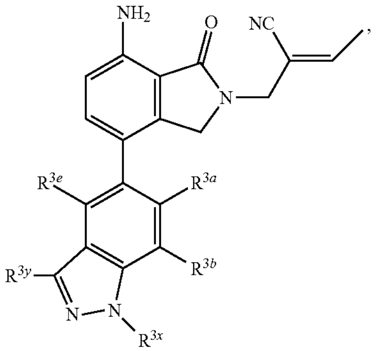

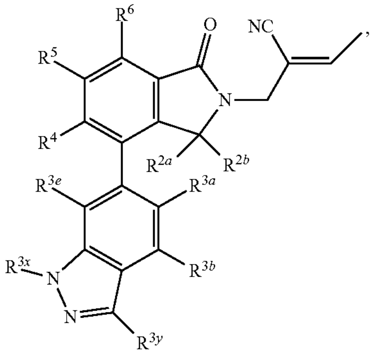

or

-continued

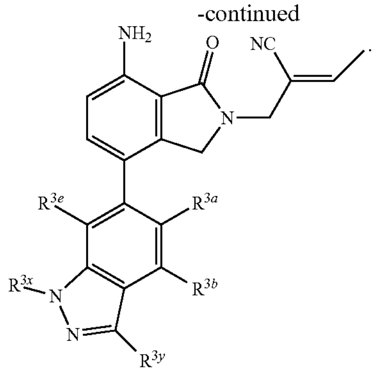

Several moieties described herein may be substituted or unsubstituted. Non-limiting examples of optional substituents include hydroxyl groups, sulfhydryl groups, halogens, amino groups, nitro groups, nitroso groups, cyano groups, azido groups, sulfoxide groups, sulfone groups, sulfonamide groups, carboxyl groups, carboxaldehyde groups, imine groups, alkyl groups, halo-alkyl groups, alkenyl groups, halo-alkenyl groups, alkynyl groups, halo-alkynyl groups, alkoxy groups, aryl groups, aryloxy groups, aralkyl groups, arylalkoxy groups, heterocyclyl groups, acyl groups, acyloxy groups, carbamate groups, amide groups, ureido groups, epoxy groups, and ester groups.

Non-limiting examples of alkyl and alkylene groups include straight, branched, and cyclic alkyl and alkylene groups. An alkyl or alkylene group can be, for example, a $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{15}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ group that is substituted or unsubstituted.

Non-limiting examples of straight alkyl groups include methyl, ethyl, propyl, butyl, pentyl, hexyl, heptyl, octyl, nonyl, and decyl.

Branched alkyl groups include any straight alkyl group substituted with any number of alkyl groups. Non-limiting examples of branched alkyl groups include isopropyl, isobutyl, sec-butyl, and t-butyl.

Non-limiting examples of substituted alkyl groups includes hydroxymethyl, chloromethyl, trifluoromethyl, aminomethyl, 1-chloroethyl, 2-hydroxyethyl, 1,2-difluoroethyl, and 3-carboxypropyl.

Non-limiting examples of cyclic alkyl groups include cyclopropyl, cyclobutyl, cyclopentyl, cyclohexyl, cycloheptyl, and cyclooctyl groups. Cyclic alkyl groups also include fused-, bridged-, and spiro-bicycles and higher fused-, bridged-, and spiro-systems. A cyclic alkyl group can be substituted with any number of straight, branched, or cyclic alkyl groups. Non-limiting examples of cyclic alkyl groups include cyclopropyl, 2-methyl-cycloprop-1-yl, cycloprop-2-en-1-yl, cyclobutyl, 2,3-dihydroxycyclobut-1-yl, cyclobut-2-en-1-yl, cyclopentyl, cyclopent-2-en-1-yl, cyclopenta-2,4-dien-1-yl, cyclohexyl, cyclohex-2-en-1-yl, cycloheptyl, cyclooctanyl, 2,5-dimethylcyclopent-1-yl, 3,5-dichlorocyclohex-1-yl, 4-hydroxycyclohex-1-yl, 3,3,5-trimethylcyclohex-1-yl, octahydropentalenyl, octahydro-1H-indenyl, 3a,4,5,6,7,7a-hexahydro-3H-inden-4-yl, decahydroazulenyl, bicyclo-[2.1.1]hexanyl, bicyclo[2.2.1]heptanyl, bicyclo[3.1.1]heptanyl, 1,3-dimethyl[2.2.1]heptan-2-yl, bicyclo[2.2.2]octanyl, and bicyclo[3.3.3]undecanyl.

Non-limiting examples of alkenyl and alkenylene groups include straight, branched, and cyclic alkenyl groups. The olefin or olefins of an alkenyl group can be, for example, E, Z, cis, trans, terminal, or exo-methylene. An alkenyl or alkenylene group can be, for example, a $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{15}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ group that is substituted or unsubstituted. Non-limiting examples of alkenyl and alkenylene groups include ethenyl, prop-1-en-1-yl, isopropenyl, but-1-en-4-yl; 2-chloroethenyl, 4-hydroxybuten-1-yl, 7-hydroxy-7-methyloct-4-en-2-yl, and 7-hydroxy-7-methyloct-3,5-dien-2-yl.

Non-limiting examples of alkynyl or alkynylene groups include straight, branched, and cyclic alkynyl groups. The triple bond of an alkylnyl or alkynylene group can be internal or terminal. An alkylnyl or alkynylene group can be, for example, a $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ group that is substituted or unsubstituted. Non-limiting examples of alkynyl or alkynylene groups include ethynyl, prop-2-yn-1-yl, prop-1-yn-1-yl, and 2-methyl-hex-4-yn-1-yl; 5-hydroxy-5-methylhex-3-yn-1-yl, 6-hydroxy-6-methylhept-3-yn-2-yl, and 5-hydroxy-5-ethylhept-3-yn-1-yl.

A halo-alkyl group can be any alkyl group substituted with any number of halogen atoms, for example, fluorine, chlorine, bromine, and iodine atoms. A halo-alkenyl group can be any alkenyl group substituted with any number of halogen atoms. A halo-alkynyl group can be any alkynyl group substituted with any number of halogen atoms.

An alkoxy group can be, for example, an oxygen atom substituted with any alkyl, alkenyl, or alkynyl group. An ether or an ether group comprises an alkoxy group. Non-limiting examples of alkoxy groups include methoxy, ethoxy, propoxy, isopropoxy, and isobutoxy.

An aryl group can be heterocyclic or non-heterocyclic. An aryl group can be monocyclic or polycyclic. An aryl group can be substituted with any number of substituents described herein, for example, hydrocarbyl groups, alkyl groups, alkoxy groups, and halogen atoms. Non-limiting examples of aryl groups include phenyl, toluyl, naphthyl, pyrrolyl, pyridyl, imidazolyl, thiophenyl, and furyl. Non-limiting examples of substituted aryl groups include 3,4-dimethylphenyl, 4-tert-butylphenyl, 4-cyclopropylphenyl, 4-diethylaminophenyl, 4-(trifluoromethyl)phenyl, 4-(difluoromethoxy)-phenyl, 4-(trifluoromethoxy)phenyl, 3-chlorophenyl, 4-chlorophenyl, 3,4-dichlorophenyl, 2-fluorophenyl, 2-chlorophenyl, 2-iodophenyl, 3-iodophenyl, 4-iodophenyl, 2-methylphenyl, 3-fluorophenyl, 3-methylphenyl, 3-methoxyphenyl, 4-fluorophenyl, 4-methylphenyl, 4-methoxyphenyl, 2,3-difluorophenyl, 3,4-difluorophenyl, 3,5-difluorophenyl, 2,3-dichlorophenyl, 3,4-dichlorophenyl, 3,5-dichlorophenyl, 2-hydroxyphenyl, 3-hydroxyphenyl, 4-hydroxyphenyl, 2-methoxyphenyl, 3-methoxyphenyl, 4-methoxyphenyl, 2,3-dimethoxyphenyl, 3,4-dimethoxyphenyl, 3,5-dimethoxyphenyl, 2,4-difluorophenyl, 2,5-difluorophenyl, 2,6-difluorophenyl, 2,3,4-trifluorophenyl, 2,3,5-trifluorophenyl, 2,3,6-trifluorophenyl, 2,4,5-trifluorophenyl, 2,4,6-trifluorophenyl, 2,4-dichlorophenyl, 2,5-dichlorophenyl, 2,6-dichlorophenyl, 3,4-dichlorophenyl, 2,3,4-trichlorophenyl, 2,3,5-trichlorophenyl, 2,3,6-trichlorophenyl, 2,4,5-trichlorophenyl, 3,4,5-trichlorophenyl, 2,4,6-trichlorophenyl, 2,3-dimethylphenyl, 2,4-dimethylphenyl, 2,5-dimethylphenyl, 2,6-dimethylphenyl, 2,3,4-trimethylphenyl, 2,3,5-trimethylphenyl, 2,3,6- trimethylphenyl, 2,4,5-trimethylphenyl, 2,4,6-trimethylphenyl, 2-ethylphenyl, 3-ethylphenyl, 4-ethylphenyl, 2,3-diethylphenyl, 2,4-diethylphenyl, 2,5-diethylphenyl, 2,6-diethylphenyl, 3,4-diethylphenyl, 2,3,4-triethylphenyl, 2,3,5-triethylphenyl, 2,3,6-triethylphenyl, 2,4,5-triethylphenyl, 2,4,6-triethylphenyl, 2-isopropylphenyl, 3-isopropylphenyl, and 4-isopropylphenyl.

Non-limiting examples of substituted aryl groups include 2-aminophenyl, 2-(N-methylamino)phenyl, 2-(N,N-dimethylamino)phenyl, 2-(N-ethylamino)phenyl, 2-(N,N-diethylamino)phenyl, 3-aminophenyl, 3-(N-methylamino)phenyl, 3-(N,N-dimethylamino)phenyl, 3-(N-ethylamino)phenyl, 3-(N,N-diethylamino)phenyl, 4-aminophenyl, 4-(N-methylamino)phenyl, 4-(N,N-dimethylamino)phenyl, 4-(N-ethylamino)phenyl, and 4-(N,N-diethylamino)phenyl.

A heterocycle can be any ring containing a ring atom that is not carbon, for example, N, O, S, P, Si, B, or any other heteroatom. A heterocycle can be substituted with any number of substituents, for example, alkyl groups and halogen atoms. A heterocycle can be aromatic (heteroaryl) or non-aromatic. Non-limiting examples of heterocycles include pyrrole, pyrrolidine, pyridine, piperidine, succinamide, maleimide, morpholine, imidazole, thiophene, furan, tetrahydrofuran, pyran, and tetrahydropyran.

Non-limiting examples of heterocycles include: heterocyclic units having a single ring containing one or more heteroatoms, non-limiting examples of which include, diazirinyl, aziridinyl, azetidinyl, pyrazolidinyl, imidazolidinyl, oxazolidinyl, isoxazolinyl, thiazolidinyl, isothiazolinyl, oxathiazolidinonyl, oxazolidinonyl, hydantoinyl, tetrahydrofuranyl, pyrrolidinyl, morpholinyl, piperazinyl, piperidinyl, dihydropyranyl, tetrahydropyranyl, piperidin-2-onyl, 2,3,4,5-tetrahydro-1H-azepinyl, 2,3-dihydro-1H-indole, and 1,2,3,4-tetrahydroquinoline; and ii) heterocyclic units having 2 or more rings one of which is a heterocyclic ring, non-limiting examples of which include hexahydro-1H-pyrrolizinyl, 3a,4,5,6,7,7a-hexahydro-1H-benzo[d]imidazolyl, 3a,4,5,6,7,7a-hexahydro-1H-indolyl, 1,2,3,4-tetrahydroquinolinyl, and decahydro-1H-cycloocta[b]pyrrolyl.

Non-limiting examples of heteroaryl include: i) heteroaryl rings containing a single ring, non-limiting examples of which include, 1,2,3,4-tetrazolyl, [1,2,3]triazolyl, [1,2,4]triazolyl, triazinyl, thiazolyl, 1H-imidazolyl, oxazolyl, isoxazolyl, isothiazolyl, furanyl, thiophenyl, pyrimidinyl, 2-phenylpyrimidinyl, pyridinyl, 3-methylpyridinyl, and 4-dimethylaminopyridinyl; and ii) heteroaryl rings containing 2 or more fused rings one of which is a heteroaryl ring, non-limiting examples of which include: 7H-purinyl, 9H-purinyl, 6-amino-9H-purinyl, 5H-pyrrolo[3,2-d]pyrimidinyl, 7H-pyrrolo[2,3-d]pyrimidinyl, pyrido[2,3-d]pyrimidinyl, 4,5,6,7-tetrahydro-1-H-indolyl, quinoxalinyl, quinazolinyl, quinolinyl, 8-hydroxy-quinolinyl, and isoquinolinyl.

Any compound herein can be purified. A compound herein can be least 1% pure, at least 2% pure, at least 3% pure, at least 4% pure, at least 5% pure, at least 6% pure, at least 7% pure, at least 8% pure, at least 9% pure, at least 10% pure, at least 11% pure, at least 12% pure, at least 13% pure, at least 14% pure, at least 15% pure, at least 16% pure, at least 17% pure, at least 18% pure, at least 19% pure, at least 20% pure, at least 21% pure, at least 22% pure, at least 23% pure, at least 24% pure, at least 25% pure, at least 26% pure, at least 27% pure, at least 28% pure, at least 29% pure, at least 30% pure, at least 31% pure, at least 32% pure, at least 33% pure, at least 34% pure, at least 35% pure, at least 36% pure, at least 37% pure, at least 38% pure, at least 39% pure, at least 40% pure, at least 41% pure, at least 42% pure, at least 43% pure, at least 44% pure, at least 45% pure, at least 46% pure, at least 47% pure, at least 48% pure, at least 49% pure, at least 50% pure, at least 51% pure, at least 52% pure, at least 53% pure, at least 54% pure, at least 55% pure, at least 56% pure, at least 57% pure, at least 58% pure, at least 59% pure, at least 60% pure, at least 61% pure, at least 62% pure, at least 63% pure, at least 64% pure, at least 65% pure, at least 66% pure, at least 67% pure, at least 68% pure, at least 69% pure, at least 70% pure, at least 71% pure, at least 72% pure, at least 73% pure, at least 74% pure, at least 75% pure, at least 76% pure, at least 77% pure, at least 78% pure, at least 79% pure, at least 80% pure, at least 81% pure, at least 82% pure, at least 83% pure, at least 84% pure, at least 85% pure, at least 86% pure, at least 87% pure, at least 88% pure, at least 89% pure, at least 90% pure, at least 91% pure, at least 92% pure, at least 93% pure, at least 94% pure, at least 95% pure, at least 96% pure, at least 97% pure, at least 98% pure, at least 99% pure, at least 99.1% pure, at least 99.2% pure, at least 99.3% pure, at least 99.4% pure, at least 99.5% pure, at least 99.6% pure, at least 99.7% pure, at least 99.8% pure, or at least 99.9% pure.

Pharmaceutical Compositions of the Disclosure.

A pharmaceutical composition of the disclosure can be used, for example, before, during, or after treatment of a subject with, for example, another pharmaceutical agent.

Subjects can be, for example, elderly adults, adults, adolescents, pre-adolescents, children, toddlers, infants, neonates, and non-human animals. In some embodiments, a subject is a patient.

A pharmaceutical composition of the disclosure can be a combination of any pharmaceutical compounds described herein with other chemical components, such as carriers, stabilizers, diluents, dispersing agents, suspending agents, thickening agents, and/or excipients. The pharmaceutical composition facilitates administration of the compound to an organism. Pharmaceutical compositions can be administered in therapeutically-effective amounts as pharmaceutical compositions by various forms and routes including, for example, intravenous, subcutaneous, intramuscular, oral, parenteral, ophthalmic, subcutaneous, transdermal, nasal, vaginal, and topical administration.

A pharmaceutical composition can be administered in a local manner, for example, via injection of the compound directly into an organ, optionally in a depot or sustained release formulation or implant. Pharmaceutical compositions can be provided in the form of a rapid release formulation, in the form of an extended release formulation, or in the form of an intermediate release formulation. A rapid release form can provide an immediate release. An extended release formulation can provide a controlled release or a sustained delayed release.

For oral administration, pharmaceutical compositions can be formulated by combining the active compounds with pharmaceutically-acceptable carriers or excipients. Such carriers can be used to formulate liquids, gels, syrups, elixirs, slurries, or suspensions, for oral ingestion by a subject. Non-limiting examples of solvents used in an oral dissolvable formulation can include water, ethanol, isopropanol, saline, physiological saline, DMSO, dimethylformamide, potassium phosphate buffer, phosphate buffer saline (PBS), sodium phosphate buffer, 4-2-hydroxyethyl-1-piperazineethanesulfonic acid buffer (HEPES), 3-(N-morpholino)propanesulfonic acid buffer (MOPS), piperazine-N,N'-bis(2-ethanesulfonic acid) buffer (PIPES), and saline sodium citrate buffer (SSC). Non-limiting examples of cosolvents used in an oral dissolvable formulation can include sucrose, urea, cremaphor, DMSO, and potassium phosphate buffer.

Pharmaceutical preparations can be formulated for intravenous administration. The pharmaceutical compositions can be in a form suitable for parenteral injection as a sterile suspension, solution or emulsion in oily or aqueous vehicles, and can contain formulatory agents such as suspending, stabilizing and/or dispersing agents. Pharmaceutical formulations for parenteral administration include aqueous solutions of the active compounds in water-soluble form. Suspensions of the active compounds can be prepared as oily injection suspensions. Suitable lipophilic solvents or vehicles include fatty oils such as sesame oil, or synthetic fatty acid esters, such as ethyl oleate or triglycerides, or liposomes. The suspension can also contain suitable stabilizers or agents which increase the solubility of the compounds to allow for the preparation of highly concentrated solutions. Alternatively, the active ingredient can be in powder form for constitution with a suitable vehicle, e.g., sterile pyrogen-free water, before use.

The active compounds can be administered topically and can be formulated into a variety of topically administrable compositions, such as solutions, suspensions, lotions, gels, pastes, medicated sticks, balms, creams, and ointments. Such pharmaceutical compositions can contain solubilizers, stabilizers, tonicity enhancing agents, buffers and preservatives.

The compounds of the disclosure can be applied topically to the skin, or a body cavity, for example, oral, vaginal, bladder, cranial, spinal, thoracic, or pelvic cavity of a subject. The compounds of the disclosure can be applied to an accessible body cavity.

The compounds can also be formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, and PEG. In suppository forms of the compositions, a low-melting wax such as a mixture of fatty acid glycerides, optionally in combination with cocoa butter, can be melted.

In practicing the methods of treatment or use provided herein, therapeutically-effective amounts of the compounds described herein are administered in pharmaceutical compositions to a subject having a disease or condition to be treated. In some embodiments, the subject is a mammal such as a human. A therapeutically-effective amount can vary widely depending on the severity of the disease, the age and relative health of the subject, the potency of the compounds used, and other factors. The compounds can be used singly or in combination with one or more therapeutic agents as components of mixtures.

Pharmaceutical compositions can be formulated using one or more physiologically-acceptable carriers comprising excipients and auxiliaries, which facilitate processing of the active compounds into preparations that can be used pharmaceutically. Formulations can be modified depending upon the route of administration chosen. Pharmaceutical compositions comprising a compound described herein can be manufactured, for example, by mixing, dissolving, emulsifying, encapsulating, entrapping, or compression processes.

The pharmaceutical compositions can include at least one pharmaceutically-acceptable carrier, diluent, or excipient and compounds described herein as free-base or pharmaceutically-acceptable salt form. Pharmaceutical compositions can contain solubilizers, stabilizers, tonicity enhancing agents, buffers and preservatives.

Methods for the preparation of compositions comprising the compounds described herein include formulating the compounds with one or more inert, pharmaceutically-acceptable excipients or carriers to form a solid, semi-solid, or liquid composition. Solid compositions include, for example, powders, tablets, dispersible granules, capsules, and cachets. Liquid compositions include, for example, solutions in which a compound is dissolved, emulsions comprising a compound, or a solution containing liposomes, micelles, or nanoparticles comprising a compound as disclosed herein. Semi-solid compositions include, for example, gels, suspensions and creams. The compositions can be in liquid solutions or suspensions, solid forms suitable for solution or suspension in a liquid prior to use, or as emulsions. These compositions can also contain minor amounts of nontoxic, auxiliary substances, such as wetting or emulsifying agents, pH buffering agents, and other pharmaceutically-acceptable additives.

Non-limiting examples of dosage forms suitable for use in the disclosure include liquid, powder, gel, nanosuspension, nanoparticle, microgel, aqueous or oily suspensions, emulsion, and any combination thereof.

Non-limiting examples of pharmaceutically-acceptable excipients suitable for use in the disclosure include binding agents, disintegrating agents, anti-adherents, anti-static agents, surfactants, anti-oxidants, coating agents, coloring agents, plasticizers, preservatives, suspending agents, emulsifying agents, anti-microbial agents, spheronization agents, and any combination thereof.

A composition of the disclosure can be, for example, an immediate release form or a controlled release formulation. An immediate release formulation can be formulated to allow the compounds to act rapidly. Non-limiting examples of immediate release formulations include readily dissolvable formulations. A controlled release formulation can be a pharmaceutical formulation that has been adapted such that release rates and release profiles of the active agent can be matched to physiological and chronotherapeutic requirements or, alternatively, has been formulated to effect release of an active agent at a programmed rate. Non-limiting examples of controlled release formulations include granules, delayed release granules, hydrogels (e.g., of synthetic or natural origin), other gelling agents (e.g., gel-forming dietary fibers), matrix-based formulations (e.g., formulations comprising a polymeric material having at least one active ingredient dispersed through), granules within a matrix, polymeric mixtures, and granular masses.

In some, a controlled release formulation is a delayed release form. A delayed release form can be formulated to delay a compound's action for an extended period of time. A delayed release form can be formulated to delay the release of an effective dose of one or more compounds, for example, for about 4, about 8, about 12, about 16, or about 24 h.

A controlled release formulation can be a sustained release form. A sustained release form can be formulated to sustain, for example, the compound's action over an extended period of time. A sustained release form can be formulated to provide an effective dose of any compound described herein (e.g., provide a physiologically-effective blood profile) over about 4, about 8, about 12, about 16 or about 24 h.

Non-limiting examples of pharmaceutically-acceptable excipients can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), each which is incorporated by reference in its entirety.

Multiple therapeutic agents can be administered in any order or simultaneously. In some embodiments, a compound of the disclosure is administered in combination with, before, or after treatment with another therapeutic agent. If simultaneously, the multiple therapeutic agents can be provided in a single, unified form, or in multiple forms, for example, as multiple separate pills. The agents can be packed together or separately, in a single package or in a plurality of packages. One or all of the therapeutic agents can be given in multiple doses. If not simultaneous, the timing between the multiple doses can vary to as much as about a month.

Therapeutic agents described herein can be administered before, during, or after the occurrence of a disease or condition, and the timing of administering the composition containing a therapeutic agent can vary. For example, the compositions can be used as a prophylactic and can be administered continuously to subjects with a propensity to conditions or diseases in order to lessen a likelihood of the occurrence of the disease or condition. The compositions can be administered to a subject during or as soon as possible after the onset of the symptoms. The administration of the therapeutic agents can be initiated within the first 48 h of the onset of the symptoms, within the first 24 h of the onset of the symptoms, within the first 6 h of the onset of the symptoms, or within 3 h of the onset of the symptoms. The initial administration can be via any route practical, such as by any route described herein using any formulation described herein.

A compound can be administered as soon as is practical after the onset of a disease or condition is detected or suspected, and for a length of time necessary for the treatment of the disease, such as, for example, from about 1 month to about 3 months. In some embodiments, the length of time a compound can be administered can be about 1 day, about 2 days, about 3 days, about 4 days, about 5 days, about 6 days, about 1 week, about 2 weeks, about 3 weeks, about 4 weeks, about 1 month, about 5 weeks, about 6 weeks, about 7 weeks, about 8 weeks, about 2 months, about 9 weeks, about 10 weeks, about 11 weeks, about 12 weeks, about 3 months, about 13 weeks, about 14 weeks, about 15 weeks, about 16 weeks, about 4 months, about 17 weeks, about 18 weeks, about 19 weeks, about 20 weeks, about 5 months, about 21 weeks, about 22 weeks, about 23 weeks, about 24 weeks, about 6 months, about 7 months, about 8 months, about 9 months, about 10 months, about 11 months, about 1 year, about 13 months, about 14 months, about 15 months, about 16 months, about 17 months, about 18 months, about 19 months, about 20 months, about 21 months, about 22 months about 23 months, about 2 years, about 2.5 years, about 3 years, about 3.5 years, about 4 years, about 4.5 years, about 5 years, about 6 years, about 7 years, about 8 years, about 9 years, or about 10 years. The length of treatment can vary for each subject.

Pharmaceutical compositions described herein can be in unit dosage forms suitable for single administration of precise dosages. In unit dosage form, the formulation is divided into unit doses containing appropriate quantities of one or more compounds. The unit dosage can be in the form of a package containing discrete quantities of the formulation. Non-limiting examples are packaged injectables, vials, or ampoules. Aqueous suspension compositions can be packaged in single-dose non-reclosable containers. Multiple-dose reclosable containers can be used, for example, in combination with or without a preservative. Formulations for injection can be presented in unit dosage form, for example, in ampoules, or in multi-dose containers with a preservative.

Pharmaceutical compositions provided herein, can be administered in conjunction with other therapies, for example, chemotherapy, radiation, surgery, anti-inflammatory agents, and selected vitamins. The other agents can be administered prior to, after, or concomitantly with the pharmaceutical compositions.

Depending on the intended mode of administration, the pharmaceutical compositions can be in the form of solid, semi-solid or liquid dosage forms, such as, for example, tablets, suppositories, pills, capsules, powders, liquids, suspensions, lotions, creams, or gels, for example, in unit dosage form suitable for single administration of a precise dosage.

For solid compositions, nontoxic solid carriers include, for example, pharmaceutical grades of mannitol, lactose, starch, magnesium stearate, sodium saccharin, talc, cellulose, glucose, sucrose, and magnesium carbonate.

Non-limiting examples of pharmaceutically active agents suitable for combination with compositions of the disclosure include anti-infectives, i.e., aminoglycosides, antiviral agents, antimicrobials, anticholinergics/antispasmodics, antidiabetic agents, antihypertensive agents, antineoplastics, cardiovascular agents, central nervous system agents, coagulation modifiers, hormones, immunologic agents, immunosuppressive agents, and ophthalmic preparations.

Compounds can be delivered via liposomal technology. The use of liposomes as drug carriers can increase the therapeutic index of the compounds. Liposomes are composed of natural phospholipids, and can contain mixed lipid chains with surfactant properties (e.g., egg phosphatidylethanolamine). A liposome design can employ surface ligands for attaching to unhealthy tissue. Non-limiting examples of liposomes include the multilamellar vesicle (MLV), the small unilamellar vesicle (SUV), and the large unilamellar vesicle (LUV). Liposomal physicochemical properties can be modulated to optimize penetration through biological barriers and retention at the site of administration, and to reduce a likelihood of developing premature degradation and toxicity to non-target tissues. Optimal liposomal properties depend on the administration route: large-sized liposomes show good retention upon local injection, small-sized liposomes are better suited to achieve passive targeting. PEGylation reduces the uptake of the liposomes by the liver and spleen, and increases the circulation time, resulting in increased localization at the inflamed site due to the enhanced permeability and retention (EPR) effect. Additionally, liposomal surfaces can be modified to achieve selective delivery of the encapsulated drug to specific target cells. Non-limiting examples of targeting ligands include monoclonal antibodies, vitamins, peptides, and polysaccharides specific for receptors concentrated on the surface of cells associated with the disease.

Non-limiting examples of dosage forms suitable for use in the disclosure include liquid, elixir, nanosuspension, aqueous or oily suspensions, drops, syrups, and any combination thereof. Non-limiting examples of pharmaceutically-acceptable excipients suitable for use in the disclosure include granulating agents, binding agents, lubricating agents, disintegrating agents, sweetening agents, glidants, anti-adherents, anti-static agents, surfactants, anti-oxidants, gums, coating agents, coloring agents, flavoring agents, coating agents, plasticizers, preservatives, suspending agents, emulsifying agents, plant cellulosic material and spheronization agents, and any combination thereof.

Compositions of the disclosure can be packaged as a kit. In some embodiments, a kit includes written instructions on the administration/use of the composition. The written material can be, for example, a label. The written material can suggest conditions methods of administration. The instructions provide the subject and the supervising physician with the best guidance for achieving the optimal clinical outcome from the administration of the therapy. The written material can be a label. In some embodiments, the label can be approved by a regulatory agency, for example the U.S. Food and Drug Administration (FDA), the European Medicines Agency (EMA), or other regulatory agencies.

Dosing.

Pharmaceutical compositions described herein can be in unit dosage forms suitable for single administration of precise dosages. In unit dosage form, the formulation is divided into unit doses containing appropriate quantities of one or more compounds. The unit dosage can be in the form of a package containing discrete quantities of the formulation. Non-limiting examples are liquids in vials or ampoules. Aqueous suspension compositions can be packaged in single-dose non-reclosable containers. Multiple-dose reclosable containers can be used, for example, in combination with a preservative. Formulations for parenteral injection can be presented in unit dosage form, for example, in ampoules, or in multi-dose containers with a preservative.

A dose can be expressed in terms of an amount of the drug divided by the mass of the subject, for example, milligrams of drug per kilograms of subject body mass. A compound described herein can be present in a composition in a range of from about 1 mg to about 2000 mg; from about 100 mg to about 2000 mg; from about 10 mg to about 2000 mg; from about 5 mg to about 1000 mg, from about 10 mg to about 500 mg, from about 50 mg to about 250 mg, from about 100 mg to about 200 mg, from about 1 mg to about 50 mg, from about 50 mg to about 100 mg, from about 100 mg to about 150 mg, from about 150 mg to about 200 mg, from about 200 mg to about 250 mg, from about 250 mg to about 300 mg, from about 300 mg to about 350 mg, from about 350 mg to about 400 mg, from about 400 mg to about 450 mg, from about 450 mg to about 500 mg, from about 500 mg to about 550 mg, from about 550 mg to about 600 mg, from about 600 mg to about 650 mg, from about 650 mg to about 700 mg, from about 700 mg to about 750 mg, from about 750 mg to about 800 mg, from about 800 mg to about 850 mg, from about 850 mg to about 900 mg, from about 900 mg to about 950 mg, or from about 950 mg to about 1000 mg.

In some embodiments, a compound is administered in an amount ranging from about 5 mg/kg to about 50 mg/kg, 250 mg/kg to about 2000 mg/kg, about 10 mg/kg to about 800 mg/kg, about 50 mg/kg to about 400 mg/kg, about 100 mg/kg to about 300 mg/kg, or about 150 mg/kg to about 200 mg/kg. In some embodiments, a compound described herein can be present in a composition in a range of from about 20 mg/kg to about 400 mg/kg. In some embodiments, a compound described herein can be present in a composition in a range of from about 20 mg/kg to about 240 mg/kg. In some embodiments, a compound described herein can be present in a composition in a range of from about 75 mg/kg to about 150 mg/kg. In some embodiments, a compound described herein can be present in a composition in a range of from about 75 mg/kg to about 150 mg/kg. In some embodiments, a compound described herein can be present in a composition in a range of from about 100 mg/kg to about 150 mg/kg.

In some embodiments, a compound described herein can be present in a composition in an amount of about 75 mg/kg. In some embodiments, a compound described herein can be present in a composition in an amount of about 100 mg/kg. In some embodiments, a compound described herein can be present in a composition in an amount of about 150 mg/kg. In some embodiments, a compound described herein can be present in a composition in an amount of about 200 mg/kg. In some embodiments, a compound described herein can be present in a composition in an amount of about 250 mg/kg. In some embodiments, a compound described herein can be present in a composition in an amount of about 400 mg/kg.

A compound described herein can be present in a composition in an amount of about 1 mg, about 2 mg, about 3 mg, about 4 mg, about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 125 mg, about 150 mg, about 175 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, about 1000 mg, about 1050 mg, about 1100 mg, about 1150 mg, about 1200 mg, about 1250 mg, about 1300 mg, about 1350 mg, about 1400 mg, about 1450 mg, about 1500 mg, about 1550 mg, about 1600 mg, about 1650 mg, about 1700 mg, about 1750 mg, about 1800 mg, about 1850 mg, about 1900 mg, about 1950 mg, or about 2000 mg.

In some embodiments, a compound described herein can be present in a composition in an amount of about 100 mg, about 120 mg, about 140 mg, about 160 mg, about 180 mg, about 200 mg, about 220 mg, about 240 mg, about 260 mg, about 280 mg, or about 300 mg. In some embodiments, a compound described herein can be present in a composition in an amount of about 150 mg. In some embodiments, a compound described herein can be present in a composition in an amount of about 170 mg. In some embodiments, a compound described herein can be present in a composition in an amount of about 280 mg. In some embodiments, a compound described herein can be present in a composition in an amount of about 300 mg.

Methods of Use

In some embodiments, compounds of the invention can be used to treat cancer in a subject. A compound of the invention can, for example, slow the proliferation of cancer cell lines, or kill cancer cells. Non-limiting examples of cancer that can be treated by a compound of the invention include: acute lymphoblastic leukemia, acute myeloid leukemia, adrenocortical carcinoma, AIDS-related cancers, AIDS-related lymphoma, anal cancer, appendix cancer, astrocytomas, basal cell carcinoma, bile duct cancer, bladder cancer, bone cancers, brain tumors, such as cerebellar astrocytoma, cerebral astrocytoma/malignant glioma, ependymoma, medulloblastoma, supratentorial primitive neuroectodermal tumors, visual pathway and hypothalamic glioma, breast cancer, bronchial adenomas, Burkitt lymphoma, carcinoma of unknown primary origin, central nervous system lymphoma, cerebellar astrocytoma, cervical cancer, childhood cancers, chronic lymphocytic leukemia, chronic myelogenous leukemia, chronic myeloproliferative disorders, colon cancer, cutaneous T-cell lymphoma, desmoplastic small round cell tumor, endometrial cancer, ependymoma, esophageal cancer, Ewing's sarcoma, germ cell tumors, gallbladder cancer, gastric cancer, gastrointestinal carcinoid tumor, gastrointestinal stromal tumor, gliomas, hairy cell leukemia, head and neck cancer, heart cancer, hepatocellular (liver) cancer, Hodgkin lymphoma, Hypopharyngeal cancer, intraocular melanoma, islet cell carcinoma, Kaposi sarcoma, kidney cancer, laryngeal cancer, lip and oral cavity cancer, liposarcoma, liver cancer, lung cancers, such as non-small cell and small cell lung cancer, lymphomas, leukemias, macroglobulinemia, malignant fibrous histiocytoma of bone/osteosarcoma, medulloblastoma, melanomas, mesothelioma, metastatic squamous neck cancer with occult primary, mouth cancer, multiple endocrine neoplasia syndrome, myelodysplastic syndromes, myeloid leukemia, nasal cavity and paranasal sinus cancer, nasopharyngeal carcinoma, neuroblastoma, non-Hodgkin lymphoma, non-small cell lung cancer, oral cancer, oropharyngeal cancer, osteosarcoma/malignant fibrous histiocytoma of bone, ovarian cancer, ovarian epithelial cancer, ovarian germ cell tumor, pancreatic cancer, pancreatic cancer islet cell, paranasal sinus and nasal cavity cancer, parathyroid cancer, penile cancer, pharyngeal cancer, pheochromocytoma, pineal astrocytoma, pineal germinoma, pituitary adenoma, pleuropulmonary blastoma, plasma cell neoplasia, primary central nervous system lymphoma, prostate cancer, rectal cancer, renal cell carcinoma, renal pelvis and ureter transitional cell cancer, retinoblastoma, rhabdomyosarcoma, salivary gland cancer, sarcomas, skin cancers, skin carcinoma merkel cell, small intestine cancer, soft tissue sarcoma, squamous cell carcinoma, stomach cancer, T-cell lymphoma, throat cancer, thymoma, thymic carcinoma, thyroid cancer, trophoblastic tumor (gestational), cancers of unknown primary site, urethral cancer, uterine sarcoma, vaginal cancer, vulvar cancer, Waldenström macroglobulinemia, and Wilms tumor.

In some embodiments, the cancer is ovarian cancer. In some embodiments, the cancer is breast cancer. In some embodiments, the cancer is lung cancer. In some embodiments, the compounds of the invention show non-lethal toxicity.

Disclosed herein is a method of inducing apoptosis in a cell, the method comprising contacting the cell with a therapeutically-effective amount of a compound that binds a p53 mutant, wherein the compound is of the formula:

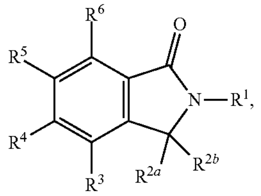

wherein:

$R^1$ is

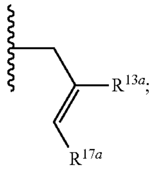

$R^{13a}$ is —C(O)$NH_2$ or —CN;

$R^{17a}$ is —CN, alkyl, aryl, heteroaryl, —$NR^7R^8$, —S(O)$_2R^7$, —$SR^7$, or $OR^7$, each which is unsubstituted or substituted, or hydrogen or halogen; and each $R^{2a}$, $R^{2b}$, $R^3$, $R^4$, $R^5$, and $R^6$ is independently alkyl, cycloalkyl, alkenyl, alkynyl, aryl, heteroaryl, heterocyclyl, —CN, —C(O)$R^9$, —C(O)$OR^9$, —C(O)$NR^9R^{10}$, —C(=N)$NR^9R^{10}$, —$OR^9$, —$SR^9$, —$NR^9R^{10}$, —$NR^9$C(O)$R^{10}$, —$NR^9$C(O)$OR^{10}$, —OC(O)$R^9$, —OC(O)$NR^9R^{10}$, —S(O)$_2R^9$, —NHS(O)$_2R^9$, —OS(O)$_2R^9$, each which is independently substituted or unsubstituted, or hydrogen or halogen; or $R^{2a}$ and $R^{2b}$ together with the carbon atom to which $R^{2a}$ and $R^{2b}$ are bound is —C=O or —C=S; or $R^3$ and $R^4$ together with the carbon atom to which $R^3$ and $R^4$ are bound form a ring, wherein the ring is unsubstituted or substituted; or $R^4$ and $R^5$ together with the carbon atom to which $R^4$ and $R^5$ are bound form a ring, wherein the ring is unsubstituted or substituted; or $R^5$ and $R^6$ together with the carbon atom to which $R^5$ and $R^6$ are bound form a ring, wherein the ring is unsubstituted or substituted, or a pharmaceutically-acceptable salt thereof.

Disclosed herein is a method of inducing apoptosis in a cell, the method comprising contacting the cell with a therapeutically-effective amount of a compound of the disclosure that binds a p53 mutant. In some embodiments, the compound is of the formula:

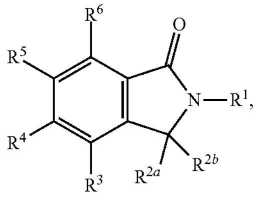

wherein:

$R^1$ is alkyl, cycloalkyl, alkenyl, alkynyl, aryl, heteroaryl, heterocyclyl, —CN, —C(O)$R^7$, —C(O)$OR^7$, —C(O)$NR^7R^8$, —C(=N)$NR^7R^8$, —$OR^7$, —$SR^7$, —$NR^7R^8$, —$NR^7$C(O)$R^8$, —$NR^7$C(O)$OR^8$, —OC(O)$R^7$, —OC(O)$NR^7R^8$, —S(O)$_2R^7$, —NHS(O)$_2R^7$, —OS(O)$_2R^7$, each which is independently substituted or unsubstituted, or hydrogen or halogen;

each $R^{2a}$, $R^{2b}$, $R^4$, $R^5$, and $R^6$ is independently alkyl, cycloalkyl, alkenyl, alkynyl, aryl, heteroaryl, heterocyclyl, —CN, —C(O)$R^9$, —C(O)$OR^9$, —C(O)$NR^9R^{10}$, —C(=N)$NR^9R^{10}$, —$OR^9$, —$SR^9$, —$NR^9R^{10}$, —$NR^9$C(O)$R^{10}$, —$NR^9$C(O)$OR^{10}$, —OC(O)$R^9$, —OC(O)$NR^9R^{10}$, —S(O)$_2R^9$, —NHS(O)$_2R^9$, —OS(O)$_2R^9$, each which is independently substituted or unsubstituted, or hydrogen or halogen; or $R^{2a}$ and $R^{2b}$ together with the carbon atom to which $R^{2a}$ and $R^{2b}$ are bound is —C=O or —C=S; or $R^4$ and $R^5$ together with the carbon atom to which $R^4$ and $R^5$ are bound form a ring, wherein the ring is unsubstituted or substituted; or $R^5$ and $R^6$ together with the carbon atom to which $R^5$ and $R^6$ are bound form a ring, wherein the ring is unsubstituted or substituted;

$R^3$ is

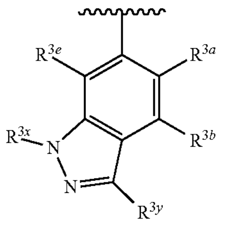 or 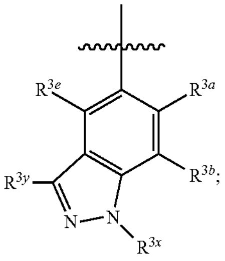

and each $R^{3a}$, $R^{3b}$, $R^{3e}$, $R^{3x}$ and $R^3$ is independently alkyl, cycloalkyl, alkenyl, alkynyl, aryl, heteroaryl, heterocyclyl, —CN, —C(O)$R^7$, —C(O)O$R^7$, —C(O)N$R^7R^8$, —C(=N)N$R^7R^8$, —O$R^7$, —S$R^7$, —N$R^7R^8$, —N$R^7$C(O)$R^8$, —N$R^7$C(O)ORB, —OC(O)$R^7$, —OC(O)N$R^7R^8$, —S$(O)_2R^7$, —NHS$(O)_2R^7$, —OS$(O)_2R^7$, each which is independently substituted or unsubstituted, or hydrogen or halogen, or a pharmaceutically-acceptable salt thereof.

Disclosed herein is a method of inducing apoptosis in a cell, the method comprising contacting the cell with a therapeutically-effective amount of a compound of the disclosure that binds a p53 mutant. In some embodiments, the compound is of the formula:

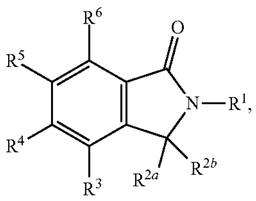

wherein:

$R^1$ is

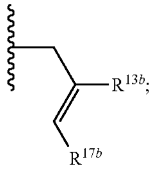

$R^{13b}$ is alkyl, cycloalkyl, alkenyl, alkynyl, aryl, heteroaryl, heterocyclyl, —CN, —C(O)$R^7$, —C(O)O$R^7$, —C(O)N$R^7R^8$, —C(=N)N$R^7R^8$, —O$R^7$, —S$R^7$, —N$R^7R^8$, —N$R^7$C(O)$R^8$, —N$R^7$C(O)O$R^8$, —OC(O)$R^7$, —OC(O)N$R^7R^8$, —S$(O)_2R^7$, —NHS$(O)_2R^7$, —OS$(O)_2R^7$, each which is independently substituted or unsubstituted, or hydrogen or halogen;

$R^{17b}$ is —CN, alkyl, aryl, heteroaryl, —N$R^7R^8$, —S$(O)_2R^7$, —S$R^7$, or O$R^7$, each which is unsubstituted or substituted, or hydrogen or halogen;

each $R^{2a}$, $R^{2b}$, $R^3$, $R^4$, and $R^5$ is independently alkyl, cycloalkyl, alkenyl, alkynyl, aryl, heteroaryl, heterocyclyl, —CN, —C(O)$R^9$, —C(O)O$R^9$, —C(O)N$R^9R^{10}$, —C(=N)N$R^9R^{10}$, —O$R^9$, —S$R^9$, —N$R^9R^{10}$, —N$R^9$C(O)$R^{10}$, —N$R^9$C(O)O$R^{10}$, —OC(O)$R^9$, —OC(O)N$R^9R^{10}$, —S$(O)_2R^9$, —NHS$(O)_2R^9$, —OS$(O)_2R^9$, each which is independently substituted or unsubstituted, or hydrogen or halogen; or $R^{2a}$ and $R^{2b}$ together with the carbon atom to which $R^{2a}$ and $R^{2b}$ are bound is C=O or —C=S; or $R^3$ and $R^4$ together with the carbon atom to which $R^3$ and $R^4$ are bound form a ring, wherein the ring is unsubstituted or substituted; or $R^4$ and $R^5$ together with the carbon atom to which $R^4$ and $R^5$ are bound form a ring, wherein the ring is unsubstituted or substituted;

$R^6$ is $NH_2$; and each $R^7$, $R^8$, $R^9$, and $R^{10}$ is independently alkyl, cycloalkyl, alkenyl, alkynyl, aryl, heteroaryl, or heterocyclyl, each which is independently substituted or unsubstituted, or hydrogen or halogen, or a pharmaceutically-acceptable salt thereof.

In some embodiments, the compound increases the ability of the p53 mutant to bind DNA. In some embodiments, wherein the cell expresses the p53. In some embodiments, the p53 mutant has a mutation at amino acid 220. In some embodiments, the p53 mutant is p53 Y220C. In some embodiments, the compound induces a conformational change in the p53 mutant. In some embodiments, the compound selectively binds the p53 mutant as compared to a wild type p53. In some embodiments, the compound increases a stability of a biologically-active conformation of the p53 mutant relative to a stability of the biologically-active conformation of the p53 mutant in an absence of the compound.

In some embodiments, the therapeutically-effective amount is about 150 mg. In some embodiments, the therapeutically-effective amount is about 300 mg. In some embodiments, the therapeutically-effective amount is about 500 mg. In some embodiments, the therapeutically-effective amount is about 1000 mg. In some embodiments, the therapeutically-effective amount is about 1500 mg. In some embodiments, the therapeutically-effective amount is about 2000 mg.

Disclosed herein is a method of treating cancer, the method comprising administering to a subject in need thereof a therapeutically-effective amount of a compound of the disclosure. In some embodiments, the compound is of the formula:

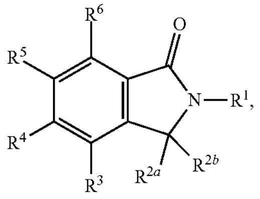

wherein:

$R^1$ is

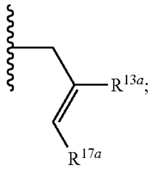

$R^{13a}$ is —C(O)$NH_2$ or —CN;

$R^{17a}$ is —CN, alkyl, aryl, heteroaryl, —$NR^7R^8$, —S$(O)_2R^7$, —$SR^7$, or $OR^7$, each which is unsubstituted or substituted, or hydrogen or halogen;

each $R^{2a}$, $R^{2b}$, $R^3$, $R^4$, $R^5$, and $R^6$ is independently alkyl, cycloalkyl, alkenyl, alkynyl, aryl, heteroaryl, heterocyclyl, —CN, —C(O)$R^9$, —C(O)$OR^9$, —C(O)$NR^9R^{10}$, —C(=N)$NR^9R^{10}$, —$OR^9$, —$SR^9$, —$NR^9R^{10}$, —$NR^9$C(O)$R^{10}$, —$NR^9$C(O)$OR^{10}$, —OC(O)$R^9$, —OC(O)$NR^9R^{10}$, —$S(O)_2R^9$, —$NHS(O)_2R^9$, —$OS(O)_2R^9$, each which is independently substituted or unsubstituted, or hydrogen or halogen; or $R^{2a}$ and $R^{2b}$ together with the carbon atom to which $R^{2a}$ and $R^{2b}$ are bound is —C=O or —C=S; or $R^3$ and $R^4$ together with the carbon atom to which $R^3$ and $R^4$ are bound form a ring, wherein the ring is unsubstituted or substituted; or $R^4$ and $R^5$ together with the carbon atom to which $R^4$ and $R^5$ are bound form a ring, wherein the ring is unsubstituted or substituted; or $R^5$ and $R^6$ together with the carbon atom to which $R^5$ and $R^6$ are bound form a ring, wherein the ring is unsubstituted or substituted;

each $R^7$, $R^8$, $R^9$, and $R^{10}$ is independently alkyl, cycloalkyl, alkenyl, alkynyl, aryl, heteroaryl, or heterocyclyl, each which is independently substituted or unsubstituted, or hydrogen or halogen, or a pharmaceutically-acceptable salt thereof.

In some embodiments, the compound is of the formula:

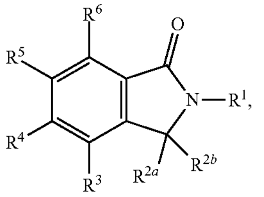

wherein:

$R^1$ is alkyl, cycloalkyl, alkenyl, alkynyl, aryl, heteroaryl, heterocyclyl, —CN, —C(O)$R^7$, —C(O)$OR^7$, —C(O)$NR^7R^8$, —C(=N)$NR^7R^8$, —$OR^7$, —$SR^7$, —$NR^7R^8$, —$NR^7$C(O)$R^8$, —$NR^7$C(O)$OR^8$, —OC(O)$R^7$, —OC(O)$NR^7R^8$, —$S(O)_2R^7$, —$NHS(O)_2R^7$, —$OS(O)_2R^7$, each which is independently substituted or unsubstituted, or hydrogen or halogen;

each $R^{2a}$, $R^{2b}$, $R^4$, $R^5$, and $R^6$ is independently alkyl, cycloalkyl, alkenyl, alkynyl, aryl, heteroaryl, heterocyclyl, —CN, —C(O)$R^9$, —C(O)$OR^9$, —C(O)$NR^9R^{10}$, —C(=N)$NR^9R^{10}$, —$OR^9$, —$SR^9$, —$NR^9R^{10}$, —$NR^9$C(O)$R^{10}$, —$NR^9$C(O)$OR^{10}$, —OC(O)$R^9$, —OC(O)$NR^9R^{10}$, —$S(O)_2R^9$, —$NHS(O)_2R^9$, —$OS(O)_2R^9$, each which is independently substituted or unsubstituted, or hydrogen or halogen; or $R^{2a}$ and $R^{2b}$ together with the carbon atom to which $R^{2a}$ and $R^{2b}$ are bound is —C=O or —C=S; or $R^4$ and $R^5$ together with the carbon atom to which $R^4$ and $R^5$ are bound form a ring, wherein the ring is unsubstituted or substituted; or $R^5$ and $R^6$ together with the carbon atom to which $R^5$ and $R^6$ are bound form a ring, wherein the ring is unsubstituted or substituted;

$R^3$ is

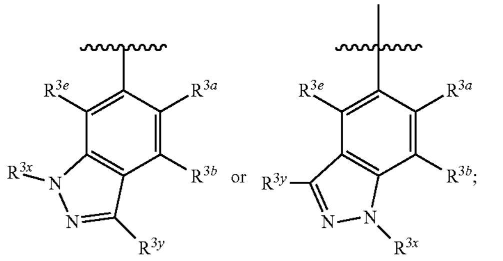

each $R^{3a}$, $R^{3b}$, $R^{3e}$, $R^{3x}$ and $R^{3y}$ is independently alkyl, cycloalkyl, alkenyl, alkynyl, aryl, heteroaryl, heterocyclyl, —CN, —C(O)$R^7$, —C(O)$OR^7$, —C(O)$NR^7R^8$, —C(=N)$NR^7R^8$, —$OR^7$, —$SR^7$, —$NR^7R^8$, —$NR^7$C(O)$R^8$, —$NR^7$C(O)ORB, —OC(O)$R^7$, —OC(O)$NR^7R^8$, —$S(O)_2R^7$, —$NHS(O)_2R^7$, —$OS(O)_2R^7$, each which is independently substituted or unsubstituted, or hydrogen or halogen;

each $R^1$, $R^8$, $R^9$, and $R^{10}$ is independently alkyl, cycloalkyl, alkenyl, alkynyl, aryl, heteroaryl, or heterocyclyl, each which is independently substituted or unsubstituted, or hydrogen or halogen, or a pharmaceutically-acceptable salt thereof.

In some embodiments, the compound is of the formula:

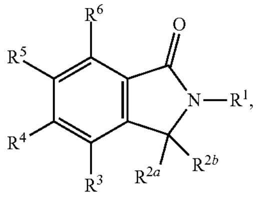

wherein:

$R^1$ is

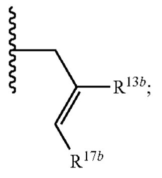

$R^{13b}$ is alkyl, cycloalkyl, alkenyl, alkynyl, aryl, heteroaryl, heterocyclyl, —CN, —C(O)$R^7$, —C(O)$OR^7$, —C(O)$NR^7R^8$, —C(=N)$NR^7R^8$, —$OR^7$, —$SR^7$, —$NR^7R^8$, —$NR^7$C(O)$R^8$, —$NR^7$C(O)$OR^8$, —OC(O)$R^7$, —OC(O)$NR^7R^8$, —$S(O)_2R^7$, —$NHS(O)_2R^7$, —$OS(O)_2R^7$, each which is independently substituted or unsubstituted, or hydrogen or halogen—

$R^{17b}$ is —CN, alkyl, aryl, heteroaryl, —$NR^7R^8$, —S$(O)_2R^7$, —$SR^7$, or $OR^7$, each which is unsubstituted or substituted, or hydrogen or halogen;

each $R^{2a}$, $R^{2b}$, $R^3$, $R^4$, and $R^5$ is independently alkyl, cycloalkyl, alkenyl, alkynyl, aryl, heteroaryl, heterocyclyl, —CN, —C(O)$R^9$, —C(O)$OR^9$, —C(O)$NR^9R^{10}$, —C(=N)$NR^9R^{10}$, —$OR^9$, —$SR^9$, —$NR^9R^{10}$, —$NR^9$C(O)$R^{10}$, —$NR^9$C(O)$OR^{10}$, —OC(O)$R^9$, —OC(O)$NR^9R^{10}$, —$S(O)_2R^9$, —$NHS(O)_2R^9$, —$OS(O)_2R^9$, each which is independently substituted or unsubstituted, or hydrogen or halogen; or $R^{2a}$ and $R^{2b}$ together with the carbon atom to which $R^{2a}$ and $R^{2b}$ are bound is —C═O or —C═S; or $R^3$ and $R^4$ together with the carbon atom to which $R^3$ and $R^4$ are bound form a ring, wherein the ring is unsubstituted or substituted; or $R^4$ and $R^5$ together with the carbon atom to which $R^4$ and $R^5$ are bound form a ring, wherein the ring is unsubstituted or substituted;

$R^6$ is $NH_2$;

each $R^7$, $R^8$, $R^9$, and $R^{10}$ is independently alkyl, cycloalkyl, alkenyl, alkynyl, aryl, heteroaryl, or heterocyclyl, each which is independently substituted or unsubstituted, or hydrogen or halogen, or a pharmaceutically-acceptable salt thereof.

In some embodiments, the cancer is ovarian cancer. In some embodiments, the cancer is breast cancer. In some embodiments, the cancer is lung cancer.

In some embodiments, the compound increases the ability of the p53 mutant to bind DNA. In some embodiments, wherein the cell expresses the p53. In some embodiments, the p53 mutant has a mutation at amino acid 220. In some embodiments, the p53 mutant is p53 Y220C. In some embodiments, the compound induces a conformational change in the p53 mutant. In some embodiments, the compound selectively binds the p53 mutant as compared to a wild type p53. In some embodiments, the compound increases a stability of a biologically-active conformation of the p53 mutant relative to a stability of the biologically-active conformation of the p53 mutant in an absence of the compound.

In some embodiments, the therapeutically-effective amount is from about 20 mg to about 2000 mg. In some embodiments, the therapeutically-effective amount is about 150 mg. In some embodiments, the therapeutically-effective amount is about 300 mg. In some embodiments, the therapeutically-effective amount is about 500 mg. In some embodiments, the therapeutically-effective amount is about 1000 mg. In some embodiments, the therapeutically-effective amount is about 1500 mg. In some embodiments, the therapeutically-effective amount is about 2000 mg.

In some embodiments, the administration is oral. In some embodiments, the administration is subcutaneous. In some embodiments, the administration is topical.

EXAMPLES

Example 1: Synthesis of Intermediates

1.1 General Scheme for Synthesis of Intermediates

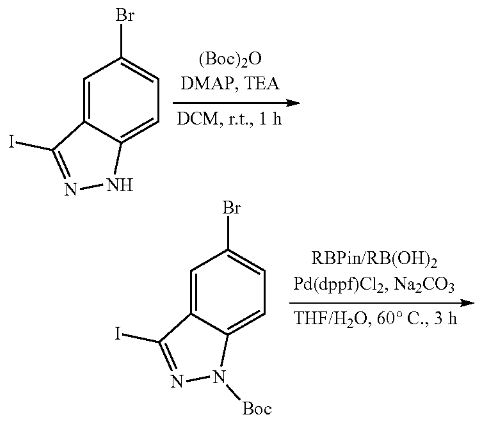

-continued

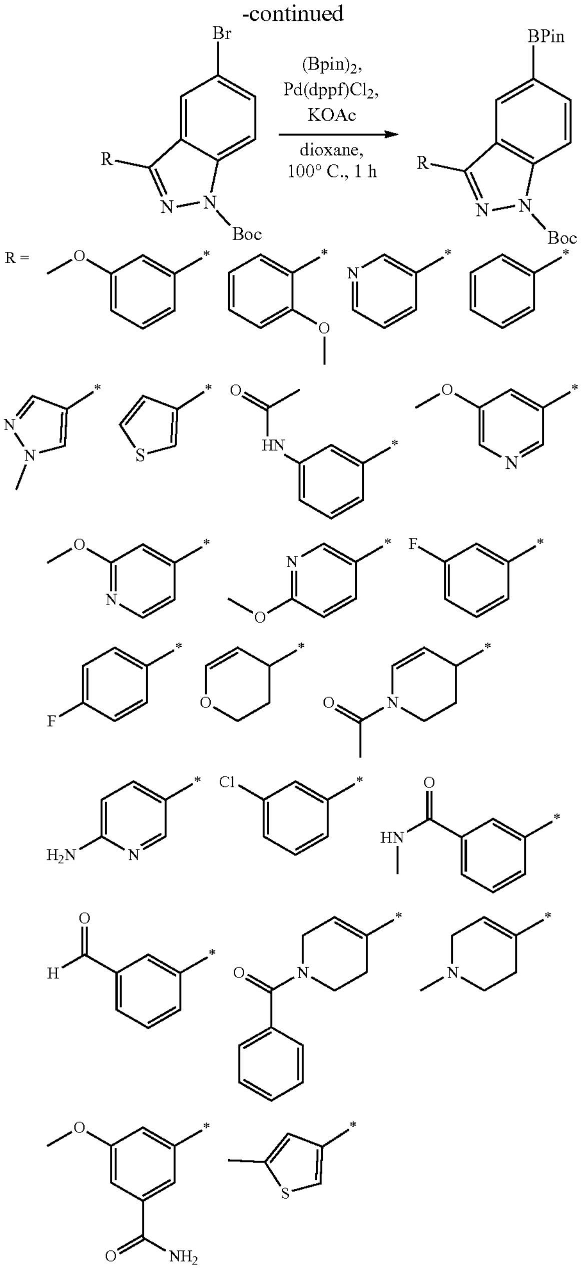

a. Preparation of tert-butyl 5-bromo-3-iodo-indazole-1-carboxylate

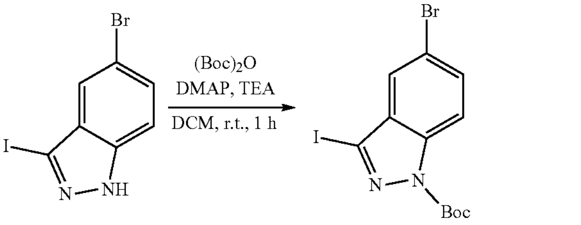 [SMILES: Brc1ccc2[nH]nc(I)c2c1 ; CC(C)(C)OC(=O)n1nc(I)c2cc(Br)ccc21]

To a solution of 5-bromo-3-iodo-1H-indazole (10 g, 30.97 mmol, 1 eq.) in DCM (100 mL) were added TEA (4.07 g, 40.26 mmol, 5.60 mL, 1.3 eq.) and DMAP (189.16 mg, 1.55 mmol, 0.05 eq.). Then $(BOC)_2O$ (7.43 g, 34.06 mmol, 7.83 mL, 1.1 eq.) was added. The mixture was stirred at 20° C. for 10 min. TLC (PE:EtOAc=1:1) showed that the reaction was complete. The reaction mixture was concentrated in vacuo to give a residue. The crude product was triturated with PE at 20° C. for 30 min, then filtered to afford the title compound as a light yellow solid (11.8 g, 27.89 mmol, 90% yield).

b. General Procedure for the Preparation of 6-bromo-indazole Derivatives

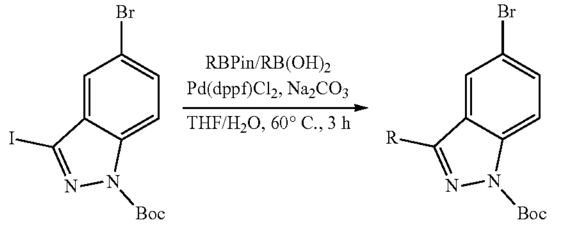

A mixture of tert-butyl 5-bromo-3-iodo-indazole-1-carboxylate (500 mg, 1.18 mmol, 1 eq.), boronic acid (1.24 mmol, 1.05 eq.), $Na_2CO_3$ (375.81 mg, 3.55 mmol, 3 eq.), and $Pd(dppf)Cl_2$ (86.48 mg, 118.19 μmol, 0.1 eq.) in THF (16 mL) and water (4 mL) was degassed and purged with nitrogen three times, and the mixture was stirred at 60° C. for 3 h under nitrogen atmosphere. TLC showed that the reaction was complete. To the reaction mixture was added 30 mL saturated aq. EDTA, and the mixture was stirred for 1 h and extracted with EtOAc (3x20 mL). The combined organic layers were washed with brine (3x20 mL), dried over anhydrous sodium sulfate, filtered, and concentrated in vacuo to give a residue. The residue was purified by prep-TLC (silica gel; PE:EtOAc=3:1) to afford the desired product.

c. General Procedure for the Preparation of Indazole Boronate Esters

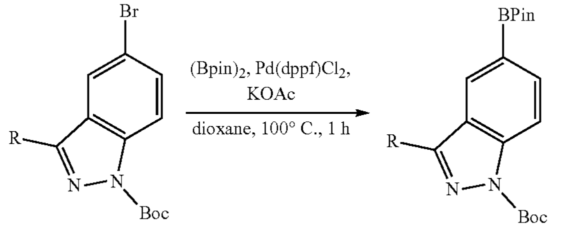

To a mixture of tert-butyl 5-bromo-3-(2-Aryl)indazole-1-carboxylate (100 mg, 263.66 μmol, 1 eq.) and $(BPin)_2$ (200.86 mg, 790.99 μmol, 3 eq.) in dioxane (2 mL) were added KOAc (77.63 mg, 790.99 μmol, 3 eq.), $Pd(dppf)Cl_2$ (19.29 mg, 26.37 μmol, 0.1 eq.) in one portion at 100° C. under nitrogen. The mixture was stirred at 100° C. for 60 min. TLC showed that the reaction was complete. The reaction was filtered, and concentrated in vacuo. The reaction was purified by prep-TLC (silica gel; PE:EtOAc=5:1) to afford the desired product.

1.2 Preparation of tert-butyl 5-bromo-3-thiazol-2-yl-indazole-1-carboxylate

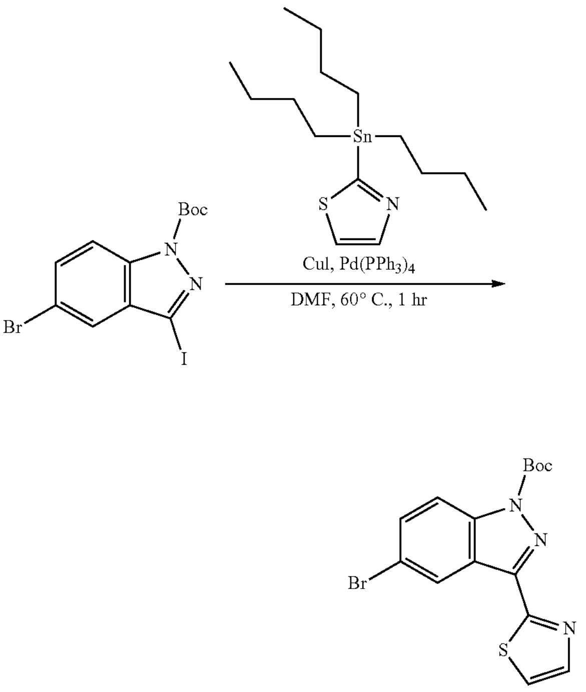

A mixture of tert-butyl 5-bromo-3-iodo-indazole-1-carboxylate (0.6 g, 1.42 mmol, 1 eq.), tributyl(thiazol-2-yl) stannane (1.06 g, 2.84 mmol, 2 eq.), $Pd(PPh_3)_4$ (327.78 mg, 283.66 μmol, 0.2 eq.), CuI (54.02 mg, 283.66 μmol, 0.2 eq.) in DMF (30 mL) was degassed and purged with nitrogen 3 times. The mixture was stirred at 60° C. for 1 h under nitrogen atmosphere. LCMS showed that the reaction was complete. To the reaction mixture was added 30 mL saturated aq. EDTA, and the mixture was stirred for 1 h and extracted with EtOAc (3x20 mL). The combined organic layers were washed with brine (3x20 mL), dried over anhydrous sodium sulfate, filtered, and concentrated in vacuo to give a residue. The residue was purified by prep-TLC (silica gel; PE:EtOAc=10:1) to afford the title compound (340 mg, 760.01 μmol, 53.59% yield, 85% purity) as a light yellow solid.

1.3 Preparation of tert-butyl 5-bromo-3-(2-phenylethynyl)indazole-1-carboxylate

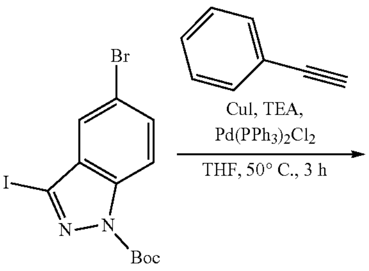

-continued

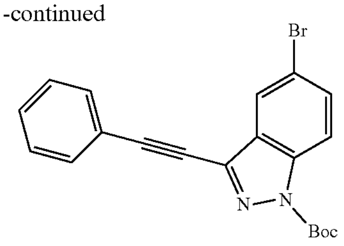

To a mixture of ethynylbenzene (96.57 mg, 945.53 μmol, 103.84 μL, 1 eq.) in THF (10 mL) was added CuI (90.04 mg, 472.76 μmol, 0.5 eq.) and TEA (478.39 mg, 4.73 mmol, 658.03 μL, 5 eq.) in one portion under nitrogen. Then tert-butyl 5-bromo-3-iodo-indazole-1-carboxylate (400 mg, 945.53 μmol, 1 eq.) and $Pd(PPh_3)_2Cl_2$ (199.10 mg, 283.66 μmol, 0.3 eq.) were added under nitrogen, and the mixture was stirred for 3 h at 50° C. TLC showed that the starting material was consumed completely and two new spots were detected. The reaction was diluted with 30 mL water, extracted with EtOAc (2×30 mL), washed with water (2×25 mL), brine (2×25 mL), dried over $Na_2SO_4$, filtered, and concentrated to give a residue. The residue was purified prep-TLC (silica gel; PE:EtOAc=8:1) to afford the title compound (280 mg, 704.82 μmol, 74.54% yield as a yellow solid.

1.4 Preparation of tert-butyl 5-bromo-3-prop-1-ynyl-indazole-1-carboxylate

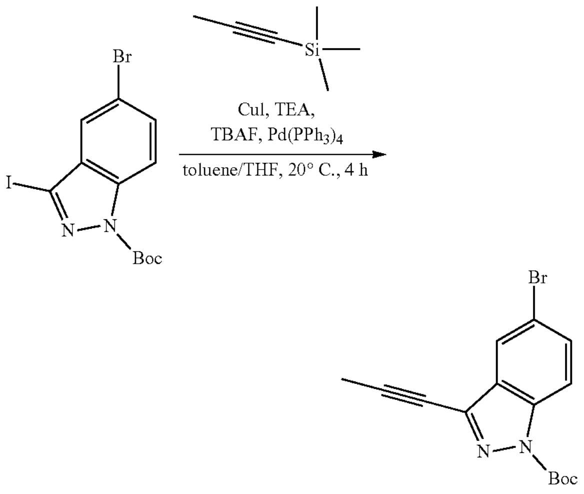

To a solution of tert-butyl 5-bromo-3-iodo-indazole-1-carboxylate (400 mg, 945.53 μmol, 1 eq.) in toluene (8 mL) and THF (6 mL) were added CuI (180.08 mg, 945.53 μmol, 1 eq.) and Pd(PPh3)4 (109.26 mg, 94.55 μmol, 0.1 eq.) under nitrogen. Then, trimethyl(prop-1-ynyl)silane (159.20 mg, 1.42 mmol, 210.02 μL, 1.5 eq.), TEA (382.71 mg, 3.78 mmol, 526.43 μL, 4 eq.) and TBAF (247.22 mg, 945.53 μmol, 1 eq.) in THF (6 mL) was added under nitrogen, and the resulting mixture was stirred at 20° C. for 4 h. TLC showed that the reaction was complete. The reaction was diluted with 30 mL water, extracted with EtOAc (2×30 mL), washed with water (2×30 mL), brine (2×30 mL), dried over anhydrous sodium sulfate, filtered, and concentrated to give a residue. The residue was purified by prep-TLC (silica gel;

PE:EtOAc=8:1) to afford the title compound (260 mg, 775.67 μmol, 82.04% yield) as a white solid.

1.5 Preparation of tert-butyl 5-bromo-3-(2-trimethylsilylethynyl)indazole-1-carboxylate

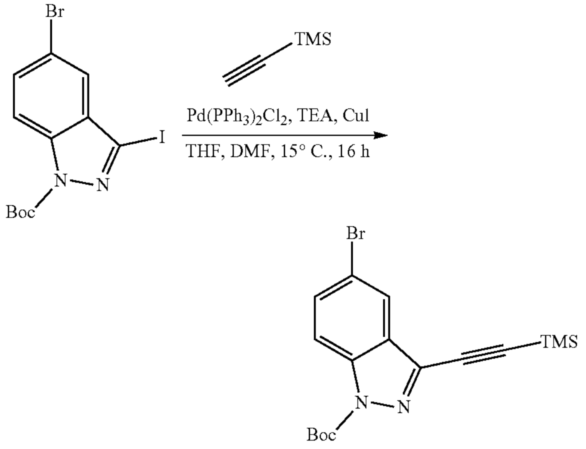

A solution of ethynyl(trimethyl)silane (696.51 mg, 7.09 mmol, 982.38 μL, 10 eq.), $Pd(PPh3)_2Cl_2$ (99.55 mg, 141.83 μmol, 0.2 eq.), CuI (135.06 mg, 709.15 μmol, 1 eq.), TEA (717.59 mg, 7.09 mmol, 10 eq.), and tert-butyl 5-bromo-3-iodo-indazole-1-carboxylate (0.3 g, 709.15 μmol, 1 eq.) in THF (2 mL) and DMF (0.2 mL) was de-gassed and stirred at 15° C. for 16 h under nitrogen. TLC (PE:EtOAc=10:1) showed the starting material was consumed completely. The reaction mixture and sat. aqueous EDTA (50 mL) were stirred for 1 h and extracted with EtOAc (2×30 mL). The combined organic phase was washed with brine (30 mL), dried over anhydrous sodium sulfate, filtered, and concentrated in vacuo. The residue was purified by prep-TLC (silica gel; PE:EtOAc=10:1 to afford the title compound (0.15 g, 305.07 μmol, 43.02% yield, 80% purity) as a brown solid.

1.6 Preparation of 1-tert-butyl 3-methyl 5-bromoindazole-1,3-dicarboxylate

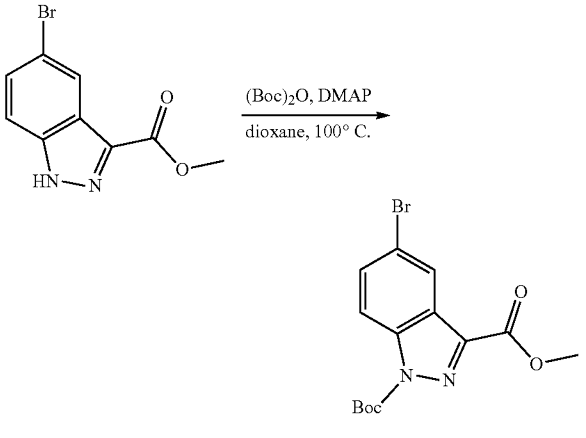

To a solution of methyl 5-bromo-1H-indazole-3-carboxylate (5 g, 19.60 mmol, 1 eq.) in dioxane (100 mL) were added $(Boc)_2O$ (5.13 g, 23.52 mmol, 5.40 mL, 1.2 eq.) and DMAP (239.48 mg, 1.96 mmol, 0.1 eq.). The resulting reaction mixture was stirred at 100° C. for 0.5 h. TLC showed that the reaction was complete. The solvent was removed in vacuo to give the crude product. The crude product was washed with PE (2×5 mL) to give the title product (5.2 g, 13.18 mmol, 67.22% yield, 90% purity) as a light yellow solid.

1.7 Preparation of tert-butyl 5-bromo-3-ethoxy-indazole-1-carboxylate

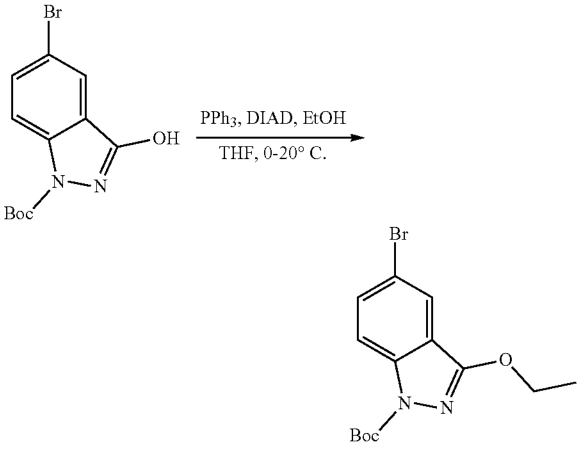

To a solution of tert-butyl 5-bromo-3-hydroxy-indazole-1-carboxylate (0.2 g, 638.68 μmol, 1 eq.), $PPh_3$ (217.77 mg, 830.28 μmol, 1.3 eq.) and EtOH (58.85 mg, 1.28 mmol, 2 eq.) in THF (2 mL) was added DIAD (193.72 mg, 958.02 μmol, 1.5 eq.) dropwise at 0° C. under nitrogen. The reaction mixture was warmed to 20° C. and stirred at 20° C. for 16 h. TLC (PE:EtOAc=5:1) showed the starting material was consumed completely. The reaction was quenched with water (20 mL) and extracted with EtOAc (2×30 mL). The combined organic phase was washed with brine (30 mL), dried over anhydrous sodium sulfate, filtered, and concentrated in vacuo. The residue was purified by prep-TLC (silica gel; PE:EtOAc=5:1) to afford the title compound as a yellow solid (0.13 g, 342.91 μmol, 53.69% yield, 90% purity).

1.8 Preparation of 1-ethyl-6-(4,4,5,5-tetramethyl-1,3,2-dioxaborolan-2-yl)-1H-indazole

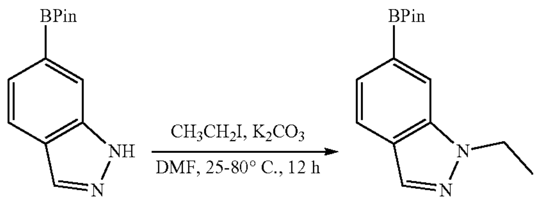

To a solution of 6-(4,4,5,5-tetramethyl-1,3,2-dioxaborolan-2-yl)-1H-indazole (0.2 g, 819.35 μmol, 1 eq.) in DMF (10 mL) was added $K_2CO_3$ (339.72 mg, 2.46 mmol, 3 eq.) in one portion at 25° C. under nitrogen. Then iodoethane (255.58 mg, 1.64 mmol, 131.07 μL, 2 eq.) was added to the mixture.

The mixture was stirred at 80° C. for 12 h. LCMS showed that the reaction was complete. The reaction mixture was poured to 20 mL water and extracted with EtOAc (3×20 mL), then washed with brine (3×10 mL). The combined organic layer was concentrated in vacuo. The residue was purified by prep-TLC (silica gel; PE:EtOAc=1:1) to afford the title compound as a colorless solid (0.1 g, 312.33 μmol, 38.12% yield, 85% purity).

1.9 Preparation of 5-bromo-1-(4-methoxybenzyl)-1H-indazole-3-carbonitrile

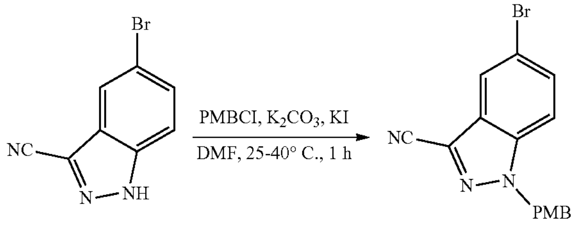

To a mixture of 5-bromo-1H-indazole-3-carbonitrile (0.2 g, 900.73 μmol, 1 eq.) and 4-methoxybenzyl chloride (169.28 mg, 1.08 mmol, 147.20 μL, 1.2 eq.) in DMF (5 mL) were added $K_2CO_3$ (622.43 mg, 4.50 mmol, 5 eq.) and KI (747.62 mg, 4.50 mmol, 5 eq.) in one portion at 25° C. under nitrogen. The mixture was stirred at 40° C. for 1 h. TLC showed that the reaction was complete. The reaction was poured to sat. $NH_4Cl$ solution (20 mL) and extracted with EtOAc (3×10 mL) then the combined organic layer was dried and concentrated in vacuo. The residue was purified by prep-TLC (silica gel; DCM:MeOH=20:1) to afford the title compound (0.19 g, 494.17 μmol, 54.86% yield, 89% purity) as a light yellow solid.

1.10 General Procedure for Alkylation of Indazole Derivatives

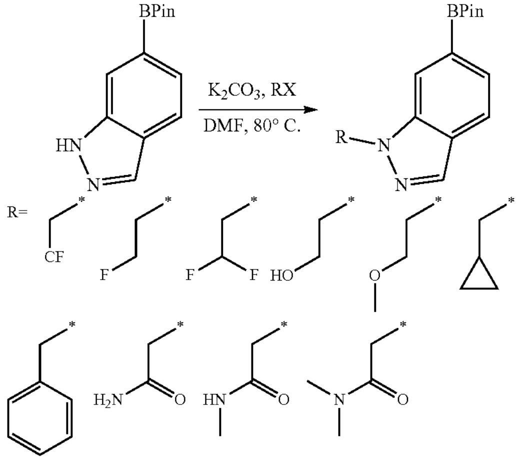

To a solution of 6-(4,4,5,5-tetramethyl-1,3,2-dioxaborolan-2-yl)-1H-indazole (0.2 g, 819.35 μmol, 1 eq.) in DMF (5 mL) were added $K_2CO_3$ (339.73 mg, 2.46 mmol, 3 eq.) and RBr (1.64 mmol, 2 eq.), then the mixture was stirred for 1 h at 80° C. LCMS showed that the reaction was complete.

The mixture was quenched with water (10 mL), then the mixture was extracted with EtOAc (3×10 mL). The combined organic phase was washed with brine (2×10 mL), dried over anhydrous sodium sulfate, filtered, and concentrated in vacuo. The residue was purified by column chromatography to afford the desired product.

1.11 Preparation of methyl 5-bromo-1-(4-methoxybenzyl)-1H-indazole-3-carboxylate

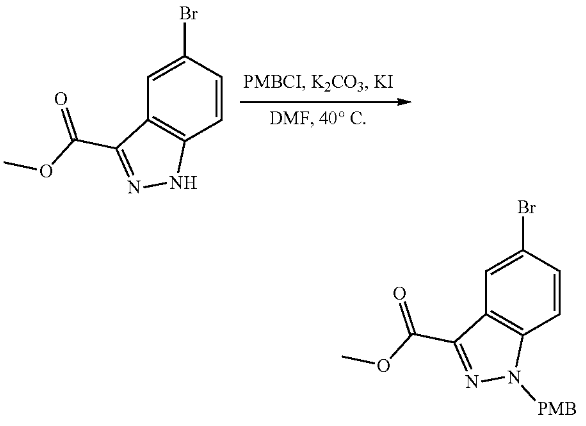

To a solution of methyl 5-bromo-1H-indazole-3-carboxylate (0.6 g, 2.35 mmol, 1 eq.) in DMF (10 mL) were added $K_2CO_3$ (975.34 mg, 7.06 mmol, 3 eq.), KI (1.17 g, 7.06 mmol, 3 eq.), and 4-methoxybenzyl chloride (552.59 mg, 3.53 mmol, 480.51 μL, 1.5 eq.), and the resulting mixture was stirred for 1 h at 40° C. TLC showed that the reaction was complete. The reaction mixture was quenched with water (20 mL) and extracted with EtOAc (3×20 mL). The combined organic phase was washed with brine (2×20 mL), dried over anhydrous sodium sulfate, filtered, and concentrated in vacuo. The residue was purified by prep-TLC (silica gel; PE:EtOAc=4:1) to afford the title compound (0.2 g, 533.03 μmol, 22.66% yield) as a white solid.

1.12 Preparation of N-[3-(4,4,5,5-tetramethyl-1,3,2-dioxaborolan-2-yl)phenyl]cyclopropanecarboxamide

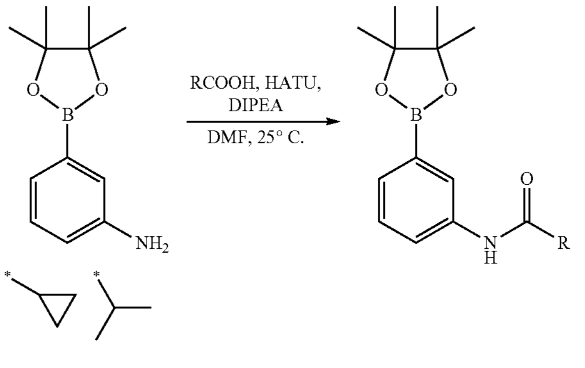

To a solution of cyclopropanecarboxylic acid (235.77 mg, 2.74 mmol, 216.30 μL, 2 eq.) in DMF (15 mL) were added DIPEA (884.87 mg, 6.85 mmol, 1.19 mL, 5 eq.) and HATU (1.56 g, 4.11 mmol, 3 eq.) in one portion at 25° C. under nitrogen. The mixture was stirred at 25° C. for 30 min, then 3-(4,4,5,5-tetramethyl-1,3,2-dioxaborolan-2-yl)aniline (300 mg, 1.37 mmol, 1 eq.) was added, and the resulting mixture was stirred for 1.5 h. TLC/LCMS showed that the reaction was complete. The reaction was diluted with 30 mL water, extracted with EtOAc (3×30 mL), washed with water (2×30 mL), brine (3×30 mL), dried over anhydrous sodium sulfate, filtered, and concentrated to give a residue. The residue was purified by prep-TLC (silica gel; DCM:MeOH=20:1) to afford the title compound (0.25 g, 740 μmol, 54.04% yield, 85% purity) as a yellow solid.

1.13 Preparation of 5-bromo-N,N-dimethyl-1H-indazole-3-carboxamide

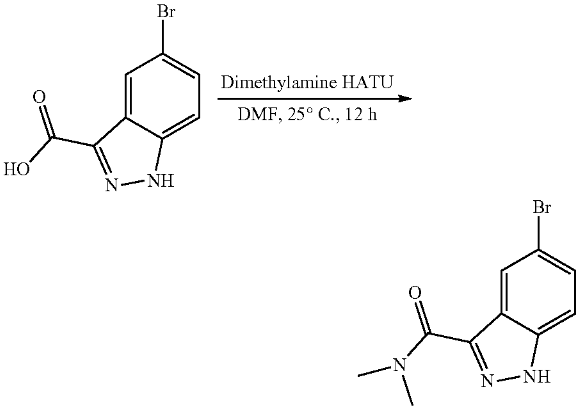

To a mixture of 5-bromo-1H-indazole-3-carboxylic acid (150 mg, 622.30 μmol, 1 eq.) and N-methylmethanamine (76.12 mg, 933.45 μmol, 85.53 μL, 1.5 eq., HCl) in DMF (3 mL) was added HATU (354.93 mg, 933.45 μmol, 1.5 eq.) and TEA (188.91 mg, 1.87 mmol, 259.85 μL, 3 eq.) in one portion at 25° C. under nitrogen. The mixture was stirred at 25° C. for 12 h. TLC and LCMS showed that the reaction was complete. The mixture was poured into water (30 mL), and the aqueous phase was extracted with EtOAc (3×30 mL). The combined organic phase was washed with brine (3×30 mL), dried over anhydrous sodium sulfate, filtered, and concentrated in vacuo. The residue was purified by prep-TLC (silica gel; DCM:MeOH=10:1) to afford the title compound (260 mg, 60% purity, 93.2% yield) as a brown solid.

1.14 Preparation of 6-bromo-9H-pyrido[3,4-b]indole

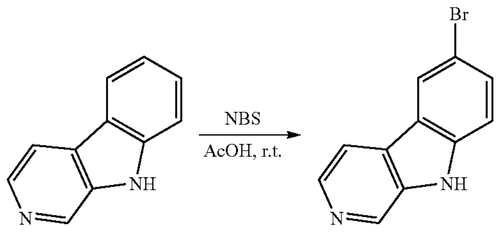

To a mixture of 9H-pyrido[3,4-b]indole (200 mg, 1.19 mmol, 1 eq.) in AcOH (5 mL) was added NBS (211.64 mg, 1.19 mmol, 1 eq.) in one portion at 25° C. The mixture was stirred at 25° C. for 12 h. LCMS showed that the reaction was complete. The residue was poured into sat. $NaHCO_3$ (60 mL) for pH=8 and the aqueous phase was extracted with EtOAc (3×30 mL). The combined organic phase was washed with brine (3×30 mL), dried over anhydrous sodium sulfate, filtered, and concentrated in vacuo. The mixture was dissolved in EtOAc (10 mL) and PE (60 mL), stirred for 30 mins, and filtered to afford (210 mg, 849.89 μmol, 71.47% yield) as a brown solid.

1.15 Preparation of 4-(4,4,5,5-tetramethyl-1,3,2-dioxaborolan-2-yl)-1,2,3,6-tetrahydropyridine

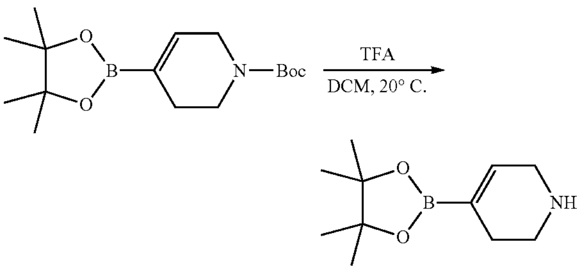

To a solution of tert-butyl 4-(4,4,5,5-tetramethyl-1,3,2-dioxaborolan-2-yl)-5,6-dihydropyridine-1(2H)-carboxylate (5 g, 16.17 mmol, 1 eq.) in DCM (20 mL) was added TFA (15.40 g, 135.06 mmol, 10 mL, 8.35 eq.). The mixture was stirred at 20° C. for 1 h. TLC showed no starting material remained, and one new spot with larger polarity was detected. The reaction mixture was concentrated in vacuo to remove the DCM. The residue was diluted with ice water (50 mL), sat. aq·$NaHCO_3$ was added to adjust the pH of the solution to 7, and extracted with DCM (3×50 mL). The combined organic layers were washed with brine (2×50 mL), dried over anhydrous sodium sulfate, filtered, and concentrated in vacuo to give a residue to afford the title compound (3 g, crude) as a light yellow gum, which was used to next step directly.

1.16 Preparation of phenyl-[4-(4,4,5,5-tetramethyl-1,3,2-dioxaborolan-2-yl)-3,6-dihydro-2H-pyridin-1-yl]methanone

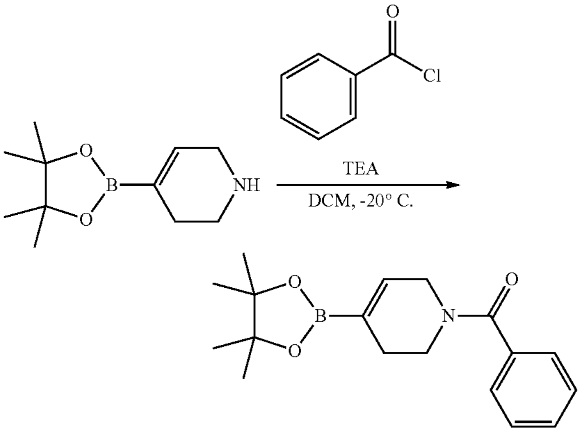

To a mixture of 4-(4,4,5,5-tetramethyl-1,3,2-dioxaborolan-2-yl)-1,2,3,6-tetrahydropyridine (1 g, 4.07 mmol, 1 eq., HCl) (100% purity) in DCM (20 mL) were added TEA (1.24 g, 12.22 mmol, 1.70 mL, 3 eq.) and benzoyl chloride (686.94 mg, 4.89 mmol, 567.72 μL, 1.2 eq.) at −20° C. The mixture was stirred at −20° C. for 0.5 h. TLC/LCMS showed that the reaction was complete. The reaction was diluted with 30 mL saturated aq·$NH_4Cl$, extracted with DCM (2×25 mL), washed with water (2×25 mL), brine (2×25 mL), dried over anhydrous sodium sulfate, filtered, and concentrated to give a residue. The residue was purified by prep-TLC (silica gel; PE:EtOAc=1:1) to afford the title compound (850 mg, 2.58 mmol, 63.31% yield, 95% purity) was obtained as a colorless gum.

1.17 Scheme for Preparation of 3-methoxy-N-methyl-5-(4,4,5,5-tetramethyl-1,3,2-dioxaborolan-2-yl)benzamide

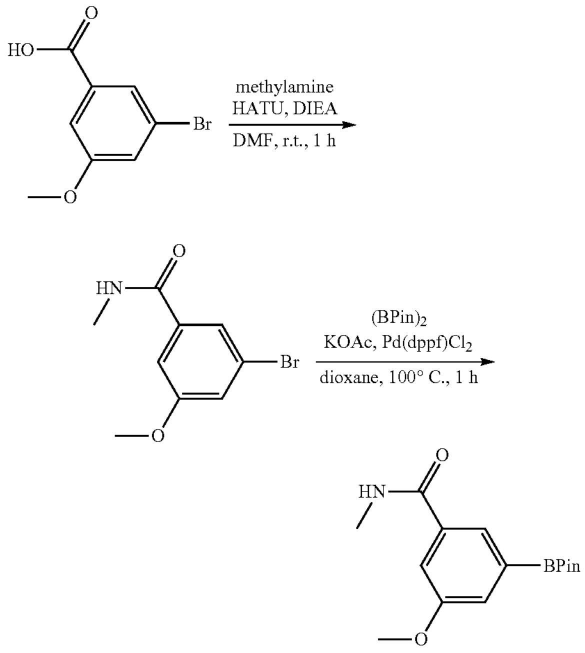

a. Procedure for Preparation of 3-bromo-5-methoxy-N-methyl-benzamide

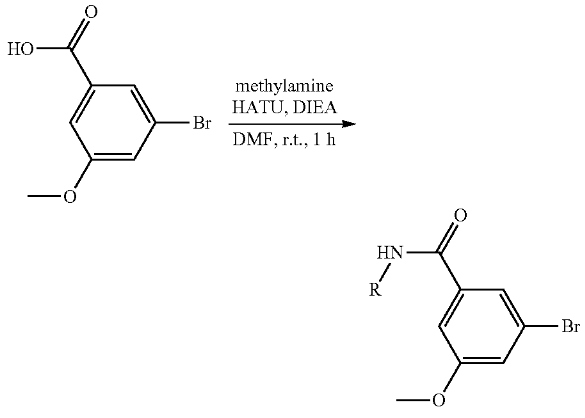

A mixture of 3-bromo-5-methoxy-benzoic acid (3 g, 12.98 mmol, 1 eq.), $MeNH_2$ (4.38 g, 64.92 mmol, 5 eq., HCl), DIEA (8.39 g, 64.92 mmol, 11.31 mL, 5 eq.), and HATU (6.42 g, 16.88 mmol, 1.3 eq.) in DMF (100 mL) was degassed and purged with nitrogen 3 times, and the mixture was stirred at 25° C. for 1 h under nitrogen atmosphere. TLC showed that the reaction was complete. To the reaction mixture was added 30 mL of a saturated EDTA solution, and the resulting mixture was stirred for 1 h. The mixture was extracted with EtOAc (3x30 mL), and the organic phase was washed with water (2x30 mL) and brine (2x30 mL), dried over anhydrous sodium sulfate, filtered, and concentrated in vacuo to give a residue. The residue was purified by column chromatography (silica gel; PE:EtOAc=3:1 to 1:1) to afford the title compound as a light yellow solid (2.1 g, 7.74 mmol, 59.63% yield, 90% purity).

b. Preparation of 3-methoxy-N-methyl-5-(4,4,5,5-tetramethyl-1,3,2-dioxaborolan-2-yl)benzamide

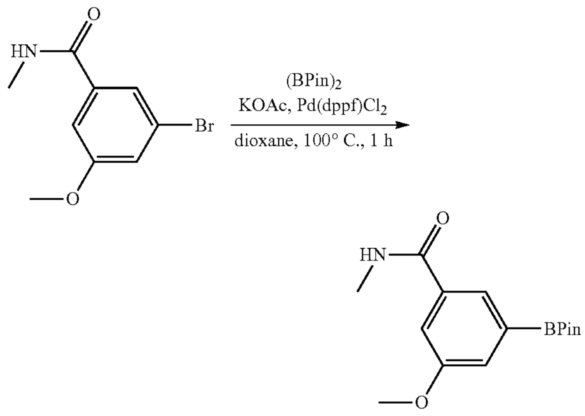

A mixture of 3-bromo-5-methoxy-N-methyl-benzamide (2.1 g, 7.74 mmol, 1 eq.) (90% purity), 4,4,5,5-tetramethyl-2-(4,4,5,5-tetramethyl-1,3,2-dioxaborolan-2-yl)-1,3,2-dioxaborolane (5.90 g, 23.23 mmol, 3 eq.), KOAc (4.56 g, 46.46 mmol, 6 eq.), and $Pd(dppf)Cl_2$ (1.13 g, 1.55 mmol, 0.2 eq.) in dioxane (50 mL) was degassed and purged with nitrogen 3 times, and the mixture was stirred at 100° C. for 1 h under nitrogen atmosphere. LCMS showed that the reaction was complete. To the reaction mixture was added 30 mL of a saturated EDTA solution, and the resulting mixture was stirred for 1 h. The mixture was extracted with EtOAc (3x30 mL), and the resulting organic phase was washed with water (2x30 mL) and brine (2x30 mL), dried over anhydrous sodium sulfate, filtered, and concentrated in vacuo to give a residue. The residue was purified by column chromatography (silica gel; PE:EtOAc=5:1 to 3:1) to afford the title compound as alight yellow solid (1.5 g, 5.15 mmol, 66.54% yield).

1.18 Preparation of 4,4,5,5-tetramethyl-2-(5-methyl-3-thienyl)-1,3,2-dioxaborolane

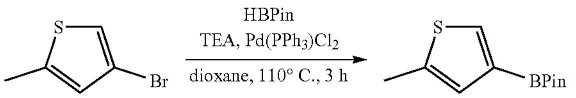

A mixture of 4-bromo-2-methyl-thiophene (2 g, 11.30 mmol, 1 eq.), 4,4,5,5-tetramethyl-1,3,2-dioxaborolane (2.89 g, 22.59 mmol, 3.28 mL, 2 eq.), TEA (3.43 g, 33.89 mmol, 4.72 mL, 3 eq.), and dichloropalladium; triphenylphosphane (7.93 g, 11.30 mmol, 1 eq.) in dioxane (50 mL) was degassed and purged with nitrogen 3 times, and the mixture was stirred at 110° C. for 3 h under nitrogen atmosphere. The reaction mixture was filtered and concentrated in vacuo to give a residue. The residue was purified by column chromatography (silica gel; PE:EtOAc=1/0 to 10:1) to afford the title compound as an off-white oil (2.5 g, 8.92 mmol, 79% yield, 80% purity).

1.19 Preparation of 3-bromo-5-methoxy-benzoyl Chloride

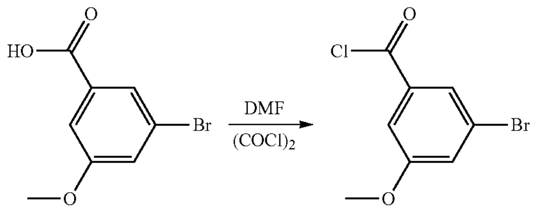

To a mixture of 3-bromo-5-methoxy-benzoic acid (3 g, 12.98 mmol, 1 eq.) in $(COCl)_2$ (43.50 g, 342.72 mmol, 30 mL, 26.39 eq.) was added DMF (0.05 mL), and the mixture was degassed and purged with nitrogen 3 times, then stirred at 25° C. for 30 min under nitrogen atmosphere. TLC showed that the reaction was complete. The reaction was quenched with methylbenzene and extracted with $NH_4Cl$. The mixture was concentrated in vacuo to remove solvent, washed with DCM (3x20 mL), and concentrated in vacuo to afford the title compound (3 g, 12.02 mmol, 92.61% yield) as a light yellow solid.

1.20 Preparation of 3-bromo-5-methoxy-benzamide

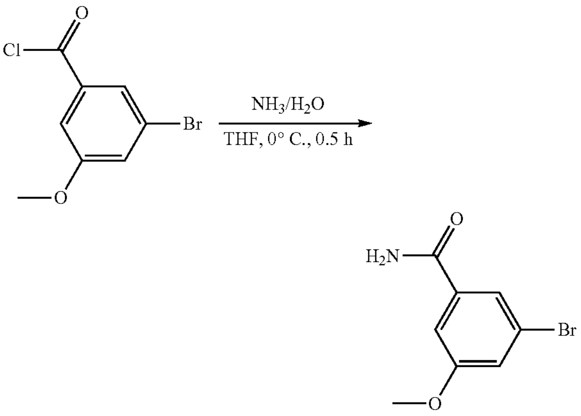

To a mixture of 3-bromo-5-methoxy-benzoyl chloride (450 mg, 1.80 mmol, 1 eq.) in THF (15 mL) was added an $NH_3$ solution (13.17 g, 150.31 mmol, 14.47 mL, 15 eq.). The mixture was slowly degassed and purged with nitrogen 3 times, and the mixture was stirred at 0° C. for 30 min under nitrogen atmosphere. TLC showed that the reaction was complete. To the reaction mixture was added 30 mL of a saturated EDTA solution, and the mixture was stirred for 1 h and extracted with EtOAc (3×30 mL). The organic phase was separated, washed with water (2×30 mL) and brine (2×30 mL), dried over anhydrous sodium sulfate, filtered, and concentrated in vacuo to give a residue. The residue was purified by column chromatography (silica gel; PE:EtOAc=3:1 to 1:1) to afford the title compound (2.5 g, 9.78 mmol, 97.60% yield, 90% purity) as a white solid.

1.21 Preparation of 3-methoxy-5-(4,4,5,5-tetramethyl-1,3,2-dioxaborolan-2-yl)benzamide

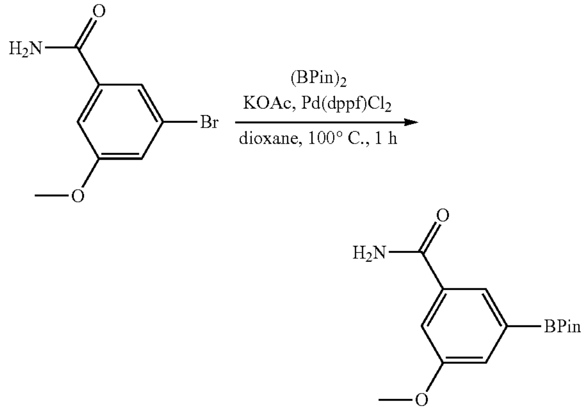

A mixture of 3-bromo-5-methoxy-benzamide (2.3 g, 9 mmol, 1 eq.)(90% purity), 4,4,5,5-tetramethyl-2-(4,4,5,5-tetramethyl-1,3,2-dioxaborolan-2-yl)-1,3,2-dioxaborolane (6.85 g, 26.99 mmol, 3 eq.), Pd(dppf)$Cl_2$ (1.32 g, 1.80 mmol, 0.2 eq.), and KOAc (5.30 g, 53.99 mmol, 6 eq.) in dioxane (80 mL) was degassed and purged with nitrogen 3 times, and the mixture was stirred at 100° C. for 1 h under nitrogen atmosphere. LCMS showed that the reaction was complete. To the reaction mixture was added 30 mL of a saturated EDTA solution, and the mixture was stirred for 1 h. The mixture was then extracted with EtOAc (3×50 mL), and the organic phase was washed with water (2×30 mL) and brine (2×30 mL), dried over anhydrous sodium sulfate, filtered, and concentrated in vacuo to give a residue. The residue was purified by column chromatography (silica gel; PE:EtOAc=3:1 to 1:1) to afford the title compound (2.15 g, 6.98 mmol, 77.60% yield, 90% purity) as a light yellow solid.

1.22 Preparation of methyl 4-bromo-2-methoxy-benzoate

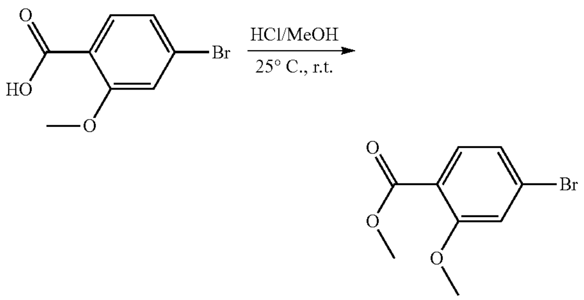

4-bromo-2-methoxy-benzoic acid (9 g, 38.95 mmol, 1 eq.) was added to HCl/MeOH (4 M, 500 mL, 51.34 eq.), and the mixture was stirred at 25° C. for 5 h. TLC showed that the reaction was complete. The mixture was dried over anhydrous sodium sulfate, filtered, and concentrated in vacuo to give a residue. Pulping by PE and concentrating the mixture in vacuo afforded the title compound as a light yellow solid (9 g, 33.05 mmol, 84.85% yield, 90% purity).

1.23 Preparation of Methyl 2-methoxy-4-(4,4,5,5-tetramethyl-1,3,2-dioxaborolan-2-yl)benzoate

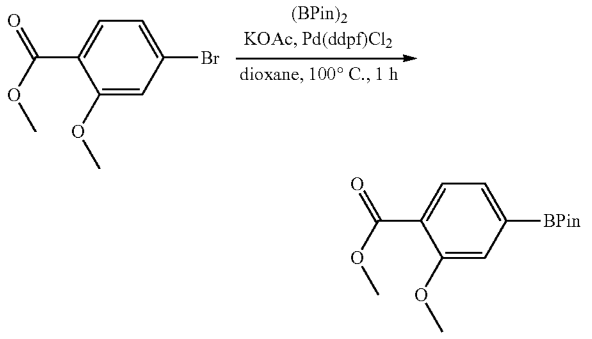

A mixture of methyl 4-bromo-2-methoxy-benzoate (8 g, 29.38 mmol, 1 eq.) (90% purity), 4,4,5,5-tetramethyl-2-(4,4,5,5-tetramethyl-1,3,2-dioxaborolan-2-yl)-1,3,2-dioxaborolane (11.19 g, 44.07 mmol, 1.5 eq.), KOAc (14.42 g, 146.90 mmol, 5 eq.), and Pd(dppf)$Cl_2$ (1.07 g, 1.47 mmol, 0.05 eq.) in dioxane (240 mL) was degassed and purged with nitrogen 3 times, and the mixture was stirred at 100° C. for 1 h under nitrogen atmosphere. TLC (PE:EtOAc=3:1) showed that the reaction was complete. To the reaction mixture was added 300 mL of a saturated EDTA solution, and the mixture was stirred for 1 h. The mixture was then extracted with EtOAc (3×300 mL), and the organic phase was washed with water (2×300 mL) and brine (2×150 mL), dried over anhydrous sodium sulfate, filtered, and concentrated in vacuo to give a residue. The residue was purified by column chromatography (silica gel; PE:EtOAc=5:0 to 5:1) to afford the title compound (11 g, 28.24 mmol, 96.12% yield, 75% purity) as a light yellow solid.

1.24 Scheme for preparation of tert-butyl4-[3-(4,4,5,5-tetramethyl-1,3,2-dioxaborolan-2-yl)phenyl]pyrazole-1-carboxylate

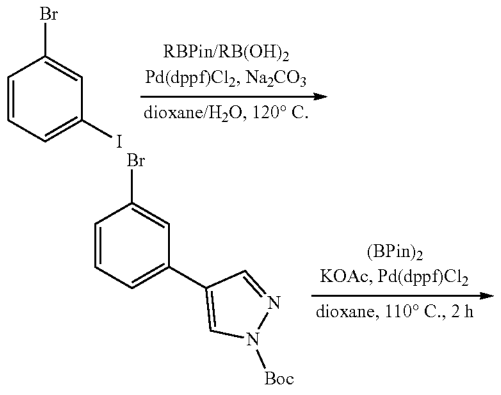

-continued

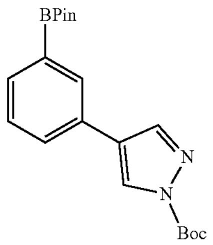

a. Preparation of tert-butyl 4-(3-bromophenyl)pyrazole-1-carboxylate

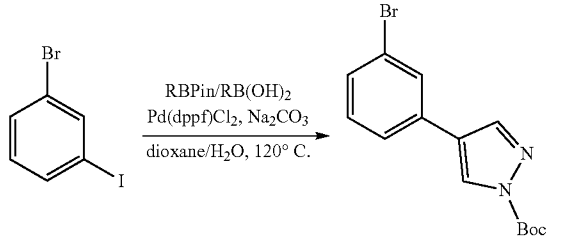 [SMILES: Brc1cccc(I)c1 ; CC(C)(C)OC(=O)n1cc(-c2cccc(Br)c2)cn1]

A mixture of 1-bromo-3-iodo-benzene (1 g, 3.53 mmol, 450.45 μL, 1 eq.), tert-butyl 4-(4,4,5,5-tetramethyl-1,3,2-dioxaborolan-2-yl)pyrazole-1-carboxylate (1.25 g, 4.24 mmol, 1.2 eq.), $Na_2CO_3$ (1.12 g, 10.60 mmol, 3 eq.), and $Pd(dppf)Cl_2$ (387.96 mg, 530.22 μmol, 0.15 eq.) in dioxane (10 mL) and water (2.5 mL) was degassed and purged with nitrogen 3 times, and the mixture was stirred at 120° C. for 15 min under nitrogen atmosphere. LCMS showed that the reaction was complete. To the reaction mixture was added 30 mL of a saturated EDTA solution, and the mixture was stirred for 1 h. The mixture was then extracted with EtOAc (3x30 mL), and the organic phase was separated, washed with water (2x30 mL) and brine (2x30 mL), dried over anhydrous sodium sulfate, filtered, and concentrated in vacuo to give a residue. The residue was purified by column chromatography (silica gel; PE:EtOAc=10:1 to 6:1) to afford the title compound as a light yellow oil (600 mg, 44.64% yield, 85% purity).

1.25 Preparation of tert-butyl4-[3-(4,4,5,5-tetramethyl-1,3,2-dioxaborolan-2-yl)phenyl]pyrazole-1-carboxylate

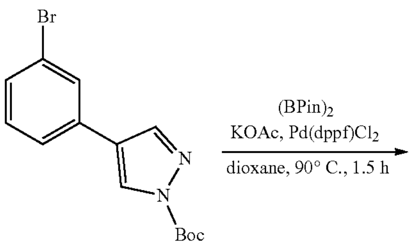

-continued

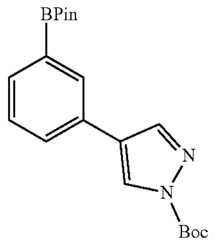

A mixture of tert-butyl 4-(3-bromophenyl)pyrazole-1-carboxylate (400 mg, 1.24 mmol, 1 eq.), 4,4,5,5-tetramethyl-2-(4,4,5,5-tetramethyl-1,3,2-dioxaborolan-2-yl)-1,3,2-dioxaborolane (2.51 g, 9.90 mmol, 8 eq.), KOAc (1.21 g, 12.38 mmol, 10 eq.), and $Pd(dppf)Cl_2$ (271.69 mg, 371.30 μmol, 0.3 eq.) in dioxane (20 mL) was degassed and purged with nitrogen 3 times, and the mixture was stirred at 90° C. for 1.5 h under nitrogen atmosphere. LCMS showed that the reaction was complete. The reaction mixture was filtered, and concentrated in vacuo to give a residue. The residue was purified by column chromatography (silica gel; PE:EtOAc=20/1 to 8:1) afford the title compound as a light yellow solid (200 mg, 405.13 μmol, 32.73% yield, 75% purity).

1.26 Preparation of 2-(5-bromo-1H-indazol-3-yl)propan-2-ol

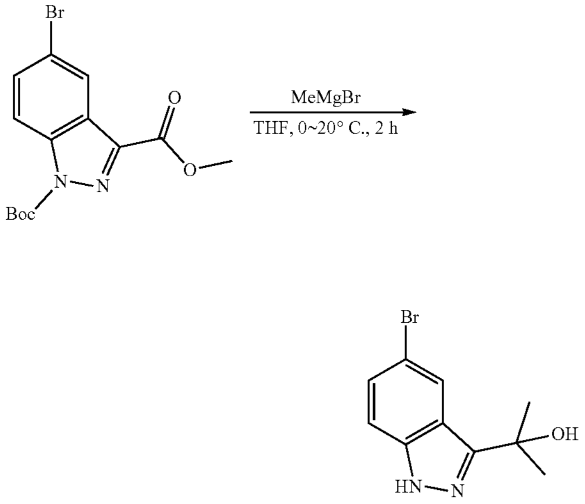

To a solution of O1-tert-butyl O3-methyl 5-bromoindazole-1,3-dicarboxylate (1 g, 2.53 mmol, 1 eq.) in THF (20 mL) was added MeMgBr (3 M, 4.22 mL, 5 eq.) at 0° C. The resulting reaction mixture was stirred at 20° C. for 2 h. TLC showed that the reaction was complete. The reaction mixture was poured into 80 mL of ice water. The aqueous phase was extracted with EtOAc (2x20 mL). The combined organic layer was washed with water (2x20 mL) and brine (20 mL), dried over anhydrous sodium sulfate, filtered, and concentrated to give the crude product afford the title compound (460 mg, crude) as an off-white solid.

1.27 Preparation of methyl 6-bromo-1-methyl-1H-indazole-4-carboxylate

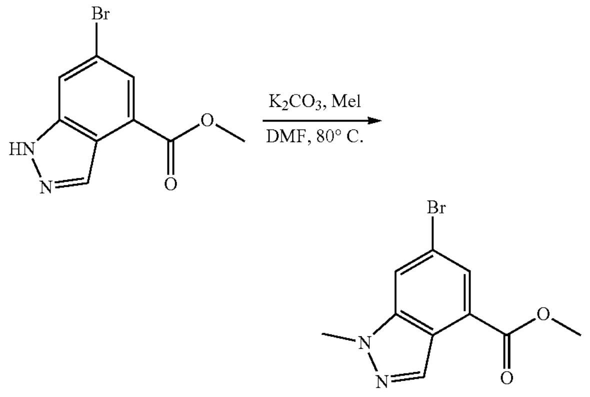

To a solution of methyl 6-bromo-1H-indazole-4-carboxylate (10 g, 39.21 mmol, 1 eq.) in DMF (50 mL) was added $K_2CO_3$ (16.26 g, 117.62 mmol, 3 eq.) and iodomethane (8.35 g, 58.81 mmol, 3.66 mL, 1.5 eq.), and the mixture was stirred for 1 h at 80° C. TLC showed that the reaction was complete. The reaction mixture was quenched with water (100 mL) and extracted with EtOAc (3×3×50 mL). The combined organic phase was washed with brine (2×100 mL), dried over anhydrous sodium sulfate, filtered, and concentrated in vacuo. The residue was purified by column chromatography (silica gel; PE:EtOAc=10:1 to 4:1) to afford the title compound (4.8 g, 17.84 mmol, 46% yield) as a yellow solid.

1.28 Preparation of 6-bromo-1-methyl-1H-indazole-4-carboxylic acid

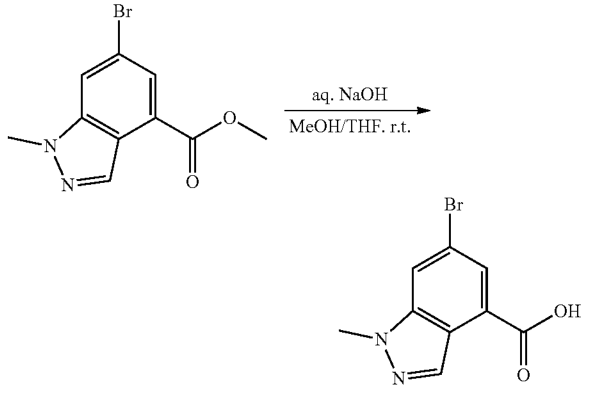

To a solution of methyl 6-bromo-1-methyl-1H-indazole-4-carboxylate (3 g, 11.15 mmol, 1 eq.) in THF (10 mL) and MeOH (10 mL) was added NaOH·aq (11.15 mmol, 10 mL, 1 eq.), then the mixture was stirred for 2 h at 20° C. TLC showed that the reaction was complete. The reaction was quenched with water (100 mL), the mixture was adjusted PH=3 with 12N HCl. Solid comes out and filtered the solid give the product to afford the title compound (2.9 g, crude) as a yellow solid.

1.29 Preparation of 6-bromo-1-methyl-indazole-4-carboxamide

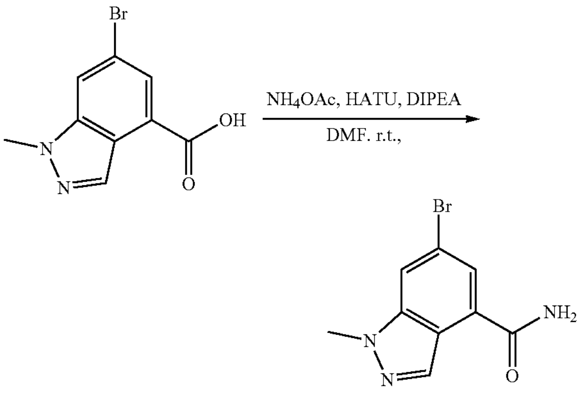

To a solution of 6-bromo-1-methyl-indazole-4-carboxylic acid (0.6 g, 2.35 mmol, 1 eq.) in DMF (10 mL) was added DIPEA (912.06 mg, 7.06 mmol, 1.23 mL, 3 eq.), HATU (1.34 g, 3.53 mmol, 1.5 eq.) and $NH_4OAc$ (906.61 mg, 11.76 mmol, 5 eq.), then the mixture was stirred for 2 h at 20° C. under nitrogen. TLC showed that the reaction was complete. The reaction was quenched with water (20 mL), the mixture was extracted with EtOAc (3×20 mL). The combined organic phase was washed with brine (2×30 mL), dried over anhydrous sodium sulfate, filtered, and concentrated in vacuo. Washed by EtOH (5 mL), to afford the title compound (0.26 g, 1.02 mmol, 43.5% yield) as a yellow solid.

1.30 Preparation of 2-(5-bromo-1-(4-methoxybenzyl)-1H-indazol-3-yl)propan-2-ol

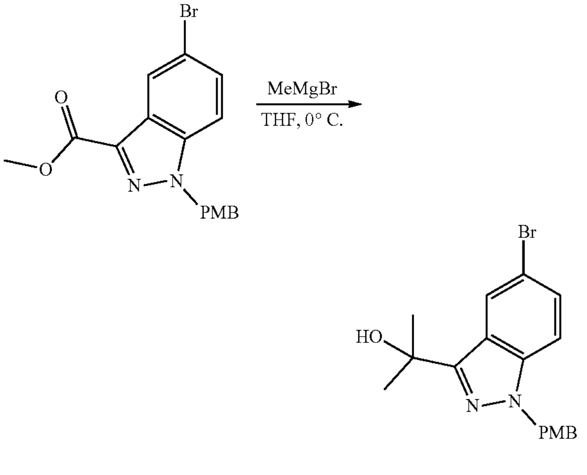

To a solution of methyl 5-bromo-1-(4-methoxybenzyl)-1H-indazole-3-carboxylate (0.17 g, 453.07 μmol, 1 eq.) in THF (10 mL) was added dropwise bromo(methyl)magnesium (3 M, 453.07 μL, 3 eq.) at 0° C. under nitrogen, then the reaction was stirred for 1 h at 0° C. under nitrogen. LCMS showed that the reaction was complete. The reaction was quenched with water (20 mL), then the mixture was extracted with EtOAc (3×10 mL). The combined organic phase was washed with brine (2×10 mL), dried over anhydrous sodium sulfate, filtered, and concentrated in vacuo.

The residue was purified by prep-TLC (silica gel; PE:EtOAc=4:1) to afford the title compound (0.17 g, 453.02 μmol, 99.99% yield) as a yellow solid.

1.31 Preparation of 5-bromo-3-isopropyl-1-(4-methoxybenzyl)-1H-indazole

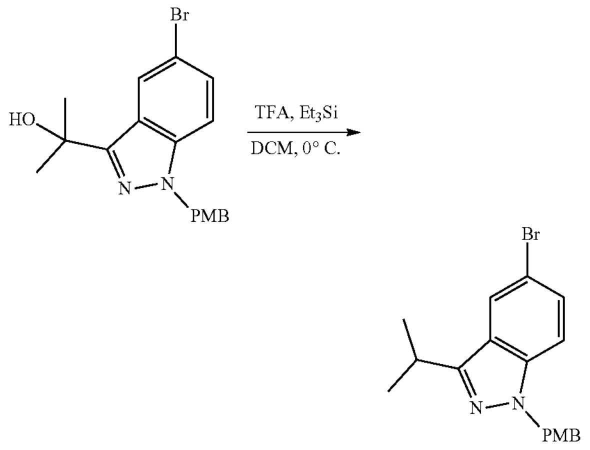

To a solution of 2-(5-bromo-1-(4-methoxybenzyl)-1H-indazol-3-yl)propan-2-ol (0.15 g, 399.72 μmol, 1 eq.) in DCM (5 mL) was added TFA (227.88 mg, 2 mmol, 147.98 μL, 5 eq.) and triethylsilane (232.40 mg, 2 mmol, 319.23 μL, 5 eq.) at 0° C., then the mixture was stirred for 15 min at 0° C. TLC showed that the reaction was complete. The reaction was quenched with sat. $NaHCO_3$ (10 mL), then the mixture was extracted with DCM (3×10 m) The combined organic phase was washed with brine (2×10 mL), dried over anhydrous sodium sulfate, filtered, and concentrated in vacuo. The residue was purified by prep-TLC (silica gel; PE:EtOAc=4:1) to afford the title compound (0.12 g, 334.02 μmol, 83.56% yield) as a yellow oil.

1.32 Preparation of 5-bromo-N-cyclopropyl-2-nitroaniline

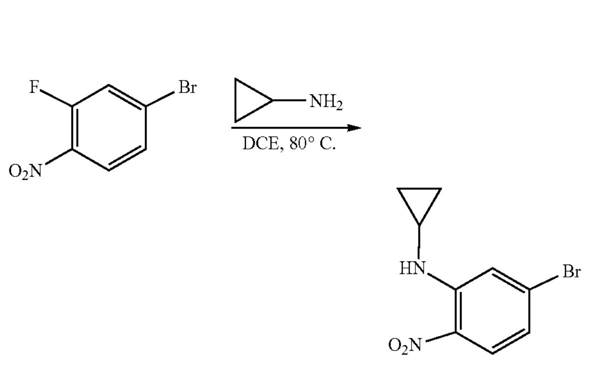

To a mixture of 4-bromo-2-fluoro-1-nitrobenzene (5 g, 22.73 mmol, 1 eq.) in DCE (50 mL) was added cyclopropanamine (2.60 g, 45.46 mmol, 3.15 mL, 2 eq.) in one portion at 80° C. under nitrogen. The mixture was stirred at 80° C. for 3 h. LCMS showed that the reaction was complete. The reaction was poured into was water (50 mL). The aqueous phase was extracted with DCM (3×3×50 mL). The combined organic phase was washed with brine (2×40 mL) dried over anhydrous sodium sulfate, filtered, and concentrated in vacuo to afford the title compound (5.8 g, crude) as a yellow solid.

1.33 Preparation of 5-bromo-N1-cyclopropylbenzene-1,2-diamine

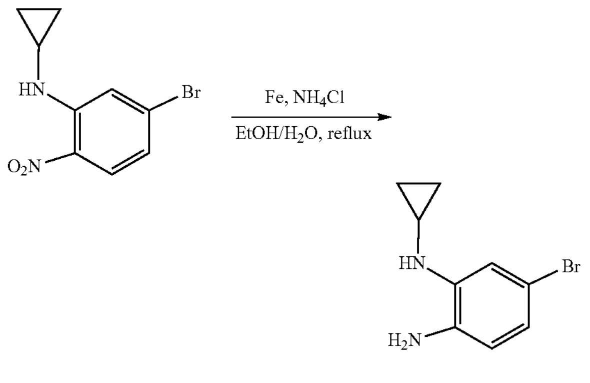

To a mixture of 5-bromo-N-cyclopropyl-2-nitroaniline (5.8 g, 22.56 mmol, 1 eq.) in EtOH (40 mL), water (10 mL) was added $NH_4Cl$ (7.24 g, 135.36 mmol, 4.73 Ml, 6 eq.) in one portion at 90° C. under nitrogen. Then Fe (7.56 g, 135.36 mmol, 6 eq.) was added in portions. The mixture was stirred at 90° C. for 1 h. TLC showed that the reaction was complete. The reaction was poured into EtOAc (60 mL), filtered by Celite. The aqueous phase was extracted with EtOAc (3×80 mL). The combined organic phase was washed with brine (2×60 mL), dried over anhydrous sodium sulfate, filtered, and concentrated in vacuo. The residue was purified by column chromatography (silica gel; PE:EtOAc=5:1 to 1:1) to afford the title compound (3.3 g, 14.53 mmol, 64.41% yield) as a brown oil.

1.34 Preparation of 6-bromo-1-cyclopropyl-1H-benzo[d]imidazol-2(3H)-one

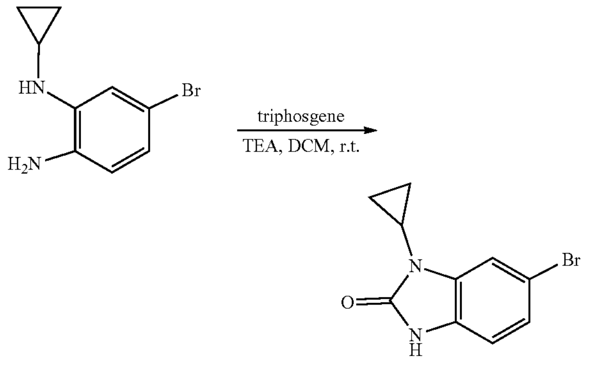

To a mixture of 5-bromo-N1-cyclopropylbenzene-1,2-diamine (3 g, 13.21 mmol, 1 eq.) in DCM (30 mL) was added TEA (1.60 g, 15.85 mmol, 2.21 mL, 1.2 eq.), triphosgene (1.96 g, 6.61 mmol, 0.5 eq.) in one portion at 25° C. under nitrogen. The mixture was stirred at 25° C. for 1 h. TLC showed that the reaction was complete. The reaction was poured into sat. $NaHCO_3$ (50 mL). The aqueous phase was extracted with EtOAc (3×50 mL). The combined organic phase was washed with brine (2×50 mL), dried over anhydrous sodium sulfate, filtered, and concentrated in vacuo. The residue was purified by column chromatography (silica gel; PE:EtOAc=5:1 to 1:1) to afford the title compound (1.1 g, 4.35 mmol, 32.90% yield) as a white solid.

1.35 Preparation of 6-bromo-2-cyclopropylimidazo[1,2-a]pyridine

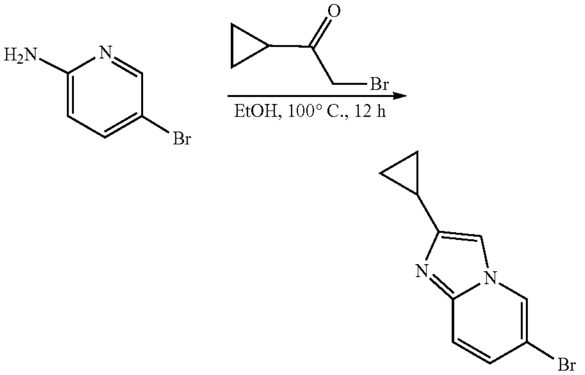

To a mixture of 2-bromo-1-cyclopropylethanone (0.05 g, 306.73 μmol, 1 eq.) and 5-bromopyridin-2-amine (53.07 mg, 306.73 μmol, 1 eq.) in EtOH (2 mL) in one portion at 100° C. under nitrogen. The mixture was stirred at 100° C. for 12 h. LCMS showed that the reaction was complete. The reaction was purified by prep-TLC (PE:EtOAc=1:1) to afford the title compound (0.04 g, 168.71 μmol, 55% yield) as a yellow oil.

1.36 Preparation of 5-bromo-N,N-dimethyl-1H-indazole-3-carboxamide

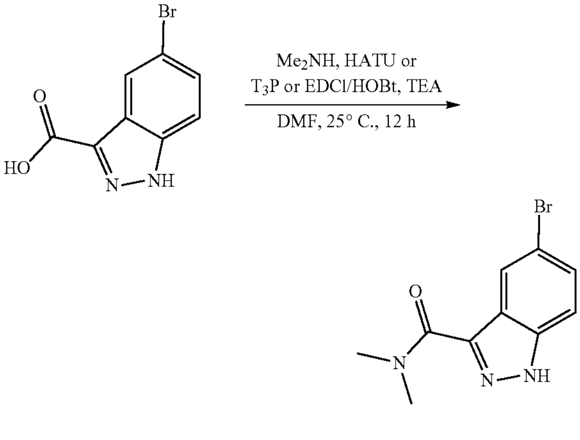

To a mixture of 5-bromo-1H-indazole-3-carboxylic acid (150 mg, 622.30 μmol, 1 eq.) and N-methylmethanamine (76.12 mg, 933.45 μmol, 85.53 μL, 1.5 eq., HCl) in DMF (3 mL) was added HATU (354.93 mg, 933.45 μmol, 1.5 eq.) and TEA (188.91 mg, 1.87 mmol, 259.85 μL, 3 eq.) in one portion at 25° C. under nitrogen. The mixture was stirred at 25° C. for 12 h. TLC and LCMS showed that the reaction was complete. The mixture was poured into water (30 mL) and the aqueous phase was extracted with EtOAc (3×30 mL). The combined organic phase was washed with brine (3×30 mL), dried over anhydrous sodium sulfate, filtered, and concentrated in vacuo. The residue was purified by prep-TLC (silica gel; DCM:MeOH=10:1) to afford the title compound (260 mg, 60% purity, 93.2% yield) as a brown solid.

1.37 Preparation of tert-butyl 5-bromo-3-(dimethylcarbamoyl)indazole-1-carboxylate

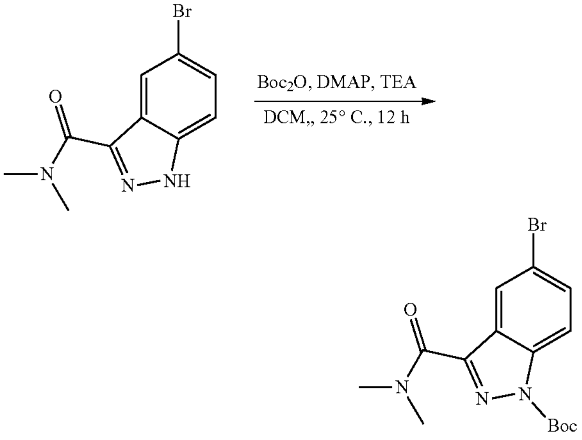

To a mixture of 5-bromo-N,N-dimethyl-1H-indazole-3-carboxamide (260 mg, 969.75 μmol, 1 eq.) and $Boc_2O$ (423.29 mg, 1.94 mmol, 445.57 μL, 2 eq.) in DCM (5 mL) was added DMAP (11.85 mg, 96.98 μmol, 0.1 eq.) and TEA (196.26 mg, 1.94 mmol, 269.96 μL, 2 eq.) in one portion at 25° C. The mixture was stirred at 25° C. for 12 h. TLC and LCMS showed that the reaction was complete. The residue was poured into water (10 mL) and the aqueous phase was extracted with EtOAc (3×30 mL). The combined organic phase was washed with brine (3×30 mL), dried over anhydrous sodium sulfate, filtered, and concentrated in vacuo. The mixture was purified by prep-TLC (silica gel; DCM:MeOH=20:1) to afford the title compound (300 mg, 814.72 μmol, 84.01% yield) as a yellow oil.

1.38 Preparation of 6-bromo-9H-pyrido[3,4-b]indole

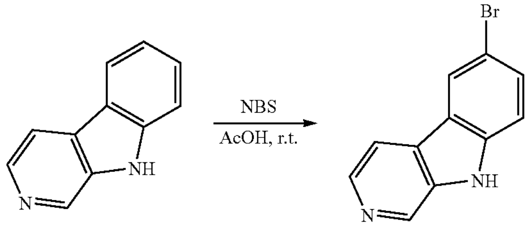

To a mixture of 9H-pyrido[3,4-b]indole (200 mg, 1.19 mmol, 1 eq.) in AcOH (5 mL) was added NBS (211.64 mg, 1.19 mmol, 1 eq.) in one portion at 25° C. The mixture was stirred at 25° C. for 12 h. LCMS showed that the reaction was complete. The residue was poured into sat. $NaHCO_3$ (60 mL) for pH=8 and the aqueous phase was extracted with EtOAc (3×30 mL). The combined organic phase was washed with brine (3×30 mL), dried over anhydrous sodium sulfate, filtered, and concentrated in vacuo. The mixture was dissolved in EtOAc (10 mL) and PE (60 mL) and the mixture was stirred for 30 mins, filtered to afford (210 mg, 849.89 μmol, 71.47% yield) was obtained as a brown solid.

1.39 Scheme for Preparation of tert-butyl 5-bromo-3-cyclobutyl-1H-indazole-1-carboxylate

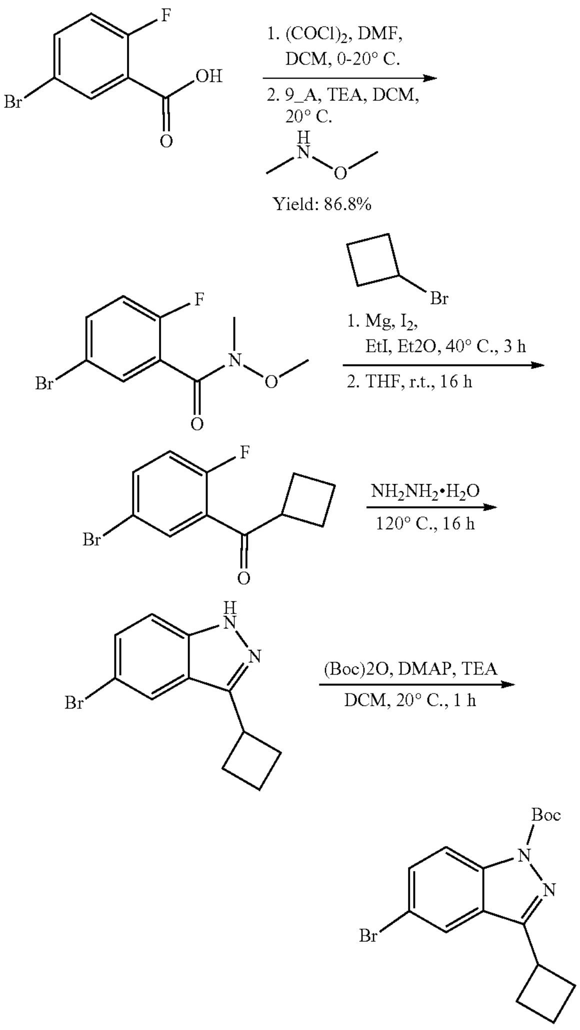

a. Preparation of 5-bromo-2-fluoro-N-methoxy-N-methyl-benzamide

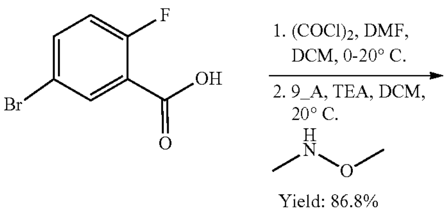

-continued

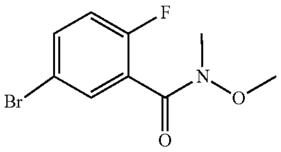

To a mixture of 5-bromo-2-fluorobenzoic acid (2 g, 9.13 mmol) in DCM (20 mL) was added $(COCl)_2$ (2.32 g, 18.26 mmol, 1.60 mL) and DMF (66.75 mg, 913.21 μmol, 70.26 uL) dropwise at 0° C. under nitrogen. The mixture was stirred at 20° C. for 1 h, LCMS shown the starting material was consumed, then the mixture was concentrated to give residue. The residue was dissolved with DCM (20 mL), then N-methoxymethanamine; hydrochloride (1.78 g, 18.26 mmol, 2 eq.) and TEA (2.77 g, 27.40 mmol, 3.81 mL, 3 eq.) was added to above mixture and stirred at 20° C. for 3 h. LCMS showed that the reaction was complete. The mixture was washed with water (10 mL) and brine (10 mL), dried over anhydrous sodium sulfate, filtered, and concentrated in vacuo. The residue was purified by column chromatography (silica gel; PE:EtOAc=50/1 to 20:1) to afford the title compound (1.7 g, 5.84 mmol, 63.93% yield, 90% purity).

b. Preparation of (5-bromo-2-fluoro-phenyl)-cyclobutyl-methanone

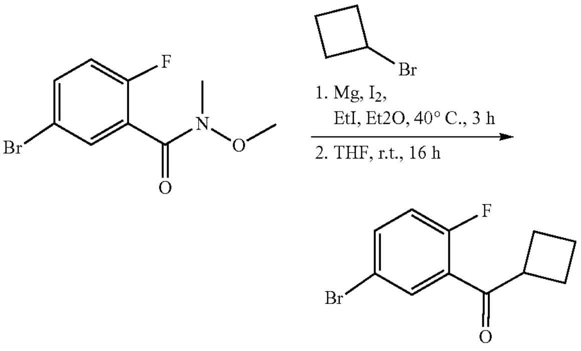

To a solution of Mg (2.06 g, 84.80 mmol, 20 eq.) in Et2O (35 mL) was added $I_2$ (538.08 mg, 2.12 mmol, 427.05 uL) and bromocyclobutane (2.86 g, 21.20 mmol, 2 mL) dropwise at 40° C. under nitrogen. EtI (991.97 mg, 6.36 mmol, 508.70 uL) was added to above mixture followed by bromocyclobutane (2.86 g, 21.20 mmol, 2 mL). Then iodoethane (1.98 g, 12.72 mmol, 1.0 mL) was added to the reaction mixture and stirred at 40° C. for another 2 hrs. The reaction mixture was cooled to 20° C. then 5-bromo-2-fluoro-N-methoxy-N-methyl-benzamide (1.11 g, 4.24 mmol, 1 eq.) in THF (10 mL) was added before stirring for another 16 hrs. TLC (PE:EtOAc=5:1) showed the starting material was consumed. The reaction was quenched with $NH_4Cl$ (20 mL) and extracted with EtOAc (5 mL×2). The combined organic phase was washed with brine (5 mL), dried over anhydrous sodium sulfate, filtered, and concentrated in vacuo. The reaction mixture was purified by prep-TLC (silica gel; PE:EtOAc=20:1) to afford the title compound (0.9 g, 2.63 mmol, 61.92% yield, 75% purity) as a yellow oil.

c. Preparation of 5-bromo-3-cyclobutyl-1H-indazole

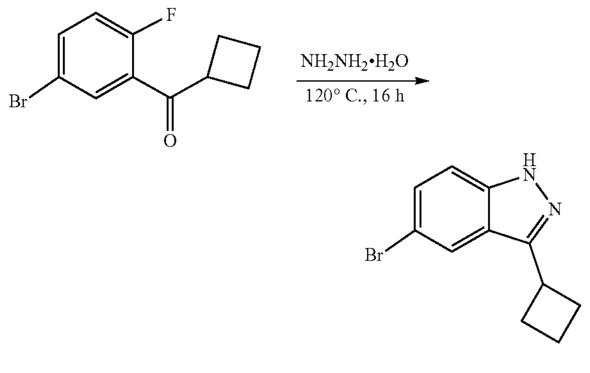

Compound (5-bromo-2-fluoro-phenyl)-cyclobutyl-methanone (0.8 g, 3.11 mmol) was dissolved in $NH_2NH_2 \cdot H_2O$ (7.79 g, 155.58 mmol, 7.56 mL) with single-necked round bottom flask. The mixture was stirred at 120° C. for 16 h under nitrogen. TLC (PE:EtOAc=20:1) showed the starting material was consumed completely. The reaction was quenched with water (20 mL) and extracted with EtOAc (5 mL×2). The combined organic phase was washed with brine (5 mL), dried over anhydrous sodium sulfate, filtered, and concentrated in vacuo. The residue was purified by prep-TLC (silica gel; PE:EtOAc=10:1) to give compound (0.28 g, 1.11 mmol, 35.83% yield) as a white solid.

d. Preparation of tert-butyl 5-bromo-3-cyclobutyl-1H-indazole-1-carboxylate

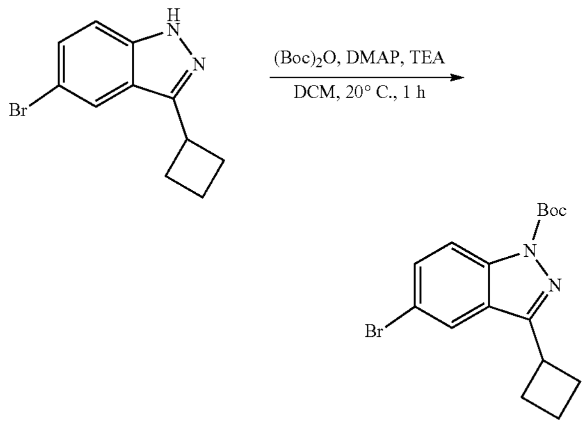

To a solution of compound 5-bromo-3-cyclobutyl-1H-indazole (0.1 g, 398.21 μmol) and TEA (52.38 mg, 517.68 μmol, 72.05 uL) in DCM (10 mL) was added DMAP (4.86 mg, 39.82 μmol) and $Boc_2O$ (104.29 mg, 477.86 μmol, 109.78 uL) dropwise at 20° C. under nitrogen. The reaction mixture was stirred at 20° C. for 1 h. TLC (PE:EtOAc=5:1) showed the starting material was consumed completely. The reaction was washed with water (10 mL), dried over anhydrous sodium sulfate, filtered, and concentrated in vacuo. The residue was purified by prep-TLC (silica gel; PE:EtOAc=10:1) to afford the title compound (0.13 g, 333.11 μmol, 83.65% yield, 90% purity) as a yellow oil.

1.40 Scheme for Preparation of [1-methyl-4-(3-pyridyl)indazol-6-yl]trifluoromethanesulfonate

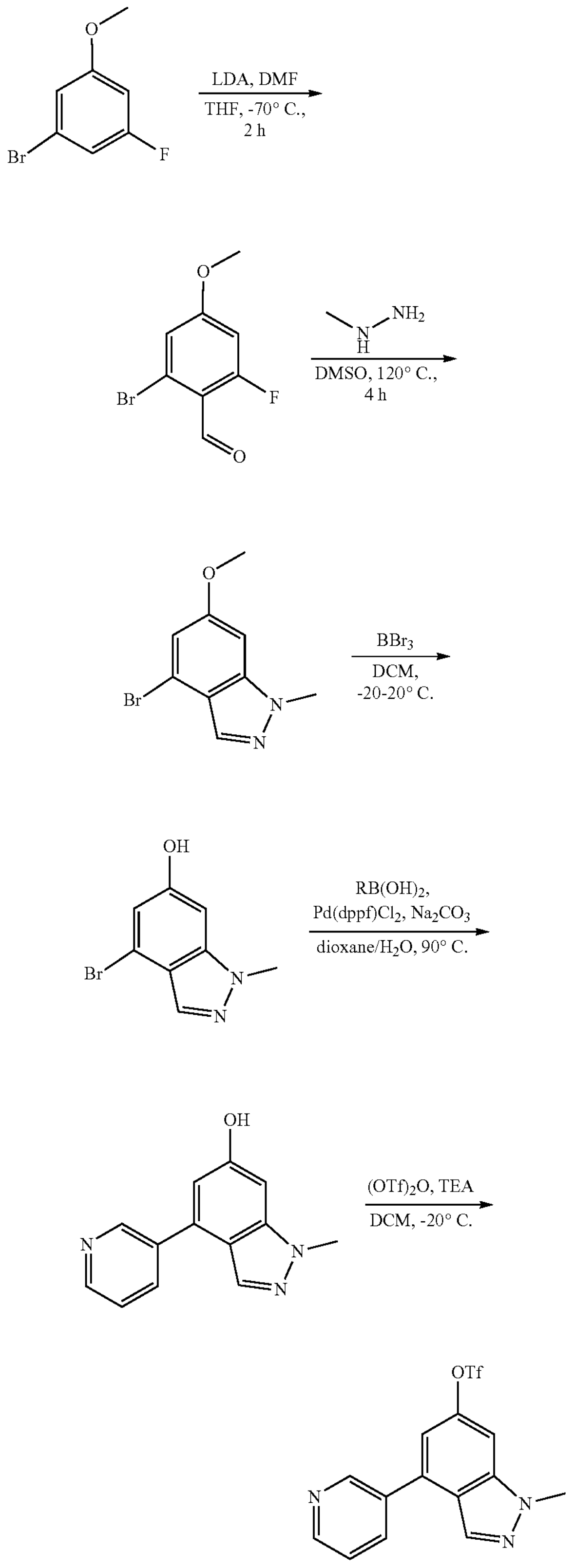

a. Preparation of 2-bromo-6-fluoro-4-methoxy-benzaldehyde

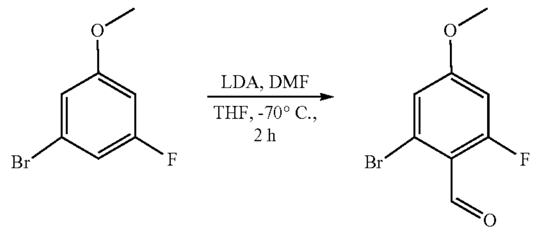

To a solution of 1-bromo-3-fluoro-5-methoxy-benzene (5 g, 24.39 mmol, 1 eq.) in THF (20 mL) was added LDA (2 M, 14.63 mL, 1.2 eq.) dropwise at −70° C. under nitrogen. During which the temperature was maintained below −70° C. The reaction mixture was stirred at −70° C. for 1 h. Then N,N-dimethylformamide (8.91 g, 121.94 mmol, 9.38 mL, 5 eq.) was added to above reaction mixture and stirred at −70° C. for another 1 hrs. TLC (PE:EtOAc=20:1) showed the starting material was consumed completely. The reaction was quenched with aqueous $NH_4Cl$ (50 mL) and extracted with EtOAc (2×100 mL). The combined organic phase was washed with brine (100 mL), dried over anhydrous sodium sulfate, filtered, and concentrated in vacuo. The residue was purified by prep-TLC (silica gel; PE:EtOAc=5:1). The residue was purified by re-crystallization from PE:EtOAc=40:1 (40 mL/1 mL) to afford the title compound (2.1 g, 8.11 mmol, 33.26% yield, 90% purity) as a white solid.

b. Preparation of 4-bromo-6-methoxy-1-methyl-indazole

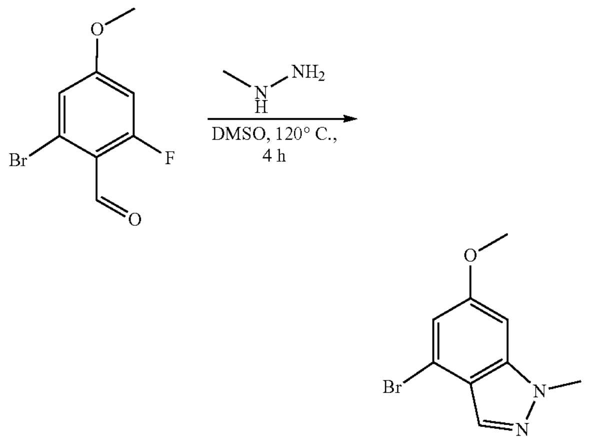

To a mixture of 2-bromo-6-fluoro-4-methoxy-benzaldehyde (3 g, 12.87 mmol, 1 eq.) in DMSO (30 mL) was added methylhydrazine (26.25 g, 569.76 mmol, 30 mL, 44.26 eq.). The mixture was stirred at 120° C. for 4 h. TLC showed the starting material was consumed completely and two main spots was detected. The reaction was poured into 200 mL water slowly, white solid was formed, filtered, and concentrated. The residue was purified by column chromatography (silica gel; PE:EtOAc=6/1 to 4:1) to afford the title compound (1.8 g, 7.09 mmol, 55.10% yield, 95% purity) as a white solid.

c. Preparation of 4-bromo-1-methyl-indazol-6-ol

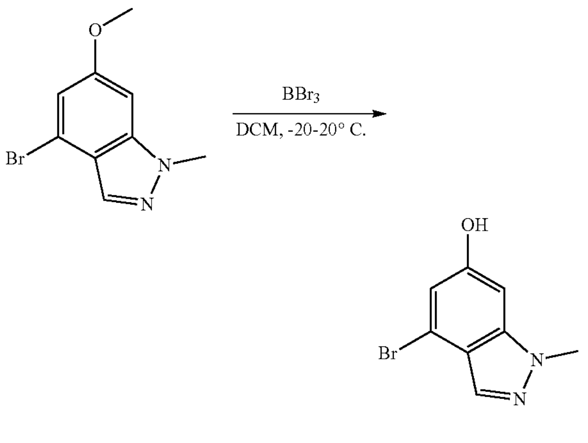

To a mixture of 4-bromo-6-methoxy-1-methyl-indazole (800 mg, 3.15 mmol, 1 eq.) (95% purity) in DCM (10 mL) was added $BBr_3$ (13 g, 51.89 mmol, 5 mL, 16.46 eq.) in one portion at −20° C. under nitrogen. The mixture was stirred at 20° C. for 12 h. LCMS showed 80% desired product and 10% R1 was remained. the reaction was stirred for another 12 h, TLC showed that the reaction was complete. The reaction was quenched with 100 mL saturated aq. $NaHCO_3$, adjust to PH=8, extracted with DCM:MeOH=10:1 (4×35 mL), washed with water (3×30 mL), brine (3×30 mL), dried over anhydrous sodium sulfate, filtered, and concentrated to give crude to afford the title compound (750 mg, crude) as a pink solid.

d. Preparation of 1-methyl-4-(3-pyridyl)indazol-6-ol

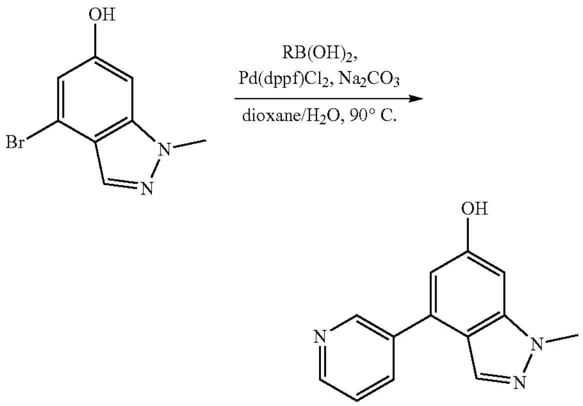

To a mixture of 4-bromo-1-methyl-indazol-6-ol (600 mg, 2.64 mmol, 1 eq.) and 3-pyridylboronic acid (649.62 mg, 5.29 mmol, 2 eq.) in dioxane (12 mL) and water (3 mL) was added $Na_2CO_3$ (1.40 g, 13.21 mmol, 5 eq.) and $Pd(dppf)Cl_2$ (290.03 mg, 396.38 μmol, 0.15 eq.) in one portion under nitrogen. The mixture was stirred at 90° C. for 1 h under nitrogen. LCMS showed 70% desired product. The reaction was diluted with 30 mL water, extracted with EtOAc (3×30 mL), washed with water (3×30 mL), brine (2×30 mL), dried over anhydrous sodium sulfate, filtered, and concentrated to give a residue. The residue was purified by prep-TLC (silica gel; DCM:MeOH=10:1) to afford the title compound (200 mg, 887.92 μmol, 33.60% yield, 100% purity) as a yellow solid.

e. Preparation of [1-methyl-4-(3-pyridyl)indazol-6-yl]trifluoromethanesulfonate

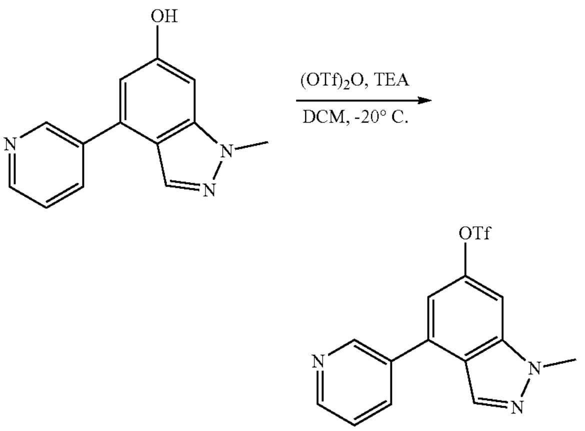

To a mixture of 1-methyl-4-(3-pyridyl)indazol-6-ol (170 mg, 754.73 μmol, 1 eq.) in DCM (5 mL) was added TEA (152.74 mg, 1.51 mmol, 210.10 μL, 2 eq.) and $Tf_2O$ (319.41 mg, 1.13 mmol, 186.79 μL, 1.5 eq.) in one portion at −20° C. under nitrogen. The mixture was stirred at −20° C. for 30 min. LCMS showed 80% desired product. The reaction was quenched with 20 mL saturated aq·$NH_4Cl$, adjust to PH=8 with 10 mL saturated aq·NaHCO3, extracted with DCM (3×30 mL), washed with water (2×25 mL), brine (2×25 mL), dried over anhydrous sodium sulfate, filtered, and concentrated to give a residue. The residue was purified prep-TLC (according to TLC plate 1, Rf=0.54, silica gel; DCM: MeOH=15:1) to afford the title compound (70 mg, 195.91 μmol, 25.96% yield) as a red gum compound (0.016 g, 44.37 μmol, 74.53% yield, 98% purity) as a white solid.

1.41 Scheme for Preparation of (1-methyl-4-phenyl-indazol-6-yl) trifluoromethanesulfonate

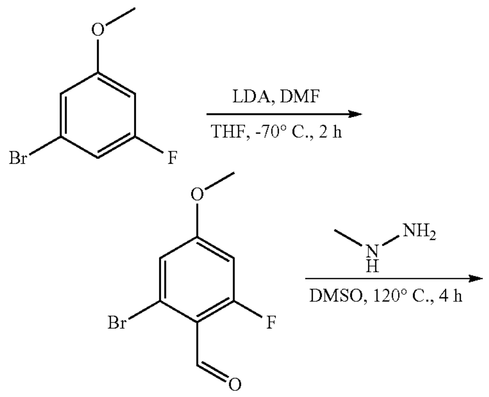

-continued

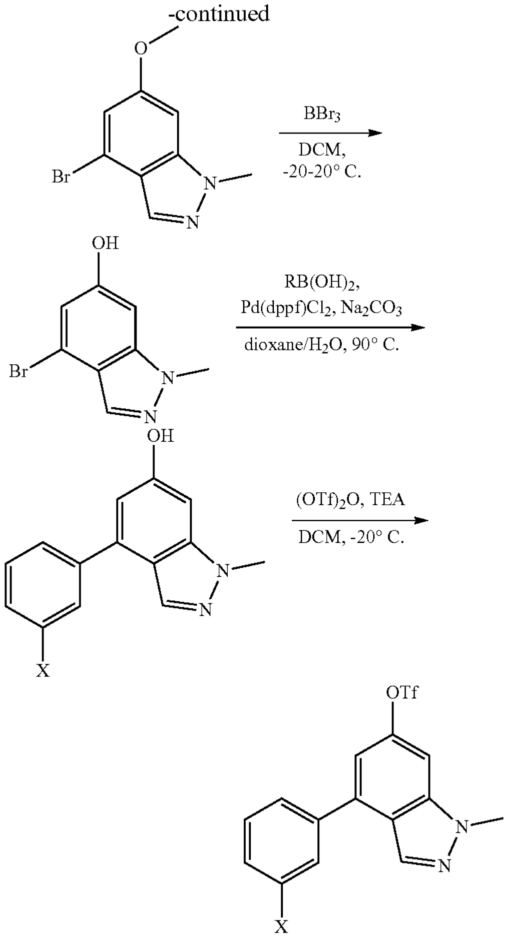

X = CN, Cl, H a. Preparation of 2-bromo-6-fluoro-4-methoxy-benzaldehyde

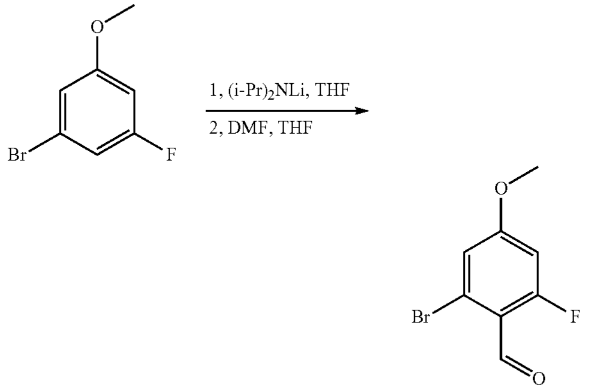

To a solution of 1-bromo-3-fluoro-5-methoxy-benzene (5 g, 24.39 mmol, 1 eq.) in THF (20 mL) was added LDA (2 M, 14.63 mL, 1.2 eq.) dropwise at −70° C. under nitrogen. The reaction mixture was stirred at −70° C. for 1 h. Then N,N-dimethylformamide (8.91 g, 121.94 mmol, 9.38 mL, 5 eq.) was added to above reaction mixture and stirred at −70° C. for another 1 hrs. TLC (PE:EtOAc=20:1) showed the starting material was consumed completely. The reaction was quenched with aqueous $NH_4Cl$ (150 mL) and extracted with EtOAc (2×100 mL). The combined organic phase was washed with brine (100 mL), dried over anhydrous sodium sulfate, filtered, and concentrated in vacuo. The residue was purified by prep-TLC (silica gel; PE:EtOAc=5:1). The residue was purified by re-crystallization from PE:EtOAc=40:1 (40 mL/1 mL) to afford the title compound (2.1 g, 8.11 mmol, 33.26% yield, 90% purity) as a white solid.

b. Preparation of 4-bromo-6-methoxy-1-methyl-indazole

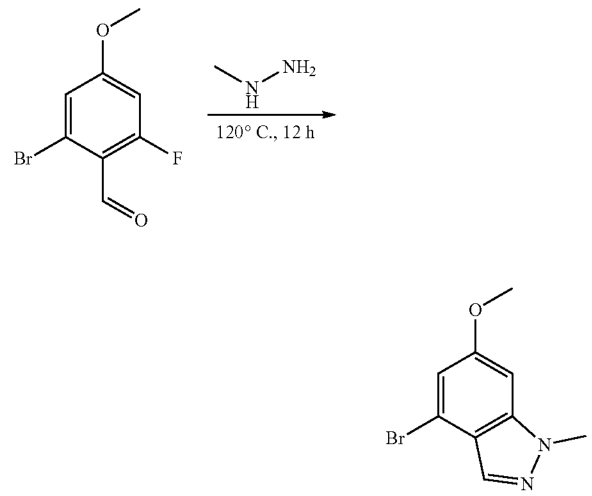

2-bromo-6-fluoro-4-methoxy-benzaldehyde (1 g, 3.86 mmol, 1 eq.) was dissolved in methylhydrazine (17.79 g, 386.21 mmol, 20.34 mL, 100 eq.) in single-necked round bottom flask. The mixture was stirred at 120° C. for 12 hrs under nitrogen. TLC (PE:EtOAc=5:1) showed the starting material was consumed completely. The mixture was cooled and concentrated in reduced pressure. The residue was purified by prep-TLC (silica gel; PE:EtOAc=5:1 to afford the title compound (0.66 g, 2.46 mmol, 63.80% yield, 90% purity) as a white solid.

c. Preparation of 6-methoxy-1-methyl-4-phenyl-indazole

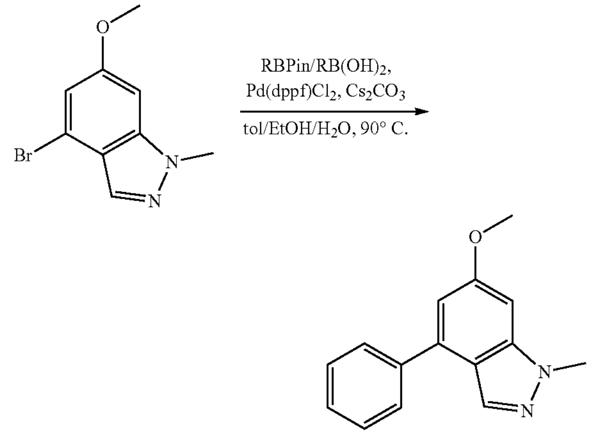

Phenylboronic acid (121.38 mg, 995.50 μmol, 1.2 eq.), 4-bromo-6-methoxy-1-methyl-indazole (0.2 g, 829.59 μmol, 1 eq.), $Pd(dppf)Cl_2$ (121.40 mg, 165.92 μmol, 0.2 eq.) and $Na_2CO_3$ (105.51 mg, 995.50 μmol, 1.2 eq.) in EtOH (5 mL) and water (2 mL) and toluene (5 mL) was de-gassed and heated to 90° C. for 2 h under nitrogen. TLC (PE:EtOAc=1:1) showed the starting material was consumed completely. The reaction mixture was poured into sat. EDTA (30 mL) and stirred for 1 h. The mixture was extracted with EtOAc (2×20 mL). The organic phase was washed with brine (2×25 mL), dried over anhydrous sodium sulfate, concentrated in vacuo to give a residue. The residue was purified by prep-TLC (silica gel; PE:EtOAc=1:1) to afford the title compound (0.16 g, 570.75 μmol, 68.80% yield, 85% purity) as a white solid.

d. Preparation of 1-methyl-4-phenyl-indazol-6-ol

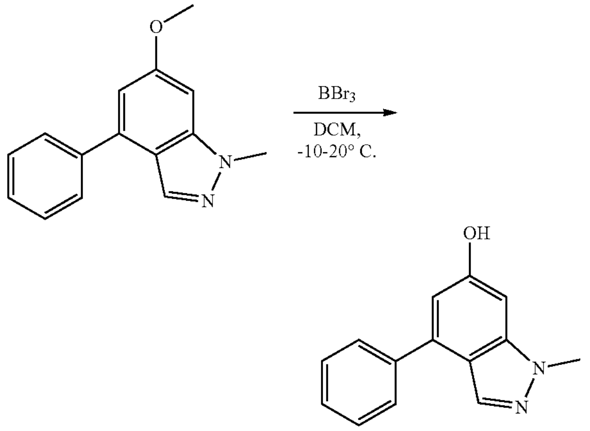

To a solution of 6-methoxy-1-methyl-4-phenyl-indazole (0.13 g, 545.57 μmol, 1 eq.) in DCM (1 mL) was added $BBr_3$ (683.38 mg, 2.73 mmol, 262.84 μL, 5 eq.) dropwise at −10° C. under nitrogen. The reaction mixture was warmed to 20° C. over a period of 60 mins and stirred at 20° C. for 15 h. TLC (PE:EtOAc=1:1) showed the starting material was consumed completely. The reaction was quenched with ice slowly and extracted with DCM (2×25 mL). The combined organic phase was washed with brine (2×25 mL), dried over anhydrous sodium sulfate, filtered, and concentrated in vacuo to afford the title compound (0.1 g, 401.32 μmol, 73.56% yield, 90% purity) as a white solid. The crude product was used in the next step without purification.

e. Preparation (1-methyl-4-phenyl-indazol-6-yl) trifluoromethanesulfonate

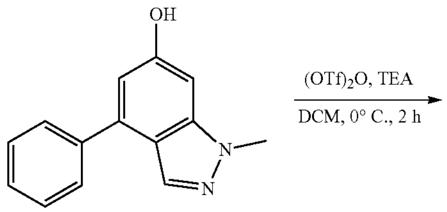

-continued

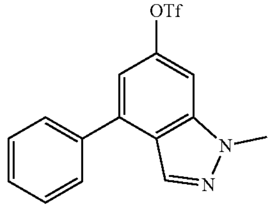

To a solution of 1-methyl-4-phenyl-indazol-6-ol (0.1 g, 445.92 μmol, 1 eq.) and trifluoromethylsulfonyl trifluoromethanesulfonate (163.55 mg, 579.69 μmol, 95.65 μL, 1.3 eq.) in DCM (4 mL) was added TEA (112.81 mg, 1.11 mmol, 155.17 μL, 2.5 eq.) dropwise at 0° C. under nitrogen. During which the temperature was maintained below 0° C. The reaction mixture was stirred at 0° C. for 2 h. TLC (PE:EtOAc=1:1) showed the starting material was consumed completely. The reaction was quenched with ice slowly and extracted with DCM (2×15 mL). The combined organic phase was washed with brine (2×15 mL), dried over anhydrous sodium sulfate, filtered, and concentrated in vacuo. The residue was purified by prep-TLC (silica gel; PE:EtOAc=1:1) to afford the title compound (0.1 g, 252.58 μmol, 56.64% yield, 90% purity) as a white solid.

1.42 Scheme for Preparation of tert-butyl 5-bromo-3-(oxetan-3-yl)indazole-1-carboxylate

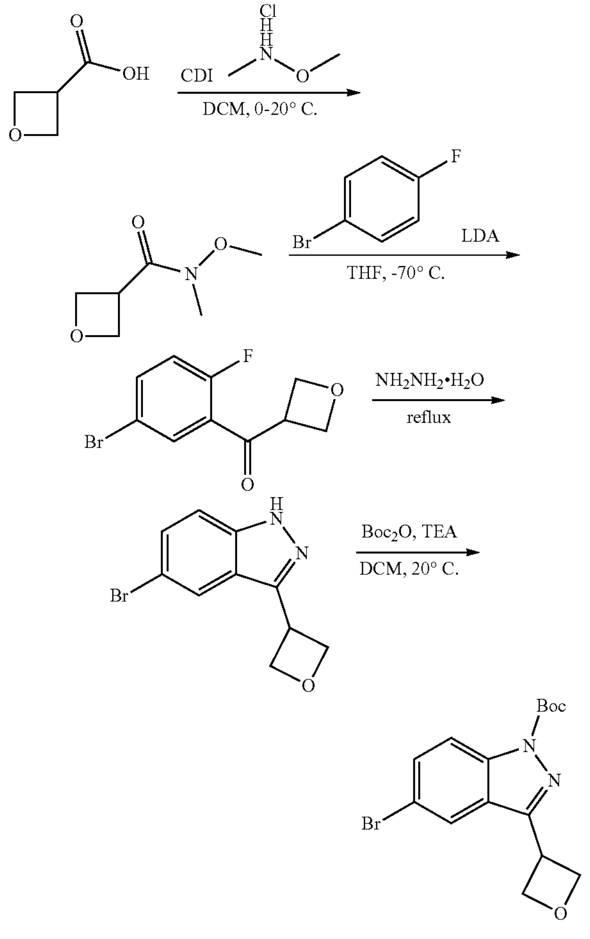

a. Preparation of N-methoxy-N-methyl-oxetane-3-carboxamide

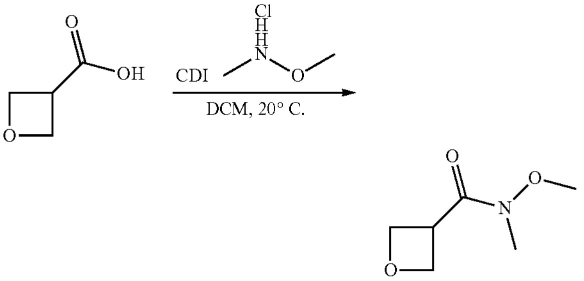

To a solution of oxetane-3-carboxylic acid (0.9 g, 8.82 mmol, 1 eq.) and N-methoxymethan amine; hydrochloride (859.93 mg, 8.82 mmol, 1 eq.) in DCM (20 mL) was added CDI (1.72 g, 10.58 mmol, 1.2 eq.) in portions at 20° C. under nitrogen. The reaction mixture was stirred at 20° C. for 16 h. TLC (PE:EtOAc=0:1) showed the starting material was consumed completely. The reaction was washed with 1N HCl (10 mL) and brine (10 mL), dried over anhydrous sodium sulfate, filtered, and concentrated in vacuo to afford the title compound (0.9 g, 5.58 mmol, 63.30% yield, 90% purity) as yellow liquid, which was used to next step without purification.

b. Preparation of (5-bromo-2-fluoro-phenyl)-(oxetan-3-yl)methanone

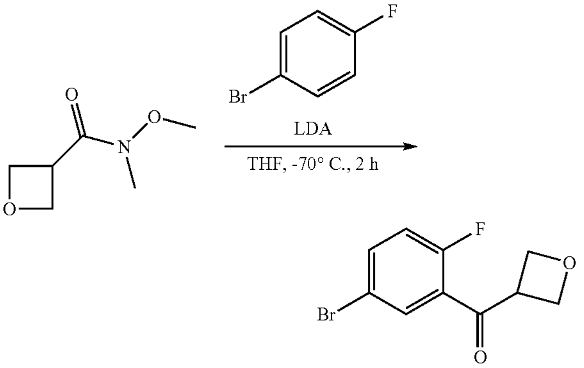

To a solution of 1-bromo-4-fluoro-benzene (1.09 g, 6.20 mmol, 682.41 μL, 2 eq.) in THF (10 mL) was added LDA (2 M, 3.41 mL, 2.2 eq.) in THF (10 mL) dropwise at −70° C. under nitrogen. The reaction mixture was stirred at −70° C. for 1 h. Then N-methoxy-N-methyl-oxetane-3-carboxamide (0.5 g, 3.10 mmol, 1 eq.) in THF (10 mL) was added to above reaction mixture and stirred at −70° C. for another 1 hrs. TLC (PE:EtOAc=20:1) showed the starting material was consumed completely. The reaction was quenched with aqueous $NH_4Cl$ (50 mL) and extracted with EtOAc (2×50 mL). The combined organic phase was washed with brine (2×50 mL), dried over anhydrous sodium sulfate, filtered, and concentrated in vacuo. The residue was purified by prep-TLC (silica gel; PE:EtOAc=5:1) to afford the title compound (0.62 g, 2.15 mmol, 69.48% yield, 90% purity) as a yellow oil.

c. Preparation of 5-bromo-3-(oxetan-3-yl)-1H-indazole

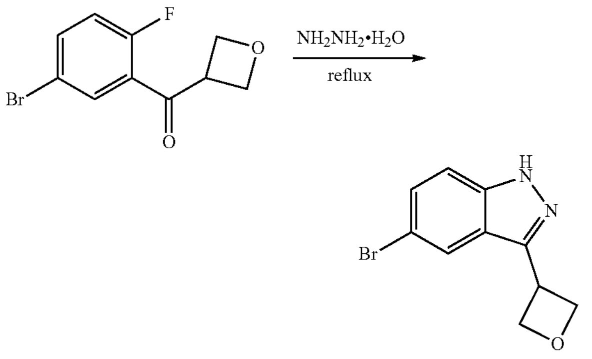

(5-bromo-2-fluoro-phenyl)-(oxetan-3-yl)methanone (0.4 g, 1.39 mmol, 1 eq.) was dissolved in $NH_2NH_2 \cdot H_2O$ (6.96 g, 138.96 mmol, 6.75 mL, 100 eq.) with single-necked round bottom flask. The mixture was stirred at 120° C. for 5 mins under nitrogen. TLC (PE:EtOAc=20:1) showed the starting material was consumed completely. The mixture was cooled and concentrated in reduced pressure. The residue was purified by prep-TLC (silica gel; PE:EtOAc=5:1) to afford the title compound (0.2 g, 671.68 μmol, 48.34% yield, 85% purity) as a yellow solid.

d. Preparation of tert-butyl 5-bromo-3-(oxetan-3-yl)indazole-1-carboxylate

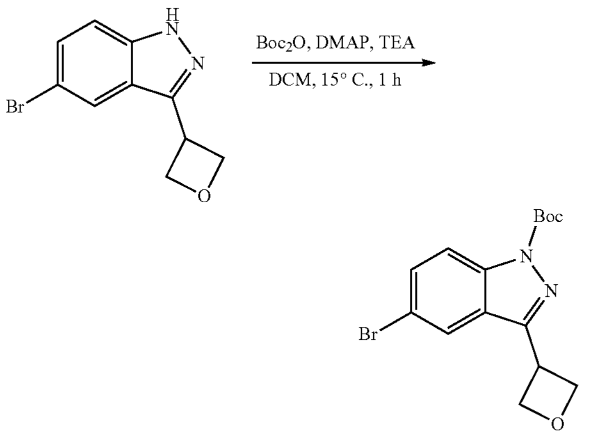

To a solution of 5-bromo-3-(oxetan-3-yl)-1H-indazole (0.1 g, 335.84 μmol, 1 eq.) and TEA (50.98 mg, 503.76 μmol, 1.5 eq.) in DCM (10 mL) was added DMAP (4.10 mg, 33.58 μmol, 0.1 eq.) and $Boc_2O$ (87.96 mg, 403.01 μmol, 1.2 eq.) at 15° C. under nitrogen. The reaction mixture was stirred at 15° C. for 1 h. TLC (PE:EtOAc=1:1) showed the starting material was consumed completely. The reaction was washed with brine (10 mL), dried over anhydrous sodium sulfate, filtered, and concentrated in vacuo. The residue was purified by prep-TLC (silica gel; PE:EtOAc=5:1) to afford the title compound (0.08 g, 203.84 μmol, 60.70% yield, 90% purity) as a yellow solid.

1.43 Scheme for preparation of 5-bromo-3-phenyl-1,2-benzoxazole

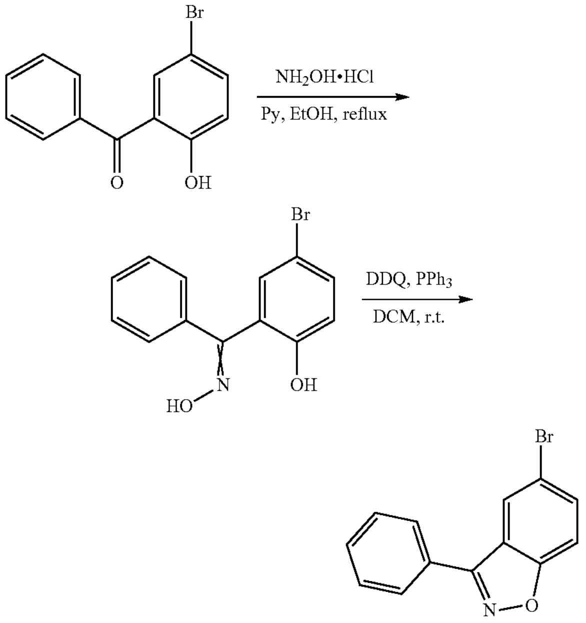

a. Preparation of (5-bromo-2-hydroxy-phenyl)-phenyl-methanone Oxime

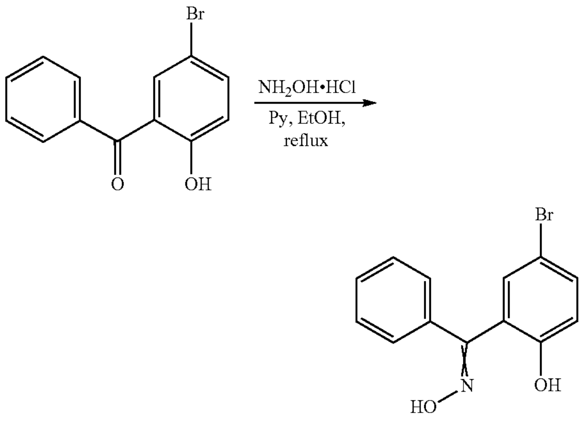

To a mixture of (5-bromo-2-hydroxy-phenyl)-phenyl-methanone (500 mg, 1.80 mmol, 1 eq.) in Py (5 mL), EtOH (30 mL) was added hydroxylamine·HCl (877.69 mg, 12.63 mmol, 7 eq.) in one portion at 90° C. under nitrogen. The mixture was stirred at 90° C. for 2 h. LCMS showed that the reaction was complete. The reaction was poured into 1 M HCl adjust to pH=6-7. The aqueous phase was extracted with EtOAc (3×50 mL). The combined organic phase was washed with brine (3×50 mL), dried over anhydrous sodium sulfate, filtered, and concentrated in vacuo to afford the title compound (500 mg, crude) as a white solid.

b. Preparation of 5-bromo-3-phenyl-1,2-benzoxazole

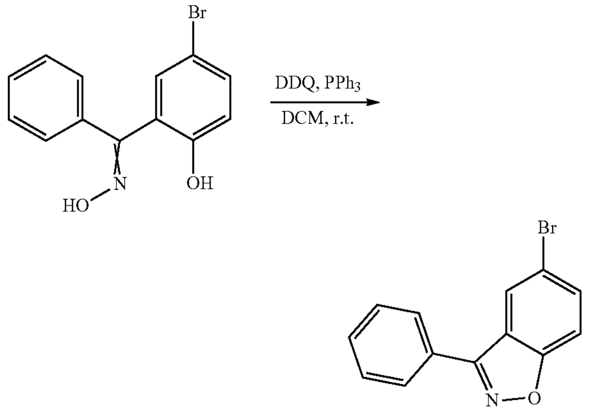

To a mixture of DDQ (233.12 mg, 1.03 mmol, 1.5 eq.), $PPh_3$ (269.35 mg, 1.03 mmol, 1.5 eq.) in DCM (10 mL) The mixture was stirred at 15° C. for 15 min, and added (5-bromo-2-hydroxy-phenyl)-phenyl-methanone oxime (200 mg, 684.63 μmol, 1 eq.), the mixture was stirred for 1 h. LCMS showed that the reaction was complete. The reaction was filtered, and concentrated in vacuo. The residue was purified by silica gel chromatography (column height: 250 mm, diameter: 100 mm, 100-200 mesh silica gel, PE:EtOAc=20/1, 1/1) to afford the title compound (70 mg, 255.37 μmol, 37.30% yield) as a white solid.

1.44 Preparation of 6-bromo-1-cyclopropyl-indazole

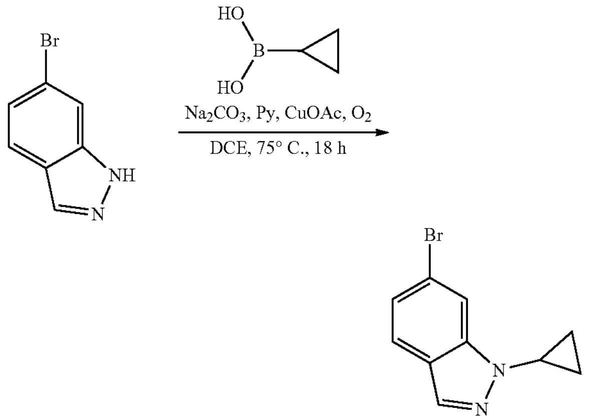

To a mixture of 6-bromo-1H-indazole (1 g, 5.08 mmol, 1 eq.) and cyclopropylboronic acid (523.15 mg, 6.09 mmol, 1.2 eq.) in 1,2-dichloroethane (10 mL) added $Na_2CO_3$ (1.08 g, 10.15 mmol, 2 eq.) in one portion under oxygen (162.40 mg, 5.08 mmol, 1 eq.) stirred for 10 min, followed by the addition of hot solution of diacetoxycopper (921.85 mg, 5.08 mmol, 1 eq.) and pyridine (401.46 mg, 5.08 mmol, 409.65 μL, 1 eq.) in 1,2-dichloroethane (10 mL). The reaction mixture was heated to 75° C. for 18 h. LCMS showed that the reaction was complete. The reaction mixture was quenched with saturated ammonium chloride solution, diluted with DCM (30 mL) and filtered through celite. The separated organic extracts were washed with brine (3×30 mL), dried over anhydrous sodium sulfate and evaporated in vacuo. The reaction was purified by prep-TLC ($SiO_2$; PE:EtOAc=5:1) (500 mg, 2.11 mmol, 41.55% yield) as a yellow oil.

1.45 Preparation of 1-cyclopropyl-6-(4,4,5,5-tetramethyl-1,3,2-dioxaborolan-2-yl)indazole

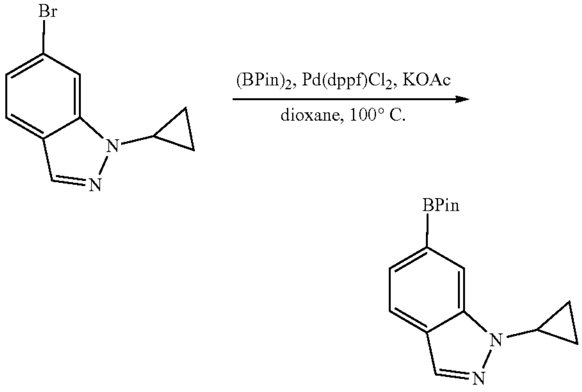

To a mixture of 6-bromo-1-cyclopropyl-indazole (300 mg, 1.27 mmol, 1 eq.) and $(BPin)_2$ (967.51 mg, 3.81 mmol, 3 eq.) in dioxane (4 mL) was added KOAc (373.91 mg, 3.81 mmol, 3 eq.), $Pd(dppf)Cl_2$ (92.93 mg, 127 μmol, 0.1 eq.) in one portion at 100° C. under nitrogen. The mixture was stirred at 100° C. for 1 h. LCMS showed that the reaction was complete. The reaction was poured water (25 mL). The aqueous phase was extracted with EtOAc (3×25 mL). The combined organic phase was washed with brine (2×10 mL), dried over anhydrous sodium sulfate, filtered, and concentrated in vacuo. The reaction was purified by prep-TLC (silica gel; PE:EtOAc=5:1) to afford the title compound (300 mg, 1.06 mmol, 83.13% yield) as a yellow oil.

1.46 Preparation of N-(2-methyl-3-(4,4,5,5-tetramethyl-1,3,2-dioxaborolan-2-yl)phenyl)acetamide

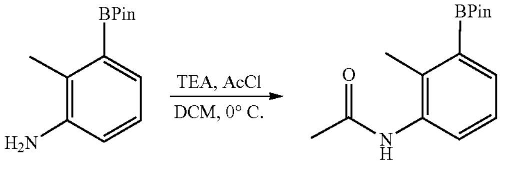

To a mixture of 2-methyl-3-(4,4,5,5-tetramethyl-1,3,2-dioxaborolan-2-yl)aniline (0.2 g, 857.95 μmol, 1 eq.) in DCM (4 mL), then added TEA (260.45 mg, 2.57 mmol, 358.25 μL, 3 eq.) and acetyl chloride (134.69 mg, 1.72 mmol, 122.45 μL, 2 eq.), the mixture was stirred at 0° C. for 1 h under nitrogen. TLC showed that the reaction was complete. The reaction mixture was diluted with water 50 mL and extracted with EtOAc (2×25 mL), the combined organic layers were washed with water (2×50 mL) and brine (2×50 mL) in turn. Then dried over anhydrous sodium sulfate, filtered, and concentrated in vacuo to give a residue. The residue was purified by prep-TLC (silica gel; PE:E- tOAc=1:1) to afford the title compound (0.2 g, 726.88 μmol, 84.72% yield) as a yellow oil.

1.47 Preparation of 6-bromo-1-methyl-N-phenyl-1H-indazole-4-carboxamide

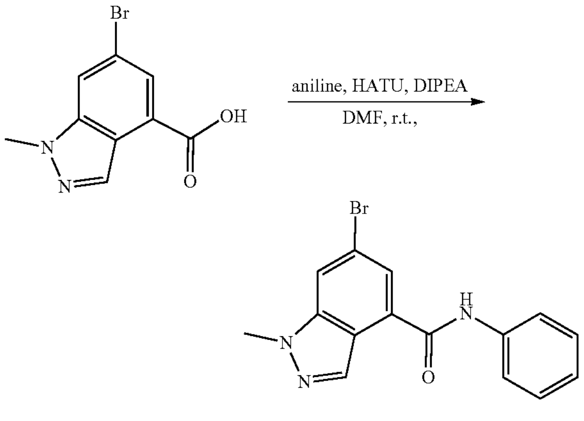

To a solution of 6-bromo-1-methyl-1H-indazole-4-carboxylic acid (0.42 g, 1.65 mmol, 1 eq.) in DMF (10 mL) was added DIPEA (1.06 g, 8.23 mmol, 1.43 mL, 5 eq.) and HATU (939.14 mg, 2.47 mmol, 1.5 eq.), the mixture was stirred at 20° C. for 15 minutes under nitrogen. Then aniline (460.03 mg, 4.94 mmol, 451.01 μL, 3 eq.) was and the reaction stirred for 1 h and 45 minutes. TLC showed that the reaction was complete. The reaction mixture was diluted with water 50 mL and extracted with EtOAc (2×25 mL), the combined organic layers were washed with water (2×50 mL) and brine (2×50 mL) in turn. Then dried over anhydrous sodium sulfate, filtered, and concentrated in vacuo to give a residue. The residue was purified by prep-TLC (silica gel; PE:EtOAc=1:1) to afford the title compound (0.5 g, 1.51 mmol, 91.97% yield) as a yellow solid.

1.48 Preparation of tert-butyl 5-bromo-3-methoxy-1H-indazole-1-carboxylate and tert-butyl 5-bromo-2-methyl-3-oxo-2,3-dihydro-1H-indazole-1-carboxylate

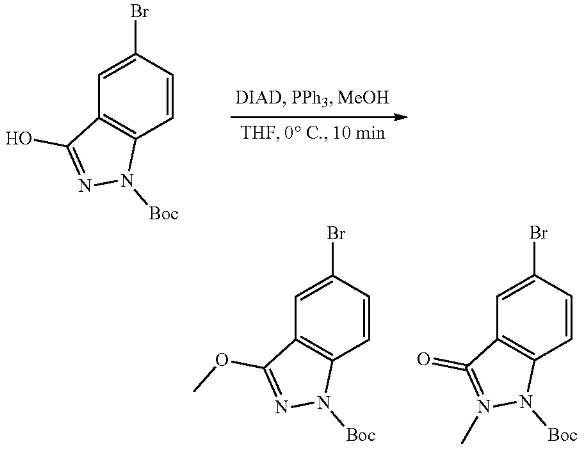

A B

To a solution of tert-butyl 5-bromo-3-hydroxy-1H-indazole-1-carboxylate (0.23 g, 697.76 μmol, 1 eq.), methanol (67.07 mg, 2.09 mmol, 84.71 μL, 3 eq.) and $PPh_3$ (237.92 mg, 907.08 μmol, 1.3 eq.) in THF (2 mL) was added DIAD (211.64 mg, 1.05 mmol, 203.50 μL, 1.5 eq.) at 0° C. for 10 min under nitrogen. TLC indicated was consumed completely. The reaction mixture was concentrated in vacuo to give a residue which was purified by prep-TLC (PE:EtOAc=3:1, $R_f$=0.4) to afford the title compound A (0.06 g, 165.05 μmol, 23.65% yield, 90% purity) and byproduct B (0.15 g, 412.63 μmol, 59.14% yield, 90% purity) as a yellow solid.

1.49 Preparation of 5-bromo-3-iodo-pyrazolo[1,5-a]pyridine

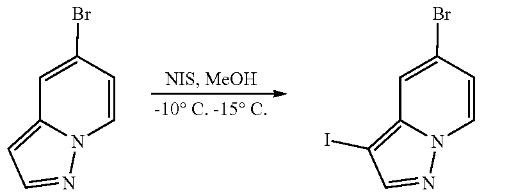 [SMILES: Brc1ccn2nccc2c1 ; Brc1ccn2ncc(I)c2c1]

To a mixture of 5-bromopyrazolo[1,5-a]pyridine (0.5 g, 2.54 mmol, 1 eq.) in MeOH (10 mL) was added NIS (570.93 mg, 2.54 mmol, 1 eq.) slowly in one portion at −10° C. under nitrogen. The mixture was stirred 0.5 h. The mixture was stirred at 15° C. for 17.5 h. LCMS showed that the reaction was complete. The reaction was poured into sat. $Na_2SO_3$ aqueous solution (10 mL). The aqueous phase was extracted with DCM (3×30 mL). The combined organic phase was washed with brine (3×30 mL), dried over anhydrous sodium sulfate, filtered, and concentrated in vacuo. The residue was washed with $CH_2Cl_2$ (15 mL) to afford the title compound (0.4 g, 1.24 mmol, 48.81% yield) as a light yellow solid.

1.50 Preparation of 5-bromo-3-(2-thienyl)pyrazolo[1,5-a]pyridine

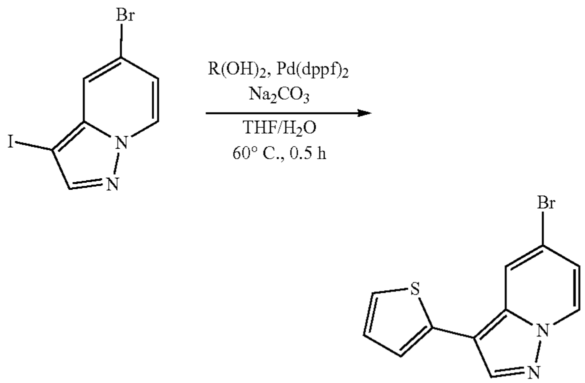

To a mixture of 5-bromo-3-iodo-pyrazolo[1,5-a]pyridine (0.4 g, 1.24 mmol, 1 eq.), 2-thienylboronic acid (237.74 mg, 1.86 mmol, 1.5 eq.) in THF (5 mL), water (1 mL) was added $Na_2CO_3$ (393.86 mg, 3.72 mmol, 3 eq.), $Pd(dppf)Cl_2$ (453.17 mg, 619.33 μmol, 0.5 eq.) one portion at 60° C. under nitrogen. The mixture was stirred at 60° C. for 30 min. LCMS showed that the reaction was complete. The reaction was poured into water (10 mL). The aqueous phase was extracted with EtOAc (3x25 mL). The combined organic phase was washed with brine (2x20 mL), dried over anhydrous sodium sulfate, filtered, and concentrated in vacuo. The residue was purified by prep-TLC (PE:EtOAc=5:1) to afford the title compound (120 mg, 429.87 μmol, 34.70% yield) as a white solid.

1.51 Preparation of 5-(4,4,5,5-tetramethyl-1,3,2-dioxaborolan-2-yl)-3-(2-thienyl)pyrazolo[1,5-a]pyridine

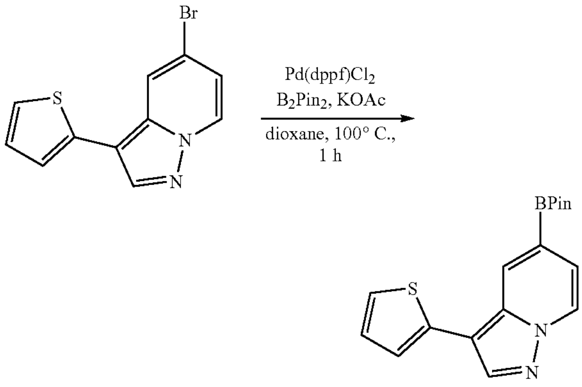

To a mixture of 5-bromo-3-(2-thienyl)pyrazolo[1,5-a]pyridine (120 mg, 429.87 μmol, 1 eq.), $(BPin)_2$ (330.33 mg, 1.29 mmol, 3 eq.) in dioxane (2 mL) was added KOAc (126.56 mg, 1.29 mmol, 3 eq.), $Pd(dppf)Cl_2$ (157.27 mg, 214.93 μmol, 0.5 eq.) in one portion at 100° C. under nitrogen. The mixture was stirred at 100° C. for 60 min. LCMS showed that the reaction was complete. The reaction was filtered, and concentrated in vacuo. The residue was purified by prep-TLC (PE:EtOAc=5:1) to afford the title compound (120 mg, 367.85 μmol, 85.57% yield) as a green oil.

1.52 Preparation of (5-bromo-2-hydroxy-phenyl)-(4-methoxyphenyl)methanone

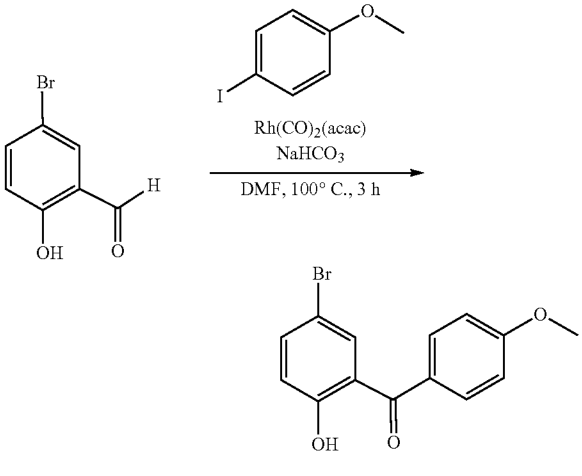

A mixture of 5-bromo-2-hydroxy-benzaldehyde (0.5 g, 2.49 mmol, 1 eq.), 1-iodo-4-methoxy-benzene (640.34 mg, 2.74 mmol, 68.69 μL, 1.1 eq.), carbon monoxide; [(Z)-1-methyl-3-oxo-but-1-enoxy]rhodium (64.18 mg, 248.73 μmol, 0.1 eq.), $NaHCO_3$ (229.86 mg, 2.74 mmol, 106.42 μL, 1.1 eq.) in DMF (3 mL) was degassed and purged with nitrogen 3 times, and the mixture was stirred at 100° C. for 1 h under nitrogen atmosphere. LCMS showed that the reaction was complete. The reaction mixture was added 30 mL saturated aq. EDTA and stirred for 1 h, extracted with EtOAc (3x20 mL). The combined organic layers were washed with brine (3x20 mL), dried over anhydrous sodium sulfate, filtered, and concentrated in vacuo to give a residue. The residue was purified by prep-TLC (silica gel; PE:EtOAc=4:1) to afford the title compound (300 mg, 898.62 μmol, 36.13% yield, 92% purity) as a light yellow solid.

1.53 Preparation of 4-(5-bromo-2-hydroxy-benzoyl)benzonitrile

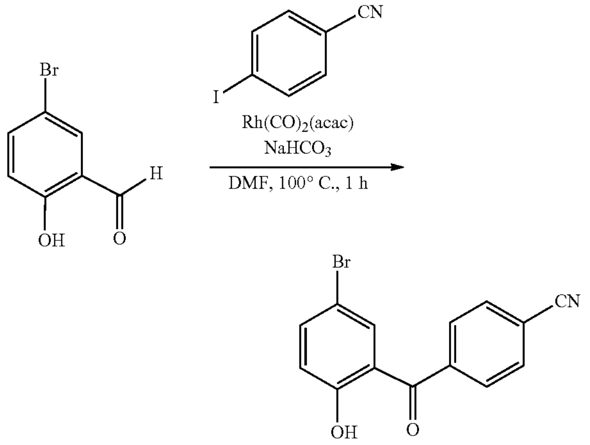

A mixture of 5-bromo-2-hydroxy-benzaldehyde (0.5 g, 2.49 mmol, 1 eq.), 4-iodobenzonitrile (626.61 mg, 2.74 mmol, 1.1 eq.), carbon monoxide; [(Z)-1-methyl-3-oxo-but-1-enoxy]rhodium (64.18 mg, 248.74 μmol, 0.1 eq.), $NaHCO_3$ (229.85 mg, 2.74 mmol, 106.41 μL, 1.1 eq.) in DMF (10 mL) was degassed and purged with nitrogen 3 times, and the mixture was stirred at 100° C. for 1 h under nitrogen atmosphere. TLC showed that the reaction was complete. The reaction mixture was added 30 mL saturated aq. EDTA and stirred for 1 h, extracted with EtOAc (3x20 mL). The combined organic layers were washed with brine (3x20 mL), dried over anhydrous sodium sulfate, filtered, and concentrated in vacuo to give a residue. The residue was purified by prep-TLC (silica gel; PE:EtOAc=10:1) to afford the title compound (150 mg, 446.84 μmol, 17.96% yield, 90% purity) as a light yellow solid.

1.54 Procedure for Preparation of 4-[2-hydroxy-5-(4,4,5,5-tetramethyl-1,3,2-dioxaborolan-2-yl)benzoyl]benzonitrile

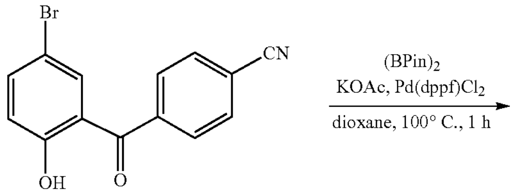

-continued

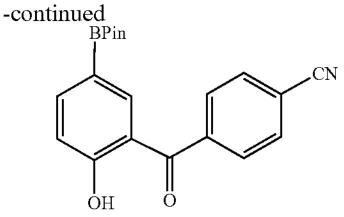

To a mixture of 4-(5-bromo-2-hydroxy-benzoyl)benzonitrile (130 mg, 430.29 μmol, 1 eq.), 4,4,5,5-tetramethyl-2-(4,4,5,5-tetramethyl-1,3,2-dioxaborolan-2-yl)-1,3,2-dioxaborolane (327.80 mg, 1.29 mmol, 3 eq.), KOAc (126.69 mg, 1.29 mmol, 3 eq.), Pd(dppf)$Cl_2$ (62.97 mg, 86.06 μmol, 0.2 eq.) in dioxane (10 mL) was degassed and purged with nitrogen 3 times, and the mixture was stirred at 100° C. for 1 h under nitrogen atmosphere. LCMS showed that the reaction was complete. The reaction mixture was filtered, and concentrated in vacuo to give a residue. The residue was purified by prep-TLC (silica gel; PE:EtOAc=4:1) to afford the title compound (100 mg, 286.38 μmol, 66.56% yield) as a light yellow solid.

1.55 Preparation of 1-(5-bromo-2-fluoro-phenyl)propan-1-one

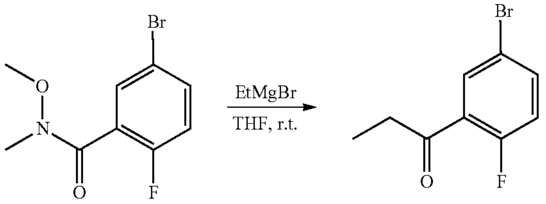

To a mixture of 5-bromo-2-fluoro-N-methoxy-N-methylbenzamide (1 g, 3.82 mmol) in THF (20 mL) was added EtMgBr (3 M, 1.91 mL, 1.5 eq.) in one portion at 25° C. under nitrogen. The mixture was stirred at 25° C. for 2 h. The reaction mixture was poured into sat·aq. $NH_4Cl$ (30 mL), then extracted with EtOAc (3×20 mL) and the combined organic layer was concentrated in vacuo. The residue was purified by column chromatography (silica gel; PE:EtOAc=10:1 to 8:1) to afford the title compound (0.58 g, 2.26 mmol, 59.21% yield, 90% purity) as a yellow oil.

1.56 Preparation of 5-bromo-3-ethyl-1H-indazole

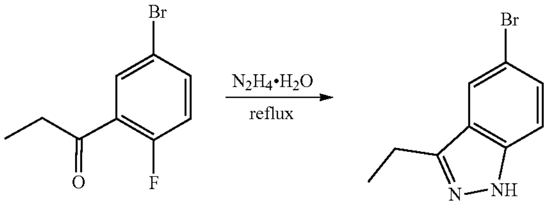

A mixture of 1-(5-bromo-2-fluoro-phenyl)propan-1-one (500 mg, 2.16 mmol) in $N_2H_4$·$H_2O$ (25 mL) was degassed and purged with nitrogen 3 times, then stirred at 120° C. for 1 h under nitrogen. The reaction mixture was quenched with water (30 mL), diluted with EtOAc (20 mL), and extracted with EtOAc (3×50 mL). The combined organic layers were washed with water (3×30 mL) and brine (3×30 mL), dried over anhydrous sodium sulfate, filtered, and concentrated in vacuo. The residue was purified by prep-TLC (silica gel; PE:EtOAc=10:1) to afford the title compound (200 mg, 888.55 μmol, 41.06% yield) as a light yellow solid.

1.57 Preparation of tert-butyl 5-bromo-3-ethyl-indazole-1-carboxylate

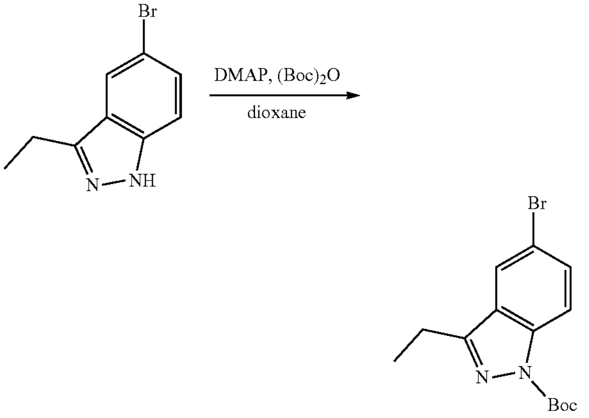

To a solution of 5-bromo-3-ethyl-2H-indazole (100 mg, 444.28 μmol) in dioxane (6 mL) was added DMAP (5.43 mg, 44.43 μmol) and $(Boc)_2O$ (145.44 mg, 666.42 μmol). The mixture was stirred at 90° C. for 1 h. The reaction mixture was quenched with water (20 mL) and extracted with EtOAc (2×20 mL). The combined organic layers were washed with brine (2×20 mL), dried over anhydrous sodium sulfate, filtered, and concentrated in vacuo. The residue was purified by prep-TLC (silica gel; PE:EtOAc=5:1) to afford the title compound (100 mg, 307.50 μmol, 69.21% yield) as a white solid.

1.58 Preparation of tert-butyl 3-ethyl-5-(4,4,5,5-tetramethyl-1,3,2-dioxaborolan-2-yl)indazole-1-carboxylate

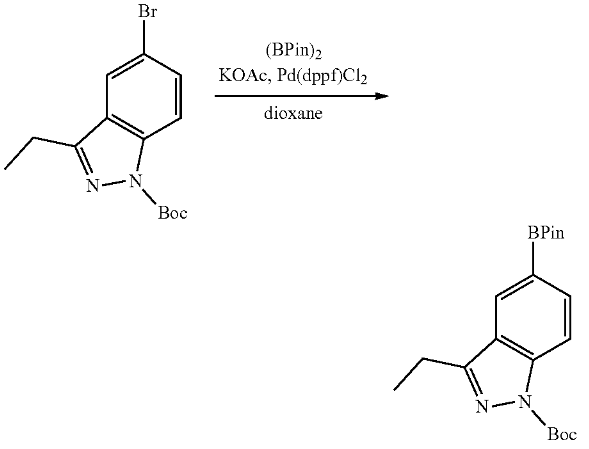

A mixture of tert-butyl 5-bromo-3-ethyl-indazole-1-carboxylate (90 mg, 276.75 μmol), 4,4,5,5-tetramethyl-2-(4,4, 5,5-tetramethyl-1,3,2-dioxaborolan-2-yl)-1,3,2-dioxaborolane (210.83 mg, 830.26 μmol), KOAc (81.48 mg, 830.26 μmol) and Pd(dppf)$Cl_2$ (40.50 mg, 55.35 μmol) in dioxane (6 mL) was degassed and purged with nitrogen 3 times. The mixture was stirred at 90° C. for 1 h under nitrogen. The reaction mixture was concentrated in vacuo. The residue was purified by prep-TLC (silica gel; PE:EtOAc=5:1) to afford the title compound (80 mg, 214.90 μmol, 77.65% yield) as a white solid.

1.59 General Procedure for Preparation of 5-bromo-2-hydroxy-N-methyl-benzamide

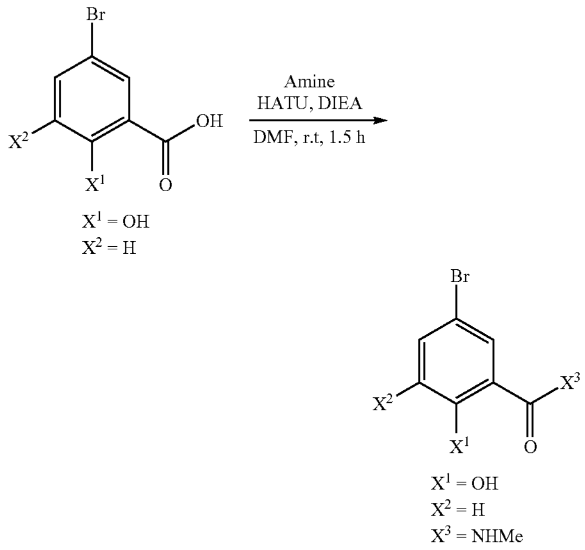

To a mixture of 5-bromo-2-hydroxy-benzoic acid (2 g, 9.22 mmol, 1 eq.) in DMF (20 mL) was added HATU (5.26 g, 13.82 mmol, 1.5 eq.) and DIPEA (3.57 g, 27.65 mmol, 4.82 mL, 3 eq.) in one portion at 25° C. under nitrogen. The mixture was stirred for 30 min, and the amine (27.65 mmol, 3 eq.) was added. The mixture was stirred further at 25° C. for another 1.5 h. TLC and showed that the reaction was complete. The reaction was diluted with 50 mL water, extracted with EtOAc (3×50 mL), washed with brine (3×50 mL), dried over anhydrous sodium sulfate, filtered, and concentrated to give a residue. The residue was purified by column chromatography (silica gel; PE:EtOAc=10:1 to 1:1) to afford the title the desired product.

1.60 Preparation of 2-hydroxy-N-methyl-5-(4,4,5,5-tetramethyl-1,3,2-dioxaborolan-2-yl)benzamide

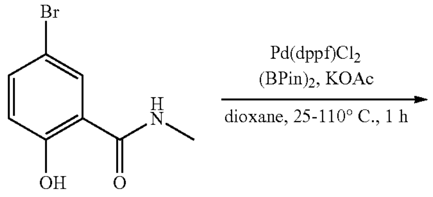

-continued

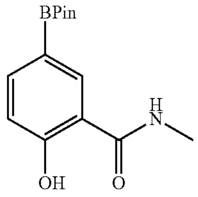

To a mixture of 5-bromo-2-hydroxy-N-methyl-benzamide (500 mg, 2.17 mmol, 1 eq.) and 4,4,5,5-tetramethyl-2-(4,4,5,5-tetramethyl-1,3,2-dioxaborolan-2-yl)-1,3,2-dioxaborolane (883.04 mg, 3.48 mmol, 1.6 eq.) in dioxane (2 mL) was added KOAc (1.07 g, 10.87 mmol, 5 eq.), followed added Pd(dppf)$Cl_2$ (159.03 mg, 217.34 μmol, 0.1 eq.) at 25° C. The mixture was stirred at 110° C. for 1 h. TLC showed that the reaction was complete. DCM (3×30 mL) was added, and the mixture was filtered. The residue was purified by column chromatography (silica gel; PE:EtOAc=10:1 to 1:1) to afford the title compound (300 mg, 1.08 mmol, 49% yield).

1.61 Preparation of 2-amino-5-bromo-N,N-dimethyl-benzamide

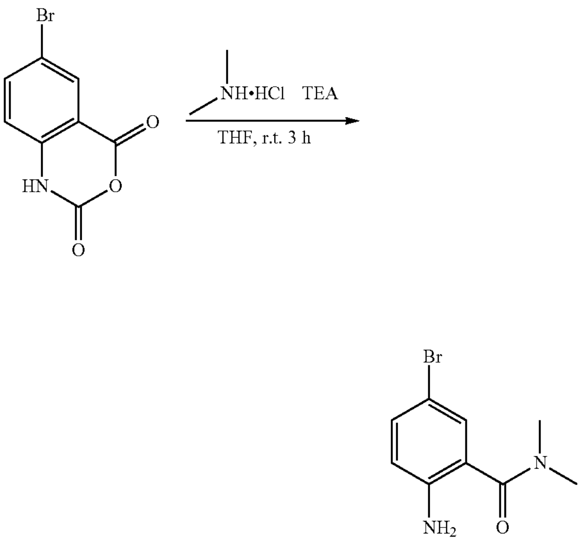

To a mixture of 6-bromo-1H-3,1-benzoxazine-2,4-dione (400 mg, 1.65 mmol, 1 eq.) and N-methylmethanamine; hydrochloride (202.15 mg, 2.48 mmol, 1.5 eq.) in THF (6 mL) was added TEA (1 g, 9.92 mmol, 1.38 mL, 6 eq.) in one portion at 25° C. under nitrogen. The mixture was stirred at 25° C. for 3 h. TLC showed that the reaction was complete. The reaction was diluted with 50 mL water, extracted with EtOAc (3×50 mL), washed with brine (3×50 mL), dried over anhydrous sodium sulfate, filtered, and concentrated to give a residue. The residue was purified by column chromatography (silica gel; PE:EtOAc=10:1 to 1:1) to afford the title compound (390 mg, 1.60 mmol, 97.07% yield) as a white solid.

1.62 Preparation of 2-amino-N,N-dimethyl-5-(4,4,5,5-tetramethyl-1,3,2-dioxaborolan-2-yl)benzamide

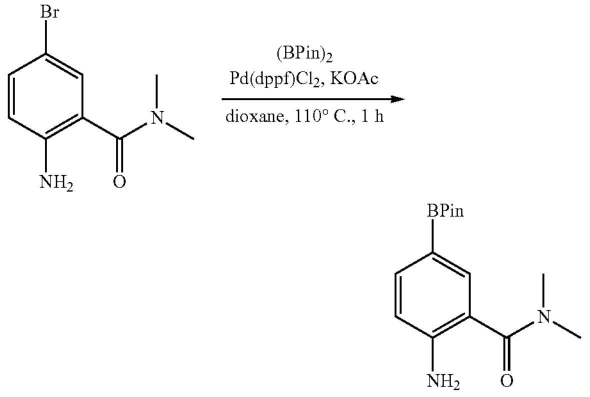

To a mixture of 2-amino-5-bromo-N,N-dimethyl-benzamide (250 mg, 1.03 mmol, 1 eq.) and 4,4,5,5-tetramethyl-2-(4,4,5,5-tetramethyl-1,3,2-dioxaborolan-2-yl)-1,3,2-dioxaborolane (443.95 mg, 1.75 mmol, 1.7 eq.) in dioxane (6 mL) was added KOAc (504.63 mg, 5.14 mmol, 5 eq.) followed by $Pd(dppf)Cl_2$ (150.50 mg, 205.68 μmol, 0.2 eq.) at 25° C. The mixture was stirred at 110° C. for 1 h. TLC showed that the reaction was complete. DCM (3×30 mL) was added, and the resulting mixture was filtered. The residue was purified by column chromatography (silica gel; PE:EtOAc=10:1 to 1:1) to afford the title compound (250 mg, 861.58 μmol, 83.78% yield) as a white solid.

1.63 Preparation of 4-bromo-2-chloro-6-fluoro-aniline

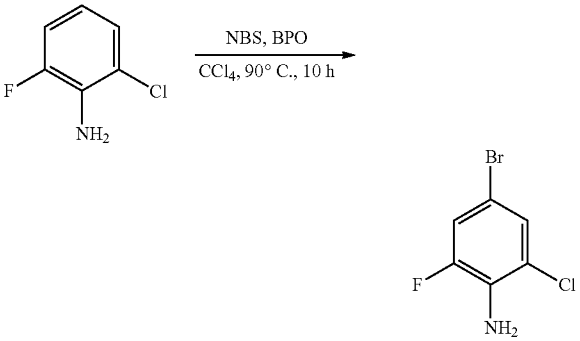

To a mixture of 2-chloro-6-fluoro-aniline (2 g, 13.74 mmol, 1 eq.) and NBS (2.69 g, 15.11 mmol, 1.1 eq.) in $CCl_4$ (20 mL) was added BPO (332.82 mg, 1.37 mmol, 0.1 eq.) at 90° C. The reaction mixture was stirred for 10 h. TLC showed that the reaction was complete. The reaction was diluted with 50 mL water, extracted with EtOAc (3×50 mL), washed with brine (3×30 mL), dried over anhydrous sodium sulfate, filtered, and concentrated to give a residue. The residue was purified by column chromatography (silica gel; PE:EtOAc=0:1) to afford the title compound (2.2 g, 9.80 mmol, 71.34% yield) as a red solid.

1.64 Preparation of 2-chloro-6-fluoro-4-(4,4,5,5-tetramethyl-1,3,2-dioxaborolan-2-yl)aniline

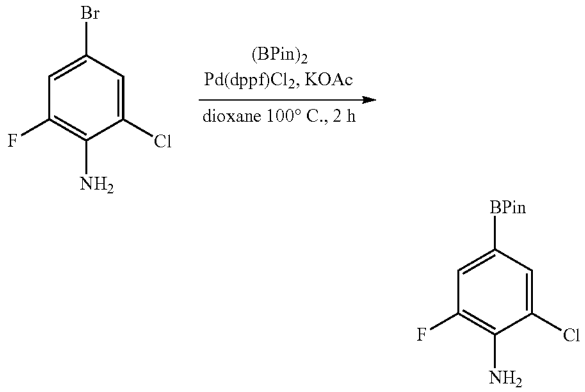

To a mixture of 4-bromo-2-chloro-6-fluoro-aniline (1 g, 4.46 mmol, 1 eq.) and $(BPin)_2$ (1.24 g, 4.90 mmol, 1.1 eq.) in dioxane (10 mL) was added KOAc (2.19 g, 22.28 mmol, 5 eq.), followed $Pd(dppf)Cl_2$ (325.99 mg, 445.52 μmol, 0.1 eq.) at 25° C. The mixture was stirred at 100° C. for 2 h. LCMS showed that the reaction was complete. DCM (3×50 mL) was added, and the resulting mixture was filtered. The residue was purified by column chromatography (silica gel; PE:EtOAc=10:1 to 1:1) to afford the title compound (840 mg, 3.09 mmol, 69.44% yield) as a red solid.

1.65 Preparation of N-[2-chloro-4-(4,4,5,5-tetramethyl-1,3,2-dioxaborolan-2-yl)phenyl]acetamide

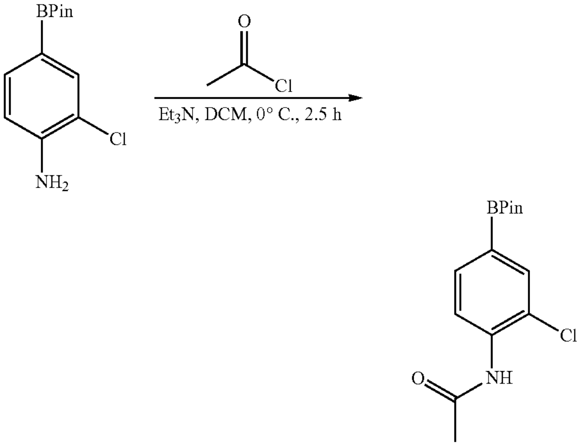

To a mixture 2-chloro-4-(4,4,5,5-tetramethyl-1,3,2-dioxaborolan-2-yl)aniline (150 mg, 591.64 μmol, 1 eq.) in DCM (2 mL) was added TEA (179.60 mg, 1.77 mmol, 247.05 μL, 3 eq.), followed by acetyl chloride (232.21 mg, 2.96 mmol, 211.10 μL, 5 eq.) at 0° C. The mixture was stirred for 2.5 h. TLC and LCMS showed that the reaction was complete. The reaction was diluted with 20 mL water, extracted with DCM (3×20 mL), washed with brine (3×10 mL), dried over anhydrous sodium sulfate, filtered, and concentrated to afford the title compound (260 mg, crude) as a light yellow solid.

1.66 Preparation of N-(3-methoxy-5-(4,4,5,5-tetramethyl-1,3,2-dioxaborolan-2-yl)phenyl)acetamide

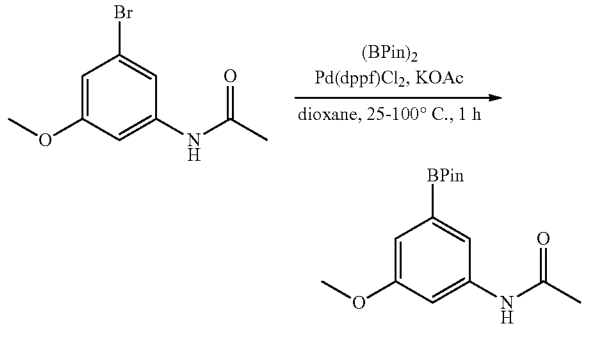

To a mixture of N-(3-bromo-5-methoxyphenyl)acetamide (0.5 g, 2.05 mmol, 1 eq.) and $(BPin)_2$ (1.04 g, 4.10 mmol, 2 eq.) in dioxane (8 mL) was added KOAc (1.01 g, 10.24 mmol, 5 eq.), followed by $Pd(dppf)Cl_2$ (149.89 mg, 204.85 µmol, 0.1 eq.) at 25° C. The mixture was stirred at 100° C. for 1 h. TLC showed that the reaction was complete. DCM (30 mL×3) was added, and the resulting mixture was filtered. The residue was purified by column chromatography (silica gel; PE:EtOAc=10:1 to 1:1) to afford the title compound (530 mg, 1.82 mmol, 88.86% yield) as a yellow solid.

1.67 Scheme for the Preparation of 2-(anilinomethyl)-4-(4,4,5,5-tetramethyl-1,3,2-dioxaborolan-2-yl)aniline

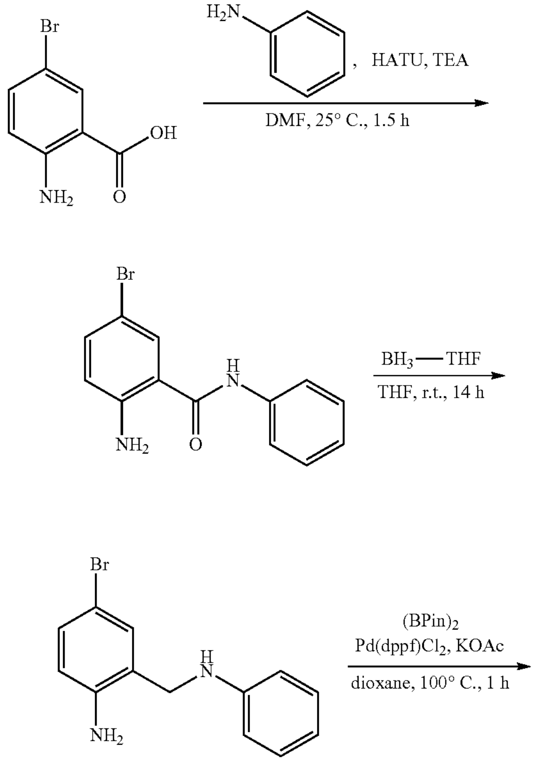

-continued

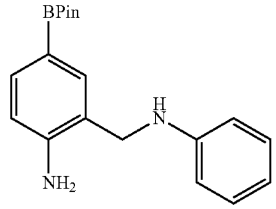

a. Preparation of 2-amino-5-bromo-N-phenyl-benzamide

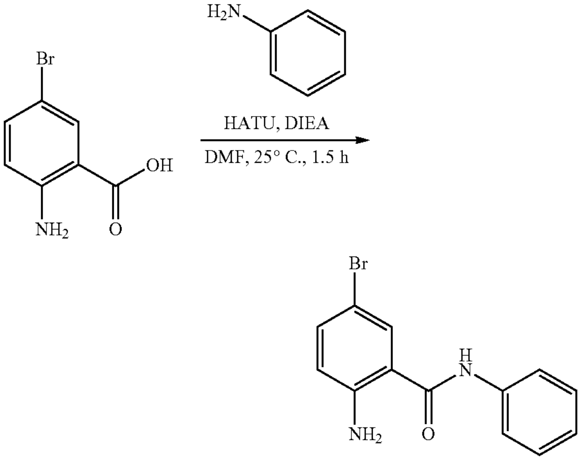

To a mixture of 2-amino-5-bromo-benzoic acid (3 g, 13.89 mmol, 1 eq.) in DMF (30 mL) were added HATU (7.92 g, 20.83 mmol, 1.5 eq.) and DIEA (17.95 g, 138.87 mmol, 24.19 mL, 10 eq.) at 25° C. The mixture was stirred at 25° C. for 0.5 h, then aniline (3.88 g, 41.66 mmol, 3.80 mL, 3 eq.) was added, and the mixture was stirred at 25° C. for 1 h. TLC (EtOAc, $R_f$=0.8) showed that the reaction was complete. The residue was poured into water (50 mL), and the aqueous phase was extracted with EtOAc (3×50 mL). The combined organic phase was washed with brine (3×50 mL), dried over anhydrous sodium sulfate, filtered, and concentrated in vacuo. The residue was purified by silica gel chromatography (PE:EtOAc=1:0 to 5:1) to afford the title compound (2.5 g, 8.59 mmol, 61.83% yield) as a brown solid.

b. Preparation of 2-(anilinomethyl)-4-bromo-aniline

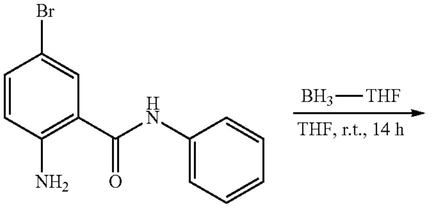

-continued

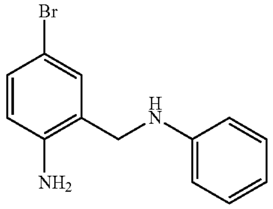

To a solution of 2-amino-5-bromo-N-phenyl-benzamide (1 g, 3.43 mmol, 1 eq.) in THF (10 mL) was added $BH_3$·THF (1 M, 20.61 mL, 6 eq.) at 25° C. The mixture was stirred at 25° C. for 2 h. LCMS showed 60% of the starting material remained. Then, $BH_3$·THF (1 M, 17.17 mL, 5 eq.) was added, and the resulting mixture was stirred at 25° C. for 12 h. The residue was poured into sat. $Na_2CO_3$ (20 mL), and the aqueous phase was extracted with EtOAc (3×20 mL). The combined organic phase was washed with brine (3×30 mL), dried over anhydrous sodium sulfate, filtered, and concentrated in vacuo. The residue was purified by silica gel chromatography (silica gel, PE:EtOAc=10:1, 8/1) to afford the title compound (0.7 g, 2.27 mmol, 66.18% yield, 90% purity) as a white solid.

c. Preparation of 2-(anilinomethyl)-4-(4,4,5,5-tetramethyl-1,3,2-dioxaborolan-2-yl)aniline

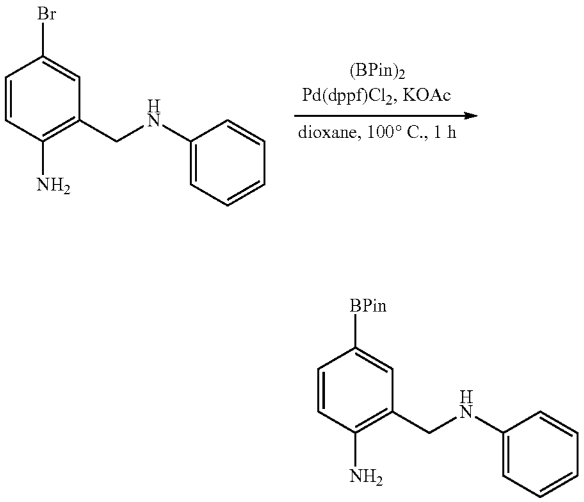

To a solution of 2-(anilinomethyl)-4-bromo-aniline (250 mg, 902.01 μmol, 48.65 μL, 1 eq.) in dioxane (10 mL) were added $Pin_2B_2$ (458.11 mg, 1.80 mmol, 2 eq.), KOAc (442.62 mg, 4.51 mmol, 5 eq.), Pd(dppf)$Cl_2$ (66 mg, 90.20 μmol, 0.1 eq.) under nitrogen. The mixture was stirred at 100° C. for 1 h. LCMS showed that the reaction was complete. The residue was poured into water (20 mL) and the aqueous phase was extracted with EtOAc (3×3×15 mL). The combined organic phase was washed with brine (3×3×15 mL), dried over anhydrous sodium sulfate, filtered, and concentrated in vacuo. The residue was purified by prep-TLC (PE:EtOAc=4:1) to afford the title compound (200 mg, 431.80 μmol, 47.87% yield, 70% purity) as a yellow oil.

1.68 Preparation of 3-bromo-5-methoxy-N-methyl-benzamide

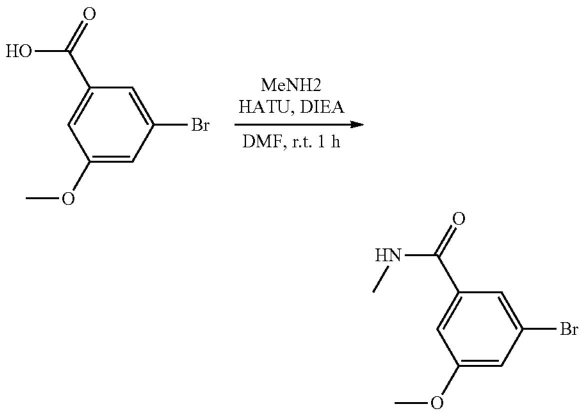

To a mixture of 3-bromo-5-methoxy-benzoic acid (3 g, 12.98 mmol, 1 eq.) and $MeNH_2$ (4.38 g, 64.92 mmol, 5 eq., HCl) in DMF (100 mL), were added DIEA (8.39 g, 64.92 mmol, 11.31 mL, 5 eq.) and HATU (6.42 g, 16.88 mmol, 1.3 eq.). The reaction mixture was degassed and purged with nitrogen 3 times, and the mixture was stirred at 25° C. for 1 h under nitrogen atmosphere. TLC showed that the reaction was complete. To the reaction mixture was added 30 mL of a saturated EDTA solution, and the mixture was stirred for 1 h. The mixture was extracted with EtOAc (3×30 mL), and the organic phase was washed with water (2×30 mL) and brine (2×30 mL), dried over anhydrous sodium sulfate, filtered, and concentrated in vacuo to give a residue. The residue was purified by column chromatography (silica gel; PE:EtOAc=3:1 to 1:1) to afford the title compound (2.1 g, 7.74 mmol, 59.63% yield, 90% purity) as a light yellow solid.

1.69 Preparation of 6-trimethylstannylpyridin-3-amine

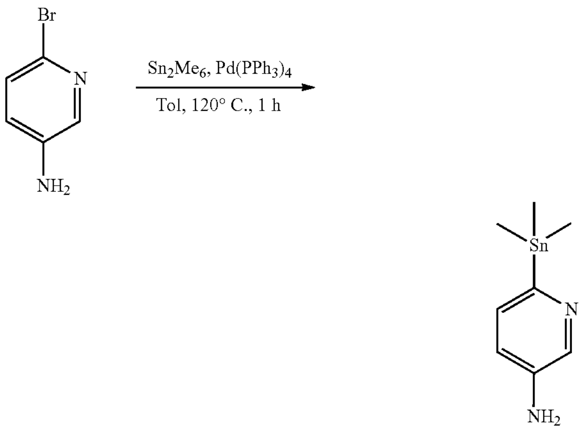

A mixture of 6-bromopyridin-3-amine (0.5 g, 2.89 mmol, 1 eq.), trimethyl(trimethylstannyl) stannane (1.14 g, 3.47 mmol, 719.12 μL, 1.2 eq.), and Pd($PPh_3$)$_4$ (667.91 mg, 578 μmol, 0.2 eq.) in toluene (15 mL) was degassed and purged with nitrogen 3 times. The mixture was stirred at 120° C. for 1 h under nitrogen atmosphere. TLC showed that the reaction was complete, and a new spot was detected with lower polarity. The reaction mixture was filtered and concentrated in vacuo to afford the title compound (0.8 g, crude) as a black brown gum.

Example 2: Synthesis of Compounds of the Disclosure: Method A

2A. General Scheme for Method A: Route 1

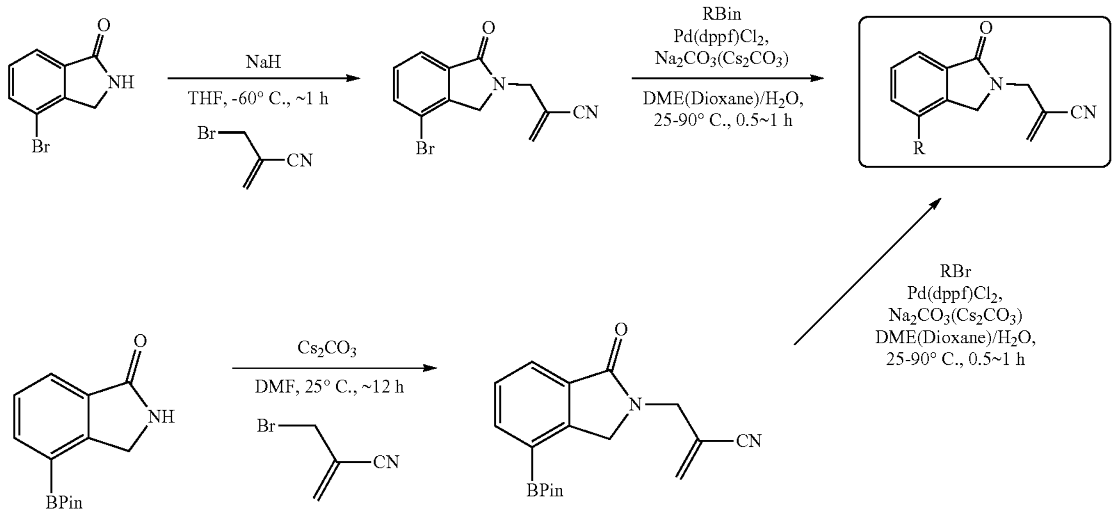

2.A.1. Preparation of 2-[[4-(3,3-dimethyl-2-oxo-indolin-6-yl)-1-oxo-isoindolin-2-yl]methyl]prop-2-enenitrile (Compound 55)

a. Preparation of 2-[(4-bromo-1-oxo-isoindolin-2-yl)methyl]prop-2-enenitrile

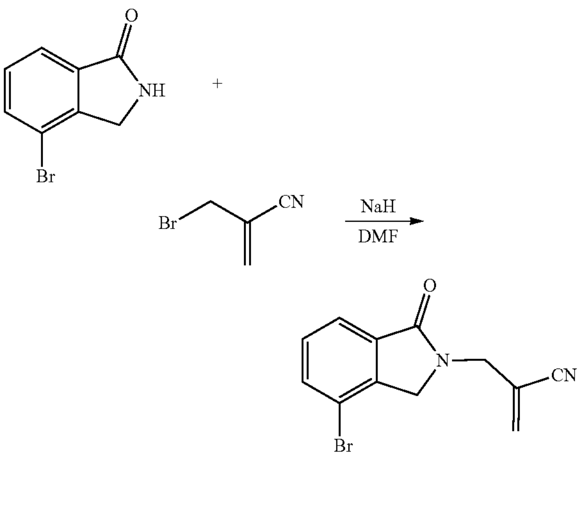

To a solution of 4-bromoisoindolin-1-one (1 g, 4.72 mmol) in DMF (10 mL) at 0° C. was added NaH (0.28 g, 60% purity, 7.07 mmol). The mixture was stirred at r.t. for 10 min. The mixture was cooled to −60° C., and 2-(bromomethyl) prop-2-enenitrile (1.03 g, 7.07 mmol) in DMF (0.5 mL) was added dropwise. The resulting mixture was stirred at −60° C. for 1 h. 8 mL of THF was added, and the mixture was stirred at −65° C. for another 3 h then partitioned between EtOAc and water. The aqueous phase was extracted with EtOAc. The combined organic phase was washed with water and brine, dried over $MgSO_4$, filtered, and concentrated in vacuo. The residue was purified by chromatography on silica gel eluting with 10-70% EtOAc/hexane to afford the title compound (1.31 g, Yield 100%).

b. Preparation of 2-{[1-oxo-4-(4,4,5,5-tetramethyl-1,3,2-dioxaborolan-2-yl)-2,3-dihydro-1H-isoindol-2-yl]methyl}prop-2-enenitrile

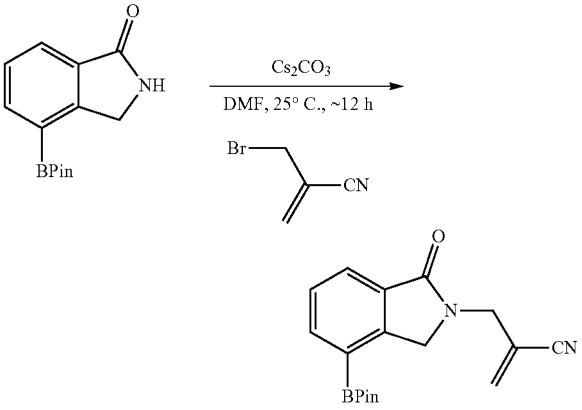

To a solution of 4-(4,4,5,5-tetramethyl-1,3,2-dioxaborolan-2-yl)-2,3-dihydro-1H-isoindol-1-one (0.2 g, 771.88 μmol, 1 eq.) in DMF (10 mL) was added $Cs_2CO_3$ (754.48 mg, 2.32 mmol, 3 eq.) in one portion at 25° C. under nitrogen. Then 2-(bromomethyl)acrylonitrile (169.02 mg, 1.16 mmol, 1.5 eq.) was added to the mixture. The mixture was stirred at 25° C. for 12 h. LCMS showed that the reaction was complete. The reaction mixture was diluted with sat. $NH_4Cl$ (30 mL) and extracted with DCM (3×20 mL). The combined organic layer was washed with brine (3×10 mL), dried with sodium sulfate, filtered, and concentrated in vacuo to afford the title compound (0.12 g, crude) as a white solid, which was used in following steps without purification.

c. Preparation of 2-[[1-oxo-4-(4,4,5,5-tetramethyl-1,3,2-dioxaborolan-2-yl) isoindolin-2-yl]methyl]prop-2-enenitrile

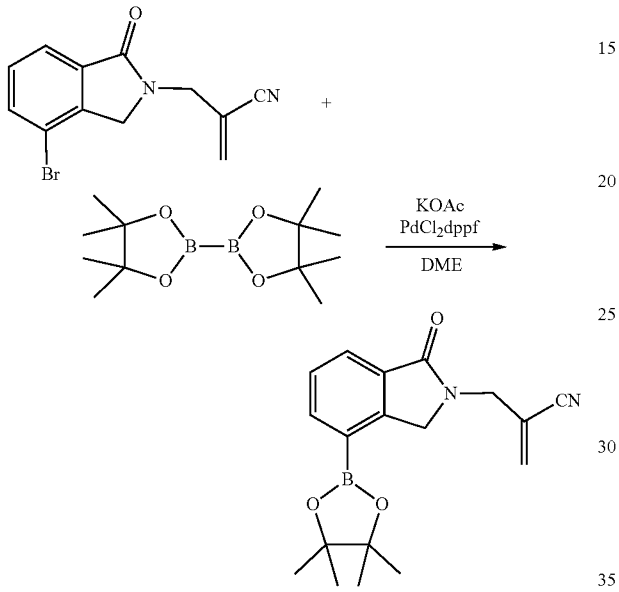

To a solution of 2-[(4-bromo-1-oxo-isoindolin-2-yl) methyl]prop-2-enenitrile (260 mg, 0.938 mmol) in DME (8 mL) were added 4,4,5,5-tetramethyl-2-(4,4,5,5-tetramethyl-1,3,2-dioxaborolan-2-yl)-1,3,2-dioxaborolane (0.357 g, 1.407 mmol), KOAc (276 mg, 2.814 mmol) and $PdCl_2dppf$ (84 mg, 103 μmol). The reaction was heated to 90° C. and stirred for 6 h. The reaction mixture was passed through a celite pad, and the solvent was removed in vacuo. The residue was purified by chromatography on silica gel eluting with 20-100% EtOAc/hexane to afford the title compound (0.265 g, Yield 87%).

d. Preparation of 2-[[4-(3,3-dimethyl-2-oxo-indolin-6-yl)-1-oxo-isoindolin-2-yl]methyl]prop-2-enenitrile (Compound 55)

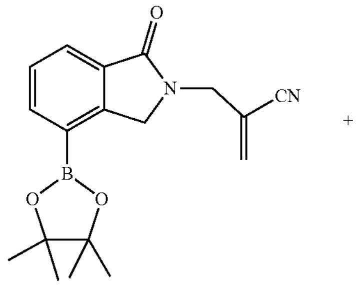

-continued

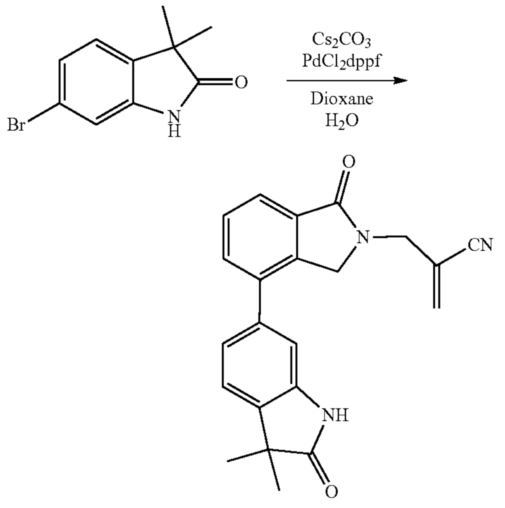

To a solution of 2-[[1-oxo-4-(4,4,5,5-tetramethyl-1,3,2-dioxaborolan-2-yl)isoindolin-2-yl]methyl]prop-2-enenitrile (53.3 mg, 164 μmol) in dioxane (1 mL) and water (0.2 mL) were added 6-bromo-3,3-dimethyl-indolin-2-one (59.2 mg, 247 μmol), $Cs_2CO_3$ (186 mg, 574 mmol) and $PdCl_2dppf$ (18 mg, 22.1 μmol). The reaction was heated to 100° C. and stirred for 30 min in a microwave. The reaction mixture was passed through a celite pad, and 2 mL of 0.5 M EDTA was added. The resulting solution was stirred at r.t. for 30 min. The solution was washed with brine, and the organic phase was dried over anhydrous sodium sulfate, filtered, and concentrated in vacuo. The residue was purified by chromatography on silica gel eluting with 40-100% EtOAc/hexane to afford the title compound (26.7 mg, Yield 46%). LC-MS: $[M+H]^+$ 358.

2A.2. Preparation of 2-[[4-(1H-indazol-6-yl)-1-oxo-isoindolin-2-yl]methyl]prop-2-enenitrile (Compound 57)

a. Preparation of tert-butyl 6-[2-(2-cyanoallyl)-1-oxo-isoindolin-4-yl]indazole-1-carboxylate

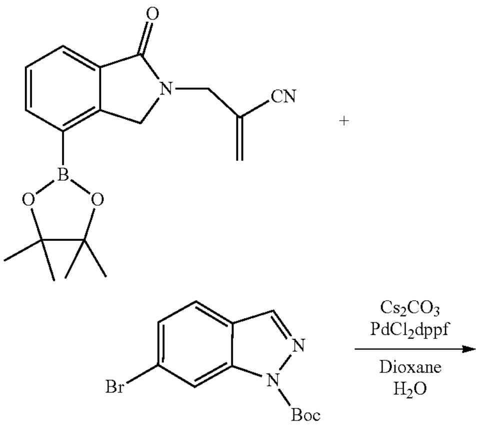

-continued

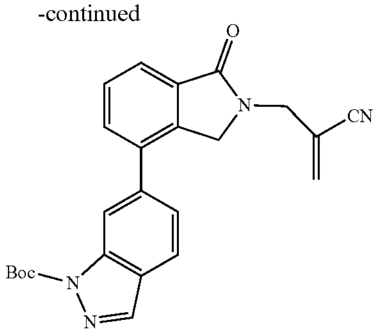

To a solution of 2-[[1-oxo-4-(4,4,5,5-tetramethyl-1,3,2-dioxaborolan-2-yl)isoindolin-2-yl]methyl]prop-2-enenitrile (51.2 mg, 158 μmol) in dioxane (1 mL) and water (0.2 mL) were added tert-butyl 6-bromoindazole-1-carboxylate (70.4 mg, 237 μmol), $Cs_2CO_3$ (180 mg, 553 mmol) and $PdCl_2dppf$ (18 mg, 22.1 μmol). The reaction was heated to 100° C. and stirred for 30 min in a microwave. The reaction mixture was passed through a celite pad, and 2 mL of 0.5 M EDTA was added. The resulting solution was stirred at r.t. for 30 min. The solution was washed with brine, and the organic phase was dried over anhydrous sodium sulfate, filtered, and concentrated in vacuo. The residue was purified by chromatography on silica gel eluting with 10-100% EtOAc/hexane to afford the title compound (30.5 mg, Yield 47%).

b. Preparation of 2-[[4-(1H-indazol-6-yl)-1-oxo-isoindolin-2-yl]methyl]prop-2-enenitrile (Compound 27)

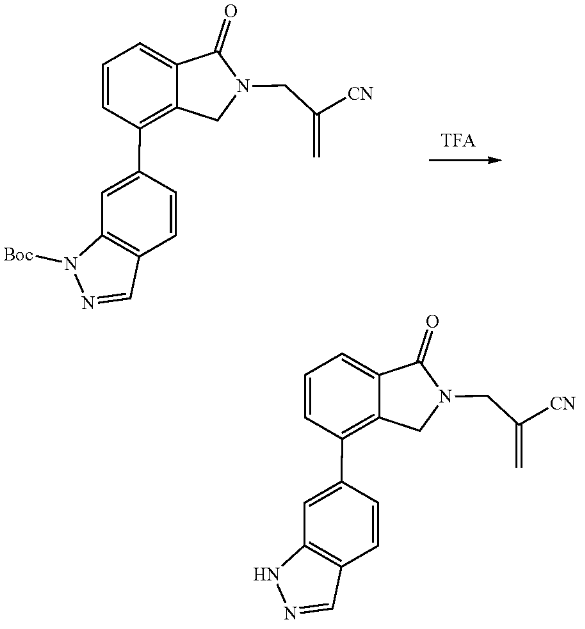

To a solution of tert-butyl 6-[2-(2-cyanoallyl)-1-oxo-isoindolin-4-yl]indazole-1-carboxylate (30.5 mg, 73 μmol) in DCM (1.6 mL) was added trifluoroacetic acid (0.4 mL) at 0° C. The resulting solution was stirred at r.t. for 2 h. The reaction mixture was concentrated in vacuo, and the residue was diluted with DCM, washed with sat. $NaHCO_3$ and brine, dried over anhydrous sodium sulfate, and concentrated. The residue was purified by chromatography on silica gel eluting with 40-100% EtOAc/hexane to afford the title compound (13.6 mg, Yield 59%). LC-MS: $[M+H]^+$ 315.

2A.3. Preparation of 2-[[4-(1H-indazol-5-yl)-1-oxo-isoindolin-2-yl]methyl]prop-2-enenitrile (Compound 58)

a. Preparation of tert-butyl 5-bromoindazole-1-carboxylate

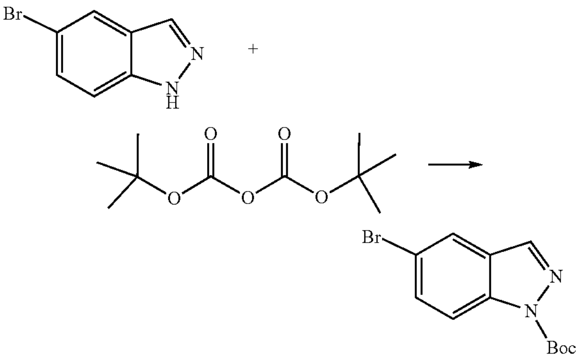

To a solution of 5-bromo-1H-indazole (500 mg, 2.538 mmol) in MeCN (10 mL) were added tert-butoxycarbonyl tert-butyl carbonate (830 mg, 3.807 mmol), TEA (900 mg, 8.838 mmol) and DMAP (61.9 mg, 0.508 mmol). The resulting mixture was stirred at r.t. for 18 h and concentrated in vacuo. The residue was purified by chromatography on silica gel eluting with 0-20% EtOAc/hexane to afford the title compound (282 mg, Yield 37%).

b. Preparation of tert-butyl 5-[2-(2-cyano-2-methylideneethyl)-1H-oxo-2,3-dihydro-1H-isoindol-4-yl]-1H-indazole-1-carboxylate

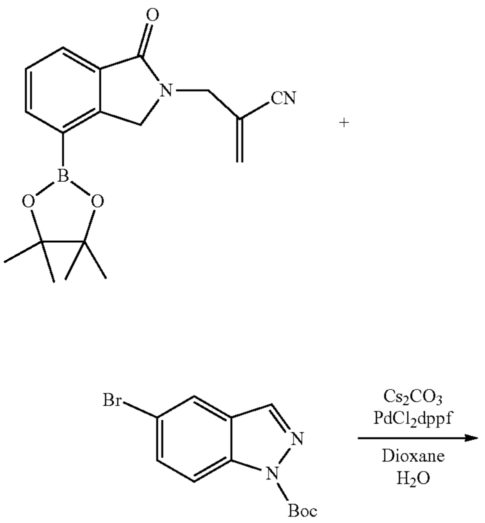

-continued

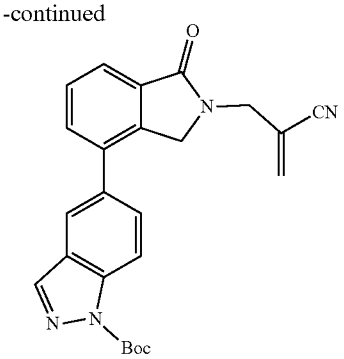

To a solution of 2-[[1-oxo-4-(4,4,5,5-tetramethyl-1,3,2-dioxaborolan-2-yl)isoindolin-2-yl]methyl]prop-2-enenitrile (49.7 mg, 153 μmol) in dioxane (1 mL) and water (0.2 mL) were added tert-butyl 5-bromoindazole-1-carboxylate (68.3 mg, 230 μmol), $Cs_2CO_3$ (174 mg, 536 mmol), and $PdCl_2$dppf (18 mg, 22.1 μmol). The reaction was heated to 100° C. for 30 min in a microwave. The reaction mixture was passed through a celite pad, and 2 mL of 0.5 M EDTA was added. The resulting solution was stirred at r.t. for 30 min. The solution was washed with brine, and The organic phase was dried over anhydrous sodium sulfate, filtered, and concentrated in vacuo. The residue was purified by chromatography on silica gel eluting with 10-100% EtOAc/hexane to afford the title compound (29.7 mg, Yield 47%).

c. Preparation of 2-[[4-(1H-indazol-5-yl)-1-oxo-isoindolin-2-yl]methyl]prop-2-enenitrile (Compound 58)

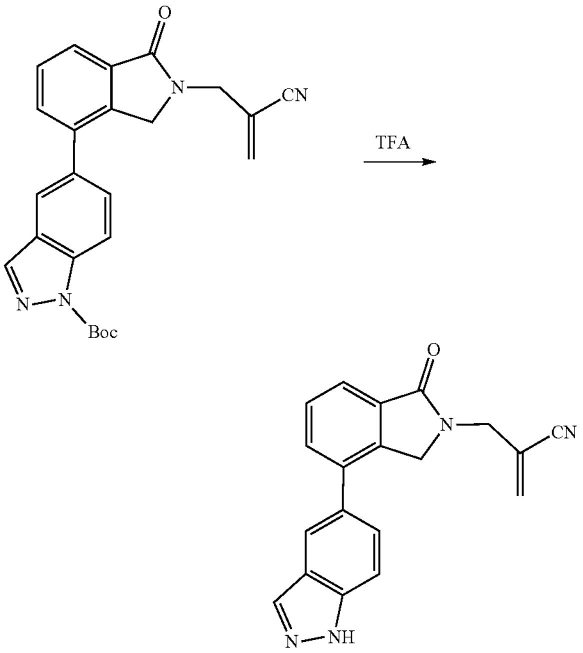

To a solution of tert-butyl 5-[2-(2-cyano-2-methylidene-ethyl)-1-oxo-2,3-dihydro-1H-isoindol-4 yl]-1H-indazole-1-carboxylate (29.7 mg, 72 μmol) in DCM (1.6 mL) was added trifluoroacetic acid (0.4 mL) at 0° C. The resulting solution was stirred at r.t. for 2 h. The reaction mixture was concentrated in vacuo and the residue was diluted with DCM, washed with sat. $NaHCO_3$ and brine, dried over anhydrous sodium sulfate, filtered, and concentrated. The residue was purified by chromatography on silica gel eluting with 40-100% EtOAc/hexane to afford the title compound (15.1 mg, Yield 67%). LC-MS: [M+H]+ 315.

2A.4. Preparation of 2-[[4-(3-methyl-1H-pyrazolo[3,4-c]pyridin-5-yl)-1-oxo-isoindolin-2-yl]methyl]prop-2-enenitrile (Compound 59)

a. Preparation of tert-butyl 5-bromo-3-methyl-pyrazolo[3,4-c]pyridine-1-carboxylate

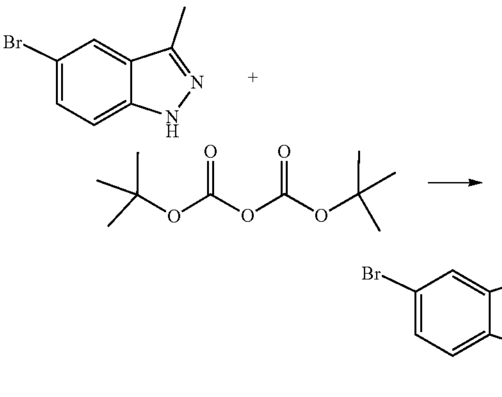

To a solution of 5-bromo-3-methyl-1H-pyrazolo[3,4-c]pyridine (400 mg, 1.886 mmol) in MeCN (6 mL) was added tert-butoxycarbonyl tert-butyl carbonate (617 mg, 2.83 mmol), TEA (668 mg, 6.601 mmol) and DMAP (46 mg, 0.377 mmol). The resulting mixture was stirred at r.t. for 18 h and concentrated in vacuo. The residue was purified by chromatography on silica gel eluting with 0-20% EtOAc/hexane to afford the title compound (473 mg, Yield 81%).

b. Preparation of tert-butyl 5-[2-(2-cyanoallyl)-1-oxo-isoindolin-4-yl]-3-methyl-pyrazolo[3,4-c]pyridine-1-carboxylate

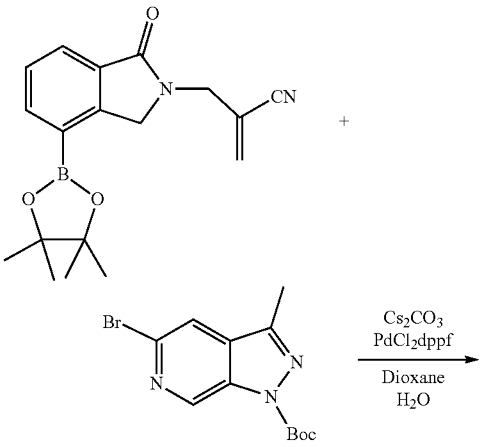

-continued

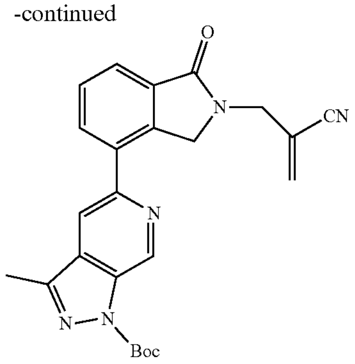

To a solution of 2-[[1-oxo-4-(4,4,5,5-tetramethyl-1,3,2-dioxaborolan-2-yl)isoindolin-2-yl]methyl]prop-2-enenitrile (51 mg, 157 μmol) in dioxane (1 mL) and water (0.2 mL) were added tert-butyl 5-bromo-3-methyl-pyrazolo[3,4-c]pyridine-1-carboxylate (73.6 mg, 236 μmol), $Cs_2CO_3$ (179 mg, 550 mmol), and $PdCl_2dppf$ (18 mg, 22.1 μmol). The reaction was heated to 100° C. for 30 min in a microwave. The reaction mixture was passed through a celite pad, and 2 mL of 0.5 M EDTA was added. The resulting solution was stirred at r.t. for 30 min. The solution was washed with brine, and the organic phase was dried over anhydrous sodium sulfate, filtered, and concentrated in vacuo. The residue was purified by chromatography on silica gel eluting with 10-100% EtOAc/hexane to afford the title compound (14.7 mg, Yield 22%).

c. Preparation of 2-[[4-(3-methyl-1H-pyrazolo[3,4-c]pyridin-5-yl)-1-oxo-isoindolin-2-yl]methyl]prop-2-enenitrile (Compound 59)

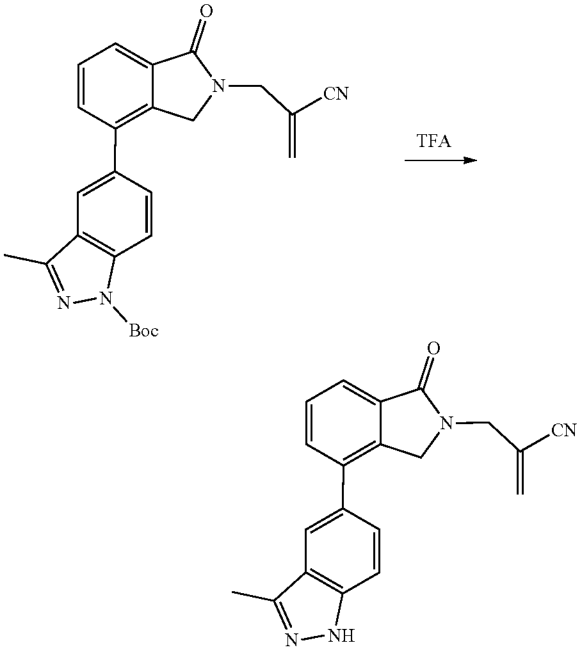

To a solution of tert-butyl 5-[2-(2-cyanoallyl)-1-oxo-isoindolin-4-yl]-3-methyl-pyrazolo[3,4-c]pyridine-1-carboxylate (14.7 mg, 34 μmol) in DCM (1.6 mL) was added trifluoroacetic acid (0.4 mL) at 0° C. The resulting solution was stirred at r.t. for 2 h. The reaction mixture was concentrated in vacuo, and the residue was diluted with DCM, washed with sat. $NaHCO_3$ and brine, dried over anhydrous sodium sulfate, filtered, and concentrated. The residue was purified by chromatography on silica gel eluting with 40-100% EtOAc/hexane to afford the title compound (8.2 mg, Yield 73%). LC-MS: $[M+H]^+$ 330.

2A.5. Preparation of 2-[[1-oxo-4-[1-(2,2,2-trifluoroethyl) indazol-6-yl]isoindolin-2-yl]methyl]prop-2-enenitrile (Compound 65)

a. Preparation of 6-bromo-1-(2,2,2-trifluoroethyl) indazole

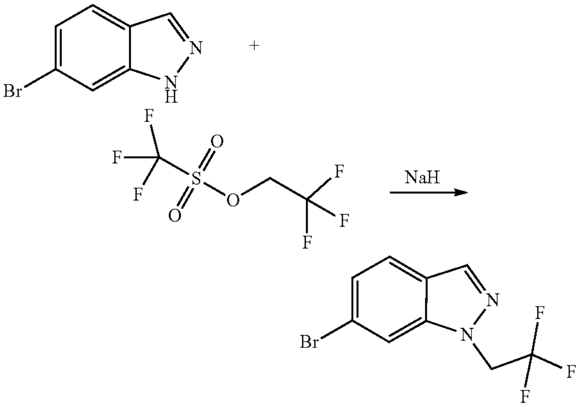

To a solution of 6-bromo-1H-indazole (500 mg, 2.54 mmol) in DMF (8 mL) was added NaH (0.203 g, 5.08 mmol). The mixture was stirred at r.t. for 10 min. The mixture was cooled to 0° C., and 2,2,2-trifluoroethyl trifluoromethanesulfonate (0.884 g, 3.81 mmol) in DMF (0.5 mL) was added dropwise. The resulting mixture was stirred at 0° C. for 3 h. The mixture was partitioned between EtOAc and water. The aqueous phase was extracted with EtOAc (3×). The combined organic phase was washed with water and brine, dried over ($MgSO_4$), filtered, and concentrated in vacuo. The residue was purified by chromatography on silica gel eluting with 10-60% EtOAc/hexane to afford the title compound (0.439 g, Yield 62%).

b. Preparation of 2-[[1-oxo-4-[1-(2,2,2-trifluoroethyl) indazol-6-yl]isoindolin-2-yl]methyl]prop-2-enenitrile (Compound 65)

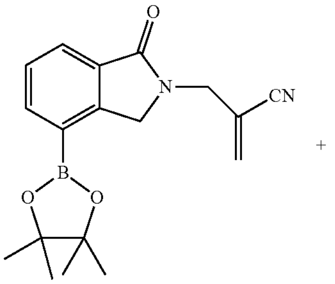

-continued

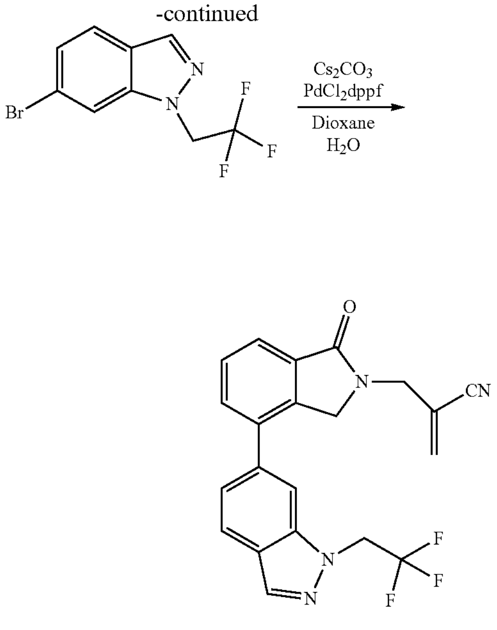

To a solution of 2-[[1-oxo-4-(4,4,5,5-tetramethyl-1,3,2-dioxaborolan-2-yl)isoindolin-2-yl]methyl]prop-2-enenitrile (51 mg, 157 μmol) in dioxane (1 mL) and water (0.2 mL) were added 6-bromo-1-(2,2,2-trifluoroethyl)indazole (65.9 mg, 236 μmol), $Cs_2CO_3$ (179 mg, 550 mmol), and $PdCl_2dppf$ (18 mg, 22.1 μmol). The reaction was heated to 100° C. for 30 min in a microwave. The reaction mixture was passed through a celite pad, and 2 mL of 0.5 M EDTA was added. The resulting solution was stirred at r.t. for 30 min. The solution was washed with brine, and the organic phase was dried over anhydrous sodium sulfate, filtered, and concentrated in vacuo. The residue was purified by reverse phase HPLC using a gradient of water 0.1% FA/acetonitrile 0.1% FA to afford the title compound (16.7 mg, Yield 27%). LC-MS: $[M+H]^+$ 397.

2A.6. Preparation of 2-[[1-oxo-4-([1,2,4]triazolo[4,3-a]pyridin-6-yl isoindolin-2-yl]methyl]prop-2-enenitrile (Compound 66)

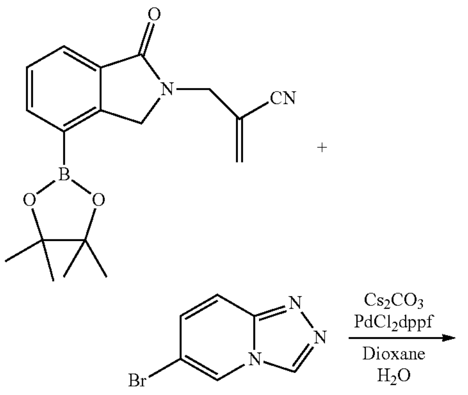

-continued

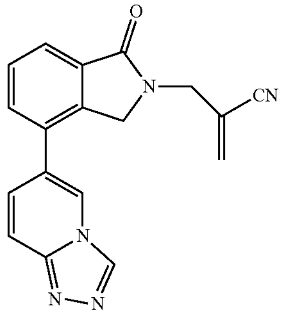

To a solution of 2-[[1-oxo-4-(4,4,5,5-tetramethyl-1,3,2-dioxaborolan-2-yl)isoindolin-2-yl]methyl]prop-2-enenitrile (52.9 mg, 163 μmol) in dioxane (1 mL) and water (0.2 mL) were added 6-bromo-[1,2,4]triazolo[4,3-a]pyridine (48.5 mg, 245 μmol), $Cs_2CO_3$ (185 mg, 571 mmol) and $PdCl_2dppf$ (18 mg, 22.1 μmol). The reaction was heated to 100° C. for 30 min in a microwave. The reaction mixture was passed through a celite pad, and 2 mL of 0.5 M EDTA was added. The resulting solution was stirred at r.t. for 30 min. The solution was washed with brine, and the organic phase was dried over anhydrous sodium sulfate, filtered, and concentrated in vacuo. The residue was purified by reverse phase HPLC using a gradient of water 0.1% FA/acetonitrile 0.1% FA to afford the title compound (11 mg, Yield 21%). LC-MS: $[M+H]^+$ 316.

2A.7. Preparation of 2-[[4-(3-meth-[1,2,4]triazolo[4,3-a]pyridin-6-yl)-1-oxo-isoindolin-2-yl]methyl]prop-2-enenitrile (Compound 67)

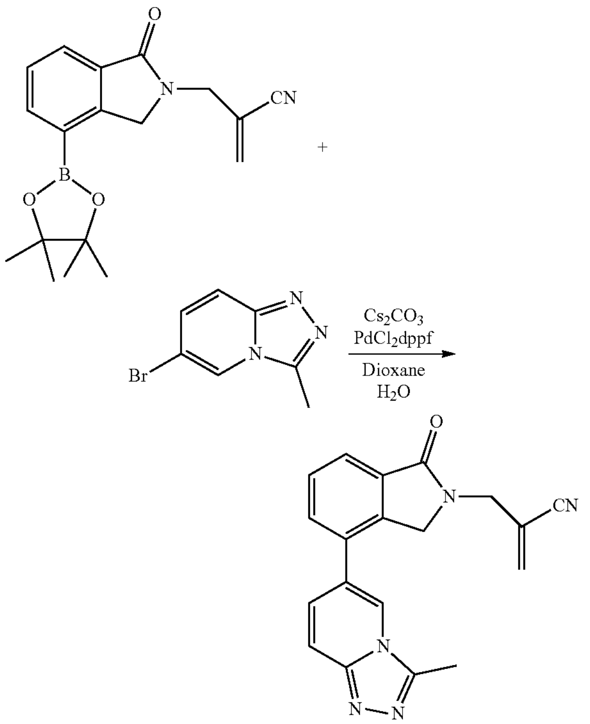 [SMILES: C=C(C#N)CN1Cc2c(B3OC(C)(C)C(C)(C)O3)cccc2C1=O ; Cc1nnc2ccc(Br)cn12 ; C=C(C#N)CN1Cc2c(cccc2-c2ccc3nnc(C)n3c2)C1=O]

To a solution of 2-[[1-oxo-4-(4,4,5,5-tetramethyl-1,3,2-dioxaborolan-2-yl)isoindolin-2-yl]methyl]prop-2-enenitrile (52.2 mg, 161 μmol) in dioxane (1 mL) and water (0.2 mL) were added 6-bromo-3-methyl-[1,2,4]triazolo[4,3-a]pyridine (51.2 mg, 242 μmol), $Cs_2CO_3$ (183 mg, 564 mmol), and $PdCl_2dppf$ (18 mg, 22.1 μmol). The reaction was heated to 100° C. for 30 min in a microwave. The reaction mixture was passed through a celite pad, and 2 mL of 0.5 M EDTA was added. The resulting solution was stirred at r.t. for 30 min. The solution was washed with brine, and the organic phase was dried over anhydrous sodium sulfate, filtered, and concentrated in vacuo. The residue was purified by reverse phase HPLC using a gradient of water 0.1% FA/acetonitrile 0.1% FA to afford the title compound (7.3 mg, Yield 14%). LC-MS: $[M+H]^+$ 330.

2A.8 Preparation of 2-[(3-oxo-8-quinoxalin-2-yl-1H-benzo[e]isoindol-2-yl)methyl]prop-2-enenitrile (Compound 68)

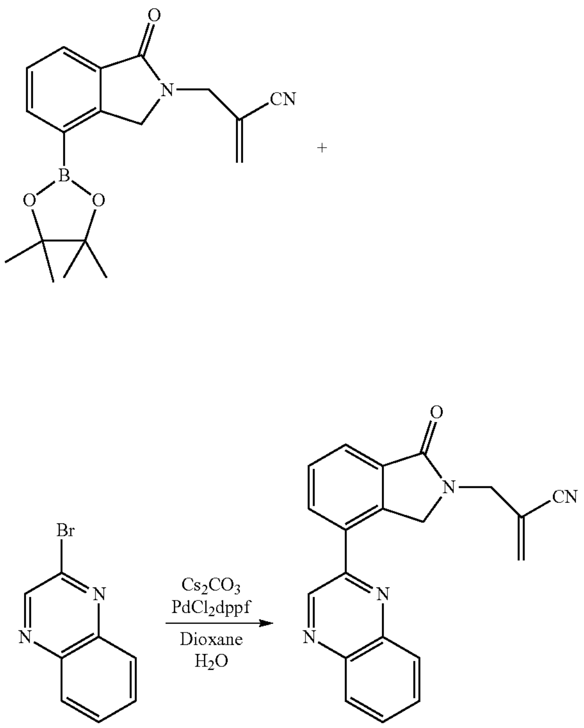

To a solution of 2-[[1-oxo-4-(4,4,5,5-tetramethyl-1,3,2-dioxaborolan-2-yl)isoindolin-2-yl]methyl]prop-2-enenitrile (55.2 mg, 170 μmol) in dioxane (1 mL) and water (0.2 mL) were added 2-bromoquinoxaline (53.4 mg, 255 μmol), $Cs_2CO_3$ (193 mg, 595 mmol), and $PdCl_2dppf$ (18 mg, 22.1 μmol). The reaction was heated to 100° C. for 30 min in a microwave. The reaction mixture was passed through a celite pad, and 2 mL of 0.5 M EDTA was added. The resulting solution was stirred at r.t. for 30 min. The solution was washed with brine, and the organic phase was dried over anhydrous sodium sulfate, filtered, and concentrated in vacuo. The residue was purified by chromatography on silica gel eluting with 20-80% EtOAc/hexane to afford the title compound (15.2 mg, Yield 27%). LC-MS: $[M+H]^+$ 327.

2A.9. Preparation of 2-[[1-oxo-4-(2-oxo-1H-quinolin-6-yl) isoindolin-2-yl]methyl]prop-2-enenitrile (Compound 59)

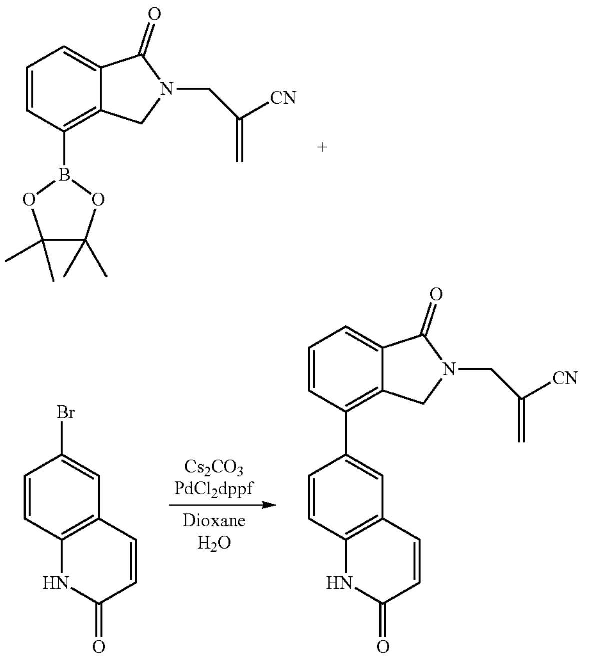

To a solution of 2-[[1-oxo-4-(4,4,5,5-tetramethyl-1,3,2-dioxaborolan-2-yl)isoindolin-2-yl]methyl]prop-2-enenitrile (52.3 mg, 161 μmol) in dioxane (1 mL) and water (0.2 mL) were added 6-bromo-1H-quinolin-2-one (54.2 mg, 242 μmol), $Cs_2CO_3$ (183 mg, 564 mmol), and $PdCl_2dppf$ (18 mg, 22.1 μmol). The reaction was heated to 100° C. for 30 min in a microwave. The reaction mixture was passed through a celite pad, and 2 mL of 0.5 M EDTA was added. The resulting solution was stirred at r.t. for 30 min. The solution was washed with brine, and the organic phase was dried over anhydrous sodium sulfate, filtered, and concentrated in vacuo. The residue was purified by reverse phase HPLC using a gradient of water 0.1% FA/acetonitrile 0.1% FA to afford the title compound (7.2 mg, Yield 13%). LC-MS: $[M+H]^+$ 342.

2A.10. Preparation of 2-[[1-oxo-4-(2-oxo-quinolin-6-yl) isoindolin-2-yl]methyl]prop-2-enenitrile (Compound 70)

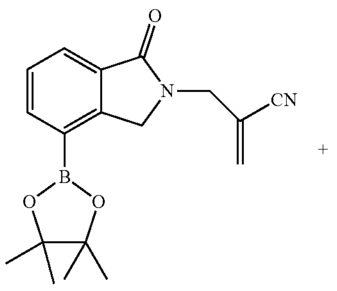

-continued

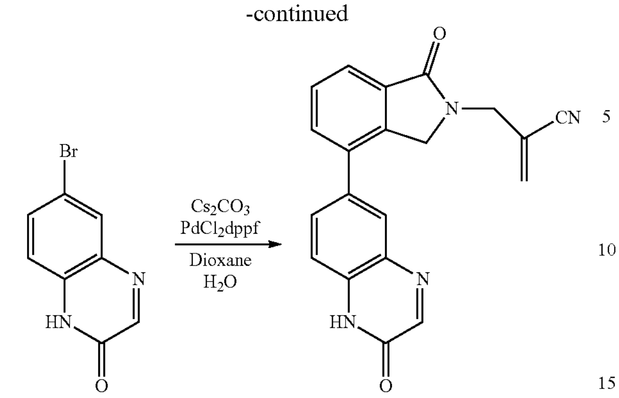

To a solution of 2-[[1-oxo-4-(4,4,5,5-tetramethyl-1,3,2-dioxaborolan-2-yl)isoindolin-2-yl]methyl]prop-2-enenitrile (50.9 mg, 157 mol) in dioxane (1 mL) and water (0.2 mL) were added 6-bromo-1H-quinoxalin-2-one (53 mg, 236 µmol), $Cs_2CO_3$ (179 mg, 550 mmol), and $PdCl_2$dppf (18 mg, 22.1 µmol). The reaction was heated to 100° C. for 30 min in a microwave. The reaction mixture was passed through a celite pad, and 2 mL of 0.5 M EDTA was added. The resulting solution was stirred at r.t. for 30 min. The solution was washed with brine, and the organic phase was dried over anhydrous sodium sulfate, filtered, and concentrated in vacuo. The residue was purified by reverse phase HPLC using a gradient of water 0.1% FA/acetonitrile 0.1% FA to afford the title compound (3.0 mg, Yield 6%). LC-MS: $[M+H]^+$ 343.

2A.11. 2-[[4-(3-methyl-2-oxo-indolin-5-yl)-1-oxo-isoindolin-2-yl]methyl]prop-2-enenitrile (Compound 76)

a. Preparation of tert-butyl 5-bromo-3-methyl-2-oxo-indoline-1-carboxylate

Boc

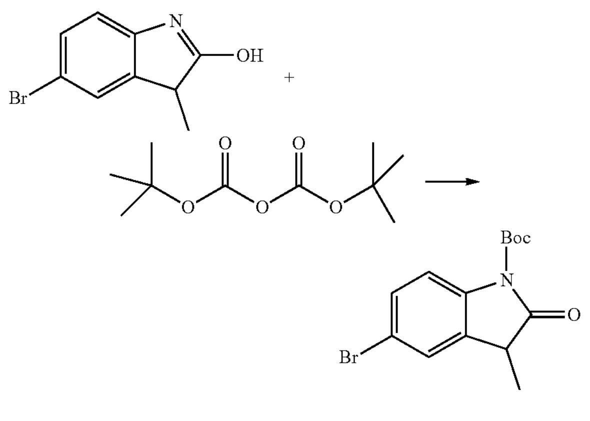

To a solution of 5-bromo-3-methyl-3H-indol-2-ol (200 mg, 0.884 mmol) in MeCN (6 mL) was added tert-butoxycarbonyl tert-butyl carbonate (289 mg, 1.327 mmol), TEA (313 mg, 3.094 mmol), and DMAP (21.6 mg, 0.177 mmol). The resulting mixture was stirred at r.t. for 18 h and concentrated in vacuo. The residue was purified by chromatography on silica gel eluting with 0-20% EtOAc/hexane to afford the title compound (245 mg, Yield 85%).

b. Preparation of tert-butyl 5-[2-(2-cyanoallyl)-1-oxo-isoindol-4-yl]-3-methy-2-oxo-indoline-1-carboxylate

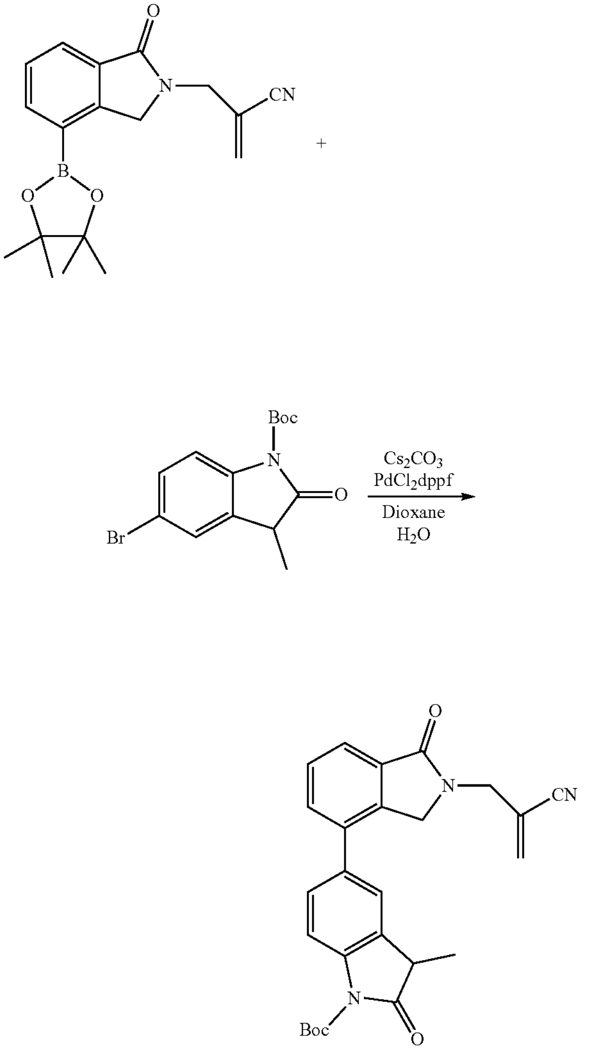

To a solution of 2-[[1-oxo-4-(4,4,5,5-tetramethyl-1,3,2-dioxaborolan-2-yl)isoindolin-2-yl]methyl]prop-2-enenitrile (76.4 mg, 236 µmol) in dioxane (1 mL) and water (0.2 mL) were added tert-butyl 5-bromo-3-methyl-2-oxo-indoline-1-carboxylate (115 mg, 353 µmol), $Cs_2CO_3$ (268 mg, 826 mmol) and $PdCl_2$dppf (18 mg, 22.1 µmol). The reaction was heated to 100° C. for 30 min in a microwave. The reaction mixture was passed through a celite pad, and 2 mL of 0.5 M EDTA was added. The resulting solution was stirred at r.t. for 30 min. The solution was washed with brine, and the organic phase was dried over anhydrous sodium sulfate, filtered, and concentrated in vacuo. The residue was purified by chromatography on silica gel eluting with 20-80% EtOAc/hexane to afford the title compound (32.8 mg, Yield 31%).

c. 2-[[4-(3-methyl-2-oxo-indolin-5-yl)-1-oxo-isoindolin-2-yl]methyl]prop-2-enenitrile (Compound 76)

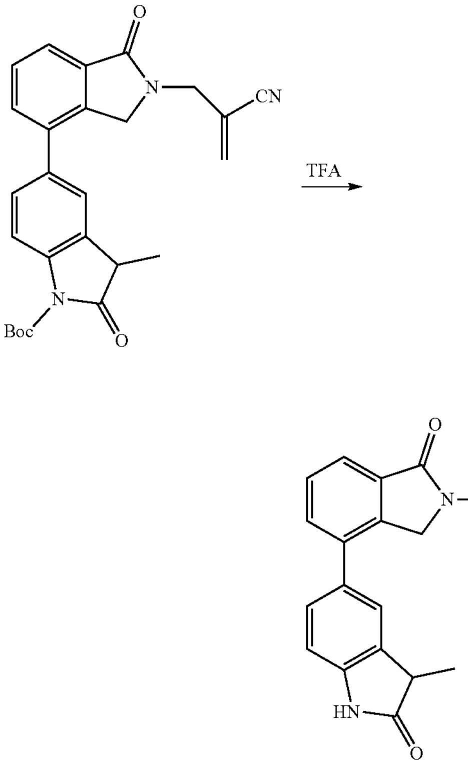

To a solution of tert-butyl 5-[2-(2-cyanoallyl)-1-oxo-isoindolin-4-yl]-3-methyl-2-oxo-indoline-1-carboxylate (32.8 mg, 74 µmol) in DCM (1.6 mL) was added trifluoroacetic acid (0.4 mL) at 0° C. The resulting solution was stirred at r.t. for 4 h. The reaction mixture was concentrated in vacuo and the residue was diluted with DCM, washed with sat. $NaHCO_3$ and brine, dried over anhydrous sodium sulfate, filtered, and concentrated. The residue was purified by chromatography on silica gel eluting with 40-80% EtOAc/hexane to afford the title compound (12.3 mg, Yield 48%). LC-MS: $[M+H]^+$ 344.

2A.12. Preparation of 2-[[4-(3-cyclopropyl-[1,2,4]triazolo[4,3-a]pyridin-6-yl)-1-oxo-isoindolin-2-yl]methyl]prop-2-enenitrile (Compound 77)

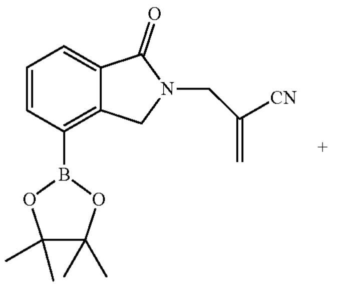

-continued

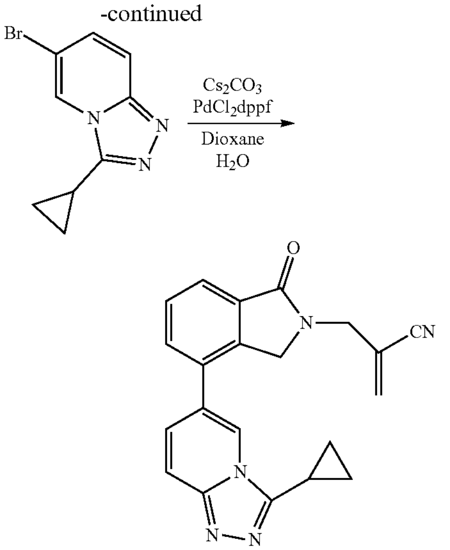

To a solution of 2-[[1-oxo-4-(4,4,5,5-tetramethyl-1,3,2-dioxaborolan-2-yl)isoindolin-2-yl]methyl]prop-2-enenitrile (57 mg, 176 µmol) in dioxane (1 mL) and water (0.2 mL) were added 6-bromo-3-cyclopropyl-[1,2,4]triazolo[4,3-a]pyridine (62.8 mg, 264 µmol), $Cs_2CO_3$ (200 mg, 616 mmol), and $PdCl_2$dppf (18 mg, 22.1 µmol). The reaction was heated to 100° C. for 30 min in a microwave. The reaction mixture was passed through a celite pad, and 2 mL of 0.5 M EDTA was added. The resulting solution was stirred at r.t. for 30 min. The solution was washed with brine, and the organic phase was dried over anhydrous sodium sulfate, filtered, and concentrated in vacuo. The residue was purified by reverse phase HPLC using a gradient of water 0.1% FA/acetonitrile 0.1% FA to afford the title compound (2.8 mg, Yield 5%). LC-MS: $[M+H]^+$ 356.

2A.13. Preparation of 2-[[4-[1-(2-fluoroethyl)indazol-6-yl]-1-oxo-isoindolin-2-yl]methyl]prop-2-enenitrile (Compound 78)

a. Preparation of 6-bromo-1-(2-fluoroethyl)indazole

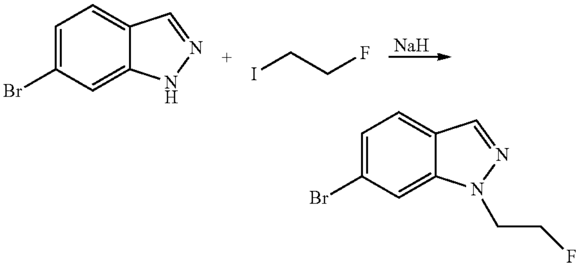

To a solution of 6-bromo-1H-indazole (500 mg, 2.54 mmol) in DMF (8 mL) was added NaH (0.203 g, 5.08 mmol). The mixture was stirred at r.t. for 10 min. The mixture was cooled to 0° C. and 1-fluoro-2-iodo-ethane (0.662 g, 3.81 mmol) in DMF (0.5 mL) was added dropwise. The resulting mixture was stirred at r.t. for 18 h. The mixture was partitioned between EtOAc and water. The aqueous phase was extracted with EtOAc (3×). The combined organic phase was washed with water and brine, dried over ($MgSO_4$), filtered, and concentrated in vacuo. The residue was purified by chromatography on silica gel eluting with 20-60% EtOAc/hexane to afford the title compound (0.365 g, Yield 59%).

b. Preparation of 2-[[4-[1-(2-fluoroethyl) indazol-6-yl]-1-oxo-isoindolin-2-yl]methyl]prop-2-enenitrile (Compound 78)

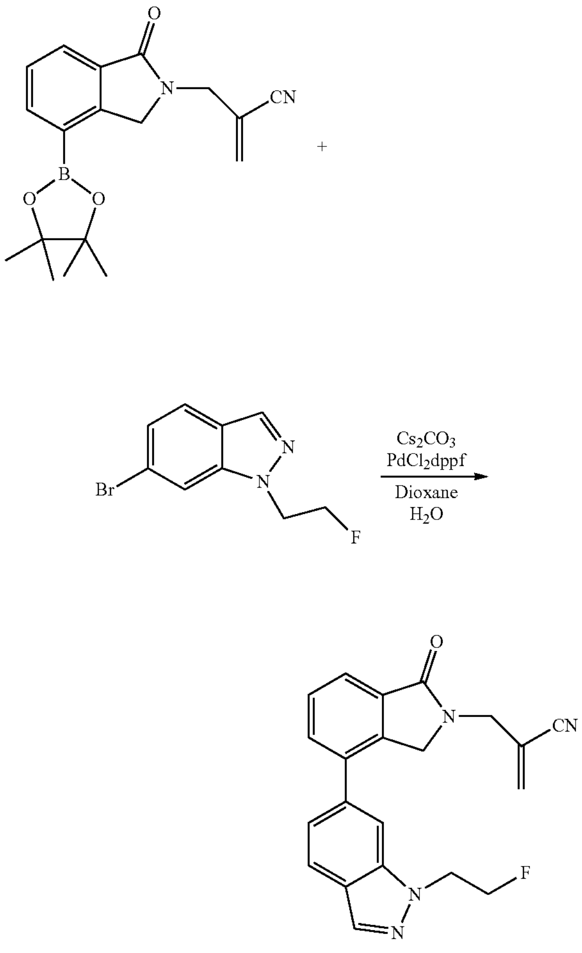

To a solution of 2-[[1-oxo-4-(4,4,5,5-tetramethyl-1,3,2-dioxaborolan-2-yl)isoindolin-2-yl]methyl]prop-2-enenitrile (51.7 mg, 158 μmol) in dioxane (1 mL) and water (0.2 mL) were added 6-bromo-1-(2-fluoroethyl)indazole (57.7 mg, 237 μmol), $Cs_2CO_3$ (179 mg, 550 mmol), and $PdCl_2dppf$ (18 mg, 22.1 μmol). The reaction was heated to 100° C. for 30 min in a microwave. The reaction mixture was passed through a celite pad, and 2 mL of 0.5 M EDTA was added. The resulting solution was stirred at r.t. for 30 min. The solution was washed with brine, and the organic phase was dried over anhydrous sodium sulfate, filtered, and concentrated in vacuo. The residue was purified by chromatography on silica gel eluting with 20-80% EtOAc/hexane to afford the title compound (13.7 mg, Yield 24%). LC-MS: $[M+H]^+$ 361.

2A.14. Preparation of 2-[[4-(1-cyclopropylindazol-6-yl)-1-oxo-isoindolin-2-yl]methyl]prop-2 enenitrile (Compound 85)

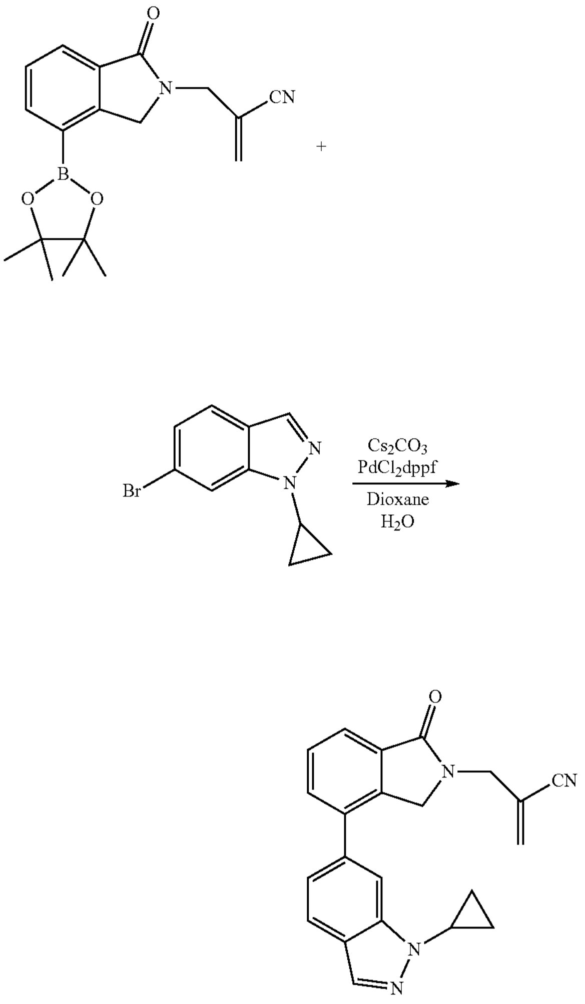

To a solution of 2-[[1-oxo-4-(4,4,5,5-tetramethyl-1,3,2-dioxaborolan-2-yl)isoindolin-2-yl]methyl]prop-2-enenitrile (50.5 mg, 156 μmol) in dioxane (1 mL) and water (0.2 mL) were added 6-bromo-1-cyclopropyl-indazole (55.4 mg, 234 μmol), $Cs_2CO_3$ (177 mg, 546 mmol), and $PdCl_2dppf$ (18 mg, 22.1 μmol). The reaction was heated to 100° C. for 30 min in a microwave. The reaction mixture was passed through a celite pad, and 2 mL of 0.5 M EDTA was added. The resulting solution was stirred at r.t. for 30 min. The solution was washed with brine, and the organic phase was dried over anhydrous sodium sulfate, filtered, and concentrated in vacuo. The residue was purified by reverse phase HPLC using a gradient of water 0.1% FA/acetonitrile 0.1% FA to afford the title compound (8 mg, Yield 15%). LC-MS: $[M+H]^+$ 355.

2A.15. 2-[[1-oxo-4-(3-oxo-2H-[1,2,4]triazolo[4,3-a]pyridin-6-yl)isoindolin-2-yl]methyl]prop-2-enenitrile (Compound 90)

a. Preparation of tert-butyl 6-bromo-3-oxo-[1,2,4]triazolo[4,3-a]pyridine-2-carboxylate

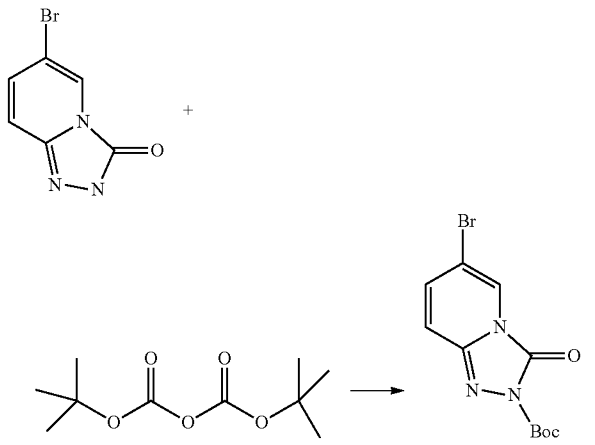

To a solution of 6-bromo-2H-[1,2,4]triazolo[4,3-a]pyridin-3-one (300 mg, 1.402 mmol) in MeCN (6 mL) were added tert-butoxycarbonyl tert-butyl carbonate (458 mg, 2.103 mmol), TEA (497 mg, 4.907 mmol) and DMAP (34.2 mg, 0.28 mmol). The resulting mixture was stirred at r.t. for 18 h and concentrated in vacuo. The residue was purified by chromatography on silica gel eluting with 0-40% EtOAc/hexane to afford the title compound (230 mg, Yield 52%).

b. Preparation of tert-butyl 6-[2-(2-cyanoallyl)-1-oxo-isoindolin-4-yl]-3-oxo-[1,2,4]triazolo[4,3-a]pyridine-2-carboxylate

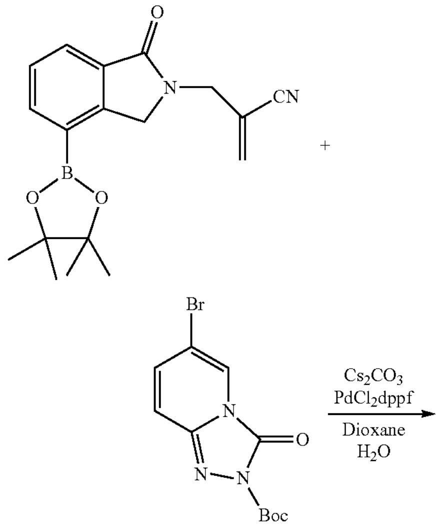

-continued

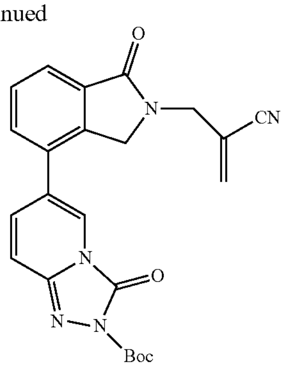

To a solution of 2-[[1-oxo-4-(4,4,5,5-tetramethyl-1,3,2-dioxaborolan-2-yl)isoindolin-2-yl]methyl]prop-2-enenitrile (58.9 mg, 182 μmol) in dioxane (1 mL) and water (0.2 mL) were added tert-butyl 6-bromo-3-oxo-[1,2,4]triazolo[4,3-a]pyridine-2-carboxylate (85.7 mg, 273 μmol), $Cs_2CO_3$ (207 mg, 637 mmol) and $PdCl_2dppf$ (18 mg, 22.1 μmol). The reaction was heated to 100° C. for 30 min in a microwave. The reaction mixture was passed through a celite pad, and 2 mL of 0.5 M EDTA was added.

The resulting solution was stirred at r.t. for 30 min. The solution was washed with brine, and the organic phase was dried over anhydrous sodium sulfate, filtered, and concentrated in vacuo. The residue was purified by chromatography on silica gel eluting with 20-80% EtOAc/hexane to afford the title compound (6.8 mg, Yield 9%).

c. 2-[[1-oxo-4-(3-oxo-2H-[1,2,4]triazolo[4,3-a]pyridin-6-yl)isoindolin-2-yl]methyl]prop-2-enenitrile (Compound 90)

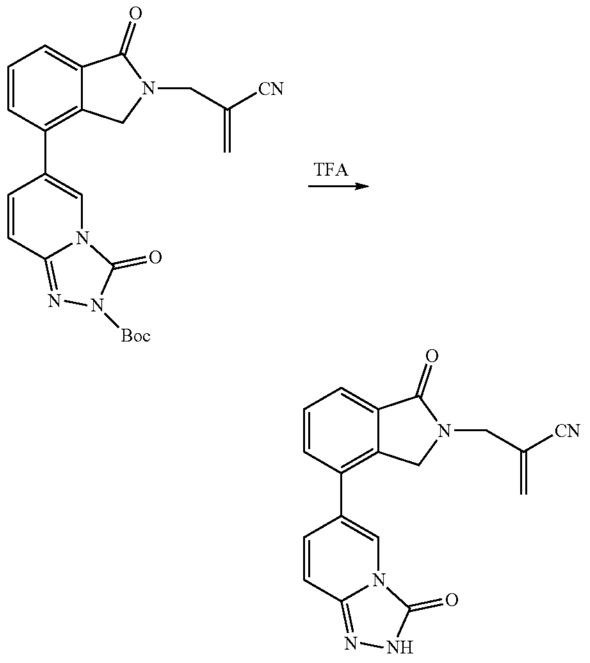 [SMILES: C=C(C#N)CN1Cc2c(cccc2-c2ccc3nn(C(=O)OC(C)(C)C)c(=O)n3c2)C1=O ; C=C(C#N)CN1Cc2c(cccc2-c2ccc3n[nH]c(=O)n3c2)C1=O]

To a solution of tert-butyl 6-[2-(2-cyanoallyl)-1-oxo-isoindolin-4-yl]-3-oxo-[1,2,4]triazolo[4,3-a]pyridine-2-carboxylate (6.8 mg, 16 μmol) in DCM (1.6 mL) was added trifluoroacetic acid (0.4 mL) at 0° C. The resulting solution was stirred at r.t. for 2 h. The reaction mixture was concentrated in vacuo and the residue was diluted with DCM, washed with sat. $NaHCO_3$ and brine, dried over anhydrous sodium sulfate, filtered, and concentrated. The residue was purified by reverse phase HPLC using a gradient of water 0.1% FA/acetonitrile 0.1% FA to afford the title compound (2.4 mg, Yield 46%). LC-MS: $[M+H]^+$ 332.

2A.16. Preparation of 2-{[4-(3-methyl-1-benzothiophen-5-yl)-1-oxo-2,3-dihydro-1H-isoindol-2-yl]methyl}prop-2-enenitrile (Compound 19)

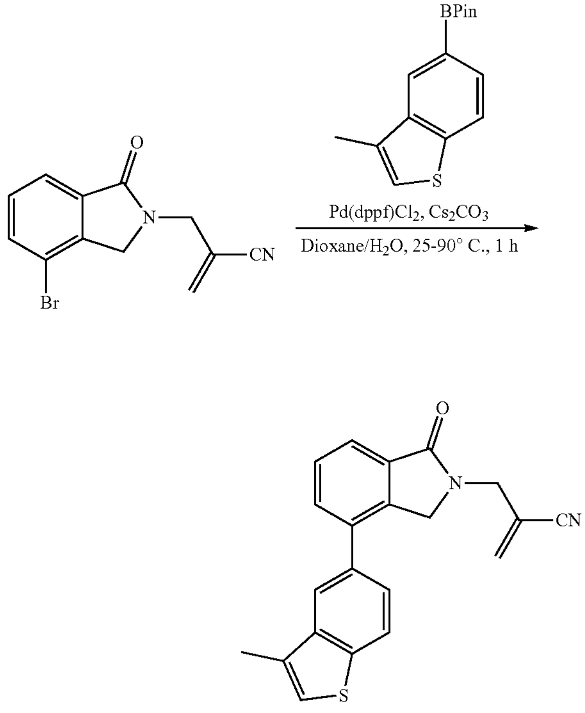

To a mixture of 2-[(4-bromo-1-oxo-2,3-dihydro-1H-isoindol-2-yl)methyl]prop-2-enenitrile (0.05 g, 155.17 μmol, 1 eq.) and 4,4,5,5-tetramethyl-2-(3-methyl-1-benzothiophen-5-yl)-1,3-dioxolane (79.77 mg, 232.75 μmol, 1.5 eq.) in dioxane (4 mL) and water (1 mL) was added $Cs_2CO_3$ (151.67 mg, 465.51 μmol, 3 eq.) in one portion at 25° C. under nitrogen. Then, $Pd(dppf)Cl_2$ (5.68 mg, 7.76 μmol, 0.05 eq.) was added to the mixture. The mixture was stirred at 90° C. for 1 h. LCMS showed that the reaction was complete. The reaction was poured into 10 mL sat EDTA, and diluted with 10 mL EtOAc, then the mixture was stirred at 25° C. for 1 h. The aqueous layer was extracted with EtOAc (3×10 mL), the combined organic layer was washed with brine 10 mL, filtered, and concentrated in vacuo. The crude product was purified by prep-TLC (silica gel; PE:EtOAc=1:2), and 60 mg purified product was purified by prep-HPLC to afford the title compound (5.10 mg, 14.81 μmol, 9.54% yield, 100% purity) as a white solid. LC-MS: $[M+H]^+$ 345.

2A.17. General Procedure for Acylation

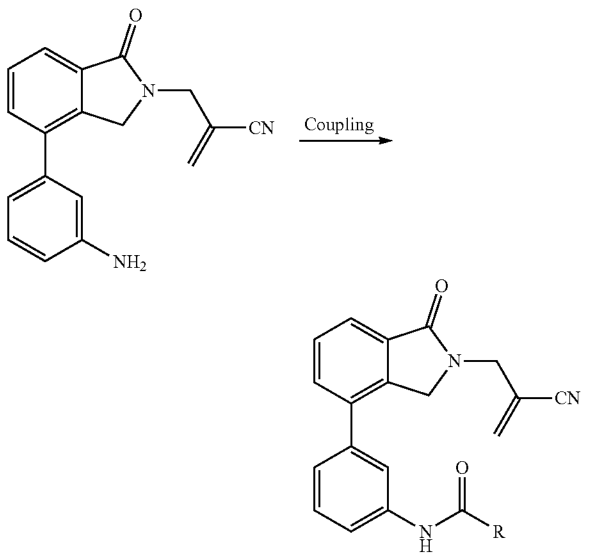

Condition 1. RCl, TEA, DCM, 0° C.
Condition 2. RCOOH, HATU, DIPEA, DMF

Condition 1:

To a mixture of 2-{[4-(3-aminophenyl)-1-oxo-2,3-dihydro-1H-isoindol-2-yl]methyl}prop-2-enenitrile (50 mg, 1 eq.) in DCM (2 mL) were added TEA (3 eq.) and RCl (2 eq.), the mixture was stirred at 0° C. for 1-2 h under nitrogen. LCMS showed that the reaction was complete. The reaction mixture was extracted with DCM (25 mL×2), then the combined organic layers were washed with water (50 mL×2) and brine (50 mL×2), dried over anhydrous sodium sulfate, filtered, and concentrated in vacuo to give a residue. The residue was purified by prep-HPLC.

Condition 2:

To a solution of 2-{[4-(3-aminophenyl)-1-oxo-2,3-dihydro-1H-isoindol-2-yl]methyl}prop-2-enenitrile (20 mg, 69.13 μmol, 1 eq.) in DMF (2 mL) were added DIPEA (5 eq.) and HATU (1.5 eq.). The mixture was stirred at 25° C. for 15 minutes under nitrogen, then 1-methylpyrazole-4-carboxylic acid (1.2 eq.) was added and the reaction was stirred for 12 h. TLC and LCMS showed that the reaction was complete. The reaction mixture was extracted with EtOAc (3×15 mL), the combined organic layers were washed with water (3×50 mL) and brine (3×50 mL) then dried over anhydrous sodium sulfate, filtered, and concentrated in vacuo to give a residue. The residue was purified by prep-TLC. The product was further separated by prep-HPLC.

2A.18. Preparation of tert-butyl 3-[2-(2-cyano-2-methylideneethyl)-1-oxo-2,3-dihydro-1H-isoindol-4-yl]benzoate

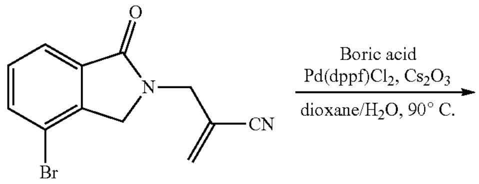

-continued

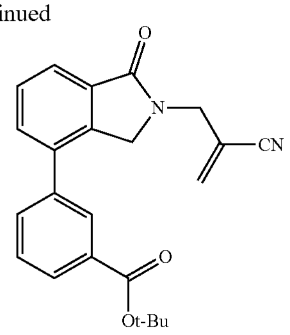

To a mixture of 2-[(4-bromo-1-oxo-2,3-dihydro-1H-isoindol-2-yl)methyl]prop-2-enenitrile (150 mg, 460.10 μmol, 1 eq.) and (3-tert-butoxycarbonylphenyl)boronic acid (204.32 mg, 920.19 μmol, 2 eq.) in dioxane (4 mL) and water (1 mL) were added $Cs_2CO_3$ (449.72 mg, 1.38 mmol, 3 eq.) and Pd(dppf)$Cl_2$ (16.83 mg, 23 μmol, 0.05 eq.). The mixture was heated to 90° C. under nitrogen and stirred for 1 h. TLC showed that the reaction was complete. The reaction mixture was stirred by addition sat. EDTA solution (25 mL) and EtOAc (25 mL) at 25° C. for 1 h, and extracted with EtOAc (30 mL×2). The combined organic layers were washed with water (50 mL×2) and brine (50 mL×2), dried over anhydrous sodium sulfate, filtered, and concentrated in vacuo to give a residue. The residue was purified by prep-TLC (silica gel; DCM:MeOH=30:1) to afford the title compound (0.15 g, 400.61 μmol, 87.07% yield) as a yellow oil.

2A.19. Preparation of 3-[2-(2-cyano-2-methylidene-ethyl)-1-oxo-2,3-dihydro-1H-isoindol-4-yl]benzoic acid

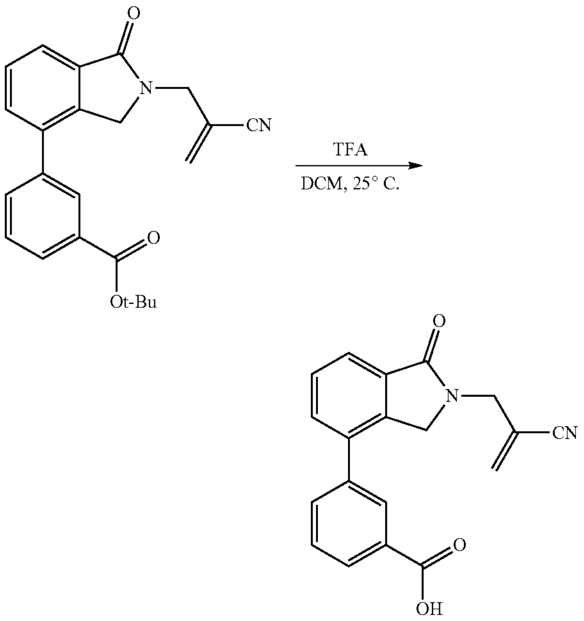 [SMILES: C=C(C#N)CN1Cc2c(cccc2-c2cccc(C(=O)OC(C)(C)C)c2)C1=O ; C=C(C#N)CN1Cc2c(cccc2-c2cccc(C(=O)O)c2)C1=O]

To a solution of tert-butyl 3-[2-(2-cyano-2-methylidene-ethyl)-1-oxo-2,3-dihydro-1H-isoindol-4-yl]benzoate (0.15 g, 400.61 μmol, 1 eq.) in DCM (4 mL) was added trifluoroacetic acid (1.54 g, 13.51 mmol, 1 mL, 33.71 eq.). The mixture was stirred at 25° C. for 12 h under nitrogen. LCMS indicated that the reaction was complete. The reaction mixture was concentrated in vacuo to afford the title compound (0.12 g, crude) as a brown oil, which was used directly without any further purification.

2A.20. General Procedure for Coupling with Amine

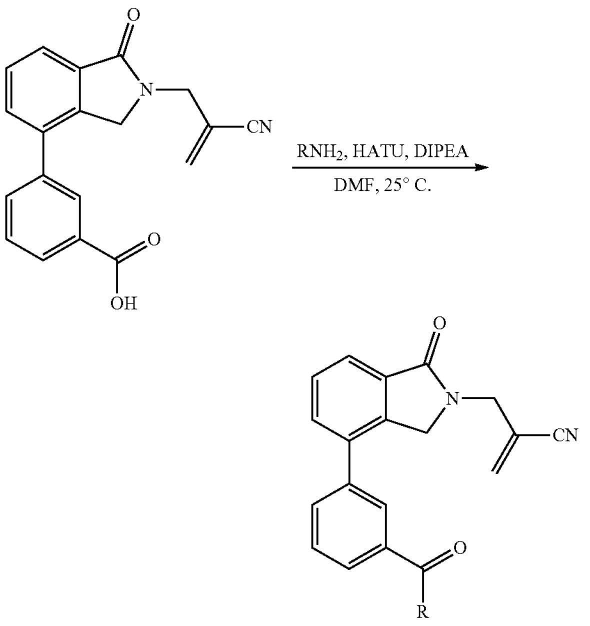

To a solution of 3-[2-(2-cyano-2-methylideneethyl)-1-oxo-2,3-dihydro-1H-isoindol-4-yl]benzoic acid (50 mg, 1 eq.) in DMF (5 mL) were added DIPEA (5 eq.) and HATU (1.5 eq.). The mixture was stirred at 25° C. for 15 minutes under nitrogen, and $RNH_2$ (1.5 eq.) was added. The reaction was stirred for 5 h. TLC and LCMS showed that the reaction was complete. The reaction mixture was diluted with water (20 mL) and extracted with EtOAc (15 mL×2). The combined organic layers were washed with water (25 mL×2) and brine (25 mL×2), dried over anhydrous sodium sulfate, filtered, and concentrated in vacuo to give a residue. The residue was purified by prep-TLC to afford the title compound (6.4 mg, 14.47 μmol, 9.21% yield, 93.7% purity) as a white solid.

2A.21. General Procedure for Boc Deprotection

Preparation of 2-[[4-(1H-indazol-6-yl)-1-oxo-isoindolin-2-yl]methyl]prop-2-enenitrile (Compound 57)

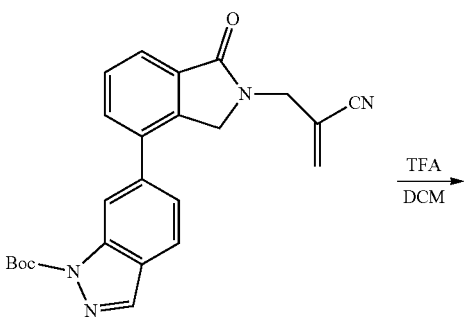

-continued

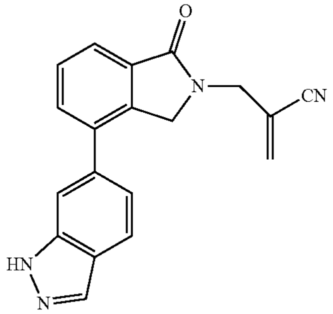

To a solution of tert-butyl 6-[2-(2-cyanoallyl)-1-oxo-isoindolin-4-yl]indazole-1-carboxylate (30.5 mg, 73 μmol) in DCM (1.6 mL) was added trifluoroacetic acid (0.4 mL) at 0° C. The resulting solution was stirred at r.t. for 2 h. The reaction mixture was concentrated in vacuo and the residue was diluted with DCM washed with sat. $NaHCO_3$ and brine, dried over anhydrous sodium sulfate, filtered, and concentrated. The residue was purified by chromatography on silica gel eluting with 40-100% EtOAc/hexane to afford the title compound (13.6 mg, Yield 59%), LC-MS: $[M+H]^+$ 315.

2B. Preparation of Compounds

TABLE 1 shows compounds containing an isoindolinone core.

TABLE 1

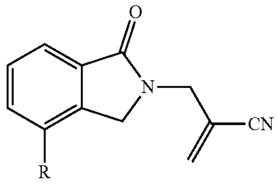

| Cpd. No. | Structure | IUPAC | LC-MS (ES+, m/z) |
|---|---|---|---|
| 1 | 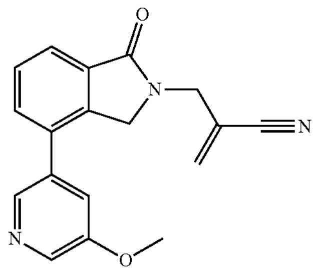 [SMILES: C=C(C#N)CN1Cc2c(cccc2-c2cncc(OC)c2)C1=O] | 2-{[4-(5-methoxypyridin-3-yl)-1-oxo-2,3-dihydro-1H-isoindol-2-yl]methyl}prop-2-enenitrile | 306.1 |
| 2 | 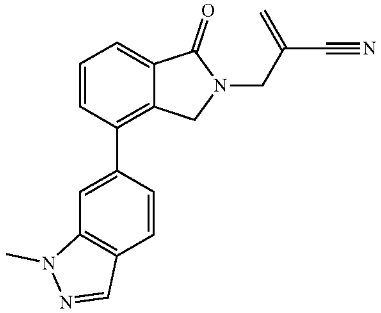 | 2-{[4-(1-methyl-1H-indazol-6-yl)-1-oxo-2,3-dihydro-1H-isoindol-2-yl]methyl}prop-2-enenitrile | 329.1 |
| 3 | 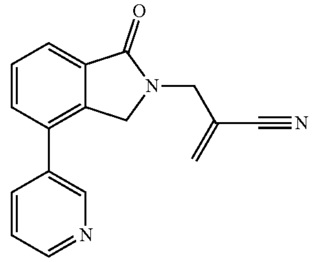 [SMILES: C=C(C#N)CN1Cc2c(cccc2-c2cccnc2)C1=O] | 2-{[1-oxo-4-(pyridin-3-yl)-2,3-dihydro-1H-isoindol-2-yl]methyl}prop-2-enenitrile | 276.1 |

TABLE 1-continued
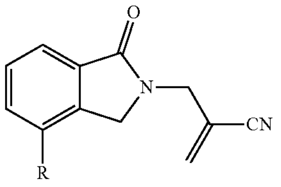
| Cpd. No. | Structure | IUPAC | LC-MS (ES+, m/z) |
|---|---|---|---|
| 4 | 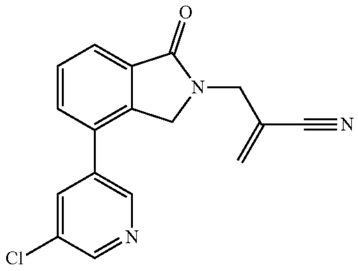 [SMILES: C=C(C#N)CN1Cc2c(cccc2-c2cncc(Cl)c2)C1=O] | 2-{[4-(5-chloropyridin-3-yl)-1-oxo-2,3-dihydro-1H-isoindol-2-yl]methyl}prop-2-enenitrile | 310 |
| 5 | 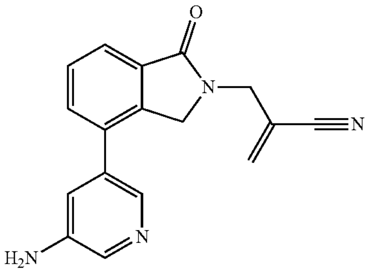 [SMILES: C=C(C#N)CN1Cc2c(cccc2-c2cncc(N)c2)C1=O] | 2-{[4-(5-aminopyridin-3-yl)-1-oxo-2,3-dihydro-1H-isoindol-2-yl]methyl}prop-2-enenitrile | 291.1 |
| 6 | 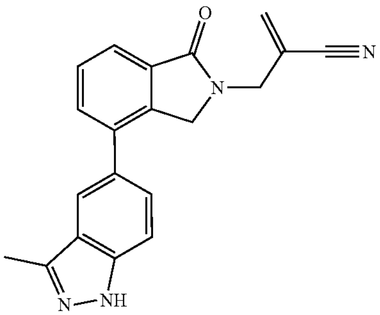 [SMILES: C=C(C#N)CN1Cc2c(cccc2-c2ccc3[nH]nc(C)c3c2)C1=O] | 2-{[4-(3-methyl-1H-indazol-5-yl)-1-oxo-2,3-dihydro-1H-isoindol-2-yl]methyl}prop-2-enenitrile | 329.1 |
| 7 | 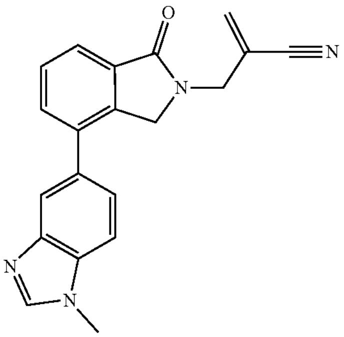 [SMILES: C=C(C#N)CN1Cc2c(cccc2-c2ccc3c(c2)ncn3C)C1=O] | 2-{[4-(1-methyl-1H-1,3-benzodiazol-5-yl)-1-oxo-2,3-dihydro-1H-isoindol-2-yl]methyl}prop-2-enenitrile | 329.1 |

TABLE 1-continued
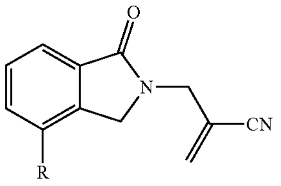
| Cpd. No. | Structure | IUPAC | LC-MS (ES+, m/z) |
|---|---|---|---|
| 8 | 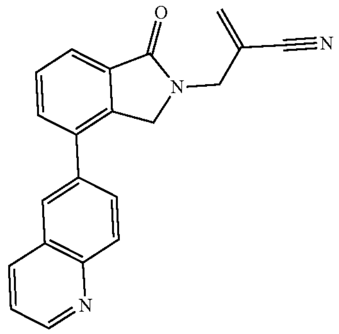 [SMILES: C=C(C#N)CN1Cc2c(cccc2-c2ccc3ncccc3c2)C1=O] | 2-{[1-oxo-4-(quinolin-6-yl)-2,3-dihydro-1H-isoindol-2-yl]methyl}prop-2-enenitrile | 326.1 |
| 9 | 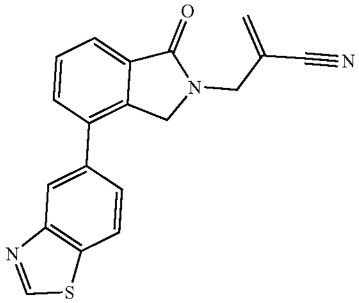 [SMILES: C=C(C#N)CN1Cc2c(cccc2-c2ccc3scnc3c2)C1=O] | 2-{[4-(1,3-benzothiazol-5-yl)-1-oxo-2,3-dihydro-1H-isoindol-2-yl]methyl}prop-2-enenitrile | 332 |
| 10 | 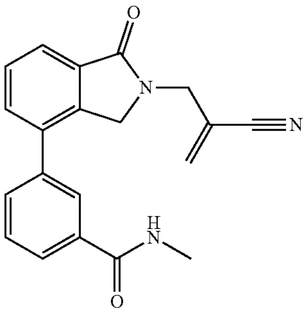 [SMILES: C=C(C#N)CN1Cc2c(cccc2-c2cccc(C(=O)NC)c2)C1=O] | 3-[2-(2-cyano-2-methylideneethyl)-1-oxo-2,3-dihydro-1H-isoindol-4-yl]-N-methylbenzamide | 332.1 |
| 11 | 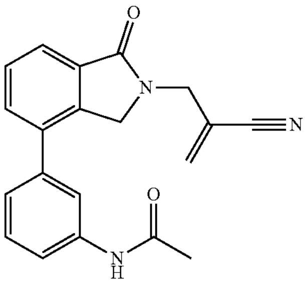 [SMILES: C=C(C#N)CN1Cc2c(cccc2-c2cccc(NC(C)=O)c2)C1=O] | N-{3-[2-(2-cyano-2-methylideneethyl)-1-oxo-2,3-dihydro-1H-isoindol-4-yl]phenyl}acetamide | 332 |

TABLE 1-continued
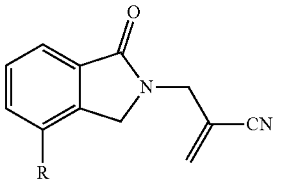
| Cpd. No. | Structure | IUPAC | LC-MS (ES+, m/z) |
|---|---|---|---|
| 12 | 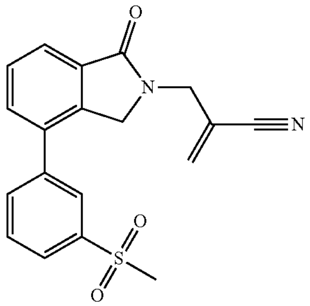 [SMILES: C=C(C#N)CN1Cc2c(cccc2-c2cccc(S(C)(=O)=O)c2)C1=O] | 2-{[4-(3-methanesulfonylphenyl)-1-oxo-2,3-dihydro-1H-isoindol-2-yl]methyl}prop-2-enenitrile | 353 |
| 13 | 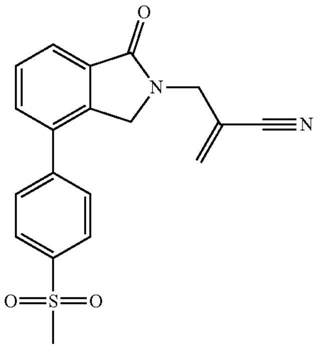 [SMILES: C=C(C#N)CN1Cc2c(cccc2-c2ccc(S(C)(=O)=O)cc2)C1=O] | 2-{[4-(4-methanesulfonylphenyl)-1-oxo-2,3-dihydro-1H-isoindol-2-yl]methyl}prop-2-enenitrile | 353 |
| 14 | 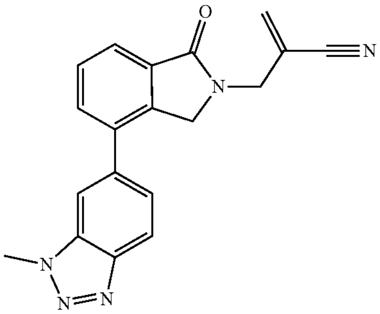 [SMILES: C=C(C#N)CN1Cc2c(cccc2-c2ccc3nnn(C)c3c2)C1=O] | 2-{[4-(1-methyl-1H-1,2,3-benzotriazol-6-yl)-1-oxo-2,3-dihydro-1H-isoindol-2-yl]methyl}prop-2-enenitrile | 330.1 |
| 15 | 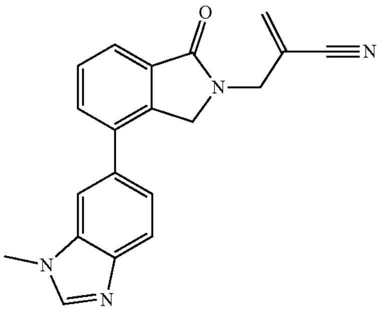 [SMILES: C=C(C#N)CN1Cc2c(cccc2-c2ccc3ncn(C)c3c2)C1=O] | 2-{[4-(1-methyl-1H-1,3-benzodiazol-6-yl)-1-oxo-2,3-dihydro-1H-isoindol-2-yl]methyl}prop-2-enenitrile | 329.1 |

TABLE 1-continued
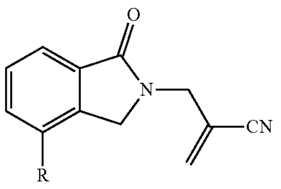
| Cpd. No. | Structure | IUPAC | LC-MS (ES+, m/z) |
|---|---|---|---|
| 16 | 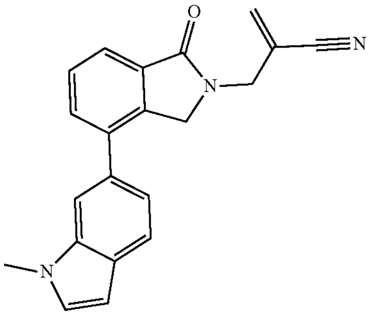 [SMILES: C=C(C#N)CN1Cc2c(cccc2-c2ccc3ccn(C)c3c2)C1=O] | 2-{[4-(1-methyl-1H-indol-6-yl)-1-oxo-2,3-dihydro-1H-isoindol-2-yl]methyl}prop-2-enenitrile | 328.1 |
| 17 | 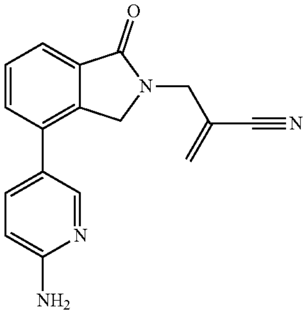 [SMILES: C=C(C#N)CN1Cc2c(cccc2-c2ccc(N)nc2)C1=O] | 2-{[4-(6-aminopyridin-3-yl)-1-oxo-2,3-dihydro-1H-isoindol-2-yl]methyl}prop-2-enenitrile | 291.1 |
| 18 | 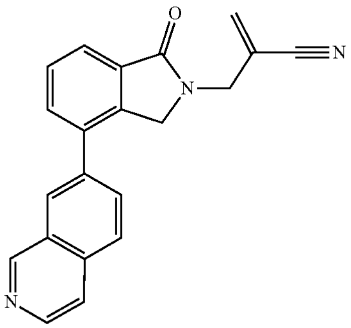 | 2-{[4-(isoquinolin-7-yl)-1-oxo-2,3-dihydro-1H-isoindol-2-yl]methyl}prop-2-enenitrile | 326.2 |
| 19 | 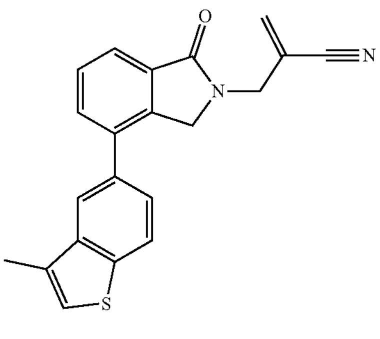 [SMILES: C=C(C#N)CN1Cc2c(cccc2-c2ccc3scc(C)c3c2)C1=O] | 2-{[4-(3-methyl-1-benzothiophen-5-yl)-1-oxo-2,3-dihydro-1H-isoindol-2-yl]methyl}prop-2-enenitrile | 345 |

TABLE 1-continued
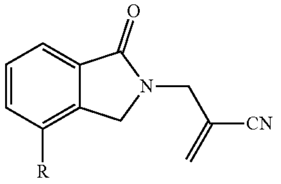
| Cpd. No. | Structure | IUPAC | LC-MS (ES+, m/z) |
|---|---|---|---|
| 20 | 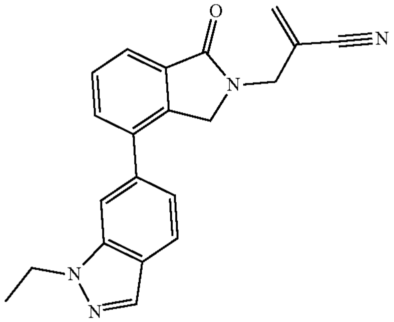 [SMILES: C=C(C#N)CN1Cc2c(cccc2-c2ccc3cnn(CC)c3c2)C1=O] | 2-{[4-(1-ethyl-1H-indazol-6-yl)-1-oxo-2,3-dihydro-1H-isoindol-2-yl]methyl}prop-2-enenitrile | 343.1 |
| 21 | 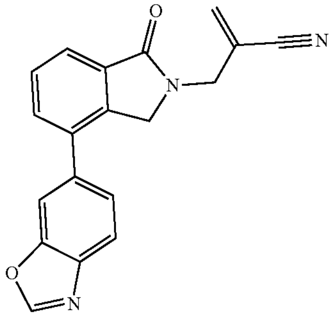 [SMILES: C=C(C#N)CN1Cc2c(cccc2-c2ccc3ncoc3c2)C1=O] | 2-{[4-(1,3-benzoxazol-6-yl)-1-oxo-2,3-dihydro-1H-isoindol-2-yl]methyl}prop-2-enenitrile | 316.2 |
| 22 | 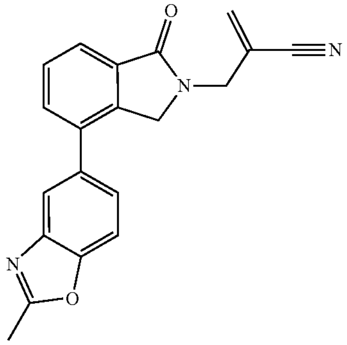 [SMILES: C=C(C#N)CN1Cc2c(cccc2-c2ccc3oc(C)nc3c2)C1=O] | 2-{[4-(2-methyl-1,3-benzoxazol-5-yl)-1-oxo-2,3-dihydro-1H-isoindol-2-yl]methyl}prop-2-enenitrile | 330.1 |
| 23 | 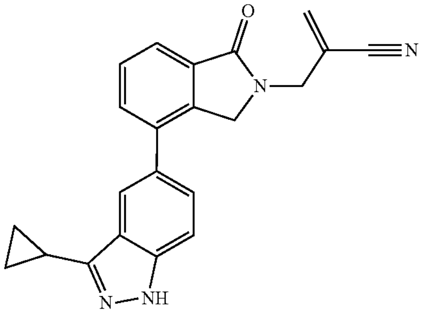 [SMILES: C=C(C#N)CN1Cc2c(cccc2-c2ccc3[nH]nc(C4CC4)c3c2)C1=O] | 2-{[4-(3-cyclopropyl-1H-indazol-5-yl)-1-oxo-2,3-dihydro-1H-isoindol-2-yl]methyl}prop-2-enenitrile | 355.1 |

TABLE 1-continued
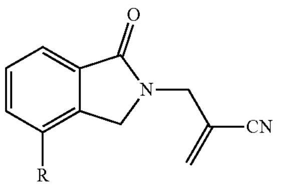
| Cpd. No. | Structure | IUPAC | LC-MS (ES+, m/z) |
|---|---|---|---|
| 24 | 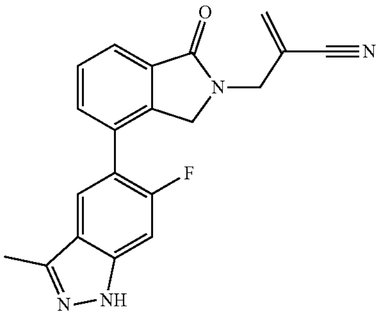 [SMILES: C=C(C#N)CN1Cc2c(cccc2-c2cc3c(C)n[nH]c3cc2F)C1=O] | 2-{[4-(6-fluoro-3-methyl-1H-indazol-5-yl)-1-oxo-2,3-dihydro-1H-isoindol-2-yl]methyl}prop-2-enenitrile | 347.2 |
| 25 | 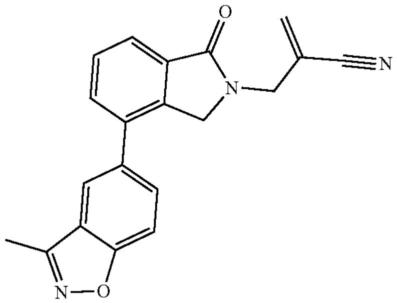 [SMILES: C=C(C#N)CN1Cc2c(cccc2-c2ccc3onc(C)c3c2)C1=O] | 2-{[4-(3-methyl-1,2-benzoxazol-5-yl)-1-oxo-2,3-dihydro-1H-isoindol-2-yl]methyl}prop-2-enenitrile | 330.1 |
| 26 | 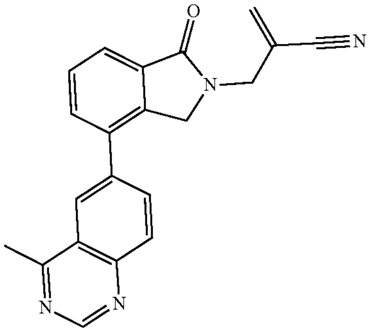 [SMILES: C=C(C#N)CN1Cc2c(cccc2-c2ccc3ncnc(C)c3c2)C1=O] | 2-{[4-(4-methylquinazolin-6-yl)-1-oxo-2,3-dihydro-1H-isoindol-2-yl]methyl}prop-2-enenitrile | 341.1 |
| 27 | 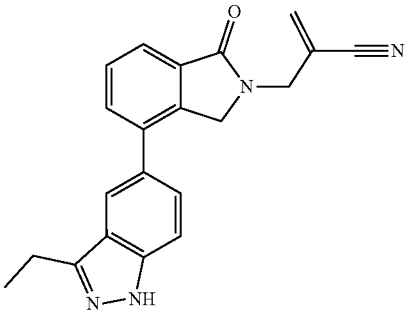 [SMILES: C=C(C#N)CN1Cc2c(cccc2-c2ccc3[nH]nc(CC)c3c2)C1=O] | 2-{[4-(3-ethyl-1H-indazol-5-yl)-1-oxo-2,3-dihydro-1H-isoindol-2-yl]methyl}prop-2-enenitrile | 343.1 |

TABLE 1-continued
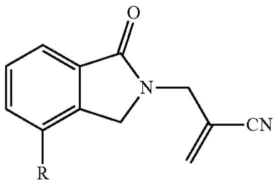
| Cpd. No. | Structure | IUPAC | LC-MS (ES+, m/z) |
|---|---|---|---|
| 28 | 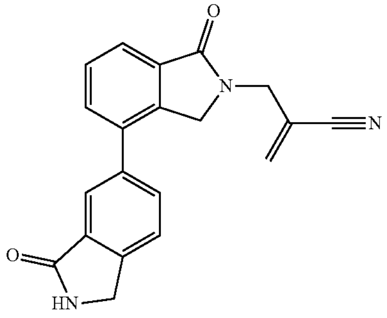 [SMILES: C=C(C#N)CN1Cc2c(cccc2-c2ccc3c(c2)C(=O)NC3)C1=O] | 2-({1,3'-dioxo-1H,1'H,2H,2'H,3H,3'H-[4,5'-biisoindol]-2-yl}methyl)prop-2-enenitrile | 330.2 |
| 29 | 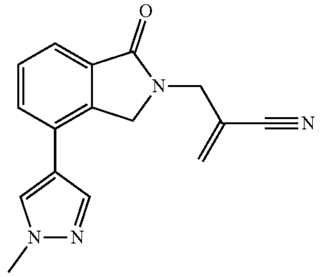 [SMILES: C=C(C#N)CN1Cc2c(cccc2-c2cnn(C)c2)C1=O] | 2-{[4-(1-methyl-1H-pyrazol-4-yl)-1-oxo-2,3-dihydro-1H-isoindol-2-yl]methyl}prop-2-enenitrile | 279 |
| 30 | 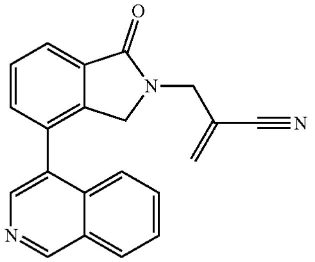 [SMILES: C=C(C#N)CN1Cc2c(cccc2-c2cncc3ccccc23)C1=O] | 2-{[4-(isoquinolin-4-yl)-1-oxo-2,3-dihydro-1H-isoindol-2-yl]methyl}prop-2-enenitrile | 326.1 |
| 31 | 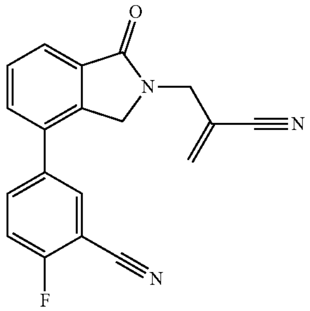 [SMILES: C=C(C#N)CN1Cc2c(cccc2-c2ccc(F)c(C#N)c2)C1=O] | 5-[2-(2-cyano-2-methylideneethyl)-1-oxo-2,3-dihydro-1H-isoindol-4-yl]-2-fluorobenzonitrile | 318 |

TABLE 1-continued
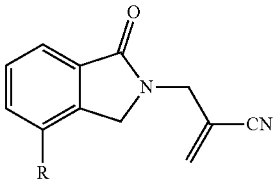
| Cpd. No. | Structure | IUPAC | LC-MS (ES+, m/z) |
|---|---|---|---|
| 32 | 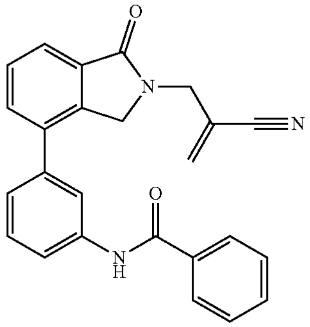 [SMILES: C=C(C#N)CN1Cc2c(cccc2-c2cccc(NC(=O)c3ccccc3)c2)C1=O] | N-{3-[2-(2-cyano-2-methylideneethyl)-1-oxo-2,3-dihydro-1H-isoindol-4-yl]phenyl}benzamide | 394 |
| 33 | 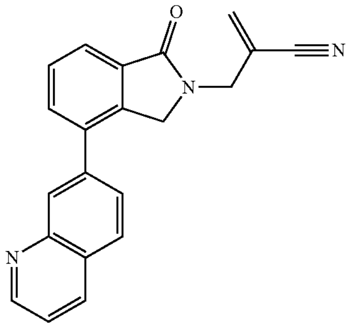 [SMILES: C=C(C#N)CN1Cc2c(cccc2-c2ccc3cccnc3c2)C1=O] | 2-{[1-oxo-4-(quinolin-7-yl)-2,3-dihydro-1H-isoindol-2-yl]methyl}prop-2-enenitrile | 326.1 |
| 34 | 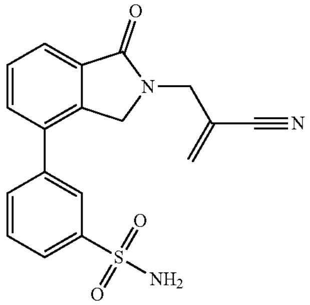 [SMILES: C=C(C#N)CN1Cc2c(cccc2-c2cccc(S(N)(=O)=O)c2)C1=O] | 3-[2-(2-cyano-2-methylideneethyl)-1-oxo-2,3-dihydro-1H-isoindol-4-yl]benzene-1-sulfonamide | 352 |
| 35 | 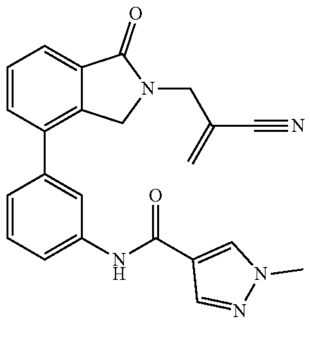 [SMILES: C=C(C#N)CN1Cc2c(cccc2-c2cccc(NC(=O)c3cnn(C)c3)c2)C1=O] | N-{3-[2-(2-cyano-2-methylideneethyl)-1-oxo-2,3-dihydro-1H-isoindol-4-yl]phenyl}-1-methyl-1H-pyrazole-4-carboxamide | 398.1 |

TABLE 1-continued
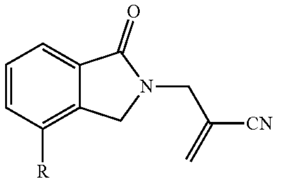
| Cpd. No. | Structure | IUPAC | LC-MS (ES+, m/z) |
|---|---|---|---|
| 36 | 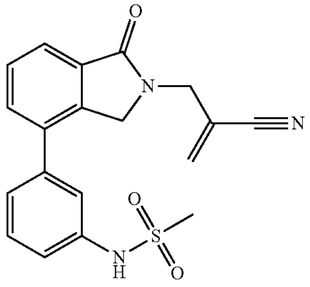 [SMILES: C=C(C#N)CN1Cc2c(cccc2-c2cccc(NS(C)(=O)=O)c2)C1=O] | N-{3-[2-(2-cyano-2-methylideneethyl)-1-oxo-2,3-dihydro-1H-isoindol-4-yl]phenyl}methanesulfonamide | 368 |
| 37 | 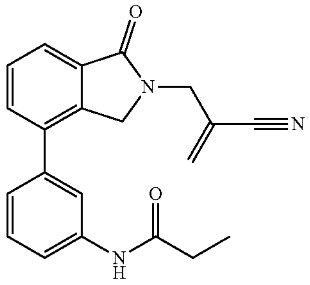 [SMILES: C=C(C#N)CN1Cc2c(cccc2-c2cccc(NC(=O)CC)c2)C1=O] | N-{3-[2-(2-cyano-2-methylideneethyl)-1-oxo-2,3-dihydro-1H-isoindol-4-yl]phenyl}propanamide | 346.1 |
| 38 | 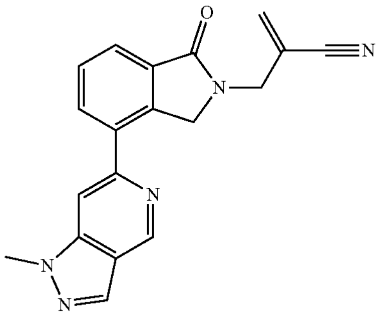 | 2-[(4-{1-methyl-1H-pyrazolo[4,3-c]pyridin-6-yl}-1-oxo-2,3-dihydro-1H-isoindol-2-yl)methyl]prop-2-enenitrile | 330.2 |
| 39 | 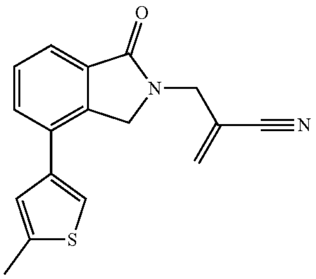 [SMILES: C=C(C#N)CN1Cc2c(cccc2-c2csc(C)c2)C1=O] | 2-{[4-(5-methylthiophen-3-yl)-1-oxo-2,3-dihydro-1H-isoindol-2-yl]methyl}prop-2-enenitrile | 295.1 |

TABLE 1-continued
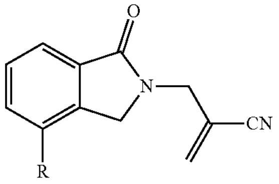
| Cpd. No. | Structure | IUPAC | LC-MS (ES+, m/z) |
|---|---|---|---|
| 40 | 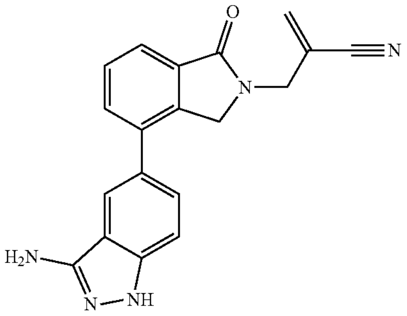 [SMILES: C=C(C#N)CN1Cc2c(cccc2-c2ccc3[nH]nc(N)c3c2)C1=O] | 2-{[4-(3-amino-1H-indazol-5-yl)-1-oxo-2,3-dihydro-1H-isoindol-2-yl]methyl}prop-2-enenitrile | 330.2 |
| 41 | 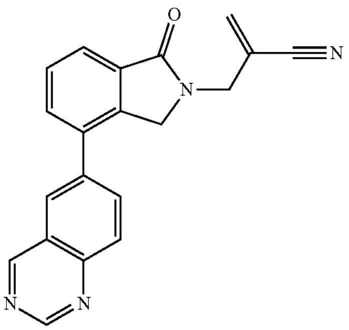 [SMILES: C=C(C#N)CN1Cc2c(cccc2-c2ccc3ncncc3c2)C1=O] | 2-{[1-oxo-4-(quinazolin-6-yl)-2,3-dihydro-1H-isoindol-2-yl]methyl}prop-2-enenitrile | 327.1 |
| 42 | 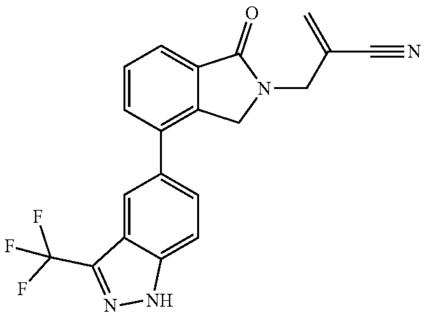 [SMILES: C=C(C#N)CN1Cc2c(cccc2-c2ccc3[nH]nc(C(F)(F)F)c3c2)C1=O] | 2-({1-oxo-4-[3-(trifluoromethyl)-1H-indazol-5-yl]-2,3-dihydro-1H-isoindol-2-yl}methyl)prop-2-enenitrile | 383.1 |
| 43 | 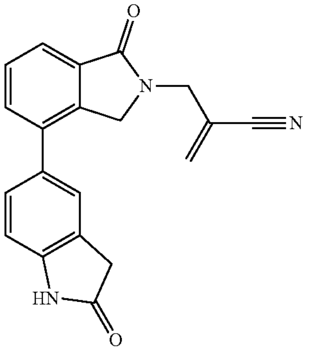 [SMILES: C=C(C#N)CN1Cc2c(cccc2-c2ccc3c(c2)CC(=O)N3)C1=O] | 2-{[1-oxo-4-(2-oxo-2,3-dihydro-1H-indol-5-yl)-2,3-dihydro-1H-isoindol-2-yl]methyl}prop-2-enenitrile | 330.1 |

TABLE 1-continued
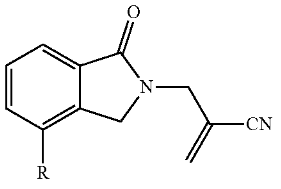
| Cpd. No. | Structure | IUPAC | LC-MS (ES+, m/z) |
|---|---|---|---|
| 44 | 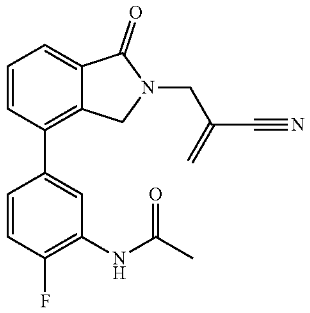 [SMILES: C=C(C#N)CN1Cc2c(cccc2-c2ccc(F)c(NC(C)=O)c2)C1=O] | N-{5-[2-(2-cyano-2-methylideneethyl)-1-oxo-2,3-dihydro-1H-isoindol-4-yl]-2-fluorophenyl}acetamide | 350 |
| 45 | 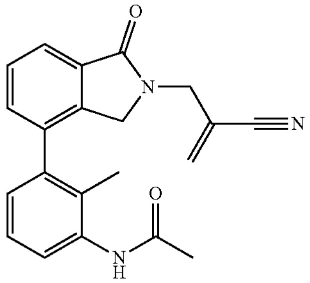 [SMILES: C=C(C#N)CN1Cc2c(cccc2-c2cccc(NC(C)=O)c2C)C1=O] | N-{3-[2-(2-cyano-2-methylideneethyl)-1-oxo-2,3-dihydro-1H-isoindol-4-yl]-2-methylphenyl}acetamide | 346.1 |
| 46 | 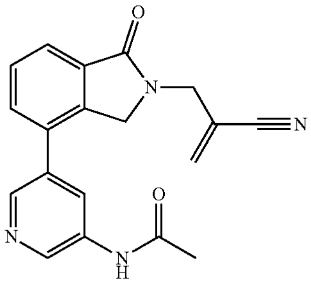 [SMILES: C=C(C#N)CN1Cc2c(cccc2-c2cncc(NC(C)=O)c2)C1=O] | N-{5-[2-(2-cyano-2-methylideneethyl)-1-oxo-2,3-dihydro-1H-isoindol-4-yl]pyridin-3-yl}acetamide | 333.1 |
| 47 | 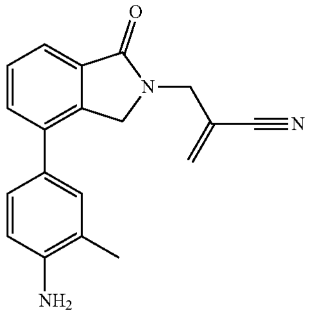 [SMILES: C=C(C#N)CN1Cc2c(cccc2-c2ccc(N)c(C)c2)C1=O] | 2-{[4-(4-amino-3-methylphenyl)-1-oxo-2,3-dihydro-1H-isoindol-2-yl]methyl}prop-2-enenitrile | 304.1 |

TABLE 1-continued
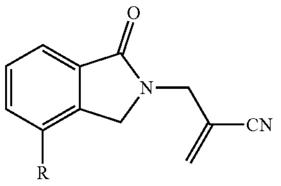
| Cpd. No. | Structure | IUPAC | LC-MS (ES+, m/z) |
| --- | --- | --- | --- |
| 48 | 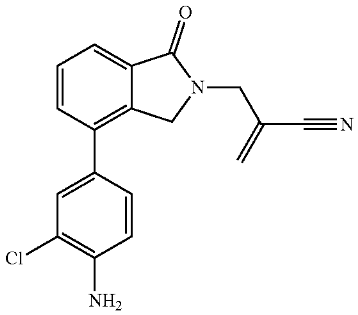 [SMILES: C=C(C#N)CN1Cc2c(cccc2-c2ccc(N)c(Cl)c2)C1=O] | 2-{[4-(4-amino-3-chlorophenyl)-1-oxo-2,3-dihydro-1H-isoindol-2-yl]methyl}prop-2-enenitrile | 324 |
| 49 | 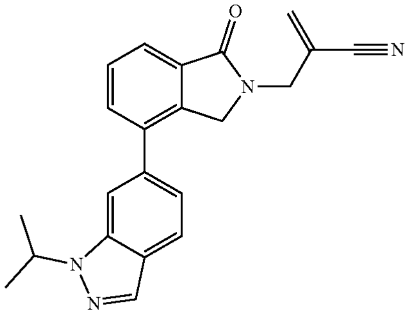 [SMILES: C=C(C#N)CN1Cc2c(cccc2-c2ccc3cnn(C(C)C)c3c2)C1=O] | 2-({1-oxo-4-[1-(propan-2-yl)-1H-indazol-6-yl]-2,3-dihydro-1H-isoindol-2-yl}methyl)prop-2-enenitrile | 357.1 |
| 50 | 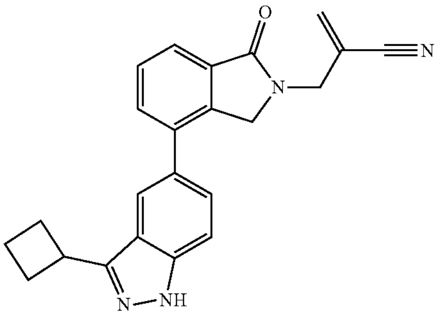 [SMILES: C=C(C#N)CN1Cc2c(cccc2-c2ccc3[nH]nc(C4CCC4)c3c2)C1=O] | 2-{[4-(3-cyclobutyl-1H-indazol-5-yl)-1-oxo-2,3-dihydro-1H-isoindol-2-yl]methyl}prop-2-enenitrile | 369.2 |
| 51 | 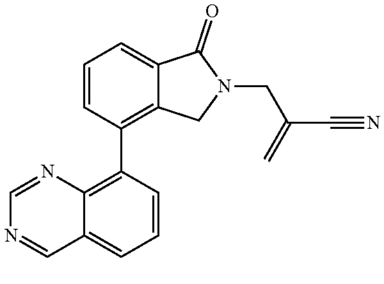 [SMILES: C=C(C#N)CN1Cc2c(cccc2-c2cccc3cncnc23)C1=O] | 2-{[1-oxo-4-(quinazolin-8-yl)-2,3-dihydro-1H-isoindol-2-yl]methyl}prop-2-enenitrile | 327.1 |

TABLE 1-continued
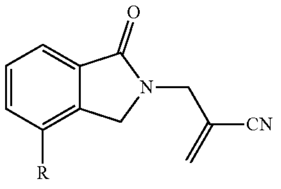
| Cpd. No. | Structure | IUPAC | LC-MS (ES+, m/z) |
|---|---|---|---|
| 52 | 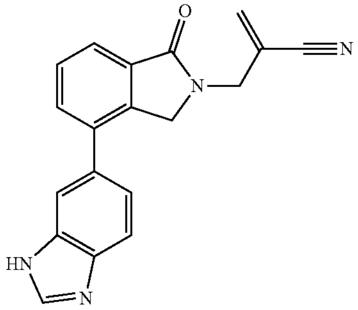 [SMILES: C=C(C#N)CN1Cc2c(cccc2-c2ccc3nc[nH]c3c2)C1=O] | 2-{[4-(1H-1,3-benzodiazol-6-yl)-1-oxo-2,3-dihydro-1H-isoindol-2-yl]methyl}prop-2-enenitrile | 315 |
| 53 | 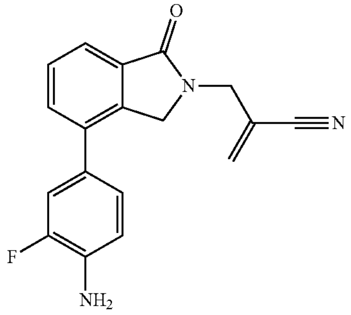 [SMILES: C=C(C#N)CN1Cc2c(cccc2-c2ccc(N)c(F)c2)C1=O] | 2-{[4-(4-amino-3-fluorophenyl)-1-oxo-2,3-dihydro-1H-isoindol-2-yl]methyl}prop-2-enenitrile | 308.1 |
| 54 | 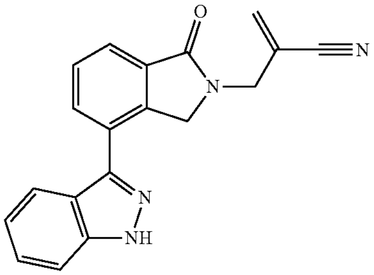 [SMILES: C=C(C#N)CN1Cc2c(cccc2-c2n[nH]c3ccccc23)C1=O] | 2-{[4-(1H-indazol-3-yl)-1-oxo-2,3-dihydro-1H-isoindol-2-yl]methyl}prop-2-enenitrile | 315 |
| 55 | 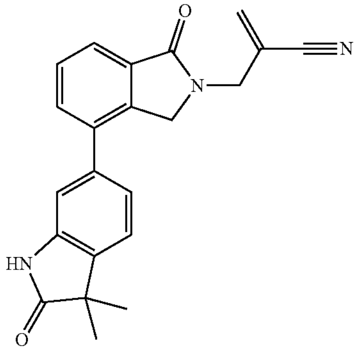 [SMILES: C=C(C#N)CN1Cc2c(cccc2-c2ccc3c(c2)NC(=O)C3(C)C)C1=O] | 2-{[4-(3,3-dimethyl-2-oxo-2,3-dihydro-1H-indol-6-yl)-1-oxo-2,3-dihydro-1H-isoindol-2-yl]methyl}prop-2-enenitrile | 358.2 |

TABLE 1-continued
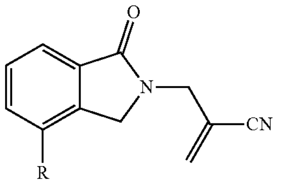
| Cpd. No. | Structure | IUPAC | LC-MS (ES+, m/z) |
|---|---|---|---|
| 56 | 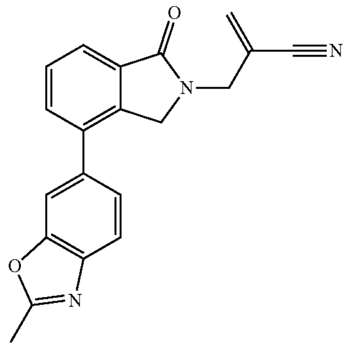 [SMILES: C=C(C#N)CN1Cc2c(cccc2-c2ccc3nc(C)oc3c2)C1=O] | 2-{[4-(2-methyl-1,3-benzoxazol-6-yl)-1-oxo-2,3-dihydro-1H-isoindol-2-yl]methyl}prop-2-enenitrile | 330.2 |
| 57 | 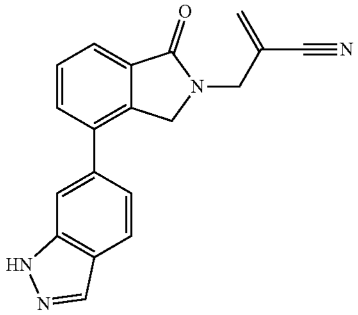 [SMILES: C=C(C#N)CN1Cc2c(cccc2-c2ccc3cn[nH]c3c2)C1=O] | 2-{[4-(1H-indazol-6-yl)-1-oxo-2,3-dihydro-1H-isoindol-2-yl]methyl}prop-2-enenitrile | 315.1 |
| 58 | 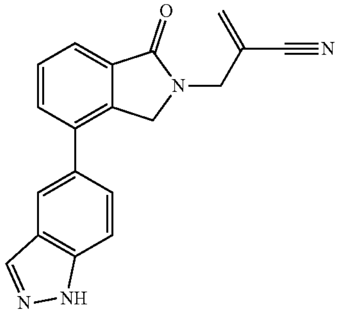 [SMILES: C=C(C#N)CN1Cc2c(cccc2-c2ccc3[nH]ncc3c2)C1=O] | 2-{[4-(1H-indazol-5-yl)-1-oxo-2,3-dihydro-1H-isoindol-2-yl]methyl}prop-2-enenitrile | 313.1 (negative ion) |
| 59 | 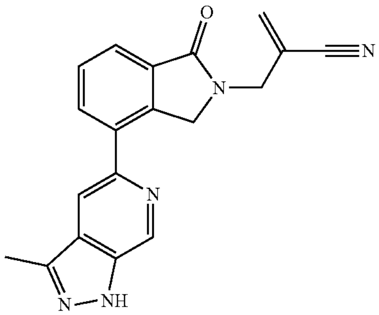 [SMILES: C=C(C#N)CN1Cc2c(cccc2-c2cc3c(C)n[nH]c3cn2)C1=O] | 2-[(4-{3-methyl-1H-pyrazolo[3,4-c]pyridin-5-yl}-1-oxo-2,3-dihydro-1H-isoindol-2-yl)methyl]prop-2-enenitrile | 330.2 |

TABLE 1-continued
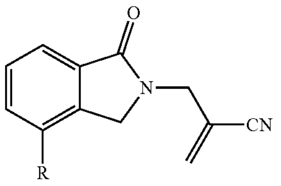
| Cpd. No. | Structure | IUPAC | LC-MS (ES+, m/z) |
|---|---|---|---|
| 60 | 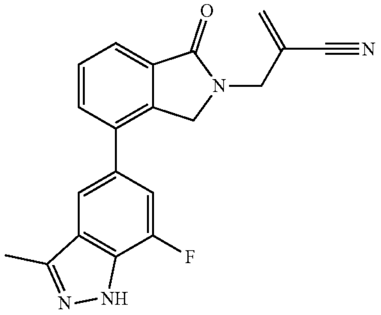 [SMILES: C=C(C#N)CN1Cc2c(cccc2-c2cc(F)c3[nH]nc(C)c3c2)C1=O] | 2-{[4-(7-fluoro-3-methyl-1H-indazol-5-yl)-1-oxo-2,3-dihydro-1H-isoindol-2-yl]methyl}prop-2-enenitrile | 347.1 |
| 61 | 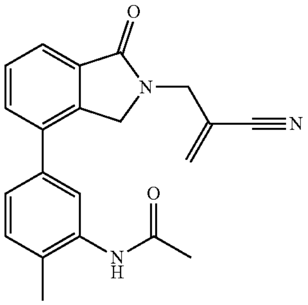 [SMILES: C=C(C#N)CN1Cc2c(cccc2-c2ccc(C)c(NC(C)=O)c2)C1=O] | N-{5-[2-(2-cyano-2-methylideneethyl)-1-oxo-2,3-dihydro-1H-isoindol-4-yl]-2-methylphenyl}acetamide | 346.1 |
| 62 | 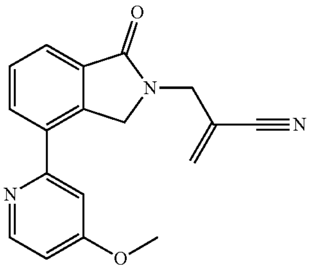 [SMILES: C=C(C#N)CN1Cc2c(cccc2-c2cc(OC)ccn2)C1=O] | 2-{[4-(4-methoxypyridin-2-yl)-1-oxo-2,3-dihydro-1H-isoindol-2-yl]methyl}prop-2-enenitrile | 306 |
| 63 | 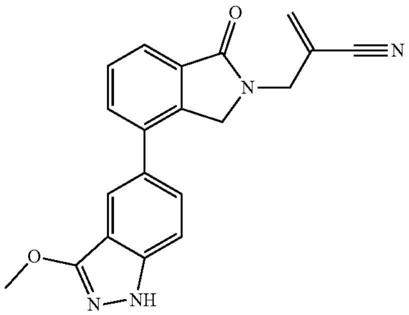 | 2-{[4-(3-methoxy-1H-indazol-5-yl)-1-oxo-2,3-dihydro-1H-isoindol-2-yl]methyl}prop-2-enenitrile | 345.1 |

TABLE 1-continued
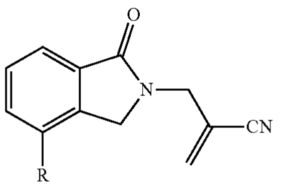
| Cpd. No. | Structure | IUPAC | LC-MS (ES+, m/z) |
|---|---|---|---|
| 64 | 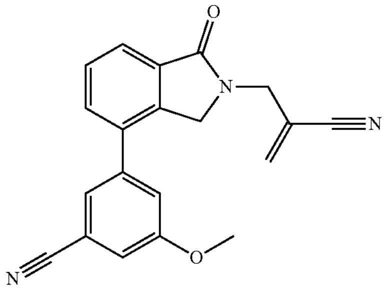 [SMILES: C=C(C#N)CN1Cc2c(cccc2-c2cc(C#N)cc(OC)c2)C1=O] | 3-[2-(2-cyano-2-methylideneethyl)-1-oxo-2,3-dihydro-1H-isoindol-4-yl]-5-methoxybenzonitrile | 330.1 |
| 65 | 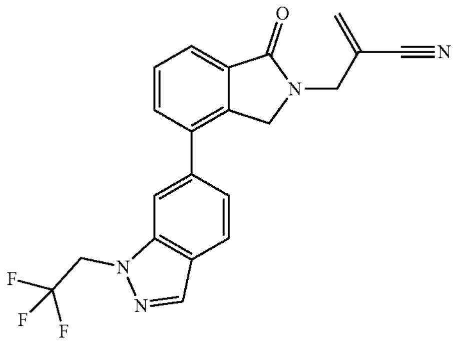 [SMILES: C=C(C#N)CN1Cc2c(cccc2-c2ccc3cnn(CC(F)(F)F)c3c2)C1=O] | 2-({1-oxo-4-[1-(2,2,2-trifluoroethyl)-1H-indazol-6-yl]-2,3-dihydro-1H-isoindol-2-yl}methyl)prop-2-enenitrile | 397.2 |
| 66 | 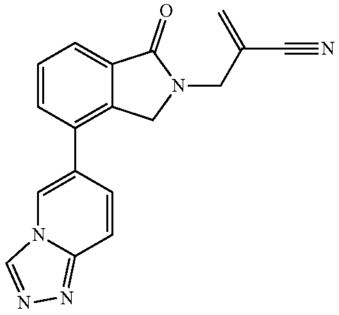 [SMILES: C=C(C#N)CN1Cc2c(cccc2-c2ccc3nncn3c2)C1=O] | 2-[(1-oxo-4-{[1,2,4]triazolo[4,3-a]pyridin-6-yl}-2,3-dihydro-1H-isoindol-2-yl)methyl]prop-2-enenitrile | 316.1 |
| 67 | 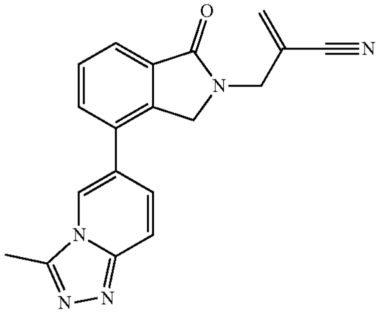 [SMILES: C=C(C#N)CN1Cc2c(cccc2-c2ccc3nnc(C)n3c2)C1=O] | 2-[(4-{3-methyl-[1,2,4]triazolo[4,3-a]pyridin-6-yl}-1-oxo-2,3-dihydro-1H-isoindol-2-yl)methyl]prop-2-enenitrile | 330.1 |

TABLE 1-continued
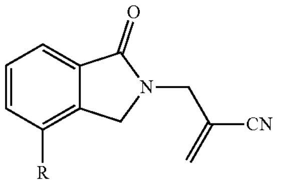
| Cpd. No. | Structure | IUPAC | LC-MS (ES+, m/z) |
|---|---|---|---|
| 68 | 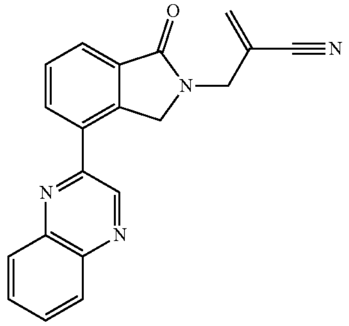 [SMILES: C=C(C#N)CN1Cc2c(cccc2-c2cnc3ccccc3n2)C1=O] | 2-{[1-oxo-4-(quinoxalin-2-yl)-2,3-dihydro-1H-isoindol-2-yl]methyl}prop-2-enenitrile | 327.1 |
| 69 | 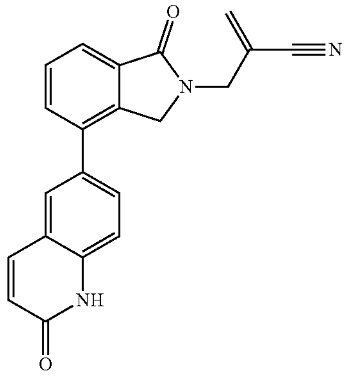 [SMILES: C=C(C#N)CN1Cc2c(cccc2-c2ccc3[nH]c(=O)ccc3c2)C1=O] | 2-{[1-oxo-4-(2-oxo-1,2-dihydroquinolin-6-yl)-2,3-dihydro-1H-isoindol-2-yl]methyl}prop-2-enenitrile | 342.2 |
| 70 | 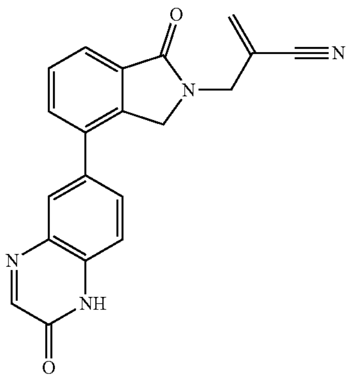 [SMILES: C=C(C#N)CN1Cc2c(cccc2-c2ccc3[nH]c(=O)cnc3c2)C1=O] | 2-{[1-oxo-4-(2-oxo-1,2-dihydroquinoxalin-6-yl)-2,3-dihydro-1H-isoindol-2-yl]methyl}prop-2-enenitrile | 343.2 |

TABLE 1-continued
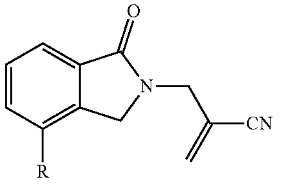
| Cpd. No. | Structure | IUPAC | LC-MS (ES+, m/z) |
|---|---|---|---|
| 71 | 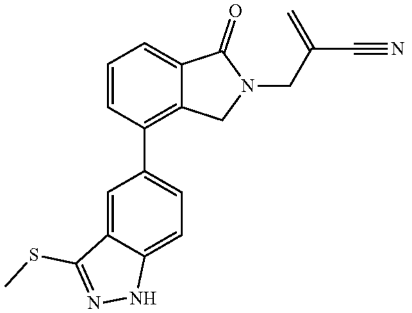 [SMILES: C=C(C#N)CN1Cc2c(cccc2-c2ccc3[nH]nc(SC)c3c2)C1=O] | 2-({4-[3-(methylsulfanyl)-1H-indazol-5-yl]-1-oxo-2,3-dihydro-1H-isoindol-2-yl}methyl)prop-2-enenitrile | 361.1 |
| 72 | 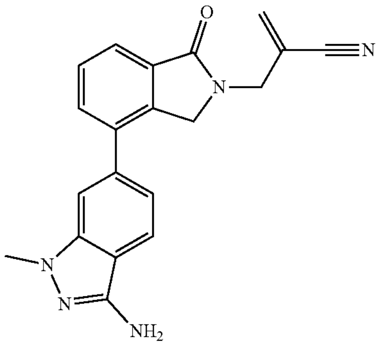 [SMILES: C=C(C#N)CN1Cc2c(cccc2-c2ccc3c(N)nn(C)c3c2)C1=O] | 2-{[4-(3-amino-1-methyl-1H-indazol-6-yl)-1-oxo-2,3-dihydro-1H-isoindol-2-yl]methyl}prop-2-enenitrile | 344.2 |
| 73 | 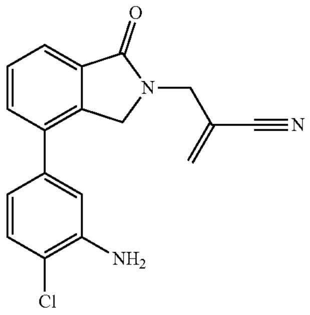 [SMILES: C=C(C#N)CN1Cc2c(cccc2-c2ccc(Cl)c(N)c2)C1=O] | 2-{[4-(3-amino-4-chlorophenyl)-1-oxo-2,3-dihydro-1H-isoindol-2-yl]methyl}prop-2-enenitrile | 324.1 |
| 74 | 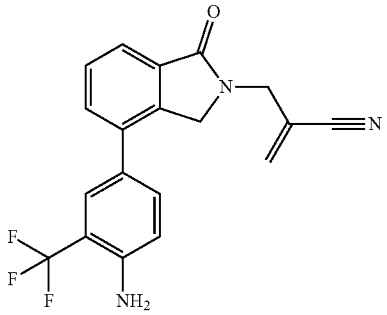 [SMILES: C=C(C#N)CN1Cc2c(cccc2-c2ccc(N)c(C(F)(F)F)c2)C1=O] | 2-({4-[4-amino-3-(trifluoromethyl)phenyl]-1-oxo-2,3-dihydro-1H-isoindol-2-yl}methyl)prop-2-enenitrile | 358.1 |

TABLE 1-continued

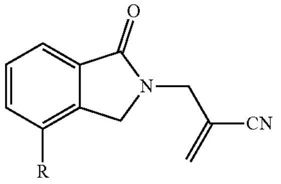

| Cpd. No. | Structure | IUPAC | LC-MS (ES+, m/z) |
|---|---|---|---|
| 75 | 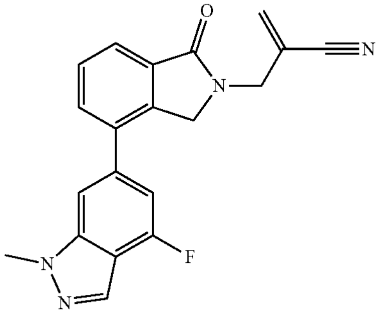 [SMILES: C=C(C#N)CN1Cc2c(cccc2-c2cc(F)c3cnn(C)c3c2)C1=O] | 2-{[4-(4-fluoro-1-methyl-1H-indazol-6-yl)-1-oxo-2,3-dihydro-1H-isoindol-2-yl]methyl}prop-2-enenitrile | 347.1 |
| 76 | 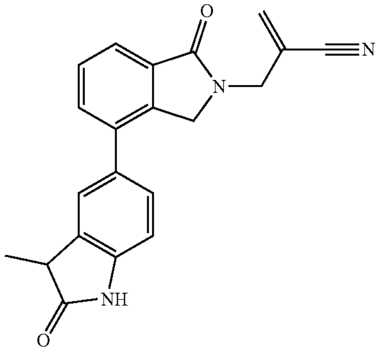 [SMILES: C=C(C#N)CN1Cc2c(cccc2-c2ccc3c(c2)C(C)C(=O)N3)C1=O] | 2-{[4-(3-methyl-2-oxo-2,3-dihydro-1H-indol-5-yl)-1-oxo-2,3-dihydro-1H-isoindol-2-yl]methyl}prop-2-enenitrile | 344.2 |
| 77 | 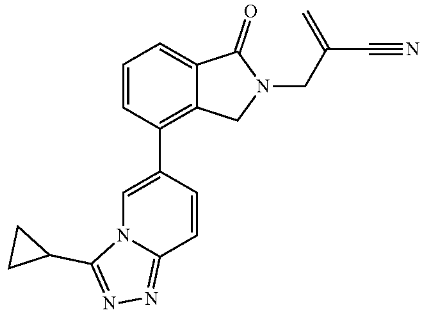 [SMILES: C=C(C#N)CN1Cc2c(cccc2-c2ccc3nnc(C4CC4)n3c2)C1=O] | 2-[(4-{3-cyclopropyl-[1,2,4]triazolo[4,3-a]pyridin-6-yl}-1-oxo-2,3-dihydro-1H-isoindol-2-yl)methyl]prop-2-enenitrile | 356.2 |
| 78 | 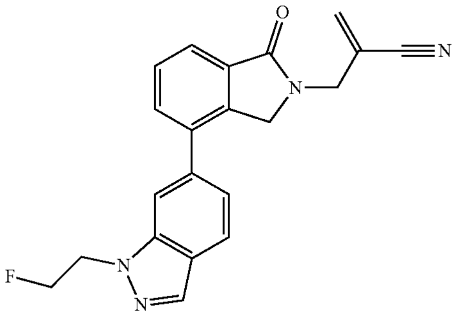 [SMILES: C=C(C#N)CN1Cc2c(cccc2-c2ccc3cnn(CCF)c3c2)C1=O] | 2-({4-[1-(2-fluoroethyl)-1H-indazol-6-yl]-1-oxo-2,3-dihydro-1H-isoindol-2-yl}methyl)prop-2-enenitrile | 361.1 |

TABLE 1-continued
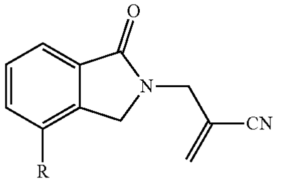
| Cpd. No. | Structure | IUPAC | LC-MS (ES+, m/z) |
|---|---|---|---|
| 79 | 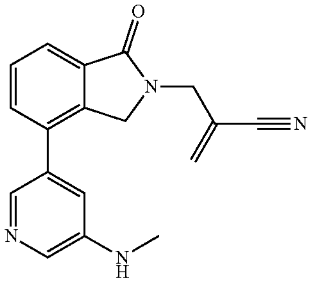 [SMILES: C=C(C#N)CN1Cc2c(cccc2-c2cncc(NC)c2)C1=O] | 2-({4-[5-(methylamino)pyridin-3-yl]-1-oxo-2,3-dihydro-1H-isoindol-2-yl}methyl)prop-2-enenitrile | 305.1 |
| 80 | 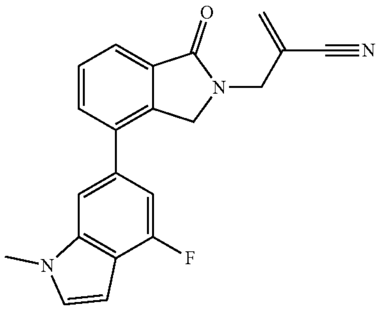 [SMILES: C=C(C#N)CN1Cc2c(cccc2-c2cc(F)c3ccn(C)c3c2)C1=O] | 2-{[4-(4-fluoro-1-methyl-1H-indol-6-yl)-1-oxo-2,3-dihydro-1H-isoindol-2-yl]methyl}prop-2-enenitrile | 346.1 |
| 81 | 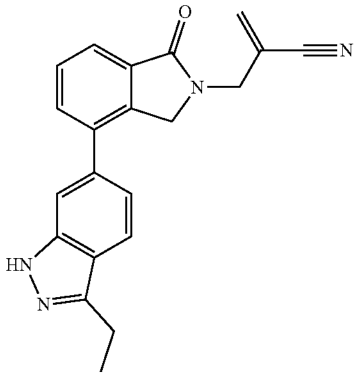 [SMILES: C=C(C#N)CN1Cc2c(cccc2-c2ccc3c(CC)n[nH]c3c2)C1=O] | 2-{[4-(3-ethyl-1H-indazol-6-yl)-1-oxo-2,3-dihydro-1H-isoindol-2-yl]methyl}prop-2-enenitrile | 343.1 |
| 82 | 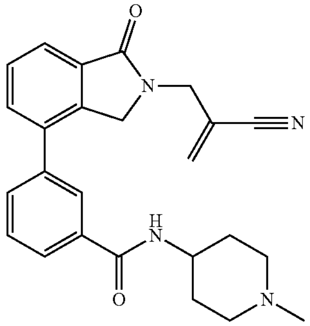 [SMILES: C=C(C#N)CN1Cc2c(cccc2-c2cccc(C(=O)NC3CCN(C)CC3)c2)C1=O] | 3-[2-(2-cyano-2-methylideneethyl)-1-oxo-2,3-dihydro-1H-isoindol-4-yl]-N-(1-methylpiperidin-4-yl)benzamide | 415.1 |

TABLE 1-continued
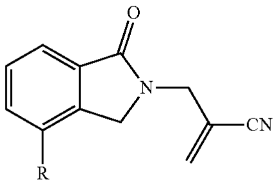
| Cpd. No. | Structure | IUPAC | LC-MS (ES+, m/z) |
| --- | --- | --- | --- |
| 83 | 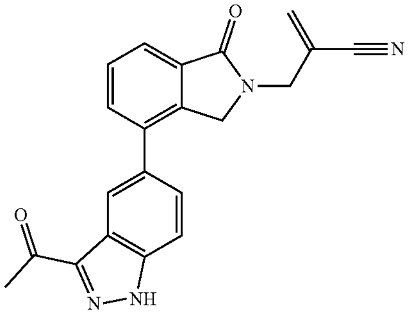 [SMILES: C=C(C#N)CN1Cc2c(cccc2-c2ccc3[nH]nc(C(C)=O)c3c2)C1=O] | 2-{[4-(3-acetyl-1H-indazol-5-yl)-1-oxo-2,3-dihydro-1H-isoindol-2-yl]methyl}prop-2-enenitrile | 357.1 |
| 84 | 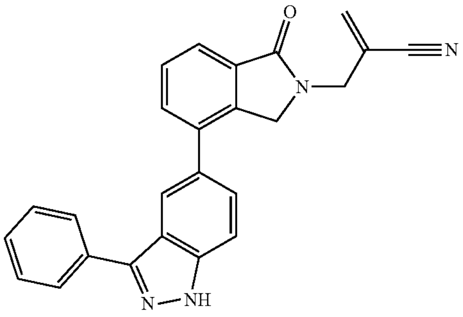 [SMILES: C=C(C#N)CN1Cc2c(cccc2-c2ccc3[nH]nc(-c4ccccc4)c3c2)C1=O] | 2-{[1-oxo-4-(3-phenyl-1H-indazol-5-yl)-2,3-dihydro-1H-isoindol-2-yl]methyl}prop-2-enenitrile | 391.2 |
| 85 | 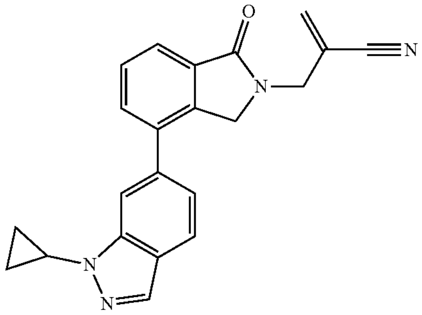 [SMILES: C=C(C#N)CN1Cc2c(cccc2-c2ccc3cnn(C4CC4)c3c2)C1=O] | 2-{[4-(1-cyclopropyl-1H-indazol-6-yl)-1-oxo-2,3-dihydro-1H-isoindol-2-yl]methyl}prop-2-enenitrile | 355.1 |
| 86 | 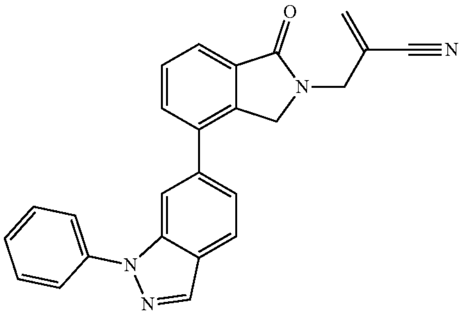 [SMILES: C=C(C#N)CN1Cc2c(cccc2-c2ccc3cnn(-c4ccccc4)c3c2)C1=O] | 2-{[1-oxo-4-(1-phenyl-1H-indazol-6-yl)-2,3-dihydro-1H-isoindol-2-yl]methyl}prop-2-enenitrile | 391.2 |

TABLE 1-continued

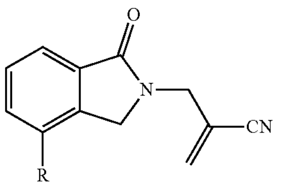

| Cpd. No. | Structure | IUPAC | LC-MS (ES+, m/z) |
|---|---|---|---|
| 87 | 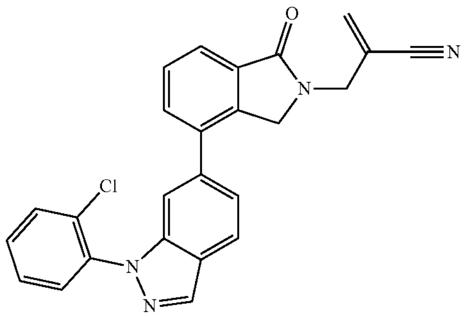 [SMILES: C=C(C#N)CN1Cc2c(cccc2-c2ccc3cnn(-c4ccccc4Cl)c3c2)C1=O] | 2-({4-[1-(2-chlorophenyl)-1H-indazol-6-yl]-1-oxo-2,3-dihydro-1H-isoindol-2-yl}methyl)prop-2-enenitrile | 423.1 |
| 88 | 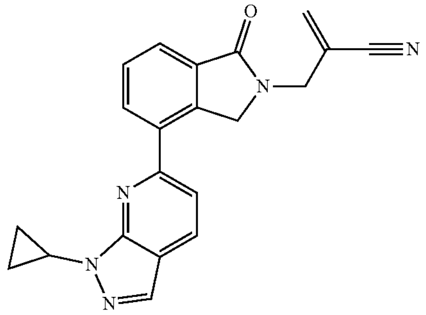 [SMILES: C=C(C#N)CN1Cc2c(cccc2-c2ccc3cnn(C4CC4)c3n2)C1=O] | 2-[(4-{1-cyclopropyl-1H-pyrazolo[3,4-b]pyridin-6-yl}-1-oxo-2,3-dihydro-1H-isoindol-2-yl)methyl]prop-2-enenitrile | 356.2 |
| 89 | 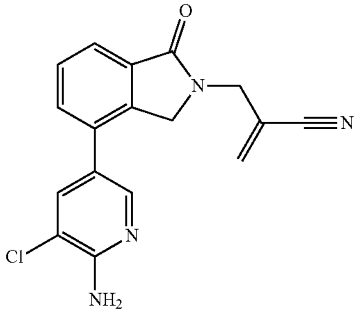 | 2-{[4-(6-amino-5-chloropyridin-3-yl)-1-oxo-2,3-dihydro-1H-isoindol-2-yl]methyl}prop-2-enenitrile | 325.1 |
| 90 | 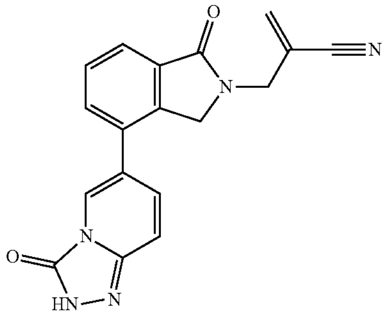 [SMILES: C=C(C#N)CN1Cc2c(cccc2-c2ccc3n[nH]c(=O)n3c2)C1=O] | 2-[(1-oxo-4-{3-oxo-2H,3H-[1,2,4]triazolo[4,3-a]pyridin-6-yl}-2,3-dihydro-1H-isoindol-2-yl)methyl]prop-2-enenitrile | 332.1 |

TABLE 1-continued

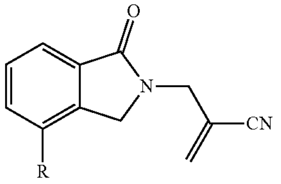

| Cpd. No. | Structure | IUPAC | LC-MS (ES+, m/z) |
|---|---|---|---|
| 91 | 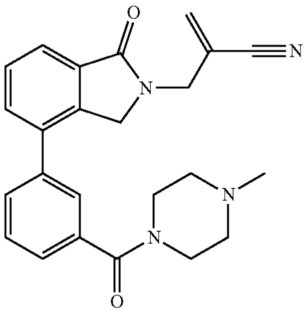 [SMILES: C=C(C#N)CN1Cc2c(cccc2-c2cccc(C(=O)N3CCN(C)CC3)c2)C1=O] | 2-({4-[3-(4-methylpiperazine-1-carbonyl)phenyl]-1-oxo-2,3-dihydro-1H-isoindol-2-yl}methyl)prop-2-enenitrile | 401.2 |
| 92 | 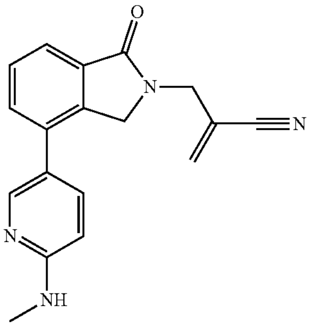 [SMILES: C=C(C#N)CN1Cc2c(cccc2-c2ccc(NC)nc2)C1=O] | 2-({4-[6-(methylamino)pyridin-3-yl]-1-oxo-2,3-dihydro-1H-isoindol-2-yl}methyl)prop-2-enenitrile | 305.1 |
| 93 | 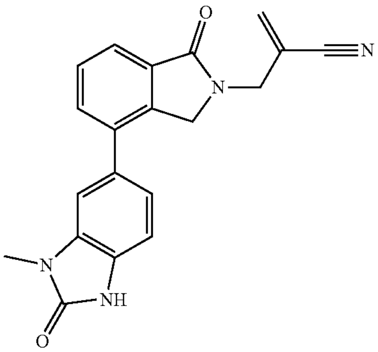 | 2-{[4-(3-methyl-2-oxo-2,3-dihydro-1H-1,3-benzodiazol-5-yl)-1-oxo-2,3-dihydro-1H-isoindol-2-yl]methyl}prop-2-enenitrile | 345.1 |
| 94 | 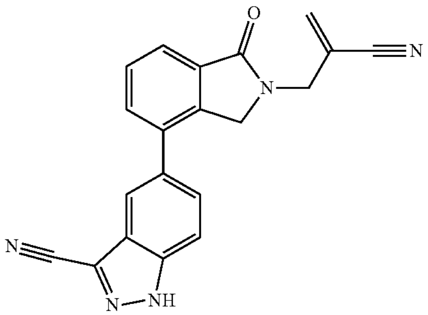 [SMILES: C=C(C#N)CN1Cc2c(cccc2-c2ccc3[nH]nc(C#N)c3c2)C1=O] | 5-[2-(2-cyano-2-methylideneethyl)-1-oxo-2,3-dihydro-1H-isoindol-4-yl]-1H-indazole-3-carbonitrile | 340.1 |

TABLE 1-continued

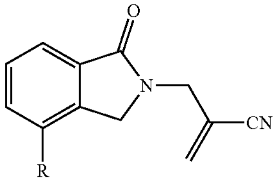

| Cpd. No. | Structure | IUPAC | LC-MS (ES+, m/z) |
|---|---|---|---|
| 95 | 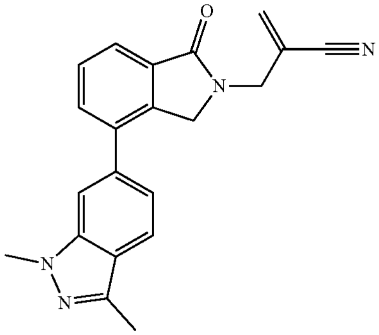 [SMILES: C=C(C#N)CN1Cc2c(cccc2-c2ccc3c(C)nn(C)c3c2)C1=O] | 2-{[4-(1,3-dimethyl-1H-indazol-6-yl)-1-oxo-2,3-dihydro-1H-isoindol-2-yl]methyl}prop-2-enenitrile | 343.2 |
| 96 | 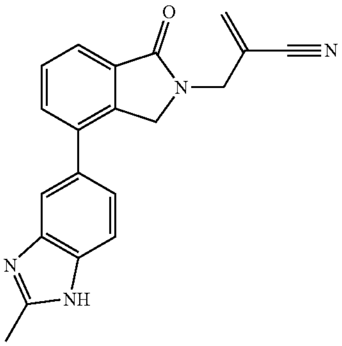 [SMILES: C=C(C#N)CN1Cc2c(cccc2-c2ccc3[nH]c(C)nc3c2)C1=O] | 2-{[4-(2-methyl-1H-1,3-benzodiazol-5-yl)-1-oxo-2,3-dihydro-1H-isoindol-2-yl]methyl}prop-2-enenitrile | 329.2 |
| 97 | 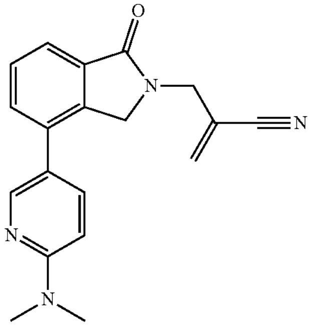 [SMILES: C=C(C#N)CN1Cc2c(cccc2-c2ccc(N(C)C)nc2)C1=O] | 2-({4-[6-(dimethylamino)pyridin-3-yl]-1-oxo-2,3-dihydro-1H-isoindol-2-yl}methyl)prop-2-enenitrile | 319 |
| 98 | 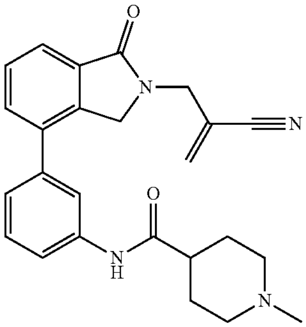 [SMILES: C=C(C#N)CN1Cc2c(cccc2-c2cccc(NC(=O)C3CCN(C)CC3)c2)C1=O] | N-{3-[2-(2-cyano-2-methylideneethyl)-1-oxo-2,3-dihydro-1H-isoindol-4-yl]phenyl}-1-methylpiperidine-4-carboxamide | 415.2 |

TABLE 1-continued

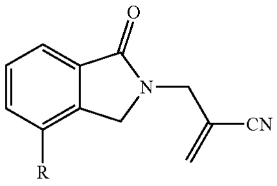

| Cpd. No. | Structure | IUPAC | LC-MS (ES+, m/z) |
|---|---|---|---|
| 99 | 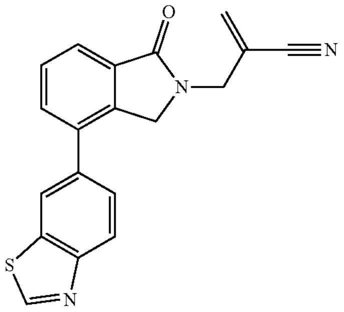 [SMILES: C=C(C#N)CN1Cc2c(cccc2-c2ccc3ncsc3c2)C1=O] | 2-{[4-(1,3-benzothiazol-6-yl)-1-oxo-2,3-dihydro-1H-isoindol-2-yl]methyl}prop-2-enenitrile | 332.1 |
| 100 | 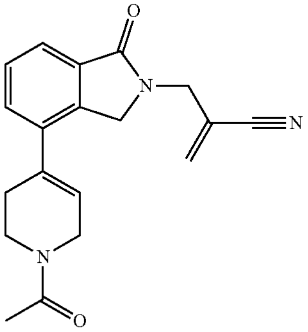 [SMILES: C=C(C#N)CN1Cc2c(cccc2C2=CCN(C(C)=O)CC2)C1=O] | 2-{[4-(1-acetyl-1,2,3,6-tetrahydropyridin-4-yl)-1-oxo-2,3-dihydro-1H-isoindol-2-yl]methyl}prop-2-enenitrile | 322.1 |
| 101 | 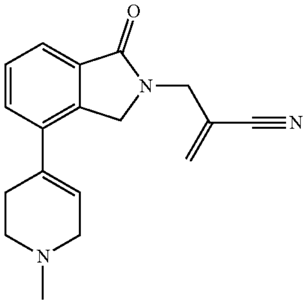 [SMILES: C=C(C#N)CN1Cc2c(cccc2C2=CCN(C)CC2)C1=O] | 2-{[4-(1-methyl-1,2,3,6-tetrahydropyridin-4-yl)-1-oxo-2,3-dihydro-1H-isoindol-2-yl]methyl}prop-2-enenitrile | 294.2 |
| 102 | 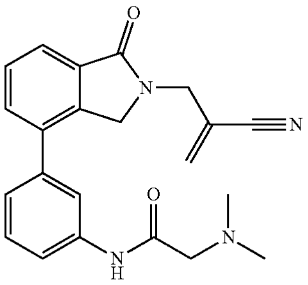 [SMILES: C=C(C#N)CN1Cc2c(cccc2-c2cccc(NC(=O)CN(C)C)c2)C1=O] | N-{3-[2-(2-cyano-2-methylideneethyl)-1-oxo-2,3-dihydro-1H-isoindol-4-yl]phenyl}-2-(dimethylamino)acetamide | 375.1 |

TABLE 1-continued

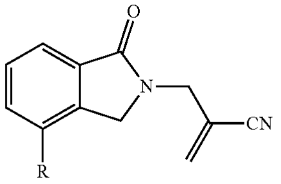

| Cpd. No. | Structure | IUPAC | LC-MS (ES+, m/z) |
|---|---|---|---|
| 103 | 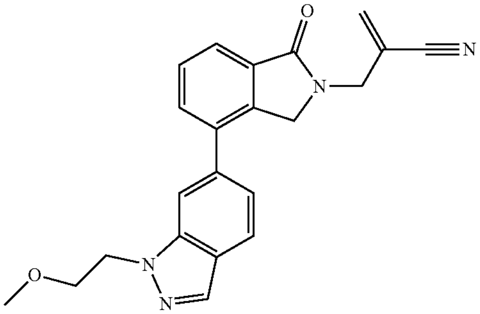 [SMILES: C=C(C#N)CN1Cc2c(cccc2-c2ccc3cnn(CCOC)c3c2)C1=O] | 2-({4-[1-(2-methoxyethyl)-1H-indazol-6-yl]-1-oxo-2,3-dihydro-1H-isoindol-2-yl}methyl)prop-2-enenitrile | 373.1 |
| 104 | 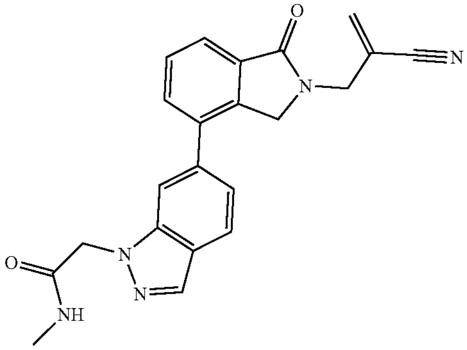 [SMILES: C=C(C#N)CN1Cc2c(cccc2-c2ccc3cnn(CC(=O)NC)c3c2)C1=O] | 2-{6-[2-(2-cyano-2-methylideneethyl)-1-oxo-2,3-dihydro-1H-isoindol-4-yl]-1H-indazol-1-yl}-N-methylacetamide | 386.2 |
| 105 | 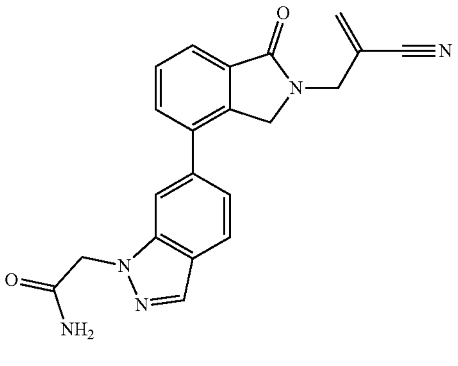 [SMILES: C=C(C#N)CN1Cc2c(cccc2-c2ccc3cnn(CC(N)=O)c3c2)C1=O] | 2-{6-[2-(2-cyano-2-methylideneethyl)-1-oxo-2,3-dihydro-1H-isoindol-4-yl]-1H-indazol-1-yl}acetamide | 372.1 |
| 106 | 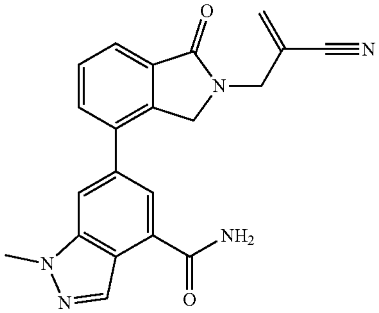 [SMILES: C=C(C#N)CN1Cc2c(cccc2-c2cc(C(N)=O)c3cnn(C)c3c2)C1=O] | 6-[2-(2-cyano-2-methylideneethyl)-1-oxo-2,3-dihydro-1H-isoindol-4-yl]-1-methyl-1H-indazole-4-carboxamide | 372.1 |

TABLE 1-continued

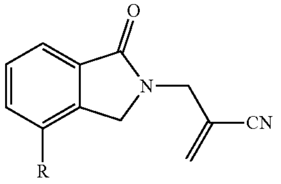

| Cpd. No. | Structure | IUPAC | LC-MS (ES+, m/z) |
|---|---|---|---|
| 107 | 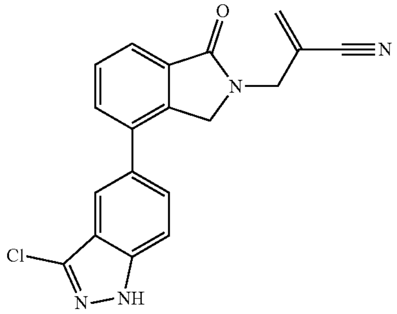 [SMILES: C=C(C#N)CN1Cc2c(cccc2-c2ccc3[nH]nc(Cl)c3c2)C1=O] | 2-{[4-(3-chloro-1H-indazol-5-yl)-1-oxo-2,3-dihydro-1H-isoindol-2-yl]methyl}prop-2-enenitrile | 349 |
| 108 | 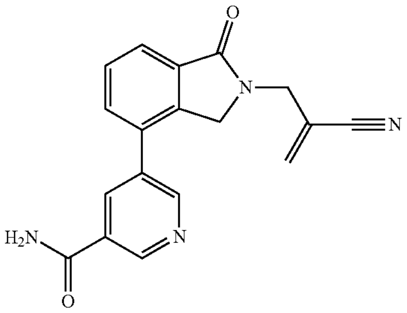 [SMILES: C=C(C#N)CN1Cc2c(cccc2-c2cncc(C(N)=O)c2)C1=O] | 5-[2-(2-cyano-2-methylideneethyl)-1-oxo-2,3-dihydro-1H-isoindol-4-yl]pyridine-3-carboxamide | 319.1 |
| 109 | 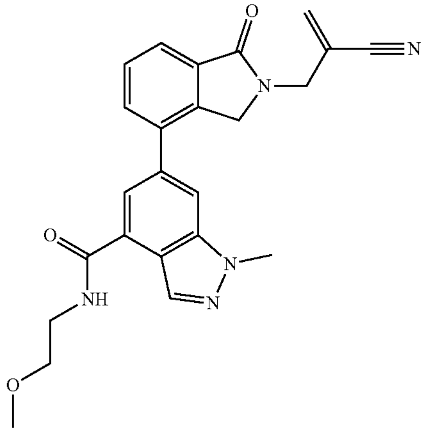 [SMILES: C=C(C#N)CN1Cc2c(cccc2-c2cc(C(=O)NCCOC)c3cnn(C)c3c2)C1=O] | 6-[2-(2-cyano-2-methylideneethyl)-1-oxo-2,3-dihydro-1H-isoindol-4-yl]-N-(2-methoxyethyl)-1-methyl-1H-indazole-4-carboxamide | 430.1 |
| 110 | 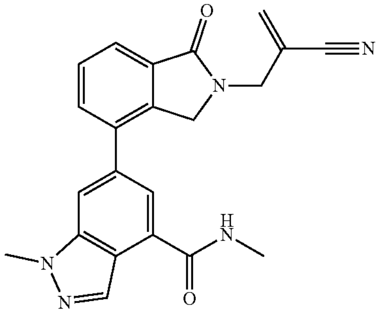 [SMILES: C=C(C#N)CN1Cc2c(cccc2-c2cc(C(=O)NC)c3cnn(C)c3c2)C1=O] | 6-[2-(2-cyano-2-methylideneethyl)-1-oxo-2,3-dihydro-1H-isoindol-4-yl]-N,1-dimethyl-1H-indazole-4-carboxamide | 386.1 |

TABLE 1-continued
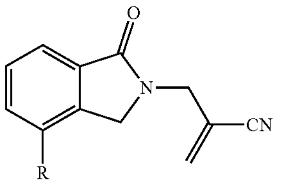
| Cpd. No. | Structure | IUPAC | LC-MS (ES+, m/z) |
|---|---|---|---|
| 111 | 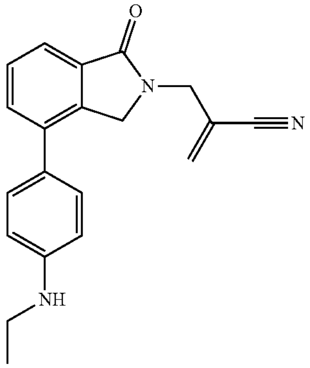 [SMILES: C=C(C#N)CN1Cc2c(cccc2-c2ccc(NCC)cc2)C1=O] | 2-({4-[4-(ethylamino)phenyl]-1-oxo-2,3-dihydro-1H-isoindol-2-yl}methyl)prop-2-enenitrile | 318.1 |
| 112 | 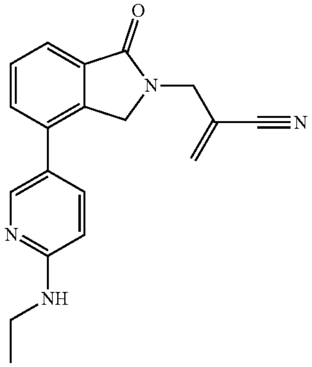 [SMILES: C=C(C#N)CN1Cc2c(cccc2-c2ccc(NCC)nc2)C1=O] | 2-({4-[6-(ethylamino)pyridin-3-yl]-1-oxo-2,3-dihydro-1H-isoindol-2-yl}methyl)prop-2-enenitrile | 319.1 |

Example 3: Synthesis of Compounds of the Disclosure: Method B

3A. General Scheme for Method B: Route 1

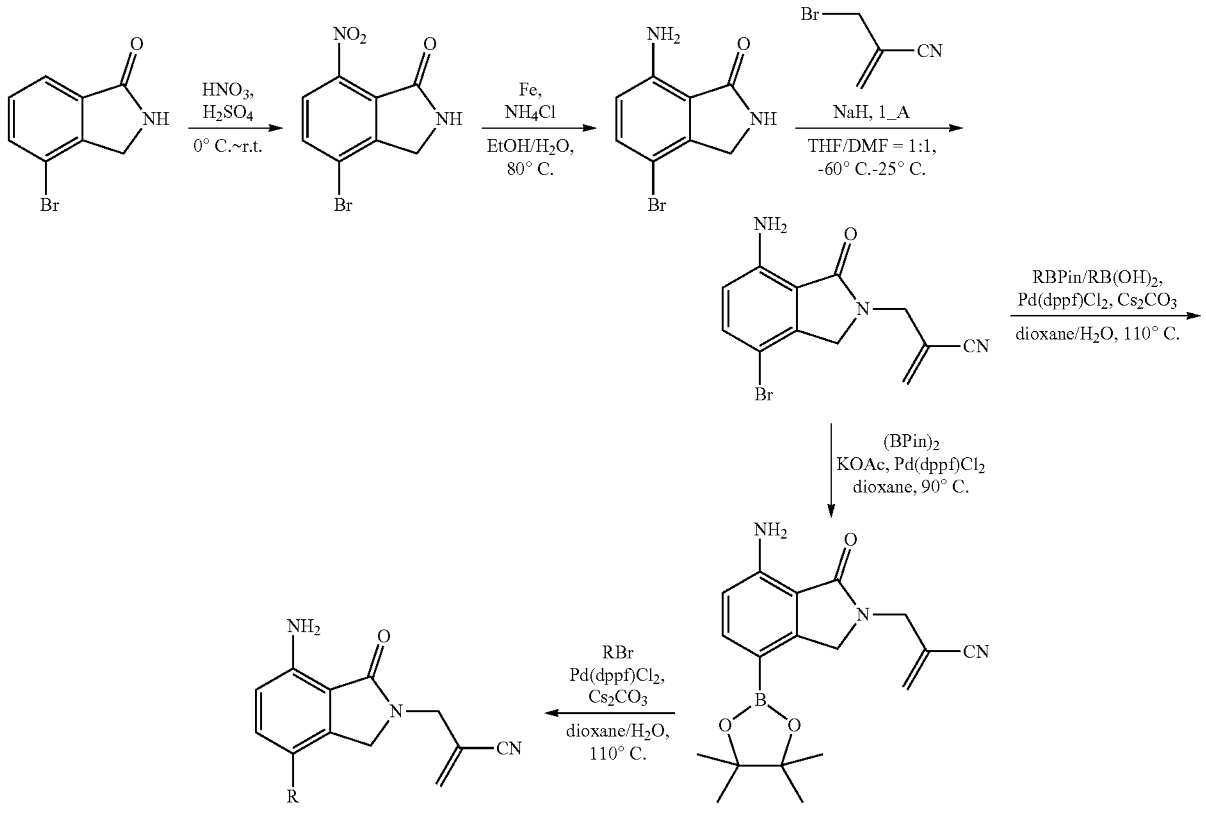

3A.1. Preparation of 2-[[7-amino-4-(3-methyl-1H-indazol-5-yl)-1-oxo-isoindolin-2-yl]methyl]prop-2-enenitrile (Compound 116)

a. Preparation of 4-bromo-7-nitro-2,3-dihydro-1H-isoindol-1-one

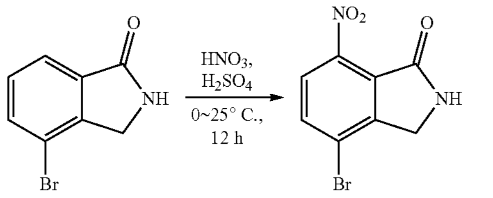 [SMILES: O=C1NCc2c(Br)cccc21 ; O=C1NCc2c(Br)ccc([N+](=O)[O-])c21]

To a solution of 4-bromoisoindolin-1-one (6 g, 28.30 mmol, 1 eq.) in concentrated $H_2SO_4$ (20 mL) at 0° C. was added $HNO_3$ (2.52 g, 39.99 mmol, 1.80 mL, 1.41 eq.) dropwise in concentrated $H_2SO_4$ (20 mL). The resulting mixture was then stirred at 25° C. for 12 h. LCMS showed that the reaction was complete. The reaction was diluted with 100 mL water, and the resulting precipitation was filtered, and concentrated to give the crude product. The crude material was washed with water (20 mL×6) and EtOH (20 mL×2), and was filtered to afford the title compound (5.1 g, 17.86 mmol, 63.11% yield, 90% purity) as a yellow solid.

Preparation of 7-amino-4-bromo-2,3-dihydro-1H-isoindol-1-one

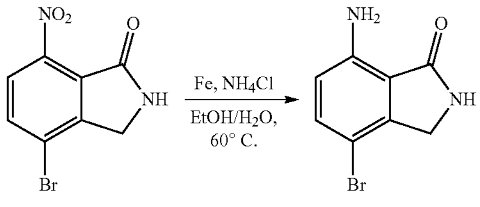 [SMILES: O=C1NCc2c(Br)ccc([N+](=O)[O-])c21 ; Nc1ccc(Br)c2c1C(=O)NC2]

To a suspension solution of 4-bromo-7-nitro-isoindolin-1-one (500 mg, 1.75 mmol, 1 eq.) in EtOH (12 mL) and saturated aq. $NH_4Cl$ (4.59 g, 85.81 mmol, 3 mL, 49.01 eq.) was added Fe (488.84 mg, 8.75 mmol, 5 eq.) in portions at 60° C. The reaction mixture was stirred for another 1 h at 60° C. LCMS showed that the reaction was complete. The reaction was filtered when the mixture was hot, and the filtered liquor was diluted with 30 mL water, extracted with EtOAc (25 mL×3), washed with water (25 mL×2), brine (25 mL×2), dried over anhydrous sodium sulfate, filtered, and concentrated to afford the title compound (330 mg, crude) as a yellow solid, which was used directly without further purification.

c. Preparation of 2-[(7-amino-4-bromo-1-oxo-isoindolin-2-yl)methyl]prop-2-enenitrile

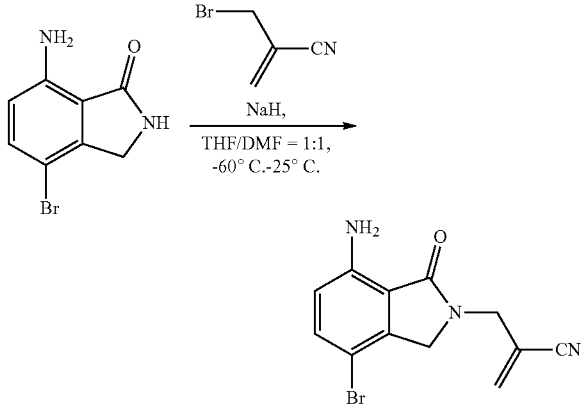

To a mixture of 7-amino-4-bromo-isoindolin-1-one (200 mg, 880.83 μmol, 1 eq.) in DMF (8 mL) and THF (8 mL) was added NaH (105.69 mg, 2.64 mmol, 60% purity, 3 eq.) at 25° C. The mixture was stirred at 25° C. for 0.5 h, and the mixture was cooled to −60° C. Then, 2-(bromomethyl)prop-2-enenitrile (128.59 mg, 880.83 μmol, 1 eq.) was added, and the mixture was stirred further at −60° C. for 1 h. TLC showed that the reaction was complete. The reaction mixture was quenched with 30 mL saturated aq. NH4Cl, extracted with EtOAc (30 mL×2), washed with water (25 mL×2) and brine (25 mL×2), dried with sodium sulfate, filtered, and concentrated to give a residue. The residue was purified by prep-TLC (silica gel; PE:EtOAc=1/1) to afford the title compound (150 mg, 462.12 μmol, 52.46% yield, 90% purity) as a yellow solid.

d. Preparation of 2-[[7-amino-1-oxo-4-(4,4,5,5-tetramethyl-1,3,2-dioxaborolan-2-yl) isoindolin-2-yl]methyl]prop-2-enenitrile

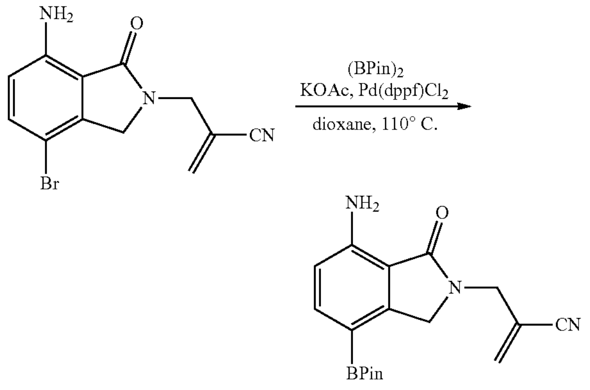

To a mixture of 2-[(7-amino-4-bromo-1-oxo-isoindolin-2-yl)methyl]prop-2-enenitrile (1 g, 3.25 mmol, 1 eq.) and 4,4,5,5-tetramethyl-2-(4,4,5,5-tetramethyl-1,3,2-dioxaborolan-2-yl)-1,3,2-dioxaborolane (2.06 g, 8.13 mmol, 2.5 eq.) in dioxane (40 mL) was added KOAc (957.47 mg, 9.76 mmol, 3 eq.) and Pd(dppf)$Cl_2$ (118.97 mg, 162.60 μmol, 0.05 eq.) in one portion. The mixture was stirred at 110° C. for 2 h. LCMS showed 10% starting material was remained and 80% product was detected. The reaction mixture was diluted with 40 mL water, extracted with EtOAc (40 mL×3), washed with water (40 mL×2), brine (40 mL×2), dried over anhydrous sodium sulfate, filtered, and concentrated to give a residue. The residue was purified by prep-TLC (silica gel; PE:EtOAc=4:1) to afford the title (0.75 g, 2.21 mmol, 67.99% yield) as a white solid.

e. Preparation of tert-butyl 5-[7-amino-2-(2-cyanoallyl)-1-oxo-isoindolin-4-yl]-3-methyl-indazole-1-carboxylate

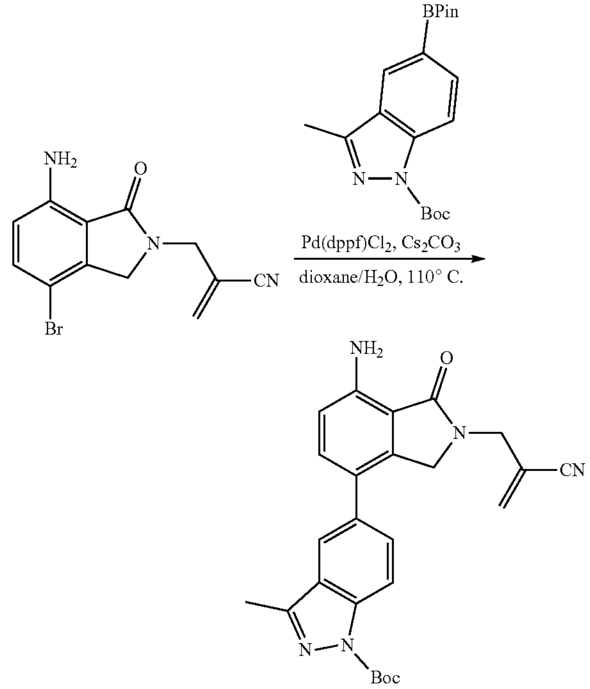

To a mixture of 2-[(7-amino-4-bromo-1-oxo-isoindolin-2-yl)methyl]prop-2-enenitrile (100 mg, 342.31 μmol, 1 eq.) and tert-butyl 3-methyl-5-(4,4,5,5-tetramethyl-1,3,2-dioxaborolan-2-yl) indazole-1-carboxylate (183.94 mg, 513.47 μmol, 1.5 eq.) in dioxane (4 mL) and water (1 mL) was added $Cs_2CO_3$ (557.66 mg, 1.71 mmol, 5 eq.) and Pd(dppf) $Cl_2$ (37.57 mg, 51.35 μmol, 0.15 eq.) and in one portion under nitrogen. The mixture was stirred at 110° C. for 3 h. TLC showed that the reaction was complete. The reaction mixture was diluted with 20 mL EtOAc, poured into 20 mL sat. EDTA and stirred for 0.5 h. The resulting solution was separated. The organic layer was poured into 20 mL sat. EDTA and stirred for 1 h and extracted with EtOAc (20 mL×3). The combined organic layer was washed with water (25 mL×3) and brine (25 mL×3) dried over anhydrous sodium sulfate, filtered, and concentrated to give the residue. The residue was purified by prep-TLC (silica gel; DCM: MeOH=20:1) to afford the title compound (65 mg, 131.91 μmol, 38.53% yield, 90% purity) as a yellow solid.

f. Preparation of 2-[[7-amino-4-(3-methyl-1H-indazol-5-yl)-1-oxo-isoindolin-2-yl]methyl]prop-2-enenitrile (Compound 116)

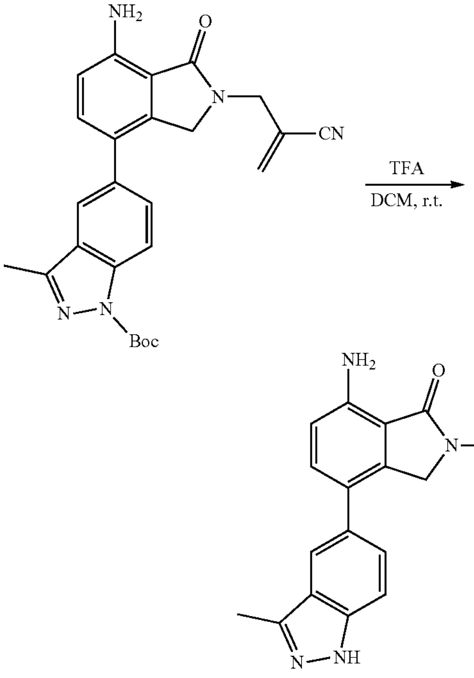

To a mixture of tert-butyl 5-[7-amino-2-(2-cyanoallyl)-1-oxo-isoindolin-4-yl]-3-methyl-indazole-1-carboxylate (55 mg, 111.61 μmol, 1 eq.) in DCM (4 mL) was added 2,2,2-trifluoroacetic acid (1.54 g, 13.51 mmol, 1 mL, 121.01 eq.) in one portion at 25° C. under nitrogen. The mixture was stirred at 25° C. for 30 min. LCMS and HPLC showed that the reaction was complete. The reaction was quenched with 10 mL saturated aqueous $NaHCO_3$. The residue was adjusted to pH=8, extracted with EtOAc (15 mL×2), washed with water (15 mL×2), extracted with EtOAc (15 mL×2), dried with sodium sulfate, filtered, and concentrated to give a residue. The residue was purified by Prep-HPLC to afford the title compound (9.4 mg, 27.21 μmol, 24.38% yield, 99.4% purity) as a white solid. LC-MS: $[M+H]^+$ 344.1.

3A.2. Preparation of 2-[[7-amino-4-[1-(2-fluoroethyl)indazol-6-yl]-1-oxo-isoindolin-1-yl]methyl]prop-2-enenitrile (Compound 1)

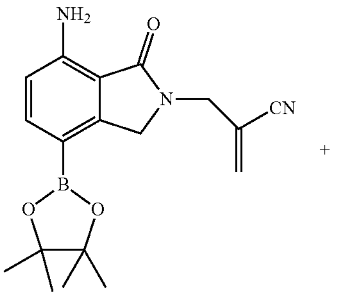

-continued

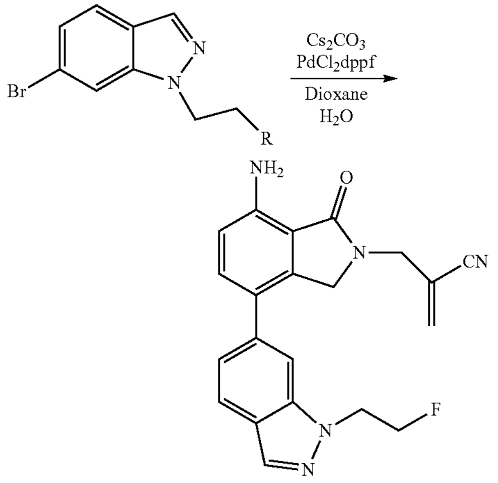

To a solution of 2-[[7-amino-1-oxo-4-(4,4,5,5-tetramethyl-1,3,2-dioxaborolan-2-yl)isoindolin-2-yl]methyl]prop-2-enenitrile (49.2 mg, 145 μmol) in dioxane (1 mL) and water (0.2 mL) were added 6-bromo-1-(2-fluoroethyl)indazole (52.9 mg, 217 μmol), $Cs_2CO_3$ (164 mg, 508 mmol) and $PdCl_2dppf$ (18 mg, 22.1 μmol). The reaction was heated to 100° C. for 30 min in a microwave. The reaction mixture was passed through a celite pad, and 2 mL of 0.5 M EDTA was added. The resulting solution was stirred at r.t. for 30 min. The solution was washed with brine, and the organic phase was dried over anhydrous sodium sulfate, filtered, and concentrated in vacuo. The residue was purified by chromatography on silica gel eluting with 20-80% EtOAc/hexane to afford the title compound (32.6 mg, Yield 60%). LC-MS: $[M+H]^+$ 376.

3A.3. Preparation of 2-[(7-amino-1-oxo-4-pyrazolo[1,5-a]pyridin-5-yl-isoindolin-2-yl)methyl]prop-2-enenitrile (Compound 152)

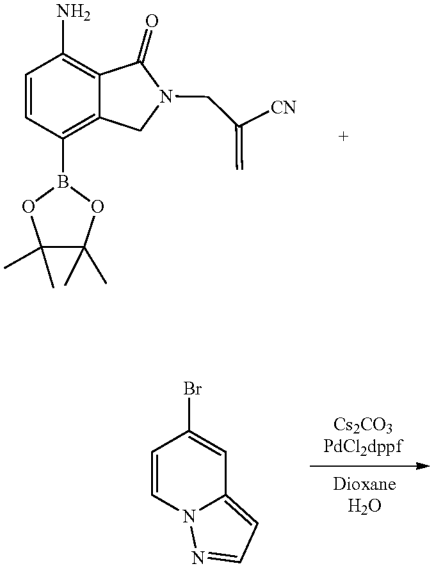

-continued

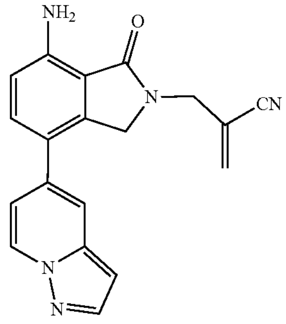

To a solution of 2-[[7-amino-1-oxo-4-(4,4,5,5-tetramethyl-1,3,2-dioxaborolan-2-yl)isoindolin-2-yl]methyl]prop-2-enenitrile (48.3 mg, 142 mol) in dioxane (1 mL) and water (0.2 mL) were added 5-bromopyrazolo[1,5-a]pyridine (42.1 mg, 213 μmol), $Cs_2CO_3$ (160 mg, 494 mmol) and $PdCl_2$dppf (18 mg, 22.1 μmol). The reaction was heated to 100° C. for 30 min in a microwave. The reaction mixture was passed through a celite pad, and 2 mL of 0.5 M EDTA was added. The resulting solution was stirred at r.t. for 30 min. The solution was washed with brine, and the organic phase was dried over anhydrous sodium sulfate, filtered, and concentrated in vacuo. The residue was purified by chromatography on silica gel eluting with 20-80% EtOAc/hexane to afford the title compound (26.5 mg, Yield 58%). LC-MS: $[M+H]^+$ 330.

3A.4. Preparation of 2-[[7-amino-4-(3-methyl-1H-pyrazolo[3,4-c]pyridin-5-yl)-1-oxo-isoindolin-2-yl]methyl]prop-2-enenitrile (Compound 167)

a. Preparation of tert-butyl 5-[7-amino-2-(2-cyanoallyl)-1-oxo-isoindolin-4-yl]-3-methyl-pyrazolo[3,4-c]pyridine-1-carboxylate

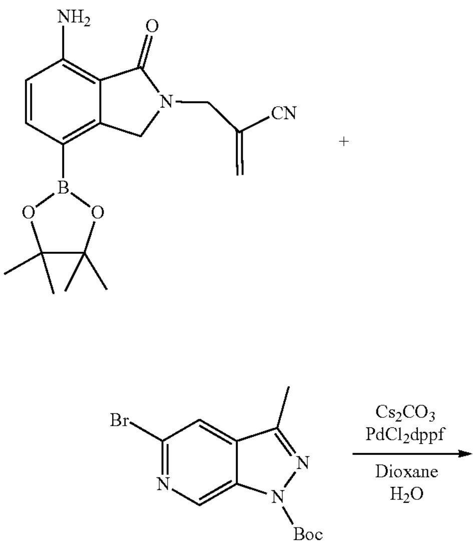

-continued

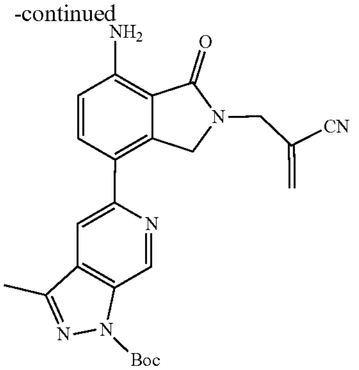

To a solution of 2-[[7-amino-1-oxo-4-(4,4,5,5-tetramethyl-1,3,2-dioxaborolan-2-yl)isoindolin-2-yl]methyl]prop-2-enenitrile (60 mg, 177 μmol) in dioxane (1 mL) and water (0.2 mL) were added tert-butyl 5-bromo-3-methyl-pyrazolo[3,4-c]pyridine-1-carboxylate (82.8 mg, 265 μmol), $Cs_2CO_3$ (172 mg, 531 mmol) and $PdCl_2$dppf (18 mg, 22.1 μmol). The reaction was heated to 100° C. for 30 min in a microwave. The reaction mixture was passed through a celite pad, and 2 mL of 0.5 M EDTA was added. The resulting solution was stirred at r.t. for 30 min. The solution was washed with brine, and the organic phase was dried over anhydrous sodium sulfate, filtered, and concentrated in vacuo. The residue was purified by chromatography on silica gel eluting with 20-80% EtOAc/hexane to afford the title compound (25.8 mg, Yield 33%).

b. Preparation of 2-[[7-amino-4-(3-methyl-1H-pyrazolo[3,4-c]pyridin-5-yl)-1-oxo-isoindolin-2-yl]methyl]prop-2-enenitrile (Compound 167)

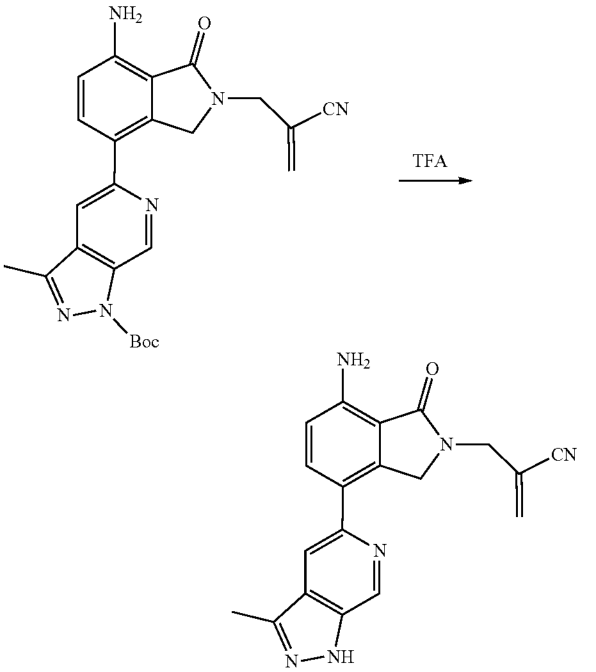

To a solution of tert-butyl 5-[7-amino-2-(2-cyanoallyl)-1-oxo-isoindolin-4-yl]-3-methyl-pyrazolo[3,4-c]pyridine-1-carboxylate (25.8 mg, 58 μmol) in DCM (1.6 mL) was added trifluoroacetic acid (0.4 mL) at 0° C. The resulting solution was stirred at r.t. for 2 h. The reaction mixture was concentrated in vacuo and the residue was diluted with DCM, washed with sat. $NaHCO_3$ and brine, dried over anhydrous sodium sulfate, filtered, and concentrated. The residue was purified by chromatography on silica gel eluting with 20-80% EtOAc/hexane to afford the title compound (16 mg, Yield 80%). LC-MS: $[M+H]^+$ 345.

3A.5. Preparation of 2-[[7-amino-4-(1-cyclopropylindazol)-6-yl)-1-oxo-isoindolin-2-yl]methyl]prop-2-enenitrile (Compound 168)

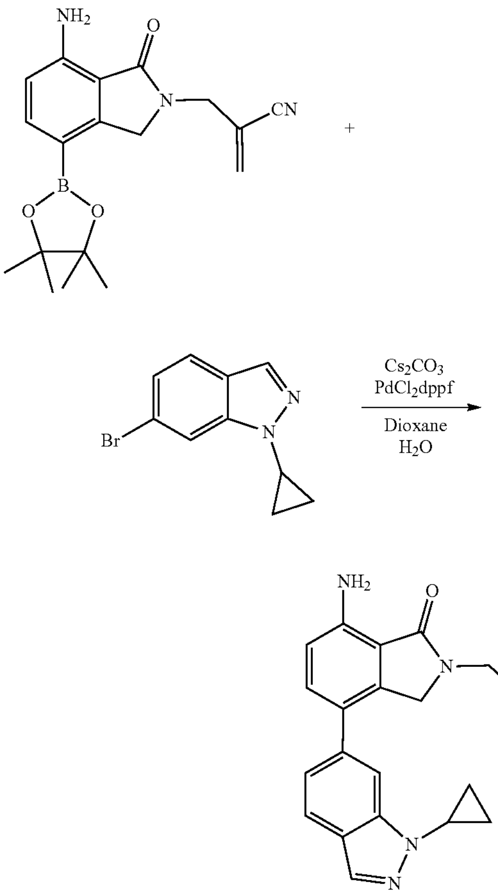

To a solution of 2-[[7-amino-1-oxo-4-(4,4,5,5-tetramethyl-1,3,2-dioxaborolan-2-yl)isoindolin-2-yl]methyl]prop-2-enenitrile (42.6 mg, 126 μmol) in dioxane (1 mL) and water (0.2 mL) were added 6-bromo-1-cyclopropyl-indazole (44.7 mg, 188 μmol), $Cs_2CO_3$ (142 mg, 432 mmol) and $PdCl_2dppf$ (18 mg, 22.1 μmol). The reaction was heated to 100° C. for 30 min in a microwave. The reaction mixture was passed through a celite pad, and 2 mL of 0.5 M EDTA was added. The resulting solution was stirred at r.t. for 30 min. The solution was washed with brine, and the organic phase was dried over anhydrous sodium sulfate, filtered, and concentrated in vacuo. The residue was purified by chromatography on silica gel eluting with 20-80% EtOAc/hexane to afford the title compound (19.2 mg, Yield 41%). LC-MS: $[M+H]^+$ 370.

3A.6. Preparation of 2-[[7-amino-4-[1-(2,2-difluoroethyl) indazol-6-yl]-1-oxo-isoindolin-2-yl]methyl] prop-2-enenitrile (Compound 180)

a. Preparation of 6-bromo-1-(2,2-difluoroethyl) indazole

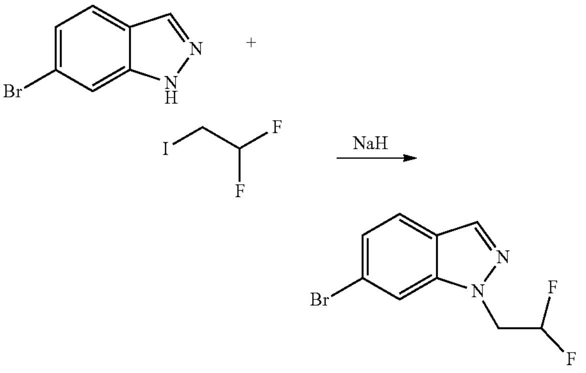

To a solution of 6-bromo-1H-indazole (500 mg, 2.54 mmol) in DMF (8 mL) was added NaH (0.203 g, 5.08 mmol). The mixture was stirred at r.t. for 10 min. The mixture was cooled to 0° C. and 1,1-difluoro-2-iodo-ethane (0.73 g, 3.81 mmol) in DMF (0.5 mL) was added dropwise. The resulting mixture was stirred at r.t. for 18 h. The mixture was partitioned between EtOAc and water. The aqueous phase was extracted with EtOAc (3x). The combined organic phase was washed with water and brine, dried over ($MgSO_4$), filtered, and concentrated in vacuo. The residue was purified by chromatography on silica gel eluting with 20-60% EtOAc/hexane to afford the title compound (0.365 g, Yield 41%).

b. Preparation of 2-[[7-amino-4-[1-(2,2-difluoroethyl) indazol-6-yl]-1-oxo-isoindolin-2-yl]methyl] prop-2-enenitrile (Compound 180)

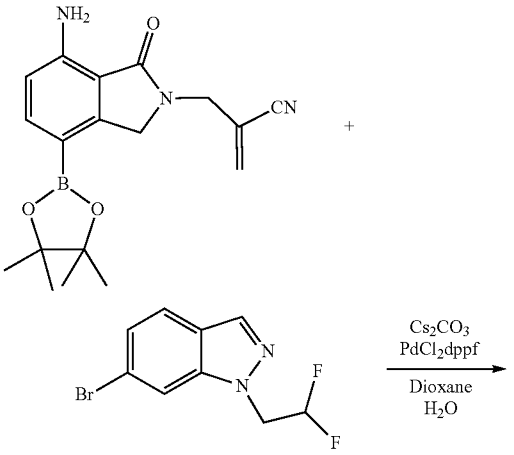

-continued

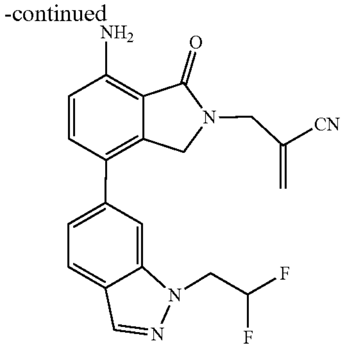

To a solution of 2-[[7-amino-1-oxo-4-(4,4,5,5-tetramethyl-1,3,2-dioxaborolan-2-yl)isoindolin-2-yl]methyl]prop-2-enenitrile (31.3 mg, 92 μmol) in dioxane (1 mL) and water (0.2 mL) were added 6-bromo-1-(2,2-difluoroethyl)indazole (36.1 mg, 138 μmol), $Cs_2CO_3$ (104 mg, 322 mmol) and $PdCl_2$dppf (15 mg, 18.3 μmol). The reaction was heated to 100° C. for 30 min in a microwave. The reaction mixture was passed through a celite pad, and 2 mL of 0.5 M EDTA was added. The resulting solution was stirred at r.t. for 30 min. The solution was washed with brine, and the organic phase was dried over anhydrous sodium sulfate, filtered, and concentrated in vacuo. The residue was purified by reverse phase HPLC using a gradient of water 0.1% FA/acetonitrile 0.1% FA to afford the title compound (3.2 mg, Yield 9%).

LC-MS: $[M+H]^+$ 394.

3A.7. Preparation of 2-[[7-amino-4-(1-cyclobutylindazol-6-yl)-1-oxo-isoindolin-2-yl]methyl]prop-2-enenitrile (Compound 181)

a. Preparation of 6-bromo-1-cyclobutyl-indazole

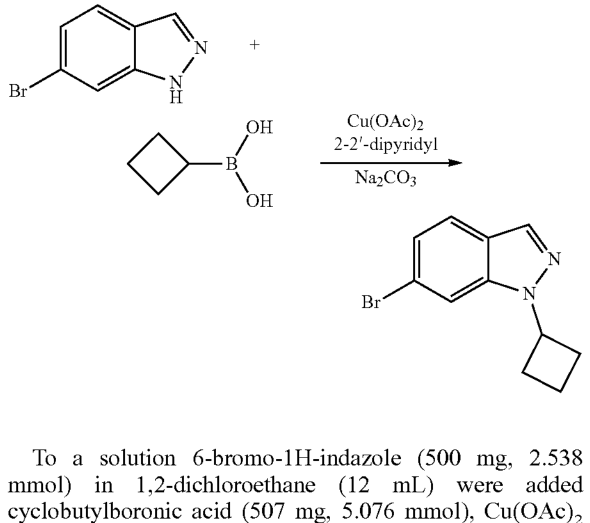

To a solution 6-bromo-1H-indazole (500 mg, 2.538 mmol) in 1,2-dichloroethane (12 mL) were added cyclobutylboronic acid (507 mg, 5.076 mmol), $Cu(OAc)_2$ (461 mg, 2.538 mmol), 2-2'-dipyridyl (396 mg, 2.538 mmol) and $Na_2CO_3$ (538 mg, 5.076 mmol). The reaction was heated to 70° C. for 6 h. The solvent was removed in vacuo. The residue was purified by chromatography on silica gel eluting with 10-80% EtOAc/hexane to afford the title compound (180 mg, Yield 28%).

b. Preparation of 2-[[7-amino-4-(1-cyclobutylindazol-6-yl)-1-oxo-isoindolin-2-yl]methyl]prop-2-enenitrile (Compound 181)

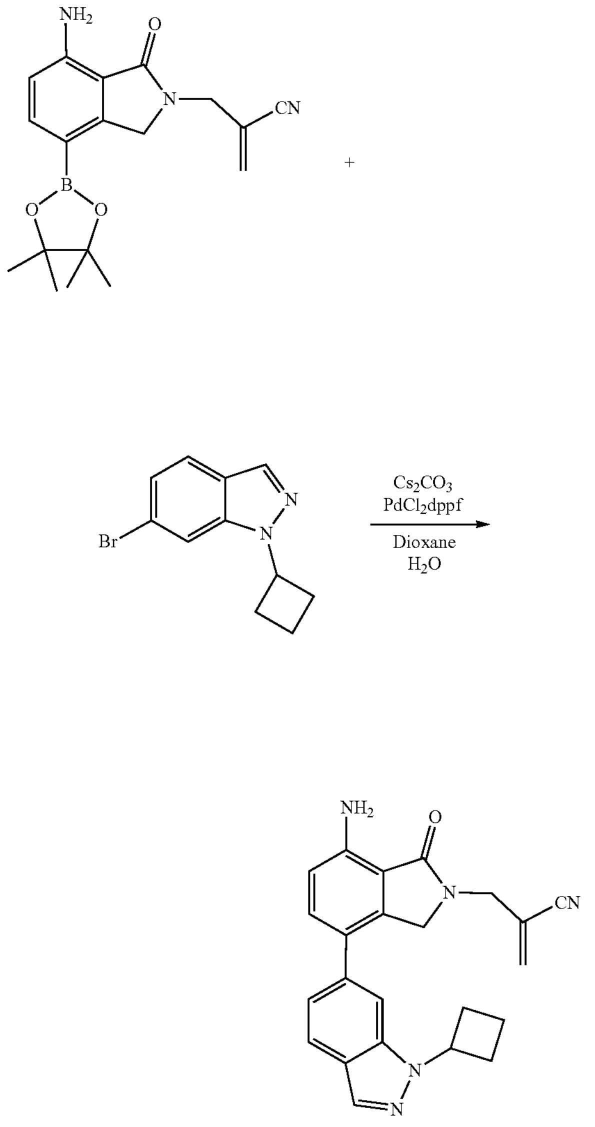

To a solution of 2-[[7-amino-1-oxo-4-(4,4,5,5-tetramethyl-1,3,2-dioxaborolan-2-yl)isoindolin-2-yl]methyl]prop-2-enenitrile (40 mg, 118 μmol) in dioxane (1 mL) and water (0.2 mL) were added 6-bromo-1-cyclobutyl-indazole (44.4 mg, 177 μmol), $Cs_2CO_3$ (134 mg, 415 mmol) and $PdCl_2$dppf (16 mg, 20 μmol). The reaction was heated to 100° C. for 30 min in a microwave. The reaction mixture was passed through a celite pad, and 2 mL of 0.5 M EDTA was added. The resulting solution was stirred at r.t. for 30 min. The solution was washed with brine, and the organic phase was dried over anhydrous sodium sulfate, filtered, and concentrated in vacuo. The residue was purified by reverse phase HPLC using a gradient of water 0.1% FA/acetonitrile 0.1% FA to afford the title compound (15.1 mg, Yield 33%). LC-MS: $[M+H]^+$ 384.

3A.8. Preparation of 2-[[7-amino-4-[3-(1-methylpyrazol-4-yl)-1H-indazol-5-yl]-1-oxo-isoindolin-2-yl]methyl]prop-2-enenitrile (Compound 182)

a. Preparation of tert-butyl 5-[7-amino-2-(2-cyanoallyl)-1-oxo-isoindolin-4-yl]-3-(1-methylpyrazol-4-yl) indazole-1-carboxylate

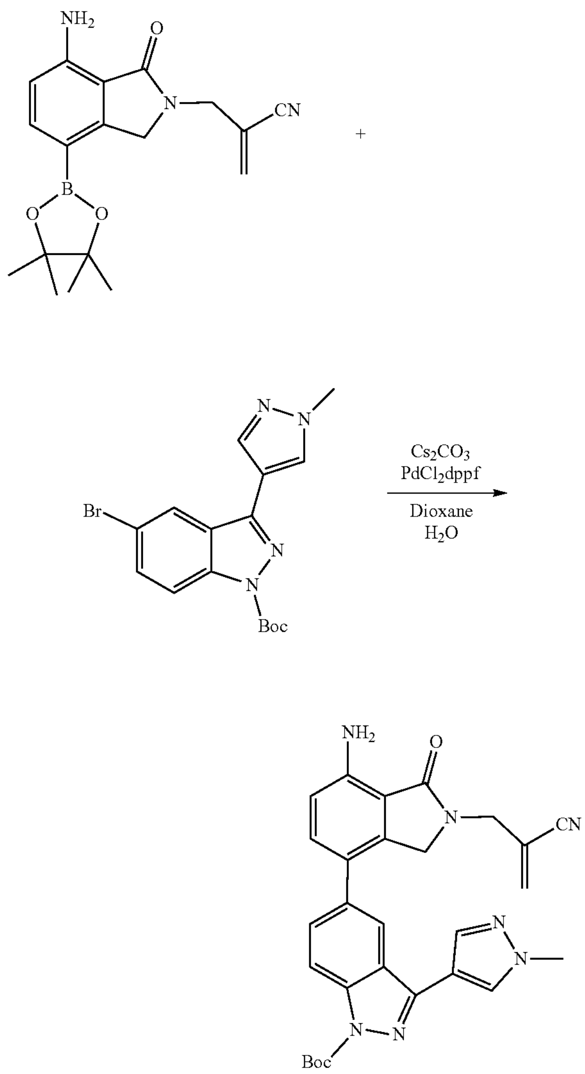

To a solution of 2-[[7-amino-1-oxo-4-(4,4,5,5-tetramethyl-1,3,2-dioxaborolan-2-yl)isoindolin-2-yl]methyl]prop-2-enenitrile (49.9 mg, 147 μmol) in dioxane (1 mL) and water (0.2 mL) were added tert-butyl 5-bromo-3-(1-methylpyrazol-4-yl)indazole-1-carboxylate (78.1 mg, 221 μmol), $Cs_2CO_3$ (167 mg, 515 mmol) and $PdCl_2dppf$ (18 mg, 22 μmol). The reaction was heated to 100° C. for 30 min in a microwave. The reaction mixture was passed through a celite pad, and 2 mL of 0.5 M EDTA was added. The resulting solution was stirred at r.t. for 30 min. The solution was washed with brine, and the organic phase was dried over anhydrous sodium sulfate, filtered, and concentrated in vacuo. The residue was purified by chromatography on silica gel eluting with 40-100% EtOAc/hexane to afford the title compound (50.6 mg, Yield 68%).

b. Preparation of 2-[[7-amino-4-[3-(1-methylpyrazol-4-yl)-1H-indazol-5-yl]-1-oxo-isoindolin-2-yl]methyl]prop-2-enenitrile (Compound 182)

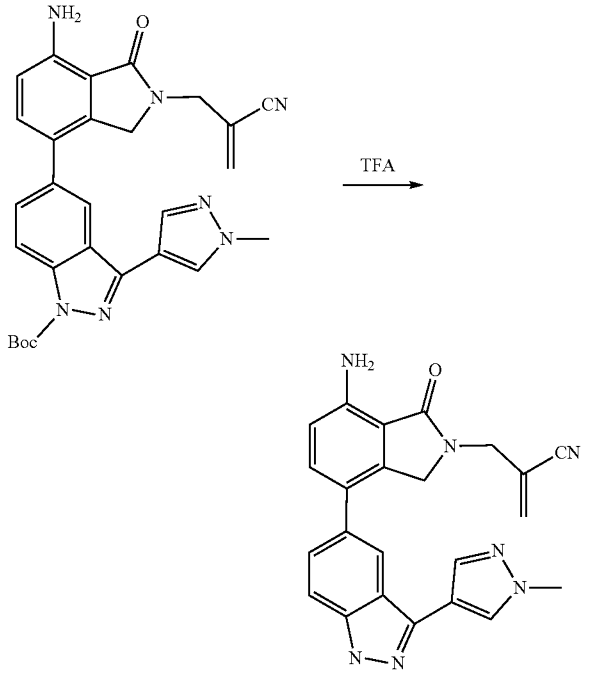

To a solution of tert-butyl 5-[7-amino-2-(2-cyanoallyl)-1-oxo-isoindolin-4-yl]-3-(1-methylpyrazol-4-yl) indazole-1-carboxylate (50.6 mg, 99 μmol) in DCM (1.6 mL) was added trifluoroacetic acid (0.4 mL) at 0° C. The resulting solution was stirred at r.t. for 2 h. The reaction mixture was concentrated in vacuo and the residue was diluted with DCM, washed with sat. $NaHCO_3$ and brine, dried over anhydrous sodium sulfate, filtered, and concentrated. The residue was purified by reverse phase HPLC using a gradient of water 0.1% FA/acetonitrile 0.1% FA to afford the title compound (9.3 mg, Yield 19%). LC-MS: $[M+H]^+$ 410.

3A.9. Preparation of 2-[[7-amino-4-(9H-carbazol-3-yl)-1-oxo-isoindolin-2-yl]methyl]prop-2-enenitrile (Compound 184)

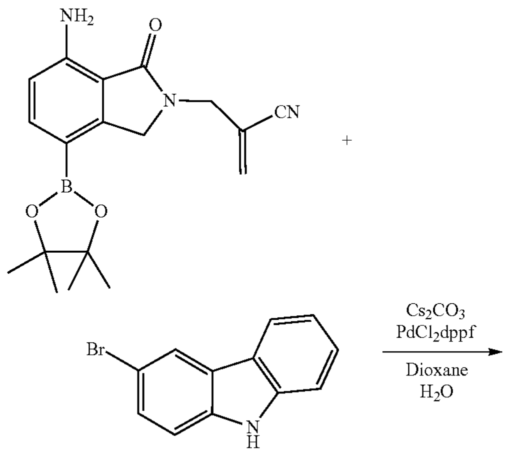

-continued

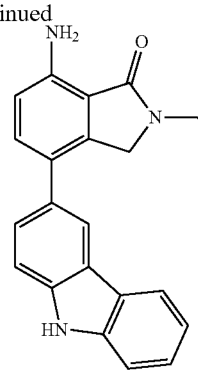

To a solution of 2-[[7-amino-1-oxo-4-(4,4,5,5-tetramethyl-1,3,2-dioxaborolan-2-yl)isoindolin-2-yl]methyl]prop-2-enenitrile (31.5 mg, 93 μmol) in dioxane (1 mL) and water (0.2 mL) were added 3-bromo-9H-carbazole (34.3 mg, 139 μmol), $Cs_2CO_3$ (105 mg, 326 mmol) and $PdCl_2dppf$ (15 mg, 18 mol). The reaction was heated to 100° C. for 30 min in a microwave. The reaction mixture was passed through a celite pad, and 2 mL of 0.5 M EDTA was added. The resulting solution was stirred at r.t. for 30 min. The solution was washed with brine, and the organic phase was dried over anhydrous sodium sulfate, filtered, and concentrated in vacuo. The residue was purified by reverse phase HPLC using a gradient of water 0.1% FA/acetonitrile 0.1% FA to afford the title compound (8 mg, Yield 23%). LC-MS: $[M+H]^+$ 379.

3A.10. Preparation of 2-[[7-amino-1-oxo-4-(3-phenyl-1H-pyrazolo[4,3-b]pyridin-5-yl) isoindolin-2-yl]methyl]prop-2-enenitrile (Compound 247)

a. Preparation of tert-butyl 5-bromo-3-phenyl-pyrazolo[4,3-b]pyridine-1-carboxylate

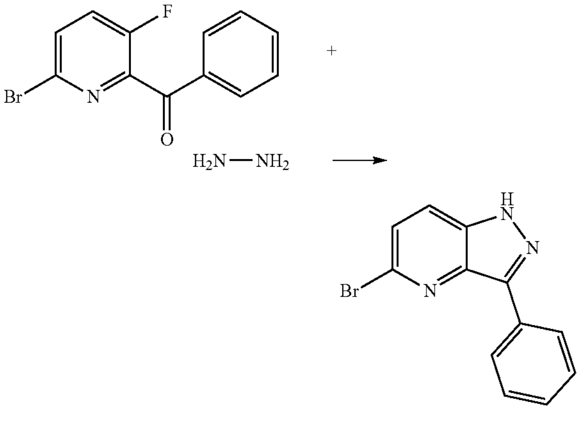

A mixture of (6-bromo-3-fluoro-2-pyridyl)-phenyl-methanone (75.4 mg, 27 μmol) and hydrazine (20.3 mg, 405 μmol) in ethylene glycol (3 mL) was heated to 170° C. for 7 h. The mixture was partitioned between EtOAc and water. The aqueous phase was extracted with EtOAc (3×). The combined organic phase was washed with water and brine, dried over ($MgSO_4$), filtered, and concentrated in vacuo. The residue (64.6 mg, Yield 87%) was used to next step without further purification.

b. Preparation of tert-butyl 5-bromo-3-phenyl-pyrazolo[4,3-b]pyridine-1-carboxylate

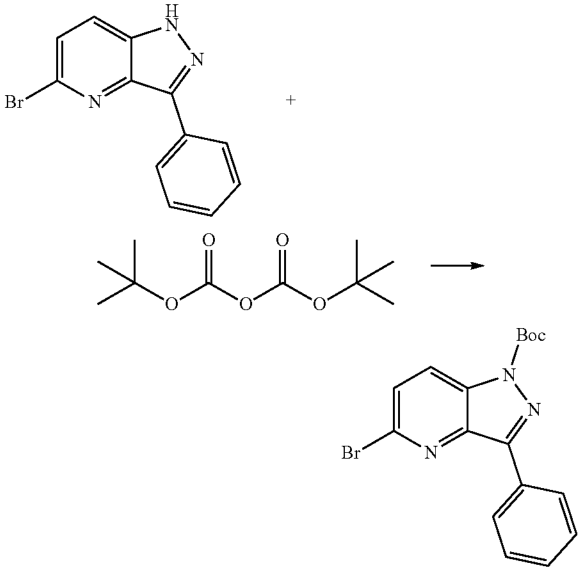

To a solution of 5-bromo-3-phenyl-1H-pyrazolo[4,3-b]pyridine (64.6 mg, 0.236 mmol) in MeCN (3 mL) was added tert-butoxycarbonyl tert-butyl carbonate (102 mg, 0.471 mmol), TEA (83.7 mg, 0.826 mmol) and DMAP (5.8 mg, 0.047 mmol). The resulting mixture was stirred at r.t. for 5 h and concentrated in vacuo. The residue was purified by chromatography on silica gel eluting with 0-20% EtOAc/hexane to afford the title compound (64 mg, Yield 73%).

c. Preparation of tert-butyl 5-[7-amino-2-(2-cyanoallyl)-1-oxo-isoindolin-4-yl]-3-phenyl-pyrazolo[4,3-b]pyridine-1-carboxylate

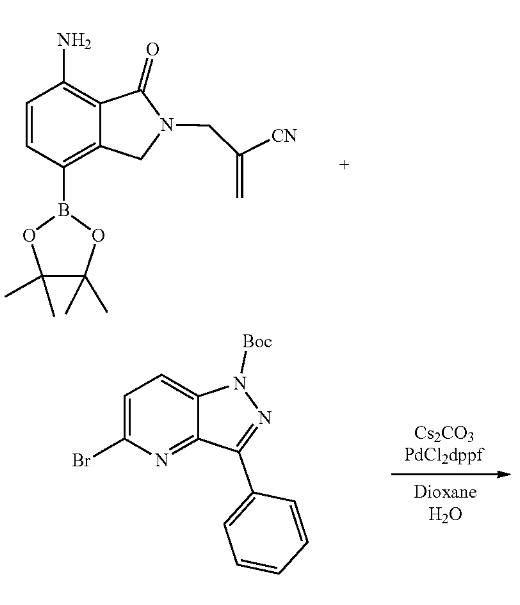

-continued

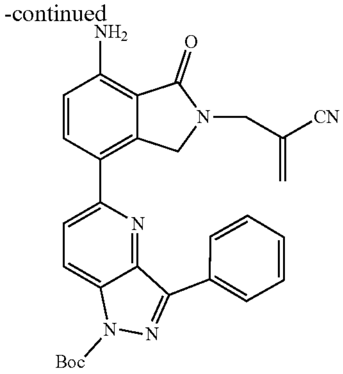

To a solution of 2-[[7-amino-1-oxo-4-(4,4,5,5-tetramethyl-1,3,2-dioxaborolan-2-yl)isoindolin-2-yl]methyl]prop-2-enenitrile (58 mg, 171 μmol) in dioxane (1 mL) and water (0.2 mL) were added tert-butyl 5-bromo-3-phenyl-pyrazolo[4,3-b]pyridine-1-carboxylate (64 mg, 171 μmol), $Cs_2CO_3$ (194 mg, 589 mmol) and $PdCl_2$dppf (18 mg, 22 μmol). The reaction was heated to 100° C. for 30 min in a microwave. The reaction mixture was passed through a celite pad, and 2 mL of 0.5 M EDTA was added. The resulting solution was stirred at r.t. for 30 min. The solution was washed with brine, and the organic phase was dried over anhydrous sodium sulfate, filtered, and concentrated in vacuo. The residue was purified by chromatography on silica gel eluting with 40-100% EtOAc/hexane to afford the title compound (15 mg, Yield 17%).

d. Preparation of 2-[[7-amino-1-oxo-4-(3-phenyl-1H-pyrazolo[4,3-b]pyridin-5-yl) isoindolin-2-yl] methyl]prop-2-enenitrile (Compound 247)

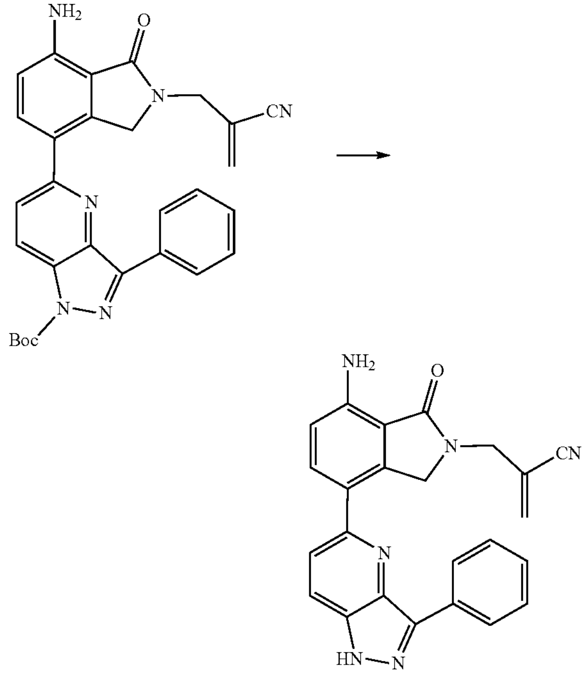

To a solution of tert-butyl 5-[7-amino-2-(2-cyanoallyl)-1-oxo-isoindolin-4-yl]-3-phenyl-pyrazolo[4,3-b]pyridine-1-carboxylate (15 mg, 30 μmol) in DCM (1.6 mL) was added trifluoroacetic acid (0.4 mL) at 0° C. The resulting solution was stirred at r.t. for 2 h. The reaction mixture was concentrated in vacuo and the residue was diluted with DCM, washed with sat. $NaHCO_3$ and brine, dried over anhydrous sodium sulfate, filtered, and concentrated. The residue was purified by reverse phase HPLC using a gradient of water 0.1% FA/acetonitrile 0.1% FA to afford the title compound (2 mg, Yield 17%). LC-MS: $[M+H]^+$ 407.

3A.11. Preparation of 2-[[7-amino-1-oxo-[3-(2-thienyl) pyrazolo[1,5-a]pyridin-5-yl]isoindolin-2-yl] methyl]prop-2-enenitrile (Compound 248)

a. Preparation of 5-bromo-3-(2-thienyl) pyrazolo[1,5-a]pyridine

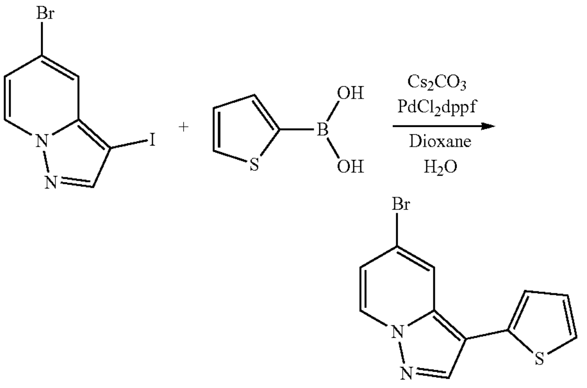

To a solution 5-bromo-3-iodo-pyrazolo[1,5-a]pyridine (150 mg, 464 μmol) in dioxane (3 mL) and water (0.6 mL) were added 2-thienylboronic acid (89.1 mg, 697 μmol), $Cs_2CO_3$ (528 mg, 1.624 mmol) and $PdCl_2$dppf (40 mg, 44 μmol). The reaction was heated to 100° C. for 1 h in a microwave. The reaction mixture was passed through a celite pad, and 2 mL of 0.5 M EDTA was added. The resulting solution was stirred at r.t. for 30 min. The solution was washed with brine, and the organic phase was dried over anhydrous sodium sulfate, filtered, and concentrated in vacuo. The residue was purified by chromatography on silica gel eluting with 0-70% EtOAc/hexane to afford the title compound (46.7 mg, Yield 36%).

b. Preparation of 2-[[7-amino-1-oxo-4-[2-thienyl) pyrazolo[1,5-a]pyridin-5-yl]isoindolin-2-yl]methyl] prop-2-enenitrile (Compound 248)

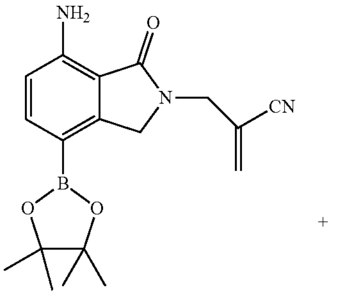

-continued

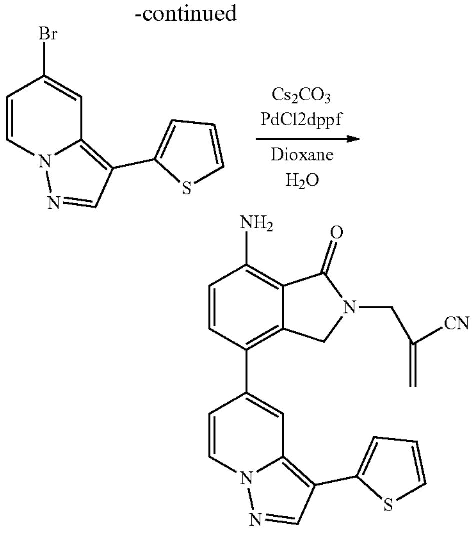

To a solution of 2-[[7-amino-1-oxo-4-(4,4,5,5-tetramethyl-1,3,2-dioxaborolan-2-yl)isoindolin-2-yl]methyl]prop-2-enenitrile (43.7 mg, 129 μmol) in dioxane (1.5 mL) and water (0.3 mL) were added 5-bromo-3-(2-thienyl)pyrazolo[1,5-a]pyridine 46.7 mg, 167 μmol), $Cs_2CO_3$ (146 mg, 452 mmol) and $PdCl_2dppf$ (18 mg, 22 μmol). The reaction was heated to 100° C. for 30 min in a microwave. The reaction mixture was passed through a celite pad, and 2 mL of 0.5 M EDTA was added. The resulting solution was stirred at r.t. for 30 min. The solution was washed with brine, and the organic phase was dried over anhydrous sodium sulfate, filtered, and concentrated in vacuo. The residue was purified by chromatography on silica gel eluting with 40-100% EtOAc/hexane to afford the title compound (9.1 mg, Yield 19%). LC-MS: $[M+H]^+$ 412.

3A.12. Preparation of 2-[[7-amino-1-oxo-4-[3-(3-thienyl) pyrazolo[1,5-a]pyridin-5-yl]isoindolin-2-yl]methyl]prop-2-enenitrile (Compound 249)

a. Preparation of 5-bromo-3-(3-thienyl)pyrazolo[1,5-a]pyridine

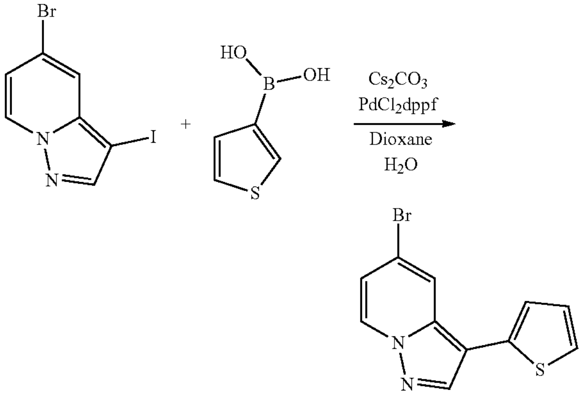

To a solution 5-bromo-3-iodo-pyrazolo[1,5-a]pyridine (150 mg, 464 μmol) in dioxane (3 mL) and water (0.6 mL) were added 3-thienylboronic acid (89.1 mg, 697 μmol), $Cs_2CO_3$ (528 mg, 1.624 mmol) and $PdCl_2dppf$ (40 mg, 44 μmol). The reaction was heated to 100° C. for 1 h in a microwave. The reaction mixture was passed through a celite pad, and 2 mL of 0.5 M EDTA was added. The resulting solution was stirred at r.t. for 30 min. The solution was washed with brine, and the organic phase was dried over anhydrous sodium sulfate, filtered, and concentrated in vacuo. The residue was purified by chromatography on silica gel eluting with 0-70% EtOAc/hexane to afford the title compound (57.2 mg, Yield 44%).

b. Preparation of 2-[[7-amino-1-oxo-4-[3-(3-thienyl) pyrazolo[1,5-a]pyridin-5-yl]isoindolin-2-yl]methyl] prop-2-enenitrile (Compound 249)

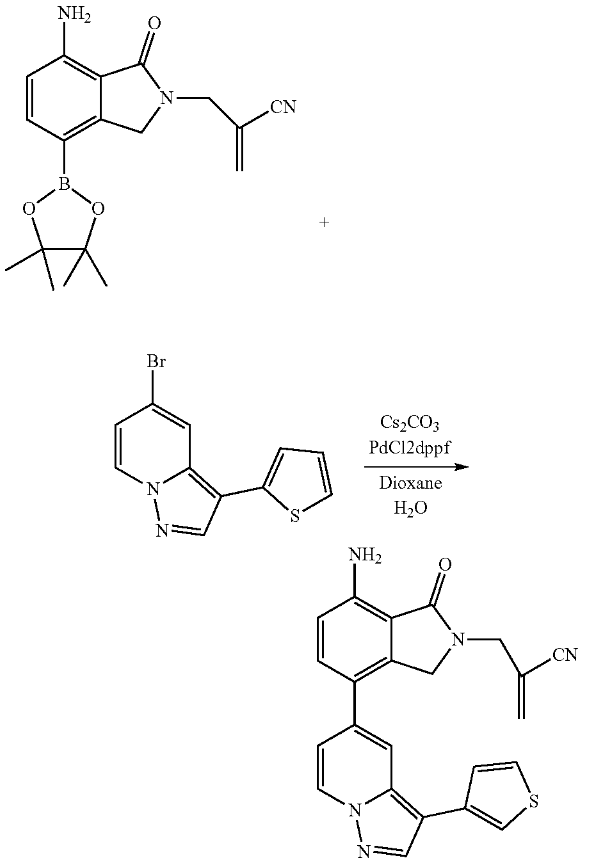

To a solution of 2-[[7-amino-1-oxo-4-(4,4,5,5-tetramethyl-1,3,2-dioxaborolan-2-yl)isoindolin-2-yl]methyl]prop-2-enenitrile (53.5 mg, 158 μmol) in dioxane (1.5 mL) and water (0.3 mL) were added 5-bromo-3-(3-thienyl)pyrazolo[1,5-a]pyridine (57.2 mg, 205 μmol), $Cs_2CO_3$ (180 mg, 553 mmol) and $PdCl_2dppf$ (18 mg, 22 μmol). The reaction was heated to 100° C. for 30 min in a microwave. The reaction mixture was passed through a celite pad, and 2 mL of 0.5 M EDTA was added. The resulting solution was stirred at r.t. for 30 min. The solution was washed with brine, and the organic phase was dried over anhydrous sodium sulfate, filtered, and concentrated in vacuo. The residue was purified by chromatography on silica gel eluting with 40-100% EtOAc/hexane to afford the title compound (10.6 mg, Yield 16%). LC-MS: $[M+H]^+$ 412.

3B. General Scheme for Method B: Route 2

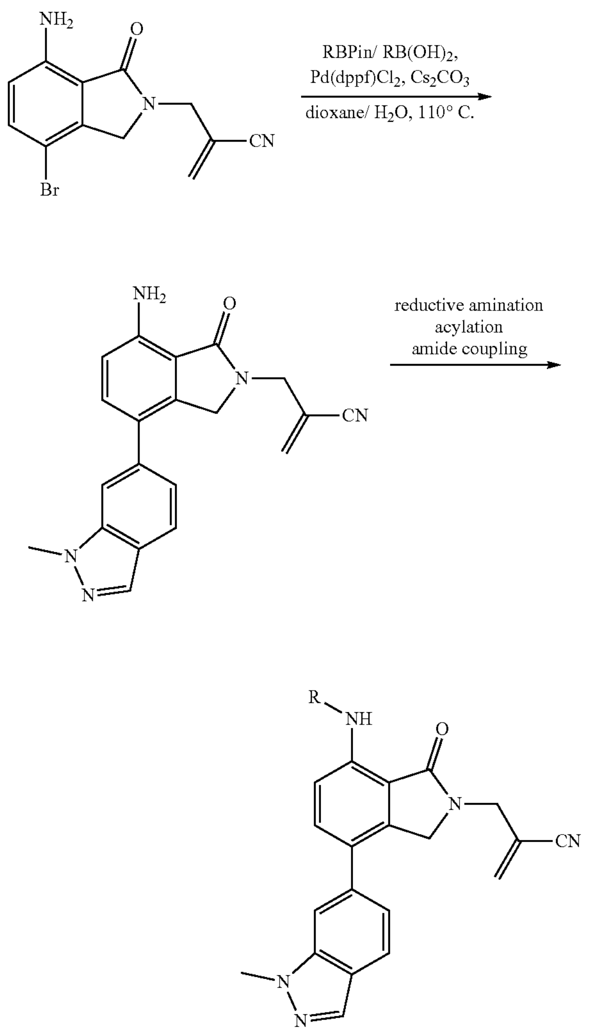

3B.1. Preparation of N-[2-(2-cyanoallyl)-7-(1-methylindazol-6-yl)-3-oxo-isoindolin-4-yl]acetamide (Compound 117)

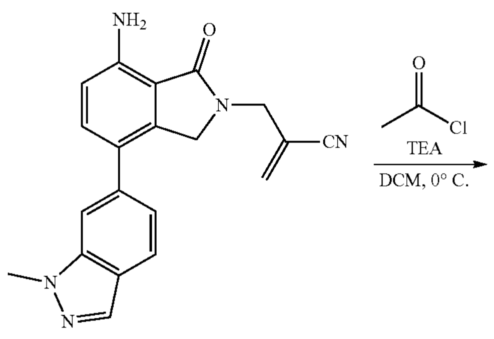

-continued

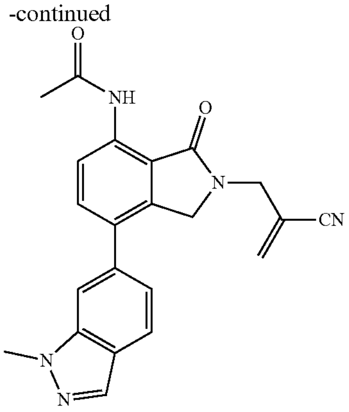

To a mixture of 2-[[7-amino-4-(1-methylindazol-6-yl)-1-oxo-isoindolin-2-yl]methyl]prop-2-enenitrile (50 mg, 131.05 μmol, 1 eq.) in DCM (2 mL) were added TEA (39.78 mg, 393.15 μmol, 54.72 μL, 3 eq.) and acetyl chloride (102.87 mg, 1.31 mmol, 93.52 μL, 10 eq.) in one portion at 0° C. under nitrogen. The mixture was stirred at 0° C. for 30 min. LCMS showed that the reaction was complete. The reaction was poured into 15 mL aq·$NH_4Cl$, extracted with DCM (15 mL×2), washed with water (15 mL×2) and brine (15 mL×2), dried over anhydrous sodium sulfate, filtered, and concentrated to give a residue. The residue was purified by prep-HPLC to afford the title compound (5.9 mg, 14.70 μmol, 11.21% yield, 96.0% purity) as a white solid. LC-MS: $[M+H]^+$ 386.1.

3B.2. Preparation of 2-[[4-(1-methylindazol-6-yl)-7-[(1-methyl-4-piperidyl)amino]-1-oxo-isoindolin-2-yl]methyl]prop-2-enenitrile (Compound 120)

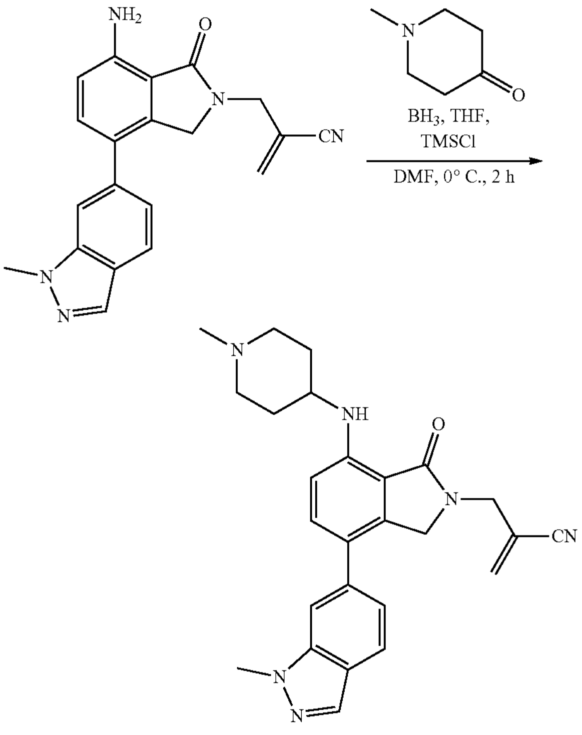

To a mixture of 2-[[7-amino-4-(1-methylindazol-6-yl)-1-oxo-isoindolin-2-yl]methyl]prop-2-enenitrile (40 mg, 104.84 μmol, 1 eq.) and 1-methylpiperidin-4-one (23.73 mg, 209.68 μmol, 24.39 μL, 2 eq.) in DMF (1.5 mL) was added TMSCl (28.48 mg, 262.10 μmol, 33.27 μL, 2.5 eq.) in one portion at 0° C. under nitrogen. The mixture was stirred at 0° C. for 1 h, then $BH_3$·THF (1 M in THF solution, 314.52 μL, 3 eq.) was added and stirred for 1 h at 0° C. LCMS showed no starting material remained. The reaction was poured into 15 mL water, and the pH of the mixture was adjusted to 8. After adding 5 mL saturated aq. $NaHCO_3$, the mixture was extracted with EtOAc (3×15 mL), and the organic layer was washed with water (15 mL×2) and brine (3×15 mL), dried over anhydrous sodium sulfate, filtered, and concentrated to give a residue. The residue was purified by prep-HPLC to afford the title compound (5.6 mg, 11.95 μmol, 11.40% yield, 94.0% purity) as a white solid. LC-MS: $[M+H]^+$ 441.2.

3C. Preparation of Compounds

TABLE 2 shows compounds containing the 7-amino-isoindolinone core and acrylonitrile moiety.

TABLE 2

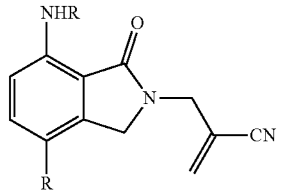

| Cpd. No. | Structure | IUPAC | LC-MS (ES+, m/z) |
|---|---|---|---|
| 113. | 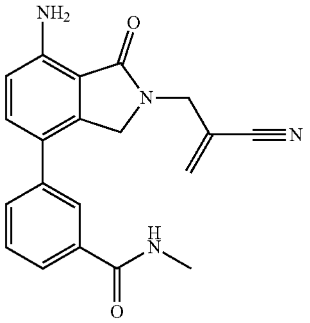 [SMILES: C=C(C#N)CN1Cc2c(-c3cccc(C(=O)NC)c3)ccc(N)c2C1=O] | 3-[7-amino-2-(2-cyano-2-methylideneethyl)-1-oxo-2,3-dihydro-1H-isoindol-4-yl]-N-methylbenzamide | 347 |
| 114. | 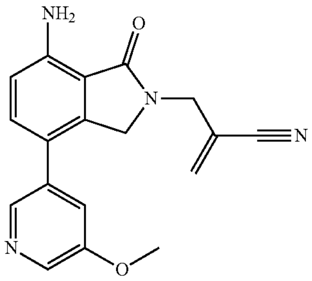 [SMILES: C=C(C#N)CN1Cc2c(-c3cncc(OC)c3)ccc(N)c2C1=O] | 2-{[7-amino-4-(5-methoxypyridin-3-yl)-1-oxo-2,3-dihydro-1H-isoindol-2-yl]methyl}prop-2-enenitrile | 321 |
| 115. | 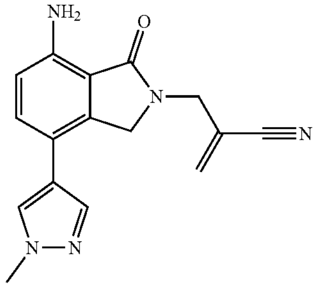 [SMILES: C=C(C#N)CN1Cc2c(-c3cnn(C)c3)ccc(N)c2C1=O] | 2-{[7-amino-4-(1-methyl-1H-pyrazol-4-yl)-1-oxo-2,3-dihydro-1H-isoindol-2-yl]methyl}prop-2-enenitrile | 294.1 |

TABLE 2-continued
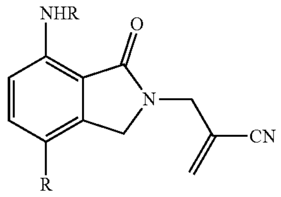
| Cpd. No. | Structure | IUPAC | LC-MS (ES+, m/z) |
|---|---|---|---|
| 116. | 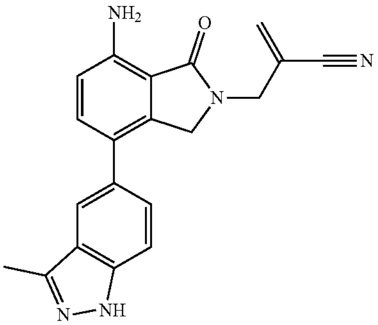 [SMILES: C=C(C#N)CN1Cc2c(-c3ccc4[nH]nc(C)c4c3)ccc(N)c2C1=O] | 2-{[7-amino-4-(3-methyl-1H-indazol-5-yl)-1-oxo-2,3-dihydro-1H-isoindol-2-yl]methyl}prop-2-enenitrile | 344.1 |
| 117. | 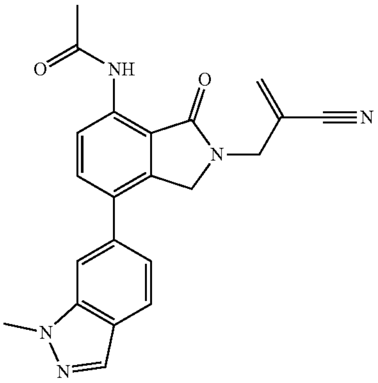 [SMILES: C=C(C#N)CN1Cc2c(-c3ccc4cnn(C)c4c3)ccc(NC(C)=O)c2C1=O] | N-[2-(2-cyano-2-methylideneethyl)-7-(1-methyl-1H-indazol-6-yl)-3-oxo-2,3-dihydro-1H-isoindol-4-yl]acetamide | 386.1 |
| 118. | 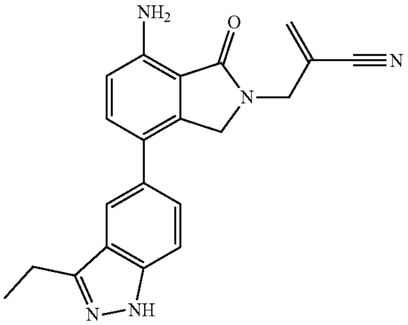 [SMILES: C=C(C#N)CN1Cc2c(-c3ccc4[nH]nc(CC)c4c3)ccc(N)c2C1=O] | 2-{[7-amino-4-(3-ethyl-1H-indazol-5-yl)-1-oxo-2,3-dihydro-1H-isoindol-2-yl]methyl}prop-2-enenitrile | 358.1 |
| 119. | 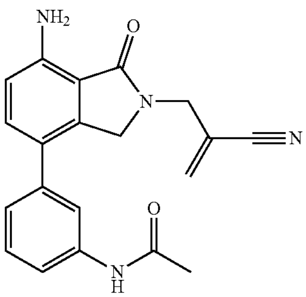 [SMILES: C=C(C#N)CN1Cc2c(-c3cccc(NC(C)=O)c3)ccc(N)c2C1=O] | N-{3-[7-amino-2-(2-cyano-2-methylideneethyl)-1-oxo-2,3-dihydro-1H-isoindol-4-yl]phenyl}acetamide | 347.1 |

TABLE 2-continued
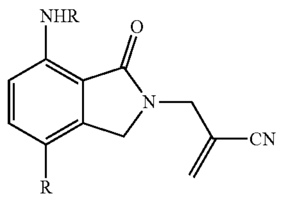
| Cpd. No. | Structure | IUPAC | LC-MS (ES+, m/z) |
|---|---|---|---|
| 120. | 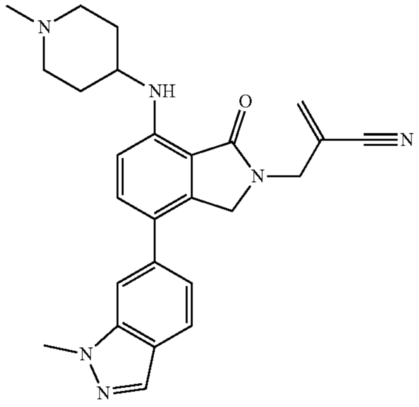 [SMILES: C=C(C#N)CN1Cc2c(-c3ccc4cnn(C)c4c3)ccc(NC3CCN(C)CC3)c2C1=O] | 2-{[4-(1-methyl-1H-indazol-6-yl)-7-[(1-methylpiperidin-4-yl)amino]-1-oxo-2,3-dihydro-1H-isoindol-2-yl]methyl}prop-2-enenitrile | 441.2 |
| 121. | 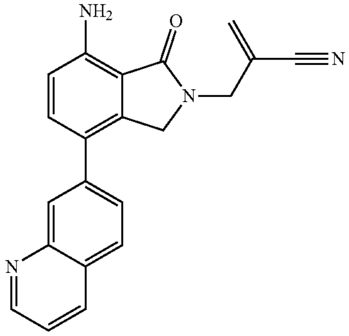 [SMILES: C=C(C#N)CN1Cc2c(-c3ccc4cccnc4c3)ccc(N)c2C1=O] | 2-{[7-amino-1-oxo-4-(quinolin-7-yl)-2,3-dihydro-1H-isoindol-2-yl]methyl}prop-2-enenitrile | 341.1 |
| 122. | 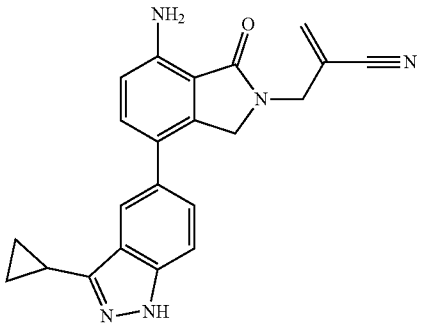 [SMILES: C=C(C#N)CN1Cc2c(-c3ccc4[nH]nc(C5CC5)c4c3)ccc(N)c2C1=O] | 2-{[7-amino-4-(3-cyclopropyl-1H-indazol-5-yl)-1-oxo-2,3-dihydro-1H-isoindol-2-yl]methyl}prop-2-enenitrile | 370.1 |

TABLE 2-continued

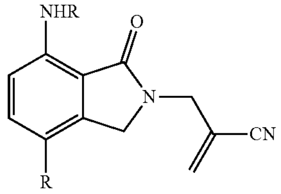

| Cpd. No. | Structure | IUPAC | LC-MS (ES+, m/z) |
|---|---|---|---|
| 123. | 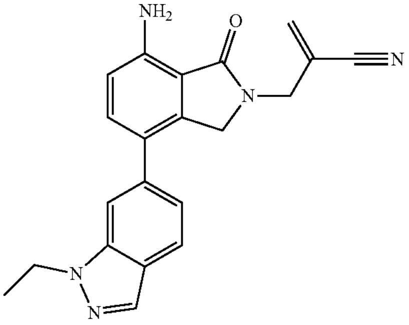 [SMILES: C=C(C#N)CN1Cc2c(-c3ccc4cnn(CC)c4c3)ccc(N)c2C1=O] | 2-{[7-amino-4-(1-ethyl-1H-indazol-6-yl)-1-oxo-2,3-dihydro-1H-isoindol-2-yl]methyl}prop-2-enenitrile | 358.1 |
| 124. | 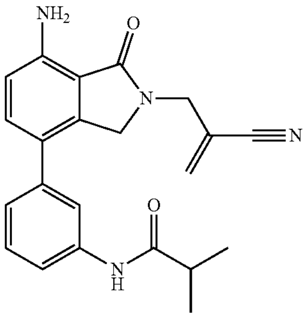 [SMILES: C=C(C#N)CN1Cc2c(-c3cccc(NC(=O)C(C)C)c3)ccc(N)c2C1=O] | N-{3-[7-amino-2-(2-cyano-2-methylideneethyl)-1-oxo-2,3-dihydro-1H-isoindol-4-yl]phenyl}-2-methylpropanamide | 375.1 |
| 125. | 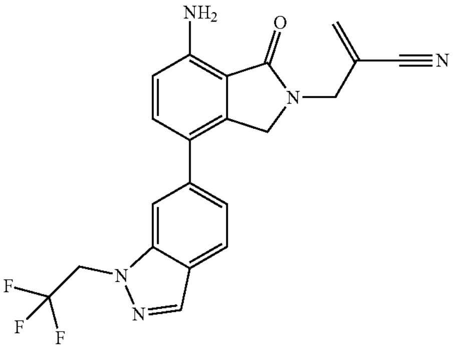 [SMILES: C=C(C#N)CN1Cc2c(-c3ccc4cnn(CC(F)(F)F)c4c3)ccc(N)c2C1=O] | 2-({7-amino-1-oxo-4-[1-(2,2,2-trifluoroethyl)-1H-indazol-6-yl]-2,3-dihydro-1H-isoindol-2-yl}methyl)prop-2-enenitrile | 412.1 |
| 126. | 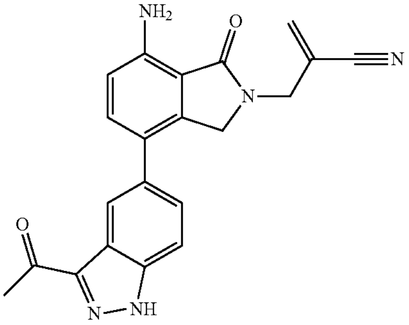 [SMILES: C=C(C#N)CN1Cc2c(-c3ccc4[nH]nc(C(C)=O)c4c3)ccc(N)c2C1=O] | 2-{[4-(3-acetyl-1H-indazol-5-yl)-7-amino-1-oxo-2,3-dihydro-1H-isoindol-2-yl]methyl}prop-2-enenitrile | 372.1 |

TABLE 2-continued
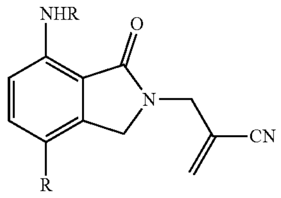
| Cpd. No. | Structure | IUPAC | LC-MS (ES+, m/z) |
|---|---|---|---|
| 127. | 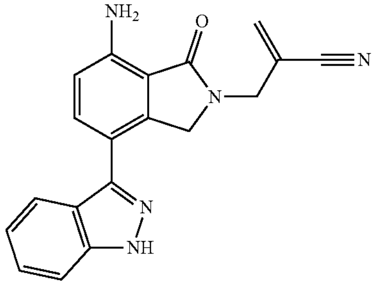 [SMILES: C=C(C#N)CN1Cc2c(-c3n[nH]c4ccccc34)ccc(N)c2C1=O] | 2-{[7-amino-4-(1H-indazol-3-yl)-1-oxo-2,3-dihydro-1H-isoindol-2-yl]methyl}prop-2-enenitrile | 330 |
| 128. | 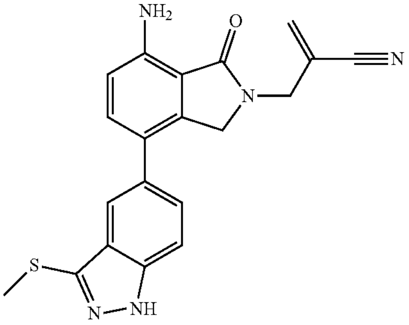 [SMILES: C=C(C#N)CN1Cc2c(-c3ccc4[nH]nc(SC)c4c3)ccc(N)c2C1=O] | 2-({7-amino-4-[3-(methylsulfanyl)-1H-indazol-5-yl]-1-oxo-2,3-dihydro-1H-isoindol-2-yl}methyl)prop-2-enenitrile | 376.1 |
| 129. | 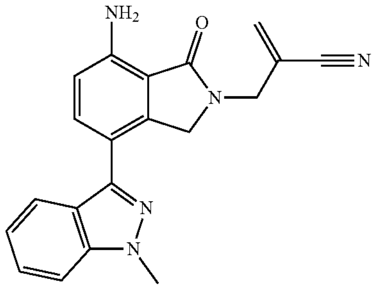 [SMILES: C=C(C#N)CN1Cc2c(-c3nn(C)c4ccccc34)ccc(N)c2C1=O] | 2-{[7-amino-4-(1-methyl-1H-indazol-3-yl)-1-oxo-2,3-dihydro-1H-isoindol-2-yl]methyl}prop-2-enenitrile | 344.1 |
| 130. | 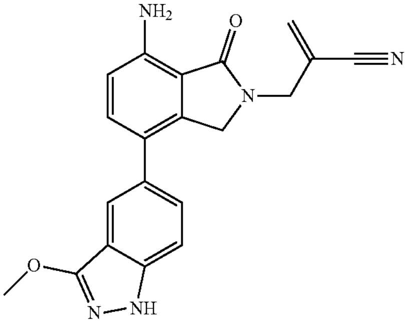 | 2-{[7-amino-4-(3-methoxy-1H-indazol-5-yl)-1-oxo-2,3-dihydro-1H-isoindol-2-yl]methyl}prop-2-enenitrile | 360.1 |

TABLE 2-continued
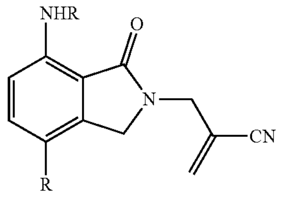
| Cpd. No. | Structure | IUPAC | LC-MS (ES+, m/z) |
|---|---|---|---|
| 131. | 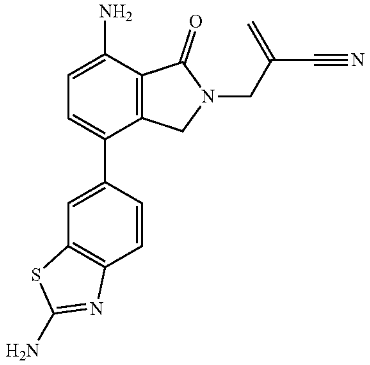 [SMILES: C=C(C#N)CN1Cc2c(-c3ccc4nc(N)sc4c3)ccc(N)c2C1=O] | 2-{[7-amino-4-(2-amino-1,3-benzothiazol-6-yl)-1-oxo-2,3-dihydro-1H-isoindol-2-yl]methyl}prop-2-enenitrile | 362 |
| 132. | 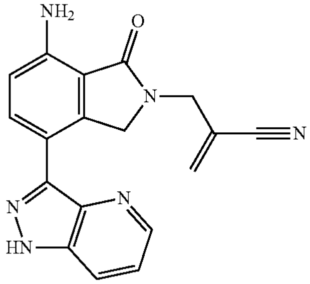 [SMILES: C=C(C#N)CN1Cc2c(-c3n[nH]c4cccnc34)ccc(N)c2C1=O] | 2-[(7-amino-1-oxo-4-{1H-pyrazolo[4,3-b]pyridin-3-yl}-2,3-dihydro-1H-isoindol-2-yl)methyl]prop-2-enenitrile | 331.1 |
| 133. | 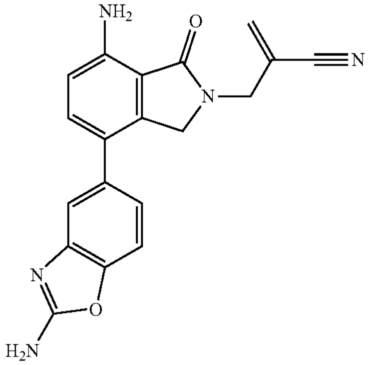 [SMILES: C=C(C#N)CN1Cc2c(-c3ccc4oc(N)nc4c3)ccc(N)c2C1=O] | 2-{[7-amino-4-(2-amino-1,3-benzoxazol-5-yl)-1-oxo-2,3-dihydro-1H-isoindol-2-yl]methyl}prop-2-enenitrile | 346 |
| 134. | 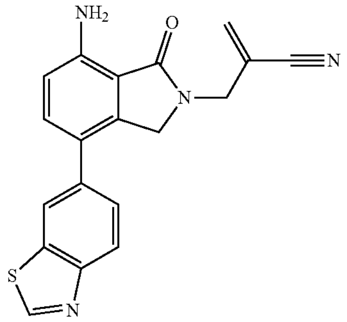 [SMILES: C=C(C#N)CN1Cc2c(-c3ccc4ncsc4c3)ccc(N)c2C1=O] | 2-{[7-amino-4-(1,3-benzothiazol-6-yl)-1-oxo-2,3-dihydro-1H-isoindol-2-yl]methyl}prop-2-enenitrile | 347.1 |

TABLE 2-continued
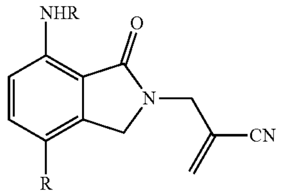
| Cpd. No. | Structure | IUPAC | LC-MS (ES+, m/z) |
| --- | --- | --- | --- |
| 135. | 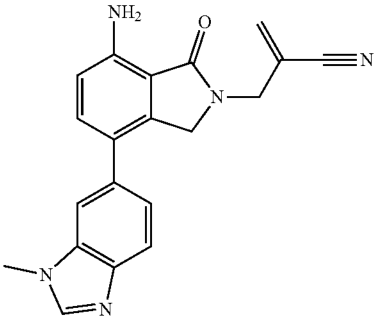 [SMILES: C=C(C#N)CN1Cc2c(-c3ccc4ncn(C)c4c3)ccc(N)c2C1=O] | 2-{[7-amino-4-(1-methyl-1H-1,3-benzodiazol-6-yl)-1-oxo-2,3-dihydro-1H-isoindol-2-yl]methyl}prop-2-enenitrile | 344.1 |
| 136. | 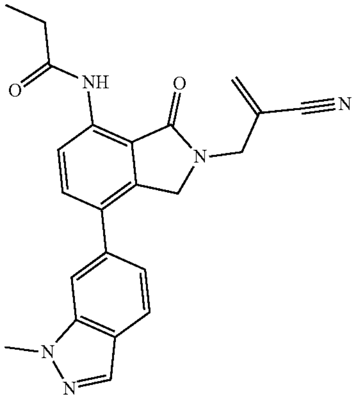 [SMILES: C=C(C#N)CN1Cc2c(-c3ccc4cnn(C)c4c3)ccc(NC(=O)CC)c2C1=O] | N-[2-(2-cyano-2-methylideneethyl)-7-(1-methyl-1H-indazol-6-yl)-3-oxo-2,3-dihydro-1H-isoindol-4-yl]propanamide | 400.1 |
| 137. | 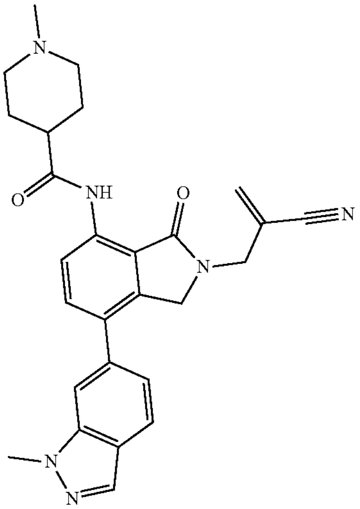 [SMILES: C=C(C#N)CN1Cc2c(-c3ccc4cnn(C)c4c3)ccc(NC(=O)C3CCN(C)CC3)c2C1=O] | N-[2-(2-cyano-2-methylideneethyl)-7-(1-methyl-1H-indazol-6-yl)-3-oxo-2,3-dihydro-1H-isoindol-4-yl]-1-methylpiperidine-4-carboxamide | 469.2 |

TABLE 2-continued

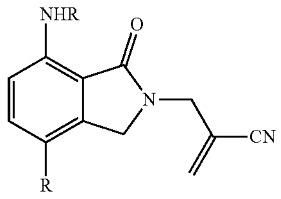

| Cpd. No. | Structure | IUPAC | LC-MS (ES+, m/z) |
|---|---|---|---|
| 138. | 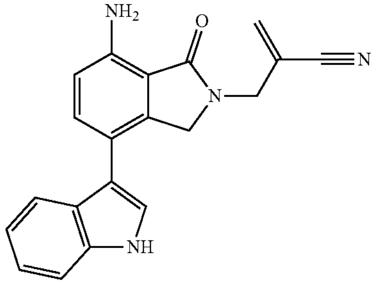 [SMILES: C=C(C#N)CN1Cc2c(-c3c[nH]c4ccccc34)ccc(N)c2C1=O] | 2-{[7-amino-4-(1H-indol-3-yl)-1-oxo-2,3-dihydro-1H-isoindol-2-yl]methyl}prop-2-enenitrile | 329.1 |
| 139. | 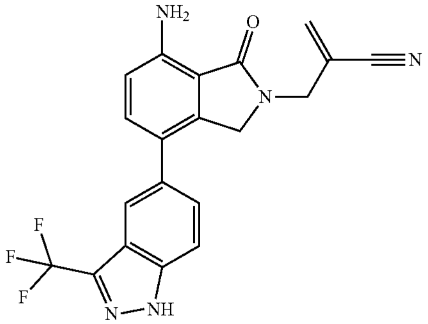 [SMILES: C=C(C#N)CN1Cc2c(-c3ccc4[nH]nc(C(F)(F)F)c4c3)ccc(N)c2C1=O] | 2-({7-amino-1-oxo-4-[3-(trifluoromethyl)-1H-indazol-5-yl]-2,3-dihydro-1H-isoindol-2-yl}methyl)prop-2-enenitrile | 398 |
| 140. | 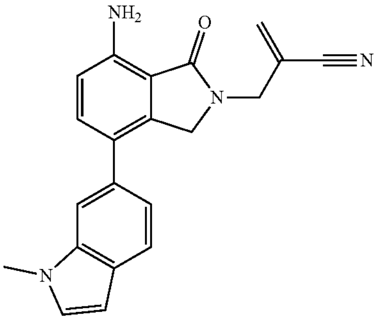 [SMILES: C=C(C#N)CN1Cc2c(-c3ccc4ccn(C)c4c3)ccc(N)c2C1=O] | 2-{[7-amino-4-(1-methyl-1H-indol-6-yl)-1-oxo-2,3-dihydro-1H-isoindol-2-yl]methyl}prop-2-enenitrile | 343.2 |
| 141. | 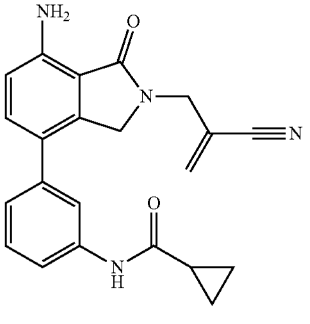 [SMILES: C=C(C#N)CN1Cc2c(-c3cccc(NC(=O)C4CC4)c3)ccc(N)c2C1=O] | N-{3-[7-amino-2-(2-cyano-2-methylideneethyl)-1-oxo-2,3-dihydro-1H-isoindol-4-yl]phenyl}cyclopropanecarboxamide | 373.2 |

TABLE 2-continued
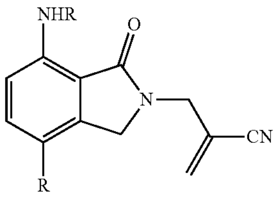
| Cpd. No. | Structure | IUPAC | LC-MS (ES+, m/z) |
|---|---|---|---|
| 142. | 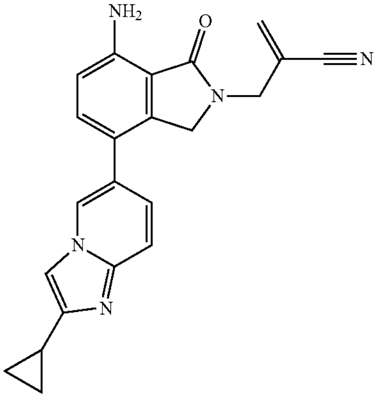 [SMILES: C=C(C#N)CN1Cc2c(-c3ccc4nc(C5CC5)cn4c3)ccc(N)c2C1=O] | 2-[(7-amino-4-{2-cyclopropylimidazo[1,2-a]pyridin-6-yl}-1-oxo-2,3-dihydro-1H-isoindol-2-yl)methyl]prop-2-enenitrile | 370.2 |
| 143. | 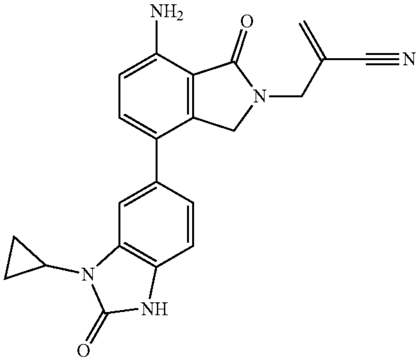 [SMILES: C=C(C#N)CN1Cc2c(-c3ccc4[nH]c(=O)n(C5CC5)c4c3)ccc(N)c2C1=O] | 2-{[7-amino-4-(3-cyclopropyl-2-oxo-2,3-dihydro-1H-1,3-benzodiazol-5-yl)-1-oxo-2,3-dihydro-1H-isoindol-2-yl]methyl}prop-2-enenitrile | 386 |
| 144. | 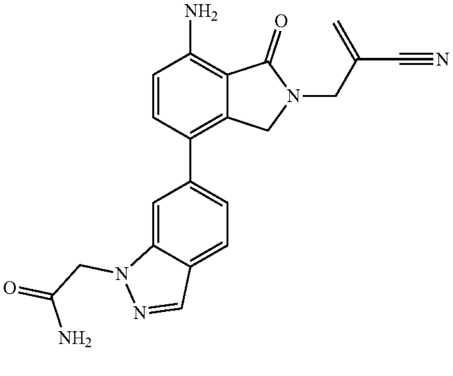 [SMILES: C=C(C#N)CN1Cc2c(-c3ccc4cnn(CC(N)=O)c4c3)ccc(N)c2C1=O] | 2-{6-[7-amino-2-(2-cyano-2-methylideneethyl)-1-oxo-2,3-dihydro-1H-isoindol-4-yl]-1H-indazol-1-yl}acetamide | 387.1 |

TABLE 2-continued

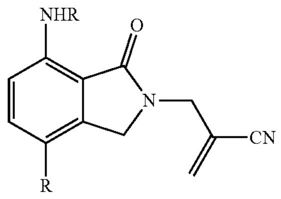

| Cpd. No. | Structure | IUPAC | LC-MS (ES+, m/z) |
|---|---|---|---|
| 145. | 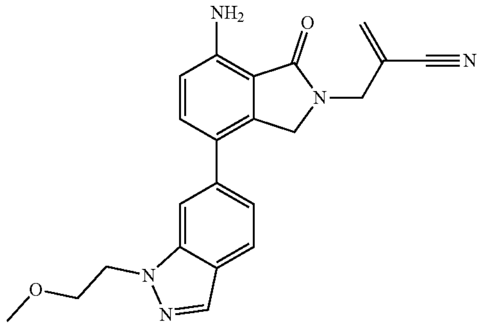 [SMILES: C=C(C#N)CN1Cc2c(-c3ccc4cnn(CCOC)c4c3)ccc(N)c2C1=O] | 2-({7-amino-4-[1-(2-methoxyethyl)-1H-indazol-6-yl]-1-oxo-2,3-dihydro-1H-isoindol-2-yl}methyl)prop-2-enenitrile | 388.1 |
| 146. | 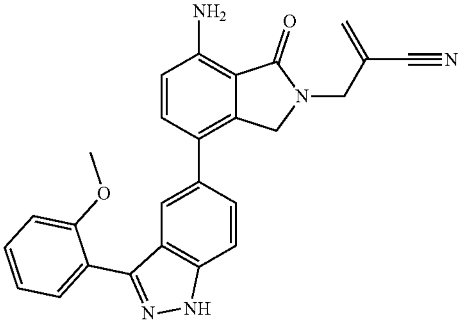 [SMILES: C=C(C#N)CN1Cc2c(-c3ccc4[nH]nc(-c5ccccc5OC)c4c3)ccc(N)c2C1=O] | 2-({7-amino-4-[3-(2-methoxyphenyl)-1H-indazol-5-yl]-1-oxo-2,3-dihydro-1H-isoindol-2-yl}methyl)prop-2-enenitrile | 436.2 |
| 147. | 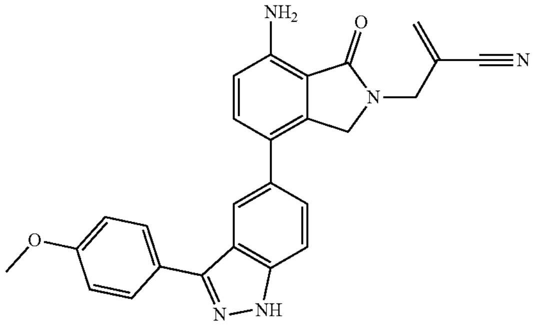 [SMILES: C=C(C#N)CN1Cc2c(-c3ccc4[nH]nc(-c5ccc(OC)cc5)c4c3)ccc(N)c2C1=O] | 2-({7-amino-4-[3-(4-methoxyphenyl)-1H-indazol-5-yl]-1-oxo-2,3-dihydro-1H-isoindol-2-yl}methyl)prop-2-enenitrile | 436.1 |
| 148. | 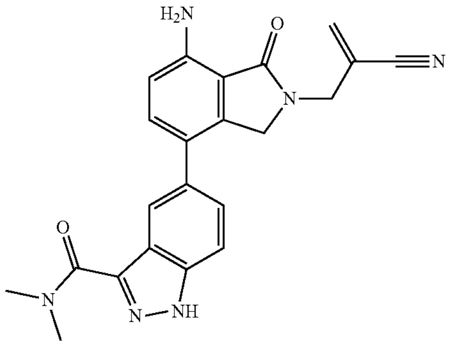 [SMILES: C=C(C#N)CN1Cc2c(-c3ccc4[nH]nc(C(=O)N(C)C)c4c3)ccc(N)c2C1=O] | 5-[7-amino-2-(2-cyano-2-methylideneethyl)-1-oxo-2,3-dihydro-1H-isoindol-4-yl]-N,N-dimethyl-1H-indazole-3-carboxamide | 401.2 |

TABLE 2-continued

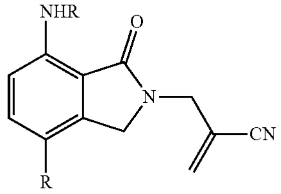

| Cpd. No. | Structure | IUPAC | LC-MS (ES+, m/z) |
|---|---|---|---|
| 149. | 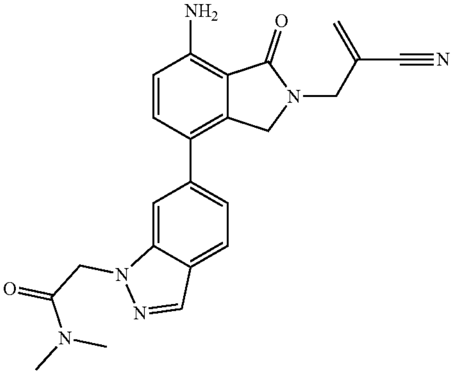 | 2-{6-[7-amino-2-(2-cyano-2-methylideneethyl)-1-oxo-2,3-dihydro-1H-isoindol-4-yl]-1H-indazol-1-yl}-N,N-dimethylacetamide | 415.1 |
| 150. | 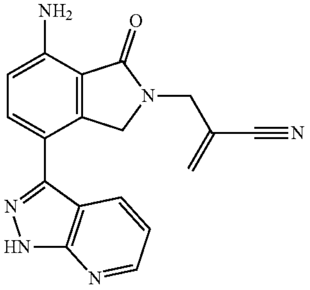 [SMILES: C=C(C#N)CN1Cc2c(-c3n[nH]c4ncccc34)ccc(N)c2C1=O] | 2-[(7-amino-1-oxo-4-{1H-pyrazolo[3,4-b]pyridin-3-yl}-2,3-dihydro-1H-isoindol-2-yl)methyl]prop-2-enenitrile | 331.1 |
| 151. | 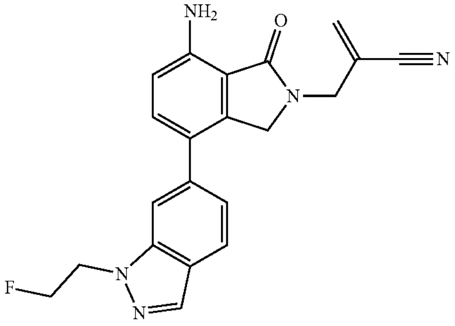 [SMILES: C=C(C#N)CN1Cc2c(-c3ccc4cnn(CCF)c4c3)ccc(N)c2C1=O] | 2-({7-amino-4-[1-(2-fluoroethyl)-1H-indazol-6-yl]-1-oxo-2,3-dihydro-1H-isoindol-2-yl}methyl)prop-2-enenitrile | 376.1 |
| 152. | 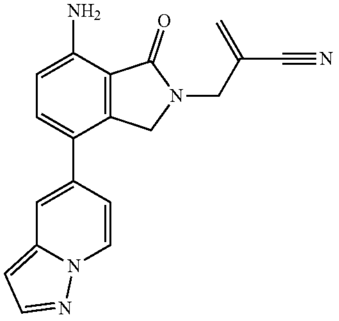 [SMILES: C=C(C#N)CN1Cc2c(-c3ccn4nccc4c3)ccc(N)c2C1=O] | 2-[(7-amino-1-oxo-4-{pyrazolo[1,5-a]pyridin-5-yl}-2,3-dihydro-1H-isoindol-2-yl)methyl]prop-2-enenitrile | 330.1 |

TABLE 2-continued
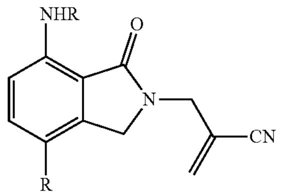
| Cpd. No. | Structure | IUPAC | LC-MS (ES+, m/z) |
|---|---|---|---|
| 153. | 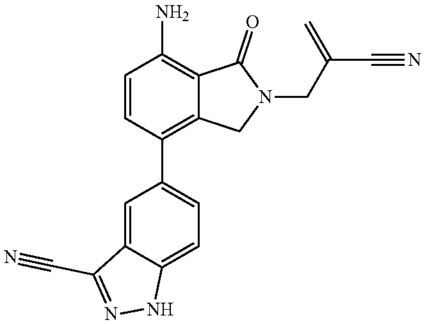 [SMILES: C=C(C#N)CN1Cc2c(-c3ccc4[nH]nc(C#N)c4c3)ccc(N)c2C1=O] | 5-[7-amino-2-(2-cyano-2-methylideneethyl)-1-oxo-2,3-dihydro-1H-isoindol-4-yl]-1H-indazole-3-carbonitrile | 355.1 |
| 154. | 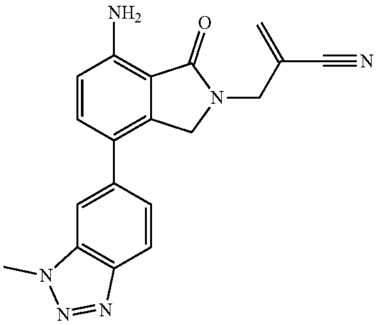 [SMILES: C=C(C#N)CN1Cc2c(-c3ccc4nnn(C)c4c3)ccc(N)c2C1=O] | 2-{[7-amino-4-(1-methyl-1H-1,2,3-benzotriazol-6-yl)-1-oxo-2,3-dihydro-1H-isoindol-2-yl]methyl}prop-2-enenitrile | 345.1 |
| 155. | 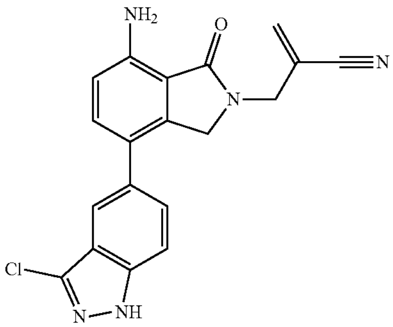 [SMILES: C=C(C#N)CN1Cc2c(-c3ccc4[nH]nc(Cl)c4c3)ccc(N)c2C1=O] | 2-{[7-amino-4-(3-chloro-1H-indazol-5-yl)-1-oxo-2,3-dihydro-1H-isoindol-2-yl]methyl}prop-2-enenitrile | 364.1 |
| 156. | 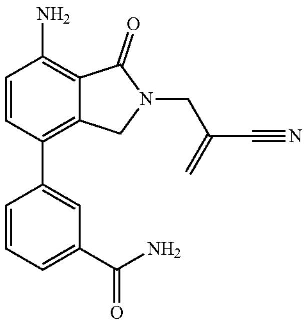 [SMILES: C=C(C#N)CN1Cc2c(-c3cccc(C(N)=O)c3)ccc(N)c2C1=O] | 3-[7-amino-2-(2-cyano-2-methylideneethyl)-1-oxo-2,3-dihydro-1H-isoindol-4-yl]benzamide | 333.2 |

TABLE 2-continued
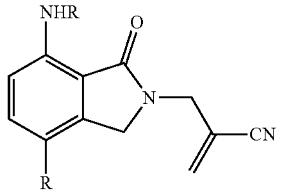
| Cpd. No. | Structure | IUPAC | LC-MS (ES+, m/z) |
|---|---|---|---|
| 157. | 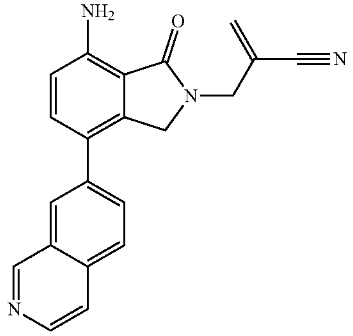 [SMILES: C=C(C#N)CN1Cc2c(-c3ccc4ccncc4c3)ccc(N)c2C1=O] | 2-{[7-amino-4-(isoquinolin-7-yl)-1-oxo-2,3-dihydro-1H-isoindol-2-yl]methyl}prop-2-enenitrile | 341.1 |
| 158. | 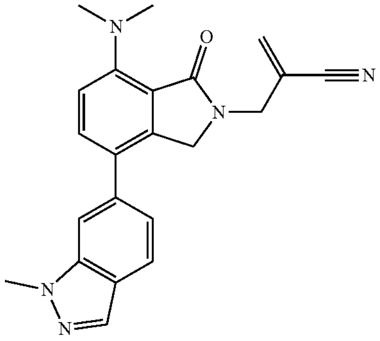 [SMILES: C=C(C#N)CN1Cc2c(-c3ccc4cnn(C)c4c3)ccc(N(C)C)c2C1=O] | 2-{[7-(dimethylamino)-4-(1-methyl-1H-indazol-6-yl)-1-oxo-2,3-dihydro-1H-isoindol-2-yl]methyl}prop-2-enenitrile | 372.1 |
| 159. | 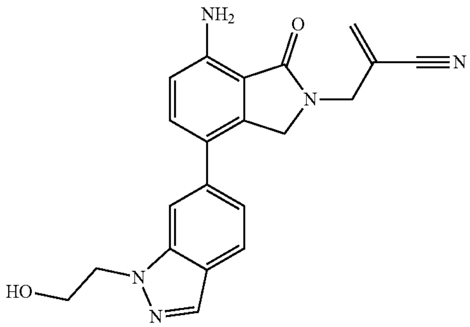 [SMILES: C=C(C#N)CN1Cc2c(-c3ccc4cnn(CCO)c4c3)ccc(N)c2C1=O] | 2-({7-amino-4-[1-(2-hydroxyethyl)-1H-indazol-6-yl]-1-oxo-2,3-dihydro-1H-isoindol-2-yl}methyl)prop-2-enenitrile | 374.2 |

TABLE 2-continued
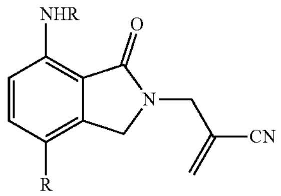
| Cpd. No. | Structure | IUPAC | LC-MS (ES+, m/z) |
|---|---|---|---|
| 160. | 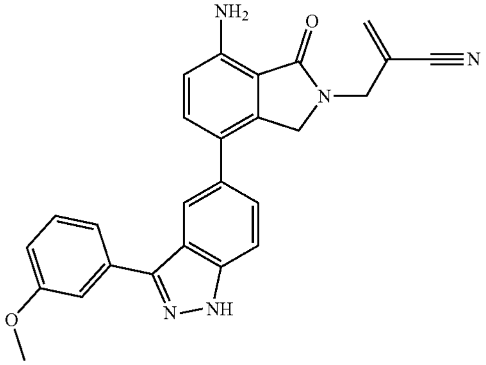 [SMILES: C=C(C#N)CN1Cc2c(-c3ccc4[nH]nc(-c5cccc(OC)c5)c4c3)ccc(N)c2C1=O] | 2-({7-amino-4-[3-(3-methoxyphenyl)-1H-indazol-5-yl]-1-oxo-2,3-dihydro-1H-isoindol-2-yl}methyl)prop-2-enenitrile | 436.1 |
| 161. | 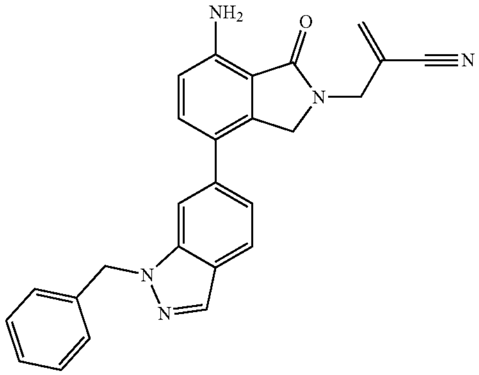 [SMILES: C=C(C#N)CN1Cc2c(-c3ccc4cnn(Cc5ccccc5)c4c3)ccc(N)c2C1=O] | 2-{[7-amino-4-(1-benzyl-1H-indazol-6-yl)-1-oxo-2,3-dihydro-1H-isoindol-2-yl]methyl}prop-2-enenitrile | 420.1 |
| 162. | 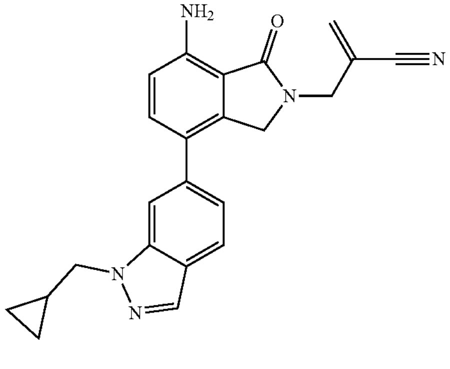 [SMILES: C=C(C#N)CN1Cc2c(-c3ccc4cnn(CC5CC5)c4c3)ccc(N)c2C1=O] | 2-({7-amino-4-[1-(cyclopropylmethyl)-1H-indazol-6-yl]-1-oxo-2,3-dihydro-1H-isoindol-2-yl}methyl)prop-2-enenitrile | 384.2 |

TABLE 2-continued
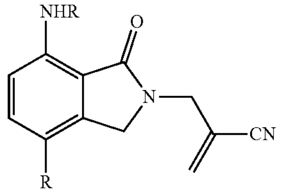
| Cpd. No. | Structure | IUPAC | LC-MS (ES+, m/z) |
|---|---|---|---|
| 163. | 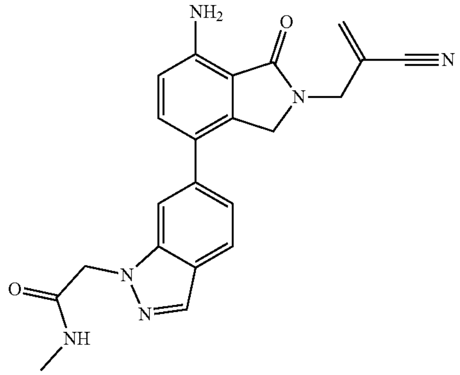 [SMILES: C=C(C#N)CN1Cc2c(-c3ccc4cnn(CC(=O)NC)c4c3)ccc(N)c2C1=O] | 2-{6-[7-amino-2-(2-cyano-2-methylideneethyl)-1-oxo-2,3-dihydro-1H-isoindol-4-yl]-1H-indazol-1-yl}-N-methylacetamide | 401.2 |
| 164. | 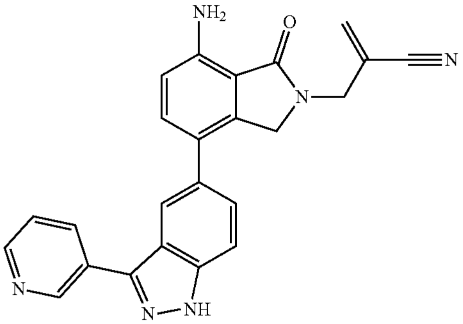 [SMILES: C=C(C#N)CN1Cc2c(-c3ccc4[nH]nc(-c5cccnc5)c4c3)ccc(N)c2C1=O] | 2-({7-amino-1-oxo-4-[3-(pyridin-3-yl)-1H-indazol-5-yl]-2,3-dihydro-1H-isoindol-2-yl}methyl)prop-2-enenitrile | 407.1 |
| 165. | 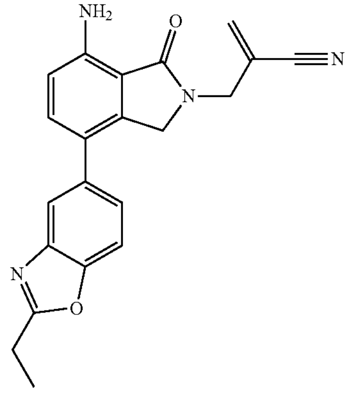 [SMILES: C=C(C#N)CN1Cc2c(-c3ccc4oc(CC)nc4c3)ccc(N)c2C1=O] | 2-{[7-amino-4-(2-ethyl-1,3-benzoxazol-5-yl)-1-oxo-2,3-dihydro-1H-isoindol-2-yl]methyl}prop-2-enenitrile | 359.2 |

TABLE 2-continued

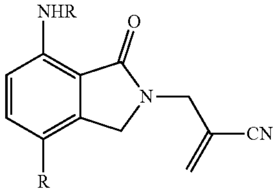

| Cpd. No. | Structure | IUPAC | LC-MS (ES+, m/z) |
|---|---|---|---|
| 166. | 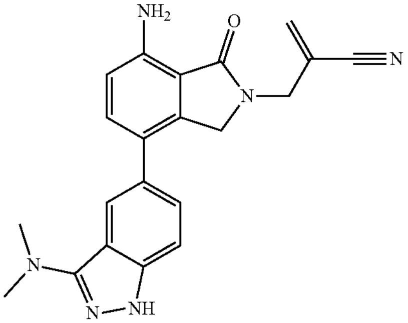 [SMILES: C=C(C#N)CN1Cc2c(-c3ccc4[nH]nc(N(C)C)c4c3)ccc(N)c2C1=O] | 2-({7-amino-4-[3-(dimethylamino)-1H-indazol-5-yl]-1-oxo-2,3-dihydro-1H-isoindol-2-yl}methyl)prop-2-enenitrile | 373.2 |
| 167. | 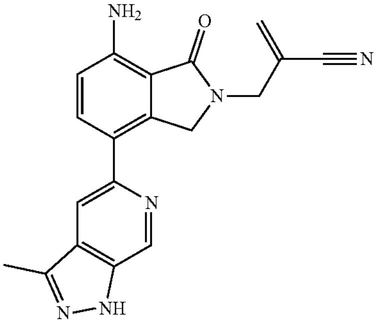 [SMILES: C=C(C#N)CN1Cc2c(-c3cc4c(C)n[nH]c4cn3)ccc(N)c2C1=O] | 2-[(7-amino-4-{3-methyl-1H-pyrazolo[3,4-c]pyridin-5-yl}-1-oxo-2,3-dihydro-1H-isoindol-2-yl)methyl]prop-2-enenitrile | 345.1 |
| 168. | 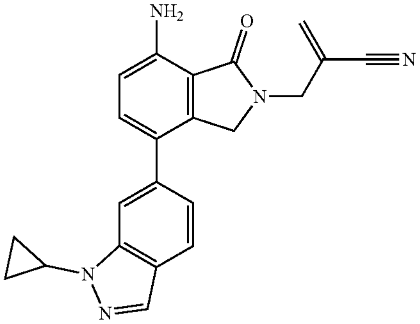 [SMILES: C=C(C#N)CN1Cc2c(-c3ccc4cnn(C5CC5)c4c3)ccc(N)c2C1=O] | 2-{[7-amino-4-(1-cyclopropyl-1H-indazol-6-yl)-1-oxo-2,3-dihydro-1H-isoindol-2-yl]methyl}prop-2-enenitrile | 370.2 |
| 169. | 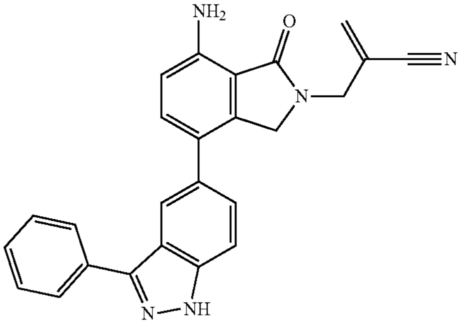 [SMILES: C=C(C#N)CN1Cc2c(-c3ccc4[nH]nc(-c5ccccc5)c4c3)ccc(N)c2C1=O] | 2-{[7-amino-1-oxo-4-(3-phenyl-1H-indazol-5-yl)-2,3-dihydro-1H-isoindol-2-yl]methyl}prop-2-enenitrile | 406.2 |

TABLE 2-continued
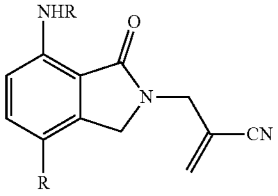
| Cpd. No. | Structure | IUPAC | LC-MS (ES+, m/z) |
|---|---|---|---|
| 170. | 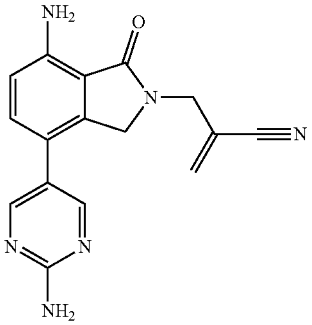 [SMILES: C=C(C#N)CN1Cc2c(-c3cnc(N)nc3)ccc(N)c2C1=O] | 2-{[7-amino-4-(2-aminopyrimidin-5-yl)-1-oxo-2,3-dihydro-1H-isoindol-2-yl]methyl}prop-2-enenitrile | 307.2 |
| 171. | 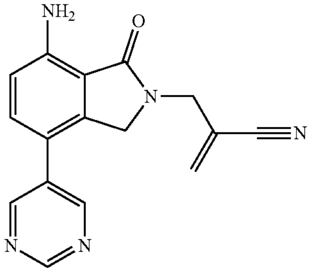 [SMILES: C=C(C#N)CN1Cc2c(-c3cncnc3)ccc(N)c2C1=O] | 2-{[7-amino-1-oxo-4-(pyrimidin-5-yl)-2,3-dihydro-1H-isoindol-2-yl]methyl}prop-2-enenitrile | 292.2 |
| 172. | 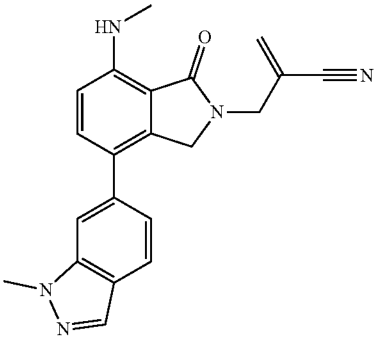 [SMILES: C=C(C#N)CN1Cc2c(-c3ccc4cnn(C)c4c3)ccc(NC)c2C1=O] | 2-{[4-(1-methyl-1H-indazol-6-yl)-7-(methylamino)-1-oxo-2,3-dihydro-1H-isoindol-2-yl]methyl}prop-2-enenitrile | 358.1 |
| 173. | 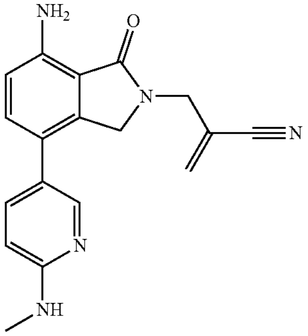 [SMILES: C=C(C#N)CN1Cc2c(-c3ccc(NC)nc3)ccc(N)c2C1=O] | 2-({7-amino-4-[6-(methylamino)pyridin-3-yl]-1-oxo-2,3-dihydro-1H-isoindol-2-yl}methyl)prop-2-enenitrile | 320.1 |

TABLE 2-continued

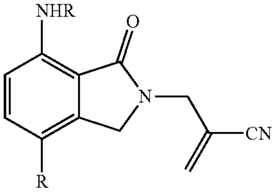

| Cpd. No. | Structure | IUPAC | LC-MS (ES+, m/z) |
|---|---|---|---|
| 174. | 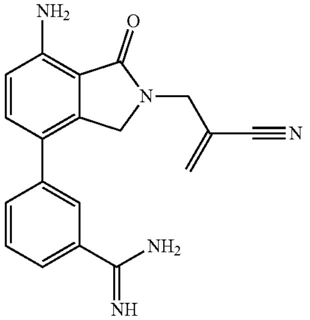 [SMILES: C=C(C#N)CN1Cc2c(-c3cccc(C(=N)N)c3)ccc(N)c2C1=O] | 3-[7-amino-2-(2-cyano-2-methylideneethyl)-1-oxo-2,3-dihydro-1H-isoindol-4-yl]benzene-1-carboximidamide | 332.1 |
| 175. | 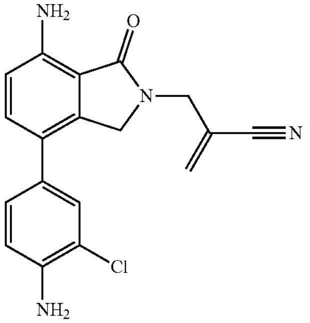 [SMILES: C=C(C#N)CN1Cc2c(-c3ccc(N)c(Cl)c3)ccc(N)c2C1=O] | 2-{[7-amino-4-(4-amino-3-chlorophenyl)-1-oxo-2,3-dihydro-1H-isoindol-2-yl]methyl}prop-2-enenitrile | 339 |
| 176. | 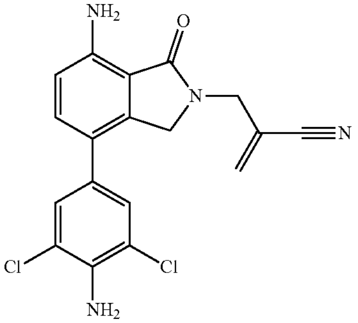 [SMILES: C=C(C#N)CN1Cc2c(-c3cc(Cl)c(N)c(Cl)c3)ccc(N)c2C1=O] | 2-{[7-amino-4-(4-amino-3,5-dichlorophenyl)-1-oxo-2,3-dihydro-1H-isoindol-2-yl]methyl}prop-2-enenitrile | 373 |
| 177. | 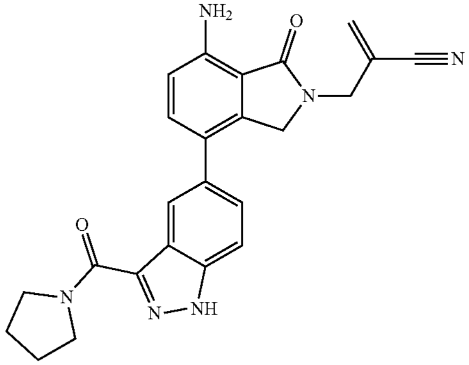 [SMILES: C=C(C#N)CN1Cc2c(-c3ccc4[nH]nc(C(=O)N5CCCC5)c4c3)ccc(N)c2C1=O] | 2-({7-amino-1-oxo-4-[3-(pyrrolidine-1-carbonyl)-1H-indazol-5-yl]-2,3-dihydro-1H-isoindol-2-yl}methyl)prop-2-enenitrile | 427.1 |

TABLE 2-continued

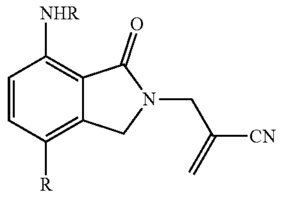

| Cpd. No. | Structure | IUPAC | LC-MS (ES+, m/z) |
|---|---|---|---|
| 178. | 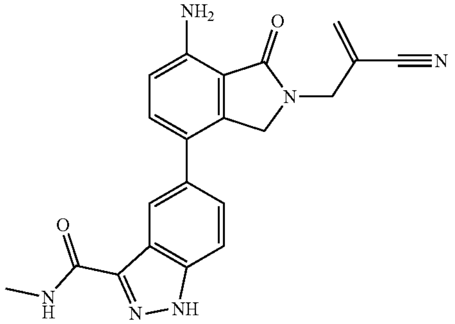 [SMILES: C=C(C#N)CN1Cc2c(-c3ccc4[nH]nc(C(=O)NC)c4c3)ccc(N)c2C1=O] | 5-[7-amino-2-(2-cyano-2-methylideneethyl)-1-oxo-2,3-dihydro-1H-isoindol-4-yl]-N-methyl-1H-indazole-3-carboxamide | 387.2 |
| 179. | 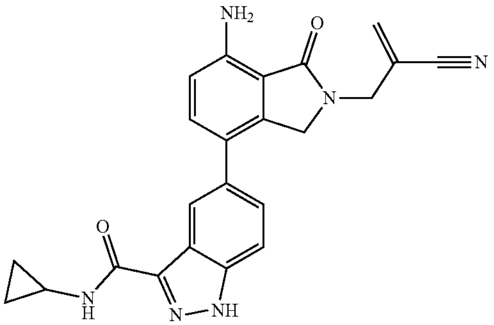 [SMILES: C=C(C#N)CN1Cc2c(-c3ccc4[nH]nc(C(=O)NC5CC5)c4c3)ccc(N)c2C1=O] | 5-[7-amino-2-(2-cyano-2-methylideneethyl)-1-oxo-2,3-dihydro-1H-isoindol-4-yl]-N-cyclopropyl-1H-indazole-3-carboxamide | 413.1 |
| 180. | 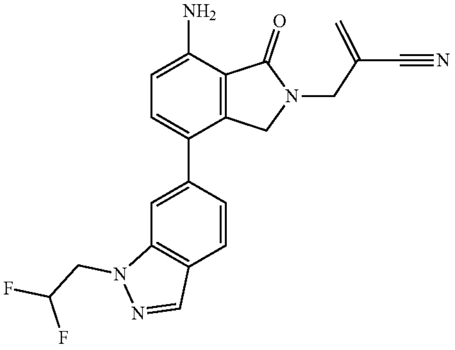 [SMILES: C=C(C#N)CN1Cc2c(-c3ccc4cnn(CC(F)F)c4c3)ccc(N)c2C1=O] | 2-({7-amino-4-[1-(2,2-difluoroethyl)-1H-indazol-6-yl]-1-oxo-2,3-dihydro-1H-isoindol-2-yl}methyl)prop-2-enenitrile | 394.2 |
| 181. | 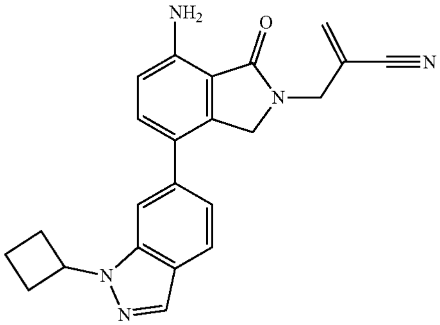 [SMILES: C=C(C#N)CN1Cc2c(-c3ccc4cnn(C5CCC5)c4c3)ccc(N)c2C1=O] | 2-{[7-amino-4-(1-cyclobutyl-1H-indazol-6-yl)-1-oxo-2,3-dihydro-1H-isoindol-2-yl]methyl}prop-2-enenitrile | 384.2 |

TABLE 2-continued

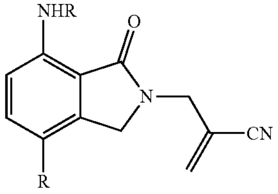

| Cpd. No. | Structure | IUPAC | LC-MS (ES+, m/z) |
|---|---|---|---|
| 182. | 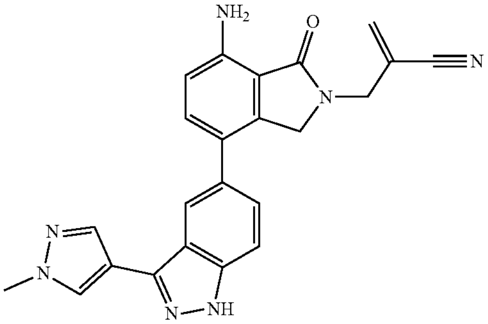 [SMILES: C=C(C#N)CN1Cc2c(-c3ccc4[nH]nc(-c5cnn(C)c5)c4c3)ccc(N)c2C1=O] | 2-({7-amino-4-[3-(1-methyl-1H-pyrazol-4-yl)-1H-indazol-5-yl]-1-oxo-2,3-dihydro-1H-isoindol-2-yl}methyl)prop-2-enenitrile | 410.2 |
| 183. | 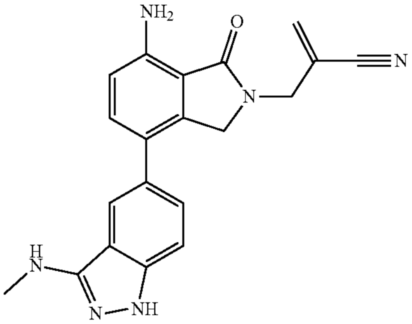 [SMILES: C=C(C#N)CN1Cc2c(-c3ccc4[nH]nc(NC)c4c3)ccc(N)c2C1=O] | 2-({7-amino-4-[3-(methylamino)-1H-indazol-5-yl]-1-oxo-2,3-dihydro-1H-isoindol-2-yl}methyl)prop-2-enenitrile | 359.2 |
| 184. | 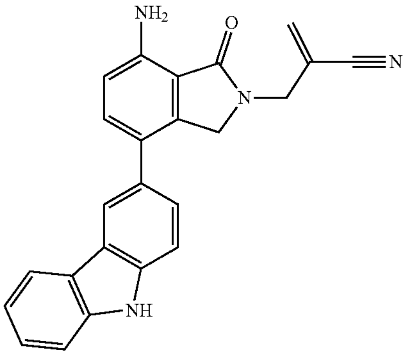 [SMILES: C=C(C#N)CN1Cc2c(-c3ccc4[nH]c5ccccc5c4c3)ccc(N)c2C1=O] | 2-{[7-amino-4-(9H-carbazol-3-yl)-1-oxo-2,3-dihydro-1H-isoindol-2-yl]methyl}prop-2-enenitrile | 379.2 |
| 185. | 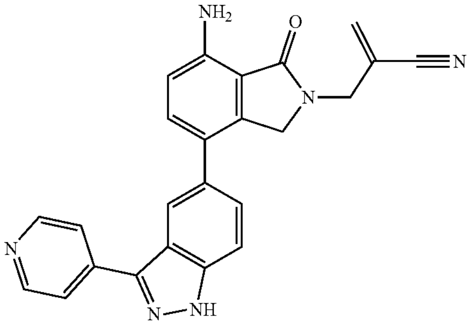 [SMILES: C=C(C#N)CN1Cc2c(-c3ccc4[nH]nc(-c5ccncc5)c4c3)ccc(N)c2C1=O] | 2-({7-amino-1-oxo-4-[3-(pyridin-4-yl)-1H-indazol-5-yl]-2,3-dihydro-1H-isoindol-2-yl}methyl)prop-2-enenitrile | 407.2 |

TABLE 2-continued
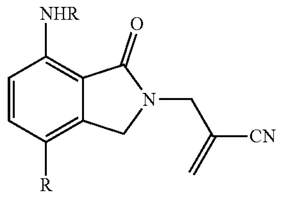
| Cpd. No. | Structure | IUPAC | LC-MS (ES+, m/z) |
|---|---|---|---|
| 186. | 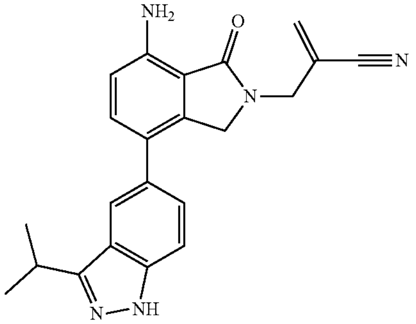 [SMILES: C=C(C#N)CN1Cc2c(-c3ccc4[nH]nc(C(C)C)c4c3)ccc(N)c2C1=O] | 2-({7-amino-1-oxo-4-[3-(propan-2-yl)-1H-indazol-5-yl]-2,3-dihydro-1H-isoindol-2-yl}methyl)prop-2-enenitrile | 372.12 |
| 187. | 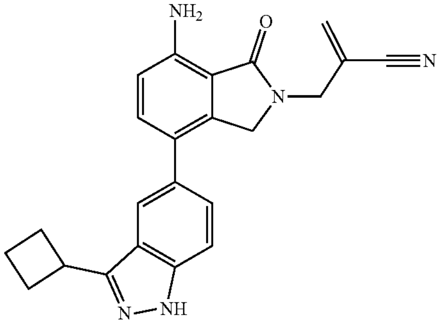 [SMILES: C=C(C#N)CN1Cc2c(-c3ccc4[nH]nc(C5CCC5)c4c3)ccc(N)c2C1=O] | 2-{[7-amino-4-(3-cyclobutyl-1H-indazol-5-yl)-1-oxo-2,3-dihydro-1H-isoindol-2-yl]methyl}prop-2-enenitrile | 384.2 |
| 188. | 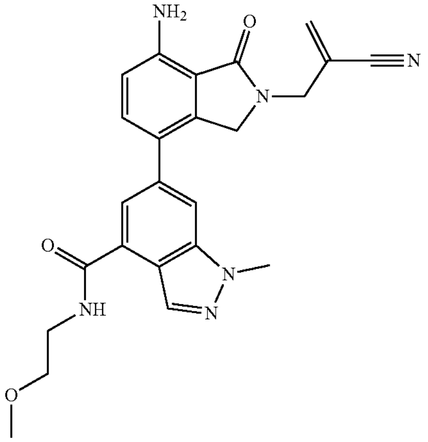 [SMILES: C=C(C#N)CN1Cc2c(-c3cc(C(=O)NCCOC)c4cnn(C)c4c3)ccc(N)c2C1=O] | 6-[7-amino-2-(2-cyano-2-methylideneethyl)-1-oxo-2,3-dihydro-1H-isoindol-4-yl]-N-(2-methoxyethyl)-1-methyl-1H-indazole-4-carboxamide | 445.1 |

TABLE 2-continued

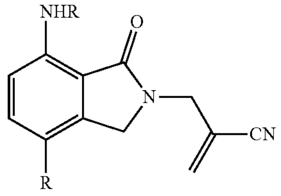

| Cpd. No. | Structure | IUPAC | LC-MS (ES+, m/z) |
|---|---|---|---|
| 189. | 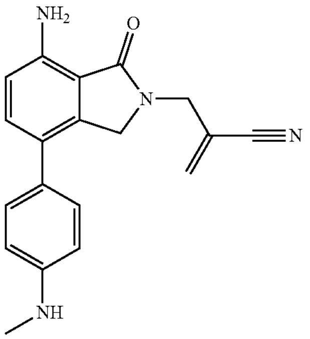 [SMILES: C=C(C#N)CN1Cc2c(-c3ccc(NC)cc3)ccc(N)c2C1=O] | 2-({7-amino-4-[4-(methylamino)phenyl]-1-oxo-2,3-dihydro-1H-isoindol-2-yl}methyl)prop-2-enenitrile | 319.2 |
| 190. | 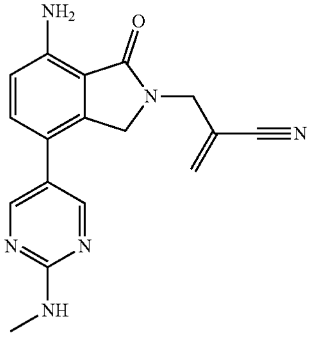 [SMILES: C=C(C#N)CN1Cc2c(-c3cnc(NC)nc3)ccc(N)c2C1=O] | 2-({7-amino-4-[2-(methylamino)pyrimidin-5-yl]-1-oxo-2,3-dihydro-1H-isoindol-2-yl}methyl)prop-2-enenitrile | 321.1 |
| 191. | 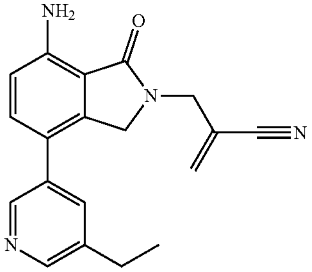 [SMILES: C=C(C#N)CN1Cc2c(-c3cncc(CC)c3)ccc(N)c2C1=O] | 2-{[7-amino-4-(5-ethylpyridin-3-yl)-1-oxo-2,3-dihydro-1H-isoindol-2-yl]methyl}prop-2-enenitrile | 319.2 |
| 192. | 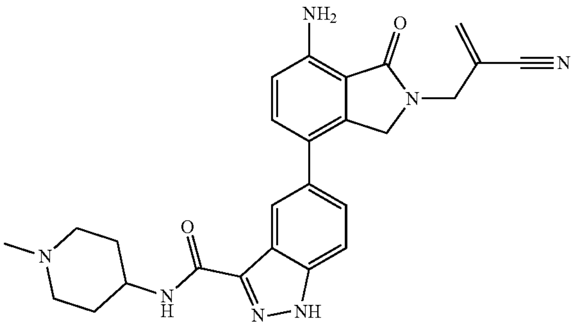 [SMILES: C=C(C#N)CN1Cc2c(-c3ccc4[nH]nc(C(=O)NC5CCN(C)CC5)c4c3)ccc(N)c2C1=O] | 5-[7-amino-2-(2-cyano-2-methylideneethyl)-1-oxo-2,3-dihydro-1H-isoindol-4-yl]-N-(1-methylpiperidin-4-yl)-1H-indazole-3-carboxamide | 470.2 |

TABLE 2-continued

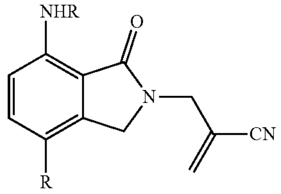

| Cpd. No. | Structure | IUPAC | LC-MS (ES+, m/z) |
|---|---|---|---|
| 193. | 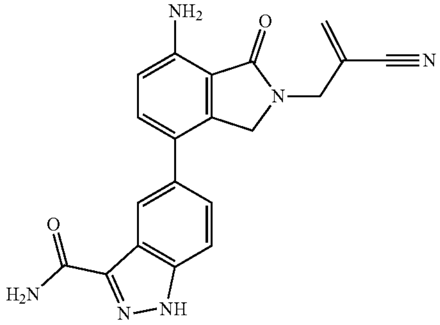 [SMILES: C=C(C#N)CN1Cc2c(-c3ccc4[nH]nc(C(N)=O)c4c3)ccc(N)c2C1=O] | 5-[7-amino-2-(2-cyano-2-methylideneethyl)-1-oxo-2,3-dihydro-1H-isoindol-4-yl]-1H-indazole-3-carboxamide | 373.1 |
| 194. | 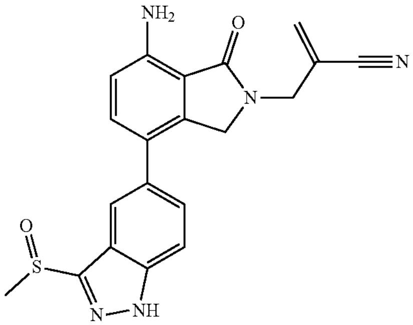 [SMILES: C=C(C#N)CN1Cc2c(-c3ccc4[nH]nc(S(C)=O)c4c3)ccc(N)c2C1=O] | 2-{[7-amino-4-(3-methanesulfinyl-1H-indazol-5-yl)-1-oxo-2,3-dihydro-1H-isoindol-2-yl]methyl}prop-2-enenitrile | 392.1 |
| 195. | 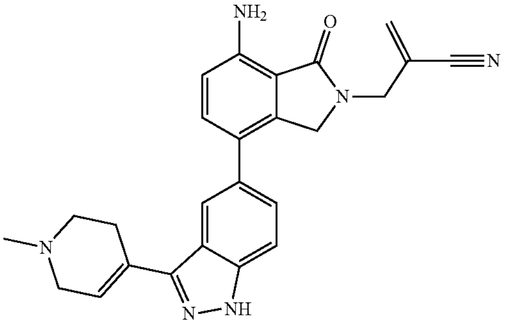 [SMILES: C=C(C#N)CN1Cc2c(-c3ccc4[nH]nc(C5=CCN(C)CC5)c4c3)ccc(N)c2C1=O] | 2-({7-amino-4-[3-(1-methyl-1,2,3,6-tetrahydropyridin-4-yl)-1H-indazol-5-yl]-1-oxo-2,3-dihydro-1H-isoindol-2-yl}methyl)prop-2-enenitrile | 425.2 |
| 196. | 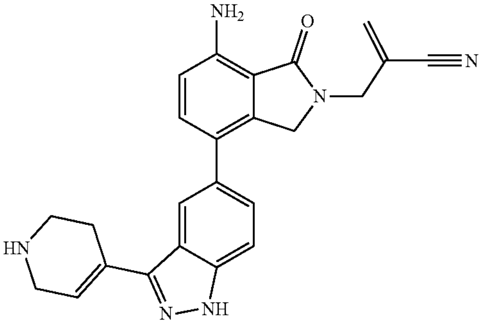 [SMILES: C=C(C#N)CN1Cc2c(-c3ccc4[nH]nc(C5=CCNCC5)c4c3)ccc(N)c2C1=O] | 2-({7-amino-1-oxo-4-[3-(1,2,3,6-tetrahydropyridin-4-yl)-1H-indazol-5-yl]-2,3-dihydro-1H-isoindol-2-yl}methyl)prop-2-enenitrile | 411.2 |

TABLE 2-continued

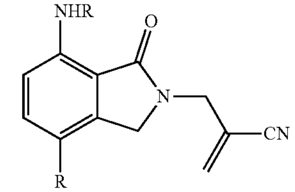

| Cpd. No. | Structure | IUPAC | LC-MS (ES+, m/z) |
|---|---|---|---|
| 197. | 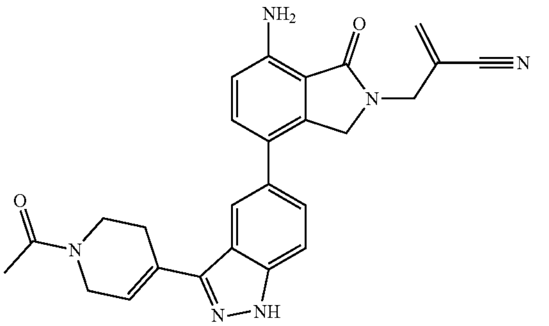 [SMILES: C=C(C#N)CN1Cc2c(-c3ccc4[nH]nc(C5=CCN(C(C)=O)CC5)c4c3)ccc(N)c2C1=O] | 2-({4-[3-(1-acetyl-1,2,3,6-tetrahydropyridin-4-yl)-1H-indazol-5-yl]-7-amino-1-oxo-2,3-dihydro-1H-isoindol-2-yl}methyl)prop-2-enenitrile | 453.2 |
| 198. | 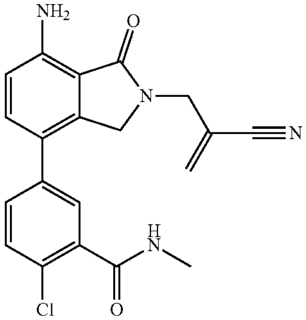 | 5-[7-amino-2-(2-cyano-2-methylideneethyl)-1-oxo-2,3-dihydro-1H-isoindol-4-yl]-2-chloro-N-methylbenzamide | 381.1 |
| 199. | 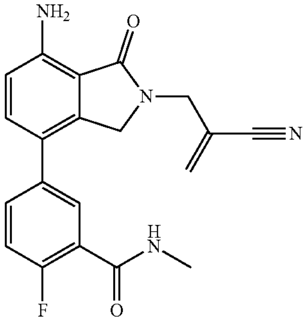 [SMILES: C=C(C#N)CN1Cc2c(-c3ccc(Cl)c(C(=O)NC)c3)ccc(N)c2C1=O] | 5-[7-amino-2-(2-cyano-2-methylideneethyl)-1-oxo-2,3-dihydro-1H-isoindol-4-yl]-2-fluoro-N-methylbenzamide | 365.2 |
| 200. | 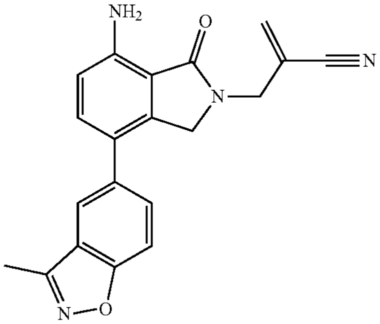 [SMILES: C=C(C#N)CN1Cc2c(-c3ccc4onc(C)c4c3)ccc(N)c2C1=O] | 2-{[7-amino-4-(3-methyl-1,2-benzoxazol-5-yl)-1-oxo-2,3-dihydro-1H-isoindol-2-yl]methyl}prop-2-enenitrile | 345.2 |

TABLE 2-continued

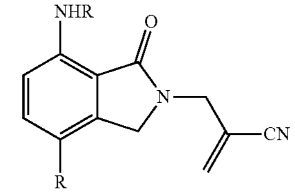

| Cpd. No. | Structure | IUPAC | LC-MS (ES+, m/z) |
|---|---|---|---|
| 201. | 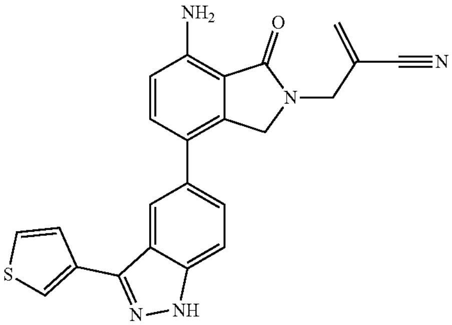 [SMILES: C=C(C#N)CN1Cc2c(-c3ccc4[nH]nc(-c5ccsc5)c4c3)ccc(N)c2C1=O] | 2-({7-amino-1-oxo-4-[3-(thiophen-3-yl)-1H-indazol-5-yl]-2,3-dihydro-1H-isoindol-2-yl}methyl)prop-2-enenitrile | 412.1 |
| 202. | 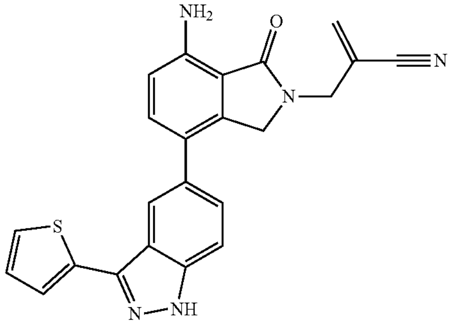 [SMILES: C=C(C#N)CN1Cc2c(-c3ccc4[nH]nc(-c5cccs5)c4c3)ccc(N)c2C1=O] | 2-({7-amino-1-oxo-4-[3-(thiophen-2-yl)-1H-indazol-5-yl]-2,3-dihydro-1H-isoindol-2-yl}methyl)prop-2-enenitrile | 412.1 |
| 203. | 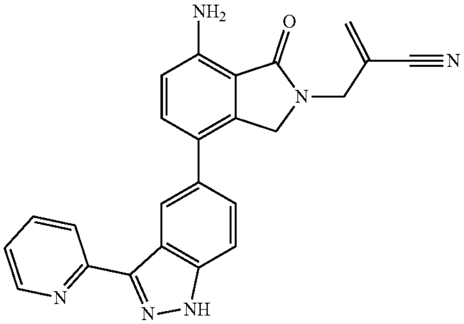 [SMILES: C=C(C#N)CN1Cc2c(-c3ccc4[nH]nc(-c5ccccn5)c4c3)ccc(N)c2C1=O] | 2-({7-amino-1-oxo-4-[3-(pyridin-2-yl)-1H-indazol-5-yl]-2,3-dihydro-1H-isoindol-2-yl}methyl)prop-2-enenitrile | 407.1 |
| 204. | 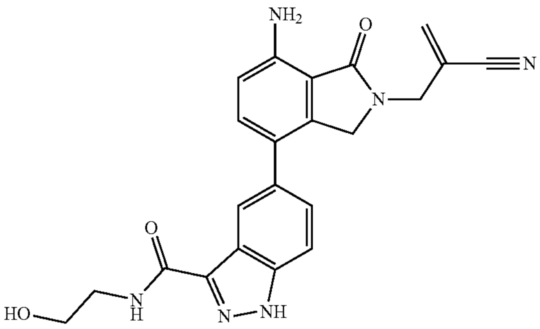 [SMILES: C=C(C#N)CN1Cc2c(-c3ccc4[nH]nc(C(=O)NCCO)c4c3)ccc(N)c2C1=O] | 5-[7-amino-2-(2-cyano-2-methylideneethyl)-1-oxo-2,3-dihydro-1H-isoindol-4-yl]-N-(2-hydroxyethyl)-1H-indazole-3-carboxamide | 417.1 |

TABLE 2-continued

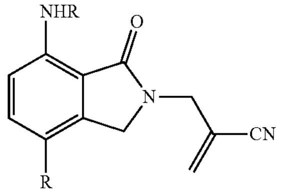

| Cpd. No. | Structure | IUPAC | LC-MS (ES+, m/z) |
| --- | --- | --- | --- |
| 205. | 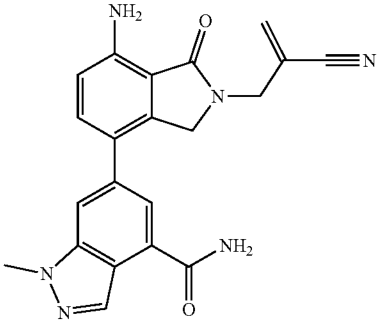 [SMILES: C=C(C#N)CN1Cc2c(-c3cc(C(N)=O)c4cnn(C)c4c3)ccc(N)c2C1=O] | 6-[7-amino-2-(2-cyano-2-methylideneethyl)-1-oxo-2,3-dihydro-1H-isoindol-4-yl]-1-methyl-1H-indazole-4-carboxamide | 387.1 |
| 206. | 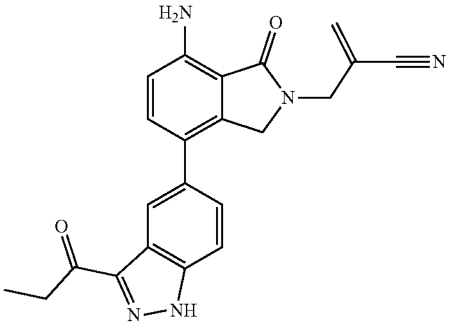 [SMILES: C=C(C#N)CN1Cc2c(-c3ccc4[nH]nc(C(=O)CC)c4c3)ccc(N)c2C1=O] | 2-{[7-amino-1-oxo-4-(3-propanoyl-1H-indazol-5-yl)-2,3-dihydro-1H-isoindol-2-yl]methyl}prop-2-enenitrile | 386.1 |
| 207. | 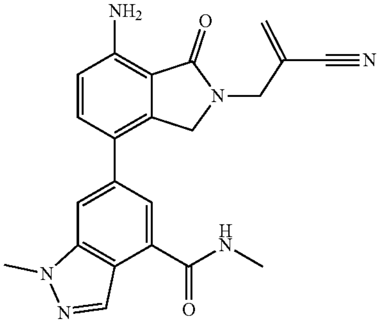 [SMILES: C=C(C#N)CN1Cc2c(-c3cc(C(=O)NC)c4cnn(C)c4c3)ccc(N)c2C1=O] | 6-[7-amino-2-(2-cyano-2-methylideneethyl)-1-oxo-2,3-dihydro-1H-isoindol-4-yl]-N,1-dimethyl-1H-indazole-4-carboxamide | 401.1 |
| 208. | 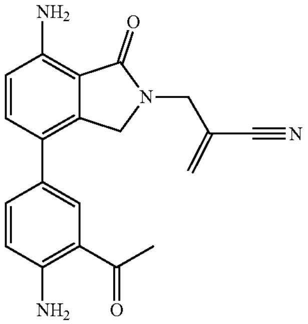 [SMILES: C=C(C#N)CN1Cc2c(-c3ccc(N)c(C(C)=O)c3)ccc(N)c2C1=O] | 2-{[4-(3-acetyl-4-aminophenyl)-7-amino-1-oxo-2,3-dihydro-1H-isoindol-2-yl]methyl}prop-2-enenitrile | 347.1 |

TABLE 2-continued

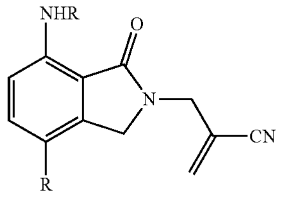

| Cpd. No. | Structure | IUPAC | LC-MS (ES+, m/z) |
|---|---|---|---|
| 209. | 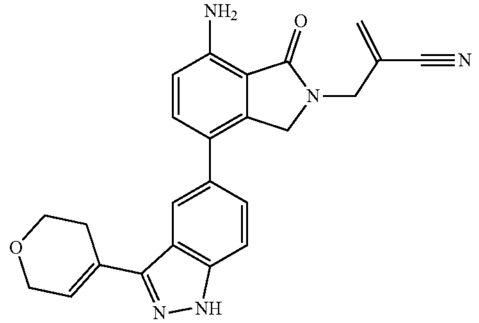 [SMILES: C=C(C#N)CN1Cc2c(-c3ccc4[nH]nc(C5=CCOCC5)c4c3)ccc(N)c2C1=O] | 2-({7-amino-4-[3-(3,6-dihydro-2H-pyran-4-yl)-1H-indazol-5-yl]-1-oxo-2,3-dihydro-1H-isoindol-2-yl}methyl)prop-2-enenitrile | 412.1 |
| 210. | 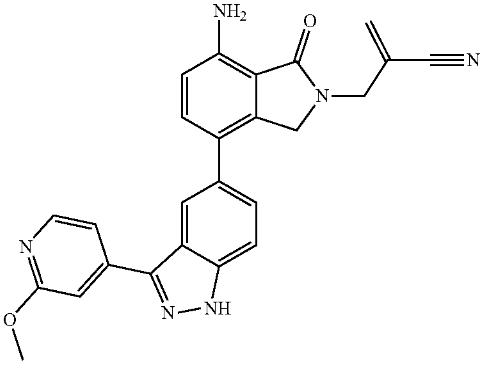 [SMILES: C=C(C#N)CN1Cc2c(-c3ccc4[nH]nc(-c5ccnc(OC)c5)c4c3)ccc(N)c2C1=O] | 2-({7-amino-4-[3-(2-methoxypyridin-4-yl)-1H-indazol-5-yl]-1-oxo-2,3-dihydro-1H-isoindol-2-yl}methyl)prop-2-enenitrile | 437.2 |
| 211. | 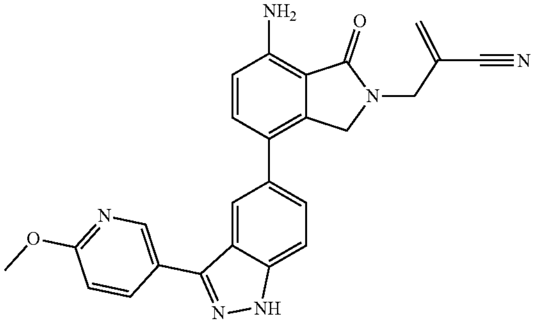 [SMILES: C=C(C#N)CN1Cc2c(-c3ccc4[nH]nc(-c5ccc(OC)nc5)c4c3)ccc(N)c2C1=O] | 2-({7-amino-4-[3-(6-methoxypyridin-3-yl)-1H-indazol-5-yl]-1-oxo-2,3-dihydro-1H-isoindol-2-yl}methyl)prop-2-enenitrile | 437.2 |
| 212. | 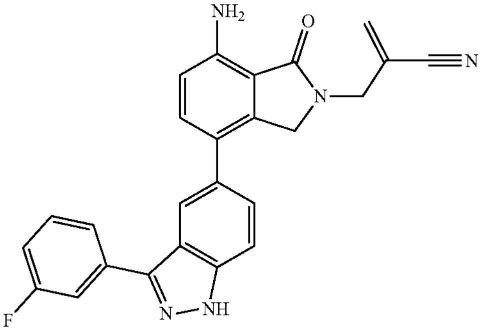 [SMILES: C=C(C#N)CN1Cc2c(-c3ccc4[nH]nc(-c5cccc(F)c5)c4c3)ccc(N)c2C1=O] | 2-({7-amino-4-[3-(3-fluorophenyl)-1H-indazol-5-yl]-1-oxo-2,3-dihydro-1H-isoindol-2-yl}methyl)prop-2-enenitrile | 424.2 |

TABLE 2-continued
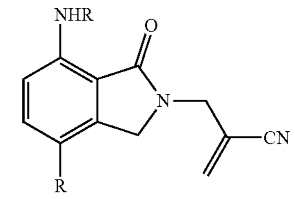
| Cpd. No. | Structure | IUPAC | LC-MS (ES+, m/z) |
|---|---|---|---|
| 213. | 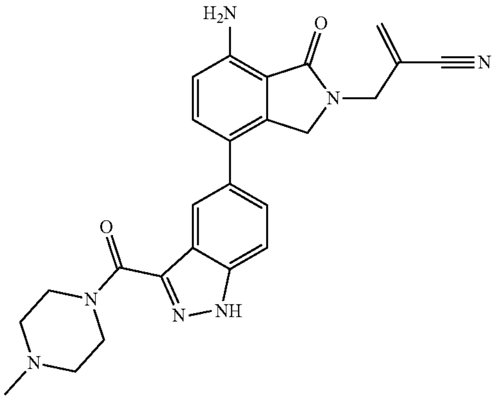 [SMILES: C=C(C#N)CN1Cc2c(-c3ccc4[nH]nc(C(=O)N5CCN(C)CC5)c4c3)ccc(N)c2C1=O] | 2-({7-amino-4-[3-(4-methylpiperazine-1-carbonyl)-1H-indazol-5-yl]-1-oxo-2,3-dihydro-1H-isoindol-2-yl}methyl)prop-2-enenitrile | 456.2 |
| 214. | 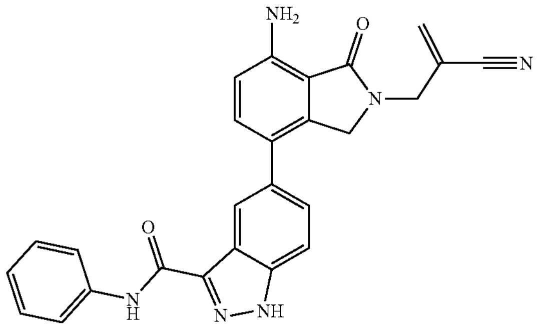 [SMILES: C=C(C#N)CN1Cc2c(-c3ccc4[nH]nc(C(=O)Nc5ccccc5)c4c3)ccc(N)c2C1=O] | 5-[7-amino-2-(2-cyano-2-methylideneethyl)-1-oxo-2,3-dihydro-1H-isoindol-4-yl]-N-phenyl-1H-indazole-3-carboxamide | 449.2 |
| 215. | 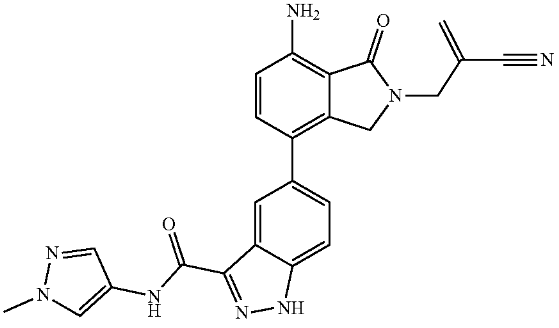 [SMILES: C=C(C#N)CN1Cc2c(-c3ccc4[nH]nc(C(=O)Nc5cnn(C)c5)c4c3)ccc(N)c2C1=O] | 5-[7-amino-2-(2-cyano-2-methylideneethyl)-1-oxo-2,3-dihydro-1H-isoindol-4-yl]-N-(1-methyl-1H-pyrazol-4-yl)-1H-indazole-3-carboxamide | 453.2 |

TABLE 2-continued

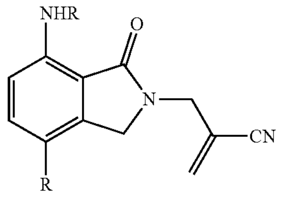

| Cpd. No. | Structure | IUPAC | LC-MS (ES+, m/z) |
|---|---|---|---|
| 216. | 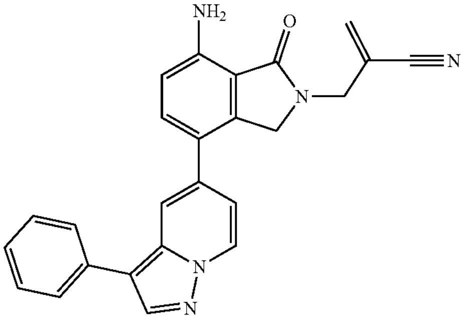 [SMILES: C=C(C#N)CN1Cc2c(-c3ccn4ncc(-c5ccccc5)c4c3)ccc(N)c2C1=O] | 2-[(7-amino-1-oxo-4-{3-phenylpyrazolo[1,5-a]pyridin-5-yl}-2,3-dihydro-1H-isoindol-2-yl)methyl]prop-2-enenitrile | 406.2 |
| 217. | 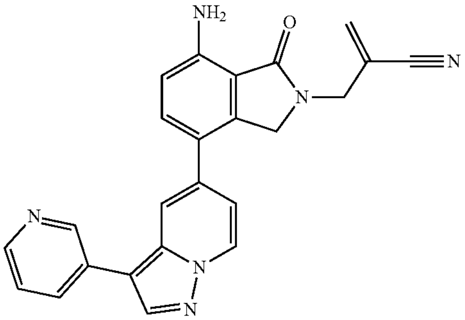 | 2-({7-amino-1-oxo-4-[3-(pyridin-3-yl)pyrazolo[1,5-a]pyridin-5-yl]-2,3-dihydro-1H-isoindol-2-yl}methyl)prop-2-enenitrile | 407.2 |
| 218. | 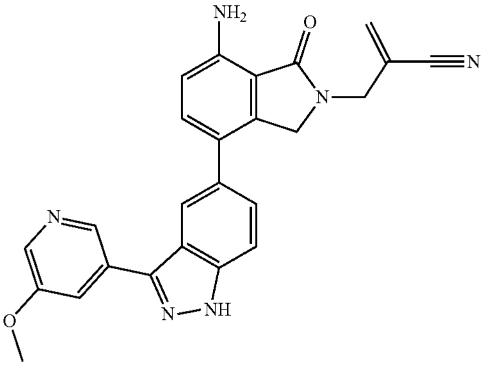 [SMILES: C=C(C#N)CN1Cc2c(-c3ccc4[nH]nc(-c5cncc(OC)c5)c4c3)ccc(N)c2C1=O] | 2-({7-amino-4-[3-(5-methoxypyridin-3-yl)-1H-indazol-5-yl]-1-oxo-2,3-dihydro-1H-isoindol-2-yl}methyl)prop-2-enenitrile | 437.2 |
| 219. | 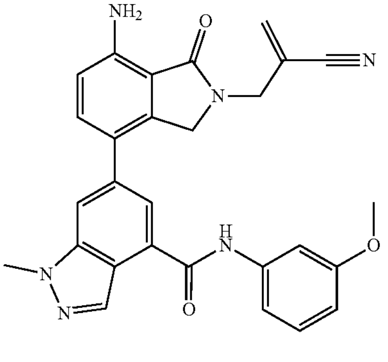 | 6-[7-amino-2-(2-cyano-2-methylideneethyl)-1-oxo-2,3-dihydro-1H-isoindol-4-yl]-N-(3-methoxyphenyl)-1-methyl-1H-indazole-4-carboxamide | 493.2 |

TABLE 2-continued

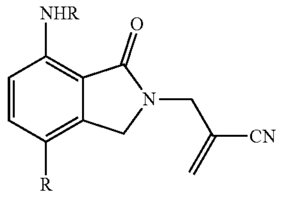

| Cpd. No. | Structure | IUPAC | LC-MS (ES+, m/z) |
|---|---|---|---|
| 220. | 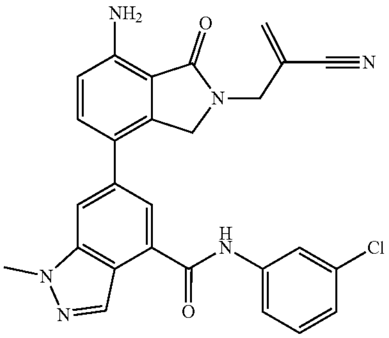 [SMILES: C=C(C#N)CN1Cc2c(-c3cc(C(=O)Nc4cccc(Cl)c4)c4cnn(C)c4c3)ccc(N)c2C1=O] | 6-[7-amino-2-(2-cyano-2-methylideneethyl)-1-oxo-2,3-dihydro-1H-isoindol-4-yl]-N-(3-chlorophenyl)-1-methyl-1H-indazole-4-carboxamide | 497.1 |
| 221. | 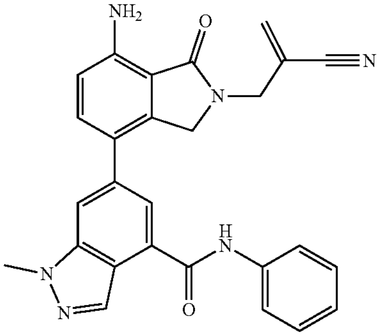 [SMILES: C=C(C#N)CN1Cc2c(-c3cc(C(=O)Nc4ccccc4)c4cnn(C)c4c3)ccc(N)c2C1=O] | 6-[7-amino-2-(2-cyano-2-methylideneethyl)-1-oxo-2,3-dihydro-1H-isoindol-4-yl]-1-methyl-N-phenyl-1H-indazole-4-carboxamide | 463.2 |
| 222. | 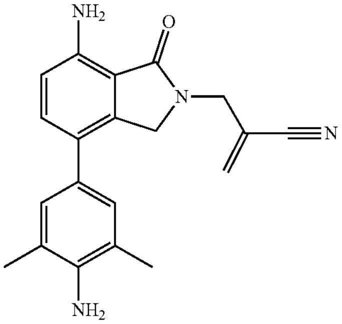 [SMILES: C=C(C#N)CN1Cc2c(-c3cc(C)c(N)c(C)c3)ccc(N)c2C1=O] | 2-{[7-amino-4-(4-amino-3,5-dimethylphenyl)-1-oxo-2,3-dihydro-1H-isoindol-2-yl]methyl}prop-2-enenitrile | 333.1 |
| 223. | 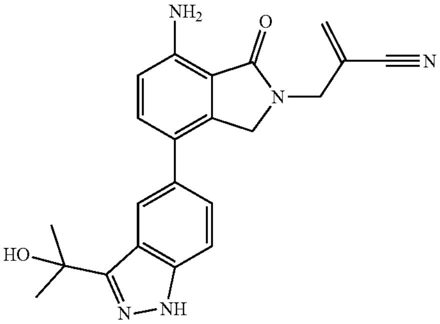 [SMILES: C=C(C#N)CN1Cc2c(-c3ccc4[nH]nc(C(C)(C)O)c4c3)ccc(N)c2C1=O] | 2-({7-amino-4-[3-(2-hydroxypropan-2-yl)-1H-indazol-5-yl]-1-oxo-2,3-dihydro-1H-isoindol-2-yl}methyl)prop-2-enenitrile | 388.1 |

TABLE 2-continued
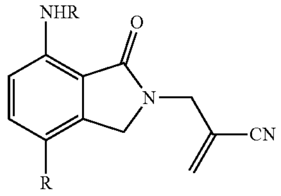
| Cpd. No. | Structure | IUPAC | LC-MS (ES+, m/z) |
|---|---|---|---|
| 224. | 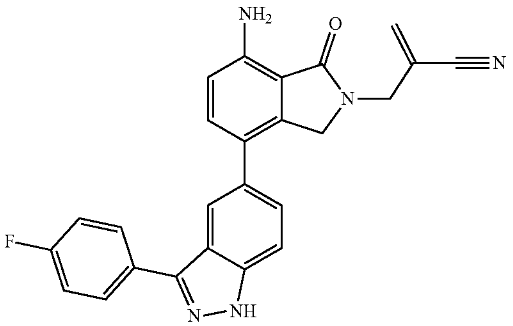 [SMILES: C=C(C#N)CN1Cc2c(-c3ccc4[nH]nc(-c5ccc(F)cc5)c4c3)ccc(N)c2C1=O] | 2-({7-amino-4-[3-(4-fluorophenyl)-1H-indazol-5-yl]-1-oxo-2,3-dihydro-1H-isoindol-2-yl}methyl)prop-2-enenitrile | 424.1 |
| 225. | 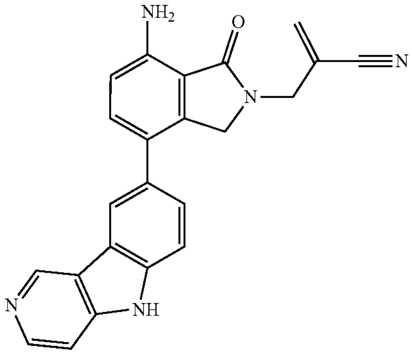 [SMILES: C=C(C#N)CN1Cc2c(-c3ccc4[nH]c5ccncc5c4c3)ccc(N)c2C1=O] | 2-[(7-amino-1-oxo-4-{5H-pyrido[4,3-b]indol-8-yl}-2,3-dihydro-1H-isoindol-2-yl)methyl]prop-2-enenitrile | 380 |
| 226. | 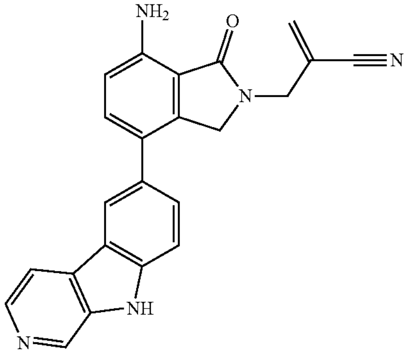 [SMILES: C=C(C#N)CN1Cc2c(-c3ccc4[nH]c5cnccc5c4c3)ccc(N)c2C1=O] | 2-[(7-amino-1-oxo-4-{9H-pyrido[3,4-b]indol-6-yl}-2,3-dihydro-1H-isoindol-2-yl)methyl]prop-2-enenitrile | 380.1 |

TABLE 2-continued

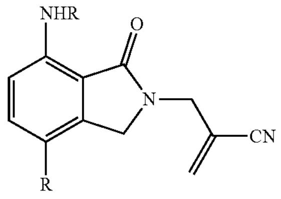

| Cpd. No. | Structure | IUPAC | LC-MS (ES+, m/z) |
| --- | --- | --- | --- |
| 227. | 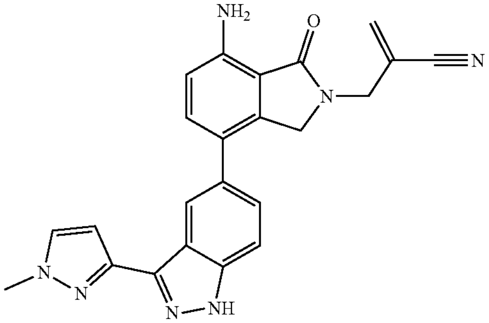 [SMILES: C=C(C#N)CN1Cc2c(-c3ccc4[nH]nc(-c5ccn(C)n5)c4c3)ccc(N)c2C1=O] | 2-({7-amino-4-[3-(1-methyl-1H-pyrazol-3-yl)-1H-indazol-5-yl]-1-oxo-2,3-dihydro-1H-isoindol-2-yl}methyl)prop-2-enenitrile | 410.1 |
| 228. | 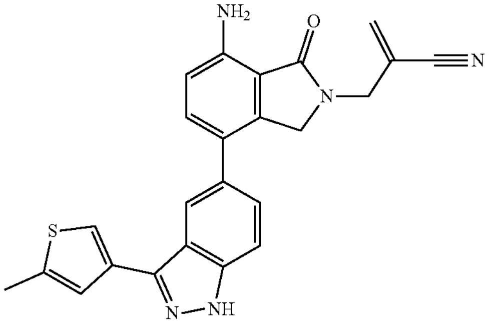 [SMILES: C=C(C#N)CN1Cc2c(-c3ccc4[nH]nc(-c5csc(C)c5)c4c3)ccc(N)c2C1=O] | 2-({7-amino-4-[3-(5-methylthiophen-3-yl)-1H-indazol-5-yl]-1-oxo-2,3-dihydro-1H-isoindol-2-yl}methyl)prop-2-enenitrile | 426.1 |
| 229. | 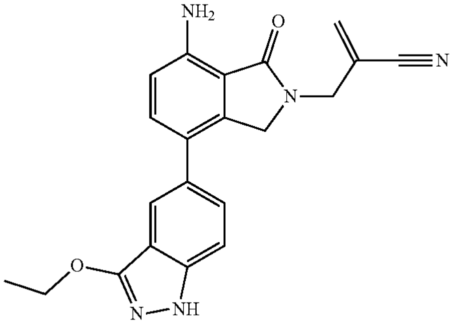 [SMILES: C=C(C#N)CN1Cc2c(-c3ccc4[nH]nc(OCC)c4c3)ccc(N)c2C1=O] | 2-{[7-amino-4-(3-ethoxy-1H-indazol-5-yl)-1-oxo-2,3-dihydro-1H-isoindol-2-yl]methyl}prop-2-enenitrile | 374 |
| 230. | 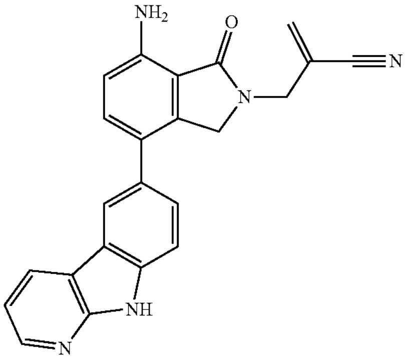 [SMILES: C=C(C#N)CN1Cc2c(-c3ccc4[nH]c5ncccc5c4c3)ccc(N)c2C1=O] | 2-[(7-amino-1-oxo-4-{9H-pyrido[2,3-b]indol-6-yl}-2,3-dihydro-1H-isoindol-2-yl)methyl]prop-2-enenitrile | 380.1 |

TABLE 2-continued

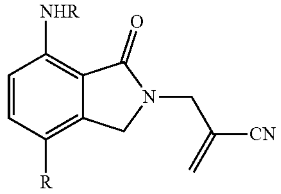

| Cpd. No. | Structure | IUPAC | LC-MS (ES+, m/z) |
|---|---|---|---|
| 231. | 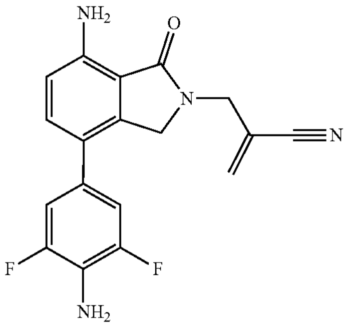 [SMILES: C=C(C#N)CN1Cc2c(-c3cc(F)c(N)c(F)c3)ccc(N)c2C1=O] | 2-{[7-amino-4-(4-amino-3,5-difluorophenyl)-1-oxo-2,3-dihydro-1H-isoindol-2-yl]methyl}prop-2-enenitrile | 341.1 |
| 232. | 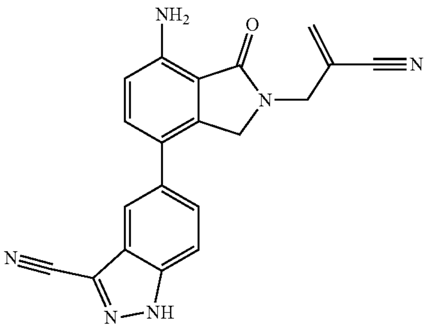 [SMILES: C=C(C#N)CN1Cc2c(-c3ccc4[nH]nc(C#N)c4c3)ccc(N)c2C1=O] | 2-{[7-amino-4-(3-ethynyl-1H-indazol-5-yl)-1-oxo-2,3-dihydro-1H-isoindol-2-yl]methyl}prop-2-enenitrile | 354.1 |
| 233. | 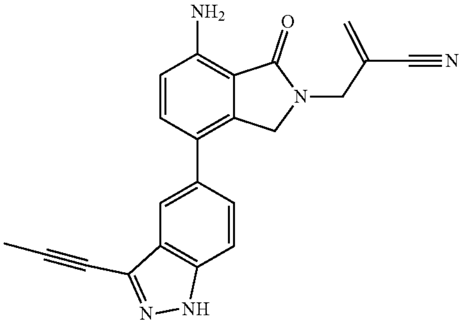 [SMILES: C=C(C#N)CN1Cc2c(-c3ccc4[nH]nc(C#CC)c4c3)ccc(N)c2C1=O] | 2-({7-amino-1-oxo-4-[3-(prop-1-yn-1-yl)-1H-indazol-5-yl]-2,3-dihydro-1H-isoindol-2-yl}methyl)prop-2-enenitrile | 368.1 |
| 234. | 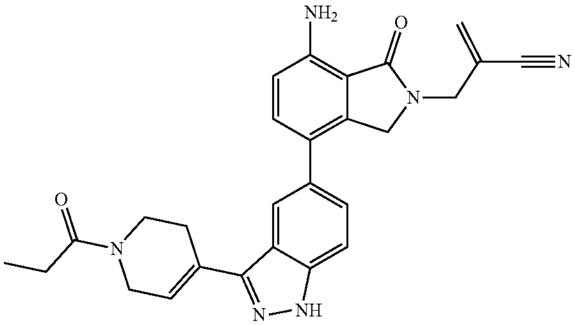 [SMILES: C=C(C#N)CN1Cc2c(-c3ccc4[nH]nc(C5=CCN(C(=O)CC)CC5)c4c3)ccc(N)c2C1=O] | 2-({7-amino-1-oxo-4-[3-(1-propanoyl-1,2,3,6-tetrahydropyridin-4-yl)-1H-indazol-5-yl]-2,3-dihydro-1H-isoindol-2-yl}methyl)prop-2-enenitrile | 467.1 |

TABLE 2-continued

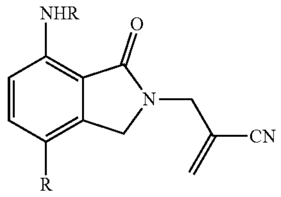

| Cpd. No. | Structure | IUPAC | LC-MS (ES+, m/z) |
|---|---|---|---|
| 235. | 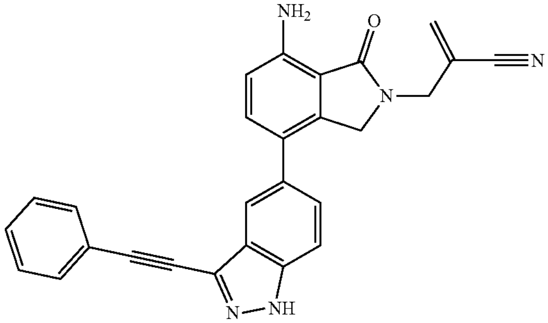 [SMILES: C=C(C#N)CN1Cc2c(-c3ccc4[nH]nc(C#Cc5ccccc5)c4c3)ccc(N)c2C1=O] | 2-({7-amino-1-oxo-4-[3-(2-phenylethynyl)-1H-indazol-5-yl]-2,3-dihydro-1H-isoindol-2-yl}methyl)prop-2-enenitrile | 430.1 |
| 236. | 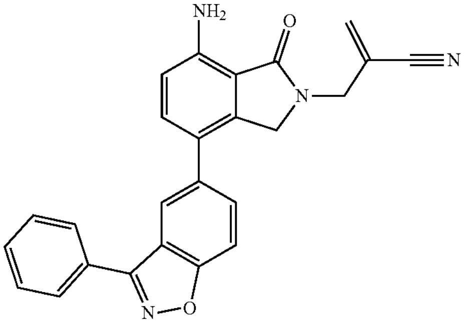 [SMILES: C=C(C#N)CN1Cc2c(-c3ccc4onc(-c5ccccc5)c4c3)ccc(N)c2C1=O] | 2-{[7-amino-1-oxo-4-(3-phenyl-1,2-benzoxazol-5-yl)-2,3-dihydro-1H-isoindol-2-yl]methyl}prop-2-enenitrile | 407.1 |
| 237. | 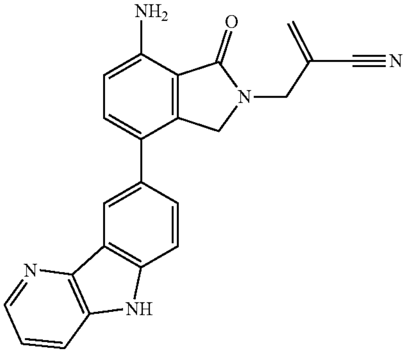 | 2-[(7-amino-1-oxo-4-{5H-pyrido[3,2-b]indol-8-yl}-2,3-dihydro-1H-isoindol-2-yl)methyl]prop-2-enenitrile | 380.1 |
| 238. | 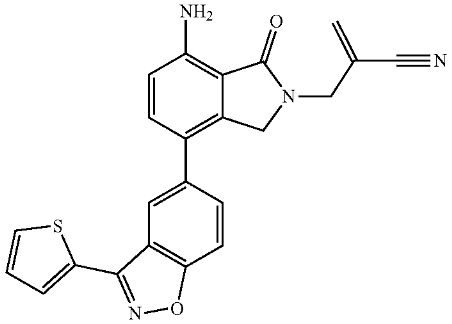 [SMILES: C=C(C#N)CN1Cc2c(-c3ccc4onc(-c5cccs5)c4c3)ccc(N)c2C1=O] | 2-({7-amino-1-oxo-4-[3-(thiophen-2-yl)-1,2-benzoxazol-5-yl]-2,3-dihydro-1H-isoindol-2-yl}methyl)prop-2-enenitrile | 413.1 |

TABLE 2-continued

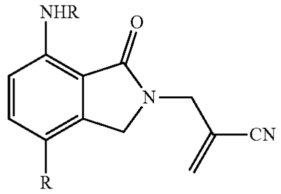

| Cpd. No. | Structure | IUPAC | LC-MS (ES+, m/z) |
|---|---|---|---|
| 239. | 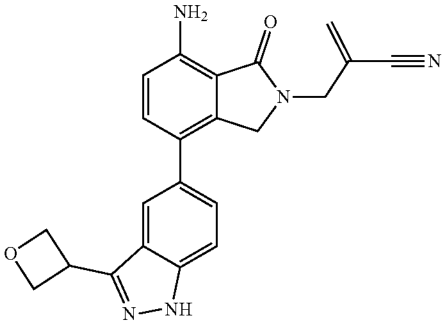 [SMILES: C=C(C#N)CN1Cc2c(-c3ccc4[nH]nc(C5COC5)c4c3)ccc(N)c2C1=O] | 2-({7-amino-4-[3-(oxetan-3-yl)-1H-indazol-5-yl]-1-oxo-2,3-dihydro-1H-isoindol-2-yl}methyl)prop-2-enenitrile | 386.1 |
| 240. | 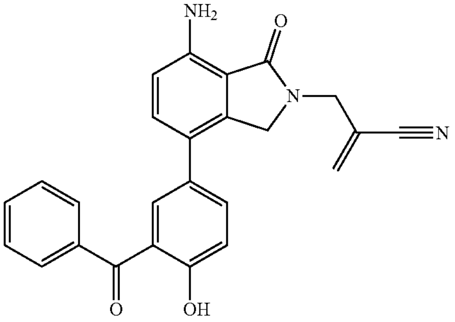 [SMILES: C=C(C#N)CN1Cc2c(-c3ccc(O)c(C(=O)c4ccccc4)c3)ccc(N)c2C1=O] | 2-{[7-amino-4-(3-benzoyl-4-hydroxyphenyl)-1-oxo-2,3-dihydro-1H-isoindol-2-yl]methyl}prop-2-enenitrile | 410.1 |
| 241. | 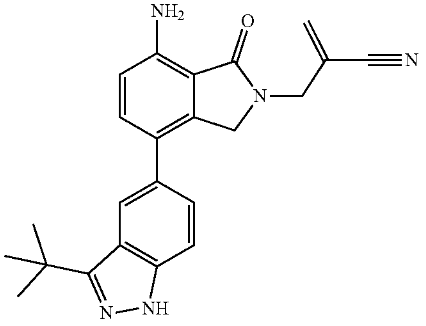 [SMILES: C=C(C#N)CN1Cc2c(-c3ccc4[nH]nc(C(C)(C)C)c4c3)ccc(N)c2C1=O] | 2-{[7-amino-4-(3-tert-butyl-1H-indazol-5-yl)-1-oxo-2,3-dihydro-1H-isoindol-2-yl]methyl}prop-2-enenitrile | 386.1 |
| 242. | 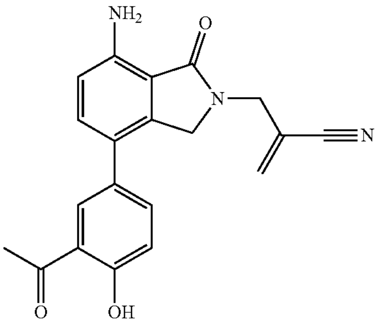 [SMILES: C=C(C#N)CN1Cc2c(-c3ccc(O)c(C(C)=O)c3)ccc(N)c2C1=O] | 2-{[4-(3-acetyl-4-hydroxyphenyl)-7-amino-1-oxo-2,3-dihydro-1H-isoindol-2-yl]methyl}prop-2-enenitrile | 348.1 |

TABLE 2-continued

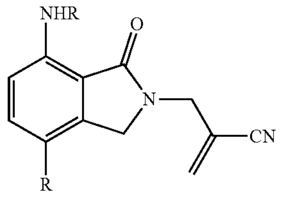

| Cpd. No. | Structure | IUPAC | LC-MS (ES+, m/z) |
|---|---|---|---|
| 243. | 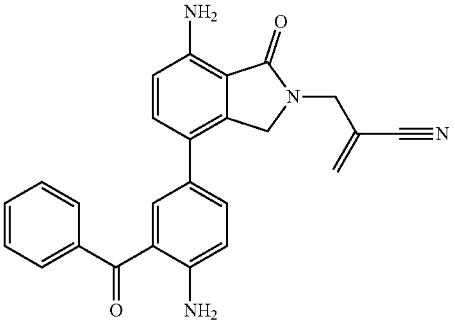 [SMILES: C=C(C#N)CN1Cc2c(-c3ccc(N)c(C(=O)c4ccccc4)c3)ccc(N)c2C1=O] | 2-{[7-amino-4-(4-amino-3-benzoylphenyl)-1-oxo-2,3-dihydro-1H-isoindol-2-yl]methyl}prop-2-enenitrile | 409.1 |
| 244. | 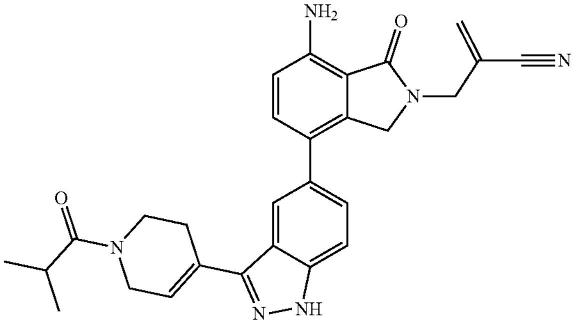 [SMILES: C=C(C#N)CN1Cc2c(-c3ccc4[nH]nc(C5=CCN(C(=O)C(C)C)CC5)c4c3)ccc(N)c2C1=O] | 2-[(7-amino-4-{3-[1-(2-methylpropanoyl)-1,2,3,6-tetrahydropyridin-4-yl]-1H-indazol-5-yl}-1-oxo-2,3-dihydro-1H-isoindol-2-yl)methyl]prop-2-enenitrile | 481.2 |
| 245. | 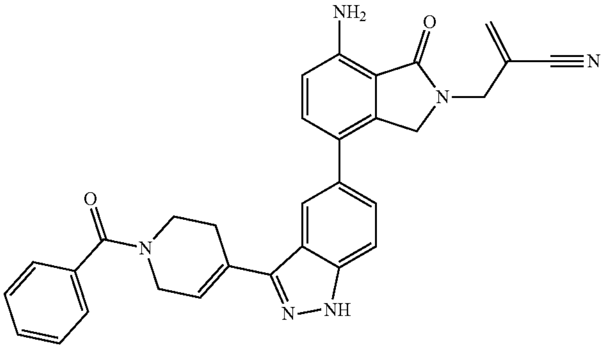 [SMILES: C=C(C#N)CN1Cc2c(-c3ccc4[nH]nc(C5=CCN(C(=O)c6ccccc6)CC5)c4c3)ccc(N)c2C1=O] | 2-({7-amino-4-[3-(1-benzoyl-1,2,3,6-tetrahydropyridin-4-yl)-1H-indazol-5-yl]-1-oxo-2,3-dihydro-1H-isoindol-2-yl}methyl)prop-2-enenitrile | 515.2 |
| 246. | 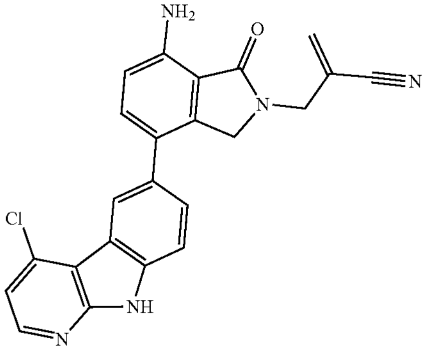 [SMILES: C=C(C#N)CN1Cc2c(-c3ccc4[nH]c5nccc(Cl)c5c4c3)ccc(N)c2C1=O] | 2-[(7-amino-4-{4-chloro-9H-pyrido[2,3-b]indol-6-yl}-1-oxo-2,3-dihydro-1H-isoindol-2-yl)methyl]prop-2-enenitrile | 414.2 |

TABLE 2-continued

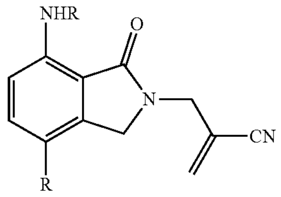

| Cpd. No. | Structure | IUPAC | LC-MS (ES+, m/z) |
|---|---|---|---|
| 247. | 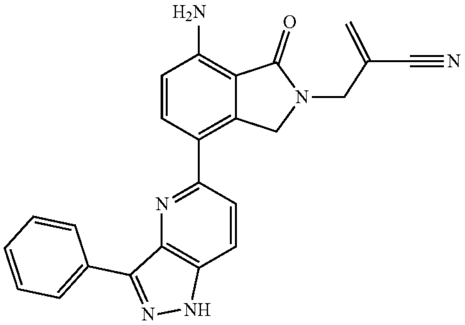 [SMILES: C=C(C#N)CN1Cc2c(-c3ccc4[nH]nc(-c5ccccc5)c4n3)ccc(N)c2C1=O] | 2-[(7-amino-1-oxo-4-{3-phenyl-1H-pyrazolo[4,3-b]pyridin-5-yl}-2,3-dihydro-1H-isoindol-2-yl)methyl]prop-2-enenitrile | 407.2 |
| 248. | 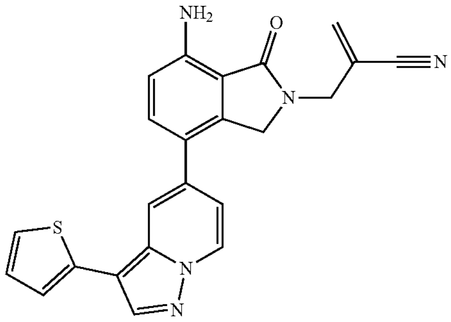 [SMILES: C=C(C#N)CN1Cc2c(-c3ccn4ncc(-c5cccs5)c4c3)ccc(N)c2C1=O] | 2-({7-amino-1-oxo-4-[3-(thiophen-2-yl)pyrazolo[1,5-a]pyridin-5-yl]-2,3-dihydro-1H-isoindol-2-yl}methyl)prop-2-enenitrile | 412.2 |
| 249. | 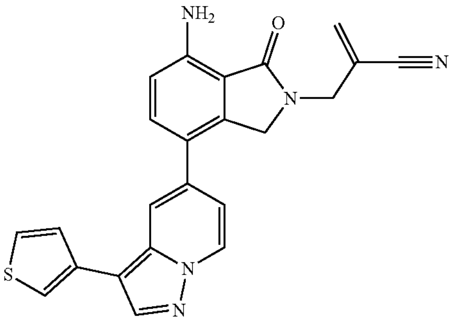 [SMILES: C=C(C#N)CN1Cc2c(-c3ccn4ncc(-c5ccsc5)c4c3)ccc(N)c2C1=O] | 2-({7-amino-1-oxo-4-[3-(thiophen-3-yl)pyrazolo[1,5-a]pyridin-5-yl]-2,3-dihydro-1H-isoindol-2-yl}methyl)prop-2-enenitrile | 412.2 |
| 250. | 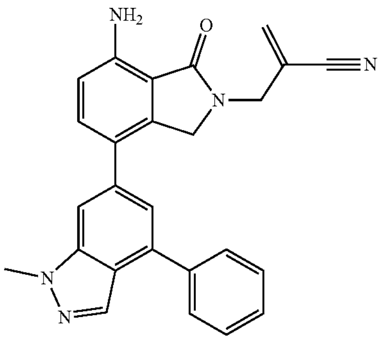 [SMILES: C=C(C#N)CN1Cc2c(-c3cc(-c4ccccc4)c4cnn(C)c4c3)ccc(N)c2C1=O] | 2-{[7-amino-4-(1-methyl-4-phenyl-1H-indazol-6-yl)-1-oxo-2,3-dihydro-1H-isoindol-2-yl]methyl}prop-2-enenitrile | 420.1 |

TABLE 2-continued
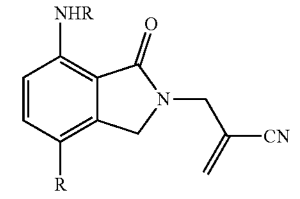
| Cpd. No. | Structure | IUPAC | LC-MS (ES+, m/z) |
|---|---|---|---|
| 251. | 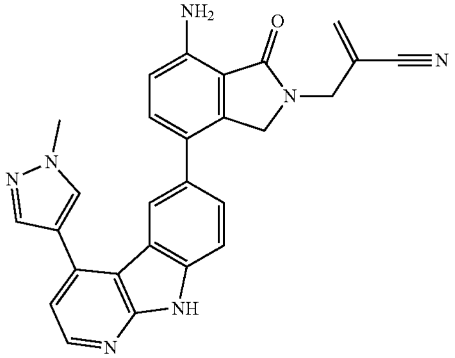 [SMILES: C=C(C#N)CN1Cc2c(-c3ccc4[nH]c5nccc(-c6cnn(C)c6)c5c4c3)ccc(N)c2C1=O] | 2-({7-amino-4-[4-(1-methyl-1H-pyrazol-4-yl)-9H-pyrido[2,3-b]indol-6-yl]-1-oxo-2,3-dihydro-1H-isoindol-2-yl}methyl)prop-2-enenitrile | 460.2 |
| 252. | 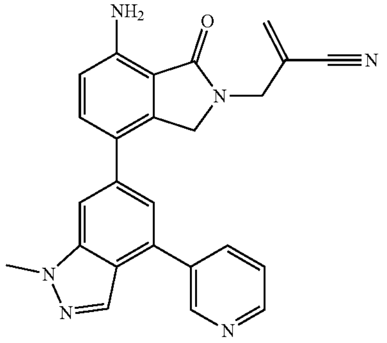 [SMILES: C=C(C#N)CN1Cc2c(-c3cc(-c4cccnc4)c4cnn(C)c4c3)ccc(N)c2C1=O] | 2-({7-amino-4-[1-methyl-4-(pyridin-3-yl)-1H-indazol-6-yl]-1-oxo-2,3-dihydro-1H-isoindol-2-yl}methyl)prop-2-enenitrile | 421.1 |
Example 4: Synthesis of Compounds of the Disclosure: Method C
4A. General Scheme for Method C: Route 1
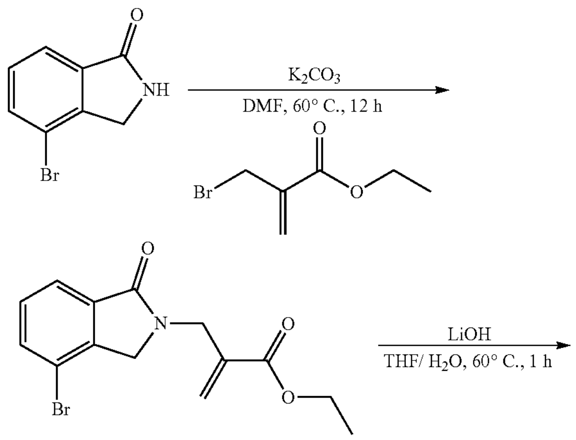
-continued
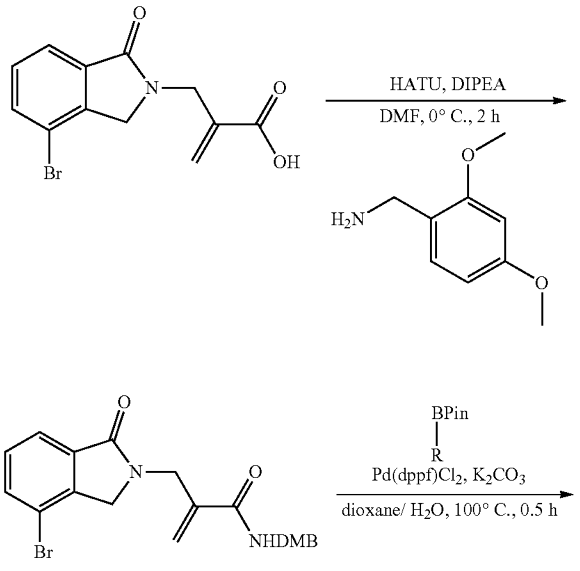

-continued

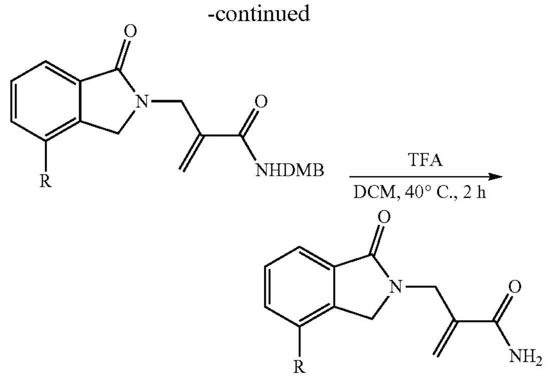

4A.1. Preparation of 2-{[1-oxo-4-(3-phenyl-1H-indazol-5-yl)-2,3-dihydro-1H-isoindol-2-yl]methyl}prop-2-enamide (Compound 258)

a. Preparation of Ethyl 2-[(4-bromo-1-oxo-2,3-dihydro-1H-isoindol-2-yl)methyl]prop-2-enoate

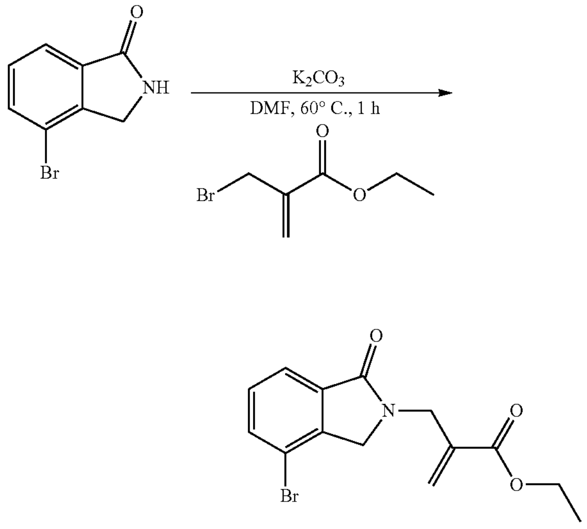

To a solution of 4-bromo-2,3-dihydro-1H-isoindol-1-one (5 g, 23.58 mmol, 1 eq.) and ethyl 2-(bromomethyl)prop-2-enoate (9.10 g, 47.16 mmol, 2 eq.) in DMF (50 mL) was added $K_2CO_3$ (9.78 g, 70.74 mmol, 3 eq.). The reaction mixture was stirred at 60° C. for 1 h, and LCMS showed that the reaction was complete. The mixture was extracted with DCM (50 mL×2), and the organic phase was washed with water (50 mL) and brine (50 mL), and dried over anhydrous sodium sulfate. The solids were filtered off, and the filtrate was concentrated in vacuo. The crude residue was purified by column chromatography (silica gel; PE:EtOAc=1/1) to afford the title compound (7 g, 21.59 mmol, 92% yield) as a yellow oil.

b. Preparation of 2-[(4-bromo-1-oxo-2,3-dihydro-1H-isoindol-2-yl)methyl]prop-2-enoic acid

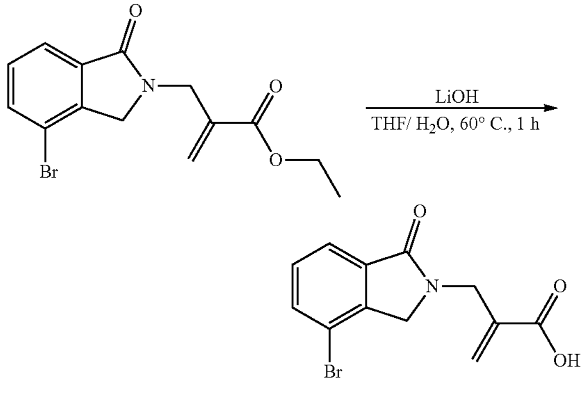

To a solution of ethyl 2-[(4-bromo-1-oxo-2,3-dihydro-1H-isoindol-2-yl)methyl]prop-2-enoate (3.5 g, 10.80 mmol, 1 eq.) in THF (30 mL) and water (15 mL) was added $LiOH \cdot H_2O$ (907.2 mg, 21.6 mmol, 1 eq.). The reaction mixture was stirred further at 60° C. for 1 h. LCMS showed that the reaction was complete. Aqueous HCl solution (1N) was added to acidify the mixture until pH~3. Then mixture was extracted with DCM (10 mL×2), and the combined organic phases were washed with water (10 mL) and brine (10 mL), dried over anhydrous sodium sulfate, filtered, and concentrated. The solids were filtered off, and the filtrate was concentrated in vacuo to give the crude. The residue was purified by prep-HPLC to afford the title compound (3 g, 93.7% yield) as a white solid.

c. Preparation of 2-[(4-bromo-1-oxo-2,3-dihydro-1H-isoindol-2-yl)methyl]-N-[(2,4-dimethoxyphenyl)methyl]prop-2-enamide

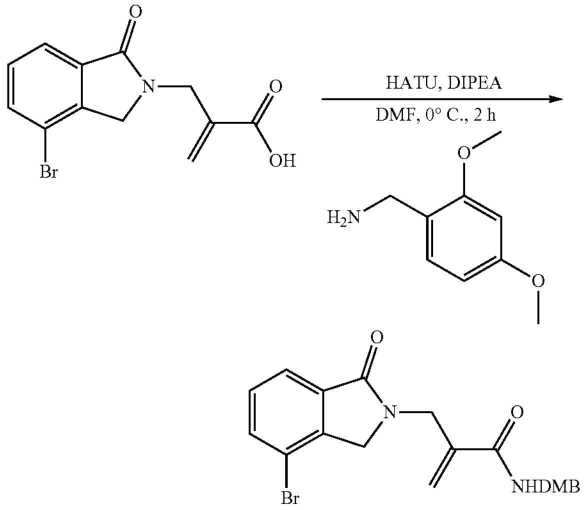

To a solution of 2-[(4-bromo-1-oxo-2,3-dihydro-1H-isoindol-2-yl)methyl]prop-2-enoic acid (3 g, 10.13 mmol, 1 eq.) and (2,4-dimethoxyphenyl)benzylamine (2.54 g, 15.20 mmol, 2.29 mL, 1.5 eq.) in DMF (40 mL) were added DIPEA (2.62 g, 20.26 mmol, 3.53 mL, 2 eq.) and HATU (5.78 g, 15.20 mmol, 1.5 eq.). The mixture was stirred at 0° C. for 1 h, and TLC showed that the reaction was complete. The mixture was extracted with DCM (10 mL×2), and the combined organic phases were washed with water (10 mL) and brine (10 mL), dried over anhydrous sodium sulfate, filtered, and concentrated. The solids were filtered off, and the filtrate was concentrated in vacuo to give the crude. The crude residue was purified by column chromatography (silica gel; PE:EtOAc=1/1) to afford the title compound (3 g, 6.74 mmol, 66.50% yield) as a yellow solid.

d. Preparation of tert-butyl 5-[2-[2-[(2,4-dimethoxyphenyl)methylcarbamoyl]allyl]-1-oxo-isoindolin-4-yl]-3-phenyl-indazole-1-carboxylate

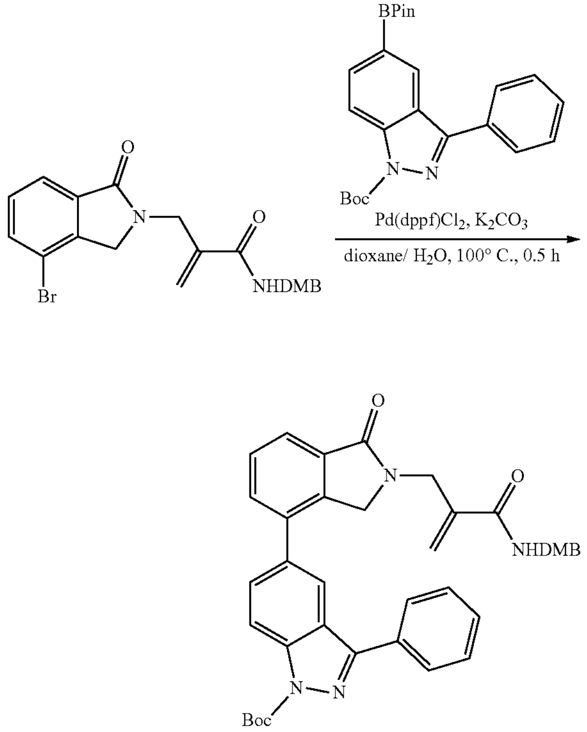

To a solution of 2-[(4-bromo-1-oxo-2,3-dihydro-1H-isoindol-2-yl)methyl]-N-[(2,4-dimethoxyphenyl)methyl]prop-2-enamide (80 mg, 179.65 μmol, 1 eq.) and 3-phenyl-5-(4,4,5,5-tetramethyl-1,3,2-dioxaborolan-2-yl)-1H-indazole-1-carboxylate (226 mg, 538.95 μmol, 3 eq.) in dioxane (2 mL) and water (0.5 mL) were added $K_2CO_3$ (74.49 mg, 538.95 μmol, 3 eq) and $Pd(dppf)Cl_2$ (6.57 mg, 8.98 μmol, 0.05 eq.). The reaction mixture was stirred at 100° C. for 1 h. LCMS showed that the reaction was complete. The mixture was extracted with DCM (10 mL×2), and the organic phase was washed with water (10 mL) and brine (10 mL), dried over anhydrous sodium sulfate, filtered, and concentrated. The solids were filtered off, and the filtrate was concentrated in vacuo to give the crude. The crude residue was purified by column chromatography (silica gel; PE:EtOAc=1/1) to afford the title compound (65 mg, 71% yield).

e. Preparation of 2-{[1-oxo-4-(3-phenyl-1H-indazol-5-yl)-2,3-dihydro-1H-isoindol-2-yl]methyl}prop-2-enamide (Compound 258)

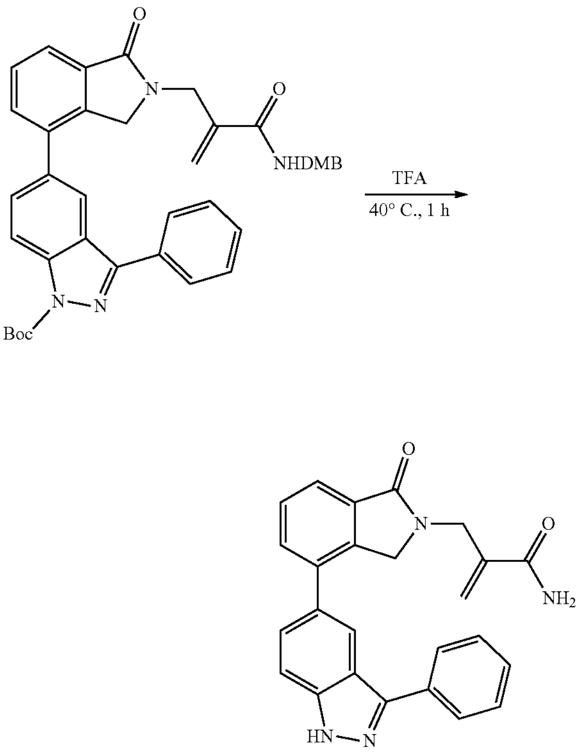

The solution of tert-butyl 5-[2-[2-[(2,4-dimethoxyphenyl)methylcarbamoyl]allyl]-1-oxo-isoindolin-4-yl]-3-phenyl-indazole-1-carboxylate (47.12 μmol, 1 eq.) in trifluoroacetic acid (2 mL) was stirred at 40° C. for 1 h. LCMS and TLC showed that the reaction was complete. The mixture was extracted with DCM (10 mL×2), and the combined organic phases were washed with water (10 mL) and brine (10 mL), dried over anhydrous sodium sulfate, filtered, and concentrated. The solids were filtered off, and the filtrate was concentrated in vacuo to give the crude. The residue was purified by HPLC to afford the desired product. LC-MS (ES+, m/z): 409.1.

4A.2, Preparation of 2-[[4-(4-amino-3,5-dichlorophenyl)-1-oxo-isoindolin-2-yl]methyl]prop-2-enamide (Compound 263)

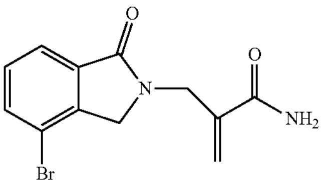

+

-continued

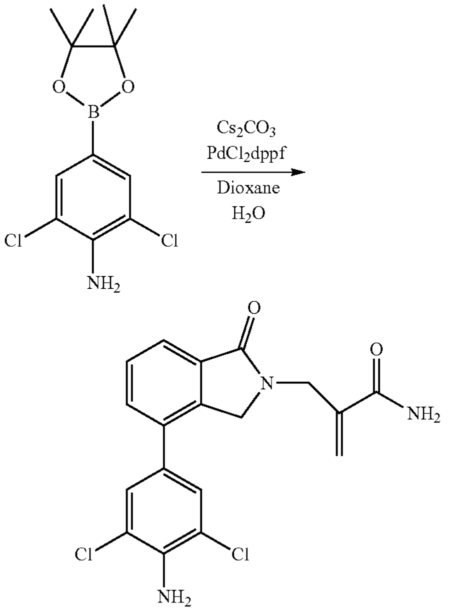

To a solution of 2-[(4-bromo-1-oxo-isoindolin-2-yl) methyl]prop-2-enamide (30 mg, 102 μmol) in dioxane (1.0 mL) and water (0.2 mL) were added 2,6-dichloro-4-(4,4,5,5-tetramethyl-1,3,2-dioxaborolan-2-yl)aniline (43.9 mg, 152 μmol), $Cs_2CO_3$ (99.5 mg, 0.306 mmol) and $PdCl_2$dppf (18 mg, 22 μmol). The reaction was heated to 100° C. for 25 min. The reaction mixture was passed through a celite pad, and 2 mL of 0.5 M EDTA was added. The resulting solution was stirred at r.t. for 30 min. The solution was washed with brine, and the organic phase was dried over anhydrous sodium sulfate, filtered, and concentrated in vacuo. The residue was purified by reverse phase HPLC using a gradient of water 0.1% FA/acetonitrile 0.1% FA to afford the title compound (17 mg, Yield 44%). LC-MS: $[M+H]^+$ 377.

4A3. Preparation of 2-[[4-[4-(aminomethyl)phenyl]-1-oxo-isoindolin-2-yl]methyl]prop-2-enamide (Compound 264)

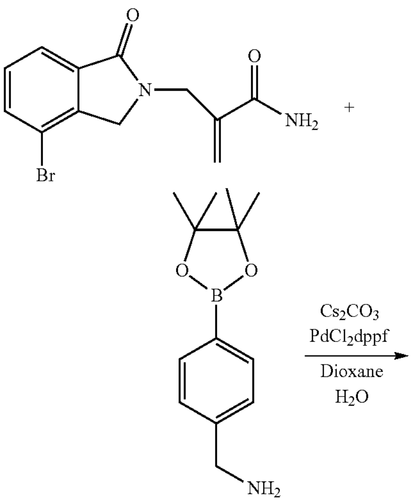

-continued

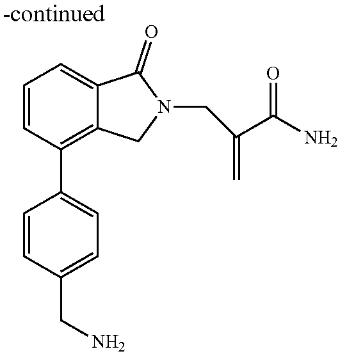

To a solution of 2-[(4-bromo-1-oxo-isoindolin-2-yl) methyl]prop-2-enamide (30 mg, 102 μmol) in dioxane (1.0 mL) and water (0.2 mL) were added [4-(4,4,5,5-tetramethyl-1,3,2-dioxaborolan-2-yl)phenyl]methanamine (35.4 mg, 152 μmol), $Cs_2CO_3$ (99.5 mg, 0.306 mmol) and $PdCl_2$dppf (18 mg, 22 μmol). The reaction was heated to 100° C. for 25 min. The reaction mixture was passed through a celite pad, and 2 mL of 0.5 M EDTA was added. The resulting solution was stirred at r.t. for 30 min. The solution was washed with brine, and the organic phase was dried over anhydrous sodium sulfate, filtered, and concentrated in vacuo. The residue was purified by reverse phase HPLC using a gradient of water 0.1% FA/acetonitrile 0.1% FA to afford the title compound (4 mg, Yield 12%). LC-MS: $[M+H]^+$ 322.

4A.4 Preparation of 2-[[4-(3-methyl-1H-indazol-5-yl)-1-oxo-isoindolin-2-yl]methyl]prop-2-enamide (Compound 265)

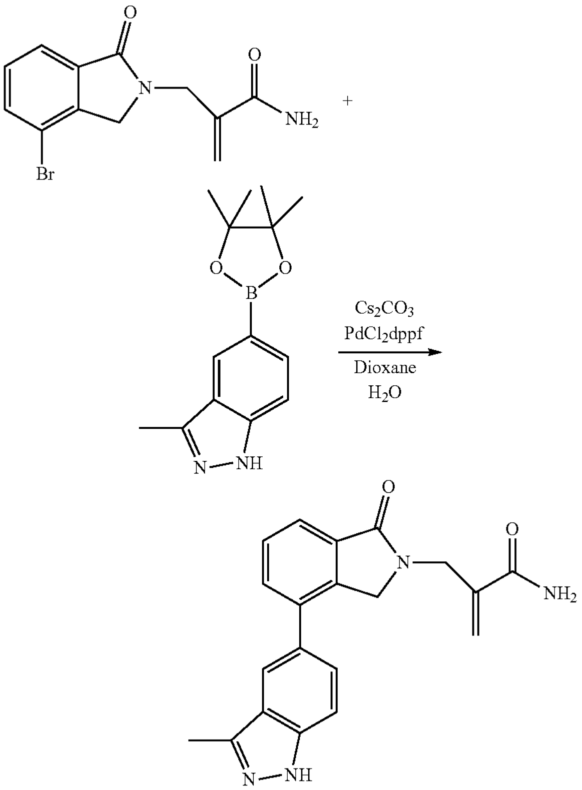

To a solution of 2-[(4-bromo-1-oxo-isoindolin-2-yl)methyl]prop-2-enamide (30 mg, 102 μmol) in dioxane (1.0 mL) and water (0.2 mL) were added 3-methyl-5-(4,4,5,5-tetramethyl-1,3,2-dioxaborolan-2-yl)-1H-indazole (39.2 mg, 152 μmol), $Cs_2CO_3$ (99.5 mg, 0.306 mmol) and $PdCl_2dppf$ (18 mg, 22 μmol). The reaction was heated to 100° C. for 25 min. The reaction mixture was passed through a celite pad, and 2 mL of 0.5 M EDTA was added. The resulting solution was stirred at r.t. for 30 min. The solution was washed with brine, dried over anhydrous sodium sulfate, filtered, and concentrated in vacuo. The residue was purified by reverse phase HPLC using a gradient of water 0.1% FA/acetonitrile 0.1% FA to afford the title compound (16.9 mg, Yield 48%). LC-MS: $[M+H]^+$ 347.

4A.5. Preparation of 2-[[4-(6-amino-5-chloro-3-pyridyl)-1-oxo-isoindolin-2-yl]methyl]prop-2-enamide (Compound 266)

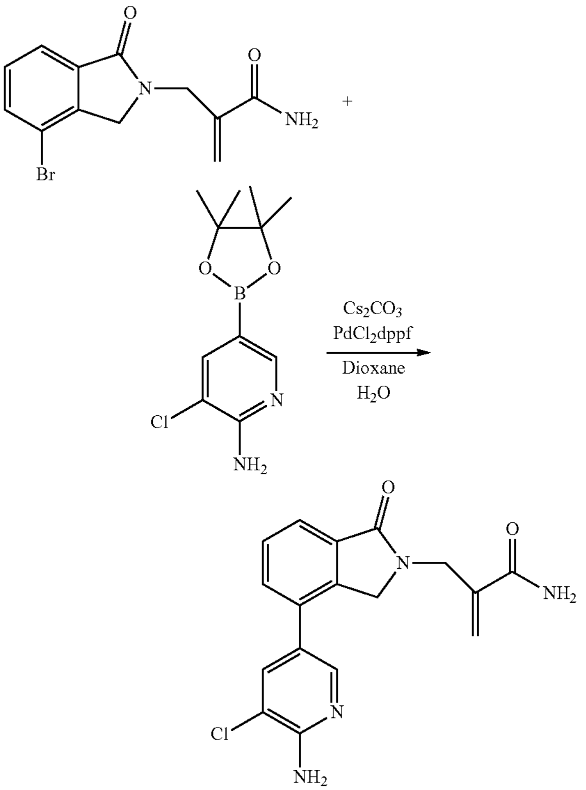

To a solution of 2-[(4-bromo-1-oxo-isoindolin-2-yl)methyl]prop-2-enamide (30 mg, 102 μmol) in dioxane (1.0 mL) and water (0.2 mL) were added 3-chloro-5-(4,4,5,5-tetramethyl-1,3,2-dioxaborolan-2-yl)pyridin-2-amine (38.7 mg, 152 μmol), $Cs_2CO_3$ (99.5 mg, 0.306 mmol) and $PdCl_2dppf$ (18 mg, 22 μmol). The reaction was heated to 100° C. for 25 min. The reaction mixture was passed through a celite pad, and 2 mL of 0.5 M EDTA was added. The resulting solution was stirred at r.t. for 30 min. The solution was washed with brine, and the organic phase was dried over anhydrous sodium sulfate, filtered, and concentrated in vacuo. The residue was purified by reverse phase HPLC using a gradient of water 0.1% FA/acetonitrile 0.1% FA to afford the title compound (16.5 mg, Yield 47%). LC-MS: $[M+H]^+$ 343.

4A.6. Preparation of 2-[[4-(4-amino-3-chloro-phenyl)-1-oxo-isoindolin-2-yl]methyl]prop-2-enamide (Compound 267)

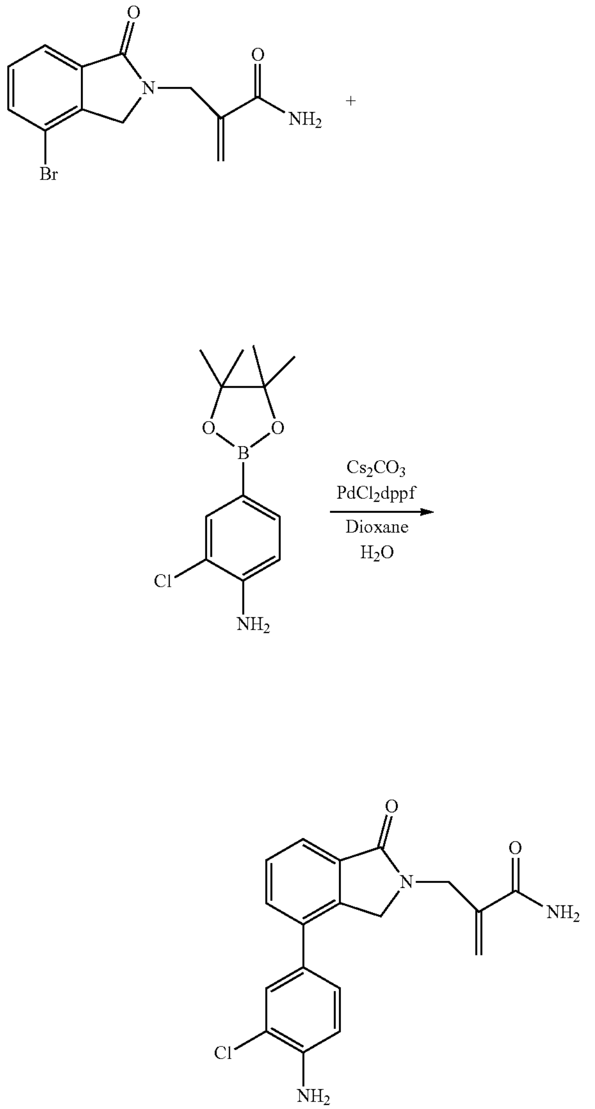

To a solution of 2-[(4-bromo-1-oxo-isoindolin-2-yl)methyl]prop-2-enamide (30 mg, 102 μmol) in dioxane (1.0 mL) and water (0.2 mL) were added 2-chloro-4-(4,4,5,5-tetramethyl-1,3,2-dioxaborolan-2-yl)aniline (38.5 mg, 152 μmol), $Cs_2CO_3$ (99.5 mg, 0.306 mmol) and $PdCl_2dppf$ (18 mg, 22 μmol). The reaction was heated to 100° C. for 25 min. The reaction mixture was passed through a celite pad, and 2 mL of 0.5 M EDTA was added. The resulting solution was stirred at r.t. for 30 min. The solution was washed with brine, and the organic phase was dried over anhydrous sodium sulfate, filtered, and concentrated in vacuo. The residue was purified by reverse phase HPLC using a gradient of water 0.1% FA/acetonitrile 0.1% FA to afford the title compound (22 mg, Yield 63%). LC-MS: $[M+H]^+$ 342.

4A.7. Preparation of 2-[[4-(6-amino-2-naphthyl)-1-oxo-isoindolin-2-yl]methyl]prop-2-enamide (Compound 268)

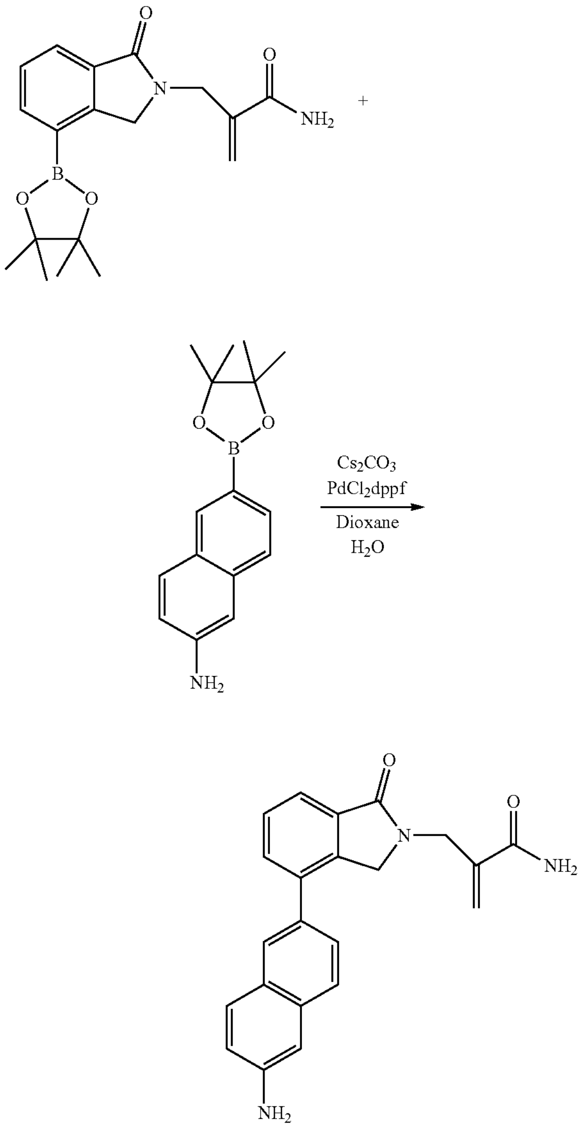

To a solution of 2-[[1-oxo-4-(4,4,5,5-tetramethyl-1,3,2-dioxaborolan-2-yl)isoindolin-2-yl]methyl]prop-2-enamide (50 mg, 146 μmol) in dioxane (1.0 mL) and water (0.2 mL) were added 6-(4,4,5,5-tetramethyl-1,3,2-dioxaborolan-2-yl) naphthalen-2-amine (48.7 mg, 219 μmol), $Cs_2CO_3$ (142 mg, 0.438 mmol) and $PdCl_2dppf$ (18 mg, 22 μmol). The reaction was heated to 100° C. for 25 min. The reaction mixture was passed through a celite pad, and 2 mL of 0.5 M EDTA was added. The resulting solution was stirred at r.t. for 30 min. The solution was washed with brine, and the organic phase was dried over anhydrous sodium sulfate, filtered, and concentrated in vacuo. The residue was purified by reverse phase HPLC using a gradient of water 0.1% FA/acetonitrile 0.1% FA to afford the title compound (3 mg, Yield 6%). LC-MS: $[M+H]^+$ 358.

4.A.8. Preparation of 2-[[4-[3-(3-aminophenyl)-1H-indazol-5-yl]-1-oxo-isoindolin-2-yl]methyl]prop-2-enamide (Compound 269)

a. Preparation of tert-butyl N-[3-(5-bromo-1H-indazol-3-yl)phenyl]carbamate

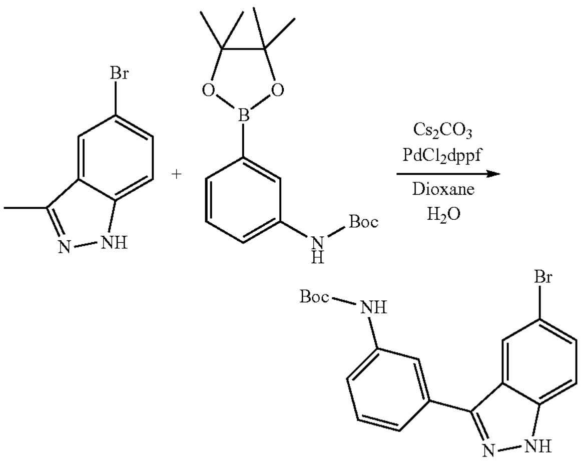

To a solution 5-bromo-3-iodo-1H-indazole (100 mg, 310 μmol) in dioxane (2.0 mL) and water (0.4 mL) were added tert-butyl N-[3-(4,4,5,5-tetramethyl-1,3,2-dioxaborolan-2-yl)phenyl]carbamate (148 mg, 465 μmol), $Cs_2CO_3$ (302 mg, 0.93 mmol) and $PdCl_2dppf$ (40 mg, 45 μmol). The reaction was heated to 120° C. for 30 min. The reaction mixture was passed through a celite pad, and 2 mL of 0.5 M EDTA was added. The resulting solution was stirred at r.t. for 30 min. The solution was washed with brine, and the organic phase was dried over anhydrous sodium sulfate, filtered, and concentrated in vacuo. The residue was purified by chromatography on silica gel eluting with 0-60% EtOAc/hexane to afford the title compound (52.6 mg, Yield 44%).

b. Preparation of tert-butyl N-[3-[5-[2-(2-carbamoylallyl)-1-oxo-isoindolin-4-yl]-1H-indazol-3-yl]phenyl]carbamate

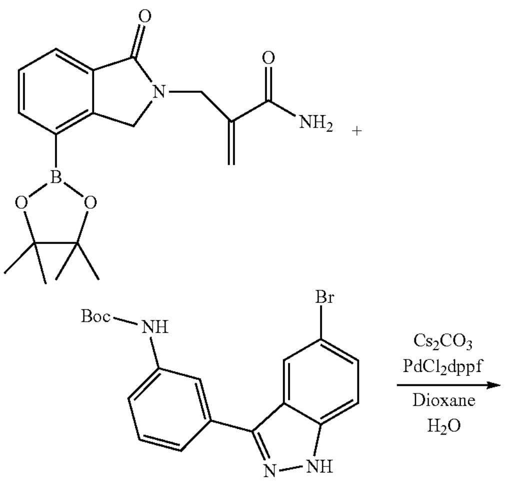

-continued

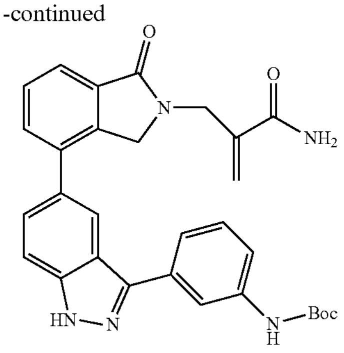

To a solution of 2-[[1-oxo-4-(4,4,5,5-tetramethyl-1,3,2-dioxaborolan-2-yl)isoindolin-2-yl]methyl]prop-2-enamide (50 mg, 146 μmol) in dioxane (1.0 mL) and water (0.2 mL) were added tert-butyl N-[3-(5-bromo-1H-indazol-3-yl)phenyl]carbamate (68 mg, 175 μmol), $Cs_2CO_3$ (142 mg, 0.438 mmol) and $PdCl_2dppf$ (18 mg, 22 μmol). The reaction was heated to 100° C. for 25 min. The reaction mixture was passed through a celite pad, and 2 mL of 0.5 M EDTA was added. The resulting solution was stirred at r.t. for 30 min. The solution was washed with brine, and the organic phase was dried over anhydrous sodium sulfate, filtered, and concentrated in vacuo. The residue was purified by chromatography on silica gel eluting with 0-5% MeOH/DCM to afford the title compound (45.2 mg, Yield 59%).

c. Preparation of 2-[[4-[3-(3-aminophenyl)-1H-indazol-5-yl]-1-oxo-isoindolin-2-yl]methyl]prop-2-enamide (Compound 269)

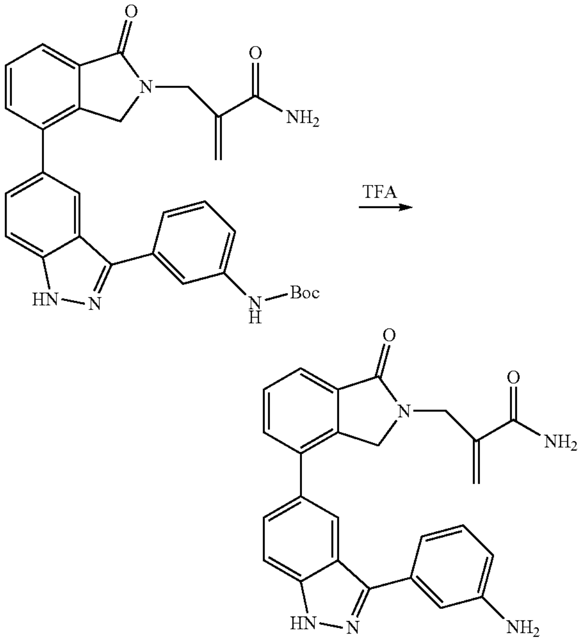

To a solution of tert-butyl N-[3-[5-[2-(2-carbamoylallyl)-1-oxo-isoindolin-4-yl]-1H-indazol-3-yl]phenyl]carbamate (45.2 mg, 86 μmol) in DCM (2 mL) was added trifluoroacetic acid (0.5 mL) at 0° C. The resulting solution was stirred at 0° C. for 1 h and at r.t. for 1 h. The reaction mixture was concentrated in vacuo and the residue was diluted with DCM, washed with sat. $NaHCO_3$ and brine, dried over anhydrous sodium sulfate, filtered, and concentrated. The residue was purified by reverse phase HPLC using a gradient of water 0.1% FA/acetonitrile 0.1% FA to afford the title compound (20.1 mg, Yield 55%). LC-MS: $[M+H]^+$ 424.

4A.9. Preparation of N-[3-[2-(2-carbanoylallyl)-1-oxo-isoindolin-4-yl]phenyl]tetrahydropyran-4-carboxamide (Compound 270)

a. Preparation of N-(3-bromophenyl)tetrahydropyran-4-carboxamide

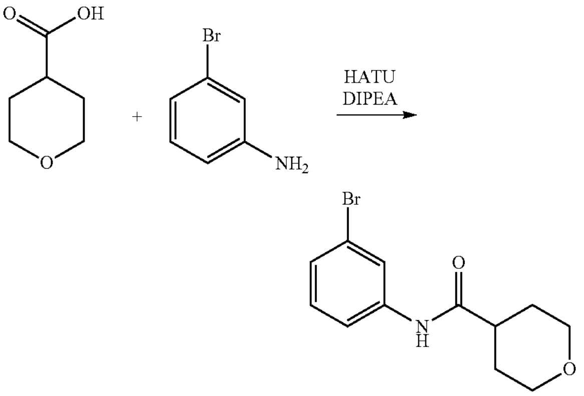

A mixture of tetrahydropyran-4-carboxylic acid (200 mg, 1.537 mmol), HATU (1.169 g, 3.074 mmol) and DIPEA (0.595 g, 4.611 mmol) in DMF (8 mL) was stirred at r.t. for 30 min. 3-Bromoaniline (0.397 g, 2.306 mmol) was added. The resulting mixture was stirred at r.t. for 18 h and partitioned between EtOAc and water. The aqueous phase was extracted with EtOAc (3×). The combined organic phase was washed with sat. $NaHCO_3$ and brine, dried over ($MgSO_4$), filtered, and concentrated in vacuo. The residue was purified by chromatography on silica gel eluting with 20-80% EtOAc/hexane to afford the title compound (0.401 g, Yield 92%).

b. Preparation of N-[3-[2-(2-carbamoylallyl)-1-oxo-isoindolin-4-yl]phenyl]tetrahydropyran-4-carboxamide (Compound 270)

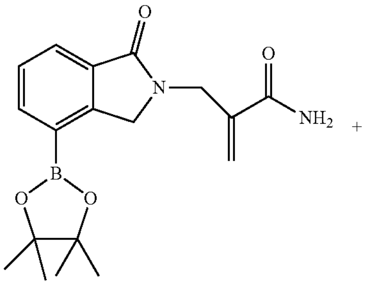
+

-continued

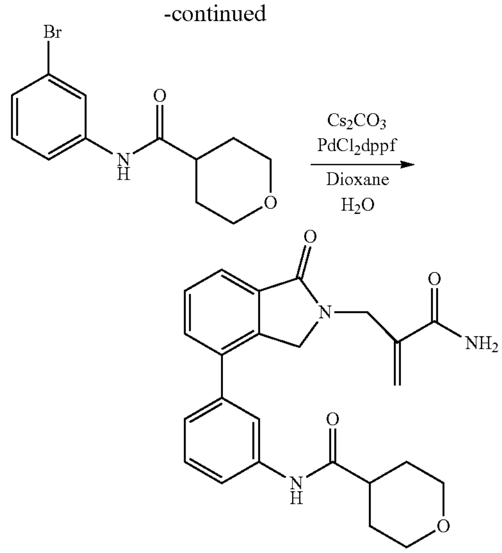

To a solution of 2-[[1-oxo-4-(4,4,5,5-tetramethyl-1,3,2-dioxaborolan-2-yl)isoindolin-2-yl]methyl]prop-2-enamide (40 mg, 117 μmol) in dioxane (1.0 mL) and water (0.2 mL) were added N-(3-bromophenyl)tetrahydropyran-4-carboxamide (49.9 mg, 176 μmol), $Cs_2CO_3$ (114 mg, 0.351 mmol) and $PdCl_2$dppf (18 mg, 22 μmol). The reaction was heated to 100° C. for 25 min. The reaction mixture was passed through a celite pad, and 2 mL of 0.5 M EDTA was added. The resulting solution was stirred at r.t. for 30 min. The solution was washed with brine, and the organic phase was dried over anhydrous sodium sulfate, filtered, and concentrated in vacuo. The residue was purified by reverse phase HPLC using a gradient of water 0.1% FA/acetonitrile 0.1% FA to afford the title compound (11 mg, Yield 22%). LC-MS: $[M+H]^+$ 420.

4A.10. N-{3-[2-(2-carbamoyl-2-methylideneethyl)-1-oxo-2,3-dihydro-1H-isoindol-4-yl]phenyl}piperidine-4-carboxamide (Compound 271)

a. Preparation of tert-butyl 4-[(3-bromophenyl)carbamoyl]piperidine-1-carboxylate

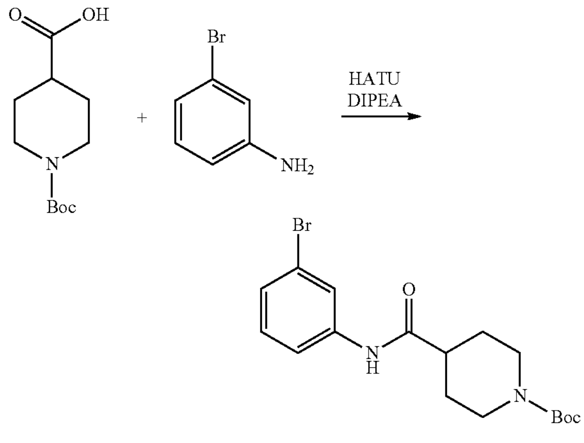

A mixture of 1-tert-butoxycarbonylpiperidine-4-carboxylic acid (200 mg, 0.872 mmol), HATU (0.663 g, 1.744 mmol) and DIPEA (0.337 g, 4.611 mmol) in DMF (8 mL) was stirred at r.t. for 30 min. 3-Bromoaniline (0.225 g, 1.308 mmol) was added. The resulting mixture was stirred at r.t. for 18 h and partitioned between EtOAc and water. The aqueous phase was extracted with EtOAc (3×). The combined organic phase was washed with sat. $NaHCO_3$ and brine, dried over ($MgSO_4$), filtered, and concentrated in vacuo. The residue was purified by chromatography on silica gel eluting with 0-50% EtOAc/hexane to afford the title compound (0.334 g, Yield 100%).

b. Preparation of tert-butyl 4-[[3-[2-(2-carbamoylallyl)-1-oxo-isoindolin-4-yl]phenyl]carbamoyl]piperidine-1-carboxylate

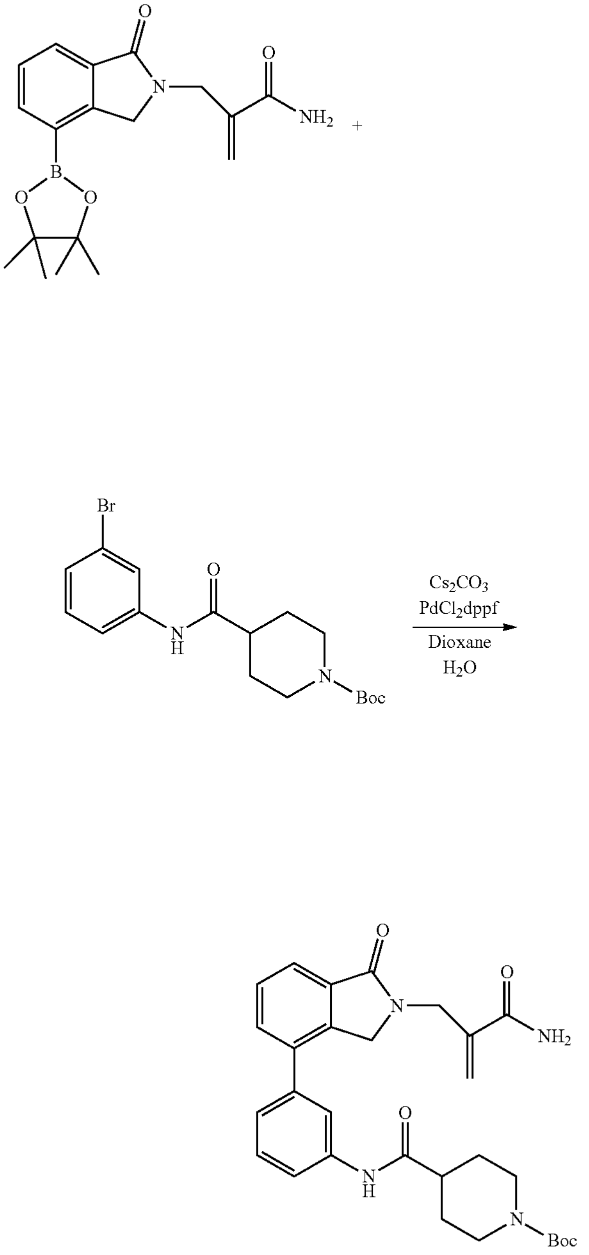

To a solution of 2-[[1-oxo-4-(4,4,5,5-tetramethyl-1,3,2-dioxaborolan-2-yl)isoindolin-2-yl]methyl]prop-2-enamide (50 mg, 146 μmol) in dioxane (1.0 mL) and water (0.2 mL) were added tert-butyl 4-[(3-bromophenyl)carbamoyl]piperidine-1-carboxylate (84 mg, 219 μmol), $Cs_2CO_3$ (142 mg, 0.438 mmol) and $PdCl_2dppf$ (18 mg, 22 μmol). The reaction was heated to 100° C. for 25 min. The reaction mixture was passed through a celite pad, and 2 mL of 0.5 M EDTA was added. The resulting solution was stirred at r.t. for 30 min. The solution was washed with brine, and the organic phase was dried over anhydrous sodium sulfate, filtered, and concentrated in vacuo. The residue was purified by chromatography on silica gel eluting with 50-100% EtOAc/hexane and 10% MeOH in DCM to afford the title compound (41.2 mg, Yield 55%).

c. N-{3-[2-(2-carbamoyl-2-methylideneethyl)-1-oxo-2,3-dihydro-1H-isoindol-4-yl]phenyl}piperidine-4-carboxamide (Compound 271)

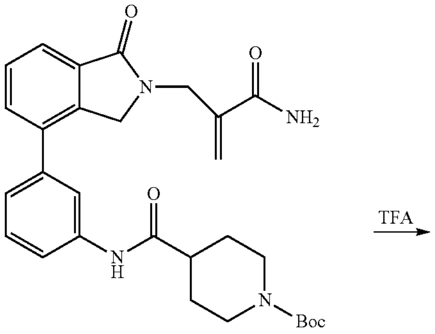

-continued

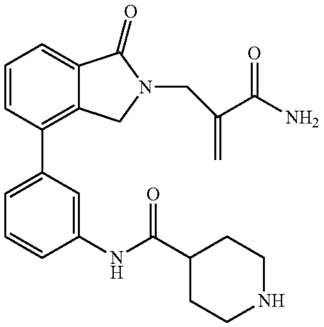

To a solution of tert-butyl 4-[[3-[2-(2-carbamoylallyl)-1-oxo-isoindolin-4-yl]phenyl]carbamoyl]piperidine-1-carboxylate (41.2 mg, 79 μmol) in DCM (2 mL) was added trifluoroacetic acid (0.5 mL) at 0° C. The resulting solution was stirred at 0° C. for 1 h and r.t. for 1 h. The reaction mixture was concentrated in vacuo and the residue was diluted with DCM, washed with sat. $NaHCO_3$ and brine, dried over anhydrous sodium sulfate, filtered, and concentrated. The residue was purified by reverse phase HPLC using a gradient of water 0.100 FA/acetonitrile 0.1% FA to afford the title compound (2.1 mg, Yield 6%). LC-MS: $[M+H]^+$ 419.

4B. Synthesis of Compounds of the Disclosure

TABLE 3 shows compounds containing an isoindolinone core and acrylamide moiety prepared using the methods described above.

TABLE 3

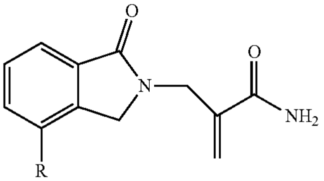

| Cpd. No. | Structure | IUPAC | LC-MS (ES+, m/z) |
|---|---|---|---|
| 253. | 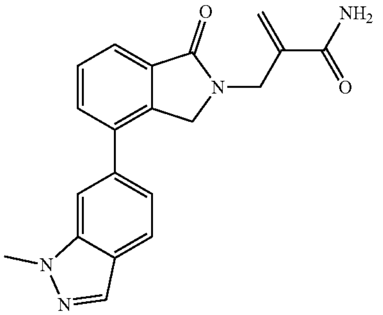 [SMILES: C=C(CN1Cc2c(cccc2-c2ccc3cnn(C)c3c2)C1=O)C(N)=O] | 2-{[4-(1-methyl-1H-indazol-6-yl)-1-oxo-2,3-dihydro-1H-isoindol-2-yl]methyl}prop-2-enamide | 347.1 |

TABLE 3-continued
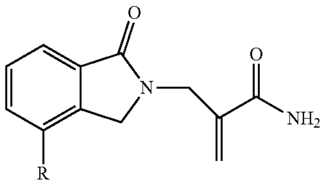
| Cpd. No. | Structure | IUPAC | LC-MS (ES+, m/z) |
|---|---|---|---|
| 254. | 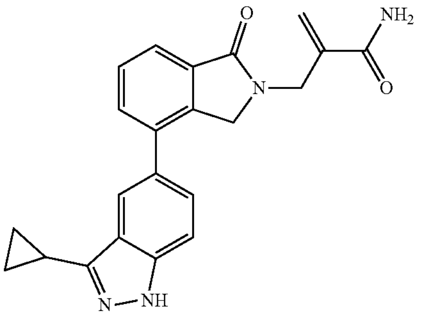 [SMILES: C=C(CN1Cc2c(cccc2-c2ccc3[nH]nc(C4CC4)c3c2)C1=O)C(N)=O] | 2-{[4-(3-cyclopropyl-1H-indazol-5-yl)-1-oxo-2,3-dihydro-1H-isoindol-2-yl]methyl}prop-2-enamide | 373.2 |
| 255. | 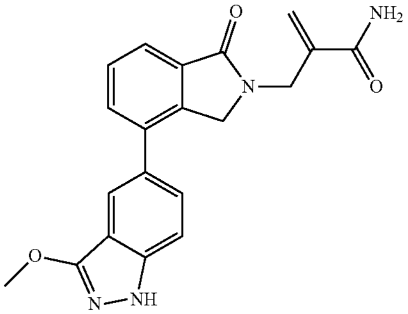 [SMILES: C=C(CN1Cc2c(cccc2-c2ccc3[nH]nc(OC)c3c2)C1=O)C(N)=O] | 2-{[4-(3-methoxy-1H-indazol-5-yl)-1-oxo-2,3-dihydro-1H-isoindol-2-yl]methyl}prop-2-enamide | 363.2 |
| 256. | 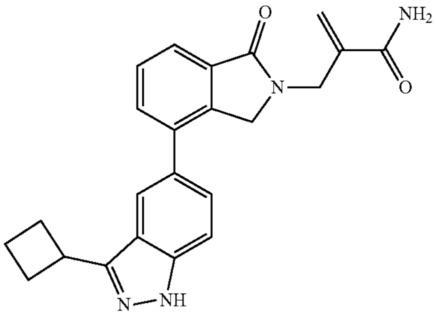 [SMILES: C=C(CN1Cc2c(cccc2-c2ccc3[nH]nc(C4CCC4)c3c2)C1=O)C(N)=O] | 2-{[4-(3-cyclobutyl-1H-indazol-5-yl)-1-oxo-2,3-dihydro-1H-isoindol-2-yl]methyl}prop-2-enamide | 387.1 |
| 257. | 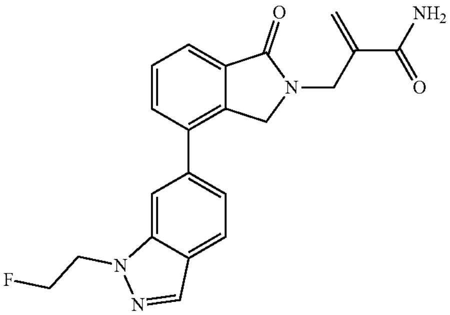 [SMILES: C=C(CN1Cc2c(cccc2-c2ccc3cnn(CCF)c3c2)C1=O)C(N)=O] | 2-({4-[1-(2-fluoroethyl)-1H-indazol-6-yl]-1-oxo-2,3-dihydro-1H-isoindol-2-yl}methyl)prop-2-enamide | 379.2 |

TABLE 3-continued
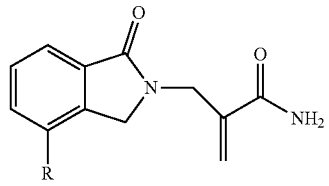
| Cpd. No. | Structure | IUPAC | LC-MS (ES+, m/z) |
|---|---|---|---|
| 258. | 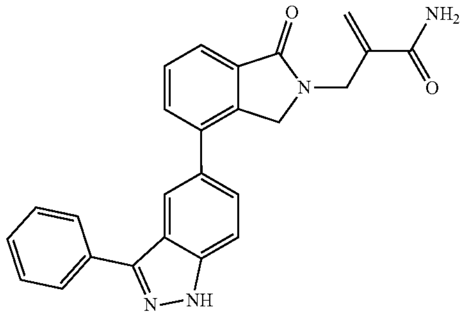 [SMILES: C=C(CN1Cc2c(cccc2-c2ccc3[nH]nc(-c4ccccc4)c3c2)C1=O)C(N)=O] | 2-{[1-oxo-4-(3-phenyl-1H-indazol-5-yl)-2,3-dihydro-1H-isoindol-2-yl]methyl}prop-2-enamide | 409.1 |
| 259. | 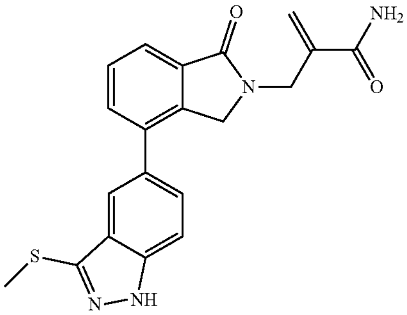 | 2-({4-[3-(methylsulfanyl)-1H-indazol-5-yl]-1-oxo-2,3-dihydro-1H-isoindol-2-yl}methyl)prop-2-enamide | 379.1 |
| 260. | 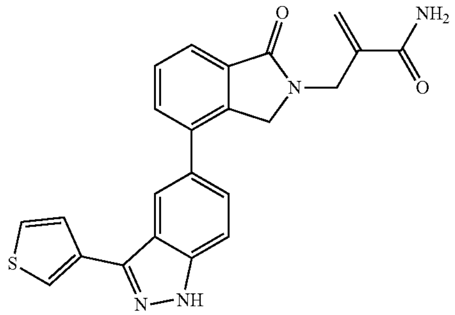 [SMILES: C=C(CN1Cc2c(cccc2-c2ccc3[nH]nc(-c4ccsc4)c3c2)C1=O)C(N)=O] | 2-({1-oxo-4-[3-(thiophen-3-yl)-1H-indazol-5-yl]-2,3-dihydro-1H-isoindol-2-yl}methyl)prop-2-enamide | 415 |
| 261. | 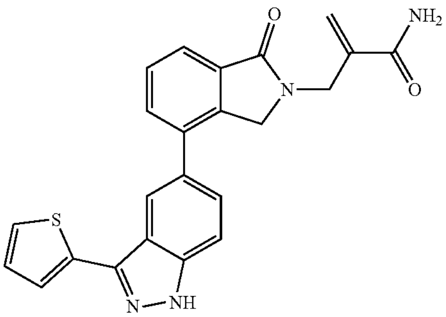 [SMILES: C=C(CN1Cc2c(cccc2-c2ccc3[nH]nc(-c4cccs4)c3c2)C1=O)C(N)=O] | 2-({1-oxo-4-[3-(thiophen-2-yl)-1H-indazol-5-yl]-2,3-dihydro-1H-isoindol-2-yl}methyl)prop-2-enamide | 415.1 |

TABLE 3-continued
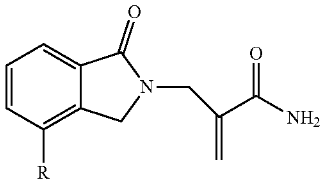
| Cpd. No. | Structure | IUPAC | LC-MS (ES+, m/z) |
|---|---|---|---|
| 262. | 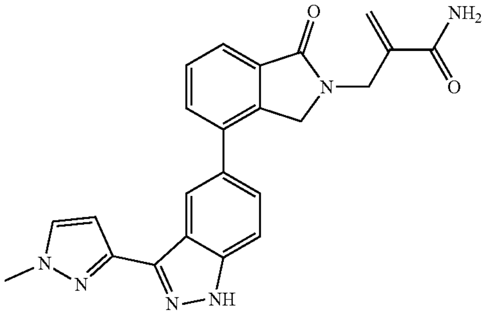 [SMILES: C=C(CN1Cc2c(cccc2-c2ccc3[nH]nc(-c4ccn(C)n4)c3c2)C1=O)C(N)=O] | 2-({4-[3-(1-methyl-1H-pyrazol-3-yl)-1H-indazol-5-yl]-1-oxo-2,3-dihydro-1H-isoindol-2-yl}methyl)prop-2-enamide | 413.1 |
| 263. | 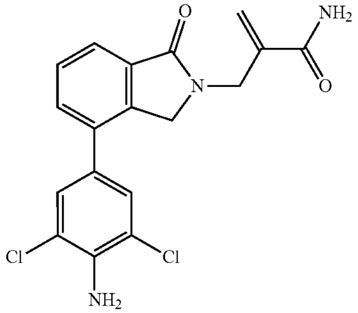 [SMILES: C=C(CN1Cc2c(cccc2-c2cc(Cl)c(N)c(Cl)c2)C1=O)C(N)=O] | 2-{[4-(4-amino-3,5-dichlorophenyl)-1-oxo-2,3-dihydro-1H-isoindol-2-yl]methyl}prop-2-enamide | 375.8 |
| 264. | 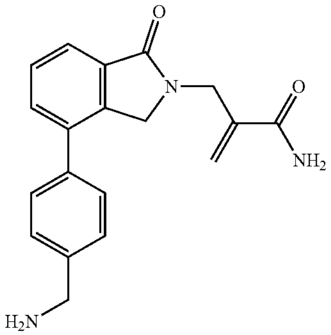 [SMILES: C=C(CN1Cc2c(cccc2-c2ccc(CN)cc2)C1=O)C(N)=O] | 2-({4-[4-(aminomethyl)phenyl]-1-oxo-2,3-dihydro-1H-isoindol-2-yl}methyl)prop-2-enamide | 322 |
| 265. | 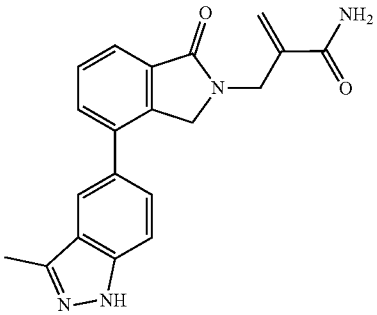 [SMILES: C=C(CN1Cc2c(cccc2-c2ccc3[nH]nc(C)c3c2)C1=O)C(N)=O] | 2-{[4-(3-methyl-1H-indazol-5-yl)-1-oxo-2,3-dihydro-1H-isoindol-2-yl]methyl}prop-2-enamide | 347 |

TABLE 3-continued
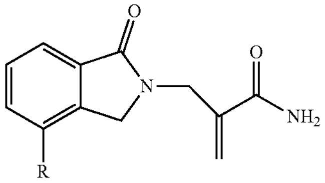
| Cpd. No. | Structure | IUPAC | LC-MS (ES+, m/z) |
|---|---|---|---|
| 266. | 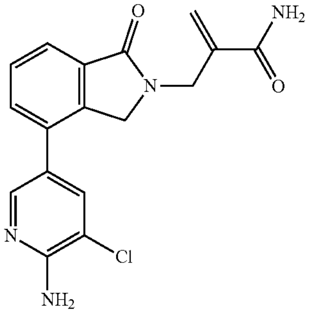 [SMILES: C=C(CN1Cc2c(cccc2-c2cnc(N)c(Cl)c2)C1=O)C(N)=O] | 2-{[4-(6-amino-5-chloropyridin-3-yl)-1-oxo-2,3-dihydro-1H-isoindol-2-yl]methyl}prop-2-enamide | 342.9 |
| 267. | 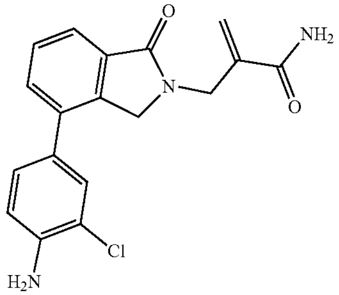 [SMILES: C=C(CN1Cc2c(cccc2-c2ccc(N)c(Cl)c2)C1=O)C(N)=O] | 2-{[4-(4-amino-3-chlorophenyl)-1-oxo-2,3-dihydro-1H-isoindol-2-yl]methyl}prop-2-enamide | 341.9 |
| 268. | 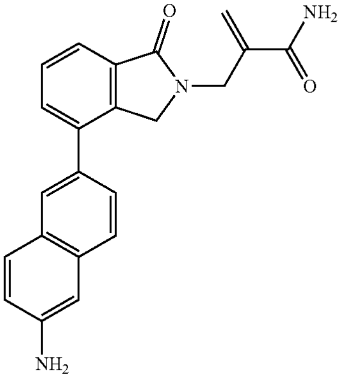 [SMILES: C=C(CN1Cc2c(cccc2-c2ccc3cc(N)ccc3c2)C1=O)C(N)=O] | 2-{[4-(6-aminonaphthalen-2-yl)-1-oxo-2,3-dihydro-1H-isoindol-2-yl]methyl}prop-2-enamide | 358 |
| 269. | 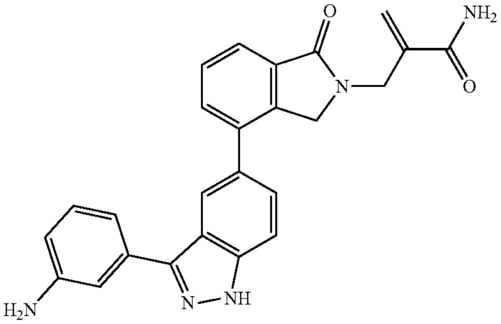 [SMILES: C=C(CN1Cc2c(cccc2-c2ccc3[nH]nc(-c4cccc(N)c4)c3c2)C1=O)C(N)=O] | 2-({4-[3-(3-aminophenyl)-1H-indazol-5-yl]-1-oxo-2,3-dihydro-1H-isoindol-2-yl}methyl)prop-2-enamide | 423.9 |

TABLE 3-continued
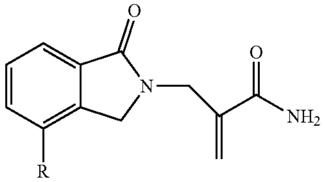
| Cpd. No. | Structure | IUPAC | LC-MS (ES+, m/z) |
|---|---|---|---|
| 270. | 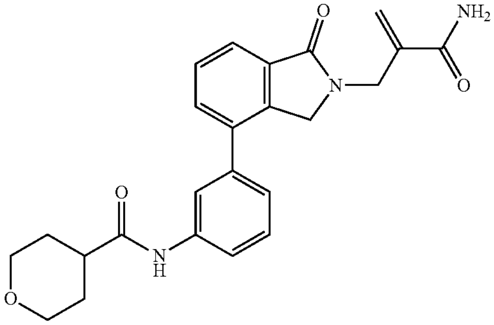 [SMILES: C=C(CN1Cc2c(cccc2-c2cccc(NC(=O)C3CCOCC3)c2)C1=O)C(N)=O] | N-{3-[2-(2-carbamoyl-2-methylideneethyl)-1-oxo-2,3-dihydro-1H-isoindol-4-yl]phenyl}oxane-4-carboxamide | 419.9 |
| 271. | 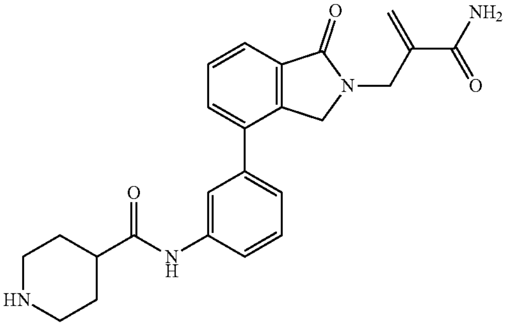 [SMILES: C=C(CN1Cc2c(cccc2-c2cccc(NC(=O)C3CCNCC3)c2)C1=O)C(N)=O] | N-{3-[2-(2-carbamoyl-2-methylideneethyl)-1-oxo-2,3-dihydro-1H-isoindol-4-yl]phenyl}piperidine-4-carboxamide | 419 |
Example 5: Synthesis of Compounds of the Disclosure: Method D
5A. General Scheme for Method D: Route 1
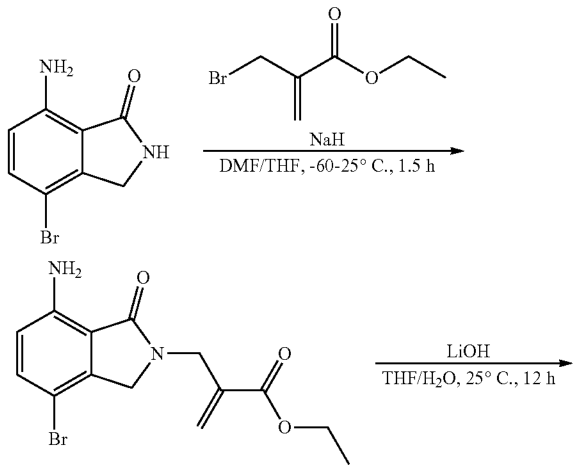
-continued
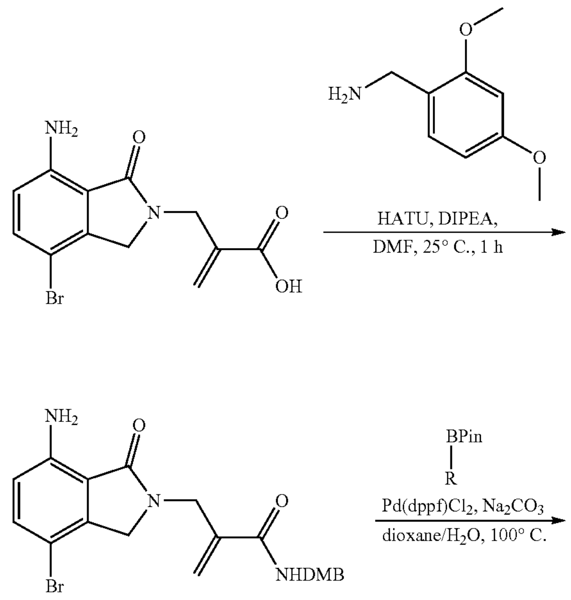

-continued

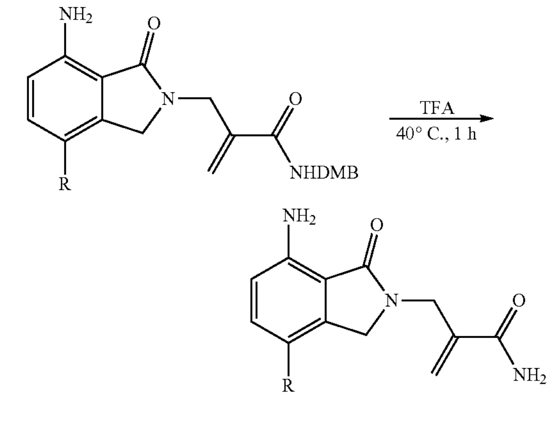

5A.1. Preparation of 2-[[7-amino-4-(1-methylindazol-6-yl)-1-oxo-isoindolin-2-yl]methyl]prop-2-enamide (Compound 272)

a. Preparation of ethyl 2-[(7-amino-4-bromo-1-oxo-isoindolin-2-yl)methyl]prop-2-enoate

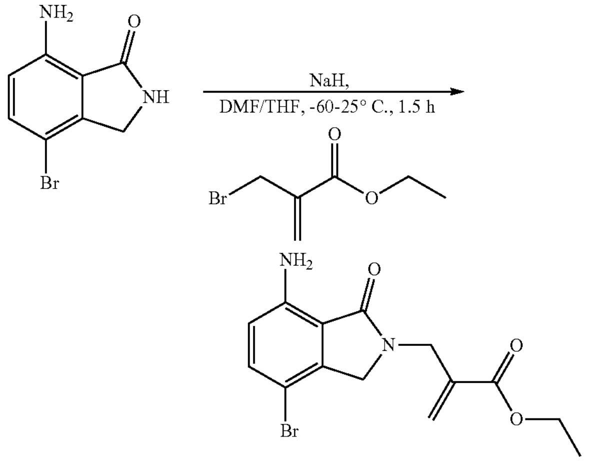

To a mixture of 7-amino-4-bromo-isoindolin-1-one (2 g, 8.81 mmol, 1 eq.) in DMF (80 mL) and THF (80 mL) was added NaH (880.75 mg, 22.02 mmol, 60% purity, 2.5 eq.) in one portion at 25° C. under nitrogen. The mixture was stirred at 25° C. for 0.5 h, and cold to −60° C. and added ethyl 2-(bromomethyl)prop-2-enoate (1.87 g, 9.69 mmol, 1.1 eq.). The mixture was stirred at −60° C. for 1 h. TLC (PE:EtOAc=1:1) showed that the reaction was complete. The residue was poured into ice-water (w/w=1/1) and aq. $NH_4Cl$ (300 mL) and stirred for 5 min. The aqueous phase was extracted with EtOAc (100 mL×3). The combined organic phase was washed with brine (100 mL×2), dried over anhydrous sodium sulfate, filtered, and concentrated in vacuo. The reaction was purified by silica gel chromatography (column height: 50 mm, diameter: 30 mm, 100-200 mesh silica gel, PE:EtOAc=5:1 to 1:1) to afford the title compound (1.44 g, 4.25 mmol, 48.20% yield) as a yellow solid.

b. Preparation of 2-[(7-amino-4-bromo-1-oxo-isoindolin-2-yl)methyl]prop-2-enoic Acid

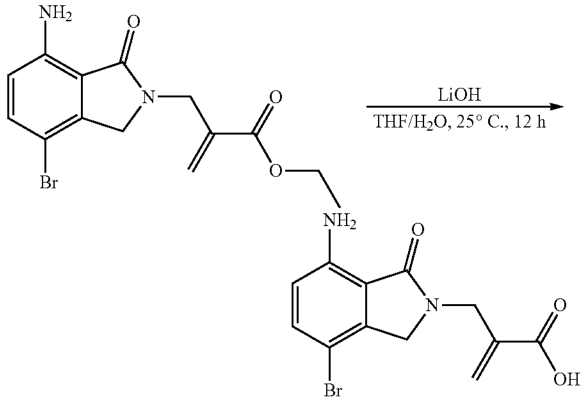

To a mixture of ethyl 2-[(7-amino-4-bromo-1-oxo-isoindolin-2-yl)methyl]prop-2-enoate (1.44 g, 4.25 mmol, 1 eq.) in THF (10 mL) and water (5 mL) was added $LiOH \cdot H_2O$ (409.76 mg, 9.76 mmol, 2.3 eq.) in one portion at 25° C. under nitrogen. The mixture was stirred at 25° C. for 12 h. LCMS showed that the reaction was complete. The reaction mixture was adjusted by 1N HCl to pH=7. The resulting solution was extracted with EtOAc:THF=2:1 (3×50 mL), washed with brine (3×50 mL), dried over anhydrous sodium sulfate, filtered, and concentrated to afford the title compound (1.13 g, 3.63 mmol, 85.55% yield) as a yellow solid.

c. Preparation of 2-[(7-amino-4-bromo-1-oxo-isoindolin-2-yl)methyl]-N-[(2,4-dimethoxyphenyl)methyl]prop-2-enamide

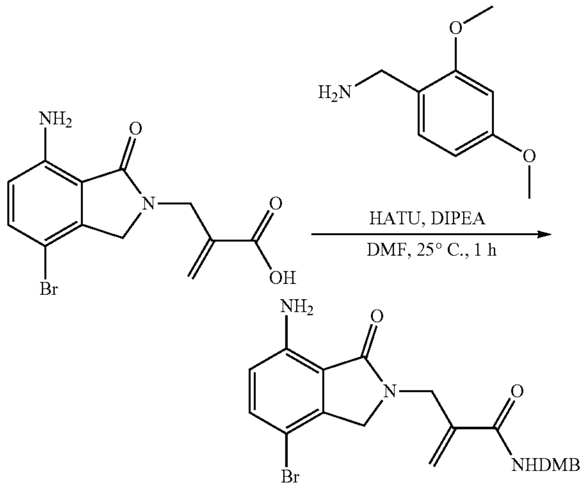

To a mixture of 2-[(7-amino-4-bromo-1-oxo-isoindolin-2-yl)methyl]prop-2-enoic acid (0.9 g, 2.89 mmol, 1 eq.) and (2,4-dimethoxyphenyl)methanamine (967.34 mg, 5.79 mmol, 871.47 μL, 2 eq.) in DMF (20 mL) was added HATU (1.65 g, 4.34 mmol, 1.5 eq.) and TEA (1.46 g, 14.46 mmol, 2.01 mL, 5 eq.) in one portion at 25° C. under nitrogen. The mixture was stirred at 25° C. for 1 h. TLC (PE:EtOAc=1:1) showed that the reaction was complete. The residue was poured into ice-water (w/w=1/1) (30 mL) and stirred for 5 min. The aqueous phase was extracted with EtOAc (20 mL×2). The combined organic phase was washed with brine (20 mL×2), dried over anhydrous sodium sulfate, filtered, and concentrated in vacuo. The reaction was purified by silica gel chromatography (column height: 50 mm, diameter: 30 mm, 100-200 mesh silica gel, PE:EtOAc=5:1 to 1:1) to afford the title compound (1.03 g, 2.24 mmol, 77.35% yield) as a yellow solid.

d. Preparation of 2-[[7-amino-4-(1-methylindazol-6-yl)-1-oxo-isoindolin-2-yl]methyl]-N-[(2,4-dimethoxyphenyl)methyl]prop-2-enamide

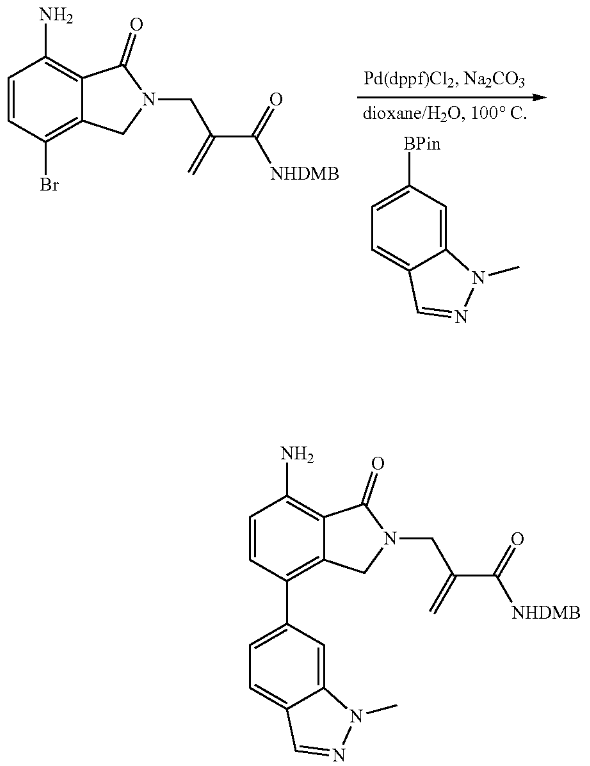

To a mixture of 2-[(7-amino-4-bromo-1-oxo-isoindolin-2-yl)methyl]-N-[(2,4-dimethoxyphenyl)methyl]prop-2-enamide (100 mg, 217.24 μmol, 1 eq.) and 1-methyl-6-(4,4,5,5-tetramethyl-1,3,2-dioxaborolan-2-yl)indazole (67.29 mg, 260.69 μmol, 1.2 eq.) in dioxane (2 mL) and water (0.5 mL) were added Pd(dppf)$Cl_2$ (7.95 mg, 10.86 μmol, 0.05~0.1 eq.) and $Cs_2CO_3$ (212.34 mg, 651.72 μmol, 3 eq.) in one portion under nitrogen. The mixture was stirred at 100° C. for 10 min. LCMS showed that the reaction was complete. The residue was poured into aq·EDTA (20~30 mL) and stirred for 60 min. The aqueous phase was extracted with EtOAc (10 mL×2~3). The combined organic phase was washed with brine (10 mL×2), dried over anhydrous sodium sulfate, filtered, and concentrated in vacuo. The reaction was purified by prep-TLC (DCM:MeOH=20:1 to 10:1) to afford the title compound (0.05 g, 97.74 μmol, 44.99% yield) as a yellow solid.

e. Preparation of 2-[[7-amino-4-(1-methylindazol-6-yl)-1-oxo-isoindolin-2-yl]methyl]prop-2-enamide (Compound 272)

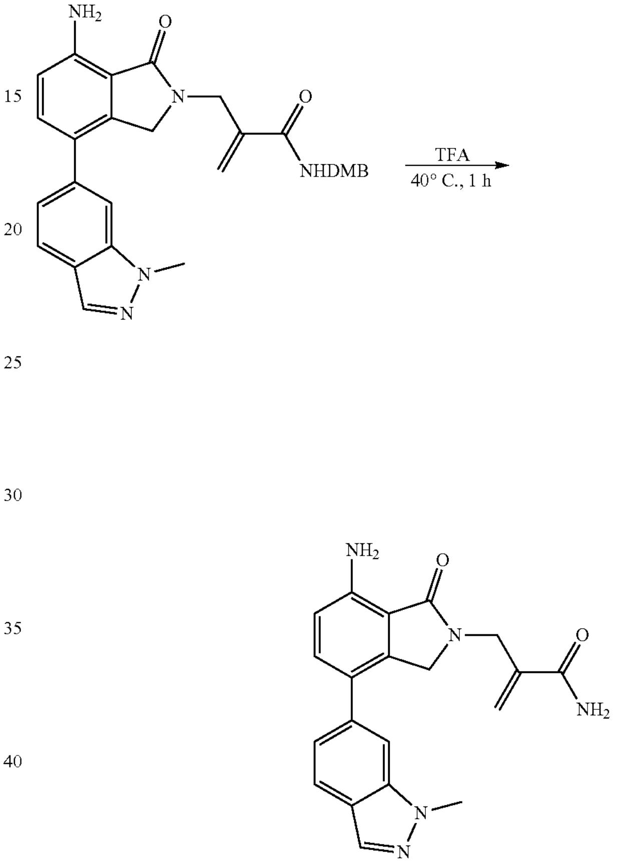

A mixture of 2-[[7-amino-4-(1-methylindazol-6-yl)-1-oxo-isoindolin-2-yl]methyl]-N-[(2,4-dimethoxyphenyl)methyl]prop-2-enamide (0.04 g, 78.19 μmol, 1 eq.) in trifluoroacetic acid (6.16 g, 54.02 mmol, 4 mL, 690.93 eq.) was stirred at 40° C. for 1 h. LCMS showed that the reaction was complete. The residue was poured into ice-water (w/w=1/1) (20 mL) and stirred for 5 min. TLC show the reaction was complete. The mixture was adjusted to pH=7~8 by adding 2N aq $Na_2CO_3$ or $NaHCO_3$.

The aqueous phase was extracted with EtOAc (10 mL×2). The combined organic phase was washed with brine (10 mL×2), dried over anhydrous sodium sulfate, filtered, and concentrated in vacuo and purified by prep-HPLC or by prep-TLC to afford the title compound (20 mg, 55.06 μmol, 70.42% yield, 99.5% purity) as a yellow solid. LC-MS: $[M+H]^+$ 362.1.

General Procedure for PMB Deprotection 5A.2. Preparation of 2-[[7-amino-4-(3-cyano-1H-indazol-5-yl)-1-oxo-isoindolin-2-yl]methyl]prop-2-enamide (Compound 290)

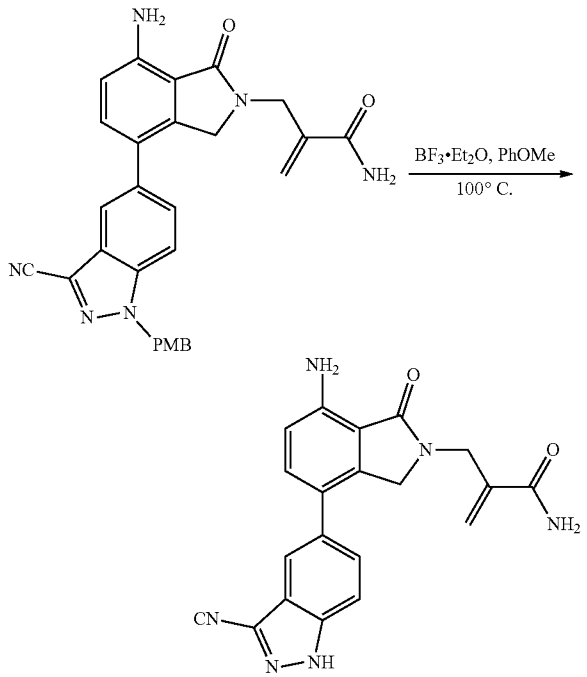

To a mixture of 2-[[7-amino-4-[3-cyano-1-[(4-methoxyphenyl)methyl]indazol-5-yl]-1-oxo-isoindolin-2-yl]methyl]prop-2-enamide (0.04 g, 81.21 μmol, 1 eq.) in PhOMe (1 mL) was added $BF_3 \cdot Et_2O$ (2 mL) in one portion at 100° C. under nitrogen. The mixture was stirred at 100° C. for 30 min LCMS showed that the reaction was complete. The residue was poured into 2 M $Na_2CO_3$ (50 mL) and stirred for 5 min. The aqueous phase was extracted with EtOAc (3×15 mL). The combined organic phase was washed with brine (2×15 mL), dried over anhydrous sodium sulfate, filtered, and concentrated in vacuo. The reaction was purified by prep-TLC (DCM:MeOH=20:1) to afford the title compound (4.4 mg, 11.34 μmol, 13.97% yield, 96% purity) as a yellow solid. LC-MS: $[M+H]^+$ 373.1.

5B. General Scheme for Method D: Route 2

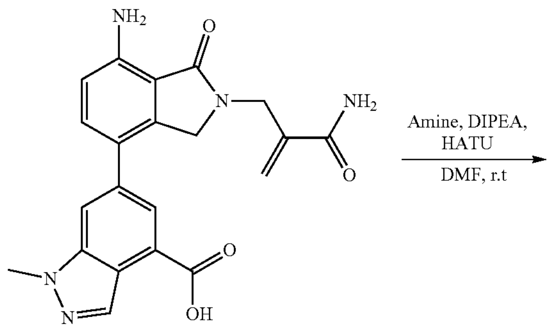

-continued

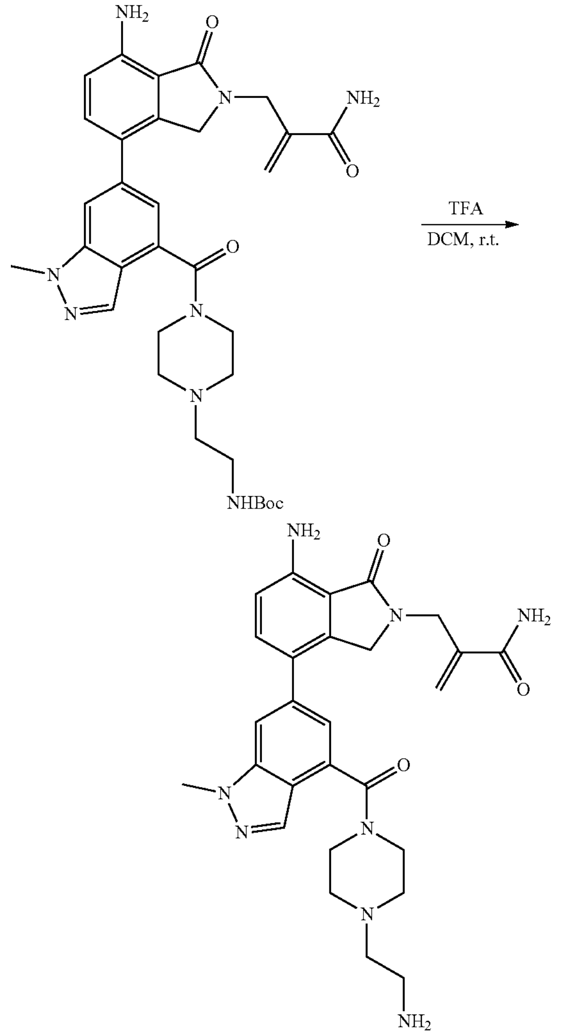

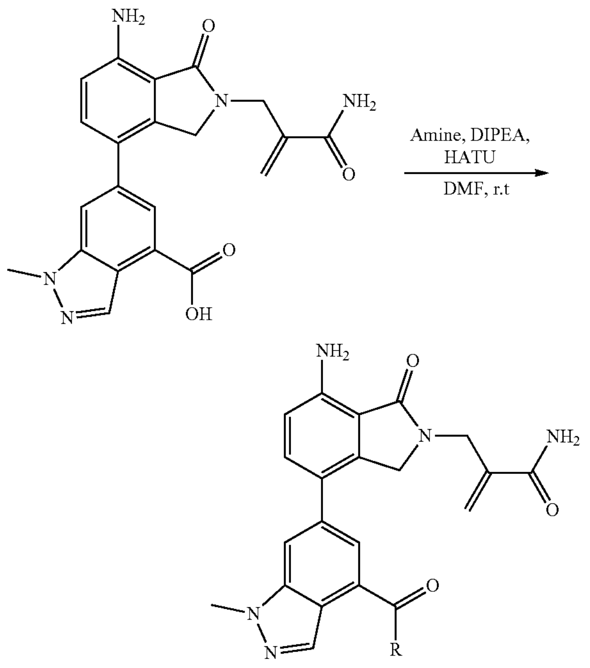

-continued

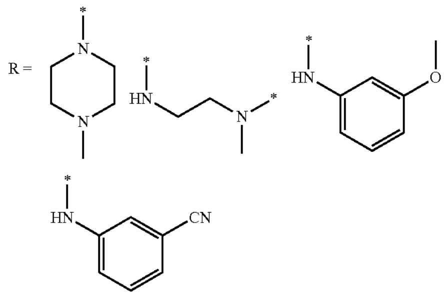

To a mixture of 6-[7-amino-2-(2-carbamoylallyl)-1-oxo-isoindolin-4-yl]-1-methyl-indazole-4-carboxylic acid (0.04 g, 98.67 μmol, 1 eq.) and 1-methylpiperazine (14.82 mg, 148 μmol, 16.42 μL, 1.5 eq.) in DMF (3 mL) were added HATU (56.27 mg, 148 μmol, 1.5 eq.) and TEA (49.92 mg, 493.33 μmol, 68.67 μL, 5 eq.) in one portion at 25° C. under nitrogen. The mixture was stirred at 25° C. for 1 h. LCMS showed that the reaction was complete. the reaction was poured to sat. aqueous $NH_4Cl$ (30 mL) then extracted with EtOAc (3×10 mL) the combined organic layer was concentrated in vacuo. The product was purified by prep-HPLC to afford the title compound (0.0127 g, 25.63 μmol, 25.98% yield, 98.4% purity) as a white solid. LCMS and $^1H$ NMR showed the product was desired product.

5B.1. General Procedure for Route 2 a. Preparation of tert-butyl N-[2-[4-[6-[7-amino-2-(2-carbamoylallyl)-1-oxo-isoindolin-4-yl]-1-methyl-indazole-4-carbonyl]piperazin-1-yl]ethyl]carbamate -continued

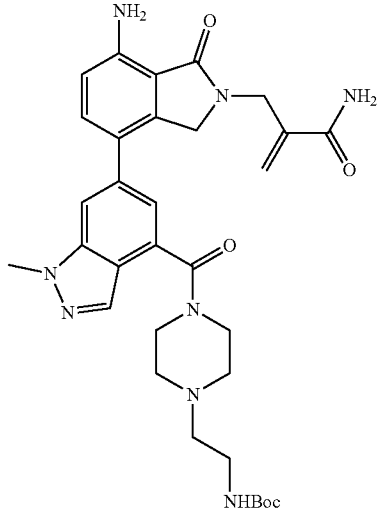

To a mixture of 6-[7-amino-2-(2-carbamoylallyl)-1-oxo-isoindolin-4-yl]-1-methyl-indazole-4-carboxylic acid (0.1 g, 246.67 μmol, 1 eq.) and tert-butyl N-(2-piperazin-1-ylethyl) carbamate (113.13 mg, 493.33 μmol, 2 eq.) in DMF (15 mL) were added HATU (140.68 mg, 370 μmol, 1.5 eq.) and TEA (124.80 mg, 1.23 mmol, 171.67 μL, 5 eq.) in one portion at 25° C. under nitrogen. The mixture was stirred at 25° C. for 1 h. LCMS showed that the reaction was complete. the reaction was poured to water, then extracted with EtOAc (3×10 mL). The combined organic layer was concentrated in vacuo to afford the title compound (0.15 g, crude) as a yellow solid, which was used directly without further purification.

b. General Procedure for 2-[[7-amino-4-[4-[4-(2-aminoethyl)piperazine-1-carbonyl]-1-methyl-indazol-6-yl]-1-oxo-isoindolin-2-yl]methyl]prop-2-enamide (Compound 313)

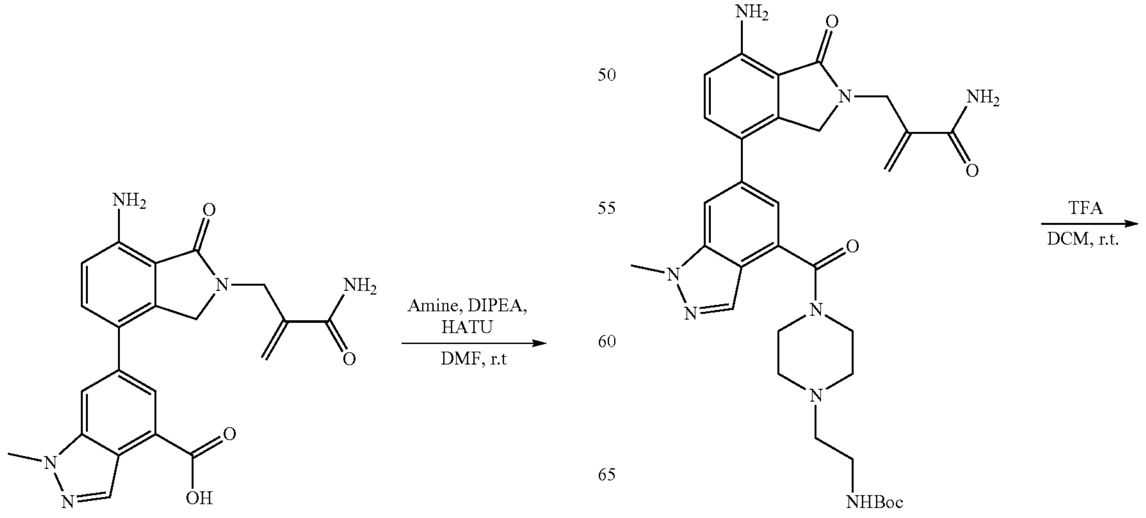

-continued

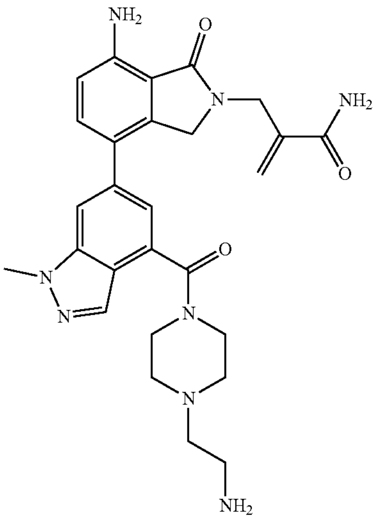

To a mixture of tert-butyl N-[2-[4-[6-[7-amino-2-(2-carbamoylallyl)-1-oxo-isoindolin-4-yl]-1-methyl-indazole-4-carbonyl]piperazin-1-yl]ethyl]carbamate (0.1 g, 162.15 μmol, 1 eq.) in DCM (4 mL) was added trifluoroacetic acid (1.54 g, 13.51 mmol, 1 mL, 83.29 eq.) in one portion at 25° C. under nitrogen. The mixture was stirred at 25° C. for 1 h. LCMS showed that the reaction was complete. The reaction was poured into a sat. $NaHCO_3$ solution (30 mL) then extracted with EtOAc (3×10 mL). The combined organic layer was concentrated in vacuo. The crude product was purified by prep-HPLC to afford the title compound (0.01 g, 19.36 μmol, 11.94% yield, 100% purity) as a white solid. LC-MS: $[M+H]^+$ 517.2.

5C. General Scheme for Method D: Route 3

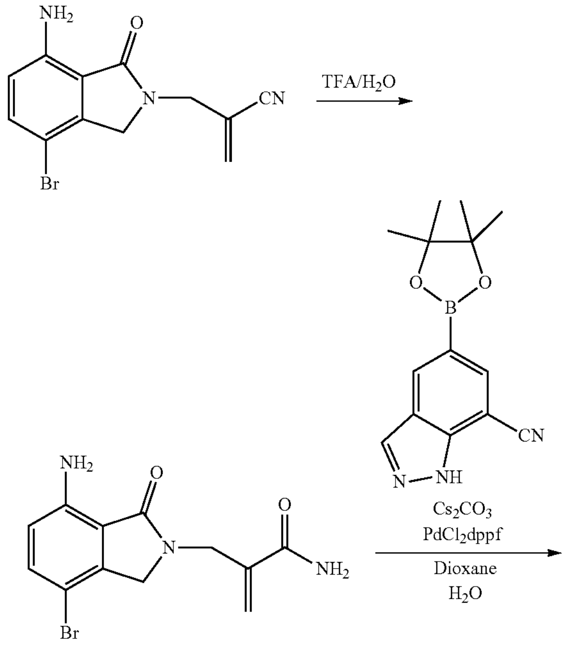

-continued

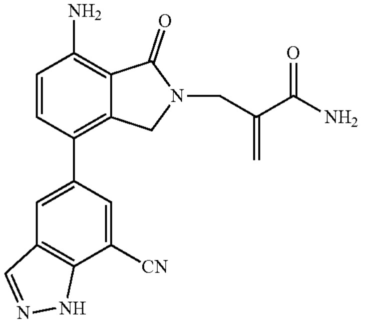

5C.1. Preparation of 2-[[7-amino-4-(7-cyano-1H-indazol-1-yl)-1-oxo-isoindolin-2-yl]methyl]prop-2-enamide (Compound 316)

a. Preparation of 2-[(7-amino-4-bromo-1-oxo-isoindolin-2-yl)methyl]prop-2-enamide

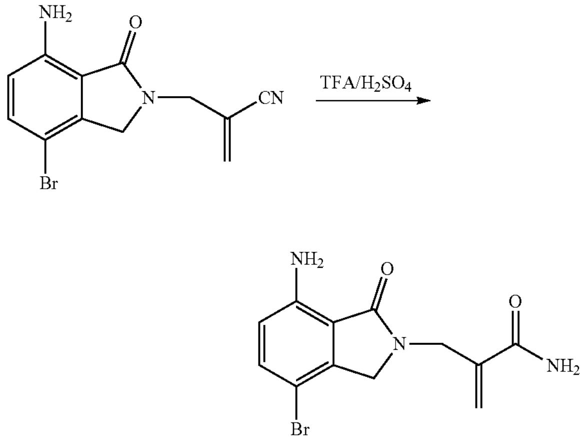

To a solution of 2-[(7-amino-4-bromo-1-oxo-isoindolin-2-yl)methyl]prop-2-enenitrile (200 mg, 685 μmol) in trifluoroacetic acid (3 mL) was added $H_2SO_4$ (0.6 mL). The mixture was stirred at r.t. for 3 h. The reaction mixture was concentrated in vacuo and sat. $NaHCO_3$ was added. The solid was filtered, washed with water, and dried in vacuo to the title compound (196 mg, Yield 92%).

b. Preparation of 5-(4,4,5,5-tetramethyl-1,3,2-dioxaborolan-2-yl)-1H-indazole-7-carbonitrile

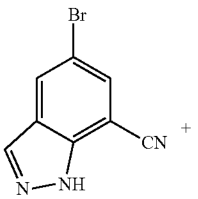

-continued

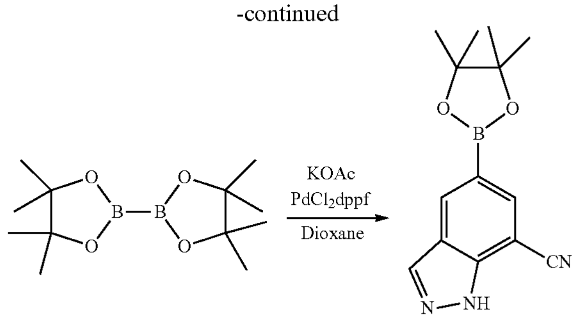

To a solution of 5-bromo-1H-indazole-7-carbonitrile (100 mg, 455 μmol) in dioxane (3 mL) were added 4,4,5,5-tetramethyl-2-(4,4,5,5-tetramethyl-1,3,2-dioxaborolan-2-yl)-1,3,2-dioxaborolane (346 mg, 1.365 mmol), KOAc (223 mg, 2.275 mmol) and $PdCl_2dppf$ (40 mg, 49 μmol). The reaction was heated to 100° C. for 1 h. The reaction mixture was passed through a celite pad, and the solvent was removed in vacuo. The residue was purified by chromatography on silica gel eluting with 0-40% EtOAc/hexane to afford the title compound (100 mg, Yield 82%).

c. Preparation of 2-[[7-anno-4-(7-cyano-1H-indazol-5-yl)-1-oxo-isoindolin-2-yl]methyl]prop-2-enamide (Compound 316)

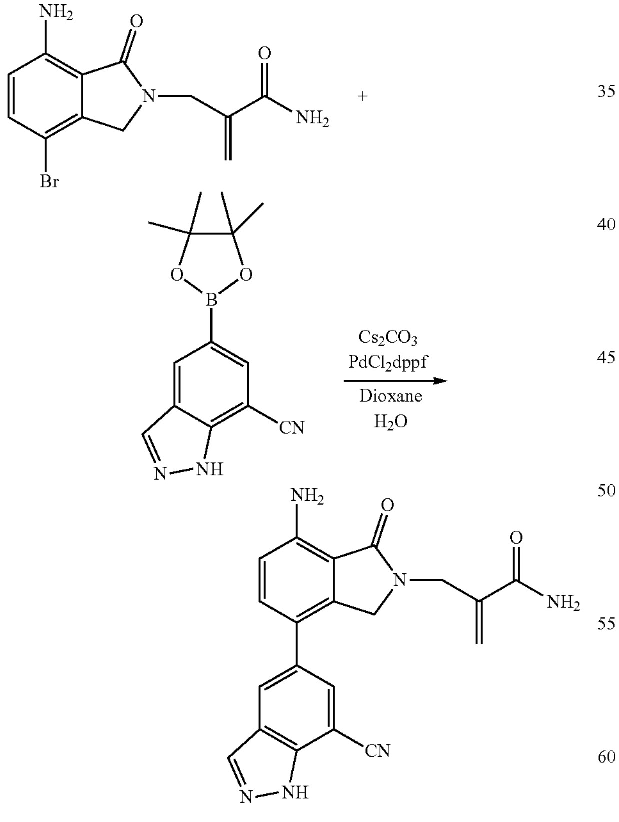

To a solution of 2-[(7-amino-4-bromo-1-oxo-isoindolin-2-yl)methyl]prop-2-enamide (50 mg, 161 μmol) in dioxane (1.5 mL) and water (0.3 mL) were added 5-(4,4,5,5-tetramethyl-1,3,2-dioxaborolan-2-yl)-1H-indazole-7-carbonitrile (106 mg, 394 μmol), $Cs_2CO_3$ (157 mg, 0.484 mmol) and $PdCl_2dppf$ (18 mg, 22 μmol). The reaction was heated to 120° C. for 30 min. The reaction mixture was passed through a celite pad, and 2 mL of 0.5 M EDTA was added. The resulting solution was stirred at r.t. for 30 min. The solution was washed with brine, and the organic phase was dried over anhydrous sodium sulfate, filtered, and concentrated in vacuo. The residue was purified by reverse phase HPLC using a gradient of water 0.1% FA/acetonitrile 0.1% FA to afford the title compound (2.8 mg, Yield 5%). LC-MS: $[M+H]^+$ 373.

5.C.2. Procedure for Preparation of 2-[[7-(methylamino)-4-(1-methylindazol-6-yl)-1-oxo-isoindolin-2-yl]methyl]prop-2-enamide (Compound 360)

a. Preparation of 2-[[7-amino-4-(1-methylindazol-6-yl)-1-oxo-isoindolin-2-yl]methyl]prop-2-enenitrile

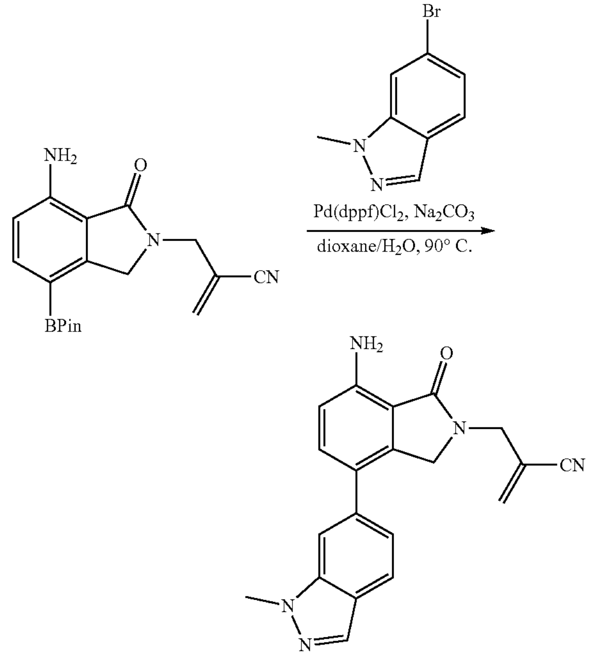

To a mixture of 2-[[7-amino-1-oxo-4-(4,4,5,5-tetramethyl-1,3,2-dioxaborolan-2-yl)isoindolin-2-yl]methyl]prop-2-enenitrile (674.99 mg, 1.99 mmol, 1.05 eq.) and 6-bromo-1-methyl-indazole (0.4 g, 1.90 mmol, 1 eq.) in dioxane (8 mL) and water (2 mL) were added $Na_2CO_3$ (602.61 mg, 5.69 mmol, 3 eq.) and $Pd(dppf)Cl_2$ (277.35 mg, 379.04 μmol, 0.2 eq.) The reaction mixture was degassed and purged with nitrogen 3 times, and the mixture was stirred at 120° C. for 0.5 h under nitrogen atmosphere. TLC showed that the reaction was complete. The reaction mixture was added 30 mL aq·EDTA and stirred for 1 h, extracted with EtOAc (3×20 mL). The combined organic layers were washed with brine (3×20 mL), dried over anhydrous sodium sulfate, filtered, and concentrated in vacuo to give a residue. The residue was purified by prep-TLC (silica gel; DCM: MeOH=30:1) to afford the title compound (280 mg, 774.65 μmol, 40.87% yield, 95% purity) was obtained as a light yellow solid.

b. Procedure for Preparation of 2-[[7-(methylamino)-4-(1-methylindazol-6-yl)-1-oxo-isoindolin-2-yl]methyl]prop-2-enamide (Compound 360)

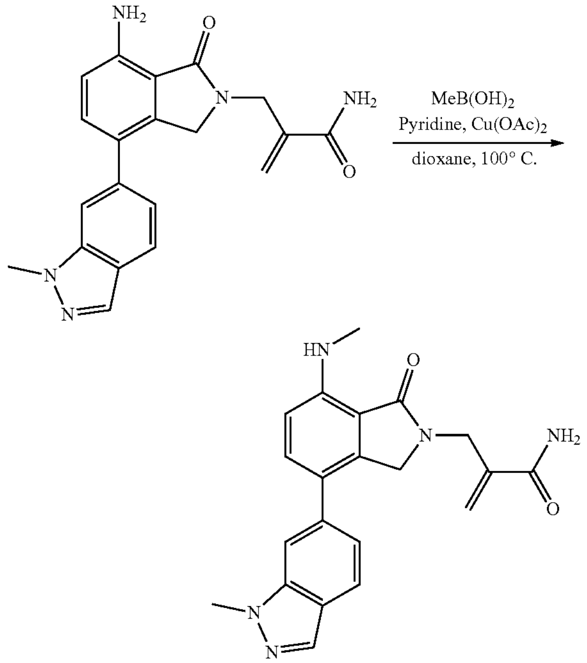

To a solution of 2-[[7-amino-4-(1-methylindazol-6-yl)-1-oxo-isoindolin-2-yl]methyl]prop-2-enamide (50 mg, 138.35 μmol, 1 eq.) in dioxane (3 mL) was added PYRIDINE (32.83 mg, 415.06 μmol, 33.50 μL, 3 eq.) and diacetoxycopper (75.39 mg, 415.06 μmol, 3 eq.) after 30 min, added methylboronic acid (24.85 mg, 415.06 μmol, 3 eq.) in dioxane (0.2 mL) The mixture was stirred at 100° C. for 4.5 h. TLC showed that the reaction was complete The reaction mixture was added to 30 mL sat. EDTA and stirred for 1 h. The resulting solution was extracted with EtOAc (3×20 mL). The combined organic layers were washed with brine (3×20 mL), dried over anhydrous sodium sulfate, filtered, and concentrated in vacuo to give a residue. The residue was purified by prep-TLC (silica gel; DCM:MeOH=10:1), then the residue was purified by prep-HPLC to afford the title compound (6.0 mg, 15.98 μmol, 11.55% yield, 100% purity) as a white solid. LC-MS: $[M+H]^+$ 376.1.

5D. General Scheme for Method D: Route 4

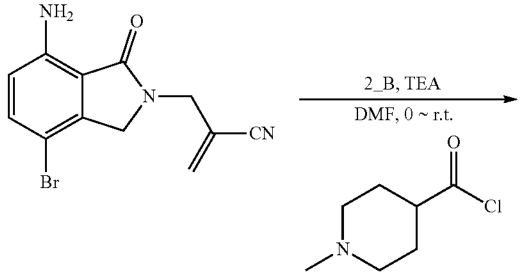

-continued

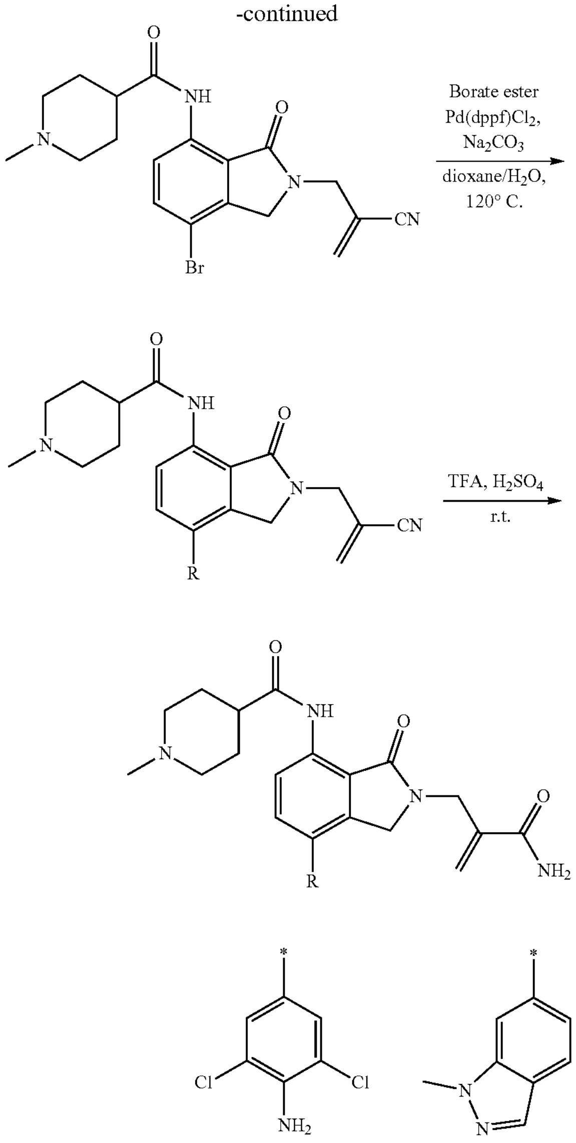

5D.1. Preparation of N-[2-(2-carbamoylallyl)-7-(1-methylindazol-6-yl)-3-oxo-isoindolin-4-yl]-1-methyl-piperidine-4-carboxamide (Compound 361)

a. Preparation of N-[7-bromo-2-(2-cyanoallyl)-3-oxo-isoindolin-4-yl]-1-methyl-piperidine-4-carboxamide

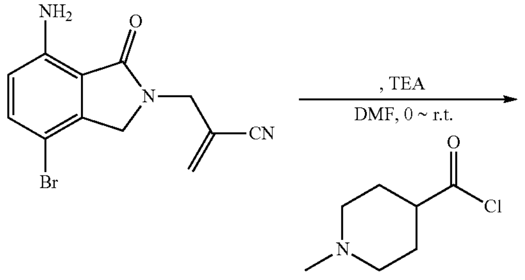

-continued

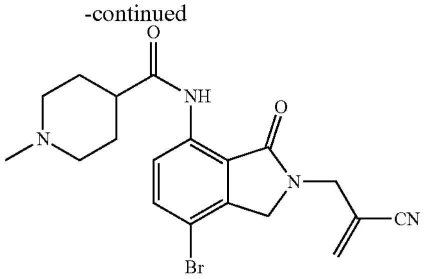

To a solution of 2-[(7-amino-4-bromo-1-oxo-isoindolin-2-yl)methyl]prop-2-enenitrile (0.3 g, 872.90 μmol, 1 eq.) in DMF (10 mL) was added TEA (441.64 mg, 4.36 mmol, 607.49 μL, 5 eq.) then added 1-methylpiperidine-4-carbonyl chloride (282.17 mg, 1.75 mmol, 2 eq.) at 0° C. The mixture was stirred at 0-20° C. for 12 h. TLC showed 50% of the starting material remained. The reaction mixture was quenched with additional ice water, and the resulting solution was extracted with EtOAc (3×50 mL). The combined organic layers were washed with water (2×50 mL), dried over anhydrous sodium sulfate, filtered, and concentrated in vacuo to give a residue. The residue was purified by prep-TLC (silica gel; DCM:MeOH=30:1) to afford the title compound (60 mg, 143.78 μmol, 16.47% yield) as a light yellow gum.

b. Preparation of N-[7-(4-amino-3,5-dichloro-phenyl)-2-(2-cyanoallyl)-3-oxo-isoindolin-4-yl]-1-methyl-piperidine-4-carboxamide

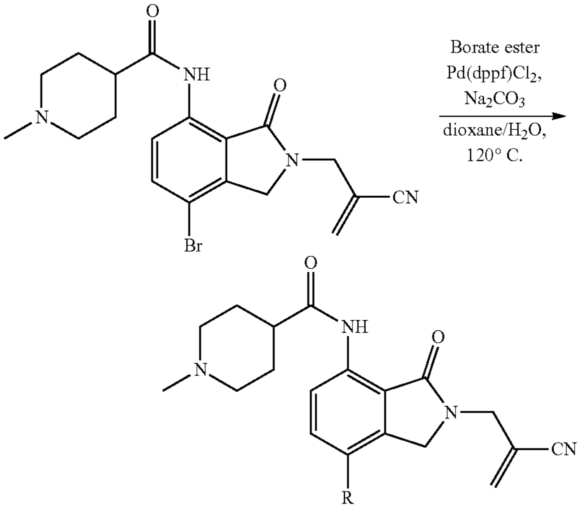

A mixture of N-[7-bromo-2-(2-cyanoallyl)-3-oxo-isoindolin-4-yl]-1-methyl-piperidine-4-carboxamide (100 mg, 239.64 μmol, 1 eq.) and 2,6-dichloro-4-(4,4,5,5-tetramethyl-1,3,2-dioxaborolan-2-yl)aniline (103.51 mg, 359.45 μmol, 1.5 eq.) in dioxane (4 mL) and water (1 mL) were added $Na_2CO_3$ (76.20 mg, 718.91 μmol, 3 eq.), Pd(dppf)$Cl_2$ (17.53 mg, 23.96 μmol, 0.1 eq.). The reaction mixture was degassed and purged with nitrogen 3 times, and the mixture was stirred at 120° C. for 20 min under nitrogen atmosphere. LCMS showed that the reaction was complete. To the reaction mixture was added 30 mL of sat. EDTA, and the resulting mixture was stirred for 1 h and extracted with EtOAc (20 mL×3). The combined organic layers were washed with brine (3×20 mL), dried over anhydrous sodium sulfate, filtered, and concentrated in vacuo to give a residue. The residue was purified by prep-TLC (silica gel; DCM:MeOH=20:1) to afford the title compound (50 mg, 100.32 μmol, 41.86% yield) was obtained as a light yellow gum.

c. Preparation of N-[2-(2-carbamoylallyl)-7-(1-methylindazol-6-yl)-3-oxo-isoindolin-4-yl]-1-methyl-piperidine-4-carboxamide (Compound 361)

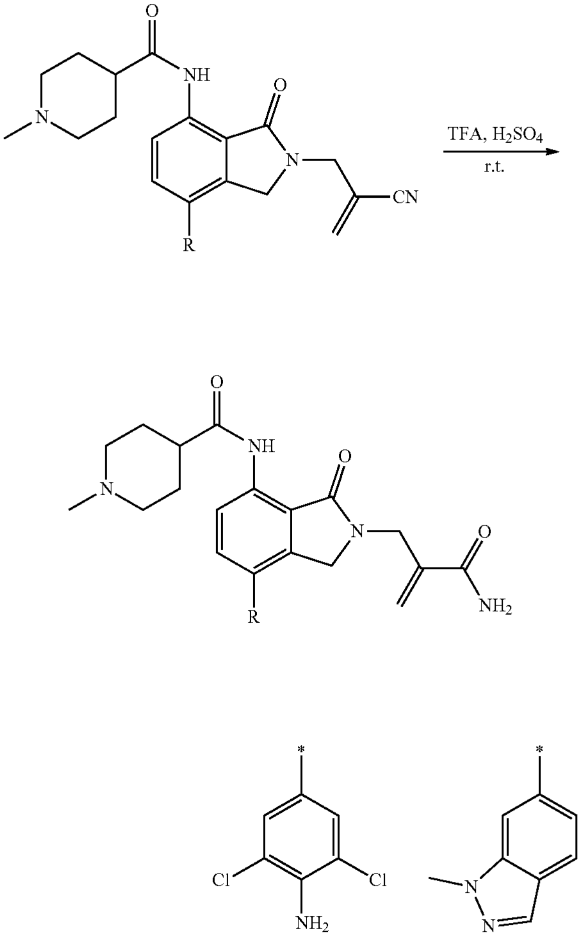

The solution of N-[2-(2-cyanoallyl)-7-(1-methylindazol-6-yl)-3-oxo-isoindolin-4-yl]-1-methyl-piperidine-4-carboxamide (30 mg, 64.03 μmol, 1 eq.) in trifluoroacetic acid (2 mL) and $H_2SO_4$ (2 mL) was stirred at 50° C. for 1 h. LCMS showed that the reaction was complete. The reaction mixture was quenched with addition ice water 10 mL at 0° C., and added sat. $Na_2CO_3$ to adjust pH=8, and extracted with DCM (3×50 mL). The combined organic layers were washed with brine (100 mL), dried over anhydrous sodium sulfate, filtered, and concentrated in vacuo to give a residue. The residue was purified by prep-HPLC to afford the title compound (5.5 mg, 11.15 μmol, 17.41% yield, 98.6% purity) as a white solid. LC-MS: $[M+H]^+$ 487.2.

5E. General Scheme for Method D: Route 5

5.E.1. Preparation of 2-[[4-(1-methylindazol-6-yl)-1-oxo-7-(4-piperidylamino)isoindolin-2-yl]methyl]prop-2-enamide (Compound 363)

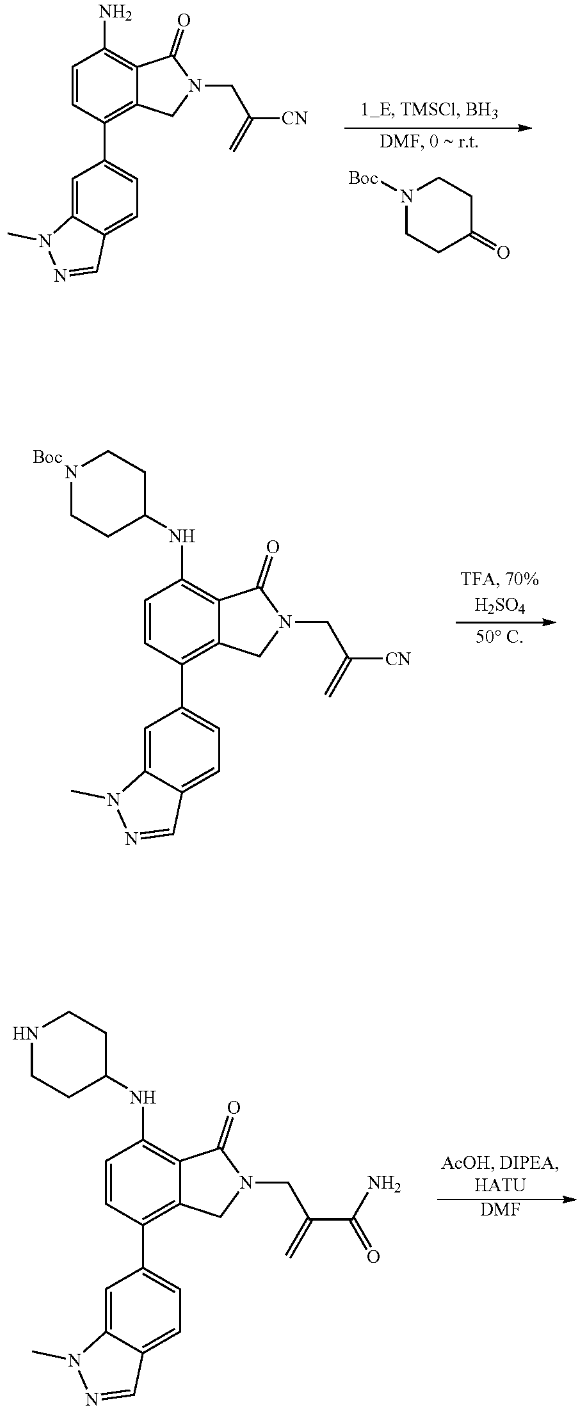

-continued

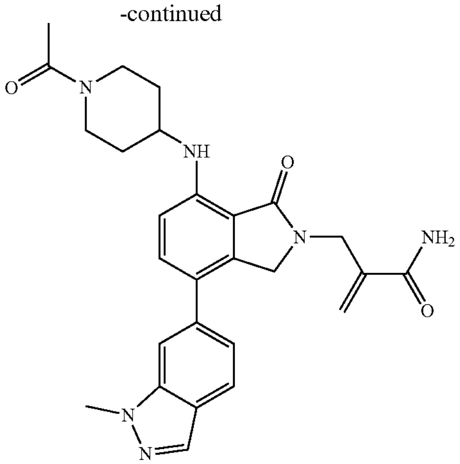

a. Preparation of tert-butyl 4-[[2-(2-cyanoallyl)-7-(1-methylindazol-6-yl)-3-oxo-isoindolin-4-yl]amino]piperidine-1-carboxylate

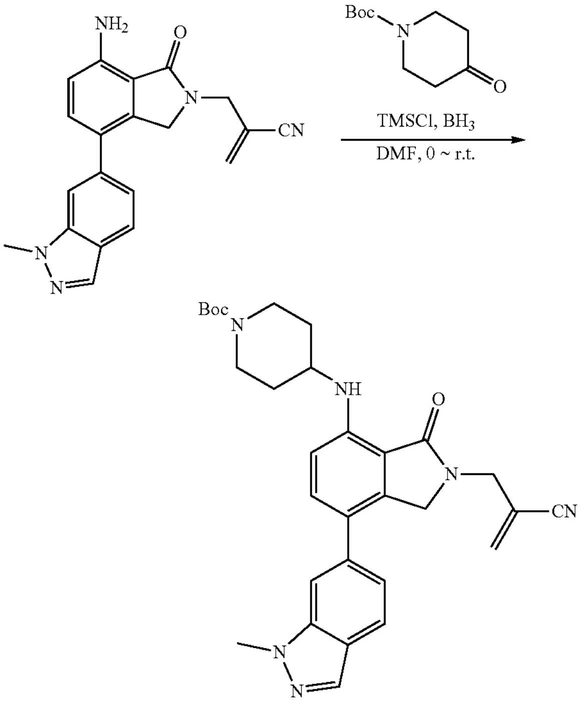

To a solution of 2-[[7-amino-4-(1-methylindazol-6-yl)-1-oxo-isoindolin-2-yl]methyl]prop-2 enenitrile (240 mg, 663.99 μmol, 1 eq.; 95% purity) and tert-butyl 4-oxopiperidine-1-carboxylate (1.06 g, 5.31 mmol, 67.74 μL, 8 eq.) in DMF (10 mL) was added TMSCl (577.08 mg, 5.31 mmol, 674.16 μL, 8 eq.) at 0° C. After stirring the mixture for 1 h, $BH_3$-$Me_2S$ (10 M, 1.5 mL, 22.59 eq.) was added. The mixture was stirred at 0° C. for 1 hr. TLC showed that the reaction was complete. The reaction mixture was quenched with ice water (50 mL) at 0° C., and added saturated $NaHCO_3$ solution was added to adjust the solution to pH=7~8. The mixture was extracted with EtOAc (3×50 mL), and the combined organic layers were washed with brine (100 mL), dried over anhydrous sodium sulfate, filtered, and concentrated in vacuo to give a residue. The residue was purified by prep-TLC (silica gel; DCM:MeOH=30:1) to afford the title compound (200 mg, 379.77 μmol, 57.20% yield) as a light yellow solid.

b. Preparation of 2-[[4-(1-methylindazol-6-yl)-1-oxo-7-(4-piperidylamino)isoindolin-2-yl]methyl]prop-2-enamide (Compound 363)

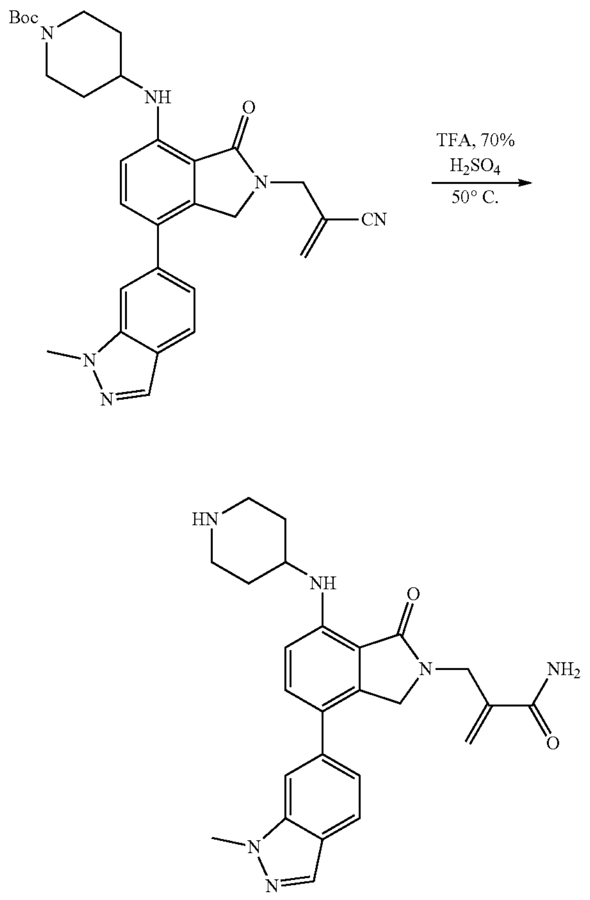

A solution of tert-butyl 4-[[2-(2-cyanoallyl)-7-(1-methylindazol-6-yl)-3-oxo-isoindolin-4-yl]amino]piperidine-1-carboxylate (160 mg, 303.82 μmol, 1 eq.) in trifluoroacetic acid (3 mL) and $H_2SO_4$ (3 mL) was stirred at 50° C. for 1 h. LCMS showed that the reaction was complete. The reaction mixture was quenched with ice water (10 mL) at 0° C., and added sat. $Na_2CO_3$ to was added to adjust the mixture to pH=9. The mixture was extracted with DCM (3×15 mL), and the combined organic layers were washed with brine (10 mL), dried over anhydrous sodium sulfate, filtered, and concentrated in vacuo to give a residue. The residue was purified by prep-TLC (silica gel; DCM:MeOH: trifluoroacetic acid=10:1:0.1) to get 40 mg of a crude product. The 30 mg of product was purified by prep-HPLC to afford the title compound (5 mg, 10.54 μmol, 3.47% yield, 93.7% purity) as a white solid. LC-MS: $[M+H]^+$ 445.1.

5.E.2. Preparation of 2-[[7-[(1-acetyl-4-piperidyl)amino]-4-(1-methylindazol-6-yl)-1-oxo-isoindolin-2-yl]methyl]prop-2-enamide (Compound 364)

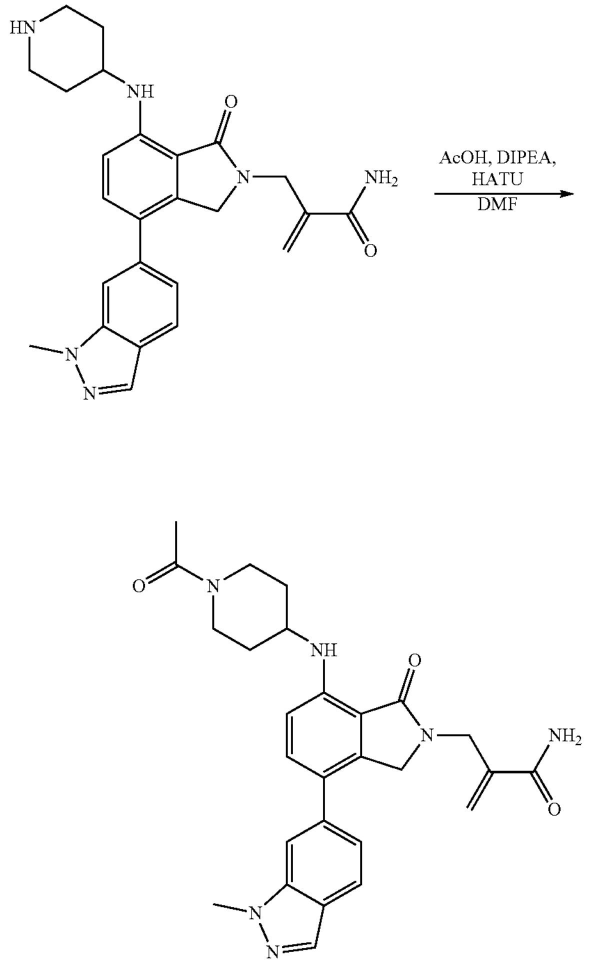

To a mixture of 2-[[4-(1-methylindazol-6-yl)-1-oxo-7-(4-piperidylamino)isoindolin-2-yl]methyl]prop-2-enamide (0.1 g, 179.97 μmol, 1 eq.) and AcOH (54.04 mg, 899.83 μmol, 51.46 μL, 5 eq.) in DMF (2 mL) were added DIPEA (186.08 mg, 1.44 mmol, 250.78 μL, 8 eq.) and HATU (102.64 mg, 269.95 μmol, 1.5 eq.). The reaction mixture was degassed and purged with nitrogen 3 times, and the mixture was stirred at 20° C. for 1 h under nitrogen atmosphere. LCMS showed that the reaction was complete. The reaction mixture was extracted with EtOAc (3×50 mL). The combined organic layers were washed with water (3×50 mL) and brine (50 mL×3), dried over anhydrous sodium sulfate, filtered, and concentrated in vacuo to give a residue. The residue was purified by prep-HPLC to afford the title compound (5.3 mg, 10.89 μmol, 6.05% yield, 100% purity) as a white solid. LC-MS: $[M+H]^+$ 487.1.

5F. General Scheme for Method D: Route 6

5.F.1. Preparation of 2-[[4-(4-amino-3,5-dichloro-phenyl)-7-(benzylamino)-1-oxo-isoindolin-2-yl]methyl]prop-2-enamide (Compound 365)

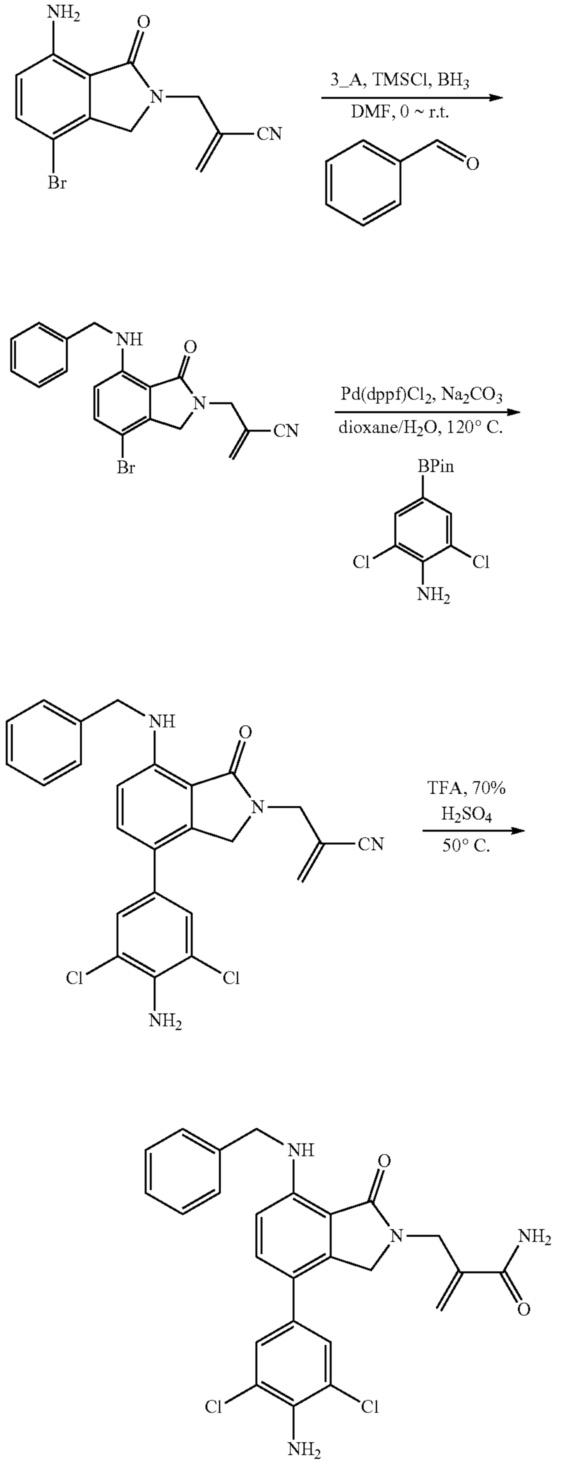

a. Preparation of 2-[[7-(benzylamino)-4-bromo-1-oxo-isoindolin-2-yl]methyl]prop-2-enenitrile

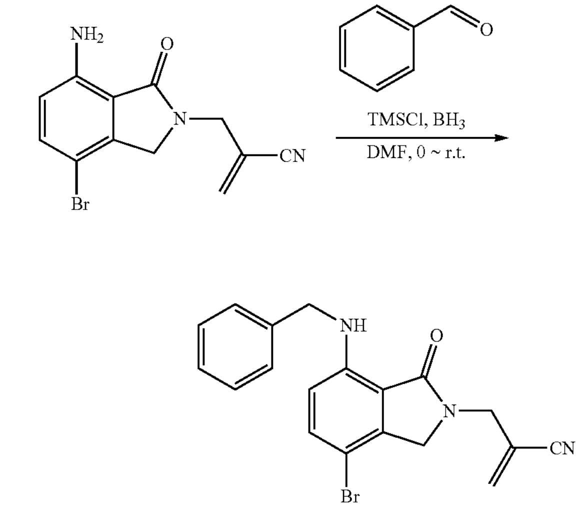

To a solution of 2-[(7-amino-4-bromo-1-oxo-isoindolin-2-yl)methyl]prop-2-enenitrile (200 mg, 581.93 μmol, 1 eq.) (85% purity) in DMF (10 mL) were added benzaldehyde (617.55 mg, 5.82 mmol, 588.15 μL, 10 eq.) and TMSCl (632.22 mg, 5.82 mmol, 738.58 μL, 10 eq.) at 0° C. After 1 h, $BH_3$-$Me_2S$ (10 M, 1.27 mL, 21.91 eq.) was added, and the resulting mixture was stirred at 0~10° C. for 2 h. TLC showed that the reaction was complete. The reaction mixture was quenched with ice water (10 mL) at 0° C., and a saturated $NaHCO_3$ solution was added to adjust the solution to pH=7~8. The mixture was extracted with EtOAc (50 mL×3), and the combined organic layers were washed with brine (50 mL), dried over anhydrous sodium sulfate, filtered, and concentrated in vacuo to give a residue. The residue was purified by prep-TLC (silica gel; DCM:MeOH=30:1) to afford the title compound (160 mg, 376.71 μmol, 64.74% yield, 90% purity) as a light yellow solid.

b. Preparation of 2-[[4-(4-amino-3,5-dichloro-phenyl)-7-(benzylamino)-1-oxo-isoindolin-2-yl]methyl]prop-2-enenitrile

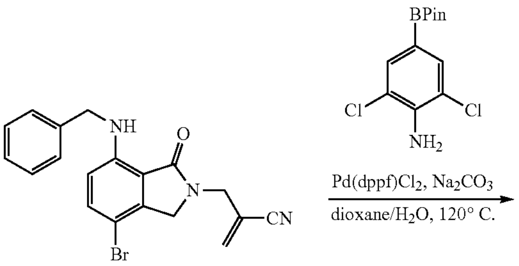

-continued

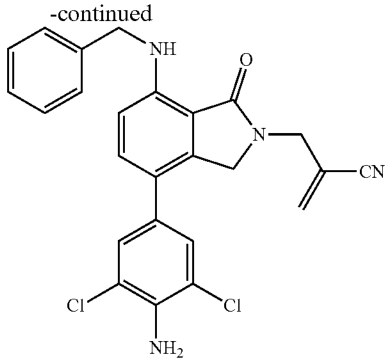

To the mixture of 2-[[7-(benzylamino)-4-bromo-1-oxo-isoindolin-2-yl]methyl]prop-2-enenitrile (120 mg, 282.54 μmol, 1 eq.) (90% purity) and 2,6-dichloro-4-(4,4,5,5-tetramethyl-1,3,2-dioxaborolan-2-yl)aniline (97.64 mg, 339.04 μmol, 1.2 eq.) in dioxane (2 mL) and water (0.5 mL) were added $Na_2CO_3$ (89.84 mg, 847.61 μmol, 3 eq.) and $Pd(dppf)Cl_2$ (20.67 mg, 28.25 μmol, 0.1 eq.) The reaction mixture was degassed and purged with nitrogen 3 times, and the mixture was stirred at 120° C. for 0.5 h under nitrogen atmosphere. TLC showed that the reaction was complete. To the reaction mixture was added 30 mL of sat. EDTA, and the mixture was stirred for 1 h. The mixture was then extracted with EtOAc (3×20 mL), and the combined organic layers were washed with brine (3×20 mL), dried over anhydrous sodium sulfate, filtered, and concentrated in vacuo to give a residue. The residue was purified by prep-TLC (silica gel; PE:EtOAc=4:1) to afford the title compound (70 mg, 135.96 μmol, 48.12% yield, 90% purity) as a light yellow gum.

c. Preparation of 2-[[4-(4-amino-3,5-dichloro-phenyl)-7-(benzylamino)-1-oxo-isoindolin-2-yl]methyl]prop-2-enamide (Compound 365)

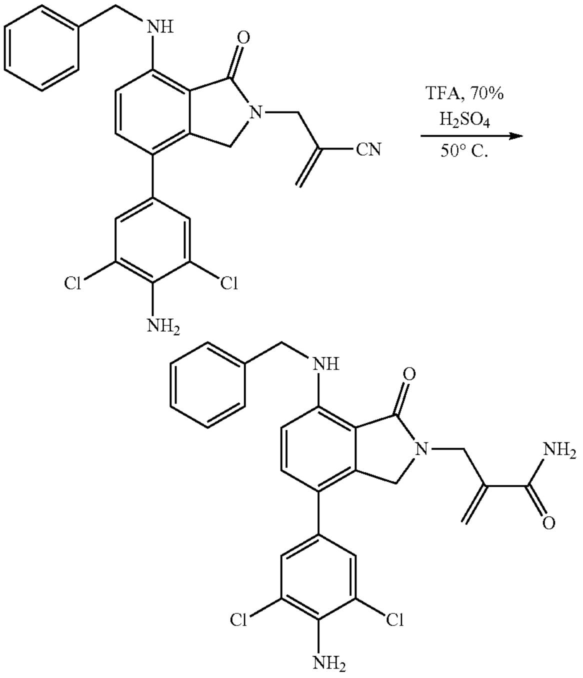

A mixture of 2-[[4-(4-amino-3,5-dichloro-phenyl)-7-(benzylamino)-1-oxo-isoindolin-2-yl]methyl]prop-2-enenitrile (50 mg, 107.91 μmol, 1 eq.) in trifluoroacetic acid (3 mL) and $H_2SO_4$ (3 mL) was stirred at 50° C. for 1 h. LCMS showed that the reaction was complete. The reaction mixture was quenched with ice water (30 mL) at 0° C., and sat. $Na_2CO_3$ was added to adjust the solution to pH=8. The resulting mixture was extracted with DCM (3×20 mL), and the combined organic layers were washed with brine (30 mL), dried over anhydrous sodium sulfate, filtered, and concentrated in vacuo to give a residue. The residue was purified by prep-HPLC column to afford the title compound (16.3 mg, 33.86 μmol, 31.38% yield, 100% purity) as a white solid. LC-MS: $[M+H]^+$ 481.

5G. General Scheme for Method D: Route 7

5G.1. Preparation of 3-[7-amino-2-(2-carbamoylallyl)-1-oxo-isoindolin-4-yl]-N-(2-methylsulfanylethyl)benzamide (Compound 302)

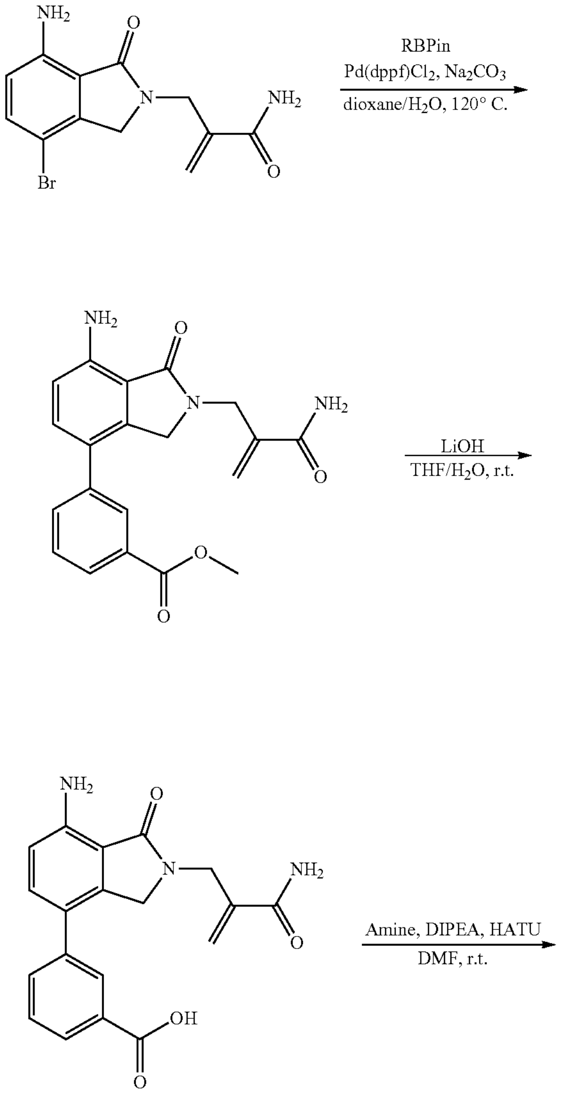

-continued

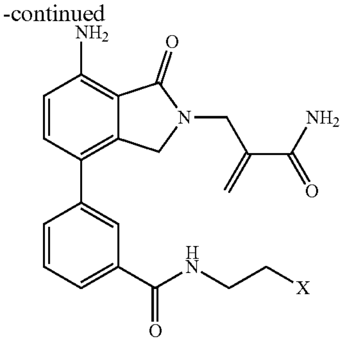

X = SMe
X = OMe
X = N(Me)2 a. Procedure for Preparation of methyl 3-[7-amino-2-(2-carbamoylallyl)-1-oxo-isoindolin-4-yl]benzoate

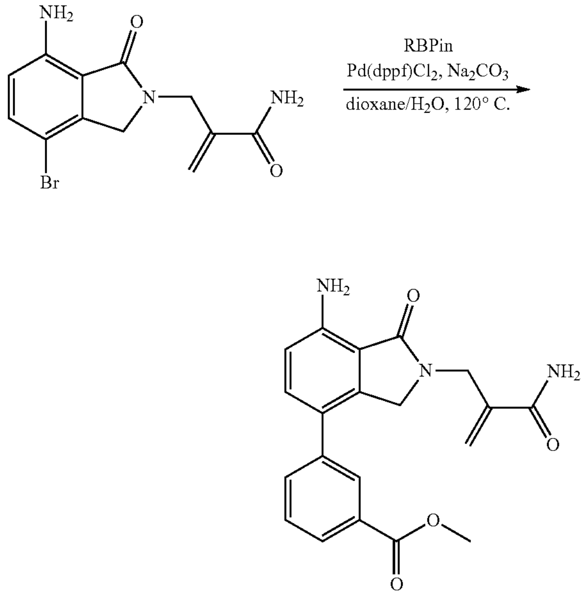 [SMILES: C=C(CN1Cc2c(Br)ccc(N)c2C1=O)C(N)=O ; C=C(CN1Cc2c(-c3cccc(C(=O)OC)c3)ccc(N)c2C1=O)C(N)=O]

To a mixture of 2-[(7-amino-4-bromo-1-oxo-isoindolin-2-yl)methyl]prop-2-enamide (400 mg, 1.29 mmol, 1 eq.) and (3-methoxycarbonylphenyl)boronic acid (255.37 mg, 1.42 mmol, 1.1 eq.) in dioxane (10 mL) and water (2.5 mL) were added $Na_2CO_3$ (410.09 mg, 3.87 mmol, 3 eq.) and ditert-butyl(cyclopentyl)phosphane; dichloro palladium; iron (84.06 mg, 128.97 μmol, 0.1 eq.) The reaction mixture was degassed and purged with nitrogen 3 times, and the mixture was stirred at 120° C. for 20 min under nitrogen atmosphere. LCMS showed that the reaction was complete. The reaction mixture was added into 30 mL of sat. EDTA and stirred for 1 h. The mixture was extracted with EtOAc (3×20 mL), and the combined organic layers were washed with brine (3×20 mL), dried over anhydrous sodium sulfate, filtered, and concentrated in vacuo to give a residue. The residue was purified by prep-TLC (silica gel; DCM:MeOH=10:1) to afford the title compound (210 mg, 574.74 μmol, 44.56% yield) as a light yellow solid.

b. Preparation of 3-[7-amino-2-(2-carbamoylallyl)-1-oxo-isoindolin-4-yl]benzoic Acid

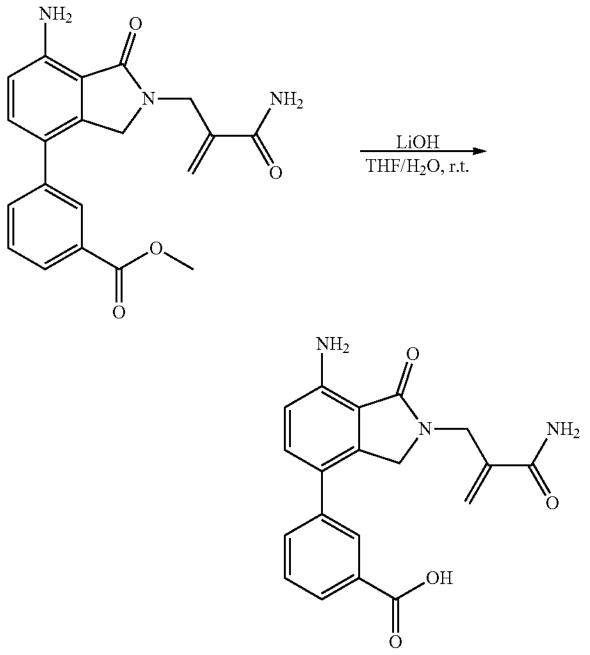

To a solution of methyl 3-[7-amino-2-(2-carbamoylallyl)-1-oxo-isoindolin-4-yl]benzoate (250 mg, 684.22 μmol, 1 eq.) in THF (6 mL) and was added LiOH·$H_2O$ (86.14 mg, 2.05 mmol, 3 eq.) in water (6 mL). The mixture was stirred at 20° C. for 12 h. LCMS showed that the reaction was complete. The reaction mixture was quenched with ice water (20 mL) at 0° C., and 2 M HCl was added dropwise to adjust the solution to pH=3~4. The mixture was extracted with EtOAc (3×30 mL), and the combined organic layers were washed with brine (2×50 mL), dried over anhydrous sodium sulfate, filtered, and concentrated in vacuo to afford the crude compound (470 mg, crude) as a light yellow solid, which was used directly without further purification.

c. Preparation of 3-[7-amino-2-(2-carbamoylallyl)-1-oxo-isoindolin-4-yl]-N-(2-methylsulfanylethyl) benzamide (Compound 302)

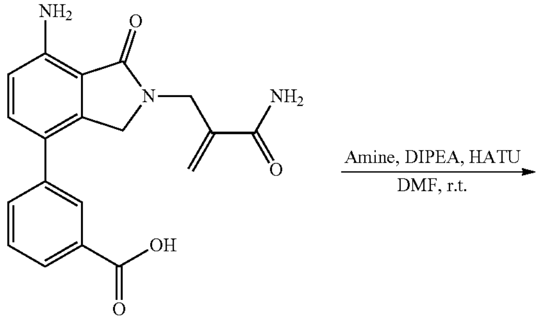

-continued

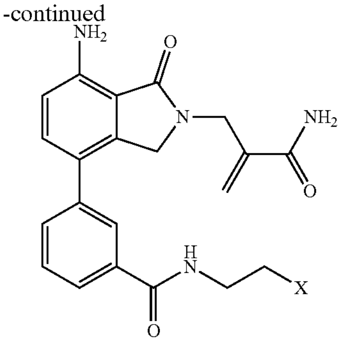

X = SMe
X = OMe
X = N(Me)$_2$

Procedure for X=SMe:

To a solution of 3-[7-amino-2-(2-carbamoylallyl)-1-oxo-isoindolin-4-yl]benzoic acid (100 mg, 142.31 μmol, 1 eq.) (50%, purity) in DMF (5 mL) were added 2-methylsulfanylethanamine (5 eq.), DIPEA (3 eq.) and HATU (1.5 eq.). The mixture was stirred at 20° C. for 1 h. LCMS showed that the reaction was complete. The reaction mixture was quenched with water (20 mL), and extracted with EtOAc (3×20 mL). The combined organic layers were washed with brine (3×20 mL), dried over anhydrous sodium sulfate, filtered, and concentrated in vacuo to give a residue. The residue was purified by prep-TLC (silica gel; DCM: MeOH=10:1) to afford the title compound (22.1 mg, 51.28 μmol, 36.03% yield, 98.5% purity) as a white solid. LC-MS: $[M+H]^+$ 425.1.

5H. General Scheme for Method D: Route 8

5H.1. Preparation of 2-[[4-(3-acetyl-4-hydroxy-phenyl)-7-amino-1-oxo-isoindolin-2-yl]methyl]prop-2-enenitrile (Compound 314)

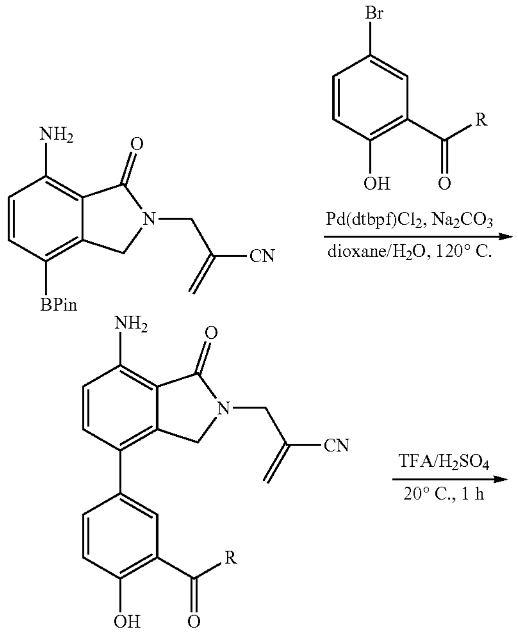

-continued

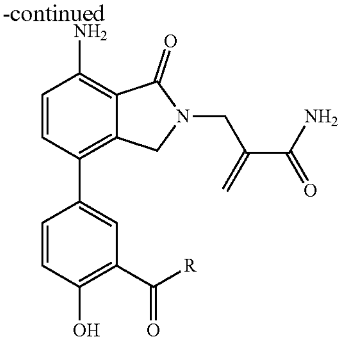

R:

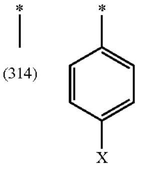

(314)

X: OMe
X: CN
X: H a. Preparation of 2-[[4-(3-acetyl-4-hydroxy-phenyl)-7-amino-1-oxo-isoindolin-2-yl]methyl]prop-2-enenitrile

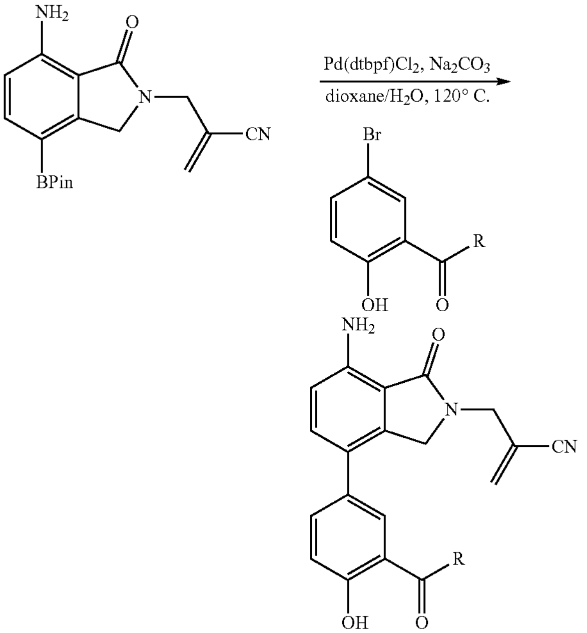

Procedure (R=Me):

To a mixture of 2-[[7-amino-1-oxo-4-(4,4,5,5-tetramethyl-1,3,2-dioxaborolan-2-yl)isoindolin-2-yl]methyl]prop-2-enenitrile (102.06 mg, 255.76 μmol, 1.1 eq.) and 1-(5-bromo-2-hydroxy-phenyl)ethanone (50 mg, 232.51 μmol, 1 eq.) in dioxane (4 mL) and water (1 mL) were added ditert-butyl(cyclopentyl)phosphane; dichloropalladium; iron (7.58 mg, 11.63 μmol, 0.05 eq.) and $Na_2CO_3$ (73.93 mg, 697.53 μmol, 3 eq.) under nitrogen. The mixture was heated to 120° C. and stirred for 10 min under nitrogen. TLC showed that the reaction was complete and detected the desired product. The residue was poured into saturated EDTA (10 mL) and stirred for 2 h. The aqueous phase was extracted with EtOAc (10 mL×3). The combined organic phase was washed with brine (10 mL×3), dried over anhydrous sodium sulfate, filtered, and concentrated in vacuo. the product was purified by prep-TLC (silica gel; DCM:Methanol=20:1) to afford the title compound (57 mg, 164.09 μmol, 70.57% yield) as a yellow solid.

b. Preparation of 2-[[4-(3-acetyl-4-hydroxy-phenyl)-7-amino-1-oxo-isoindolin-2-yl]methyl]prop-2-enenitrile (Compound 314)

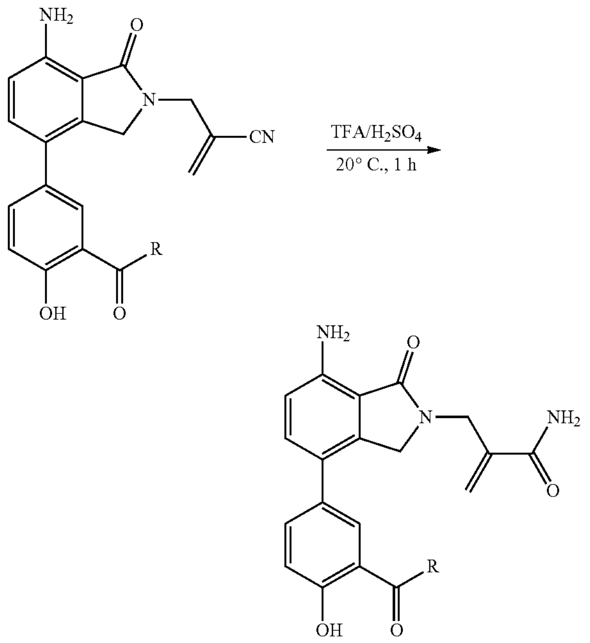

R:

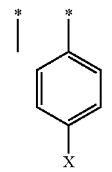

X = OMe, CN, H

Procedure ofr R=Me:

To a mixture of trifluoroacetic acid (380.92 mg, 3.34 mmol, 247.35 μL, 23.21 eq.) and $H_2SO_4$ (455.12 mg, 4.64 mmol, 247.35 μL, 32.24 eq.) was added 2-[[4-(3-acetyl-4-hydroxy-phenyl)-7-amino-1-oxo-isoindolin-2-yl]methyl]prop-2-enenitrile (50 mg, 143.94 μmol, 1 eq.). The mixture was stirred at 20° C. for 1 h. TLC showed that the reaction was complete The residue was poured into ice-water (10 mL), then sat. $Na_2CO_3$ was added to the mixture to adjust the solution to pH~8. The aqueous phase was extracted with EtOAc (3×20 mL), and the combined organic phase was washed with brine (3×20 mL), dried over anhydrous sodium sulfate, filtered, and concentrated in vacuo. The residue was purified by prep-HPLC to afford the title compound (15.5 mg, 44.62 μmol, 100% purity) was a yellow solid. LC-MS: $[M+H]^+$ 366.1.

5I. General Scheme for Method D: Route 9

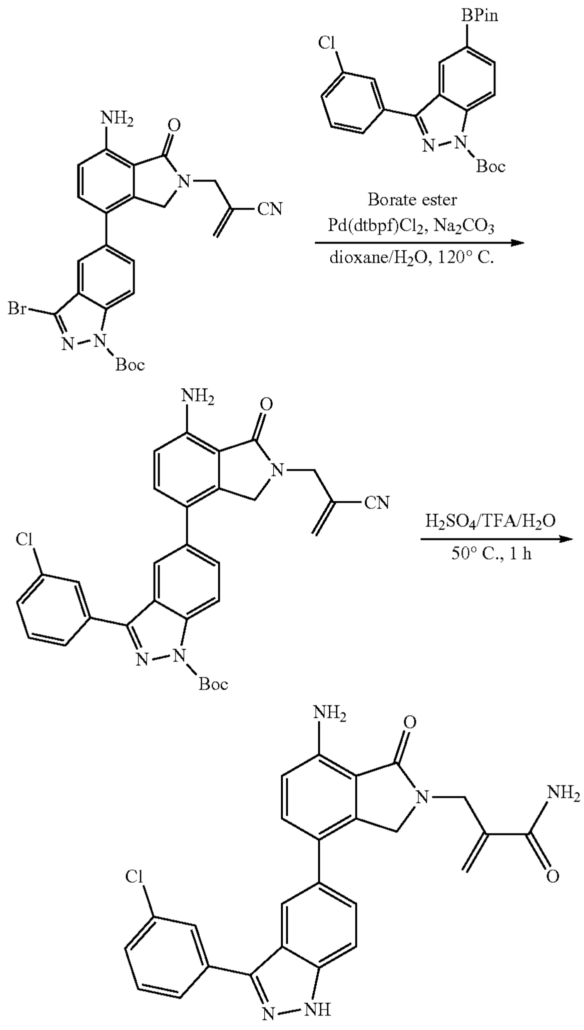

Procedure for Preparation of 2-[[7-amino-4-[3-(3-chlorophenyl)-1H-indazol-5-yl]-1-oxo-isoindolin-2-yl]methyl]prop-2-enamide (Compound 320)

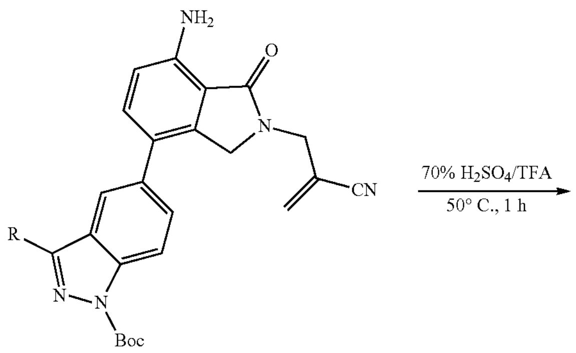

-continued

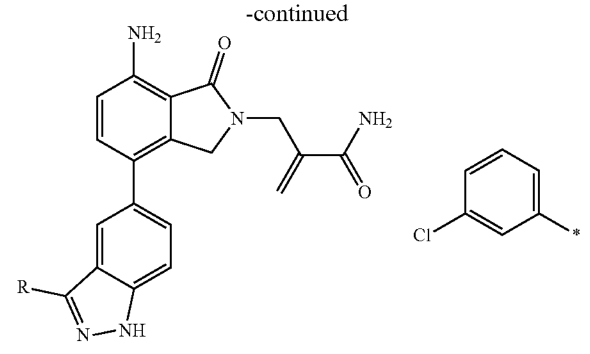

A mixture of tert-butyl 5-[7-amino-2-(2-cyanoallyl)-1-oxo-isoindolin-4-yl]-3-(3-chlorophenyl)indazole-1-carboxylate (80 mg, 148.15 μmol, 1 eq.) in trifluoroacetic acid (1.5 mL) and $H_2SO_4$ (1.5 mL) was stirred at 50° C. for 1 h. TLC showed that the reaction was complete. The reaction mixture was added to 30 mL of sat. EDTA and stirred for 1 h, and extracted with EtOAc (3×20 mL). The combined organic layers were washed with brine (3×20 mL), dried over anhydrous sodium sulfate, filtered, and concentrated in vacuo to give a residue. The residue was purified by prep-TLC (silica gel; DCM:MeOH=10:1) to afford the title compound (5.2 mg, 11.36 μmol, 7.67% yield, 100% purity) as a light yellow solid. LC-MS: $[M+H]^+$ 458.

5J. General Scheme for Method D: Route 10

5J.1. Preparation of 2-[[4-[3-[3-[(4-acetylpiperazin-1-yl)methyl]phenyl]-1H-indazol-5-yl]-7-amino-1-oxo-isoindolin-2-yl]methyl]prop-2-enamide (Compound 351)

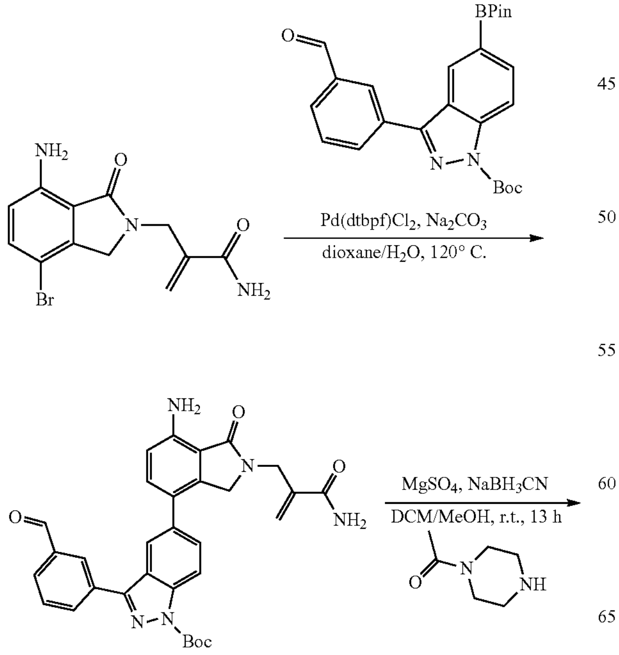

-continued

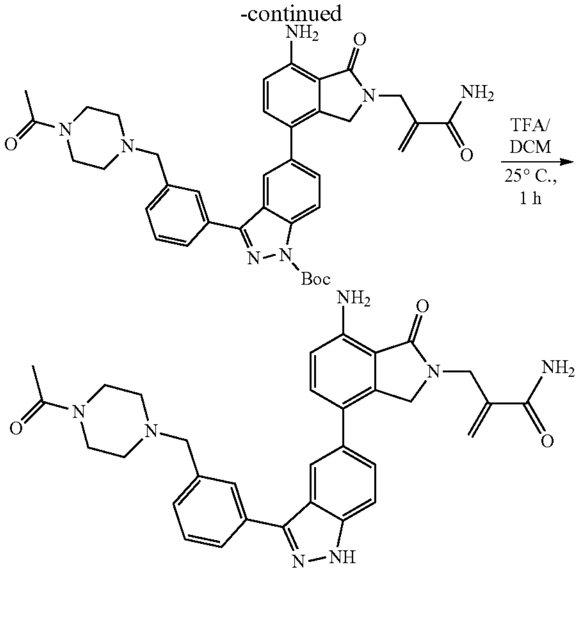

a. Procedure for Preparation of tert-butyl 3-(3-formylphenyl)-5-(4,4,5,5-tetramethyl-1,3,2-dioxaborolan-2-yl)indazole-1-carboxylate

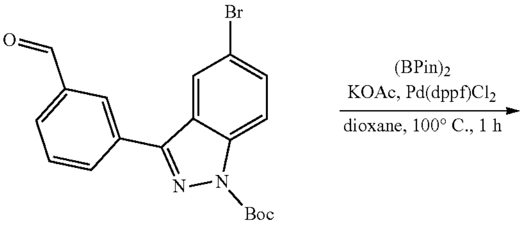

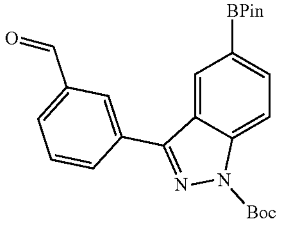

To a mixture of tert-butyl 5-bromo-3-(3-formylphenyl)indazole-1-carboxylate (0.8 g, 1.99 mmol, 1 eq.) and 4,4,5,5-tetramethyl-2-(4,4,5,5-tetramethyl-1,3,2-dioxaborolan-2-yl)-1,3,2-dioxaborolane (1.52 g, 5.98 mmol, 3 eq.) in dioxane (40 mL) were added AcOK (587 mg, 5.98 mmol, 3 eq.) and Pd(dppf)$Cl_2$ (291.77 mg, 398.75 μmol, 0.2 eq.). The reaction mixture was degassed and purged with nitrogen 3 times, and the mixture was stirred at 100° C. for 1 h under nitrogen atmosphere. TLC showed that the reaction was complete. The reaction mixture was filtered, and concentrated in vacuo to give a residue. The residue was purified by column chromatography (silica gel; PE:EtOAc=10:1 to 3:1) to afford the title compound (550 mg, 1.04 mmol, 52.30% yield, 85% purity) as an off-white oil.

b. Procedure for Preparation of tert-butyl 5-[7-amino-2-(2-carbamoylallyl)-1-oxo-isoindolin-4-yl]-3-(3-formylphenyl)indazole-1-carboxylate

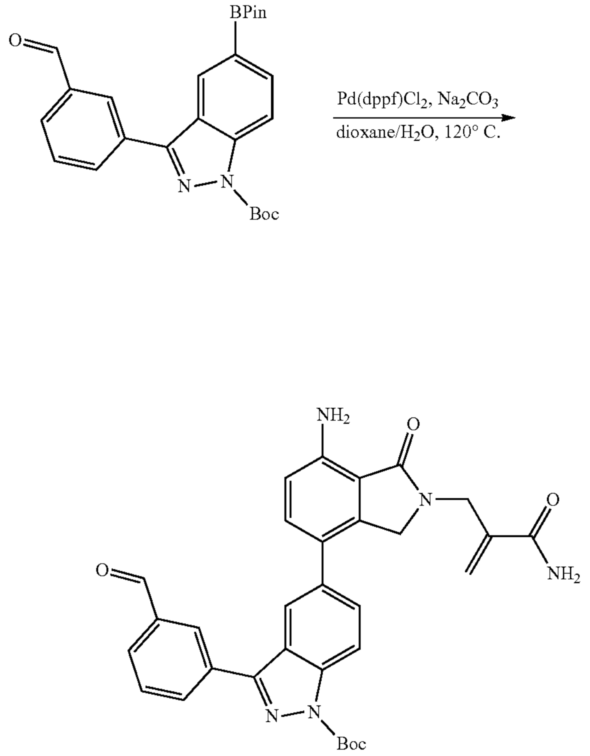

To a mixture of tert-butyl 3-(3-formylphenyl)-5-(4,4,5,5-tetramethyl-1,3,2-dioxaborolan-2-yl)indazole-1-carboxylate (408.14 mg, 773.83 μmol, 1.2 eq.) (85% purity) and 2-[(7-amino-4-bromo-1-oxo-isoindolin-2-yl)methyl]prop-2-enamide (0.2 g, 644.86 μmol, 1 eq.) in dioxane (3 mL) and water (0.75 mL), were added $Na_2CO_3$ (205.05 mg, 1.93 mmol, 3 eq.) and Pd(dppf)$Cl_2$ (94.37 mg, 128.97 μmol, 0.2 eq.). The reaction mixture was degassed and purged with nitrogen 3 times, and the mixture was stirred at 100° C. for 20 min under nitrogen atmosphere. LCMS showed that the reaction was complete. The reaction mixture was added to 30 mL of saturated aq. EDTA and stirred for 1 h. The resulting solution was extracted with EtOAc (3×20 mL), and the combined organic layer was washed with brine (3×20 mL), dried over anhydrous sodium sulfate, filtered, and concentrated in vacuo to give a residue. The residue was purified by prep-TLC (silica gel; DCM:MeOH=15:1) to afford the title compound (160 mg, 246.56 μmol, 38.23% yield, 85% purity) as a light yellow gum.

c. Procedure for Preparation of tert-butyl 3-[3-[(4-acetylpiperazin-1-yl)methyl]phenyl]-5-[7-amino-2-(2-carbamoylallyl)-1-oxo-isoindolin-4-yl]indazole-1-carboxylate

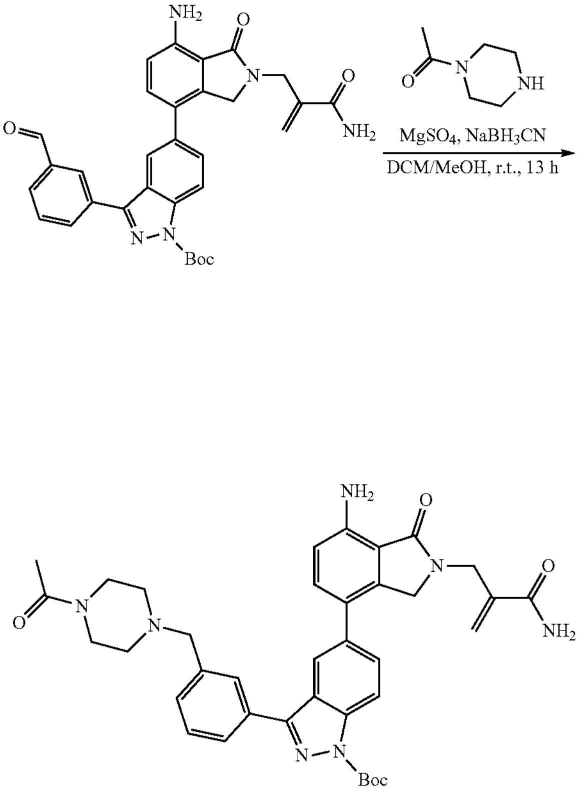

To a solution of tert-butyl 5-[7-amino-2-(2-carbamoylallyl)-1-oxo-isoindolin-4-yl]-3-(3-formylphenyl)indazole-1-carboxylate (80 mg, 123.28 μmol, 1 eq.) (85% purity) and 1-piperazin-1-ylethanone (79 mg, 616.40 μmol, 5 eq.) in DCM (3 mL) and MeOH (3 mL) was added $MgSO_4$ (148.39 mg, 1.23 mmol, 10 eq.). The reaction mixture was stirred at 20° C. for 12 h, and $NaBH_3CN$ (38.73 mg, 616.40 μmol, 5 eq.) was added. The mixture was stirred at 20° C. for 1 h. LCMS showed that the reaction was complete. The reaction mixture was extracted with EtOAc (3×50 mL), and the combined organic layers were washed with water (3×50 mL) and brine (3×50 mL), dried over anhydrous sodium sulfate, filtered, and concentrated in vacuo to give a residue. The residue was purified by prep-TLC (silica gel; DCM: MeOH=15:1) to afford the title compound (70 mg, 94.91 μmol, 76.99% yield, 90% purity) as a light yellow gum.

d. Preparation of 2-[[4-[3-[3-[(4-acetylpiperazin-1-yl)methyl]phenyl]-1H-indazol-5-yl]-7-amino-1-oxo-isoindolin-2-yl]methyl]prop-2-enamide (Compound 351)

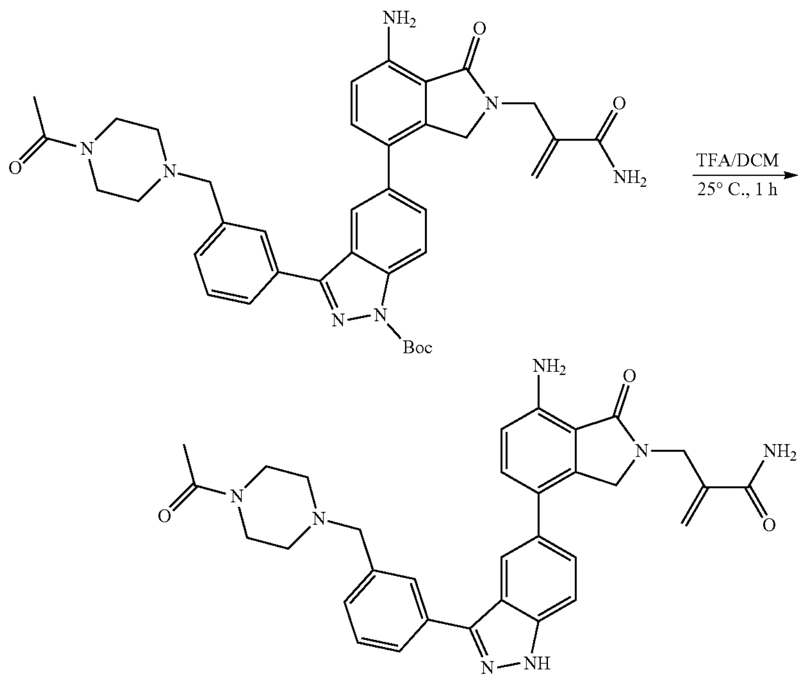

A solution of tert-butyl 3-[3-[(4-acetylpiperazin-1-yl)methyl]phenyl]-5-[7-amino-2-(2-carbamoylallyl)-1-oxo-isoindolin-4-yl]indazole-1-carboxylate (50 mg, 67.80 μmol, 1 eq.) (90% purity) in trifluoroacetic acid (2 mL) and DCM (2 mL) was stirred at 20° C. for 1 h. LCMS showed that the reaction was complete. The reaction mixture was quenched with addition ice water 10 mL at 0° C., and $Na_2CO_3$ was added to adjust the solution to pH=8. The mixture was extracted with DCM (15 mL×3), and the combined organic layers were washed with brine (10 mL), dried over anhydrous sodium sulfate, filtered, and concentrated in vacuo to give a residue. The residue was purified by prep-HPLC to afford the title compound (13.1 mg, 23.24 μmol, 34.28% yield, 100% purity) as a white solid. LC-MS: $[M+H]^+$ 564.3.

Route 11:

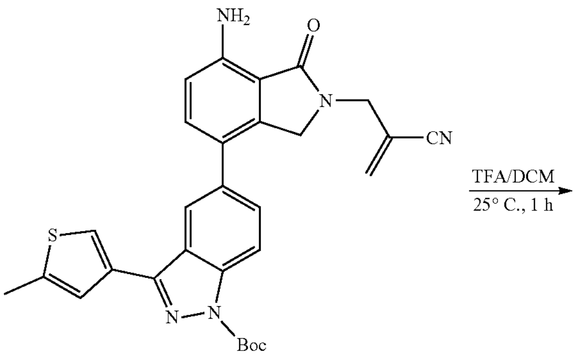

-continued

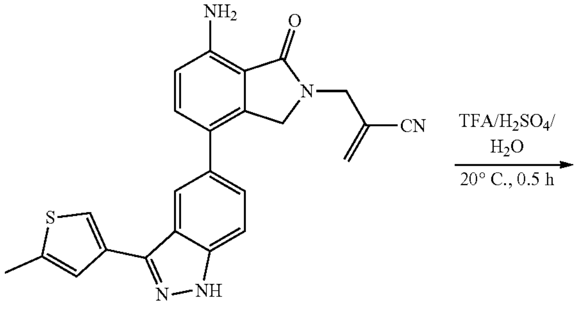

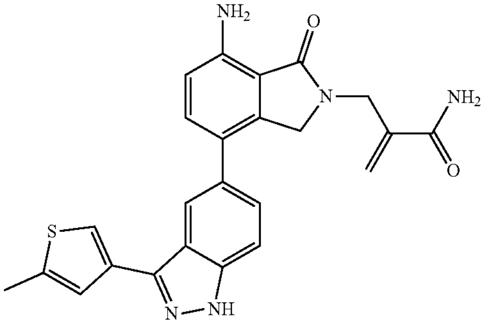

a. Preparation of 2-[[7-amino-4-[3-(5-methyl-3-thienyl)-1H-indazol-5-yl]-1-oxo-isoindolin-2-yl]methyl]prop-2-enenitrile

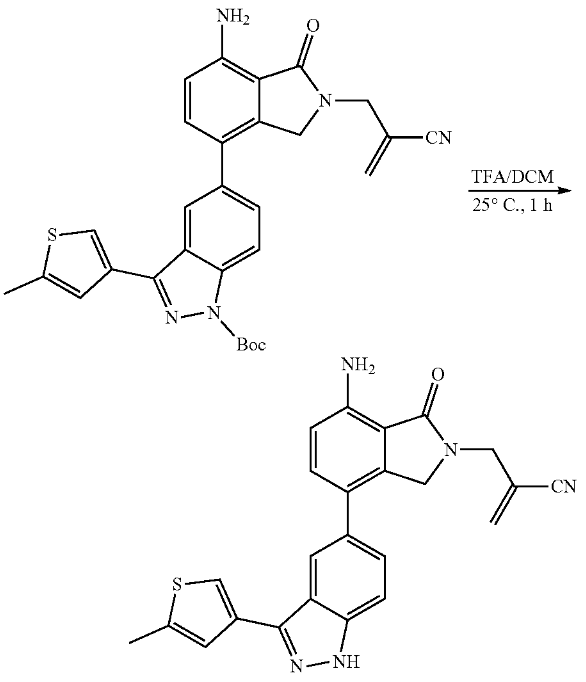

A solution of tert-butyl 5-[7-amino-2-(2-cyanoallyl)-1-oxo-isoindolin-4-yl]-3-(5-methyl-3-thienyl)indazole-1-carboxylate (60 mg, 91.32 μmol, 1 eq.) (80% purity) in trifluoroacetic acid (3 mL) and DCM (3 mL) was stirred at 20° C. for 1 h. TLC and LCMS showed that the reaction was complete. The reaction mixture was quenched with addition ice water 10 mL at 0° C., and added $Na_2CO_3$ to adjust pH=8, and extracted with DCM (3x15 mL). The combined organic layers were washed with brine (10 mL), dried over anhydrous sodium sulfate, filtered, and concentrated in vacuo to give a residue. The residue was purified by prep-TLC (silica gel; DCM:MeOH=10:1) to afford the title compound (45 mg, 84.61 μmol, 92.65% yield, 80% purity) as a white solid.

Preparation of 2-[[7-amino-4-[3-(5-methyl-3-thienyl)-1H-indazol-5-yl]-1-oxo-isoindolin-2-yl]methyl]prop-2-enamide (Compound 346)

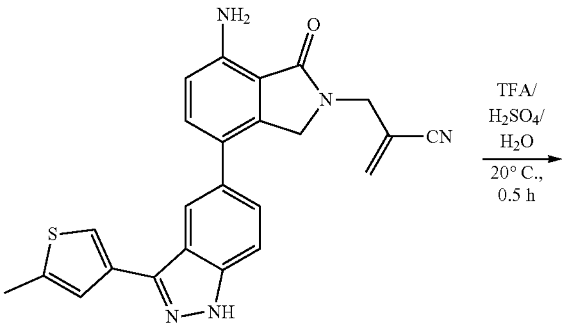

-continued

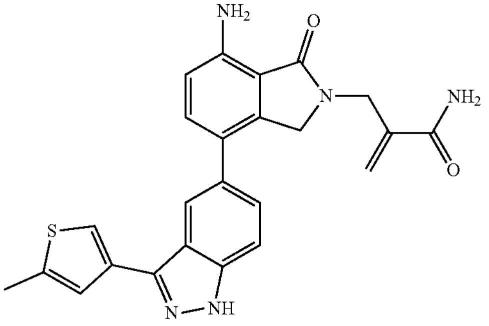

A solution of 2-[[7-amino-4-[3-(5-methyl-3-thienyl)-1H-indazol-5-yl]-1-oxo-isoindolin-2-yl]methyl]prop-2-enenitrile (40 mg, 75.20 μmol, 1 eq.) (80% purity) in trifluoroacetic acid (3 mL) and $H_2SO_4$ (3 mL) was stirred at 20° C. for 0.5 h. HPLC showed that the reaction was complete. The reaction mixture was The reaction was quenched by adding ice water 10 mL at 0° C., and sat. $Na_2CO_3$ was added to adjust the mixture to pH=8. The mixture was extracted with DCM (3x15 mL). The combined organic layers were washed with brine (10 mL), dried over anhydrous sodium sulfate, filtered, and concentrated in vacuo to give a residue. The residue was purified by prep-HPLC to afford the title compound (7.2 mg, 16.23 μmol, 21.59% yield, 100% purity) as a white solid. LC-MS: $[M+H]^+$ 444.1.

Route 12:

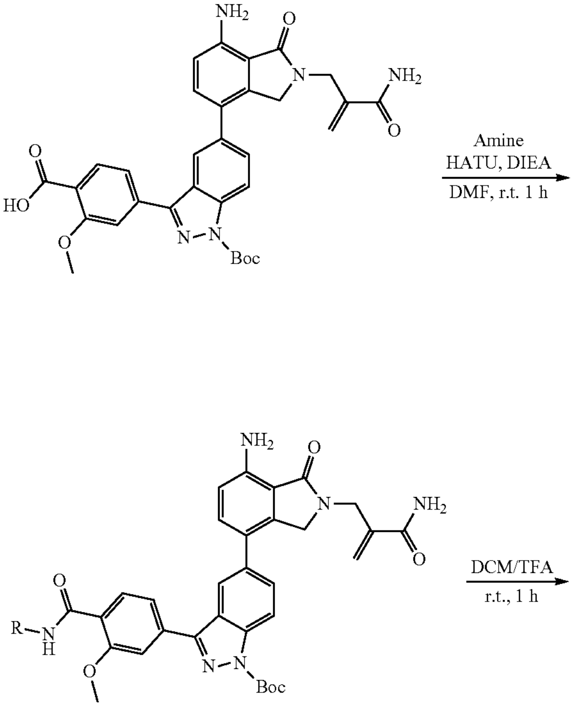

-continued

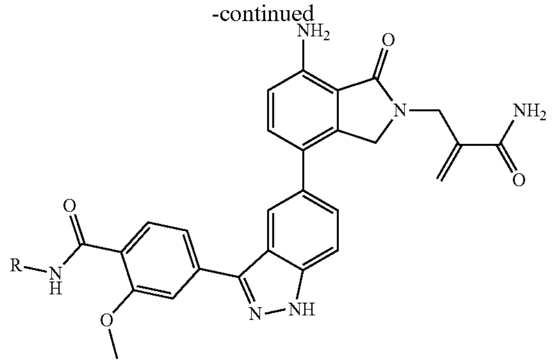

R = H
R = Me a. Procedure for Preparation of tert-butyl 5-[7-amino-2-(2-carbamoylallyl)-1-oxo-isoindolin-4-yl]-3-(4-carbamoyl-3-methoxy-phenyl)indazole-1-carboxylate

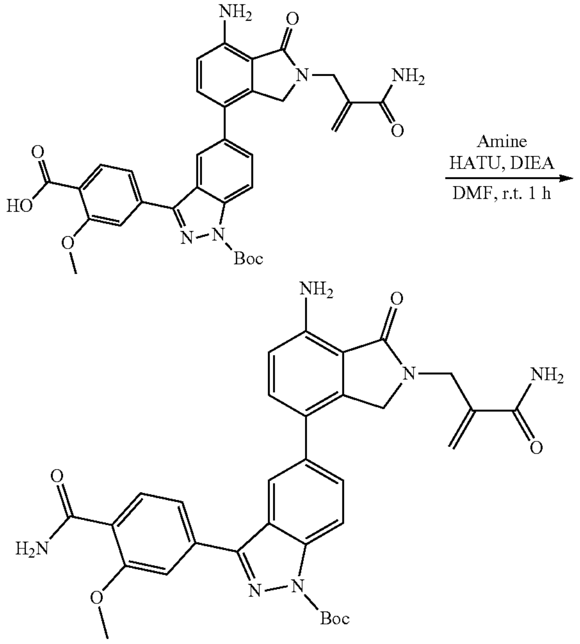

To a mixture of 4-[5-[7-amino-2-(2-carbamoylallyl)-1-oxo-isoindolin-4-yl]-1-tert-butoxycarbonyl-indazol-3-yl]-2-methoxy-benzoic acid (100 mg, 167.33 mol, 1 eq.) and $CH_3COONH_4$ (64.49 mg, 836.66 μmol, 5 eq.) in DMF (10 mL) were added DIEA (151.38 mg, 1.17 mmol, 204.02 μL, 7 eq.) and HATU (82.71 mg, 217.53 μmol, 1.3 eq.). The reaction mixture was degassed and purged with nitrogen 3 times, and the mixture was stirred at 25° C. for 1 h under nitrogen atmosphere. LCMS showed that the reaction was complete. The reaction mixture was added to 30 mL saturated EDTA, stirred for 1 h, then extracted with EtOAc (3×30 mL). The organic phase was separated, washed with water (2×30 mL) and brine (2×30 mL), dried over anhydrous sodium sulfate, filtered, and concentrated in vacuo to give a residue. The residue was purified by prep-TLC (silica gel; DCM:MeOH=10:1) to afford the title compound (90 mg, 150.85 μmol, 90.15% yield) as a light yellow solid.

Procedure for Preparation of 4-[5-[7-amino-2-(2-carbamoylallyl)-1-oxo-isoindolin-4-yl]-1H-indazol-3-yl]-2-methoxy-benzamide (Compound 350)

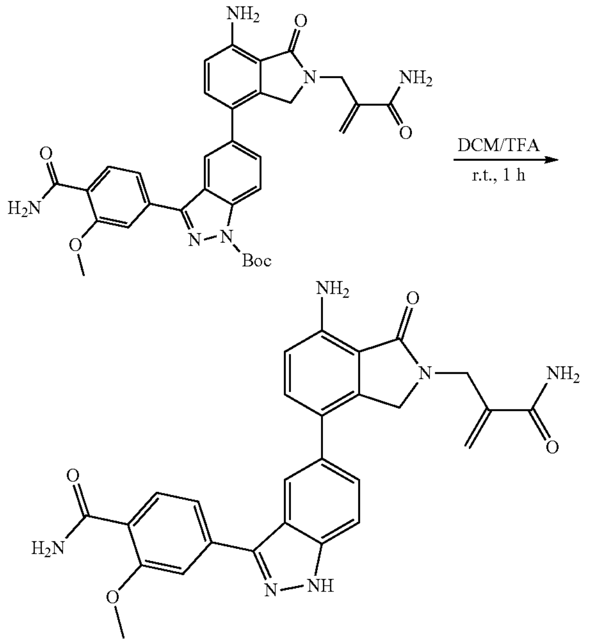

A mixture of tert-butyl 5-[7-amino-2-(2-carbamoylallyl)-1-oxo-isoindolin-4-yl]-3-(4-carbamoyl-3-methoxy-phenyl)indazole-1-carboxylate (90 mg, 150.85 μmol, 1 eq.) in DCM (2.5 mL) and trifluoroacetic acid (2.5 mL) was stirred at 25° C. for 1 h under nitrogen atmosphere. LCMS showed that the reaction was complete. The reaction mixture was added to ice water, then sat. $Na_2CO_3$ was slowly added to adjust the mixture to pH=8~9. The resulting solution was extracted with DCM (3×30 mL). The organic phase was separated and washed with water (2×30 mL) and brine (2×30 mL), dried over anhydrous sodium sulfate, filtered, and concentrated in vacuo to give a residue. The residue was purified by prep-HPLC to afford the title compound as a light yellow solid (5.3 mg, 10.57 mol, 7.01% yield, 99% purity). LC-MS: $[M+H]^+$ 497.1.

Procedure for Preparation of tert-butyl 5-[7-amino-2-(2-carbamoylallyl)-1-oxo-isoindolin-4-yl]-3-[3-methoxy-4-(methylcarbamoyl)phenyl]indazole-1-carboxylate

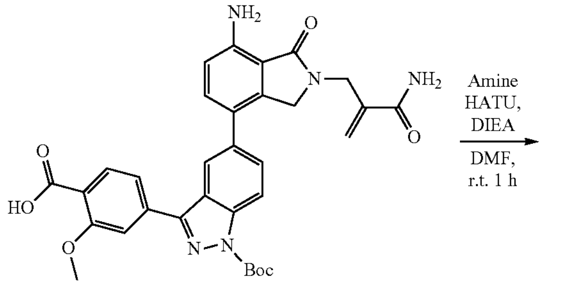

-continued

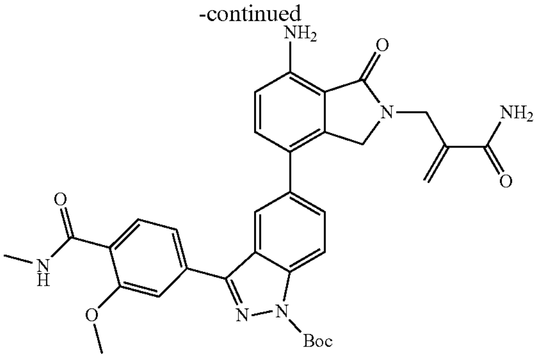

To a mixture of 4-[5-[7-amino-2-(2-carbamoylallyl)-1-oxo-isoindolin-4-yl]-1-tert-butoxycarbonyl-indazol-3-yl]-2-methoxy-benzoic acid (80 mg, 133.87 μmol, 1 eq.) and methanamine (45.19 mg, 669.33 μmol, 5 eq., HCl) in DMF (8 mL) were added HATU (66.17 mg, 174.02 μmol, 1.3 eq.) and DIEA (121.11 mg, 937.06 μmol, 163.2 μL, 7 eq.). The mixture was stirred at 25° C. for 1 h under nitrogen atmosphere. LCMS showed that the reaction was complete. The reaction mixture was added to 30 mL saturated EDTA and stirred for 1 h. The mixture was then extracted with EtOAc (3x30 mL). The organic phase was separated, washed with water (2x30 mL) and brine (2x30 mL), dried over anhydrous sodium sulfate, filtered, and concentrated in vacuo to give a residue. The residue was purified by prep-TLC (silica gel; DCM:MeOH=10:1) to afford the title compound (60 mg, 88.43 mol, 66.06% yield, 90% purity) as a light yellow solid.

Procedure for Preparation of 4-[5-[7-amino-2-(2-carbamoylallyl)-1-oxo-isoindolin-4-yl]-1H-indazol-3-yl]-2-methoxy-N-methyl-benzamide (Compound 353)

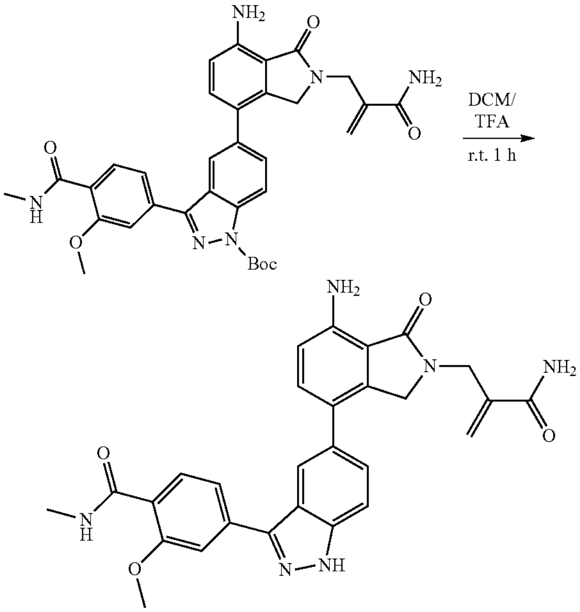

A mixture of tert-butyl 5-[7-amino-2-(2-carbamoylallyl)-1-oxo-isoindolin-4-yl]-3-[3-methoxy-4-(methylcarbamoyl)phenyl]indazole-1-carboxylate (50 mg, 73.69 μmol, 1 eq.) in DCM (2 mL) and trifluoroacetic acid (2 mL) was stirred at 25° C. for 1 h under nitrogen atmosphere. LCMS and TLC (DCM:MeOH=10:1) showed that the reaction was complete. The reaction mixture was added to ice water, and sat. $Na_2CO_3$ was slowly added to adjust the mixture to pH=8~9. The resulting solution was extracted with DCM (3x30 mL). The organic phase was separated, washed with water (2x30 mL) and brine (2x30 mL), dried over anhydrous sodium sulfate, filtered, and concentrated in vacuo to give a residue. The residue was purified by prep-HPLC to afford the title compound (13.4 mg, 25.72 μmol, 34.90% yield, 98% purity) as a light yellow solid. LC-MS: $[M+H]^+$ 511.1.

Route 13

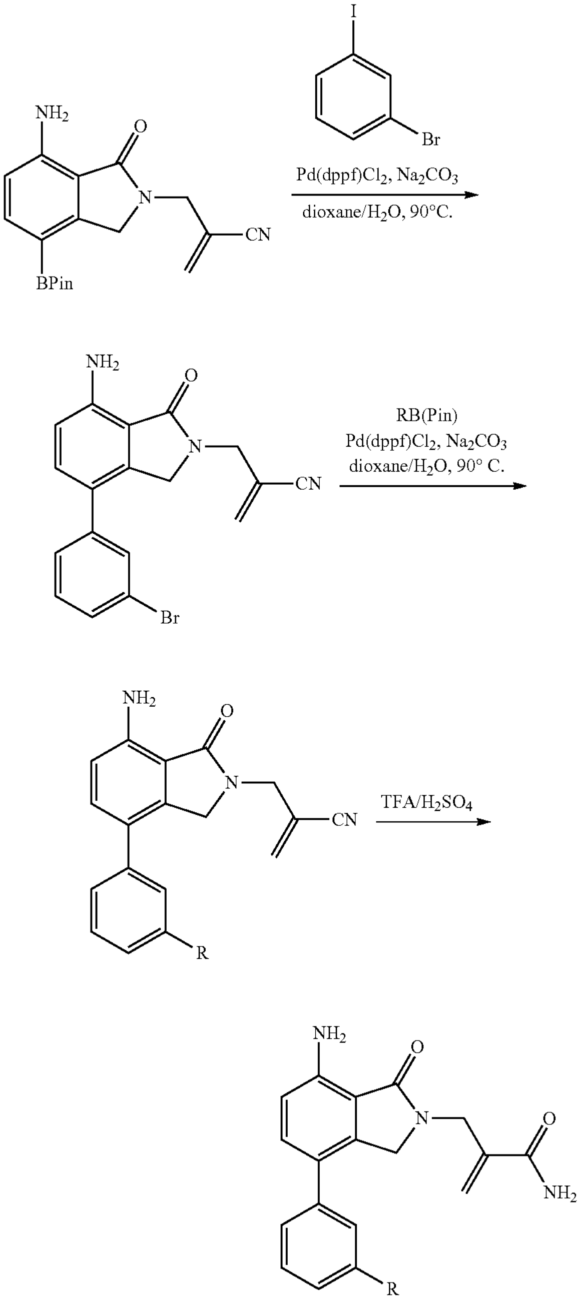

-continued

R:

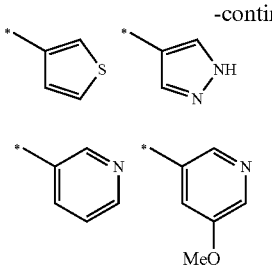

b. Procedure for Preparation of 2-[[7-amino-4-(3-bromophenyl)-1-oxo-isoindolin-2-yl]methyl]prop-2-enenitrile

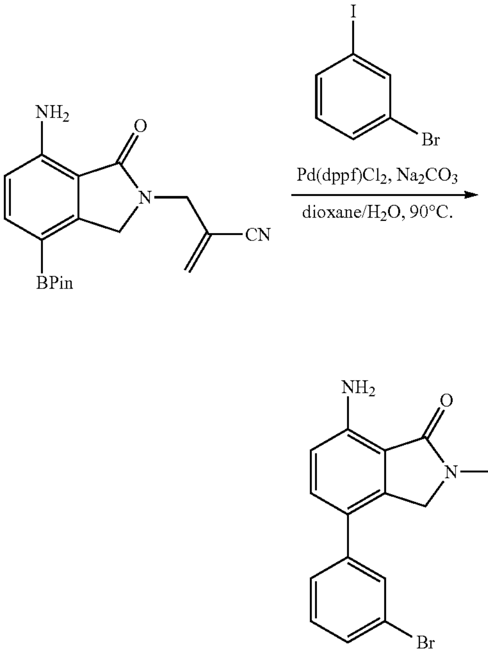

To a mixture of 2-[[7-amino-1-oxo-4-(4,4,5,5-tetramethyl-1,3,2-dioxaborolan-2-yl)isoindolin-2-yl]methyl]prop-2-enenitrile (0.4 g, 1.06 mmol, 1 eq.) (90% purity) and 1-bromo-3-iodo-benzene (1.50 g, 5.31 mmol, 676.25 μL, 5 eq.) in dioxane (40 mL) and water (10 mL) were added $Na_2CO_3$ (337.47 mg, 3.18 mmol, 3 eq.) and $Pd(dppf)Cl_2$ (155.32 mg, 212.27 μmol, 0.2 eq.). The reaction mixture was degassed and purged with nitrogen 3 times, and the mixture was stirred at 90° C. for 15 min under nitrogen atmosphere. LCMS showed that the reaction was complete. The reaction mixture was added to 30 mL EDTA and stirred for 1 h, and extracted with EtOAc (3x20 mL). The combined organic layers were washed with brine (3x20 mL), dried over anhydrous sodium sulfate, filtered, and concentrated in vacuo to give a residue. The residue was purified by prep-TLC (silica gel; DCM:MeOH=20:1) to afford the title compound (200 mg, 488.83p mol, 46.06% yield, 90% purity) as a light yellow gum.

Procedure for Preparation of 2-[[7-amino-1-oxo-4-[3-(3-thienyl)phenyl]isoindolin-2-yl]methyl]prop-2-enenitrile

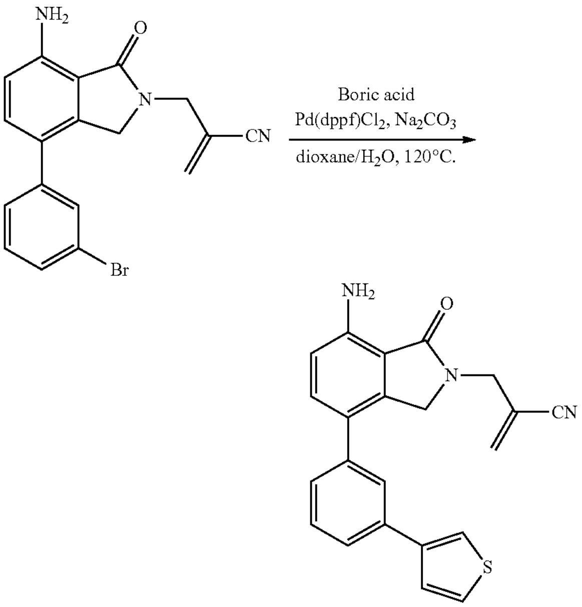

To a mixture of 2-[[7-amino-4-(3-bromophenyl)-1-oxo-isoindolin-2-yl]methyl]prop-2-enenitrile (60 mg, 162.94 μmol, 1 eq.) and 3-thienylboronic acid (72.97 mg, 570.30 mol, 3.5 eq.) in dioxane (4 mL) and water (1 mL) were added $Na_2CO_3$ (51.81 mg, 488.83 μmol, 3 eq.) and Pd(dppf) $Cl_2$ (23.85 mg, 32.59 μmol, 0.2 eq.). The reaction mixture was degassed and purged with nitrogen 3 times, and the mixture was stirred at 120° C. for 15 min under nitrogen atmosphere. LCMS showed that the reaction was complete. The reaction mixture was added to 30 mL of a saturated EDTA solution stirred for 1 h, then extracted with EtOAc (3x30 mL). The organic phase was separated and washed with water (2x30 mL) and brine (2x30 mL), dried over anhydrous sodium sulfate, filtered, and concentrated in vacuo to give a residue. The residue was purified by prep-TLC (silica gel; DCM:MeOH=10:1) to afford the title compound (70 mg, 135.68 μmol, 83.27% yield, 72% purity) as a light yellow solid.

Procedure for Preparation of 2-[[7-amino-1-oxo-4-[3-(3-thienyl)phenyl]isoindolin-2-yl]methyl]prop-2-enamide (Compound 354)

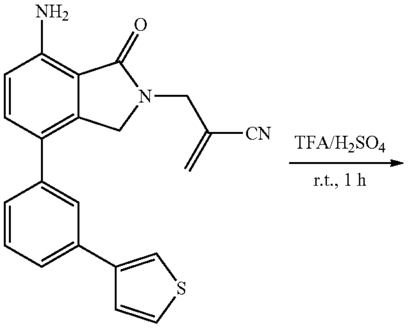

-continued

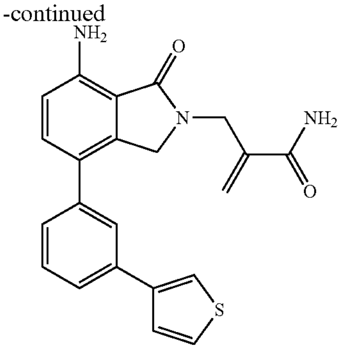

A mixture of 2-[[7-amino-1-oxo-4-[3-(3-thienyl)phenyl]isoindolin-2-yl]methyl]prop-2-enenitrile (50 mg, 96.92 μmol, 1 eq.) (72% purity) in $H_2SO_4$ (0.5 mL) and trifluoroacetic acid (0.5 mL) was stirred at 25° C. for 1 h under nitrogen atmosphere. LCMS showed that the reaction was complete. The reaction mixture was added to ice water, and sat. $Na_2CO_3$ was slowly added to adjust the mixture to pH=8~9. The resulting solution was extracted with DCM (3x30 mL). The organic phase was separated and washed with water (2x30 mL) and brine (2x30 mL), dried over anhydrous sodium sulfate, filtered, and concentrated in vacuo to give a residue. The residue was purified by prep-TLC (silica gel; DCM:MeOH=20:1), then further purified by prep-HPLC to afford the title compound (2.1 mg, 5.39 μmol, 5.56% yield, 100% purity) as a light yellow solid. LC-MS: $[M+H]^+$ 390.1.

Procedure for Preparation of 2-[[7-amino-1-oxo-4-[3-(3-pyridyl)phenyl]isoindolin-2-yl]methyl]prop-2-enenitrile

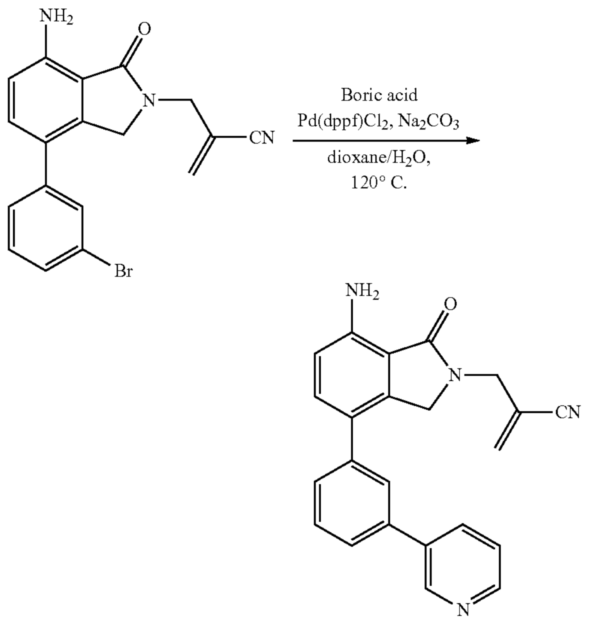

To a mixture of 2-[[7-amino-4-(3-bromophenyl)-1-oxo-isoindolin-2-yl]methyl]prop-2-enenitrile (50 mg, 135.79 μmol, 1 eq.) and 3-pyridylboronic acid (25.04 mg, 203.68 μmol, 1.5 eq.) in dioxane (4 mL) and water (1 mL) were added $Na_2CO_3$ (43.18 mg, 407.36 mol, 3 eq.) and Pd(dppf)$Cl_2$ (29.81 mg, 40.74 μmol, 0.3 eq.). The reaction mixture was degassed and purged with nitrogen 3 times, and the mixture was stirred at 120° C. for 20 min under nitrogen atmosphere. LCMS showed that the reaction was complete. The reaction mixture was added to 30 mL saturated EDTA and stirred for 1 h. The mixture was extracted with EtOAc (3x30 mL). The organic phase was separated and washed with water (2x30 mL) and brine (2x30 mL), dried over anhydrous sodium sulfate, filtered, and concentrated in vacuo to give a residue. The residue was purified by prep-TLC (silica gel; DCM:MeOH=10:1) to afford the title compound (50 mg, 122.81p mol, 90.45% yield, 90% purity) as a light yellow solid.

Procedure for Preparation of 2-[[7-amino-1-oxo-4-[3-(3-pyridyl)phenyl]isoindolin-2-yl]methyl]prop-2-enamide] (Compound 355)

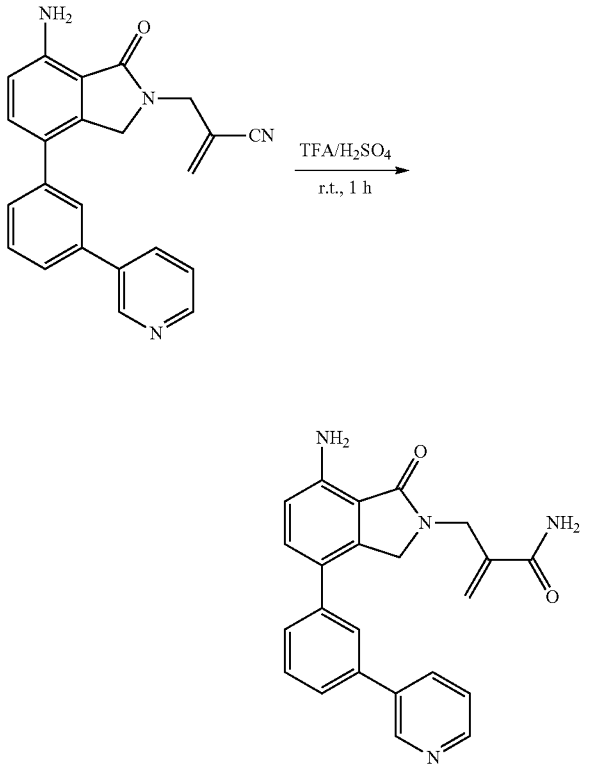 [SMILES: C=C(C#N)CN1Cc2c(-c3cccc(-c4cccnc4)c3)ccc(N)c2C1=O ; C=C(CN1Cc2c(-c3cccc(-c4cccnc4)c3)ccc(N)c2C1=O)C(N)=O]

A mixture of 2-[[7-amino-1-oxo-4-[3-(3-pyridyl)phenyl]isoindolin-2-yl]methyl]prop-2-enenitrile (40 mg, 98.25 μmol, 1 eq.) (90% purity) in trifluoroacetic acid (1.5 mL) and $H_2SO_4$ (1.5 mL) was stirred at 25° C. for 1 h under nitrogen atmosphere. LCMS showed that the reaction was complete. The reaction mixture was added to ice water, then sat. $Na_2CO_3$ was slowly added to adjust the mixture to pH=8~9. The resulting solution was extracted with DCM (3x30 mL). The organic phase was separated, washed with water (2x30 mL) and brine (2x30 mL), dried over anhydrous sodium sulfate, filtered, and concentrated in vacuo to give a residue. The residue was purified by prep-HPLC to afford the title compound as a white solid (14 mg, 36.42 μmol, 37.07% yield, 100% purity). LC-MS: $[M+H]^+$ 385.1.

Procedure for Preparation of tert-butyl 4-[3-[7-amino-2-(2-carbamoylallyl)-1-oxo-isoindolin-4-yl]phenyl]pyrazole-1-carboxylate

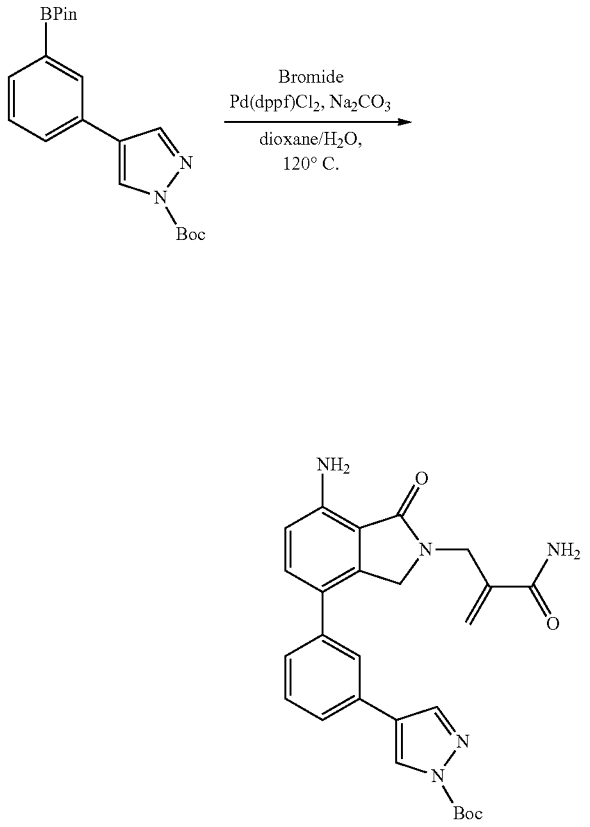

To a mixture of tert-butyl 4-[3-(4,4,5,5-tetramethyl-1,3,2-dioxaborolan-2-yl)phenyl]pyrazole-1-carboxylate (143.25 mg, 386.91 μmol, 1.5 eq.) and 2-[(7-amino-4-bromo-1-oxo-isoindolin-2-yl)methyl]prop-2-enamide (80 mg, 257.94 mol, 1 eq.) in dioxane (2 mL) and water (0.5 mL) were added $Na_2CO_3$ (82.02 mg, 773.83 mol, 3 eq.) and Pd(dppf)$Cl_2$ (56.62 mg, 77.38 μmol, 0.3 eq.). The reaction mixture was degassed and purged with nitrogen 3 times, and the mixture was stirred at 100° C. for 15 min under nitrogen atmosphere. TLC (EtOAc:PA=1:0) showed that the reaction was complete. The reaction mixture was added to 30 mL saturated EDTA and stirred for 1 h, then extracted with EtOAc (3×30 mL). The organic phase was separated, washed with water (2×30 mL) and brine (2×30 mL), dried over anhydrous sodium sulfate, filtered, and concentrated in vacuo to give a residue. The residue was purified by prep-TLC (silica gel; EtOAc:PE=1:0) to afford the title compound (50 mg, 84.47 mol, 32.75% yield, 80% purity) as a light yellow solid.

Procedure for Preparation of 2-[[7-amino-1-oxo-4-[3-(1H-pyrazol-4-yl)phenyl]isoindolin-2-yl]methyl]prop-2-enamide (Compound 359)

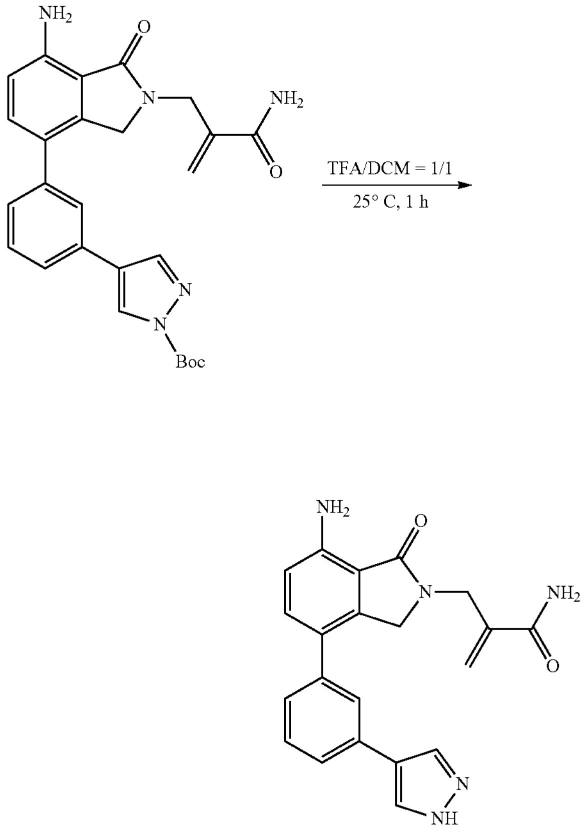

A mixture of tert-butyl 4-[3-[7-amino-2-(2-carbamoylallyl)-1-oxo-isoindolin-4-yl]phenyl]pyrazole-1-carboxylate (40 mg, 67.58 mol, 1 eq.) (80% purity) in DCM (0.5 mL) and trifluoroacetic acid (0.5 mL) was stirred at 25° C. for 1 h under nitrogen atmosphere. LCMS showed that the reaction was complete. The reaction mixture was added to ice water, then sat. $Na_2CO_3$ was slowly added to adjust the mixture to pH=8~9. The resulting solution was extracted with DCM (3×30 mL). The organic phase was separated, washed with water (2×30 mL) and brine (2×30 mL), dried over anhydrous sodium sulfate, filtered, and concentrated in vacuo to give a residue. The residue was purified by prep-HPLC to afford the title compound (1.5 mg, 3.94 μmol, 5.83% yield, 98% purity) as a light yellow solid. LC-MS: $[M+H]^+$ 374.1.

Route 14

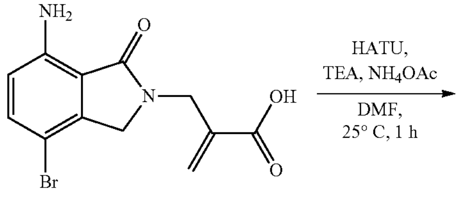

-continued

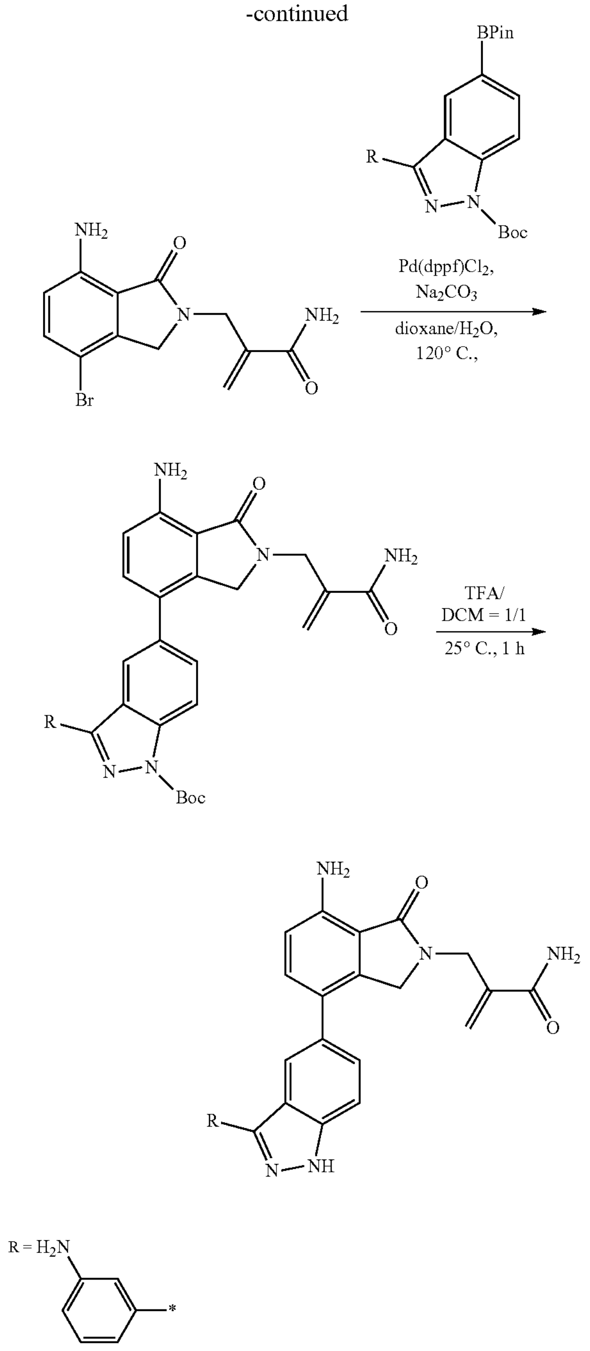

a. Preparation of 2-[(7-amino-4-bromo-1-oxo-isoindolin-2-yl)methyl]prop-2-enamide

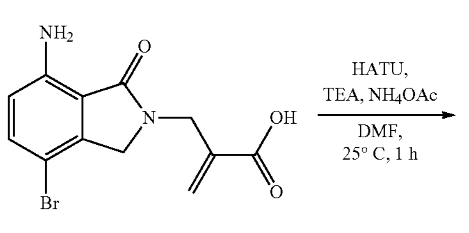

-continued

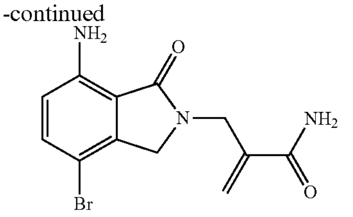

To a mixture of 2-[(7-amino-4-bromo-1-oxo-isoindolin-2-yl)methyl]prop-2-enoic acid (2.7 g, 8.68 mmol, 1 eq.) in DMF (100 mL) were added HATU (4.95 g, 13.02 mmol, 1.5 eq.) and TEA (4.39 g, 43.39 mmol, 6.04 mL, 5 eq.) in one portion at 25° C. under nitrogen. The mixture was stirred at 25° C. for 15 min, then $NH_4OAc$ (1 g, 13.02 mmol, 1.5 eq.) was added to the mixture. The mixture was stirred at 25° C. for 1 h. LCMS showed that the reaction was complete. The reaction was poured into water (100 mL) then extracted with EtOAc (3×50 mL). The combined organic layer was concentrated in vacuo. The residue was purified by column chromatography (silica gel; PE:EtOAc=5:1 to 0:1) to afford the title compound (1.1 g, 3.19 mmol, 36.78% yield, 90% purity) as a yellow solid.

b. Preparation of tert-butyl 5-[7-amino-2-(2-carbamoylallyl)-1-oxo-isoindolin-4-yl]-3-(3-aminophenyl)indazole-1-carboxylate

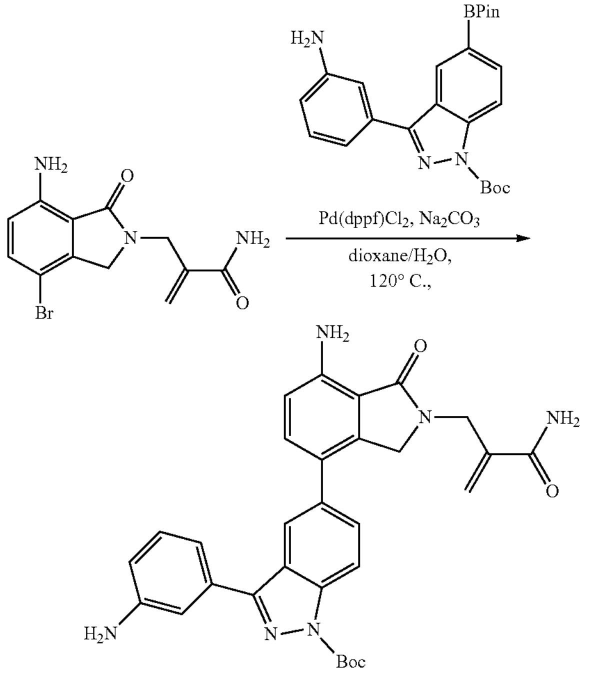

To a mixture of 2-[(7-amino-4-bromo-1-oxo-isoindolin-2-yl)methyl]prop-2-enamide (0.1 g, 322.43 μmol, 1 eq.) and tert-butyl 3-(3-aminophenyl)-5-(4,4,5,5-tetramethyl-1,3,2-dioxaborolan-2-yl)indazole-1-carboxylateBromide (140.36 mg, 322.43 μmol, 1 eq.) in dioxane (8 mL) and water (2 mL) were added $Cs_2CO_3$ (315.16 mg, 967.29 μmol, 3 eq.) and $Pd(dppf)Cl_2$ (23.59 mg, 32.24 μmol, 0.1 eq.) in one portion at 25° C. under nitrogen. The mixture was stirred at 100° C. for 10 min. LCMS showed that the reaction was complete.

The reaction was poured into 20 mL sat. EDTA, and diluted with 20 mL EtOAc. The mixture was then stirred at 25° C. for 1 h, and the aqueous layer was extracted with EtOAc (3×20 mL). The combined organic layer was washed with brine 20 mL, filtered, and concentrated in vacuo. The residue was purified by prep-TLC (silica gel; DCM:MeOH=10:1) to afford the title compound (0.08 g, 126.25 μmol, 39.16% yield, 85% purity) as a yellow solid.

General Procedure for 2-[[7-amino-4-[3-(3-amino-phenyl)-1H-indazol-5-yl]-1-oxo-isoindolin-2-yl] methyl]prop-2-enamide (Compound 342)

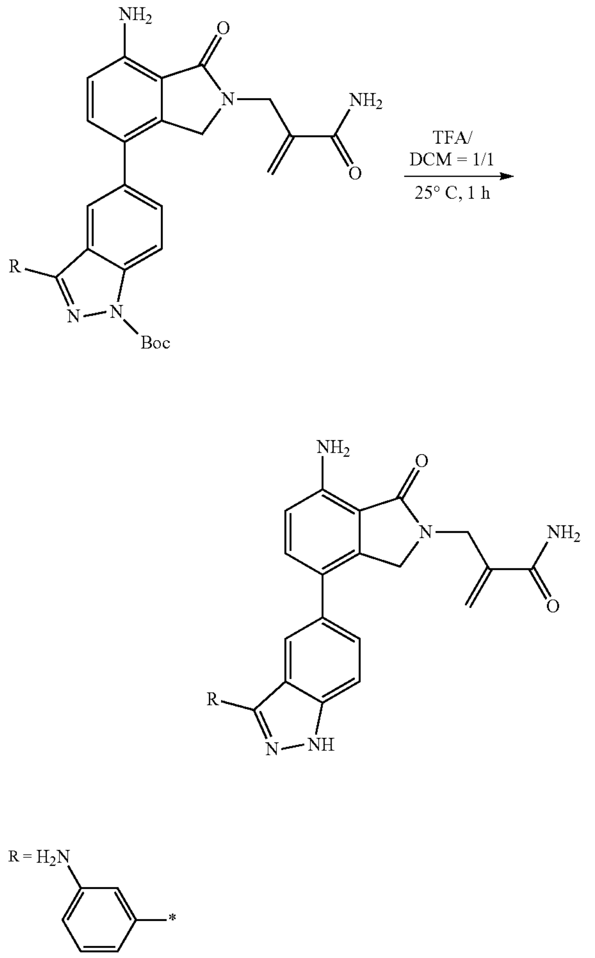

To a mixture of tert-butyl 5-[7-amino-2-(2-carbamoylallyl)-1-oxo-isoindolin-4-yl]-3-(3-aminophenyl)indazole-1-carboxylate (0.06, 111.40 μmol, 1 eq.) in DCM (3 mL) was added trifluoroacetic acid (1.54 g, 13.51 mmol, 1 mL, 121.24 eq.) in one portion at 25° C. under nitrogen. The mixture was stirred at 25° C. for 1 hrs. HPLC showed that the reaction was complete. The reaction was poured into sat. $NH_4Cl$ (30 mL) and extracted with EtOAc (3×20 mL). The combined organic layer was concentrated in vacuo. The residue was purified by prep-TLC (silica gel; DCM: MeOH=10:1) to afford the title compound (0.0052 g, 11.11 μmol, 9.97% yield, 93.7% purity) as a white solid. LC-MS: $[M+H]^+$ 439.3.

Preparation of tert-butyl 5-bromo-3-[3-(morpholinomethyl)phenyl]indazole-1-carboxylate

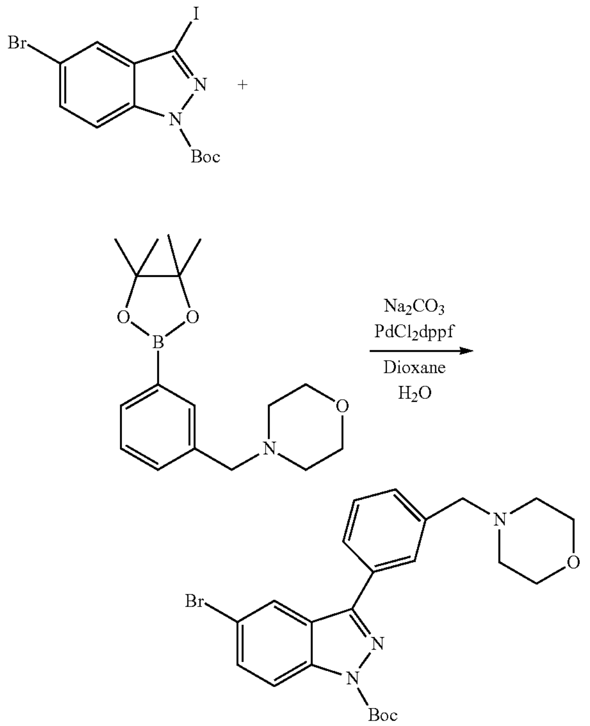

To a solution tert-butyl 5-bromo-3-iodo-indazole-1-carboxylate (300 mg, 708 μmol) in dioxane (8 mL) and water (1.6 mL) were added 4-[[3-(4,4,5,5-tetramethyl-1,3,2-dioxaborolan-2-yl)phenyl]methyl]morpholine (321.8 mg, 1.062 mmol), $Na_2CO_3$ (225 mg, 2.124 mmol) and $PdCl_2dppf$ (58 mg, 71 μmol). The reaction was heated to 100° C. for 3 h. The reaction mixture was passed through a celite pad. The solution was washed with brine, and the organic phase was dried over anhydrous sodium sulfate, filtered, and concentrated in vacuo. The residue was purified by chromatography on silica gel eluting with 0-50% EtOAc/hexane to afford the title compound (312 mg, Yield 93%).

Preparation of tert-butyl 5-[7-amino-2-(2-cyanoallyl)-1-oxo-isoindolin-4-yl]-3-[3-(morpholinomethyl) phenyl]indazole-1-carboxylate

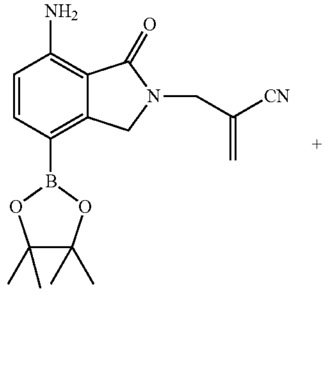

-continued

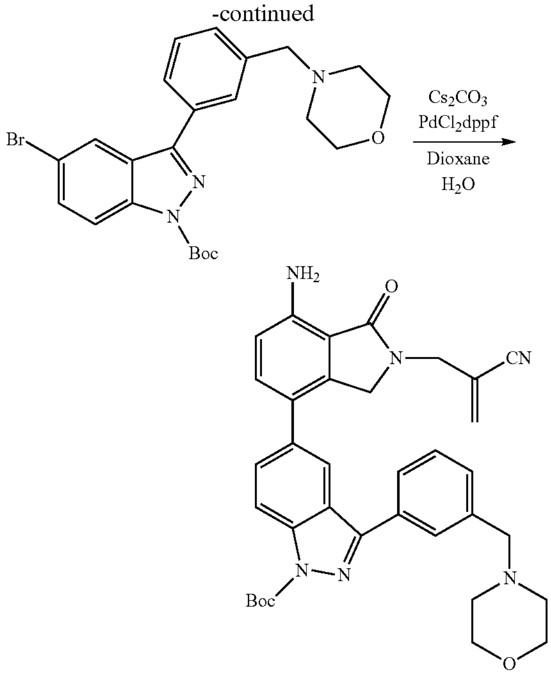

To a solution of 2-[[7-amino-1-oxo-4-(4,4,5,5-tetramethyl-1,3,2-dioxaborolan-2-yl)isoindolin-2-yl]methyl]prop-2-enenitrile (112 mg, 332 μmol) in dioxane (1 mL) and water (0.2 mL) were added tert-butyl 5-bromo-3-[3-(morpholinomethyl)phenyl]indazole-1-carboxylate (188 mg, 398 μmol), $Cs_2CO_3$ (324 mg, 996 mmol) and $PdCl_2$dppf (40 mg, 49 μmol). The reaction was heated to 100° C. for 1 h in a microwave. The reaction mixture was passed through a celite pad, and 2 mL of 0.5 M EDTA was added. The resulting solution was stirred at r.t. for 30 min. The solution was washed with brine, and the organic phase was dried over anhydrous sodium sulfate, filtered, and concentrated in vacuo. The residue was purified by chromatography on silica gel eluting with 50-100% EtOAc/hexane to afford the title compound (27.5 mg, Yield 14%).

Preparation of 2-[[7-amino-4-[3-[3-(morpholinomethyl)phenyl]-1H-indazol-5-yl]-1-oxo-isoindolin-2-yl]methyl]prop-2-enamide (Compound 291

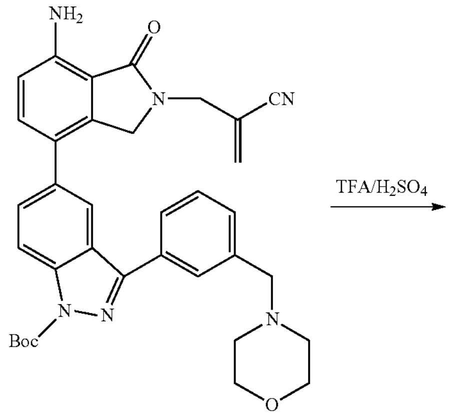

-continued

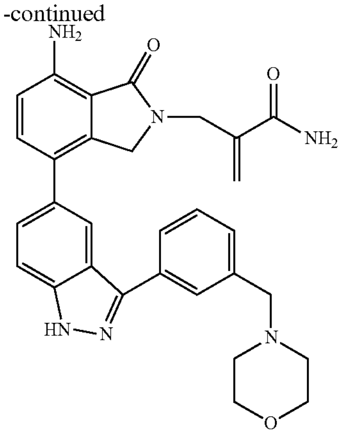

To a solution of tert-butyl 5-[7-amino-2-(2-cyanoallyl)-1-oxo-isoindolin-4-yl]-3-[3-(morpholinomethyl)phenyl]indazole-1-carboxylate (15 mg, 25 μmol) in trifluoroacetic acid (0.5 mL) was added one drop of $H_2SO_4$. The mixture was stirred at r.t. for 1 h. The reaction mixture was concentrated in vacuo and the mixture was partitioned between EtOAc and sat. $NaHCO_3$. The aqueous phase was extracted with EtOAc (2×). The combined organic phase was washed with water and brine, dried over ($MgSO_4$), filtered, and concentrated in vacuo. The residue was purified by reverse phase HPLC using a gradient of water 0.1% FA/acetonitrile 0.1% FA to afford the title compound (7.3 mg, Yield 56%). LC-MS: $[M+H]^+$ 523.3.

Preparation of tert-butyl 5-bromo-3-[5-(morpholinomethyl)-2-thienyl]indazole-1-carboxylate

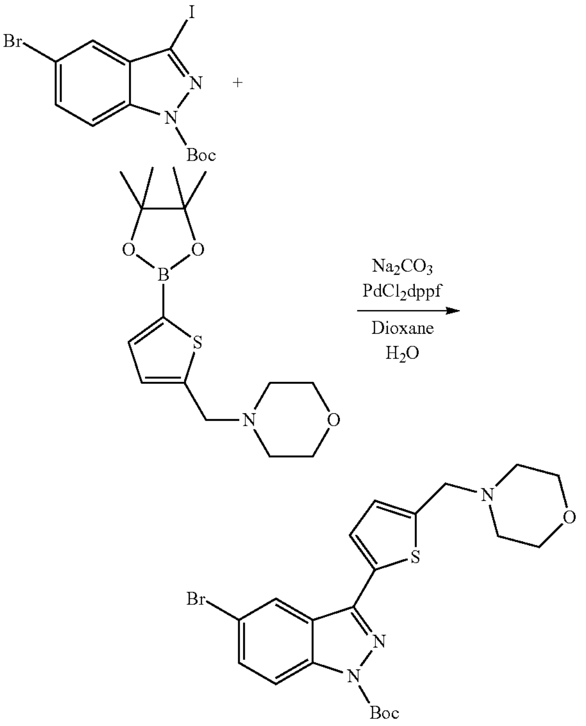

To a solution tert-butyl 5-bromo-3-iodo-indazole-1-carboxylate (200 mg, 472 μmol) in dioxane (2 mL) and water (0.4 mL) were added 4-[[5-(4,4,5,5-tetramethyl-1,3,2-dioxaborolan-2-yl)-2-thienyl]methyl]morpholine (218 mg, 0.708 mmol), $Na_2CO_3$ (150 mg, 1.416 mmol) and $PdCl_2$dppf (50 mg, 61 μmol). The reaction was heated to 100° C. for 3 h. The reaction mixture was passed through a celite pad. The solution was washed with brine, and the organic phase was dried over anhydrous sodium sulfate, filtered, and concentrated in vacuo. The residue was purified by chromatography on silica gel eluting with 0-50% EtOAc/hexane to afford the title compound (140 mg, Yield 62%).

Preparation of tert-butyl 5-[7-amino-2-(2-cyanoallyl)-1-oxo-isoindolin-4-yl]-3-[5-(morpholinomethyl)-2-thienyl]indazole-1-carboxylate

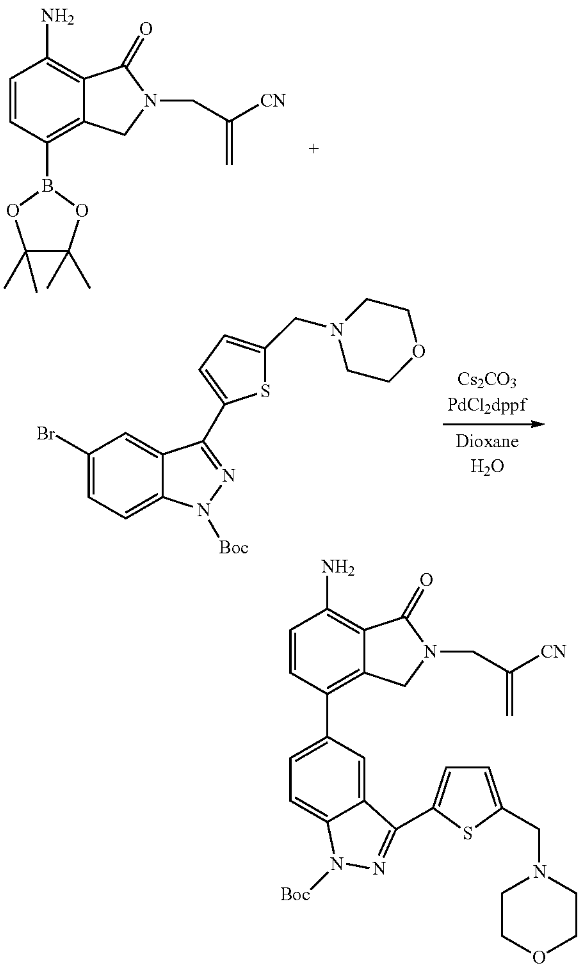

To a solution of 2-[[7-amino-1-oxo-4-(4,4,5,5-tetramethyl-1,3,2-dioxaborolan-2-yl)isoindolin-2-yl]methyl]prop-2-enenitrile (82.8 mg, 244 μmol) in dioxane (2 mL) and water (0.4 mL) were added tert-butyl 5-bromo-3-[5-(morpholinomethyl)-2-thienyl]indazole-1-carboxylate (140 mg, 293 μmol), $Cs_2CO_3$ (238 mg, 732 mmol) and $PdCl_2$dppf (40 mg, 49 μmol). The reaction was heated to 100° C. for 1 h in a microwave. The reaction mixture was passed through a celite pad, and 2 mL of 0.5 M EDTA was added. The resulting solution was stirred at r.t. for 30 min. The solution was washed with brine, and the organic phase was dried over anhydrous sodium sulfate, filtered, and concentrated in vacuo. The residue was purified by chromatography on silica gel eluting with 20-80% EtOAc/hexane to afford the title compound (59.2 mg, Yield 40%).

Preparation of 2-[[7-amino-4-[3-[5-(morpholinomethyl)-2-thienyl]-1H-indazol-5-yl]-1-oxo-isoindolin-2-yl]methyl]prop-2-enamide (Compound 292)

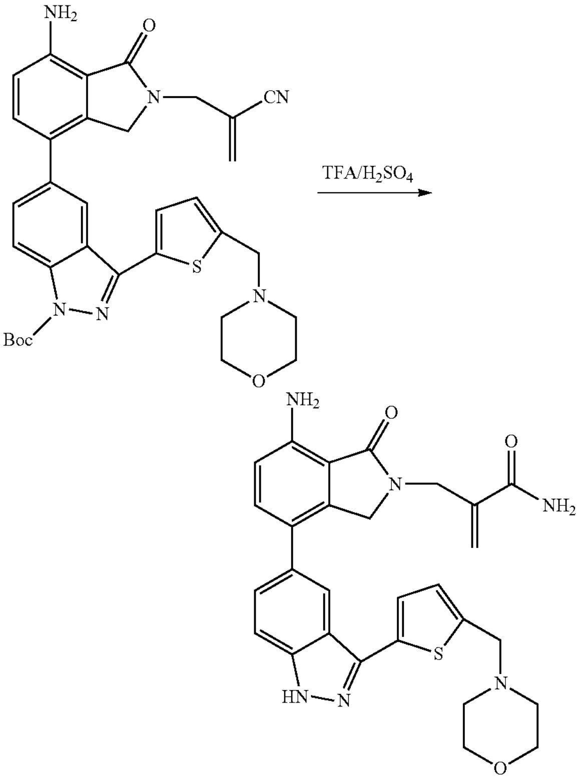

To a solution of tert-butyl 5-[7-amino-2-(2-cyanoallyl)-1-oxo-isoindolin-4-yl]-3-[5-(morpholinomethyl)-2-thienyl] indazole-1-carboxylate (20 mg, 32 μmol) in trifluoroacetic acid (0.5 mL) was added one drop of $H_2SO_4$. The mixture was stirred at r.t. for 1 h. The reaction mixture was concentrated in vacuo and The mixture was partitioned between EtOAc and sat. $NaHCO_3$. The aqueous phase was extracted with EtOAc (2×). The combined organic phase was washed with water and brine, dried over ($MgSO_4$), filtered, and concentrated in vacuo. The residue was purified by reverse phase HPLC using a gradient of water 0.1% FA/acetonitrile 0.1% FA to afford the title compound (3 mg, Yield 17%). LC-MS: $[M+H]^+$ 529.

Preparation of tert-butyl 3-[7-amino-2-(2-cyanoallyl)-1-oxo-isoindolin-4-yl]benzoate

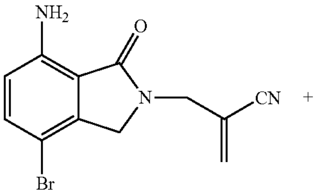

-continued

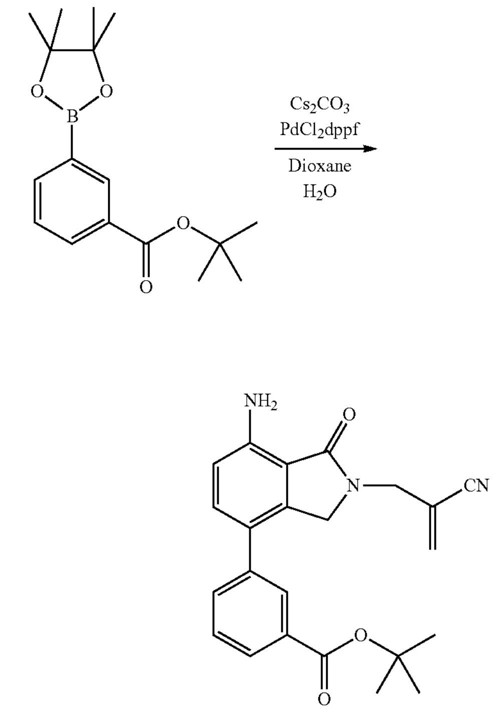

To a solution of 2-[(7-amino-4-bromo-1-oxo-isoindolin-2-yl)methyl]prop-2-enenitrile (60 mg, 205 μmol) in dioxane (3 mL) and water (0.3 mL) were added tert-butyl 3-(4,4,5,5-tetramethyl-1,3,2-dioxaborolan-2-yl)benzoate (93.7 mg, 308 μmol), $Cs_2CO_3$ (200 mg, 615 mmol) and $PdCl_2$dppf (18 mg, 22 μmol). The reaction was heated to 100° C. for 30 min in a microwave. The reaction mixture was passed through a celite pad, and 2 mL of 0.5 M EDTA was added. The resulting solution was stirred at r.t. for 30 min. The solution was washed with brine, and the organic phase was dried over anhydrous sodium sulfate, filtered, and concentrated in vacuo. The residue was purified by chromatography on silica gel eluting with 00-40% EtOAc/hexane to afford the title compound (67.5 mg, Yield 85%).

Preparation of 3-[7-amino-2-(2-carbamoylallyl)-1-oxo-isoindolin-4-yl]benzoic Acid (Compound 301)

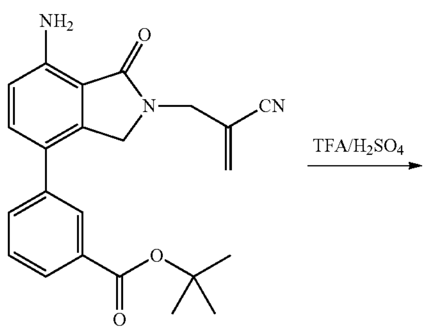

-continued

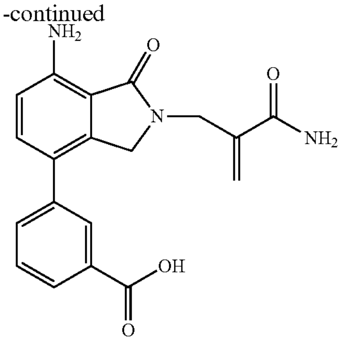

To a solution of tert-butyl 3-[7-amino-2-(2-cyanoallyl)-1-oxo-isoindolin-4-yl]benzoate (30 mg, 77 μmol) in trifluoroacetic acid (1.0 mL) was added 0.2 mL of $H_2SO_4$. The mixture was stirred at r.t. for 1 h. The reaction mixture was concentrated in vacuo and the mixture was partitioned between EtOAc and sat. $NaHCO_3$. The aqueous phase was extracted with EtOAc (2×). The combined organic phase was washed with water and brine, dried over ($MgSO_4$), filtered, and concentrated in vacuo. The residue was purified by reverse phase HPLC using a gradient of water 0.1% FA/acetonitrile 0.1% FA to afford the title compound (25 mg, Yield 93%). LC-MS: $[M+H]^+$ 352.

Preparation of 2-[[7-amino-4-(3,7-dimethyl-1H-indazol-5-yl)-oxo-isoindolin-2-yl]methyl]prop-2-enenitrile

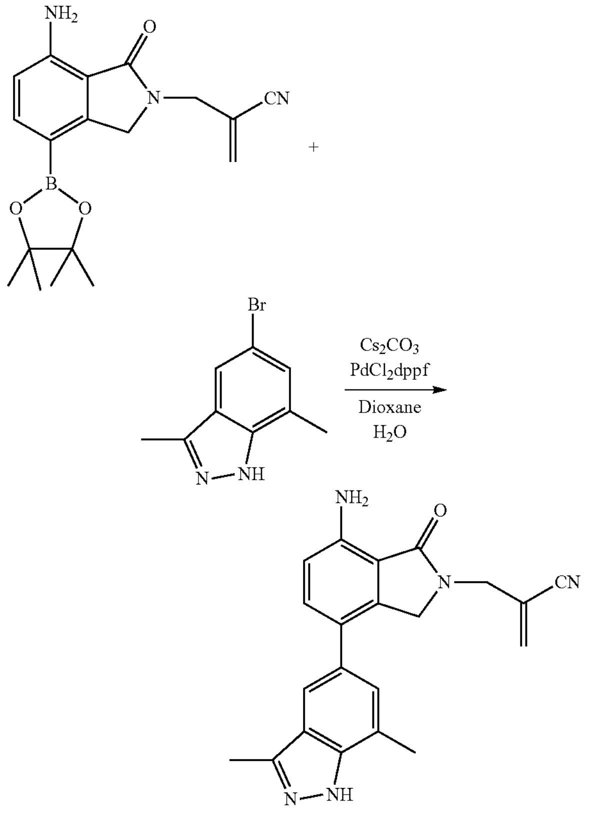

To a solution of 2-[[7-amino-1-oxo-4-(4,4,5,5-tetramethyl-1,3,2-dioxaborolan-2-yl)isoindolin-2-yl]methyl]prop- 2-enenitrile (50 mg, 147 μmol) in dioxane (1 mL) and water (0.2 mL) were added 5-bromo-3,7-dimethyl-1H-indazole (49.7 mg, 2221 μmol), $Cs_2CO_3$ (143 mg, 441 mmol) and $PdCl_2dppf$ (18 mg, 22 μmol). The reaction was heated to 100° C. for 1 h in a microwave. The reaction mixture was passed through a celite pad, and 2 mL of 0.5 M EDTA was added. The resulting solution was stirred at r.t. for 30 min. The solution was washed with brine, and the organic phase was dried over anhydrous sodium sulfate, filtered, and concentrated in vacuo. The residue was purified by chromatography on silica gel eluting with 20-100% EtOAc/hexane to afford the title compound (19.7 mg, Yield 38%).

Preparation of 2-[[7-amino-4-(3,7-dimethyl-1H-indazol-5-yl)-1-oxo-isoindolin-2-yl]methyl]prop-2-enamide (Compound 304)

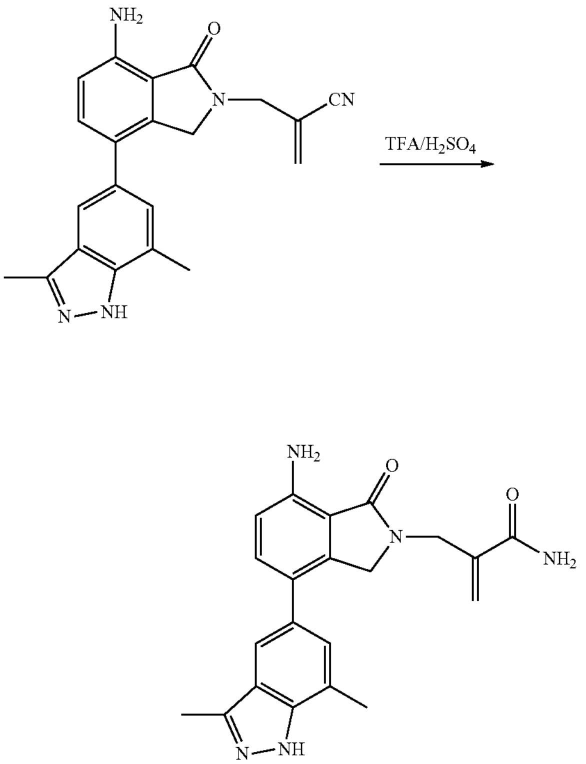 [SMILES: C=C(C#N)CN1Cc2c(-c3cc(C)c4[nH]nc(C)c4c3)ccc(N)c2C1=O ; C=C(CN1Cc2c(-c3cc(C)c4[nH]nc(C)c4c3)ccc(N)c2C1=O)C(N)=O]

To a solution of 2-[[7-amino-4-(3,7-dimethyl-1H-indazol-5-yl)-1-oxo-isoindolin-2-yl]methyl]prop-2-enenitrile (19.7 mg, 55 μmol) in trifluoroacetic acid (1.0 mL) was added one drop of $H_2SO_4$. The mixture was stirred at r.t. for 1 h. The reaction mixture was concentrated in vacuo and the mixture was partitioned between EtOAc and sat. $NaHCO_3$. The aqueous phase was extracted with EtOAc (2×). The combined organic phase was washed with water and brine, dried over ($MgSO_4$), filtered, and concentrated in vacuo. The residue was purified by reverse phase HPLC using a gradient of water 0.1% FA/acetonitrile 0.1% FA to afford the title compound (11.1 mg, Yield 54%). LC-MS: $[M+H]^+$ 376.2.

Preparation of 7-isopropyl-5-(4,4,5,5-tetramethyl-1,3,2-dioxaborolan-2-yl)-1H-indazole

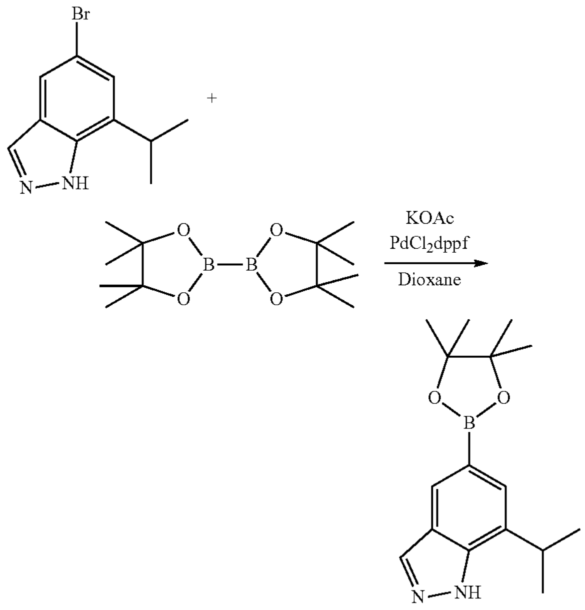

To a solution of 5-bromo-7-isopropyl-1H-indazole (100 mg, 418 μmol) in dioxane (2 mL) were added 4,4,5,5-tetramethyl-2-(4,4,5,5-tetramethyl-1,3,2-dioxaborolan-2-yl)-1,3,2-dioxaborolane (399 mg, 1.571 mmol), KOAc (123 mg, 1.254 mmol) and $PdCl_2dppf$ (19 mg, 23 μmol). The reaction was heated to 100° C. for 2 h in a microwave. The reaction mixture was passed through a celite pad, and the solvent was removed in vacuo. The residue was purified by chromatography on silica gel eluting with 10-60% EtOAc/hexane to afford the title compound (95 mg, Yield 79%).

Preparation of 2-[[7-amino-4-(7-isopropyl-1H-indazol-5-yl)-1-oxo-isoindolin-2-yl]methyl]prop-2-enenitrile

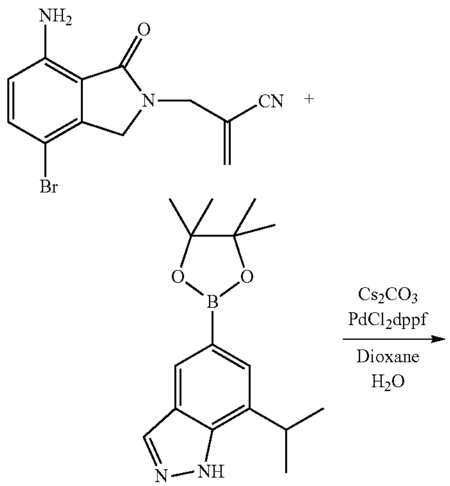

-continued

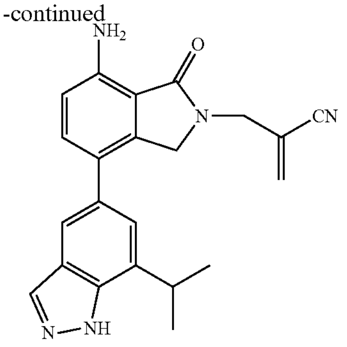

To a solution of 2-[(7-amino-4-bromo-1-oxo-isoindolin-2-yl)methyl]prop-2-enenitrile (50 mg, 171 μmol) in dioxane (2 mL) and water (0.4 mL) were added 7-isopropyl-5-(4,4,5,5-tetramethyl-1,3,2-dioxaborolan-2-yl)-1H-indazole (59.8 mg, 209 μmol), $Cs_2CO_3$ (166 mg, 513 μmol) and $PdCl_2dppf$ (18 mg, 22 μmol). The reaction was heated to 100° C. for 30 min in a microwave. The reaction mixture was passed through a celite pad, and 2 mL of 0.5 M EDTA was added. The resulting solution was stirred at r.t. for 30 min. The solution was washed with brine, and the organic phase was dried over anhydrous sodium sulfate, filtered, and concentrated in vacuo. The residue was purified by chromatography on silica gel eluting with 20-80% EtOAc/hexane to afford the title compound (13.6 mg, Yield 21%).

Preparation of 2-[[7-amino-4-(7-isopropyl-1H-indazol-5-yl)-1-oxo-isoindolin-2-yl]methyl]prop-2-enamide (Compound 308)

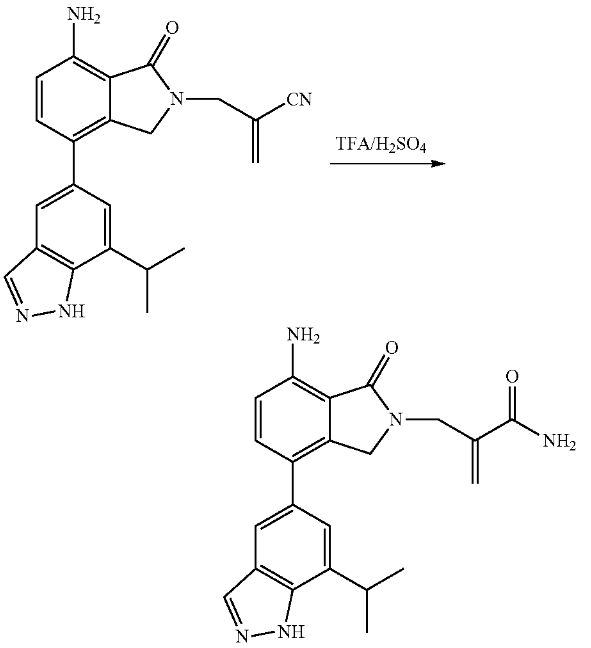

To a solution of 2-[[7-amino-4-(7-isopropyl-1H-indazol-5-yl)-1-oxo-isoindolin-2-yl]methyl]prop-2-enenitrile (13.6 mg, 37 μmol) in trifluoroacetic acid (1.0 mL) was added one drop of $H_2SO_4$. The mixture was stirred at r.t. for 2 h. The reaction mixture was concentrated in vacuo and the mixture was partitioned between EtOAc and sat. $NaHCO_3$. The aqueous phase was extracted with EtOAc (2×). The combined organic phase was washed with water and brine, dried over ($MgSO_4$), filtered, and concentrated in vacuo. The residue was purified by reverse phase HPLC using a gradient of water 0.1% FA/acetonitrile 0.1% FA to afford the title compound (7 mg, Yield 49%). LC-MS: $[M+H]^+$ 390.2.

Preparation of 7-chloro-5-(4,4,5,5-tetramethyl-1,3,2-dioxaborolan-2-yl)-1H-indazole

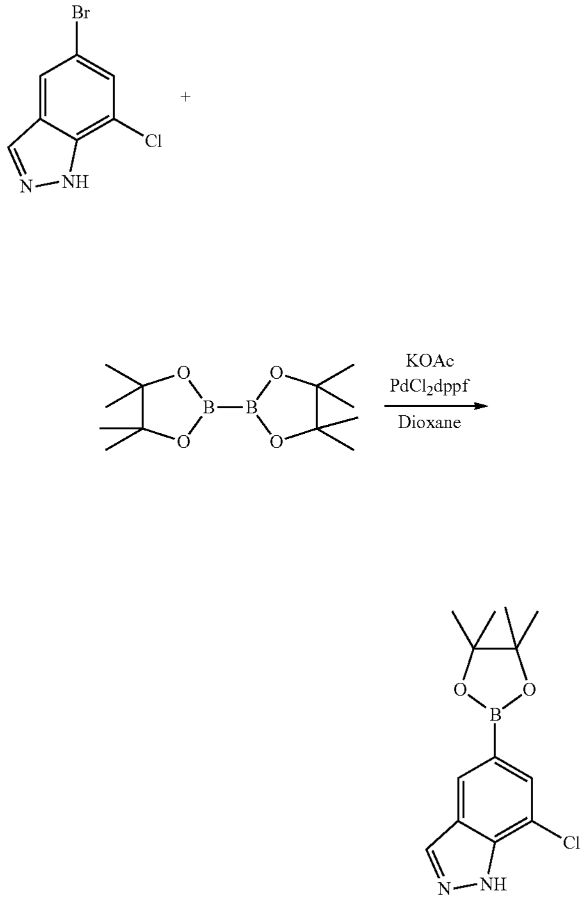

To a solution of 5-bromo-5-chloro-1H-indazole (200 mg, 864 μmol) in dioxane (10 mL) were added 4,4,5,5-tetramethyl-2-(4,4,5,5-tetramethyl-1,3,2-dioxaborolan-2-yl)-1,3,2-dioxaborolane (658 mg, 2.592 mmol), KOAc (424 mg, 4.32 mmol) and $PdCl_2dppf$ (80 mg, 98 μmol). The reaction was heated to 100° C. for 2 h. The reaction mixture was passed through a celite pad, and the solvent was removed in vacuo. The residue was purified by chromatography on silica gel eluting with 0-20% EtOAc/hexane to afford the title compound (163 mg, Yield 68%).

Preparation of 2-[[7-amino-4-(7-chloro-1H-indazol-5-yl)-1-oxo-isoindolin-2-yl]methyl]prop-2-enenitrile

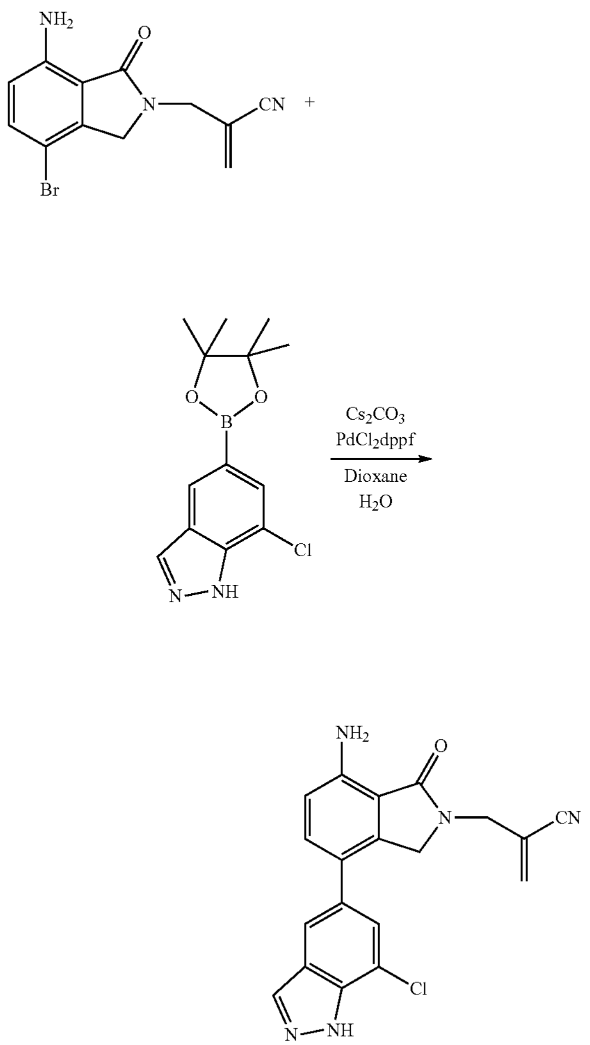

To a solution of 2-[(7-amino-4-bromo-1-oxo-isoindolin-2-yl)methyl]prop-2-enenitrile (100 mg, 342 μmol) in dioxane (2 mL) and water (0.4 mL) were added 7-chloro-5-(4,4,5,5-tetramethyl-1,3,2-dioxaborolan-2-yl)-1H-indazole (163 mg, 585 μmol), $Cs_2CO_3$ (333 mg, 1.026 mmol) and $PdCl_2dppf$ (40 mg, 49 μmol). The reaction was heated to 120° C. for 1 h a microwave. The reaction mixture was passed through a celite pad, and 2 mL of 0.5 M EDTA was added. The resulting solution was stirred at r.t. for 30 min. The solution was washed with brine, and the organic phase was dried over anhydrous sodium sulfate, filtered, and concentrated in vacuo. The residue was purified by chromatography on silica gel eluting with 20-80% EtOAc/hexane to afford the title compound (56 mg, Yield 45%).

Preparation of 2-[[7-amino-4-(7-chloro-1H-indazol-5-yl)-1-oxo-isoindolin-2-yl]methyl]prop-2-enamide (Compound 311)

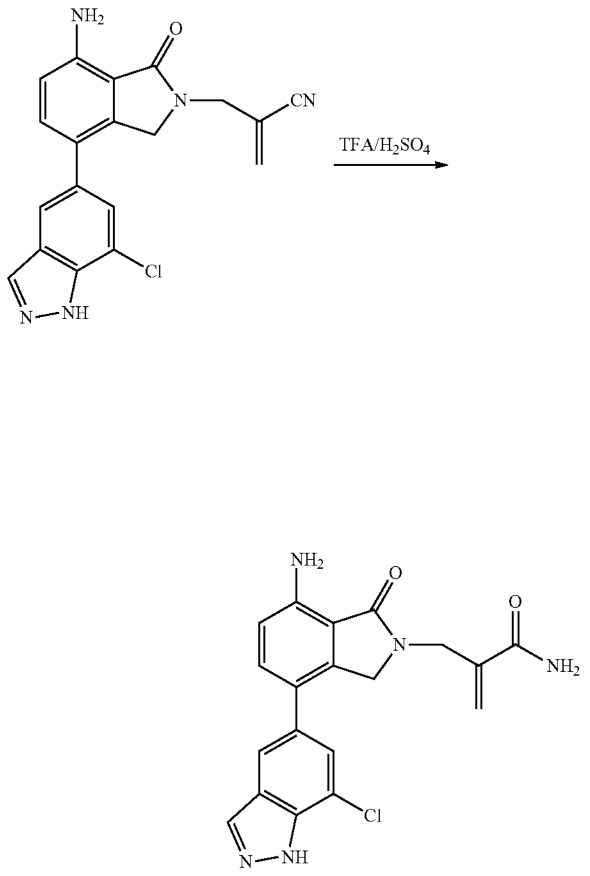

To a solution of 2-[[7-amino-4-(7-chloro-1H-indazol-5-yl)-1-oxo-isoindolin-2-yl]methyl]prop-2-enenitrile (26.7 mg, 73 μmol) in trifluoroacetic acid (1.0 mL) was added two drops of $H_2SO_4$. The mixture was stirred at r.t. for 2 h. The reaction mixture was concentrated in vacuo and the mixture was partitioned between EtOAc and sat. $NaHCO_3$. The aqueous phase was extracted with EtOAc (2×). The combined organic phase was washed with water and brine, dried over ($MgSO_4$), filtered, and concentrated in vacuo. The residue was purified by reverse phase HPLC using a gradient of water 0.1% FA/acetonitrile 0.1% FA to afford the title compound (6.7 mg, Yield 24%). LC-MS: $[M+H]^+$ 382.1.

TABLE 4 shows compounds comprising an amine-substituted isoindolinone core and acrylamide moiety prepared using the methods described above.

TABLE 4
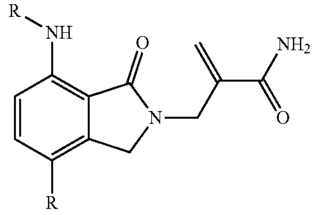
| Cpd. No. | Structure | IUPAC | LC-MS (ES+, m/z) |
|---|---|---|---|
| 272. | 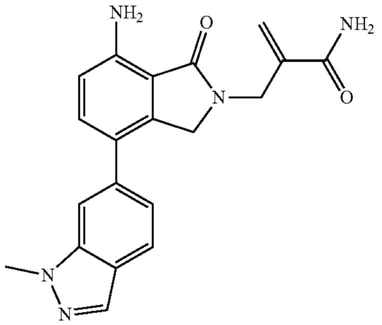 [SMILES: C=C(CN1Cc2c(-c3ccc4cnn(C)c4c3)ccc(N)c2C1=O)C(N)=O] | 2-{[7-amino-4-(1-methyl-1H-indazol-6-yl)-1-oxo-2,3-dihydro-1H-isoindol-2-yl]methyl}prop-2-enamide | 362.1 |
| 273. | 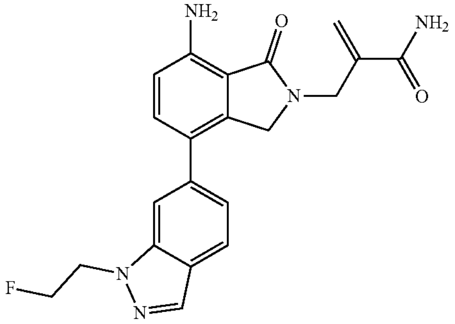 [SMILES: C=C(CN1Cc2c(-c3ccc4cnn(CCF)c4c3)ccc(N)c2C1=O)C(N)=O] | 2-({7-amino-4-[1-(2-fluoroethyl)-1H-indazol-6-yl]-1-oxo-2,3-dihydro-1H-isoindol-2-yl}methyl)prop-2-enamide | 394.1 |
| 274. | 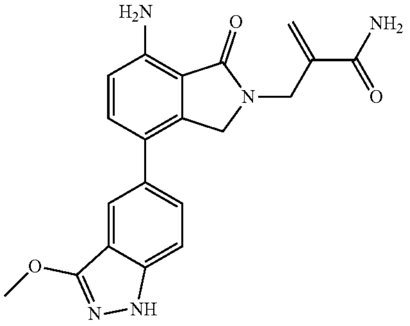 [SMILES: C=C(CN1Cc2c(-c3ccc4[nH]nc(OC)c4c3)ccc(N)c2C1=O)C(N)=O] | 2-{[7-amino-4-(3-methoxy-1H-indazol-5-yl)-1-oxo-2,3-dihydro-1H-isoindol-2-yl]methyl}prop-2-enamide | 378.1 |
| 275. | 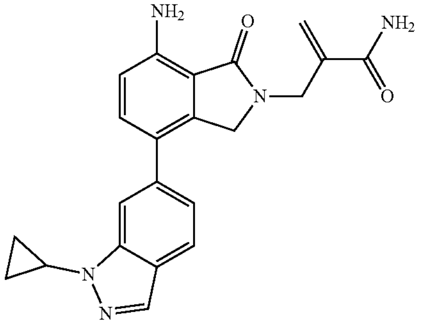 [SMILES: C=C(CN1Cc2c(-c3ccc4cnn(C5CC5)c4c3)ccc(N)c2C1=O)C(N)=O] | 2-{[7-amino-4-(1-cyclopropyl-1H-indazol-6-yl)-1-oxo-2,3-dihydro-1H-isoindol-2-yl]methyl}prop-2-enamide | 388.1 |

TABLE 4-continued
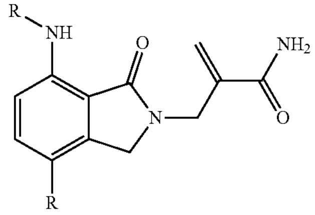
| Cpd. No. | Structure | IUPAC | LC-MS (ES+, m/z) |
|---|---|---|---|
| 276. | 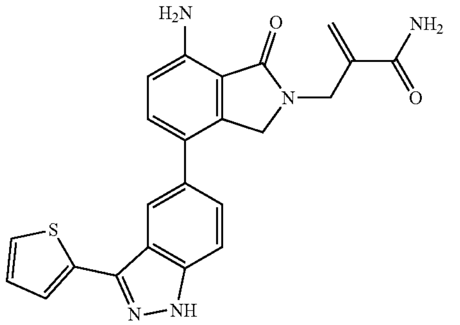 [SMILES: C=C(CN1Cc2c(-c3ccc4[nH]nc(-c5cccs5)c4c3)ccc(N)c2C1=O)C(N)=O] | 2-({7-amino-1-oxo-4-[3-(thiophen-2-yl)-1H-indazol-5-yl]-2,3-dihydro-1H-isoindol-2-yl}methyl)prop-2-enamide | 430.1 |
| 277. | 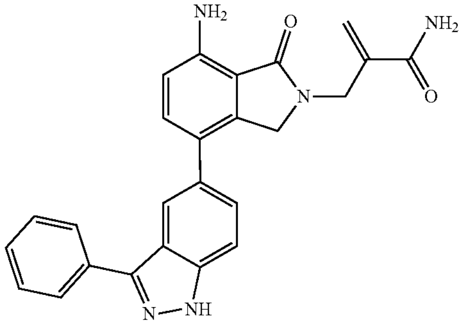 [SMILES: C=C(CN1Cc2c(-c3ccc4[nH]nc(-c5ccccc5)c4c3)ccc(N)c2C1=O)C(N)=O] | 2-{[7-amino-1-oxo-4-(3-phenyl-1H-indazol-5-yl)-2,3-dihydro-1H-isoindol-2-yl]methyl}prop-2-enamide | 424.2 |
| 278. | 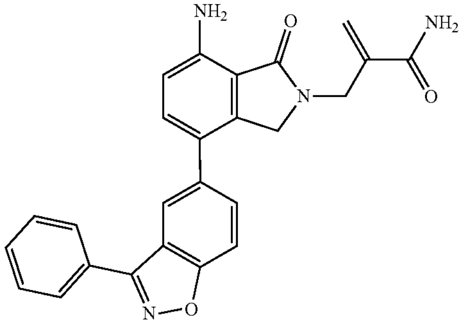 [SMILES: C=C(CN1Cc2c(-c3ccc4onc(-c5ccccc5)c4c3)ccc(N)c2C1=O)C(N)=O] | 2-{[7-amino-1-oxo-4-(3-phenyl-1,2-benzoxazol-5-yl)-2,3-dihydro-1H-isoindol-2-yl]methyl}prop-2-enamide | 425.1 |
| 279. | 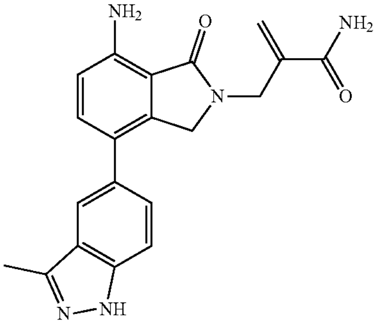 [SMILES: C=C(CN1Cc2c(-c3ccc4[nH]nc(C)c4c3)ccc(N)c2C1=O)C(N)=O] | 2-{[7-amino-4-(3-methyl-1H-indazol-5-yl)-1-oxo-2,3-dihydro-1H-isoindol-2-yl]methyl}prop-2-enamide | 362.1 |

TABLE 4-continued

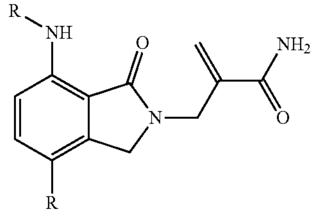

| Cpd. No. | Structure | IUPAC | LC-MS (ES+, m/z) |
|---|---|---|---|
| 280. | 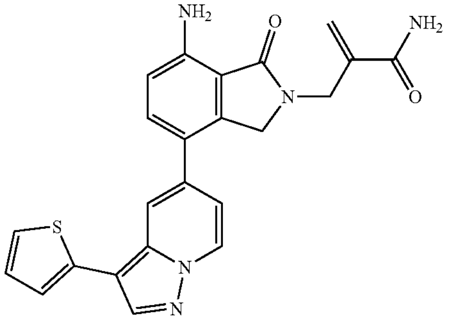 [SMILES: C=C(CN1Cc2c(-c3ccn4ncc(-c5cccs5)c4c3)ccc(N)c2C1=O)C(N)=O] | 2-({7-amino-1-oxo-4-[3-(thiophen-2-yl)pyrazolo[1,5-a]pyridin-5-yl]-2,3-dihydro-1H-isoindol-2-yl}methyl)prop-2-enamide | 430 |
| 281. | 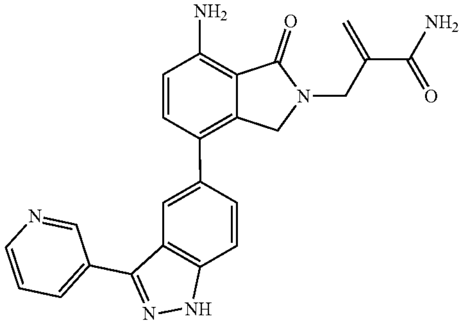 [SMILES: C=C(CN1Cc2c(-c3ccc4[nH]nc(-c5cccnc5)c4c3)ccc(N)c2C1=O)C(N)=O] | 2-({7-amino-1-oxo-4-[3-(pyridin-3-yl)-1H-indazol-5-yl]-2,3-dihydro-1H-isoindol-2-yl}methyl)prop-2-enamide | 425.1 |
| 282. | 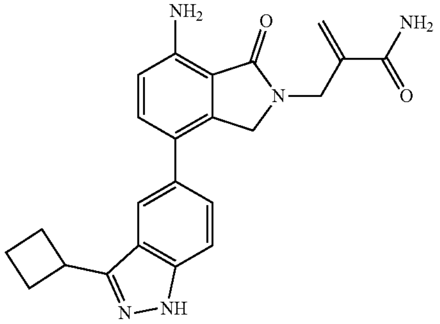 [SMILES: C=C(CN1Cc2c(-c3ccc4[nH]nc(C5CCC5)c4c3)ccc(N)c2C1=O)C(N)=O] | 2-{[7-amino-4-(3-cyclobutyl-1H-indazol-5-yl)-1-oxo-2,3-dihydro-1H-isoindol-2-yl]methyl}prop-2-enamide | 402.1 |
| 283. | 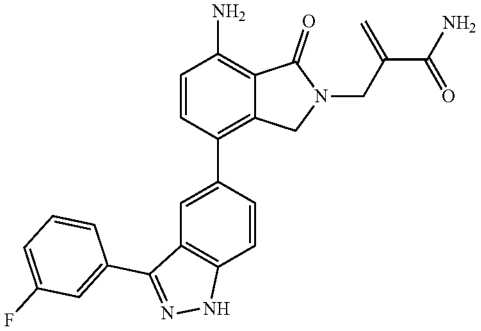 [SMILES: C=C(CN1Cc2c(-c3ccc4[nH]nc(-c5cccc(F)c5)c4c3)ccc(N)c2C1=O)C(N)=O] | 2-({7-amino-4-[3-(3-fluorophenyl)-1H-indazol-5-yl]-1-oxo-2,3-dihydro-1H-isoindol-2-yl}methyl)prop-2-enamide | 442.1 |

TABLE 4-continued

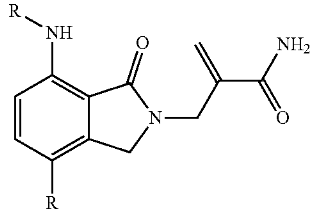

| Cpd. No. | Structure | IUPAC | LC-MS (ES+, m/z) |
|---|---|---|---|
| 284. | 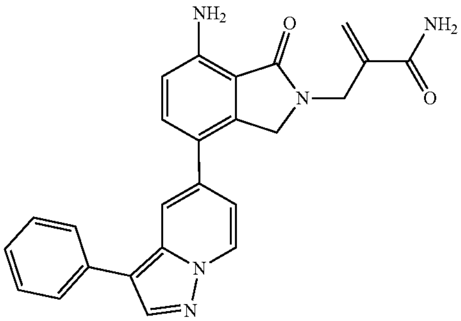 [SMILES: C=C(CN1Cc2c(-c3ccn4ncc(-c5ccccc5)c4c3)ccc(N)c2C1=O)C(N)=O] | 2-[(7-amino-1-oxo-4-{3-phenylpyrazolo[1,5-a]pyridin-5-yl}-2,3-dihydro-1H-isoindol-2-yl)methyl]prop-2-enamide | 424.1 |
| 285. | 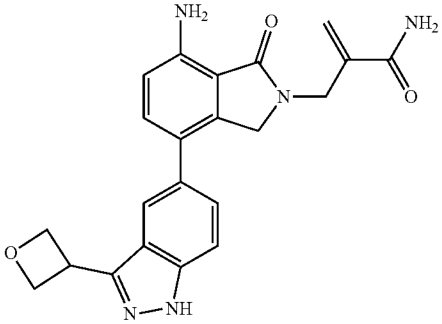 [SMILES: C=C(CN1Cc2c(-c3ccc4[nH]nc(C5COC5)c4c3)ccc(N)c2C1=O)C(N)=O] | 2-({7-amino-4-[3-(oxetan-3-yl)-1H-indazol-5-yl]-1-oxo-2,3-dihydro-1H-isoindol-2-yl}methyl)prop-2-enamide | 404.1 |
| 286. | 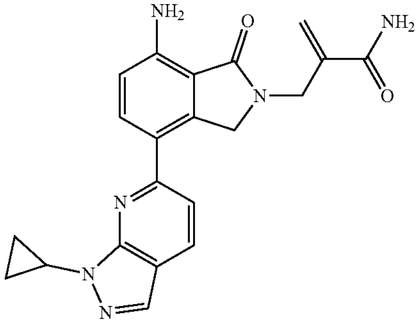 [SMILES: C=C(CN1Cc2c(-c3ccc4cnn(C5CC5)c4n3)ccc(N)c2C1=O)C(N)=O] | 2-[(7-amino-4-{1-cyclopropyl-1H-pyrazolo[3,4-b]pyridin-6-yl}-1-oxo-2,3-dihydro-1H-isoindol-2-yl)methyl]prop-2-enamide | 389.1 |
| 287. | 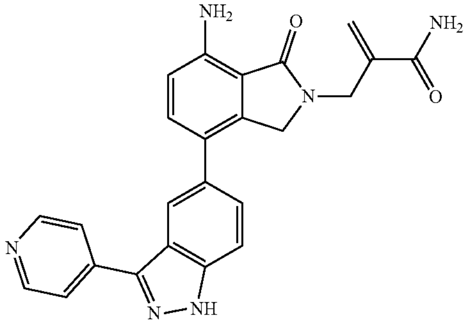 [SMILES: C=C(CN1Cc2c(-c3ccc4[nH]nc(-c5ccncc5)c4c3)ccc(N)c2C1=O)C(N)=O] | 2-({7-amino-1-oxo-4-[3-(pyridin-4-yl)-1H-indazol-5-yl]-2,3-dihydro-1H-isoindol-2-yl}methyl)prop-2-enamide | 425.1 |

TABLE 4-continued

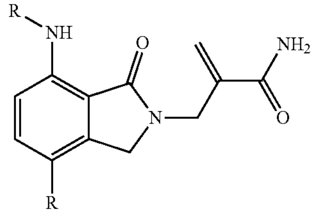

| Cpd. No. | Structure | IUPAC | LC-MS (ES+, m/z) |
|---|---|---|---|
| 288. | 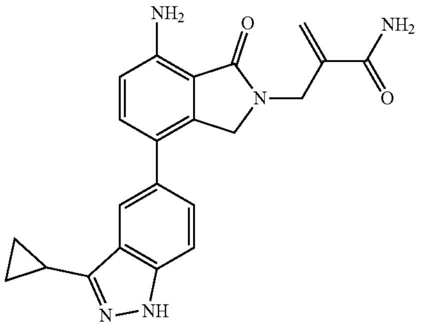 [SMILES: C=C(CN1Cc2c(-c3ccc4[nH]nc(C5CC5)c4c3)ccc(N)c2C1=O)C(N)=O] | 2-{[7-amino-4-(3-cyclopropyl-1H-indazol-5-yl)-1-oxo-2,3-dihydro-1H-isoindol-2-yl]methyl}prop-2-enamide | 388.1 |
| 289. | 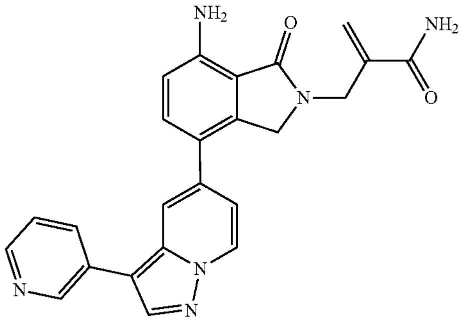 [SMILES: C=C(CN1Cc2c(-c3ccn4ncc(-c5cccnc5)c4c3)ccc(N)c2C1=O)C(N)=O] | 2-({7-amino-1-oxo-4-[3-(pyridin-3-yl)pyrazolo[1,5-a]pyridin-5-yl]-2,3-dihydro-1H-isoindol-2-yl}methyl)prop-2-enamide | 425.2 |
| 290. | 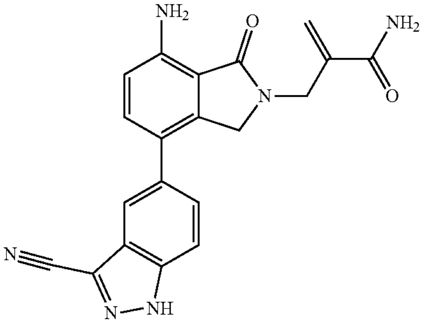 [SMILES: C=C(CN1Cc2c(-c3ccc4[nH]nc(C#N)c4c3)ccc(N)c2C1=O)C(N)=O] | 2-{[7-amino-4-(3-cyano-1H-indazol-5-yl)-1-oxo-2,3-dihydro-1H-isoindol-2-yl]methyl}prop-2-enamide | 373.1 |
| 291. | 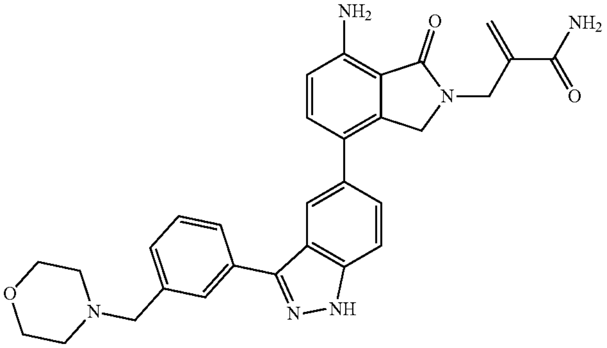 [SMILES: C=C(CN1Cc2c(-c3ccc4[nH]nc(-c5cccc(CN6CCOCC6)c5)c4c3)ccc(N)c2C1=O)C(N)=O] | 2-{[7-amino-4-(3-{3-[(morpholin-4-yl)methyl]phenyl}-1H-indazol-5-yl)-1-oxo-2,3-dihydro-1H-isoindol-2-yl]methyl}prop-2-enamide | 523.3 |

TABLE 4-continued
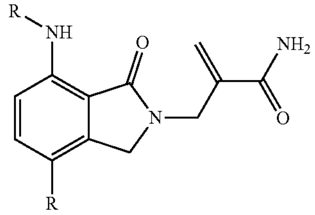
| Cpd. No. | Structure | IUPAC | LC-MS (ES+, m/z) |
|---|---|---|---|
| 292. | 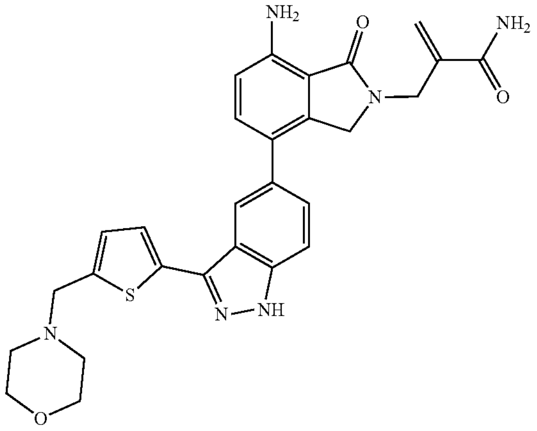 [SMILES: C=C(CN1Cc2c(-c3ccc4[nH]nc(-c5ccc(CN6CCOCC6)s5)c4c3)ccc(N)c2C1=O)C(N)=O] | 2-{[7-amino-4-(3-{5-[(morpholin-4-yl)methyl]thiophen-2-yl}-1H-indazol-5-yl)-1-oxo-2,3-dihydro-1H-isoindol-2-yl]methyl}prop-2-enamide | 529.2 |
| 293. | 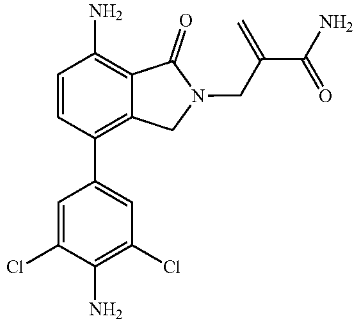 [SMILES: C=C(CN1Cc2c(-c3cc(Cl)c(N)c(Cl)c3)ccc(N)c2C1=O)C(N)=O] | 2-{[7-amino-4-(4-amino-3,5-dichlorophenyl)-1-oxo-2,3-dihydro-1H-isoindol-2-yl]methyl}prop-2-enamide | 391 |
| 294. | 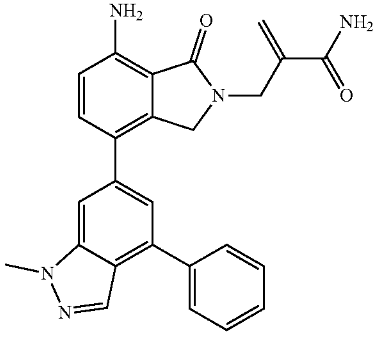 [SMILES: C=C(CN1Cc2c(-c3cc(-c4ccccc4)c4cnn(C)c4c3)ccc(N)c2C1=O)C(N)=O] | 2-{[7-amino-4-(1-methyl-4-phenyl-1H-indazol-6-yl)-1-oxo-2,3-dihydro-1H-isoindol-2-yl]methyl}prop-2-enamide | 438.1 |

TABLE 4-continued
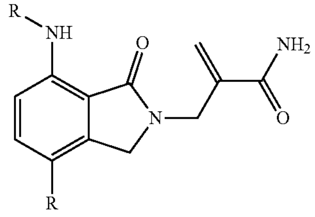
| Cpd. No. | Structure | IUPAC | LC-MS (ES+, m/z) |
|---|---|---|---|
| 295. | 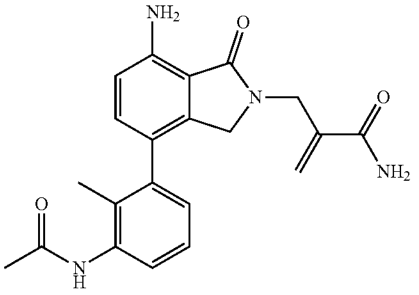 [SMILES: C=C(CN1Cc2c(-c3cccc(NC(C)=O)c3C)ccc(N)c2C1=O)C(N)=O] | 2-{[7-amino-4-(3-acetamido-2-methylphenyl)-1-oxo-2,3-dihydro-1H-isoindol-2-yl]methyl}prop-2-enamide | 379.1 |
| 296. | 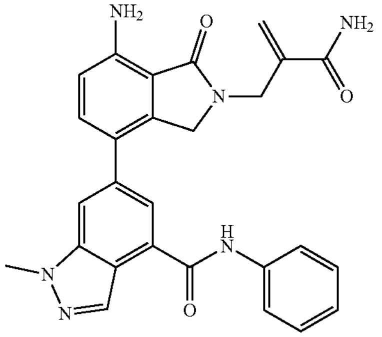 [SMILES: C=C(CN1Cc2c(-c3cc(C(=O)Nc4ccccc4)c4cnn(C)c4c3)ccc(N)c2C1=O)C(N)=O] | 6-[7-amino-2-(2-carbamoyl-2-methylideneethyl)-1-oxo-2,3-dihydro-1H-isoindol-4-yl]-1-methyl-N-phenyl-1H-indazole-4-carboxamide | 481.1 |
| 297. | 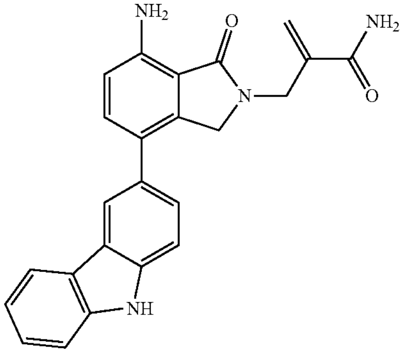 [SMILES: C=C(CN1Cc2c(-c3ccc4[nH]c5ccccc5c4c3)ccc(N)c2C1=O)C(N)=O] | 2-{[7-amino-4-(9H-carbazol-3-yl)-1-oxo-2,3-dihydro-1H-isoindol-2-yl]methyl}prop-2-enamide | 397.1 |

TABLE 4-continued
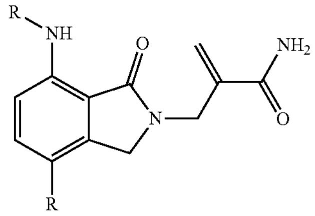
| Cpd. No. | Structure | IUPAC | LC-MS (ES+, m/z) |
|---|---|---|---|
| 298. | 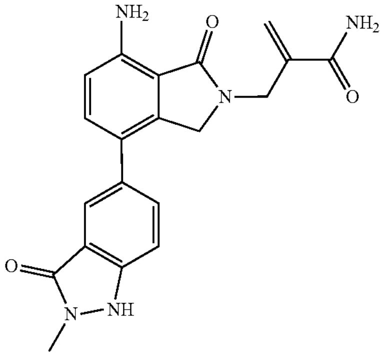 [SMILES: C=C(CN1Cc2c(-c3ccc4[nH]n(C)c(=O)c4c3)ccc(N)c2C1=O)C(N)=O] | 2-{[7-amino-4-(2-methyl-3-oxo-2,3-dihydro-1H-indazol-5-yl)-1-oxo-2,3-dihydro-1H-isoindol-2-yl]methyl}prop-2-enamide | 378.1 |
| 299. | 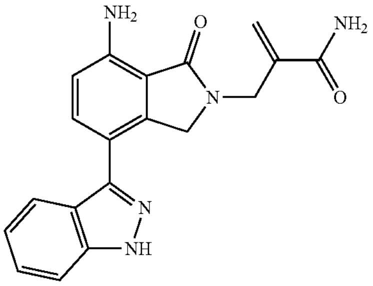 [SMILES: C=C(CN1Cc2c(-c3n[nH]c4ccccc34)ccc(N)c2C1=O)C(N)=O] | 2-{[7-amino-4-(1H-indazol-3-yl)-1-oxo-2,3-dihydro-1H-isoindol-2-yl]methyl}prop-2-enamide | 348.1 |
| 300. | 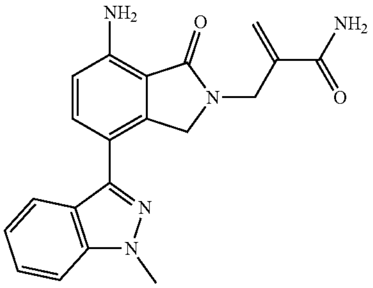 [SMILES: C=C(CN1Cc2c(-c3nn(C)c4ccccc34)ccc(N)c2C1=O)C(N)=O] | 2-{[7-amino-4-(1-methyl-1H-indazol-3-yl)-1-oxo-2,3-dihydro-1H-isoindol-2-yl]methyl}prop-2-enamide | 362.1 |
| 301. | 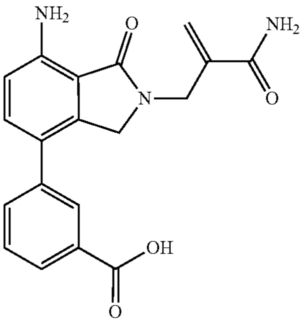 [SMILES: C=C(CN1Cc2c(-c3cccc(C(=O)O)c3)ccc(N)c2C1=O)C(N)=O] | 3-[7-amino-2-(2-carbamoyl-2-methylideneethyl)-1-oxo-2,3-dihydro-1H-isoindol-4-yl]benzoic acid | 352.2 |

TABLE 4-continued
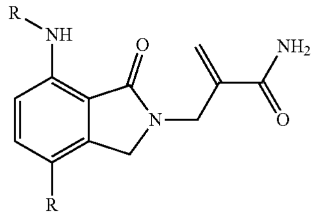
| Cpd. No. | Structure | IUPAC | LC-MS (ES+, m/z) |
|---|---|---|---|
| 302. | 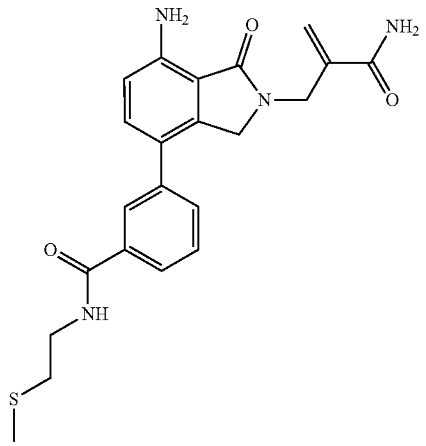 [SMILES: C=C(CN1Cc2c(-c3cccc(C(=O)NCCSC)c3)ccc(N)c2C1=O)C(N)=O] | 3-[7-amino-2-(2-carbamoyl-2-methylideneethyl)-1-oxo-2,3-dihydro-1H-isoindol-4-yl]-N-[2-(methylsulfanyl)ethyl]benzamide | 425.1 |
| 303. | 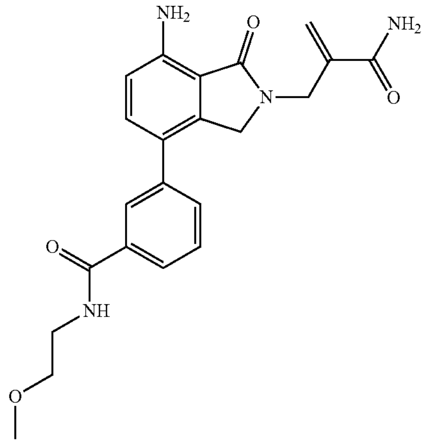 [SMILES: C=C(CN1Cc2c(-c3cccc(C(=O)NCCOC)c3)ccc(N)c2C1=O)C(N)=O] | 3-[7-amino-2-(2-carbamoyl-2-methylideneethyl)-1-oxo-2,3-dihydro-1H-isoindol-4-yl]-N-(2-methoxyethyl)benzamide | 409.1 |
| 304. | 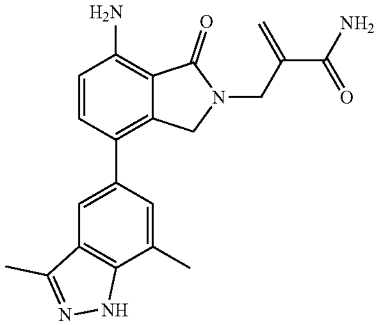 [SMILES: C=C(CN1Cc2c(-c3cc(C)c4[nH]nc(C)c4c3)ccc(N)c2C1=O)C(N)=O] | 2-{[7-amino-4-(3,7-dimethyl-1H-indazol-5-yl)-1-oxo-2,3-dihydro-1H-isoindol-2-yl]methyl}prop-2-enamide | 376.2 |

TABLE 4-continued
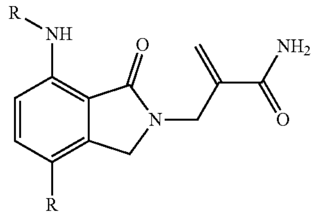
| Cpd. No. | Structure | IUPAC | LC-MS (ES+, m/z) |
|---|---|---|---|
| 305. | 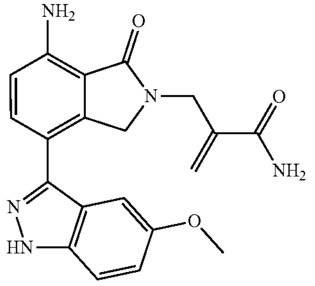 [SMILES: C=C(CN1Cc2c(-c3n[nH]c4ccc(OC)cc34)ccc(N)c2C1=O)C(N)=O] | 2-{[7-amino-4-(5-methoxy-1H-indazol-3-yl)-1-oxo-2,3-dihydro-1H-isoindol-2-yl]methyl}prop-2-enamide | 378.1 |
| 306. | 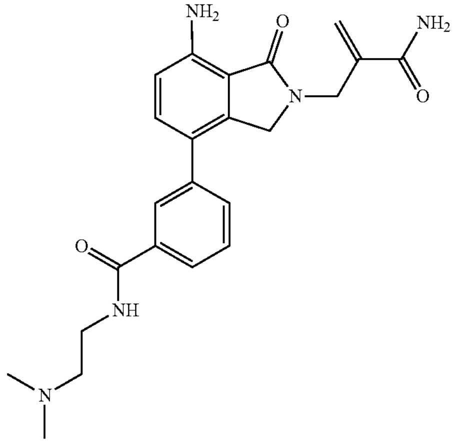 [SMILES: C=C(CN1Cc2c(-c3cccc(C(=O)NCCN(C)C)c3)ccc(N)c2C1=O)C(N)=O] | 3-[7-amino-2-(2-carbamoyl-2-methylideneethyl)-1-oxo-2,3-dihydro-1H-isoindol-4-yl]-N-[2-(dimethylamino)ethyl]benzamide | 422.2 |
| 307. | 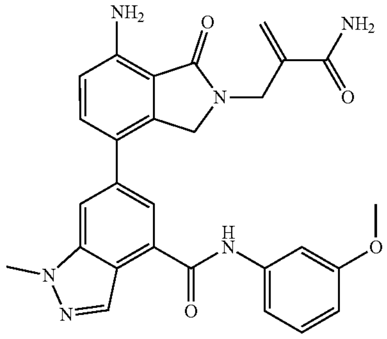 | 6-[7-amino-2-(2-carbamoyl-2-methylideneethyl)-1-oxo-2,3-dihydro-1H-isoindol-4-yl]-N-(3-methoxyphenyl)-1-methyl-1H-indazole-4-carboxamide | 511.3 |

TABLE 4-continued
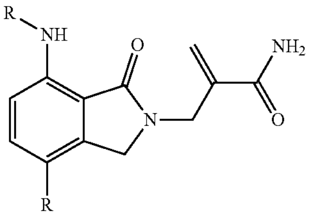
| Cpd. No. | Structure | IUPAC | LC-MS (ES+, m/z) |
|---|---|---|---|
| 308. | 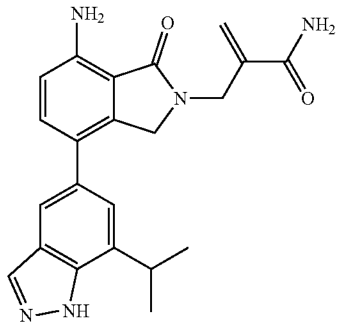 [SMILES: C=C(CN1Cc2c(-c3cc(C(C)C)c4[nH]ncc4c3)ccc(N)c2C1=O)C(N)=O] | 2-({7-amino-1-oxo-4-[7-(propan-2-yl)-1H-indazol-5-yl]-2,3-dihydro-1H-isoindol-2-yl}methyl)prop-2-enamide | 390.2 |
| 309. | 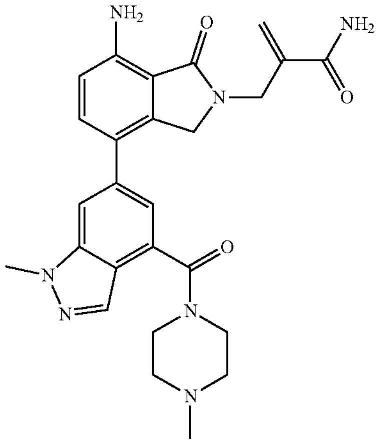 [SMILES: C=C(CN1Cc2c(-c3cc(C(=O)N4CCN(C)CC4)c4cnn(C)c4c3)ccc(N)c2C1=O)C(N)=O] | 2-({7-amino-4-[1-methyl-4-(4-methylpiperazine-1-carbonyl)-1H-indazol-6-yl]-1-oxo-2,3-dihydro-1H-isoindol-2-yl}methyl)prop-2-enamide | 488.2 |
| 310. | 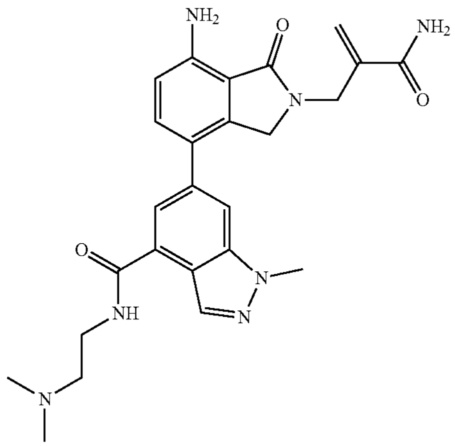 [SMILES: C=C(CN1Cc2c(-c3cc(C(=O)NCCN(C)C)c4cnn(C)c4c3)ccc(N)c2C1=O)C(N)=O] | 6-[7-amino-2-(2-carbamoyl-2-methylideneethyl)-1-oxo-2,3-dihydro-1H-isoindol-4-yl]-N-[2-(dimethylamino)ethyl]-1-methyl-1H-indazole-4-carboxamide | 476.2 |

TABLE 4-continued
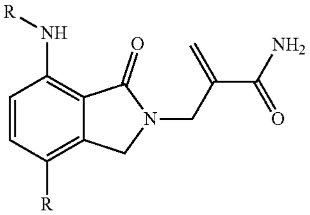
| Cpd. No. | Structure | IUPAC | LC-MS (ES+, m/z) |
| --- | --- | --- | --- |
| 311. | 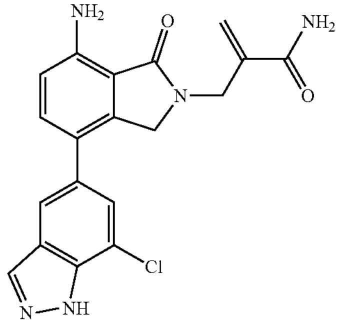 [SMILES: C=C(CN1Cc2c(-c3cc(Cl)c4[nH]ncc4c3)ccc(N)c2C1=O)C(N)=O] | 2-{[7-amino-4-(7-chloro-1H-indazol-5-yl)-1-oxo-2,3-dihydro-1H-isoindol-2-yl]methyl}prop-2-enamide | 382.1 |
| 312. | 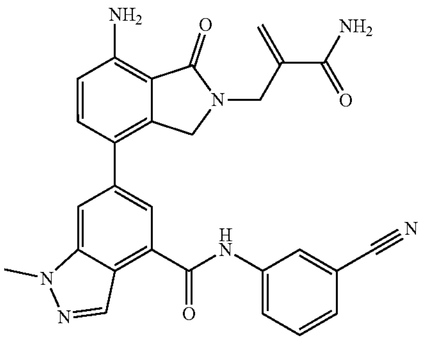 [SMILES: C=C(CN1Cc2c(-c3cc(C(=O)Nc4cccc(C#N)c4)c4cnn(C)c4c3)ccc(N)c2C1=O)C(N)=O] | 6-[7-amino-2-(2-carbamoyl-2-methylideneethyl)-1-oxo-2,3-dihydro-1H-isoindol-4-yl]-N-(3-cyanophenyl)-1-methyl-1H-indazole-4-carboxamide | 506.2 |
| 313. | 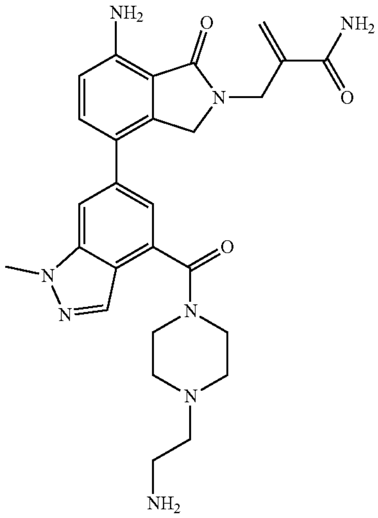 [SMILES: C=C(CN1Cc2c(-c3cc(C(=O)N4CCN(CCN)CC4)c4cnn(C)c4c3)ccc(N)c2C1=O)C(N)=O] | 2-[(7-amino-4-{4-[4-(2-aminoethyl)piperazine-1-carbonyl]-1-methyl-1H-indazol-6-yl}-1-oxo-2,3-dihydro-1H-isoindol-2-yl)methyl]prop-2-enamide | 517.2 |

TABLE 4-continued
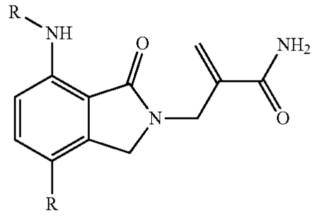
| Cpd. No. | Structure | IUPAC | LC-MS (ES+, m/z) |
|---|---|---|---|
| 314. | 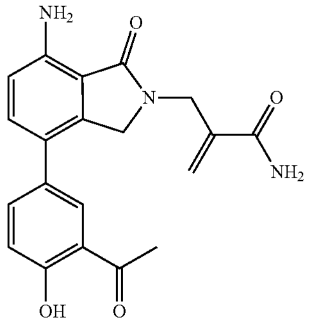 [SMILES: C=C(CN1Cc2c(-c3ccc(O)c(C(C)=O)c3)ccc(N)c2C1=O)C(N)=O] | 2-{[4-(3-acetyl-4-hydroxyphenyl)-7-amino-1-oxo-2,3-dihydro-1H-isoindol-2-yl]methyl}prop-2-enamide | 366.1 |
| 315. | 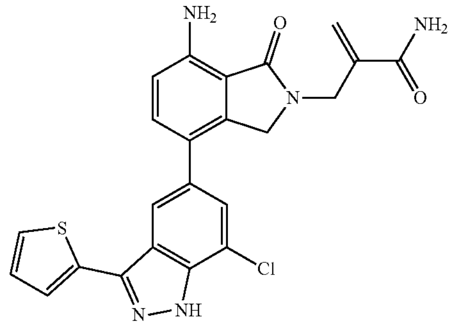 [SMILES: C=C(CN1Cc2c(-c3cc(Cl)c4[nH]nc(-c5cccs5)c4c3)ccc(N)c2C1=O)C(N)=O] | 2-({7-amino-4-[7-chloro-3-(thiophen-2-yl)-1H-indazol-5-yl]-1-oxo-2,3-dihydro-1H-isoindol-2-yl}methyl)prop-2-enamide | 464.1 |
| 316. | 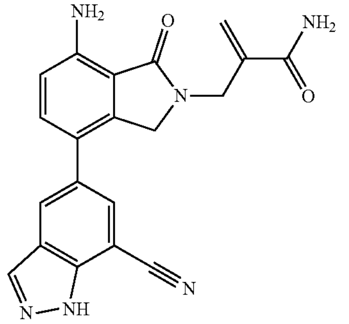 [SMILES: C=C(CN1Cc2c(-c3cc(C#N)c4[nH]ncc4c3)ccc(N)c2C1=O)C(N)=O] | 2-{[7-amino-4-(7-cyano-1H-indazol-5-yl)-1-oxo-2,3-dihydro-1H-isoindol-2-yl]methyl}prop-2-enamide | 373.1 |
| 317. | 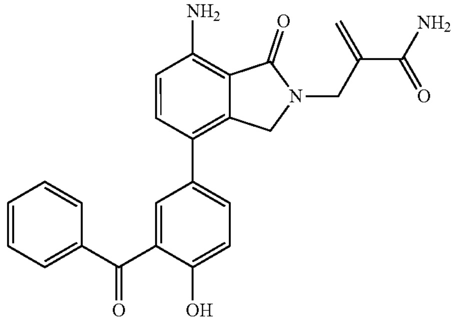 [SMILES: C=C(CN1Cc2c(-c3ccc(O)c(C(=O)c4ccccc4)c3)ccc(N)c2C1=O)C(N)=O] | 2-{[7-amino-4-(3-benzoyl-4-hydroxyphenyl)-1-oxo-2,3-dihydro-1H-isoindol-2-yl]methyl}prop-2-enamide | 428.1 |

TABLE 4-continued
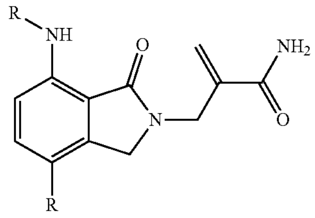
| Cpd. No. | Structure | IUPAC | LC-MS (ES+, m/z) |
|---|---|---|---|
| 318. | 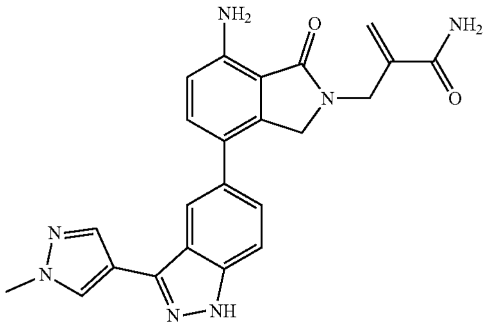 [SMILES: C=C(CN1Cc2c(-c3ccc4[nH]nc(-c5cnn(C)c5)c4c3)ccc(N)c2C1=O)C(N)=O] | 2-({7-amino-4-[3-(1-methyl-1H-pyrazol-4-yl)-1H-indazol-5-yl]-1-oxo-2,3-dihydro-1H-isoindol-2-yl}methyl)prop-2-enamide | 428.1 |
| 319. | 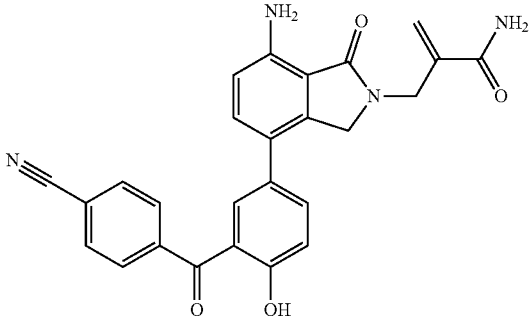 [SMILES: C=C(CN1Cc2c(-c3ccc(O)c(C(=O)c4ccc(C#N)cc4)c3)ccc(N)c2C1=O)C(N)=O] | 2-({7-amino-4-[3-(4-cyanobenzoyl)-4-hydroxyphenyl]-1-oxo-2,3-dihydro-1H-isoindol-2-yl}methyl)prop-2-enamide | 453.1 |
| 320. | 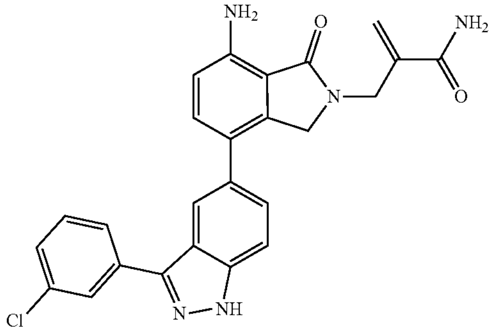 [SMILES: C=C(CN1Cc2c(-c3ccc4[nH]nc(-c5cccc(Cl)c5)c4c3)ccc(N)c2C1=O)C(N)=O] | 2-({7-amino-4-[3-(3-chlorophenyl)-1H-indazol-5-yl]-1-oxo-2,3-dihydro-1H-isoindol-2-yl}methyl)prop-2-enamide | 458 |

TABLE 4-continued
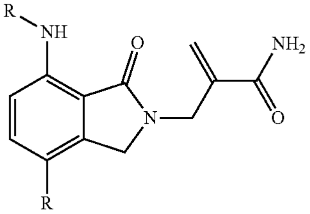
| Cpd. No. | Structure | IUPAC | LC-MS (ES+, m/z) |
|---|---|---|---|
| 321. | 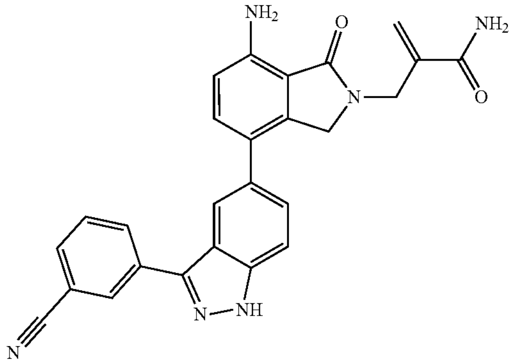 [SMILES: C=C(CN1Cc2c(-c3ccc4[nH]nc(-c5cccc(C#N)c5)c4c3)ccc(N)c2C1=O)C(N)=O] | 2-({7-amino-4-[3-(3-cyanophenyl)-1H-indazol-5-yl]-1-oxo-2,3-dihydro-1H-isoindol-2-yl}methyl)prop-2-enamide | 449.1 |
| 322. | 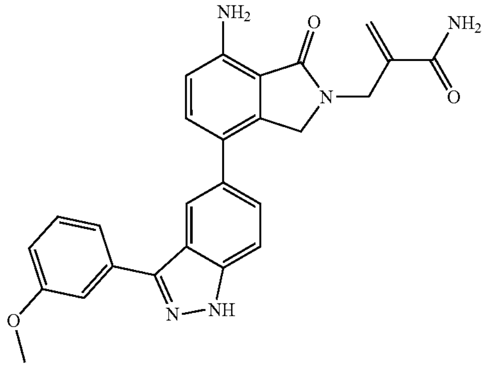 [SMILES: C=C(CN1Cc2c(-c3ccc4[nH]nc(-c5cccc(OC)c5)c4c3)ccc(N)c2C1=O)C(N)=O] | 2-({7-amino-4-[3-(3-methoxyphenyl)-1H-indazol-5-yl]-1-oxo-2,3-dihydro-1H-isoindol-2-yl}methyl)prop-2-enamide | 454.2 |
| 323. | 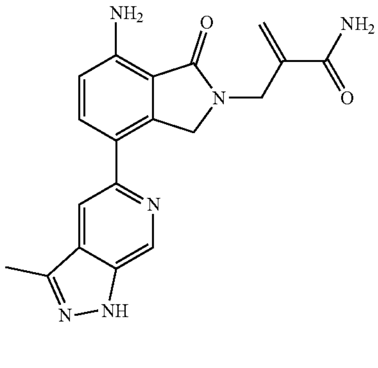 [SMILES: C=C(CN1Cc2c(-c3cc4c(C)n[nH]c4cn3)ccc(N)c2C1=O)C(N)=O] | 2-[(7-amino-4-{3-methyl-1H-pyrazolo[3,4-c]pyridin-5-yl}-1-oxo-2,3-dihydro-1H-isoindol-2-yl)methyl]prop-2-enamide | 363.1 |

TABLE 4-continued

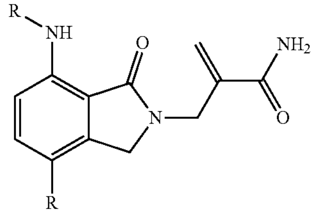

| Cpd. No. | Structure | IUPAC | LC-MS (ES+, m/z) |
|---|---|---|---|
| 324. | 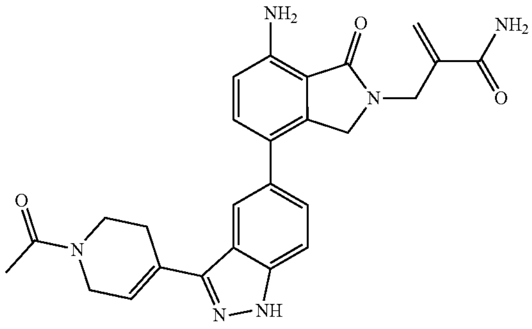 [SMILES: C=C(CN1Cc2c(-c3ccc4[nH]nc(C5=CCN(C(C)=O)CC5)c4c3)ccc(N)c2C1=O)C(N)=O] | 2-({4-[3-(1-acetyl-1,2,3,6-tetrahydropyridin-4-yl)-1H-indazol-5-yl]-7-amino-1-oxo-2,3-dihydro-1H-isoindol-2-yl}methyl)prop-2-enamide | 471.2 |
| 325. | 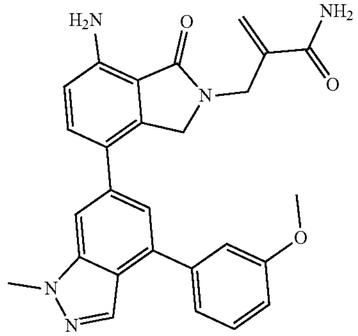 [SMILES: C=C(CN1Cc2c(-c3cc(-c4cccc(OC)c4)c4cnn(C)c4c3)ccc(N)c2C1=O)C(N)=O] | 2-({7-amino-4-[4-(3-methoxyphenyl)-1-methyl-1H-indazol-6-yl]-1-oxo-2,3-dihydro-1H-isoindol-2-yl}methyl)prop-2-enamide | 468.1 |
| 326. | 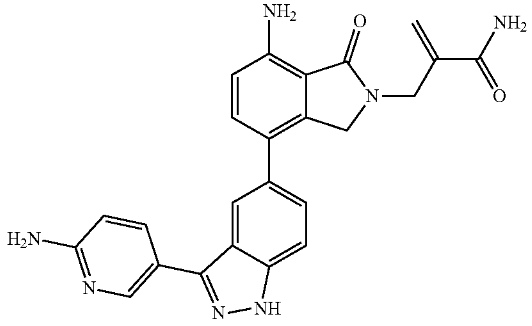 [SMILES: C=C(CN1Cc2c(-c3ccc4[nH]nc(-c5ccc(N)nc5)c4c3)ccc(N)c2C1=O)C(N)=O] | 2-({7-amino-4-[3-(6-aminopyridin-3-yl)-1H-indazol-5-yl]-1-oxo-2,3-dihydro-1H-isoindol-2-yl}methyl)prop-2-enamide | 440.1 |
| 327. | 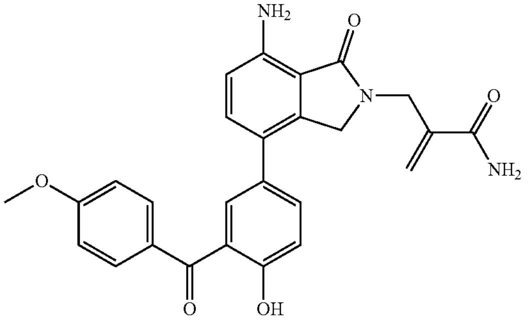 [SMILES: C=C(CN1Cc2c(-c3ccc(O)c(C(=O)c4ccc(OC)cc4)c3)ccc(N)c2C1=O)C(N)=O] | 2-({7-amino-4-[4-hydroxy-3-(4-methoxybenzoyl)phenyl]-1-oxo-2,3-dihydro-1H-isoindol-2-yl}methyl)prop-2-enamide | 458.2 |

TABLE 4-continued

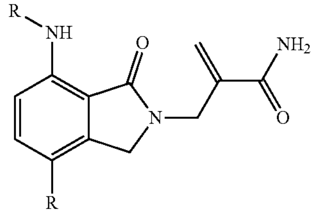

| Cpd. No. | Structure | IUPAC | LC-MS (ES+, m/z) |
|---|---|---|---|
| 328. | 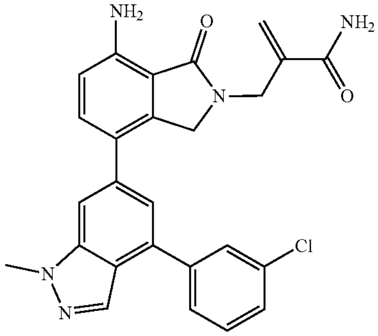 [SMILES: C=C(CN1Cc2c(-c3cc(-c4cccc(Cl)c4)c4cnn(C)c4c3)ccc(N)c2C1=O)C(N)=O] | 2-({7-amino-4-[4-(3-chlorophenyl)-1-methyl-1H-indazol-6-yl]-1-oxo-2,3-dihydro-1H-isoindol-2-yl}methyl)prop-2-enamide | 472.1 |
| 329. | 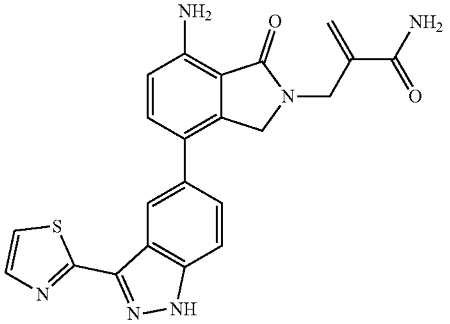 [SMILES: C=C(CN1Cc2c(-c3ccc4[nH]nc(-c5nccs5)c4c3)ccc(N)c2C1=O)C(N)=O] | 2-({7-amino-1-oxo-4-[3-(1,3-thiazol-2-yl)-1H-indazol-5-yl]-2,3-dihydro-1H-isoindol-2-yl}methyl)prop-2-enamide | 431.1 |
| 330. | 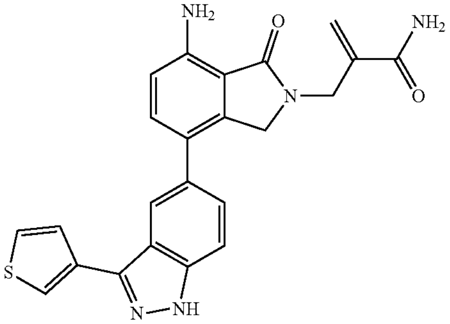 [SMILES: C=C(CN1Cc2c(-c3ccc4[nH]nc(-c5ccsc5)c4c3)ccc(N)c2C1=O)C(N)=O] | 2-({7-amino-1-oxo-4-[3-(thiophen-3-yl)-1H-indazol-5-yl]-2,3-dihydro-1H-isoindol-2-yl}methyl)prop-2-enamide | |
| 331. | 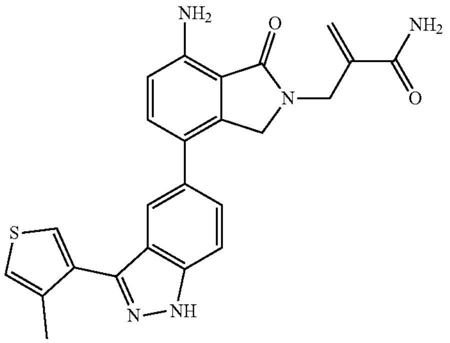 [SMILES: C=C(CN1Cc2c(-c3ccc4[nH]nc(-c5cscc5C)c4c3)ccc(N)c2C1=O)C(N)=O] | 2-({7-amino-4-[3-(4-methylthiophen-3-yl)-1H-indazol-5-yl]-1-oxo-2,3-dihydro-1H-isoindol-2-yl}methyl)prop-2-enamide | 444.1 |

TABLE 4-continued
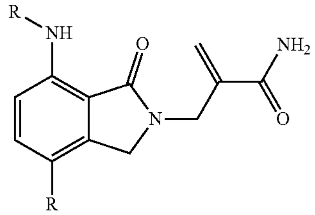
| Cpd. No. | Structure | IUPAC | LC-MS (ES+, m/z) |
|---|---|---|---|
| 332. | 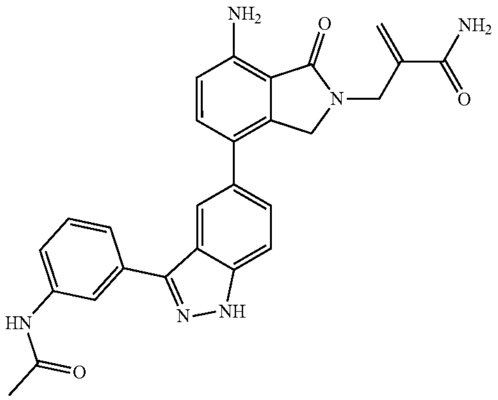 [SMILES: C=C(CN1Cc2c(-c3ccc4[nH]nc(-c5cccc(NC(C)=O)c5)c4c3)ccc(N)c2C1=O)C(N)=O] | 2-({7-amino-4-[3-(3-acetamidophenyl)-1H-indazol-5-yl]-1-oxo-2,3-dihydro-1H-isoindol-2-yl}methyl)prop-2-enamide | 481.2 |
| 333. | 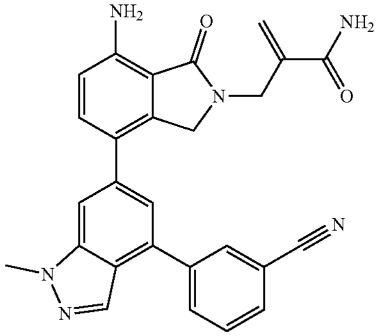 [SMILES: C=C(CN1Cc2c(-c3cc(-c4cccc(C#N)c4)c4cnn(C)c4c3)ccc(N)c2C1=O)C(N)=O] | 2-({7-amino-4-[4-(3-cyanophenyl)-1-methyl-1H-indazol-6-yl]-1-oxo-2,3-dihydro-1H-isoindol-2-yl}methyl)prop-2-enamide | 463.2 |
| 334. | 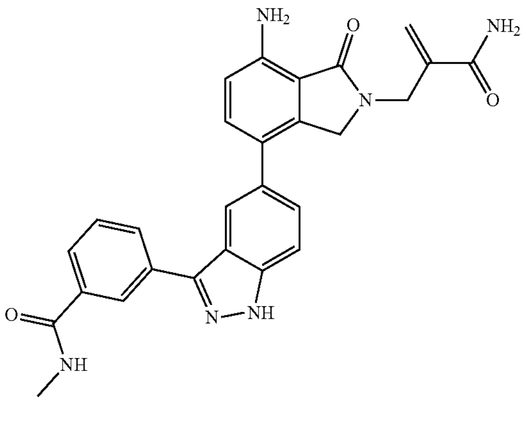 [SMILES: C=C(CN1Cc2c(-c3ccc4[nH]nc(-c5cccc(C(=O)NC)c5)c4c3)ccc(N)c2C1=O)C(N)=O] | 3-{5-[7-amino-2-(2-carbamoyl-2-methylideneethyl)-1-oxo-2,3-dihydro-1H-isoindol-4-yl]-1H-indazol-3-yl}-N-methylbenzamide | 481.1 |

TABLE 4-continued
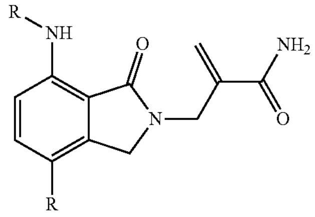
| Cpd. No. | Structure | IUPAC | LC-MS (ES+, m/z) |
| --- | --- | --- | --- |
| 335. | 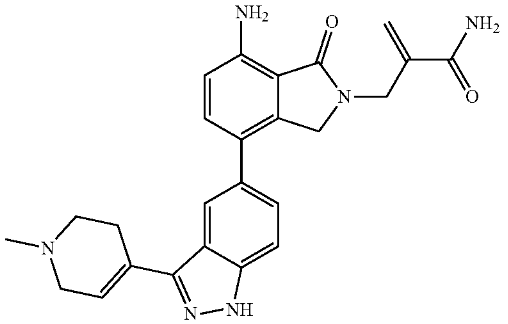 [SMILES: C=C(CN1Cc2c(-c3ccc4[nH]nc(C5=CCN(C)CC5)c4c3)ccc(N)c2C1=O)C(N)=O] | 2-({7-amino-4-[3-(1-methyl-1,2,3,6-tetrahydropyridin-4-yl)-1H-indazol-5-yl]-1-oxo-2,3-dihydro-1H-isoindol-2-yl}methyl)prop-2-enamide | 443.1 |
| 336. | 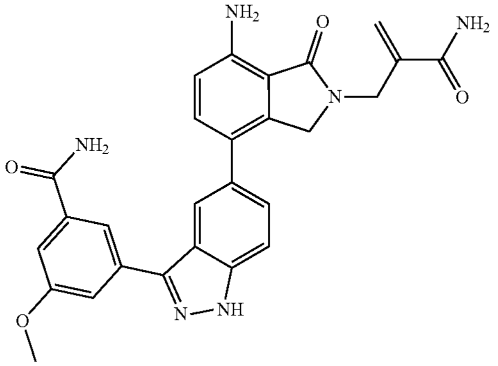 [SMILES: C=C(CN1Cc2c(-c3ccc4[nH]nc(-c5cc(OC)cc(C(N)=O)c5)c4c3)ccc(N)c2C1=O)C(N)=O] | 3-{5-[7-amino-2-(2-carbamoyl-2-methylideneethyl)-1-oxo-2,3-dihydro-1H-isoindol-4-yl]-1H-indazol-3-yl}-5-methoxybenzamide | 497.1 |
| 337. | 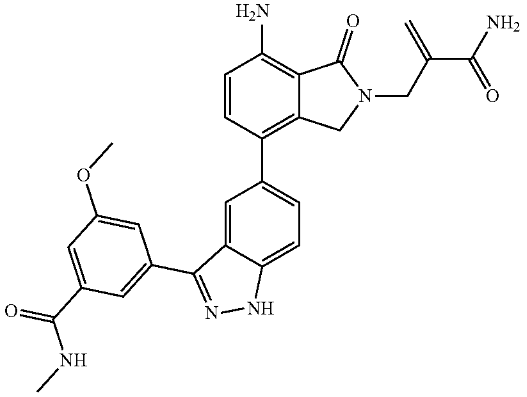 [SMILES: C=C(CN1Cc2c(-c3ccc4[nH]nc(-c5cc(OC)cc(C(=O)NC)c5)c4c3)ccc(N)c2C1=O)C(N)=O] | 3-{5-[7-amino-2-(2-carbamoyl-2-methylideneethyl)-1-oxo-2,3-dihydro-1H-isoindol-4-yl]-1H-indazol-3-yl}-5-methoxy-N-methylbenzamide | 511.2 |

TABLE 4-continued
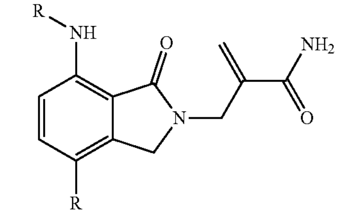
| Cpd. No. | Structure | IUPAC | LC-MS (ES+, m/z) |
|---|---|---|---|
| 338. | 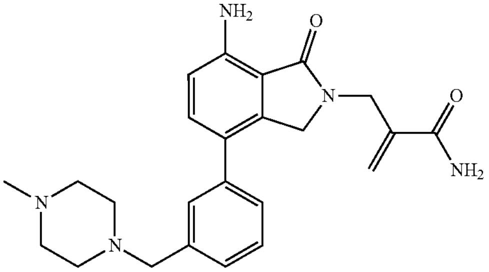 [SMILES: C=C(CN1Cc2c(-c3cccc(CN4CCN(C)CC4)c3)ccc(N)c2C1=O)C(N)=O] | 2-[(7-amino-4-{3-[(4-methylpiperazin-1-yl)methyl]phenyl}-1-oxo-2,3-dihydro-1H-isoindol-2-yl)methyl]prop-2-enamide | 420.2 |
| 339. | 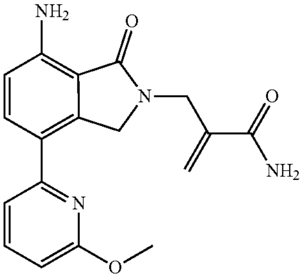 [SMILES: C=C(CN1Cc2c(-c3cccc(OC)n3)ccc(N)c2C1=O)C(N)=O] | 2-{[7-amino-4-(6-methoxypyridin-2-yl)-1-oxo-2,3-dihydro-1H-isoindol-2-yl]methyl}prop-2-enamide | 339.1 |
| 340. | 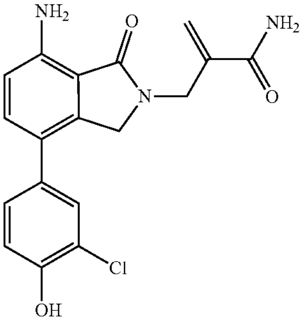 [SMILES: C=C(CN1Cc2c(-c3ccc(O)c(Cl)c3)ccc(N)c2C1=O)C(N)=O] | 2-{[7-amino-4-(3-chloro-4-hydroxyphenyl)-1-oxo-2,3-dihydro-1H-isoindol-2-yl]methyl}prop-2-enamide | 358 |
| 341. | 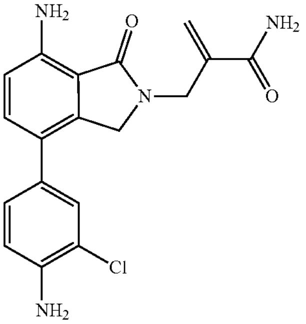 [SMILES: C=C(CN1Cc2c(-c3ccc(N)c(Cl)c3)ccc(N)c2C1=O)C(N)=O] | 2-{[7-amino-4-(4-amino-3-chlorophenyl)-1-oxo-2,3-dihydro-1H-isoindol-2-yl]methyl}prop-2-enamide | 357.1 |

TABLE 4-continued
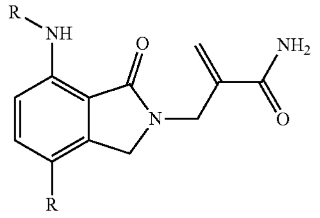
| Cpd. No. | Structure | IUPAC | LC-MS (ES+, m/z) |
|---|---|---|---|
| 342. | 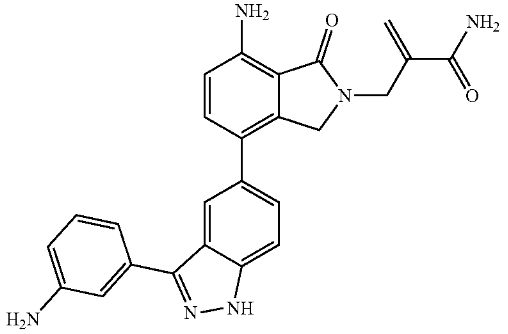 [SMILES: C=C(CN1Cc2c(-c3ccc4[nH]nc(-c5cccc(N)c5)c4c3)ccc(N)c2C1=O)C(N)=O] | 2-({7-amino-4-[3-(3-aminophenyl)-1H-indazol-5-yl]-1-oxo-2,3-dihydro-1H-isoindol-2-yl}methyl)prop-2-enamide | 439.3 |
| 343. | 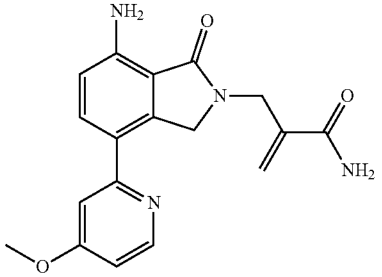 [SMILES: C=C(CN1Cc2c(-c3cc(OC)ccn3)ccc(N)c2C1=O)C(N)=O] | 2-{[7-amino-4-(4-methoxypyridin-2-yl)-1-oxo-2,3-dihydro-1H-isoindol-2-yl]methyl}prop-2-enamide | 339.1 |
| 344. | 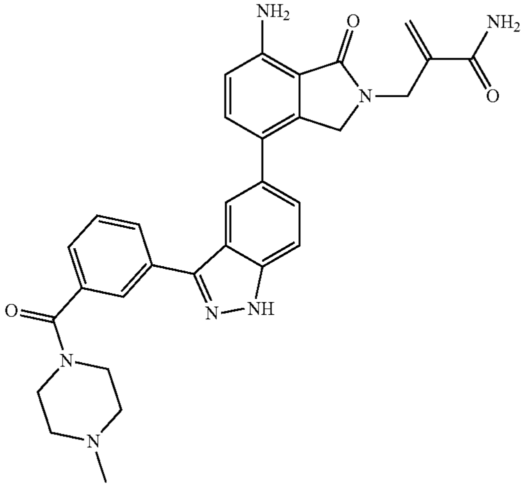 [SMILES: C=C(CN1Cc2c(-c3ccc4[nH]nc(-c5cccc(C(=O)N6CCN(C)CC6)c5)c4c3)ccc(N)c2C1=O)C(N)=O] | 2-[(7-amino-4-{3-[3-(4-methylpiperazine-1-carbonyl)phenyl]-1H-indazol-5-yl}-1-oxo-2,3-dihydro-1H-isoindol-2-yl)methyl]prop-2-enamide | 550.3 |

TABLE 4-continued
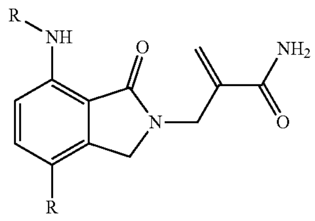
| Cpd. No. | Structure | IUPAC | LC-MS (ES+, m/z) |
|---|---|---|---|
| 345. | 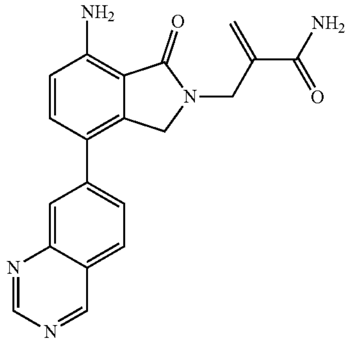 [SMILES: C=C(CN1Cc2c(-c3ccc4cncnc4c3)ccc(N)c2C1=O)C(N)=O] | 2-{[7-amino-1-oxo-4-(quinazolin-7-yl)-2,3-dihydro-1H-isoindol-2-yl]methyl}prop-2-enamide | 360.1 |
| 346. | 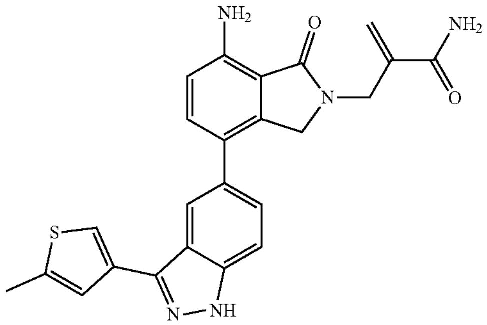 [SMILES: C=C(CN1Cc2c(-c3ccc4[nH]nc(-c5csc(C)c5)c4c3)ccc(N)c2C1=O)C(N)=O] | 2-({7-amino-4-[3-(5-methylthiophen-3-yl)-1H-indazol-5-yl]-1-oxo-2,3-dihydro-1H-isoindol-2-yl}methyl)prop-2-enamide | 444.1 |
| 347. | 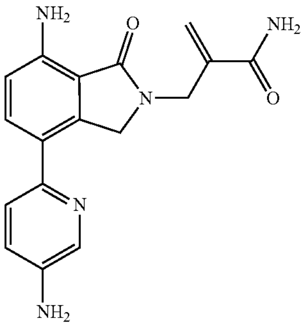 [SMILES: C=C(CN1Cc2c(-c3ccc(N)cn3)ccc(N)c2C1=O)C(N)=O] | 2-{[7-amino-4-(5-aminopyridin-2-yl)-1-oxo-2,3-dihydro-1H-isoindol-2-yl]methyl}prop-2-enamide | 324.1 |

TABLE 4-continued
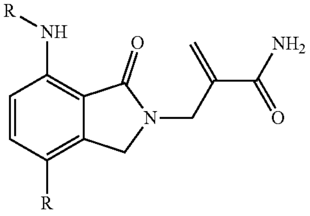
| Cpd. No. | Structure | IUPAC | LC-MS (ES+, m/z) |
|---|---|---|---|
| 348. | 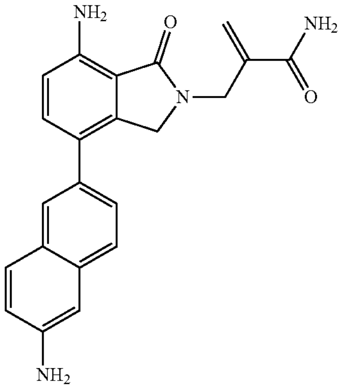 [SMILES: C=C(CN1Cc2c(-c3ccc4cc(N)ccc4c3)ccc(N)c2C1=O)C(N)=O] | 2-{[7-amino-4-(6-aminonaphthalen-2-yl)-1-oxo-2,3-dihydro-1H-isoindol-2-yl]methyl}prop-2-enamide | 373.1 |
| 349. | 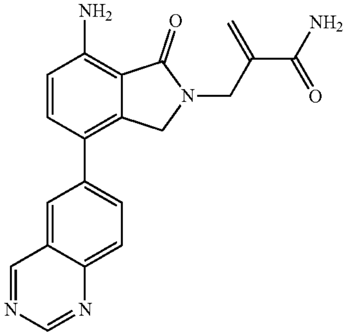 [SMILES: C=C(CN1Cc2c(-c3ccc4ncncc4c3)ccc(N)c2C1=O)C(N)=O] | 2-{[7-amino-1-oxo-4-(quinazolin-6-yl)-2,3-dihydro-1H-isoindol-2-yl]methyl}prop-2-enamide | 360.1 |
| 350. | 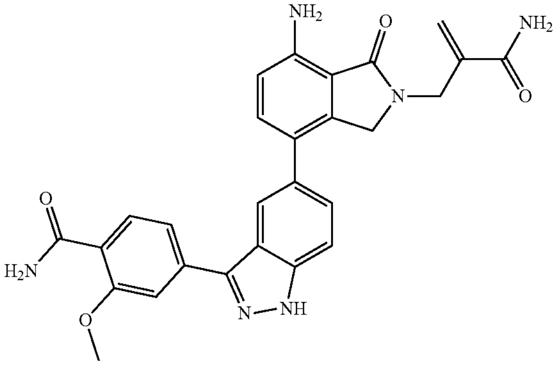 [SMILES: C=C(CN1Cc2c(-c3ccc4[nH]nc(-c5ccc(C(N)=O)c(OC)c5)c4c3)ccc(N)c2C1=O)C(N)=O] | 4-{5-[7-amino-2-(2-carbamoyl-2-methylideneethyl)-1-oxo-2,3-dihydro-1H-isoindol-4-yl]-1H-indazol-3-yl}-2-methoxybenzamide | 497.1 |

TABLE 4-continued
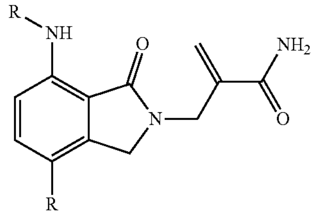
| Cpd. No. | Structure | IUPAC | LC-MS (ES+, m/z) |
|---|---|---|---|
| 351. | 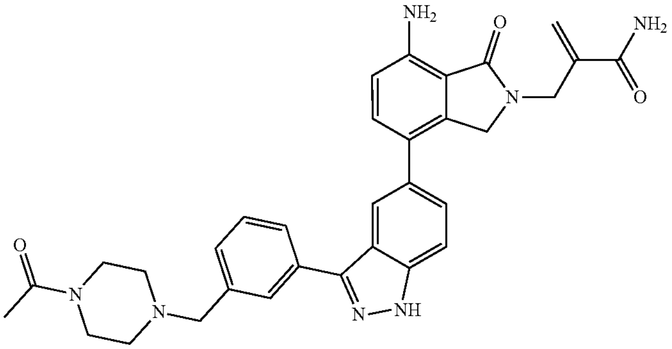 [SMILES: C=C(CN1Cc2c(-c3ccc4[nH]nc(-c5cccc(CN6CCN(C(C)=O)CC6)c5)c4c3)ccc(N)c2C1=O)C(N)=O] | 2-{[4-(3-{3-[(4-acetylpiperazin-1-yl)methyl]phenyl}-1H-indazol-5-yl)-7-amino-1-oxo-2,3-dihydro-1H-isoindol-2-yl]methyl}prop-2-enamide | 564.3 |
| 352. | 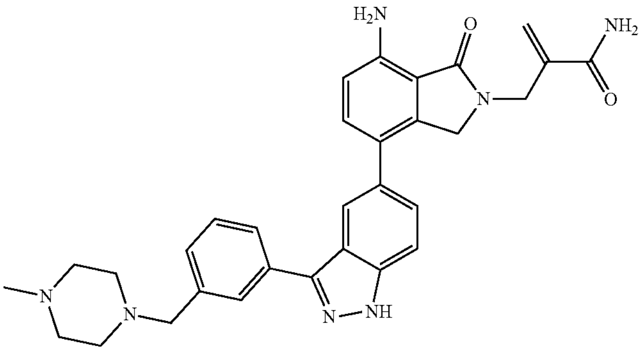 [SMILES: C=C(CN1Cc2c(-c3ccc4[nH]nc(-c5cccc(CN6CCN(C)CC6)c5)c4c3)ccc(N)c2C1=O)C(N)=O] | 2-{[7-amino-4-(3-{3-[(4-methylpiperazin-1-yl)methyl]phenyl}-1H-indazol-5-yl)-1-oxo-2,3-dihydro-1H-isoindol-2-yl]methyl}prop-2-enamide | 536.3 |
| 353. | 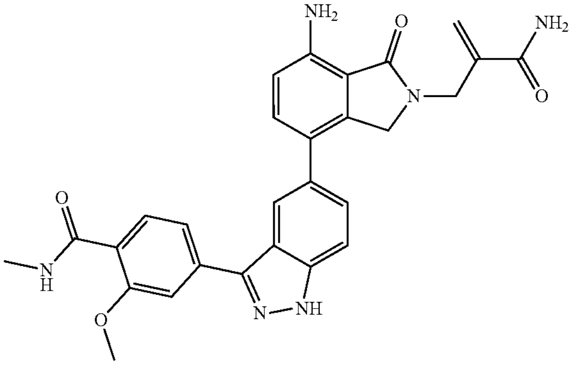 [SMILES: C=C(CN1Cc2c(-c3ccc4[nH]nc(-c5ccc(C(=O)NC)c(OC)c5)c4c3)ccc(N)c2C1=O)C(N)=O] | 4-{5-[7-amino-2-(2-carbamoyl-2-methylideneethyl)-1-oxo-2,3-dihydro-1H-isoindol-4-yl]-1H-indazol-3-yl}-2-methoxy-N-methylbenzamide | 511.1 |

TABLE 4-continued
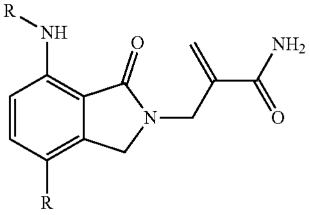
| Cpd. No. | Structure | IUPAC | LC-MS (ES+, m/z) |
|---|---|---|---|
| 354. | 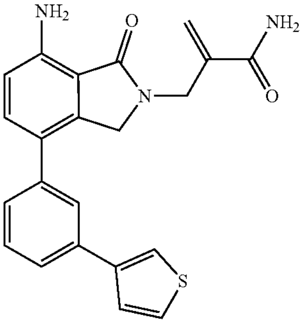 [SMILES: C=C(CN1Cc2c(-c3cccc(-c4ccsc4)c3)ccc(N)c2C1=O)C(N)=O] | 2-({7-amino-1-oxo-4-[3-(thiophen-3-yl)phenyl]-2,3-dihydro-1H-isoindol-2-yl}methyl)prop-2-enamide | 390.1 |
| 355. | 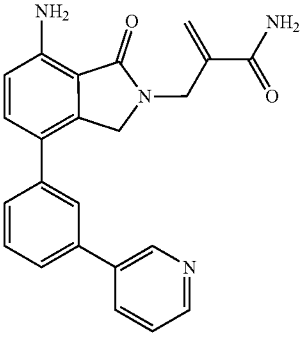 [SMILES: C=C(CN1Cc2c(-c3cccc(-c4cccnc4)c3)ccc(N)c2C1=O)C(N)=O] | 2-({7-amino-1-oxo-4-[3-(pyridin-3-yl)phenyl]-2,3-dihydro-1H-isoindol-2-yl}methyl)prop-2-enamide | 385.1 |
| 356. | 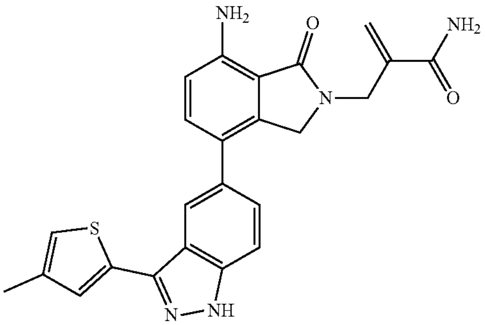 [SMILES: C=C(CN1Cc2c(-c3ccc4[nH]nc(-c5cc(C)cs5)c4c3)ccc(N)c2C1=O)C(N)=O] | 2-({7-amino-4-[3-(4-methylthiophen-2-yl)-1H-indazol-5-yl]-1-oxo-2,3-dihydro-1H-isoindol-2-yl}methyl)prop-2-enamide | 444.1 |
| 357. | 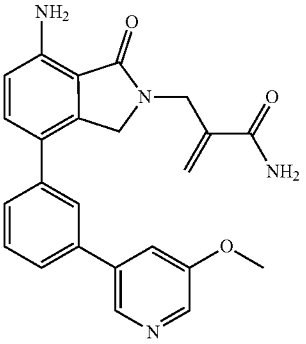 [SMILES: C=C(CN1Cc2c(-c3cccc(-c4cncc(OC)c4)c3)ccc(N)c2C1=O)C(N)=O] | 2-({7-amino-4-[3-(5-methoxypyridin-3-yl)phenyl]-1-oxo-2,3-dihydro-1H-isoindol-2-yl}methyl)prop-2-enamide | 415.1 |

TABLE 4-continued
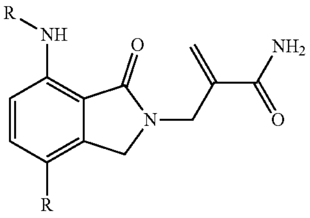
| Cpd. No. | Structure | IUPAC | LC-MS (ES+, m/z) |
|---|---|---|---|
| 358. | 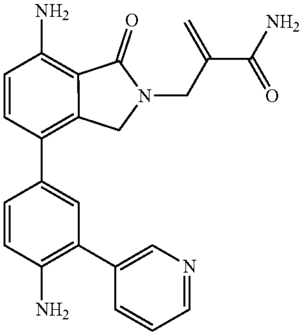 [SMILES: C=C(CN1Cc2c(-c3ccc(N)c(-c4cccnc4)c3)ccc(N)c2C1=O)C(N)=O] | 2-({7-amino-4-[4-amino-3-(pyridin-3-yl)phenyl]-1-oxo-2,3-dihydro-1H-isoindol-2-yl}methyl)prop-2-enamide | 400.2 |
| 359. | 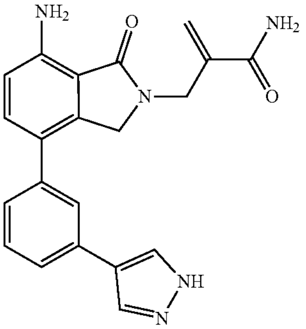 [SMILES: C=C(CN1Cc2c(-c3cccc(-c4cn[nH]c4)c3)ccc(N)c2C1=O)C(N)=O] | 2-({7-amino-1-oxo-4-[3-(1H-pyrazol-4-yl)phenyl]-2,3-dihydro-1H-isoindol-2-yl}methyl)prop-2-enamide | 374.1 |
| 360. | 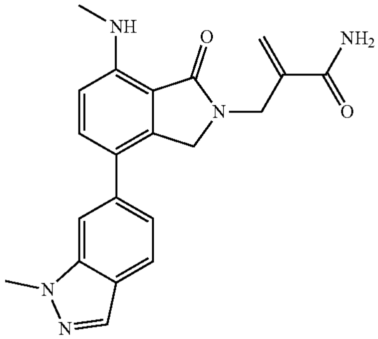 [SMILES: C=C(CN1Cc2c(-c3ccc4cnn(C)c4c3)ccc(NC)c2C1=O)C(N)=O] | 2-{[4-(1-methyl-1H-indazol-6-yl)-7-(methylamino)-1-oxo-2,3-dihydro-1H-isoindol-2-yl]methyl}prop-2-enamide | 376.1 |

TABLE 4-continued
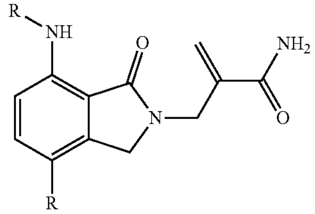
| Cpd. No. | Structure | IUPAC | LC-MS (ES+, m/z) |
| --- | --- | --- | --- |
| 361. | 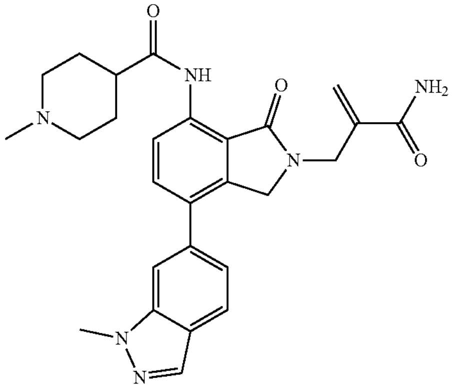 [SMILES: C=C(CN1Cc2c(-c3ccc4cnn(C)c4c3)ccc(NC(=O)C3CCN(C)CC3)c2C1=O)C(N)=O] | N-[2-(2-carbamoyl-2-methylideneethyl)-7-(1-methyl-1H-indazol-6-yl)-3-oxo-2,3-dihydro-1H-isoindol-4-yl]-1-methylpiperidine-4-carboxamide | 487.2 |
| 362. | 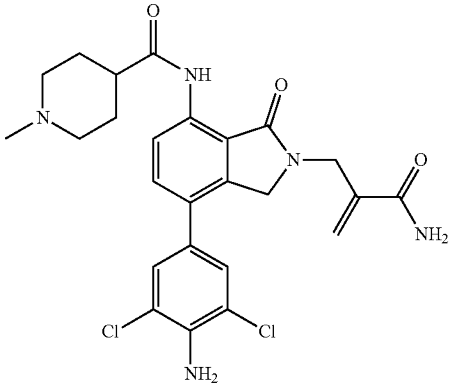 [SMILES: C=C(CN1Cc2c(-c3cc(Cl)c(N)c(Cl)c3)ccc(NC(=O)C3CCN(C)CC3)c2C1=O)C(N)=O] | N-[7-(4-amino-3,5-dichlorophenyl)-2-(2-carbamoyl-2-methylideneethyl)-3-oxo-2,3-dihydro-1H-isoindol-4-yl]-1-methylpiperidine-4-carboxamide | 516.1 |
| 363. | 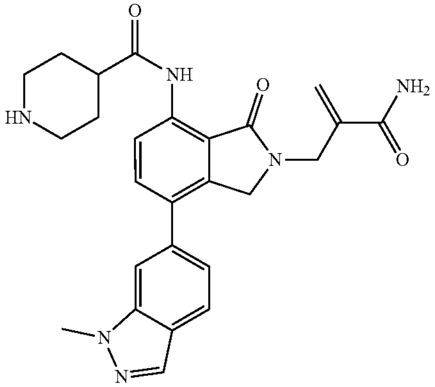 [SMILES: C=C(CN1Cc2c(-c3ccc4cnn(C)c4c3)ccc(NC(=O)C3CCNCC3)c2C1=O)C(N)=O] | 2-{[4-(1-methyl-1H-indazol-6-yl)-1-oxo-7-[(piperidin-4-yl)amino]-2,3-dihydro-1H-isoindol-2-yl]methyl}prop-2-enamide | 445.1 |

TABLE 4-continued
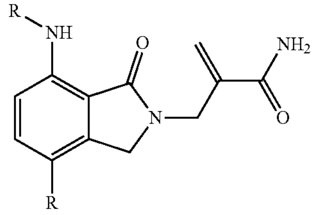
| Cpd. No. | Structure | IUPAC | LC-MS (ES+, m/z) |
|---|---|---|---|
| 364. | 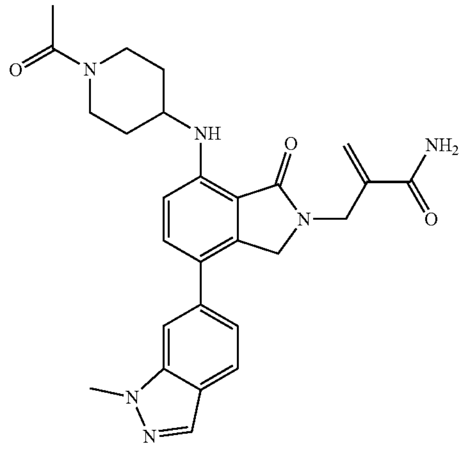 [SMILES: C=C(CN1Cc2c(-c3ccc4cnn(C)c4c3)ccc(NC3CCN(C(C)=O)CC3)c2C1=O)C(N)=O] | 2-({7-[(1-acetylpiperidin-4-yl)amino]-4-(1-methyl-1H-indazol-6-yl)-1-oxo-2,3-dihydro-1H-isoindol-2-yl}methyl)prop-2-enamide | 487.1 |
| 365. | 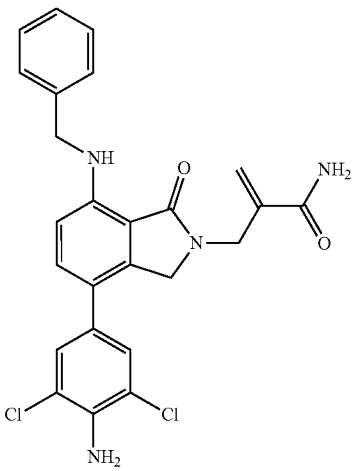 [SMILES: C=C(CN1Cc2c(-c3cc(Cl)c(N)c(Cl)c3)ccc(NCc3ccccc3)c2C1=O)C(N)=O] | 2-{[4-(4-amino-3,5-dichlorophenyl)-7-(benzylamino)-1-oxo-2,3-dihydro-1H-isoindol-2-yl]methyl}prop-2-enamide | 481 |
Example 6: Method E
General Scheme for Method E
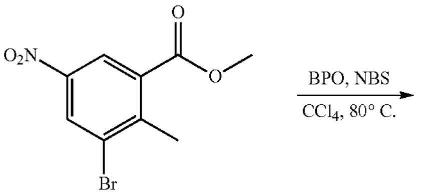
-continued
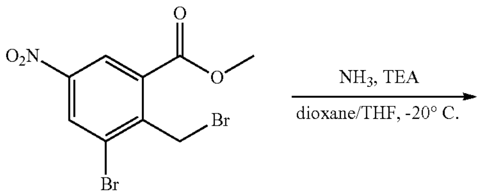

-continued

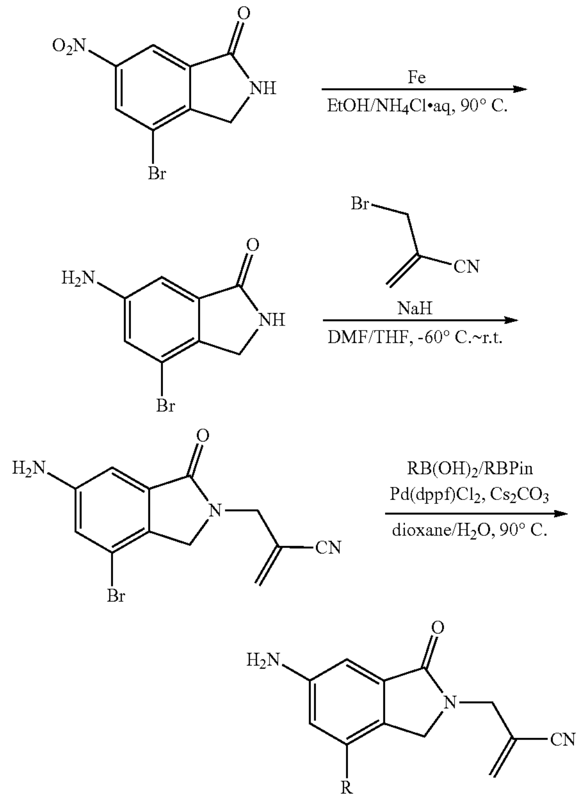

a. Preparation of methyl 3-bromo-2-(bromomethyl)-5-nitro-benzoate

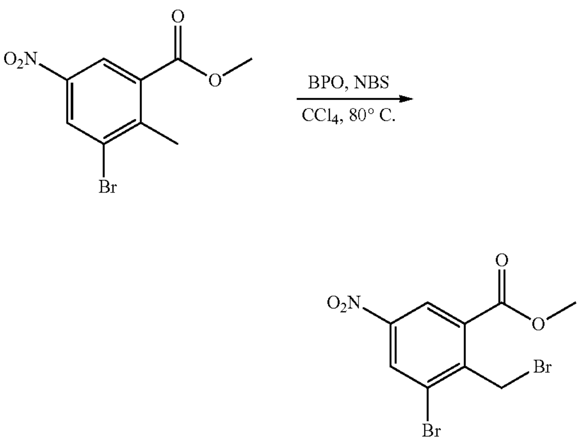

To a solution of methyl 3-bromo-2-methyl-5-nitro-benzoate (20 g, 72.97 mmol, 1 eq.) in $CCl_4$ (200 mL) were added NBS (15.59 g, 87.57 mmol, 1.2 eq.) and BPO (1.77 g, 7.30 mmol, 0.1 eq.). The mixture was stirred at 80° C. for 12 h under nitrogen. The reaction mixture was filtered to remove the solid, then the solution was concentrated in vacuo to afford the title compound (30 g, crude) as a yellow solid and was used for the next step directly without further purification.

b. Preparation of 4-bromo-6-nitro-isoindolin-1-one

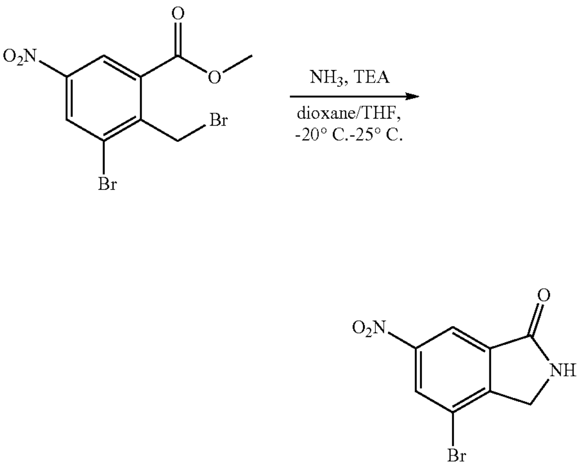

To a solution of methyl 3-bromo-2-(bromomethyl)-5-nitro-benzoate (5 g, 12.75 mmol, 1 eq.) in THF (100 mL) at −20° C. under nitrogen were added TEA (6.45 g, 63.75 mmol, 8.87 mL, 5 eq.), $NH_3$ (10 M, 1.27 mL, 1 eq.), and dioxane (80 mL). The mixture was stirred at 25° C. for 12 h. The reaction mixture was filtered and concentrated in vacuo to afford the title compound (2.6 g, crude) as a yellow solid, which was used for the next step directly without further purification.

c. Preparation of 6-amino-4-bromo-isoindolin-1-one

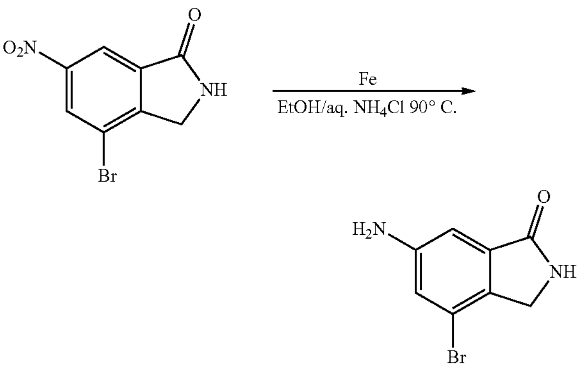

To a mixture of 4-bromo-6-nitro-isoindolin-1-one (1 g, 3.50 mmol, 1 eq.) in EtOH (20 mL) were added sat. $NH_4Cl$ (5 mL) and Fe (977.68 mg, 17.51 mmol, 5 eq.) in one portion at 25° C. The mixture was stirred at 90° C. for 1 h. The reaction mixture was filtered and concentrated in vacuo. The residue washed with ACN (30 mL), and the solution was concentrated in vacuo to afford the title compound (0.4 g, 1.59 mmol, 45.28% yield, 90% purity) as a red solid.

d. Preparation of 2-[(6-amino-4-bromo-1-oxo-isoindolin-2-yl)methyl]prop-2-enenitrile

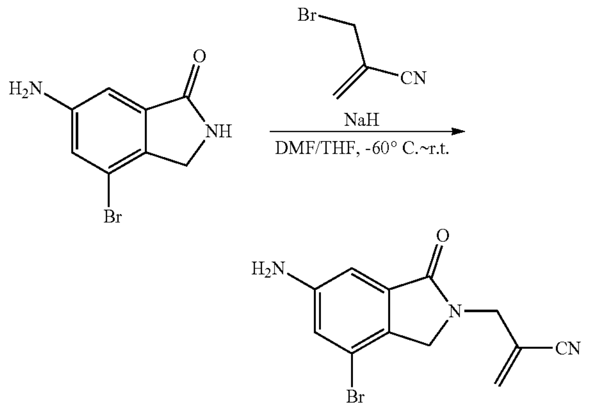

To a mixture of 6-amino-4-bromo-isoindolin-1-one (0.5 g, 2.36 mmol) in THF (30 mL)/DMF (30 mL) was added NaH (141.5 mg, 3.54 mmol, 60% purity) in one portion at r.t. under nitrogen. The mixture was stirred at r.t. for 30 min. After cooling to −60° C., 2-(bromomethyl)acrylonitrile (378.7 mg, 2.59 mmol) was added to the reaction mixture. The mixture was stirred at −60° C. for 20 min. The reaction mixture was diluted with sat. $NH_4Cl$ (30 mL) and extracted with DCM (3×20 mL). The combined organic layer was washed with brine, dried with sodium sulfate, filtered, and concentrated in vacuo to afford the title compound (550 mg, Yield 80%), which was used for the next step without further purification.

General Procedure for Suzuki Coupling

Preparation of 2-{[6-amino-4-(1-methyl-1H-indazol-6-yl)-1-oxo-2,3-dihydro-1H-isoindol-2-yl]methyl}prop-2-enenitrile (Compound 366)

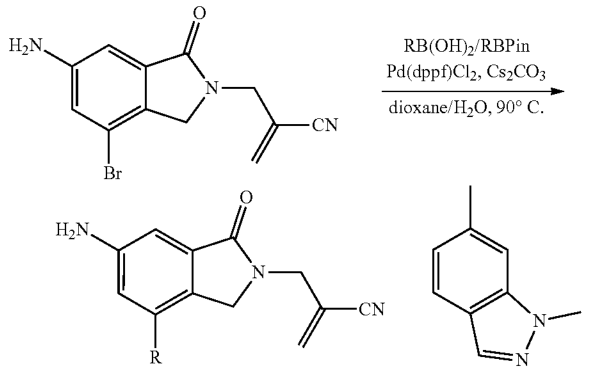

To a mixture of 2-[(6-amino-4-bromo-1-oxo-isoindolin-2-yl)methyl]prop-2-enenitrile (0.05 g, 171.16 μmol, 1 eq.) and (1-methylindazol-6-yl)boronic acid (45.18 mg, 256.73 μmol, 1.5 eq.) in dioxane (4 mL)/water (1 mL) were added $Cs_2CO_3$ (167.30 mg, 513.47 μmol, 3 eq.) and $Pd(dppf)Cl_2$ (12.52 mg, 17.12 μmol, 0.1 eq.) under nitrogen. The mixture was stirred at 90° C. for 30 min under nitrogen. The reaction mixture was poured into 20 mL of sat EDTA, and 20 mL of EtOAc was added. The mixture was stirred at r.t. for 1 h. The aqueous phase was extracted with EtOAc (3×20 mL). The combined organic layer was washed with brine, filtered, and concentrated in vacuo. The residue was purified by prep-HPLC to afford the title compound (0.0081 g, 23.33 μmol, 13.63% yield, 98.9% purity) as a white solid. LC-MS: $[M+H]^+$ 344.1.

Route 2

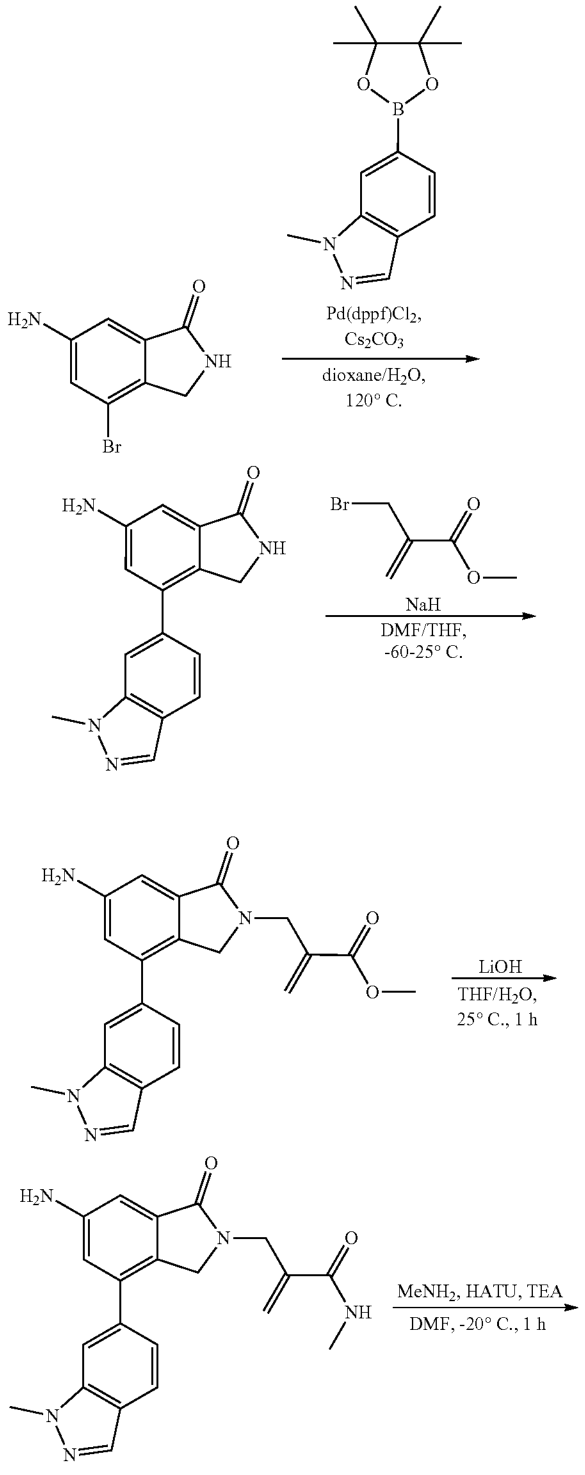

-continued

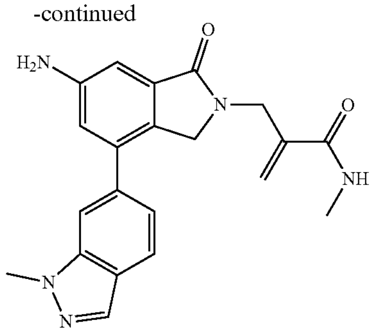

a. Preparation of 6-amino-4-(1-methylindazol-6-yl) isoindolin-1-one

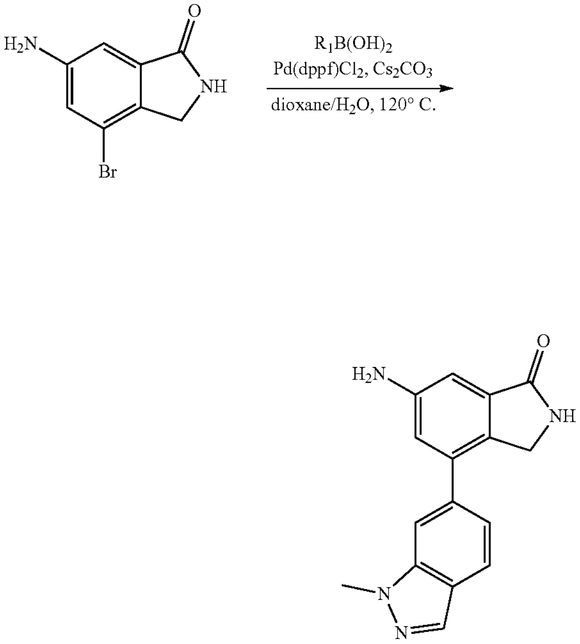 [SMILES: Nc1cc(Br)c2c(c1)C(=O)NC2 ; Cn1ncc2ccc(-c3cc(N)cc4c3CNC4=O)cc21]

To a mixture of 6-amino-4-bromoisoindolin-1-one (600 mg, 2.64 mmol) and (1-methylindazol-6-yl)boronic acid (232 mg, 1.32 mmol) in dioxane (4 mL)/water (1 mL) were added $Cs_2CO_3$ (1.29 g, 3.96 mmol) and $Pd(dppf)Cl_2$ (96.7 mg, 132.1 μmol). The mixture was degassed and purged with nitrogen 3 times. Then the mixture was stirred at 120° C. for 20 min. The reaction mixture was poured into 30 mL of water. The aqueous phase was extracted with EtOAc (30 mL×3). The combined organic layer was washed with brine, dried over anhydrous sodium sulfate, filtered, and concentrated in vacuo. The residue was washed with 10 mL of DCM:MeOH (30:1) to afford the title compound (74.9 mg, 20.4% Yield) as a gray solid.

Preparation of methyl 2-[[6-amino-4-(1-methylindazol-6-yl)-1-oxo-isoindolin-2-yl]methyl]prop-2-enoate (Compound 371)

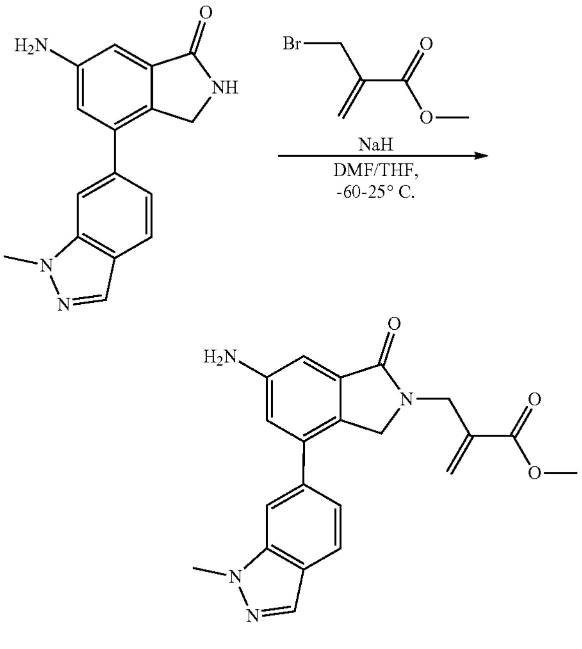

To a mixture of 6-amino-4-(1-methylindazol-6-yl)isoindolin-1-one (0.2 g, 718.63 μmol, 1 eq.) in DMF (20 mL) and THF (20 mL) was added NaH (43.11 mg, 1.08 mmol, 60% purity, 1.5 eq.) in one portion at 25° C. under nitrogen. The mixture was stirred at 25° C. for 30 min. Then the mixture was cooled to −60° C., and methyl 2-(bromomethyl)prop-2-enoate (128.64 mg, 718.63 μmol, 1 eq.) was added. The mixture was stirred further at −60° C. for 15 min, then at r.t. for 30 min. LCMS showed that the reaction was complete. The reaction mixture was poured into sat. aq. $NH_4Cl$ (30 mL), then extracted with DCM (3×20 mL), and washed with brine (3×10 mL). The combined organic layer was concentrated in vacuo. The residue was purified by prep-TLC (silica gel; DCM:MeOH=20:1) to afford the title compound (0.16 g, 382.56 μmol, 53.24% yield, 90% purity) as a yellow solid. LC-MS: $[M+H]^+$ 377.1.

Preparation of 2-[[6-amino-4-(1-methylindazol-6-yl)-1-oxo-isoindolin-2-yl]methyl]prop-2-enoic Acid

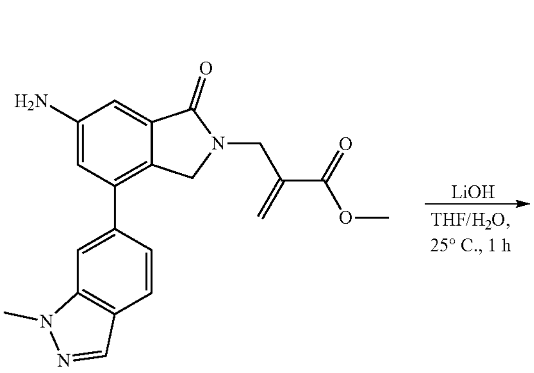

-continued

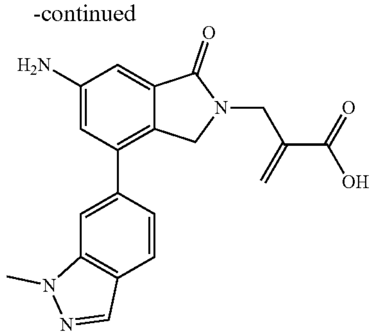

To a mixture of methyl 2-[[6-amino-4-(1-methylindazol-6-yl)-1-oxo-isoindolin-2-yl]methyl]prop-2-enoate (0.13 g, 345.37 μmol, 1 eq.) in THF (9 mL)/water (2.25 mL) was added $LiOH \cdot H_2O$ (43.48 mg, 1.04 mmol, 3 eq.) at 25° C. The mixture was stirred at 25° C. for 1 h. The reaction mixture was poured into sat. aq. $NH_4Cl$ (30 mL), then extracted with EtOAc (3×10 mL). The combined organic layer was concentrated in vacuo to afford the title compound (0.12 g, crude), which was used for the next step without further purification.

Preparation of 2-[[6-amino-4-(1-methylindazol-6-yl)-1-oxo-isoindolin-2-yl]methyl]-N-methyl-prop-2-enamide (Compound 378)

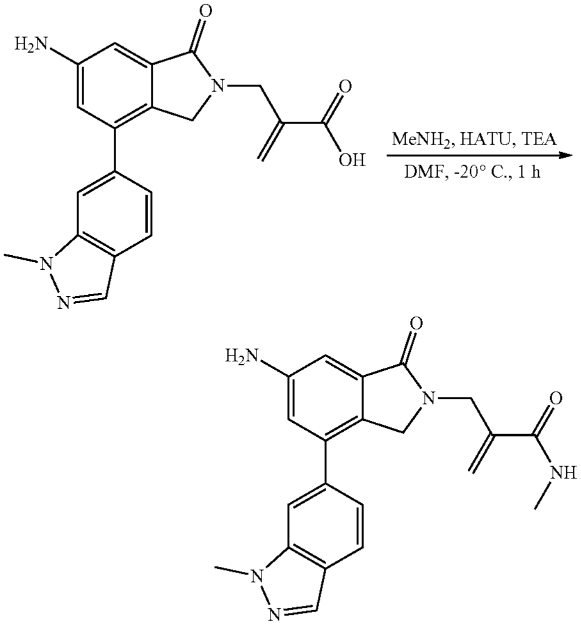

To a mixture of 2-[[6-amino-4-(1-methylindazol-6-yl)-1-oxo-isoindolin-2-yl]methyl]prop-2-enoic acid (0.02 g, 55.19 μmol, 1 eq.) in DMF (4 mL) was added TEA (27.92 mg, 275.95 μmol, 38.41 μL, 5 eq.) at −20° C. under nitrogen. Then, HATU (31.48 mg, 82.79 μmol, 1.5 eq.) was added to the reaction, and the mixture was stirred at −20° C. for 30 min, and $MeNH_2$ (4.47 mg, 66.23 μmol) was added. The mixture was stirred at −20° C. for 30 min. The reaction mixture was poured into sat. $NH_4Cl$ (30 mL) and extracted with DCM (3×10 mL). The combined organic layer was concentrated in vacuo. The residue was purified by prep- TLC (silica gel; DCM:MeOH=20:1) to afford the title compound (0.0053 g, 14.12 μmol, 25.58% yield, 100% purity) as a white solid. LC-MS: $[M+H]^+$ 376.1.

Preparation of N-[2-(2-cyanoallyl)-7-(1-methylindazol-6-yl)-3-oxo-isoindolin-5-yl]acetamide (Compound 372)

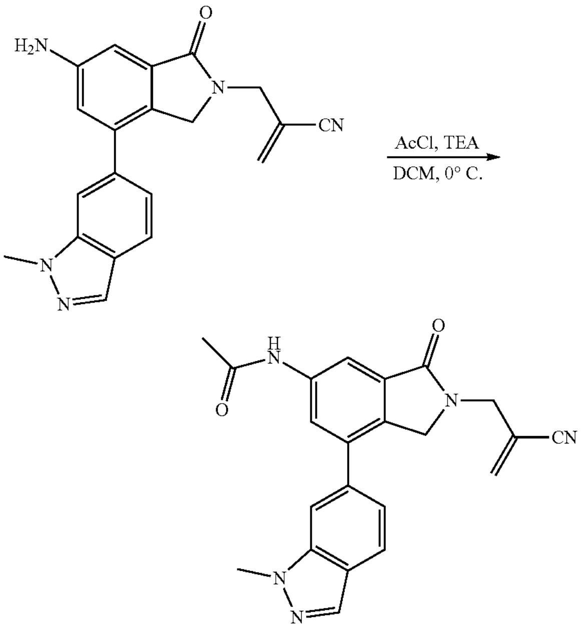

To a mixture of 2-[[6-amino-4-(1-methylindazol-6-yl)-1-oxo-isoindolin-2-yl]methyl]prop-2-enenitrile (0.03 g, 87.37 μmol, 1 eq.) in DCM (2 mL) at 0° C. was added TEA (10.61 mg, 104.84 μmol, 14.59 μL, 1.2 eq.) and acetyl chloride (6.86 mg, 87.37 μmol, 6.23 μL, 1 eq.). The mixture was stirred at 0° C. for 1 h. The reaction mixture was concentrated in vacuo, and the residue was purified by prep-HPLC to afford the title compound (0.0085 g, 21.41 μmol, 24.51% yield, 97.1% purity) as a white solid. LC-MS: $[M+H]^+$ 386.1.

Route 3

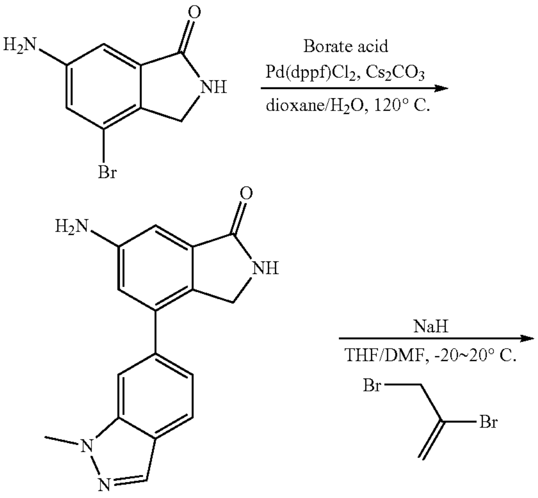

-continued

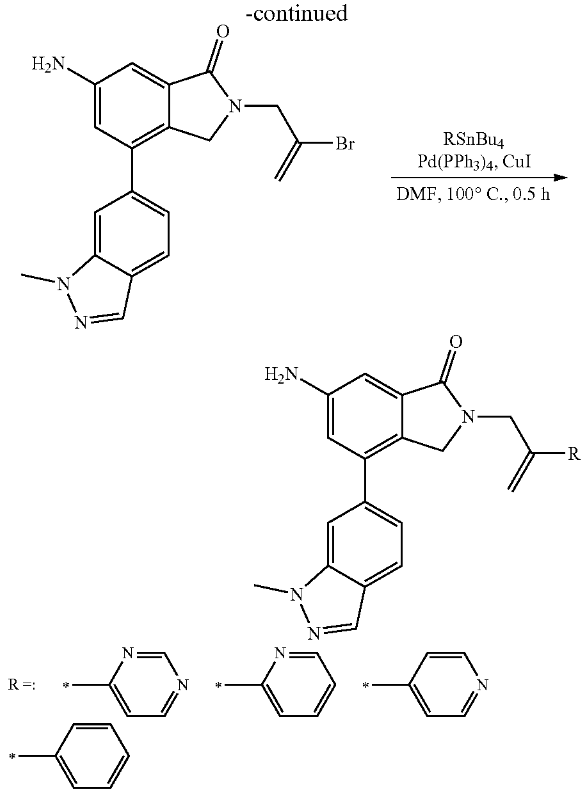

a. Preparation of 6-amino-2-(2-bromoallyl)-4-(1-methylindazol-6-yl)isoindolin-1-one

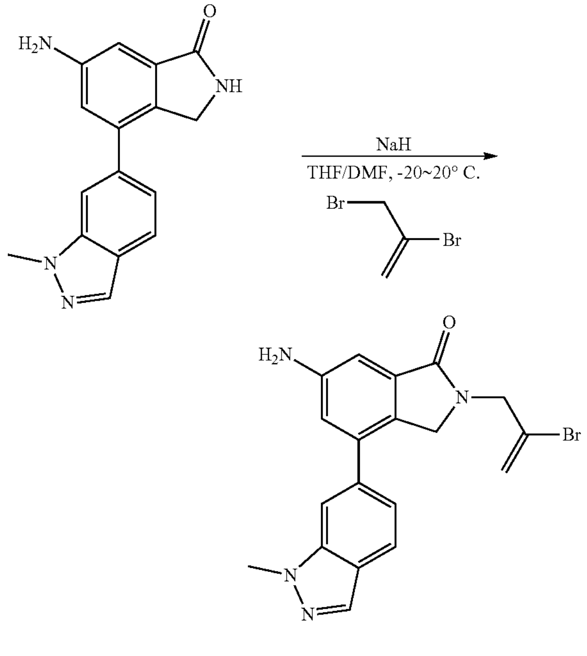

To a solution of 6-amino-4-(1-methylindazol-6-yl)isoindolin-1-one (100 mg, 323.38 μmol, 1 eq.) (90% purity) in THF (5 mL) and DMF (5 mL) was added NaH (38.80 mg, 970.15 μmol, 60% purity, 3 eq.) at 20° C. The reaction mixture was stirred for 0.5 h, then added 2,3-dibromoprop-1-ene (64.64 mg, 323.38 μmol, 31.53 μL, 1 eq.) in THF (0.5 mL) added dropwise at −20° C. The mixture was stirred at −20° C. for 1 h. LCMS showed 20% of the starting material remained. The reaction mixture was The reaction was quenched by adding sat. $NH_4Cl$ 20 mL at 0° C., and the mixture was extracted with EtOAc (3×20 mL). The combined organic layers were washed with brine (3×20 mL×3), dried over anhydrous sodium sulfate, filtered, and concentrated in vacuo to give a residue. The residue was purified by prep-TLC (silica gel; DCM:MeOH=10:1) to afford the title compound (150 mg, 377.58 μmol, 38.92% yield) as a light yellow solid.

Preparation of 6-amino-4-(1-methylindazol-6-yl)-2-(2-pyrimidin-4-ylallyl)isoindolin-1-one (Compound 379)

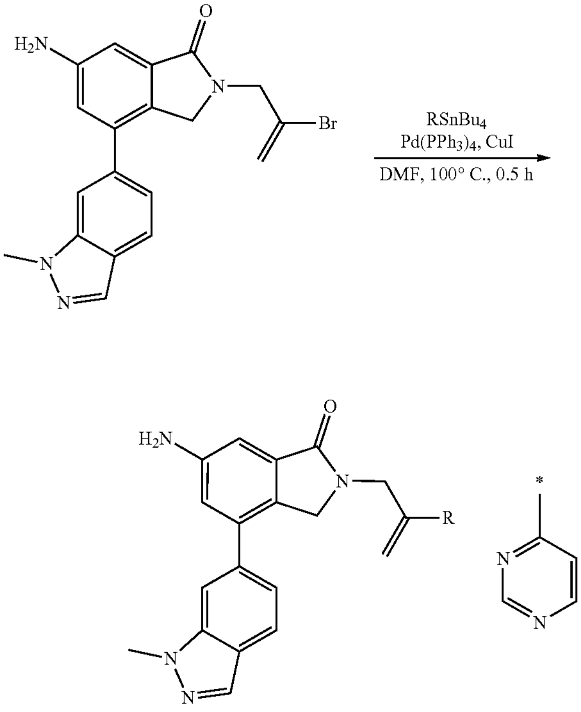

To a mixture solution of 6-amino-2-(2-bromoallyl)-4-(1-methylindazol-6-yl)isoindolin-1-one (40 mg, 100.69 μmol, 1 eq.) in DMF (4 mL) were added tributyl(pyrimidin-4-yl) stannane (74.33 mg, 201.38 μmol, 2 eq.), CuI (3.84 mg, 20.14 μmol, 0.2 eq.), $Pd(PPh_3)_4$ (11.64 mg, 10.07 μmol, 0.1 eq.). The mixture was degassed and purged with nitrogen 3 times, and the mixture was stirred at 100° C. for 0.5 h under nitrogen atmosphere. LCMS showed that the reaction was complete. The reaction mixture was added to 30 mL sat. EDTA and stirred for 1 h, and extracted with EtOAc (20 mL×3). The combined organic layers were washed with brine (3×20 mL), dried over anhydrous sodium sulfate, filtered, and concentrated in vacuo to give a residue. The residue was purified by prep-TLC (silica gel; DCM: MeOH=10:1) to afford the title compound (6.6 mg, 16.46 μmol, 16.355% yield, 98.9% purity) as a white solid. LC-MS: $[M+H]^+$ 397.1.

Route 4:

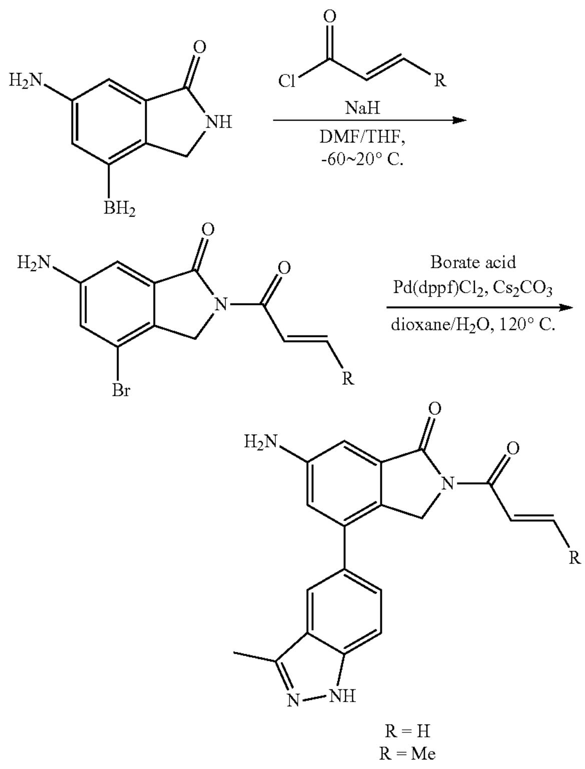

General Procedure for 6-amino-4-bromo-2-prop-2-enoyl-isoindolin-1-one

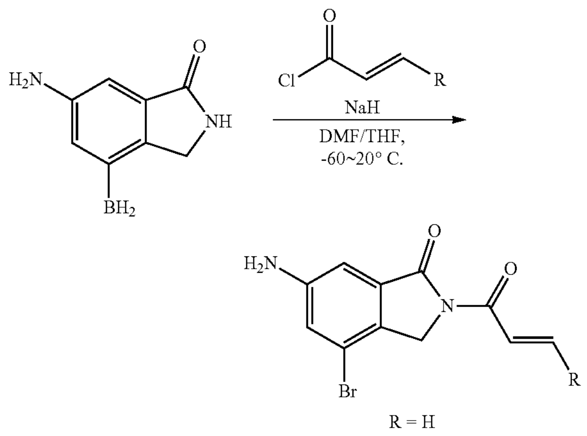

To a solution of 6-amino-4-bromo-isoindolin-1-one (100 mg, 440.42 μmol, 1 eq.) in DMF (3 mL) and THF (3 mL) was added NaH (52.84 mg, 1.32 mmol, 60% purity, 3 eq.). The reaction was stirred at 20° C. for 0.5 h, and prop-2-enoyl chloride (39.86 mg, 440.42 μmol, 35.91 μL, 1 eq.) in THF (0.5 mL) was added at −60° C. The mixture was stirred further at −60° C. for 1 h. LCMS showed no starting material remained. The reaction mixture was The reaction was quenched by adding sat. aq. $NH_4Cl$ 10 mL at 0° C., and the mixture was extracted with EtOAc (15 mL×3). The combined organic layers were washed with brine (30 mL), dried over anhydrous sodium sulfate, filtered, and concentrated in vacuo to give a residue. The residue was purified by prep-TLC (silica gel; DCM:MeOH=10:1) to afford the title compound (40 mg, 135.18 μmol, 30.69% yield, 95% purity) as a light yellow solid.

Preparation of 6-amino-4-(3-methyl-1H-indazol-5-yl)-2-prop-2-enoyl-isoindolin-1-one (Compound 383)

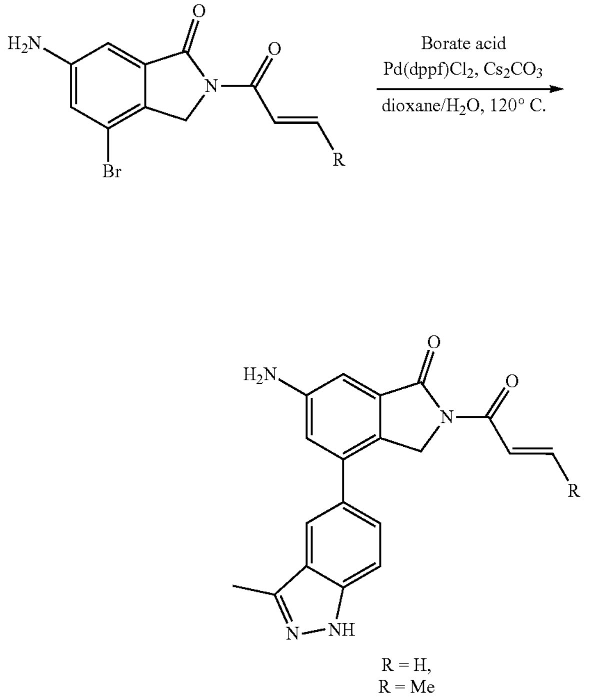

Procedure for R=H:

To a mixture of 6-amino-4-bromo-2-prop-2-enoyl-isoindolin-1-one (30 mg, 106.72 μmol, 1 eq.) and (3-methyl-1H-indazol-5-yl)boronic acid (18.78 mg, 106.72 μmol, 1 eq.) in dioxane (3 mL) and water (0.75 mL) were added $Cs_2CO_3$ (104.32 mg, 320.17 μmol, 3 eq.) and Pd(dppf)$Cl_2$ (7.81 mg, 10.67 μmol, 0.1 eq.). The mixture was degassed and purged with nitrogen 3 times and stirred at 120° C. for 20 min under nitrogen atmosphere. LCMS showed no starting material remained. The reaction mixture was poured into 30 mL saturated aq. EDTA and stirred for 1 h, and extracted with EtOAc (20 mL×3). The combined organic layers were washed with brine (20 mL×3), dried over anhydrous sodium sulfate, filtered, and concentrated in vacuo to give a residue. The residue was purified by prep-TLC (silica gel; DCM: MeOH=10:1) then purified by prep-HPLC to afford the title compound (3.0 mg, 8.79 μmol, 8.24% yield, 97.4% purity) as a light yellow solid. LC-MS: $[M+H]^+$ 347.1.

Preparation of tert-butyl 5-[2-(2-carbamoylallyl)-6-(methylamino)-1-oxo-isoindolin-4-yl]-3-methyl-indazole-1-carboxylate

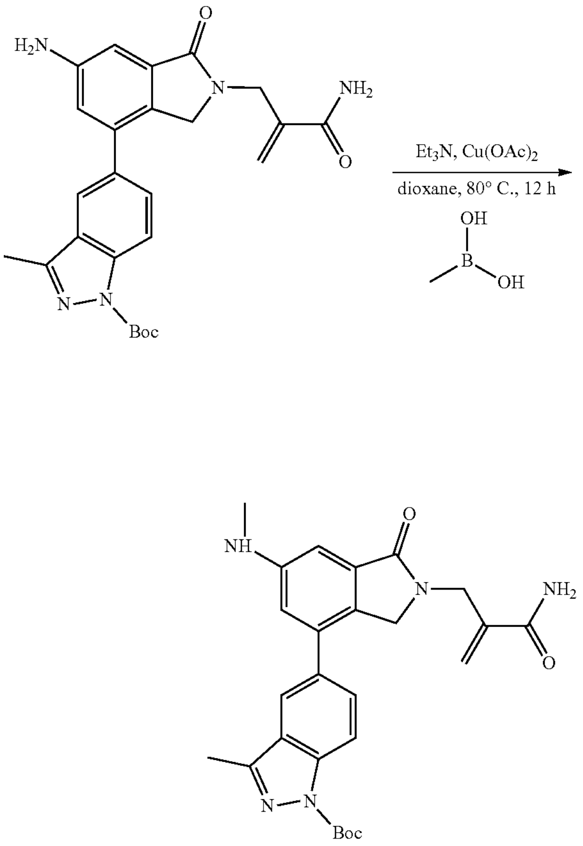

To a solution of tert-butyl 5-[6-amino-2-(2-carbamoylallyl)-1-oxo-isoindolin-4-yl]-3-methyl-indazole-1-carboxylate (100 mg, 216.68 μmol, 1 eq.) in dioxane (3 mL) were added TEA (109.63 mg, 1.08 mmol, 150.80 μL, 5 eq.), $Cu(OAc)_2$ (118.07 mg, 650.04 μmol, 3 eq.) in one portion under nitrogen. The mixture was stirred for 30 min, then methylboronic acid (38.91 mg, 650.04 μmol, 3 eq.) in dioxane (0.2 mL) was added. The reaction mixture was stirred for at 80° C. for 11.5 h under $O_2$ balloon. TLC showed that the reaction was complete. 20 mL of EtOAc poured into the mixture, and the resulting mixture was poured into a sat EDTA solution (30 mL) and stirred for 1 h. The aqueous phase was extracted with EtOAc (3×20 mL). The combined organic phase was washed with brine (3×30 mL), dried over anhydrous sodium sulfate and concentrated in vacuo. The residue was purified by prep-TLC (silica gel; DCM:MeOH=10:1) to afford the title compound (45 mg, 94.63 μmol, 43.67% yield) as a yellow solid.

Preparation of 2-[[6-(methylamino)-4-(3-methyl-1H-indazol-5-yl)-1-oxo-isoindolin-2-yl]methyl]prop-2-enamide (Compound 387)

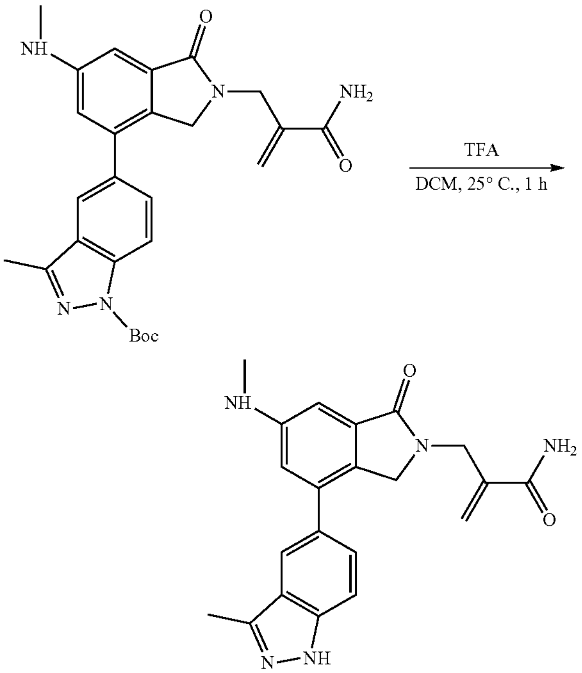

To a mixture of tert-butyl 5-[2-(2-carbamoylallyl)-6-(methylamino)-1-oxo-isoindolin-4-yl]-3-methyl-indazole-1-carboxylate (40 mg, 84.12 μmol, 1 eq.) in DCM (0.75 mL) was added trifluoroacetic acid (385 mg, 3.38 mmol, 0.25 mL, 40.14 eq.) in one portion. The mixture was stirred at 25° C. for 60 min, LCMS and HPLC showed that the reaction was complete. The reaction mixture was adjusted to pH=8 with saturated aq. $Na_2CO_3$. The mixture was extracted with EtOAc (3×20 mL). The combined organic phase was washed with brine (3×30 mL), dried over anhydrous sodium sulfate and active carbon to remove color, then concentrated in vacuo. The residue was purified by prep-HPLC to afford the title compound (5.1 mg, 13.44 μmol, 15.97% yield, 98.9% purity) as a white solid. LC-MS: $[M+H]^+$ 376.2.

Route 5

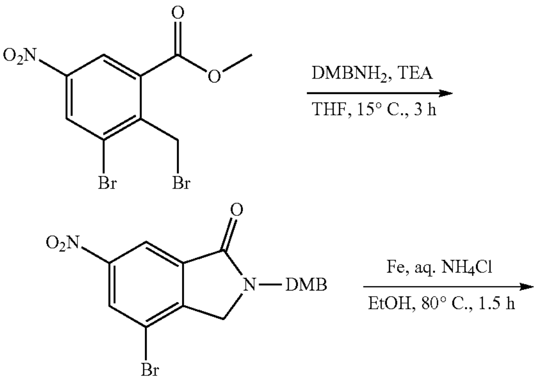

-continued

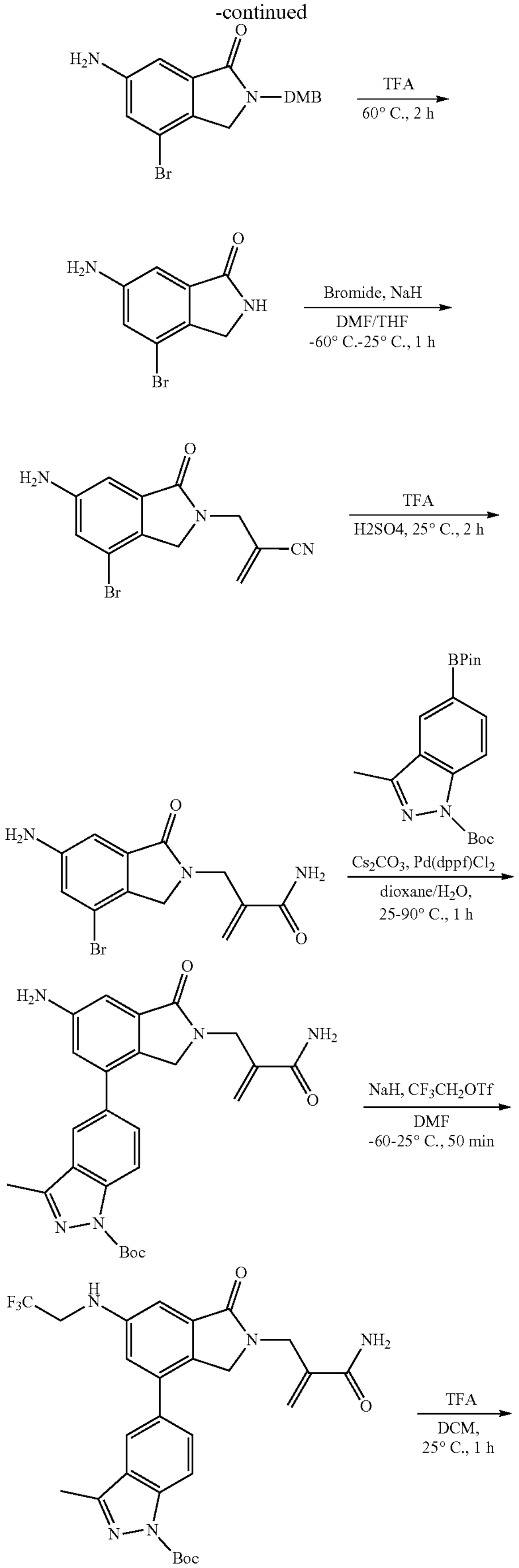

-continued

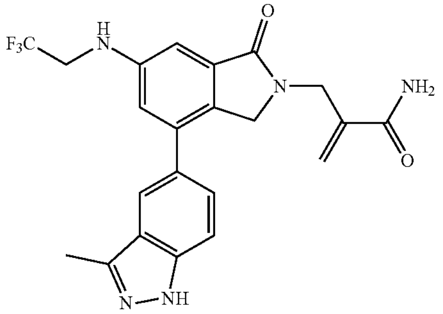

a. Preparation of 4-bromo-2-[(2,4-dimethoxyphenyl) methyl]-6-nitro-isoindolin-1-one

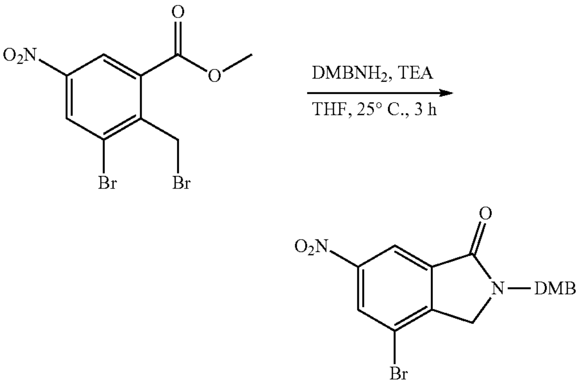

To a mixture of methyl 3-bromo-2-(bromomethyl)-5-nitrobenzoate (10 g, 28.33 mmol, 1 eq.) and 2,4-dimethoxybenzylamine (5.02 g, 30.03 mmol, 4.52 mL, 1.06 eq.) in THF (300 mL) was added TEA (14.33 g, 141.66 mmol, 19.72 mL, 5 eq.) in one portion at 25° C. under nitrogen. The mixture was stirred at 25° C. for 3 h. TLC showed that the reaction was complete. The reaction was quenched with ice water (100 mL) and extracted with EtOAc (3×100 mL). The combined organic layer was washed with brine (3×50 mL), dried over anhydrous sodium sulfate, filtered, and concentrated. The residue was purified by column chromatography (silica gel; PE:EtOAc=1/0 to 4:1) to afford the title compound (9 g, 18.79 mmol, 66.31% yield, 85% purity) as a yellow solid.

b. Preparation of 6-amino-4-bromo-2-[(2,4-dimethoxyphenyl)methyl]isoindolin-1-one

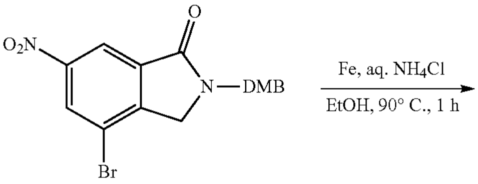

-continued

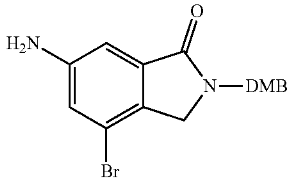

To a mixture of 4-bromo-2-[(2,4-dimethoxyphenyl)methyl]-6-nitro-isoindolin-1-one (9 g, 18.79 mmol, 1 eq.) (85% purity) in EtOH (320 mL) was added $NH_4Cl$ (1 g, 18.79 mmol, 1 eq.) in water (80 mL), then Fe (5.25 g, 93.93 mmol, 5 eq.) was added in portions at 90° C. The mixture was stirred at 90° C. for 1 h. TLC showed that the reaction was complete. The reaction was filtered, and the filter cake was washed with hot EtOAc/EtOH=1/1 (3×200 mL). The combined organic layer was concentrated. 100 mL of water was added to the reaction mixture, and the mixture was extracted with EtOAc (4×100 mL). The combined organic layer was washed with brine (3×50 mL), dried over anhydrous sodium sulfate, filtered, and concentrated. the crude product was washed with PE (3×50 mL) to afford the title compound (8 g, 18.03 mmol, 95.95% yield, 85% purity) as a yellow solid.

b. Preparation of 6-amino-4-bromo-isoindolin-1-one

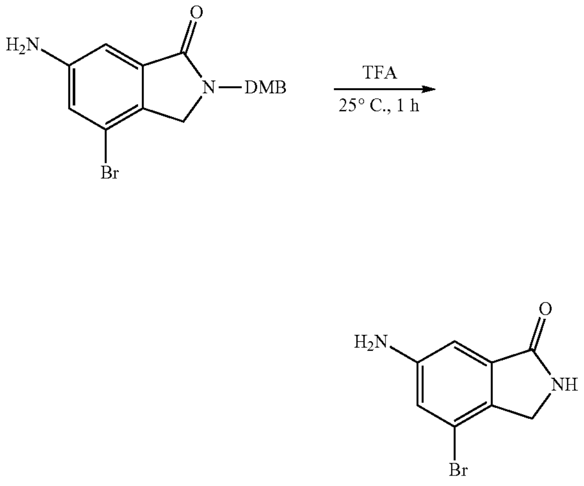

6-amino-4-bromo-2-[(2,4-dimethoxyphenyl)methyl]isoindolin-1-one (8 g, 21.21 mmol, 1 eq.) was dissolved in trifluoroacetic acid (200 mL) at 25° C. The mixture was stirred at 25° C. for 1 h. LCMS showed that the reaction was complete. The reaction was poured to water (200 mL) and 2N aq. NaOH was added to adjust pH of the mixture to 8. A solid formed, and the solution was filtered in vacuo to remove solvent. The crude product was washed with DCM (3×20 mL) and water (3×20 mL) to afford the title compound (4 g, 15.86 mmol, 74.76% yield, 90% purity) as a white solid.

c. Preparation of 2-[(6-amino-4-bromo-1-oxo-isoindolin-2-yl)methyl]prop-2-enenitrile

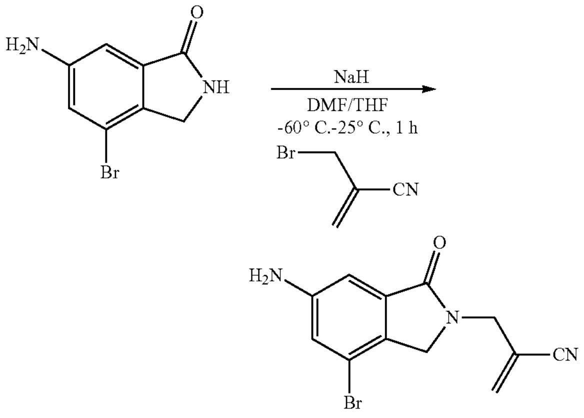

To a mixture of 6-amino-4-bromo-isoindolin-1-one (2 g, 8.81 mmol, 1 eq.) in THF (40 mL), DMF (40 mL) was added NaH (528.45 mg, 13.21 mmol, 60% purity, 1.5 eq.) in one portion at 25° C. under nitrogen. The mixture was stirred at 25° C. for 30 min, then (bromomethyl)prop-2-enenitrile (1.29 g, 8.81 mmol, 1 eq.) was added to the mixture. The mixture was stirred at −60° C. for 30 min. LCMS showed that the reaction was complete. The reaction was poured to sat. $NH_4Cl$ (300 mL) and extracted with EtOAc (3×100 mL). The combined organic layer was concentrated in vacuo. The residue was purified by column chromatography (silica gel; DCM/MeOH=60/1 to 30:1) to afford the title compound (1.2 g, 4.11 mmol, 46.63% yield) as a white solid.

d. Preparation of 2-[(6-amino-4-bromo-1-oxo-isoindolin-2-yl)methyl]prop-2-enamide

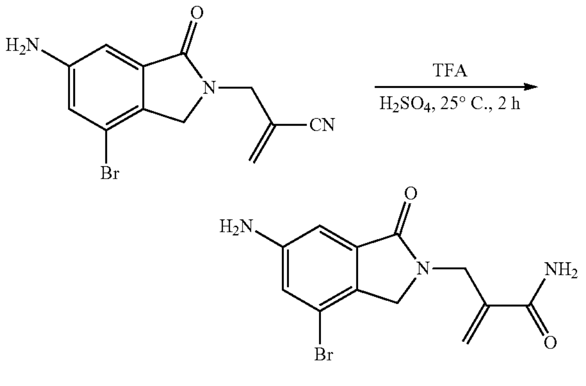

To a mixture of 2-[(6-amino-4-bromo-1-oxo-isoindolin-2-yl)methyl]prop-2-enenitrile (1.1 g, 3.77 mmol, 1 eq.) in $H_2SO_4$ (20.24 g, 144.46 mmol, 11 mL, 70% purity, 38.36 eq.) was added trifluoroacetic acid (16.94 g, 148.57 mmol, 11 mL, 39.46 eq.) in one portion at 25° C. The mixture was stirred at 25° C. for 2 h. LCMS showed that the reaction was complete. The reaction mixture was poured into ice water (20 mL) and 2N aq. NaOH was added to adjust the mixture to pH=8. The resulting precipitate was filtered in vacuo, and the crude product was washed with water (3×20 mL) to afford the title compound (1 g, 3.22 mmol, 85.63% yield) as a white solid.

e. Preparation of tert-butyl 5-[6-amino-2-(2-carbamoylallyl)-1-oxo-isoindolin-4-yl]-3-methyl-indazole-1-carboxylate

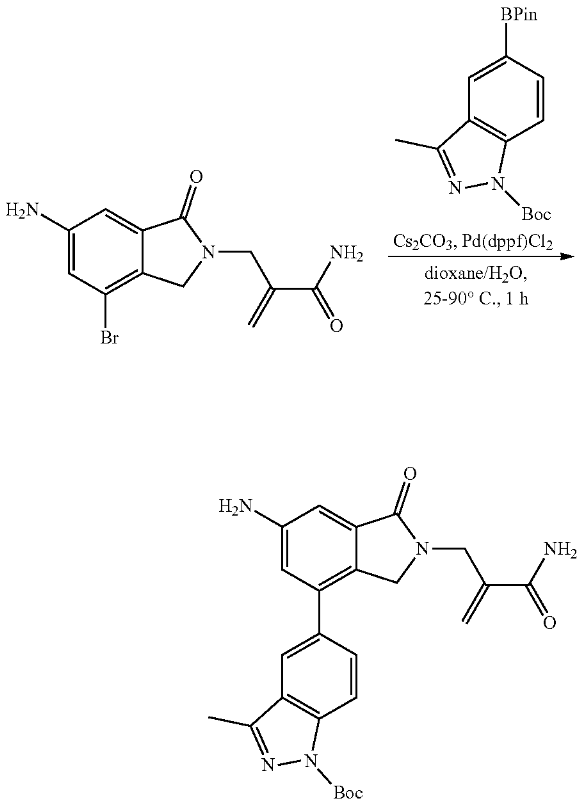

To a mixture of 2-[(6-amino-4-bromo-1-oxo-isoindolin-2-yl)methyl]prop-2-enamide (1 g, 3.22 mmol, 1 eq.) and tert-butyl 3-methyl-5-(4,4,5,5-tetramethyl-1,3,2-dioxaborolan-2-yl)indazole-1-carboxylate (1.39 g, 3.87 mmol, 1.2 eq.) in dioxane (20 mL) and water (5 mL) were added $Cs_2CO_3$ (3.15 g, 9.67 mmol, 3 eq.) and Pd(dppf)$Cl_2$ (235.92 mg, 322.43 μmol, 0.1 eq.) in one portion at 25° C. under nitrogen. The mixture was stirred at 90° C. for 1 h. LCMS showed that the reaction was complete. The reaction was poured to sat. EDTA (20 mL), diluted with 20 mL EtOAc, then the mixture was stirred at 25° C. for 1 h. The aqueous layer was extracted with EtOAc (3×20 mL). The combined organic layer was washed with brine 20 mL, filtered, and concentrated in vacuo. The residue was purified by column chromatography (silica gel; DCM/MeOH=40/1 to 20:1) to afford the title compound (1.2 g, 2.60 mmol, 80.64% yield) as a yellow solid.

f. Preparation of tert-butyl 5-[2-(2-carbamoylallyl)-1-oxo-6-(2,2,2-trifluoroethylamino) isoindolin-4-yl]-3-methyl-indazole-1-carboxylate

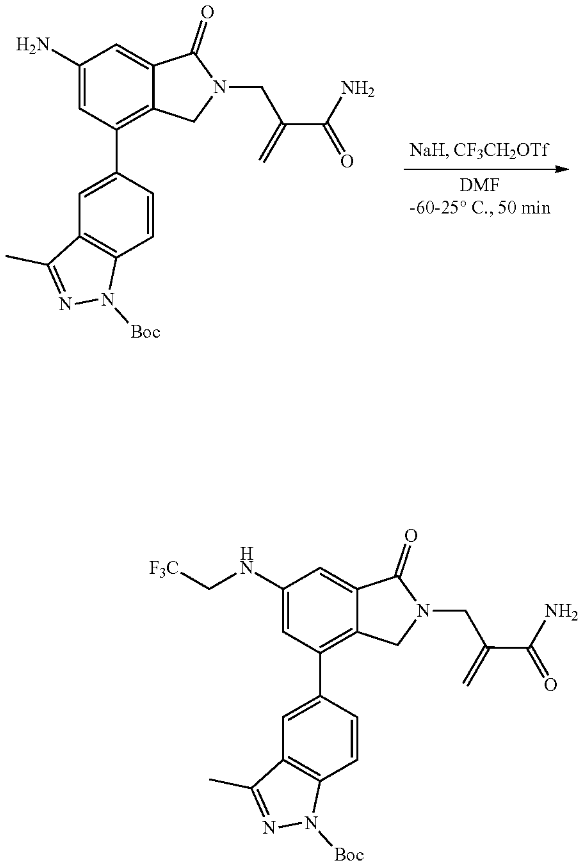

To a mixture of tert-butyl 5-[6-amino-2-(2-carbamoylallyl)-1-oxo-isoindolin-4-yl]-3-methyl-indazole-1-carboxylate (0.06 g, 130.01 μmol, 1 eq.) in DMF (3 mL) was added NaH (7.80 mg, 195.01 μmol, 60% purity, 1.5 eq.) in one portion at 25° C. under nitrogen. The mixture was stirred at 25° C. for 30 min, then $CF_3CH_2OTf$ (33.19 mg, 143.01 μmol, 1.1 eq.) was added to the mixture at −60° C. The mixture was stirred at −60° C. for 20 min. TLC showed that the reaction was complete. The reaction mixture was poured into sat. $NH_4Cl$ (300 mL) and extracted with EtOAc (3×100 mL). The combined organic layer was concentrated in vacuo. The residue was purified by prep-TLC (silica gel; DCM:MeOH=10:1) to afford the title compound (0.05 g, 91.99 μmol, 70.76% yield) as a yellow solid. LC-MS: $[M+H]^+$ 444.2.

Preparation of 2-[[6-amino-4-[3-methyl-1-(2,2,2-trifluoroethyl)indazol-5-yl]-1-oxo-isoindolin-2-yl]methyl]prop-2-enamide (Compound 392)

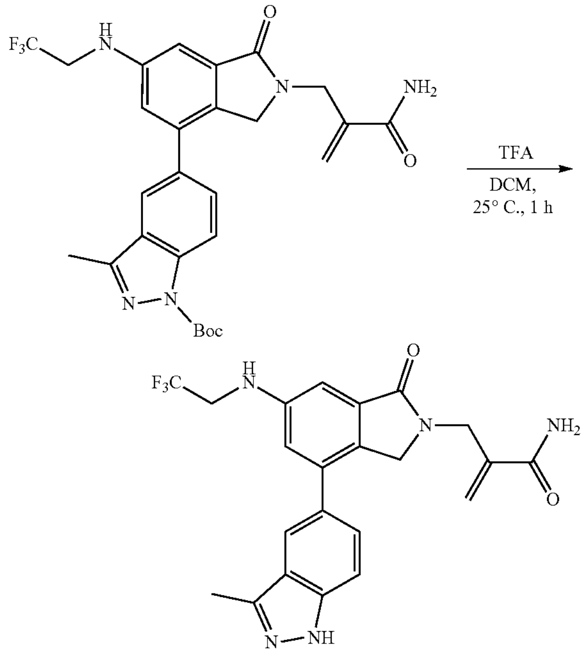

To a mixture of tert-butyl 5-[2-(2-carbamoylallyl)-1-oxo-6-(2,2,2-trifluoroethylamino)isoindolin-4-yl]-3-methyl-indazole-1-carboxylate (0.05 g, 91.99 μmol, 1 eq.) in DCM (3 mL) was added trifluoroacetic acid (1.54 g, 13.51 mmol, 1 mL, 146.82 eq.) in one portion at 25° C. The mixture was stirred at 25° C. for 1 h. LCMS showed that the reaction was complete. The reaction mixture was concentrated in vacuo. The crude product was purified by prep-HPLC to afford the title compound (0.0055 g, 12.24 μmol, 13.31% yield, 98.7% purity) as a white solid. LC-MS: $[M+H]^+$ 444.1.

Preparation of 2-[[4-bromo-1-oxo-6-(2,2,2-trifluoroethylamino)isoindolin-2-yl]methyl]prop-2-enamide

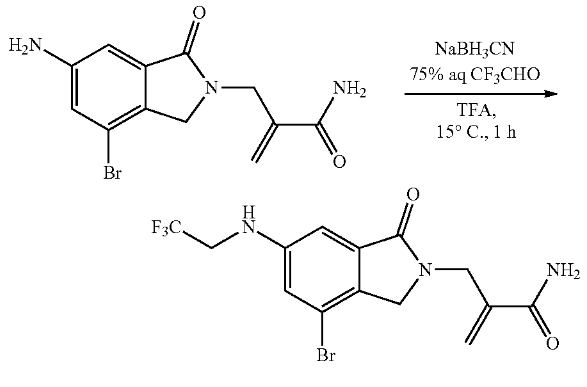

To a solution of 2-[(6-amino-4-bromo-1-oxo-isoindolin-2-yl)methyl]prop-2-enamide (300 mg, 580.37 μmol, 1 eq.) and $NaBH_3CN$ (324 mg, 5.16 mmol, 8.88 eq.) in trifluoroacetic acid (5 mL) was added 2,2,2-trifluoroacetaldehyde (250 mg, 1.91 mmol, 3.30 eq.) (75% aq in 0.8 mL trifluoroacetic acid). The reaction was stirred at 15° C. for 1 h. TLC showed 60% of the desired compound. The reaction was quenched with water (3×20 mL), and the resulting mixture was adjusted pH=8 with solid $Na_2CO_3$. Then the reaction was extracted with DCM/MeOH=10:1 (5×20 mL). The combined organic phase was dried over anhydrous sodium sulfate, filtered, and concentrated. The residue was purified by prep-TLC (silica gel; DCM/MeOH=10:1) to afford the title compound (100 mg, 254.99 μmol, 43.94% yield) as a white solid.

Preparation of tert-butyl 5-[2-(2-carbamoylallyl)-1-oxo-6-(2,2,2-trifluoroethylamino) isoindolin-4-yl]-3-methyl-indazole-1-carboxylate

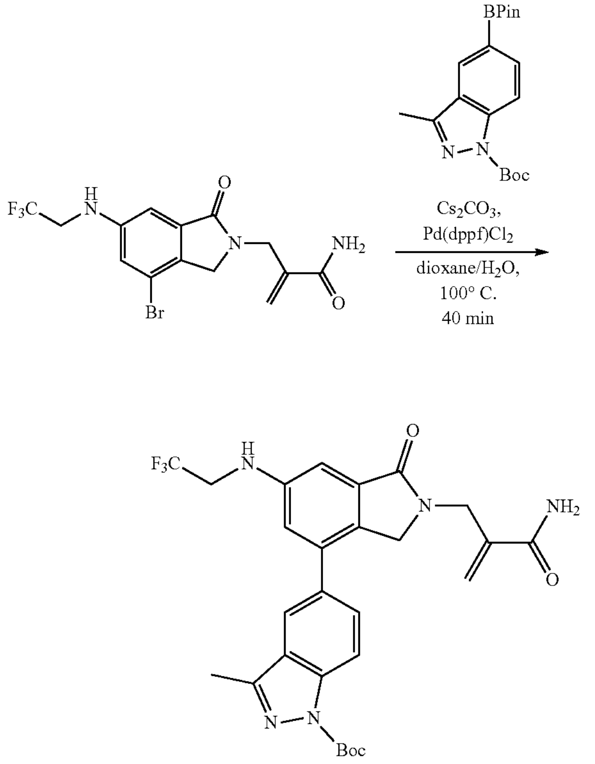

To a solution of 2-[[4-bromo-1-oxo-6-(2,2,2-trifluoroethylamino)isoindolin-2-yl]methyl]prop-2-enamide (80 mg, 203.99 μmol, 1 eq.) and tert-butyl 3-methyl-5-(4,4,5,5-tetramethyl-1,3,2-dioxaborolan-2-yl)indazole-1-carboxylate (157 mg, 438.26 μmol, 2.15 eq.) in dioxane (6.4 mL) and water (1.6 mL) were added $Cs_2CO_3$ (199.39 mg, 611.98 μmol, 3 eq.) and $Pd(dppf)Cl_2$ (14.93 mg, 20.40 μmol, 0.1 eq.). The reaction was stirred at 100° C. for 40 min under nitrogen atmosphere. TLC and LCMS showed 70% of the desired product. 20 mL EtOAc and 20 mL sat. EDTA were added to the reaction, and the reaction was stirred at 15° C. for 1 h. The reaction mixture was extracted with DCM (5×20 mL). The combined organic layer was washed with brine (3×20 mL), dried over anhydrous sodium sulfate, filtered, and concentrated. The crude was purified by prep-TLC (silica gel; DCM/MeOH=10:1) to afford the title compound (50 mg, 91.99 μmol, 45.09% yield) as a white solid.

Preparation of 2-{[4-(3-methyl-1H-indazol-5-yl)-1-oxo-6-[(2,2,2-trifluoroethyl)amino]-2,3-dihydro-1H-isoindol-2-yl]methyl}prop-2-enamide (Compound 403)

Title compound was obtained using the same procedure described for Compound 392. LC-MS: $[M+H]^+$ 444.2.

Condition 1: Preparation of tert-butyl 5-[6-benzamido-2-(2-carbamoylallyl)-1-oxo-isoindolin-4-yl]-3-methyl-indazole-1-carboxylate

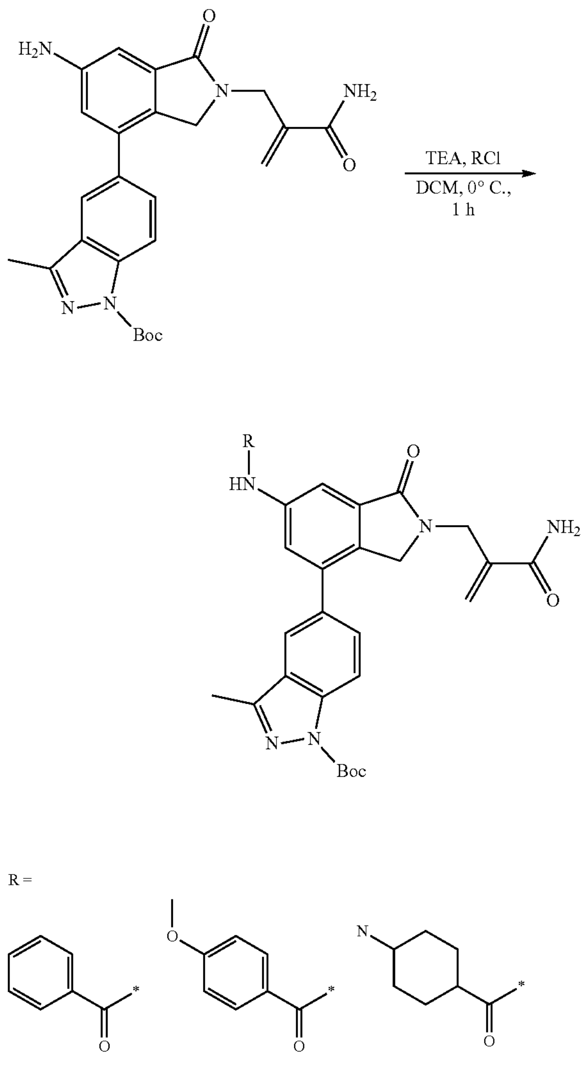

To a mixture of tert-butyl 5-[6-amino-2-(2-carbamoylallyl)-1-oxo-isoindolin-4-yl]-3-methyl-indazole-1-carboxylate (0.05 g, 108.34 μmol, 1 eq.) and benzoyl chloride (18.27 mg, 130.01 μmol, 15.10 μL, 1.2 eq.) in DCM (4 mL) was added TEA (13.16 mg, 130.01 μmol, 18.10 μL, 1.2 eq.) in one portion at 0° C. under nitrogen. The mixture was stirred at 0° C. for 1 h. The reaction was concentrated in vacuo and purified by prep-TLC (silica gel; DCM:MeOH=10:1) to afford the title compound (0.05 g, 88.40 μmol, 81.59% yield) as a yellow solid.

Condition 2:

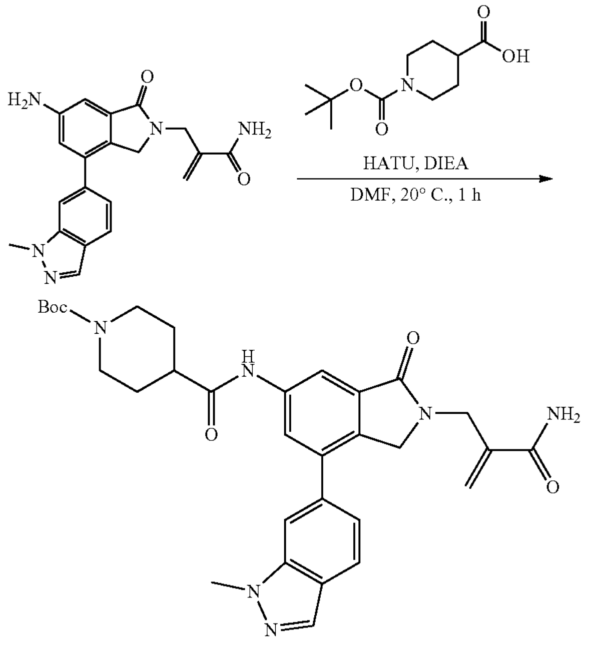

To a solution of 2-[[6-amino-4-(1-methylindazol-6-yl)-1-oxo-isoindolin-2-yl]methyl]prop-2-enamide (80 mg, 221.36 μmol, 1 eq.), 1-tert-butoxycarbonylpiperidine-4-carboxylic acid (76.13 mg, 332.05 μmol, 1.5 eq.) in DMF (4 mL) were added HATU (126.25 mg, 332.05 μmol, 1.5 eq.) and DIPEA (143.05 mg, 1.11 mmol, 192.79 μL, 5 eq.). The mixture was stirred at 20° C. for 1 h. TLC showed that the reaction was complete. The reaction mixture was poured into water (30 mL), extracted with EtOAc (3×50 mL). The combined organic layers were washed with water (3×50 mL), and washed with brine (3×50 mL), dried over anhydrous sodium sulfate, filtered, and concentrated in vacuo to afford the title compound (70 mg, crude) as a light yellow solid, which was used to next step directly without further purification.

Preparation of N-[2-(2-carbamoyl-2-methylidene-ethyl)-7-(3-methyl-1H-indazol-5-yl)-3-oxo-2,3-dihydro-1H-isoindol-5-yl]benzamide (Compound 385)

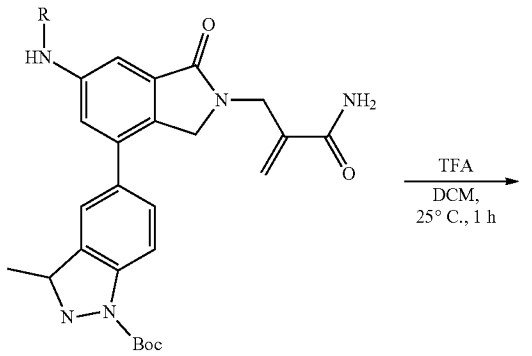

-continued

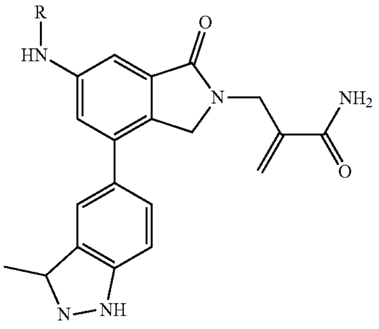

R =

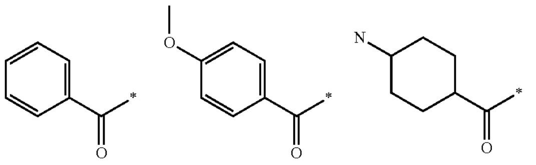

To a mixture of tert-butyl 5-[6-benzamido-2-(2-carbamoylallyl)-1-oxo-isoindolin-4-yl]-3-methyl-indazole-1-carboxylate (0.04 g, 70.72 μmol, 1 eq.) in DCM (4 mL) was added trifluoroacetic acid (1.54 g, 13.51 mmol, 1 mL, 190.98 eq.) in one portion at 25° C. The mixture was stirred at 25° C. for 1 h. TLC and LCMS showed that the reaction was complete. The reaction was poured to water (10 mL) and sat. $Na_2CO_3$ was added to adjust the solution to pH=7. The mixture was then extracted with EtOAc (3×20 mL). The combined organic layer was concentrated in vacuo. The residue was purified by prep-HPLC to afford the title compound (0.006 g, 12.62 μmol, 17.84% yield, 97.9% purity) as a white solid. LC-MS: $[M+H]^+$ 466.1.

Example 7: General Procedure for Reductive Amination

General Procedure for tert-butyl 5-[2-(2-carbamoylallyl)-1-oxo-6-(tetrahydropyran-4-ylmethylamino)isoindolin-4-yl]-3-methyl-indazole-1-carboxylate

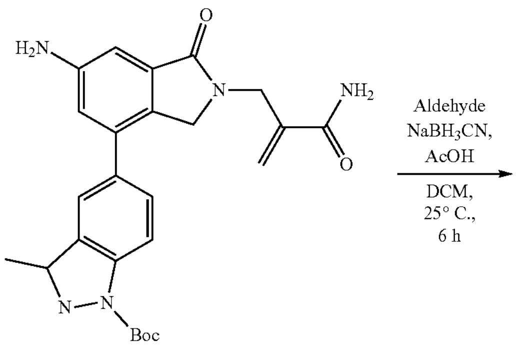

-continued

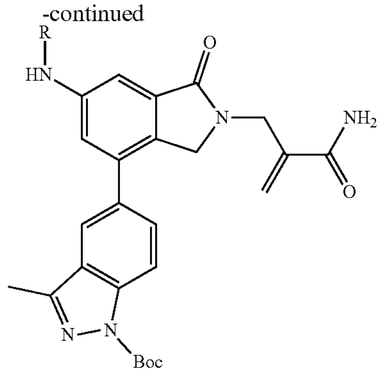

R =

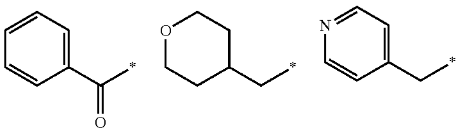

To a mixture of tert-butyl 5-[6-amino-2-(2-carbamoylallyl)-1-oxo-isoindolin-4-yl]-3-methyl-indazole-1-carboxylate (0.06 g, 130.01 μmol, 1 eq.) and tetrahydropyran-4-carbaldehyde (29.68 mg, 260.01 μmol, 2 eq.) in DCE (6 mL) was added $NaBH(OAc)_3$ (82.66 mg, 390.02 μmol, 3 eq.) in one portion at 25° C. under nitrogen. The mixture was stirred at 25° C. for 6 h. TLC and LCMS showed that the reaction was complete. The reaction mixture was poured into a sat. $NaHCO_3$ solution (30 mL), then extracted with DCM (3×30 mL). The combined organic layer was concentrated in vacuo. The residue was purified by prep-TLC (silica gel; DCM:MeOH=10:1) to afford the title compound (0.05 g, 89.34 μmol, 68.72% yield) as a yellow solid.

Preparation of tert-butyl 5-[6-amino-2-(2-carbamoylallyl)-1-oxo-isoindolin-4-yl]-3-(3-pyridyl)indazole-1-carboxylate

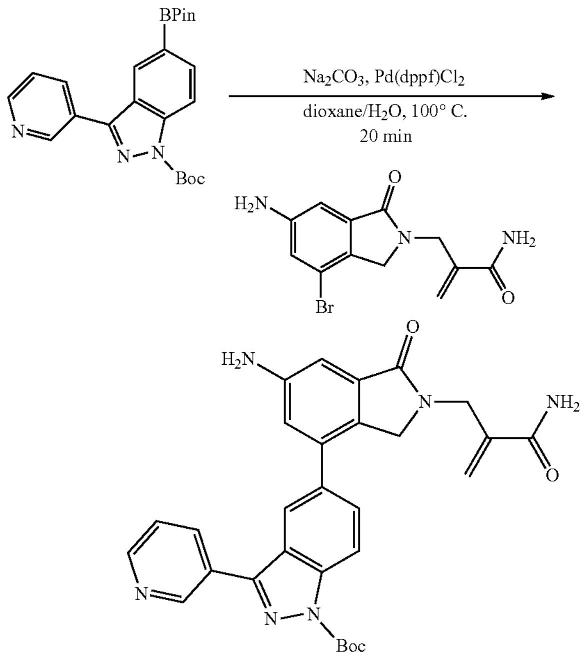

To a mixture of 2-[(6-amino-4-bromo-1-oxo-isoindolin-2-yl)methyl]prop-2-enamide (60 mg, 193.46 μmol, 1 eq.) and tert-butyl 3-(3-pyridyl)-5-(4,4,5,5-tetramethyl-1,3,2-dioxaborolan-2-yl)indazole-1-carboxylate (203.76 mg, 386.91 μmol, 2 eq.) (80% purity) in dioxane (3 mL) and water (0.75 mL) were added $Na_2CO_3$ (61.51 mg, 580.37 μmol, 3 eq.), $Pd(dppf)Cl_2$ (28.31 mg, 38.69 μmol, 0.2 eq.). The mixture was degassed and purged with nitrogen 3 times, and the mixture was stirred at 100° C. for 20 min. TLC showed that the reaction was complete. The reaction mixture was added to 30 mL of saturated aq. EDTA and stirred for 1 h, and extracted with EtOAc (3×20 mL). The combined organic layers were washed with brine (3×20 mL), dried over anhydrous sodium sulfate, filtered, and concentrated in vacuo to give a residue. The residue was purified by prep-TLC (silica gel; DCM:MeOH=15:1) to afford the title compound (60 mg, 114.38 μmol, 59.12% yield) as a light yellow solid.

TABLE 5 shows compounds described using the methods of EXAMPLE 6 and 7.

TABLE 5

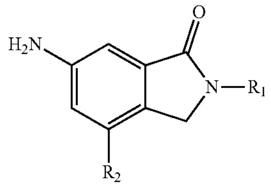

| Cpd. No. | Structure | IUPAC | LC-MS (ES+, m/z) |
|---|---|---|---|
| 366. | 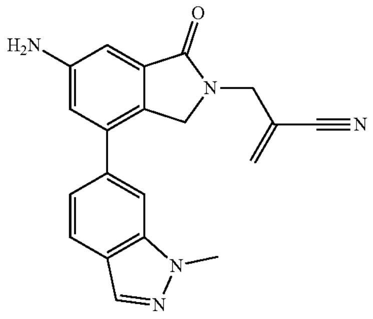 [SMILES: C=C(C#N)CN1Cc2c(cc(N)cc2-c2ccc3cnn(C)c3c2)C1=O] | 2-{[6-amino-4-(1-methyl-1H-indazol-6-yl)-1-oxo-2,3-dihydro-1H-isoindol-2-yl]methyl}prop-2-enenitrile | 344.1 |
| 367. | 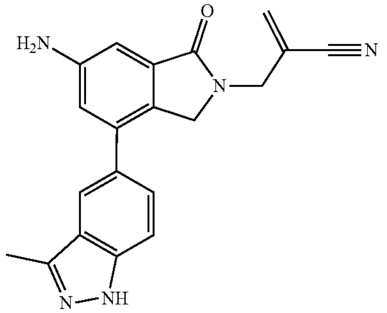 [SMILES: C=C(C#N)CN1Cc2c(cc(N)cc2-c2ccc3[nH]nc(C)c3c2)C1=O] | 2-{[6-amino-4-(3-methyl-1H-indazol-5-yl)-1-oxo-2,3-dihydro-1H-isoindol-2-yl]methyl}prop-2-enenitrile | 344.1 |
| 368. | 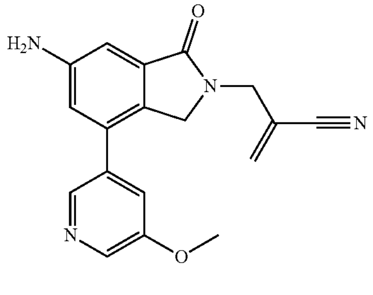 [SMILES: C=C(C#N)CN1Cc2c(cc(N)cc2-c2cncc(OC)c2)C1=O] | 2-{[6-amino-4-(5-methoxypyridin-3-yl)-1-oxo-2,3-dihydro-1H-isoindol-2-yl]methyl}prop-2-enenitrile | 321.1 |

TABLE 5-continued

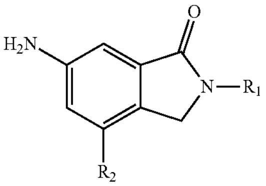

| Cpd. No. | Structure | IUPAC | LC-MS (ES+, m/z) |
|---|---|---|---|
| 369. | 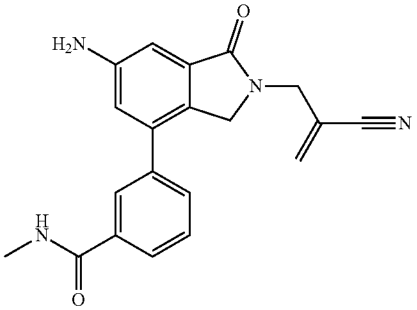 [SMILES: C=C(C#N)CN1Cc2c(cc(N)cc2-c2cccc(C(=O)NC)c2)C1=O] | 3-[6-amino-2-(2-cyano-2-methylideneethyl)-1-oxo-2,3-dihydro-1H-isoindol-4-yl]-N-methylbenzamide | 347.1 |
| 370. | 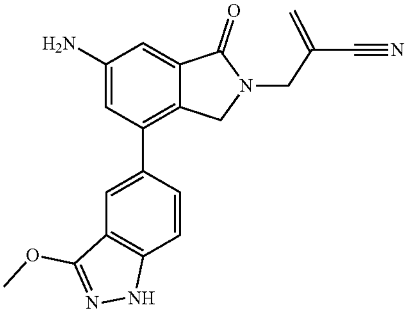 | 2-{[6-amino-4-(3-methoxy-1H-indazol-5-yl)-1-oxo-2,3-dihydro-1H-isoindol-2-yl]methyl}prop-2-enenitrile | 360.1 |
| 371. | 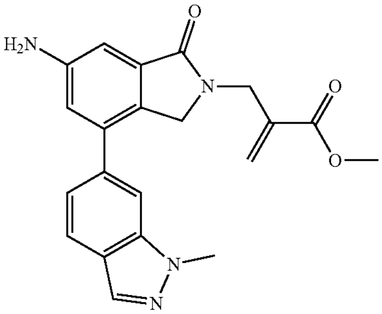 [SMILES: C=C(CN1Cc2c(cc(N)cc2-c2ccc3cnn(C)c3c2)C1=O)C(=O)OC] | methyl 2-{[6-amino-4-(1-methyl-1H-indazol-6-yl)-1-oxo-2,3-dihydro-1H-isoindol-2-yl]methyl}prop-2-enoate | 377.1 |
| 372. | 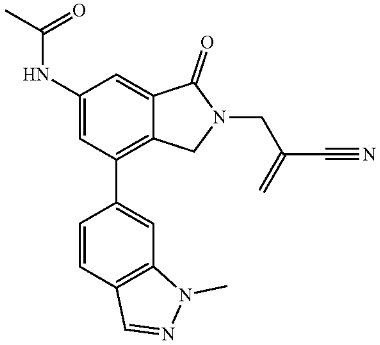 [SMILES: C=C(C#N)CN1Cc2c(cc(NC(C)=O)cc2-c2ccc3cnn(C)c3c2)C1=O] | N-[2-(2-cyano-2-methylideneethyl)-7-(1-methyl-1H-indazol-6-yl)-3-oxo-2,3-dihydro-1H-isoindol-5-yl]acetamide | 386.1 |

TABLE 5-continued
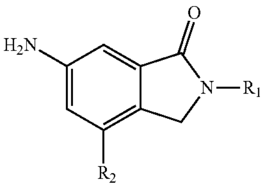
| Cpd. No. | Structure | IUPAC | LC-MS (ES+, m/z) |
|---|---|---|---|
| 373. | 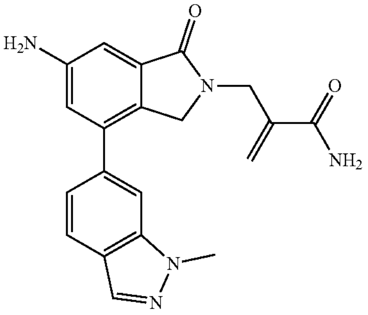 [SMILES: C=C(CN1Cc2c(cc(N)cc2-c2ccc3cnn(C)c3c2)C1=O)C(N)=O] | 2-{[6-amino-4-(1-methyl-1H-indazol-6-yl)-1-oxo-2,3-dihydro-1H-isoindol-2-yl]methyl}prop-2-enamide | 362.1 |
| 374. | 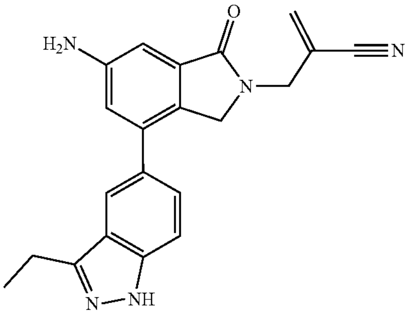 [SMILES: C=C(C#N)CN1Cc2c(cc(N)cc2-c2ccc3[nH]nc(CC)c3c2)C1=O] | 2-{[6-amino-4-(3-ethyl-1H-indazol-5-yl)-1-oxo-2,3-dihydro-1H-isoindol-2-yl]methyl}prop-2-enenitrile | 358.1 |
| 375. | 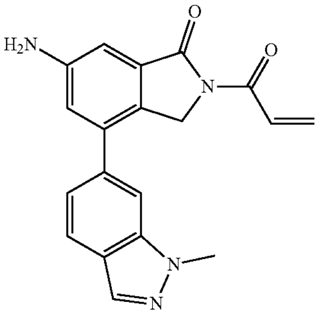 [SMILES: C=CC(=O)N1Cc2c(cc(N)cc2-c2ccc3cnn(C)c3c2)C1=O] | 6-amino-4-(1-methyl-1H-indazol-6-yl)-2-(prop-2-enoyl)-2,3-dihydro-1H-isoindol-1-one | 333.1 |
| 376. | 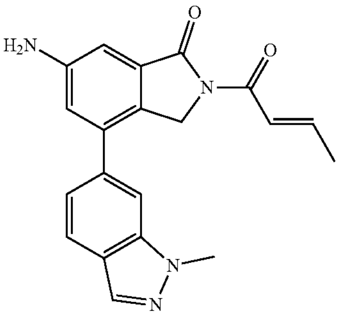 [SMILES: C/C=C/C(=O)N1Cc2c(cc(N)cc2-c2ccc3cnn(C)c3c2)C1=O] | 6-amino-2-[(2E)-but-2-enoyl]-4-(1-methyl-1H-indazol-6-yl)-2,3-dihydro-1H-isoindol-1-one | 347.1 |

TABLE 5-continued
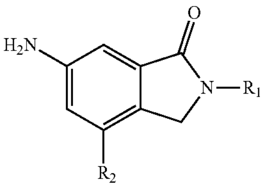
| Cpd. No. | Structure | IUPAC | LC-MS (ES+, m/z) |
|---|---|---|---|
| 377. | 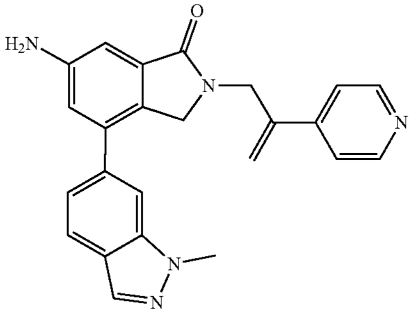 [SMILES: C=C(CN1Cc2c(cc(N)cc2-c2ccc3cnn(C)c3c2)C1=O)c1ccncc1] | 6-amino-4-(1-methyl-1H-indazol-6-yl)-2-[2-(pyridin-4-yl)prop-2-en-1-yl]-2,3-dihydro-1H-isoindol-1-one | 396.1 |
| 378. | 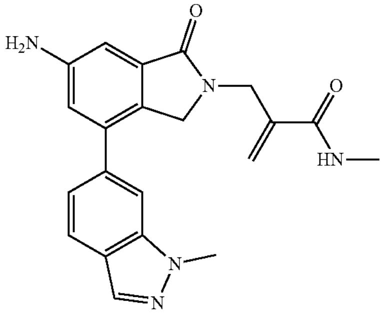 | 2-{[6-amino-4-(1-methyl-1H-indazol-6-yl)-1-oxo-2,3-dihydro-1H-isoindol-2-yl]methyl}-N-methylprop-2-enamide | 376.1 |
| 379. | 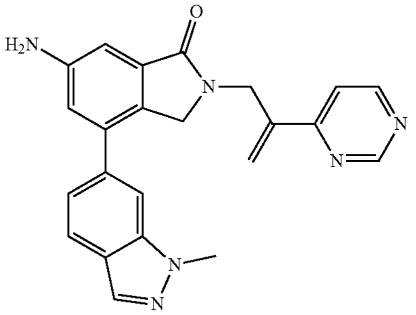 [SMILES: C=C(CN1Cc2c(cc(N)cc2-c2ccc3cnn(C)c3c2)C1=O)c1ccncn1] | 6-amino-4-(1-methyl-1H-indazol-6-yl)-2-[2-(pyrimidin-4-yl)prop-2-en-1-yl]-2,3-dihydro-1H-isoindol-1-one | 397.1 |
| 380. | 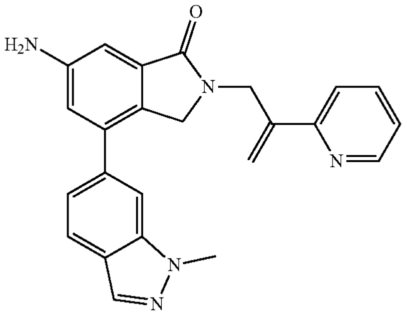 [SMILES: C=C(CN1Cc2c(cc(N)cc2-c2ccc3cnn(C)c3c2)C1=O)c1ccccn1] | 6-amino-4-(1-methyl-1H-indazol-6-yl)-2-[2-(pyridin-2-yl)prop-2-en-1-yl]-2,3-dihydro-1H-isoindol-1-one | 396.1 |

TABLE 5-continued
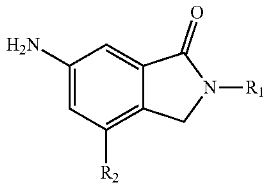
| Cpd. No. | Structure | IUPAC | LC-MS (ES+, m/z) |
| --- | --- | --- | --- |
| 381. | 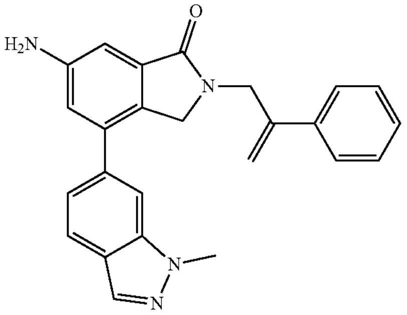 [SMILES: C=C(CN1Cc2c(cc(N)cc2-c2ccc3cnn(C)c3c2)C1=O)c1ccccc1] | 6-amino-4-(1-methyl-1H-indazol-6-yl)-2-(2-phenylprop-2-en-1-yl)-2,3-dihydro-1H-isoindol-1-one | 395.1 |
| 382. | 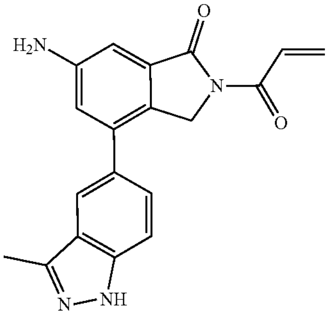 [SMILES: C=CC(=O)N1Cc2c(cc(N)cc2-c2ccc3[nH]nc(C)c3c2)C1=O] | 6-amino-4-(3-methyl-1H-indazol-5-yl)-2-(prop-2-enoyl)-2,3-dihydro-1H-isoindol-1-one | 333 |
| 383. | 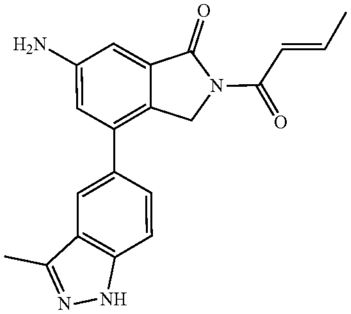 [SMILES: C/C=C/C(=O)N1Cc2c(cc(N)cc2-c2ccc3[nH]nc(C)c3c2)C1=O] | 6-amino-2-[(2E)-but-2-enoyl]-4-(3-methyl-1H-indazol-5-yl)-2,3-dihydro-1H-isoindol-1-one | 347.1 |
| 384. | 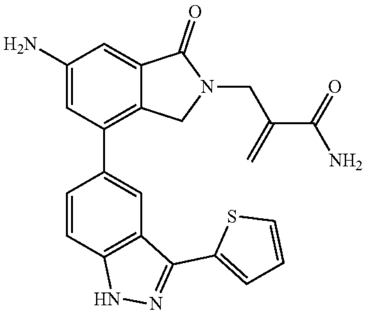 [SMILES: C=C(CN1Cc2c(cc(N)cc2-c2ccc3[nH]nc(-c4cccs4)c3c2)C1=O)C(N)=O] | 2-({6-amino-1-oxo-4-[3-(thiophen-2-yl)-1H-indazol-5-yl]-2,3-dihydro-1H-isoindol-2-yl}methyl)prop-2-enamide | 430.1 |

TABLE 5-continued

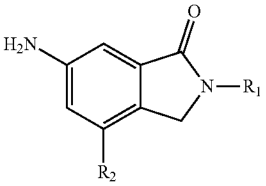

| Cpd. No. | Structure | IUPAC | LC-MS (ES+, m/z) |
|---|---|---|---|
| 385. | 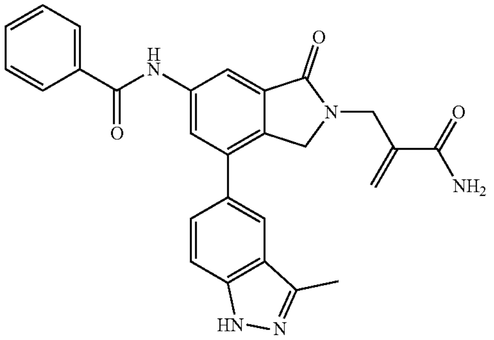 [SMILES: C=C(CN1Cc2c(cc(NC(=O)c3ccccc3)cc2-c2ccc3[nH]nc(C)c3c2)C1=O)C(N)=O] | N-[2-(2-carbamoyl-2-methylideneethyl)-7-(3-methyl-1H-indazol-5-yl)-3-oxo-2,3-dihydro-1H-isoindol-5-yl]benzamide | 466.1 |
| 386. | 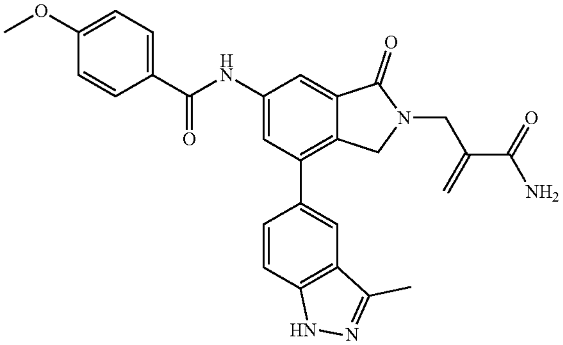 [SMILES: C=C(CN1Cc2c(cc(NC(=O)c3ccc(OC)cc3)cc2-c2ccc3[nH]nc(C)c3c2)C1=O)C(N)=O] | N-[2-(2-carbamoyl-2-methylideneethyl)-7-(3-methyl-1H-indazol-5-yl)-3-oxo-2,3-dihydro-1H-isoindol-5-yl]-4-methoxybenzamide | 496.1 |
| 387. | 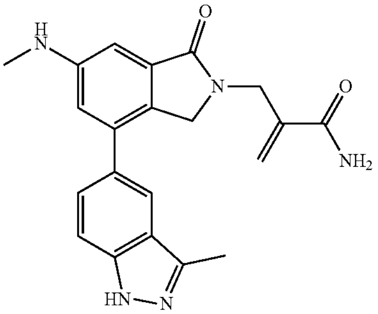 [SMILES: C=C(CN1Cc2c(cc(NC)cc2-c2ccc3[nH]nc(C)c3c2)C1=O)C(N)=O] | 2-{[4-(3-methyl-1H-indazol-5-yl)-6-(methylamino)-1-oxo-2,3-dihydro-1H-isoindol-2-yl]methyl}prop-2-enamide | 376.2 |
| 388. | 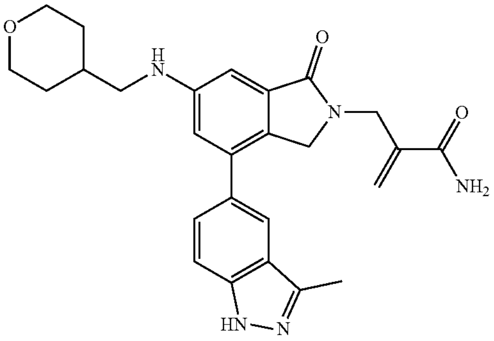 [SMILES: C=C(CN1Cc2c(cc(NCC3CCOCC3)cc2-c2ccc3[nH]nc(C)c3c2)C1=O)C(N)=O] | 2-{[4-(3-methyl-1H-indazol-5-yl)-6-{[(oxan-4-yl)methyl]amino}-1-oxo-2,3-dihydro-1H-isoindol-2-yl]methyl}prop-2-enamide | 460.1 |

TABLE 5-continued
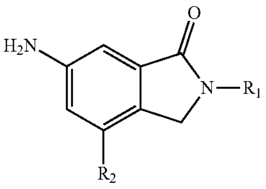
| Cpd. No. | Structure | IUPAC | LC-MS (ES+, m/z) |
|---|---|---|---|
| 389. | 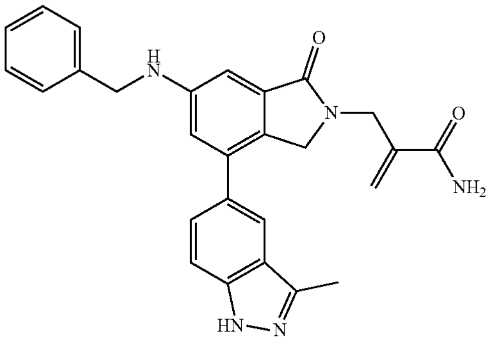 [SMILES: C=C(CN1Cc2c(cc(NCc3ccccc3)cc2-c2ccc3[nH]nc(C)c3c2)C1=O)C(N)=O] | 2-{[6-(benzylamino)-4-(3-methyl-1H-indazol-5-yl)-1-oxo-2,3-dihydro-1H-isoindol-2-yl]methyl}prop-2-enamide | 452.2 |
| 390. | 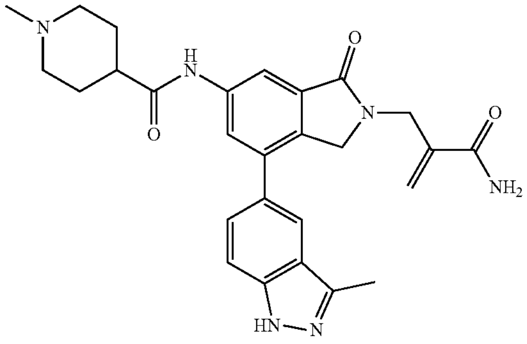 [SMILES: C=C(CN1Cc2c(cc(NC(=O)C3CCN(C)CC3)cc2-c2ccc3[nH]nc(C)c3c2)C1=O)C(N)=O] | N-[2-(2-carbamoyl-2-methylideneethyl)-7-(3-methyl-1H-indazol-5-yl)-3-oxo-2,3-dihydro-1H-isoindol-5-yl]-1-methylpiperidine-4-carboxamide | 487.2 |
| 391. | 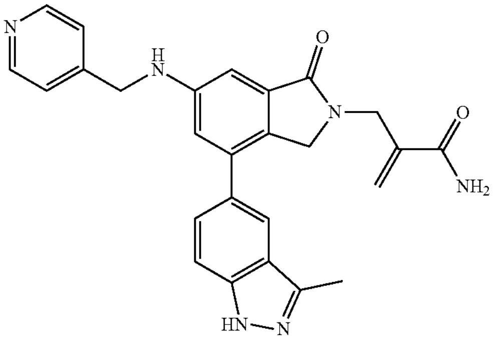 [SMILES: C=C(CN1Cc2c(cc(NCc3ccncc3)cc2-c2ccc3[nH]nc(C)c3c2)C1=O)C(N)=O] | 2-{[4-(3-methyl-1H-indazol-5-yl)-1-oxo-6-{[(pyridin-4-yl)methyl]amino}-2,3-dihydro-1H-isoindol-2-yl]methyl}prop-2-enamide | 453.1 |

TABLE 5-continued

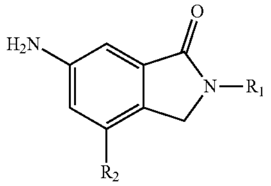

| Cpd. No. | Structure | IUPAC | LC-MS (ES+, m/z) |
|---|---|---|---|
| 392. | 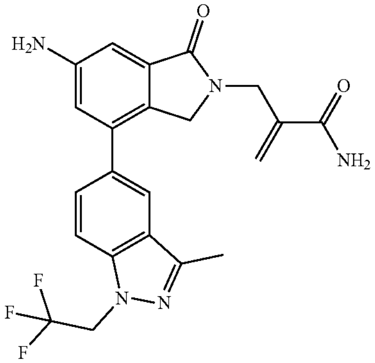 [SMILES: C=C(CN1Cc2c(cc(N)cc2-c2ccc3c(c2)c(C)nn3CC(F)(F)F)C1=O)C(N)=O] | 2-({6-amino-4-[3-methyl-1-(2,2,2-trifluoroethyl)-1H-indazol-5-yl]-1-oxo-2,3-dihydro-1H-isoindol-2-yl}methyl)prop-2-enamide | 444.1 |
| 393. | 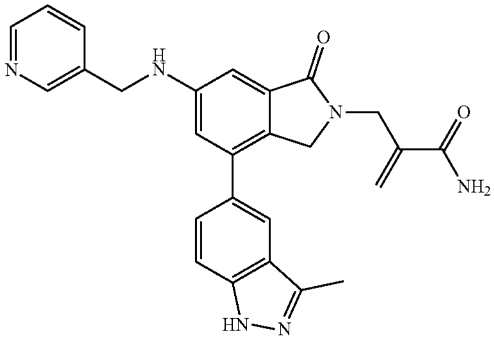 [SMILES: C=C(CN1Cc2c(cc(NCc3cccnc3)cc2-c2ccc3[nH]nc(C)c3c2)C1=O)C(N)=O] | 2-{[4-(3-methyl-1H-indazol-5-yl)-1-oxo-6-{[(pyridin-3-yl)methyl]amino}-2,3-dihydro-1H-isoindol-2-yl]methyl}prop-2-enamide | 453.1 |
| 394. | 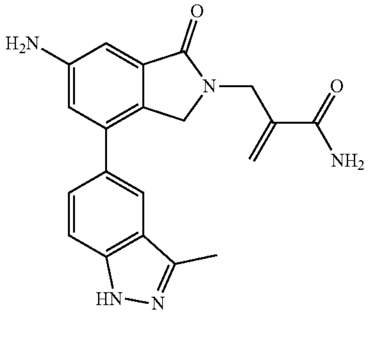 [SMILES: C=C(CN1Cc2c(cc(N)cc2-c2ccc3[nH]nc(C)c3c2)C1=O)C(N)=O] | 2-{[6-amino-4-(3-methyl-1H-indazol-5-yl)-1-oxo-2,3-dihydro-1H-isoindol-2-yl]methyl}prop-2-enamide | 362.1 |
| 395. | 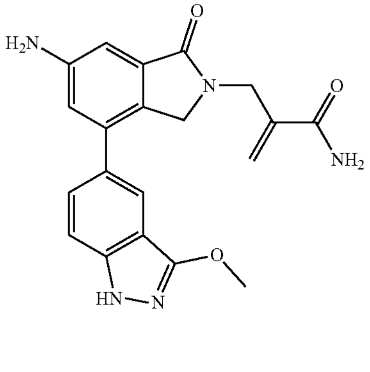 [SMILES: C=C(CN1Cc2c(cc(N)cc2-c2ccc3[nH]nc(OC)c3c2)C1=O)C(N)=O] | 2-{[6-amino-4-(3-methoxy-1H-indazol-5-yl)-1-oxo-2,3-dihydro-1H-isoindol-2-yl]methyl}prop-2-enamide | 378.1 |

TABLE 5-continued
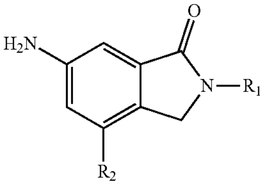
| Cpd. No. | Structure | IUPAC | LC-MS (ES+, m/z) |
|---|---|---|---|
| 396. | 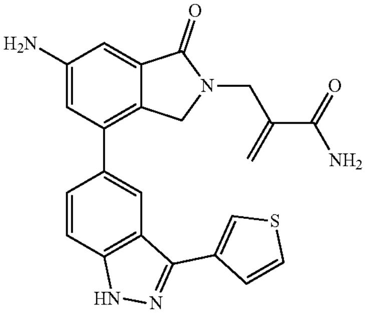 [SMILES: C=C(CN1Cc2c(cc(N)cc2-c2ccc3[nH]nc(-c4ccsc4)c3c2)C1=O)C(N)=O] | 2-({6-amino-1-oxo-4-[3-(thiophen-3-yl)-1H-indazol-5-yl]-2,3-dihydro-1H-isoindol-2-yl}methyl)prop-2-enamide | 430 |
| 397. | 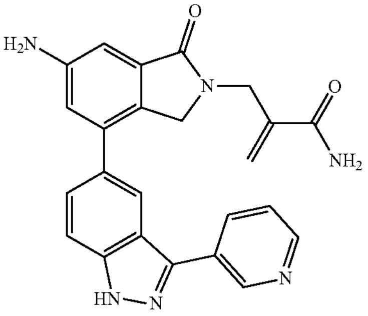 [SMILES: C=C(CN1Cc2c(cc(N)cc2-c2ccc3[nH]nc(-c4cccnc4)c3c2)C1=O)C(N)=O] | 2-({6-amino-1-oxo-4-[3-(pyridin-3-yl)-1H-indazol-5-yl]-2,3-dihydro-1H-isoindol-2-yl}methyl)prop-2-enamide | 425.2 |
| 398. | 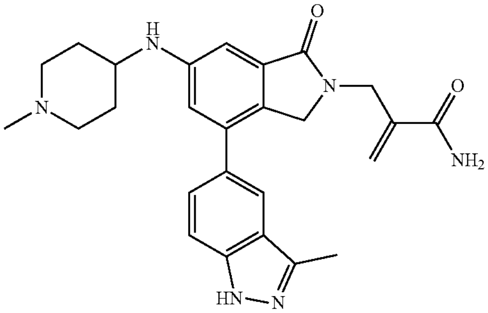 [SMILES: C=C(CN1Cc2c(cc(NC3CCN(C)CC3)cc2-c2ccc3[nH]nc(C)c3c2)C1=O)C(N)=O] | 2-{[4-(3-methyl-1H-indazol-5-yl)-6-[(1-methylpiperidin-4-yl)amino]-1-oxo-2,3-dihydro-1H-isoindol-2-yl]methyl}prop-2-enamide | 459.3 |

TABLE 5-continued
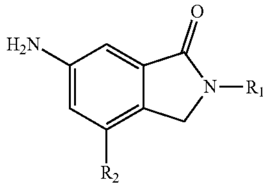
| Cpd. No. | Structure | IUPAC | LC-MS (ES+, m/z) |
|---|---|---|---|
| 399. | 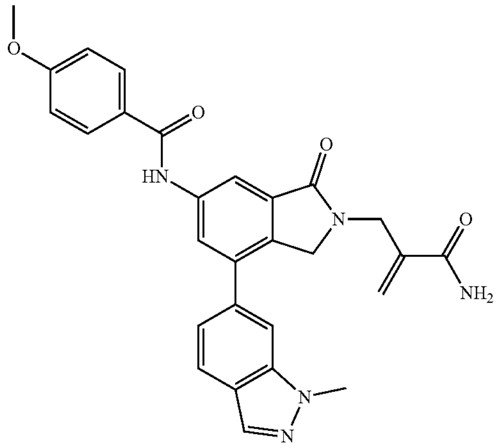 [SMILES: C=C(CN1Cc2c(cc(NC(=O)c3ccc(OC)cc3)cc2-c2ccc3cnn(C)c3c2)C1=O)C(N)=O] | N-[2-(2-carbamoyl-2-methylideneethyl)-7-(1-methyl-1H-indazol-6-yl)-3-oxo-2,3-dihydro-1H-isoindol-5-yl]-4-methoxybenzamide | 496.2 |
| 400. | 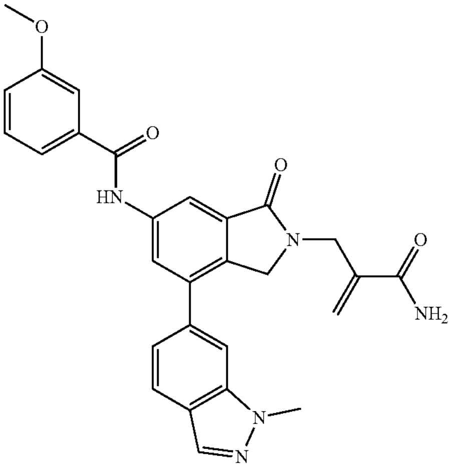 [SMILES: C=C(CN1Cc2c(cc(NC(=O)c3cccc(OC)c3)cc2-c2ccc3cnn(C)c3c2)C1=O)C(N)=O] | N-[2-(2-carbamoyl-2-methylideneethyl)-7-(1-methyl-1H-indazol-6-yl)-3-oxo-2,3-dihydro-1H-isoindol-5-yl]-3-methoxybenzamide | 496.2 |
| 401. | 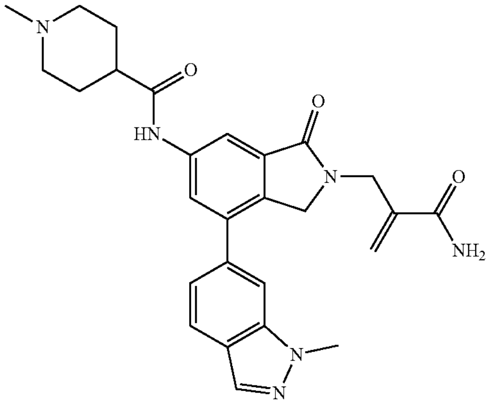 [SMILES: C=C(CN1Cc2c(cc(NC(=O)C3CCN(C)CC3)cc2-c2ccc3cnn(C)c3c2)C1=O)C(N)=O] | N-[2-(2-carbamoyl-2-methylideneethyl)-7-(1-methyl-1H-indazol-6-yl)-3-oxo-2,3-dihydro-1H-isoindol-5-yl]-1-methylpiperidine-4-carboxamide | 487.2 |

TABLE 5-continued
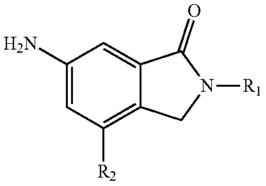
| Cpd. No. | Structure | IUPAC | LC-MS (ES+, m/z) |
|---|---|---|---|
| 402. | 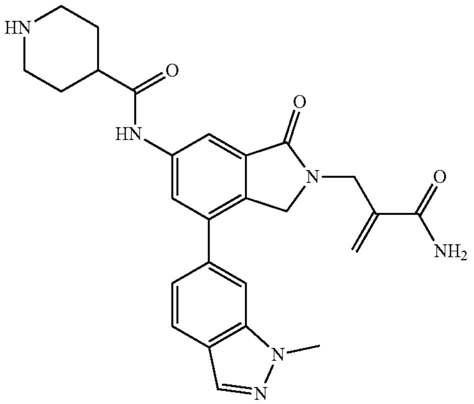 [SMILES: C=C(CN1Cc2c(cc(NC(=O)C3CCNCC3)cc2-c2ccc3cnn(C)c3c2)C1=O)C(N)=O] | N-[2-(2-carbamoyl-2-methylideneethyl)-7-(1-methyl-1H-indazol-6-yl)-3-oxo-2,3-dihydro-1H-isoindol-5-yl]piperidine-4-carboxamide | 473.2 |
| 403. | 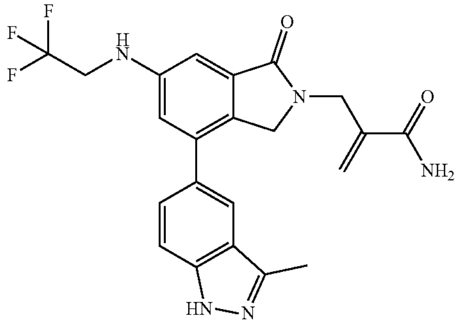 [SMILES: C=C(CN1Cc2c(cc(NCC(F)(F)F)cc2-c2ccc3[nH]nc(C)c3c2)C1=O)C(N)=O] | 2-{[4-(3-methyl-1H-indazol-5-yl)-1-oxo-6-[(2,2,2-trifluoroethyl)amino]-2,3-dihydro-1H-isoindol-2-yl]methyl}prop-2-enamide | 444.2 |
Example 8: Method F
Route 1:

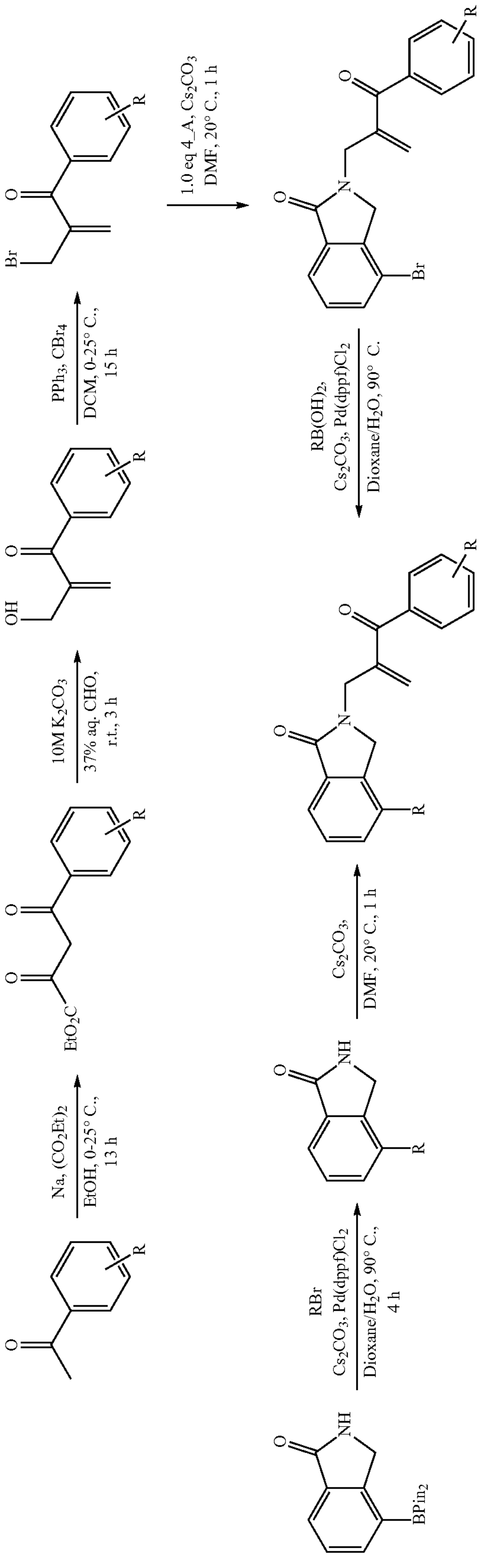
Na, $(CO_2Et)_2$
EtOH, 0-25° C.,
13 h
10M $K_2CO_3$
37% aq. CHO,
r.t., 3 h
$PPh_3$, $CBr_4$
DCM, 0-25° C.,
15 h
1.0 eq 4_A, $Cs_2CO_3$
DMF, 20° C., 1 h
$RB(OH)_2$,
$Cs_2CO_3$, $Pd(dppf)Cl_2$
Dioxane/$H_2O$, 90° C.
RBr
$Cs_2CO_3$, $Pd(dppf)Cl_2$
Dioxane/$H_2O$, 90° C.,
4 h
$Cs_2CO_3$,
DMF, 20° C., 1 h a. Preparation of 2-(bromomethyl)-1-phenylprop-2-en-1-one

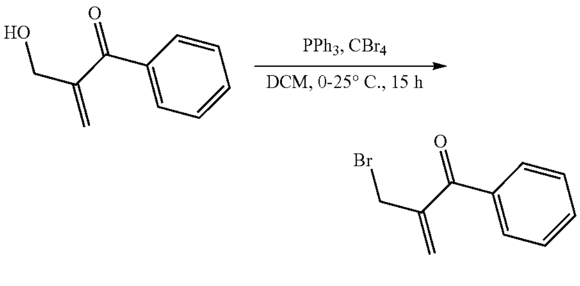

To a solution of $PPh_3$ (405.59 mg, 1.55 mmol, 1.1 eq.) in DCM (3.0 mL) was added a solution of $CBr_4$ (512.82 mg, 1.55 mmol, 1.1 eq.) in 1 mL DCM at 0° C. under nitrogen. The reaction mixture turned yellow. To the above reaction was added a solution of 2-(hydroxymethyl)-1-phenylprop-2-en-1-one (100 mg, 585.75 μmol, 1 eq.) (90% purity) in 1 mL DCM at 0° C. under nitrogen atmosphere. The reaction was stirred at 0° C. for 1 h and at 20° C. for 14 h. White solid was formed, and TLC showed a new spot. The reaction mixture was filtrated, and the filtrate was concentrated. The residue was purified by prep-TLC (silica gel; PE:EtOAc=10:1, Rf=0.5) to afford the title compound (45 mg, 179.93 μmol, 30.72% yield, 90% purity) as a colorless oil.

b. Preparation of 4-bromo-2-(2-methylidene-3-oxo-3-phenylpropyl)-2,3-dihydro-1H-isoindol-1-one

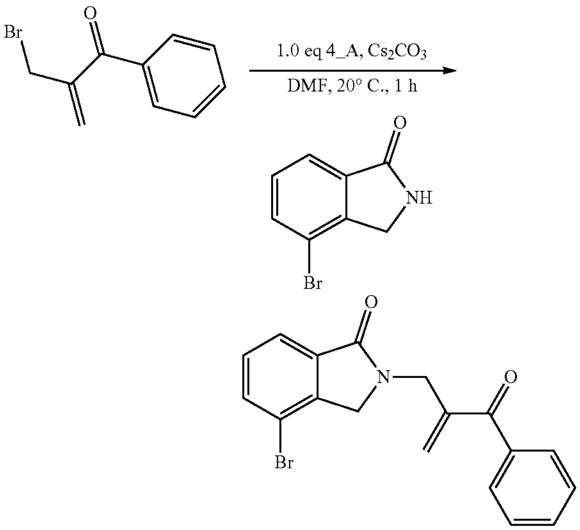

To a solution of 4-bromoisoindolin-1-one (40 mg, 188.64 μmol, 1.10 eq.) and 2-(bromomethyl)-1-phenyl-prop-2-en-1-one (43 mg, 171.94 μmol, 1 eq.) in DMF (2.0 mL) was added $Cs_2CO_3$ (112.04 mg, 343.88 μmol, 2 eq.) at 20° C. The reaction was stirred at 20° C. for 1 h. TLC showed a new spot. The reaction was poured into ice-water (10 mL) and extracted with EtOAc (3×10 mL). The organic layer was washed with brine (3×10 mL), dried over anhydrous sodium sulfate, filtered, and concentrated to give the crude compound. The crude compound was purified by prep-TLC (silica gel; PE:EtOAc=1.2:1) to afford the title compound (25 mg, 70.18 μmol, 40.82% yield) as a light yellow oil.

Preparation of N-{3-[2-(2-methylidene-3-oxo-3-phenylpropyl)-1-oxo-2,3-dihydro-1H-isoindol-4-yl]phenyl}acetamide (Compound 405)

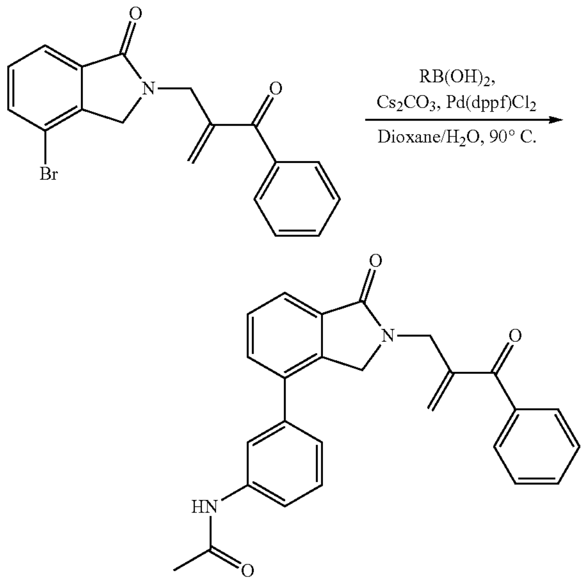

To a solution of 2-(2-benzoylallyl)-4-bromo-isoindolin-1-one (25 mg, 70.18 μmol, 1 eq.) in dioxane (1.6 mL) and water (0.4 mL) and (3-acetamidophenyl)boronic acid (18.84 mg, 105.27 μmol, 1.5 eq.) were added $Pd(dppf)Cl_2$ (2.57 mg, 3.51 μmol, 0.05 eq.) and $Cs_2CO_3$ (68.60 mg, 210.55 μmol, 3 eq.). The reaction was stirred at 90° C. for 1 h under nitrogen. LCMS and TLC showed that the reaction was complete. 5 mL sat. EDTA was added to the reaction, and the reaction was stirred at 20° C. for 2 h. The reaction mixture was extracted with EtOAc (3×20 mL). The combined organic layer was washed with water (3×10 mL) and brine (3×10 mL), dried over anhydrous sodium sulfate, filtered, and concentrated to give the crude compound. The crude compound was purified by prep-TLC (silica gel; DCM:MeOH=20:1, Rf=0.4) to afford the title compound (15.4 mg, 36.39 μmol, 51.85% yield, 97% purity) as a yellow solid. LC-MS (ES+, m/z): 411.1.

Preparation of 4-(1-methyl-1H-indazol-6-yl)-2,3-dihydro-1H-isoindol-1-one

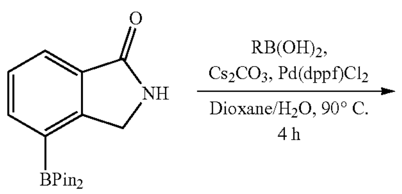

-continued

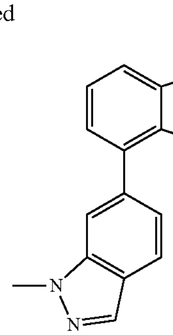

To a solution of 4-(4,4,5,5-tetramethyl-1,3,2-dioxaborolan-2-yl)isoindolin-1-one (1.08 g, 4.17 mmol, 1.1 eq.) and 6-bromo-1-methyl-indazole (800 mg, 3.79 mmol, 1 eq.) in dioxane (32 mL) and water (8 mL) was added $Cs_2CO_3$ (3.70 g, 11.37 mmol, 3 eq.) and $Pd(dppf)Cl_2$ (138.67 mg, 189.52 μmol, 0.05 eq.). Then the reaction was stirred at 90° C. for 4 h. TLC and LCMS showed about 60% of the desired product. Sat. EDTA (15 mL) was added to the reaction, and the reaction was stirred at 20° C. for 2 h. The reaction mixture was then extracted with EtOAc (20 mL×3). The combined organic layer was washed with brine (20 mL×3), dried over anhydrous sodium sulfate, filtered, and concentrated. The crude compound was purified by silica gel chromatography (DCM/MeOH=15:1) and washed with PE:EtOAc=3:1 (10 mL) to afford the title compound (370 mg, 1.34 mmol, 35.22% yield, 95% purity) as a yellow solid.

Preparation of 4-(1-methyl-1H-indazol-6-yl)-2-(2-methylidene-3-oxo-3-phenylpropyl)-2,3-dihydro-1H-isoindol-1-one (Compound 404)

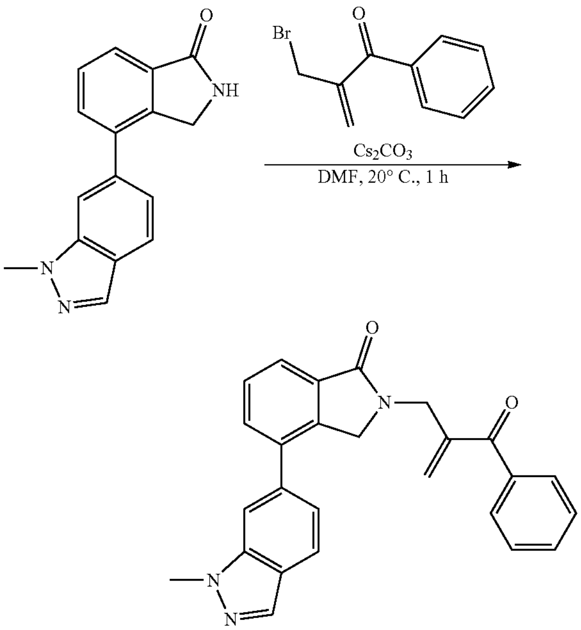

To a solution of 4-(1-methylindazol-6-yl)isoindolin-1-one (20.59 mg, 78.19 μmol, 0.8 eq.) and 2-(bromomethyl)-1-phenyl-prop-2-en-1-one (22 mg, 97.74 μmol, 1 eq.) in DMF (1 mL) was added $Cs_2CO_3$ (63.69 mg, 195.48 μmol, 2 eq.). Then the reaction was stirred at 20° C. for 1 h. LCMS and TLC showed 50% of the desired product. The reaction was poured into ice-water (5.0 mL) and extracted with EtOAc (10 mL×3). The combined organic layer was washed with water (10 mL×3) and brine (10 mL×3), dried over anhydrous sodium sulfate, filtered, and concentrated to give the crude compound. The crude compound was purified by prep-TLC (PE:EtOAc=1:1, Rf=0.38) to afford the title compound (5.0 mg, 11.87 μmol, 12.14% yield, 96.7% purity) as a white solid. LC-MS (ES+, m/z): 408.1.

Route 2

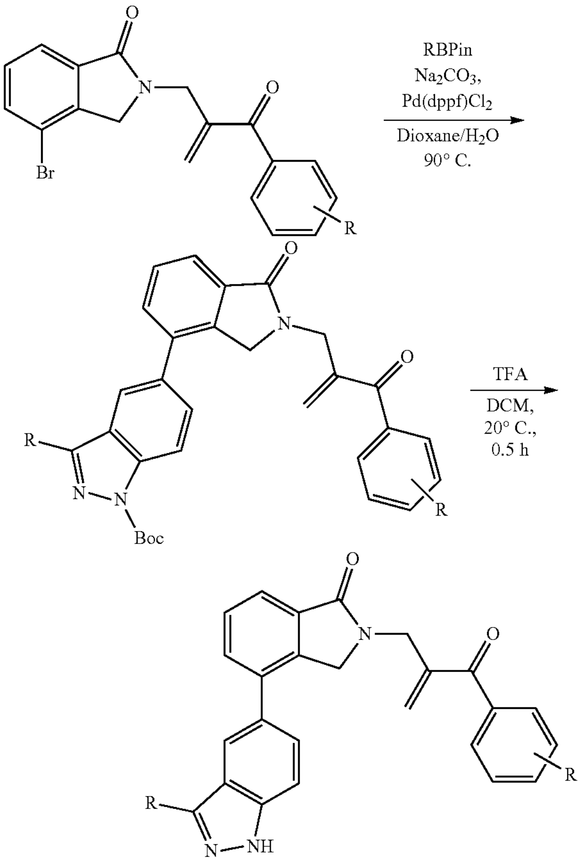

Preparation of tert-butyl 3-cyclopropyl-5-[2-(2-methylidene-3-oxo-3-phenylpropyl)-1-oxo-2,3-dihydro-1H-isoindol-4-yl]-1H-indazole-1-carboxylate

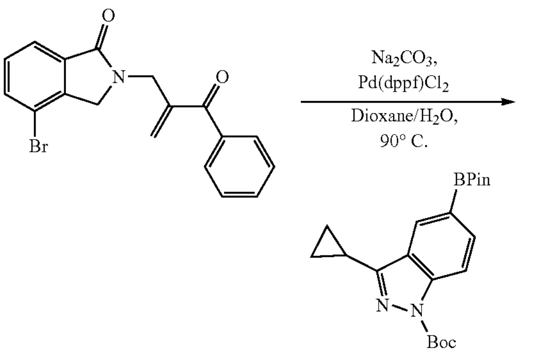

-continued

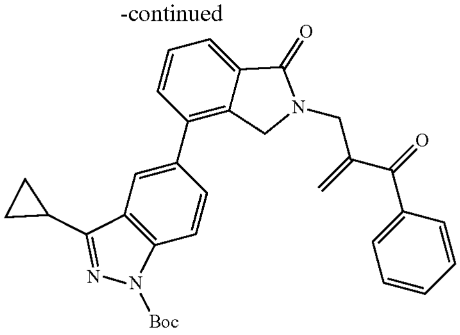

To a solution of 2-(2-benzoylallyl)-4-bromo-isoindolin-1-one (50 mg, 140.37 μmol, 6.74 e-1 eq.) in dioxane (2.4 mL) and water (0.6 mL) were added tert-butyl 3-cyclopropyl-5-(4,4,5,5-tetramethyl-1,3,2-dioxaborolan-2-yl)indazole-1-carboxylate (80 mg, 208.18 μmol, 1 eq.) and $Na_2CO_3$ (66.20 mg, 624.55 μmol, 3 eq.). Then, $Pd(dppf)Cl_2$ (7.62 mg, 10.41 μmol, 0.05 eq.) was added to the reaction, and the reaction was stirred at 120° C. for 5 min under nitrogen atmosphere. TLC showed that the reaction was complete. 10 mL EtOAc was added to the reaction, followed by 20 mL sat. EDTA. The reaction mixture was stirred at 20° C. for 1 h. Then the reaction mixture was extracted with EtOAc (20 mL×3). The combined organic layer was washed with brine (20 mL×3), dried over anhydrous sodium sulfate, filtered, and concentrated. The residue was purified by prep-TLC (silica gel; PE:EtOAc=1:1) to afford the title compound (80 mg, 134.93 μmol, 64.81% yield, 90% purity) as a yellow oil.

Preparation of 4-(3-cyclopropyl-1H-indazol-5-yl)-2-(2-methylidene-3-oxo-3-phenylpropyl)-2,3-dihydro-1H-isoindol-1-one (Compound 408)

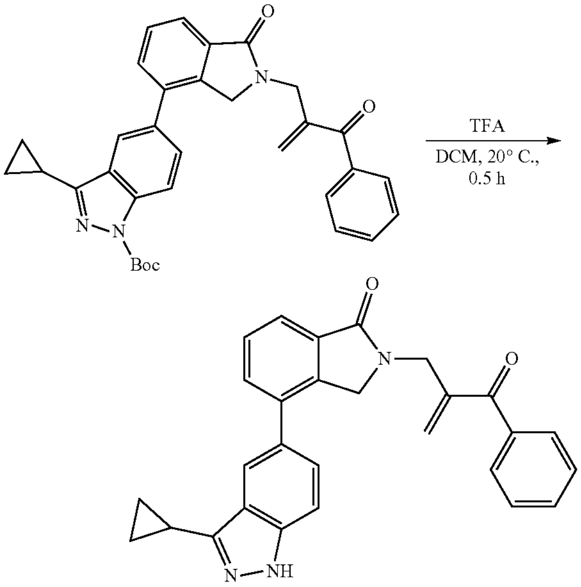

To a solution of tert-butyl 5-[2-(2-benzoylallyl)-1-oxo-isoindolin-4-yl]-3-cyclopropyl-indazole-1-carboxylate (70 mg, 118.06 μmol, 1 eq.) (90% purity) in DCM (2 mL) was added trifluoroacetic acid (616 mg, 5.40 mmol, 0.4 mL, 45.76 eq.) at 20° C. The reaction was stirred at 20° C. for 0.5 h. TLC showed that the reaction was complete. The reaction was adjusted pH=9 with sat. $NaHCO_3$ (~10 mL). The reaction was extracted with EtOAc (10 mL×3). The combined organic layer was washed with brine (10 mL×3), dried over anhydrous sodium sulfate, filtered, and concentrated. The residue was purified by prep-TLC (silica gel; PE:EtOAc=1:1) to afford the title compound (16.3 mg, 36.47 μmol, 30.89% yield, 97.0% purity) as a white solid. LC-MS (ES+, m/z): 434.1.

Route 3

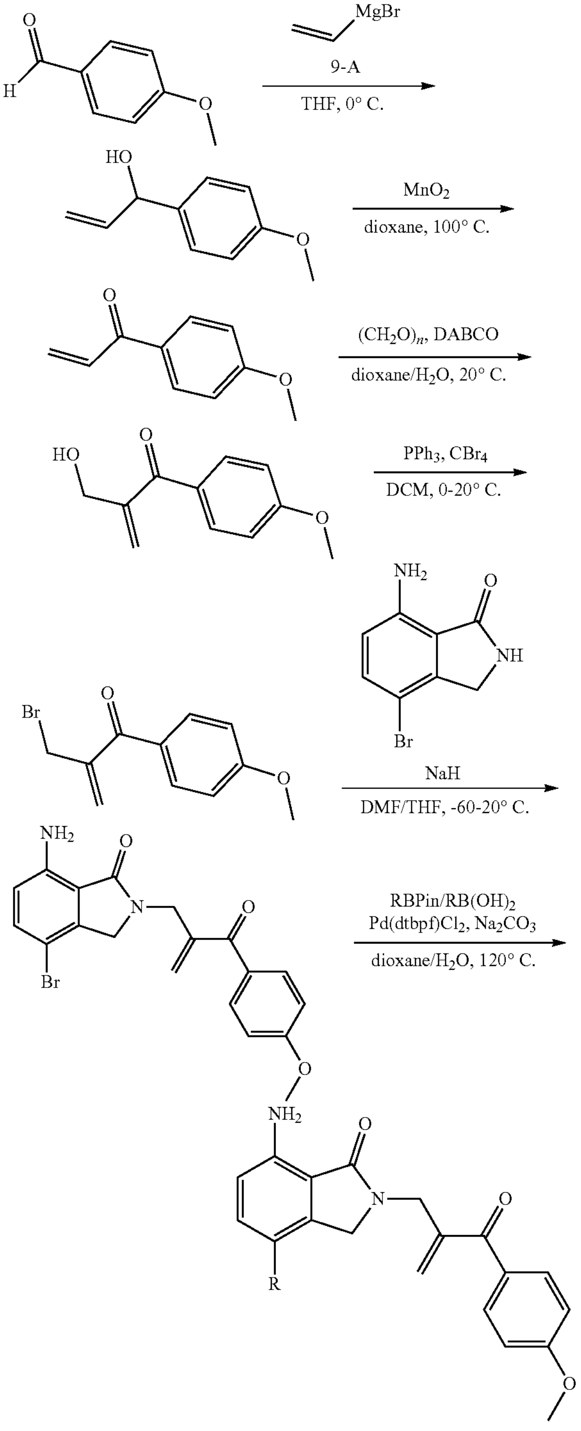

Preparation of 2-(hydroxymethyl)-1-(3-methoxyphenyl)prop-2-en-1-one

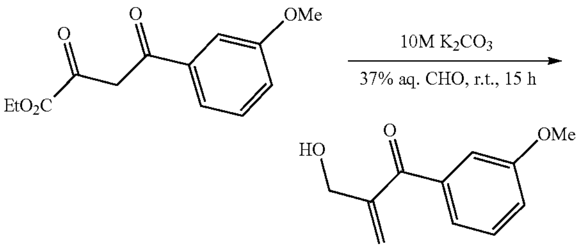

To a suspension of ethyl 3-(3-methoxyphenyl)-3-oxopropanoate (1.5 g, 5.09 mmol, 1 eq.) (85% purity) in formaldehyde (1.65 g, 20.38 mmol, 1.52 mL, 4 eq.) (37% aqueous solution) was added $K_2CO_3$ (10 M, 1.02 mL, 2 eq.) (aqueous solution) dropwise at 25° C. The reaction was stirred at 25° C. for 15 h. TLC showed about 30% of the desired product. The reaction was extracted with EtOAc (20 mL×3). The combined organic layer was washed with brine (20 mL×3), dried over anhydrous sodium sulfate, filtered, and concentrated to give the crude compound. The crude compound was purified by prep-TLC (silica gel; PE:EtOAc=1:1, Rf=0.36) to afford the title compound (240 mg, 1.19 mmol, 23.28% yield, 95% purity) as a yellow oil.

Preparation of 2-(bromomethyl)-1-(3-methoxyphenyl)prop-2-en-1-one

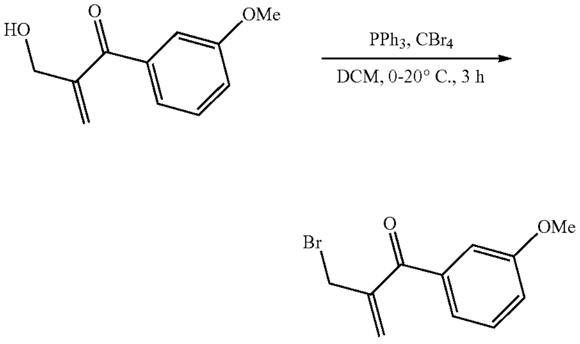

To a solution of $PPh_3$ (336 mg, 1.28 mmol, 1.23 eq.) in DCM (3.0 mL) was added a solution of $CBr_4$ (451.50 mg, 1.36 mmol, 1.31 eq.) at 0° C. under nitrogen atmosphere. The reaction turned yellow. Then, a solution of 2-(hydroxymethyl)-1-(3-methoxyphenyl)prop-2-en-1-one (210 mg, 1.04 mmol, 1 eq.) (95% purity) in 1 mL DCM was added to the reaction at 0° C. under nitrogen atmosphere. The reaction was stirred at 0° C. for 1 h and at 20° C. for 2 h. TLC showed a new spot. The reaction was concentrated, and the resulting residue was purified by prep-TLC (silica gel; PE:EtOAc=10:1, Rf=0.47) to afford the title compound (83 mg, 325.35 µmol, 31.355% yield) as a colorless oil.

Preparation of tert-butyl 5-{2-[3-(3-methoxyphenyl)-2-methylidene-3-oxopropyl]-1-oxo-2,3-dihydro-1H-isoindol-4-yl}-3-methyl-1H-indazole-1-carboxylate

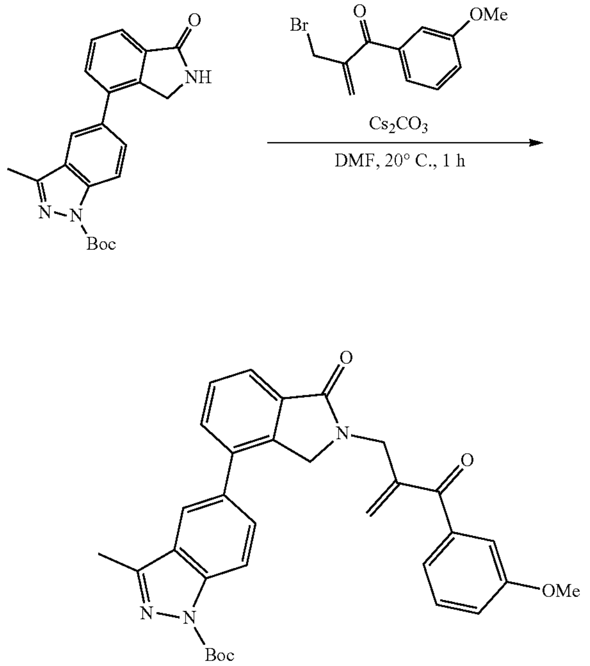

To a solution of 2-(bromomethyl)-1-(3-methoxyphenyl)prop-2-en-1-one (35.10 mg, 137.59 µmol, 1 eq.) and tert-butyl 3-methyl-5-(1-oxoisoindolin-4-yl)indazole-1-carboxylate (50 mg, 137.59 µmol, 1 eq.) in DMF (3.0 mL) was added $Cs_2CO_3$ (134.48 mg, 412.76 µmol, 3 eq.). Then the reaction was stirred at 20° C. for 1 h. TLC showed about 40% of the desired product. Water (5 mL) was added to the reaction, and the reaction mixture was extracted with EtOAc (10 mL×3). The combined organic layer was washed with water (10 mL×3) and brine (10 mL×3), dried over anhydrous sodium sulfate, filtered, and concentrated. The crude compound was purified by prep-TLC (silica gel; PE:EtOAc=1:1, Rf=0.53) to afford the title compound (25 mg, 46.50 µmol, 33.80% yield) as a red solid.

Preparation of 2-[3-(3-methoxyphenyl)-2-methylidene-3-oxopropyl]-4-(3-methyl-1H-indazol-5-yl)-2,3-dihydro-1H-isoindol-1-one (Compound 470)

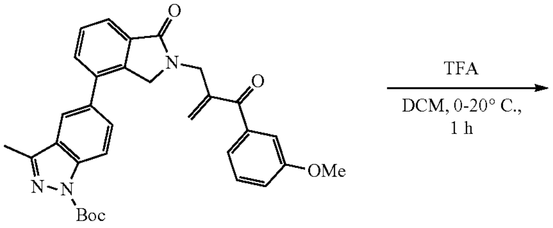

-continued

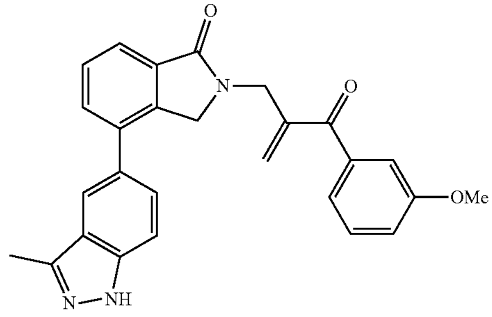

To a solution of tert-butyl 5-[2-[2-(3-methoxybenzoyl) allyl]-1-oxo-isoindolin-4-yl]-3-methyl-indazole-1-carboxylate (18 mg, 33.48 μmol, 1 eq.) in DCM (2 mL) was added trifluoroacetic acid (0.4 mL) at 0° C. The reaction was stirred at 20° C. for 1 h. TLC showed that the reaction was complete. The reaction was poured into sat. $NaHCO_3$ (20 mL) and extracted with EtOAc (20 mL×3). The combined organic layer was washed with brine (10 mL×3), dried over anhydrous sodium sulfate, filtered, and concentrated. The crude compound was purified by prep-TLC (silica gel; DCM:MeOH=20:1, Rf=0.40) to afford the title compound (6.4 mg, 13.72 μmol, 40.98% yield, 93.8% purity) as a white solid. LC-MS (ES+, m/z): 438.2.

Route 4:

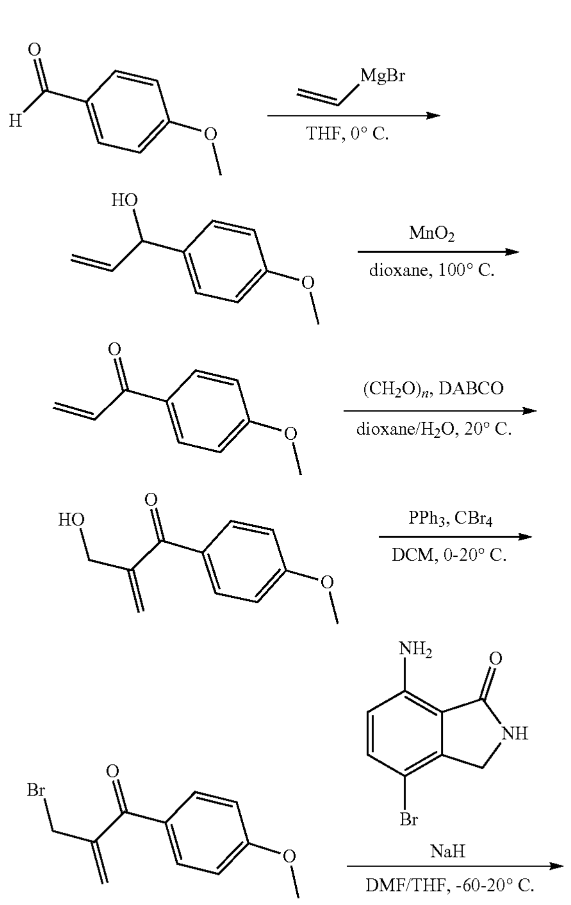

-continued

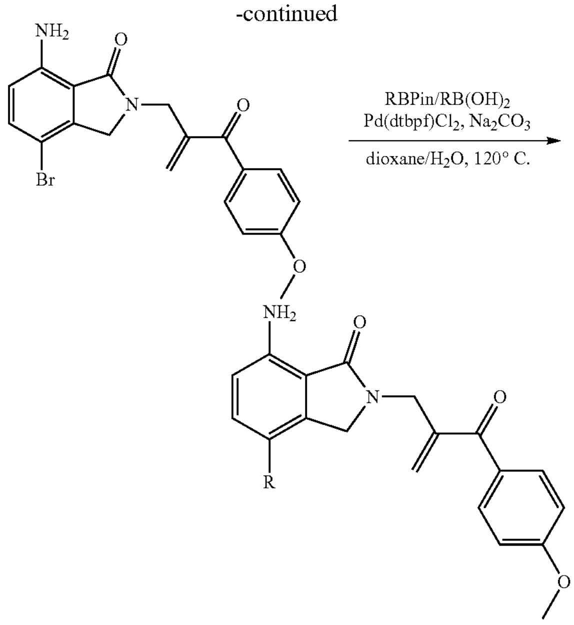

a. Preparation of 1-(4-methoxyphenyl)prop-2-en-1-ol

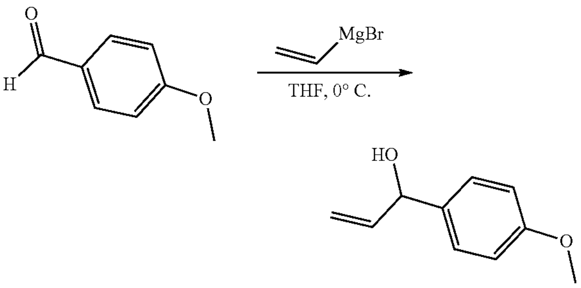

To a solution of 4-methoxybenzaldehyde (10 g, 73.45 mmol, 8.93 mL, 1 eq.) in THF (100 mL) was added bromo(vinyl)magnesium (1 M, 110.17 mL, 1.5 eq.) at 0° C., and the resulting reaction mixture was stirred at 0° C. for 0.5 h. TLC showed that the reaction was complete. The reaction mixture was poured into 200 mL of ice water. The aqueous phase was extracted with EtOAc (2×100 mL). The combined organic layer was washed with water (2×100 mL) and brine (100 mL), dried over anhydrous sodium sulfate, filtered, and concentrated to give the crude title compound (13 g, crude) as a light yellow oil, which was used for the next step directly without further purification.

b. Preparation of 1-(4-methoxyphenyl)prop-2-en-1-one

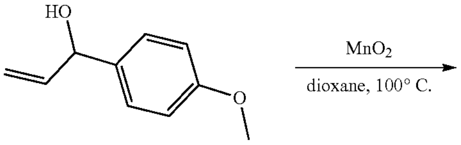

-continued

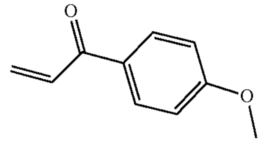

To a solution of 1-(4-methoxyphenyl)prop-2-en-1-ol (13 g, 79.17 mmol, 1 eq.) in dioxane (20 mL) was added $MnO_2$ (34.41 g, 395.86 mmol, 5 eq.). The resulting reaction mixture was stirred at 100° C. for 1 h. TLC showed that the reaction was complete. The reaction mixture was filtered, and the filtrate was concentrated to give a residue. The residue was purified by column chromatography (silica gel; PE:EtOAc=10:1 to 4:1) to afford the title product (4.2 g, 23.31 mmol, 29.44% yield, 90% purity) as a light yellow oil.

c. Preparation of 2-(hydroxymethyl)-1-(4-methoxyphenyl) prop-2-en-1-one

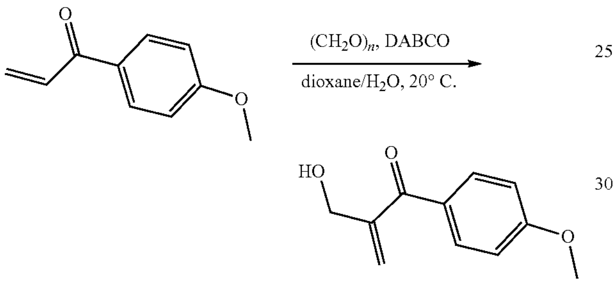

To a solution of 1-(4-methoxyphenyl)prop-2-en-1-one (4.2 g, 23.31 mmol, 1 eq.) in dioxane (50 mL) and water (50 mL) were added formaldehyde (769.79 mg, 25.64 mmol, 706.23 μL, 1.1 eq.) and DABCO (261.44 mg, 2.33 mmol, 256.31 μL, 0.1 eq.). The resulting reaction mixture was stirred at 20° C. for 1 h. TLC showed that the reaction was complete. The reaction mixture was poured into 200 mL ice water. The aqueous phase was extracted with EtOAc (2×80 mL). The combined organic layer was washed with water (2×80 mL) and brine (80 mL), dried over anhydrous sodium sulfate, filtered, and concentrated to give the crude product. The residue was purified by column chromatography (silica gel; PE:EtOAc=4:1 to 1:1) to afford the title compound (2 g, 9.36 mmol, 40.18% yield, 90% purity) as a colorless oil.

d. Preparation of 2-(bromomethyl)-1-(4-methoxyphenyl)prop-2-en-1-one

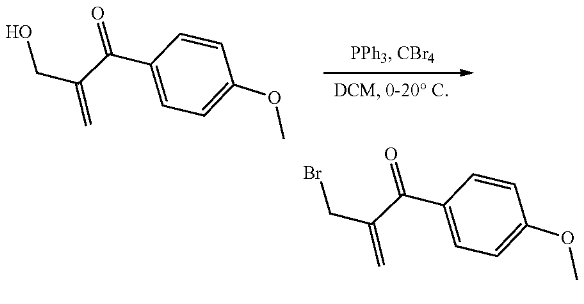

To a mixture of $PPh_3$ (525.36 mg, 2 mmol, 1.1 eq.) and $CBr_4$ (664.25 mg, 2 mmol, 1.1 eq.) in DCM (4 mL) was added 2-(hydroxymethyl)-1-(4-methoxyphenyl)prop-2-en-1-one (0.35 g, 1.82 mmol, 1 eq.). The reaction mixture was stirred at 0° C. for 1 h under nitrogen, then stirred at 20° C. for 11 h. TLC showed that the reaction was complete. The reaction was diluted with water (50 mL) and extracted with EtOAc (2×25 mL). The combined organic layers were washed with water (2×50 mL) and brine (2×50 mL), dried over anhydrous sodium sulfate, filtered, and concentrated in vacuo to give a residue. The residue was purified by prep-TLC (silica gel; PE:EtOAc=1:1) to afford the title compound (0.17 g, 666.39 μmol, 36.60% yield) as a white oil.

e. Preparation of 7-amino-4-bromo-2-[2-(4-methoxybenzoyl)allyl]isoindolin-1-one

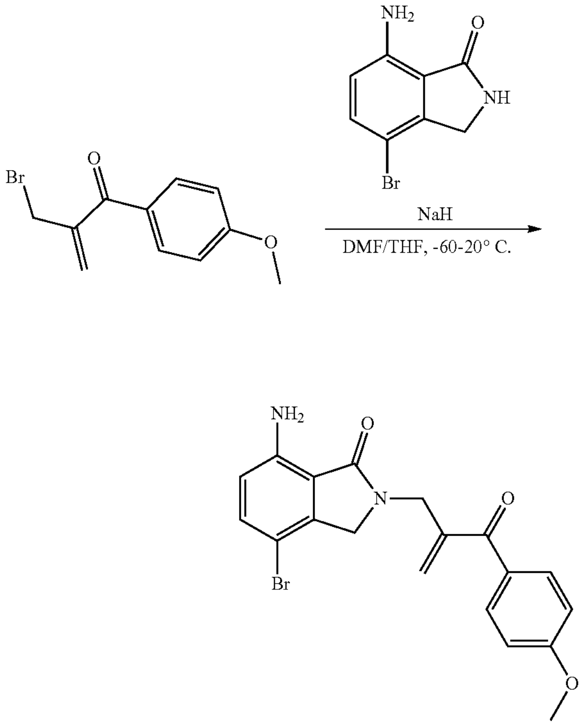

To a solution of 7-amino-4-bromo-isoindolin-1-one (0.1 g, 440.42 μmol, 1 eq.) in DMF (1.5 mL) and THF (1.5 mL) was added NaH (52.85 mg, 1.32 mmol, 60% purity, 3 eq.). The reaction was stirred at 20° C. for 20 min under nitrogen, and 2-(bromomethyl)-1-(4-methoxyphenyl)prop-2-en-1-one (123.59 mg, 484.46 μmol, 1.1 eq.) was added. The mixture was stirred further at −60° C. for 20 min. TLC showed that the reaction was complete. The reaction mixture was The reaction was quenched by adding $NH_4Cl$ (30 mL) at 0° C., and extracted with EtOAc (2×25 mL). The combined organic layers were washed with water (2×50 mL) and brine (2×50 mL), dried over anhydrous sodium sulfate, filtered, and concentrated in vacuo to give a residue to afford the title compound (0.2 g, crude) as a yellow oil, which was used directly without further purification.

Preparation of 7-amino-2-[2-(4-methoxybenzoyl)allyl]-4-(3-methyl-1H-indazol-5-yl)isoindolin-1-one (Compound 412)

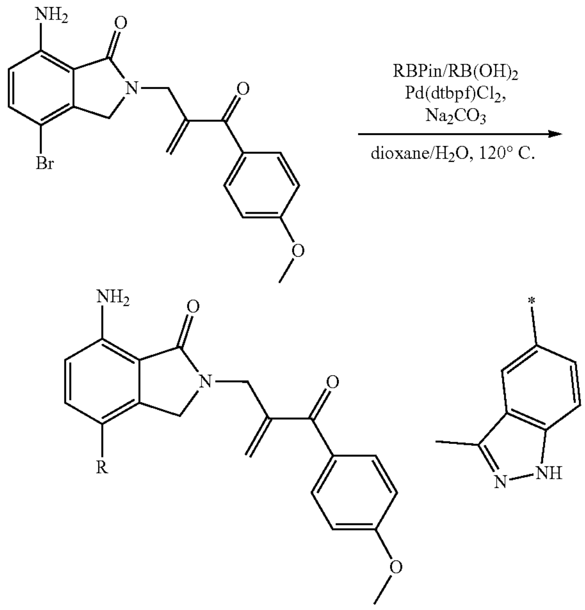

To a mixture of 7-amino-4-bromo-2-[2-(4-methoxybenzoyl)allyl]isoindolin-1-one (0.15 g, 373.83 μmol, 1 eq.) and (3-methyl-1H-indazol-5-yl)boronic acid (78.94 mg, 448.59 μmol, 1.2 eq.) in dioxane (4 mL) and water (1 mL) were added $Na_2CO_3$ (118.87 mg, 1.12 mmol, 3 eq.) and ditert-butyl(cyclopentyl)phosphane; dichloropalladium; iron (24.36 mg, 37.38 μmol, 0.1 eq.). The mixture was heated to 120° C. under nitrogen and stirred for 20 min. TLC showed that the reaction was complete. The reaction mixture was stirred by adding sat. EDTA (50 mL) and EtOAc (30 mL) at 25° C. The mixture was then extracted with EtOAc (25 mL×2). The combined organic layers were washed with water (50 mL×2) and brine (50 mL×2), dried over anhydrous sodium sulfate, filtered, and concentrated in vacuo to give a residue. The residue was purified by prep-TLC (silica gel; DCM:MeOH=15:1) to afford the title compound (14.2 mg, 28.78 μmol, 7.70% yield, 91.7% purity) as a white solid. LC-MS: $[M+H]^+$ 453.1.

Route 5:

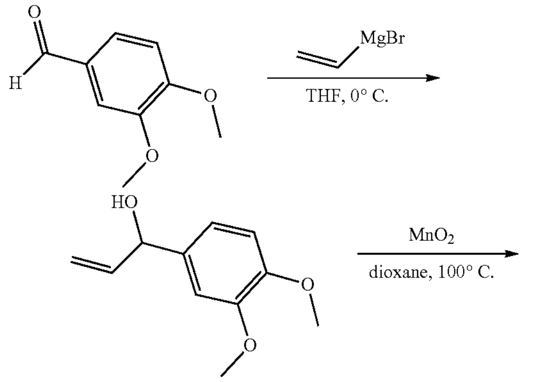

-continued

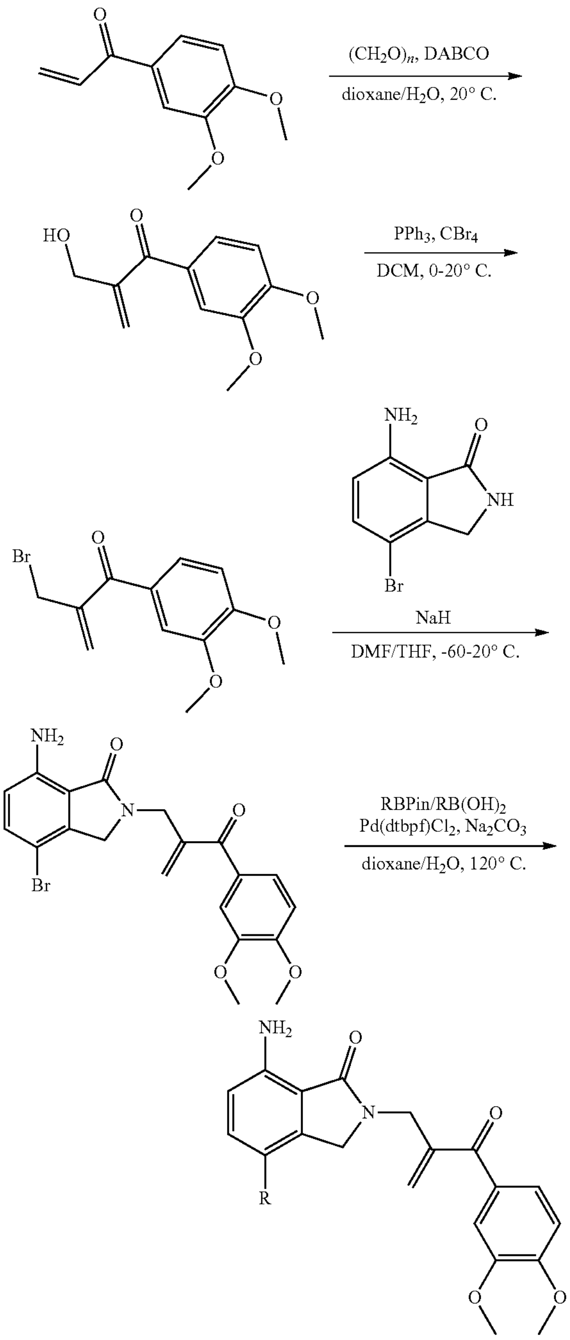

a. Preparation of 1-(3,4-dimethoxyphenyl)prop-2-en-1-ol

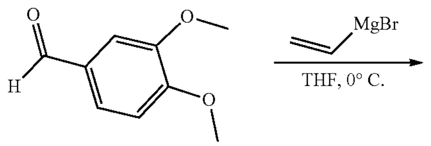

-continued

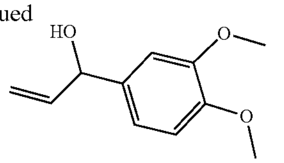

To a solution of 3,4-dimethoxybenzaldehyde (10 g, 60.18 mmol, 1 eq.) in THF (100 mL) was added vinylmagnesium bromide (1 M, 90.27 mL, 1.5 eq.), and the mixture was stirred at 0° C. for 0.5 h under nitrogen. TLC showed that the reaction was complete. The reaction mixture was poured into ice water (200 mL), then extracted with EtOAc (2×100 mL). The combined organic layers were washed with water (2×200 mL) and brine (2×200 mL), dried over anhydrous sodium sulfate, filtered, and concentrated in vacuo to give a residue to afford the title compound (11 g, crude) as a yellow oil, which was used directly without further purification.

b. Preparation of 1-(3,4-dimethoxyphenyl)prop-2-en-1-one

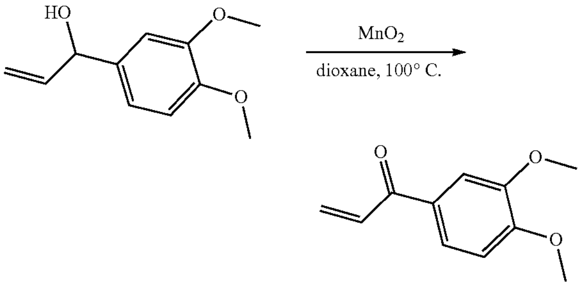

To a solution of 1-(3,4-dimethoxyphenyl)prop-2-en-1-ol (3 g, 15.45 mmol, 1 eq.) in dioxane (30 mL) was added $MnO_2$ (6.71 g, 77.23 mmol, 5 eq.), and the mixture was stirred at 100° C. for 12 h under nitrogen. TLC indicated ~40% of the starting material. The reaction mixture was filtered, and the filtrate was concentrated to give the residue. The residue was purified by column chromatography (silica gel; PE:EtOAc=1:0 to 10:1) to afford the title compound (2.1 g, 10.93 mmol, 70.73% yield) as a yellow oil.

c. Preparation of 1-(3,4-dimethoxyphenyl)-2-(hydroxymethyl)prop-2-en-1-one

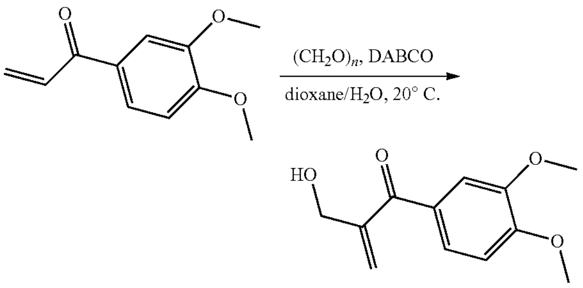

To a solution of 1-(3,4-dimethoxyphenyl)prop-2-en-1-one (2 g, 10.41 mmol, 1 eq.) in dioxane (10 mL) and water (10 mL) were added formaldehyde (343.67 mg, 11.45 mmol, 315.29 µL, 1.1 eq.) and DABCO (116.72 mg, 1.04 mmol, 114.43 µL, 0.1 eq.). The mixture was stirred at 20° C. for 1 h under nitrogen. TLC showed that the reaction was complete. The reaction mixture was poured into ice water (100 mL), then extracted with EtOAc (2×50 mL). The combined organic layers were washed with water (2×100 mL) and brine (2×100 mL), dried over anhydrous sodium sulfate, filtered, and concentrated in vacuo to give a residue. The residue was purified by column chromatography (silica gel; PE:EtOAc=4/1 to 1:1) to afford the title compound (0.7 g, 3.15 mmol, 30.27% yield) as a white oil.

d. Preparation of 2-(bromomethyl)-1-(3,4-dimethoxyphenyl)prop-2-en-1-one

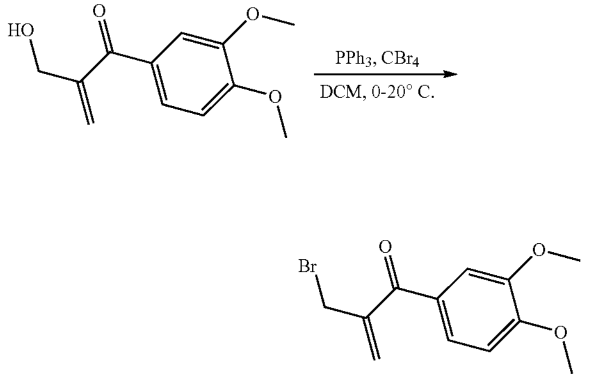

To a mixture of $PPh_3$ (908.76 mg, 3.46 mmol, 1.1 eq.) and $CBr_4$ (1.15 g, 3.46 mmol, 1.1 eq.) in DCM (5 mL) was added 1-(3,4-dimethoxyphenyl)-2-(hydroxymethyl)prop-2-en-1-one (0.7 g, 3.15 mmol, 1 eq.). The mixture was stirred at 0° C. for 1 h under nitrogen, then stirred at 20° C. for 1 h. TLC showed that the reaction was complete. The reaction was diluted with water (50 mL) and extracted with EtOAc (2×25 mL). The combined organic layers were washed with water (2×50 mL) and brine (2×50 mL), dried over anhydrous sodium sulfate, filtered, and concentrated in vacuo to give a residue. The residue was purified by prep-TLC (silica gel; PE:EtOAc=1:1) to afford the title compound (0.45 g, 1.58 mmol, 50.11% yield) as a yellow solid.

e. Preparation of 7-amino-4-bromo-2-[2-(3,4-dimethoxybenzoyl)allyl]isoindolin-1-one

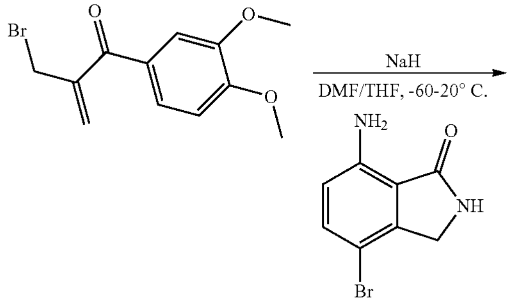

-continued

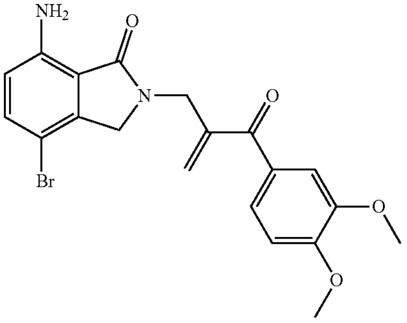

To a solution of 7-amino-4-bromo-isoindolin-1-one (0.2 g, 880.83 μmol, 1 eq.) in DMF (2 mL) and THF (2 mL) was added NaH (105.69 mg, 2.64 mmol, 60% purity, 3 eq.). The reaction was and stirred at 20° C. for 20 min under nitrogen. Then, 2-(bromomethyl)-1-(3,4-dimethoxyphenyl)prop-2-en-1-one added (276.27 mg, 968.92 μmol, 1.1 eq.) was added, and the mixture was stirred at −60° C. for 20 min. LCMS showed that the reaction was complete. The reaction mixture was The reaction was quenched by adding $NH_4Cl$ 30 mL at 0° C., and extracted with EtOAc (2×25 mL). The combined organic layers were washed with water (2×50 mL) and brine (2×50 mL), dried over anhydrous sodium sulfate, filtered, and concentrated in vacuo to afford the title compound (0.42 g, crude) as a yellow solid, which was used directly in the next step.

Preparation of 7-amino-2-[2-(3,4-dimethoxy benzoyl)allyl]-4-(3-pyridyl)isoindolin-1-one (Compound 416)

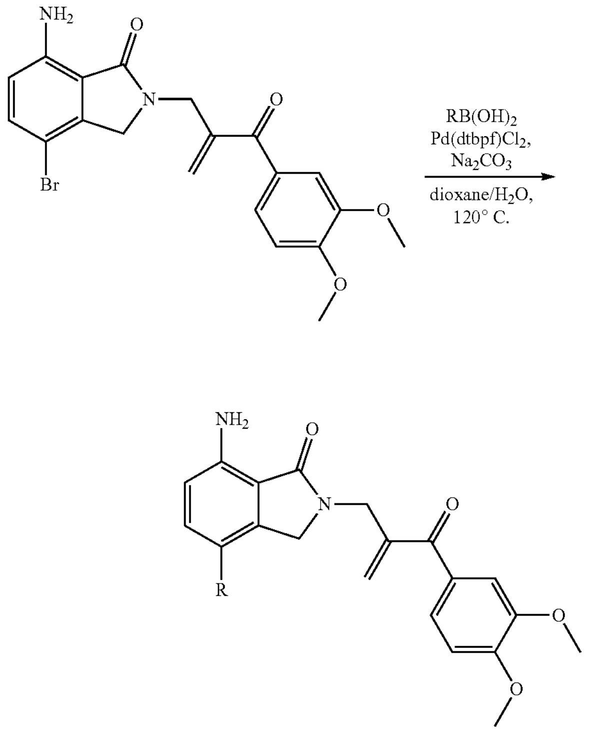

-continued

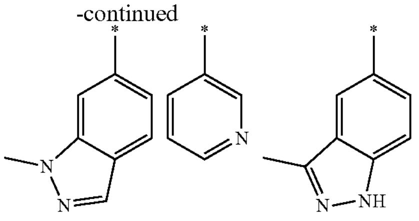

To a mixture of 7-amino-4-bromo-2-[2-(3,4-dimethoxybenzoyl)allyl]isoindolin-1-one (80 mg, 185.49 μmol, 1 eq.) and 3-pyridylboronic acid (27.36 mg, 222.59 μmol, 1.2 eq.) in dioxane (4 mL) and water (1 mL) were added $Na_2CO_3$ (58.98 mg, 556.48 μmol, 3 eq.) and ditert-butyl(cyclopentyl) phosphane; dichloropalladium; iron (12.09 mg, 18.55 μmol, 0.1 eq.). The mixture was heated to 120° C. under nitrogen and stirred for 20 min. LCMS showed that the reaction was complete. The reaction mixture was stirred after adding sat. EDTA (50 mL) and EtOAc (30 mL) at 25° C., and the resulting mixture was extracted with EtOAc (2×25 mL). The combined organic layers were washed with water (2×50 mL) and brine (2×50 mL), dried over anhydrous sodium sulfate, filtered, and concentrated in vacuo to give a residue. The residue was purified by prep-HPLC to afford the title compound (13.0 mg, 30.27 μmol, 16.32% yield, 100% purity) as a white solid. LC-MS: $[M+H]^+$ 430.1.

Preparation of 7-amino-2-[2-(3,4-dimethoxybenzoyl) allyl]-4-(1-methylindazol-6-yl)isoindolin-1-one (Compound 415)

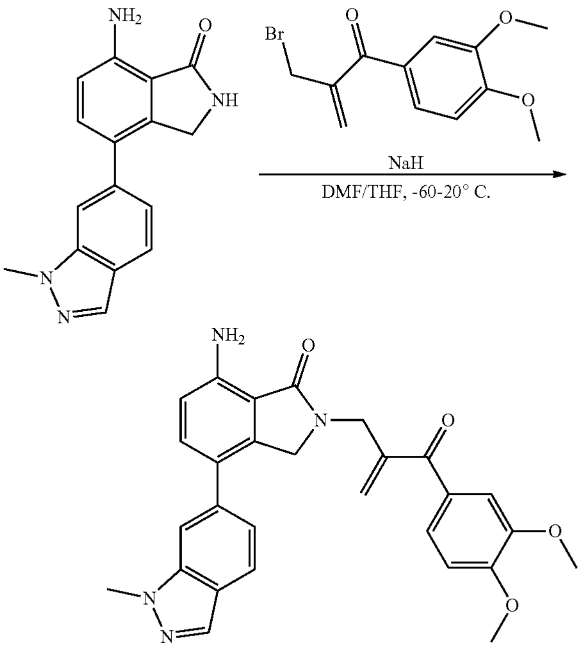

To a solution of 7-amino-4-(1-methylindazol-6-yl)isoindolin-1-one (80 mg, 287.45 μmol, 1 eq.) in DMF (2 mL) and THF (2 mL) was added NaH (34.49 mg, 862.35 μmol, 60% purity, 3 eq.). The reaction was stirred at 20° C. for 20 min under nitrogen, and 2-(bromomethyl)-1-(3,4-dimethoxyphenyl)prop-2-en-1-one (90.16 mg, 316.20 μmol, 1.1 eq.) was added. The mixture was stirred further at −60° C. for 20 min.

LCMS showed that the reaction was complete. The reaction mixture was The reaction was quenched by adding $NH_4Cl$ 30 mL at 0° C., and was extracted with EtOAc (2×25 mL). The combined organic layers were washed with water (2×50 mL) and brine (2×50 mL), dried over anhydrous sodium sulfate, filtered, and concentrated in vacuo to give a residue. The residue was purified by prep-HPLC to afford the title compound (14.3 mg, 29.64 μmol, 10.31% yield, 100% purity) as a white solid. LC-MS: $[M+H]^+$ 483.2.

Route 6

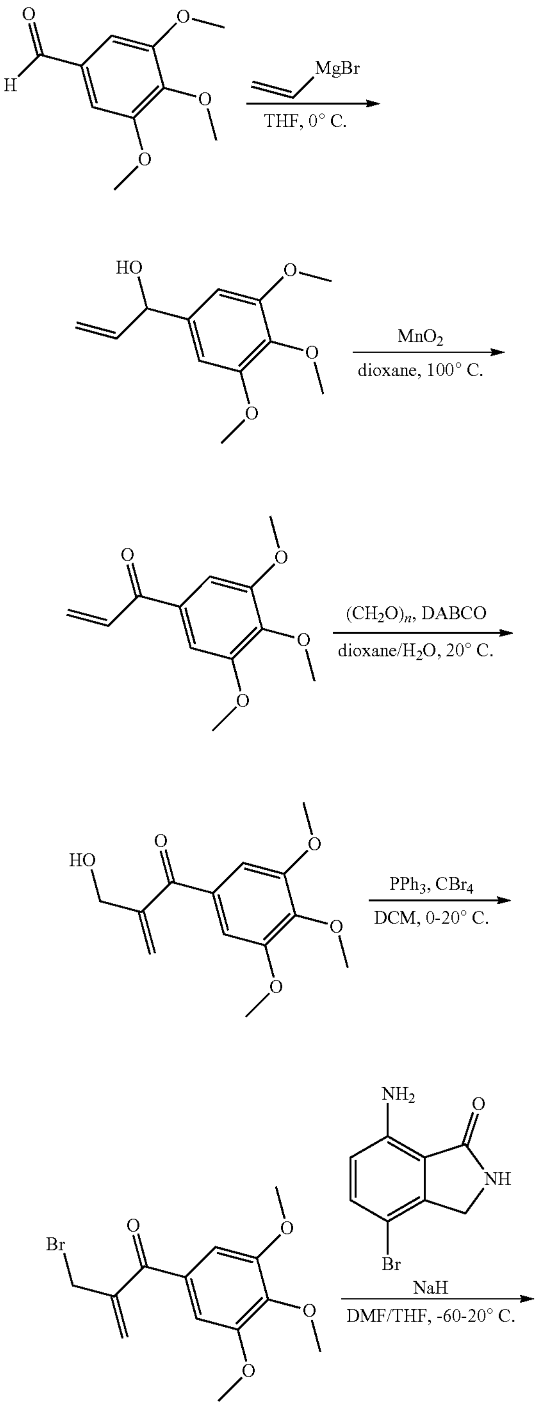

-continued

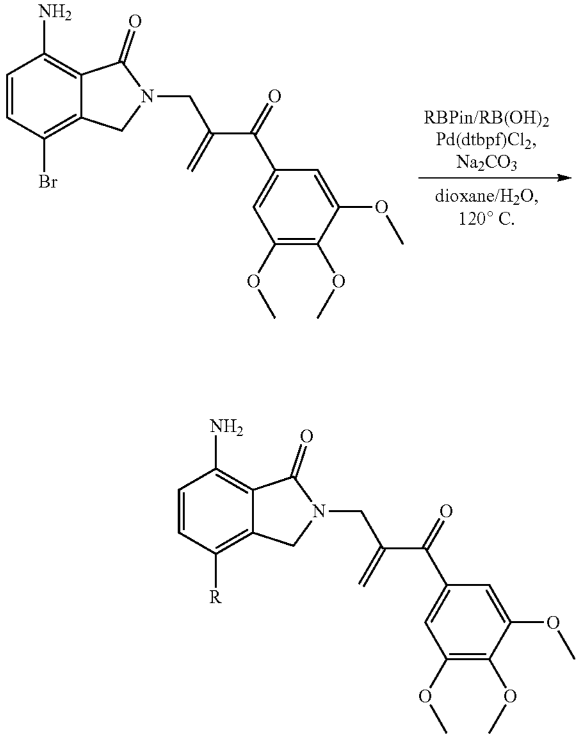

a. Preparation of 1-(3,4,5-trimethoxyphenyl)prop-2-en-1-ol

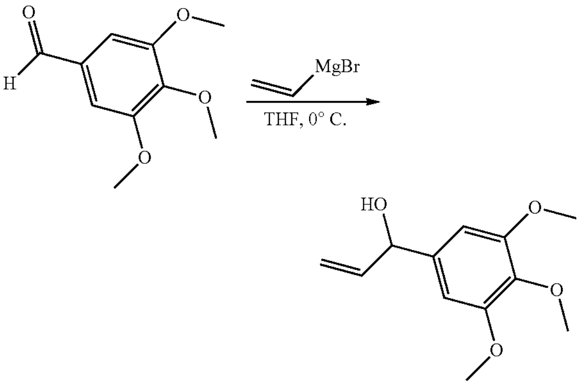

To a solution of 3,4,5-trimethoxybenzaldehyde (10 g, 50.97 mmol, 1 eq.) in THF (100 mL) was added bromo (vinyl)magnesium (1 M, 76.45 mL, 1.5 eq.). The mixture was stirred at 0° C. for 0.5 h under nitrogen. TLC showed that the reaction was complete. LCMS showed that the reaction was complete. The reaction mixture was poured into ice water (300 mL) and extracted with EtOAc (2×100 mL). The combined organic layers were washed with water (2×200 mL) and brine (2×200 mL), dried over anhydrous sodium sulfate, filtered, and concentrated in vacuo to give a residue. The residue was purified by column chromatography (silica gel; PE:EtOAc=10:1 to 4:1) to afford the title compound (11 g, 49.05 mmol, 48.12% yield) as a yellow oil.

b. Preparation of 1-(3,4,5-trimethoxyphenyl)prop-2-en-1-one

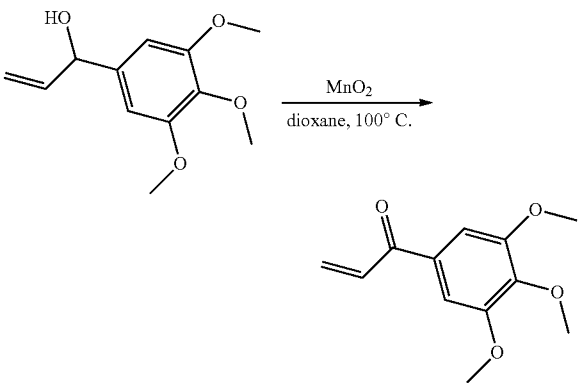

To a solution of 1-(3,4,5-trimethoxyphenyl)prop-2-en-1-ol (10 g, 44.59 mmol, 1 eq.) in dioxane (150 mL) was added $MnO_2$ (19.38 g, 222.96 mmol, 5 eq.). The mixture was stirred at 100° C. for 12 h under nitrogen. TLC showed that the reaction was complete. The reaction mixture was filtered, and the filtrate was concentrated to give a residue. The residue was purified by column chromatography (silica gel; PE:EtOAc=15:1 to 8:1) to afford the title compound (4 g, 18 mmol, 40.36% yield) as a yellow solid.

c. Preparation of 2-(hydroxymethyl)-1-(3,4,5-trimethoxyphenyl)prop-2-en-1-one

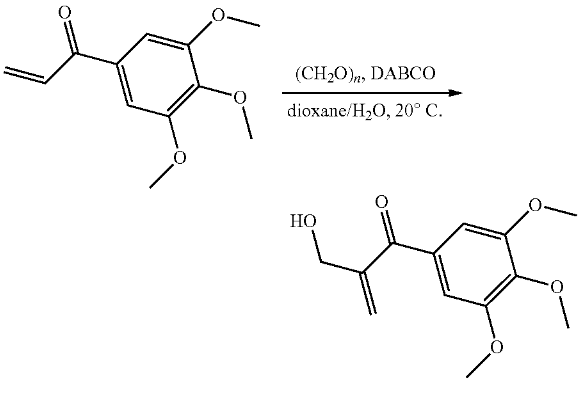 [SMILES: C=CC(=O)c1cc(OC)c(OC)c(OC)c1 ; C=C(CO)C(=O)c1cc(OC)c(OC)c(OC)c1]

To a solution of 1-(3,4,5-trimethoxyphenyl)prop-2-en-1-one (3.5 g, 15.75 mmol, 1 eq.) in dioxane (30 mL) and water (30 mL) were added formaldehyde (520.17 mg, 17.32 mmol, 477.22 μL, 1.1 eq.) and DABCO (176.66 mg, 1.57 mmol, 173.20 μL, 0.1 eq.). The mixture was stirred at 20° C. for 12 h under nitrogen. TLC and LCMS showed that the reaction was complete. The reaction mixture was poured into icewater (150 mL), then extracted with EtOAc (2×50 mL). The combined organic layers were washed with water (2×100 mL) and brine (2×100 mL), dried over anhydrous sodium sulfate, filtered, and concentrated in vacuo to give a residue. The residue was purified by column chromatography (silica gel; PE:EtOAc=8:1 to 2:1) to afford the title compound (1.1 g, 4.36 mmol, 27.69% yield) as a white oil.

d. Preparation of 2-(bromomethyl)-1-(3,4,5-trimethoxyphenyl)prop-2-en-1-one

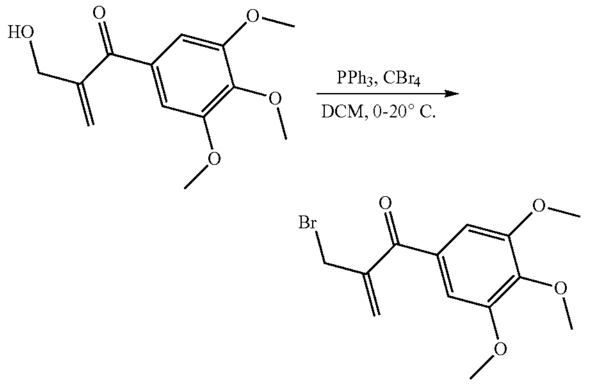 [SMILES: C=C(CO)C(=O)c1cc(OC)c(OC)c(OC)c1 ; C=C(CBr)C(=O)c1cc(OC)c(OC)c(OC)c1]

To a mixture of $PPh_3$ (800.60 mg, 3.05 mmol, 1.1 eq.) and $CBr_4$ (1.01 g, 3.05 mmol, 1.1 eq.) in DCM (10 mL) was added 2-(hydroxymethyl)-1-(3,4,5-trimethoxyphenyl)prop-2-en-1-one (0.7 g, 2.77 mmol, 1 eq.). The mixture was stirred at 0° C. for 1 h under nitrogen, then stirred at 20° C. for 1 h. TLC showed that the reaction was complete. The reaction diluted with water (50 mL) and extracted with EtOAc (2×25 mL). The combined organic layers were washed with water (2×50 mL) and brine (2×50 mL), dried over anhydrous sodium sulfate, filtered, and concentrated in vacuo to give a residue. The residue was purified by prep-TLC (silica gel; PE:EtOAc=1:1) to afford the title compound (0.4 g, 1.27 mmol, 45.74% yield) as a yellow solid.

e. Preparation of 7-amino-4-bromo-2-[2-(3,4,5-trimethoxybenzoyl)allyl]isoindolin-1-one

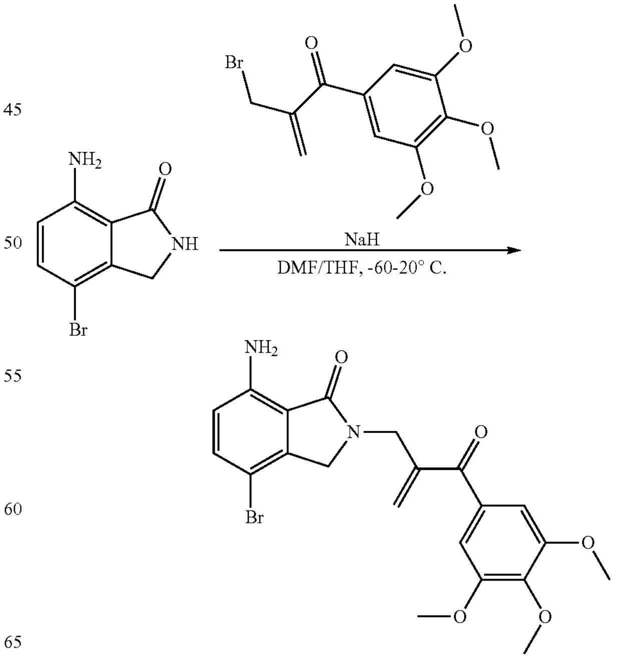

To a solution of 7-amino-4-bromo-isoindolin-1-one (0.18 g, 792.75 μmol, 1 eq.) in DMF (4 mL) and THF (4 mL) was added NaH (95.12 mg, 2.38 mmol, 60% purity, 3 eq.). The reaction was stirred at 20° C. for 20 min under nitrogen, and 2-(bromomethyl)-1-(3,4,5-trimethoxyphenyl)prop-2-en-1-one (274.83 mg, 872.03 μmol, 1.1 eq.) was added. The mixture was stirred at −60° C. for 20 min. TLC showed that the reaction was complete. The reaction diluted with water (50 mL) and extracted with EtOAc (2×25 mL). The combined organic layers were washed with water (2×50 mL) and brine (2×50 mL), dried over anhydrous sodium sulfate, filtered, and concentrated in vacuo to give a residue to afford the title compound (0.43 g, crude) as a yellow oil, which was used directly in the next step.

Preparation of 7-amino-4-(5-methoxy-3-pyridyl)-2-[2-(3,4,5-trimethoxybenzoyl)allyl]isoindolin-1-one (Compound 419)

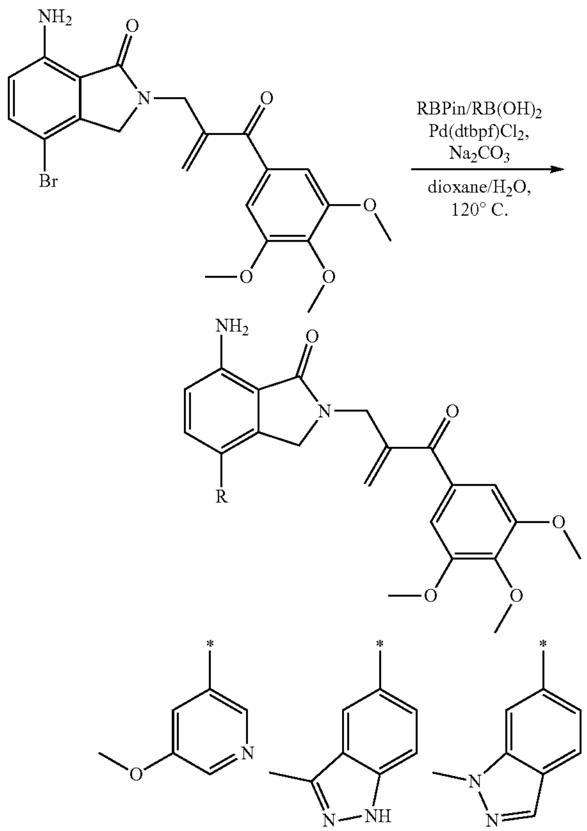

To a mixture of 7-amino-4-bromo-2-[2-(3,4,5-trimethoxybenzoyl)allyl]isoindolin-1-one (80 mg, 173.42 μmol, 1 eq.) and 3-methoxy-5-(4,4,5,5-tetramethyl-1,3,2-dioxaborolan-2-yl)pyridine (48.92 mg, 208.10 μmol, 1.2 eq.) in dioxane (2 mL) and water (0.5 mL) were added $Na_2CO_3$ (55.14 mg, 520.26 μmol, 3 eq.) and ditert-butyl (cyclopentyl)phosphane; dichloropalladium; iron (11.30 mg, 17.34 μmol, 0.1 eq.). The mixture was heated to 120° C. under nitrogen and stirred for 20 min. LCMS showed that the reaction was complete. The reaction mixture was stirred after adding sat. EDTA (50 mL) and EtOAc (25 mL) at 25° C., and was then extracted with EtOAc (2×25 mL). The combined organic layers were washed with water (2×50 mL) and brine (2×50 mL), dried over anhydrous sodium sulfate, filtered, and concentrated in vacuo to give a residue. The residue was purified by prep-HPLC to afford the title compound (9.6 mg, 18.98 μmol, 10.95% yield, 96.8% purity) as a white solid. LC-MS: $[M+H]^+$ 490.2.

Preparation of 7-amino-4-(1-methylindazol-6-yl)-2-[2-(3,4,5-trimethoxybenzoyl)allyl]isoindolin-1-one (Compound 418)

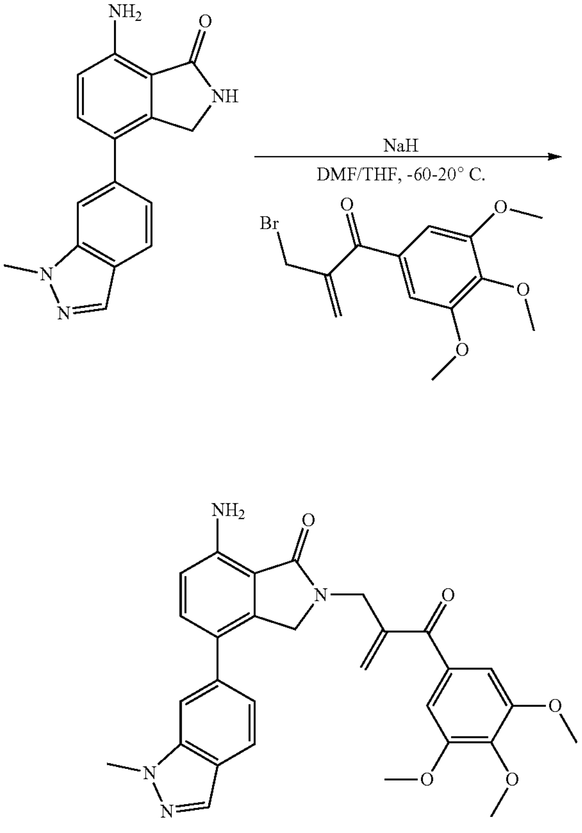

To a solution of 7-amino-4-(1-methylindazol-6-yl)isoindolin-1-one (70 mg, 251.52 μmol, 1 eq.) in DMF (1.5 mL) and THF (1.5 mL) was added NaH (30.18 mg, 754.56 μmol, 60% purity, 3 eq.). The reaction was stirred at 20° C. for 20 min under nitrogen, and 2-(bromomethyl)-1-(3,4,5-trimethoxyphenyl)prop-2-en-1-one (87.20 mg, 276.67 μmol, 1.1 eq.) was added. The mixture was stirred at −60° C. for 20 min. LCMS showed that the reaction was complete. The reaction mixture was The reaction was quenched by adding sat. $NH_4Cl$ 30 mL at 0° C., and extracted with EtOAc (2×25 mL). The combined organic layers were washed with water (2×50 mL) and brine (2×50 mL), dried over anhydrous sodium sulfate, filtered, and concentrated in vacuo to give a residue. The residue was purified by prep-HPLC to afford the title compound (14.3 mg, 27.90 μmol, 11.09% yield, 100.0% purity) as a white solid. LC-MS: $[M+H]^+$ 513.2.

TABLE 6 shows compounds prepared using the methods of EXAMPLE 8.

TABLE 6
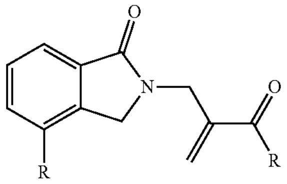
| Cpd. No. | Structure | IUPAC | LC-MS (ES+, m/z) |
|---|---|---|---|
| 404. | 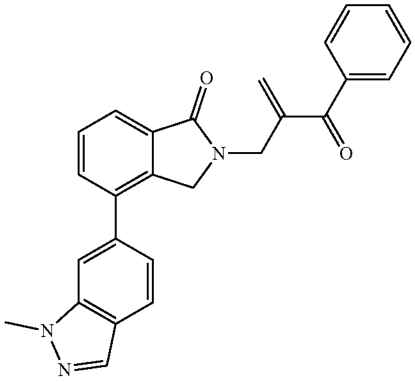 [SMILES: C=C(CN1Cc2c(cccc2-c2ccc3cnn(C)c3c2)C1=O)C(=O)c1ccccc1] | 4-(1-methyl-1H-indazol-6-yl)-2-(2-methylidene-3-oxo-3-phenylpropyl)-2,3-dihydro-1H-isoindol-1-one | 408.1 |
| 405. | 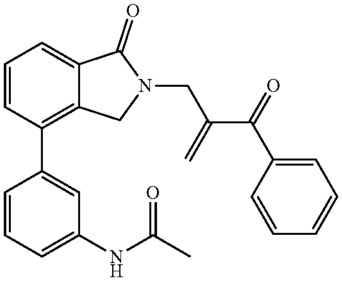 [SMILES: C=C(CN1Cc2c(cccc2-c2cccc(NC(C)=O)c2)C1=O)C(=O)c1ccccc1] | N-{3-[2-(2-methylidene-3-oxo-3-phenylpropyl)-1-oxo-2,3-dihydro-1H-isoindol-4-yl]phenyl}acetamide | 411.1 |
| 406. | 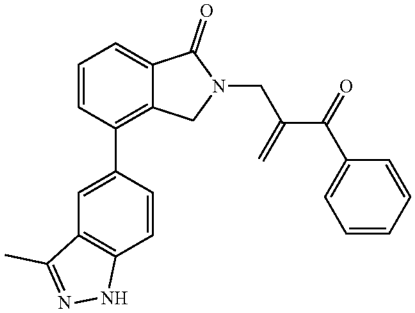 [SMILES: C=C(CN1Cc2c(cccc2-c2ccc3[nH]nc(C)c3c2)C1=O)C(=O)c1ccccc1] | 4-(3-methyl-1H-indazol-5-yl)-2-(2-methylidene-3-oxo-3-phenylpropyl)-2,3-dihydro-1H-isoindol-1-one | 408.2 |
| 407. | 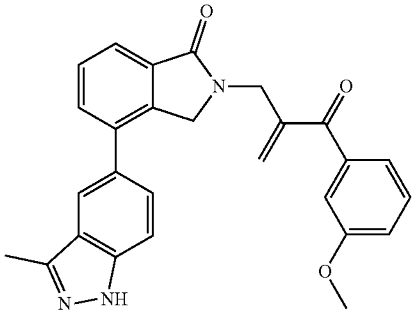 [SMILES: C=C(CN1Cc2c(cccc2-c2ccc3[nH]nc(C)c3c2)C1=O)C(=O)c1cccc(OC)c1] | 2-[3-(3-methoxyphenyl)-2-methylidene-3-oxopropyl]-4-(3-methyl-1H-indazol-5-yl)-2,3-dihydro-1H-isoindol-1-one | 438.2 |

TABLE 6-continued

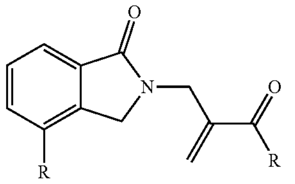

| Cpd. No. | Structure | IUPAC | LC-MS (ES+, m/z) |
|---|---|---|---|
| 408. | 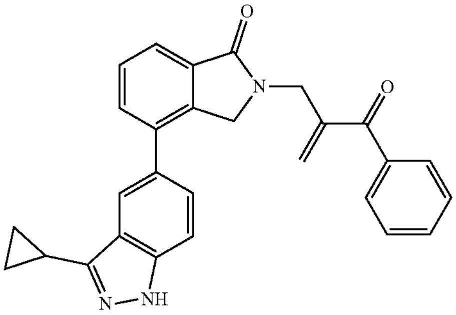 [SMILES: C=C(CN1Cc2c(cccc2-c2ccc3[nH]nc(C4CC4)c3c2)C1=O)C(=O)c1ccccc1] | 4-(3-cyclopropyl-1H-indazol-5-yl)-2-(2-methylidene-3-oxo-3-phenylpropyl)-2,3-dihydro-1H-isoindol-1-one | 434.1 |
| 409. | 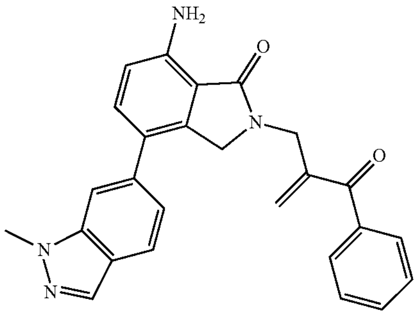 [SMILES: C=C(CN1Cc2c(-c3ccc4cnn(C)c4c3)ccc(N)c2C1=O)C(=O)c1ccccc1] | 7-amino-4-(1-methyl-1H-indazol-6-yl)-2-(2-methylidene-3-oxo-3-phenylpropyl)-2,3-dihydro-1H-isoindol-1-one | 423.2 |
| 410. | 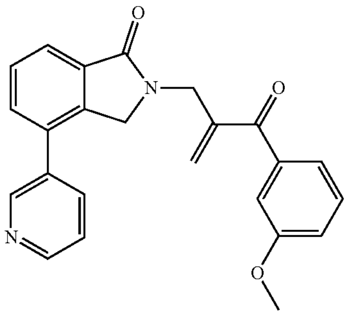 [SMILES: C=C(CN1Cc2c(cccc2-c2cccnc2)C1=O)C(=O)c1cccc(OC)c1] | 2-[3-(3-methoxyphenyl)-2-methylidene-3-oxopropyl]-4-(pyridin-3-yl)-2,3-dihydro-1H-isoindol-1-one | 385.1 |
| 411. | 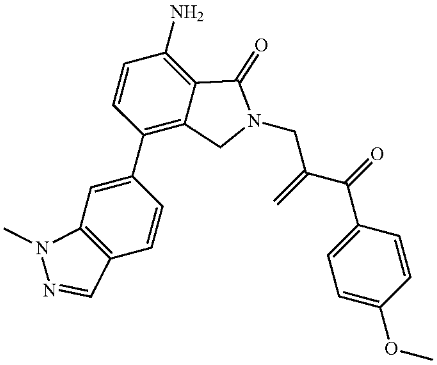 | 7-amino-2-[3-(4-methoxyphenyl)-2-methylidene-3-oxopropyl]-4-(1-methyl-1H-indazol-6-yl)-2,3-dihydro-1H-isoindol-1-one | 453.1 |

TABLE 6-continued

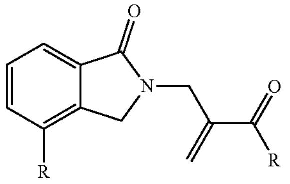

| Cpd. No. | Structure | IUPAC | LC-MS (ES+, m/z) |
| --- | --- | --- | --- |
| 412. | 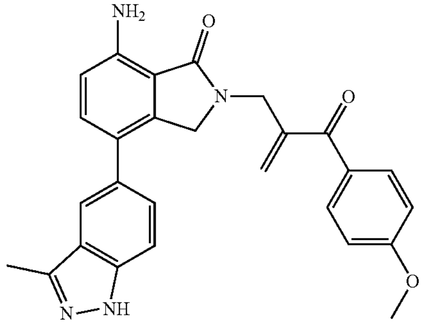 [SMILES: C=C(CN1Cc2c(-c3ccc4[nH]nc(C)c4c3)ccc(N)c2C1=O)C(=O)c1ccc(OC)cc1] | 7-amino-2-[3-(4-methoxyphenyl)-2-methylidene-3-oxopropyl]-4-(3-methyl-1H-indazol-5-yl)-2,3-dihydro-1H-isoindol-1-one | 453.1 |
| 413. | 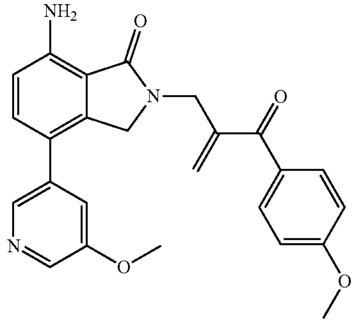 [SMILES: C=C(CN1Cc2c(-c3cncc(OC)c3)ccc(N)c2C1=O)C(=O)c1ccc(OC)cc1] | 7-amino-2-[3-(4-methoxyphenyl)-2-methylidene-3-oxopropyl]-4-(5-methoxypyridin-3-yl)-2,3-dihydro-1H-isoindol-1-one | 430.1 |
| 414. | 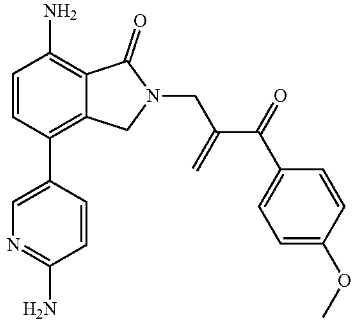 [SMILES: C=C(CN1Cc2c(-c3ccc(N)nc3)ccc(N)c2C1=O)C(=O)c1ccc(OC)cc1] | 7-amino-4-(6-aminopyridin-3-yl)-2-[3-(4-methoxyphenyl)-2-methylidene-3-oxopropyl]-2,3-dihydro-1H-isoindol-1-one | 415.1 |
| 415. | 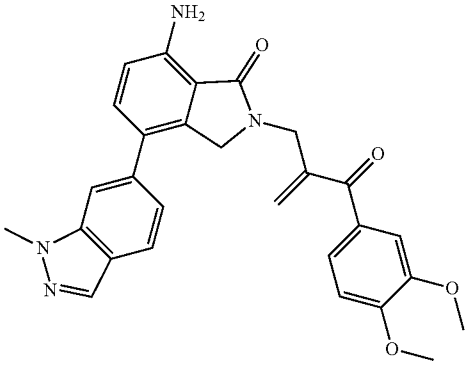 | 7-amino-2-[3-(3,4-dimethoxyphenyl)-2-methylidene-3-oxopropyl]-4-(1-methyl-1H-indazol-6-yl)-2,3-dihydro-1H-isoindol-1-one | 483.2 |

TABLE 6-continued

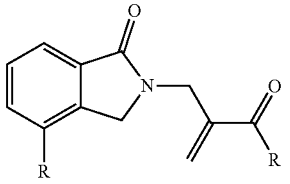

| Cpd. No. | Structure | IUPAC | LC-MS (ES+, m/z) |
|---|---|---|---|
| 416. | 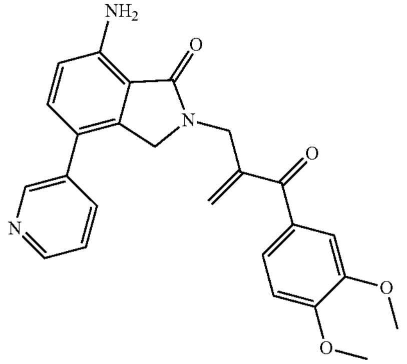 [SMILES: C=C(CN1Cc2c(-c3cccnc3)ccc(N)c2C1=O)C(=O)c1ccc(OC)c(OC)c1] | 7-amino-2-[3-(3,4-dimethoxyphenyl)-2-methylidene-3-oxopropyl]-4-(pyridin-3-yl)-2,3-dihydro-1H-isoindol-1-one | 430.1 |
| 417. | 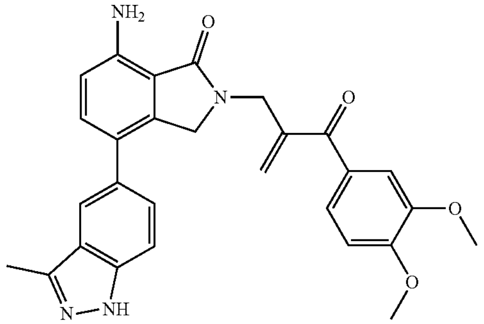 | 7-amino-2-[3-(3,4-dimethoxyphenyl)-2-methylidene-3-oxopropyl]-4-(3-methyl-1H-indazol-5-yl)-2,3-dihydro-1H-isoindol-1-one | 483.2 |
| 418. | 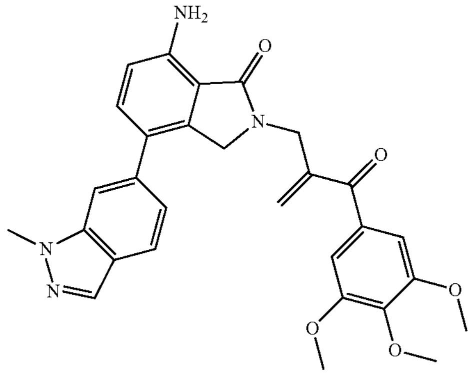 | 7-amino-4-(1-methyl-1H-indazol-6-yl)-2-[2-methylidene-3-oxo-3-(3,4,5-trimethoxyphenyl)propyl]-2,3-dihydro-1H-isoindol-1-one | 513.2 |
| 419. | 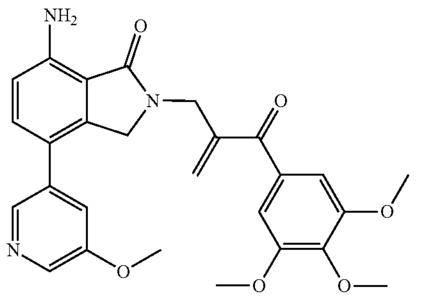 [SMILES: C=C(CN1Cc2c(-c3cncc(OC)c3)ccc(N)c2C1=O)C(=O)c1cc(OC)c(OC)c(OC)c1] | 7-amino-4-(5-methoxypyridin-3-yl)-2-[2-methylidene-3-oxo-3-(3,4,5-trimethoxyphenyl)propyl]-2,3-dihydro-1H-isoindol-1-one | 490.2 |

TABLE 6-continued
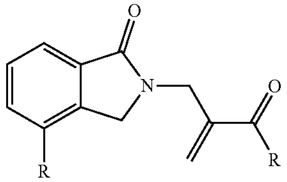
| Cpd. No. | Structure | IUPAC | LC-MS (ES+, m/z) |
|---|---|---|---|
| 420. | 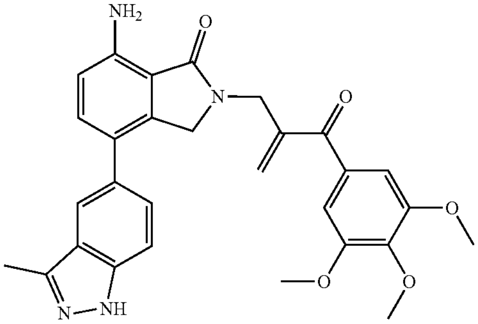 | 7-amino-4-(3-methyl-1H-indazol-5-yl)-2-[2-methylidene-3-oxo-3-(3,4,5-trimethoxyphenyl)propyl]-2,3-dihydro-1H-isoindol-1-one | 513.2 |
Example 9: Method G
General Scheme for Method G
Route 1
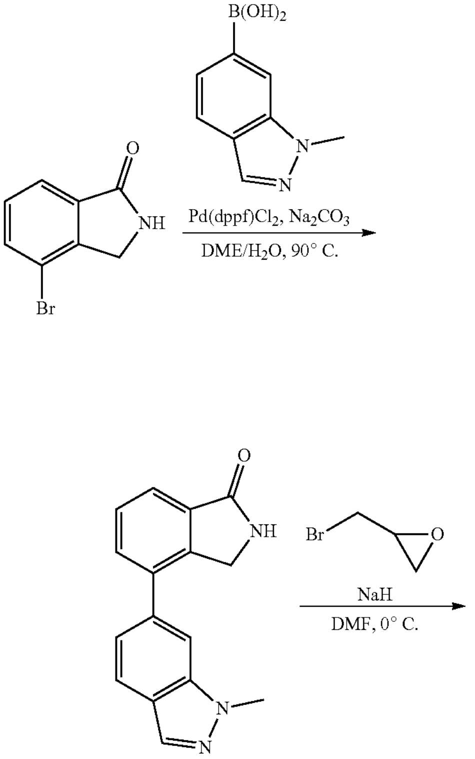
-continued
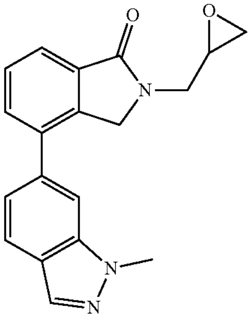
a. Preparation of 4-(1-methylindazol-6-yl)isoindolin-1-one
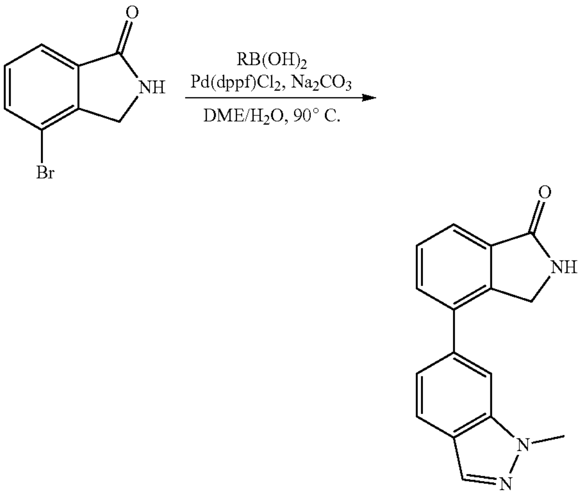 [SMILES: O=C1NCc2c(Br)cccc21 ; Cn1ncc2ccc(-c3cccc4c3CNC4=O)cc21]

To a mixture of 4-bromoisoindolin-1-one (0.3 g, 1.41 mmol, 1 eq.) and (1-methylindazol-6-yl)boronic acid (248.98 mg, 1.41 mmol, 1 eq.) in DME (8 mL) and water (2 mL) was added $Na_2CO_3$ (449.86 mg, 4.24 mmol, 3 eq.) in one portion at 25° C. under nitrogen. Then, $Pd(dppf)Cl_2$ (51.76 mg, 70.74 μmol, 0.05 eq.) was added to the mixture. The mixture was stirred at 90° C. for 1 h. LCMS showed that the reaction was complete. The reaction was poured to 20 mL sat EDTA and diluted with 20 mL EtOAc, then the mixture was stirred at 25° C. for 1 h. The aqueous layer was extracted with EtOAc (3x20 mL), and the combined organic layer was washed with brine 10 mL, filtered, and concentrated in vacuo. The residue was purified by column chromatography (silica gel; DCM/MeOH=20/1 to 10:1) to afford the title compound (0.15 g, 512.74 μmol, 90% purity) as a yellow solid.

Preparation of 4-(1-methylindazol-6-yl)-2-(oxiran-2-ylmethyl)isoindolin-1-one (Compound 421)

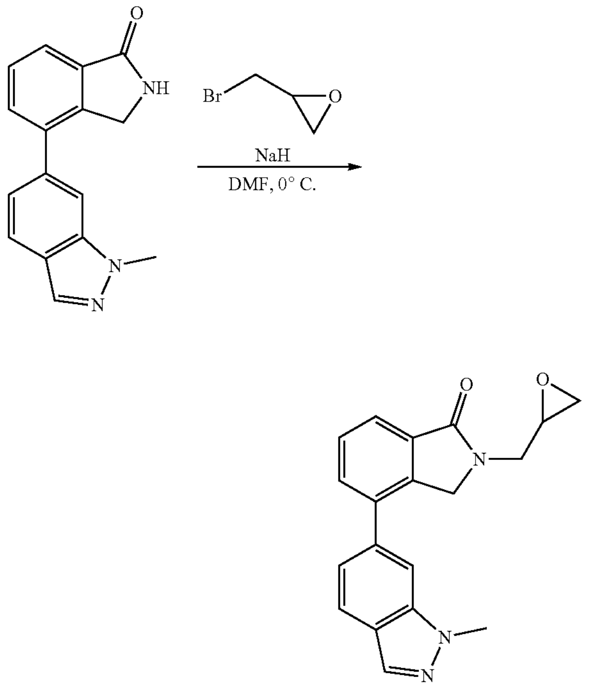

To a solution of 4-(1-methylindazol-6-yl)isoindolin-1-one (50 mg, 170.91 μmol, 1 eq.) in DMF (2 mL) was added NaH (20.51 mg, 512.74 μmol, 60% purity, 3 eq.), and the mixture was stirred at 25° C. for 30 minutes under nitrogen. Then, 2-(bromomethyl)oxirane (70.23 mg, 512.74 μmol, 42.31 μL, 3 eq.) was added, and the mixture was stirred at 0° C. for 30 minutes. TLC and LCMS showed that the reaction was complete. The reaction was quenched with saturated $NH_4Cl$ (15 mL) at 0° C., and extracted with EtOAc (3x15 mL). The combined organic layers were washed with water (2x50 mL) and brine (2x50 mL), dried over anhydrous sodium sulfate, filtered, and concentrated in vacuo to give a residue. The residue was purified by prep-TLC (silica gel; DCM: MeOH=15:1) to afford the title compound (8.1 mg, 24.81 μmol, 14.51% yield, 97.8% purity) as a white solid. LC-MS: $[M+H]^+$ 320.1.

Preparation of 4-(3-methyl-1H-indazol-5-yl)-2-[(oxiran-2-yl)methyl]-2,3-dihydro-1H-isoindol-1-one (Compound 422)

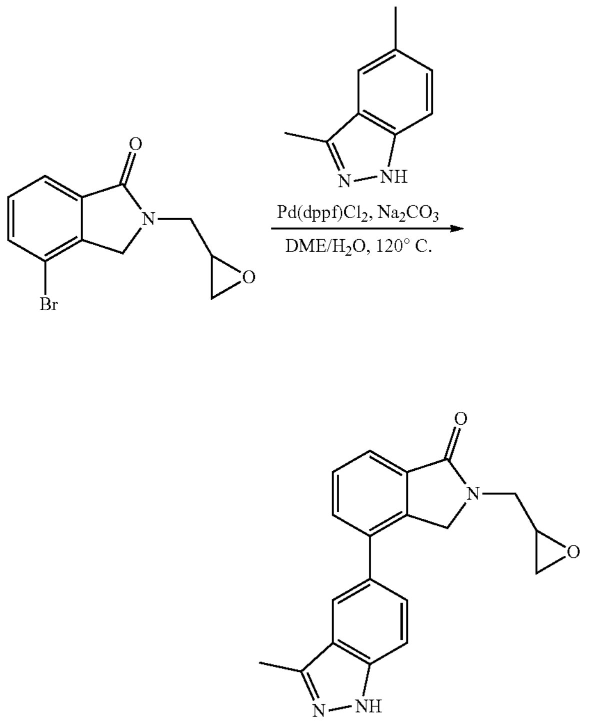

To a solution of 4-bromo-2-(oxiran-2-ylmethyl)isoindolin-1-one (50 mg, 167.84 μmol, 1 eq.) in water (0.5 mL) and DME (2 mL) were added (3-methyl-1H-indazol-5-yl)boronic acid (44.31 mg, 251.77 μmol, 1.5 eq.), $Na_2CO_3$ (44.47 mg, 419.61 μmol, 2.5 eq.) and $Pd(dppf)Cl_2$ (12.28 mg, 16.78 μmol, 0.1 eq.). The resulting reaction mixture was stirred at 120° C. for 5 min. LCMS and TLC showed that the reaction was complete. The reaction mixture was poured into 80 mL sat. EDTA, and 30 mL EtOAc was added to the mixture. The solution was stirred for 2 h, and the aqueous phase was extracted with EtOAc (2x20 mL). The combined organic layer was washed with water (2x20 mL) and brine (20 mL), dried over anhydrous sodium sulfate, filtered, and concentrated to give the crude product. The crude product was purified by prep-TLC (silica gel; DCM:MeOH=20:1) to afford the title compound (11.3 mg, 34 μmol, 20.26% yield, 96.1% purity) as an off-white solid. LC-MS: $[M+H]^+$ 320.1

Route 2

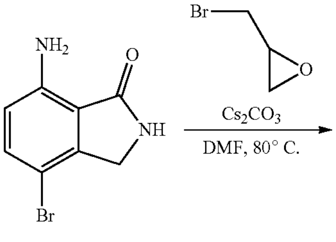

-continued

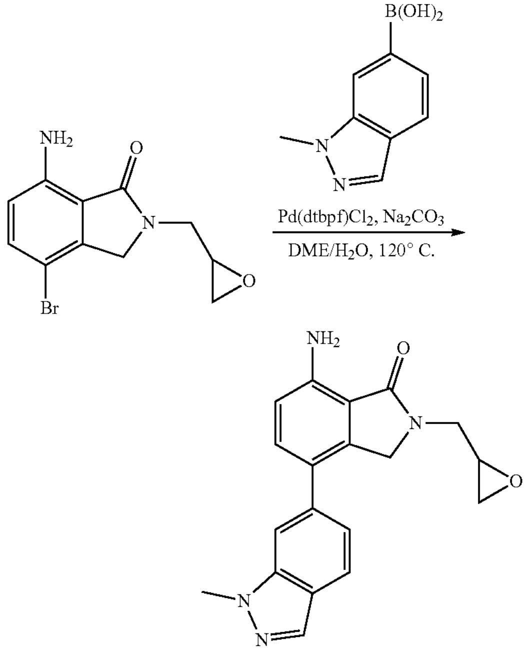

Preparation of 7-amino-4-bromo-2-(oxiran-2-ylmethyl)isoindolin-1-one

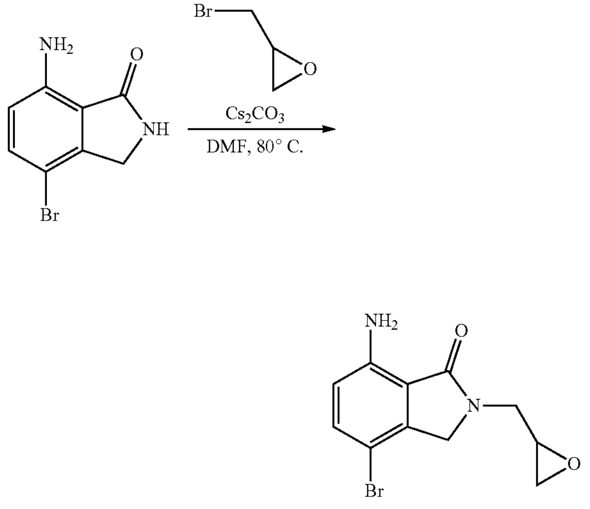

To a solution of 7-amino-4-bromo-isoindolin-1-one (1 g, 4.40 mmol, 1 eq.) in DMF (15 mL) were added $Cs_2CO_3$ (4.3 g, 13.21 mmol, 3 eq.) and 2-(bromomethyl)oxirane (6.03 g, 44.04 mmol, 3.63 mL, 10 eq.). The mixture was stirred at 80° C. for 1 h. TLC showed that the reaction was complete. The reaction mixture was diluted with water 50 mL, and extracted with EtOAc (50 mL×2). The combined organic layers were washed with water (100 mL×2) and brine (100 mL×2), dried over anhydrous sodium sulfate, filtered, and concentrated in vacuo to give a residue to afford the title compound (1.2 g, crude) as a brown oil, which was used directly in the next step.

Preparation of 7-amino-4-(1-methylindazol-6-yl)-2-(oxiran-2-ylmethyl)isoindolin-1-one (Compound 427)

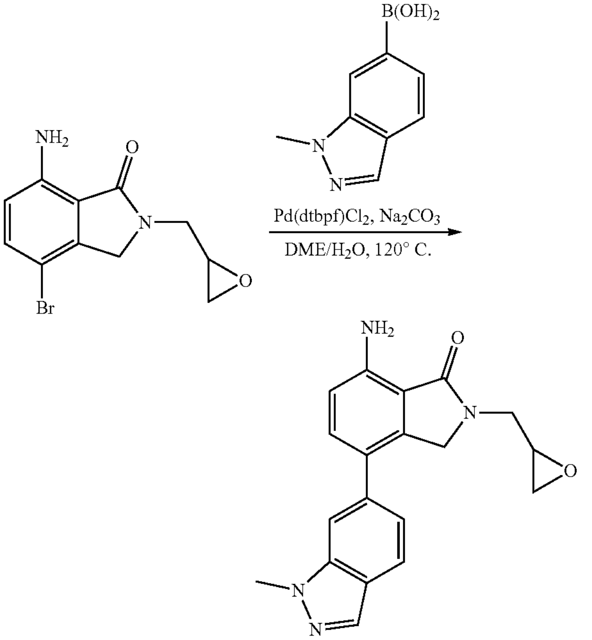

To a mixture of 7-amino-4-bromo-2-(oxiran-2-ylmethyl)isoindolin-1-one (0.2 g, 706.41 μmol, 1 eq.) and (1-methylindazol-6-yl)boronic acid (186.47 mg, 1.06 mmol, 1.5 eq.) in DME (4 mL) and water (1 mL) were added $Na_2CO_3$ (224.62 mg, 2.12 mmol, 3 eq.) and $Pd(dtbpf)Cl_2$ (46.04 mg, 70.64 μmol, 0.1 eq.), the reaction mixture was heated to 120° C. under nitrogen and stirred for 20 min. TLC showed that the reaction was complete. The reaction mixture was stirred by adding sat. EDTA (30 mL) and EtOAc (30 mL) at 25° C., and the mixture was extracted with EtOAc (2×50 mL). The combined organic layers were washed with water (2×100 mL) and brine (2×100 mL), dried over anhydrous sodium sulfate, filtered, and concentrated in vacuo to give a residue. The residue was purified by prep-TLC (silica gel; DCM: MeOH=20:1) to afford the title compound (0.05 g, 149.53 μmol, 21.17% yield) as a yellow solid. LC-MS: $[M+H]^+$ 335.1.

Route 3:

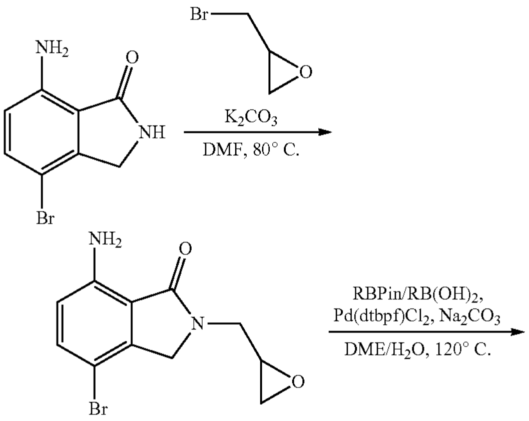

-continued

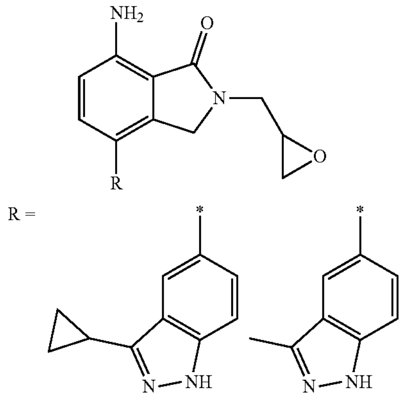

Preparation of 7-amino-4-bromo-2-(oxiran-2-ylmethyl)isoindolin-1-one

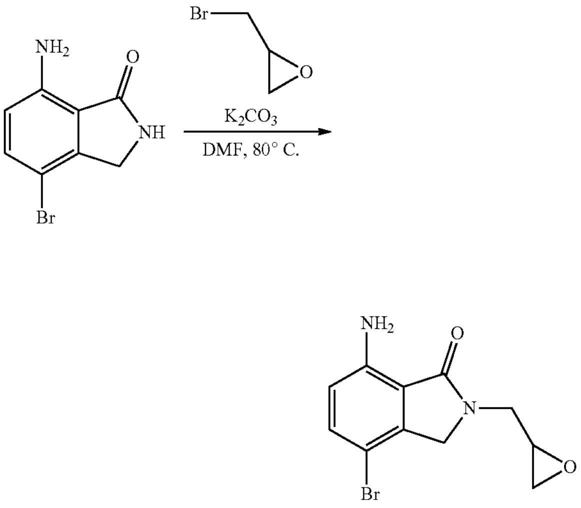

To a solution of 7-amino-4-bromo-isoindolin-1-one (0.5 g, 2.20 mmol, 1 eq.) in DMF (10 mL) were added $Cs_2CO_3$ (2.15 g, 6.61 mmol, 3 eq.) and 2-(bromomethyl)oxirane (3.02 g, 22.02 mmol, 1.82 mL, 10 eq.). The mixture was stirred at 80° C. for 1 h. TLC showed that the reaction was complete. The reaction mixture was diluted with water 50 mL, and extracted with EtOAc (2×50 mL). The combined organic layers were washed with water (2×100 mL) and brine (2×100 mL), dried over anhydrous sodium sulfate, filtered, and concentrated in vacuo to give a residue to afford the title compound (0.8 g, crude) as a brown oil, which was used directly without purification.

Preparation of 7-amino-4-(3-methyl-1H-indazol-5-yl)-2-[(oxiran-2-yl)methyl]-2,3-dihydro-1H-isoindol-1-one (Compound 428)

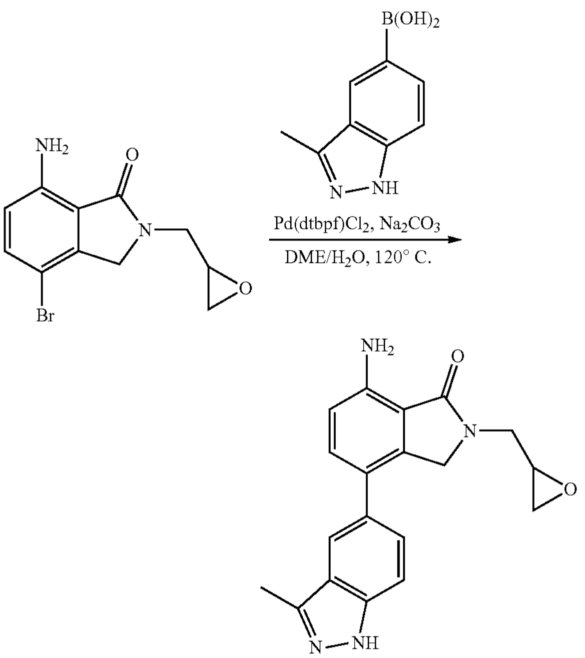 [SMILES: Nc1ccc(Br)c2c1C(=O)N(CC1CO1)C2 ; Cc1n[nH]c2ccc(B(O)O)cc12 ; Cc1n[nH]c2ccc(-c3ccc(N)c4c3CN(CC3CO3)C4=O)cc12]

To a mixture of 7-amino-4-bromo-2-(oxiran-2-ylmethyl)isoindolin-1-one (0.1 g, 353.21 μmol, 1 eq.) and (3-methyl-1H-indazol-5-yl)boronic acid (93.24 mg, 529.81 μmol, 1.5 eq.) in DME (4 mL) and water (1 mL) were added $Na_2CO_3$ (112.31 mg, 1.06 mmol, 3 eq.) and ditert-butyl(cyclopentyl) phosphane; dichloropalladium; iron (23.02 mg, 35.32 μmol, 0.1 eq.). The reaction mixture was heated to 120° C. under nitrogen and stirred for 20 min. TLC and LCMS showed that the reaction was complete. The reaction mixture was stirred with sat. EDTA (25 mL) and EtOAc (25 mL) at 25° C., and extracted with EtOAc (2×30 mL). The combined organic layers were washed with water (2×50 mL) and brine (2×50 mL), dried over anhydrous sodium sulfate, filtered, and concentrated in vacuo to give a residue. The residue was purified by prep-TLC (silica gel; DCM:MeOH=20:1) to afford the title compound (11.9 mg, 27.58 μmol, 7.81% yield, 77.5% purity) as a white solid. LC-MS: $[M+H]^+$ 335.2

Route 4

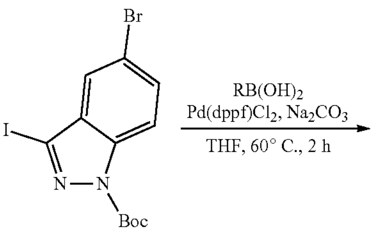

-continued

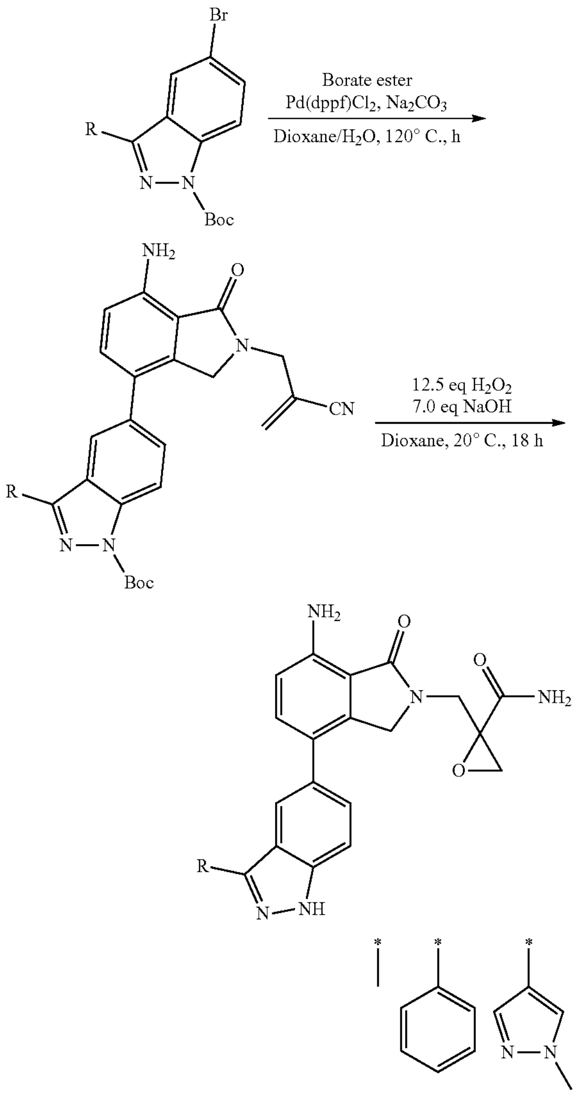

Preparation of tert-butyl 5-[7-amino-2-(2-cyanoallyl)-1-oxo-isoindolin-4-yl]-3-phenyl-indazole-1-carboxylate

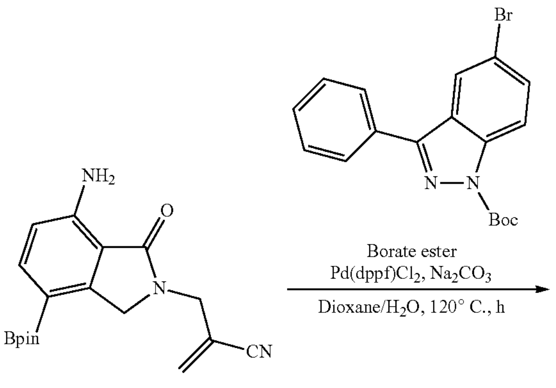

-continued

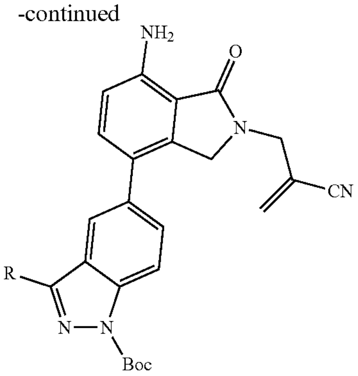

To a solution of tert-butyl 3-(1-methylpyrazol-4-yl)-5-(4,4,5,5-tetramethyl-1,3,2-dioxaborolan-2-yl)indazole-1-carboxylate (330 mg, 884.14 μmol, 1 eq.) and 2-[(7-amino-4-bromo-1-oxo-isoindolin-2-yl)methyl]prop-2-enenitrile (359.88 mg, 1.06 mmol, 1.2 eq.) in dioxane (12 mL) and water (3 mL) were added Pd(dppf)Cl2 (194.08 mg, 265.24 μmol, 0.3 eq.) and $Na_2CO_3$ (281.13 mg, 2.65 mmol, 3 eq.). Then the reaction was stirred at 120° C. for 15 min under nitrogen atmosphere. TLC showed 60% of the desired product. 20 mL sat. EDTA was added to the reaction, and the reaction mixture was stirred at 20° C. for 1 h. The reaction mixture was extracted with EtOAc (20 mL×3). The combined organic layer was washed with brine (10 mL×3), dried over anhydrous sodium sulfate, filtered, and concentrated. The crude was purified by silica gel chromatography (PE: EtOAc=3:1) and prep-TLC (silica gel; DCM/MeOH=20/1, Rf=0.5) to afford the title compound (300 mg, 593.39 μmol, 67.12% yield) as a yellow solid.

Preparation of 2-[[7-amino-1-oxo-4-(3-phenyl-1H-indazol-5-yl)isoindolin-2-yl]methyl]oxirane-2-carboxamide (Compound 435)

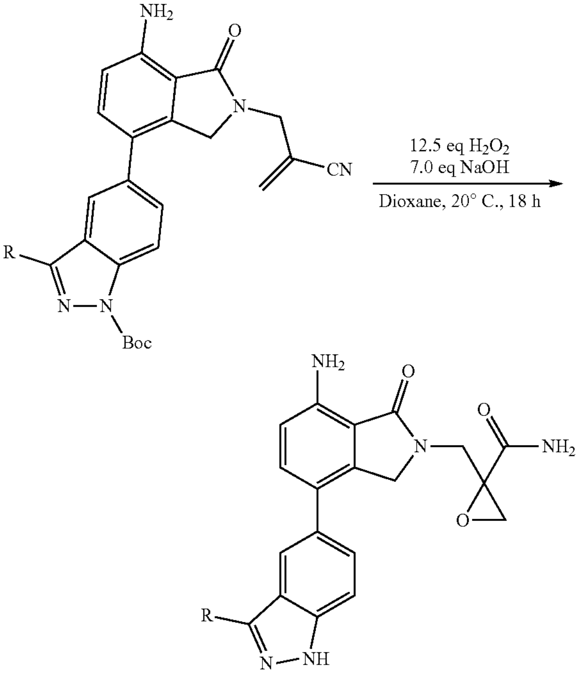

To a solution of tert-butyl 5-[7-amino-2-(2-cyanoallyl)-1-oxo-isoindolin-4-yl]-3-phenyl-indazole-1-carboxylate (120 mg, 237.36 μmol, 1 eq.) in dioxane (6.0 mL) were added water (336 mg, 2.96 mmol, 284.75 μL, 30% purity, 12.49 eq.) and NaOH (66 mg, 1.65 mmol, 0.6 mL, 6.95 eq.). The reaction was stirred at 20° C. for 2 h. TLC and LCMS showed 40% of the desired product. Then the reaction was stirred at 20° C. for another 2 h. TLC showed 40% of the desired product. 0.5 mL of the reaction mixture was added to water (0.3 mL 30% aqueous), and the reaction was stirred at 20° C. for 1 h. TLC showed no improvement to the reaction. An additional 5.0 mL of the reaction mixture was worked up by adding 10 mL Sat. $Na_2S_2O_3$ to the reaction and stirring the mixture at 20° C. for 1 h. The reaction mixture was extracted with EtOAc (20 mL×3). The combined organic layer was washed with brine (10 mL×3), dried over anhydrous sodium sulfate, filtrate and concentrated to give the crude. The crude was purified by prep-TLC and prep-HPLC to afford the title compound (5.1 mg, 11.14 μmol, 4.69% yield, 96% purity) as a white solid. LC-MS: $[M+H]^+$ 440.1.

Preparation of 2-[[7-amino-4-[3-(3,6-dihydro-2H-pyran-4-yl)-1H-indazol-5-yl]-1-oxo-isoindolin-2-yl]methyl]oxirane-2-carboxamide

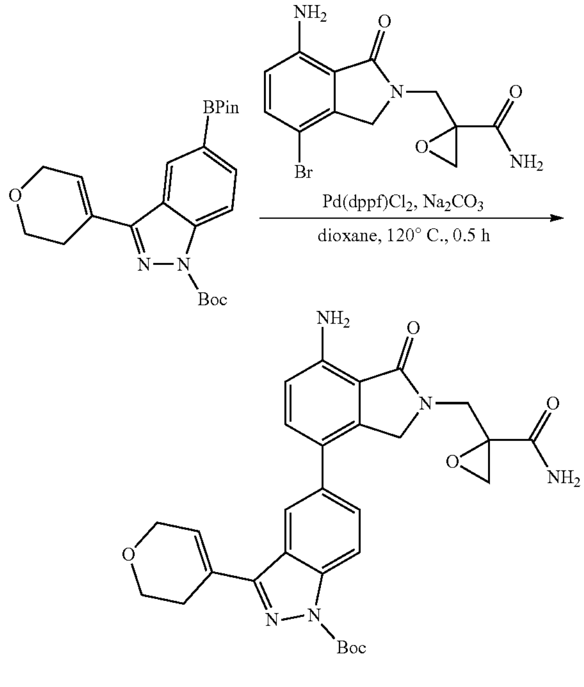

To a mixture of 2-[(7-amino-4-bromo-1-oxo-isoindolin-2-yl)methyl]oxirane-2-carboxamide (90 mg, 220.76 μmol, 1 eq.) and tert-butyl 3-(3,6-dihydro-2H-pyran-4-yl)-5-(4,4,5,5-tetramethyl-1,3,2-dioxaborolan-2-yl)indazole-1-carboxylate (166.08 mg, 331.14 μmol, 1.5 eq.) in dioxane (4 mL) and water (1 mL) were added $Na_2CO_3$ (70.19 mg, 662.28 μmol, 3 eq.) and $Pd(dppf)Cl_2$ (8.08 mg, 11.04 μmol, 0.05 eq.) under nitrogen. The mixture was stirred at 120° C. for 0.5 h. LCMS and TLC showed that the reaction was complete. Saturated EDTA (10 mL) was added to the mixture, and the mixture was cooled to 20° C. and concentrated under reduced pressure at 20° C. The residue was poured into ice-water (20 mL) and stirred for 2 h. The aqueous phase was extracted with EtOAc (3×10 mL). The combined organic phase was washed with brine (3×10 mL), dried over anhydrous sodium sulfate, filtered, and concentrated in vacuo. The residue was purified by prep-TLC to afford the title compound (40 mg, 41% yield) as a yellow solid.

Preparation of 2-[[7-amino-4-[3-(3,6-dihydro-2H-pyran-4-yl)-1H-indazol-5-yl]-1-oxo-isoindolin-2-yl]methyl]oxirane-2-carboxamide (Compound 438)

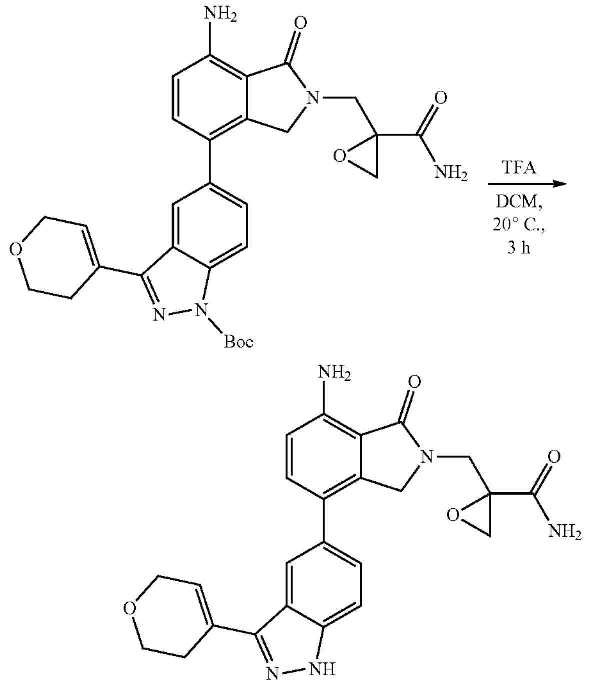 [SMILES: CC(C)(C)OC(=O)n1nc(C2=CCOCC2)c2cc(-c3ccc(N)c4c3CN(CC3(C(N)=O)CO3)C4=O)ccc21 ; NC(=O)C1(CN2Cc3c(-c4ccc5[nH]nc(C6=CCOCC6)c5c4)ccc(N)c3C2=O)CO1]

A mixture of tert-butyl 5-[7-amino-2-[(2-carbamoyloxiran-2-yl)methyl]-1-oxo-isoindolin-4-yl]-3-(3,6-dihydro-2H-pyran-4-yl)indazole-1-carboxylate (36 mg, 65.98 μmol, 1 eq.) in DCM (2 mL) and trifluoroacetic acid (308 mg, 2.70 mmol, 0.2 mL, 40.94 eq.) was stirred at 20° C. for 3 h. TLC showed that the reaction was complete. The residue was poured into saturated $NaHCO_3$ (10 mL). The aqueous phase was extracted with DCM (3×5 mL). The combined organic phase was washed with brine (3×5 mL), dried over anhydrous sodium sulfate, filtered, and concentrated in vacuo. The residue was purified by prep-TLC DCM:Methanol=10:1 to afford the title compound (14 mg, 29.23 μmol, 44.29% yield, 93% purity) as a white solid, LC-MS: $[M+H]^+$ 446.1.

Route 5

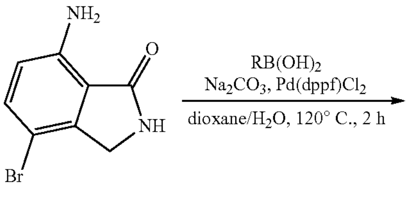

-continued

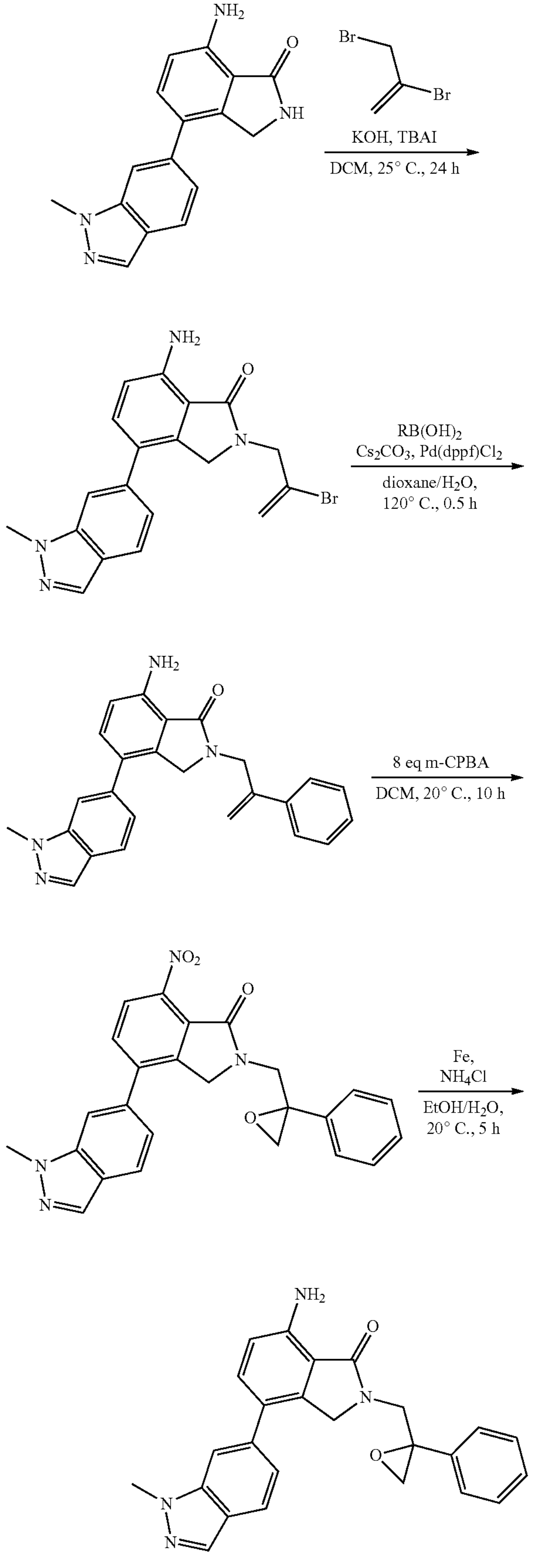

Preparation of 7-amino-4-(1-methylindazol-6-yl)isoindolin-1-one

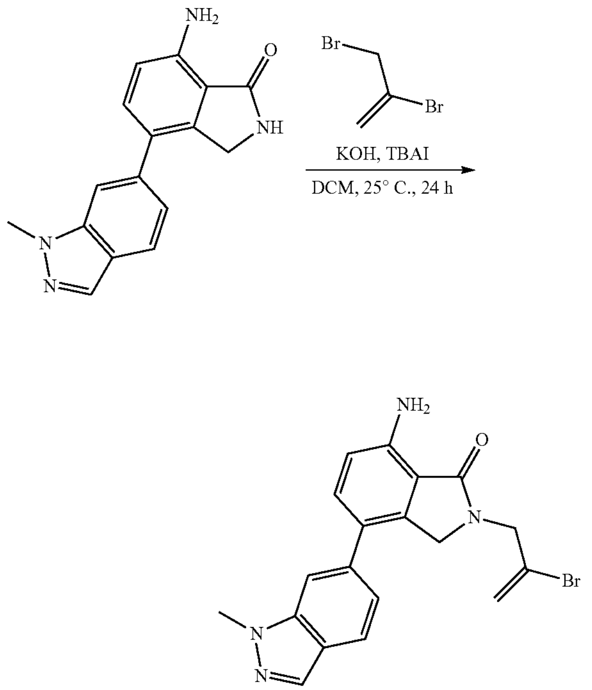

To a mixture of 7-amino-4-bromo-isoindolin-1-one (950 mg, 4.18 mmol, 1 eq.) and (1-methylindazol-6-yl) boronic acid (809.92 mg, 4.60 mmol, 1.1 eq.) in dioxane (8 mL) and water (2 mL) were added $Na_2CO_3$ (1.33 g, 12.55 mmol, 3 eq.) and $Pd(dppf)Cl_2$ (153.07 mg, 209.20 μmol, 0.05 eq.) under nitrogen. The mixture was heated to 120° C. and stirred for 2 h. TLC showed that the reaction was complete. 30 mL saturated EDTA was added to the mixture, then the mixture was stirred for 2 h. The aqueous phase was extracted with EtOAc (20 mL×3). The combined organic phase was washed with brine (20 mL×3), dried over anhydrous sodium sulfate, filtered, and concentrated in vacuo. The residue was washed with DCM (2 mL) to afford the title compound (600 mg, 2.16 mmol, 51.53% yield) as a brown solid.

Preparation of 7-amino-2-(2-bromoallyl)-4-(1-methylindazol-6-yl)isoindolin-1-one

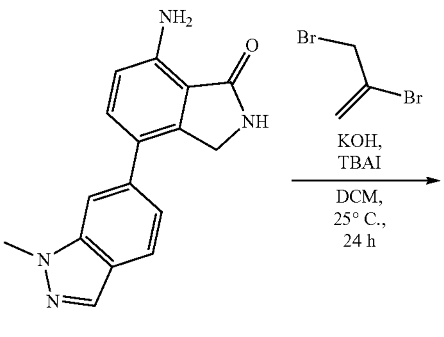

-continued

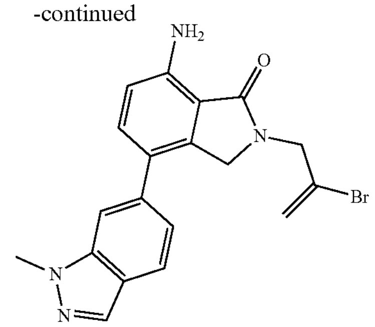

To a mixture of 7-amino-4-(1-methylindazol-6-yl)isoindolin-1-one (350 mg, 1.26 mmol, 1 eq.) in DCM (5 mL) were added TBAI (464.52 mg, 1.26 mmol, 1 eq.) and KOH (211.68 mg, 3.77 mmol, 3 eq). Then, 2,3-dibromoprop-1-ene (226.22 mg, 1.13 mmol, 110.35 μL, 0.9 eq.) was added to the mixture. The mixture was stirred at 25° C. for 24 h. TLC showed that the reaction was not completed. Water (20 mL) was added to the mixture, and the aqueous phase was extracted with DCM (20 mL×3). The combined organic phase was washed with water and brine (20 mL×3), dried over anhydrous sodium sulfate, filtered, and concentrated in vacuo. The residue was purified by prep-TLC (DCM:Methanol=20:1) to afford the title compound (200 mg, 503.44 μmol, 40.03% yield) as a yellow solid.

Preparation of 7-amino-4-(1-methylindazol-6-yl)-2-(2-phenylallyl)isoindolin-1-one

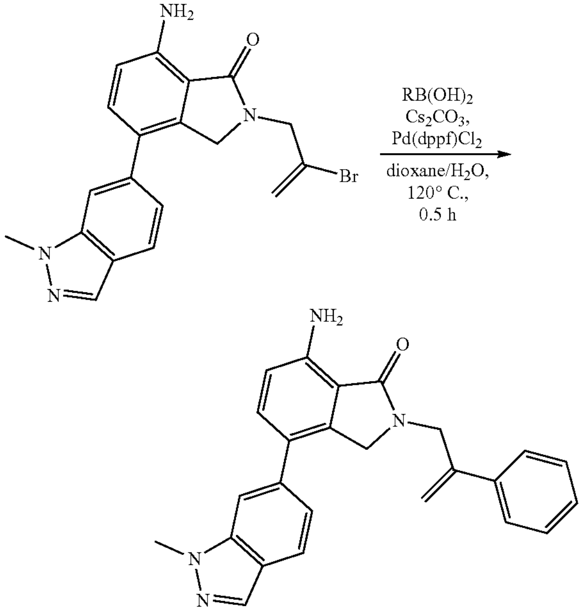

To a mixture of 7-amino-2-(2-bromoallyl)-4-(1-methylindazol-6-yl)isoindolin-1-one (200 mg, 503.44 μmol, 1 eq.) and phenylboronic acid (122.77 mg, 1.01 mmol, 2 eq.) in dioxane (4 mL) and water (1 mL) were added $Cs_2CO_3$ (492.09 mg, 1.51 mmol, 3 eq.) and Pd(dppf)$Cl_2$ (18.42 mg, 25.17 μmol, 0.05 eq.) under nitrogen. The mixture was heated to 120° C. and stirred for 0.5 h. The residue was poured into saturated EDTA (10 mL) and stirred for 2 h. The aqueous phase was extracted with EtOAc (10 mL×3). The combined organic phase was washed with brine (10 mL×3), dried over anhydrous sodium sulfate, filtered, and concentrated in vacuo. The residue was purified by prep-TLC (DCM:Methanol=10:1) to afford the title compound (100 mg, 253.51 μmol, 50.355% yield) as a yellow solid.

Preparation of 4-(1-methylindazol-6-yl)-7-nitro-2-[(2-phenyloxiran-2-yl)methyl]isoindolin-1-one

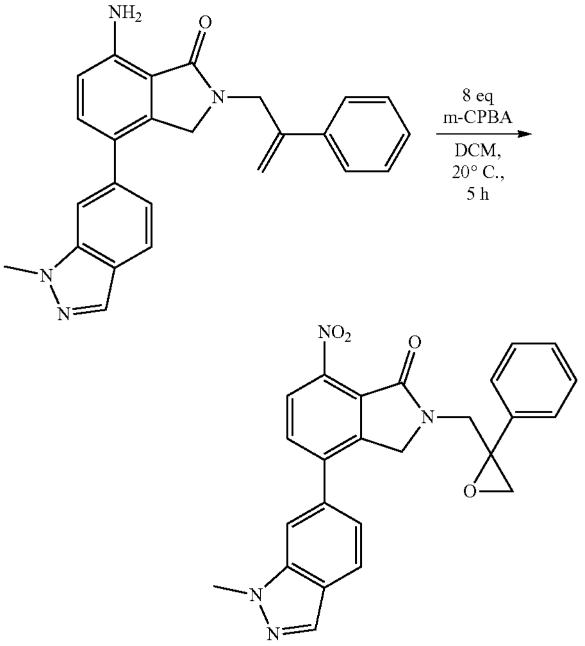

To a mixture of 7-amino-4-(1-methylindazol-6-yl)-2-(2-phenylallyl)isoindolin-1-one (90 mg, 228.16 μmol, 1 eq.) in DCM (1 mL) was added m-CPBA (314.98 mg, 1.83 mmol, 100% purity, 8 eq.). The mixture was stirred at 20° C. for 5 h. TLC showed that the reaction was complete. The residue was poured into sat. $NaHCO_3$ (10 mL). The aqueous phase was extracted with DCM (3×5 mL). The combined organic phase was washed with $NaHCO_3$ (3×5 mL), dried over anhydrous sodium sulfate, filtered, and concentrated in vacuo. The residue was purified by prep-TLC (DCM:Methanol=30:1) to afford the title compound (40 mg, 90.82 μmol, 39.80% yield) as a yellow solid.

Preparation of 7-amino-4-(1-methylindazol-6-yl)-2-[(2-phenyloxiran-2-yl)methyl]isoindolin-1-one (Compound 439)

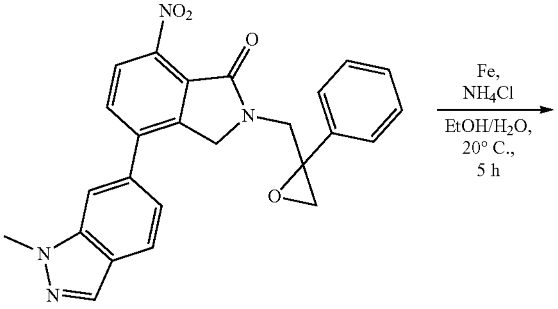

-continued

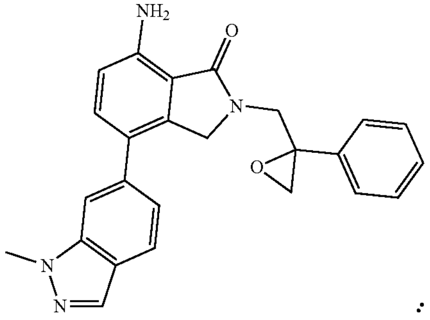

To a mixture of $NH_4Cl$ (3.64 mg, 68.11 μmol, 2.38 μL, 1 eq.) and 4-(1-methylindazol-6-yl)-7-nitro-2-[(2-phenyloxiran-2-yl)methyl]isoindolin-1-one (30 mg, 68.11 μmol, 1 eq.) in EtOH (4 mL) and water (1 mL) was added Fe (29.17 mg, 522.23 μmol, 7.67 eq.) at 20° C. The reaction was stirred for 5 h at 20° C. TLC showed that the reaction was complete. The mixture was filtered, and the solid was washed with DCM:Methanol=10:1 (5 mL×10). The combined organic phase was concentrated. The solid was purified by prep-TLC (DCM:Methanol=10:1) to afford the title compound (9 mg, 21.49 μmol, 31.55% yield, 98% purity) as a white solid. LC-MS: $[M+H]^+$ 411.2.

Route 6:

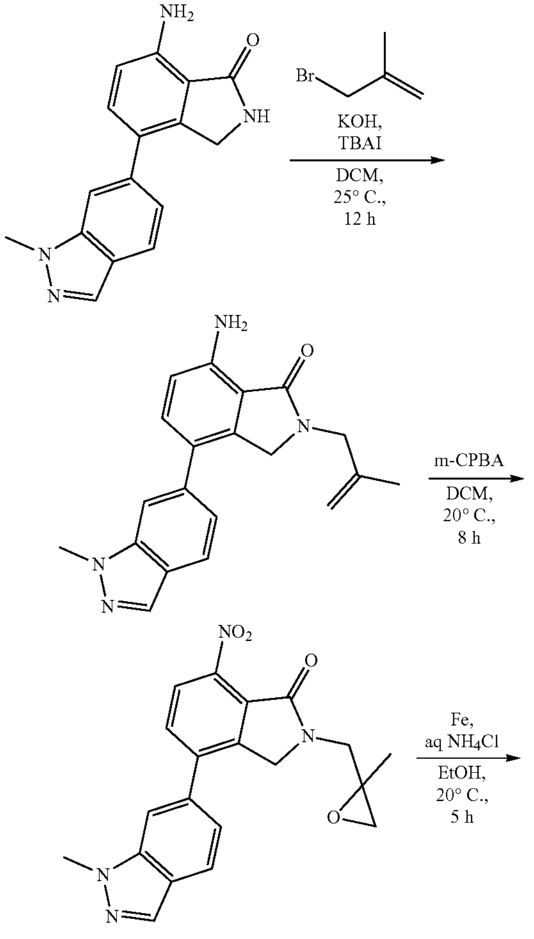

-continued

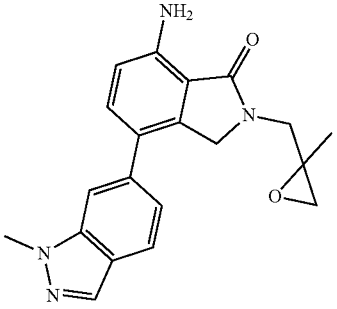

Preparation of 7-amino-2-(2-methylallyl)-4-(1-methylindazol-6-yl)isoindolin-1-one

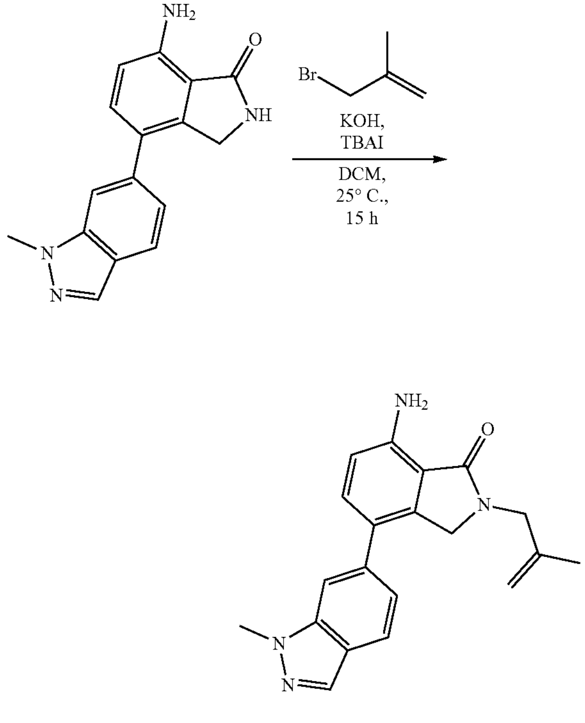

To a mixture of 7-amino-4-(1-methylindazol-6-yl)isoindolin-1-one (300 mg, 1.08 mmol, 1 eq.) in DCM (1 mL) were added TBAI (398.16 mg, 1.08 mmol, 1 eq.) and KOH (181.45 mg, 3.23 mmol, 3 eq.). Then, 3-bromo-2-methyl-prop-1-ene (145.52 mg, 1.08 mmol, 108.60 μL, 1 eq.) was added to the mixture. The mixture was stirred at 20° C. for 15 h. TLC showed that the reaction was not completed. Water (20 mL) was added to the mixture, and the aqueous phase was extracted with DCM (20 mL×3). The combined organic phase was washed with water and brine (20 mL×3), dried over anhydrous sodium sulfate, filtered, and concentrated in vacuo. The residue was purified by prep-TLC ($SiO_2$ DCM:Methanol=20:1) to afford the title compound (200 mg, 601.69 μmol, 55.82% yield) as a yellow solid.

Preparation of 4-(1-methylindazol-6-yl)-2-[(2-methyloxiran-2-yl)methyl]-7-nitro-isoindolin-1-one

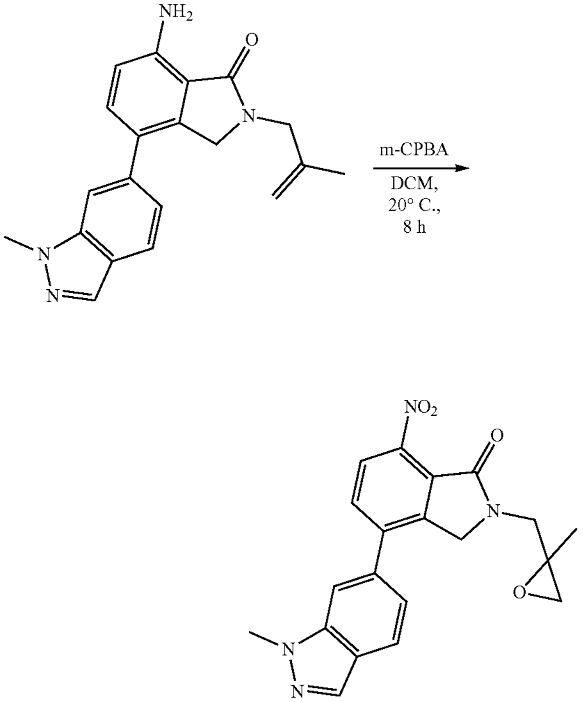

To a mixture of 7-amino-2-(2-methylallyl)-4-(1-methylindazol-6-yl)isoindolin-1-one (180 mg, 541.52 μmol, 1 eq.) in DCM (3 mL) was added m-CPBA (747.60 mg, 4.33 mmol, 100% purity, 8 eq.). The mixture was stirred at 25° C. for 5 h. LCMS and TLC showed that the reaction was complete. The reaction mixture was poured into $NaHCO_3$ (20 mL) and stirred for 15 min. The aqueous phase was extracted with DCM (10 mL×3). The combined organic phase was washed with $NaHCO_3$ (10 mL×3), dried over anhydrous sodium sulfate, filtered, and concentrated in vacuo. The residue was purified by prep-TLC (DCM:Methanol=20:1) to afford the title compound (100 mg, 264.28 μmol, 48.80% yield) as a yellow solid.

Preparation of 7-amino-4-(1-methylindazol-6-yl)-2-[(2-methyloxiran-2-yl)methyl]isoindolin-1-one (Compound 440)

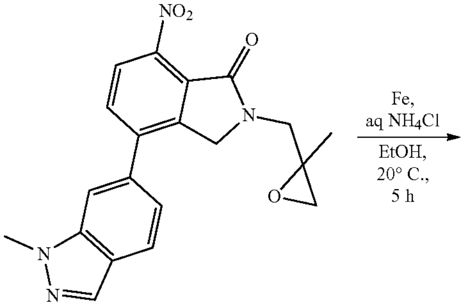

-continued

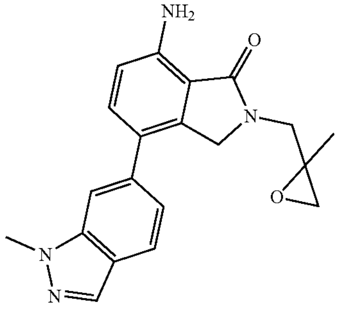

To a mixture of $NH_4Cl$ (12.72 mg, 237.86 μmol, 8.32 μL, 1 eq.) and 4-(1-methylindazol-6-yl)-2-[(2-methyloxiran-2-yl)methyl]-7-nitro-isoindolin-1-one (100 mg, 237.86 μmol, 1 eq.) in EtOH (1 mL) and water (0.25 mL) was added Fe (66.42 mg, 1.19 mmol, 5 eq.) at 20° C., and the reaction was stirred for 15 h at 20° C. TLC showed reaction was complete. The residue was filtrated, and the aqueous phase was extracted with EtOAc (10 mL×3). The combined organic phase was washed with brine (10 mL×3), dried over anhydrous sodium sulfate, filtered, and concentrated in vacuo. The residue was purified by prep-HPLC to afford the title compound (9.2 mg, 25.35 μmol, 10.66% yield, 96% purity) as a white solid. LC-MS: $[M+H]^+$ 349.1.

Route 7

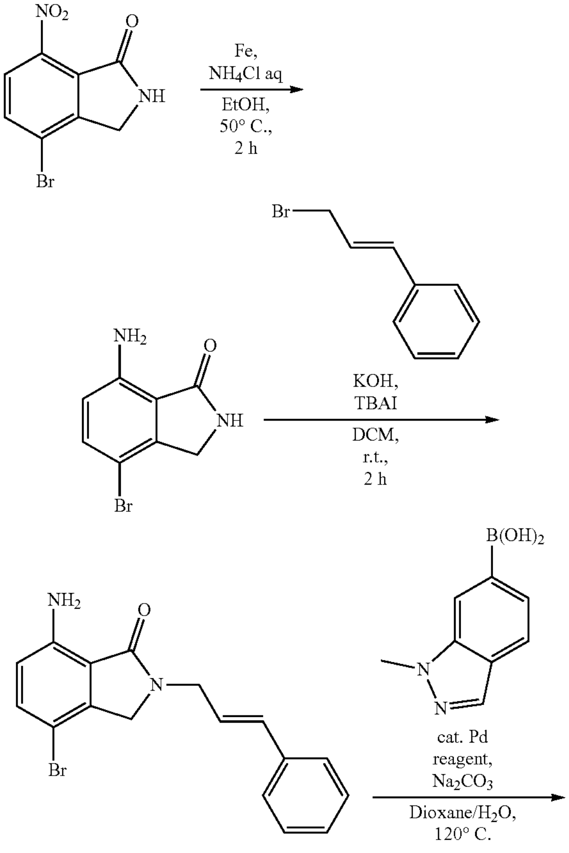

-continued

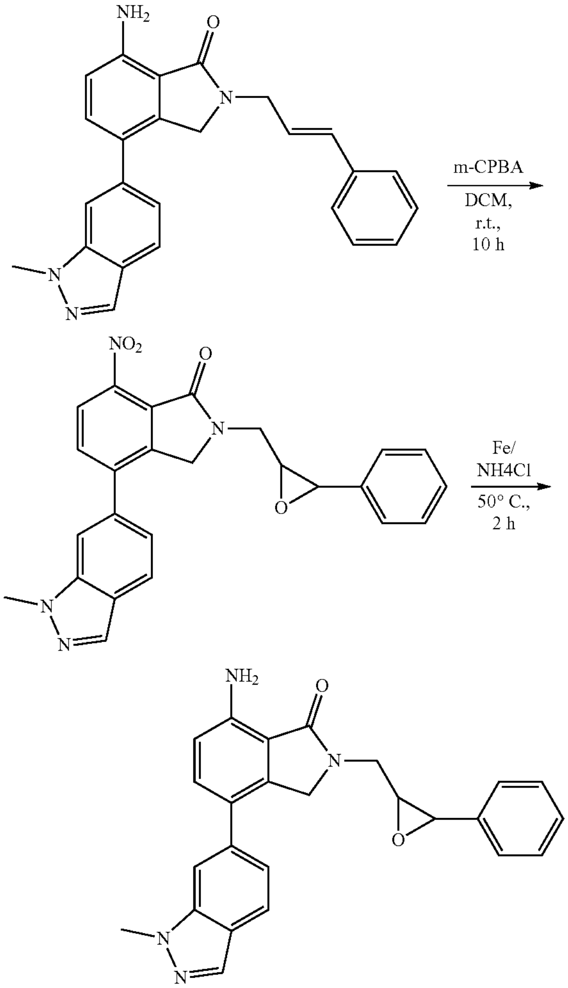

Preparation of 7-amino-4-bromo-isoindolin-1-one

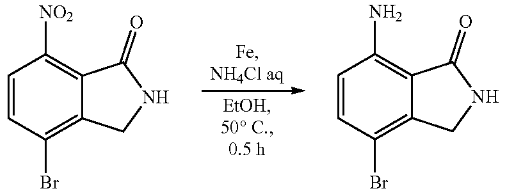 [SMILES: O=C1NCc2c(Br)ccc([N+](=O)[O-])c21 ; Nc1ccc(Br)c2c1C(=O)NC2]

To a solution of 4-bromo-7-nitro-isoindolin-1-one (0.5 g, 1.95 mmol, 1 eq.) in EtOH (10 mL) and water (2 mL) were added $NH_4Cl$ (520.25 mg, 9.73 mmol, 340.03 μL, 5 eq.) and Fe (543.20 mg, 9.73 mmol, 5 eq.). The reaction mixture was stirred at 50° C. for 0.5 h. TLC (PE:EtOAc=3:1, $R_f$=0.3) showed that the reaction was complete. 15 mL of water was added into the reaction mixture. The mixture was extracted with EtOAc (3×15 mL) to give the crude product. The crude product was dissolved in EtOAc (20 mL), and 200 mL of PE was added to the solution. The turbid solution was filtrated the cake to afford the title compound (0.4 g, 1.76 mmol, 90.56% yield) as a light yellow solid.

Preparation of 7-amino-4-bromo-2-[(Z)-cinnamyl] isoindolin-1-one

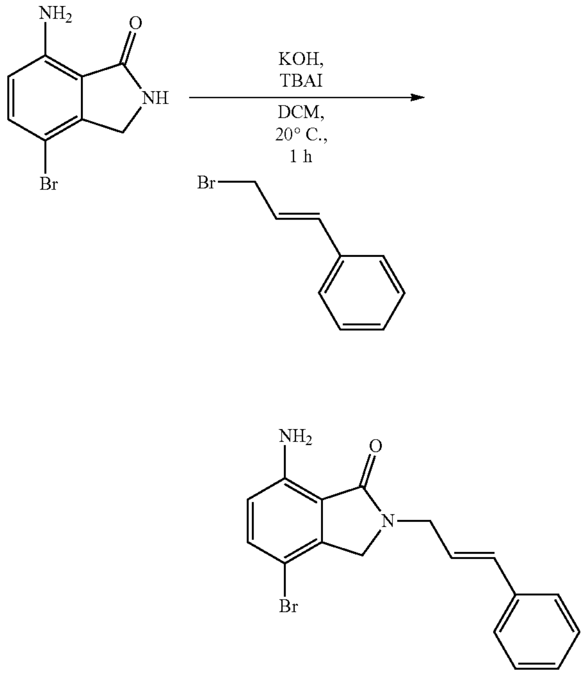

To a solution of 7-amino-4-bromo-isoindolin-1-one (400 mg, 1.76 mmol, 1 eq.) in DCM (10 mL) were added KOH (296.54 mg, 5.29 mmol, 3 eq.), TBAI (130.14 mg, 352.33 μmol, 0.2 eq.) and [(E)-3-bromoprop-1-enyl]benzene (416.61 mg, 2.11 mmol, 313.24 μL, 1.2 eq.; dropwise), and the reaction was stirred at 20° C. for 1 h. LCMS showed that the reaction was complete. The reaction was quenched with 10 mL water and extracted with EtOAc (3×20 mL) to give the crude product. The crude product was purified by prep-TLC (EtOAc, Rf=0.4) to afford the title compound (340 mg, 842.03 μmol, 47.80% yield, 85% purity) as a yellow solid.

Preparation of 7-amino-2-[(E)-cinnamyl]-4-(1-methylindazol-6-yl)isoindolin-1-one

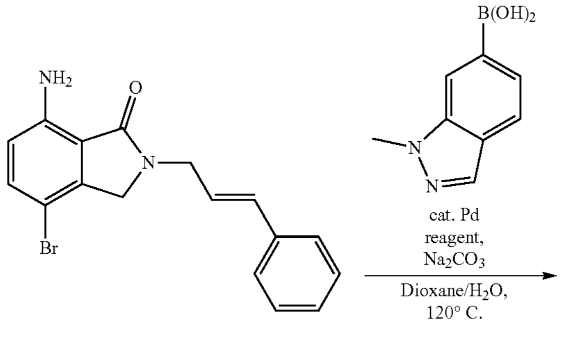

-continued

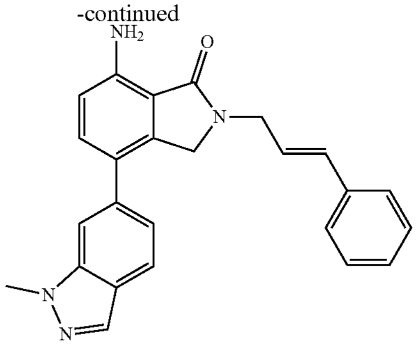

To a solution of 7-amino-4-bromo-2-[(E)-cinnamyl]isoindolin-1-one (0.4 g, 1.17 mmol, 1 eq.) in dioxane (3 mL) and water (1 mL) were added (1-methylindazol-6-yl)boronic acid (266.62 mg, 1.52 mmol, 1.3 eq.), ditert-butyl(cyclopentyl)phosphane; dichloropalladium; iron (75.96 mg, 116.54 µmol, 0.1 eq.), $Na_2CO_3$ (370.58 mg, 3.50 mmol, 3 eq.) under nitrogen. The reaction mixture was stirred at 120° C. for 20 min. LCMS showed that the reaction was complete. The reaction was quenched with 10 mL water and extracted with EtOAc (3×10 mL). The crude material was purified by prep-TLC (EtOAc, $R_f$=0.6) and prep-HPLC to afford the title compound (0.34 g, 861.92 µmol, 73.96% yield) as a white solid.

Preparation of 4-(1-methylindazol-6-yl)-7-nitro-2-[(3-phenyloxiran-2-yl)methyl]isoindolin-1-one

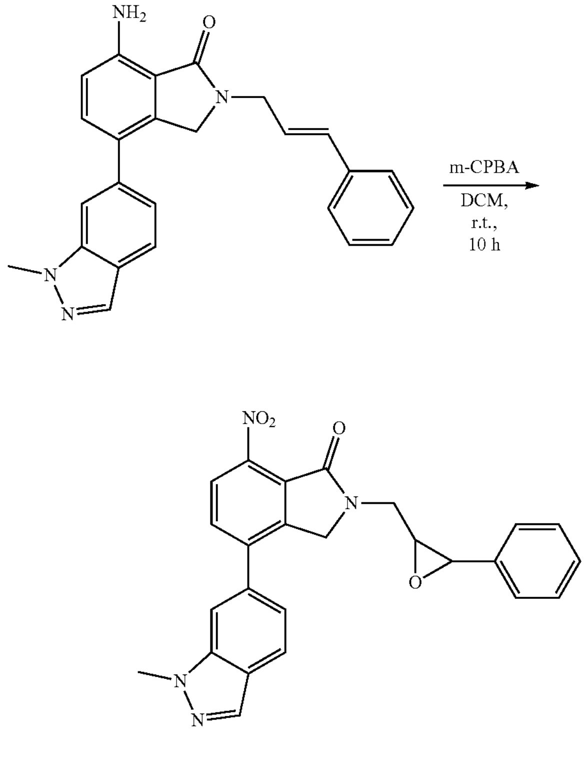

To a solution of 7-amino-2-[(Z)-cinnamyl]-4-(1-methylindazol-6-yl)isoindolin-1-one (0.2 g, 507.0 µmol, 1 eq.) in DCM (5 mL) was added m-CPBA (437.5 mg, 2.5 mmol, 100% purity, 5 eq.). The reaction was stirred at 10° C. for 10 h. LCMS showed the desired product. The reaction mixture was washed with sat. $NaHCO_3$ (3×15 mL), and the organic layer was dried and concentrated to give the crude product. The crude product was purified by prep-TLC (MeOH: DCM=20:1, Rf=0.6) to afford the title compound (0.1 g, 227.0 µmol, 44.8% yield) as a white solid.

Preparation of 7-amino-4-(1-methyl-1H-indazol-6-yl)-2-((3-phenyloxiran-2-yl)methyl)isoindolin-1-one (Compound 441)

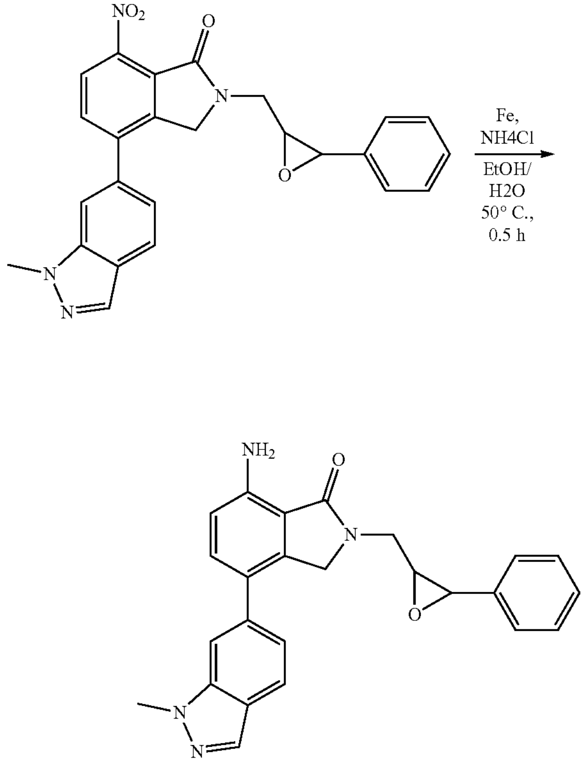

To a solution of 4-(1-methylindazol-6-yl)-7-nitro-2-[(3-phenyloxiran-2-yl)methyl]isoindolin-1-one (0.1 g, 227.0 µmol, 1 eq.) in EtOH (5 mL) and Water (1 mL) was added $NH_4Cl$ (60.7 mg, 1.1 mmol, 39.7 µL, 5 eq.) and Fe (63.4 mg, 1.1 mmol, 5 eq.), then the reaction mixture was stirred at 50° C. for 0.5 h. TLC (MeOH:DCM=20:1, Rf=0.4) showed that the reaction was complete. The reaction mixture was quenched with sat. $NaHCO_3$ (15 mL) and extracted with EtOAc (3×20 mL), dried with sodium sulfate, concentrated to give the residue. The residue was purified by prep-HPLC to afford the title compound (5.2 mg, 12.3 µmol, 5.41% yield, 97% purity) as a white solid. LC-MS: $[M+H]^+$ 411.1.

TABLE 7 shows compounds that were synthesized using the methods described in EXAMPLE 9.

TABLE 7
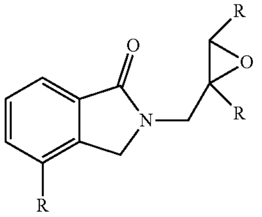
| Cpd. No. | Structure | IUPAC | LC-MS (ES+, m/z) |
| --- | --- | --- | --- |
| 421. | 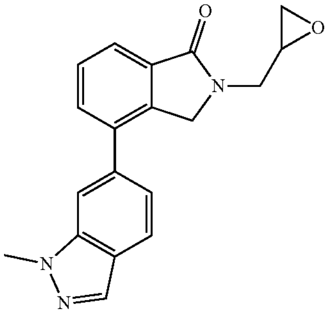 [SMILES: Cn1ncc2ccc(-c3cccc4c3CN(CC3CO3)C4=O)cc21] | 4-(1-methyl-1H-indazol-6-yl)-2-[(oxiran-2-yl)methyl]-2,3-dihydro-1H-isoindol-1-one | 320.1 |
| 422. | 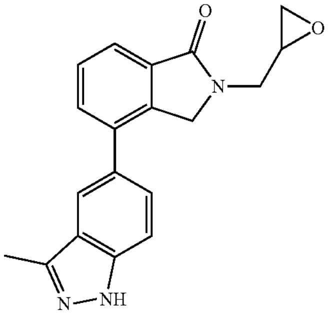 [SMILES: Cc1n[nH]c2ccc(-c3cccc4c3CN(CC3CO3)C4=O)cc12] | 4-(3-methyl-1H-indazol-5-yl)-2-[(oxiran-2-yl)methyl]-2,3-dihydro-1H-isoindol-1-one | 320.1 |
| 423. | 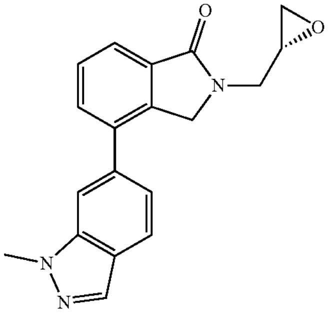 [SMILES: Cn1ncc2ccc(-c3cccc4c3CN(C[C@@H]3CO3)C4=O)cc21] | 4-(1-methyl-1H-indazol-6-yl)-2-{[(2R)-oxiran-2-yl]methyl}-2,3-dihydro-1H-isoindol-1-one | 320 |
| 424. | 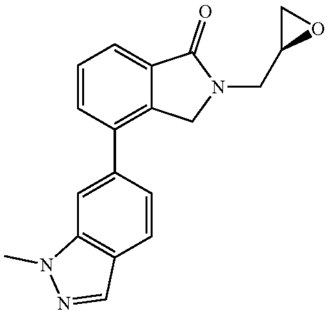 [SMILES: Cn1ncc2ccc(-c3cccc4c3CN(C[C@H]3CO3)C4=O)cc21] | 4-(1-methyl-1H-indazol-6-yl)-2-{[(2S)-oxiran-2-yl]methyl}-2,3-dihydro-1H-isoindol-1-one | 320 |

TABLE 7-continued
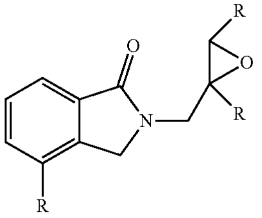
| Cpd. No. | Structure | IUPAC | LC-MS (ES+, m/z) |
|---|---|---|---|
| 425. | 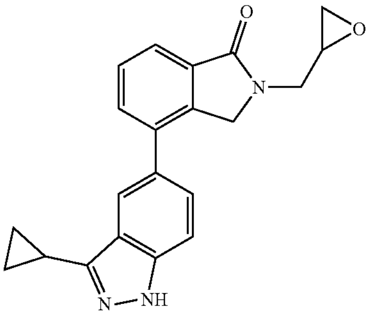 [SMILES: O=C1c2cccc(-c3ccc4[nH]nc(C5CC5)c4c3)c2CN1CC1CO1] | 4-(3-cyclopropyl-1H-indazol-5-yl)-2-[(oxiran-2-yl)methyl]-2,3-dihydro-1H-isoindol-1-one | 346.2 |
| 426. | 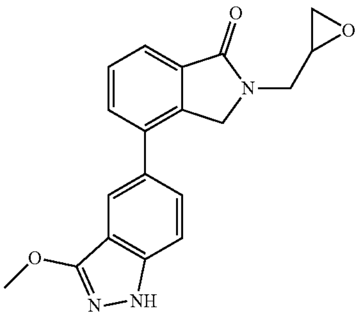 [SMILES: COc1n[nH]c2ccc(-c3cccc4c3CN(CC3CO3)C4=O)cc12] | 4-(3-methoxy-1H-indazol-5-yl)-2-[(oxiran-2-yl)methyl]-2,3-dihydro-1H-isoindol-1-one | 336.1 |
| 427. | 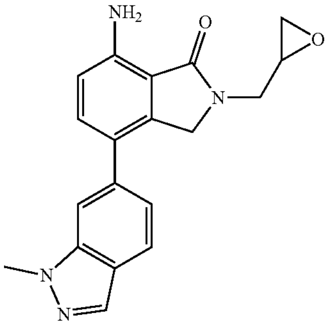 [SMILES: Cn1ncc2ccc(-c3ccc(N)c4c3CN(CC3CO3)C4=O)cc21] | 7-amino-4-(1-methyl-1H-indazol-6-yl)-2-[(oxiran-2-yl)methyl]-2,3-dihydro-1H-isoindol-1-one | 335.1 |
| 428. | 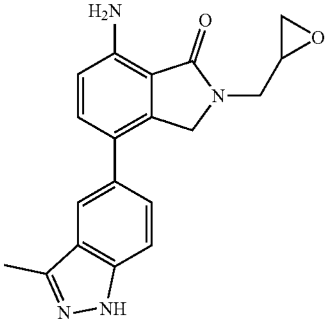 [SMILES: Cc1n[nH]c2ccc(-c3ccc(N)c4c3CN(CC3CO3)C4=O)cc12] | 7-amino-4-(3-methyl-1H-indazol-5-yl)-2-[(oxiran-2-yl)methyl]-2,3-dihydro-1H-isoindol-1-one | 335.2 |

TABLE 7-continued
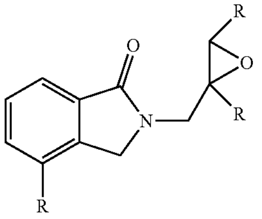
| Cpd. No. | Structure | IUPAC | LC-MS (ES+, m/z) |
|---|---|---|---|
| 429. | 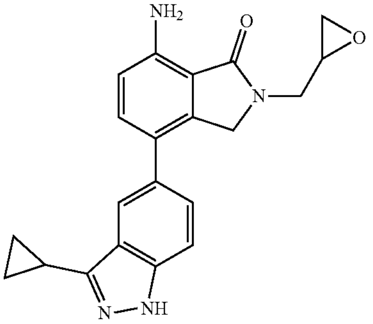 [SMILES: Nc1ccc(-c2ccc3[nH]nc(C4CC4)c3c2)c2c1C(=O)N(CC1CO1)C2] | 7-amino-4-(3-cyclopropyl-1H-indazol-5-yl)-2-[(oxiran-2-yl)methyl]-2,3-dihydro-1H-isoindol-1-one | 361.1 |
| 430. | 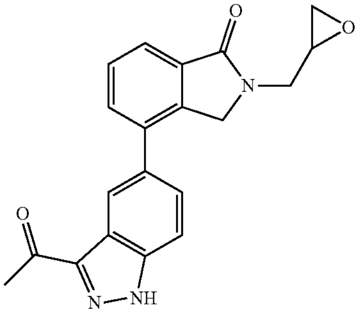 [SMILES: CC(=O)c1n[nH]c2ccc(-c3cccc4c3CN(CC3CO3)C4=O)cc12] | 4-(3-acetyl-1H-indazol-5-yl)-2-[(oxiran-2-yl)methyl]-2,3-dihydro-1H-isoindol-1-one | 348.1 |
| 431. | 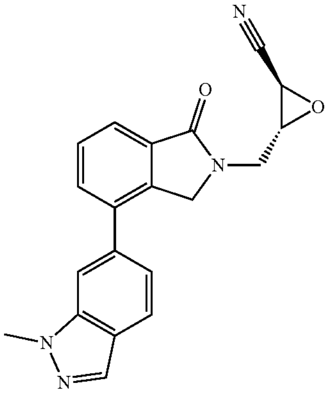 [SMILES: Cn1ncc2ccc(-c3cccc4c3CN(C[C@H]3O[C@@H]3C#N)C4=O)cc21] | (2R,3R)-3-{[4-(1-methyl-1H-indazol-6-yl)-1-oxo-2,3-dihydro-1H-isoindol-2-yl]methyl}oxirane-2-carbonitrile | 345.1 |
| 432. | 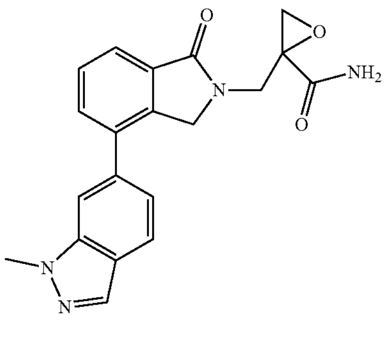 [SMILES: Cn1ncc2ccc(-c3cccc4c3CN(CC3(C(N)=O)CO3)C4=O)cc21] | 2-{[4-(1-methyl-1H-indazol-6-yl)-1-oxo-2,3-dihydro-1H-isoindol-2-yl]methyl}oxirane-2-carboxamide | 363.2 |

TABLE 7-continued
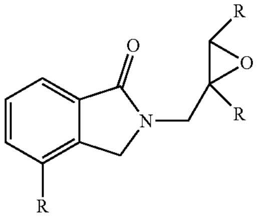
| Cpd. No. | Structure | IUPAC | LC-MS (ES+, m/z) |
|---|---|---|---|
| 433. | 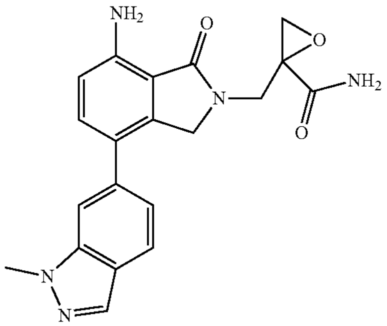 [SMILES: Cn1ncc2ccc(-c3ccc(N)c4c3CN(CC3(C(N)=O)CO3)C4=O)cc21] | 2-{[7-amino-4-(1-methyl-1H-indazol-6-yl)-1-oxo-2,3-dihydro-1H-isoindol-2-yl]methyl}oxirane-2-carboxamide | 422.2 |
| 434. | 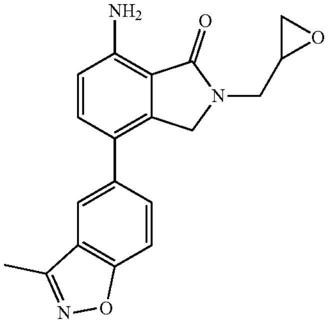 [SMILES: Cc1noc2ccc(-c3ccc(N)c4c3CN(CC3CO3)C4=O)cc12] | 7-amino-4-(3-methyl-1,2-benzoxazol-5-yl)-2-[(oxiran-2-yl)methyl]-2,3-dihydro-1H-isoindol-1-one | 336.1 |
| 435. | 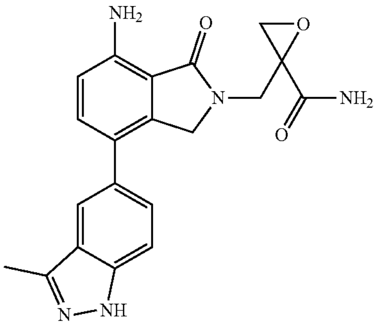 [SMILES: Cc1n[nH]c2ccc(-c3ccc(N)c4c3CN(CC3(C(N)=O)CO3)C4=O)cc12] | 2-{[7-amino-4-(3-methyl-1H-indazol-5-yl)-1-oxo-2,3-dihydro-1H-isoindol-2-yl]methyl}oxirane-2-carboxamide | 378.3 |
| 436. | 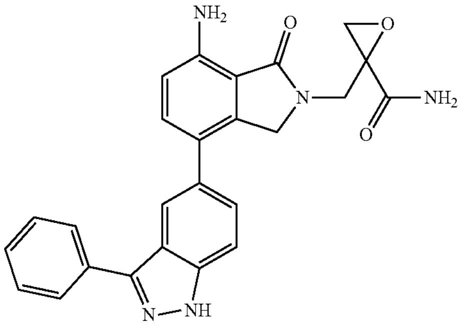 [SMILES: NC(=O)C1(CN2Cc3c(-c4ccc5[nH]nc(-c6ccccc6)c5c4)ccc(N)c3C2=O)CO1] | 2-{[7-amino-1-oxo-4-(3-phenyl-1H-indazol-5-yl)-2,3-dihydro-1H-isoindol-2-yl]methyl}oxirane-2-carboxamide | 440.1 |

TABLE 7-continued

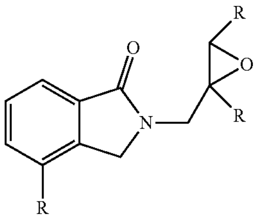

| Cpd. No. | Structure | IUPAC | LC-MS (ES+, m/z) |
| --- | --- | --- | --- |
| 437. | 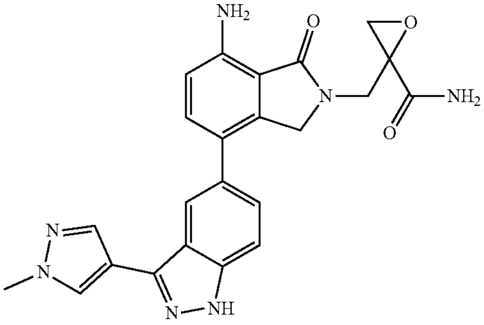 [SMILES: Cn1cc(-c2n[nH]c3ccc(-c4ccc(N)c5c4CN(CC4(C(N)=O)CO4)C5=O)cc23)cn1] | 2-({7-amino-4-[3-(1-methyl-1H-pyrazol-4-yl)-1H-indazol-5-yl]-1-oxo-2,3-dihydro-1H-isoindol-2-yl}methyl)oxirane-2-carboxamide | 444.1 |
| 438. | 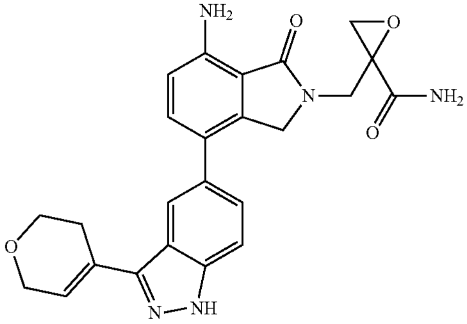 [SMILES: NC(=O)C1(CN2Cc3c(-c4ccc5[nH]nc(C6=CCOCC6)c5c4)ccc(N)c3C2=O)CO1] | 2-({7-amino-4-[3-(3,6-dihydro-2H-pyran-4-yl)-1H-indazol-5-yl]-1-oxo-2,3-dihydro-1H-isoindol-2-yl}methyl)oxirane-2-carboxamide | 446.1 |
| 439. | 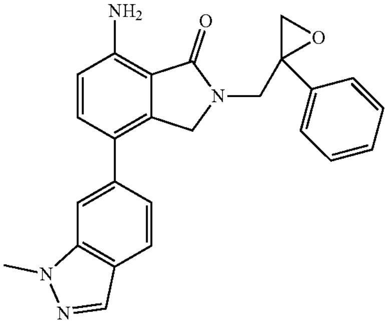 [SMILES: Cn1ncc2ccc(-c3ccc(N)c4c3CN(CC3(c5ccccc5)CO3)C4=O)cc21] | 7-amino-4-(1-methyl-1H-indazol-6-yl)-2-[(2-phenyloxiran-2-yl)methyl]-2,3-dihydro-1H-isoindol-1-one | 411.2 |
| 440. | 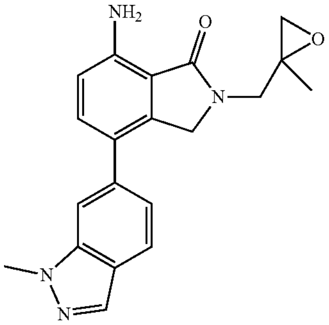 [SMILES: Cn1ncc2ccc(-c3ccc(N)c4c3CN(CC3(C)CO3)C4=O)cc21] | 7-amino-4-(1-methyl-1H-indazol-6-yl)-2-[(2-methyloxiran-2-yl)methyl]-2,3-dihydro-1H-isoindol-1-one | 349.1 |

TABLE 7-continued
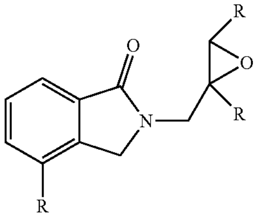
| Cpd. No. | Structure | IUPAC | LC-MS (ES+, m/z) |
|---|---|---|---|
| 441. | 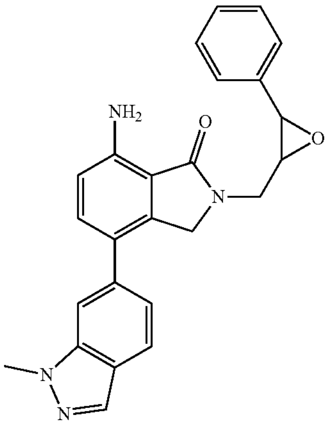 [SMILES: Cn1ncc2ccc(-c3ccc(N)c4c3CN(CC3OC3c3ccccc3)C4=O)cc21] | 7-amino-4-(1-methyl-1H-indazol-6-yl)-2-[(3-phenyloxiran-2-yl)methyl]-2,3-dihydro-1H-isoindol-1-one | 411.1 |
Example 10: Method H
General Scheme for Method H
Route 1
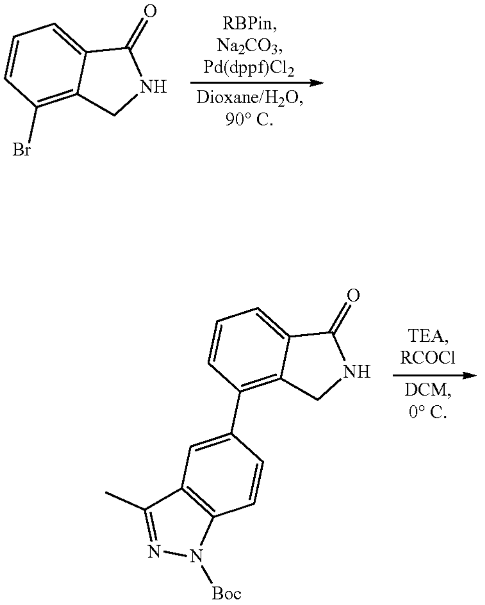
-continued
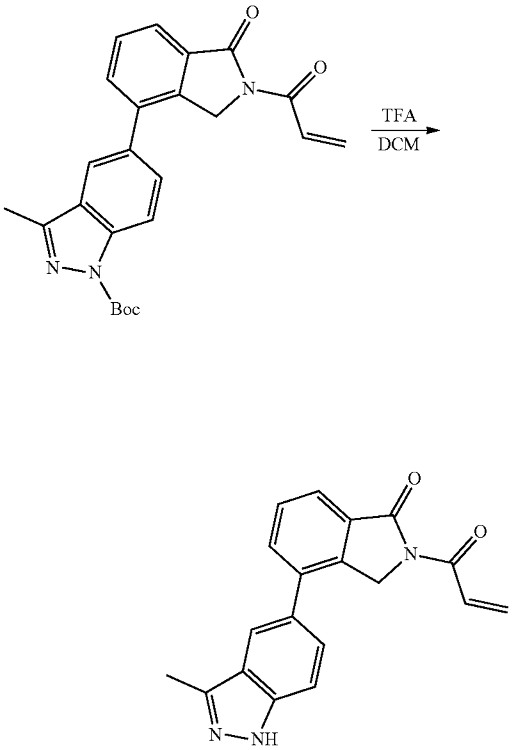

Preparation of tert-butyl 3-methyl-5-(1-oxo-2,3-dihydro-1H-isoindol-4-yl)-1H-indazole-1-carboxylate

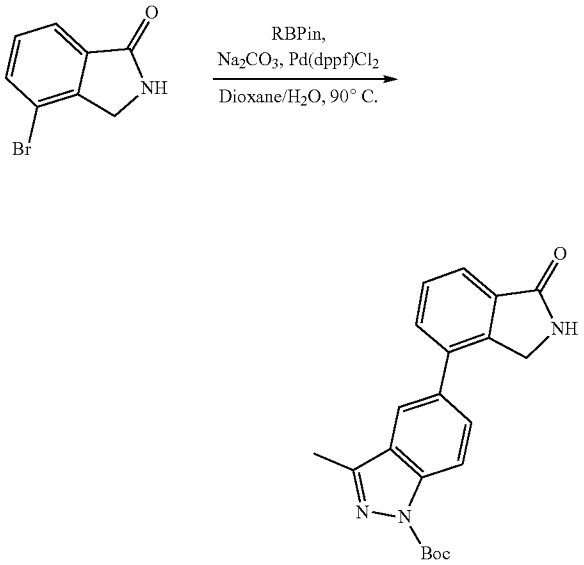 [SMILES: O=C1NCc2c(Br)cccc21 ; Cc1nn(C(=O)OC(C)(C)C)c2ccc(-c3cccc4c3CNC4=O)cc12]

To a solution of 4-bromo-2,3-dihydro-1H-isoindol-1-one (0.15 g, 707.40 μmol, 1 eq.) in dioxane (4 mL) and water (1 mL) were added tert-butyl 3-methyl-5-(4,4,5,5-tetramethyl-1,3,2-dioxaborolan-2-yl)indazole-1-carboxylate (278.76 mg, 778.14 μmol, 1.1 eq.), $Na_2CO_3$ (374.89 mg, 3.54 mmol, 5 eq.) and Pd(dppf)$Cl_2$ (51.76 mg, 70.74 μmol, 0.1 eq.), and the mixture was stirred for 1 h at 90° C. under nitrogen. LCMS showed that the reaction was complete. The reaction was diluted with 10 mL EtOAc and 20 mL sat. EDTA and stirred at 20° C. for 1 h. The reaction mixture was extracted with (3×10 mL) EtOAc and washed with 20 mL brine, dried over anhydrous sodium sulfate, filtered, and concentrated in vacuo to give a crude product. The residue was purified by prep-TLC (silica gel; DCM:MeOH=20:1) to afford the title compound (0.15 g, 412.76 μmol, 58.35% yield) as a yellow solid.

Preparation of tert-butyl 3-methyl-5-[1-oxo-2-(prop-2-enoyl)-2,3-dihydro-1H-isoindol-4-yl]-1H-indazole-1-carboxylate

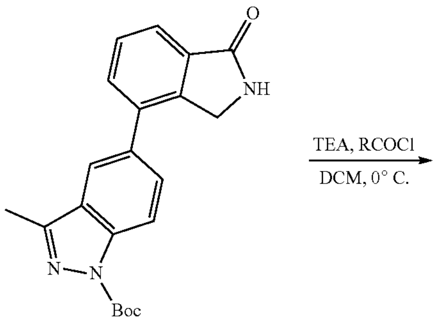

-continued

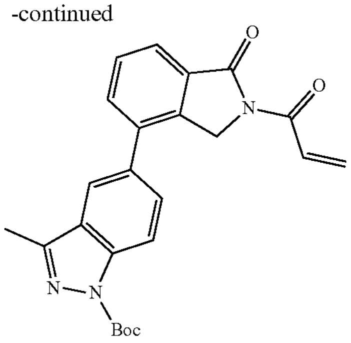

To a solution of tert-butyl 3-methyl-5-(1-oxo-2,3-dihydro-1H-isoindol-4-yl)-1H-indazole-1-carboxylate (0.09 g, 247.65 μmol, 1 eq.) in DCM (5 mL) was added TEA (125.30 mg, 1.24 mmol, 172.35 μL, 5 eq.) and prop-2-enoyl chloride (33.62 mg, 371.48 μmol, 30.29 μL, 1.5 eq.). The mixture was stirred for 0.5 h at 0° C. under nitrogen. TLC showed that the reaction was complete. The reaction was quenched with water (10 mL), then the mixture was extracted with DCM (3×10 mL). The combined organic phase was washed with brine (2×10 mL), dried over anhydrous sodium sulfate, filtered, and concentrated in vacuo. The residue was purified by prep-TLC (silica gel; DCM: MeOH=20:1) to afford the title compound (0.06 g, 143.73 μmol, 58.04% yield) as a yellow solid.

Preparation of 4-(3-methyl-1H-indazol-5-yl)-2-prop-2-enoyl-isoindolin-1-one (Compound 443)

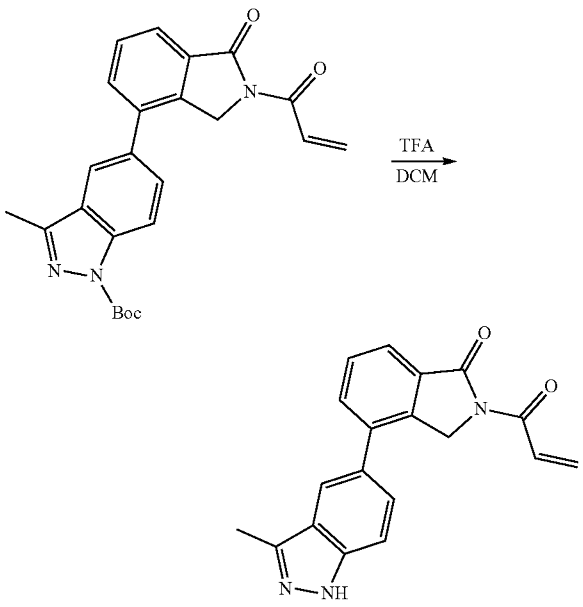

To a solution of tert-butyl 3-methyl-5-[1-oxo-2-(prop-2-enoyl)-2,3-dihydro-1H-isoindol-4-yl]-1H-indazole-1-carboxylate (0.05 g, 119.77 μmol, 1 eq.) in DCM (2 mL) was added trifluoroacetic acid (770 mg, 6.75 mmol, 0.5 mL, 56.38 eq.), and the mixture was stirred for 1 h at 20° C. under nitrogen. TLC showed that the reaction was complete. The reaction was quenched with sat. $NaHCO_3$ (10 mL), and the mixture was extracted with DCM (10 mL×3). The combined organic phase was washed with brine (10 mL×2), dried over anhydrous sodium sulfate, filtered, and concentrated in vacuo. The residue was purified by prep-TLC (silica gel; DCM:MeOH=20:1) to afford the title compound (5.90 mg, 17.01 μmol, 14.20% yield, 91.5% purity) as a white solid. LC-MS: $[M+H]^+$ 318.1.

Route 2

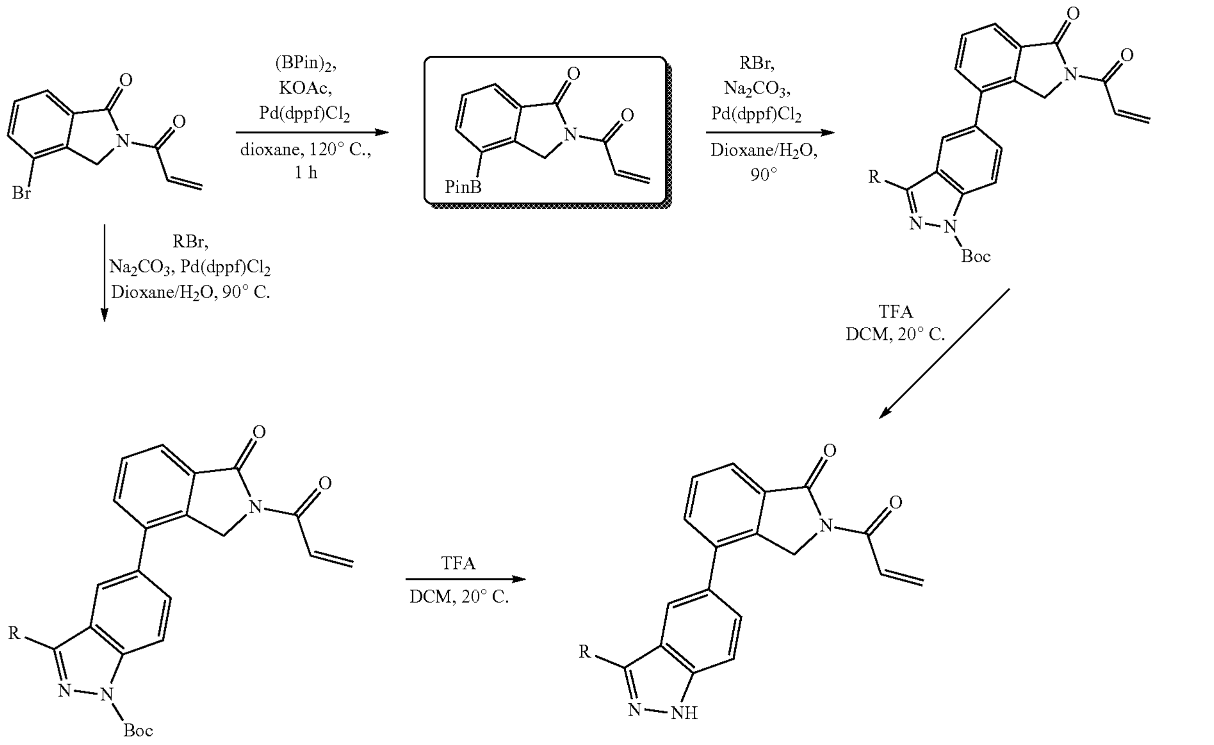

Preparation of 4-bromo-2-(prop-2-enoyl)-2,3-dihydro-1H-isoindol-1-one

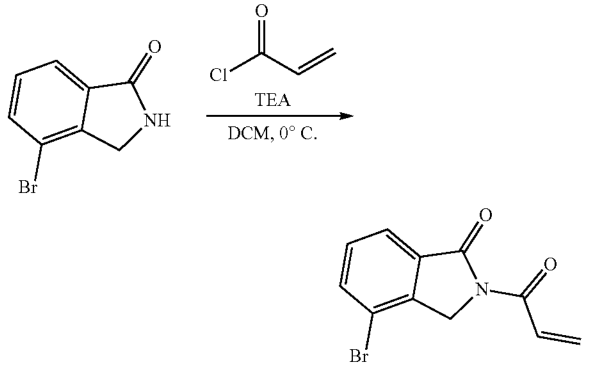

To a solution of 4-bromo-2,3-dihydro-1H-isoindol-1-one (1.5 g, 7.07 mmol, 1 eq.) in DCM (20 mL) were added TEA (3.58 g, 35.37 mmol, 4.92 mL, 5 eq.) and prop-2-enoyl chloride (960.39 mg, 10.61 mmol, 865.21 μL, 1.5 eq.), and the mixture was stirred for 0.5 h at 0° C. under nitrogen. LCMS showed that the reaction was complete. The reaction was quenched with water (30 mL), then the mixture was extracted with DCM (20 mL×3). The combined organic phase was washed with brine (30 mL×2), dried over anhydrous sodium sulfate, filtered, and concentrated in vacuo. The residue was purified by column chromatography (silica gel; PE:EtOAc=1:0 to 10:1) to afford the title compound (1 g, 3.76 mmol, 53.13% yield) as a yellow solid.

Preparation of tert-butyl 3-methoxy-5-[1-oxo-2-(prop-2-enoyl)-2,3-dihydro-1H-isoindol-4-yl]-1H-indazole-1-carboxylate

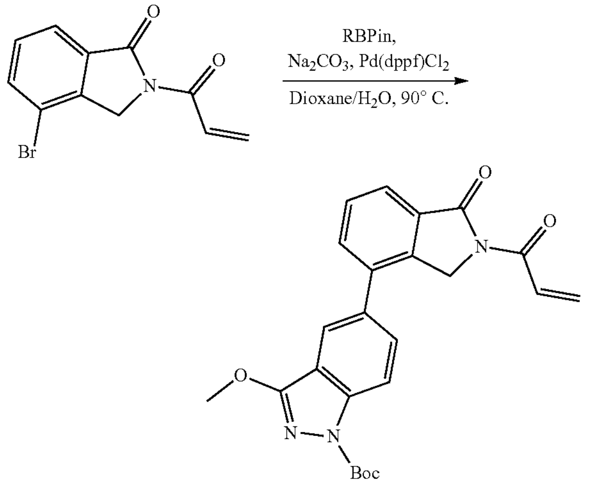

To a solution of 4-bromo-2-(prop-2-enoyl)-2,3-dihydro-1H-isoindol-1-one (0.04 g, 150.32 μmol, 1 eq.) in dioxane (1 mL) and water (0.25 mL) were added tert-butyl 3-methoxy- 5-(4,4,5,5-tetramethyl-1,3,2-dioxaborolan-2-yl)indazole-1-carboxylate (61.88 mg, 165.36 μmol, 1.1 eq.), $Na_2CO_3$ (79.66 mg, 751.62 μmol, 5 eq.), and Pd(dppf)$Cl_2$ (11 mg, 15.03 μmol, 0.1 eq.), and the mixture was stirred for 10 min at 90° C. under nitrogen. TLC showed that the reaction was complete. The reaction was diluted with 10 mL EtOAc and 20 mL sat. EDTA and stirred at 20° C. for 1 h. The reaction was extracted with (3×10 mL) EtOAc and washed with 20 mL saturated brine. The combined organic phase was dried over anhydrous sodium sulfate, filtered, and concentrated in vacuo to give a crude product. The residue was purified by prep-TLC (silica gel; DCM:MeOH=40:1) to afford the title compound (0.03 g, 69.21 μmol, 46.04% yield) as a yellow oil.

Preparation of 4-(3-methoxy-1H-indazol-5-yl)-2-prop-2-enoyl-isoindolin-1-one (Compound 231)

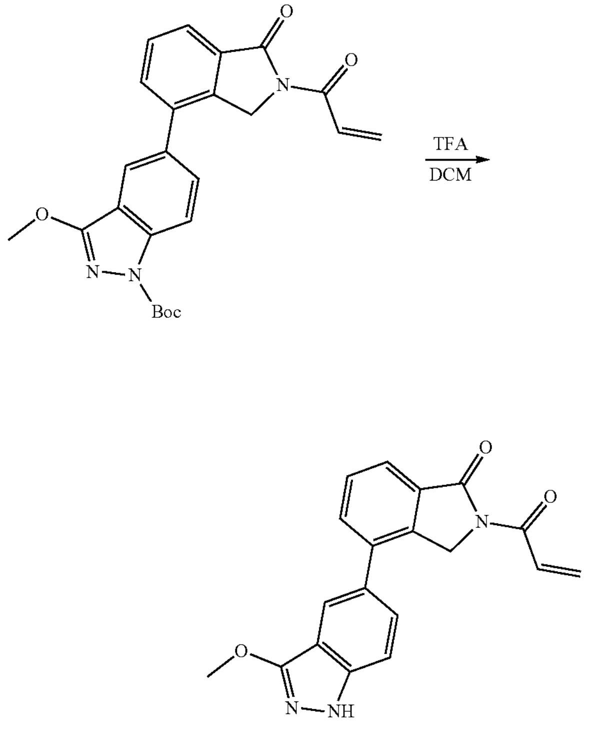

To a solution of tert-butyl 3-methoxy-5-[1-oxo-2-(prop-2-enoyl)-2,3-dihydro-1H-isoindol-4-yl]-1H-indazole-1-carboxylate (0.02 g, 46.14 μmol, 1 eq.) in DCM (2 mL) was added trifluoroacetic acid (770 mg, 6.75 mmol, 0.5 mL, 146.36 eq.), and the mixture was stirred for 0.5 h at 20° C. under nitrogen. TLC showed that the reaction was complete. The reaction was quenched with sat. $NaHCO_3$ (10 mL), then the reaction mixture was extracted with DCM (3×10 mL). The combined organic phase was washed with brine (2×10 mL), dried over anhydrous sodium sulfate, filtered, and concentrated in vacuo. The residue was purified by prep-HPLC to afford the title compound (0.0032 g, 9.60 μmol, 20.81% yield, 100% purity) as a white solid. LC-MS: $[M+H]^+$ 334.1.

Preparation of 2-(prop-2-enoyl)-4-(4,4,5,5-tetramethyl-1,3,2-dioxaborolan-2-yl)-2,3-dihydro-1H-isoindol-1-one

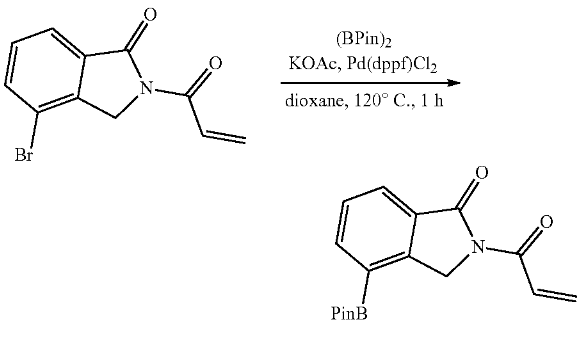

To a solution of 4-bromo-2-(prop-2-enoyl)-2,3-dihydro-1H-isoindol-1-one (420 mg, 1.58 mmol, 1 eq.) and $(BPin)_2$ (625.80 mg, 2.46 mmol, 1.56 eq.) in dioxane (20 mL) was added KOAc (630 mg, 6.42 mmol, 4.07 eq.) and Pd(dppf)$Cl_2$ (577.47 mg, 789.21 μmol, 0.5 eq.). Then the reaction was stirred at 120° C. for 1 h under nitrogen atmosphere. TLC and HPLC showed that the reaction was complete. The reaction was filtered, and the filtration was concentrated. The residue was purified by silica gel chromatography (100% PE) and prep-TLC (silica gel; PE:EtOAc=4:1, Rf=0.5) to afford the title compound (320 mg, 817.49 μmol, 51.79% yield, 80% purity) as a light yellow solid.

Preparation of tert-butyl 5-[1-oxo-2-(prop-2-enoyl)-2,3-dihydro-1H-isoindol-4-yl]-3-(pyridin-3-yl)-1H-indazole-1-carboxylate

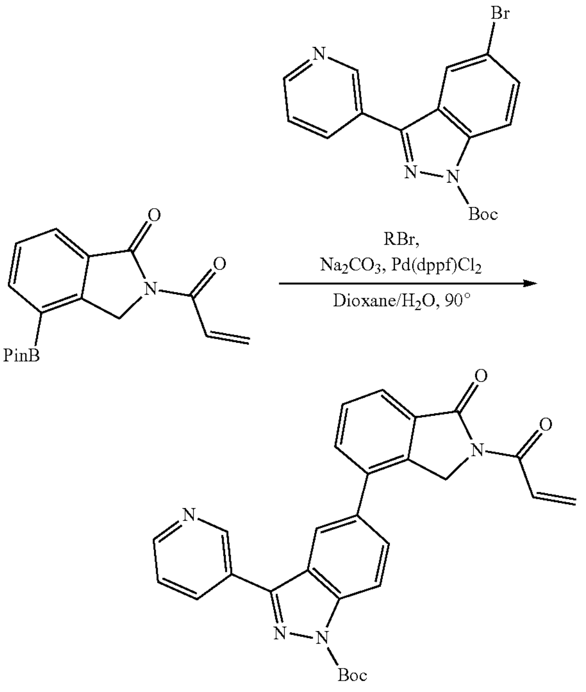

To a solution of 2-(prop-2-enoyl)-4-(4,4,5,5-tetramethyl-1,3,2-dioxaborolan-2-yl)-2,3-dihydro-1H-isoindol-1-one (70 mg, 201.18 μmol, 1.51 eq.) (90% purity) and tert-butyl 5-bromo-3-(3-pyridyl)indazole-1-carboxylate (50 mg, 133.61 μmol, 1 eq.) in dioxane (2.4 mL) and water (0.6 mL) were added Pd(dppf)$Cl_2$ (9.78 mg, 13.36 μmol, 0.1 eq.) and $Na_2CO_3$ (42.48 mg, 400.82 μmol, 3 eq.). The reaction was stirred at 120° C. for 10 min under nitrogen atmosphere. TLC showed that the reaction was complete. 10 mL EtOAc and 20 mL sat. EDTA were added to the reaction. The reaction mixture was stirred at 20° C. for 1 h. Then the reaction mixture was extracted with EtOAc (3×20 mL). The combined organic layer was washed with brine (3×10 mL), dried over anhydrous sodium sulfate, filtered, and concentrated to give the residue. The residue was purified by prep-TLC to afford the title compound (20 mg, 37.46 μmol, 28.04% yield, 90% purity) as a yellow solid.

Route 3:

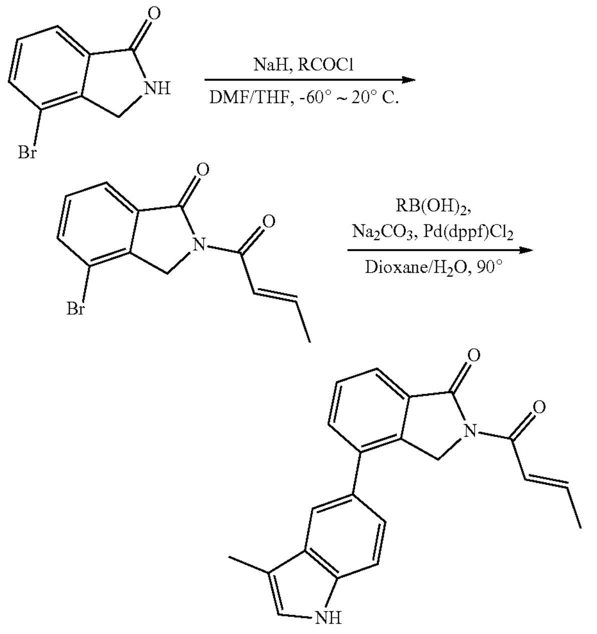

Preparation of 4-bromo-2-[(2E)-but-2-enoyl]-2,3-dihydro-1H-isoindol-1-one

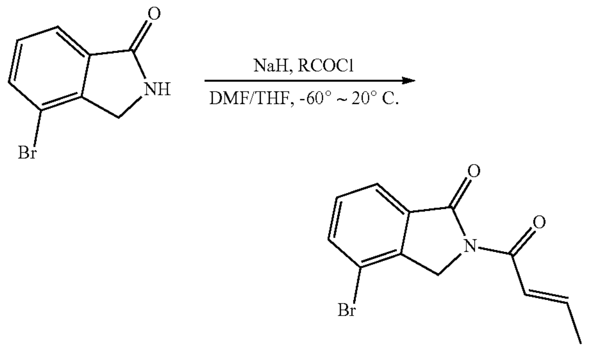

To a solution of 4-bromo-2,3-dihydro-1H-isoindol-1-one (0.15 g, 707.40 μmol, 1 eq.) in DMF (1 mL) and THF (1 mL) was added NaH (56.59 mg, 1.41 mmol, 60% purity, 2 eq.), and the mixture was stirred for 20 min at 20° C. under nitrogen. Then, (Z)-but-2-enoyl chloride (110.92 mg, 1.06 mmol, 98.18 μL, 1.5 eq.) was added, and the mixture was stirred for 10 min at −60° C. under nitrogen. LCMS showed that the reaction was complete. The reaction was quenched with sat. $NH_4Cl$ (10 mL), then the mixture was extracted with EtOAc (3×10 mL). The combined organic phase was washed with brine (3×10 mL), dried over anhydrous sodium sulfate, filtered, and concentrated in vacuo to afford the title compound (0.15 g, crude) as a light yellow solid.

Preparation of 2-[(E)-but-2-enoyl]-4-(3-methyl-1H-indazol-5-yl)isoindolin-1-one (Compound 444)

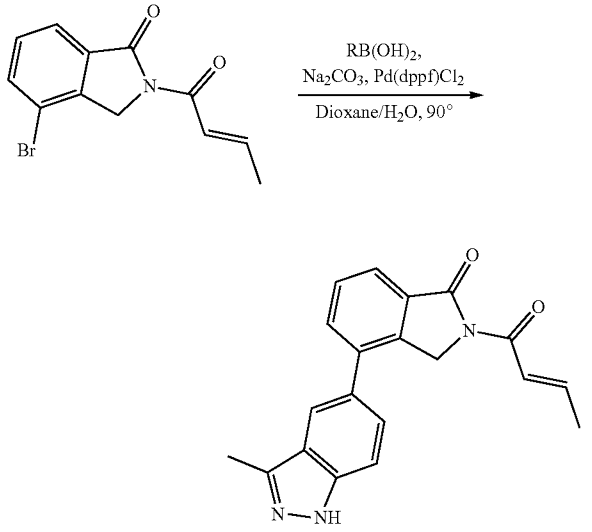 [SMILES: C/C=C/C(=O)N1Cc2c(Br)cccc2C1=O ; C/C=C/C(=O)N1Cc2c(cccc2-c2ccc3[nH]nc(C)c3c2)C1=O]

To a solution of 4-bromo-2-[(2E)-but-2-enoyl]-2,3-dihydro-1H-isoindol-1-one (0.05 g, 178.50 μmol, 1 eq.) in dioxane (2 mL) and water (0.5 mL) were added (3-methyl-1H-indazol-5-yl)boronic acid (47.12 mg, 267.75 μmol, 1.5 eq.), $Na_2CO_3$ (94.59 mg, 892.48 μmol, 5 eq.) and Pd(dppf)$Cl_2$ (13.06 mg, 17.85 μmol, 0.1 eq.), and the mixture was stirred for 0.5 h at 90° C. under nitrogen. LCMS showed that the reaction was complete. The reaction was diluted with 10 mL EtOAc and 20 mL sat. EDTA and stirred at 20° C. for 1 h. The reaction was extracted with (3×10 mL) EtOAc and washed with 20 mL saturated brine. The combined organic phase was dried over anhydrous sodium sulfate, filtered, and concentrated in vacuo to give a crude product. The residue was purified by prep-TLC (silica gel; DCM:MeOH=20:1) to afford the title compound (0.0083 g, 25.05 μmol, 14.03% yield, 100.0% purity) as a white solid. LC-MS: $[M+H]^+$ 332.1.

Route 4:

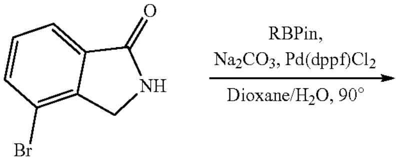

-continued

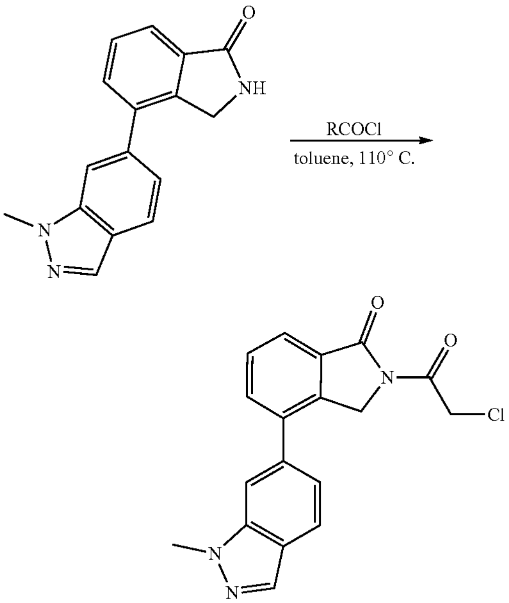

Preparation of 4-(1-methyl-1H-indazol-6-yl)-2,3-dihydro-1H-isoindol-1-one

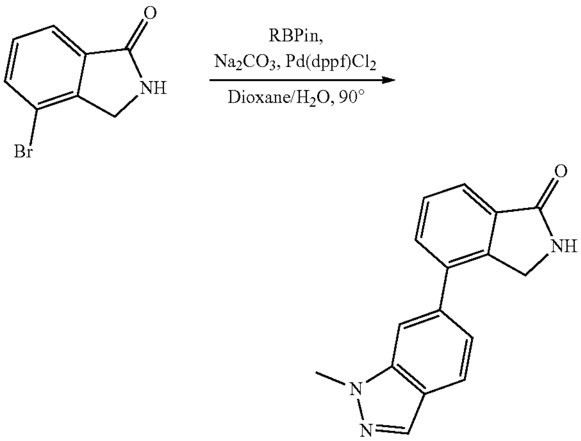

To a solution of 4-bromo-2,3-dihydro-1H-isoindol-1-one (0.2 g, 943.20 μmol, 1 eq.) in dioxane (8 mL) and water (2 mL) were added 1-methyl-6-(4,4,5,5-tetramethyl-1,3,2-dioxaborolan-2-yl)indazole (292.16 mg, 1.13 mmol, 1.2 eq.), $Na_2CO_3$ (499.85 mg, 4.72 mmol, 5 eq.) and $Pd(dppf)Cl_2$ (69.02 mg, 94.32 μmol, 0.1 eq.), and the mixture was stirred for 0.5 h at 90° C. under nitrogen. LCMS showed that the reaction was complete. The reaction was diluted with 20 mL EtOAc and 30 mL sat. EDTA and stirred at 20° C. for 1 h. Then the reaction was extracted with (3×20 mL) EtOAc and washed with 20 mL saturated brine. The combined organic phase was dried over anhydrous sodium sulfate, filtered, and concentrated in vacuo to give a crude product. The residue was purified by prep-TLC (silica gel; DCM:MeOH=20:1) to afford the title compound (0.12 g, 455.77 μmol, 48.32% yield) as a yellow solid.

Preparation of 2-(2-chloroacetyl)-4-(1-methylindazol-6-yl)isoindolin-1-one (Compound 445)

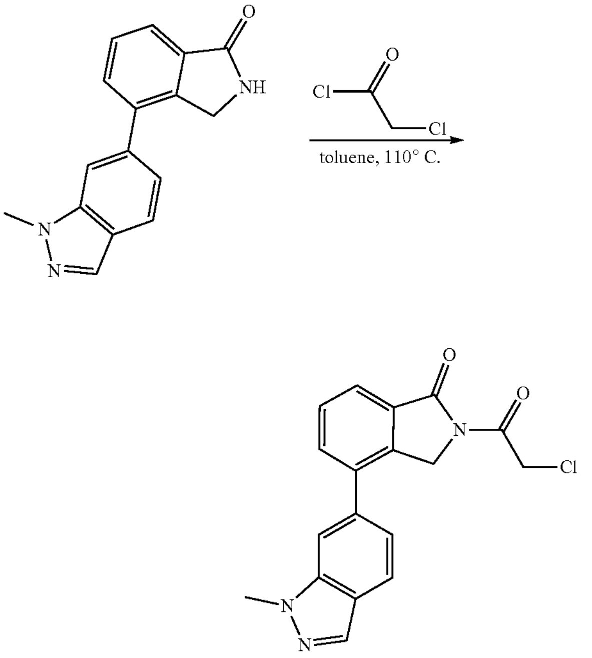 [SMILES: Cn1ncc2ccc(-c3cccc4c3CNC4=O)cc21 ; O=C(Cl)CCl ; Cn1ncc2ccc(-c3cccc4c3CN(C(=O)CCl)C4=O)cc21]

To a solution of 4-(1-methyl-1H-indazol-6-yl)-2,3-dihydro-1H-isoindol-1-one (0.03 g, 113.94 μmol, 1 eq.) in toluene (3 mL) was added 2-chloroacetyl chloride (19.30 mg, 170.91 μmol, 13.59 μL, 1.5 eq.), and the mixture was stirred for 1 h at 110° C. under nitrogen. LCMS showed that the reaction was complete. The reaction mixture was diluted with 10 mL EtOAc and 20 mL sat. EDTA and stirred at 20° C. for 1 h. The reaction was extracted with (3×10 mL) EtOAc and washed with 20 mL brine. The combined organic phase was dried over anhydrous sodium sulfate, filtered, and concentrated in vacuo to give a crude product. The residue was purified by prep-HPLC to afford the title compound (8.40 mg, 24.72 μmol, 21.70% yield) as a white solid. LC-MS: $[M+H]^+$ 340.

Route 5:

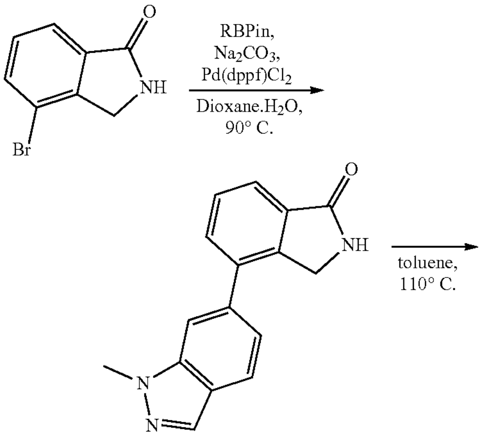

-continued

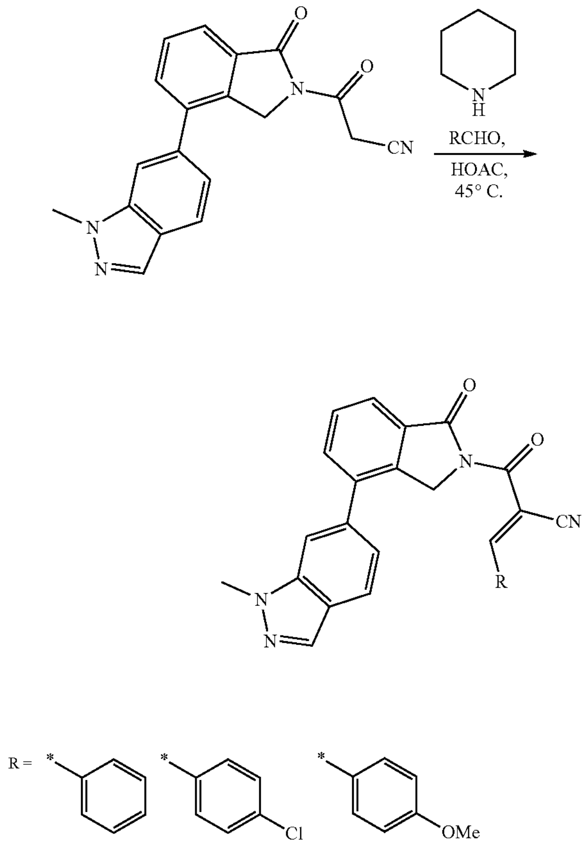

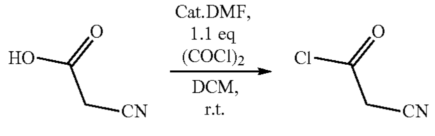

Preparation of 2-cyanoacetyl Chloride

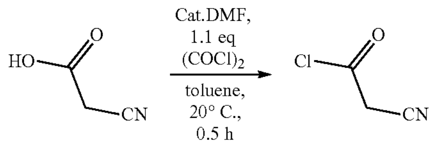 [SMILES: N#CCC(=O)O ; N#CCC(=O)Cl]

To a solution of 2-cyanoacetic acid (0.5 g, 5.88 mmol, 1 eq.) in toluene (10 mL) were added $(COCl)_2$ (820.69 mg, 6.47 mmol, 566 μL, 1.1 eq.) and DMF (42.97 mg, 587.81 μmol, 45.23 μL, 0.1 eq.), and the mixture was stirred for 0.5 h at 20° C. under nitrogen. The reaction was quenched with MeOH. TLC showed that the reaction was complete. The desired product was afforded as a yellow liquid, which was used directly in the next step.

Preparation of 3-[4-(1-methylindazol-6-yl)-1-oxo-isoindolin-2-yl]-3-oxo-propanenitrile

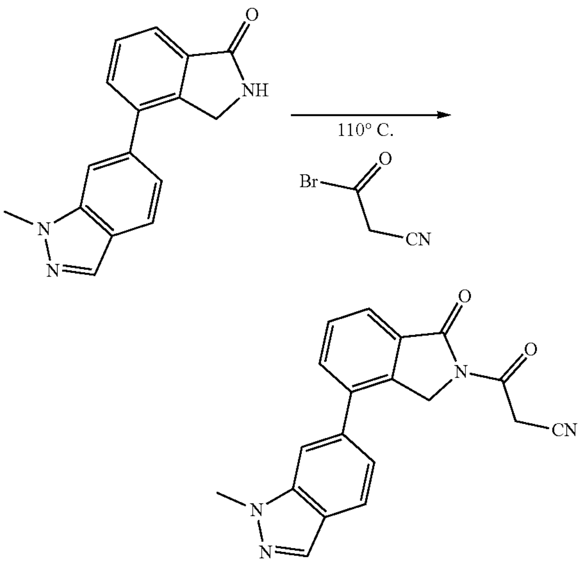

A solution of 4-(1-methylindazol-6-yl)isoindolin-1-one (0.15 g, 569.71 μmol, 1 eq.) in 2-cyanoacetyl chloride (58.97 mg, 569.71 μmol, 10 mL, 1 eq.) was stirred for 0.5 h at 110° C. under nitrogen. LCMS showed that the reaction was complete. The solvent was removed to give the crude product. The crude was washed with PE (10 mL) to afford 200 mg of the crude product, which was purified by prep-HPLC to afford the title compound (0.0251 g, 75.98 μmol, 13.34% yield, 100% purity) as a white solid.

Preparation of (E)-2-[4-(1-methylindazol-6-yl)-1-oxo-isoindoline-2-carbonyl]-3-phenyl-prop-2-enenitrile (Compound 453)

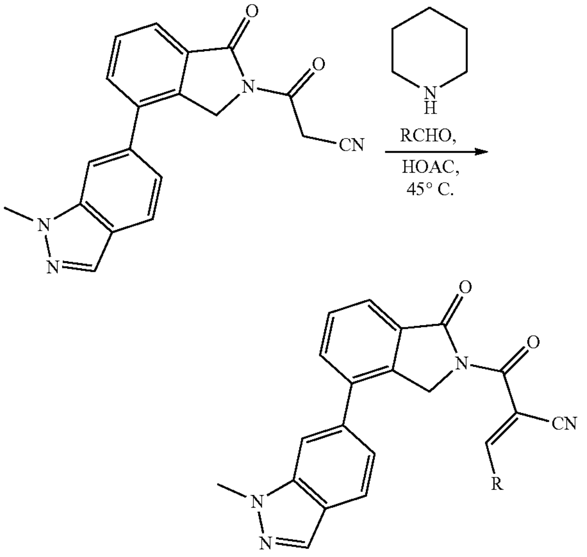

-continued

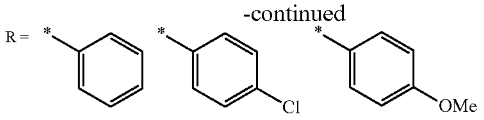

To a solution of 3-[4-(1-methylindazol-6-yl)-1-oxo-isoindolin-2-yl]-3-oxo-propanenitrile (0.05 g, 151.36 μmol, 1 eq.) in HOAc (5 mL) were added benzaldehyde (32.13 mg, 302.72 μmol, 30.60 μL, 2 eq.) and piperidine (6.44 mg, 75.68 μmol, 7.47 μL, 0.5 eq.). The mixture was stirred for 24 h at 45° C. under nitrogen. TLC showed that the reaction was complete. The reaction was quenched with water (20 mL), then the reaction was extracted with EtOAc (3×20 mL). The combined organic phase was washed with brine (2×20 mL), dried over anhydrous sodium sulfate, filtered, and concentrated in vacuo. The residue was purified by prep-HPLC to afford the title compound (0.0057 g, 13.24 μmol, 8.75% yield, 97.2% purity) as a white solid. LC-MS: $[M+H]^+$ 419.1.

Route 6:

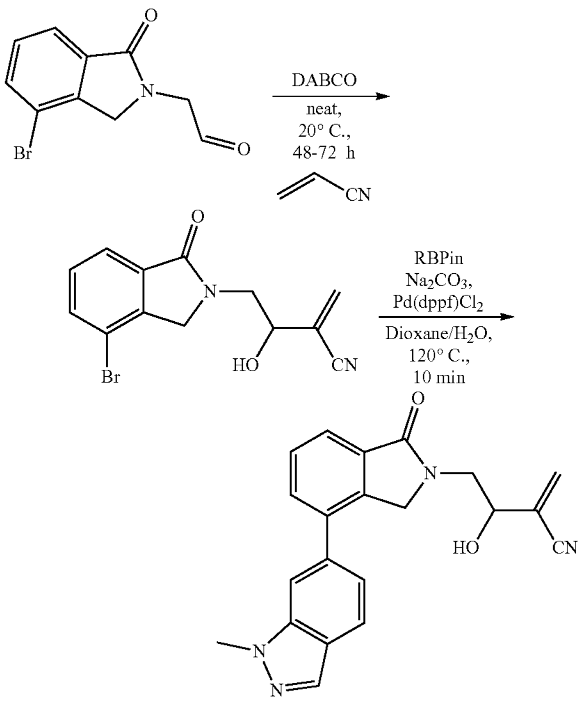

Preparation of 4-(4-bromo-1-oxo-2,3-dihydro-1H-isoindol-2-yl)-3-hydroxy-2-methylidenebutanenitrile

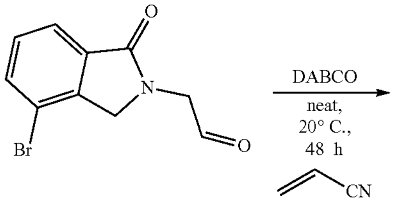

-continued

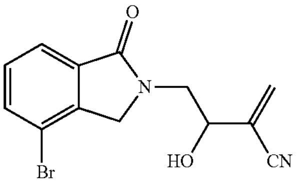

A solution of 2-(4-bromo-1-oxo-isoindolin-2-yl)acetaldehyde (200 mg, 629.72 μmol, 1 eq.) in prop-2-enenitrile (4.18 g, 78.83 mmol, 5.23 mL, 125.18 eq.) was added DABCO (141.28 mg, 1.26 mmol, 138.51 μL, 2 eq.). The reaction was stirred at 20° C. for 48 h. TLC showed that the reaction was complete. The reaction was concentrated, and the residue was purified by prep-TLC (silica gel; DCM/MeOH=20:1) to afford the title compound (30 mg, 97.67 μmol, 15.51% yield) as a light yellow solid.

Preparation of 3-hydroxy-2-methylene-4-[4-(1-methylindazol-6-yl)-1-oxo-isoindolin-2-yl]butanenitrile (Compound 446)

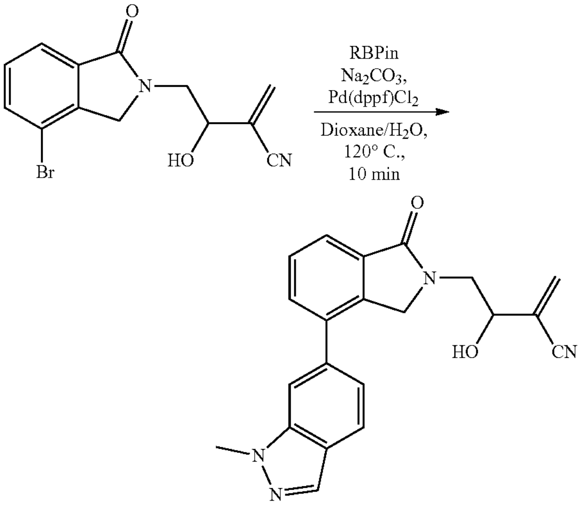

To a solution of 4-(4-bromo-1-oxo-2,3-dihydro-1H-isoindol-2-yl)-3-hydroxy-2-methylidenebutanenitrile (35 mg, 113.95 μmol, 1 eq.) and 1-methyl-6-(4,4,5,5-tetramethyl-1,3,2-dioxaborolan-2-yl)indazole (35 mg, 135.59 μmol, 1.19 eq.) in dioxane (2.4 mL) and water (0.6 mL) were added $Pd(dppf)Cl_2$ (41.69 mg, 56.98 μmol, 0.5 eq.) and $Na_2CO_3$ (6.04 mg, 56.98 μmol, 0.5 eq.). Then the reaction was stirred at 120° C. for 10 min under nitrogen atmosphere. TLC showed that the reaction was complete. 5 mL EtOAc and 20 mL sat. EDTA were added to the reaction, and the reaction was stirred at 20° C. for 1 h. The reaction was extracted with EtOAc (3×20 mL). The combined organic layer was washed with brine (3×10 mL), dried over anhydrous sodium sulfate, filtered, and concentrated to give the crude compound. The crude compound was purified by prep-TLC (silica gel; DCM/MeOH=20:1) and prep-HPLC to afford the title compound (10.3 mg, 28.74 μmol, 25.22% yield, 100.0% purity) as a white solid. LC-MS: $[M+H]^+$ 359.1.

Route 7:

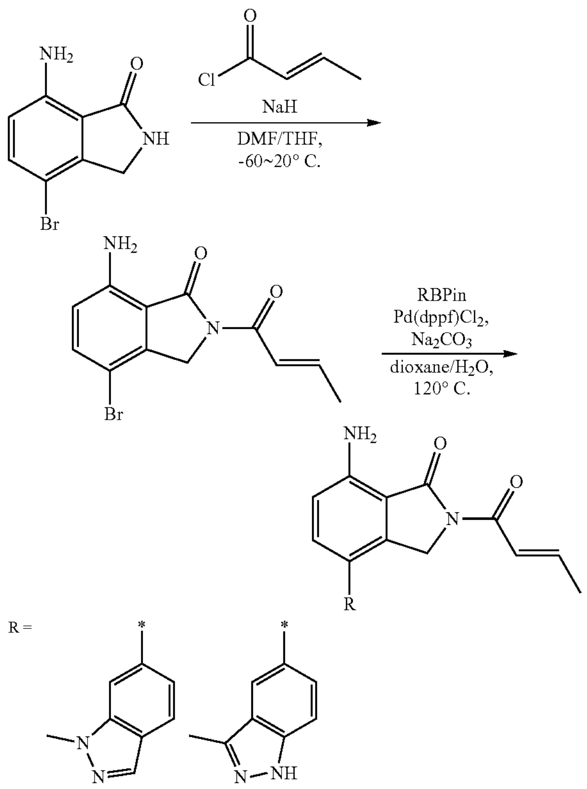

Preparation of 7-amino-4-bromo-2-[(2E)-but-2-enoyl]-2,3-dihydro-1H-isoindol-1-one

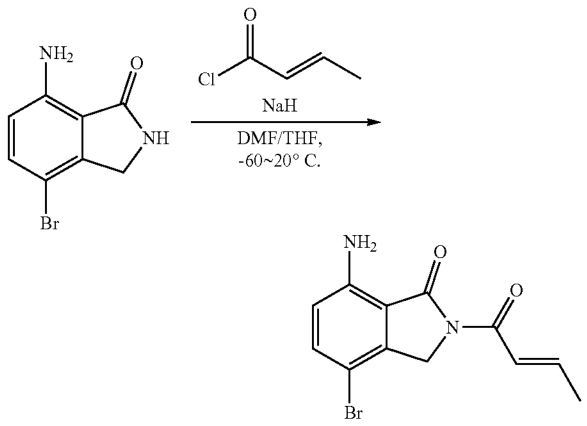

To a solution of 7-amino-4-bromo-2,3-dihydro-1H-isoindol-1-one (0.2 g, 880.83 μmol, 1 eq.) in DMF (3 mL) and THF (3 mL) was added NaH (70.47 mg, 1.76 mmol, 60% purity, 2 eq.). The mixture was stirred for 20 min at 20° C. under nitrogen, then (Z)-but-2-enoyl chloride (138.12 mg, 1.32 mmol, 107.73 μL, 1.5 eq.) was added. The resulting mixture was stirred for 10 min at −60° C. under nitrogen. LCMS/TLC showed that the reaction was complete. The reaction was quenched with $NH_4Cl$ (20 mL), and the mixture was extracted with DCM (3×10 mL). The combined organic phase was washed with brine (2×20 mL), dried over anhydrous sodium sulfate, filtered, and concentrated in vacuo. The residue was purified by prep-TLC (silica gel; DCM:MeOH=40:1) to afford the title compound (0.05 g, 169.42 μmol, 19.230% yield) as a yellow solid.

Preparation of 7-amino-2-[(2E)-but-2-enoyl]-4-(1-methyl-1H-indazol-6-yl)-2,3-dihydro-1H-isoindol-1-one (Compound 457)

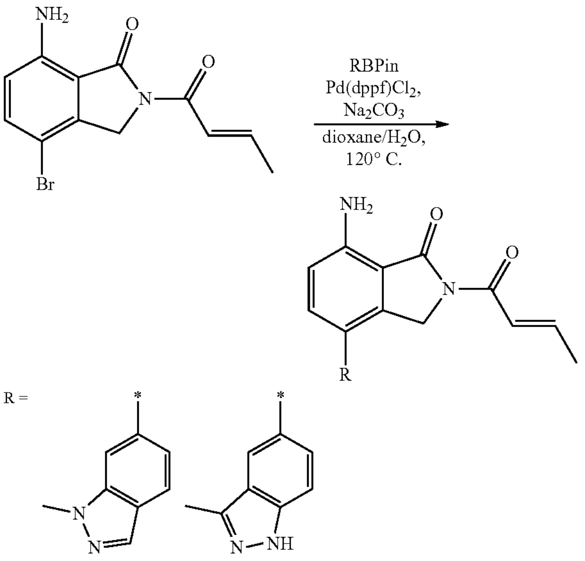

To a solution of 7-amino-4-bromo-2-[(2E)-but-2-enoyl]-2,3-dihydro-1H-isoindol-1-one (0.04 g, 135.53 μmol, 1 eq.) in dioxane (1 mL) and water (0.25 mL) were added (1-methylindazol-6-yl)boronic acid (35.78 mg, 203.30 μmol, 1.5 eq.), $Na_2CO_3$ (71.83 mg, 677.66 μmol, 5 eq.) and Pd(dppf)$Cl_2$ (49.59 mg, 67.77 μmol, 0.5 eq.). The mixture was stirred for 10 min at 120° C. under nitrogen. TLC showed that the reaction was complete. The reaction was diluted with 10 mL EtOAc and 20 mL sat. EDTA and stirred at 20° C. for 1 h. The reaction was extracted with (3×10 mL) EtOAc, and the combined organic layer was washed with 20 mL brine, dried over anhydrous sodium sulfate, filtered, and concentrated in vacuo to give a crude product. The residue was purified by prep-HPLC to afford the title compound (0.0063 g, 18.04 μmol, 13.31% yield, 99.2% purity) as a yellow solid.

Preparation of tert-butyl 5-[7-amino-2-[(E)-but-2-enoyl]-1-oxo-isoindolin-4-yl]-3-(3-pyridyl)indazole-1-carboxylate (Compound 429)

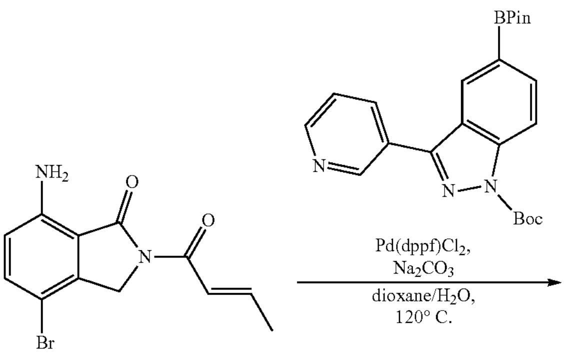

-continued

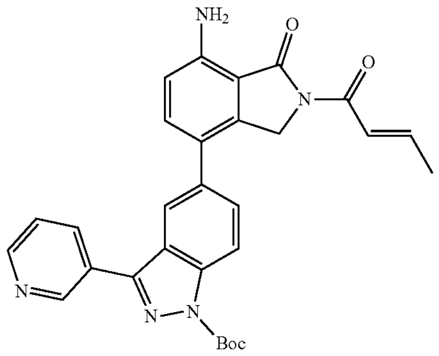

To a solution of 7-amino-4-bromo-2-[(2E)-but-2-enoyl]-2,3-dihydro-1H-isoindol-1-one (0.07 g, 237.18 μmol, 1 eq.) in dioxane (4 mL) and water (1 mL) were added tert-butyl 3-(pyridin-3-yl)-5-(4,4,5,5-tetramethyl-1,3,2-dioxaborolan-2-yl)-1H-indazole-1-carboxylate (109.92 mg, 260.90 μmol, 1.1 eq.), $Na_2CO_3$ (125.69 mg, 1.19 mmol, 5 eq.) and Pd(dppf)$Cl_2$ (86.77 mg, 118.59 μmol, 0.5 eq.). The mixture was stirred for 10 min at 120° C. under nitrogen. TLC showed that the reaction was complete. The reaction was diluted with 10 mL EtOAc and 20 mL sat. EDTA and stirred at 20° C. for 1 h. The reaction was extracted with (3×10 mL) EtOAc and washed with 20 mL saturated brine, and the combined organic phase was dried over anhydrous sodium sulfate, filtered, and concentrated in vacuo to afford the title compound (0.1 g, crude) as a yellow solid, which was used directly without any further purification. LC-MS: $[M+H]^+$ 409.1.

Route 8:

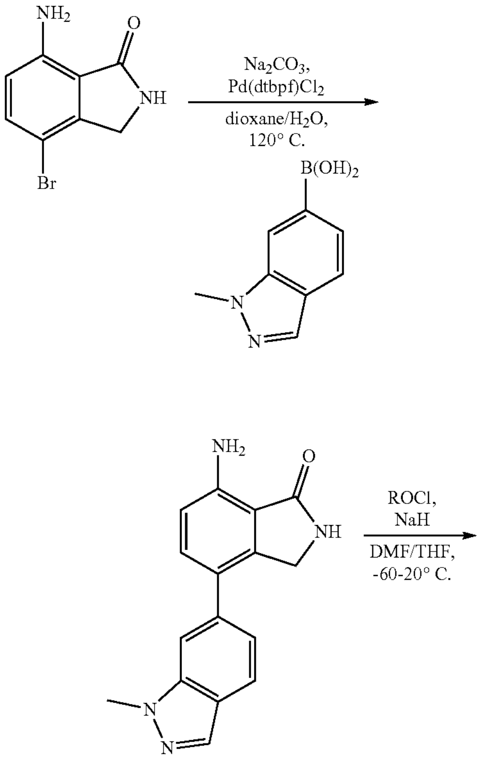

-continued

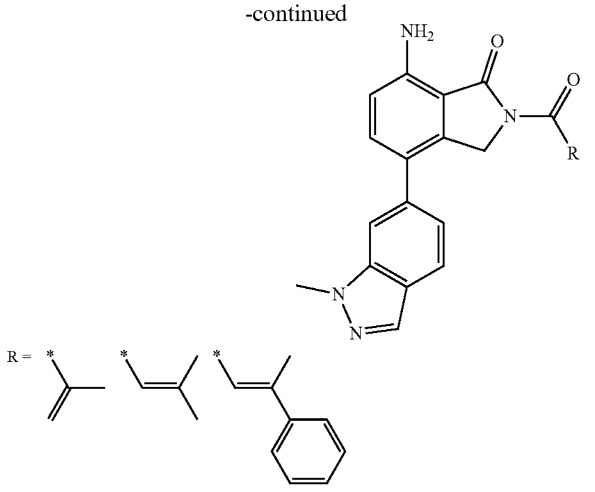

Preparation of 7-amino-4-(1-methyl-1H-indazol-6-yl)-2,3-dihydro-1H-isoindol-1-one

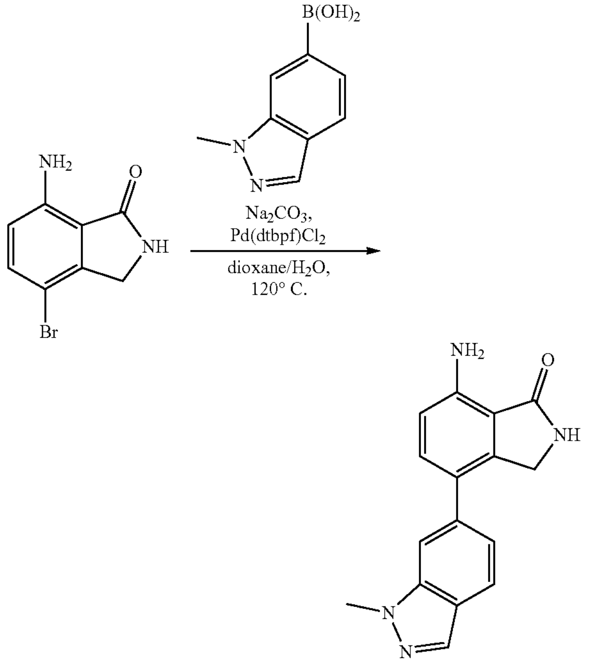

To a solution of 7-amino-4-bromo-2,3-dihydro-1H-isoindol-1-one (2 g, 8.81 mmol, 1 eq.) in dioxane (40 mL) and water (10 mL) were added (1-methylindazol-6-yl) boronic acid (1.86 g, 10.57 mmol, 1.2 eq.), $Na_2CO_3$ (4.67 g, 44.04 mmol, 5 eq.) and Pd(dppf)$Cl_2$ (3.22 g, 4.40 mmol, 0.5 eq.). The mixture was stirred for 10 min at 120° C. under nitrogen. TLC showed that the reaction was complete. The reaction was diluted with 30 mL EtOAc and 30 mL sat. EDTA and stirred at 20° C. for 1 h. The reaction was extracted with (3×30 mL) EtOAc. The combined organic phase was washed with 20 mL brine, dried over anhydrous sodium sulfate, filtered, and concentrated in vacuo to give a crude product. The crude product was washed with by DCM (20 mL) to afford the title compound (1.5 g, 5.39 mmol, 61.19% yield) as a black brown solid.

Preparation of 7-amino-4-(1-methylindazol-6-yl)-2-(2-methylprop-2-enoyl)isoindolin-1-one (Compound 463)

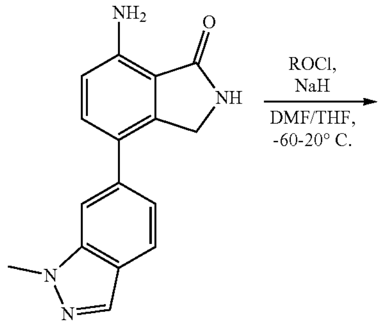

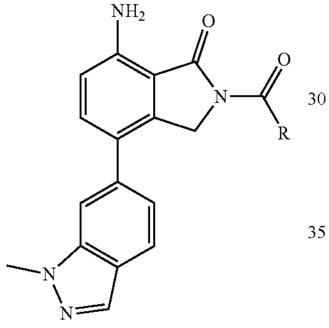

-continued

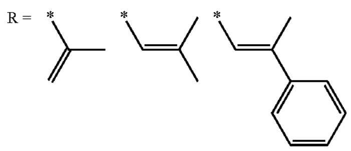

To a solution of 7-amino-4-(1-methylindazol-6-yl)isoindolin-1-one (0.05 g, 179.66 μmol, 1 eq.) in DMF (2 mL) and THF (2 mL) was added NaH (14.37 mg, 359.31 μmol, 60% purity, 2 eq.) under nitrogen. The mixture was stirred for 20 min at 20° C., and 2-methylprop-2-enoyl chloride (28.17 mg, 269.49 μmol, 26.33 μL, 1.5 eq.) was added to the reaction. The resulting mixture was stirred for 10 min at −60° C. LCMS showed that the reaction was complete. The reaction was quenched with $NH_4Cl$ (10 mL), then the mixture was extracted with EtOAc (3×10 mL). The combined organic phase was washed with brine (2×10 mL), dried over anhydrous sodium sulfate, filtered, and concentrated in vacuo. The residue was purified by prep-HPLC to afford the title compound (0.006 g, 17.01 μmol, 9.47% yield, 98.2% purity) as a yellow solid. LC-MS: $[M+H]^+$ 347.1.

TABLE 8 shows compounds prepared using the methods described in EXAMPLE 10.

TABLE 8

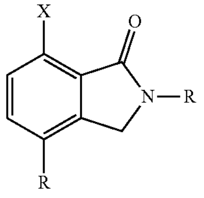

| Cpd. No. | Structure | IUPAC | LC-MS (ES+, m/z) |
|---|---|---|---|
| 442. | 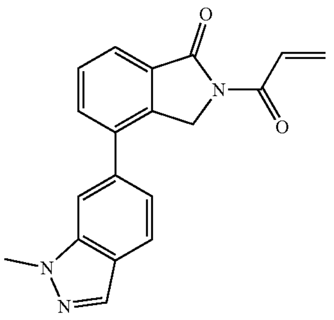 [SMILES: C=CC(=O)N1Cc2c(cccc2-c2ccc3cnn(C)c3c2)C1=O] | 4-(1-methyl-1H-indazol-6-yl)-2-(prop-2-enoyl)-2,3-dihydro-1H-isoindol-1-one | 318 |

TABLE 8-continued
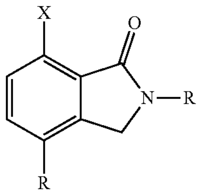
| Cpd. No. | Structure | IUPAC | LC-MS (ES+, m/z) |
|---|---|---|---|
| 443. | 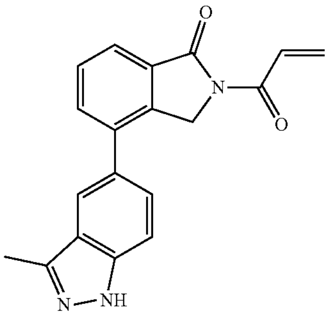 [SMILES: C=CC(=O)N1Cc2c(cccc2-c2ccc3[nH]nc(C)c3c2)C1=O] | 4-(3-methyl-1H-indazol-5-yl)-2-(prop-2-enoyl)-2,3-dihydro-1H-isoindol-1-one | 318.1 |
| 444. | 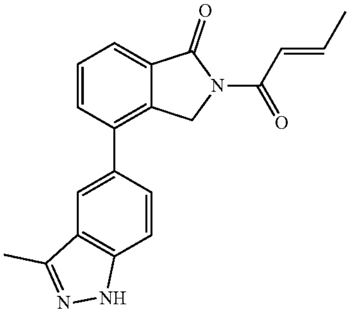 [SMILES: C/C=C/C(=O)N1Cc2c(cccc2-c2ccc3[nH]nc(C)c3c2)C1=O] | 2-[(2E)-but-2-enoyl]-4-(3-methyl-1H-indazol-5-yl)-2,3-dihydro-1H-isoindol-1-one | 332.1 |
| 445. | 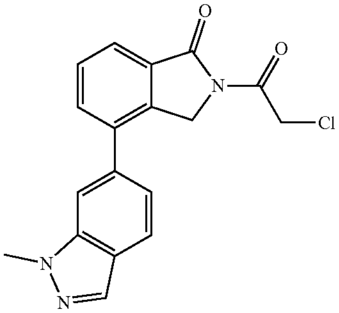 [SMILES: Cn1ncc2ccc(-c3cccc4c3CN(C(=O)CCl)C4=O)cc21] | 2-(2-chloroacetyl)-4-(1-methyl-1H-indazol-6-yl)-2,3-dihydro-1H-isoindol-1-one | 340 |
| 446. | 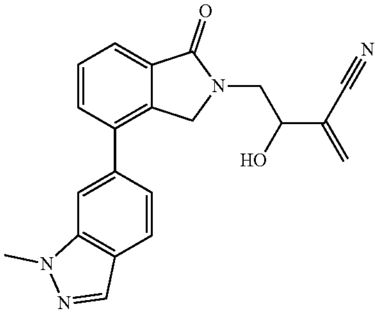 [SMILES: C=C(C#N)C(O)CN1Cc2c(cccc2-c2ccc3cnn(C)c3c2)C1=O] | 3-hydroxy-4-[4-(1-methyl-1H-indazol-6-yl)-1-oxo-2,3-dihydro-1H-isoindol-2-yl]-2-methylidenebutanenitrile | 359.1 |

TABLE 8-continued
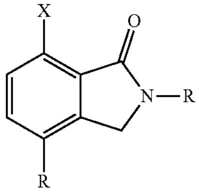
| Cpd. No. | Structure | IUPAC | LC-MS (ES+, m/z) |
|---|---|---|---|
| 447. | 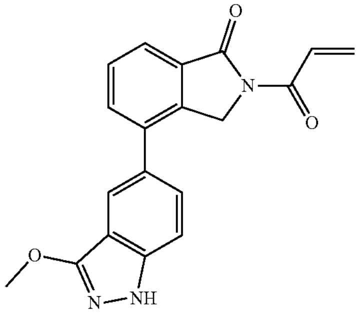 [SMILES: C=CC(=O)N1Cc2c(cccc2-c2ccc3[nH]nc(OC)c3c2)C1=O] | 4-(3-methoxy-1H-indazol-5-yl)-2-(prop-2-enoyl)-2,3-dihydro-1H-isoindol-1-one | 334.1 |
| 448. | 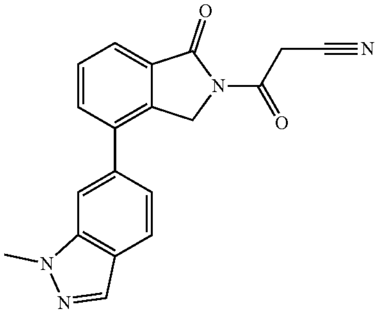 [SMILES: Cn1ncc2ccc(-c3cccc4c3CN(C(=O)CC#N)C4=O)cc21] | 3-[4-(1-methyl-1H-indazol-6-yl)-1-oxo-2,3-dihydro-1H-isoindol-2-yl]-3-oxopropanenitrile | 331.1 |
| 449. | 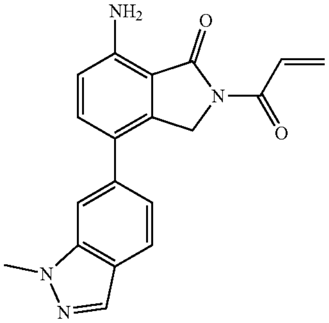 [SMILES: C=CC(=O)N1Cc2c(-c3ccc4cnn(C)c4c3)ccc(N)c2C1=O] | 7-amino-4-(1-methyl-1H-indazol-6-yl)-2-(prop-2-enoyl)-2,3-dihydro-1H-isoindol-1-one | 333.2 |
| 450. | 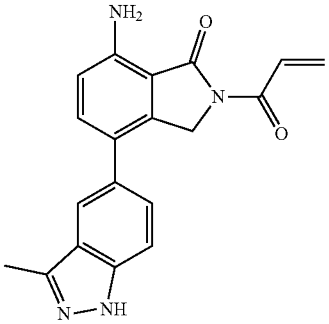 [SMILES: C=CC(=O)N1Cc2c(-c3ccc4[nH]nc(C)c4c3)ccc(N)c2C1=O] | 7-amino-4-(3-methyl-1H-indazol-5-yl)-2-(prop-2-enoyl)-2,3-dihydro-1H-isoindol-1-one | 333.1 |

TABLE 8-continued
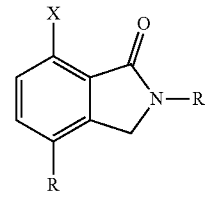
| Cpd. No. | Structure | IUPAC | LC-MS (ES+, m/z) |
|---|---|---|---|
| 451. | 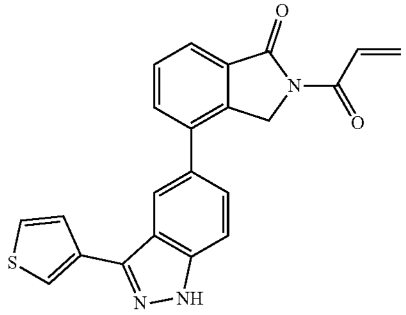 [SMILES: C=CC(=O)N1Cc2c(cccc2-c2ccc3[nH]nc(-c4ccsc4)c3c2)C1=O] | 2-(prop-2-enoyl)-4-[3-(thiophen-3-yl)-1H-indazol-5-yl]-2,3-dihydro-1H-isoindol-1-one | 386.1 |
| 452. | 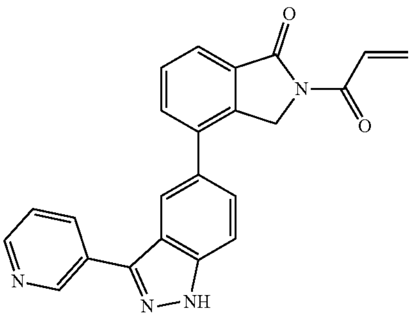 [SMILES: C=CC(=O)N1Cc2c(cccc2-c2ccc3[nH]nc(-c4cccnc4)c3c2)C1=O] | 2-(prop-2-enoyl)-4-[3-(pyridin-3-yl)-1H-indazol-5-yl]-2,3-dihydro-1H-isoindol-1-one | 381.1 |
| 453. | 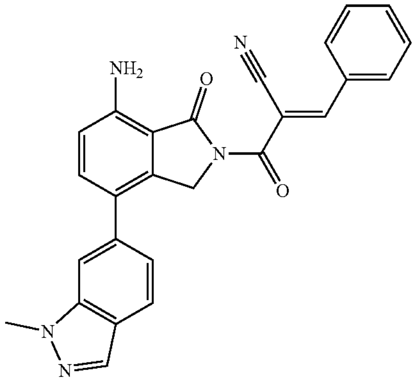 [SMILES: Cn1ncc2ccc(-c3ccc(N)c4c3CN(C(=O)/C(C#N)=C/c3ccccc3)C4=O)cc21] | (2E)-2-[(E)-4-(1-methyl-1H-indazol-6-yl)-1-oxo-2,3-dihydro-1H-isoindole-2-carbonyl]-3-phenylprop-2-enenitrile | 419.1 |

TABLE 8-continued
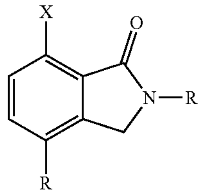
| Cpd. No. | Structure | IUPAC | LC-MS (ES+, m/z) |
|---|---|---|---|
| 454. | 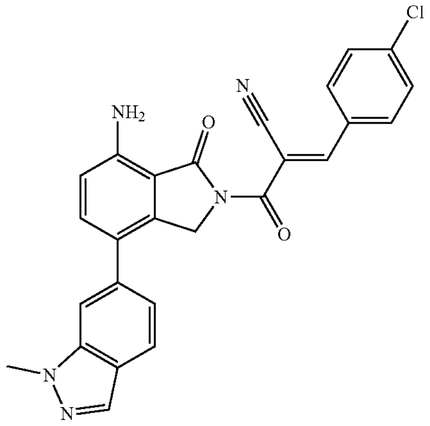 [SMILES: Cn1ncc2ccc(-c3ccc(N)c4c3CN(C(=O)/C(C#N)=C/c3ccc(Cl)cc3)C4=O)cc21] | (2E)-3-(4-chlorophenyl)-2-[(E)-4-(1-methyl-1H-indazol-6-yl)-1-oxo-2,3-dihydro-1H-isoindole-2-carbonyl]prop-2-enenitrile | 453 |
| 455. | 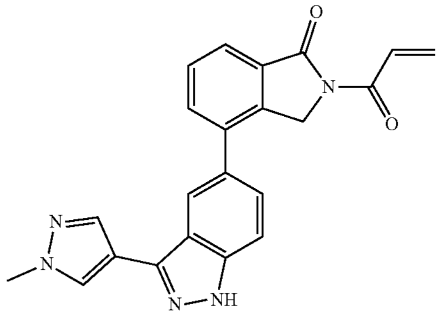 [SMILES: C=CC(=O)N1Cc2c(cccc2-c2ccc3[nH]nc(-c4cnn(C)c4)c3c2)C1=O] | 4-[3-(1-methyl-1H-pyrazol-4-yl)-1H-indazol-5-yl]-2-(prop-2-enoyl)-2,3-dihydro-1H-isoindol-1-one | 384.2 |
| 456. | 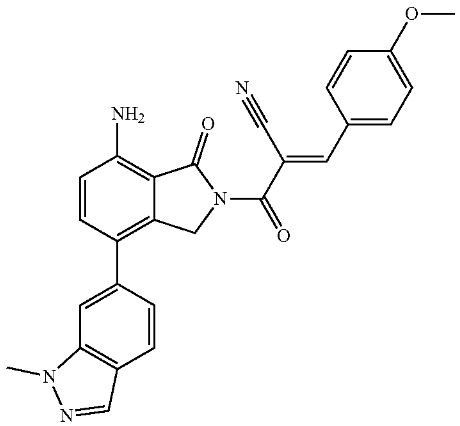 | (2E)-3-(4-methoxyphenyl)-2-[(E)-4-(1-methyl-1H-indazol-6-yl)-1-oxo-2,3-dihydro-1H-isoindole-2-carbonyl]prop-2-enenitrile | 449.1 |

TABLE 8-continued
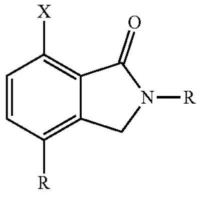
| Cpd. No. | Structure | IUPAC | LC-MS (ES+, m/z) |
|---|---|---|---|
| 457. | 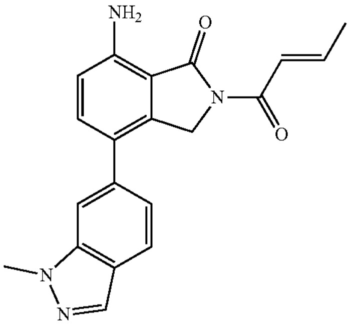 [SMILES: C/C=C/C(=O)N1Cc2c(-c3ccc4cnn(C)c4c3)ccc(N)c2C1=O] | 7-amino-2-[(2E)-but-2-enoyl]-4-(1-methyl-1H-indazol-6-yl)-2,3-dihydro-1H-isoindol-1-one | 347.1 |
| 458. | 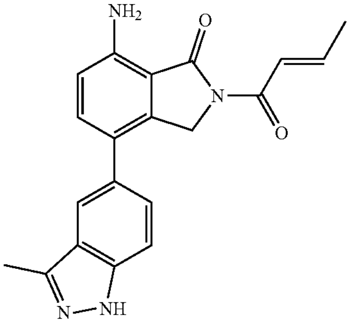 [SMILES: C/C=C/C(=O)N1Cc2c(-c3ccc4[nH]nc(C)c4c3)ccc(N)c2C1=O] | 7-amino-2-[(2E)-but-2-enoyl]-4-(3-methyl-1H-indazol-5-yl)-2,3-dihydro-1H-isoindol-1-one | 347.1 |
| 459. | 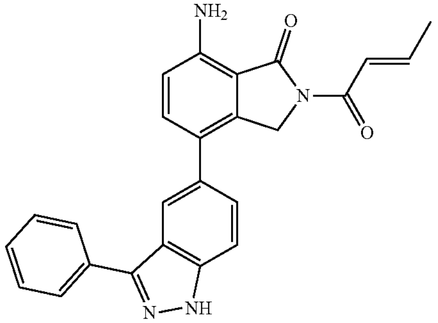 | 7-amino-2-[(2E)-but-2-enoyl]-4-(3-phenyl-1H-indazol-5-yl)-2,3-dihydro-1H-isoindol-1-one | 409.1 |
| 460. | 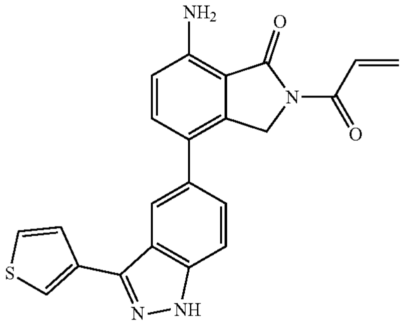 [SMILES: C=CC(=O)N1Cc2c(-c3ccc4[nH]nc(-c5ccsc5)c4c3)ccc(N)c2C1=O] | 7-amino-2-(prop-2-enoyl)-4-[3-(thiophen-3-yl)-1H-indazol-5-yl]-2,3-dihydro-1H-isoindol-1-one | 401.1 |

TABLE 8-continued
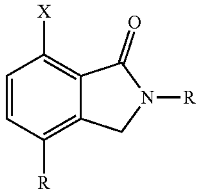
| Cpd. No. | Structure | IUPAC | LC-MS (ES+, m/z) |
|---|---|---|---|
| 461. | 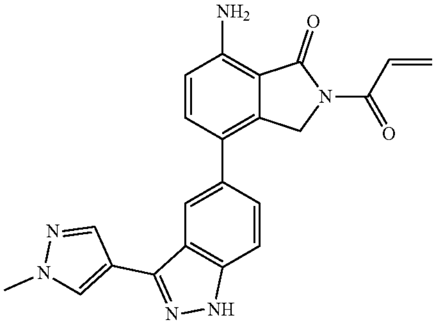 [SMILES: C=CC(=O)N1Cc2c(-c3ccc4[nH]nc(-c5cnn(C)c5)c4c3)ccc(N)c2C1=O] | 7-amino-4-[3-(1-methyl-1H-pyrazol-4-yl)-1H-indazol-5-yl]-2-(prop-2-enoyl)-2,3-dihydro-1H-isoindol-1-one | 399.1 |
| 462. | 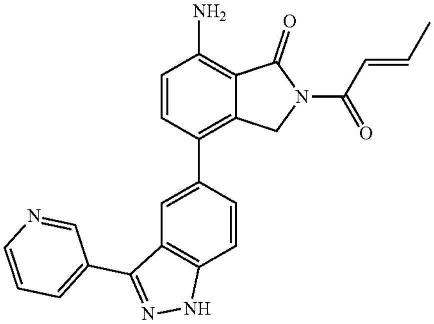 [SMILES: C/C=C/C(=O)N1Cc2c(-c3ccc4[nH]nc(-c5cccnc5)c4c3)ccc(N)c2C1=O] | 7-amino-2-[(2E)-but-2-enoyl]-4-[3-(pyridin-3-yl)-1H-indazol-5-yl]-2,3-dihydro-1H-isoindol-1-one | 410.1 |
| 463. | 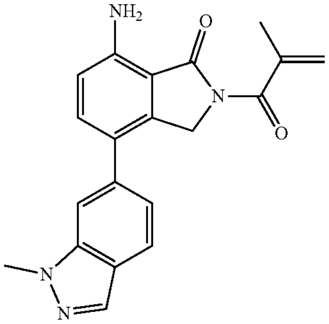 [SMILES: C=C(C)C(=O)N1Cc2c(-c3ccc4cnn(C)c4c3)ccc(N)c2C1=O] | 7-amino-4-(1-methyl-1H-indazol-6-yl)-2-(2-methylprop-2-enoyl)-2,3-dihydro-1H-isoindol-1-one | 347.1 |
| 464. | 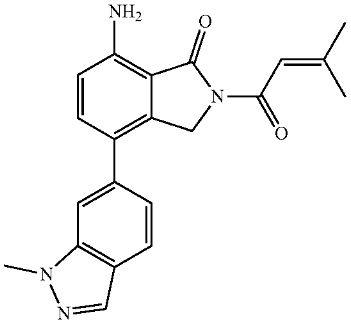 [SMILES: CC(C)=CC(=O)N1Cc2c(-c3ccc4cnn(C)c4c3)ccc(N)c2C1=O] | 7-amino-4-(1-methyl-1H-indazol-6-yl)-2-(3-methylbut-2-enoyl)-2,3-dihydro-1H-isoindol-1-one | 361.1 |

TABLE 8-continued
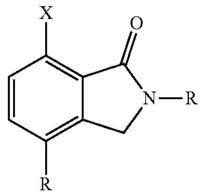
| Cpd. No. | Structure | IUPAC | LC-MS (ES+, m/z) |
|---|---|---|---|
| 465. | 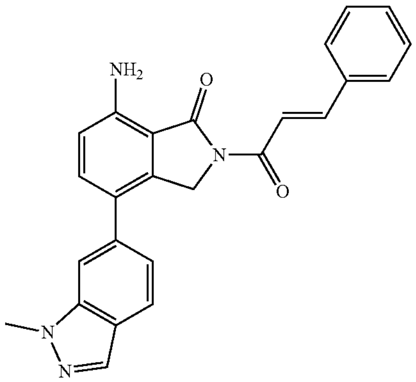 [SMILES: Cn1ncc2ccc(-c3ccc(N)c4c3CN(C(=O)/C=C/c3ccccc3)C4=O)cc21] | 7-amino-4-(1-methyl-1H-indazol-6-yl)-2-[(2E)-3-phenylprop-2-enoyl]-2,3-dihydro-1H-isoindol-1-one | 409.1 |
Example 11: Method I
General Scheme for Method I
Route 1:
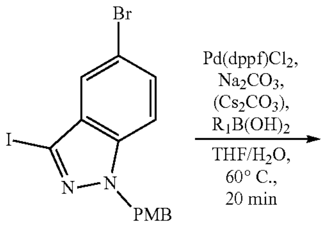
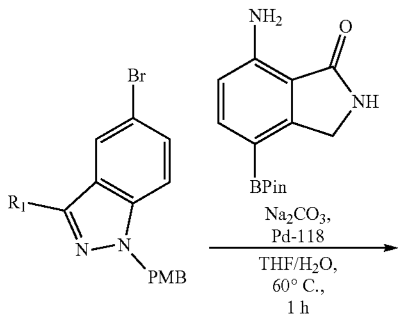
-continued
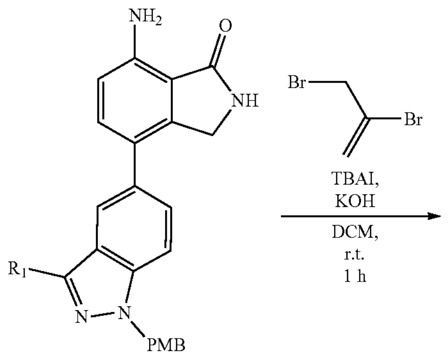
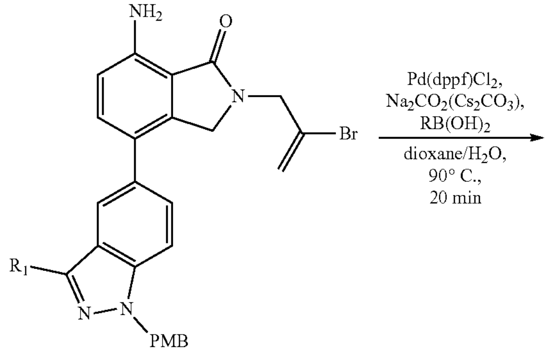

-continued

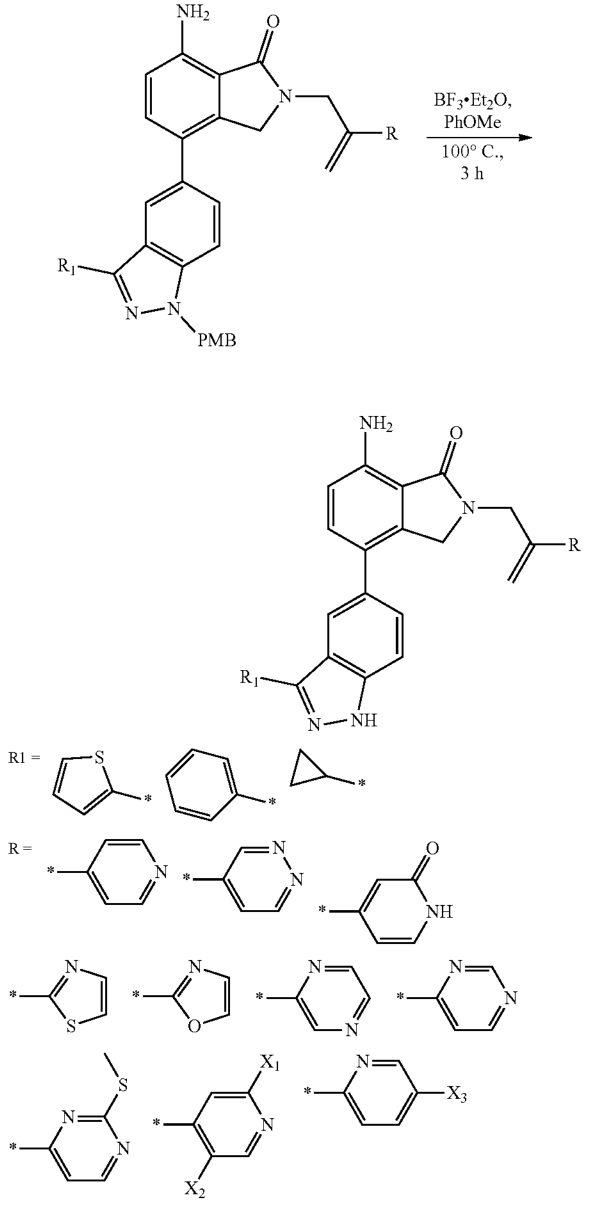

X1 = H, Cl, COMe, F, $CH_2OH$, CN, $CF_3$, NHAc, OMe, $NH_2$, Me
X2: F, CN
X3: $CONH_2$, CN, CF3

Preparation of 5-bromo-1-[(4-methoxyphenyl)methyl]-3-phenyl-indazole

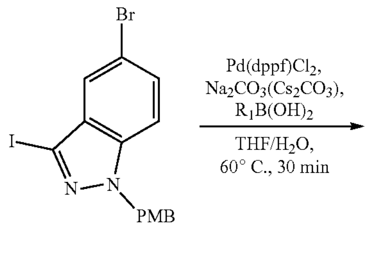

-continued

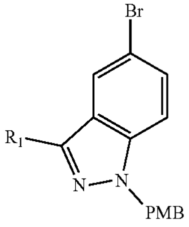

R=phenyl: To a mixture of 5-bromo-3-iodo-1-[(4-methoxyphenyl)methyl]indazole (2.5 g, 5.64 mmol, 1 eq.) and phenylboronic acid (1.38 g, 11.28 mmol, 2 eq.) in THF (20 mL) water (5 mL) was added $Na_2CO_3$ (1.79 g, 16.93 mmol, 3 eq.) in one portion at 25° C. under nitrogen. Then, Pd(dppf)$Cl_2$ (2.06 g, 2.82 mmol, 0.5 eq.) was added to the mixture. The mixture was stirred at 60° C. for 30 min. LCMS showed that the reaction was complete. The reaction was poured into 20 mL sat. EDTA and diluted with 20 mL EtOAc. The mixture was then stirred at 25° C. for 1 h, and the aqueous layer was extracted with EtOAc (3×20 mL). The combined organic layer was washed with brine 20 mL, filtered, and concentrated in vacuo. The residue was purified by column chromatography (silica gel; PE:EtOAc=4:1 to 1:1) to afford the title compound (1.6 g, 4.07 mmol, 72.10% yield) as alight yellow solid.

Preparation of 7-amino-4-[1-[(4-methoxyphenyl)methyl]-3-phenyl-indazol-5-yl]isoindolin-1-one

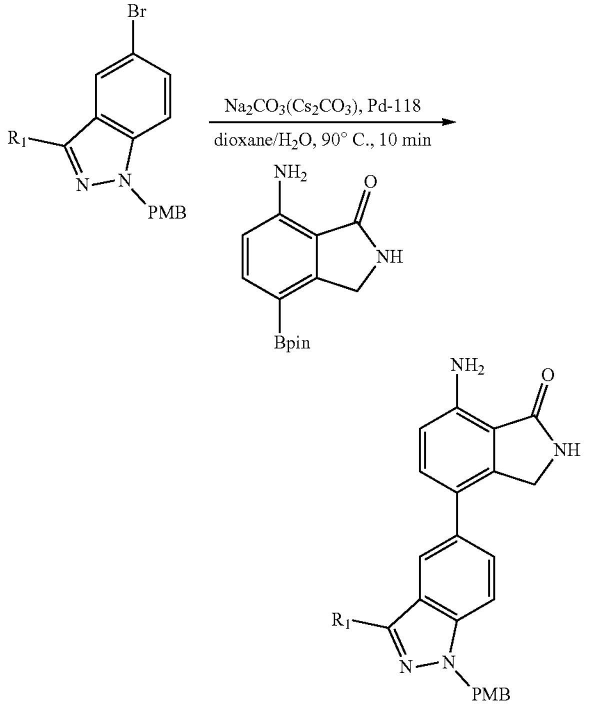

R=phenyl: To a mixture of 5-bromo-1-[(4-methoxyphenyl)methyl]-3-phenyl-indazole (0.7 g, 1.78 mmol, 1 eq.) and 7-amino-4-(4,4,5,5-tetramethyl-1,3,2-dioxaborolan-2-yl) isoindolin-1-one (585.50 mg, 2.14 mmol, 1.2 eq.) in dioxane (10 mL) and water (2.5 mL) was added $Na_2CO_3$ (565.96 mg, 5.34 mmol, 3 eq.) in one portion at 25° C. under nitrogen.

Then, $Pd(dppf)Cl_2$ (130.24 mg, 177.99 μmol, 0.1 eq.) was added to the reaction, and the mixture was stirred at 90° C. for 10 min. LCMS showed that the reaction was complete. The reaction was poured to 20 mL sat EDTA and diluted with 20 mL EtOAc, and the mixture was stirred at 25° C. for 1 h. The aqueous layer was extracted with EtOAc (3×20 mL). The combined organic layer was washed with brine 20 mL, filtered, and concentrated in vacuo. The residue was purified by column chromatography (silica gel; DCM: MeOH=30:1 to 20:1) to afford the title compound (0.6 g, 1.04 mmol, 58.56% yield, 80% purity) as a yellow solid.

Preparation of 7-amino-2-(2-bromoallyl)-4-[1-[(4-methoxyphenyl)methyl]-3-phenyl-indazol-5-yl]isoindolin-1-one

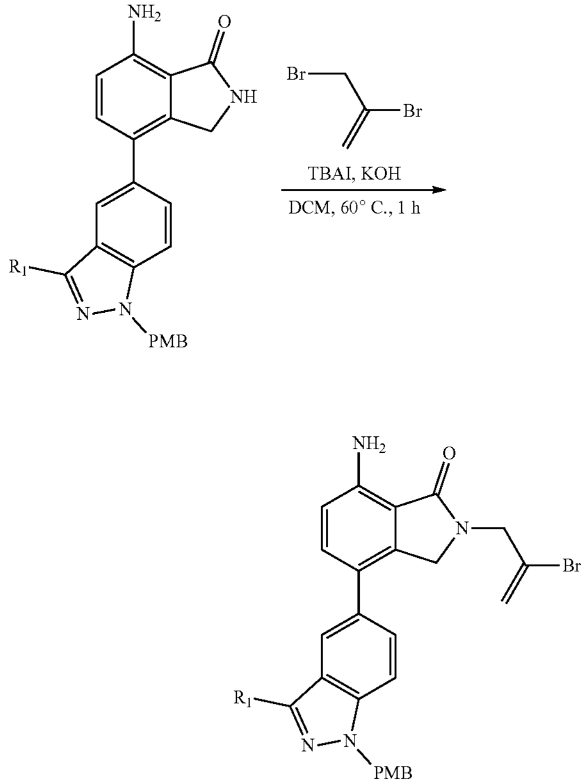

R=phenyl: To a mixture of 7-amino-4-[1-[(4-methoxyphenyl)methyl]-3-phenyl-indazol-5-yl]isoindolin-1-one (0.5 g, 1.09 mmol, 1 eq.) in DCM (10 mL) were added KOH (182.74 mg, 3.26 mmol, 3 eq.) and TBAI (401.03 mg, 1.09 mmol, 1 eq.) in one portion at 25° C. under nitrogen. Then, 2,3-dibromoprop-1-ene (195.30 mg, 977.14 μmol, 95.27 μL, 0.9 eq.) was added, and the mixture was stirred at 60° C. for 1 h. LCMS showed that the reaction was complete. The reaction was poured to sat. $NH_4Cl$ (30 mL) and extracted with DCM (3×20 mL). The combined organic layer was concentrated in vacuo. The residue was purified by prep-TLC (silica gel; DCM:MeOH=20:1) to afford the title compound (0.3 g, 440.05 μmol, 40.53% yield, 85% purity) as a light yellow solid.

Preparation of 7-amino-4-[1-[(4-methoxyphenyl)methyl]-3-phenyl-indazol-5-yl]-2-[2-(4-pyridyl)allyl]isoindolin-1-one

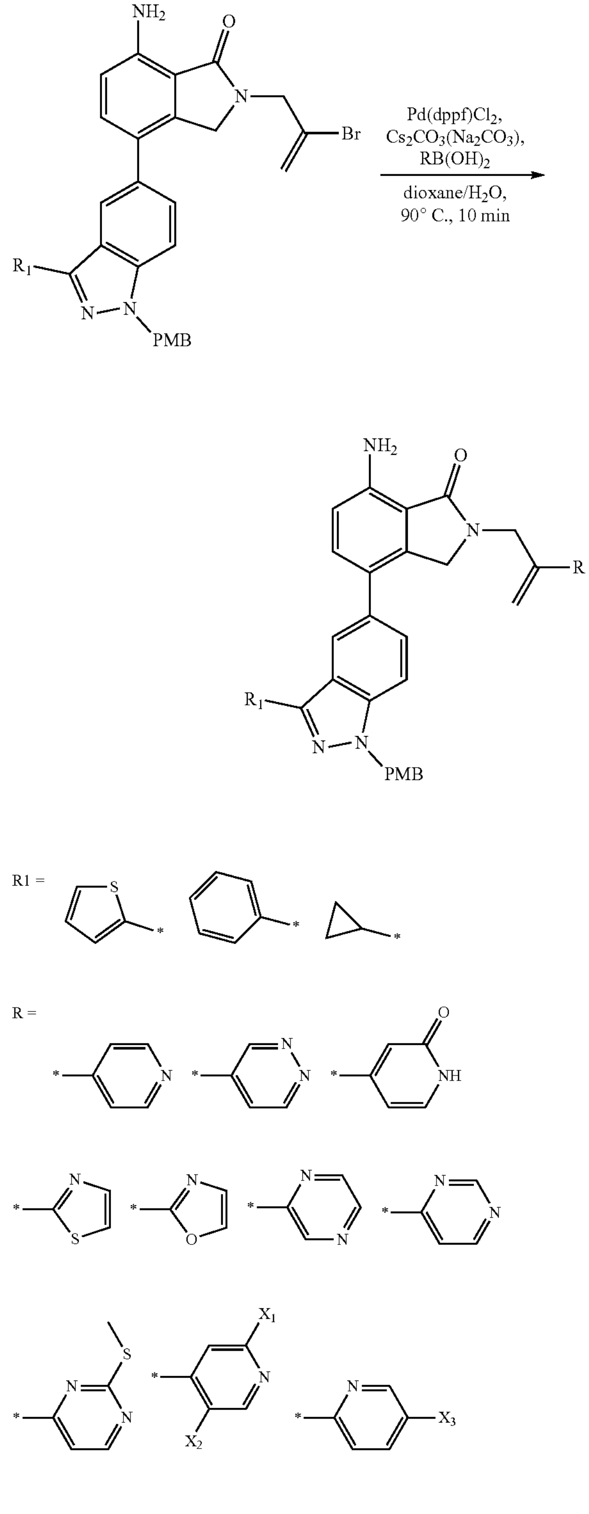

X1 = H, Cl, COMe, F, $CH_2OH$, CN, $CF_3$, NHAc, OMe, $NH_2$, Me
X2: F, CN
X3: $CONH_2$, CN, CF3

To a mixture of 7-amino-2-(2-bromoallyl)-4-[1-[(4-methoxyphenyl)methyl]-3-phenyl-indazol-5-yl]isoindolin-1-one (0.13 g, 224.34 μmol, 1 eq.) and boronic acid (33.09 mg, 269.20 μmol, 1.2 eq.) in dioxane (4 mL) water (1 mL) was added $Cs_2CO_3$ (219.28 mg, 673.01 μmol, 3 eq.) in one portion at 25° C. under nitrogen. Then, Pd(dppf)$Cl_2$ (16.41 mg, 22.43 μmol, 0.1 eq.) was added to the reaction, and the mixture was stirred at 90° C. for 10 min. LCMS showed that the reaction was complete. The reaction was poured to 20 mL sat EDTA and diluted with 20 mL EtOAc. The resulting mixture was stirred at 25° C. for 1 h, and the aqueous layer was extracted with EtOAc (3×20 mL). The combined organic layer was washed with brine 20 mL, filtered, and concentrated in vacuo. The residue was purified by prep-TLC (silica gel; DCM:MeOH=20:1) to afford the title compound (0.06 g, 103.86 μmol, 46.30% yield) was obtained as a light yellow solid.

Preparation of 7-amino-4-(3-phenyl-1H-indazol-5-yl)-2-[2-(4-pyridyl)allyl]isoindolin-1-one (Compound 466)

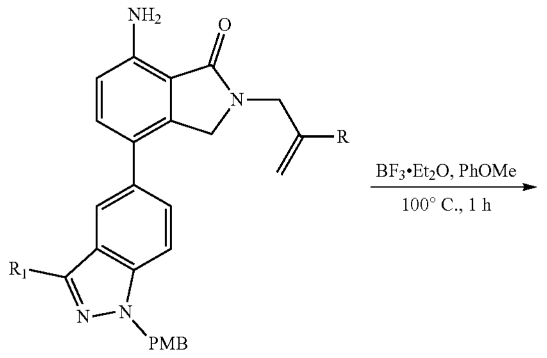

-continued

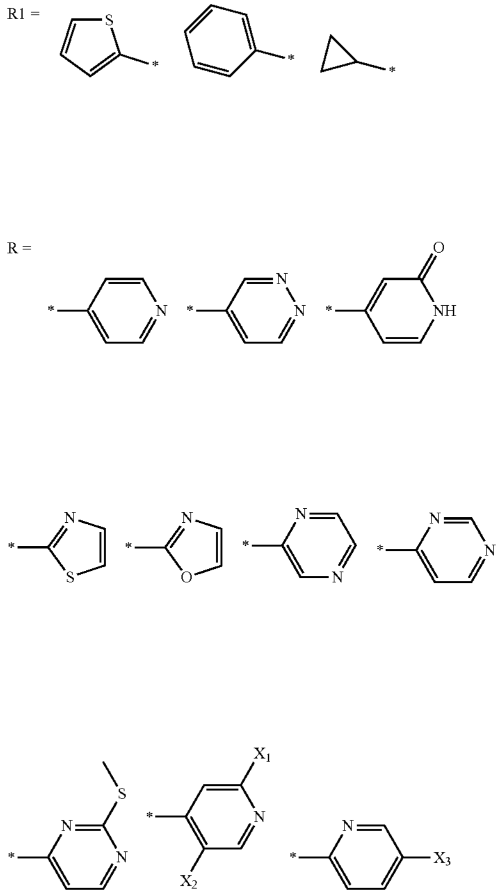

X1 = H, Cl, COMe, F, $CH_2OH$, CN, $CF_3$, NHAc, OMe, $NH_2$, Me
X2: F, CN
X3: $CONH_2$, CN, CF3

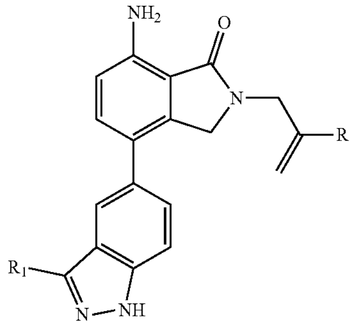

To a mixture of 7-amino-4-[1-[(4-methoxyphenyl)methyl]-3-phenyl-indazol-5-yl]-2-[2-(4-pyridyl)allyl]isoindolin-1-one (0.06 g, 103.86 μmol, 1 eq.) in $BF_3$·$Et_2O$ (4 mL) was added anisole (56.16 mg, 519.32 μmol, 56.44 μL, 5 eq.) in one portion at 25° C. under nitrogen. The mixture was stirred at 100° C. for 1 h. LCMS showed that the reaction was complete. The reaction was poured to sat. $Na_2CO_3$ (30 mL) then extracted with EtOAc (3×10 mL). The combined organic layer was concentrated in vacuo. The crude product was obtained as a yellow solid. The crude product was purified by prep-HPLC to afford the title compound (0.004 g, 8.59 μmol, 8.27% yield, 98.3% purity) as a white solid. LC-MS: $[M+H]^+$ 458.1.

TABLE 9 shows compounds prepared using the methods described in EXAMPLE 11.

TABLE 9
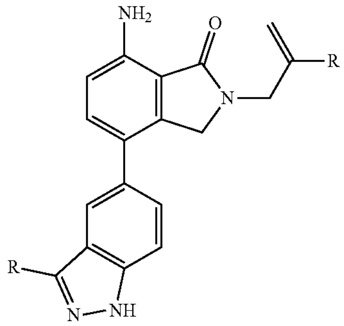
| Cpd. No. | Structure | IUPAC | LC-MS (ES+, m/z) |
|---|---|---|---|
| 466. | 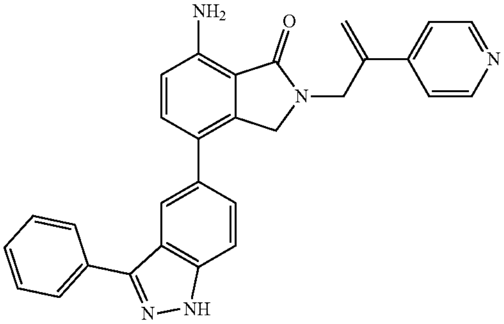 | 7-amino-4-(3-phenyl-1H-indazol-5-yl)-2-[2-(pyridin-4-yl)prop-2-en-1-yl]-2,3-dihydro-1H-isoindol-1-one | 458.1 |
| 467. | 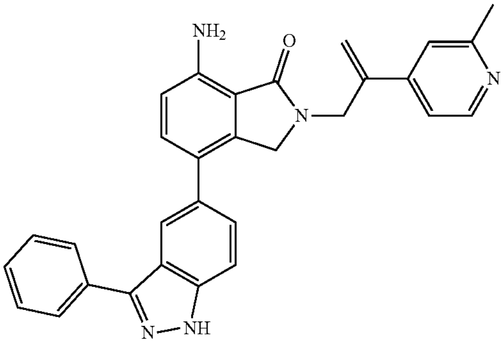 [SMILES: C=C(CN1Cc2c(-c3ccc4[nH]nc(-c5ccccc5)c4c3)ccc(N)c2C1=O)c1ccnc(C)c1] | 7-amino-2-[2-(2-methylpyridin-4-yl)prop-2-en-1-yl]-4-(3-phenyl-1H-indazol-5-yl)-2,3-dihydro-1H-isoindol-1-one | 472.1 |
| 468. | 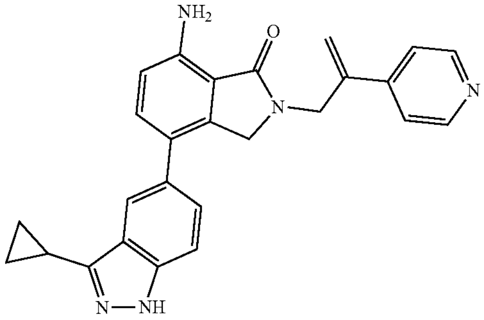 [SMILES: C=C(CN1Cc2c(-c3ccc4[nH]nc(C5CC5)c4c3)ccc(N)c2C1=O)c1ccncc1] | 7-amino-4-(3-cyclopropyl-1H-indazol-5-yl)-2-[2-(pyridin-4-yl)prop-2-en-1-yl]-2,3-dihydro-1H-isoindol-1-one | 422.1 |

TABLE 9-continued
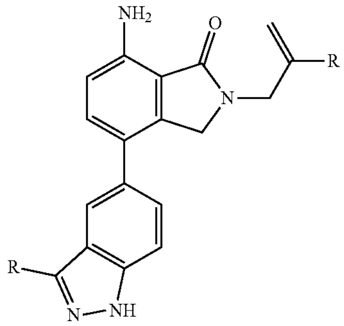
| Cpd. No. | Structure | IUPAC | LC-MS (ES+, m/z) |
| --- | --- | --- | --- |
| 469. | 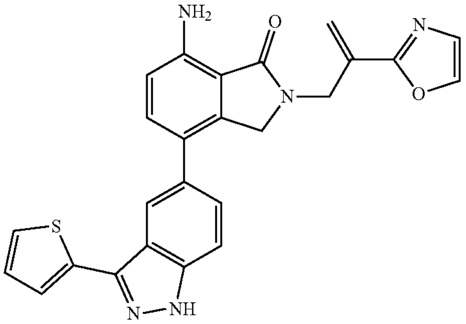 [SMILES: C=C(CN1Cc2c(-c3ccc4[nH]nc(-c5cccs5)c4c3)ccc(N)c2C1=O)c1ncco1] | 7-amino-2-[2-(1,3-oxazol-2-yl)prop-2-en-1-yl]-4-[3-(thiophen-2-yl)-1H-indazol-5-yl]-2,3-dihydro-1H-isoindol-1-one | 454.1 |
| 470. | 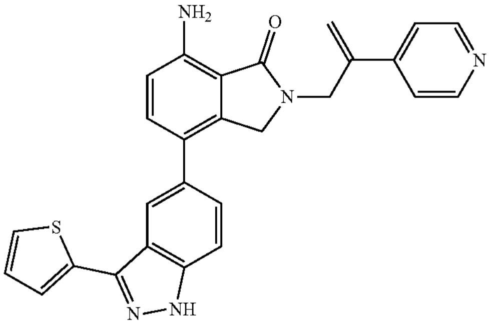 | 7-amino-2-[2-(pyridin-4-yl)prop-2-en-1-yl]-4-[3-(thiophen-2-yl)-1H-indazol-5-yl]-2,3-dihydro-1H-isoindol-1-one | 464.1 |
| 471. | 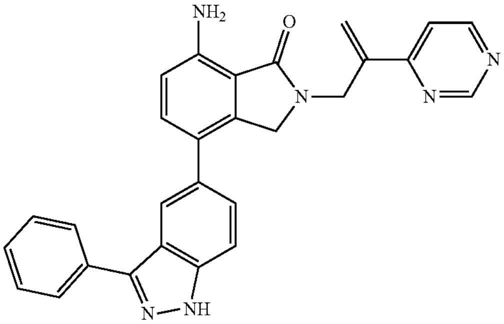 [SMILES: C=C(CN1Cc2c(-c3ccc4[nH]nc(-c5ccccc5)c4c3)ccc(N)c2C1=O)c1ccncn1] | 7-amino-4-(3-phenyl-1H-indazol-5-yl)-2-[2-(pyrimidin-4-yl)prop-2-en-1-yl]-2,3-dihydro-1H-isoindol-1-one | 459.2 |

TABLE 9-continued
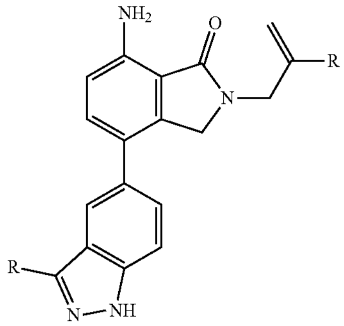
| Cpd. No. | Structure | IUPAC | LC-MS (ES+, m/z) |
|---|---|---|---|
| 472. | 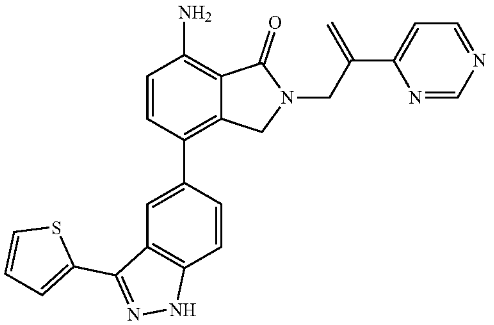 [SMILES: C=C(CN1Cc2c(-c3ccc4[nH]nc(-c5cccs5)c4c3)ccc(N)c2C1=O)c1ccncn1] | 7-amino-2-[2-(pyrimidin-4-yl)prop-2-en-1-yl]-4-[3-(thiophen-2-yl)-1H-indazol-5-yl]-2,3-dihydro-1H-isoindol-1-one | 465.1 |
| 473. | 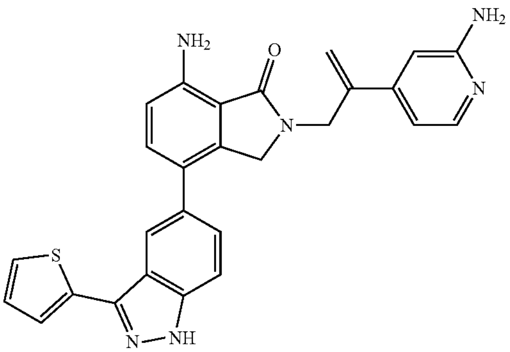 [SMILES: C=C(CN1Cc2c(-c3ccc4[nH]nc(-c5cccs5)c4c3)ccc(N)c2C1=O)c1ccnc(N)c1] | 7-amino-2-[2-(2-aminopyridin-4-yl)prop-2-en-1-yl]-4-[3-(thiophen-2-yl)-1H-indazol-5-yl]-2,3-dihydro-1H-isoindol-1-one | 479.1 |
| 474. | 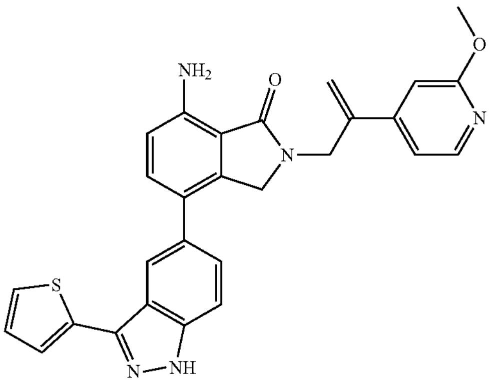 [SMILES: C=C(CN1Cc2c(-c3ccc4[nH]nc(-c5cccs5)c4c3)ccc(N)c2C1=O)c1ccnc(OC)c1] | 7-amino-2-[2-(2-methoxypyridin-4-yl)prop-2-en-1-yl]-4-[3-(thiophen-2-yl)-1H-indazol-5-yl]-2,3-dihydro-1H-isoindol-1-one | 494.1 |

TABLE 9-continued
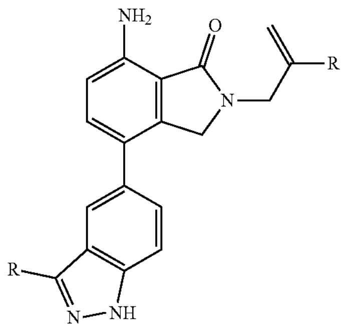
| Cpd. No. | Structure | IUPAC | LC-MS (ES+, m/z) |
|---|---|---|---|
| 475. | 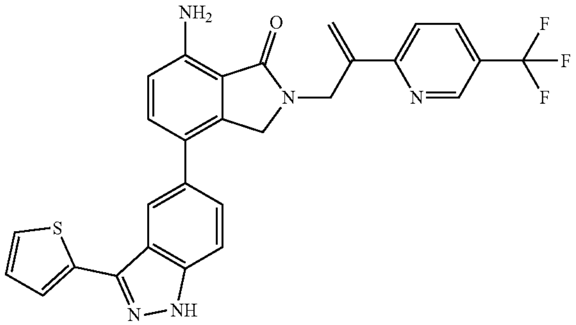 [SMILES: C=C(CN1Cc2c(-c3ccc4[nH]nc(-c5cccs5)c4c3)ccc(N)c2C1=O)c1ccc(C(F)(F)F)cn1] | 7-amino-4-[3-(thiophen-2-yl)-1H-indazol-5-yl]-2-{2-[5-(trifluoromethyl)pyridin-2-yl]prop-2-en-1-yl}-2,3-dihydro-1H-isoindol-1-one | 532.1 |
| 476. | 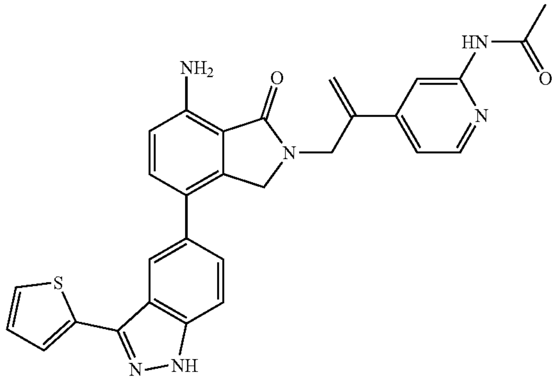 [SMILES: C=C(CN1Cc2c(-c3ccc4[nH]nc(-c5cccs5)c4c3)ccc(N)c2C1=O)c1ccnc(NC(C)=O)c1] | N-[4-(3-{7-amino-1-oxo-4-[3-(thiophen-2-yl)-1H-indazol-5-yl]-2,3-dihydro-1H-isoindol-2-yl}prop-1-en-2-yl)pyridin-2-yl]acetamide | 521.2 |
| 477. | 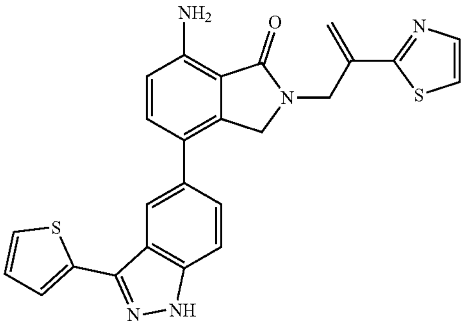 | 7-amino-2-[2-(1,3-thiazol-2-yl)prop-2-en-1-yl]-4-[3-(thiophen-2-yl)-1H-indazol-5-yl]-2,3-dihydro-1H-isoindol-1-one | 470.1 |

TABLE 9-continued
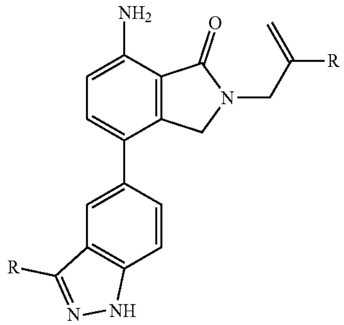
| Cpd. No. | Structure | IUPAC | LC-MS (ES+, m/z) |
|---|---|---|---|
| 478. | 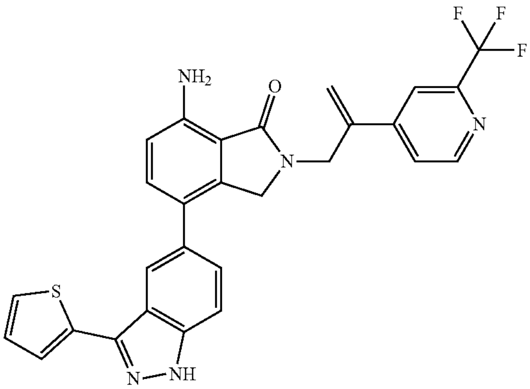 [SMILES: C=C(CN1Cc2c(-c3ccc4[nH]nc(-c5cccs5)c4c3)ccc(N)c2C1=O)c1ccnc(C(F)(F)F)c1] | 7-amino-4-[3-(thiophen-2-yl)-1H-indazol-5-yl]-2-{2-[2-(trifluoromethyl)pyridin-4-yl]prop-2-en-1-yl}-2,3-dihydro-1H-isoindol-1-one | 532.1 |
| 479. | 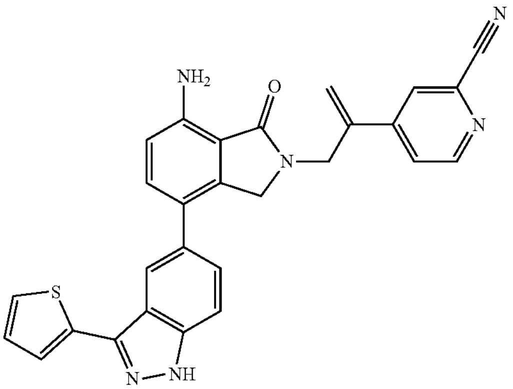 [SMILES: C=C(CN1Cc2c(-c3ccc4[nH]nc(-c5cccs5)c4c3)ccc(N)c2C1=O)c1ccnc(C#N)c1] | 4-(3-{7-amino-1-oxo-4-[3-(thiophen-2-yl)-1H-indazol-5-yl]-2,3-dihydro-1H-isoindol-2-yl}prop-1-en-2-yl)pyridine-2-carbonitrile | 489 |
| 480. | 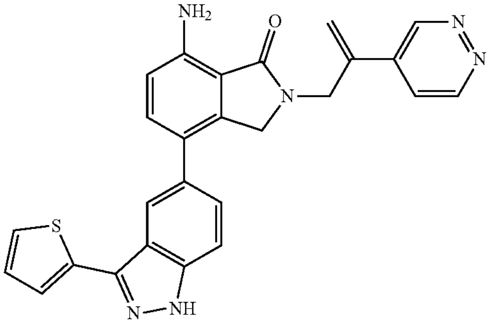 | 7-amino-2-[2-(pyridazin-4-yl)prop-2-en-1-yl]-4-[3-(thiophen-2-yl)-1H-indazol-5-yl]-2,3-dihydro-1H-isoindol-1-one | 465.1 |

TABLE 9-continued
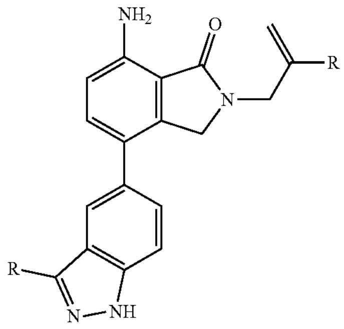
| Cpd. No. | Structure | IUPAC | LC-MS (ES+, m/z) |
|---|---|---|---|
| 481. | 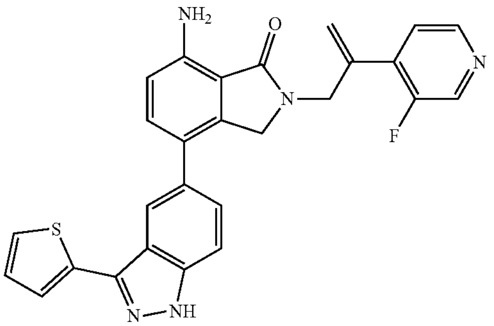 [SMILES: C=C(CN1Cc2c(-c3ccc4[nH]nc(-c5cccs5)c4c3)ccc(N)c2C1=O)c1ccncc1F] | 7-amino-2-[2-(3-fluoropyridin-4-yl)prop-2-en-1-yl]-4-[3-(thiophen-2-yl)-1H-indazol-5-yl]-2,3-dihydro-1H-isoindol-1-one | 482.1 |
| 482. | 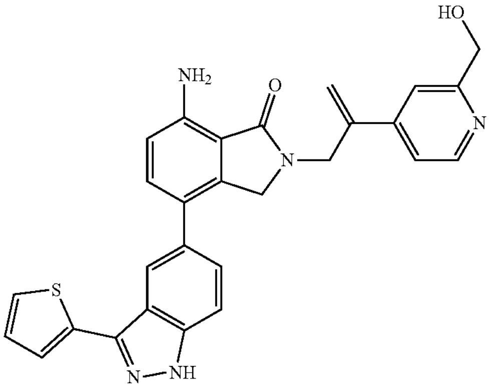 [SMILES: C=C(CN1Cc2c(-c3ccc4[nH]nc(-c5cccs5)c4c3)ccc(N)c2C1=O)c1ccnc(CO)c1] | 7-amino-2-{2-[2-(hydroxymethyl)pyridin-4-yl]prop-2-en-1-yl}-4-[3-(thiophen-2-yl)-1H-indazol-5-yl]-2,3-dihydro-1H-isoindol-1-one | 494.2 |
| 483. | 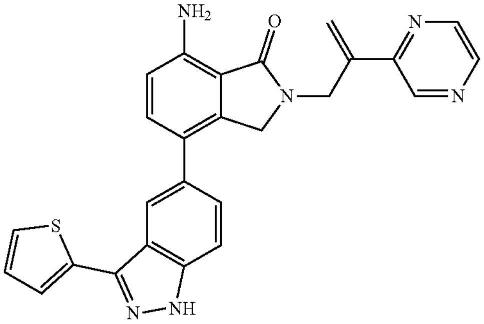 [SMILES: C=C(CN1Cc2c(-c3ccc4[nH]nc(-c5cccs5)c4c3)ccc(N)c2C1=O)c1cnccn1] | 7-amino-2-[2-(pyrazin-2-yl)prop-2-en-1-yl]-4-[3-(thiophen-2-yl)-1H-indazol-5-yl]-2,3-dihydro-1H-isoindol-1-one | 465.1 |

TABLE 9-continued
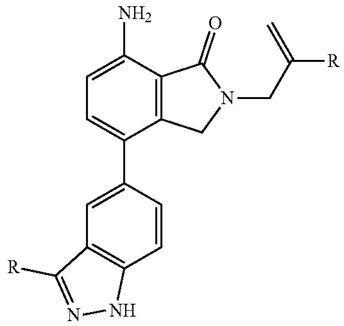
| Cpd. No. | Structure | IUPAC | LC-MS (ES+, m/z) |
| --- | --- | --- | --- |
| 484. | 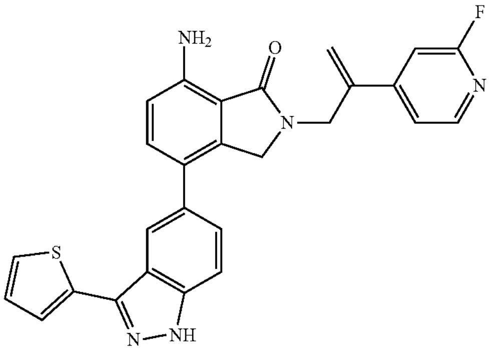 [SMILES: C=C(CN1Cc2c(-c3ccc4[nH]nc(-c5cccs5)c4c3)ccc(N)c2C1=O)c1ccnc(F)c1] | 7-amino-2-[2-(2-fluoropyridin-4-yl)prop-2-en-1-yl]-4-[3-(thiophen-2-yl)-1H-indazol-5-yl]-2,3-dihydro-1H-isoindol-1-one | 482 |
| 485. | 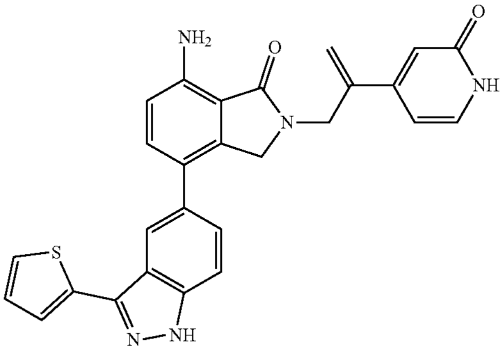 [SMILES: C=C(CN1Cc2c(-c3ccc4[nH]nc(-c5cccs5)c4c3)ccc(N)c2C1=O)c1cc[nH]c(=O)c1] | 7-amino-2-[2-(2-oxo-1,2-dihydropyridin-4-yl)prop-2-en-1-yl]-4-[3-(thiophen-2-yl)-1H-indazol-5-yl]-2,3-dihydro-1H-isoindol-1-one | 480.2 |
| 486. | 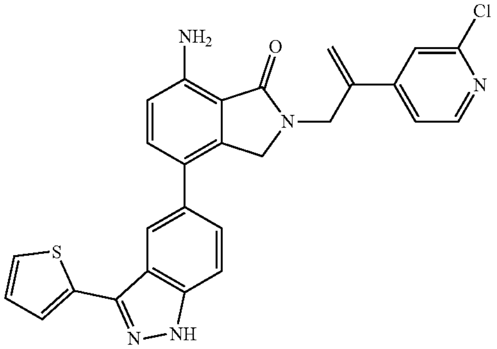 [SMILES: C=C(CN1Cc2c(-c3ccc4[nH]nc(-c5cccs5)c4c3)ccc(N)c2C1=O)c1ccnc(Cl)c1] | 7-amino-2-[2-(2-chloropyridin-4-yl)prop-2-en-1-yl]-4-[3-(thiophen-2-yl)-1H-indazol-5-yl]-2,3-dihydro-1H-isoindol-1-one | 498.1 |

TABLE 9-continued
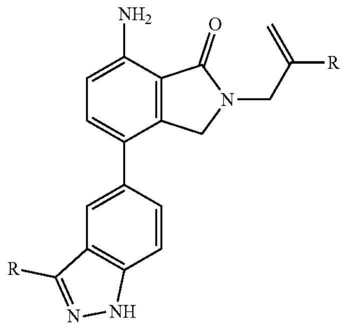
| Cpd. No. | Structure | IUPAC | LC-MS (ES+, m/z) |
|---|---|---|---|
| 487. | 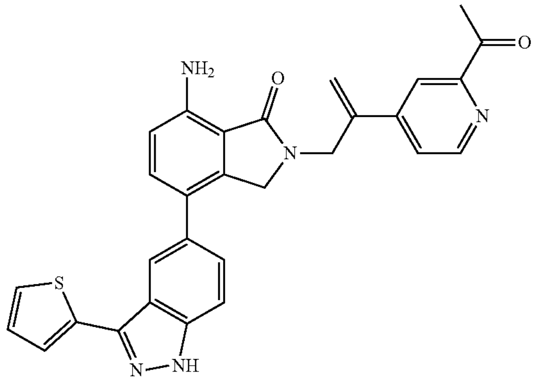 [SMILES: C=C(CN1Cc2c(-c3ccc4[nH]nc(-c5cccs5)c4c3)ccc(N)c2C1=O)c1ccnc(C(C)=O)c1] | 2-[2-(2-acetylpyridin-4-yl)prop-2-en-1-yl]-7-amino-4-[3-(thiophen-2-yl)-1H-indazol-5-yl]-2,3-dihydro-1H-isoindol-1-one | 506.1 |
| 488. | 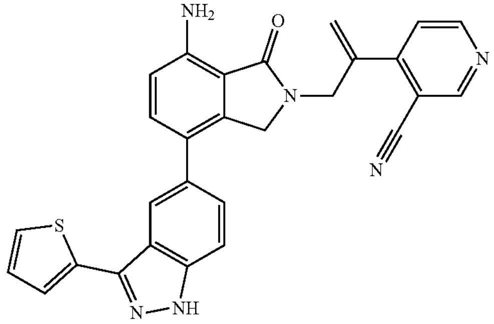 [SMILES: C=C(CN1Cc2c(-c3ccc4[nH]nc(-c5cccs5)c4c3)ccc(N)c2C1=O)c1ccncc1C#N] | 4-(3-{7-amino-1-oxo-4-[3-(thiophen-2-yl)-1H-indazol-5-yl]-2,3-dihydro-1H-isoindol-2-yl}prop-1-en-2-yl)pyridine-3-carbonitrile | 489.1 |
| 489. | 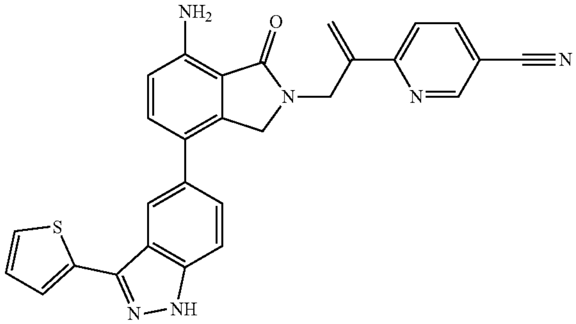 [SMILES: C=C(CN1Cc2c(-c3ccc4[nH]nc(-c5cccs5)c4c3)ccc(N)c2C1=O)c1ccc(C#N)cn1] | 6-(3-{7-amino-1-oxo-4-[3-(thiophen-2-yl)-1H-indazol-5-yl]-2,3-dihydro-1H-isoindol-2-yl}prop-1-en-2-yl)pyridine-3-carbonitrile | 489.1 |

TABLE 9-continued
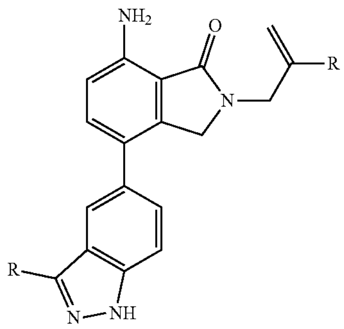
| Cpd. No. | Structure | IUPAC | LC-MS (ES+, m/z) |
|---|---|---|---|
| 490. | 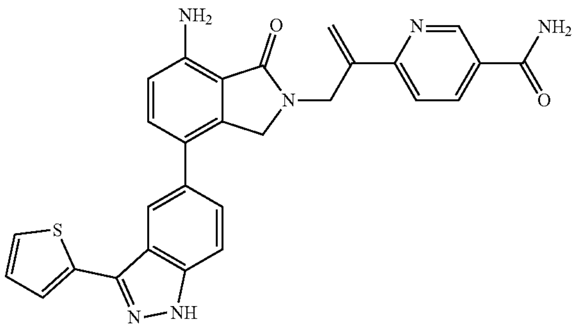 [SMILES: C=C(CN1Cc2c(-c3ccc4[nH]nc(-c5cccs5)c4c3)ccc(N)c2C1=O)c1ccc(C(N)=O)cn1] | 6-(3-{7-amino-1-oxo-4-[3-(thiophen-2-yl)-1H-indazol-5-yl]-2,3-dihydro-1H-isoindol-2-yl}prop-1-en-2-yl)pyridine-3-carboxamide | 507.2 |
| 491. | 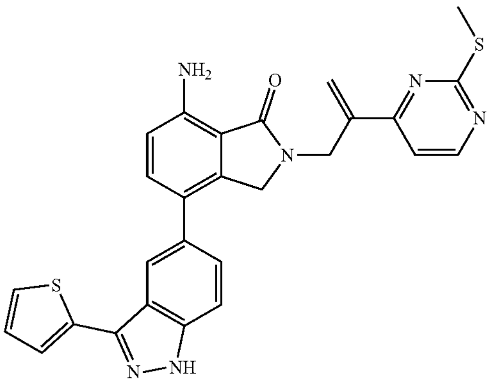 [SMILES: C=C(CN1Cc2c(-c3ccc4[nH]nc(-c5cccs5)c4c3)ccc(N)c2C1=O)c1ccnc(SC)n1] | 7-amino-2-{2-[2-(methylsulfanyl)pyrimidin-4-yl]prop-2-en-1-yl}-4-[3-(thiophen-2-yl)-1H-indazol-5-yl]-2,3-dihydro-1H-isoindol-1-one | 511.1 |
| 492. | 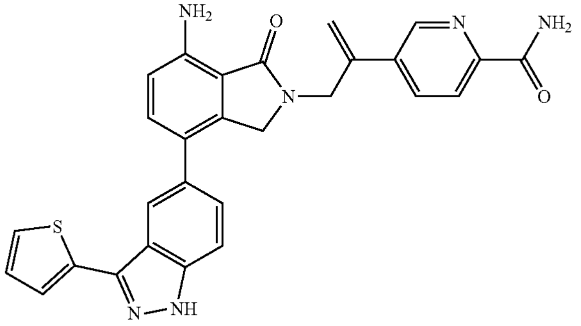 [SMILES: C=C(CN1Cc2c(-c3ccc4[nH]nc(-c5cccs5)c4c3)ccc(N)c2C1=O)c1ccc(C(N)=O)nc1] | 5-(3-{7-amino-1-oxo-4-[3-(thiophen-2-yl)-1H-indazol-5-yl]-2,3-dihydro-1H-isoindol-2-yl}prop-1-en-2-yl)pyridine-2-carboxamide | 507.1 |

Example 12: Method J

General Scheme for Method J

Route 1:

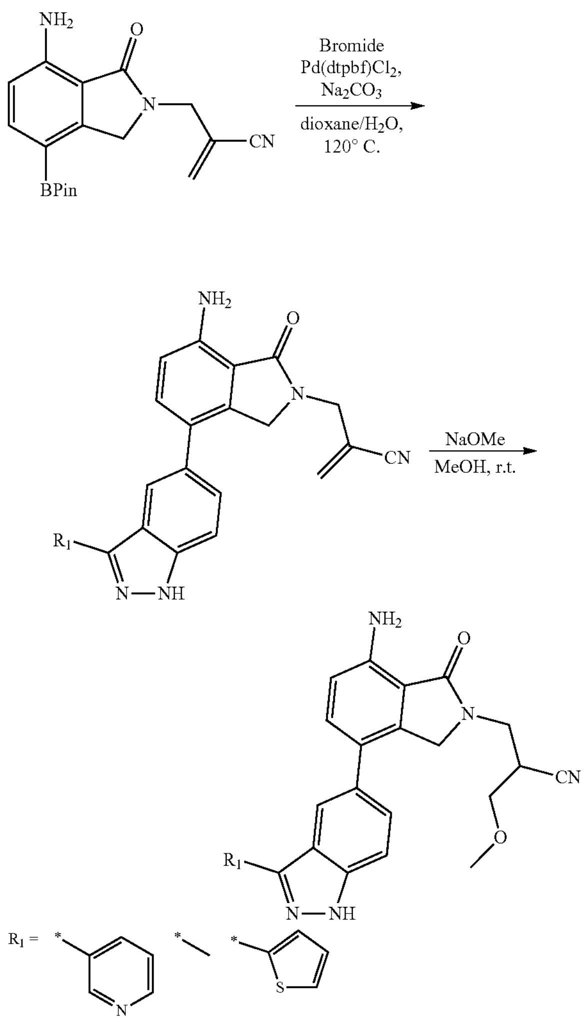

Preparation of 2-[[7-amino-1-oxo-4-[3-(3-pyridyl)-1H-indazol-5-yl]isoindolin-2-yl]methyl]-3-methoxy-propanenitrile (Compound 497)

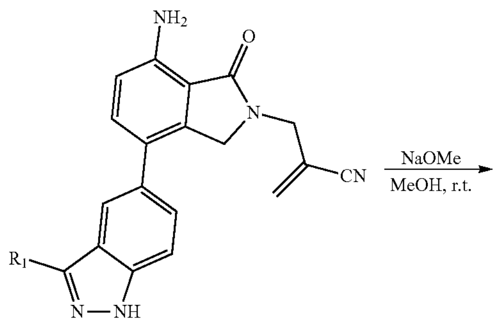

-continued

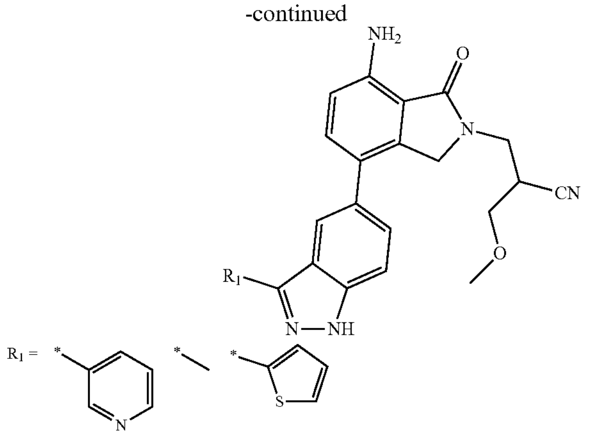

To a solution of 5-[7-amino-2-(2-cyanoallyl)-1-oxo-isoindolin-4-yl]-3-(3-pyridyl)indazole (50 mg, 93.77 μmol, 1 eq.) in MeOH (4 mL) was added NaOMe (300 mg, 5.55 mmol, 59.22 eq.). The reaction mixture was stirred at 15° C. for 0.5 hr. The reaction was quenched by adding water (10 mL) at 0° C., and the mixture was extracted with EtOAc (3×10 mL). The combined organic layers were washed with brine (30 mL), dried over anhydrous sodium sulfate, filtered, and concentrated in vacuo to give a residue. The residue was purified by HPLC to afford the title compound (5.7 mg, 12.82 μmol, 13.67% yield, 98.6% purity) as a white solid. LC-MS: $[M+H]^+$ 439.3.

Preparation of 2-[[7-amino-4-(3-methyl-1,2-benzoxazol-5-yl)-1-oxo-isoindolin-2-yl]methyl]prop-2-enenitrile

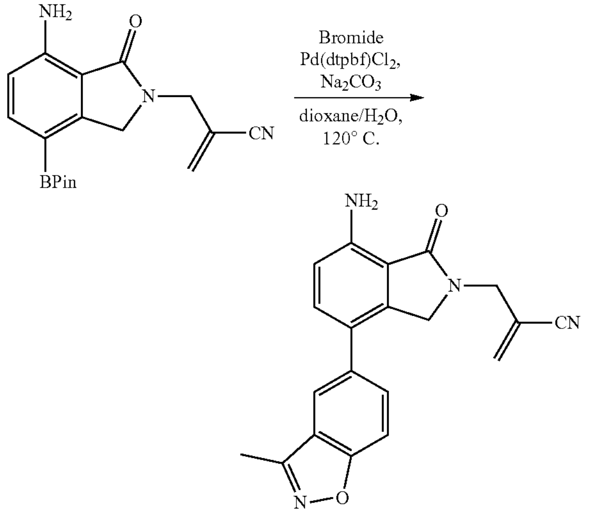

To a solution of 2-[[7-amino-1-oxo-4-(4,4,5,5-tetramethyl-1,3,2-dioxaborolan-2-yl)isoindolin-2-yl]methyl]prop-2-enenitrile (175.96 mg, 518.76 μmol, 1.1 eq.) and 5-bromo-3-methyl-1,2-benzoxazole (0.1 g, 471.60 μmol, 1 eq.) in dioxane (2 mL) and water (0.5 mL) were added $Na_2CO_3$ (149.95 mg, 1.41 mmol, 3 eq.), $Pd(dppf)Cl_2$ (15.37 mg, 23.58 μmol, 0.05 eq.). The reaction mixture was stirred at 120° C. for 0.5 hr under nitrogen. The reaction mixture was poured into sat. aq. EDTA (10 mL) and EtOAc (10 mL) was added. The solution was stirred at 20° C. for 1 h. The reaction mixture was extracted with EtOAc (3×10 mL). The organic layers was washed with water (3×20 mL) and brine (20 mL), dried over anhydrous sodium sulfate, filtered, and concentrated in vacuo to give a residue. The residue was purified by prep-TLC (silica gel; DCM:MeOH=20:1) to afford the title compound (60 mg, 174.23 μmol, 36.94% yield) as a yellow solid.

Preparation of 2-[[7-amino-4-(3-methyl-1,2-benzoxazol-5-yl)-1-oxo-isoindolin-2-yl]methyl]-3-methoxy-propanenitrile (Compound 501)

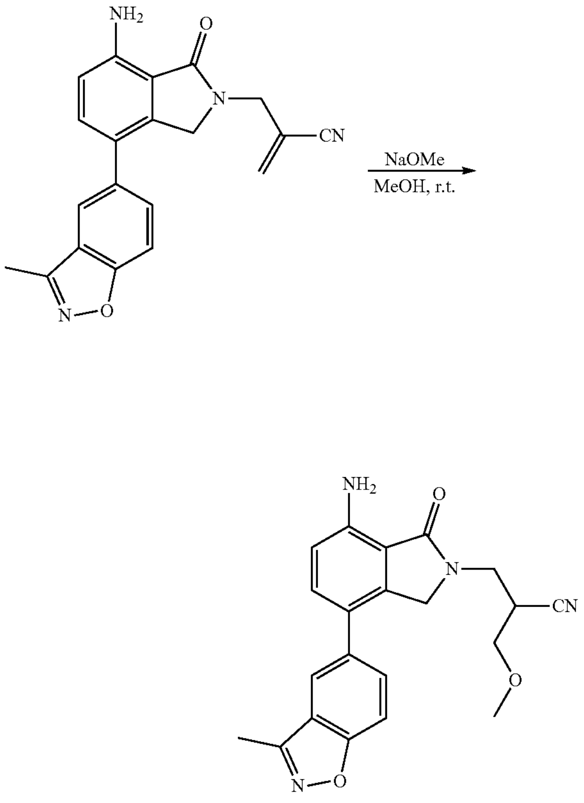

To a solution of 2-[[7-amino-4-(3-methyl-1,2-benzoxazol-5-yl)-1-oxo-isoindolin-2-yl]methyl]prop-2-enenitrile (60 mg, 174.23 μmol, 1 eq.) in MeOH (6 mL) was added NaOMe (600 mg, 11.11 mmol, 63.74 eq.). The mixture was stirred at 15° C. for 0.5 hr. The reaction was quenched with water (10 mL) at 0° C. and extracted with EtOAc (3×10 mL). The combined organic layers were washed with brine (30 mL), dried over anhydrous sodium sulfate, filtered, and concentrated in vacuo to give a residue. The residue was purified by prep-TLC (silica gel; DCM:MeOH=15:1) and SFC to afford the title compound (3.5 mg, 8.95 μmol, 96.2% purity) as a white solid. LC-MS: $[M+H]^+$ 377.1.

Preparation of 3-(7-amino-1-oxo-4-(3-(pyridin-3-yl)-1H-indazol-5-yl)isoindolin-2-yl)-2-(chloromethyl)propanenitrile (Compound 500)

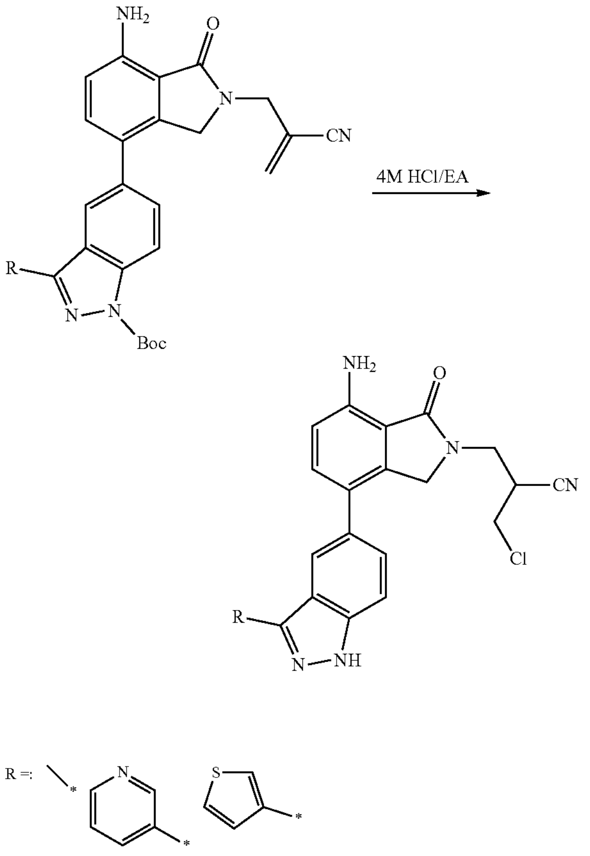

A solution of tert-butyl 5-[7-amino-2-(2-cyanoallyl)-1-oxo-isoindolin-4-yl]-3-(3-pyridyl)indazole-1-carboxylate (50 mg, 98.71 μmol, 1 eq.) in HCl/EtOAc (4 M, 10 mL, 405.24 eq.) was stirred at 70° C. for 24 h. The reaction mixture was concentrated in vacuo to remove solvent. The residue was purified by prep-HPLC to afford the title compound (10.1 mg, 21.41 μmol, 93.9% purity) as a white solid. LC-MS: $[M+H]^+$ 443.1.

General Procedure for Addition of Amines.

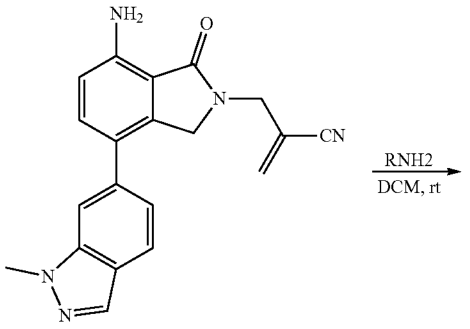

-continued

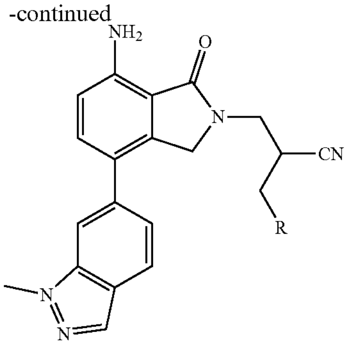

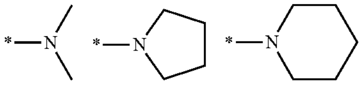

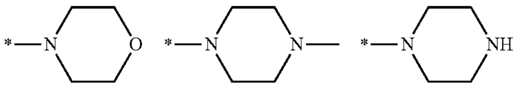

-continued

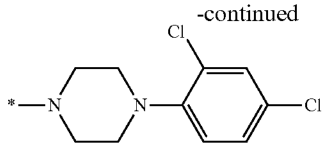

Preparation of 2-{[7-amino-4-(1-methyl-1H-indazol-6-yl)-1-oxo-2,3-dihydro-1H-isoindol-2-yl]methyl}-3-(morpholin-4-yl)propanenitrile (Compound 504)

To a solution of 2-{[7-amino-4-(1-methyl-1H-indazol-6-yl)-1-oxo-2,3-dihydro-1H-isoindol-2-yl]methyl}prop-2-enenitrile (50 mg, 146 μmol, 1 eq.) in DCM (4 mL) was added morpholine (63 μL, 146 μmol, 5 eq.). The reaction mixture was stirred at r.t. for 18 h. The reaction mixture was diluted with water and extracted with DCM (3×10 mL). The combined organic layers were washed with brine (30 mL), dried over anhydrous sodium sulfate, filtered, and concentrated in vacuo to give a residue. The residue was purified by HPLC to afford the desired product. LC-MS: $[M+H]^+$ 431.3

TABLE 10 shows compounds prepared using the methods described in EXAMPLE 12.

TABLE 10

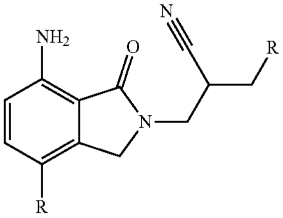

| Cpd. No. | Structure | IUPAC | LC-MS (ES+, m/z) |
|---|---|---|---|
| 493. | 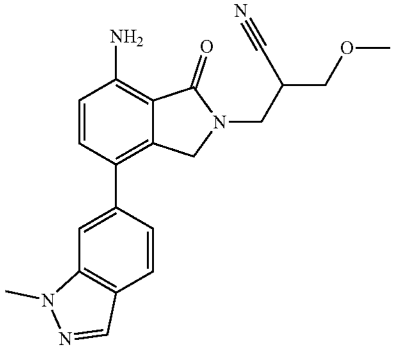 | 2-{[7-amino-4-(1-methyl-1H-indazol-6-yl)-1-oxo-2,3-dihydro-1H-isoindol-2-yl]methyl}-3-methoxypropanenitrile | 376.2 |
| 494. | 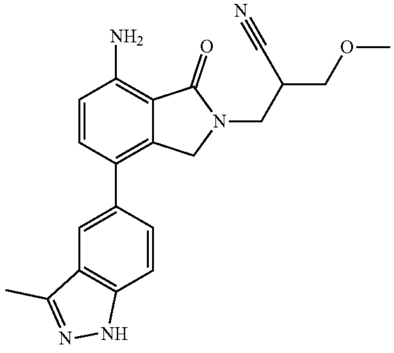 | 2-{[7-amino-4-(3-methyl-1H-indazol-5-yl)-1-oxo-2,3-dihydro-1H-isoindol-2-yl]methyl}-3-methoxypropanenitrile | 376.2 |

TABLE 10-continued
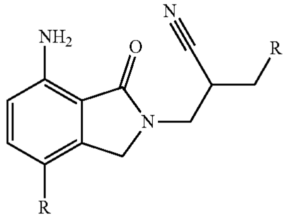
| Cpd. No. | Structure | IUPAC | LC-MS (ES+, m/z) |
|---|---|---|---|
| 495. | 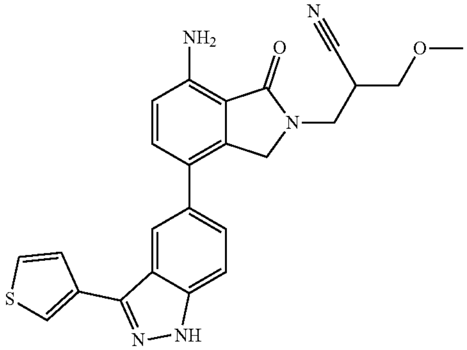 [SMILES: COCC(C#N)CN1Cc2c(-c3ccc4[nH]nc(-c5ccsc5)c4c3)ccc(N)c2C1=O] | 2-({7-amino-1-oxo-4-[3-(thiophen-3-yl)-1H-indazol-5-yl]-2,3-dihydro-1H-isoindol-2-yl}methyl)-3-methoxypropanenitrile | 444.1 |
| 496. | 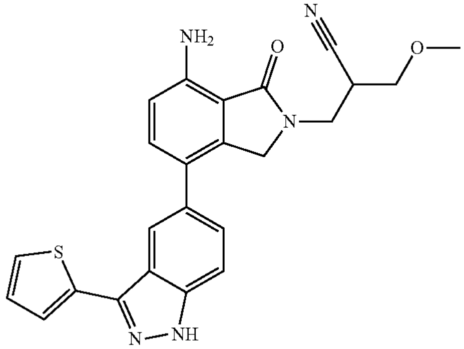 [SMILES: COCC(C#N)CN1Cc2c(-c3ccc4[nH]nc(-c5cccs5)c4c3)ccc(N)c2C1=O] | 2-({7-amino-1-oxo-4-[3-(thiophen-2-yl)-1H-indazol-5-yl]-2,3-dihydro-1H-isoindol-2-yl}methyl)-3-methoxypropanenitrile | 444.2 |
| 497. | 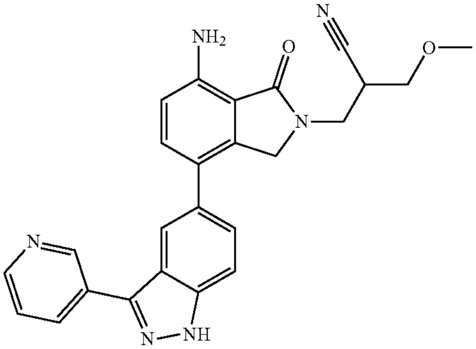 [SMILES: COCC(C#N)CN1Cc2c(-c3ccc4[nH]nc(-c5cccnc5)c4c3)ccc(N)c2C1=O] | 2-({7-amino-1-oxo-4-[3-(pyridin-3-yl)-1H-indazol-5-yl]-2,3-dihydro-1H-isoindol-2-yl}methyl)-3-methoxypropanenitrile | 439.3 |

TABLE 10-continued
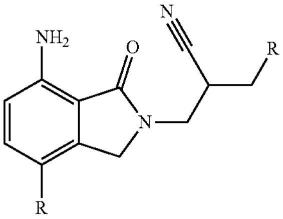
| Cpd. No. | Structure | IUPAC | LC-MS (ES+, m/z) |
|---|---|---|---|
| 498. | 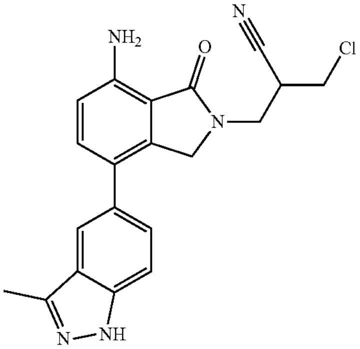 [SMILES: Cc1n[nH]c2ccc(-c3ccc(N)c4c3CN(CC(C#N)CCl)C4=O)cc12] | 2-{[7-amino-4-(3-methyl-1H-indazol-5-yl)-1-oxo-2,3-dihydro-1H-isoindol-2-yl]methyl}-3-chloropropanenitrile | 380.1 |
| 499. | 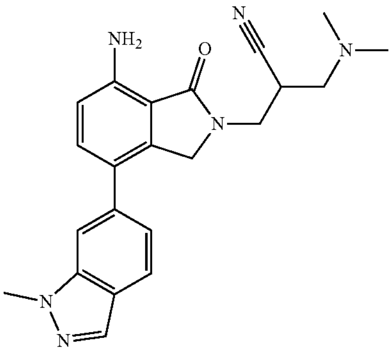 | 2-{[7-amino-4-(1-methyl-1H-indazol-6-yl)-1-oxo-2,3-dihydro-1H-isoindol-2-yl]methyl}-3-(dimethylamino)propanenitrile | 389.3 |
| 500. | 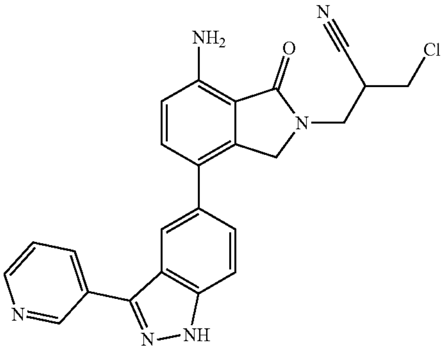 [SMILES: N#CC(CCl)CN1Cc2c(-c3ccc4[nH]nc(-c5cccnc5)c4c3)ccc(N)c2C1=O] | 2-({7-amino-1-oxo-4-[3-(pyridin-3-yl)-1H-indazol-5-yl]-2,3-dihydro-1H-isoindol-2-yl}methyl)-3-chloropropanenitrile | 443.1 |

TABLE 10-continued
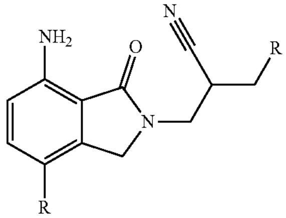
| Cpd. No. | Structure | IUPAC | LC-MS (ES+, m/z) |
|---|---|---|---|
| 501. | 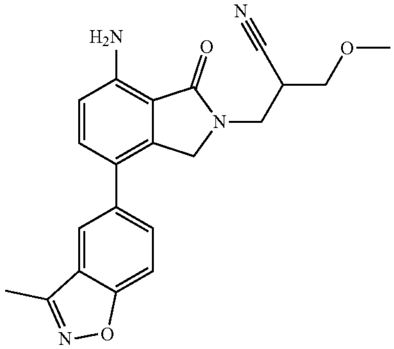 | 2-{[7-amino-4-(3-methyl-1,2-benzoxazol-5-yl)-1-oxo-2,3-dihydro-1H-isoindol-2-yl]methyl}-3-methoxypropanenitrile | 377.2 |
| 502. | 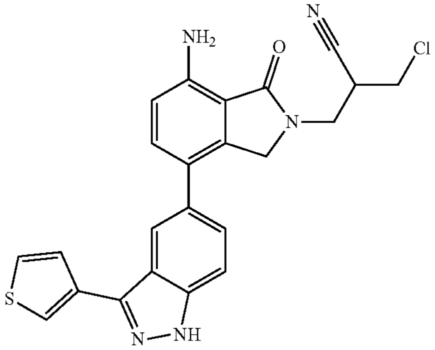 [SMILES: N#CC(CCl)CN1Cc2c(-c3ccc4[nH]nc(-c5ccsc5)c4c3)ccc(N)c2C1=O] | 2-({7-amino-1-oxo-4-[3-(thiophen-3-yl)-1H-indazol-5-yl]-2,3-dihydro-1H-isoindol-2-yl}methyl)-3-chloropropanenitrile | 448.1 |
| 503. | 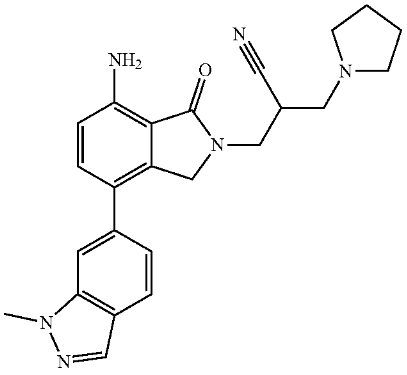 [SMILES: Cn1ncc2ccc(-c3ccc(N)c4c3CN(CC(C#N)CN3CCCC3)C4=O)cc21] | 2-{[7-amino-4-(1-methyl-1H-indazol-6-yl)-1-oxo-2,3-dihydro-1H-isoindol-2-yl]methyl}-3-(pyrrolidin-1-yl)propanenitrile | 415.2 |

TABLE 10-continued
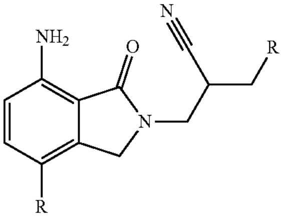
| Cpd. No. | Structure | IUPAC | LC-MS (ES+, m/z) |
|---|---|---|---|
| 504. | 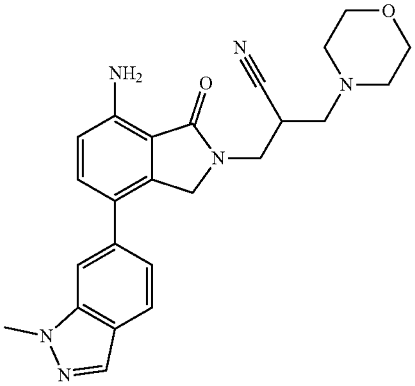 [SMILES: Cn1ncc2ccc(-c3ccc(N)c4c3CN(CC(C#N)CN3CCOCC3)C4=O)cc21] | 2-{[7-amino-4-(1-methyl-1H-indazol-6-yl)-1-oxo-2,3-dihydro-1H-isoindol-2-yl]methyl}-3-(morpholin-4-yl)propanenitrile | 431.3 |
| 505. | 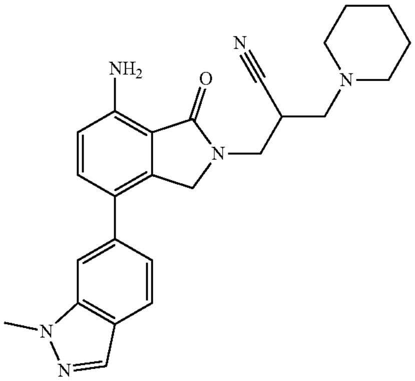 [SMILES: Cn1ncc2ccc(-c3ccc(N)c4c3CN(CC(C#N)CN3CCCCC3)C4=O)cc21] | 2-{[7-amino-4-(1-methyl-1H-indazol-6-yl)-1-oxo-2,3-dihydro-1H-isoindol-2-yl]methyl}-3-(piperidin-1-yl)propanenitrile | 429.2 |
| 506. | 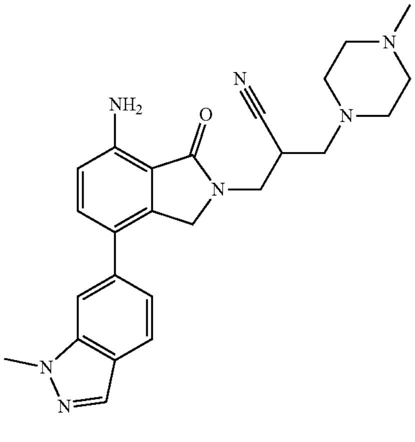 | 2-{[7-amino-4-(1-methyl-1H-indazol-6-yl)-1-oxo-2,3-dihydro-1H-isoindol-2-yl]methyl}-3-(4-methylpiperazin-1-yl)propanenitrile | 444.2 |

TABLE 10-continued
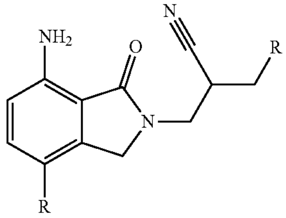
| Cpd. No. | Structure | IUPAC | LC-MS (ES+, m/z) |
|---|---|---|---|
| 507. | 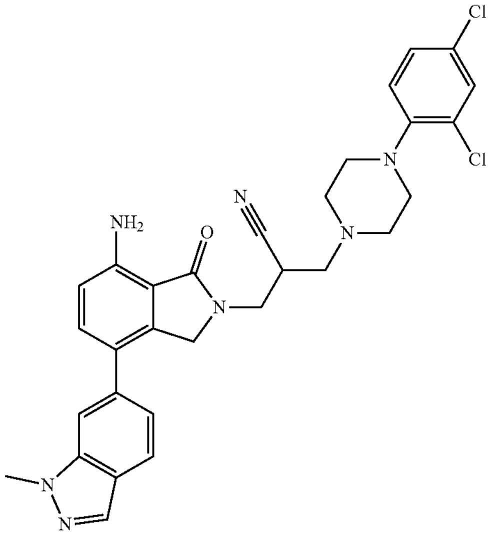 [SMILES: Cn1ncc2ccc(-c3ccc(N)c4c3CN(CC(C#N)CN3CCN(c5ccc(Cl)cc5Cl)CC3)C4=O)cc21] | 2-{[7-amino-4-(1-methyl-1H-indazol-6-yl)-1-oxo-2,3-dihydro-1H-isoindol-2-yl]methyl}-3-[4-(3,4-dichlorophenyl)piperazin-1-yl]propanenitrile | 574.2 |
| 508. | 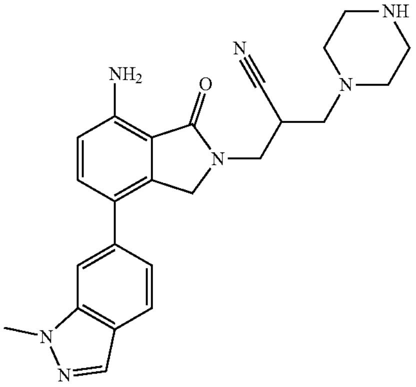 [SMILES: Cn1ncc2ccc(-c3ccc(N)c4c3CN(CC(C#N)CN3CCNCC3)C4=O)cc21] | 2-{[7-amino-4-(1-methyl-1H-indazol-6-yl)-1-oxo-2,3-dihydro-1H-isoindol-2-yl]methyl}-3-(piperazin-1-yl)propanenitrile | 430.3 |
| 509. | 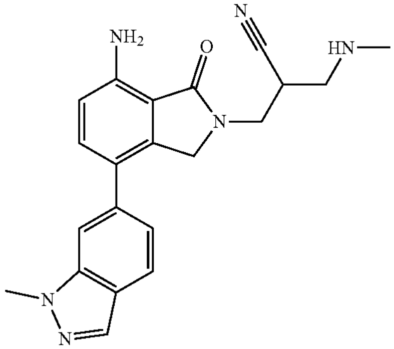 | 2-{[7-amino-4-(1-methyl-1H-indazol-6-yl)-1-oxo-2,3-dihydro-1H-isoindol-2-yl]methyl}-3-(methylamino)propanenitrile | 375.2 |

Example 13: Method K

General Scheme for Method K

Route 1:

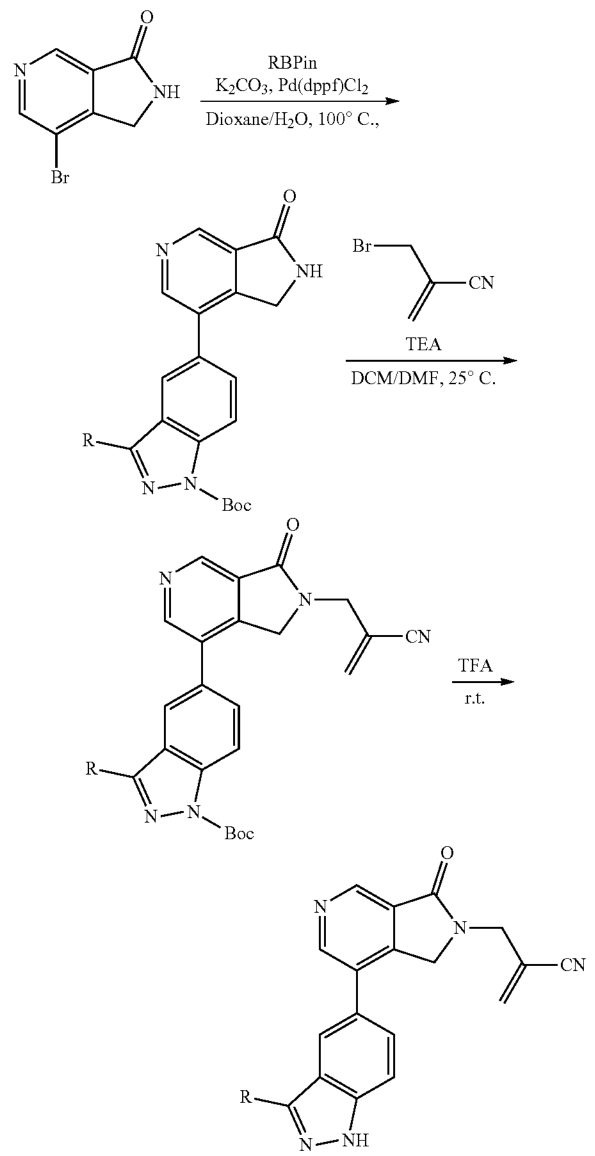

Preparation of tert-butyl 3-cyclopropyl-5-{3-oxo-1H,2H,3H-pyrrolo[3,4-c]pyridin-7-yl}-1H-indazole-1-carboxylate

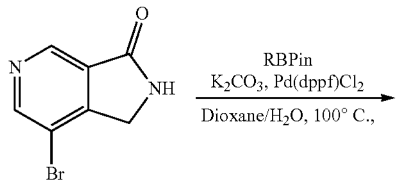

-continued

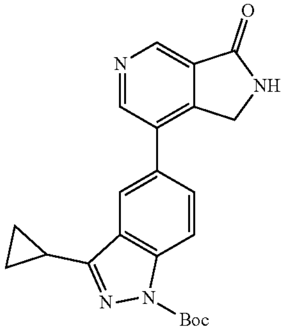

To a mixture of 7-bromo-1H,2H,3H-pyrrolo[3,4-c]pyridin-3-one (324.69 mg, 844.95 μmol, 1 eq.) in dioxane (3 mL) and water (0.6 mL) were added $K_2CO_3$ (467.12 mg, 3.38 mmol, 4 eq.), Pd(dppf)$Cl_2$ (27.53 mg, 42.25 μmol, 0.05 eq.) in one portion at 100° C. under nitrogen. The mixture was stirred at 100° C. for 5 min, TLC (DCM:MeOH=20:1) showed that the reaction was complete. The residue was poured into sat. EDTA (30 mL) and stirred for 60 min. The aqueous phase was extracted with EtOAc (3×10 mL). The combined organic phase was washed with brine (3×10 mL), dried over anhydrous sodium sulfate, filtered, and concentrated. The crude material was triturated with EtOAc (5 mL) and PE (20 mL), and the resulting solid was collected by filtration to afford the title compound (0.2 g, 512.25 μmol, 61% yield) as a yellow solid.

Preparation of tert-butyl 5-[2-(2-cyano-2-methylideneethyl)-3-oxo-1H,2H,3H-pyrrolo[3,4-c]pyridin-7-yl]-3-cyclopropyl-1H-indazole-1-carboxylate

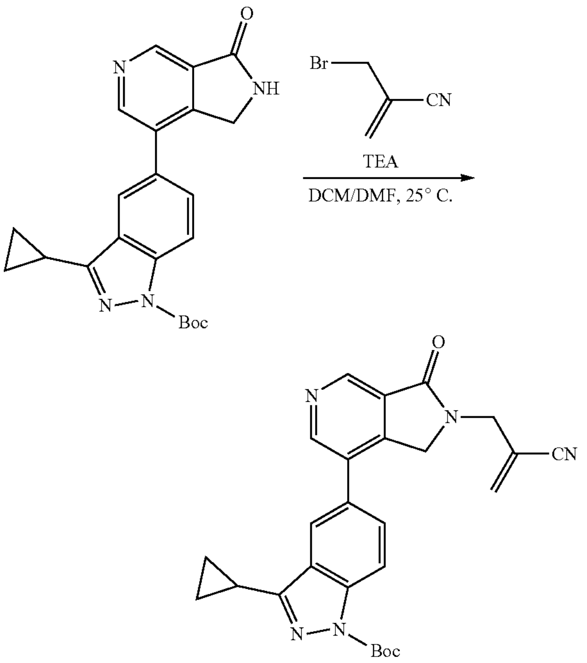

To a mixture of tert-butyl 3-cyclopropyl-5-{3-oxo-1H,2H,3H-pyrrolo[3,4-c]pyridin-7-yl}-1H-indazole-1-carboxylate (0.02 g, 51.23 μmol, 1 eq.) in DCM (0.5 mL) and DMF (0.5 mL) was added TEA (10.37 mg, 102.45 μmol, 14.26 μL, 2 eq.) in one portion at 25° C. under nitrogen. The mixture was stirred at 25° C. for 10 min, then added 2-(bromomethyl)prop-2-enenitrile (5.98 mg, 40.98 μmol, 0.8 eq.). The mixture was stirred at 25° C. for 50 min. The residue was poured into ice-water (30 mL) and stirred for 5 min. The aqueous phase was extracted with EtOAc (3×10 mL). The combined organic phase was washed with brine (3×10 mL), dried over anhydrous sodium sulfate, filtered, and concentrated. The reaction was purified by prep-TLC (DCM:MeOH=25:1) to afford the title compound (1 mg, 2.20 μmol, 4.29% yield) as a yellow solid.

Preparation of 2-{[7-(3-cyclopropyl-1H-indazol-5-yl)-3-oxo-1H,2H,3H-pyrrolo[3,4-c]pyridin-2-yl]methyl}prop-2-enenitrile (Compound 512)

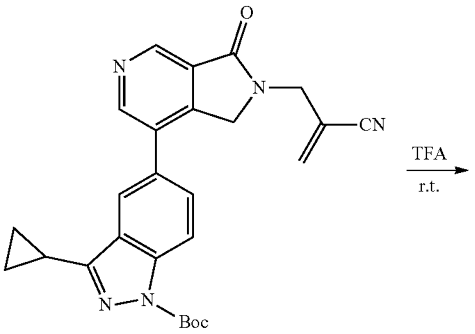

-continued

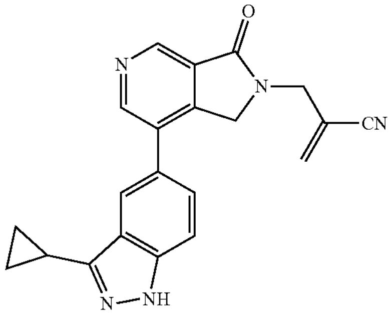

A mixture of tert-butyl 5-[2-(2-cyano-2-methylidene-ethyl)-3-oxo-1H,2H,3H-pyrrolo[3,4-c]pyridin-7-yl]-3-cyclopropyl-1H-indazole-1-carboxylate (10.61 mg, 23.28 μmol, 1 eq.) in trifluoroacetic acid (2 mL) was stirred at 25° C. for 2 h. LCMS showed that the reaction was complete. The reaction mixture was concentrated to give crude product, which was purified by prep-HPLC and lyophilized to afford the title compound (1.1 mg, 2.91 μmol, 12.5000 yield, 9400 purity) as a yellow solid. LC-MS: $[M+H]^+$ 356.1.

TABLE 11 shows compounds prepared using the methods described in EXAMPLE 13.

TABLE 11

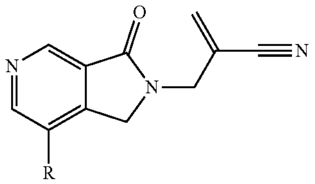

| Cpd. No. | Structure | IUPAC | LC-MS (ES+, m/z) |
|---|---|---|---|
| 510. | 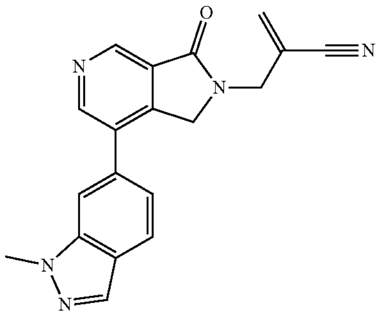 [SMILES: C=C(C#N)CN1Cc2c(cncc2-c2ccc3cnn(C)c3c2)C1=O] | 2-{[7-(1-methyl-1H-indazol-6-yl)-3-oxo-1H,2H,3H-pyrrolo[3,4-c]pyridin-2-yl]methyl}prop-2-enenitrile | 330.1 |

TABLE 11-continued
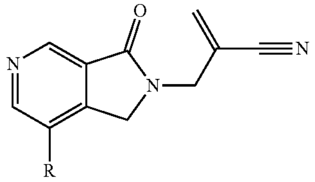
| Cpd. No. | Structure | IUPAC | LC-MS (ES+, m/z) |
|---|---|---|---|
| 511. | 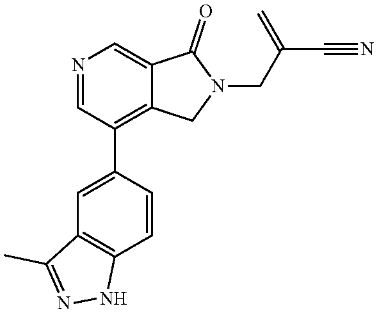 | 2-{[7-(3-methyl-1H-indazol-5-yl)-3-oxo-1H,2H,3H-pyrrolo[3,4-c]pyridin-2-yl]methyl}prop-2-enenitrile | 330.1 |
| 512. | 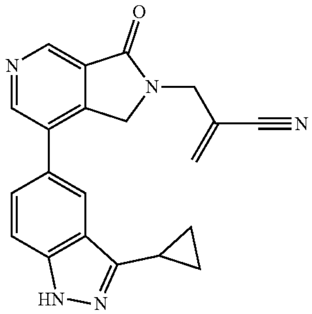 [SMILES: C=C(C#N)CN1Cc2c(cncc2-c2ccc3[nH]nc(C4CC4)c3c2)C1=O] | 2-{[7-(3-cyclopropyl-1H-indazol-5-yl)-3-oxo-1H,2H,3H-pyrrolo[3,4-c]pyridin-2-yl]methyl}prop-2-enenitrile | 356.1 |
Example 14: Method L
General Scheme for Method L
Route 1:
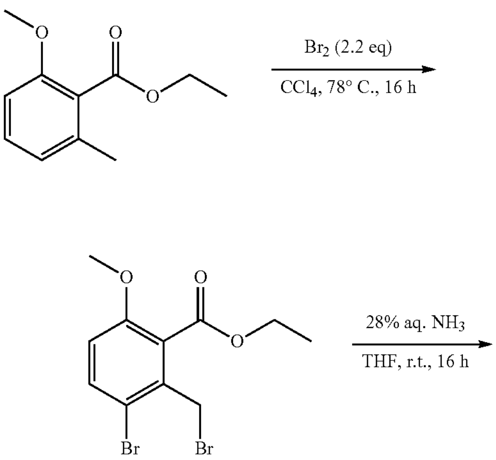
-continued
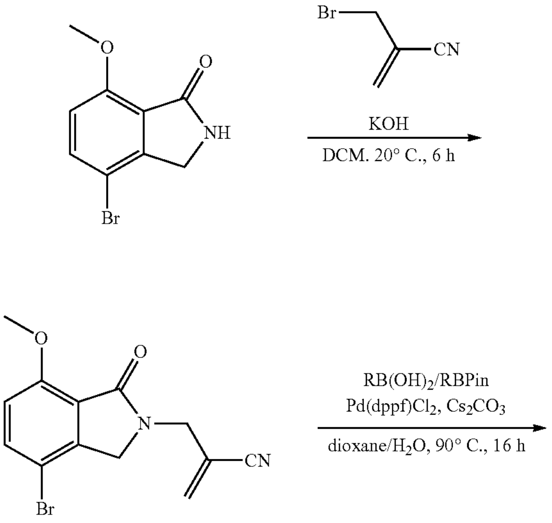

-continued

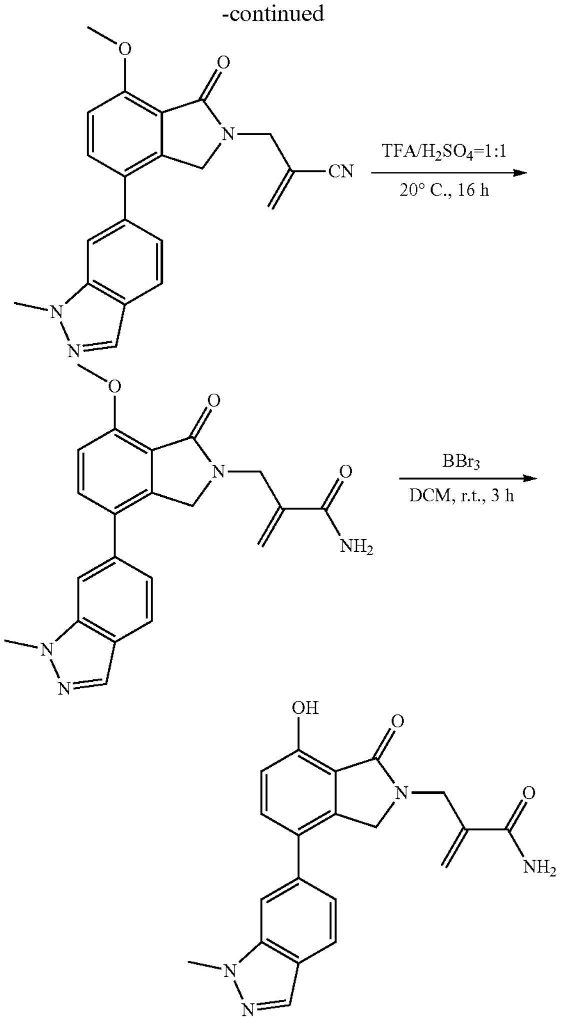

Preparation of ethyl 3-bromo-6-methoxy-2-methyl-benzoate

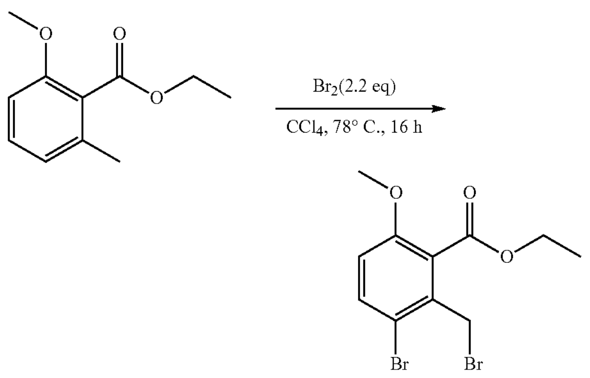

To a mixture of ethyl 2-methoxy-6-methyl-benzoate (5 g, 25.74 mmol, 1 eq.) in $CCl_4$ (100 mL) was added $Br_2$ (9.05 g, 56.63 mmol, 2.92 mL, 2.2 eq.). The mixture was stirred at 78° C. for 16 h under nitrogen atmosphere. TLC showed the starting material was consumed. The mixture was concentrated, and the residue was purified by column chromatography on silica (PE:EtOAc=15:1 to 10:1) to obtain the title compound (1.1 g, 3.12 mmol, 12.12% yield) as a white solid.

Preparation of 4-bromo-7-methoxy-isoindolin-1-one

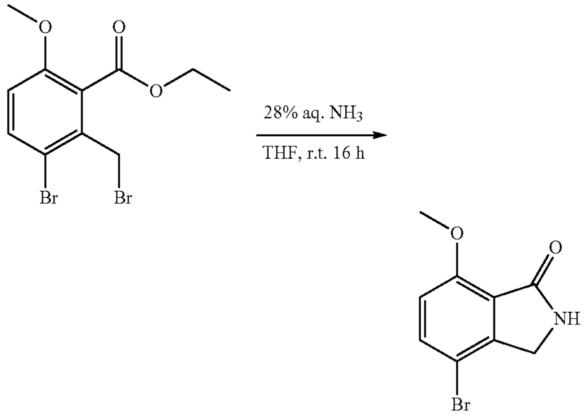

To a solution of ethyl 3-bromo-2-(bromomethyl)-6-methoxy-benzoate (1 g, 2.56 mmol, 1 eq.) in THF (10 mL) was added $NH_3$ solution (6.40 g, 51.13 mmol, 7.03 mL, 28% purity, 20 eq.) at 20° C. The mixture was stirred at for 16 h. TLC showed the starting material was consumed. The resulting precipitate was collected by filtration. The filtration cake was washed with water (20 mL) and dried in vacuo to get the product to afford the title compound (0.6 g, 2.48 mmol, 96.95% yield) as a white solid.

Preparation of 2-[(4-bromo-7-methoxy-1-oxo-isoindolin-2-yl)methyl]prop-2-enenitrile

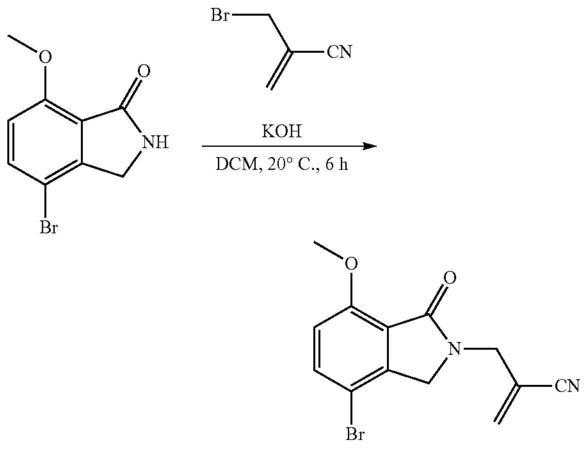

To a mixture of 4-bromo-7-methoxy-isoindolin-1-one (0.2 g, 826.21 μmol, 1 eq.), KOH (92.71 mg, 1.65 mmol, 2 eq.) and TBAI (91.55 mg, 247.86 μmol, 0.3 eq.) in DCM (20 mL) was added 2-(bromomethyl)prop-2-enenitrile (132.68 mg, 908.83 μmol, 1.1 eq.) at 20° C. The reaction mixture was stirred at 20° C. for 6 h. TLC showed that the reaction was complete. The mixture was poured into water (15 mL) and extracted with EtOAc (20 mL×3). The organic layers were washed with brine (15 mL), dried over anhydrous sodium sulfate, filtered, and concentrated to obtain the crude product. The residue was purified by column chromatography (silica gel; PE:EtOAc=4:1 to 1:1) to afford the title compound (0.11 g, 358.14 μmol, 43.35% yield) as a white solid.

Preparation of 2-[[7-methoxy-4-(1-methylindazol-6-yl)-1-oxo-isoindolin-2-yl]methyl]prop-2-enenitrile

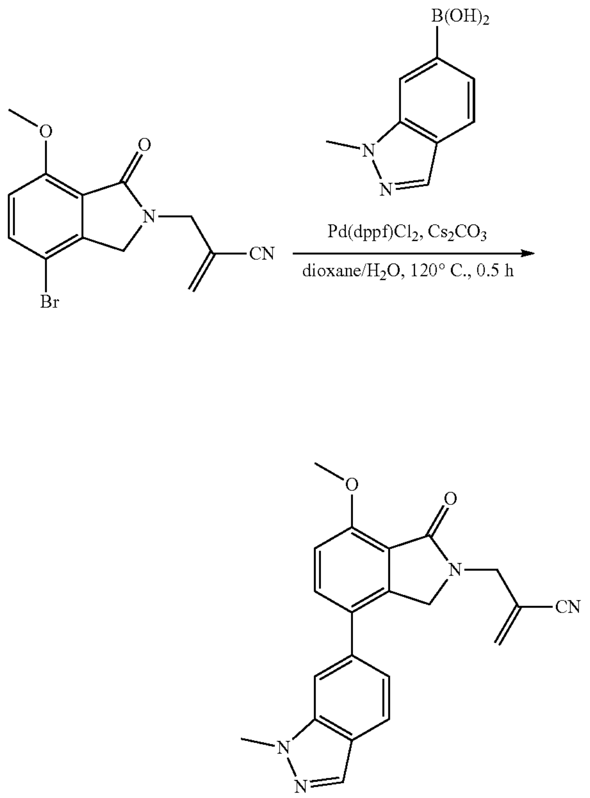

To a mixture of 2-[(4-bromo-7-methoxy-1-oxo-isoindolin-2-yl)methyl]prop-2-enenitrile (0.11 g, 358.14 μmol, 1 eq.) and (1-methylindazol-6-yl)boronic acid (75.63 mg, 429.77 μmol, 1.2 eq.) in dioxane (4 mL) and water (1 mL) were added $Na_2CO_3$ (113.88 mg, 1.07 mmol, 3 eq.) and Pd(dppf)$Cl_2$ (23.34 mg, 35.81 μmol, 0.1 eq.). The mixture was stirred at 120° C. under nitrogen for 0.5 h. TLC showed the starting material was consumed. The mixture was added to sat. EDTA (15 mL), and the resulting mixture was stirred for 1 h at 20° C. The mixture was extracted with EtOAc (5×15 mL). The organic layers were washed with brine (10 mL) and concentrated. The residue was purified by prep-TLC (silica gel; EtOAc:THF=3:1) to afford the title compound (0.06 g, 167.41 μmol, 46.75% yield) as a yellow solid.

Preparation of 2-{[7-methoxy-4-(1-methyl-1H-indazol-6-yl)-1-oxo-2,3-dihydro-1H-isoindol-2-yl]methyl}prop-2-enamide (Compound 513)

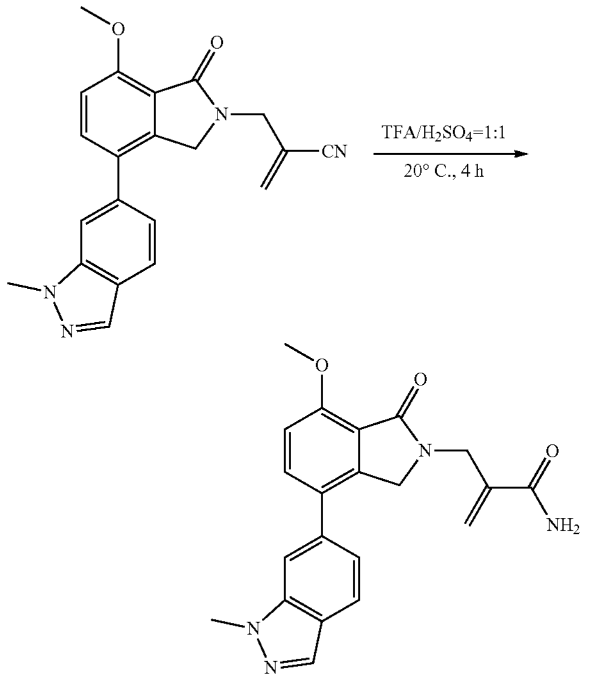

To a mixture of 2-[[7-methoxy-4-(1-methylindazol-6-yl)-1-oxo-isoindolin-2-yl]methyl]prop-2-enenitrile (0.06 g, 167.41 μmol, 1 eq.) in trifluoroacetic acid (0.3 mL) was added $H_2SO_4$ (0.3 mL), and the mixture was stirred at 20° C. for 4 h. LCMS showed that the reaction was complete. The mixture was poured into ice (10 g). The mixture was extracted with EtOAc (3×15 mL), and the aqueous layer was adjusted to pH=8 with sat. $NaHCO_3$. The mixture was extracted EtOAc (5×7 mL). The organic layers were washed with brine then concentrated. The residue was purified by prep-HPLC to afford the title compound (0.015 g, 39.28 μmol, 23.46% yield, 98.560% purity) as a white solid. LC-MS: $[M+H]^+$ 377.1.

Preparation of 2-[[7-hydroxy-4-(1-methylindazol-6-yl)-1-oxo-isoindolin-2-yl]methyl]prop-2-enamide (Compound 515)

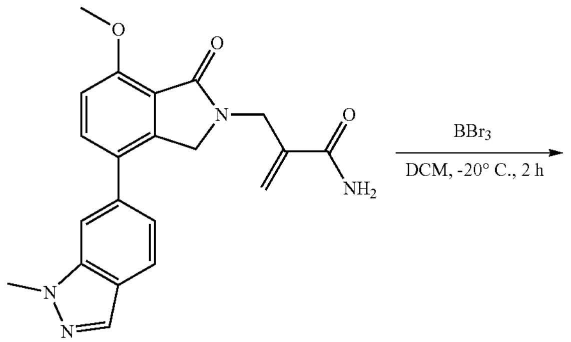

-continued

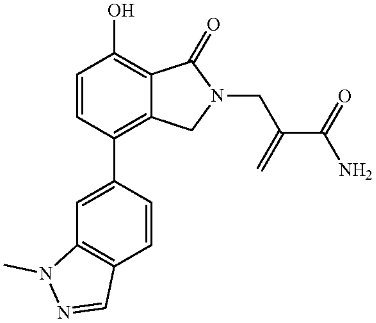

To a solution of 2-[[7-methoxy-4-(1-methylindazol-6-yl)-1-oxo-isoindolin-2-yl]methyl]prop-2-enamide (0.008 g, 21.25 μmol, 1 eq.) in DCM (2 mL) was added $BBr_3$ (15.97 mg, 63.76 μmol, 6.14 μL, 3 eq.). The mixture was stirred at −20° C. for 2 h. LCMS and HPLC showed the starting material was consumed. The mixture was poured into 5 mL of water and extracted with DCM (3×5 mL). The organic layers were concentrated. The residue was purified by prep-HPLC to afford the title compound (0.002 g, 5.36 μmol, 25.22% yield, 97.119% purity) as a white solid. LC-MS: $[M+H]^+$ 363.1.

Route 2:

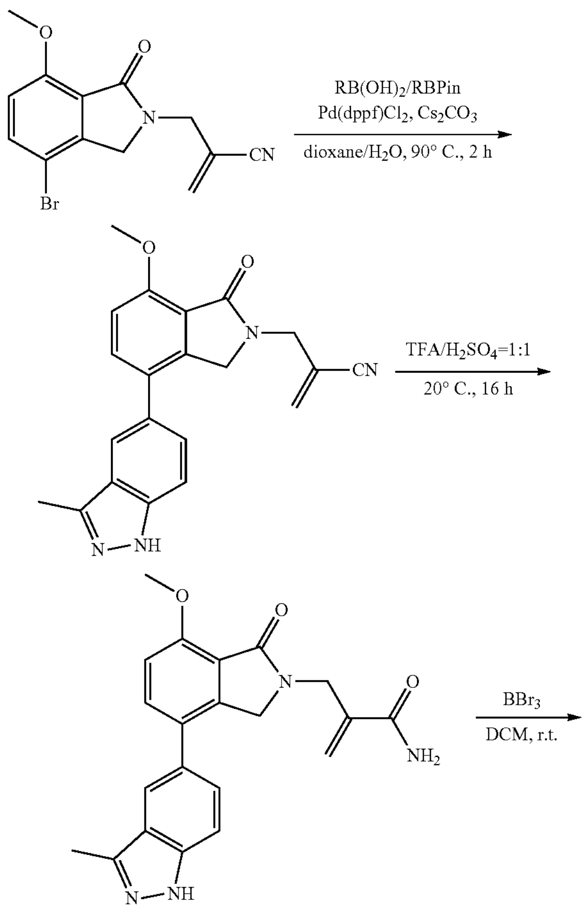

-continued

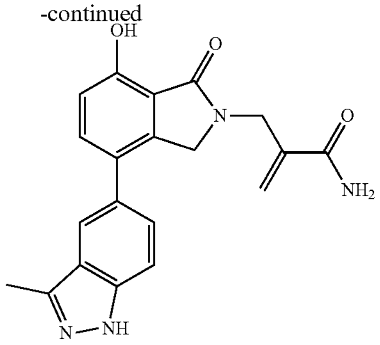

Preparation of 2-[[7-methoxy-4-(3-methyl-1H-indazol-5-yl)-1-oxo-isoindolin-2-yl]methyl]prop-2-en-enitrile

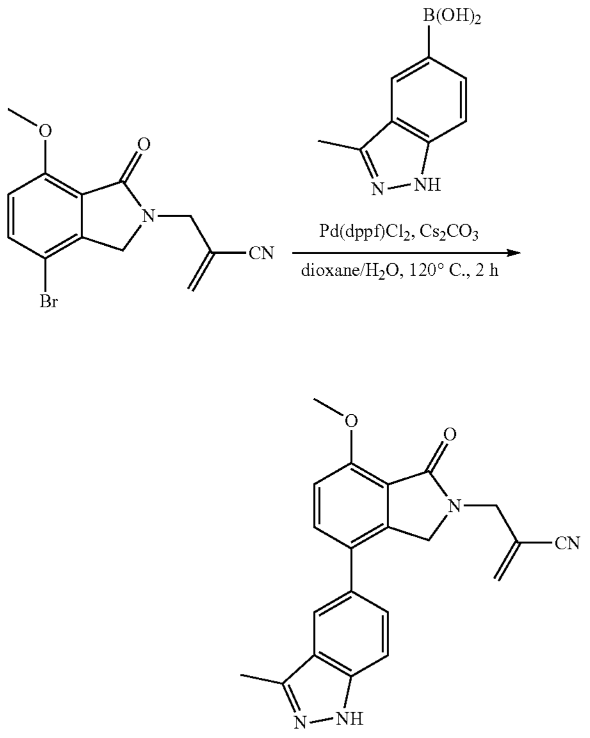

To a mixture of 2-[(4-bromo-7-methoxy-1-oxo-isoindolin-2-yl)methyl]prop-2-enenitrile (0.4 g, 1.30 mmol, 1 eq.) and (3-methyl-1H-indazol-5-yl) boronic acid (275.02 mg, 1.56 mmol, 1.2 eq.) in dioxane (12 mL) and water (3 mL) were added $Na_2CO_3$ (414.10 mg, 3.91 mmol, 3 eq.) and $Pd(dppf)Cl_2$ (84.88 mg, 130.23 μmol, 0.1 eq.). The mixture was stirred at 120° C. under nitrogen for 2 h. TLC showed the starting material was consumed. The mixture was added to sat. EDTA (25 mL) and stirred for 1 h at 20° C. and extracted with EtOAc (20 mL×5). The organic layers were washed with brine (10 mL) and concentrated. The residue was purified by prep-TLC (silica gel; EtOAc:THF=2:1) to afford the title compound (0.12 g, 301.35 μmol, 23.14% yield, 90% purity) as a yellow solid.

Preparation of 2-[[7-methoxy-4-(3-methyl-1H-indazol-5-yl)-1-oxo-isoindolin-2-yl]methyl]prop-2-enamide (Compound 514)

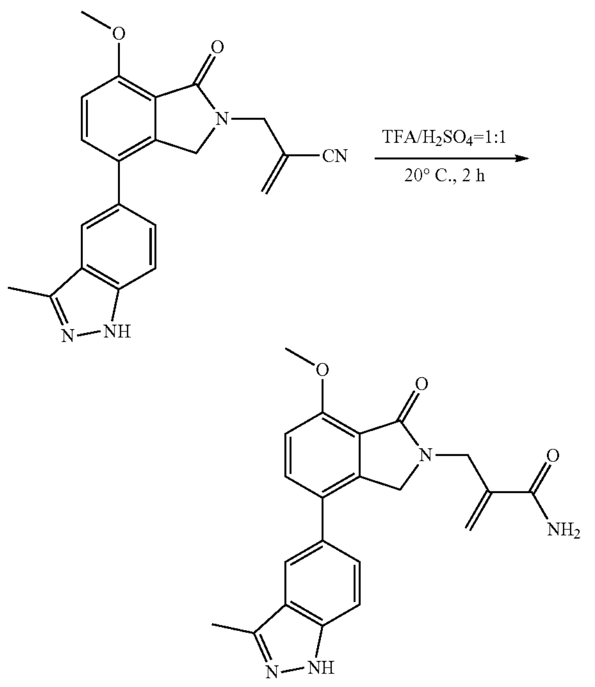

To a mixture of 2-[[7-methoxy-4-(3-methyl-1H-indazol-5-yl)-1-oxo-isoindolin-2-yl]methyl]prop-2-enenitrile (0.12 g, 334.83 μmol, 1 eq.) in trifluoroacetic acid (1.5 mL) was added $H_2SO_4$ (1.5 mL), and the mixture was stirred at 20° C. for 2 h. LCMS showed that the reaction was complete. The mixture was poured into ice (40 g), and the mixture was adjusted to pH=8 with sat. $NaHCO_3$. The mixture was extracted with EtOAc (5×25 mL). The organic layer was washed brine and concentrated. The residue was purified by prep-HPLC to afford the title compound (0.055 g, 143.26 μmol, 42.79% yield, 98.045% purity) as a white solid. LC-MS: $[M+H]^+$ 377.1.

Preparation of 2-[[7-hydroxy-4-(3-methyl-1H-indazol-5-yl)-1-oxo-isoindolin-2-yl]methyl]prop-2-enamide (Compound 515)

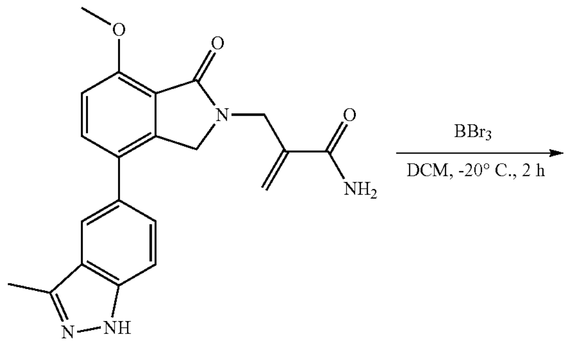

-continued

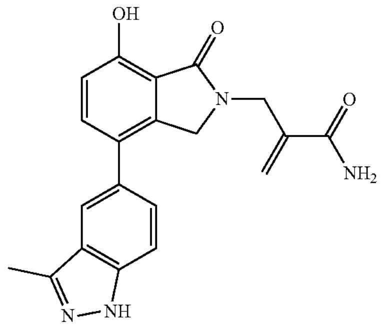

To a solution of 2-[[7-methoxy-4-(3-methyl-1H-indazol-5-yl)-1-oxo-isoindolin-2-yl]methyl]prop-2-enamide (0.045 g, 119.55 μmol, 1 eq.) in DCM (3 mL) was added $BBr_3$ (89.85 mg, 358.65 μmol, 34.56 μL, 3 eq.). The mixture was stirred at −20° C. for 2 h. LCMS showed that the reaction was complete. The mixture was poured in sat. $NaHCO_3$ (20 mL) and extracted with DCM (8×15 mL). The organic layers was washed with brine (20 mL), filtered, and concentrated. The residue was purified by prep-HPLC to afford the title compound (0.016 g, 44.08 μmol, 36.87% yield, 99.839% purity) as a white solid. LC-MS: $[M+H]^+$ 363.1.

Route 3:

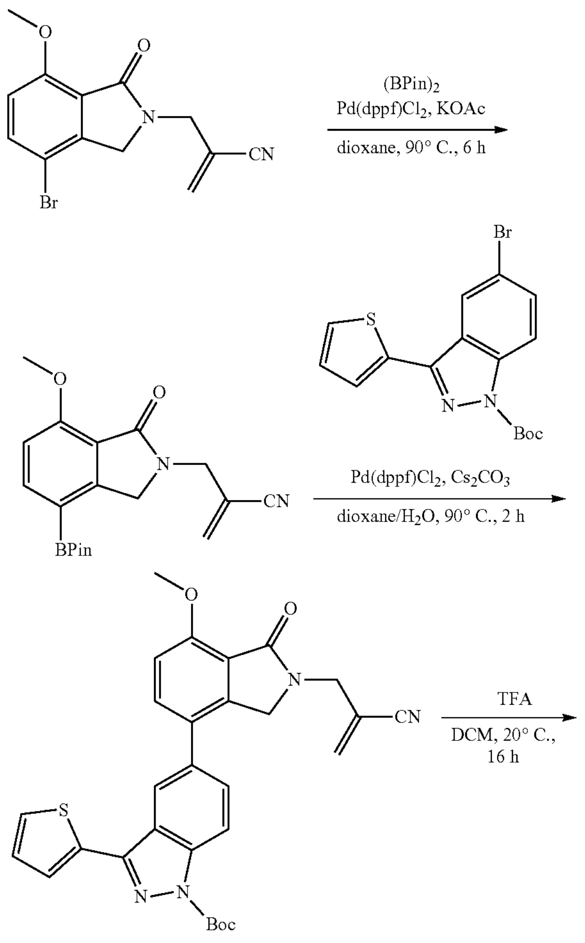

-continued

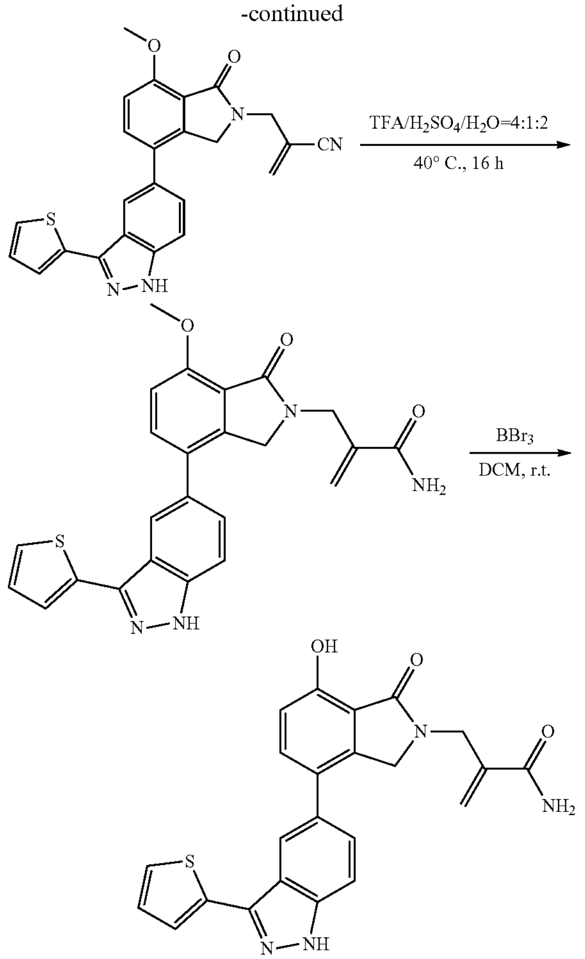

Preparation of 2-[[7-methoxy-1-oxo-4-(4,4,5,5-tetramethyl-1,3,2-dioxaborolan-2-yl)isoindolin-2-yl]methyl]prop-2-enenitrile

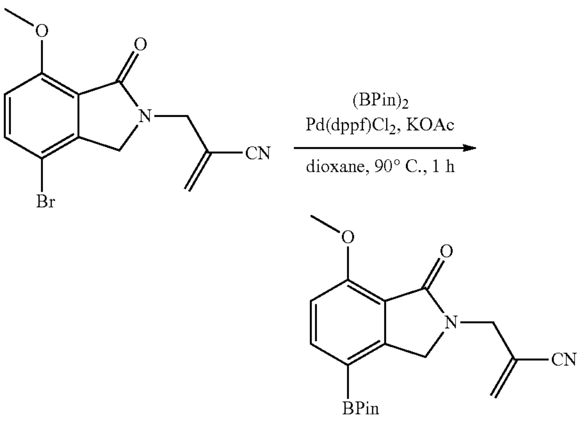

To a mixture of 2-[(4-bromo-7-methoxy-1-oxo-isoindolin-2-yl)methyl]prop-2-enenitrile (0.82 g, 2.67 mmol, 1 eq.) and 4,4,5,5-tetramethyl-2-(4,4,5,5-tetramethyl-1,3,2-dioxaborolan-2-yl)-1,3,2-dioxaborolane (1.02 g, 4 mmol, 1.5 eq.) in dioxane (20 mL) were added KOAc (524.02 mg, 5.34 mmol, 2 eq.) and $Pd(dppf)Cl_2$ (586.05 mg, 800.93 μmol, 0.3 eq.). The mixture was stirred at 90° C. under nitrogen for 1 h. LCMS showed the starting material was consumed. To the mixture was added to 40 mL of sat. EDTA at 20° C. and stirred for 1 h and extracted with EtOAc (3×40 mL). The organic layers were washed with brine (20 mL) and concentrated. The residue was purified by column chromatography (silica gel; PE:EtOAc=4:1 to 1:1) to afford the title compound (0.75 g, 1.91 mmol, 71.38% yield, 90% purity) as a yellow solid.

Preparation of tert-butyl 5-[2-(2-cyanoallyl)-7-methoxy-1-oxo-isoindolin-4-yl]-3-(2-thienyl)indazole-1-carboxylate

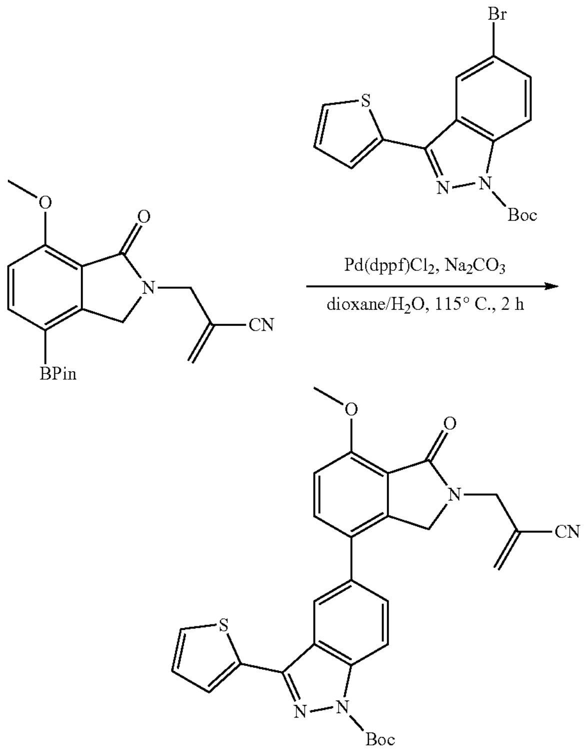

To a mixture of 2-[[7-methoxy-1-oxo-4-(4,4,5,5-tetramethyl-1,3,2-dioxaborolan-2-yl) isoindolin-2-yl]methyl]prop-2-enenitrile (0.2 g, 508.18 μmol, 1 eq.) and tert-butyl 5-bromo-3-(2-thienyl)indazole-1-carboxylate (235.57 mg, 559 μmol, 1.1 eq.) in dioxane (5 mL) and water (1 mL) were added $Na_2CO_3$ (161.58 mg, 1.52 mmol, 3 eq.) and Pd(dppf) $Cl_2$ (37.18 mg, 50.82 μmol, 0.1 eq.). The mixture was degassed and purged with nitrogen 3 times and stirred at 115° C. for 2 h under nitrogen atmosphere. LCMS showed the starting material was consumed. To the mixture was added sat. EDTA (25 mL), and the mixture was stirred for 1 h at 25° C. Then, the mixture was extracted with EtOAc (4×30 mL). The organic layers were washed with brine (15 mL), filtered, and concentrated. The residue was purified by column chromatography (silica gel; PE:EtOAc=4:1 to 1:1) to afford the title compound (0.12 g, 182.30 μmol, 35.87% yield, 80% purity) as a yellow solid.

Preparation of 2-[[7-methoxy-1-oxo-4-[3-(2-thienyl)-1H-indazol-5-yl]isoindolin-2-yl]methyl]prop-2-enenitrile

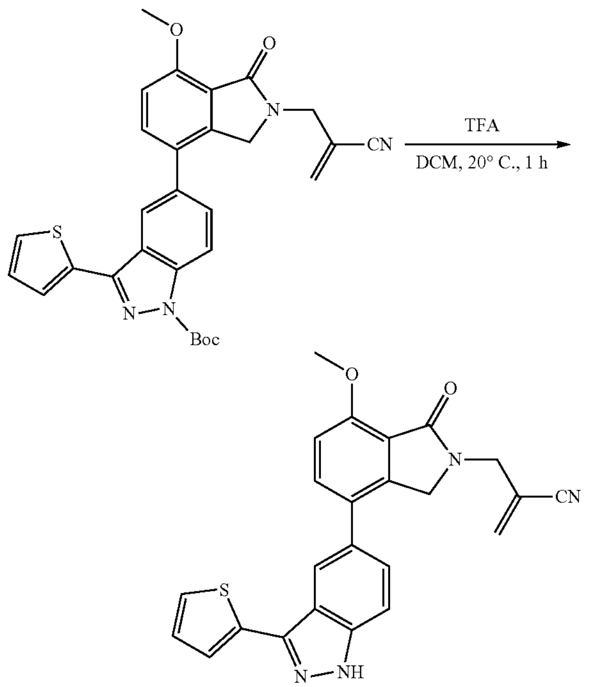

To a solution of tert-butyl 5-[2-(2-cyanoallyl)-7-methoxy-1-oxo-isoindolin-4-yl]-3-(2-thienyl) indazole-1-carboxylate (0.12 g, 227.87 μmol, 1 eq.) in DCM (10 mL) was added trifluoroacetic acid (3 mL), and the mixture was stirred at 20° C. for 1 h under nitrogen atmosphere. TLC showed the starting material was consumed. The mixture was concentrated and poured into sat. $NaHCO_3$ (15 mL), then extracted with and EtOAc (4×20 mL). The organic layers were washed with brine (10 mL), dried over anhydrous sodium sulfate, filtered, and concentrated. The residue was purified by prep-TLC (silica gel; EtOAc) to afford the title compound (0.080 g, 168.82 μmol, 74.08% yield, 90% purity) as a yellow solid.

Preparation of 2-[[7-methoxy-1-oxo-4-[3-(2-thienyl)-1H-indazol-5-yl]isoindolin-2-yl]methyl]prop-2-enamide

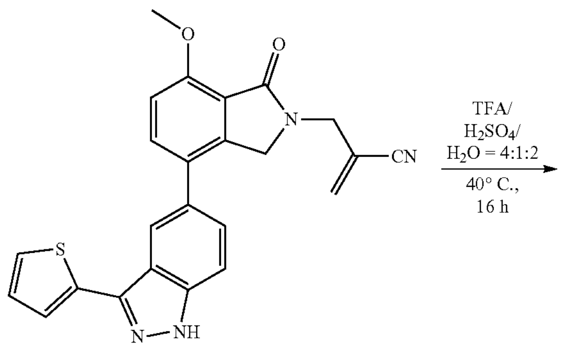

-continued

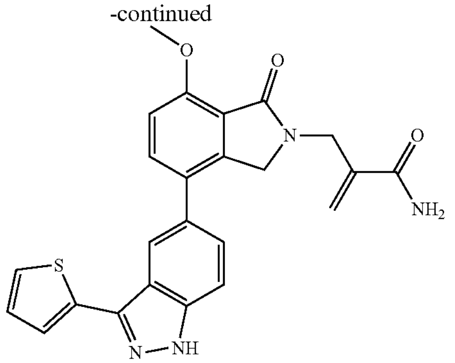

To a mixture of 2-[[7-methoxy-1-oxo-4-[3-(2-thienyl)-1H-indazol-5-yl]isoindolin-2-yl]methyl]prop-2-enenitrile (0.075 g, 175.85 μmol, 1 eq.) in trifluoroacetic acid (4 mL) was added $H_2SO_4$ (1 mL) and water (2 mL). The mixture was stirred at 50° C. for 8 h under nitrogen atmosphere. LCMS showed that the reaction was complete. 15 g of ice was added to the reaction mixture, and the mixture was adjusted to pH=9 with sat. $NaHCO_3$. The mixture was extracted with EtOAc (5×25 mL), and the organic layers were washed with brine (20 mL), dried over anhydrous sodium sulfate, filtered, and concentrated to get the crude product to afford the title compound (0.055 g, crude) as a yellow solid.

Preparation of 2-[[7-hydroxy-1-oxo-4-[3-(2-thienyl)-1H-indazol-5-yl]isoindolin-2-yl]methyl]prop-2-enamide (Compound 518)

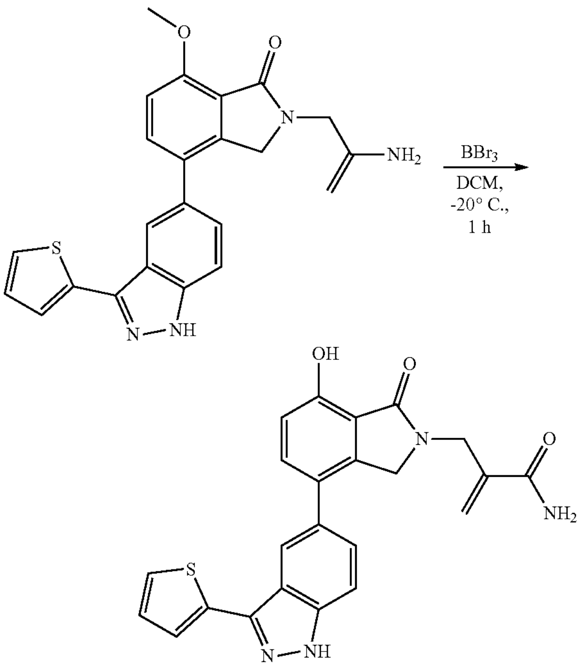

To a solution of 2-[[7-methoxy-1-oxo-4-[3-(2-thienyl)-1H-indazol-5-yl]isoindolin-2-yl]methyl]prop-2-enamide (0.05 g, 112.48 μmol, 1 eq.) in DCM (5 mL) was added $BBr_3$ (84.54 mg, 337.45 μmol, 32.52 μL, 3 eq.) at −20° C. The mixture was stirred at −20° C. for 1 h. LCMS showed the starting material was consumed. To the mixture was added 10 mL of water, and the mixture was extracted with DCM (3×20 mL). The organic layers were washed with brine (10 mL) and dried over anhydrous sodium sulfate, filtered, and concentrated. The residue was purified by prep-HPLC to afford the title compound (0.013 g, 30.20 μmol, 26.85% yield) as a white solid. LC-MS: $[M+H]^+$ 431.

Route 4:

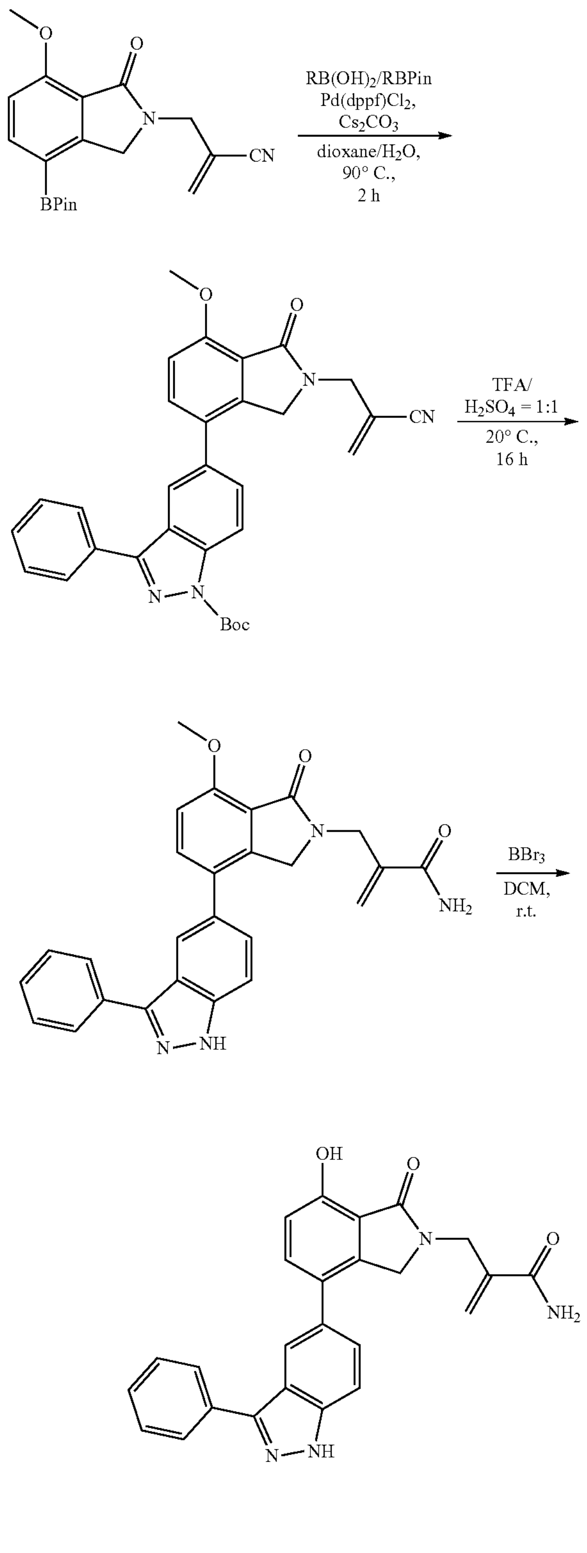

Preparation of tert-butyl 5-[2-(2-cyanoallyl)-7-methoxy-1-oxo-isoindolin-4-yl]-3-phenyl-indazole-1-carboxylate

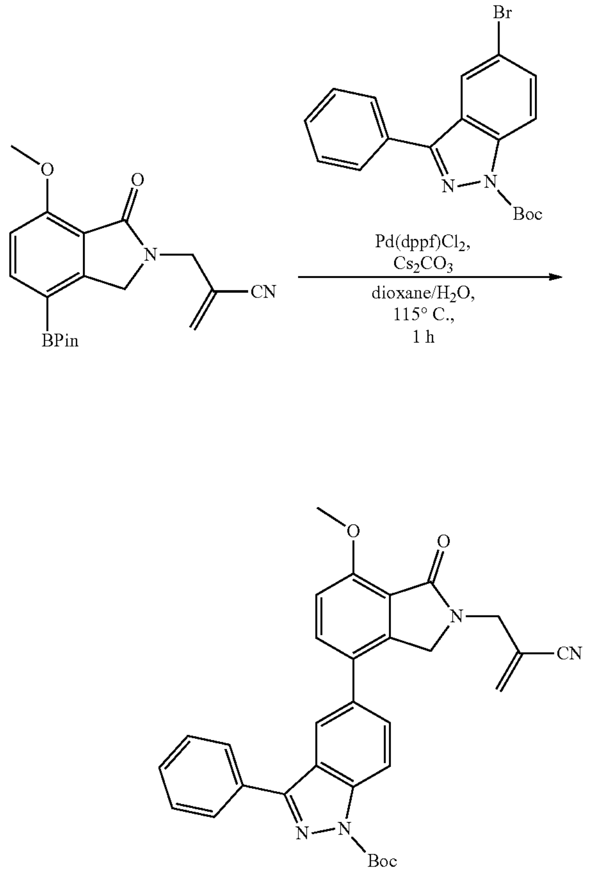

To a mixture of 2-[[7-methoxy-1-oxo-4-(4,4,5,5-tetramethyl-1,3,2-dioxaborolan-2-yl) isoindolin-2-yl]methyl]prop-2-enenitrile (0.2 g, 564.64 μmol, 1 eq.) and tert-butyl 5-bromo-3-phenyl-indazole-1-carboxylate (210.75 mg, 564.64 μmol, 1 eq.) in dioxane (5 mL) and water (1 mL) were added $Na_2CO_3$ (179.54 mg, 1.69 mmol, 3 eq.), $Pd(dppf)Cl_2$ (82.63 mg, 112.93 μmol, 0.2 eq.), then the mixture was stirred at 115° C. for 1 h under nitrogen atmosphere. LCMS showed that the starting material was completely consumed. To the mixture was added sat. EDTA (15 mL) at 20° C. and stirred for 1 h. Then the mixture was extracted with EtOAc (5×30 mL). The organic layers were washed with brine, filtered, and concentrated. The residue was purified by column chromatography (silica gel; PE:EtOAc=4:1 to 1:1) to afford the title compound (0.1, 153.68 μmol, 27.22% yield, 80% purity) as a yellow solid.

Preparation of 2-[[7-methoxy-1-oxo-4-(3-phenyl-1H-indazol-5-yl)isoindolin-2-yl]methyl]prop-2-enamide

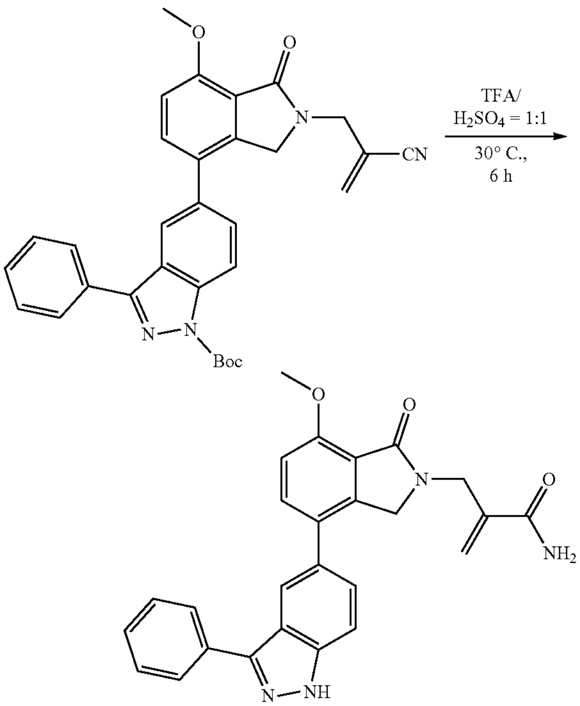

To a mixture of tert-butyl 5-[2-(2-cyanoallyl)-7-methoxy-1-oxo-isoindolin-4-yl]-3-phenyl-indazole-1-carboxylate (0.1 g, 192.09 μmol, 1 eq.) in trifluoroacetic acid (2 mL) was added $H_2SO_4$ (2 mL), and the mixture was stirred at 30° C. for 6 h. LCMS showed the starting material was consumed. The solution was poured into 25 g of ice, and the mixture was adjusted to pH=10 with sat. $NaHCO_3$. The mixture was extracted with EtOAc (3×30 mL). The organic layers were washed with brine (10 mL), dried over anhydrous sodium sulfate, filtered, concentrated. The residue was purified by column chromatography (silica gel; PE:EtOAc=3:1 to 0:1) to afford the title compound (0.065 g, 133.42 μmol, 69.45% yield, 90% purity) as a yellow solid.

Preparation of 2-[[7-hydroxyl-1-oxo-4-(3-phenyl-1H-indazol-5-yl)isoindolin-2-yl]methyl]prop-2-enamide (Compound 517)

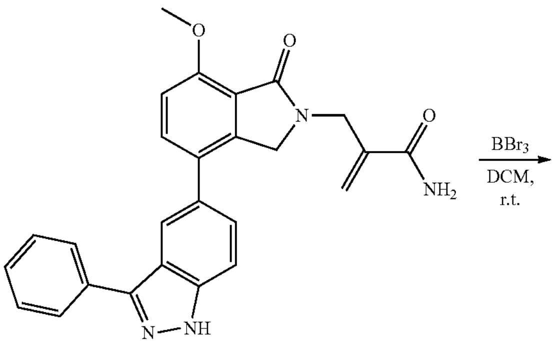

-continued

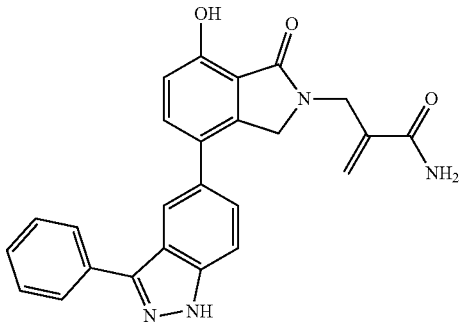

To a solution of 2-[[7-methoxy-1-oxo-4-(3-phenyl-1H-indazol-5-yl)isoindolin-2-yl]methyl]prop-2-enamide (0.065 g, 148.24 μmol, 1 eq.) in DCM (5 mL) was added $BBr_3$ (111.41 mg, 444.72 μmol, 42.85 μL, 3 eq.) in portions and stirred at 20° C. for 1 h. LCMS showed that the reaction worked well. Water (5 mL) was added to the reaction, and the mixture was extracted with DCM (4×8 mL). The organic layers was washed with brine (2×10 mL), dried over anhydrous sodium sulfate, filtered, and concentrated. The residue was purified by prep-TLC (EtOAc:THF=1:3, Rf=0.4) to afford the title compound (0.018 g, 38.59 μmol, 26.03% yield, 91% purity) as a white solid. LC-MS: $[M+H]^+$ 425.1.

Route 5:

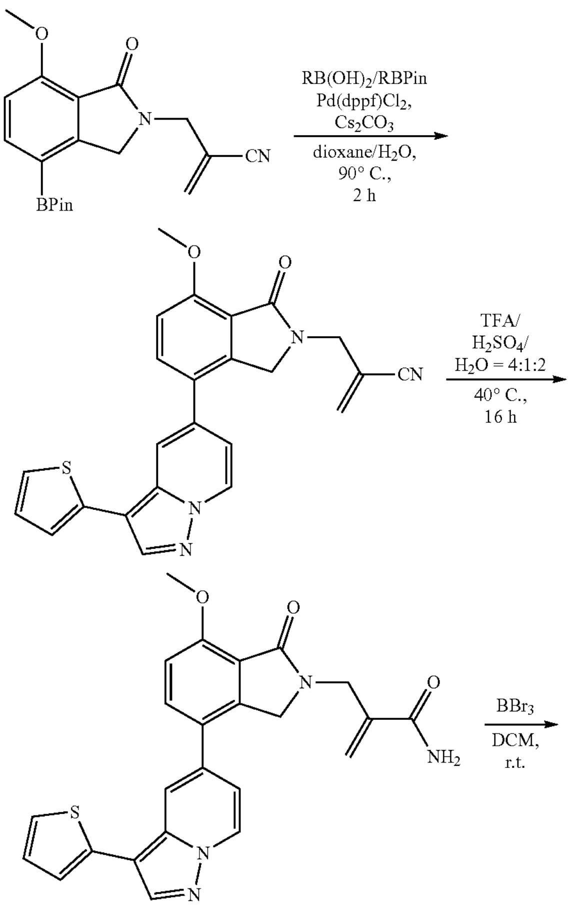

-continued

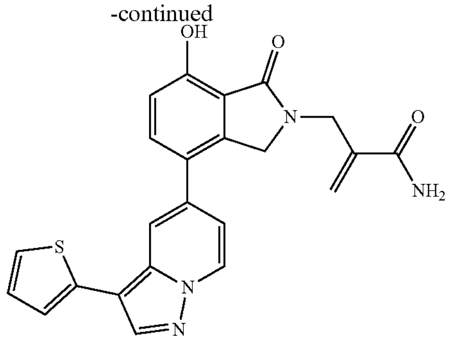

Preparation of 2-((7-methoxy-1-oxo-4-(3-(thiophen-2-yl)pyrazolo[1,5-a]pyridin-5-yl)isoindolin-2-yl) methyl)acrylonitrile

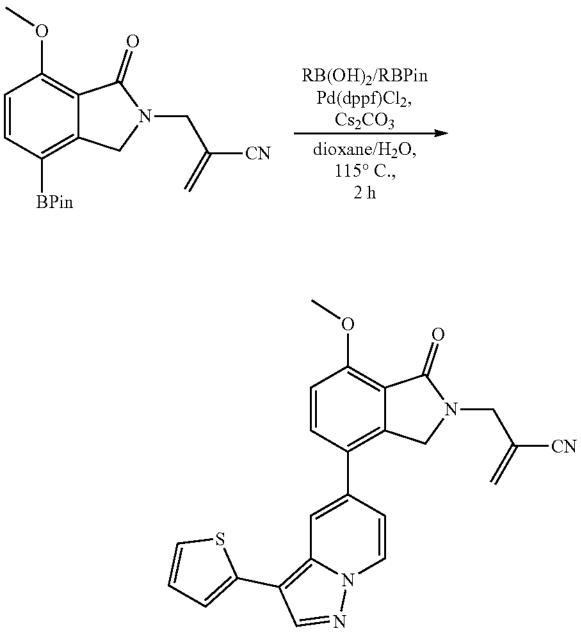

To a mixture of 2-[[7-methoxy-1-oxo-4-(4,4,5,5-tetramethyl-1,3,2-dioxaborolan-2-yl) isoindolin-2-yl]methyl]prop-2-enenitrile (0.2 g, 508.18 μmol, 1 eq.) and 5-bromo-3-(thiophen-2-yl)pyrazolo[1,5-a]pyridine (177.33 mg, 508.18 μmol, 1 eq.) in dioxane (5 mL) and water (1 mL) were added $Na_2CO_3$ (161.59 mg, 1.52 mmol, 3 eq.) and $Pd(dppf)Cl_2$ (37.18 mg, 50.82 μmol, 0.1 eq.). The mixture was degassed and purged with nitrogen 3 times, and the mixture was stirred at 115° C. for 2 h under nitrogen atmosphere. To the mixture was added sat. EDTA (15 mL) at 20° C., and the mixture was stirred for 1 h. The mixture was extracted with EtOAc (4×15 mL). The organic layers were washed with brine (8 mL), dried over anhydrous sodium sulfate, filtered, and concentrated. The residue was purified by column chromatography (silica gel; PE:EtOAc=4:1 to 0:1) to afford 85 mg of the product with 47% purity by LCMS. The product was then purified by prep-HPLC to afford the title compound (0.037 g, 78.08 μmol, 15.36% yield, 90% purity) as a yellow solid.

Preparation of 2-[[7-methoxy-1-oxo-4-[3-(2-thienyl) pyrazolo[1,5-a]pyridin-5-yl]isoindolin-2-yl]methyl] prop-2-enamide

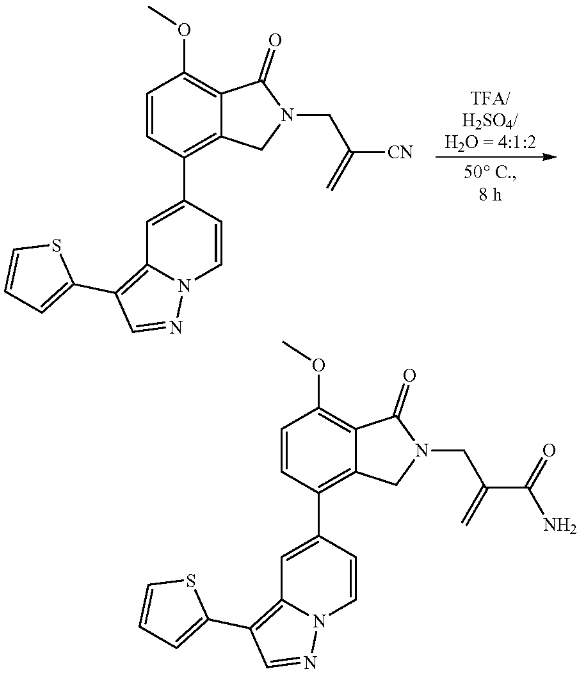

To a mixture of 2-[[7-methoxy-1-oxo-4-[3-(2-thienyl) pyrazolo[1,5-a]pyridin-5-yl]isoindolin-2-yl]methyl]prop-2-enenitrile (0.032 g, 75.03 μmol, 1 eq.) in trifluoroacetic acid (2 mL) was added $H_2SO_4$ (0.5 mL) and water (1 mL). The mixture was stirred at 50° C. for 8 h under nitrogen atmosphere. 10 g of ice was added to the reaction mixture, and the mixture was adjusted to pH=9 with sat. $NaHCO_3$. Then the mixture was extracted with EtOAc (5×20 mL). The organic layers were washed with brine (15 mL), dried over anhydrous sodium sulfate, filtered, concentrated to afford the title compound (0.028 g, 62.99 μmol, 83.95% yield) as a yellow solid.

Preparation of 2-[[7-hydroxy-1-oxo-4-[3-(2-thienyl) pyrazolo[1,5-a]pyridin-5-yl]isoindolin-2-yl]methyl] prop-2-enamide (Compound 519)

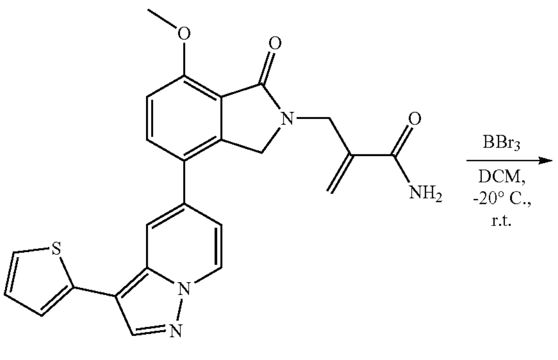

-continued

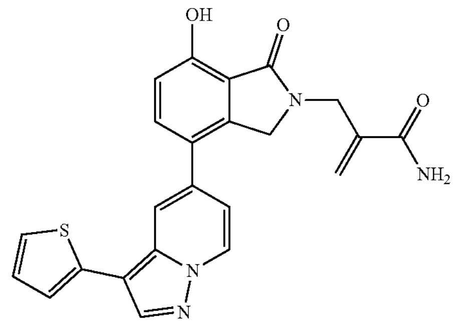

To a solution of 2-[[7-methoxy-1-oxo-4-[3-(2-thienyl)pyrazolo[1,5-a]pyridin-5-yl]isoindolin-2-yl]methyl]prop-2-enamide (0.023 g, 51.74 μmol, 1 eq.) in DCM (5 mL) was added $BBr_3$ (38.89 mg, 155.23 μmol, 14.96 μL, 3 eq.). The mixture was stirred at −20° C. for 1 h. To the mixture was added 10 mL of water, and the mixture was extracted with DCM (4×15 mL). The organic layers were washed with brine (10 mL) and dried over anhydrous sodium sulfate, filtered, and concentrated. The crude material was purified by prep-HPLC to afford the title compound (0.007 g, 16.08 μmol, 31.08% yield, 98.896% purity) as a yellow solid. LC-MS: $[M+H]^+$ 431.1

Route 6:

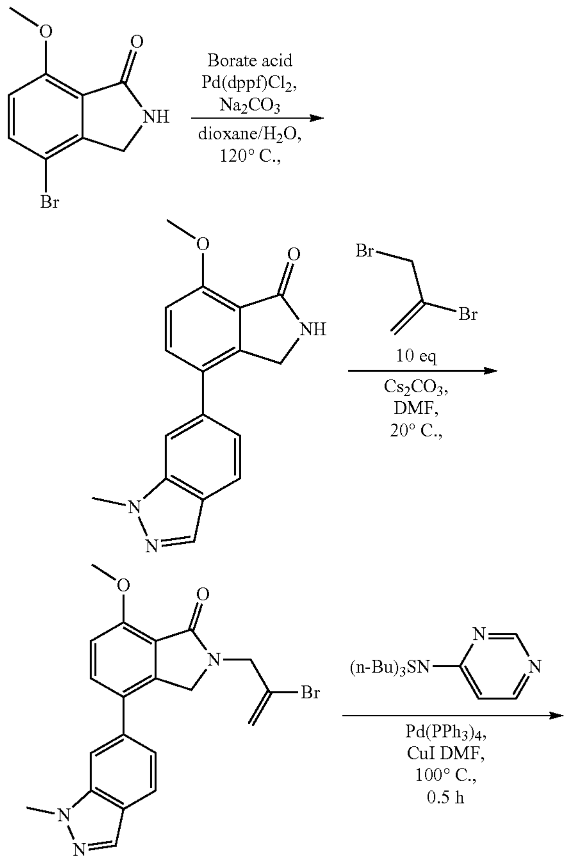

-continued

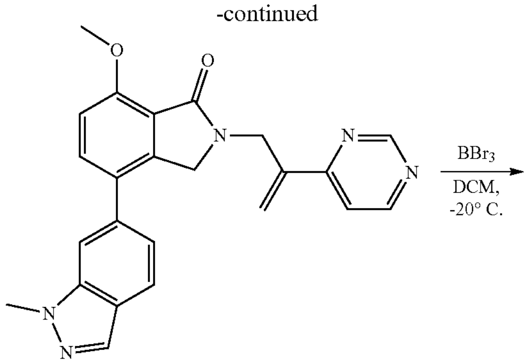

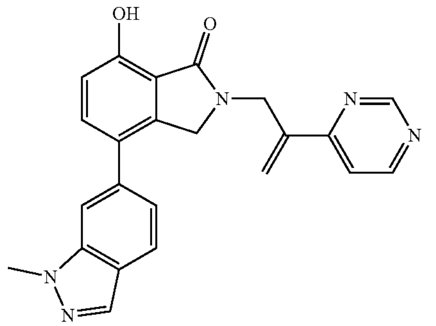

Preparation of 7-methoxy-4-(1-methylindazol-6-yl)isoindolin-1-one

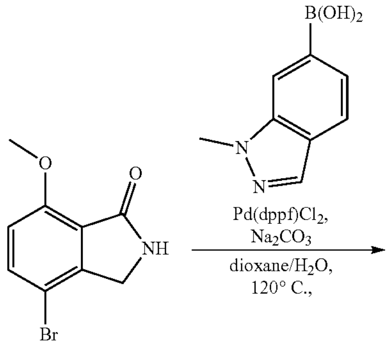

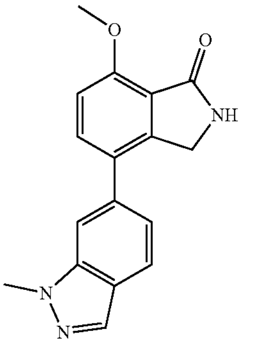

To a mixture of 4-bromo-7-methoxy-isoindolin-1-one (1 g, 4.13 mmol, 1 eq.), (1-methylindazol-6-yl) boronic acid (726.98 mg, 4.13 mmol, 1 eq.) in dioxane (30 mL) and water (6 mL) were added $Na_2CO_3$ (1.31 g, 12.39 mmol, 3 eq.), Pd(dppf)$Cl_2$ (302.27 mg, 413.11 μmol, 0.1 eq.). The mixture was degassed and purged with nitrogen 3 times, and the mixture was stirred at 120° C. for 1 h under nitrogen atmosphere. TLC (DCM:MeOH=20:1) showed the starting material was consumed. To the mixture was added sat. EDTA (30 mL), and the mixture was stirred for 1 h. The mixture was extracted with EtOAc (40 mL×3) and THF (20 mL×3). The organic layers were washed with brine (15 mL) and concentrated. The residue was purified by column chromatography (silica gel; PE:EtOAc=3:1 to 0:1) to afford the title compound (1.1 g, 3 mmol, 72.62% yield, 80% purity as a yellow solid.

Preparation of 2-(2-bromoallyl)-7-methoxy-4-(1-methylindazol-6-yl)isoindolin-1-one

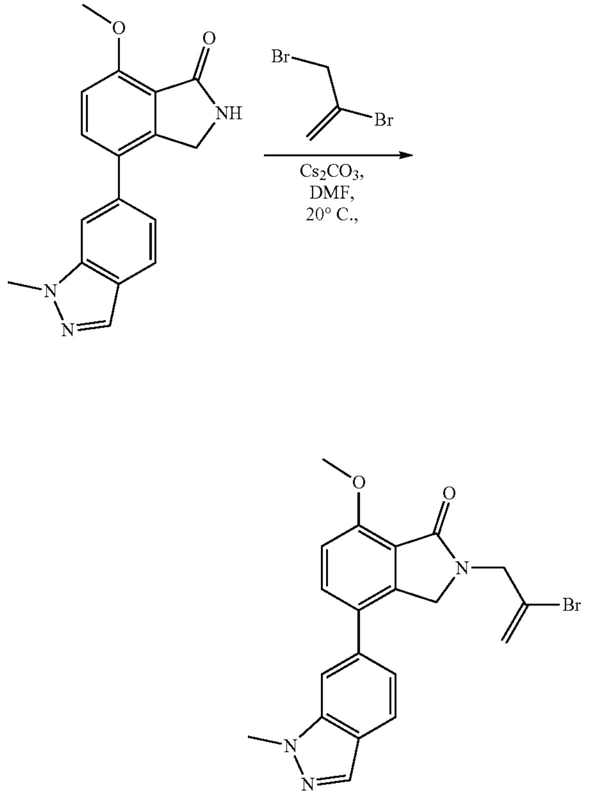

To a solution of 7-methoxy-4-(1-methylindazol-6-yl) isoindolin-1-one (0.9 g, 3.07 mmol, 1 eq.) in DMF (10 mL) were added 2,3-dibromoprop-1-ene (6.13 g, 30.68 mmol, 2.99 mL, 10 eq.) and $Cs_2CO_3$ (3 g, 9.20 mmol, 3 eq.), and the mixture was stirred at 20° C. for 72 h under nitrogen atmosphere. LCMS showed that the reaction was complete. The mixture was poured into water (50 mL) and extracted with EtOAc (3×50 mL). Then the aqueous phase was extracted with THF (3×30 mL). The organic layers were washed with water (4×20 mL) and brine (20 mL). The combined organic layer were purification directly by column chromatography (PE:EtOAc=3:1 to 1:1) to afford the title compound as a yellow solid (0.23 g, 446.30 μmol, 14.55% yield, 80% purity).

Preparation of 7-methoxy-4-(1-methylindazol-6-yl)-2-(2-pyrimidin-4-ylallyl) isoindolin-1-one

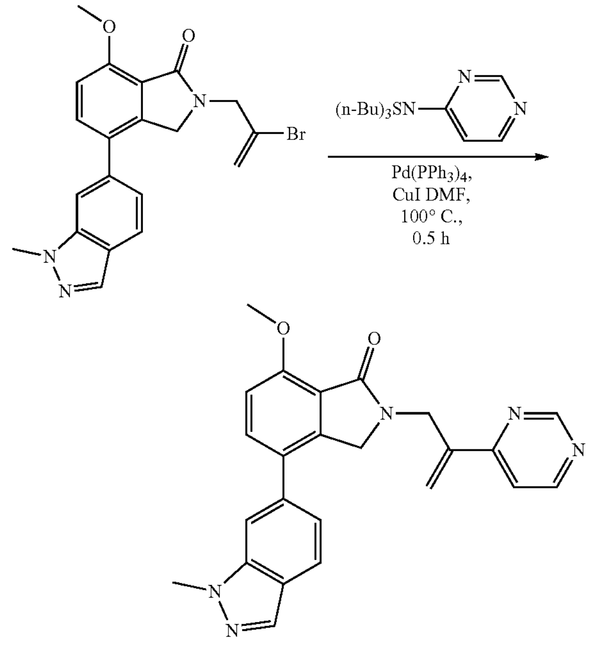

To a mixture of 2-(2-bromoallyl)-7-methoxy-4-(1-methylindazol-6-yl)isoindolin-1-one (0.1 g, 242.55 μmol, 1 eq.) and tributyl(pyrimidin-4-yl) stannane (107.44 mg, 291.06 μmol, 1.2 eq.) in DMF (4 mL) were added CuI (9.24 mg, 48.51 μmol, 0.2 eq.) and $Pd(PPh_3)_4$ (28.03 mg, 24.26 μmol, 0.1 eq.). The mixture was degassed and purged with nitrogen 3 times, and the mixture was stirred at 100° C. for 0.5 h under nitrogen atmosphere. To the mixture was added sat. EDTA (15 mL), and the resulting mixture was stirred for 1 h. Then the mixture was extracted with EtOAc (4×15 mL). The organic layers were washed with brine (8 mL), dried over anhydrous sodium sulfate, filtered, and concentrated. The residue was purified by prep-HPLC to afford the title compound (0.045 g, 109.37 μmol, 45.09% yield) as a yellow solid.

Preparation of 7-hydroxy-4-(1-methylindazol-6-yl)-2-(2-pyrimidin-4-ylallyl) isoindolin-1-one (Compound 523)

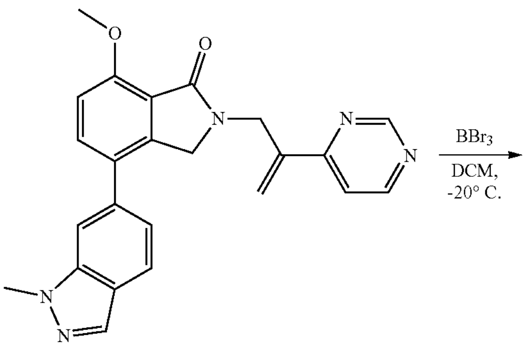

-continued

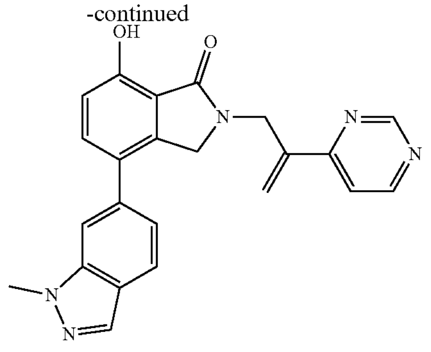

To a solution of 7-methoxy-4-(1-methylindazol-6-yl)-2-(2-pyrimidin-4-ylallyl) isoindolin-1-one (0.03 g, 72.91 μmol, 1 eq.) in DCM (10 mL) was added $BBr_3$ (54.80 mg, 218.74 μmol, 21.08 μL, 3 eq.) at −20° C. The mixture was stirred at −20° C. for 1 h. LCMS and HPLC showed some desired was detected. To the mixture was added 10 mL of water and extracted with DCM (15 mL×4), the organic layers were washed with brine (8 mL), concentrated. The residue was purified by prep-HPLC to afford the title compound (0.009 g, 22.03 μmol, 30.21% yield, 97.280% purity) as a white solid. LC-MS: $[M+H]^+$ 398.1

Route 7:

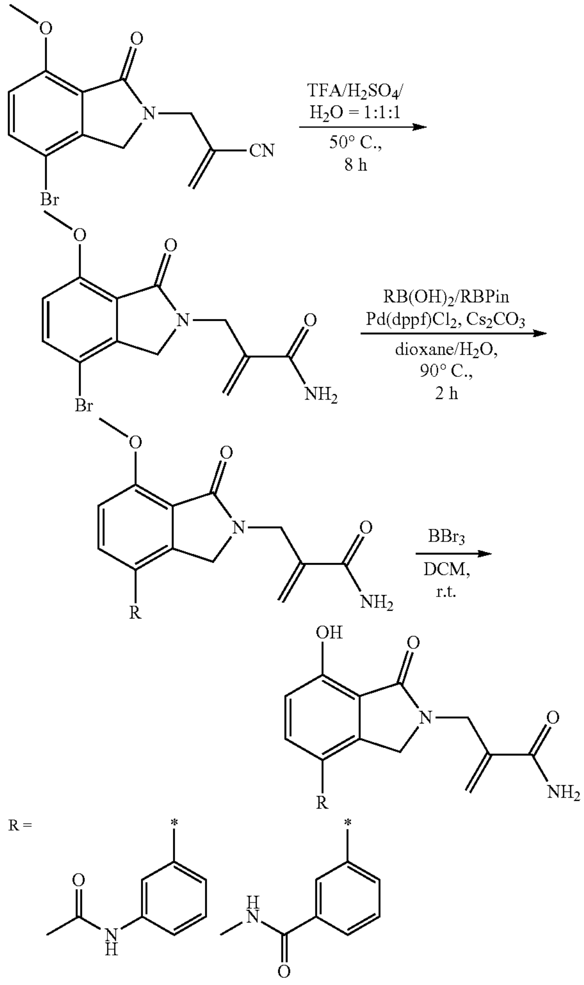

Preparation of 2-[(4-bromo-7-methoxy-1-oxo-isoindolin-2-yl)methyl]prop-2-enamide

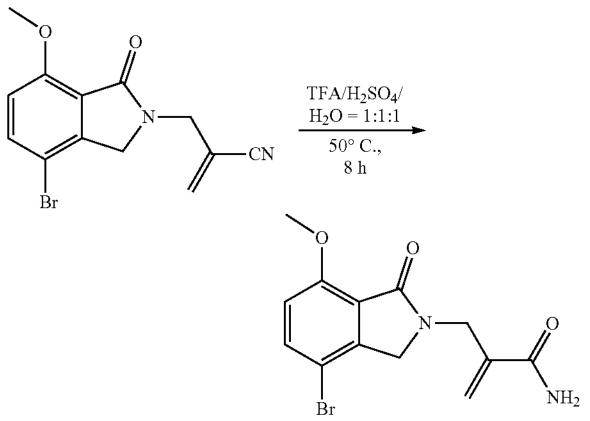

To a mixture of 2-[(4-bromo-7-methoxy-1-oxo-isoindolin-2-yl)methyl]prop-2-enenitrile (0.5 g, 1.63 mmol, 1 eq.) in trifluoroacetic acid (2 mL) was added $H_2SO_4$ (2 mL) and water (2 mL), and the mixture was stirred at 50° C. for 8 h under nitrogen atmosphere. TLC (DCM:MeOH=20:1) showed that the reaction was complete. To the mixture was added 40 mL of water, then the solution was adjusted to pH=10 with sat. $Na_2CO_3$. The mixture was extracted with EtOAc (5×50 mL). The organic layers were washed with brine (20 mL) and dried over anhydrous sodium sulfate, filtered, and concentrated to afford the title compound (630 mg, 90% purity) as a yellow solid which was used directly without any purification.

Preparation of 2-[[4-(3-acetamidophenyl)-7-methoxy-1-oxo-isoindolin-2-yl]methyl]prop-2-enamide

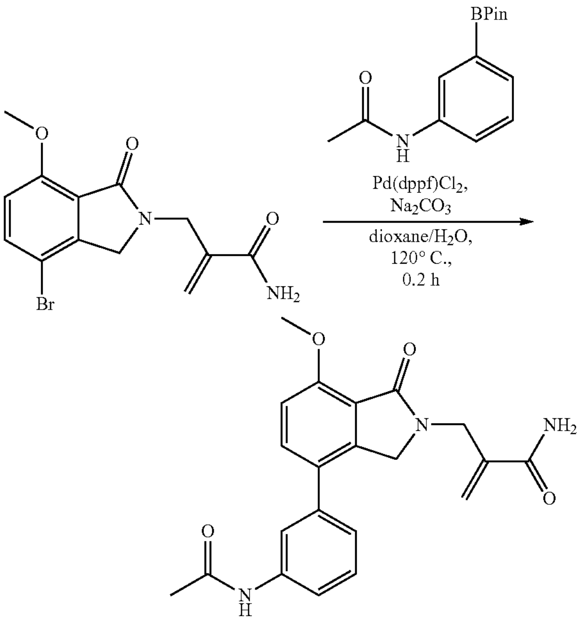

To a mixture of 2-[(4-bromo-7-methoxy-1-oxo-isoindolin-2-yl)methyl]prop-2-enamide (0.2 g, 615.09 μmol, 1 eq.), (3-acetamidophenyl) boronic acid (132.11 mg, 738.10 μmol, 1.2 eq.) in dioxane (15 mL) and water (3 mL) were added $Na_2CO_3$ (195.58 mg, 1.85 mmol, 3 eq.) and $Pd(dppf)Cl_2$ (40.09 mg, 61.51 μmol, 0.1 eq.). The mixture was degassed and purged with nitrogen 3 times, and the mixture was stirred at 120° C. for 0.2 h under nitrogen atmosphere. TLC (DCM:MeOH=20:1) showed the starting material was consumed. The reaction mixture was diluted with sat. EDTA (30 mL) and stirred for 1 h. Then the mixture was extracted with EtOAc (3x30 mL). The organic layers were washed with brine (15 mL), dried over anhydrous sodium sulfate, filtered, and concentrated. The residue was washed with EtOAc (15 mL) to get the product to afford the title compound (0.11 g, 260.93 μmol, 42.42% yield, 90% purity) as a yellow solid.

Preparation of 2-[[4-(3-acetamidophenyl)-7-hydroxy-1-oxo-isoindolin-2-yl]methyl]prop-2-enamide (Compound 520)

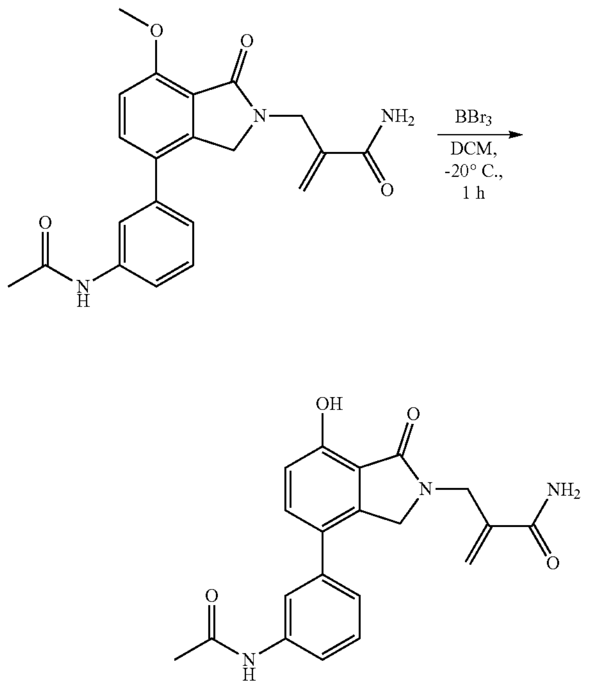

To a solution of 2-[[4-(3-acetamidophenyl)-7-methoxy-1-oxo-isoindolin-2-yl]methyl]prop-2-enamide (0.080 g, 210.85 μmol, 1 eq.) in DCM (5 mL) was added $BBr_3$ (158.47 mg, 632.56 μmol, 60.95 μL, 3 eq.) at −20° C. The mixture was stirred at −20° C. for 1 h. LCMS and HPLC showed that the reaction worked well. 8 mL of water was added, and the mixture was extracted with DCM (4x10 mL×4). The organic layers were washed with brine and dried over anhydrous sodium sulfate, filtered, and concentrated. The residue was purified by prep-HPLC to afford the title compound (0.036 g, 96.81 μmol, 45.92% yield, 98.262% purity) as a white solid. LC-MS: $[M+H]^+$ 366.1.

Preparation of 3-[2-(2-carbamoylallyl)-7-methoxy-1-oxo-isoindolin-4-yl]-N-methyl-benzamide

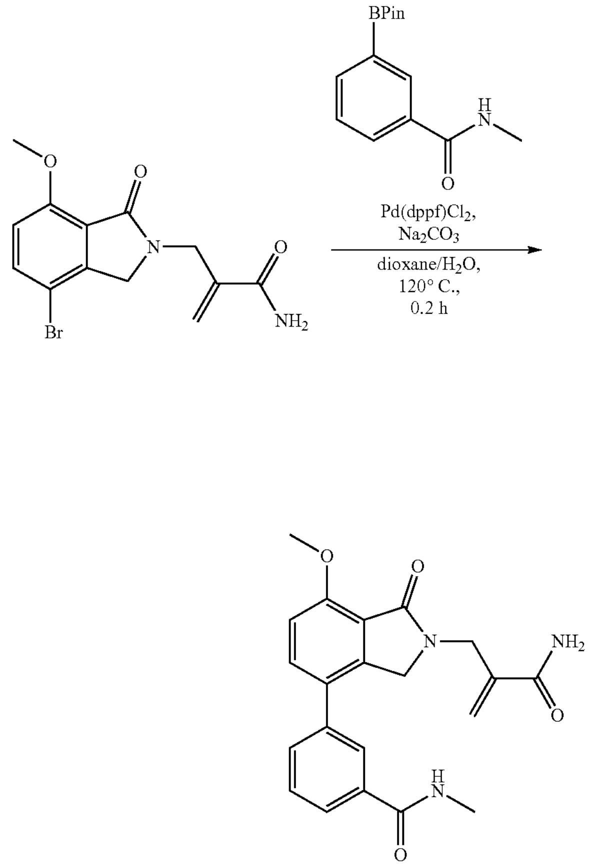

To a mixture of 2-[(4-bromo-7-methoxy-1-oxo-isoindolin-2-yl)methyl]prop-2-enamide (0.2 g, 615.09 μmol, 1 eq.), [3-(methylcarbamoyl)phenyl]boronic acid (132.11 mg, 738.10 μmol, 1.2 eq.) in dioxane (15 mL) and water (3 mL) were added $Na_2CO_3$ (195.58 mg, 1.85 mmol, 3 eq.) and ditert-butyl (cyclopentyl)phosphane; dichloropalladium; iron (40.09 mg, 61.51 μmol, 0.1 eq.). The mixture was degassed and purged with nitrogen 3 times, and the mixture was stirred at 120° C. for 0.2 h under nitrogen atmosphere. TLC (DCM:MeOH=20:1) showed that the reaction was complete. The reaction mixture was diluted with sat. EDTA (30 mL) and stirred for 1 h. Then the mixture was extracted with EtOAc (3x30 mL). The organic layers were washed with brine (15 mL), dried over anhydrous sodium sulfate, filtered, and concentrated. The residue was washed with EtOAc (15 mL) to afford the title compound (0.1 g, 237.21 μmol, 38.57% yield, 90% purity) as a yellow solid.

Preparation of 3-[2-(2-carbamoylallyl)-7-hydroxy-1-oxo-isoindolin-4-yl]-N-methyl-benzamide (Compound 521)

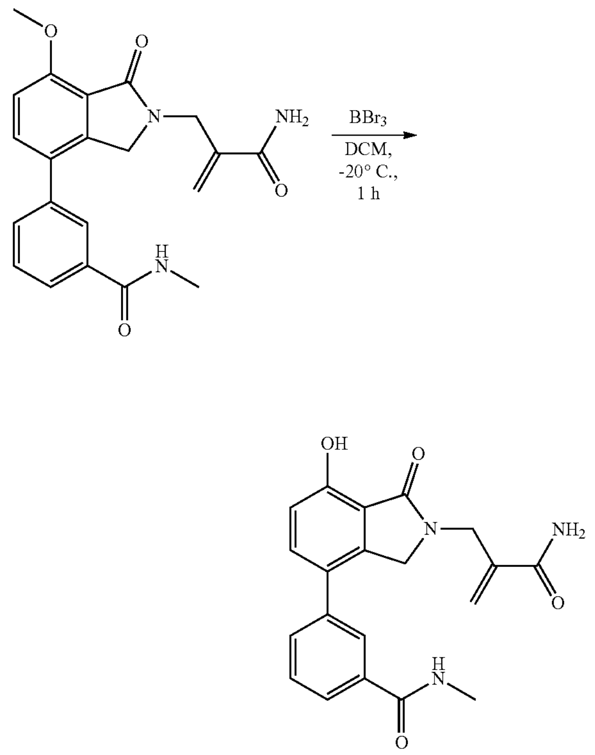

To a solution of 3-[2-(2-carbamoylallyl)-7-methoxy-1-oxo-isoindolin-4-yl]-N-methyl-benzamide (0.07 g, 184.50 μmol, 1 eq.) in DCM (5 mL) was added $BBr_3$ (138.66 mg, 553.49 μmol, 53.33 μL, 3 eq.) at −20° C. The mixture was stirred at −20° C. for 1 h. To the mixture was added 8 mL of water, then extracted with DCM (4×10 mL). The organic layers were washed with brine and dried over anhydrous sodium sulfate, filtered, and concentrated. The residue was purified by prep-HPLC to afford the title compound (0.031 g, 83.34 μmol, 45.17% yield, 98.226% purity) as a white solid. LC-MS: $[M+H]^+$ 366.1.

Route 8:

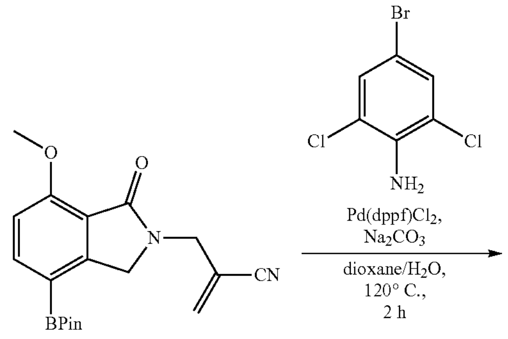

-continued

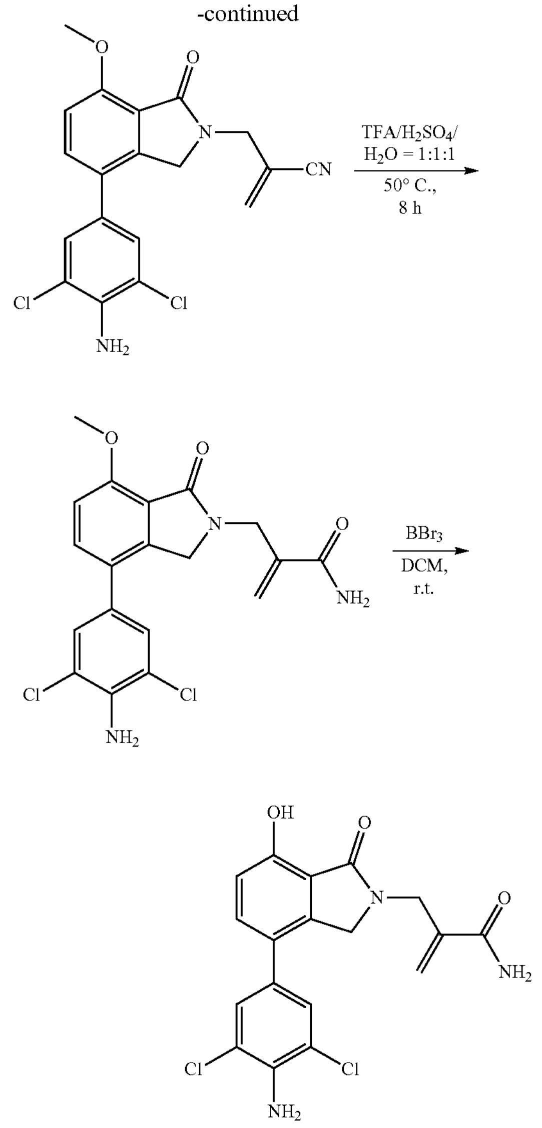

Preparation of 2-[[4-(4-amino-3,5-dichloro-phenyl)-7-methoxy-1-oxo-isoindolin-2-yl]methyl]prop-2-enenitrile

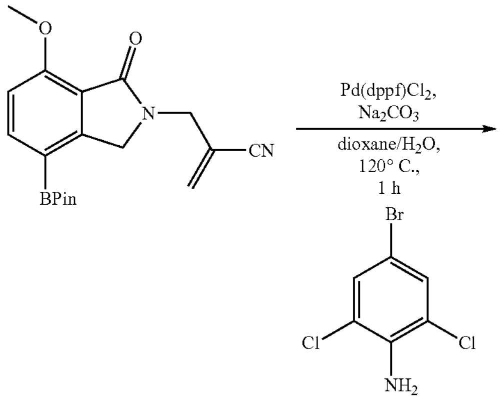

-continued

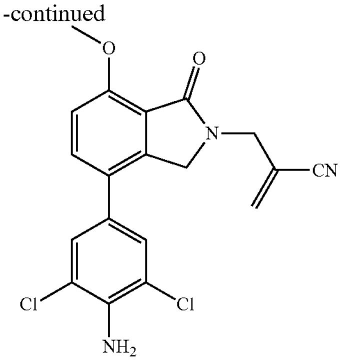

To a mixture of 2-[[7-methoxy-1-oxo-4-(4,4,5,5-tetramethyl-1,3,2-dioxaborolan-2-yl) isoindolin-2-yl]methyl]prop-2-enenitrile (0.12 g, 338.78 μmol, 1 eq.) and 4-bromo-2,6-dichloro-aniline (122.43 mg, 508.18 μmol, 1.5 eq.) in dioxane (15 mL) and water (3 mL) were added $Na_2CO_3$ (107.72 mg, 1.02 mmol, 3 eq.) and Pd(dppf)$Cl_2$ (24.79 mg, 33.88 μmol, 0.1 eq.). The mixture was degassed and purged with nitrogen 3 times, and the mixture was stirred at 120° C. for 1 h under nitrogen atmosphere. LCMS and HPLC showed that the starting material was consumed. The mixture was added to sat. EDTA (30 mL) and stirred for 1 h. The mixture was extracted with EtOAc (3×40 mL), and the organic layers were washed with brine (15 mL) and dried over anhydrous sodium sulfate, filtered, and concentrated. The residue was purified by prep-HPLC to afford the title compound (0.05 g, 115.91 μmol, 34.21% yield, 90% purity) as a yellow solid.

Preparation of 2-[[4-(4-amino-3,5-dichloro-phenyl)-7-methoxy-1-oxo-isoindolin-2-yl]methyl]prop-2-enamide

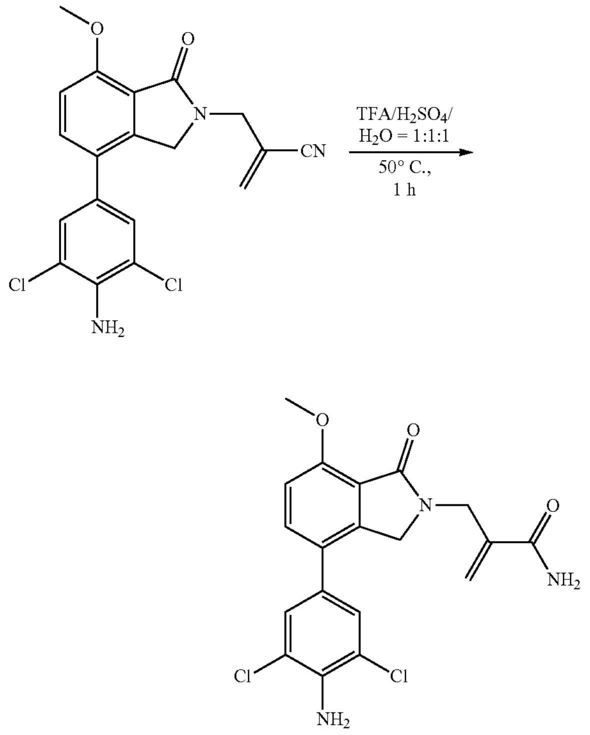

To a mixture of 2-[[4-(4-amino-3,5-dichloro-phenyl)-7-methoxy-1-oxo-isoindolin-2-yl]methyl]prop-2-enenitrile (0.045 g, 115.91 μmol, 1 eq.) in trifluoroacetic acid (1 mL) were added $H_2SO_4$ (1 mL) and water (1 mL), and the mixture was stirred at 50° C. for 1 h under nitrogen atmosphere. LCMS showed that the reaction was complete. The mixture was concentrated to remove trifluoroacetic acid under 40° C. Then to the mixture was added water (20 mL). The formed precipitation was collected by filtration. The filter cake was washed with water (5 mL) and dried in vacuo to afford the title compound (0.04 g, 98.46 μmol, 84.95% yield) as a yellow solid.

Preparation of 2-[[4-(4-amino-3,5-dichloro-phenyl)-7-hydroxy-1-oxo-isoindolin-2-yl]methyl]prop-2-enamide (Compound 522)

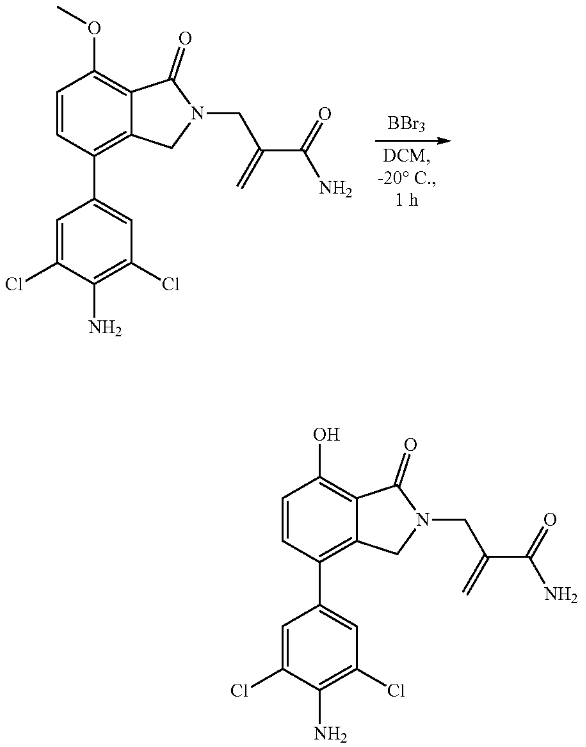

To a solution of 2-[[4-(4-amino-3,5-dichloro-phenyl)-7-methoxy-1-oxo-isoindolin-2-yl]methyl]prop-2-enamide (0.03 g, 73.84 μmol, 1 eq.) in DCM (10 mL) was added $BBr_3$ (55.50 mg, 221.53 μmol, 21.35 μL, 3 eq.). The mixture was stirred at −20° C. for 1 h. TLC showed that the reaction was complete. 10 mL of water was added, and the mixture was extracted with DCM (12 mL×4). The organic layers were washed with brine (10 mL), dried over anhydrous sodium sulfate, filtered, and concentrated. The residue was purified by prep-HPLC to afford the title compound (0.018 g, 45.18 μmol, 61.18% yield, 98.45000 purity) as a gray solid. LC-MS: $[M+H]^+$ 392.

TABLE 12 shows compounds synthesized using the methods described in EXAMPLE 14.

TABLE 12
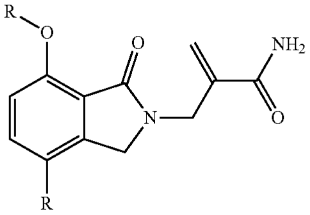
| Cpd. No. | Structure | IUPAC | LC-MS (ES+, m/z) |
|---|---|---|---|
| 513. | 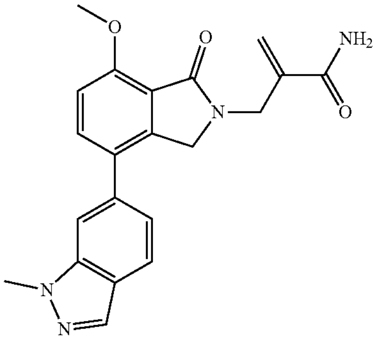 [SMILES: C=C(CN1Cc2c(-c3ccc4cnn(C)c4c3)ccc(OC)c2C1=O)C(N)=O] | 2-{[7-methoxy-4-(1-methyl-1H-indazol-6-yl)-1-oxo-2,3-dihydro-1H-isoindol-2-yl]methyl}prop-2-enamide | 377.1 |
| 514. | 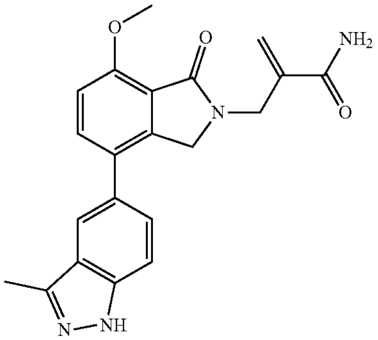 [SMILES: C=C(CN1Cc2c(-c3ccc4[nH]nc(C)c4c3)ccc(OC)c2C1=O)C(N)=O] | 2-{[7-methoxy-4-(3-methyl-1H-indazol-5-yl)-1-oxo-2,3-dihydro-1H-isoindol-2-yl]methyl}prop-2-enamide | 377.1 |
| 515. | 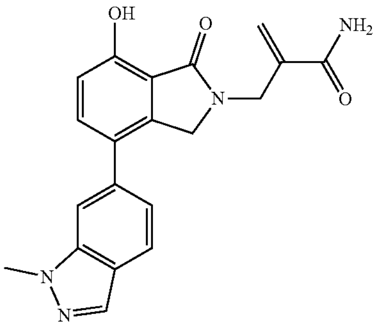 [SMILES: C=C(CN1Cc2c(-c3ccc4cnn(C)c4c3)ccc(O)c2C1=O)C(N)=O] | 2-{[7-hydroxy-4-(1-methyl-1H-indazol-6-yl)-1-oxo-2,3--dihydro-1H-isoindol-2-yl]methyl}prop-2-enamide | 363.1 |
| 516. | 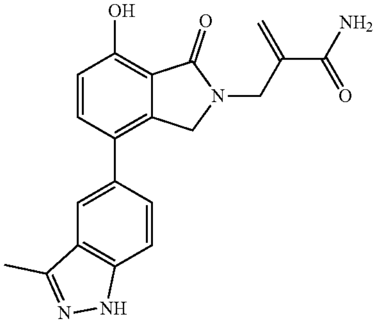 [SMILES: C=C(CN1Cc2c(-c3ccc4[nH]nc(C)c4c3)ccc(O)c2C1=O)C(N)=O] | 2-{[7-hydroxy-4-(3-methyl-1H-indazol-5-yl)-1-oxo-2,3-dihydro-1H-isoindol-2-yl]methyl}prop-2-enamide | 363.1 |

TABLE 12-continued

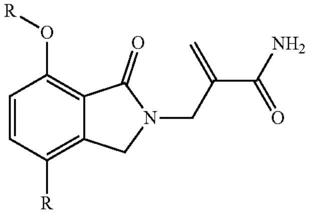

| Cpd. No. | Structure | IUPAC | LC-MS (ES+, m/z) |
|---|---|---|---|
| 517. | 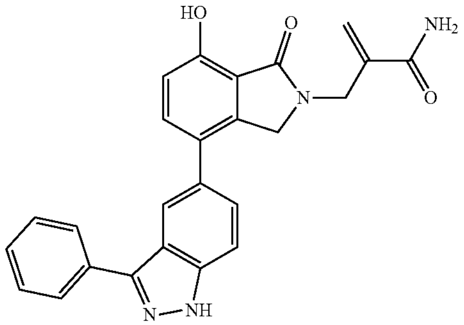 [SMILES: C=C(CN1Cc2c(-c3ccc4[nH]nc(-c5ccccc5)c4c3)ccc(O)c2C1=O)C(N)=O] | 2-{[7-hydroxy-1-oxo-4-(3-phenyl-1H-indazol-5-yl)-2,3-dihydro-1H-isoindol-2-yl]methyl}prop-2-enamide | 425.1 |
| 518. | 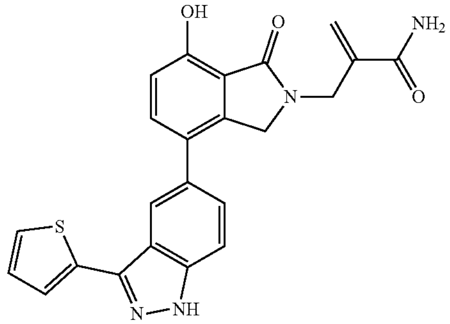 [SMILES: C=C(CN1Cc2c(-c3ccc4[nH]nc(-c5cccs5)c4c3)ccc(O)c2C1=O)C(N)=O] | 2-({7-hydroxy-1-oxo-4-[3-(thiophen-2-yl)-1H-indazol-5-yl]-2,3-dihydro-1H-isoindol-2-yl}methyl)prop-2-enamide | 431 |
| 519. | 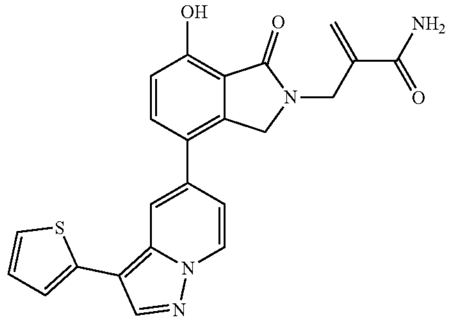 [SMILES: C=C(CN1Cc2c(-c3ccn4ncc(-c5cccs5)c4c3)ccc(O)c2C1=O)C(N)=O] | 2-({7-hydroxy-1-oxo-4-[3-(thiophen-2-yl)pyrazolo[1,5-a]pyridin-5-yl]-2,3-dihydro-1H-isoindol-2-yl}methyl)prop-2-enamide | 431.1 |
| 520. | 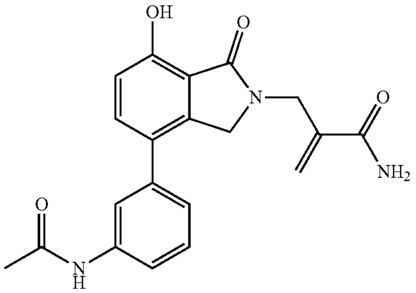 [SMILES: C=C(CN1Cc2c(-c3cccc(NC(C)=O)c3)ccc(O)c2C1=O)C(N)=O] | 2-{[4-(3-acetamidophenyl)-7-hydroxy-1-oxo-2,3-dihydro-1H-isoindol-2-yl]methyl}prop-2-enamide | 366.1 |

TABLE 12-continued
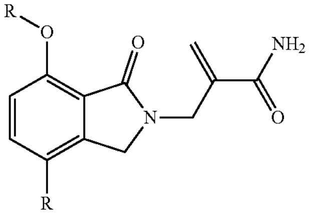
| Cpd. No. | Structure | IUPAC | LC-MS (ES+, m/z) |
|---|---|---|---|
| 521. | 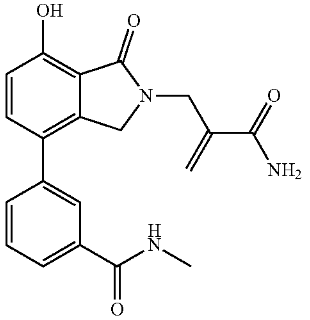 [SMILES: C=C(CN1Cc2c(-c3cccc(C(=O)NC)c3)ccc(O)c2C1=O)C(N)=O] | 3-[2-(2-carbamoyl-2-methylideneethyl)-7-hydroxy-1-oxo-2,3-dihydro-1H-isoindol-4-yl]-N-methylbenzamide | 366.1 |
| 522. | 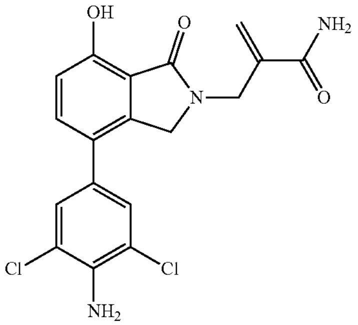 | 2-{[4-(4-amino-3,5-dichlorophenyl)-7-hydroxy-1-oxo-2,3-dihydro-1H-isoindol-2-yl]methyl}prop-2-enamide | 392 |
| 523. | 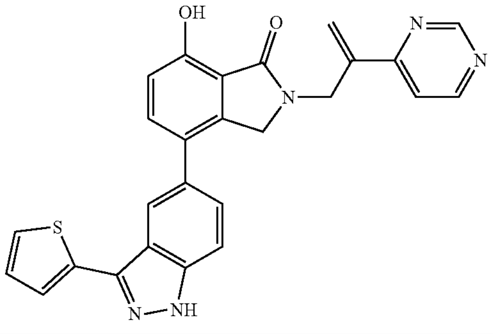 [SMILES: C=C(CN1Cc2c(-c3ccc4[nH]nc(-c5cccs5)c4c3)ccc(O)c2C1=O)c1ccncn1] | 7-hydroxy-4-(1-methyl-1H-indazol-6-yl)-2-[2-(pyrimidin-4-yl)prop-2-en-1-yl]-2,3-dihydro-1H-isoindol-1-one | 398.1 |
Example 15: Method N
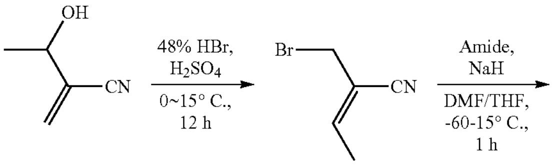
-continued
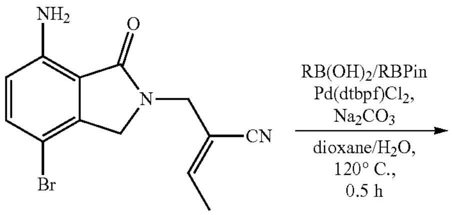

-continued

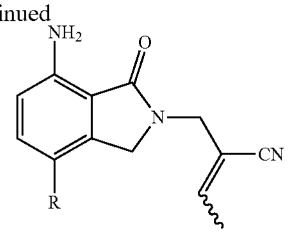

Preparation of (E)-2-(bromomethyl)but-2-enenitrile

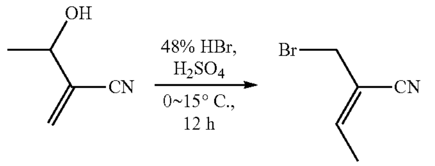

The solution of 3-hydroxy-2-methylene-butanenitrile (10 g, 102.97 mmol, 1 eq.) in DCM (20 mL) were added HBr (10 mL) and $H_2SO_4$ (10 mL) at 0° C. The mixture was stirred at 15° C. for 12 h. The reaction mixture was quenched with 50 mL of sat. $NaHCO_3$ solution at 0° C., diluted with 100 mL of water, and extracted with DCM (50 mL×3). The combined organic layers were washed with water (200 mL×3) and brine (200 mL×3), dried over anhydrous sodium sulfate, filtered, and concentrated in vacuo to give a residue. The residue was purified by column chromatography (silica gel; PE:EtOAc=10:1) to afford the title compound (15 g, Yield 90%) as a yellow oil.

Preparation of (Z)-2-[(7-amino-4-bromo-1-oxo-isoindolin-2-yl)methyl]but-2-enenitrile

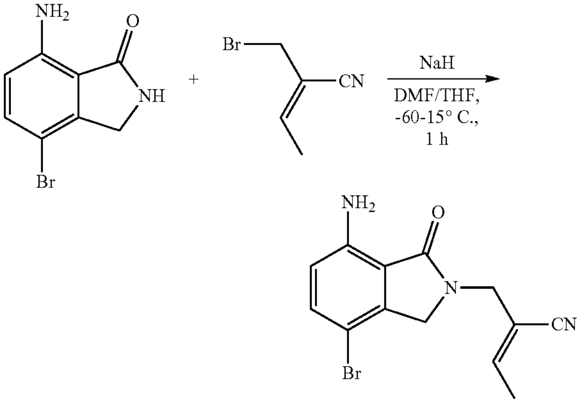

To a solution of 7-amino-4-bromo-isoindolin-1-one (2 g, 8.81 mmol, 1 eq.) in a mixture of DMF (50 mL) and THF (50 mL) was added NaH (704.60 mg, 17.62 mmol, 60% purity, 2 eq.) at 15° C. The mixture was stirred at 15° C. for 0.5 h under nitrogen. (E)-2-(bromomethyl)but-2-enenitrile (1.41 g, 8.81 mmol, 1 eq.) was added at −60° C. and stirred at −60° C. for 0.5 h. The reaction was quenched by adding of sat. $NH_4Cl$ (20 mL) at 0° C. The mixture was diluted with water (150 mL) and extracted with EtOAc (150 mL×3). The combined organic layers were washed with water (100 mL) and brine (100 mL), dried over anhydrous sodium sulfate, filtered, and concentrated in vacuo to afford the title compound (600 mg, Yield 22%).

Preparation of (Z)-2-[[7-amino-4-(4-amino-3,5-dichloro-phenyl)-1-oxo-isoindolin-2-yl]methyl]but-2-enenitrile (Compound 546)

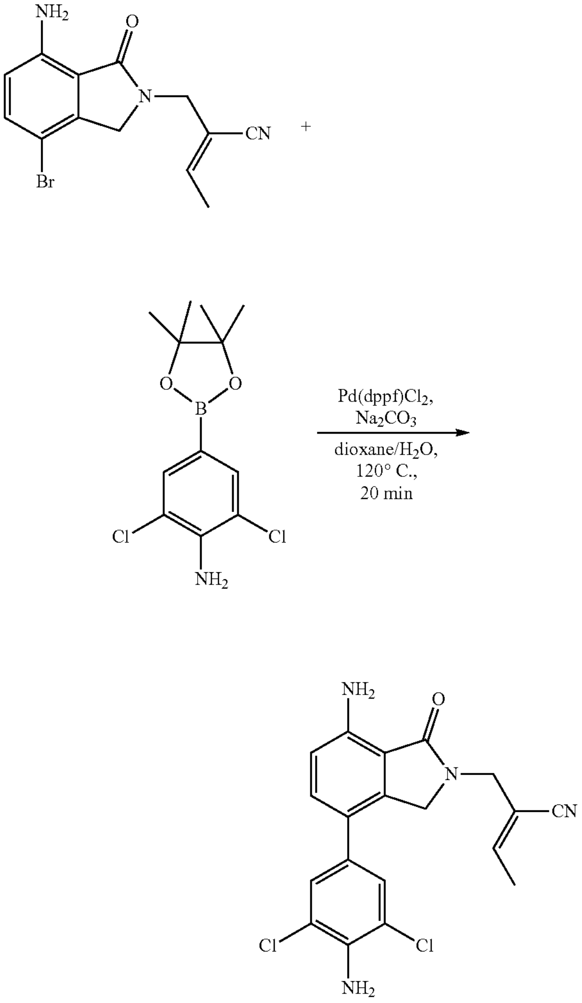

To a solution of (Z)-2-[(7-amino-4-bromo-1-oxo-isoindolin-2-yl)methyl]but-2-enenitrile (70 mg, 228.64 μmol, 1 eq.) and 2,6-dichloro-4-(4,4,5,5-tetramethyl-1,3,2-dioxaborolan-2-yl)aniline (100 mg, 275.69 μmol, 1.21 eq.) (80% purity) in dioxane (2.0 mL) and water (0.5 mL) were added Pd(dppf)$Cl_2$ (16.73 mg, 22.86 μmol, 0.1 eq.) and $Na_2CO_3$ (72.70 mg, 685.92 μmol, 3 eq.). The reaction was stirred at 120° C. for 20 min under nitrogen. 40 mL of sat. EDTA was added and the mixture was stirred at 20° C. for 1 h. The reaction mixture was extracted with EtOAc (20 mL×3). The combined organic layers were washed with brine (10 mL×3), dried over anhydrous sodium sulfate, filtered, and concentrated. The residue was purified by prep-TLC (silica gel; PE:EtOAc=2/1) to afford the title compound (70 mg, Yield 79.06%) as a yellow oil. LC-MS: $[M+H]^+$ 387.

Route 2

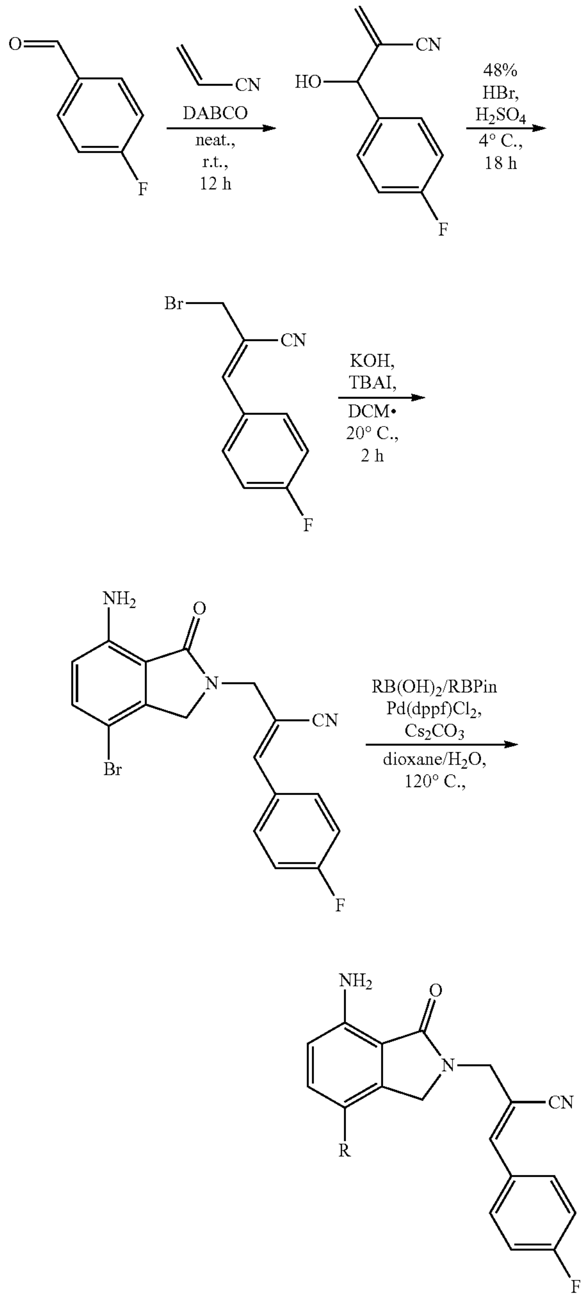

Preparation of 2-[(4-fluorophenyl)-hydroxy-methyl]prop-2-enenitrile

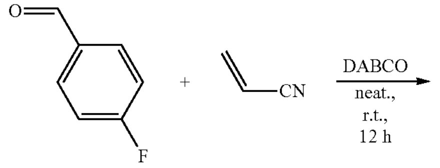

-continued

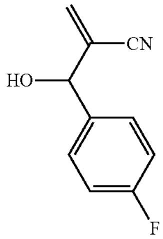

To a mixture of 4-fluorobenzaldehyde (10 g, 80.57 mmol, 8.47 mL, 1 eq.) and prop-2-enenitrile (4.28 g, 80.57 mmol, 5.34 mL, 1 eq.) was added DABCO (1.81 g, 16.11 mmol, 1.77 mL, 0.2 eq.). The reaction mixture was stirred at 20° C. for 12 h. The reaction mixture was diluted with 100 mL of EtOAc. The organic layer was washed with 5% HCl (3×50 mL), 10% $NaHCO_3$ (50 mL), and brine (50 mL), dried over anhydrous sodium sulfate, filtered, and concentrated. The residue was purified by column chromatography (silica gel; PE:EtOAc=4/1) to afford the title compound (5.2 g, Yield 32.8%) as a white solid.

Preparation of (E)-2-(bromomethyl)-3-(4-fluorophenyl)prop-2-enenitrile

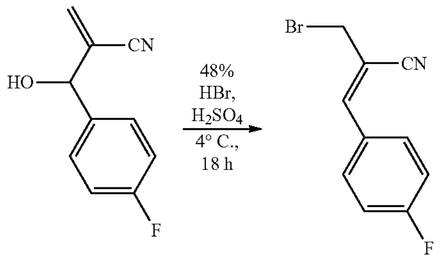

To a solution of 2-[(4-fluorophenyl)-hydroxy-methyl]prop-2-enenitrile (2 g, 11.29 mmol, 1 eq.) in DCM (10 mL) were added HBr (7.45 g, 44.20 mmol, 5 mL, 48% purity, 3.92 eq.) and $H_2SO_4$ (9.20 g, 93.80 mmol, 5 mL, 8.31 eq.) at 0° C. The reaction mixture was stirred at 15° C. for 12 hr. The reaction mixture was quenched with sat. $NaHCO_3$ (50 mL) at 0° C., diluted with water (100 mL), and extracted with DCM (50 mL×3). The combined organic layers were washed with water (200 mL×3) and brine (200 mL×3), dried over anhydrous sodium sulfate, filtered, and concentrated. The residue was purified by silica gel chromatography (PE:EtOAc:DCM 100:5:5 mL) to afford the title compound (1.4 g, Yield 51.7%) as a brown solid.

Preparation of (E)-2-(bromomethyl)but-2-enenitrile

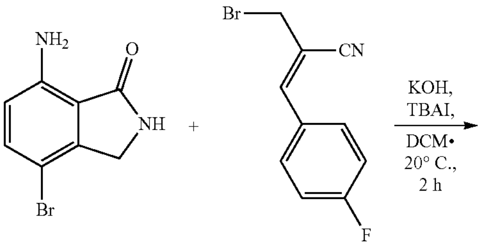

-continued

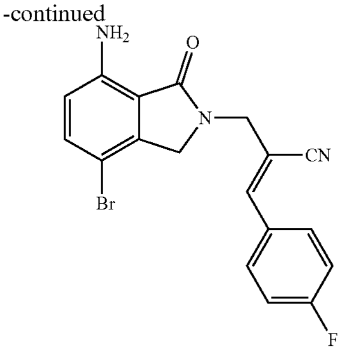

To a solution of 7-amino-4-bromo-isoindolin-1-one (200 mg, 880.83 μmol, 1 eq.) in DCM (5 mL) were added TBAI (325.35 mg, 880.83 μmol, 1 eq.) and KOH (173.46 mg, 3.09 mmol, 3.51 eq.). Then a solution of (E)-2-(bromomethyl)-3-(4-fluorophenyl)prop-2-enenitrile (213 mg, 887.24 μmol, 1.01 eq.) in DCM (2 mL) was added. The reaction mixture was stirred at 20° C. for 2 h. The reaction was quenched with ice water (5 mL) and extracted with DCM (10 mL×3). The combined organic layer was washed with water (10 mL×3) and brine (10 mL×3), dried over anhydrous sodium sulfate, filtered, and concentrated. The residue was purified by prep-TLC (silica gel; DCM:MeOH=20:1) to afford the title compound (100 mg, Yield 26.5%) as a yellow solid.

Preparation of (E)-2-(bromomethyl)but-2-enenitrile

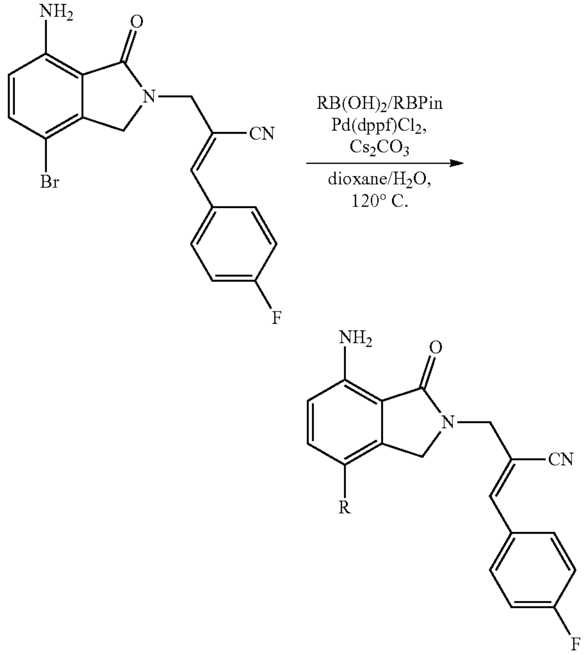

To a solution of (E)-2-(bromomethyl)but-2-enenitrile (1 eq.), $RB(OH)_2$ or RBPin (~1.0-2 eq.) in dioxane (~2.4 mL) and water (~0.6 mL) were added $Na_2CO_3$ (~3 eq.) and $Pd(dppf)Cl_2$ (~0.1 eq.). The reaction was stirred at 120° C. for 10 mins under a nitrogen atmosphere. TLC showed that the reaction was complete. ~30 mL EDTA was added to the reaction, and the reaction was stirred at 20° C. for 1 h. The reaction was extracted with EtOAc (~10 mL×3). The combined organic layer was washed with brine (~10 mL×3), dried over anhydrous sodium sulfate, filtered, and concentrated. The crude was purified by prep-TLC or prep-HPLC to obtain the desired compound.

Route 3

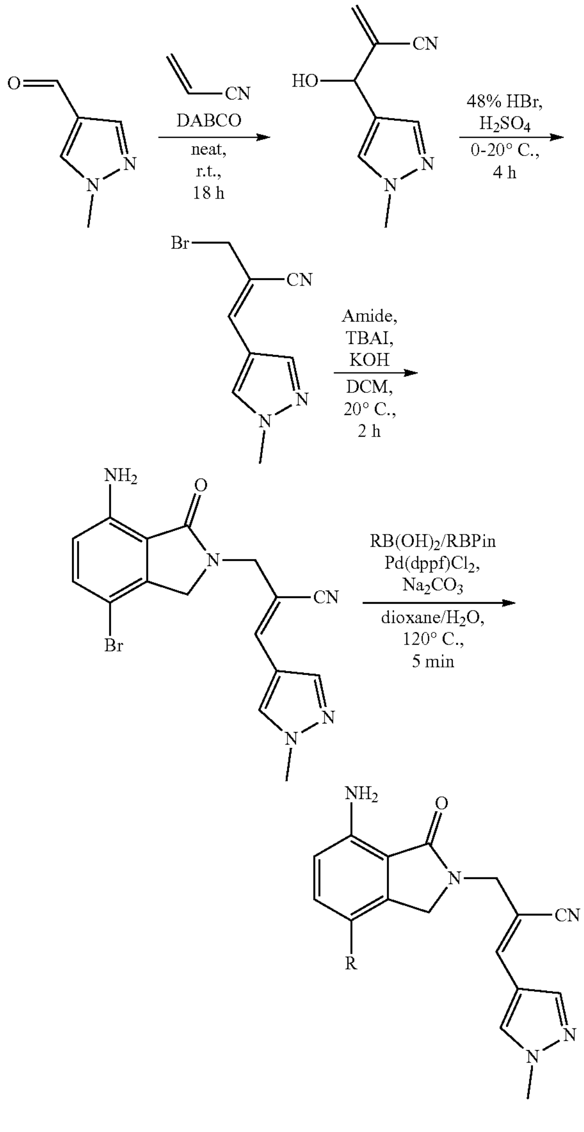

Preparation of 2-[hydroxy-(1-methylpyrazol-4-yl)methyl]prop-2-enenitrile

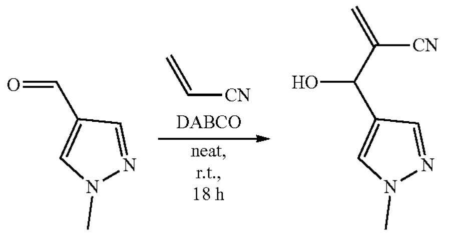

A mixture of 1-methylpyrazole-4-carbaldehyde (3 g, 27.24 mmol, 1 eq.), prop-2-enenitrile (1.45 g, 27.24 mmol, 1.81 mL, 1 eq.) and DABCO (2.44 g, 21.80 mmol, 2.40 mL, 0.8 eq.) was stirred at 20° C. for 18 h. The reaction was quenched with water (10 mL) at 0° C. and extracted with $CHCl_3$/i-PrOH 3:1 (30 mL×5). The combined organic layer was washed with brine (20 mL×3), dried over anhydrous sodium sulfate, filtered, and concentrated. The residue was purified by silica gel chromatography (PE:EtOAc=1:3) to afford the title compound (1.8 g, Yield 38.5%) as a light yellow gum.

Preparation of (E)-2-(bromomethyl)-3-(1-methylpyrazol-4-yl)prop-2-enenitrile

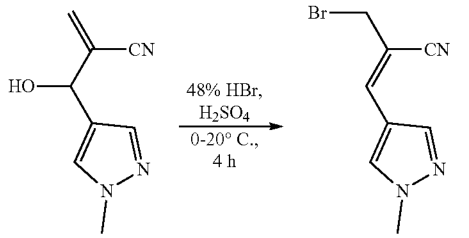

To a solution of 2-[hydroxy-(1-methylpyrazol-4-yl)methyl]prop-2-enenitrile (300 mg, 1.84 mmol, 1 eq.) in DCM (1.6 mL) were added HBr (1.19 g, 7.07 mmol, 0.8 mL, 48% purity, 3.85 eq.) and $H_2SO_4$ (1.47 g, 15.01 mmol, 0.8 mL, 8.16 eq.) at 0° C. The reaction was stirred at 20° C. for 4 h. The reaction was poured into ice-water (20 mL) and extracted with EtOAc (20 mL×3). The combined organic layer was washed with water (20 mL×3) and brine (10 mL×3), dried over anhydrous sodium sulfate, filtered, and concentrated. The residue was purified by prep-TLC (silica gel; PE:EtOAc=1:1) to afford the title compound (120 mg, Yield 28.9%) as a light yellow solid.

Preparation of (Z)-2-[(7-amino-4-bromo-1-oxo-isoindolin-2-yl)methyl]-3-(1-methylpyrazol-4-yl)prop-2-enenitrile

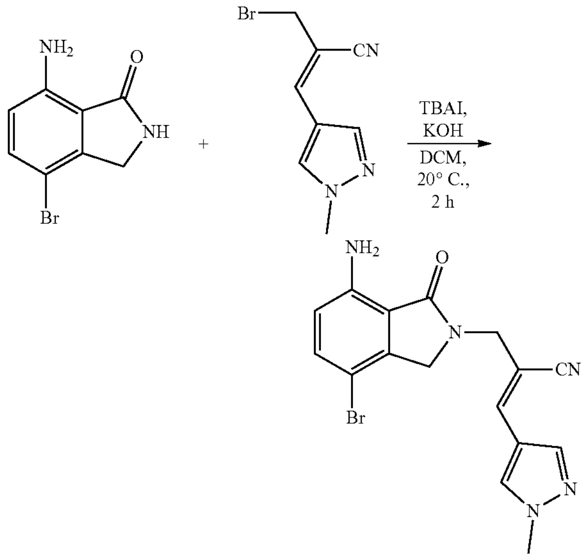

To a solution of 7-amino-4-bromo-isoindolin-1-one (40 mg, 176.17 μmol, 1 eq.), TBAI (65.07 mg, 176.17 μmol, 1 eq.) and KOH (29.65 mg, 528.50 μmol, 3 eq.) in DCM (2 mL) was stirred at 20° C. for 1 min. Then (E)-2-(bromomethyl)-3-(1-methylpyrazol-4-yl)prop-2-enenitrile (39.83 mg, 176.17 μmol, 1 eq.) in DCM (1 mL) was added. The reaction was stirred at 20° C. for 2 h, quenched with water (5 mL), and extracted with DCM (20 mL×3). The combined organic layer was washed with water (10 mL×3), birne (10 mL×3), dried over anhydrous sodium sulfate, filtered, and concentrated. The residue was purified by prep-TLC (silica gel; 100% EtOAc) to afford the title compound (50 mg, Yield 38.1%) as a yellow solid.

Preparation of (Z)-2-[[7-amino-4-(1-methylindazol-6-yl)-1-oxo-isoindolin-2-yl]methyl]-3-(1-methylpyrazol-4-yl)prop-2-enenitrile (Compound 553)

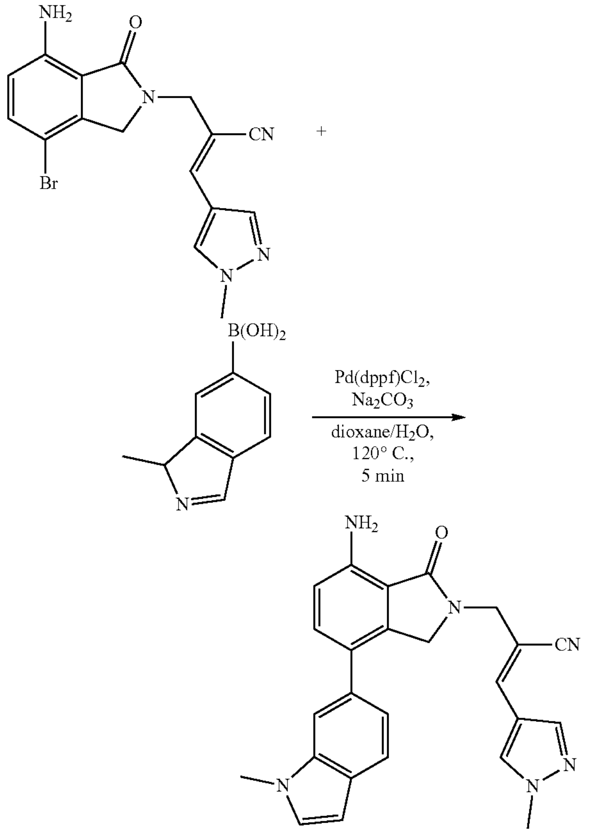

To a mixture of (Z)-2-[(7-amino-4-bromo-1-oxo-isoindolin-2-yl)methyl]-3-(1-methylpyrazol-4-yl) prop-2-enenitrile (35 mg, 94.03 μmol, 1 eq.) and (1-methylindazol-6-yl) boronic acid (19.86 mg, 112.84 μmol, 1.2 eq.) in dioxane (5 mL) and water (1 mL) were added $Na_2CO_3$ (29.90 mg, 282.09 μmol, 3 eq.) and $Pd(dppf)Cl_2$ (6.88 mg, 9.40 μmol, 0.1 eq.). The mixture was stirred at 120° C. for 20 min under nitrogen atmosphere. Sat. EDTA (25 mL) was added, and the mixture was stirred at r.t. for 1.5 h. Then the mixture was extracted with EtOAc (20 mL×3). The combined organic layer was washed with brine (10 mL), dried over anhydrous sodium sulfate, filtered, and concentrated. The residue was purified by SFC to afford the title compound (7.6 mg, Yield 18.1%) as a white solid. LC-MS: $[M+H]^+$ 424.1.

Route 4

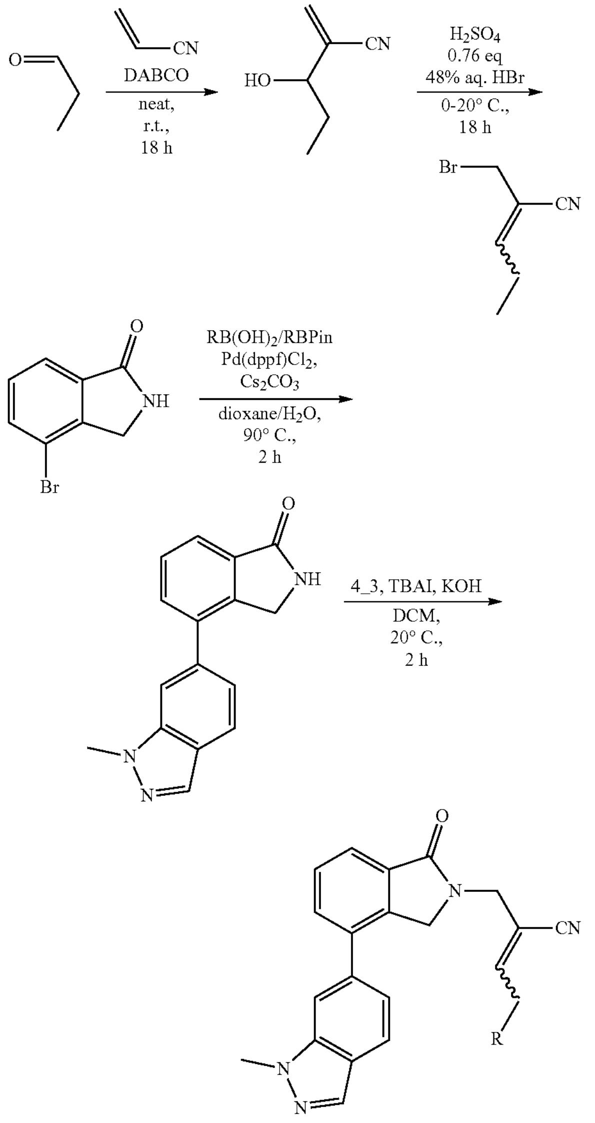

Preparation of 3-hydroxy-2-methylene-pentanenitrile

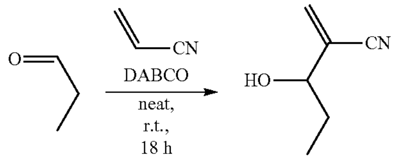

A mixture of propanal (5 g, 86.09 mmol, 6.27 mL, 1 eq.), prop-2-enenitrile (4.57 g, 86.09 mmol, 5.71 mL, 1 eq.), and DABCO (7.73 g, 68.87 mmol, 7.57 mL, 0.8 eq.) was stirred at 20° C. for 18 h. The reaction was quenched with water (10 mL) at 0° C., and the mixture was adjusted pH=4 with 12 M HCl. Then the reaction mixture was extracted with EtOAc (3×50 mL), and the combined organic layer was washed with brine (20 mL×3), dried over anhydrous sodium sulfate, filtered, and concentrated. The residue was purified by silica gel chromatography (PE:EtOAc=8:1) to afford the title compound (12 g, Yield 62.7%) as a colorless liquid.

Preparation of (E)-2-(bromomethyl)but-2-enenitrile

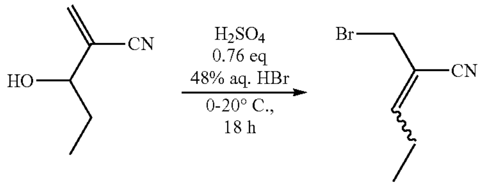

To a solution of 3-hydroxy-2-methylene-pentanenitrile (3.75 g, 26.99 mmol, 1 eq.) in DCM (4.5 mL) were added HBr (3.35 g, 19.87 mmol, 2.25 mL, 48% purity, 0.736 eq.) and $H_2SO_4$ (4.14 g, 42.21 mmol, 2.25 mL, 1.56 eq.) at 0° C. The reaction was stirred at 20° C. for 18 h. The reaction was poured into 350 mL of Sat. $NaHCO_3$ at 0° C. and extracted with EtOAc (200 mL×3). The combined organic layer was washed with sat $NaHCO_3$ (50 mL) and brine (100 mL×3), dried over anhydrous sodium sulfate, filtered, and concentrated. The residue was purified silica gel chromatography (PE:EtOAc=96:4) to afford the title compound (1.6 g, Yield 29%) as a light yellow liquid.

Preparation of 4-(1-methylindazol-6-yl)isoindolin-1-one

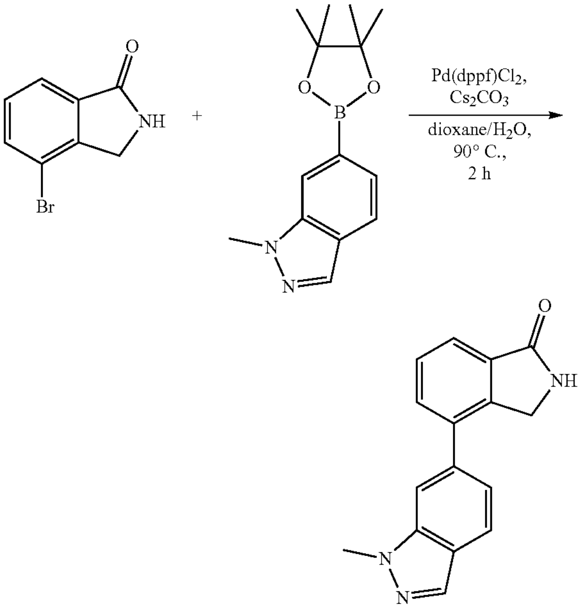

To a solution of 4-bromoisoindolin-1-one (500 mg, 2.36 mmol, 1 eq.) and 1-methyl-6-(4,4,5,5-tetramethyl-1,3,2-dioxaborolan-2-yl)indazole (727.27 mg, 2.82 mmol, 1.19 eq.) in dioxane (10 mL) and water (2.5 mL) were added $Cs_2CO_3$ (2.30 g, 7.07 mmol, 3 eq.) and $Pd(dppf)Cl_2$ (172.54 mg, 235.80 μmol, 0.1 eq.). The reaction was stirred at 90° C. for 2 h under nitrogen atmosphere. Sat. EDTA (100 mL) was added, and the reaction was stirred at 20° C. for 1 h. Then the reaction mixture was extracted with EtOAc (30 mL×5). The combined organic layer was washed with brine (30 mL×3), dried over anhydrous sodium sulfate, filtered, and concentrated. The residue was washed with DCM/MeOH (10:1.5 mL) to afford the title compound (400 mg, Yield 64.4%) as a light yellow solid.

Preparation of (2Z)-2-{[4-(1-methyl-1H-indazol-6-yl)-1-oxo-2,3-dihydro-1H-isoindol-2-yl]methyl}pent-2-enenitrile and (2E)-2-{[4-(1-methyl-1H-indazol-6-yl)-1-oxo-2,3-dihydro-1H-isoindol-2-yl]methyl}pent-2-enenitrile (Compound 556 and 557)

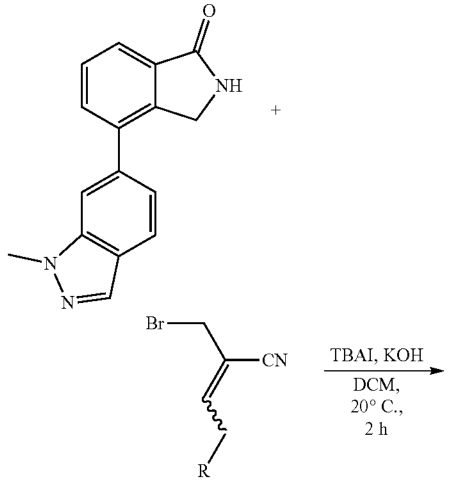

-continued

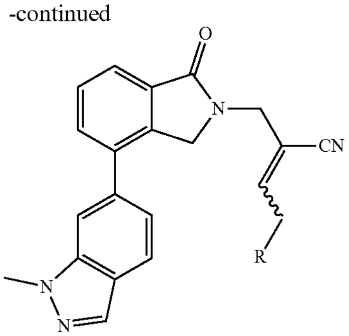

A solution of 4-(1-methylindazol-6-yl)isoindolin-1-one (80 mg, 303.84 μmol, 1 eq.), TBAI (112.23 mg, 303.84 μmol, 1 eq.) and KOH (51.15 mg, 911.53 μmol, 3 eq.) in DCM (4 mL) was stirred at 20° C. for 1 min. Then, (E)-2-(bromomethyl)pent-2-enenitrile (62.21 mg, 303.84 μmol, 1 eq.) in 1 mL DCM was added. The reaction was stirred at 20° C. for 2 h. The reaction was poured into ice-water (5 mL) and extracted with DCM (10 mL×4). The combined organic layer was washed with water (10 mL×3) and brine (10 mL×3), dried over anhydrous sodium sulfate, filtered, and concentrated. The residue was purified by prep-TLC (silica gel; DCM:MeOH=30:1) to give the mixture. The mixture was separated by SFC to afford (2Z)-2-{[4-(1-methyl-1H-indazol-6-yl)-1-oxo-2,3-dihydro-1H-isoindol-2-yl]methyl}pent-2-enenitrile (8.7 mg, Yield 8.0%) as a white solid, LC-MS: $[M+H]^+$ 372.1; and (2E)-2-{[4-(1-methyl-1H-indazol-6-yl)-1-oxo-2,3-dihydro-1H-isoindol-2-yl]methyl}pent-2-enenitrile (5.4 mg, Yield 4.99%) as a white solid, LC-MS: $[M+H]^+$ 372.1.

TABLE 13 shows compounds synthesized using the methods described in EXAMPLE 15.

TABLE 14

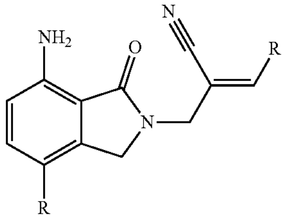

| Cpd. No. | Structure | IUPAC | LC-MS (ES+, m/z) |
|---|---|---|---|
| 534. | 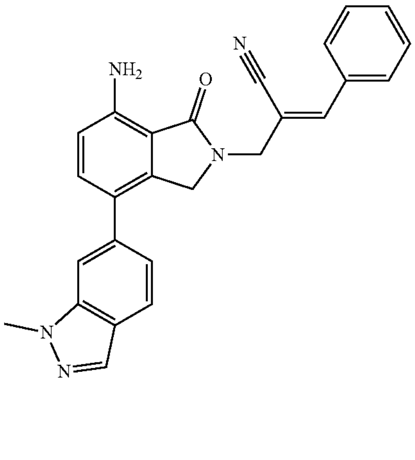 [SMILES: Cn1ncc2ccc(-c3ccc(N)c4c3CN(C/C(C#N)=C/c3ccccc3)C4=O)cc21] | (2Z)-2-{[7-amino-4-(1-methyl-1H-indazol-6-yl)-1-oxo-2,3-dihydro-1H-isoindol-2-yl]methyl}-3-phenylprop-2-enenitrile | 420.2 |

TABLE 14-continued
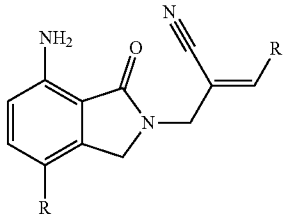
| Cpd. No. | Structure | IUPAC | LC-MS (ES+, m/z) |
|---|---|---|---|
| 535. | 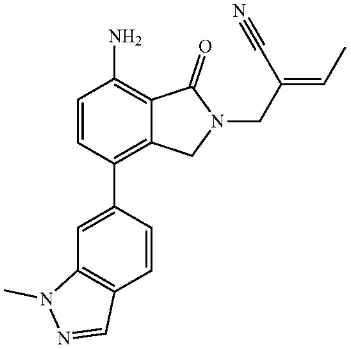 [SMILES: C/C=C(\C#N)CN1Cc2c(-c3ccc4cnn(C)c4c3)ccc(N)c2C1=O] | (2Z)-2-{[7-amino-4-(1-methyl-1H-indazol-6-yl)-1-oxo-2,3-dihydro-1H-isoindol-2-yl]methyl}but-2-enenitrile | 358.2 |
| 536. | 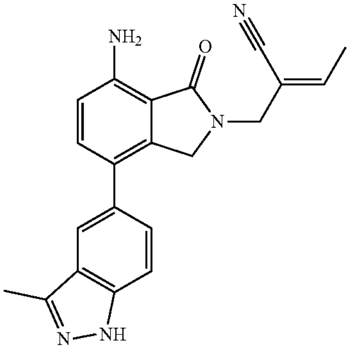 [SMILES: C/C=C(\C#N)CN1Cc2c(-c3ccc4[nH]nc(C)c4c3)ccc(N)c2C1=O] | (2Z)-2-{[7-amino-4-(3-methyl-1H-indazol-5-yl)-1-oxo-2,3-dihydro-1H-isoindol-2-yl]methyl}but-2-enenitrile | 358.2 |
| 537. | 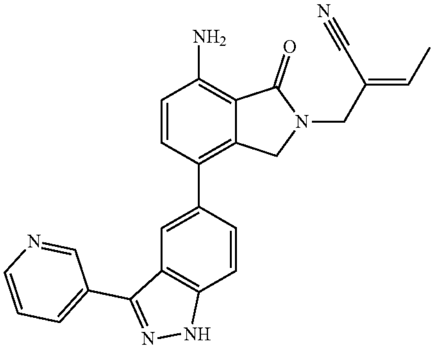 [SMILES: C/C=C(\C#N)CN1Cc2c(-c3ccc4[nH]nc(-c5cccnc5)c4c3)ccc(N)c2C1=O] | (2Z)-2-({7-amino-1-oxo-4-[3-(pyridin-3-yl)-1H-indazol-5-yl]-2,3-dihydro-1H-isoindol-2-yl}methyl)but-2-enenitrile | 421.1 |

TABLE 14-continued
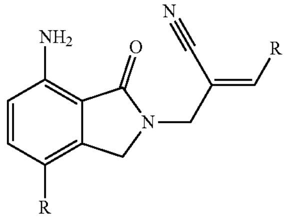
| Cpd. No. | Structure | IUPAC | LC-MS (ES+, m/z) |
|---|---|---|---|
| 538. | 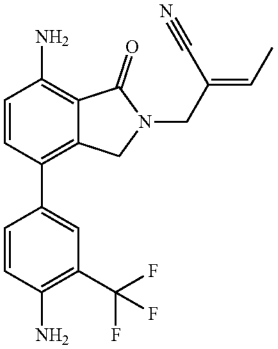 [SMILES: C/C=C(\C#N)CN1Cc2c(-c3ccc(N)c(C(F)(F)F)c3)ccc(N)c2C1=O] | (2Z)-2-({7-amino-4-[4-amino-3-(trifluoromethyl)phenyl]-1-oxo-2,3-dihydro-1H-isoindol-2-yl}methyl)but-2-enenitrile | 387.1 |
| 539. | 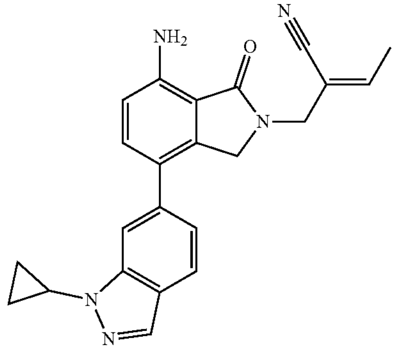 [SMILES: C/C=C(\C#N)CN1Cc2c(-c3ccc4cnn(C5CC5)c4c3)ccc(N)c2C1=O] | (2Z)-2-{[7-amino-4-(1-cyclopropyl-1H-indazol-6-yl)-1-oxo-2,3-dihydro-1H-isoindol-2-yl]methyl}but-2-enenitrile | 384.2 |
| 540. | 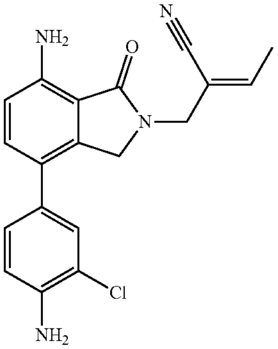 [SMILES: C/C=C(\C#N)CN1Cc2c(-c3ccc(N)c(Cl)c3)ccc(N)c2C1=O] | (2Z)-2-{[7-amino-4-(4-amino-3-chlorophenyl)-1-oxo-2,3-dihydro-1H-isoindol-2-yl]methyl}but-2-enenitrile | 353.1 |

TABLE 14-continued
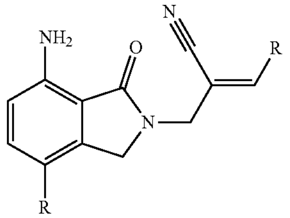
| Cpd. No. | Structure | IUPAC | LC-MS (ES+, m/z) |
|---|---|---|---|
| 541. | 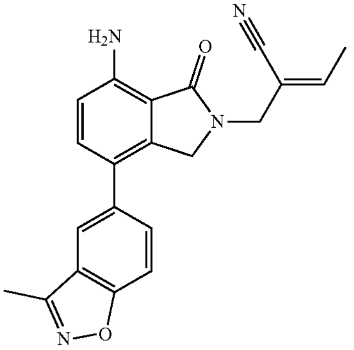 [SMILES: C/C=C(\C#N)CN1Cc2c(-c3ccc4onc(C)c4c3)ccc(N)c2C1=O] | (2Z)-2-{[7-amino-4-(3-methyl-1,2-benzoxazol-5-yl)-1-oxo-2,3-dihydro-1H-isoindol-2-yl]methyl}but-2-enenitrile | 359.1 |
| 542. | 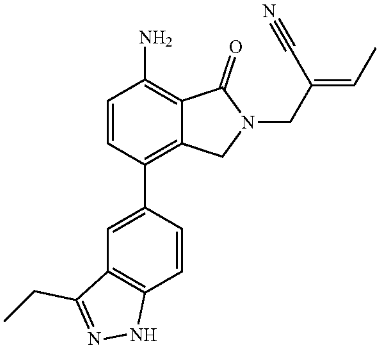 [SMILES: C/C=C(\C#N)CN1Cc2c(-c3ccc4[nH]nc(CC)c4c3)ccc(N)c2C1=O] | (2Z)-2-{[7-amino-4-(3-ethyl-1H-indazol-5-yl)-1-oxo-2,3-dihydro-1H-isoindol-2-yl]methyl}but-2-enenitrile | 372.1 |
| 543. | 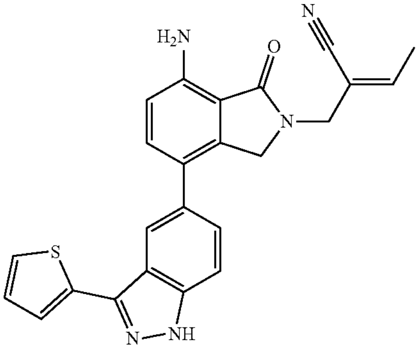 [SMILES: C/C=C(\C#N)CN1Cc2c(-c3ccc4[nH]nc(-c5cccs5)c4c3)ccc(N)c2C1=O] | (2Z)-2-({7-amino-1-oxo-4-[3-(thiophen-2-yl)-1H-indazol-5-yl]-2,3-dihydro-1H-isoindol-2-yl}methyl)but-2-enenitrile | 426.1 |

TABLE 14-continued
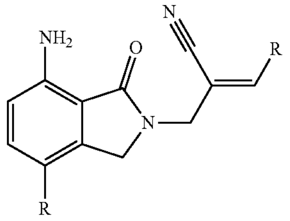
| Cpd. No. | Structure | IUPAC | LC-MS (ES+, m/z) |
|---|---|---|---|
| 544. | 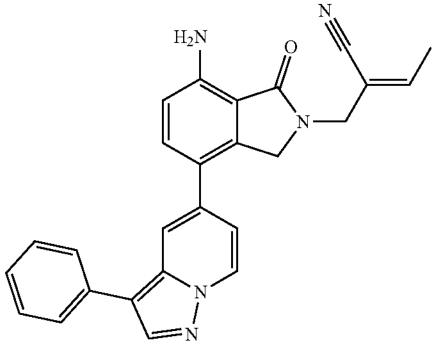 [SMILES: C/C=C(\C#N)CN1Cc2c(-c3ccn4ncc(-c5ccccc5)c4c3)ccc(N)c2C1=O] | (2Z)-2-[(7-amino-1-oxo-4-{3-phenylpyrazolo[1,5-a]pyridin-5-yl}-2,3-dihydro-1H-isoindol-2-yl)methyl]but-2-enenitrile | 420.1 |
| 545. | 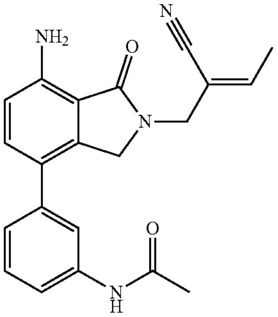 [SMILES: C/C=C(\C#N)CN1Cc2c(-c3cccc(NC(C)=O)c3)ccc(N)c2C1=O] | N-{3-[7-amino-2-(2-cyano-2-ethylideneethyl)-1-oxo-2,3-dihydro-1H-isoindol-4-yl]phenyl}acetamide | 361.2 |
| 546. | 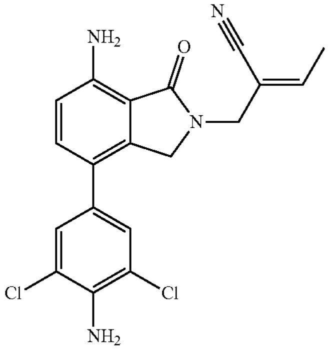 [SMILES: C/C=C(\C#N)CN1Cc2c(-c3cc(Cl)c(N)c(Cl)c3)ccc(N)c2C1=O] | (2Z)-2-{[7-amino-4-(4-amino-3,5-dichlorophenyl)-1-oxo-2,3-dihydro-1H-isoindol-2-yl]methyl}but-2-enenitrile | 387 |

TABLE 14-continued
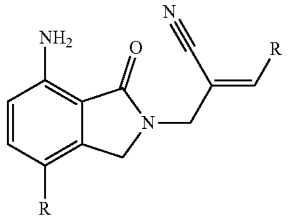
| Cpd. No. | Structure | IUPAC | LC-MS (ES+, m/z) |
|---|---|---|---|
| 547. | 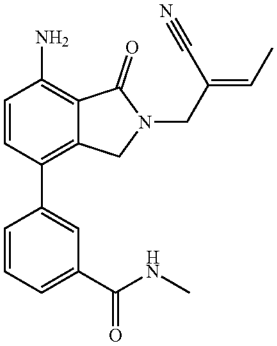 [SMILES: C/C=C(\C#N)CN1Cc2c(-c3cccc(C(=O)NC)c3)ccc(N)c2C1=O] | 3-{7-amino-2-[(2Z)-2-cyano-2-ethylideneethyl]-1-oxo-2,3-dihydro-1H-isoindol-4-yl}-N-methylbenzamide | 361.2 |
| 548. | 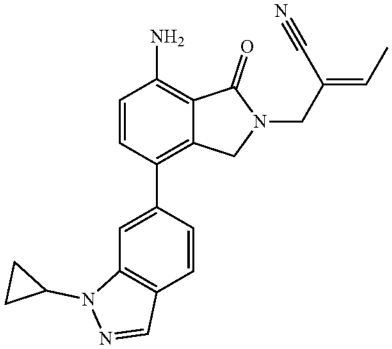 [SMILES: C/C=C(\C#N)CN1Cc2c(-c3ccc4cnn(C5CC5)c4c3)ccc(N)c2C1=O] | (2E)-2-{[7-amino-4-(1-methyl-1H-indazol-6-yl)-1-oxo-2,3-dihydro-1H-isoindol-2-yl]methyl}but-2-enenitrile | 358.1 |
| 549. | 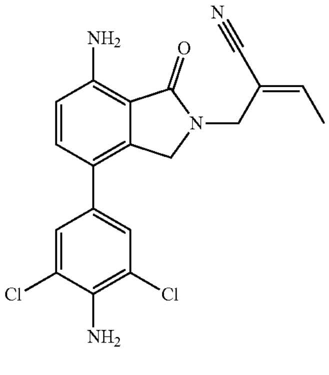 [SMILES: C/C=C(/C#N)CN1Cc2c(-c3cc(Cl)c(N)c(Cl)c3)ccc(N)c2C1=O] | (2E)-2-{[7-amino-4-(4-amino-3,5-dichlorophenyl)-1-oxo-2,3-dihydro-1H-isoindol-2-yl]methyl}but-2-enenitrile | 387 |

TABLE 14-continued
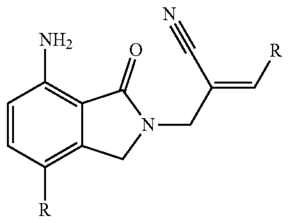
| Cpd. No. | Structure | IUPAC | LC-MS (ES+, m/z) |
|---|---|---|---|
| 550. | 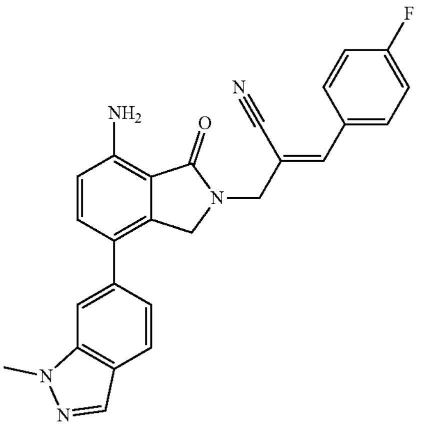 [SMILES: Cn1ncc2ccc(-c3ccc(N)c4c3CN(C/C(C#N)=C/c3ccc(F)cc3)C4=O)cc21] | (2Z)-2-{[7-amino-4-(1-methyl-1H-indazol-6-yl)-1-oxo-2,3-dihydro-1H-isoindol-2-yl]methyl}-3-(4-fluorophenyl)prop-2-enenitrile | 438.1 |
| 551. | 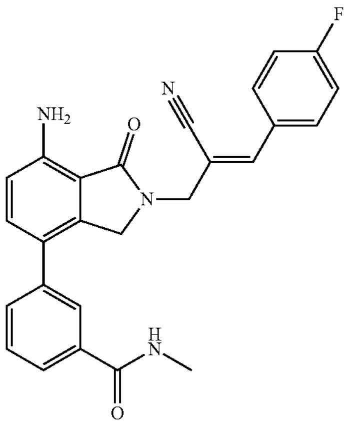 [SMILES: CNC(=O)c1cccc(-c2ccc(N)c3c2CN(C/C(C#N)=C/c2ccc(F)cc2)C3=O)c1] | 3-{7-amino-2-[(2Z)-2-cyano-2-[(4-fluorophenyl)methylidene]ethyl]-1-oxo-2,3-dihydro-1H-isoindol-4-yl}-N-methylbenzamide | 441.1 |
| 552. | 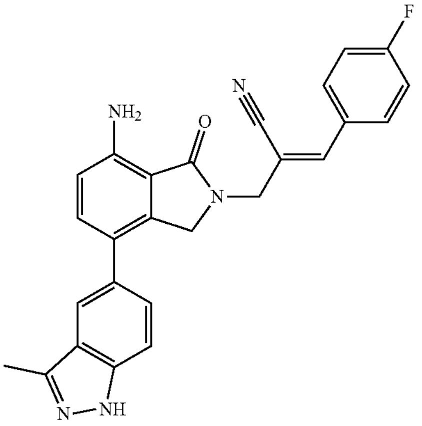 [SMILES: Cc1n[nH]c2ccc(-c3ccc(N)c4c3CN(C/C(C#N)=C/c3ccc(F)cc3)C4=O)cc12] | (2Z)-2-{[7-amino-4-(3-methyl-1H-indazol-5-yl)-1-oxo-2,3-dihydro-1H-isoindol-2-yl]methyl}-3-(4-fluorophenyl)prop-2-enenitrile | 438.1 |

TABLE 14-continued
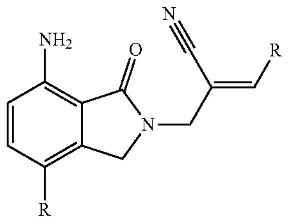
| Cpd. No. | Structure | IUPAC | LC-MS (ES+, m/z) |
|---|---|---|---|
| 553. | 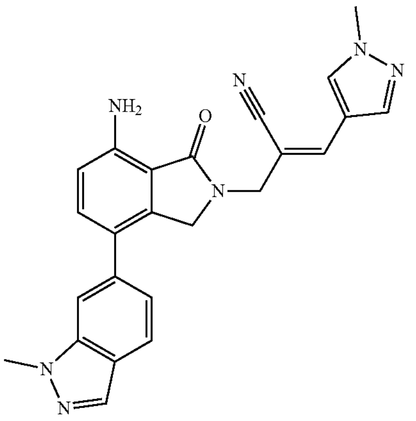 [SMILES: Cn1cc(/C=C(\C#N)CN2Cc3c(-c4ccc5cnn(C)c5c4)ccc(N)c3C2=O)cn1] | (2Z)-2-{[7-amino-4-(1-methyl-1H-indazol-6-yl)-1-oxo-2,3-dihydro-1H-isoindol-2-yl]methyl}-3-(1-methyl-1H-pyrazol-4-yl)prop-2-enenitrile | 424.1 |
| 554. | 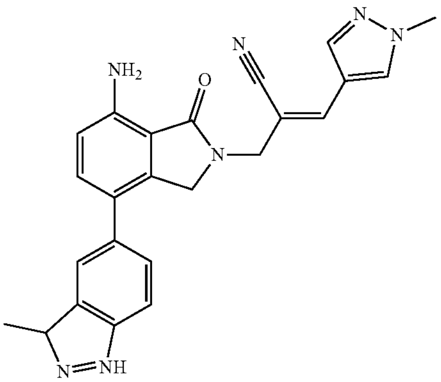 | (2Z)-2-{[7-amino-4-(3-methyl-1H-indazol-5-yl)-1-oxo-2,3-dihydro-1H-isoindol-2-yl]methyl}-3-(1-methyl-1H-pyrazol-4-yl)prop-2-enenitrile | 424.1 |
| 555. | 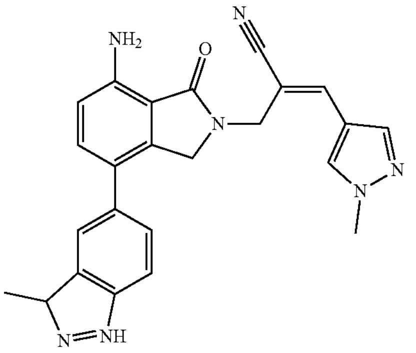 [SMILES: CC1N=Nc2ccc(-c3ccc(N)c4c3CN(C/C(C#N)=C\c3cnn(C)c3)C4=O)cc21] | (2E)-2-{[7-amino-4-(3-methyl-1H-indazol-5-yl)-1-oxo-2,3-dihydro-1H-isoindol-2-yl]methyl}-3-(1-methyl-1H-pyrazol-4-yl)prop-2-enenitrile | 424.1 |

TABLE 14-continued
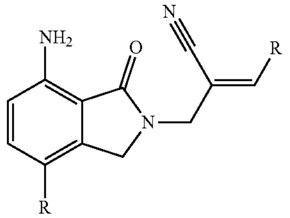
| Cpd. No. | Structure | IUPAC | LC-MS (ES+, m/z) |
|---|---|---|---|
| 556. | 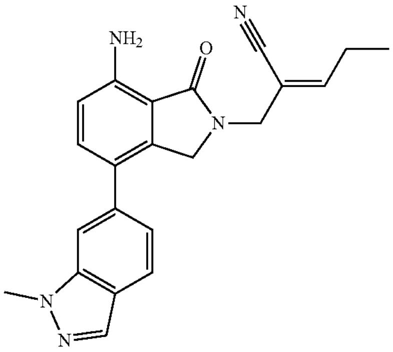 [SMILES: CC/C=C(\C#N)CN1Cc2c(-c3ccc4cnn(C)c4c3)ccc(N)c2C1=O] | (2Z)-2-{[7-amino-4-(1-methyl-1H-indazol-6-yl)-1-oxo-2,3-dihydro-1H-isoindol-2-yl]methyl}pent-2-enenitrile | 372.1 |
| 557. | 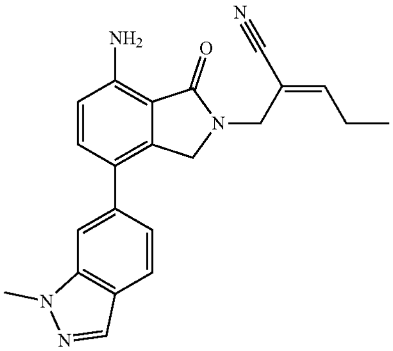 [SMILES: CC/C=C(/C#N)CN1Cc2c(-c3ccc4cnn(C)c4c3)ccc(N)c2C1=O] | (2E)-2-{[7-amino-4-(1-methyl-1H-indazol-6-yl)-1-oxo-2,3-dihydro-1H-isoindol-2-yl]methyl}pent-2-enenitrile | 372.1 |
| 558. | 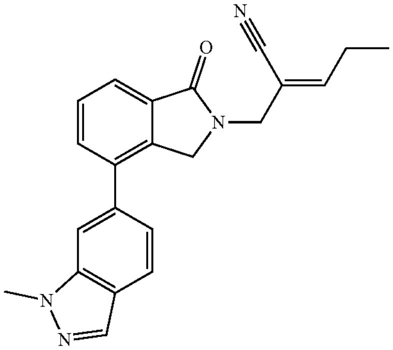 [SMILES: CC/C=C(\C#N)CN1Cc2c(cccc2-c2ccc3cnn(C)c3c2)C1=O] | (2Z)-2-{[4-(1-methyl-1H-indazol-6-yl)-1-oxo-2,3-dihydro-1H-isoindol-2-yl]methyl}pent-2-enenitrile | 357.1 |

TABLE 14-continued
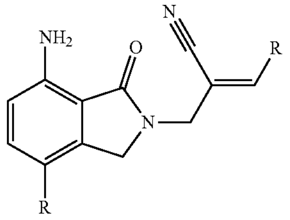
| Cpd. No. | Structure | IUPAC | LC-MS (ES+, m/z) |
|---|---|---|---|
| 559. | 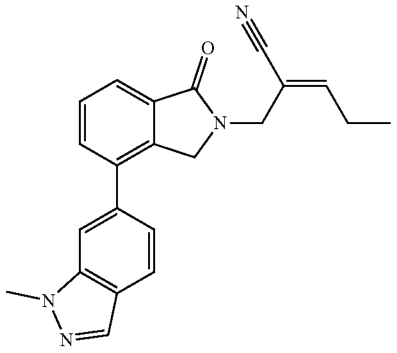 [SMILES: CC/C=C(/C#N)CN1Cc2c(cccc2-c2ccc3cnn(C)c3c2)C1=O] | (2E)-2-{[4-(1-methyl-1H-indazol-6-yl)-1-oxo-2,3-dihydro-1H-isoindol-2-yl]methyl}pent-2-enenitrile | 357.1 |
| 560. | 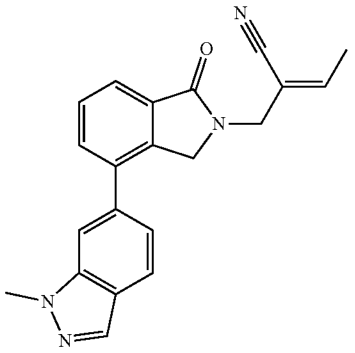 [SMILES: C/C=C(\C#N)CN1Cc2c(cccc2-c2ccc3cnn(C)c3c2)C1=O] | (2Z)-2-{[4-(1-methyl-1H-indazol-6-yl)-1-oxo-2,3-dihydro-1H-isoindol-2-yl]methyl}but-2-enenitrile | 343.1 |
| 561. | 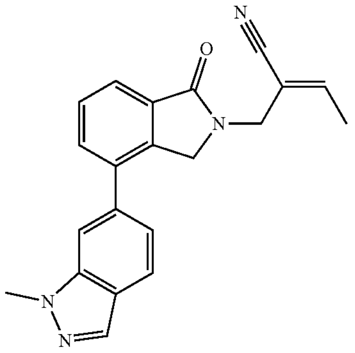 [SMILES: C/C=C(/C#N)CN1Cc2c(cccc2-c2ccc3cnn(C)c3c2)C1=O] | (2E)-2-{[4-(1-methyl-1H-indazol-6-yl)-1-oxo-2,3-dihydro-1H-isoindol-2-yl]methyl}but-2-enenitrile | 343.1 |

TABLE 14-continued
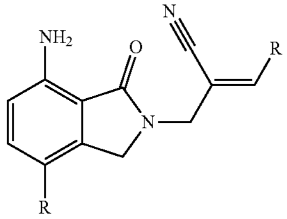
| Cpd. No. | Structure | IUPAC | LC-MS (ES+, m/z) |
|---|---|---|---|
| 562. | 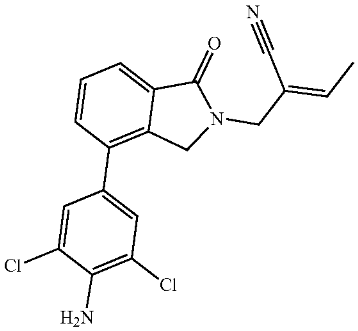 [SMILES: C/C=C(\C#N)CN1Cc2c(cccc2-c2cc(Cl)c(N)c(Cl)c2)C1=O] | (2Z)-2-{[4-(4-amino-3,5-dichlorophenyl)-1-oxo-2,3-dihydro-1H-isoindol-2-yl]methyl}but-2-enenitrile | 372 |
| 563. | 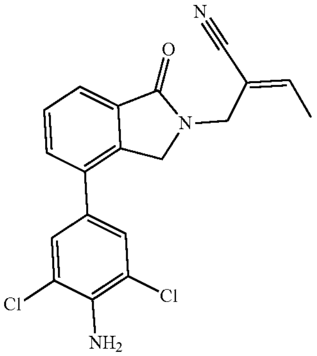 [SMILES: C/C=C(/C#N)CN1Cc2c(cccc2-c2cc(Cl)c(N)c(Cl)c2)C1=O] | (2E)-2-{[4-(4-amino-3,5-3,5-dichlorophenyl)-1-oxo-2,3-dihydro-1H-isoindol-2-yl]methyl}but-2-enamide | 372 |
| 564. | 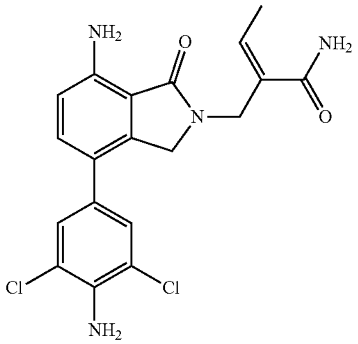 [SMILES: C/C=C(/CN1Cc2c(-c3cc(Cl)c(N)c(Cl)c3)ccc(N)c2C1=O)C(N)=O] | (2Z)-2-{[7-amino-4-(4-amino-3,5-dichlorophenyl)-1-oxo-2,3-dihydro-1H-isoindol-2-yl]methyl}but-2-enamide | 405 |

TABLE 14-continued

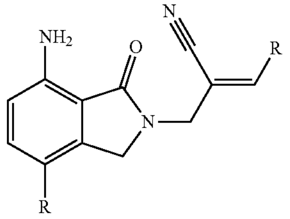

| Cpd. No. | Structure | IUPAC | LC-MS (ES+, m/z) |
|---|---|---|---|
| 565. | 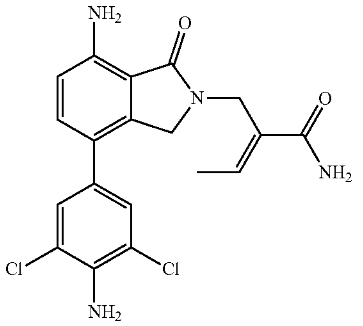 [SMILES: C/C=C(\CN1Cc2c(-c3cc(Cl)c(N)c(Cl)c3)ccc(N)c2C1=O)C(N)=O] | (2E)-2-{[7-amino-4-(4-amino-3,5-dichlorophenyl)-1-oxo-2,3-dihydro-1H-isoindol-2-yl]methyl}but-2-enamide | 405 |
| 566. | 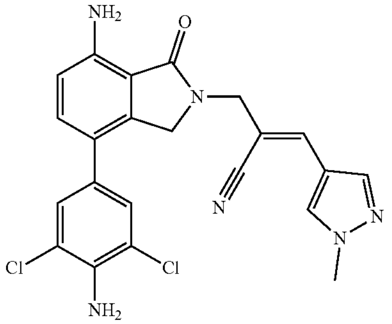 [SMILES: Cn1cc(/C=C(\C#N)CN2Cc3c(-c4cc(Cl)c(N)c(Cl)c4)ccc(N)c3C2=O)cn1] | (2Z)-2-{[7-amino-4-(4-amino-3,5-dichlorophenyl)-1-oxo-2,3-dihydro-1H-isoindol-2-yl]methyl}-3-(1-methyl-1H-pyrazol-4-yl)prop-2-enenitrile | 453.1 |
| 567. | 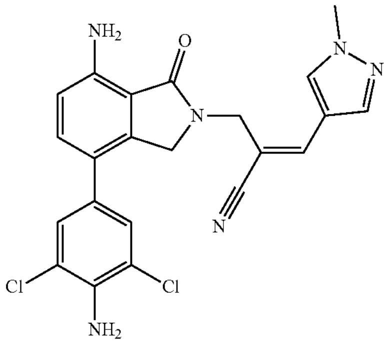 [SMILES: Cn1cc(/C=C(/C#N)CN2Cc3c(-c4cc(Cl)c(N)c(Cl)c4)ccc(N)c3C2=O)cn1] | (2E)-2-{[7-amino-4-(4-amino-3,5-dichlorophenyl)-1-oxo-2,3-dihydro-1H-isoindol-2-yl]methyl}-3-(1-methyl-1H-pyrazol-4-yl)prop-2-enenitrile | 453.1 |
| 568. | 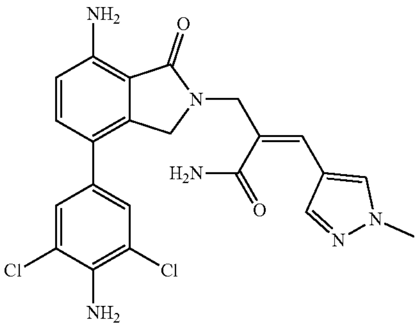 [SMILES: Cn1cc(/C=C(/CN2Cc3c(-c4cc(Cl)c(N)c(Cl)c4)ccc(N)c3C2=O)C(N)=O)cn1] | (2Z)-2-{[7-amino-4-(4-amino-3,5-dichlorophenyl)-1-oxo-2,3-dihydro-1H-isoindol-2-yl]methyl}-3-(1-methyl-1H-pyrazol-4-yl)prop-2-enamide | 471 |

TABLE 14-continued
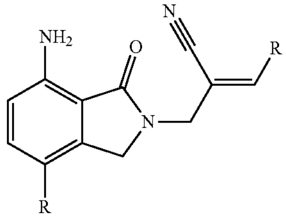
| Cpd. No. | Structure | IUPAC | LC-MS (ES+, m/z) |
|---|---|---|---|
| 569. | 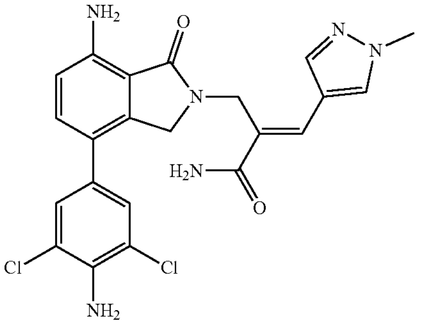 [SMILES: Cn1cc(/C=C(\CN2Cc3c(-c4cc(Cl)c(N)c(Cl)c4)ccc(N)c3C2=O)C(N)=O)cn1] | (2E)-2-{[7-amino-4-(4-amino-3,5-dichlorophenyl)-1-oxo-2,3-dihydro-1H-isoindol-2-yl]methyl}-3-(1-methyl-1H-pyrazol-4-yl)prop-2-enamide | 471 |
Example 16: Method O
General Synthetic Method:
Route 1:
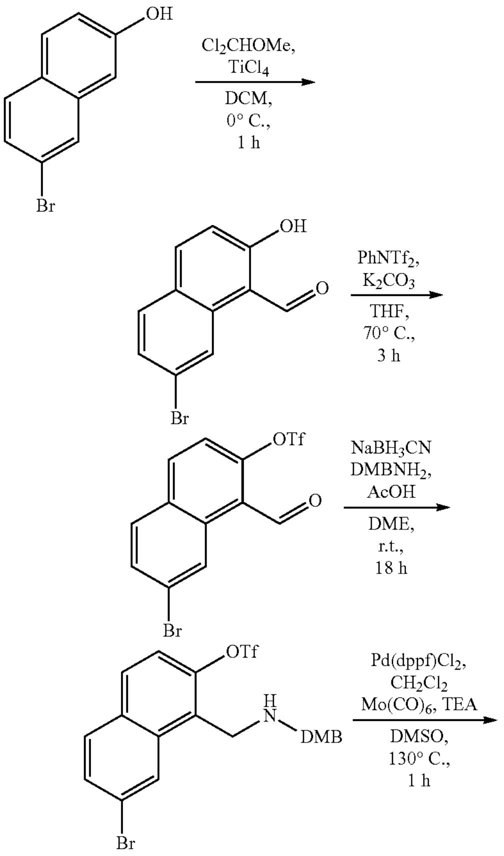
-continued
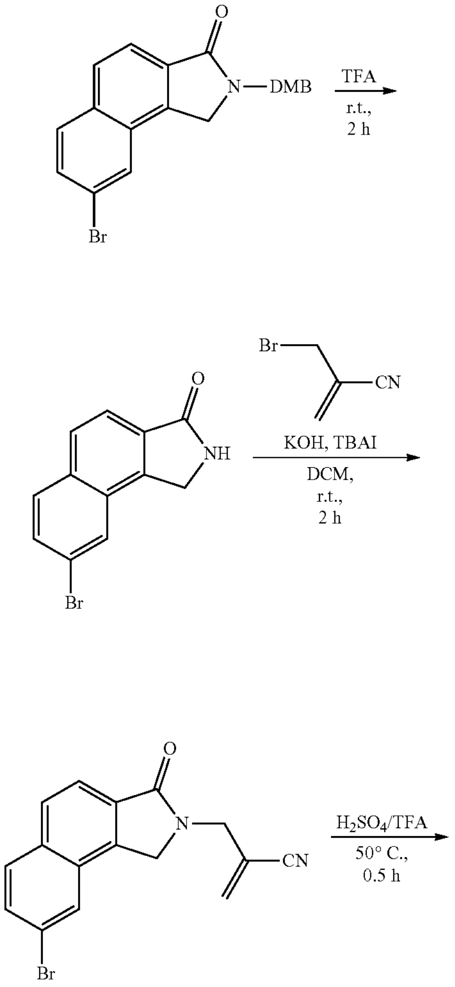

-continued

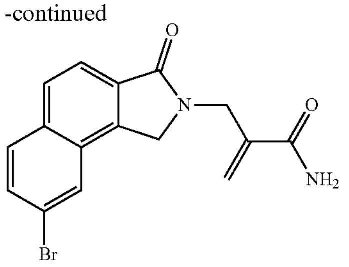

Preparation of 7-bromo-2-hydroxy-naphthalene-1-carbaldehyde

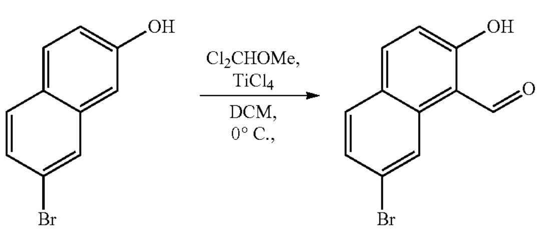 [SMILES: Oc1ccc2ccc(Br)cc2c1 ; O=Cc1c(O)ccc2ccc(Br)cc12]

To a solution of dichloro(methoxy)methane (145.6 g, 1344.9 mmol, 2 eq.) in DCM (1000 mL) was cooled to 0° C., and $TiCl_4$ (382.62 g, 2.02 mol, 3 eq.) was quickly added. The mixture was stirred at 0° C. for 20 min. 7-bromonaphthalen-2-ol (150 g, 1 eq.) in DCM (2400 mL) was added dropwise at 0° C. over a period of 10 mins under nitrogen. The mixture was stirred at 0° C. for 1 h. HPLC showed that the reaction was complete. The mixture was poured into water (2000 mL) and extracted with EtOAc (3×2000 mL). The combined organic layers were washed with brine (3×2000 mL), dried over anhydrous sodium sulfate, filtered, and concentrated in vacuo to give a residue. The crude was washed with PE (3×1000 mL) to afford the title compound (160 g, 573.53 mmol, 59% yield, 90% purity) as a brick red solid.

Preparation of (7-bromo-1-formyl-2-naphthyl)trifluoromethanesulfonate

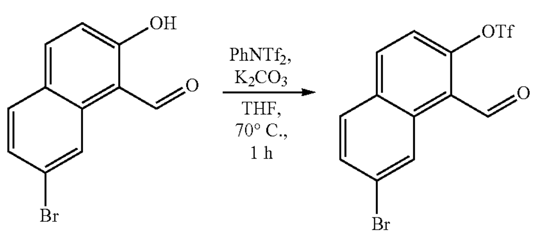 [SMILES: O=Cc1c(O)ccc2ccc(Br)cc12 ; O=Cc1c(OS(=O)(=O)C(F)(F)F)ccc2ccc(Br)cc12]

To a mixture of 7-bromo-2-hydroxy-naphthalene-1-carbaldehyde (120 g, 430.15 mmol, 1 eq.) (90% purity) and 1,1,1-trifluoro-N-phenyl-N-(trifluoromethylsulfonyl)methanesulfonamide (184.40 g, 516.18 mmol, 1.2 eq.) in THF (1500 mL) was added $K_2CO_3$ (89.17 g, 645.22 mmol, 1.5 eq.) at 70° C. The mixture was degassed and purged with nitrogen 3 times, and the mixture was stirred at 70° C. for 1 h under nitrogen atmosphere. LCMS showed that the reaction was complete. The reaction mixture was filtered to remove $K_2CO_3$. The reaction mixture was poured into water (1000 mL) and extracted with EtOAc (3×1000 mL). The combined organic layers were washed with brine (3×800 mL), dried over anhydrous sodium sulfate, filtered, and concentrated in vacuo to give a residue. The residue was washed with PE (3×800 mL) to afford the title compound (160 g, 375.84 mmol, 87.38% yield, 90% purity) as a gray solid.

Preparation of [7-bromo-1-[[(2,4-dimethoxyphenyl)methylamino]methyl]-2-naphthyl]trifluoromethanesulfonate

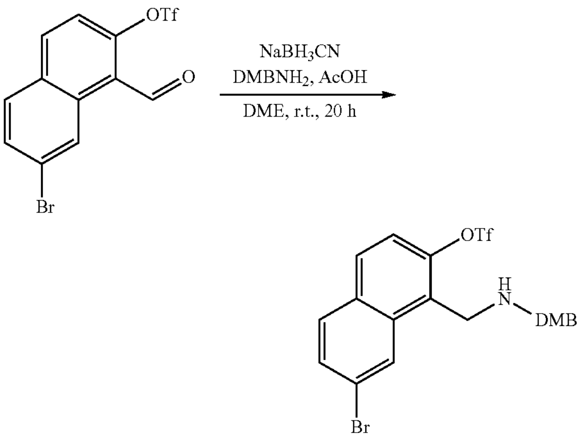

To a mixture of (7-bromo-1-formyl-2-naphthyl)trifluoromethanesulfonate (50 g, 117.45 mmol, 1 eq.) (90% purity) and (2,4-dimethoxyphenyl)methanamine (40 g, 239.23 mmol, 36.04 mL, 2.04 eq.) in DME (500 mL) was added AcOH (2.63 g, 43.71 mmol, 2.5 mL, 3.72 e-1 eq.). The mixture was stirred at 25° C. for 2 h, then $NaBH_3CN$ (22.14 g, 352.35 mmol, 3 eq.) was added to the mixture and stirred for 18 h at 25° C. TLC showed that the reaction was complete. The reaction was quenched with ice water (500 mL) slowly and extracted with DCM (3×500 mL). The combined organic phase was washed with brine (3×500 mL), dried over anhydrous sodium sulfate, filtered, and concentrated in vacuo. The residue was purified by silica gel chromatography (PE:EtOAc=40:1) to afford the title compound (60 g, 112.29 mmol, 95.60% yield) as a yellow oil.

Preparation of 8-bromo-2-[(2,4-dimethoxyphenyl)methyl]-1H-benzo[e]isoindol-3-one

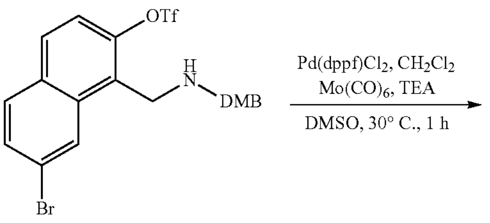

-continued

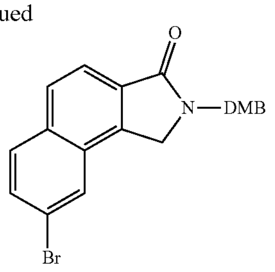

To a solution of [7-bromo-1-[[(2,4-dimethoxyphenyl) methylamino]methyl]-2-naphthyl]trifluoromethane-sulfonate (10 g, 16.84 mmol, 1 eq.) (90% purity) in DMSO (120 mL) were added Pd(dppf)$Cl_2$ (246.48 mg, 336.86 µmol, 0.02 eq.), TEA (3.58 g, 35.37 mmol, 4.92 mL, 2.1 eq.), and $Mo(CO)_6$ (889.32 mg, 3.37 mmol, 453.73 µL, 0.2 eq.). The mixture was stirred at 130° C. for 1 h under nitrogen. TLC showed that the reaction was complete. The reaction mixture was extracted with EtOAc (1000 mL×3). The combined organic layers were washed with brine (2000 mL×3), dried over anhydrous sodium sulfate, filtered, and concentrated in vacuo to give a residue. The residue was purified by column chromatography (silica gel; PE:EtOAc=1:0 to 1.5:1) to afford the title compound (4 g, 9.70 mmol, 57.60% yield) as a gray solid.

Preparation of 8-bromo-2-[(2,4-dimethoxyphenyl) methyl]-1H-benzo[e]isoindol-3-one

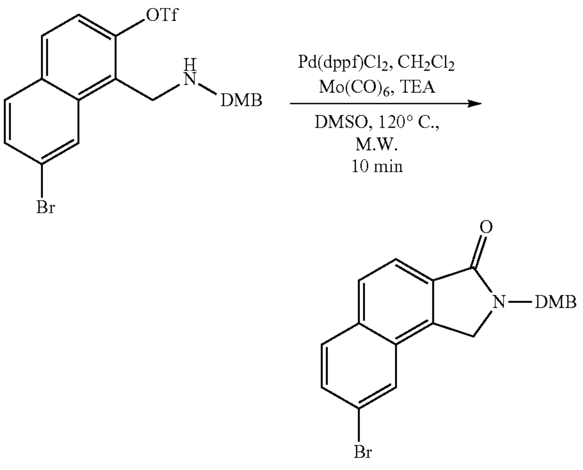

To a solution of [7-bromo-1-[[(2,4-dimethoxyphenyl) methylamino]methyl]-2-naphthyl]trifluoromethane-sulfonate (1 g, 1.68 mmol, 1 eq.) (90% purity) in DMSO (10 mL) were added Pd(dppf)$Cl_2$ (24.65 mg, 33.69 µmol, 0.02 eq.), TEA (357.91 mg, 3.54 mmol, 492.32 µL, 2.1 eq.), and $Mo(CO)_6$ (88.93 mg, 336.86 µmol, 45.37 µL, 0.2 eq.). The mixture was stirred at 120° C. for 10 min under nitrogen with microwave radiation. TLC showed that the reaction was complete. The reaction mixture was poured into water (50 mL) and extracted with EtOAc (100 mL×3). The combined organic layers were washed with brine (200 mL×3), dried over anhydrous sodium sulfate, filtered, and concentrated in vacuo to give a residue. The residue was purified by column chromatography (silica gel; PE:EtOAc=1:0 to 1.5:1) to afford the title compound (2 g, 4.61 mmol, 68.40% yield, 95% purity) as a gray solid.

Preparation of 8-bromo-1,2-dihydrobenzo[e]isoindol-3-one

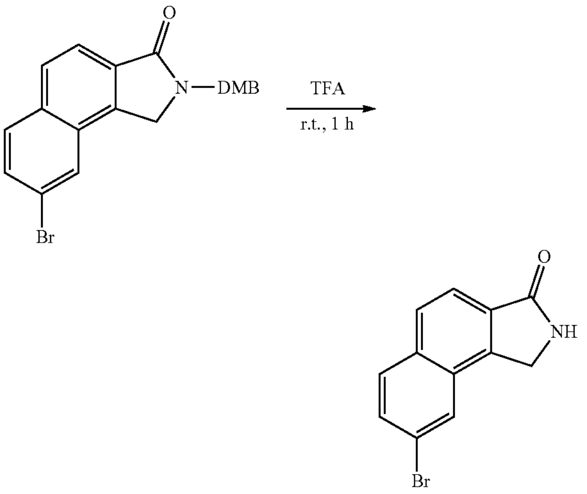

A solution of 8-bromo-2-[(2,4-dimethoxyphenyl)methyl]-1H-benzo[e]isoindol-3-one (12 g, 29.11 mmol, 1 eq.) in trifluoroacetic acid (160 mL) was stirred at 25° C. for 1 h. TLC showed that the reaction was complete. The reaction was quenched by adding ice water (500 mL) at 0° C., filtered, and concentrated in vacuo to give a residue. The residue was dissolved DCM (1000 mL), filtered, and concentrated in vacuo to give product to afford the title compound (8 g, 27.47 mmol, 94.38% yield, 90% purity) as a gray solid, which was used directly without purification.

Preparation of 2-[(8-bromo-3-oxo-1H-benzo[e] isoindol-2-yl)methyl]prop-2-enenitrile

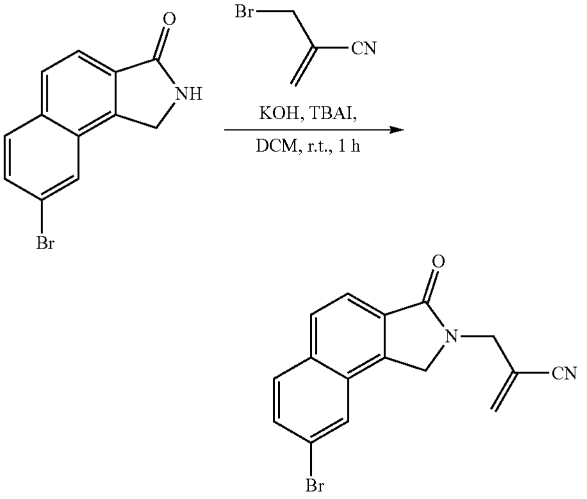

To a solution of 8-bromo-1,2-dihydrobenzo[e]isoindol-3-one (3 g, 10.30 mmol, 1 eq.) (90% purity) in DCM (60 mL) were added KOH (1.16 g, 20.60 mmol, 2 eq.), TBAI (761 mg, 2.06 mmol, 0.2 eq.), and 2-(bromomethyl)prop-2-enenitrile (1.65 g, 11.33 mmol, 1.1 eq.). The mixture was stirred at 25° C. for 1 h. TLC showed 5% of the starting material remained. The reaction was quenched with ice water (100 mL) at 0° C. and extracted with DCM (150 mL×3). The combined organic layers were washed with brine (100 mL), dried over anhydrous sodium sulfate, filtered, and concentrated in vacuo to give a residue. The residue was purified by column chromatography (silica gel; PE:EtOAc=10:1 to 1:1) to afford the title compound (5.2 g, 15.89 mmol, 77.14% yield) as a light yellow solid.

Preparation of 2-[(8-bromo-3-oxo-1H-benzo[e]isoindol-2-yl)methyl]prop-2-enamide (Compound 572)

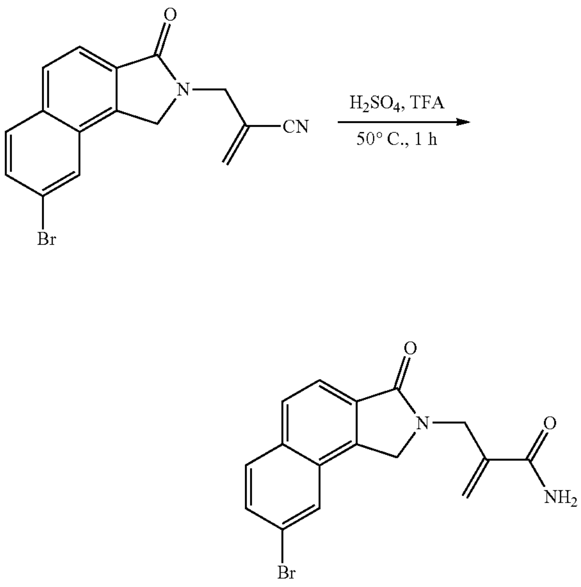 [SMILES: C=C(C#N)CN1Cc2c(ccc3ccc(Br)cc23)C1=O ; C=C(CN1Cc2c(ccc3ccc(Br)cc23)C1=O)C(N)=O]

To a solution of 2-[(8-bromo-3-oxo-1H-benzo[e]isoindol-2-yl)methyl]prop-2-enenitrile (5 g, 15.28 mmol, 1 eq.) in trifluoroacetic acid (50 mL) was added $H_2SO_4$ (50 mL). The mixture was stirred at 50° C. for 1 h. TLC showed that the reaction was complete. The reaction mixture was poured into ice water (300 mL) at 0° C. and filtered to give a residue. The crude material was washed with EtOAc (50 mL×2) to afford the title compound (5 g, 13.04 mmol, 85.30% yield, 90% purity) as a gray solid. LC-MS: $[M+H]^+$ 345.1.

Preparation of 2-[(8-bromo-3-oxo-1H-benzo[e]isoindol-2-yl)methyl]prop-2-enamide General Procedure

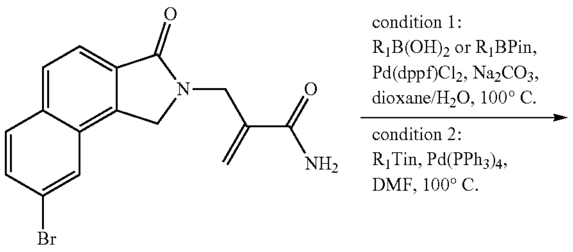

-continued

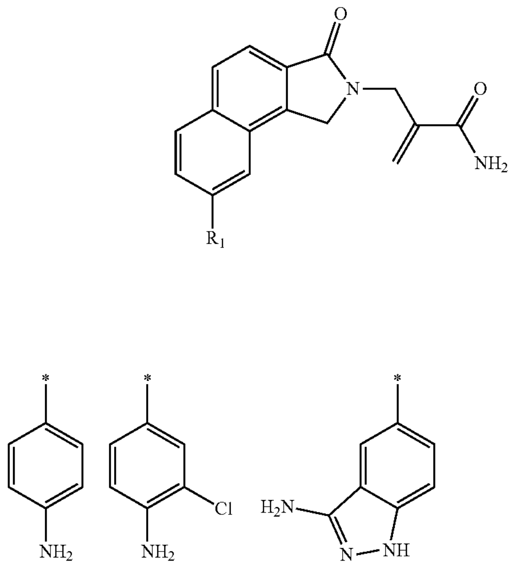

Condition 1:

To a mixture of 2-[(8-bromo-3-oxo-1H-benzo[e]isoindol-2-yl)methyl]prop-2-enamide (50 mg, 144.85 μmol, 1 eq.), 2-chloro-4-(4,4,5,5-tetramethyl-1,3,2-dioxaborolan-2-yl) aniline (55.09 mg, 217.27 μmol, 1.5 eq.) in dioxane (1 mL) water (0.25 mL) were added $Na_2CO_3$ (30.70 mg, 289.70 μmol, 2 eq.), $Pd(dppf)Cl_2$ (10.60 mg, 14.48 μmol, 0.1 eq.) at 25° C. under nitrogen. The mixture was stirred at 100° C. for 10 min. TLC/LCMS showed that the reaction was complete. 20 mL of EtOAc was poured into the mixture and stirred for 1 h. The aqueous phase was extracted with EtOAc (3×20 mL). The combined organic phase was washed with brine (3×30 mL), dried over anhydrous sodium sulfate and active carbon to remove color, then concentrated in vacuo. The residue was purified by prep-HPLC to afford the title compound (21.3 mg, 52.84 μmol, 36.48% yield, 97.207% purity) as a white solid.

Condition 2:

A mixture of 6-trimethylstannylpyridin-3-amine (372.14 mg, 1.45 mmol, 10 eq.), 2-[(8-bromo-3-oxo-1H-benzo[e]isoindol-2-yl)methyl]prop-2-enamide (50 mg, 144.85 μmol, 1 eq.), CuI (5.52 mg, 28.97 μmol, 0.2 eq.), $Pd(PPh_3)_4$ (33.48 mg, 28.97 μmol, 0.2 eq.) in DMF (5 mL) was degassed and purged with nitrogen 3 times, and the mixture was stirred at 100° C. for 1 h under nitrogen atmosphere. TLC showed that the reaction was complete. To the reaction mixture was added 30 mL saturated aq. EDTA, and the mixture was stirred for 1 h. The resulting mixture was extracted with EtOAc (20 mL×3). The combined organic layers were washed with brine (20 mL×3), dried over anhydrous sodium sulfate, filtered, and concentrated in vacuo to give a residue. The residue was purified by prep-TLC (silica gel; DCM:MeOH=10:1) and prep-HPLC to afford the title compound (13.7 mg, 38.07 μmol, 26.29% yield, 99.6% purity) as a white solid.

Preparation of 2-[[8-(1-methylindazol-5-yl)-3-oxo-1H-benzo[e]isoindol-2-yl]methyl]prop-2-enamide (Compound 589)

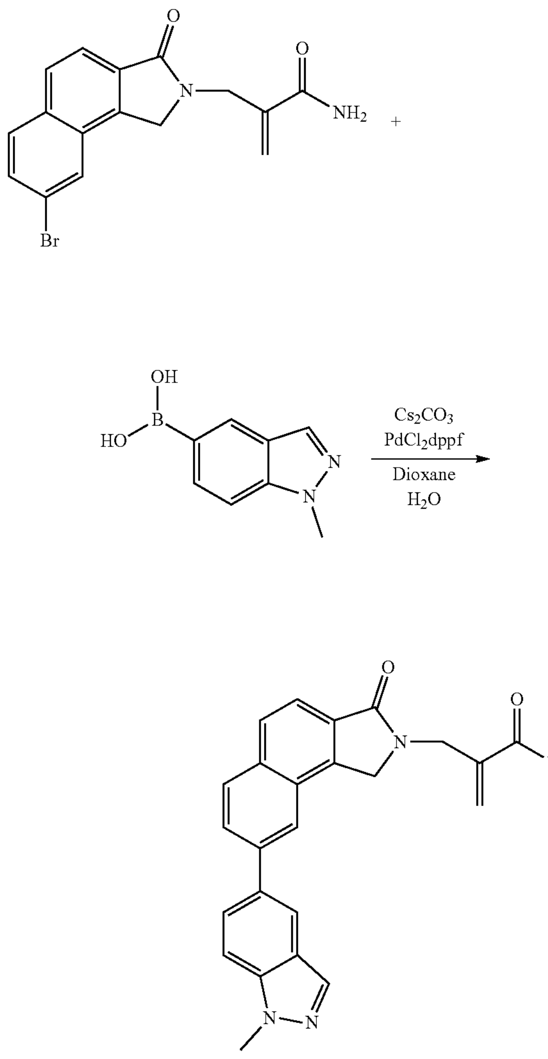

To a solution of 2-[(8-bromo-3-oxo-1H-benzo[e]isoindol-2-yl)methyl]prop-2-enamide (40 mg, 116 μmol) in dioxane (1 mL) and water (0.2 mL) were added (1-methylindazol-5-yl)boronic acid (30.6 mg, 174 μmol), $Cs_2CO_3$ (0.113 g, 348 μmol) and $PdCl_2dppf$ (18 mg, 22.06 μmol). The reaction was heated to 100° C. for 30 min in a microwave. The reaction mixture was passed through a celite pad, and 1 mL of 2 M EDTA was added. The resulting solution was stirred at r.t. for 1 h. The solution was washed with brine, and the organic phase was dried over anhydrous sodium sulfate, filtered, and concentrated in vacuo. The residue was purified by reverse phase HPLC using a gradient of water 0.1% FA/acetonitrile 0.1% FA. to afford the title compound (5.4 mg, Yield 12%). LC-MS: $[M+H]^+$ 397.

Preparation of 2-[[8-(1-methylindazol-6-yl)-3-oxo-1H-benzo[e]isoindol-2-yl]methyl]prop-2-enamide (Compound 590)

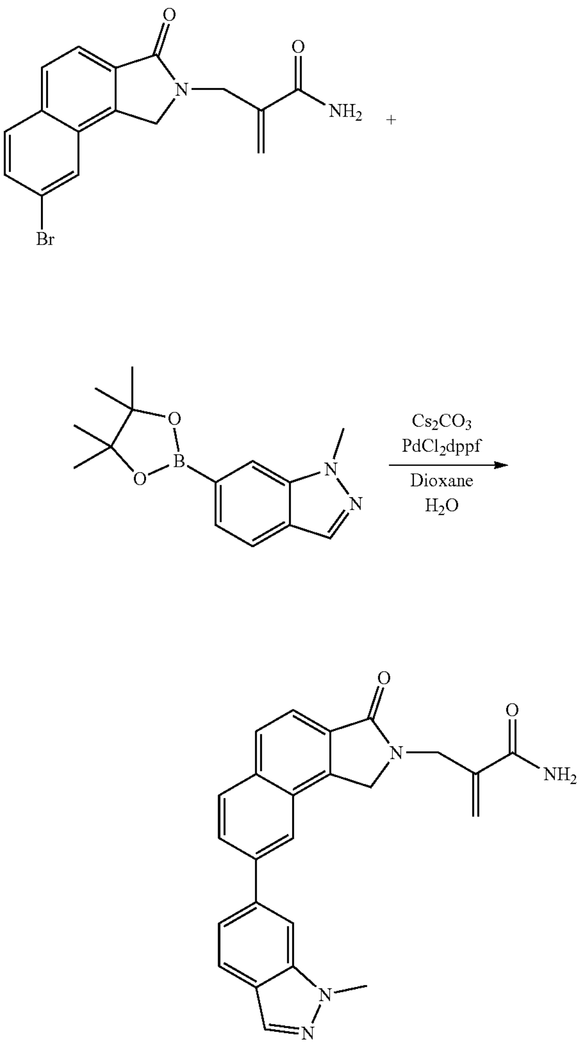

To a solution of 2-[(8-bromo-3-oxo-1H-benzo[e]isoindol-2-yl)methyl]prop-2-enamide (40 mg, 116 μmol) in dioxane (1 mL) and water (0.2 mL) were added 1-methyl-6-(4,4,5,5-tetramethyl-1,3,2-dioxaborolan-2-yl)indazole (45 mg, 174 μmol), $Cs_2CO_3$ (0.113 g, 348 μmol) and $PdCl_2dppf$ (18 mg, 22.06 μmol). The reaction was heated to 100° C. for 30 min in a microwave. The reaction mixture was passed through a celite pad, and 1 mL of 2 M EDTA was added. The resulting solution was stirred at r.t. for 1 h and was washed with brine, and the organic phase was dried over anhydrous sodium sulfate, filtered, and concentrated in vacuo. The residue was purified by reverse phase HPLC using a gradient of water 0.1% FA/acetonitrile 0.1% FA to afford the title compound (15.6 mg, Yield 34%). LC-MS: $[M+H]^+$ 397.

Preparation of 2-[(3-oxo-8-pyrazolo[1,5-a]pyridin-3-yl-1H-benzo[e]isoindol-2-yl)methyl]prop-2-enamide (Compound 593)

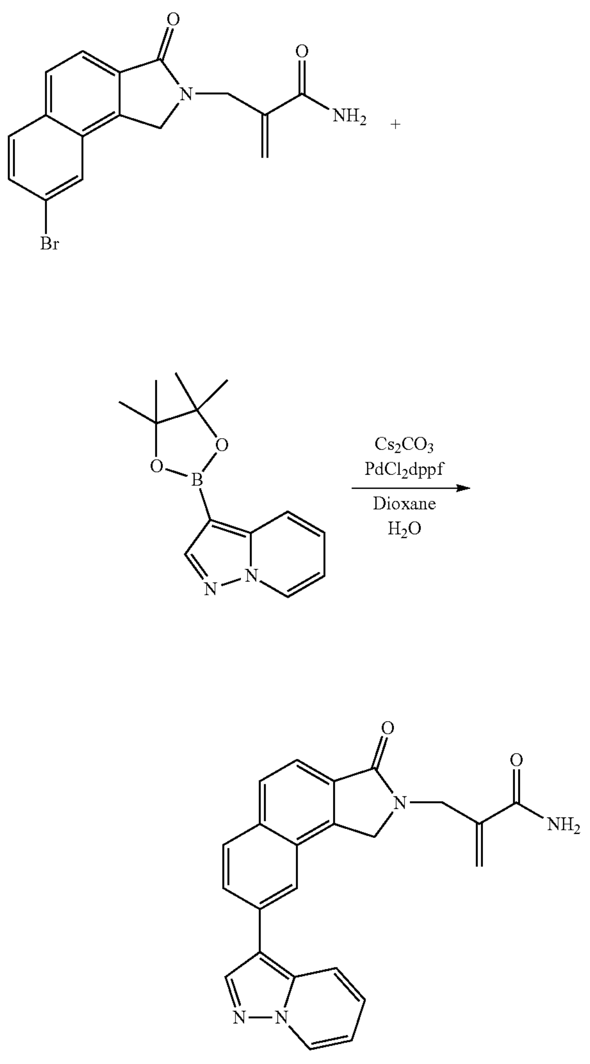

To a solution of 2-[(8-bromo-3-oxo-1H-benzo[e]isoindol-2-yl)methyl]prop-2-enamide (43.9 mg, 127 μmol) in dioxane (2 mL) and water (0.4 mL) were added 3-(4,4,5,5-tetramethyl-1,3,2-dioxaborolan-2-yl)pyrazolo [1,5-a]pyridine (46.6 mg, 191 μmol), $Cs_2CO_3$ (0.123 g, 381 μmol) and $PdCl_2dppf$ (18 mg, 22.06 μmol). The reaction was heated to 100° C. for 30 min in a microwave. The reaction mixture was passed through a celite pad, and 1 mL of 2 M EDTA was added. The resulting solution was stirred at r.t. for 1 h and washed with brine, and the organic phase was dried over anhydrous sodium sulfate, filtered, and concentrated in vacuo. The residue was purified by reverse phase HPLC using a gradient of water 0.1% FA/acetonitrile 0.1% FA to afford the title compound (6.6 mg, Yield 14%). LC-MS: $[M+H]^+$ 383.

Preparation of 2-[[3-oxo-8-(1-tetrahydropyran-4-ylpyrazol-4-yl)-1H-benzo[e]isoindol-2-yl]methyl]prop-2-enamide (Compound 602)

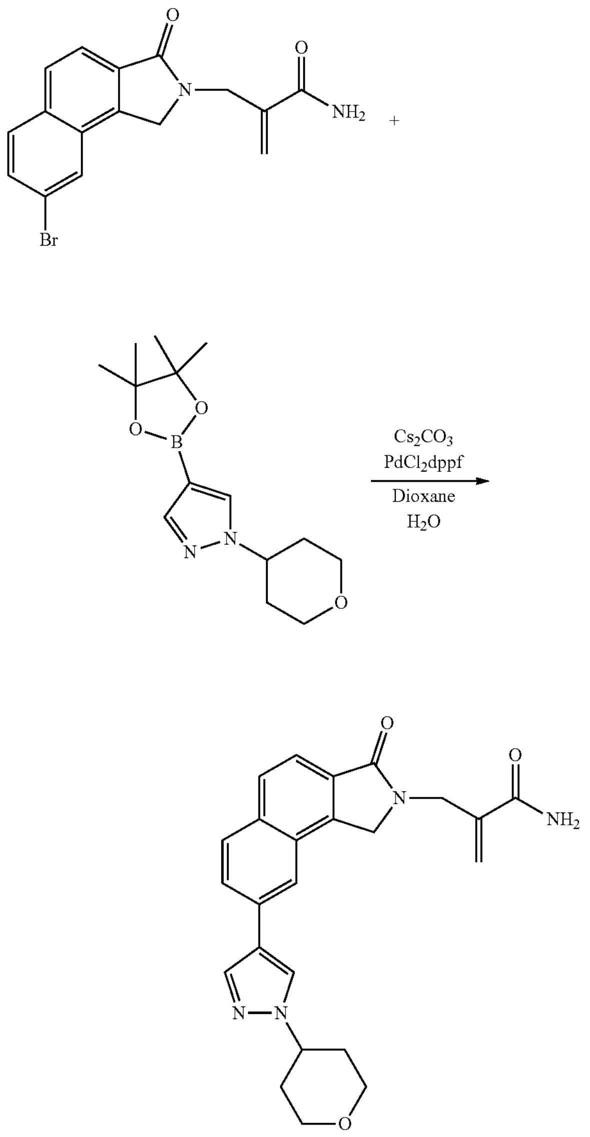

To a solution of 2-[(8-bromo-3-oxo-1H-benzo[e]isoindol-2-yl)methyl]prop-2-enamide (30 mg, 87 μmol) in dioxane (2 mL) and water (0.4 mL) were added 1-tetrahydropyran-4-yl-4-(4,4,5,5-tetramethyl-1,3,2-dioxaborolan-2-yl)pyrazole (36.4 mg, 131 μmol), $Cs_2CO_3$ (0.127 g, 390 μmol) and $PdCl_2dppf$ (18 mg, 22.06 μmol). The reaction was heated to 100° C. for 30 min in a microwave. The reaction mixture was passed through a celite pad, and 1 mL of 2 M EDTA was added. The resulting solution was stirred at r.t. for 1 h, and washed with brine, and the organic phase was dried over anhydrous sodium sulfate, filtered, and concentrated in vacuo. The residue was purified by reverse phase HPLC using a gradient of water 0.1% FA/acetonitrile 0.1% FA to afford the title compound (15.7 mg, Yield 43%). LC-MS: $[M+H]^+$ 417.

Preparation of 2-[[8-[1-(2-methoxyethyl) pyrazol-4-yl]-3-oxo-1H-benzo[e]isoindol-2-yl]methyl]prop-2-enamide (Compound 603)

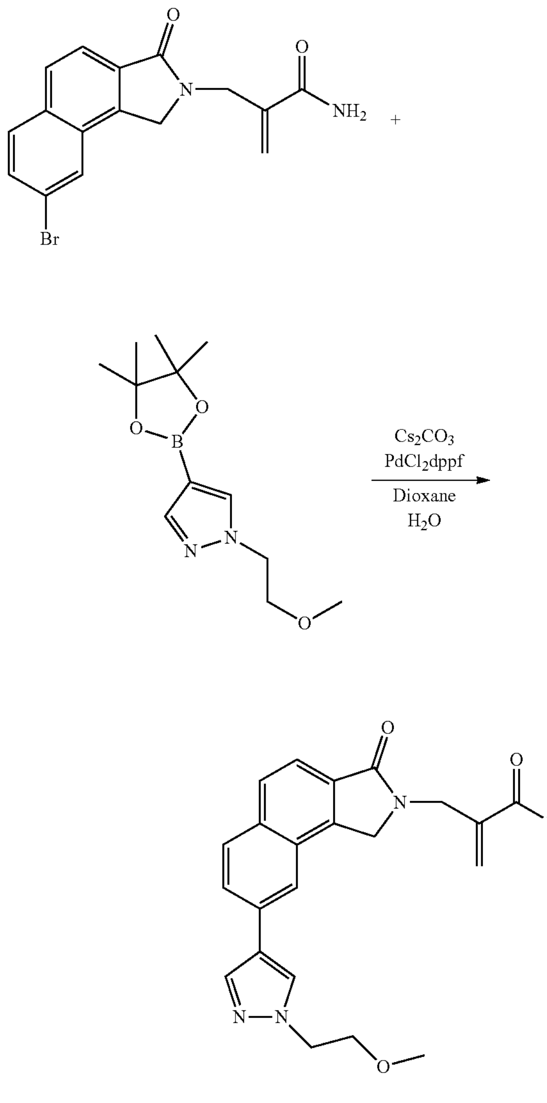

To a solution of 2-[(8-bromo-3-oxo-1H-benzo[e]isoindol-2-yl)methyl]prop-2-enamide (30 mg, 87 μmol) in dioxane (2 mL) and water (0.4 mL) were added 1-(2-methoxyethyl)-4-(4,4,5,5-tetramethyl-1,3,2-dioxaborolan-2-yl)pyrazole (33 mg, 131 μmol), $Cs_2CO_3$ (0.127 g, 390 μmol) and $PdCl_2dppf$ (18 mg, 22.06 μmol). The reaction was heated to 100° C. for 30 min in a microwave. The reaction mixture was passed through a celite pad, and 1 mL of 2 M EDTA was added. The resulting solution was stirred at r.t. for 1 h and washed with brine, and the organic phase was dried over anhydrous sodium sulfate, filtered, and concentrated in vacuo. The residue was purified by reverse phase HPLC using a gradient of water 0.1% FA/acetonitrile 0.1% FA to afford the title compound (15.0 mg, Yield 44%). LC-MS: $[M+H]^+$ 391.

Preparation of 2-[[8-[1-(2-morpholinoethyl) pyrazol-4-yl]-3-oxo-1H-benzo[e]isoindol-2-yl]methyl] prop-2-enamide (Compound 609)

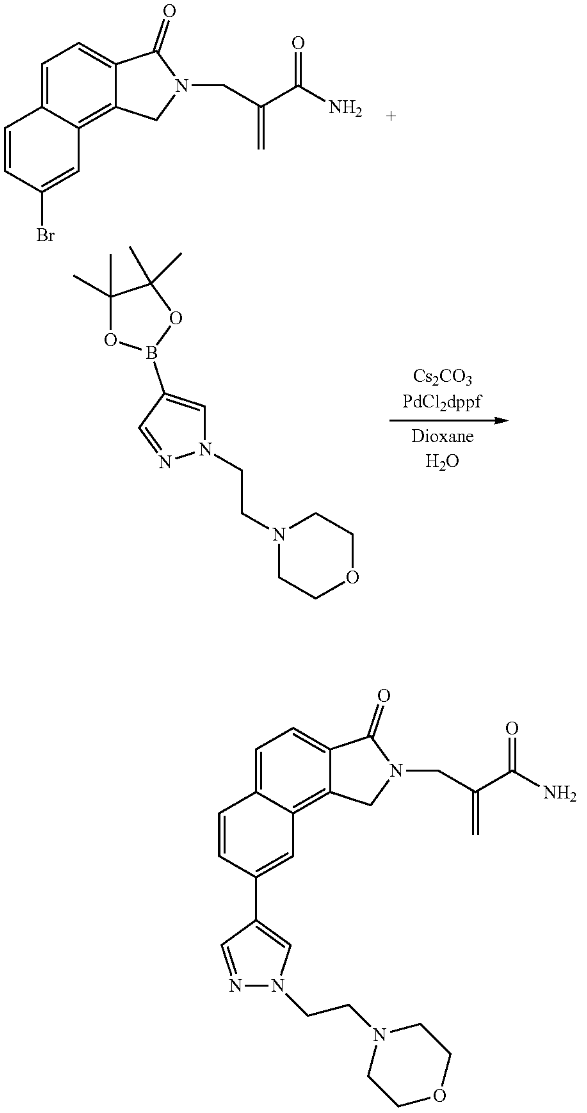

To a solution of 2-[(8-bromo-3-oxo-1H-benzo[e]isoindol-2-yl)methyl]prop-2-enamide (30 mg, 87 μmol) in dioxane (2 mL) and water (0.4 mL) were added 4-[2-[4-(4,4,5,5-tetramethyl-1,3,2-dioxaborolan-2-yl)pyrazol-1-yl]ethyl]morpholine (40.2 mg, 131 μmol), $Cs_2CO_3$ (0.127 g, 390 μmol) and $PdCl_2dppf$ (18 mg, 22.06 μmol). The reaction was heated to 100° C. for 30 min in a microwave. The reaction mixture was passed through a celite pad, and 1 mL of 2 M EDTA was added. The resulting solution was stirred at r.t. for 1 h and washed with brine, and the organic phase was dried over anhydrous sodium sulfate, filtered, and concentrated in vacuo. The residue was purified by reverse phase HPLC using a gradient of water 0.1% FA/acetonitrile 0.1% FA to afford the title compound (14.7 mg, Yield 38%). LC-MS: $[M+H]^+$ 446.

Preparation of 2-[[8-(1H-indazol-7-yl)-3-oxo-1H-benzo[e]isoindol-2-yl]methyl]prop-2-enamide (Compound 615)

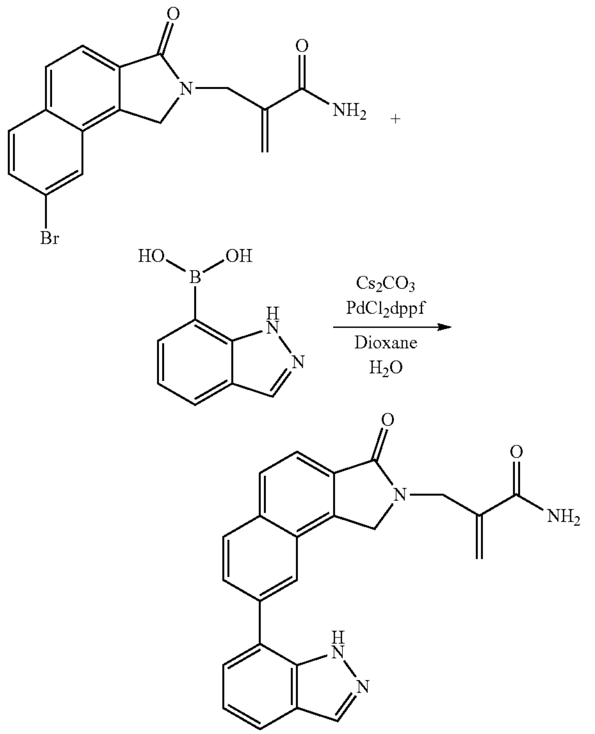

To a solution of 2-[(8-bromo-3-oxo-1H-benzo[e]isoindol-2-yl)methyl]prop-2-enamide (30 mg, 87 μmol) in dioxane (2 mL) and water (0.4 mL) were added 1H-indazol-7-ylboronic acid (21.1 mg, 131 μmol), $Cs_2CO_3$ (84.7 mg, 260 μmol) and $PdCl_2dppf$ (15 mg, 18.4 μmol). The reaction was heated to 100° C. for 30 min in a microwave. The reaction mixture was passed through a celite pad, and 1 mL of 2 M EDTA was added. The resulting solution was stirred at r.t. for 1 h and washed with brine, and the organic phase was dried over anhydrous sodium sulfate, filtered, and concentrated in vacuo. The residue was purified by reverse phase HPLC using a gradient of water 0.1% FA/acetonitrile 0.1% FA to afford the title compound (5.4 mg, Yield 16%). LC-MS: $[M+H]^+$ 383.

Preparation of 2-[[8-(1H-indazol-4-yl)-3-oxo-1H-benzo[e]isoindol-2-yl]methyl]prop-2-enamide (Compound 616)

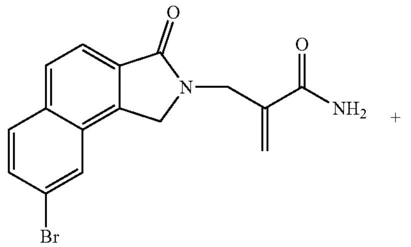

-continued

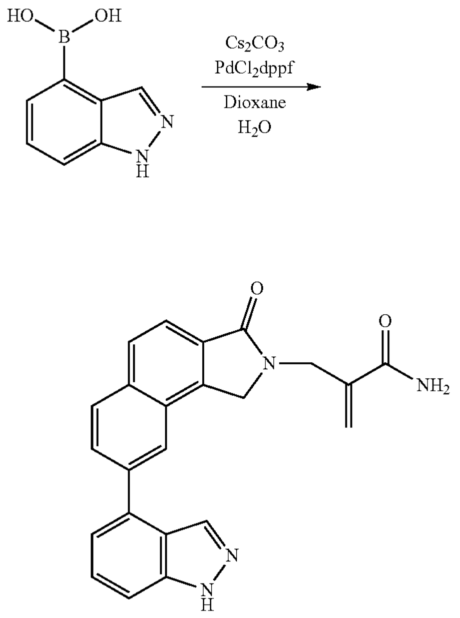

To a solution of 2-[(8-bromo-3-oxo-1H-benzo[e]isoindol-2-yl)methyl]prop-2-enamide (30 mg, 87 μmol) in dioxane (2 mL) and water (0.4 mL) were added 1H-indazol-4-ylboronic acid (21.1 mg, 131 μmol), $Cs_2CO_3$ (84.7 mg, 260 μmol) and $PdCl_2dppf$ (15 mg, 18.4 μmol). The reaction was heated to 100° C. for 30 min in a microwave. The reaction mixture was passed through a celite pad, and 1 mL of 2 M EDTA was added. The resulting solution was stirred at r.t. for 1 h and washed with brine, and the organic phase was dried over anhydrous sodium sulfate, filtered, and concentrated in vacuo. The residue was purified by reverse phase HPLC using a gradient of water 0.1% FA/acetonitrile 0.1% FA to afford the title compound (9 mg, Yield 27%). LC-MS: $[M+H]^+$ 383.

Preparation of 2-[[8-(5-chloro-3-pyridyl)-3-oxo-1H-benzo[e]isoindol-2-yl]methyl]prop-2-enamide (Compound 628)

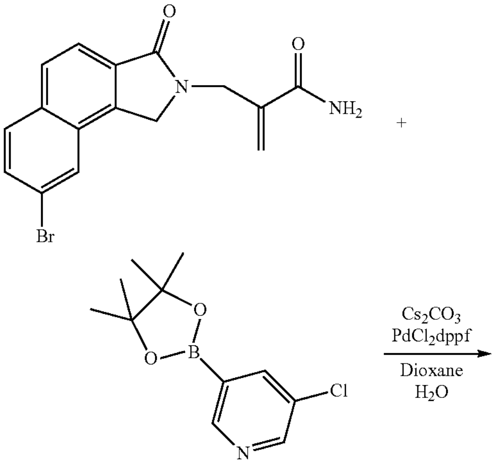

-continued

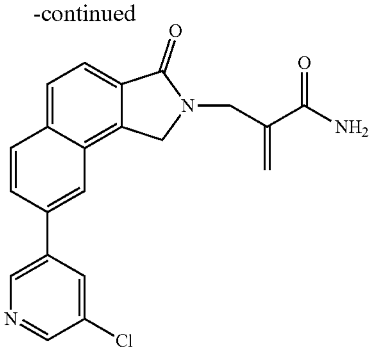

To a solution of 2-[(8-bromo-3-oxo-1H-benzo[e]isoindol-2-yl)methyl]prop-2-enamide (40 mg, 116 μmol) in dioxane (1 mL) and water (0.2 mL) were added 3-chloro-5-(4,4,5,5-tetramethyl-1,3,2-dioxaborolan-2-yl)pyridine (41.7 mg, 174 μmol), $Cs_2CO_3$ (113 mg, 348 μmol) and $PdCl_2dppf$ (18 mg, 22.4 μmol). The reaction was heated to 100° C. for 30 min in a microwave. The reaction mixture was passed through a celite pad, and 1 mL of 2 M EDTA was added. The resulting solution was stirred at r.t. for 1 h and washed with brine, and the organic phase was dried over anhydrous sodium sulfate, filtered, and concentrated in vacuo. The residue was purified by reverse phase HPLC using a gradient of water 0.1% FA/acetonitrile 0.1% FA to afford the title compound (11.1 mg, Yield 25%). LC-MS: $[M+H]^+$ 378.

Preparation of 2-[[8-(3-methylsulfonylphenyl)-3-oxo-1H-benzo[e]isoindol-2-yl]methyl]prop-2-enamide (Compound 629)

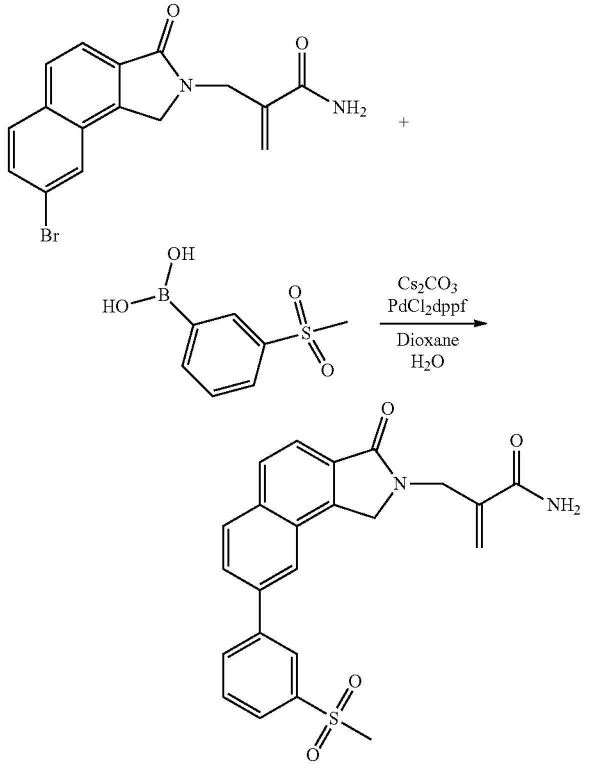

To a solution of 2-[(8-bromo-3-oxo-1H-benzo[e]isoindol-2-yl)methyl]prop-2-enamide (30 mg, 87 μmol) in dioxane (1 mL) and water (0.2 mL) were added (3-methylsulfonylphenyl)boronic acid (26 mg, 130 μmol), $Cs_2CO_3$ (84.4 mg, 261 μmol) and $PdCl_2dppf$ (18 mg, 22.4 μmol). The reaction was heated to 100° C. for 30 min in a microwave. The reaction mixture was passed through a celite pad, and 1 mL of 2 M EDTA was added. The resulting solution was stirred at r.t. for 1 h and washed with brine, and the organic phase was dried over anhydrous sodium sulfate, filtered, and concentrated in vacuo. The residue was purified by reverse phase HPLC using a gradient of water 0.1% FA/acetonitrile 0.1% FA to afford the title compound (18.6 mg, Yield 51%). LC-MS: $[M+H]^+$ 421.

Preparation of 2-[[8-(3-cyanophenyl)-3-oxo-1H-benzo[e]isoindol-2-yl]methyl]prop-2-enamide (Compound 630)

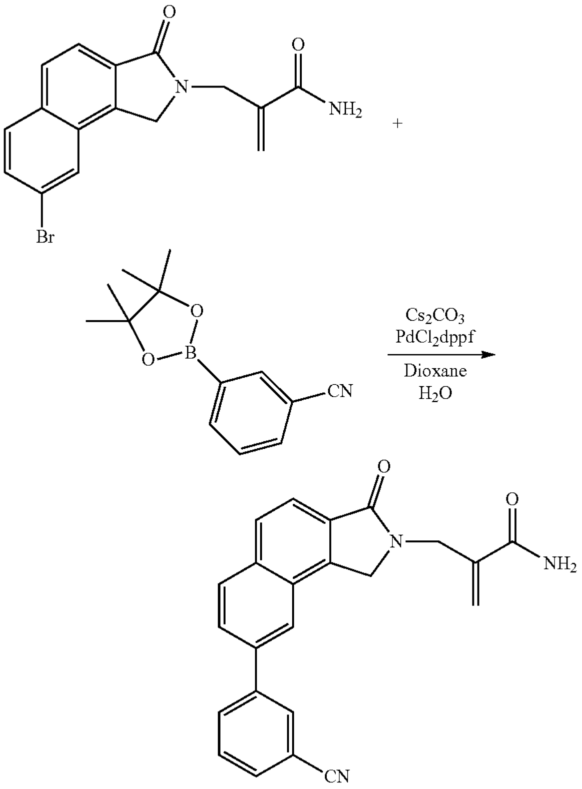

To a solution of 2-[(8-bromo-3-oxo-1H-benzo[e]isoindol-2-yl)methyl]prop-2-enamide (40 mg, 116 μmol) in dioxane (1 mL) and water (0.2 mL) were added 3-(4,4,5,5-tetramethyl-1,3,2-dioxaborolan-2-yl)benzonitrile (39.9 mg, 174 μmol), $Cs_2CO_3$ (113 mg, 348 μmol) and $PdCl_2dppf$ (18 mg, 22.4 μmol). The reaction was heated to 100° C. for 30 min in a microwave. The reaction mixture was passed through a celite pad, and 1 mL of 2 M EDTA was added. The resulting solution was stirred at r.t. for 1 h and washed with brine, and the organic phase was dried over anhydrous sodium sulfate, filtered, and concentrated in vacuo. The residue was purified by reverse phase HPLC using a gradient of water 0.1% FA/acetonitrile 0.1% FA to afford the title compound (4.0 mg, Yield 9%). LC-MS: $[M+H]^+$ 368.

Preparation of 2-[[3-oxo-8-[4-(trifluoromethyl)-3-pyridyl]-1H-benzo[e]isoindol-2-yl]methyl]prop-2-enamide (Compound 638)

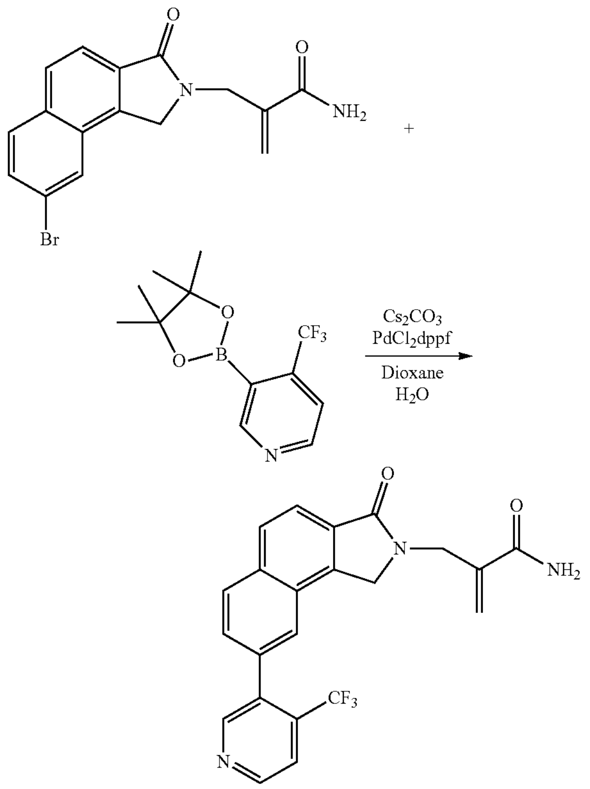

To a solution of 2-[(8-bromo-3-oxo-1H-benzo[e]isoindol-2-yl)methyl]prop-2-enamide (30 mg, 87 μmol) in dioxane (1 mL) and water (0.2 mL) were added 3-(4,4,5,5-tetramethyl-1,3,2-dioxaborolan-2-yl)-4-(trifluoromethyl)pyridine (35.5 mg, 130 μmol), $Cs_2CO_3$ (84.4 mg, 260 μmol) and $PdCl_2dppf$ (18 mg, 22.4 μmol). The reaction was heated to 100° C. for 30 min in a microwave. The reaction mixture was passed through a celite pad, and 1 mL of 2 M EDTA was added. The resulting solution was stirred at r.t. for 1 h and washed with brine, and the organic phase was dried over anhydrous sodium sulfate, filtered, and concentrated in vacuo. The residue was purified by reverse phase HPLC using a gradient of water 0.1% FA/acetonitrile 0.1% FA to afford the title compound (14.5 mg, Yield 41%) LC-MS: $[M+H]^+$ 412.

Preparation of 2-[(8-cyano-3-oxo-1H-benzo[e]isoindol-2-yl)methyl]prop-2-enamide (Compound 639)

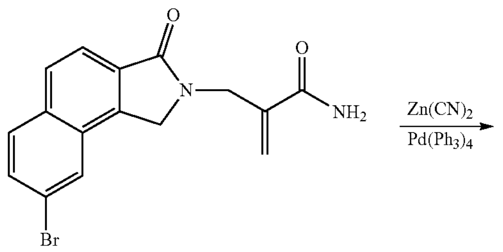

-continued

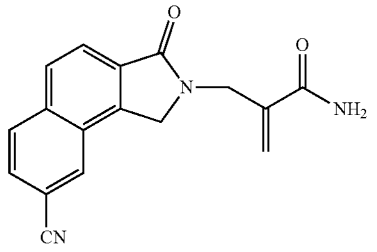

A mixture of 2-[(8-bromo-3-oxo-1H-benzo[e]isoindol-2-yl)methyl]prop-2-enamide (30 mg, 87 μmol) and $Zn(CN)_2$ (40.9 mg, 348 μmol) in DMF (2 mL) was purged with nitrogen, and Pd $(PPh_3)_4$ (5 mg, 4.35 μmol) was added. The reaction was heated to 120° C. for 40 min and Pd $(PPh_3)_4$ (5 mg, 4.35 μmol) was added and the reaction was heated to 120° C. for another 1 h. The reaction mixture was passed through a celite pad, and 1 mL of 2 M EDTA was added. The resulting solution was stirred at r.t. for 1 h and washed with brine, and the organic phase was dried over anhydrous sodium sulfate, filtered, and concentrated in vacuo. The residue was purified by reverse phase HPLC using a gradient of water 0.1% FA/acetonitrile 0.1% FA to afford the title compound (14.9 mg, Yield 59%) LC-MS: $[M+H]^+$ 292.

Preparation of tert-butyl N-[3-[2-(2-carbamoylallyl)-3-oxo-1H-benzo[e]isoindol-8-yl]phenyl]carbamate

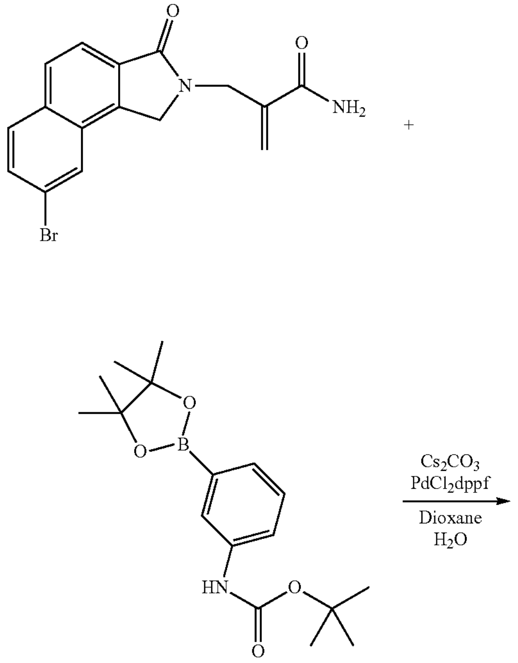

-continued

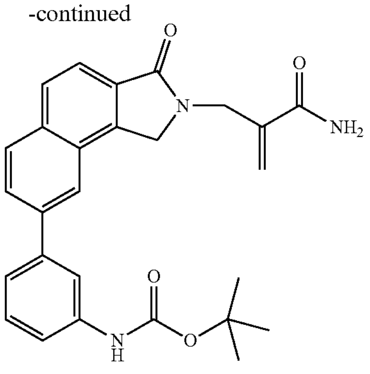

To a solution of 2-[(8-bromo-3-oxo-1H-benzo[e]isoindol-2-yl)methyl]prop-2-enamide (40 mg, 116 μmol) in dioxane (1 mL) and water (0.2 mL) were added tert-butyl N-[3-(4,4,5,5-tetramethyl-1,3,2-dioxaborolan-2-yl)phenyl]carbamate (55.5 mg, 174 μmol), $Cs_2CO_3$ (113 mg, 348 μmol) and $PdCl_2dppf$ (18 mg, 22.4 μmol). The reaction was heated to 120° C. for 25 min in a microwave. The reaction mixture was passed through a celite pad, and 1 mL of 2 M EDTA was added. The resulting solution was stirred at r.t. for 1 h and washed with brine, and the organic phase was dried over anhydrous sodium sulfate, filtered, and concentrated in vacuo. The residue was purified by chromatography on silica gel eluting with 50-100% EtOAc/hexane to afford the title compound (45.4 mg, Yield 87%).

Preparation of 2-[[8-(3-aminophenyl)-3-oxo-1H-benzo[e]isoindol-2-yl]methyl]prop-2-enamide (Compound 640)

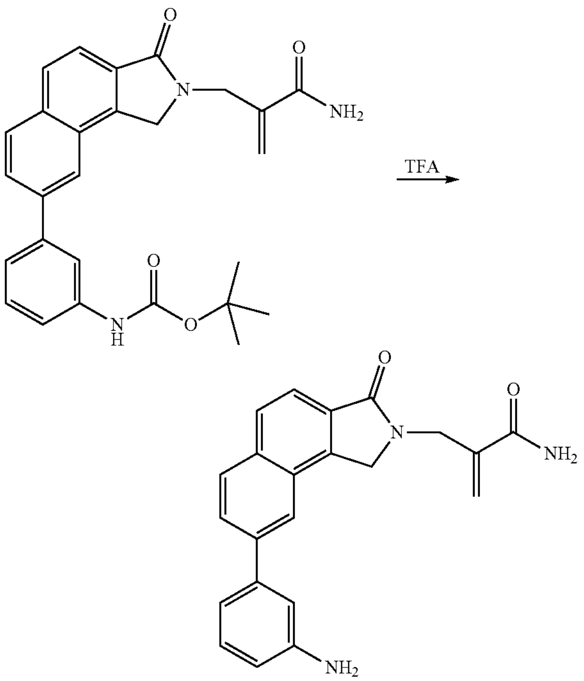

To a solution of tert-butyl N-[3-[2-(2-carbamoylallyl)-3-oxo-1H-benzo[e]isoindol-8-yl]phenyl]carbamate (45.4 mg, 99 μmol) in DCM (2 mL) was added trifluoroacetic acid (1 mL) at 0° C. The resulting solution was stirred at r.t. for 3 h. The reaction mixture was concentrated in vacuo and the residue was diluted with DCM, washed with sat. $NaHCO_3$ and brine, dried over anhydrous sodium sulfate, filtered, and concentrated. The residue was purified by reverse phase HPLC using a gradient of water 0.1% FA/acetonitrile 0.1% FA to afford the title compound (16.5 mg, Yield 46%). LC-MS: $[M+H]^+$ 358.

Preparation of 2-[[8-(6-amino-5-chloro-3-pyridyl)-3-oxo-1H-benzo[e]isoindol-2-yl]methyl]prop-2-enamide (Compound 641)

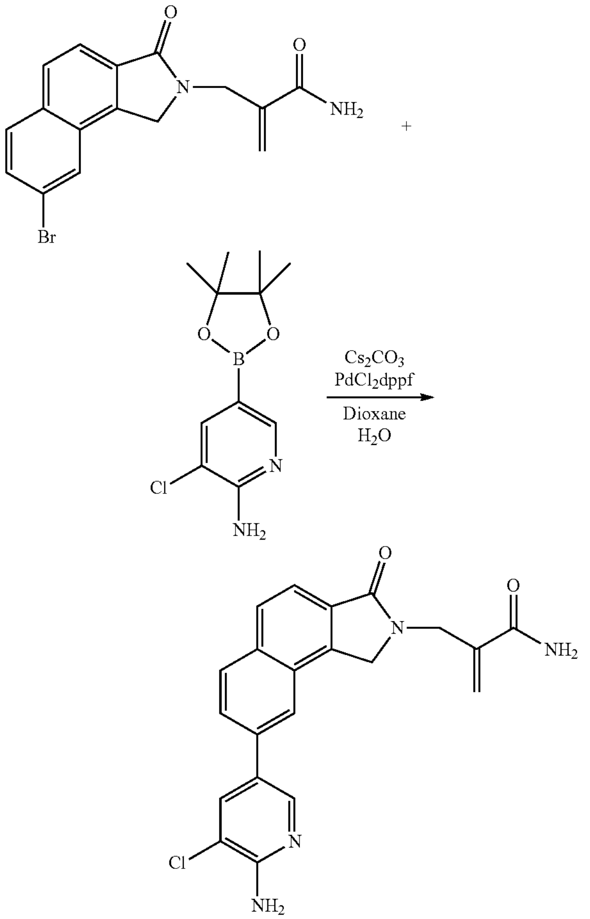

To a solution of 2-[(8-bromo-3-oxo-1H-benzo[e]isoindol-2-yl)methyl]prop-2-enamide (30 mg, 87 μmol) in dioxane (1 mL) and water (0.2 mL) were added 3-chloro-5-(4,4,5,5-tetramethyl-1,3,2-dioxaborolan-2-yl) pyridin-2-amine (33.1 mg, 130 μmol), $Cs_2CO_3$ (84.4 mg, 261 μmol) and $PdCl_2dppf$ (18 mg, 22.4 μmol). The reaction was heated to 100° C. for 30 min in a microwave. The reaction mixture was passed through a celite pad, and 1 mL of 2 M EDTA was added. The resulting solution was stirred at r.t. for 1 h and washed with brine, and the organic phase was dried over anhydrous sodium sulfate, filtered, and concentrated in vacuo The residue was purified by reverse phase HPLC using a gradient of water 0.1% FA/acetonitrile 0.1% FA to afford the title compound (23.5 mg, Yield 69%). LC-MS: $[M+H]^+$ 393.

Preparation of 2-[[8-(6-hydroxy-3-pyridyl)-3-oxo-1H-benzo[e]isoindol-2-yl]methyl]prop-2-enamide (Compound 653)

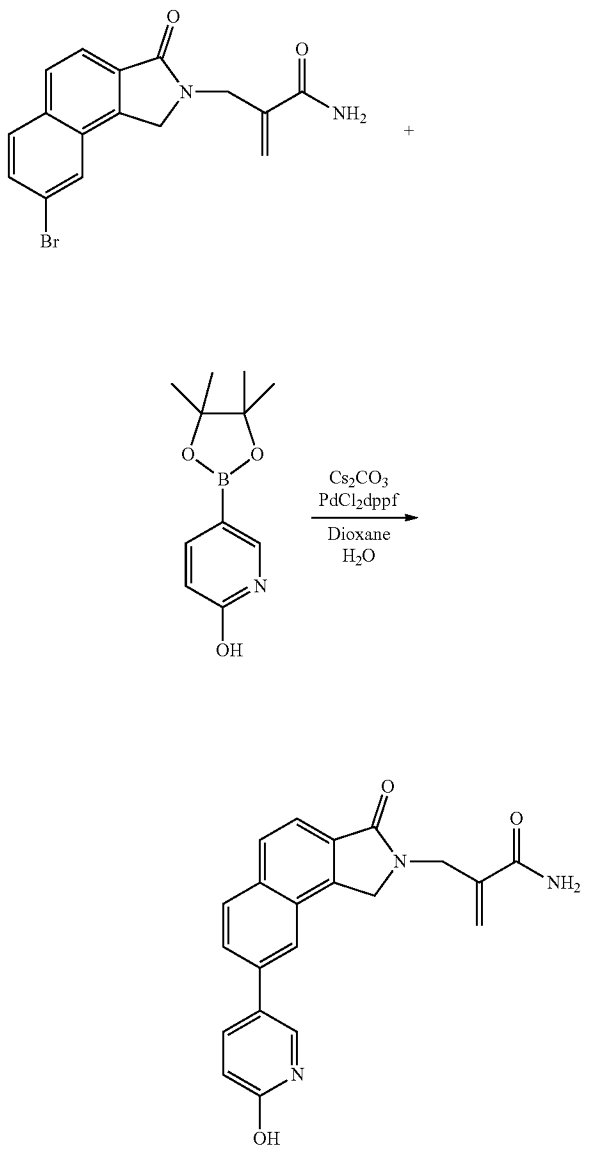

To a solution of 2-[(8-bromo-3-oxo-1H-benzo[e]isoindol-2-yl)methyl]prop-2-enamide (30 mg, 87 μmol) in dioxane (1 mL) and water (0.2 mL) were added 5-(4,4,5,5-tetramethyl-1,3,2-dioxaborolan-2-yl)pyridin-2-ol (28.7 mg, 130 μmol), $Cs_2CO_3$ (84.4 mg, 261 μmol) and $PdCl_2dppf$ (18 mg, 22.4 μmol). The reaction was heated to 100° C. for 30 min in a microwave. The reaction mixture was passed through a celite pad, and 1 mL of 2 M EDTA was added. The resulting solution was stirred at r.t. for 1 h and washed with brine, and the organic phase was dried over anhydrous sodium sulfate, filtered, and concentrated in vacuo. The residue was purified by reverse phase HPLC using a gradient of water 0.1% FA/acetonitrile 0.1% FA to afford the title compound (5.5 mg, Yield 18%). LC-MS: $[M+H]^+$ 360.

Preparation of 2-[[3-oxo-8-[6-(trifluoromethyl)-2-pyridyl]-1H-benzo[e]isoindol-2-yl]methyl]prop-2-enamide (Compound 654)

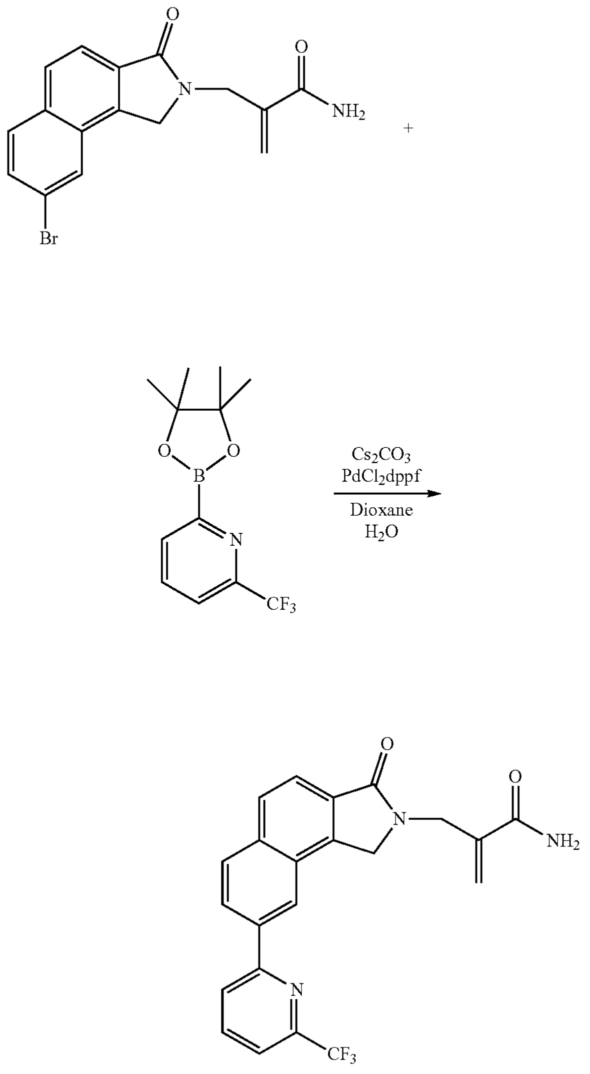

To a solution of 2-[(8-bromo-3-oxo-1H-benzo[e]isoindol-2-yl)methyl]prop-2-enamide (30 mg, 87 μmol) in dioxane (1 mL) and water (0.2 mL) were added 2-(4,4,5,5-tetramethyl-1,3,2-dioxaborolan-2-yl)-6-(trifluoromethyl)pyridine (35.5 mg, 130 μmol), $Cs_2CO_3$ (84.4 mg, 261 μmol) and $PdCl_2dppf$ (18 mg, 22.4 μmol). The reaction was heated to 100° C. for 30 min in a microwave. The reaction mixture was passed through a celite pad, and 1 mL of 2 M EDTA was added. The resulting solution was stirred at r.t. for 1 h and washed with brine, and the organic phase was dried over anhydrous sodium sulfate, filtered, and concentrated in vacuo. The residue was purified by reverse phase HPLC using a gradient of water 0.1% FA/acetonitrile 0.1% FA to afford the title compound (13.4 mg, Yield 37%). LC-MS: $[M+H]^+$ 412.

Preparation of 2-[[3-oxo-8-[6-(trifluoromethyl)-3-pyridyl]-1H-benzo[e]isoindol-2-yl]methyl]prop-2-enamide (Compound 655)

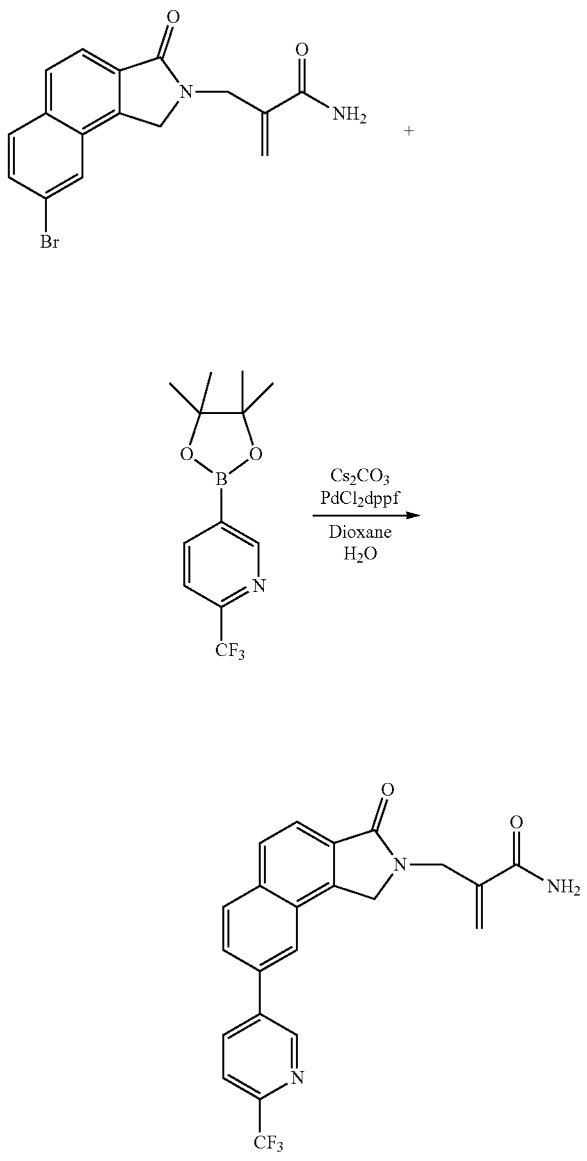

To a solution of 2-[(8-bromo-3-oxo-1H-benzo[e]isoindol-2-yl)methyl]prop-2-enamide (30 mg, 87 μmol) in dioxane (1 mL) and water (0.2 mL) were added 5-(4,4,5,5-tetramethyl-1,3,2-dioxaborolan-2-yl)-2-(trifluoromethyl)pyridine (24.8 mg, 130 μmol), $Cs_2CO_3$ (84.4 mg, 261 μmol) and $PdCl_2dppf$ (18 mg, 22.4 μmol). The reaction was heated to 100° C. for 30 min in a microwave. The reaction mixture was passed through a celite pad, and 1 mL of 2 M EDTA was added. The resulting solution was stirred at r.t. for 1 h and washed with brine, and the organic phase was dried over anhydrous sodium sulfate, filtered, and concentrated in vacuo. The residue was purified by reverse phase HPLC using a gradient of water 0.1% FA/acetonitrile 0.1% FA to afford the title compound (14.3 mg, Yield 40%). LC-MS: $[M+H]^+$ 412.

Preparation of 2-[[8-(6-cyano-3-pyridyl)-3-oxo-1H-benzo[e]isoindol-2-yl]methyl]prop-2-enamide (Compound 656)

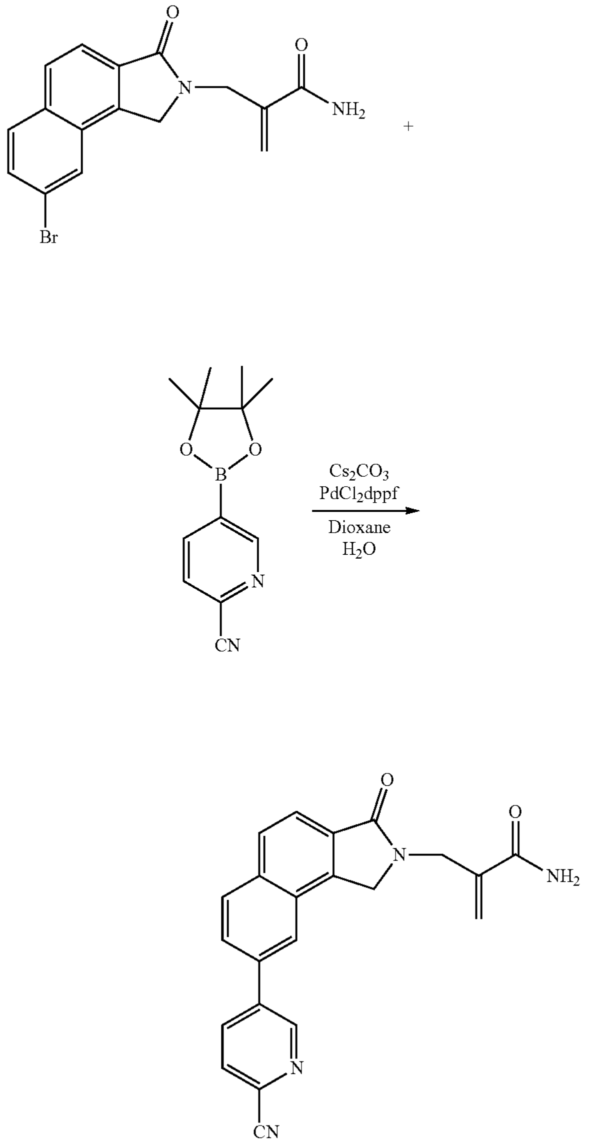

To a solution of 2-[(8-bromo-3-oxo-1H-benzo[e]isoindol-2-yl)methyl]prop-2-enamide (30 mg, 87 μmol) in dioxane (1 mL) and water (0.2 mL) were added 5-(4,4,5,5-tetramethyl-1,3,2-dioxaborolan-2-yl)pyridine-2-carbonitrile (29.9 mg, 130 μmol), $Cs_2CO_3$ (84.4 mg, 261 μmol) and $PdCl_2dppf$ (18 mg, 22.4 μmol). The reaction was heated to 100° C. for 30 min in a microwave. The reaction mixture was passed through a celite pad, and 1 mL of 2 M EDTA was added. The resulting solution was stirred at r.t. for 1 h and washed with brine, and the organic phase was dried over anhydrous sodium sulfate, filtered, and concentrated in vacuo. The residue was purified by reverse phase HPLC using a gradient of water 0.1% FA/acetonitrile 0.1% FA to afford the title compound (13.7 mg, Yield 43%). LC-MS: $[M+H]^+$ 369.

Preparation of 2-[[8-(6-methoxy-3-pyridyl)-3-oxo-1H-benzo[e]isoindol-2-yl]methyl]prop-2-enamide (Compound 659)

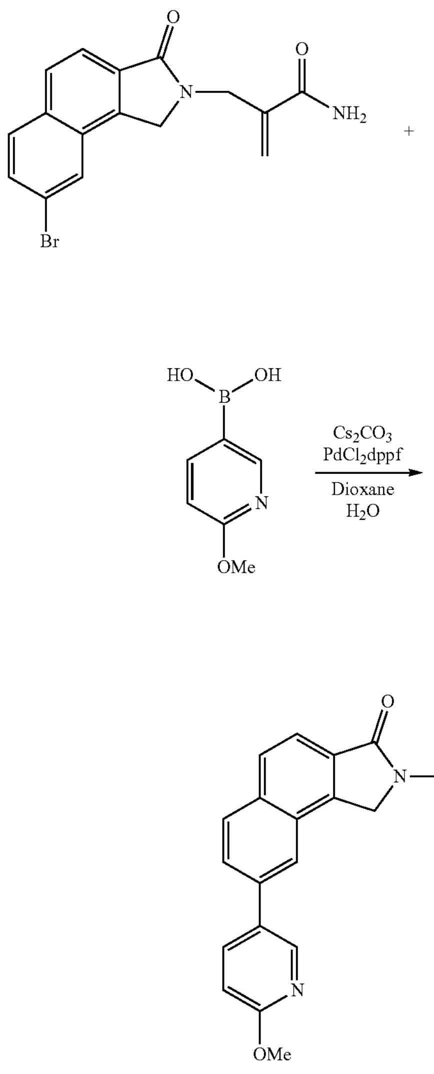

To a solution of 2-[(8-bromo-3-oxo-1H-benzo[e]isoindol-2-yl)methyl]prop-2-enamide (30 mg, 87 μmol) in dioxane (1 mL) and water (0.2 mL) were added (6-methoxy-3-pyridyl) boronic acid (19.9 mg, 130 μmol), $Cs_2CO_3$ (84.4 mg, 261 μmol) and $PdCl_2dppf$ (18 mg, 22.4 μmol). The reaction was heated to 100° C. for 25 min in a microwave. The reaction mixture was passed through a celite pad, and 1 mL of 2 M EDTA was added. The resulting solution was stirred at r.t. for 1 h and washed with brine, and the organic phase was dried over anhydrous sodium sulfate, filtered, and concentrated in vacuo. The residue was purified by reverse phase HPLC using a gradient of water 0.1% FA/acetonitrile 0.1% FA to afford the title compound (11.9 mg, Yield 37%). LC-MS: $[M+H]^+$ 374.

Preparation of 2-[[8-(6-methyl-3-pyridyl)-3-oxo-1H-benzo[e]isoindol-2-yl]methyl]prop-2-enamide (Compound 660)

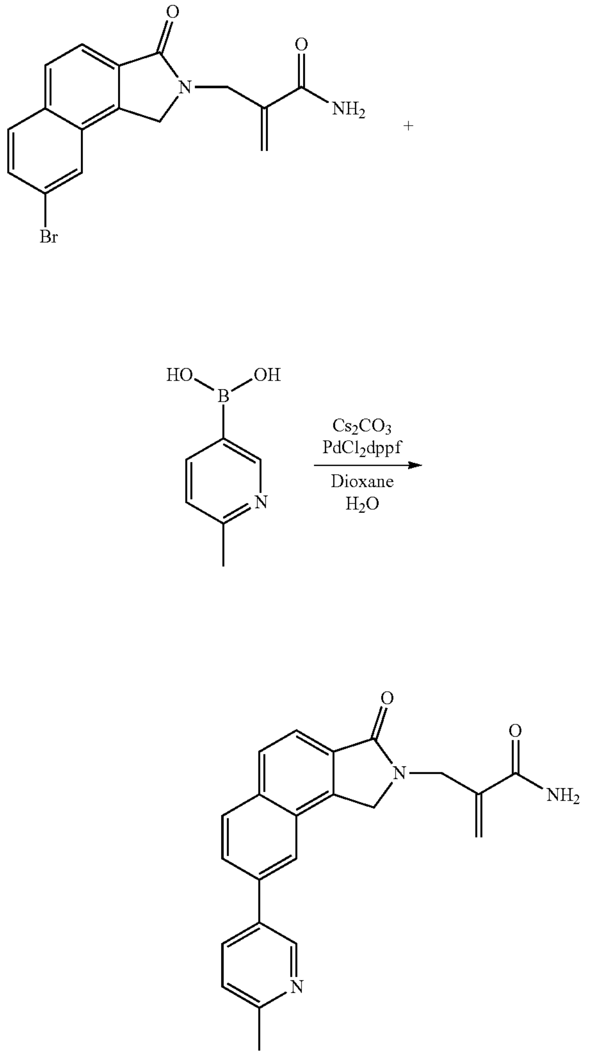

To a solution of 2-[(8-bromo-3-oxo-1H-benzo[e]isoindol-2-yl)methyl]prop-2-enamide (30 mg, 87 μmol) in dioxane (1 mL) and water (0.2 mL) were added (6-methyl-3-pyridyl) boronic acid (17.8 mg, 130 μmol), $Cs_2CO_3$ (84.4 mg, 261 μmol) and $PdCl_2dppf$ (18 mg, 22.4 μmol). The reaction was heated to 100° C. for 25 min in a microwave. The reaction mixture was passed through a celite pad, and 1 mL of 2 M EDTA was added. The resulting solution was stirred at r.t. for 1 h and washed with brine, and the organic phase was dried over anhydrous sodium sulfate, filtered, and concentrated in vacuo. The residue was purified by reverse phase HPLC using a gradient of water 0.1% FA/acetonitrile 0.1% FA to afford the title compound (8.5 mg, Yield 27%). LC-MS: $[M+H]^+$ 358.

Preparation of 2-[[8-(5-methyl-3-pyridyl)-3-oxo-1H-benzo[e]isoindol-2-yl]methyl]prop-2-enamide (Compound 661)

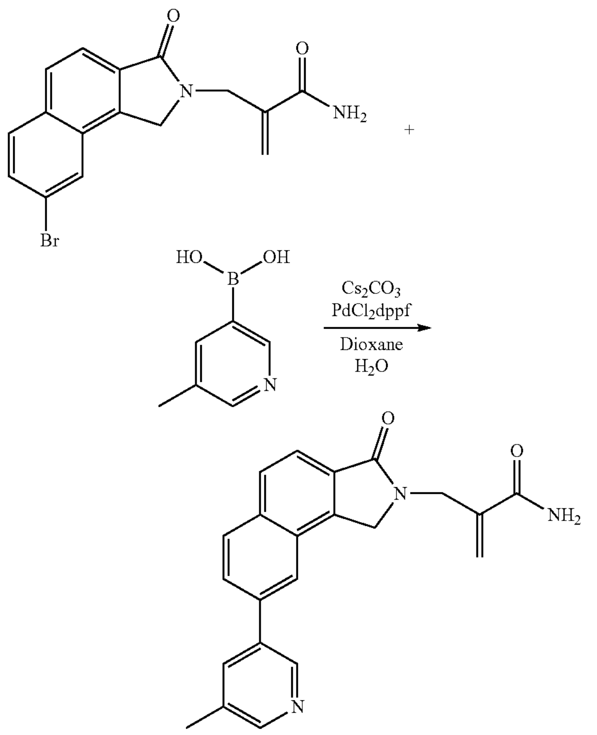

To a solution of 2-[(8-bromo-3-oxo-1H-benzo[e]isoindol-2-yl)methyl]prop-2-enamide (30 mg, 87 μmol) in dioxane (1 mL) and water (0.2 mL) were added (5-methyl-3-pyridyl) boronic acid (17.8 mg, 130 μmol), $Cs_2CO_3$ (84.4 mg, 261 μmol) and $PdCl_2dppf$ (18 mg, 22.4 μmol). The reaction was heated to 100° C. for 25 min in a microwave. The reaction mixture was passed through a celite pad, and 1 mL of 2 M EDTA was added. The resulting solution was stirred at r.t. for 1 h and washed with brine, and the organic phase was dried over anhydrous sodium sulfate, filtered, and concentrated in vacuo. The residue was purified by reverse phase HPLC using a gradient of water 0.1% FA/acetonitrile 0.1% FA to afford the title compound (14.8 mg, Yield 48%). LC-MS: $[M+H]^+$ 358.

Preparation of 2-[[8-(4-aminophenyl)-3-oxo-1H-benzo[e]isoindol-2-yl]methyl]prop-2-enamide (Compound 686)

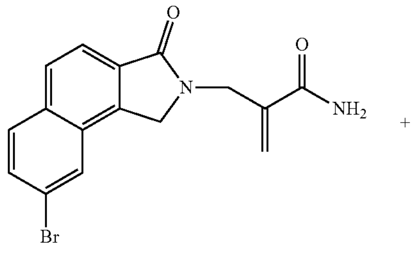

-continued

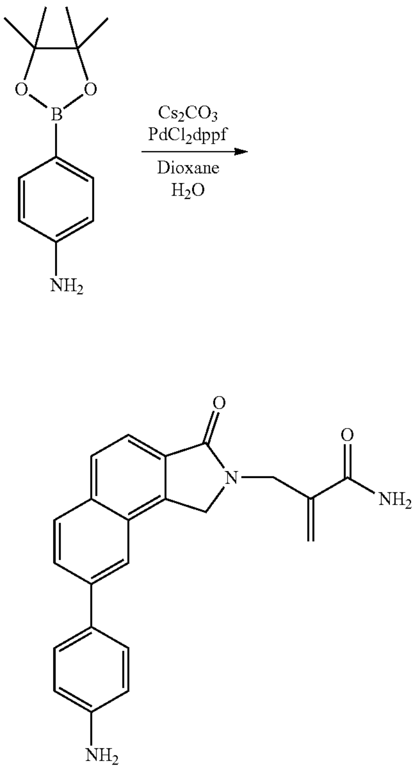

To a solution of 2-[(8-bromo-3-oxo-1H-benzo[e]isoindol-2-yl)methyl]prop-2-enamide (30 mg, 87 μmol) in dioxane (1 mL) and water (0.2 mL) were added 4-(4,4,5,5-tetramethyl-1,3,2-dioxaborolan-2-yl)aniline (28.5 mg, 130 μmol), $Cs_2CO_3$ (84.4 mg, 261 μmol) and $PdCl_2dppf$ (18 mg, 22.4 μmol). The reaction was heated to 100° C. for 25 min in a microwave. The reaction mixture was passed through a celite pad, and 1 mL of 2 M EDTA was added. The resulting solution was stirred at r.t. for 1 h and washed with brine, and the organic phase was dried over anhydrous sodium sulfate, filtered, and concentrated in vacuo. The residue was purified by reverse phase HPLC using a gradient of water 0.1% FA/acetonitrile 0.1% FA to afford the title compound (11.2 mg, Yield 36%). LC-MS: $[M+H]^+$ 358.

Preparation of 2-[[3-oxo-8-[3-(propanoylamino)phenyl]-1H-benzo[e]isoindol-2-yl]methyl]prop-2-enamide (Compound 687)

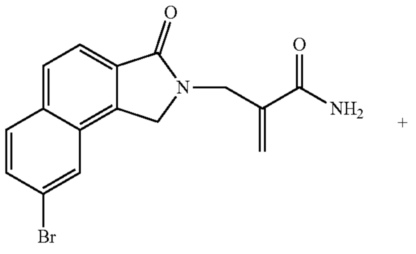

-continued

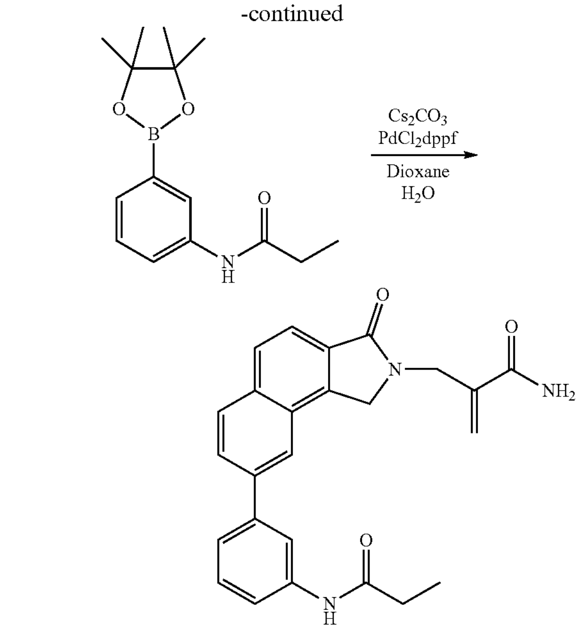

To a solution of 2-[(8-bromo-3-oxo-1H-benzo[e]isoindol-2-yl)methyl]prop-2-enamide (30 mg, 87 μmol) in dioxane (1 mL) and water (0.2 mL) were added N-[3-(4,4,5,5-tetramethyl-1,3,2-dioxaborolan-2-yl)phenyl]propanamide (35.8 mg, 130 μmol), $Cs_2CO_3$ (84.4 mg, 261 μmol) and $PdCl_2dppf$ (18 mg, 22.4 μmol). The reaction was heated to 100° C. for 25 min in a microwave. The reaction mixture was passed through a celite pad, and 1 mL of 2 M EDTA was added. The resulting solution was stirred at r.t. for 1 h and washed with brine, and the organic phase was dried over anhydrous sodium sulfate, filtered, and concentrated in vacuo. The residue was purified by reverse phase HPLC using a gradient of water 0.1% FA/acetonitrile 0.1% FA to afford the title compound (3 mg, Yield 8%).

LC-MS: $[M+H]^+$ 414.

Preparation of 2-[[8-(5-acetamido-3-pyridyl)-3-oxo-1H-benzo[e]isoindol-2-yl]methyl]prop-2-enamide (Compound 688)

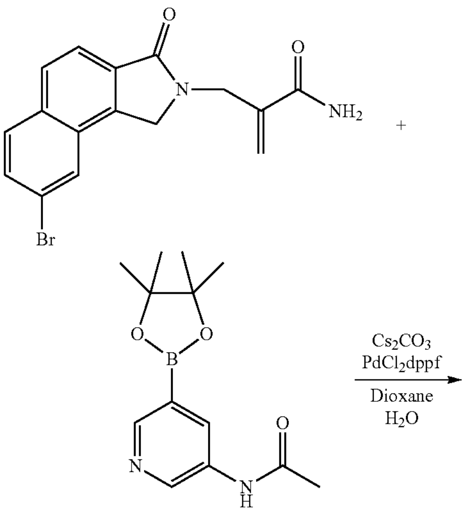

-continued

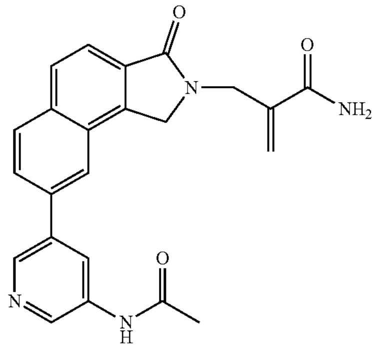

To a solution of 2-[(8-bromo-3-oxo-1H-benzo[e]isoindol-2-yl)methyl]prop-2-enamide (30 mg, 87 μmol) in dioxane (1 mL) and water (0.2 mL) were added N-[5-(4,4,5,5-tetramethyldioxaborolan-2-yl)-3-pyridyl]acetamide (34.1 mg, 130 μmol), $Cs_2CO_3$ (84.4 mg, 261 μmol) and $PdCl_2dppf$ (18 mg, 22.4 μmol). The reaction was heated to 100° C. for 25 min in a microwave. The reaction mixture was passed through a celite pad, and 1 mL of 2 M EDTA was added. The resulting solution was stirred at r.t. for 1 h and washed with brine, and the organic phase was dried over anhydrous sodium sulfate, filtered, and concentrated in vacuo. The residue was purified by reverse phase HPLC using a gradient of water 0.1% FA/acetonitrile 0.1% FA to afford the title compound (3.7 mg, Yield 11%). LC-MS: $[M+H]^+$ 401.

Preparation of 2-[[8-(4-amino-3-cyano-phenyl)-3-oxo-1H-benzo[e]isoindol-2-yl]methyl]prop-2-enamide (Compound 689)

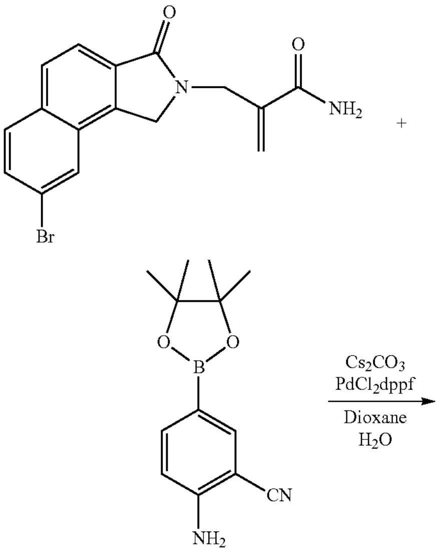

-continued

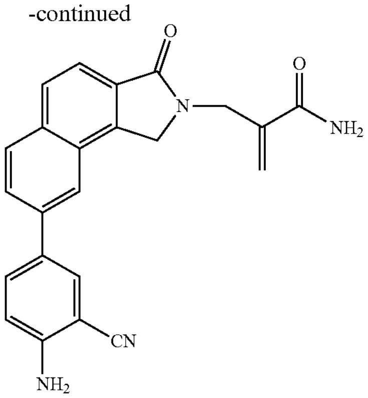

To a solution of 2-[(8-bromo-3-oxo-1H-benzo[e]isoindol-2-yl)methyl]prop-2-enamide (30 mg, 87 μmol) in dioxane (1 mL) and water (0.2 mL) were added 2-amino-5-(4,4,5,5-tetramethyl-1,3,2-dioxaborolan-2-yl)benzonitrile (31.7 mg, 130 μmol), $Cs_2CO_3$ (84.4 mg, 261 μmol) and $PdCl_2$dppf (18 mg, 22.4 μmol). The reaction was heated to 100° C. for 25 min in a microwave. The reaction mixture was passed through a celite pad, and 1 mL of 2 M EDTA was added. The resulting solution was stirred at r.t. for 1 h and washed with brine, and the organic phase was dried over anhydrous sodium sulfate, filtered, and concentrated in vacuo. The residue was purified by reverse phase HPLC using a gradient of water 0.1% FA/acetonitrile 0.1% FA to afford the title compound (18 mg, Yield 55%). LC-MS: $[M+H]^+$ 383.

Preparation of tert-butyl 4-[(3-bromophenyl) carbamoyl]piperidine-1-carboxylate

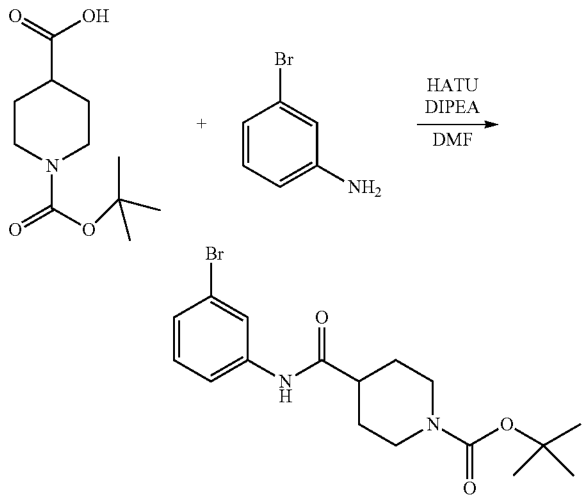

A mixture of 1-tert-butoxycarbonylpiperidine-4-carboxylic acid (200 mg, 0.872 mmol), HATU (0.663 g, 1.774 mmol) and DIPEA (337 mg, 2.616 mmol) in DMF (4 mL) was stirred at r.t. for 30 min. 3-Bromoaniline (225 mg, 1.308 mmol) was added. The resulting mixture was stirred at r.t. for 18 h and partitioned between EtOAc and water. The aqueous phase was extracted with EtOAc (3×). The combined organic phase was washed with sat. $NaHCO_3$ and brine, dried over ($MgSO_4$), filtered, and concentrated in vacuo. The residue was purified by chromatography on silica gel eluting with 0-50% EtOAc/hexane to afford the title compound (0.334 g, Yield 100%).

Preparation of tert-butyl 4-[[3-(4,4,5,5-tetramethyl-1,3,2-dioxaborolan-2-yl)phenyl]carbamoyl]piperidine-1-carboxylate

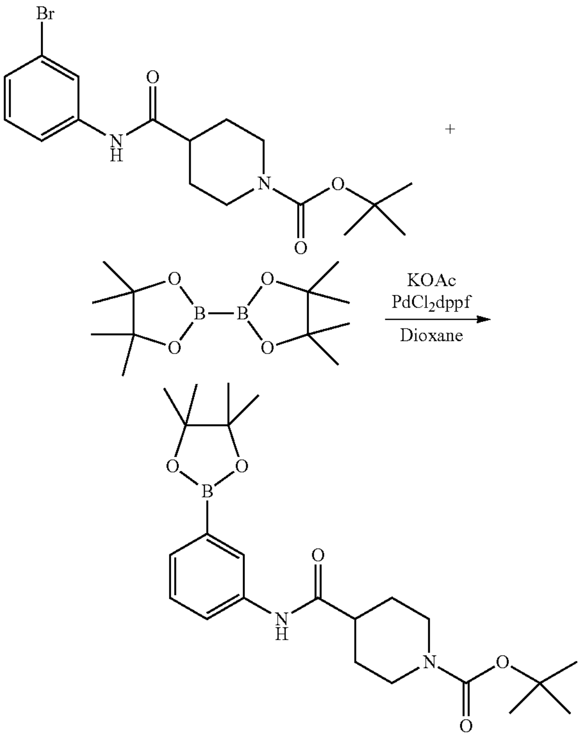

To a solution of tert-butyl 4-[(3-bromophenyl)carbamoyl] piperidine-1-carboxylate (146 mg, 382 μmol) in dioxane (3 mL) were added 4,4,5,5-tetramethyl-2-(4,4,5,5-tetramethyl-1,3,2-dioxaborolan-2-yl)-1,3,2-dioxaborolane (0.291 g, 1.146 mmol), KOAc (188 mg, 1.91 mmol) and $PdCl_2$dppf (54 mg, 66 μmol). The reaction was heated to 100° C. for 30 min in a microwave. The reaction mixture was passed through a celite pad, and the solvent was removed in vacuo. The residue was purified by chromatography on silica gel eluting with 20-80% EtOAc/hexane to afford the title compound (148 mg, Yield 90%).

Preparation of tert-butyl 4-[[3-[2-(2-carbamoylallyl)-3-oxo-1H-benzo[e]isoindol-8-yl]phenyl]carbamoyl]piperidine-1-carboxylate

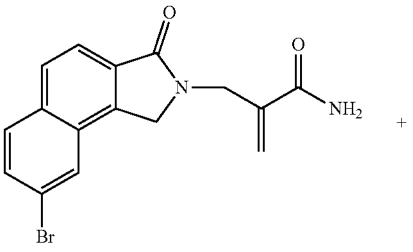

-continued

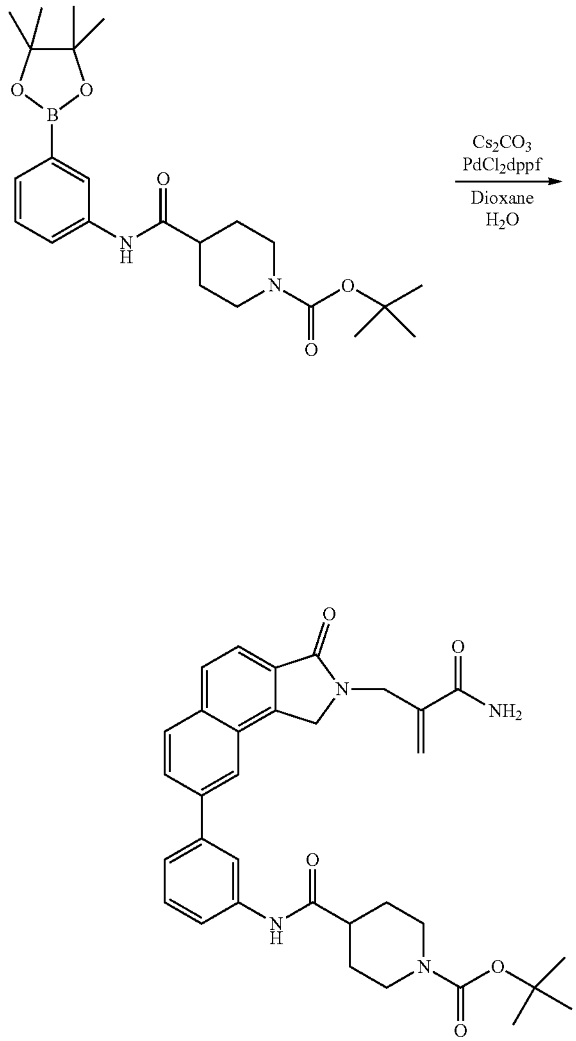

To a solution of 2-[(8-bromo-3-oxo-1H-benzo[e]isoindol-2-yl)methyl]prop-2-enamide (40 mg, 116 μmol) in dioxane (1.5 mL) and water (0.2 mL) were added tert-butyl 4-[[3-(4,4,5,5-tetramethyl-1,3,2-dioxaborolan-2-yl)phenyl]carbamoyl]piperidine-1-carboxylate (74.8 mg, 174 μmol), $Cs_2CO_3$ (113.1 mg, 348 μmol) and $PdCl_2dppf$ (18 mg, 22.4 μmol). The reaction was heated to 100° C. for 30 min in a microwave. The reaction mixture was passed through a celite pad, and 2 mL of 0.5 M EDTA was added. The resulting solution was stirred at r.t. for 40 min. The solution was washed with brine, and the organic phase was dried over anhydrous sodium sulfate, filtered, and concentrated in vacuo. The residue was purified by chromatography on silica gel eluting with 40-100% EtOAc/hexane and 0-10% MeOH/DCM to afford the title compound (56 mg, Yield 85%).

Preparation of N-[3-[2-(2-carbamoylallyl)-3-oxo-1H-benzo[e]isoindol-8-yl]phenyl]piperidine-4-carboxamide (Compound 699)

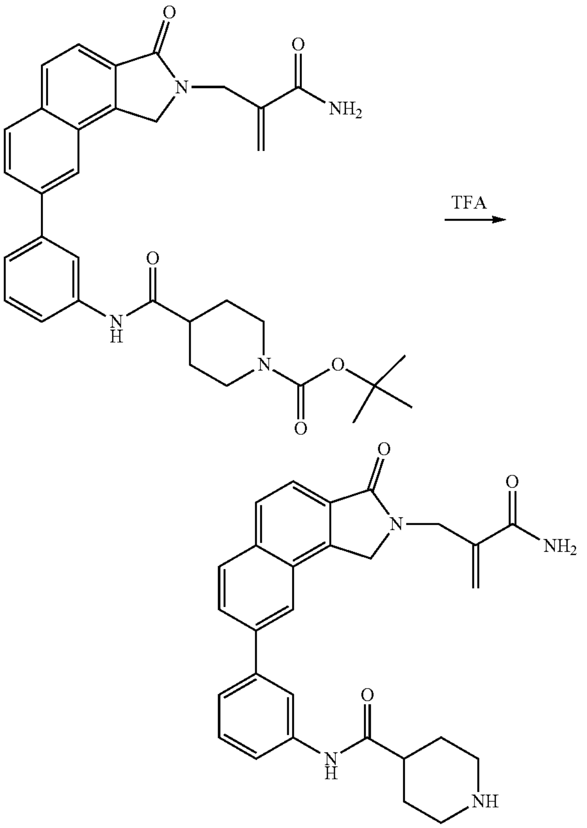

To a solution of tert-butyl 4-[[3-[2-(2-carbamoylallyl)-3-oxo-1H-benzo[e]isoindol-8-yl]phenyl]carbamoyl] piperidine-1-carboxylate (56 mg, 98 μmol) in DCM (2 mL) was added trifluoroacetic acid (0.5 mL) at 0° C. The resulting solution was stirred at 0° C. for 1 h and r.t. for 1 h. The reaction mixture was concentrated in vacuo and the residue was diluted with DCM, washed with sat. $NaHCO_3$ and brine, dried over anhydrous sodium sulfate, filtered, and concentrated. The residue was purified by reverse phase HPLC using a gradient of water 0.10% FA/acetonitrile 0.1% FA to afford the title compound (24.4 mg, Yield 53%). LC-MS: $[M+H]^+$ 469.

Preparation of 2-[[8-[4-(methylamino)phenyl]-3-oxo-1H-benzo[e]isoindol-2-yl]methyl]prop-2-enamide (Compound 706)

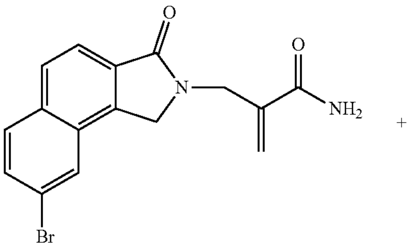

-continued

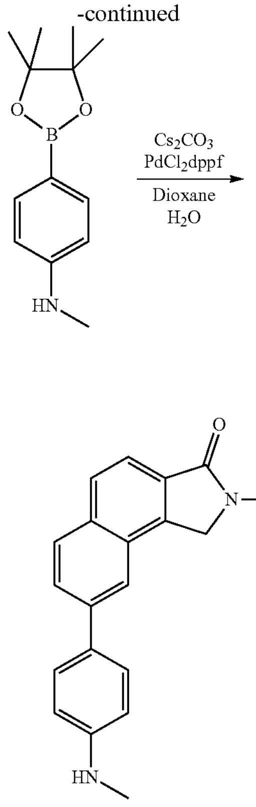

To a solution of 2-[(8-bromo-3-oxo-1H-benzo[e]isoindol-2-yl)methyl]prop-2-enamide (30 mg, 87 μmol) in dioxane (2 mL) and water (0.4 mL) were added N-methyl-4-(4,4,5,5-tetramethyl-1,3,2-dioxaborolan-2-yl)aniline (30.3 mg, 130 μmol), $Cs_2CO_3$ (84.4 mg, 261 μmol) and $PdCl_2$dppf (18 mg, 22.4 μmol). The reaction was heated to 100° C. for 40 min in a microwave. The reaction mixture was passed through a celite pad, and 2 mL of 0.5 M EDTA was added. The resulting solution was stirred at r.t. for 40 min and washed with brine, and the organic phase was dried over anhydrous sodium sulfate, filtered, and concentrated in vacuo. The residue was purified by reverse phase HPLC using a gradient of water 0.1% FA/acetonitrile 0.1% FA to afford the title compound (19 mg, Yield 59%). LC-MS: $[M+H]^+$ 372.

Preparation of 2-[[8-[4-amino-3-(trifluoromethoxy)phenyl]-3-oxo-1H-benzo[e]isoindol-2-yl]methyl]prop-2-enamide (Compound 706)

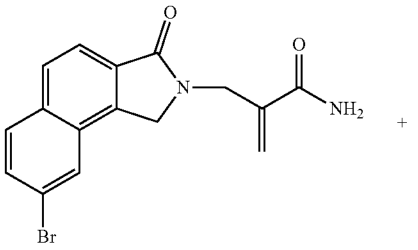

-continued

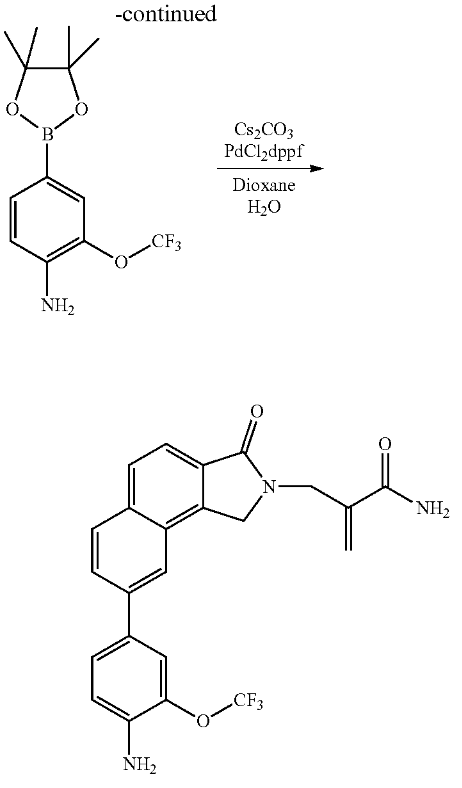

To a solution of 2-[(8-bromo-3-oxo-1H-benzo[e]isoindol-2-yl)methyl]prop-2-enamide (30 mg, 87 μmol) in dioxane (2 mL) and water (0.4 mL) were added 2-[[8-[4-amino-3-(trifluoromethoxy)phenyl]-3-oxo-1H-benzo[e]isoindol-2-yl]methyl]prop-2-enamide (39.4 mg, 130 μmol), $Cs_2CO_3$ (84.4 mg, 261 μmol) and $PdCl_2$dppf (18 mg, 22.4 μmol). The reaction was heated to 100° C. for 40 min in a microwave. The reaction mixture was passed through a celite pad, and 2 mL of 0.5 M EDTA was added. The resulting solution was stirred at r.t. for 40 min. The solution was washed with brine, and the organic phase was dried over anhydrous sodium sulfate, filtered, and concentrated in vacuo. The residue was purified by reverse phase HPLC using a gradient of water 0.10% FA/acetonitrile 0.1% FA to afford the title compound (15.1 mg, Yield 39%). LC-MS: $[M+H]^+$ 442.

Preparation of 2-[[8-(4-amino-3-fluoro-phenyl)-3-oxo-1H-benzo[e]isoindol-2-yl]methyl]prop-2-enamide (Compound 707)

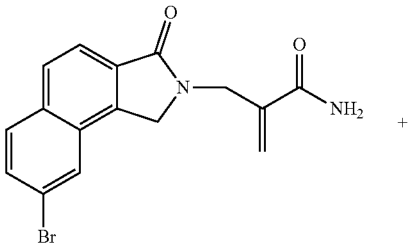

-continued

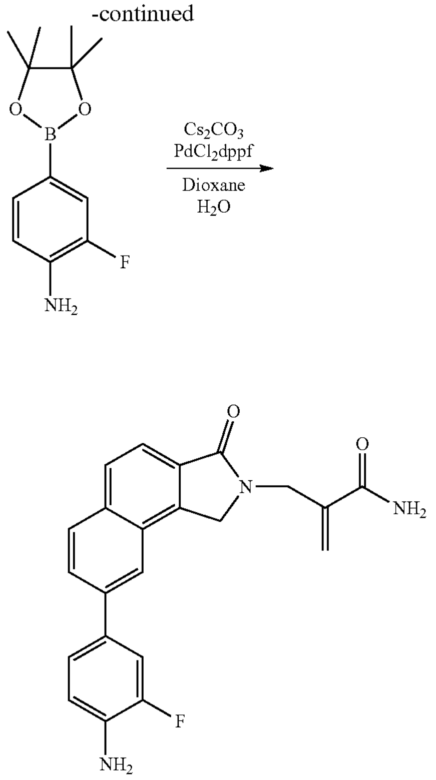

-continued

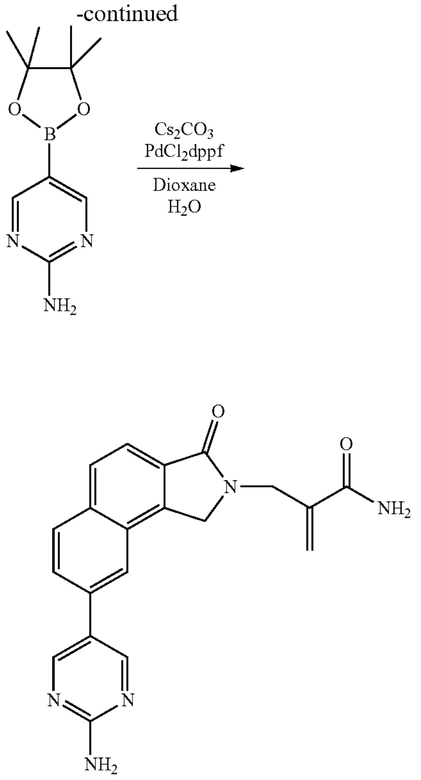

To a solution of 2-[(8-bromo-3-oxo-1H-benzo[e]isoindol-2-yl)methyl]prop-2-enamide (30 mg, 87 μmol) in dioxane (2 mL) and water (0.4 mL) were added 2-fluoro-4-(4,4,5,5-tetramethyl-1,3,2-dioxaborolan-2-yl)aniline (30.8 mg, 130 μmol), $Cs_2CO_3$ (84.4 mg, 261 μmol) and $PdCl_2dppf$ (18 mg, 22.4 μmol). The reaction was heated to 100° C. for 40 min in a microwave. The reaction mixture was passed through a celite pad, and 2 mL of 0.5 M EDTA was added. The resulting solution was stirred at r.t. for 40 min. The solution was washed with brine, and the organic phase was dried over anhydrous sodium sulfate, filtered, and concentrated in vacuo. The residue was purified by reverse phase HPLC using a gradient of water 0.1% FA/acetonitrile 0.1% FA to afford the title compound (14 mg, Yield 43%). LC-MS: $[M+H]^+$ 376.

Preparation of 2-[[8-(2-aminopyrimidin-5-yl)-3-oxo-1H-benzo[e]isoindol-2-yl]methyl]prop-2-enamide (Compound 723)

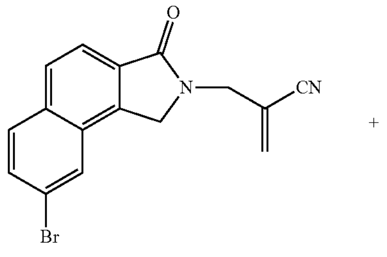

To a solution of 2-[(8-bromo-3-oxo-1H-benzo[e]isoindol-2-yl)methyl]prop-2-enamide (30 mg, 87 μmol) in dioxane (2 mL) and water (0.4 mL) were added 5-(4,4,5,5-tetramethyl-1,3,2-dioxaborolan-2-yl)pyrimidin-2-amine (28.7 mg, 130 μmol), $Cs_2CO_3$ (84.4 mg, 261 μmol) and $PdCl_2dppf$ (18 mg, 22.4 μmol). The reaction was heated to 100° C. for 40 min in a microwave. The reaction mixture was passed through a celite pad, and 2 mL of 0.5 M EDTA was added. The resulting solution was stirred at r.t. for 40 min. The solution was washed with brine, and the organic phase was dried over anhydrous sodium sulfate, filtered, and concentrated in vacuo. The residue was purified by reverse phase HPLC using a gradient of water 0.1% FA/acetonitrile 0.1% FA to afford the title compound (6.7 mg, Yield 21%). LC-MS: $[M+H]^+$ 360.

Preparation of 2-[[8-(4-amino-3-chloro-phenyl)-3-oxo-1H-benzo[e]isoindol-2-yl]methyl]prop-2-enenitrile (Compound 724)

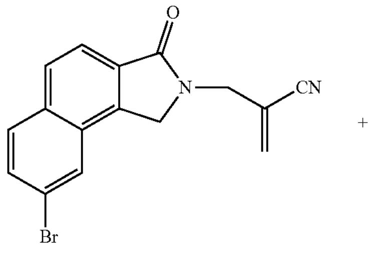

-continued

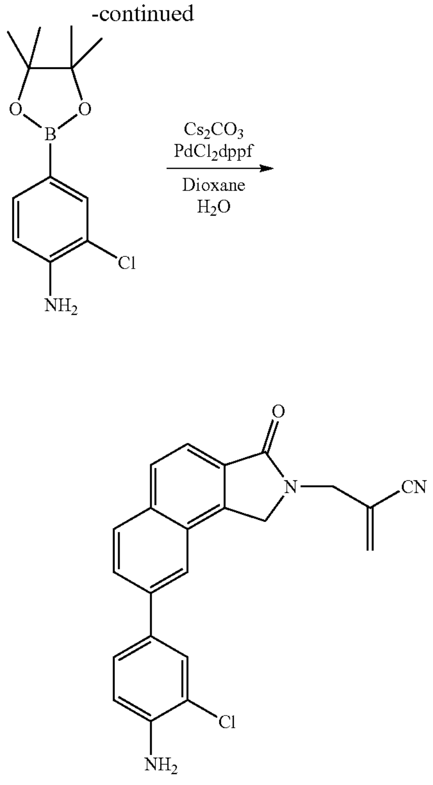

To a solution of 2-[(8-bromo-3-oxo-1H-benzo[e]isoindol-2-yl)methyl]prop-2-enenitrile (106.8 mg, 326 μmol) in dioxane (2 mL) and water (0.4 mL) were added 2-chloro-4-(4,4,5,5-tetramethyl-1,3,2-dioxaborolan-2-yl)aniline (146.5 mg, 578 μmol), $Cs_2CO_3$ (375 mg, 1.155 mmol) and $PdCl_2dppf$ (40 mg, 49 μmol). The reaction was heated to 100° C. for 30 min in a microwave. The reaction mixture was passed through a celite pad, and 2 mL of 0.5 M EDTA was added. The resulting solution was stirred at r.t. for 40 min. The solution was washed with brine, and the organic phase was dried over anhydrous sodium sulfate, filtered, and concentrated in vacuo. The residue was purified by chromatography on silica gel eluting with 10-100% EtOAc/hexane to afford the title compound (59.4 mg, Yield 49%). LC-MS: $[M+H]^+$ 374.

Preparation of 2-[[8-(3,5-dimethoxyphenyl)-3-oxo-1H-benzo[e]isoindol-2-yl]methyl]prop-2-enamide (Compound 725)

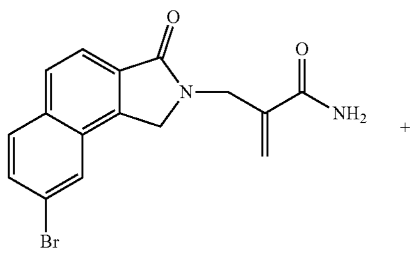

-continued

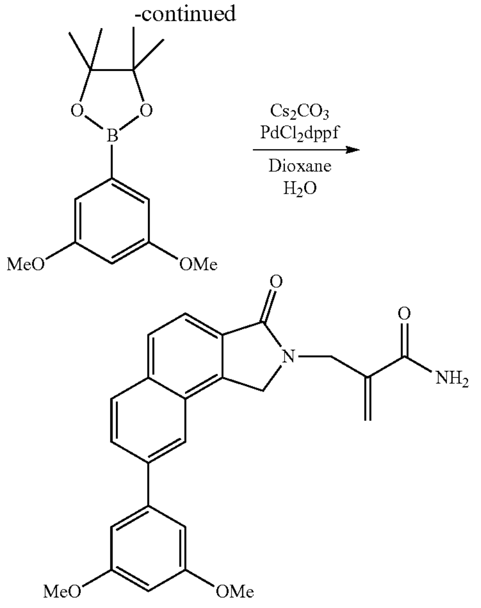

To a solution of 2-[(8-bromo-3-oxo-1H-benzo[e]isoindol-2-yl)methyl]prop-2-enamide (30 mg, 87 μmol) in dioxane (2 mL) and water (0.4 mL) were added 2-(3,5-dimethoxyphenyl)-4,4,5,5-tetramethyl-1,3,2-dioxaborolane (34.3 mg, 130 μmol), $Cs_2CO_3$ (84.4 mg, 261 μmol) and $PdCl_2dppf$ (18 mg, 22.4 μmol). The reaction was heated to 100° C. for 40 min in a microwave. The reaction mixture was passed through a celite pad, and 2 mL of 0.5 M EDTA was added. The resulting solution was stirred at r.t. for 40 min. The solution was washed with brine, and the organic phase was dried over anhydrous sodium sulfate, filtered, and concentrated in vacuo. The residue was purified by reverse phase HPLC using a gradient of water 0.1% FA/acetonitrile 0.1% FA to afford the title compound (20 mg, Yield 57%). LC-MS: $[M+H]^+$ 403.

Preparation of 3-bromo-N-methyl-5-(trifluoromethoxy)benzamide

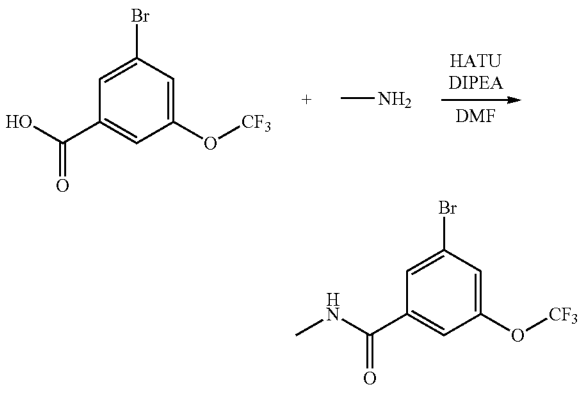

A mixture of 3-bromo-5-(trifluoromethoxy)benzoic acid (500 mg, 1.753 mmol), HATU (1.33 g, 3.506 mmol) and DIPEA (1.131 g, 8.771 mmol) in DMF (8 mL) was stirred at r.t. for 30 min. Methylamine (2 M in THF, 4.39 mL, 8.771 mmol) was added. The resulting mixture was stirred at r.t. for 18 h and partitioned between EtOAc and water. The aqueous phase was extracted with EtOAc (3×). The combined organic phase was washed with sat. $NaHCO_3$ and brine, dried over ($MgSO_4$), filtered, and concentrated in vacuo. The residue was purified by chromatography on silica gel eluting with 0-50% EtOAc/hexane to afford the title compound (0.331 g, Yield 63%).

Preparation of N-methyl-3-(4,4,5,5-tetramethyl-1,3,2-dioxaborolan-2-yl)-5-(trifluoromethoxy)benzamide

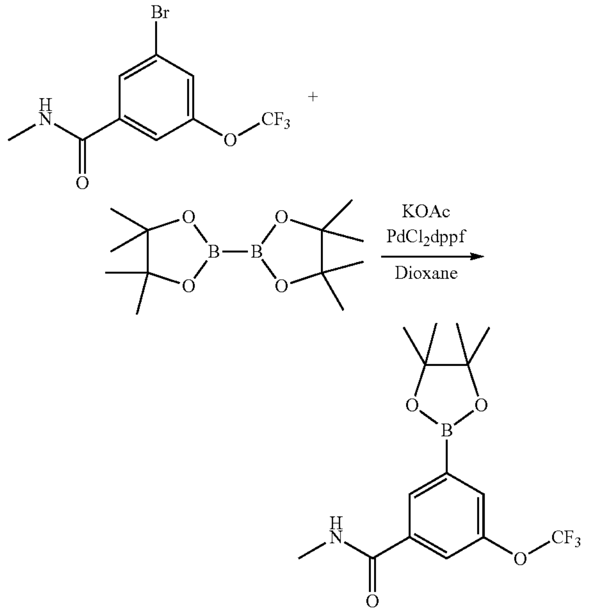

To a solution of 3-bromo-N-methyl-5-(trifluoromethoxy)benzamide (100 mg, 336 μmol) in dioxane (2 mL) were added 4,4,5,5-tetramethyl-2-(4,4,5,5-tetramethyl-1,3,2-dioxaborolan-2-yl)-1,3,2-dioxaborolane (0.128 g, 503 μmol), KOAc (99 mg, 1.008 mmol) and $PdCl_2dppf$ (40 mg, 49 μmol). The reaction was heated to 100° C. for 30 min in a microwave. The reaction mixture was passed through a celite pad, and the solvent was removed in vacuo. The residue was purified by chromatography on silica gel eluting with 0-20% MeOH/EtOAc to afford the title compound (73.3 mg, Yield 100%).

Preparation of 3-[2-(2-carbamoylallyl)-3-oxo-1H-benzo[e]isoindol-8-yl]-N-methyl-5-(trifluoromethoxy)benzamide (Compound 739)

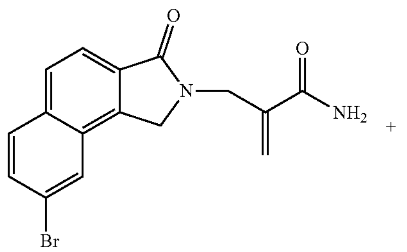

-continued

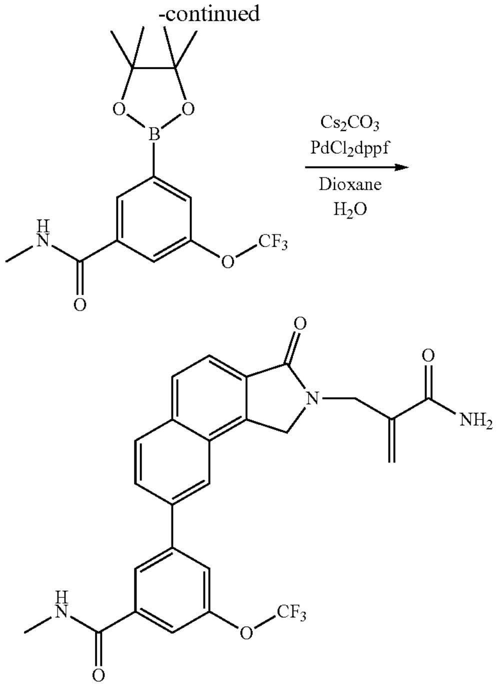

To a solution of 2-[(8-bromo-3-oxo-1H-benzo[e]isoindol-2-yl)methyl]prop-2-enamide (30 mg, 87 μmol) in dioxane (2 mL) and water (0.4 mL) were added N-methyl-3-(4,4,5,5-tetramethyl-1,3,2-dioxaborolan-2-yl)-5-(trifluoromethoxy)benzamide (28.4 mg, 130 μmol), $Cs_2CO_3$ (84.4 mg, 261 μmol) and $PdCl_2dppf$ (18 mg, 22.4 μmol). The reaction was heated to 100° C. for 40 min in a microwave. The reaction mixture was passed through a celite pad, and 2 mL of 0.5 M EDTA was added. The resulting solution was stirred at r.t. for 40 min. The solution was washed with brine, and the organic phase was dried over anhydrous sodium sulfate, filtered, and concentrated in vacuo. The residue was purified by reverse phase HPLC using a gradient of water 0.1% FA/acetonitrile 0.1% FA to afford the title compound (6.2 mg, Yield 15%). LC-MS: $[M+H]^+$ 484.

Preparation of 3-bromo-N-tetrahydropyran-4-yl-5-(trifluoromethoxy)benzamide

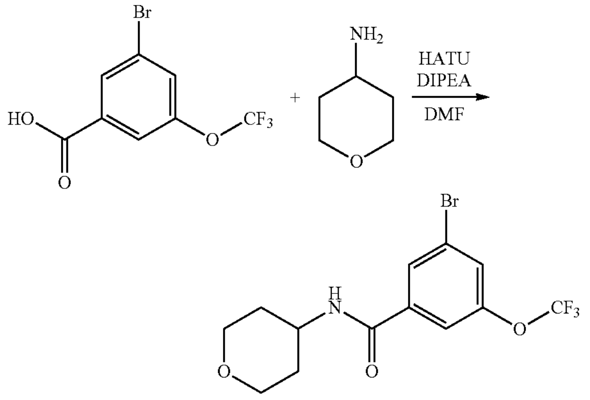

A mixture of 3-bromo-5-(trifluoromethoxy)benzoic acid (500 mg, 1.753 mmol), HATU (1.33 g, 3.506 mmol) and DIPEA (1.131 g, 8.771 mmol) in DMF (8 mL) was stirred at r.t. for 30 min. Tetrahydropyran-4-amine (0.355 g, 3.506 mmol) was added. The resulting mixture was stirred at r.t. for 18 h and partitioned between EtOAc and water. The aqueous phase was extracted with EtOAc (3×). The combined organic phase was washed with sat. $NaHCO_3$ and brine, dried over ($MgSO_4$), filtered, and concentrated in vacuo. The residue was purified by chromatography on silica gel eluting with 0-50% EtOAc/hexane to afford the title compound (0.399 g, Yield 62%).

Preparation of N-tetrahydropyran-4-yl-3-(4,4,5,5-tetramethyl-1,3,2-dioxaborolan-2-yl)-5-(trifluoromethoxy)benzamide

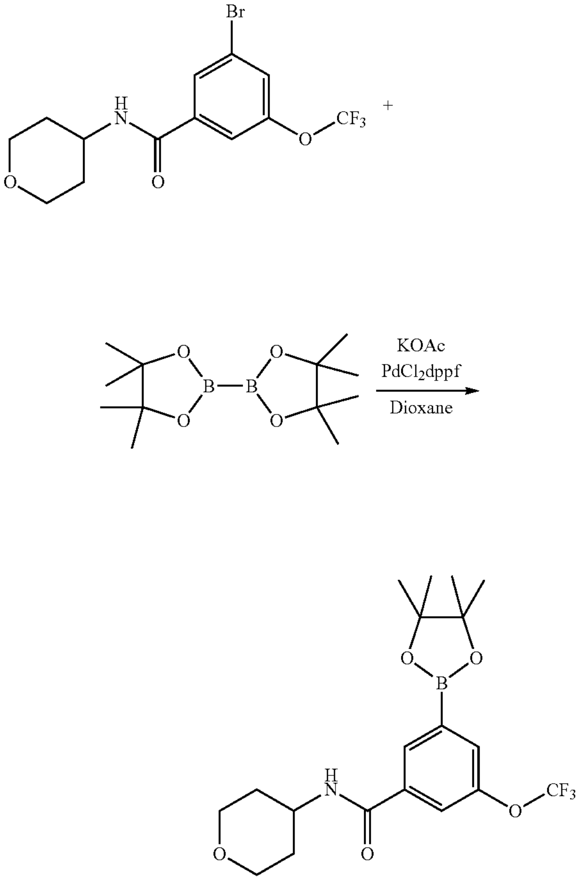

To a solution of 3-bromo-N-tetrahydropyran-4-yl-5-(trifluoromethoxy)benzamide (100 mg, 271 μmol) in dioxane (2 mL) were added 4,4,5,5-tetramethyl-2-(4,4,5,5-tetramethyl-1,3,2-dioxaborolan-2-yl)-1,3,2-dioxaborolane (0.103 g, 407 μmol), KOAc (80 mg, 0.813 mmol) and $PdCl_2dppf$ (40 mg, 49 μmol). The reaction was heated to 100° C. for 30 min in a microwave. The reaction mixture was passed through a celite pad, and the solvent was removed in vacuo. The residue was purified by chromatography on silica gel eluting with 0-20% MeOH/EtOAc to afford the title compound (44.4 mg, Yield 57%).

Preparation of 3-[2-(2-carbamoylallyl)-3-oxo-1H-benzo[e]isoindol-8-yl]-N-tetrahydropyran-4-yl-5-(trifluoromethoxy)benzamide (Compound 740)

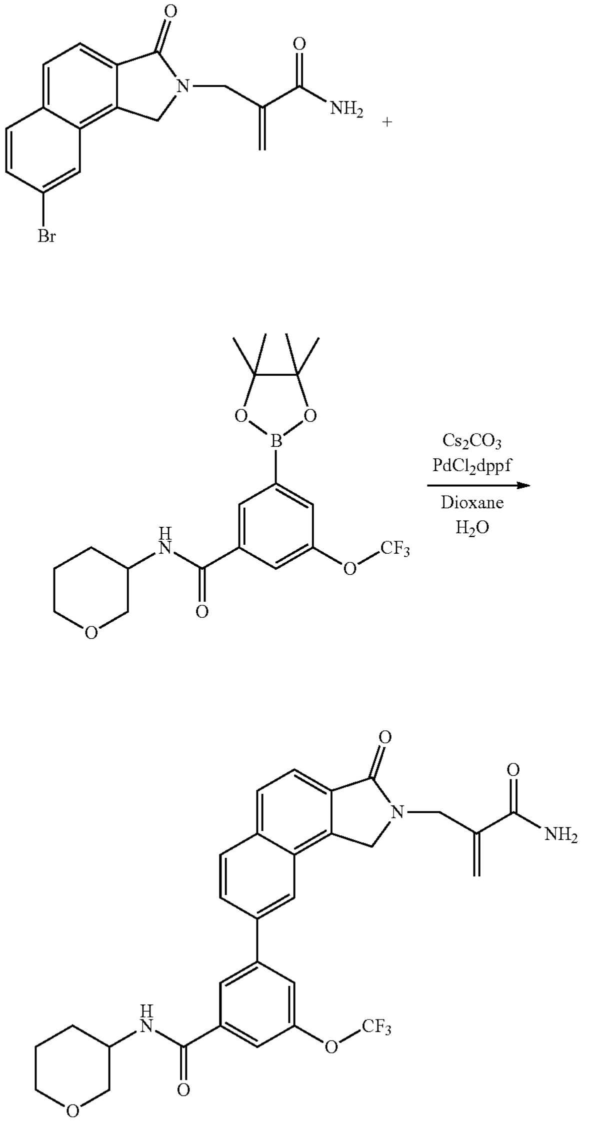

To a solution of 2-[(8-bromo-3-oxo-1H-benzo[e]isoindol-2-yl)methyl]prop-2-enamide (30 mg, 87 μmol) in dioxane (2 mL) and water (0.4 mL) were added N-tetrahydropyran-4-yl-3-(4,4,5,5-tetramethyl-1,3,2-dioxaborolan-2-yl)-5-(trifluoromethoxy)benzamide (37.5 mg, 130 μmol), $Cs_2CO_3$ (84.4 mg, 261 μmol) and $PdCl_2dppf$ (18 mg, 22.4 μmol). The reaction was heated to 100° C. for 40 min in a microwave. The reaction mixture was passed through a celite pad, and 2 mL of 0.5 M EDTA was added. The resulting solution was stirred at r.t. for 40 min. The solution was washed with brine, and the organic phase was dried over anhydrous sodium sulfate, filtered, and concentrated in vacuo. The residue was purified by reverse phase HPLC using a gradient of water 0.1% FA/acetonitrile 0.1% FA to afford the title compound (13.5 mg, Yield 28%). LC-MS: $[M+H]^+$ 554.

Preparation of 3-bromo-N-ethyl-5-(trifluoromethoxy)benzamide

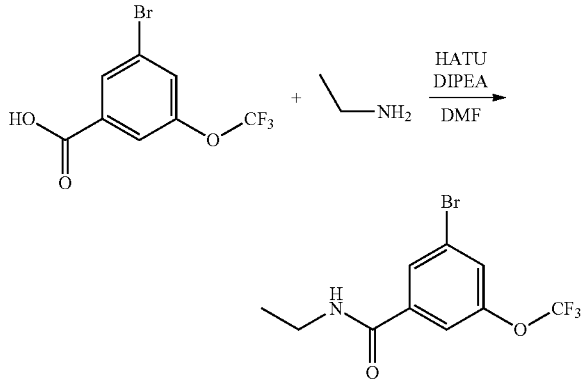

A mixture of 3-bromo-5-(trifluoromethoxy)benzoic acid (500 mg, 1.753 mmol), HATU (1.33 g, 3.506 mmol) and DIPEA (1.131 g, 8.771 mmol) in DMF (8 mL) was stirred at r.t. for 30 min. Ethylamine (2 M in THF, 4.39 mL, 8.771 mmol) was added. The resulting mixture was stirred at r.t. for 18 h and partitioned between EtOAc and water. The aqueous phase was extracted with EtOAc (3×). The combined organic phase was washed with sat. $NaHCO_3$ and brine, dried over ($MgSO_4$), filtered, and concentrated in vacuo. The residue was purified by chromatography on silica gel eluting with 0-50% EtOAc/hexane to afford the title compound (0.287 g, Yield 52%).

Preparation of N-ethyl-3-(4,4,5,5-tetramethyl-1,3,2-dioxaborolan-2-yl)-5-(trifluoromethoxy)benzamide

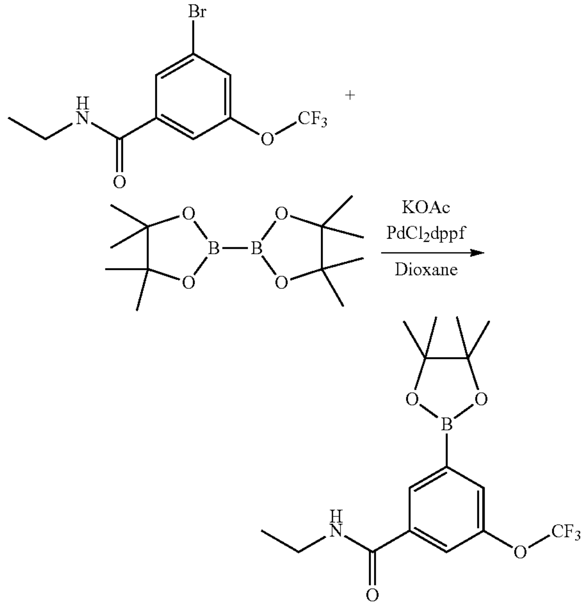

To a solution of 3-bromo-N-ethyl-5-(trifluoromethoxy)benzamide (150 mg, 480 μmol) in dioxane (3 mL) were added 4,4,5,5-tetramethyl-2-(4,4,5,5-tetramethyl-1,3,2-dioxaborolan-2-yl)-1,3,2-dioxaborolane (0.183 g, 721 μmol), KOAc (147 mg, 1.44 mmol) and $PdCl_2dppf$ (55 mg, 67 μmol). The reaction was heated to 100° C. for 30 min in a microwave. The reaction mixture was passed through a celite pad, and the solvent was removed in vacuo. The residue was purified by chromatography on silica gel eluting with 0-20% MeOH/EtOAc to afford the title compound (45 mg, Yield 41%).

Preparation of 3-[2-(2-carbamoylallyl)-3-oxo-1H-benzo[e]isoindol-8-yl]-N-ethyl-5-(trifluoromethoxy) benzamide (Compound 742)

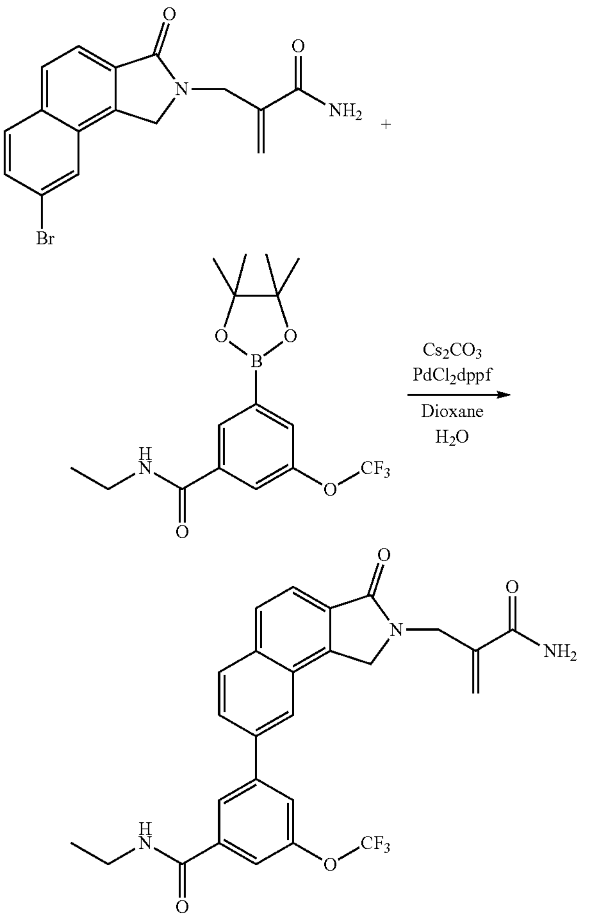

To a solution of 2-[(8-bromo-3-oxo-1H-benzo[e]isoindol-2-yl)methyl]prop-2-enamide (30 mg, 87 μmol) in dioxane (2 mL) and water (0.4 mL) were added N-ethyl-3-(4,4,5,5-tetramethyl-1,3,2-dioxaborolan-2-yl)-5-(trifluoromethoxy) benzamide (30.2 mg, 130 μmol), $Cs_2CO_3$ (84.4 mg, 261 μmol) and $PdCl_2dppf$ (18 mg, 22.4 μmol). The reaction was heated to 100° C. for 40 min in a microwave. The reaction mixture was passed through a celite pad, and 2 mL of 0.5 M EDTA was added. The resulting solution was stirred at r.t. for 40 min. The solution was washed with brine, and the organic phase was dried over anhydrous sodium sulfate, filtered, and concentrated in vacuo. The residue was purified by reverse phase HPLC using a gradient of water 0.1% FA/acetonitrile 0.1% FA to afford the title compound (12.5 mg, Yield 29%). LC-MS: $[M+H]^+$ 498.

Preparation of 2-amino-N-ethyl-3-(trifluoromethoxy)benzamide

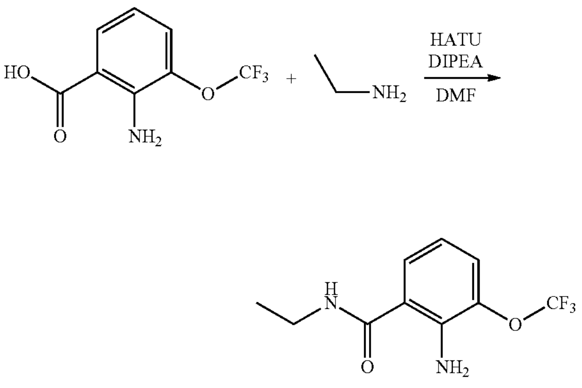

A mixture of 2-amino-3-(trifluoromethoxy)benzoic acid (500 mg, 2.261 mmol), HATU (1.72 g, 4.522 mmol) and DIPEA (1.458 g, 11.307 mmol) in DMF (8 mL) was stirred at r.t. for 30 min. Ethylamine (2 M in THF, 5.65 mL, 11.307 mmol) was added. The resulting mixture was stirred at r.t. for 18 h and partitioned between EtOAc and water. The aqueous phase was extracted with EtOAc (3×). The combined organic phase was washed with sat. $NaHCO_3$ and brine, dried over ($MgSO_4$), filtered, and concentrated in vacuo. The residue was purified by chromatography on silica gel eluting with 0-50% EtOAc/hexane to afford the title compound (0.55 g, Yield 98%).

Preparation of 2-amino-5-bromo-N-ethyl-3-(trifluoromethoxy)benzamide

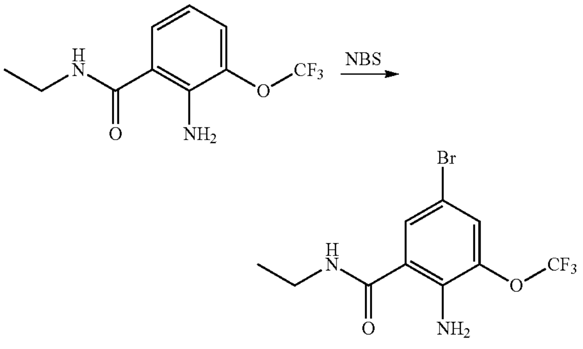

To a solution of 2-amino-N-ethyl-3-(trifluoromethoxy) benzamide (550 mg, 2.216 mmol) in DMF (10 mL) was added NBS (513 mg, 2.88 mmol) at 0° C. The resulting mixture was stirred at r.t. for 18 h and partitioned between EtOAc and water. The aqueous phase was extracted with EtOAc (3×). The combined organic phase was washed with water and brine, dried over ($MgSO_4$), filtered, and concentrated in vacuo. The residue was purified by chromatography on silica gel eluting with 0-30% EtOAc/hexane to afford the title compound (0.454 g, Yield 63%).

Preparation of 2-amino-5-[2-(2-carbamoylallyl)-3-oxo-1H-benzo[e]isoindol-8-yl]-N-ethyl-3-(trifluoromethoxy)benzamide (Compound 743)

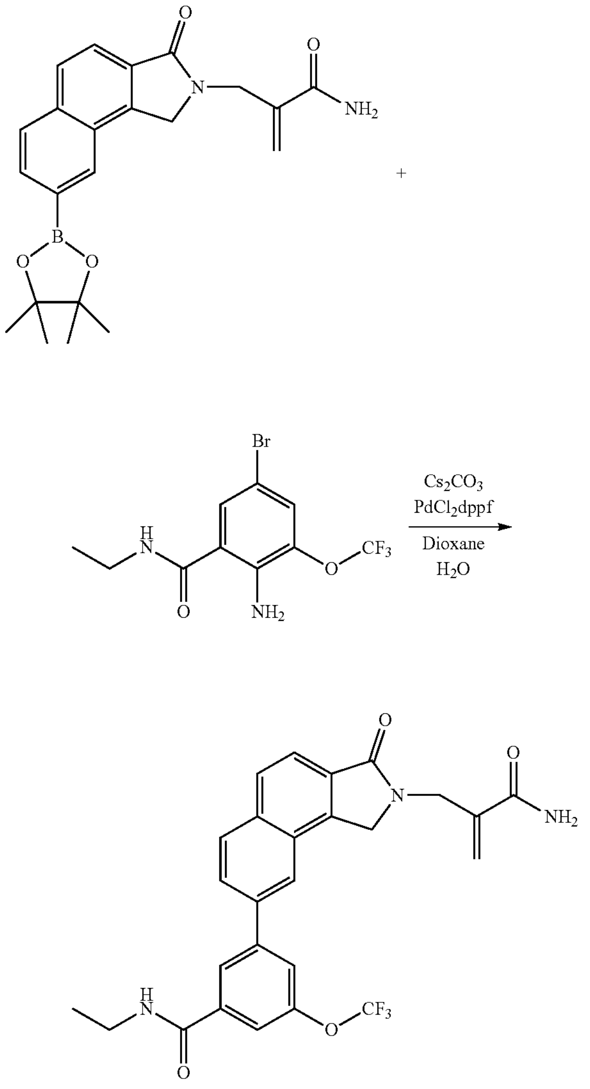

To a solution of 2-[[3-oxo-8-(4,4,5,5-tetramethyl-1,3,2-dioxaborolan-2-yl)-1H-benzo[e]isoindol-2-yl]methyl]prop-2-enamide (30 mg, 76 μmol) in dioxane (2 mL) and water (0.4 mL) were added 2-amino-5-[2-(2-carbamoylallyl)-3-oxo-1H-benzo[e]isoindol-8-yl]-N-ethyl-3-(trifluoromethoxy)benzamide (37.5 mg, 115 μmol), $Cs_2CO_3$ (74.1 mg, 228 μmol) and $PdCl_2dppf$ (18 mg, 22.4 μmol). The reaction was heated to 100° C. for 30 min in a microwave. The reaction mixture was passed through a celite pad, and 2 mL of 0.5 M EDTA was added. The resulting solution was stirred at r.t. for 40 min. The solution was washed with brine, and the organic phase was dried over anhydrous sodium sulfate, filtered, and concentrated in vacuo. The residue was purified by reverse phase HPLC using a gradient of water 0.1% FA/acetonitrile 0.1% FA to afford the title compound (3 mg, Yield 8%). LC-MS: $[M+H]^+$ 513.

Route 2:

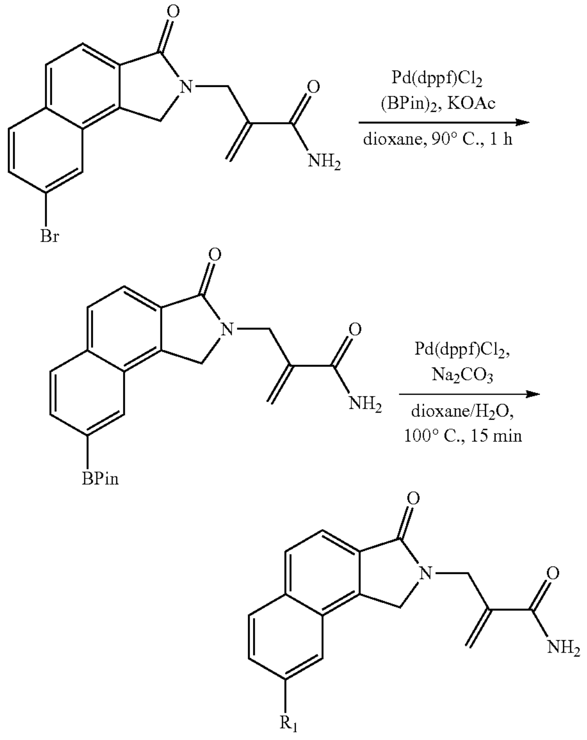

Preparation of 2-[[3-oxo-8-(4,4,5,5-tetramethyl-1,3,2-dioxaborolan-2-yl)-1H-benzo[e]isoindol-2-yl]methyl]prop-2-enamide

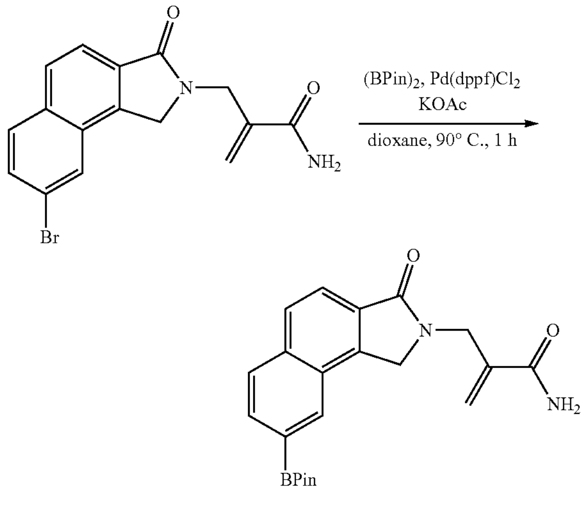

To a mixture of 2-[(8-bromo-3-oxo-1H-benzo[e]isoindol-2-yl)methyl]prop-2-enamide (100 mg, 289.70 μmol, 1 eq.) and 4,4,5,5-tetramethyl-2-(4,4,5,5-tetramethyl-1,3,2-dioxaborolan-2-yl)-1,3,2-dioxaborolane (80.92 mg, 318.66 μmol, 1.1 eq.) in dioxane (1.5 mL) were added Pd(dppf)$Cl_2$ (10.60 mg, 14.48 μmol, 0.05 eq.) and KOAc (85.29 mg, 869.09 μmol, 3 eq.) in one portion under nitrogen. The mixture was heated to 90° C. and stirred for 1 h. LCMS showed that the reaction was complete. The mixture was filtered in vacuo. The residue was purified by PE:EtOAc (V=5:1) (6 mL) to afford the title compound (500 mg, crude) as a brown solid.

General Procedure for the Suzuki Coupling

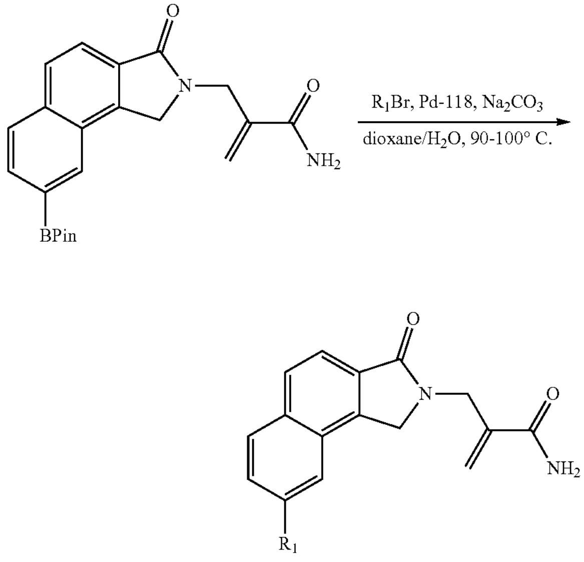

To a solution of 2-{[3-oxo-8-(4,4,5,5-tetramethyl-1,3-dioxolan-2-yl)-1H,2H,3H-benzo[e]isoindol-2-yl]methyl}prop-2-enamide (~1 eq.) in water (~0.5 mL) and dioxane (~2 mL) were added $R_1Br$ (~2 eq.), $Na_2CO_3$ (~3 eq.) and Pd-118 (~0.5 eq.) under nitrogen atmosphere. The mixture was stirred at 90~100° C. for 0.2 h. TLC or LCMS showed that the reaction was complete, EDTA (~20 mL) was added to the mixture, then the mixture was stirred for 1 hr. The reaction mixture was diluted with water ~10 mL and extracted with EtOAc 20 mL (~10 mL×2). The combined organic layers were washed with brine 10 mL, dried over anhydrous sodium sulfate, filtered, and concentrated in vacuo to give a residue. The residue was purified by prep-TLC or prep-HPLC.

General Procedure for the Suzuki Coupling

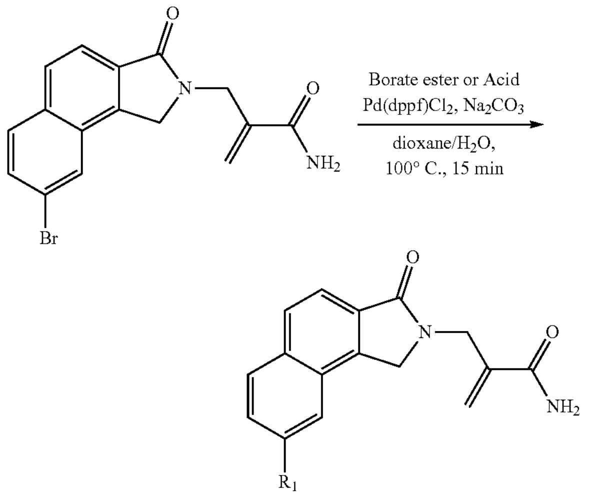

-continued

R1 =

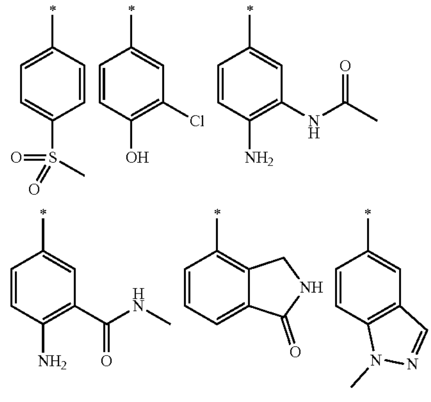

Preparation of 2-[[8-(3-acetamido-5-methoxy-phenyl)-3-oxo-1H-benzo[e]isoindol-2-yl]methyl]prop-2-enamide

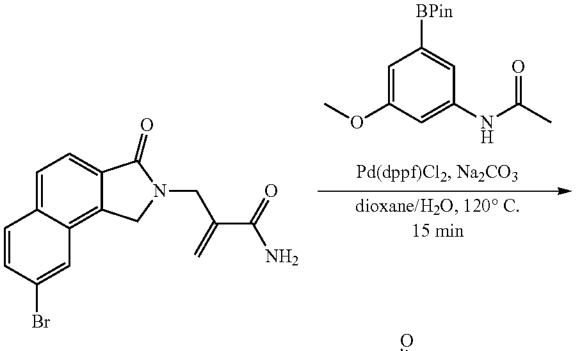

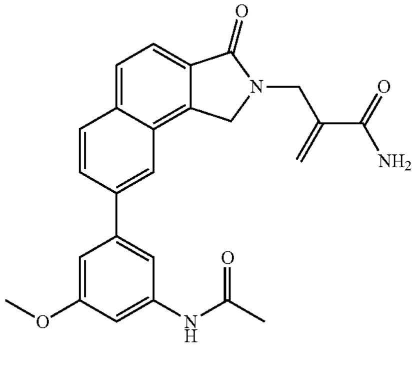

To a mixture of 2-[(8-bromo-3-oxo-1H-benzo[e]isoindol-2-yl)methyl]prop-2-enamide (50 mg, 144.85 μmol, 1 eq.), N-[3-methoxy-5-(4,4,5,5-tetramethyl-1,3,2-dioxaborolan-2-yl)phenyl]acetamide (63.26 mg, 217.27 μmol, 1.5 eq.) in dioxane (1 mL) and water (0.25 mL) were added $Na_2CO_3$ (46.06 mg, 434.54 μmol, 3 eq.), $Pd(dppf)Cl_2$ (21.20 mg, 28.97 μmol, 0.2 eq.) at 120° C. for 15 min. TLC showed that the reaction was complete. The reaction was diluted with 20 mL EtOAc and poured to 30 mL sat. EDTA, then stirred at 25° C. for 1 h and extracted with EtOAc 60 mL (20 mL×3). The combined organic layers were washed with brine (20 mL×3), filtered, and concentrated in vacuo to give a residue. The residue was purified by prep-HPLC to afford the title compound (10.2 mg, 23.51 μmol, 8.12% yield, 99% purity) as a white solid.

Preparation of 2-[[8-(4-acetamido-3-chloro-phenyl)-3-oxo-1H-benzo[e]isoindol-2-yl]methyl]prop-2-enamide (Compound 674)

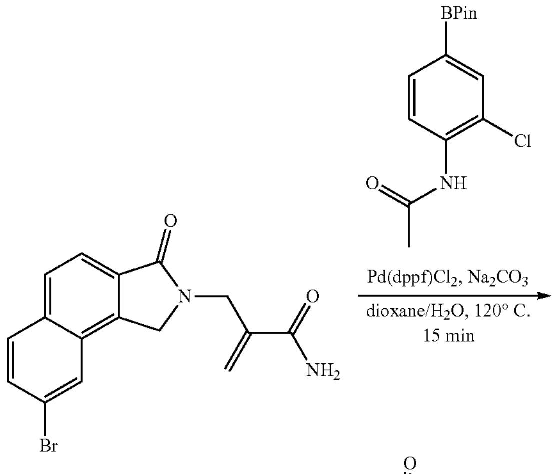

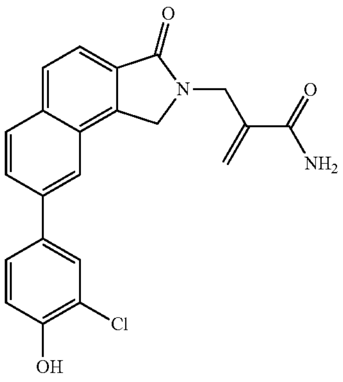

To a mixture of 2-[(8-bromo-3-oxo-1H-benzo[e]isoindol-2-yl)methyl]prop-2-enamide (50 mg, 144.85 μmol, 1 eq.) and N-[2-chloro-4-(4,4,5,5-tetramethyl-1,3,2-dioxaborolan-2-yl)phenyl]acetamide (64.22 mg, 217.27 μmol, 1.5 eq.) in dioxane (1 mL) water (0.25 mL) were added $Na_2CO_3$ (46.06 mg, 434.54 μmol, 3 eq.) and $Pd(dppf)Cl_2$ (21.20 mg, 28.97 μmol, 0.2 eq.) at 120° C. for 15 min. TLC showed that the reaction was complete. The reaction was diluted with 20 mL EtOAc and poured to 30 mL sat. EDTA, then stirred at 25° C. for 1 hr and extracted with EtOAc (20 mL×3). The combined organic layers were washed with brine (20 mL×3), filtered, and concentrated in vacuo to give a residue. The residue was purified by prep-HPLC to afford the title compound (6.7 mg, 15.29 μmol, 10.55% yield, 99% purity) as a white solid.

Preparation of N-(3-bromophenyl)tetrahydropyran-4-carboxamide

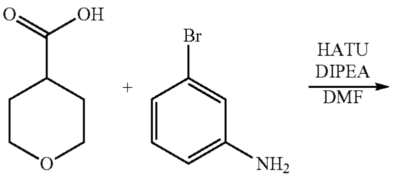

-continued

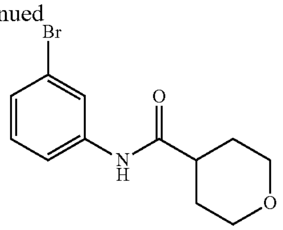

A mixture of tetrahydropyran-4-carboxylic acid (200 mg, 1.537 mmol), HATU (1.169 g, 3.074 mmol) and DIPEA (595 mg, 4.611 mmol) in DMF (5 mL) was stirred at r.t. for 30 min. 3-Bromoaniline (397 mg, 2.306 mmol) was added. The resulting mixture was stirred at r.t. for 18 h and partitioned between EtOAc and water. The aqueous phase was extracted with EtOAc (3×). The combined organic phase was washed with sat. $NaHCO_3$ and brine, dried over ($MgSO_4$), filtered, and concentrated in vacuo. The residue was purified by chromatography on silica gel eluting with 20-80% EtOAc/hexane to afford the title compound (0.401 g, Yield 92%).

Preparation of N-[3-[2-(2-carbamoylallyl)-3-oxo-1H-benzo[e]isoindol-8-yl]phenyl]tetrahydropyran-4-carboxamide (Compound 689)

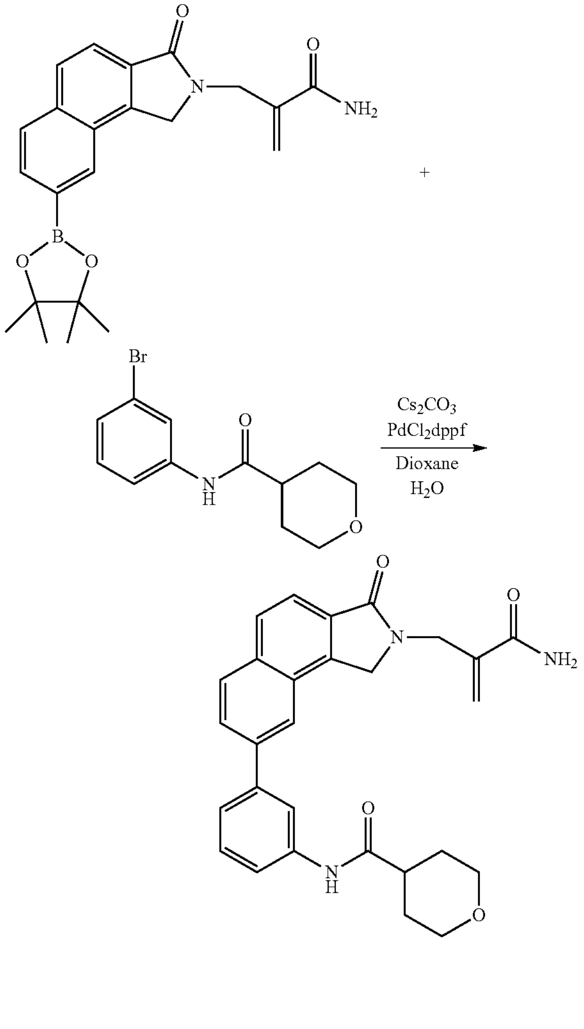

To a solution of 2-[[3-oxo-8-(4,4,5,5-tetramethyl-1,3,2-dioxaborolan-2-yl)-1H-benzo[e]isoindol-2-yl]methyl]prop-2-enamide (30 mg, 76 μmol) in dioxane (2 mL) and water (0.4 mL) were added N-(3-bromophenyl)tetrahydropyran-4-carboxamide (32.7 mg, 115 μmol), $Cs_2CO_3$ (74.1 mg, 228 μmol) and $PdCl_2dppf$ (18 mg, 22.4 μmol). The reaction was heated to 100° C. for 40 min in a microwave. The reaction mixture was passed through a celite pad, and 2 mL of 0.5 M EDTA was added. The resulting solution was stirred at r.t. for 40 min. The solution was washed with brine, and the organic phase was dried over anhydrous sodium sulfate, filtered, and concentrated in vacuo The residue was purified by reverse phase HPLC using a gradient of water 0.10% FA/acetonitrile 0.1% FA to afford the title compound (10 mg, Yield 28%). LC-MS: $[M+H]^+$ 470.

Preparation of 2-[[3-oxo-8-(3-oxo-2,4-dihydro-1H-quinoxalin-6-yl)-1H-benzo[e]isoindol-2-yl]methyl]prop-2-enamide (Compound 750)

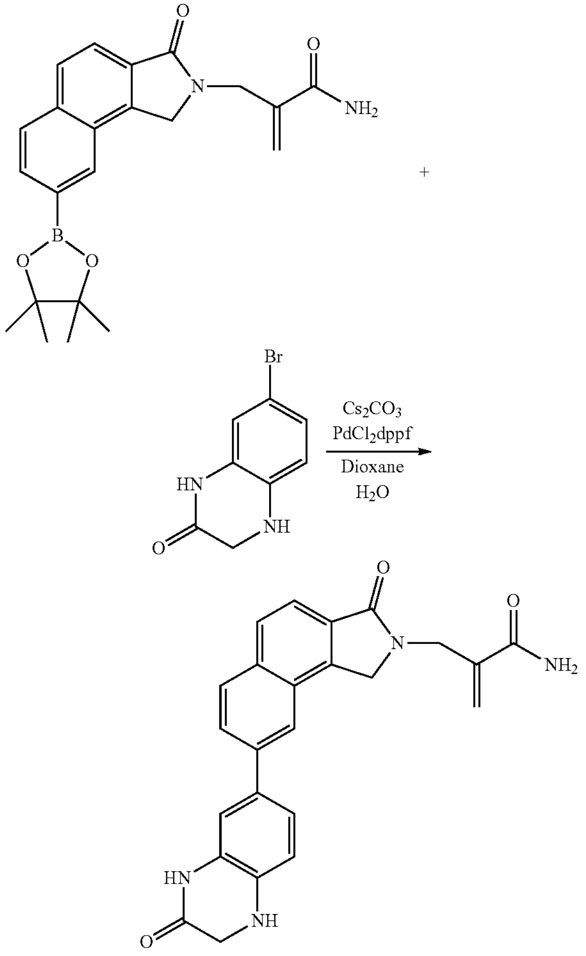

To a solution of 2-[[3-oxo-8-(4,4,5,5-tetramethyl-1,3,2-dioxaborolan-2-yl)-1H-benzo[e]isoindol-2-yl]methyl]prop-2-enamide (30 mg, 76 μmol) in dioxane (2 mL) and water (0.4 mL) were added 7-bromo-3,4-dihydro-1H-quinoxalin-2-one (26.1 mg, 114 μmol), $Cs_2CO_3$ (74.1 mg, 228 μmol) and $PdCl_2dppf$ (18 mg, 22.4 μmol). The reaction was heated to 100° C. for 30 min in a microwave. The reaction mixture was passed through a celite pad, and 2 mL of 0.5 M EDTA was added. The resulting solution was stirred at r.t. for 40 min. The solution was washed with brine, and the organic phase was dried over anhydrous sodium sulfate, filtered, and concentrated in vacuo. The residue was purified by reverse phase HPLC using a gradient of water 0.1% FA/acetonitrile 0.1% FA to afford the title compound (3 mg, Yield 10%). LC-MS: $[M+H]^+$ 413.

Preparation of 6-[2-(2-carbamoylallyl)-3-oxo-1H-benzo[e]isoindol-8-yl]-N-(1-methyl-4-piperidyl) pyridine-2-carboxamide (Compound 763)

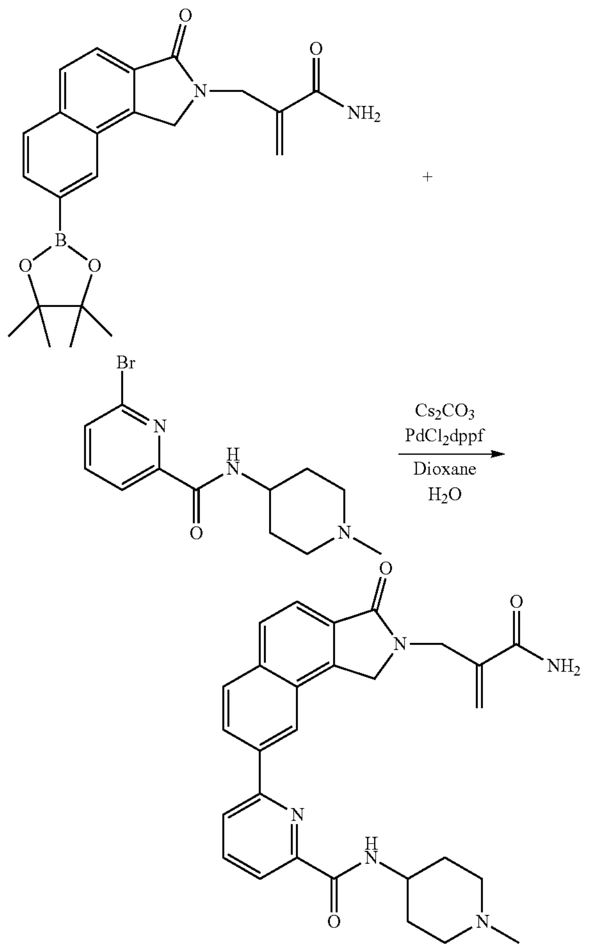

To a solution of 2-[[3-oxo-8-(4,4,5,5-tetramethyl-1,3,2-dioxaborolan-2-yl)-1H-benzo[e]isoindol-2-yl]methyl]prop-2-enamide (35.8 mg, 91 μmol) in dioxane (2 mL) and water (0.4 mL) were added 6-bromo-N-(1-methyl-4-piperidyl) pyridine-2-carboxamide (32.6 mg, 109 μmol), $Cs_2CO_3$ (89 mg, 273 μmol) and $PdCl_2dppf$ (10 mg, 9 μmol). The reaction was heated to 100° C. for 30 min in a microwave. The reaction mixture was passed through a celite pad, and 2 mL of 0.5 M EDTA was added. The resulting solution was stirred at r.t. for 40 min. The solution was washed with brine, and the organic phase was dried over anhydrous sodium sulfate, filtered, and concentrated in vacuo. The residue was purified by reverse phase HPLC using a gradient of water 0.1% FA/acetonitrile 0.1% FA to afford the title compound (7 mg, Yield 16%). LC-MS: $[M+H]^+$ 484.

Route 3:

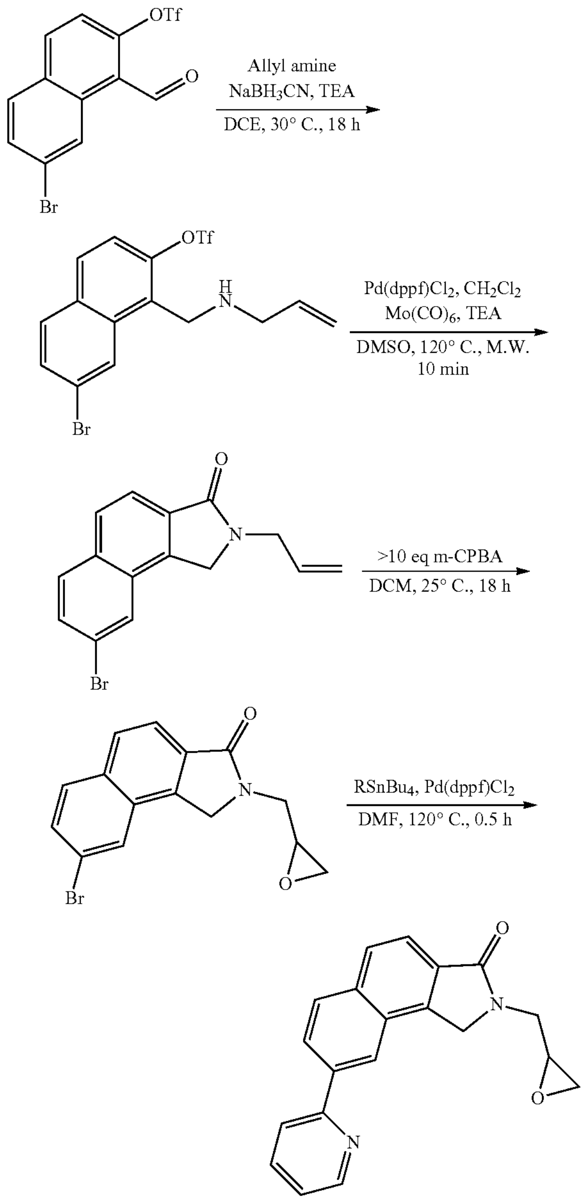

General Procedure for [1-[(allylamino)methyl]-7-bromo-2-naphthyl]trifluoromethane Sulfonate

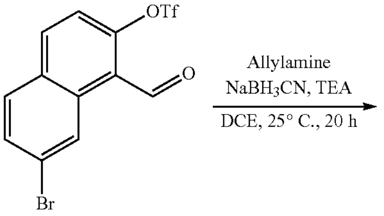

-continued

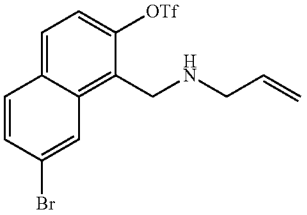

To a mixture of (7-bromo-1-formyl-2-naphthyl)trifluoromethanesulfonate (4 g, 9.40 mmol, 1 eq.) and prop-2-en-1-amine (1.32 g, 14.09 mmol, 1.73 Ml, 1.5 eq., HCl) in DME (20 mL) was added TEA (950.79 mg, 9.40 mmol, 1.31 mL, 1 eq.). The mixture was stirred for 2 h, and $NaBH_3CN$ (2.95 g, 46.98 mmol, 5 eq.) was added to the mixture and stirred for 18 h at 25° C. TLC and LCMS showed that the reaction was complete. The reaction was quenched with ice water (50 mL) slowly and extracted with DCM (3×100 mL). The combined organic phase was washed with brine (3×100 mL), dried over anhydrous sodium sulfate, filtered, and concentrated in vacuo. The residue was purified by silica gel chromatography (PE:EtOAc=40:1) to afford the title compound (2.5 g, 5.89 mmol, 62.72% yield) as a yellow oil.

General Procedure for 2-allyl-8-bromo-1H-benzo[e]isoindol-3-one

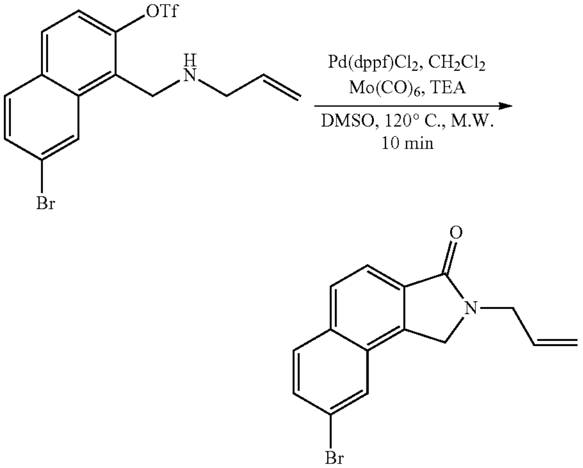

[1-[(allylamino)methyl]-7-bromo-2-naphthyl]trifluoromethanesulfonate (1 g, 2.36 mmol, 1 eq.), TEA (500.90 mg, 4.95 mmol, 689 μL, 2.1 eq.), $Pd(dppf)Cl_2$ (172.48 mg, 235.72 μmol, 0.1 eq.), and $Mo(CO)_6$ (746.76 mg, 2.83 mmol, 381 μL, 1.2 eq.) were dissolved in DMSO (10 mL) in a microwave tube. The sealed tube was heated to 120° C. for 10 min under microwave. TLC showed that the reaction was complete. The reaction was quenched with ice water (30 mL) slowly and extracted with EtOAc (3×30 mL). The combined organic phase was washed with brine (3×30 mL), dried over anhydrous sodium sulfate, filtered, and concentrated in vacuo. The crude was purified by silica gel chromatography (PE:EtOAc=3:1) to afford the title compound (500 mg, 1.65 mmol, 70.20% yield) as a yellow oil.

General Procedure for 8-bromo-2-(oxiran-2-ylmethyl)-1H-benzo[e]isoindol-3-one

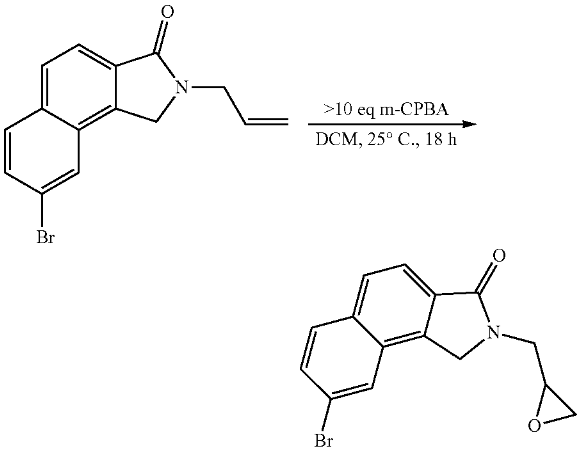

To a mixture of 2-allyl-8-bromo-1H-benzo[e]isoindol-3-one (200 mg, 661.89 μmol, 1 eq.) in DCM (20 mL) was added m-CPBA (2.14 g, 9.93 mmol, 80% purity, 15 eq.). The mixture was stirred at 25° C. for 18 h. TLC showed that the reaction was complete. The residue was poured into saturated $Na_2SO_3$ (30 mL). The aqueous phase was extracted with EtOAc (3×20 mL). The combined organic phase was washed with brine (3×20 mL) and saturated $NaHCO_3$ (3×20 mL), dried over anhydrous sodium sulfate, filtered, and concentrated in vacuo. The crude was purified by prep-TLC (silica gel; PE:EtOAc=0:1) to afford the title compound (100 mg, 314.30 μmol, 47.49% yield) as brown oil.

General Procedure for 2-(oxiran-2-ylmethyl)-8-(2-pyridyl)-1H-benzo[e]isoindol-3-one (Compound 767)

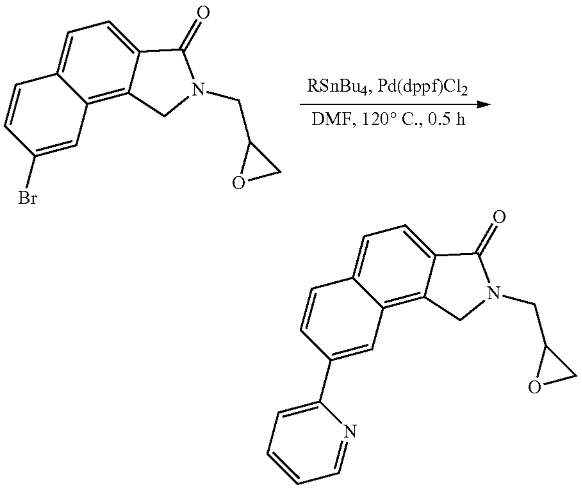

To a mixture of 8-bromo-2-(oxiran-2-ylmethyl)-1H-benzo[e]isoindol-3-one (100 mg, 314.30 μmol, 1 eq.)) and tributyl(2-pyridyl)stannane (231.42 mg, 628.61 μmol, 2 eq.) in DMF (5 mL) was added $Pd(dppf)Cl_2$ (11.50 mg, 15.72 μmol, 0.05 eq.) in a sealed tube, then the mixture was stirred for 0.5 h at 120° C. TLC and LCMS showed that the reaction was complete. The reaction was poured into saturated EDTA (50 mL) and stirred for 2 h. The aqueous phase was extracted with EtOAc (3x20 mL). The combined organic phase was washed with brine (3x20 mL), dried over anhydrous sodium sulfate, filtered, and concentrated in vacuo. The crude was purified by prep-TLC (silica gel; PE:EtOAc=0:1) then purified by prep-TLC (DCM:MeOH=20:1) to afford the title compound (5.2 mg, 16.16 μmol, 5.14% yield, 98.3% purity) as a white solid. LC-MS: $[M+H]^+$ 317.1.

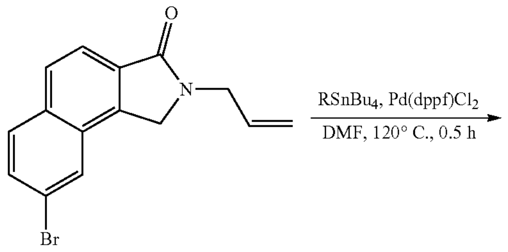

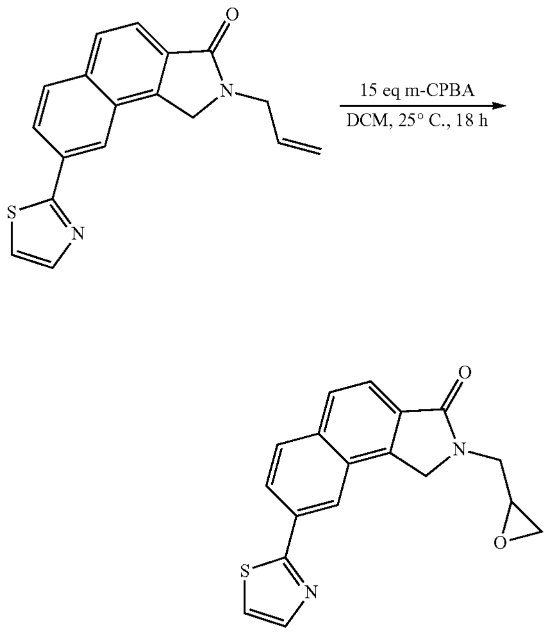

General Procedure for 2-allyl-8-thiazol-2-yl-1H-benzo[e]isoindol-3-one

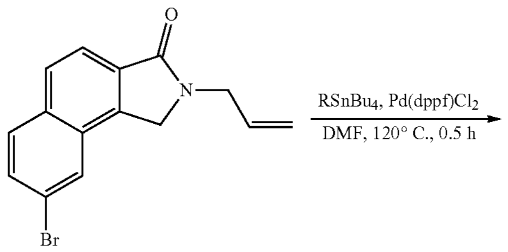

-continued

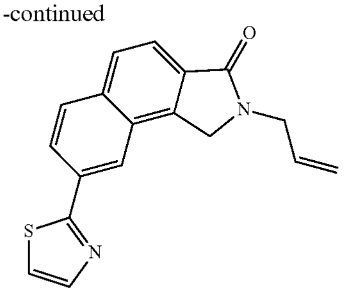

To a mixture of 2-allyl-8-bromo-1H-benzo[e]isoindol-3-one (180 mg, 595.70 μmol, 1 eq.) and tributyl(thiazol-2-yl) stannane (445.79 mg, 1.19 mmol, 2 eq.) in DMF (20 mL) was added $Pd(dppf)Cl_2$ (21.79 mg, 29.79 μmol, 0.05 eq.) in a sealed tube, then the mixture was stirred for 0.5 h at 120° C. TLC and LCMS showed that the reaction was complete. The residue was poured into saturated EDTA (50 mL) and stirred for 2 h. The aqueous phase was extracted with EtOAc (3x20 mL). The combined organic phase was washed with brine (3x20 mL), dried over anhydrous sodium sulfate, filtered, and concentrated in vacuo. The crude was purified by prep-TLC (silica gel; PE:EtOAc=0:1) to afford the title compound (150 mg, 489.59 μmol, 82.19% yield) as brown oil.

General Procedure for 2-(oxiran-2-ylmethyl)-8-thiazol-2-yl-1H-benzo[e]isoindol-3-one (Compound 766)

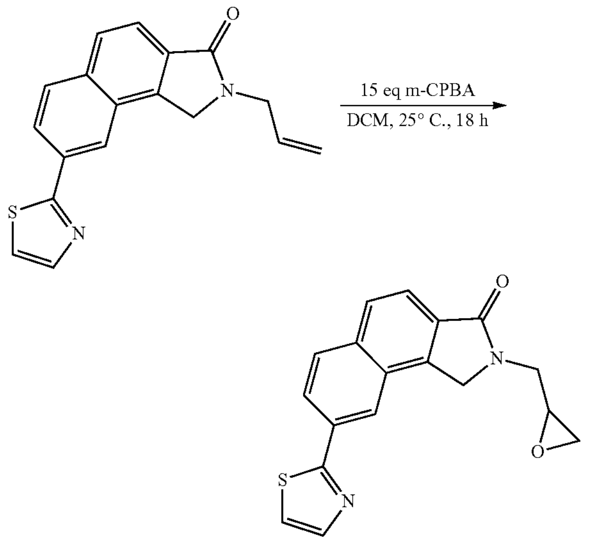

To a mixture of 2-allyl-8-thiazol-2-yl-1H-benzo[e]isoindol-3-one (100 mg, 326.39 μmol, 1 eq.) in DCM (10 mL) was added m-CPBA (844.88 mg, 3.92 mmol, 80% purity, 12 eq.). The mixture was stirred at 25° C. for 18 h. TLC and LCMS showed that the reaction was complete. The reaction was quenched with ice water (20 mL) slowly, then saturated $Na_2SO_3$ was added. The mixture was stirred for 1 h and extracted with DCM (3x20 mL). The combined organic phase was washed with brine (3x20 mL) and saturated $NaHCO_3$ (3x20 mL), dried over anhydrous sodium sulfate, filtered, and concentrated in vacuo. The crude was purified by prep-TLC (silica gel; EtOAc), then purified by prep-TLC (silica gel; DCM:MeOH=20:1) to afford the title compound (5.2 mg, 16.13 μmol, 4.94% yield, 100% purity) as a white solid. LC-MS: $[M+H]^+$ 323.

Route 4

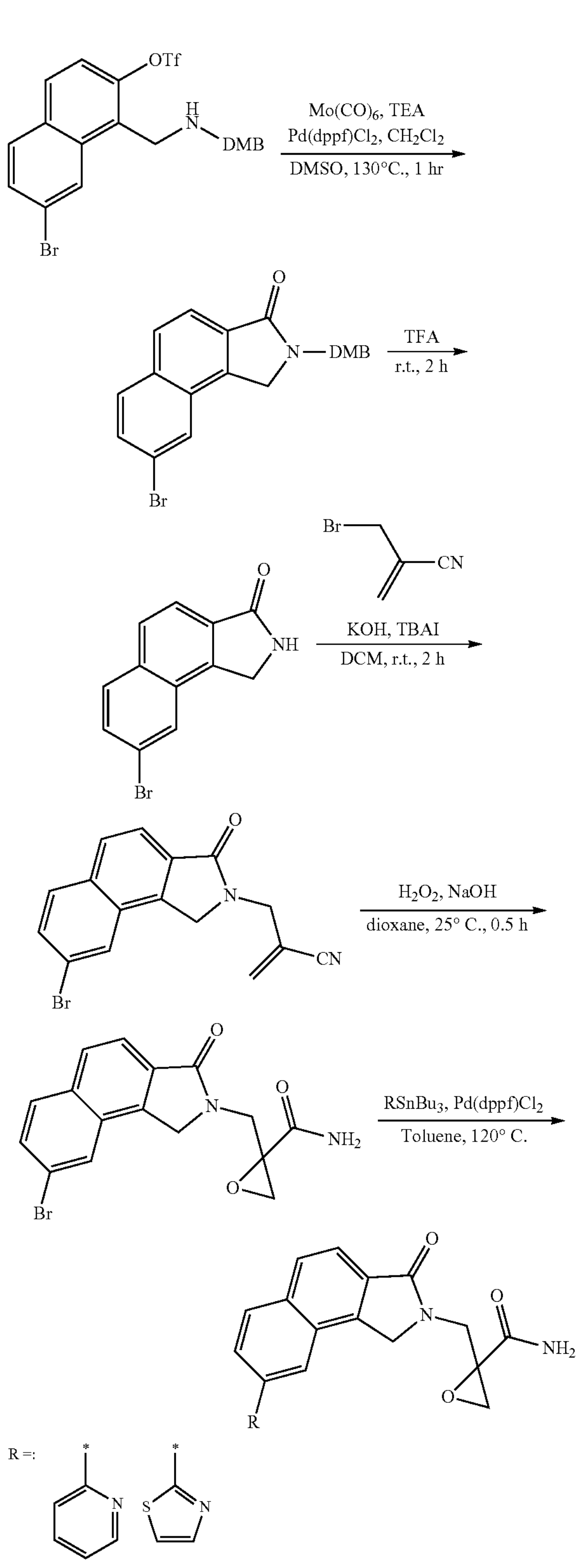

General Procedure for 8-bromo-2-[(2,4-dimethoxyphenyl)methyl]-1H-benzo[e]isoindol-3-one

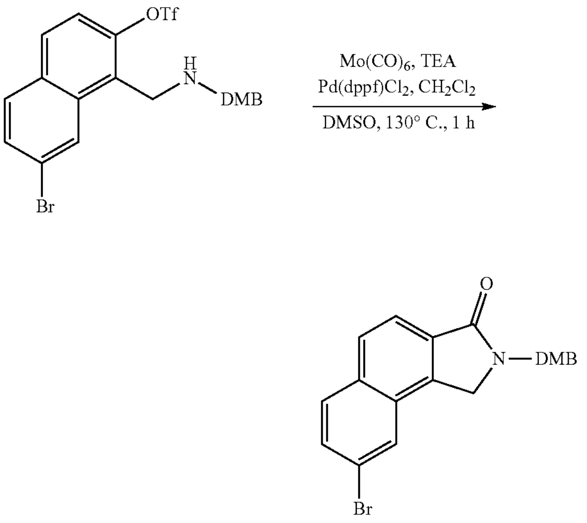

To a solution of [7-bromo-1-[[(2,4-dimethoxyphenyl)methylamino]methyl]-2-naphthyl]trifluoromethanesulfonate (10 g, 16.84 mmol, 1 eq.) (90% purity) in DMSO (120 mL) were added $Pd(dppf)Cl_2$ (246.48 mg, 336.86 μmol, 0.02 eq.), TEA (3.58 g, 35.37 mmol, 4.92 mL, 2.1 eq.), and $Mo(CO)_6$ (889.32 mg, 3.37 mmol, 453.73 μL, 0.2 eq.). The mixture was stirred at 130° C. for 1 h under nitrogen. TLC showed that the reaction was complete. The reaction mixture was extracted with EtOAc (3×300 mL). The combined organic layers were washed with brine (3×200 mL), dried over anhydrous sodium sulfate, filtered, and concentrated in vacuo to give a residue. The crude was purified by silica gel chromatography (PE:EtOAc=3:1) to afford the title compound (4 g, 9.70 mmol) as a brown solid.

General Procedure for 8-bromo-1,2-dihydrobenzo[e]isoindol-3-one

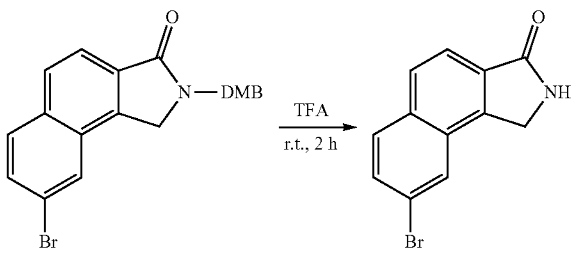

8-bromo-2-[(2,4-dimethoxyphenyl)methyl]-1H-benzo[e]isoindol-3-one (1.5 g, 3.64 mmol, 1 eq.) was added to trifluoroacetic acid (23.10 g, 202.59 mmol, 15 mL, 55.68 eq.) and stirred for 2 h at 20° C. TLC showed that the reaction was complete. The reaction was quenched with ice water (100 mL) slowly, and the crude product was obtained by filtration to afford the title compound (1.3 g, crude) as a white solid, which was used directly without purification.

General Procedure for 2-[(8-bromo-3-oxo-1H-benzo[e]isoindol-2-yl)methyl]prop-2-enenitrile

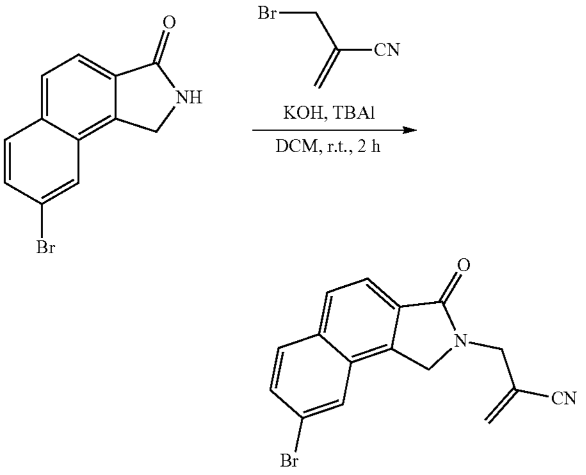

To a mixture of 8-bromo-1,2-dihydrobenzo[e]isoindol-3-one (1.3 g, 4.96 mmol, 1 eq.) in DCM (40 mL) were added KOH (556.60 mg, 9.92 mmol, 2 eq.), TBAI (366.41 mg, 991.98 μmol, 0.2 eq.), and 2-(bromomethyl)prop-2-enenitrile (868.89 mg, 5.95 mmol, 1.2 eq.). The mixture was stirred at 25° C. for 2 h. TLC showed that the reaction was complete. Sat. $NH_4Cl$ (20 mL) was added to the mixture, and the aqueous phase was extracted with DCM (3×20 mL). The combined organic phase was washed with water (3×20 mL) and brine (3×20 mL), dried over anhydrous sodium sulfate, filtered, and concentrated in vacuo. The product was purified by silica gel chromatography (PE:EtOAc=3:1) to afford the title compound (800 mg, 2.45 mmol, 49.30% yield) as a yellow solid.

General Procedure for 2-[(8-bromo-3-oxo-1H-benzo[e]isoindol-2-yl)methyl]oxirane-2-carboxamide

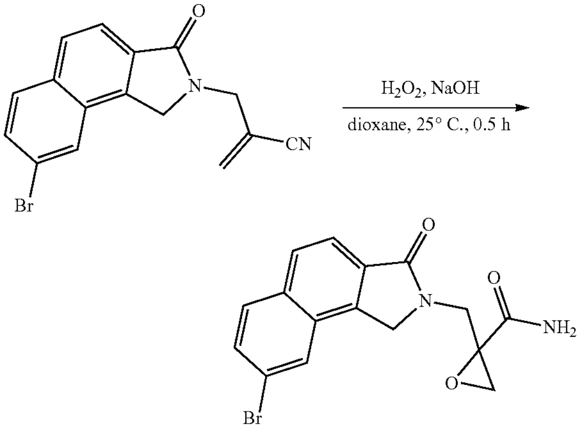

To a mixture of 2-[(8-bromo-3-oxo-1H-benzo[e]isoindol-2-yl)methyl]prop-2-enenitrile (540 mg, 1.65 mmol, 1 eq.) in dioxane (25 mL) were added water (2.43 g, 21.46 mmol, 2.06 mL, 30% purity, 13 eq.) and NaOH (481.91 mg, 12.05 mmol, 7.3 eq.). The mixture was stirred at 25° C. for 30 min. TLC and LCMS showed that the reaction was complete. The residue was poured into saturated $Na_2SO_3$ (30 mL) and stirred for 1 h. The aqueous phase was extracted with EtOAc (3×20 mL). The combined organic phase was washed with brine (3×20 mL), dried over anhydrous sodium sulfate, filtered, and concentrated in vacuo. The crude was purified by prep-TLC (silica gel; PE:EtOAc=0:1) and washed with PE:EtOAc=10:1 (2 mL) to afford the title compound (190 mg, 526.04 μmol, 31.87% yield) as a white solid, Preparation of 2-{[3-oxo-8-(pyridin-2-yl)-1H,2H,3H-benzo[e]isoindol-2-yl]methyl}oxirane-2-carboxamide (Compound 769)

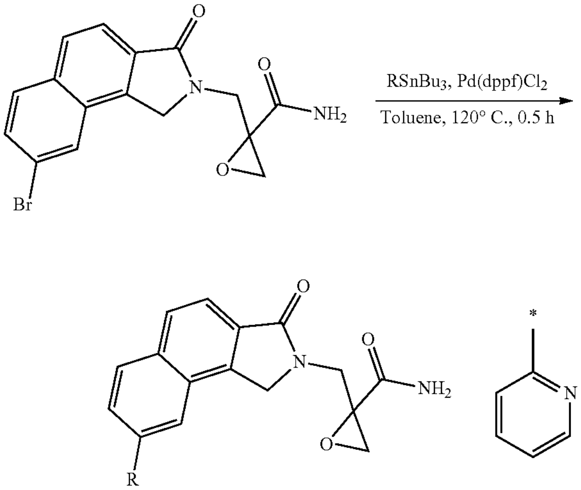

To a mixture of 2-[(8-bromo-3-oxo-1H-benzo[e]isoindol-2-yl)methyl]oxirane-2-carboxamide (80 mg, 188.27 μmol, 1 eq.) (85% purity) and tributyl(2-pyridyl)stannane (278.77 mg, 757.23 μmol, 4.02 eq.) in DMF (5 mL) was added Pd(dppf)$Cl_2$ (6.89 mg, 9.41 μmol, 0.05 eq.), then the mixture was stirred for 0.5 h at 120° C. TLC showed that the reaction was complete. The reaction was poured into saturated EDTA (30 mL) and stirred for 2 h. The aqueous phase was extracted with EtOAc (3×20 mL). The combined organic phase was washed with brine (3×20 mL), dried over anhydrous sodium sulfate, filtered, and concentrated in vacuo. The crude was purified by prep-TLC, then the crude was further purified by prep-HPLC to afford the title compound (1.1 mg, 2.85 μmol, 1.52% yield, 93.2% purity) as a white solid. LC-MS: $[M+H]^+$ 360.1

Route 5:

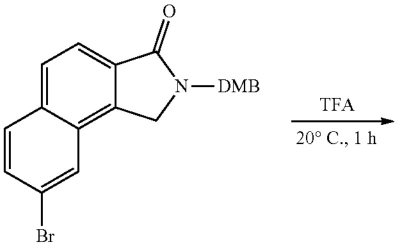

-continued

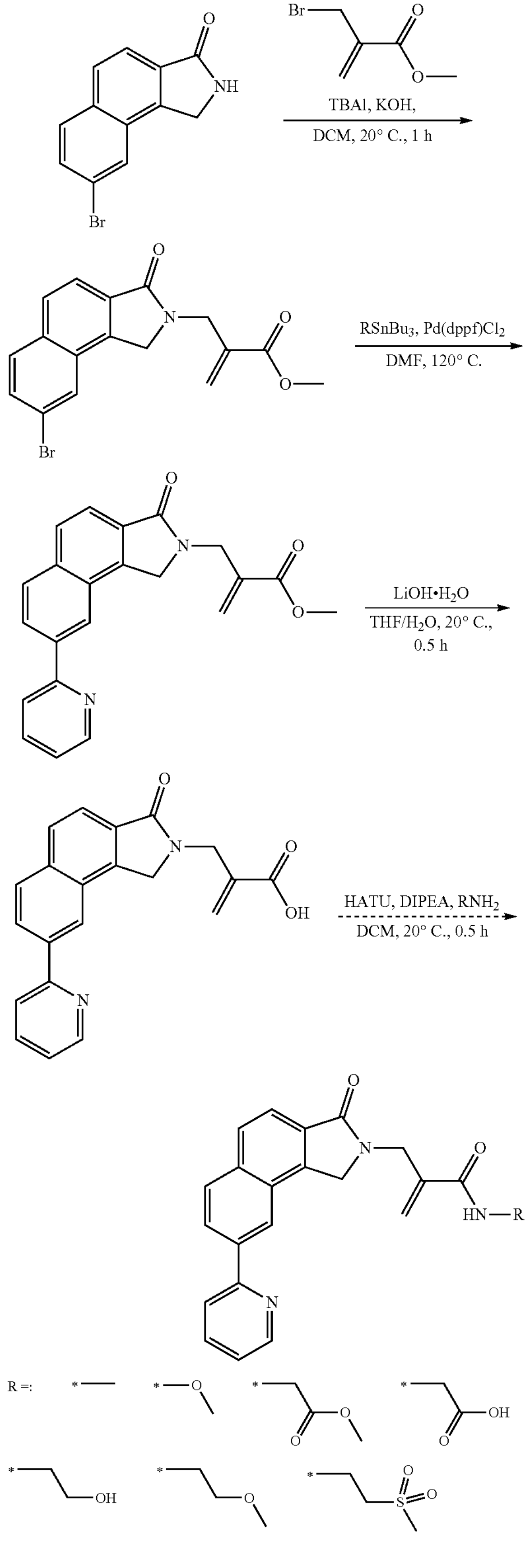

General Procedure for 8-bromo-1,2-dihydrobenzo [e]isoindol-3-one

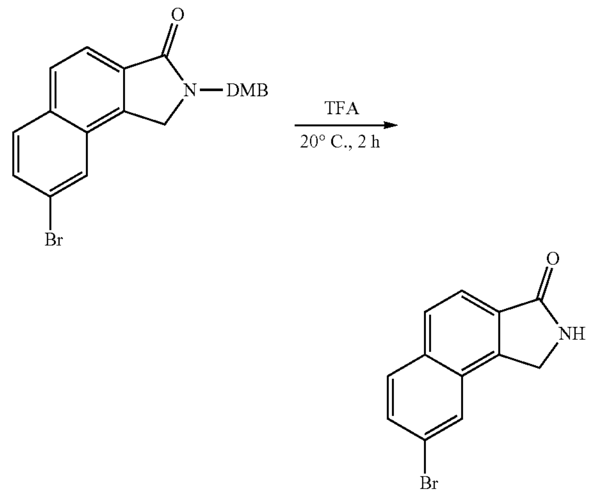

8-bromo-2-[(2,4-dimethoxyphenyl)methyl]-1H-benzo[e] isoindol-3-one (2.5 g, 6.06 mmol, 1 eq.) was added to trifluoroacetic acid (38.50 g, 337.65 mmol, 25 mL, 55.68 eq.) and stirred for 2 h at 20° C. TLC showed that the reaction was complete. The reaction was quenched with ice water (30 mL) slowly and a solid was obtained by filtration. The desired product (1.6 g, crude) was obtained as a white solid, which was used directly without any further purification.

Preparation of methyl 2-({8-bromo-3-oxo-1H,2H, 3H-benzo[e]isoindol-2-yl}methyl)prop-2-enoate (Compound 570)

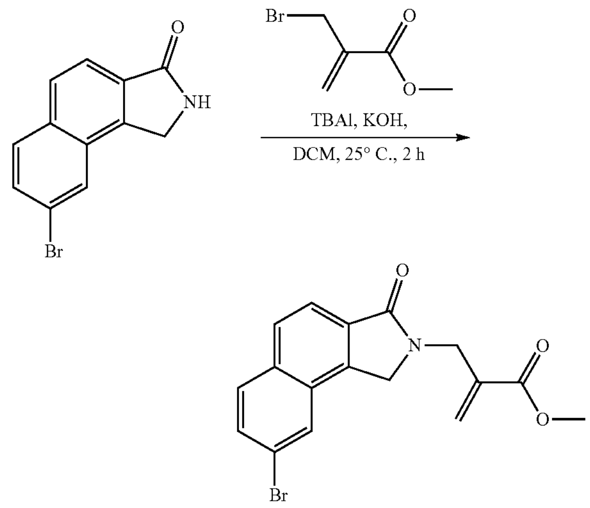

To a mixture of 8-bromo-1,2-dihydrobenzo[e]isoindol-3-one (1 g, 2.29 mmol, 1 eq.) (60% purity) in DCM (40 mL) were added KOH (256.89 mg, 4.58 mmol, 2 eq.) and TBAI (169.11 mg, 457.84 μmol, 0.2 eq.). Then, methyl 2-(bromomethyl)acrylate (491.75 mg, 2.75 mmol, 1.2 eq.) was added to the mixture, and the reaction was stirred at 25° C.

for 2 h. TLC showed that the reaction was complete. Cold Sat. $NH_4Cl$ (5 mL) was added to the mixture, and the aqueous phase was extracted with DCM (3×20 mL). The combined organic phase was washed with water (3×20 mL) and brine (3×20 mL), dried over anhydrous sodium sulfate, filtered, and concentrated in vacuo. The product was purified by silica gel chromatography (PE:EtOAc=3:1) to afford the title compound (750 mg, 1.67 mmol, 73.17% yield, 80% purity) as a yellow solid. LC-MS: $[M+H]^+$ 360.

Preparation of methyl 2-{[3-oxo-8-(pyridin-2-yl)-1H,2H,3H-benzo[e]isoindol-2-yl]methyl}prop-2-enoate (Compound 717)

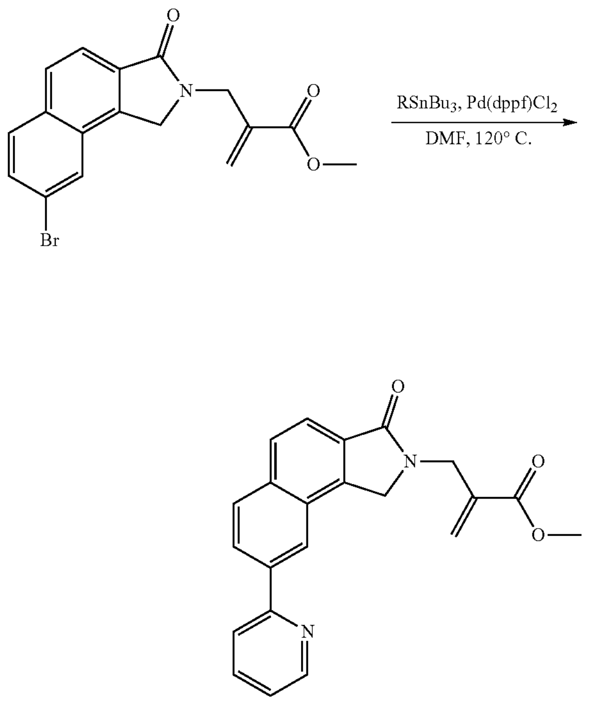

To a pressure tube was charged a mixture of methyl 2-[(8-bromo-3-oxo-1H-benzo[e]isoindol-2-yl)methyl]prop-2-enoate (700 mg, 1.55 mmol, 1 eq.) (80% purity) and tributyl(2-pyridyl)stannane (1.72 g, 4.66 mmol, 3 eq.) in DMF (10 mL), and $Pd(dppf)Cl_2$ (56.88 mg, 77.73 μmol, 0.05 eq.) was added. The tube was sealed, then the mixture was stirred for 0.5 h at 120° C. TLC showed that the reaction was complete. The residue was poured into saturated EDTA (50 mL) and stirred for 2 h. The aqueous phase was extracted with EtOAc (3×30 mL). The combined organic phase was washed with brine (3×30 mL), dried over anhydrous sodium sulfate, filtered, and concentrated in vacuo. The crude was purified by silica gel chromatography (PE:EtOAc=1/1) to afford the title compound (450 mg, 1.26 mmol, 80.76% yield) as a brown solid. LC-MS: $[M+H]^+$ 359.1.

General Procedure for 2-[[3-oxo-8-(2-pyridyl)-1H-benzo[e]isoindol-2-yl]methyl]prop-2-enoic Acid

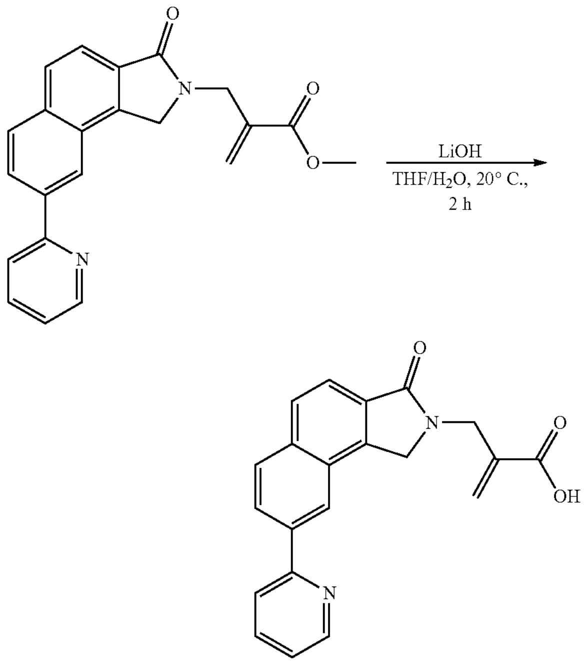

To a mixture of methyl 2-[[3-oxo-8-(2-pyridyl)-1H-benzo[e]isoindol-2-yl]methyl]prop-2-enoate (400 mg, 1.12 mmol, 1 eq in THF (8 mL) and water (2 mL) was added $LiOH{\cdot}H_2O$ (140.50 mg, 3.35 mmol, 3 eq.). The mixture was stirred at 20° C. for 2 h. TLC showed that the reaction was complete. The residue was poured into ice-water (20 mL), then saturated citric acid was added to the mixture to adjust the pH to 3. The mixture was stirred for 20 min, and the aqueous phase was extracted with EtOAc (3×20 mL). The combined organic phase was washed with brine (3×20 mL), dried over anhydrous sodium sulfate, filtered, and concentrated in vacuo to afford the title compound (370 mg, crude) as a brown solid, which was used directly without purification.

General Procedure for N-methyl-2-[[3-oxo-8-(2-pyridyl)-1H-benzo[e]isoindol-2-yl]methyl]prop-2-enamide (Compound 695)

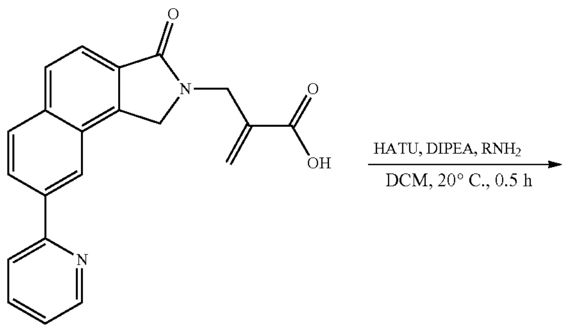

-continued

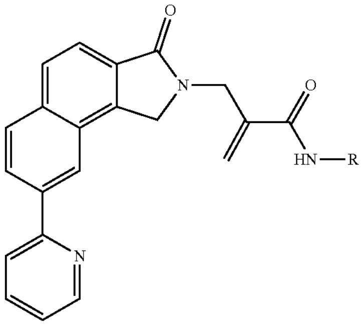

R =:

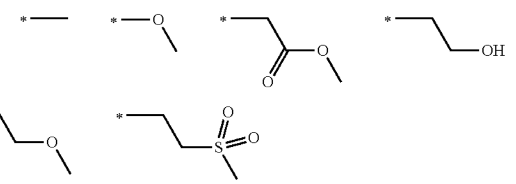

To a mixture of O-methylhydroxylamine (116.41 mg, 1.39 mmol, 6 eq., HCl) and 2-[[3-oxo-8-(2-pyridyl)-1H-benzo[e]isoindol-2-yl]methyl]prop-2-enoic acid (80 mg, 232.31 μmol, 1 eq.) in DCM (5 mL) were added DIPEA (90.07 mg, 696.94 μmol, 121.39 μL, 3 eq.) and HATU (132.50 mg, 348.47 μmol, 1.5 eq.). Then the mixture was stirred at 25° C. for 2 h. LCMS or TLC showed that the reaction was complete. The residue was poured into ice-water (20 mL). The aqueous phase was extracted with EtOAc (3×20 mL). The combined organic phase was washed with brine (3×20 mL), dried over anhydrous sodium sulfate, filtered, and concentrated in vacuo. The crude was purified by prep-HPLC to afford the title compound (6.1 mg, 16.56 μmol, 7.13% yield, 97% purity) as a white solid. LC-MS: $[M+H]^+$ 374.1

Route 6:

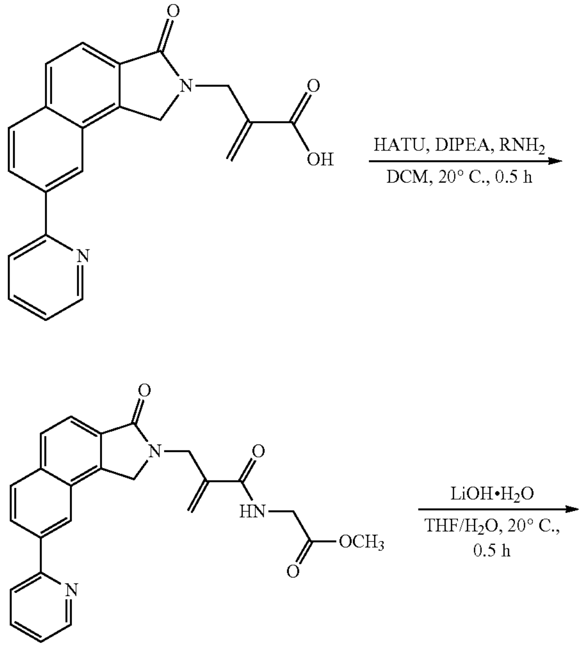

-continued

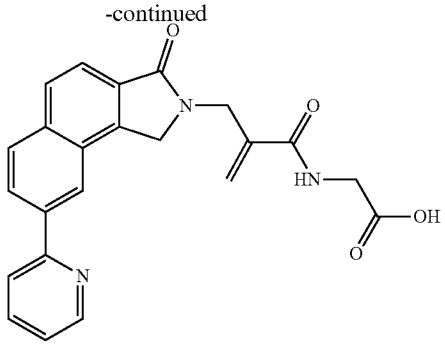

General Procedure for methyl 2-[2-[[3-oxo-8-(2-pyridyl)-1H-benzo[e]isoindol-2-yl]methyl]prop-2-enoylamino]acetate

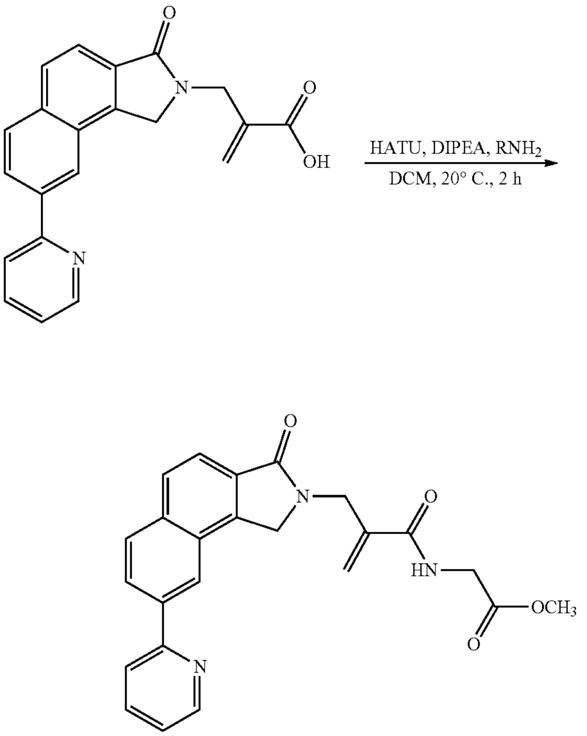 [SMILES: C=C(CN1Cc2c(ccc3ccc(-c4ccccn4)cc23)C1=O)C(=O)O ; "HATU, DIPEA, RNH2" ; C=C(CN1Cc2c(ccc3ccc(-c4ccccn4)cc23)C1=O)C(=O)NCC(=O)OC]

To a mixture of 2-[[3-oxo-8-(2-pyridyl)-1H-benzo[e]isoindol-2-yl]methyl]prop-2-enoic acid (100 mg, 290.39 μmol, 1 eq.) and methyl 2-aminoacetate; hydrochloride (218.76 mg, 1.74 mmol, 6 eq.) in DCM (5 mL) were added DIPEA (112.59 mg, 871.17 μmol, 151.74 μL, 3 eq.) and HATU (165.62 mg, 435.59 μmol, 1.5 eq.). The mixture was stirred at 20° C. for 2 h. TLC and LCMS showed that the reaction was complete. The residue was poured into ice-water (20 mL), and the aqueous phase was extracted with EtOAc (20 mL×3). The combined organic phase was washed with brine (20 mL×3), dried over anhydrous sodium sulfate, filtered, and concentrated in vacuo. The crude was purified by prep-TLC (silica gel; DCM:Methanol=10:1) to afford the title compound (70 mg, 168.50 μmol, 58.02% yield) as a white solid.

General Procedure for 2-[2-[[3-oxo-8-(2-pyridyl)-1H-benzo[e]isoindol-2-yl]methyl]prop-2-enoylamino]acetic Acid (Compound 718)

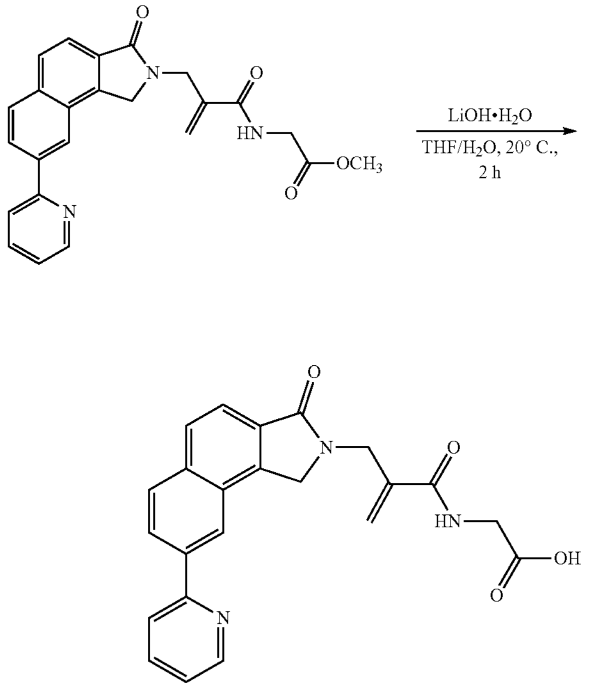

To a mixture of methyl 2-[2-[[3-oxo-8-(2-pyridyl)-1H-benzo[e]isoindol-2-yl]methyl]prop-2-enoylamino]acetate (60 mg, 144.43 μmol, 1 eq.) in THF (4 mL) and water (1 mL) was added LiOH·$H_2O$ (18.18 mg, 433.28 μmol, 3 eq.). The mixture was stirred at 20° C. for 2 h. TLC showed that the reaction was complete. Citric acid (1 mL) was added to the mixture to adjust the pH to 4~5 at 0° C. The aqueous phase was extracted with EtOAc (3×10 mL). The combined organic phase was washed with brine (3×10 mL), dried over anhydrous sodium sulfate, filtered, and concentrated in vacuo. The crude material was purified by prep-HPLC to afford the title compound (5.5 mg, 13.70 μmol, 9.49% yield, 100% purity) as a white solid. LC-MS: $[M+H]^+$ 402.1.

Route 7

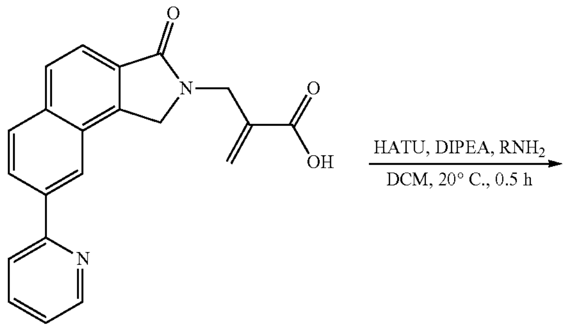

-continued

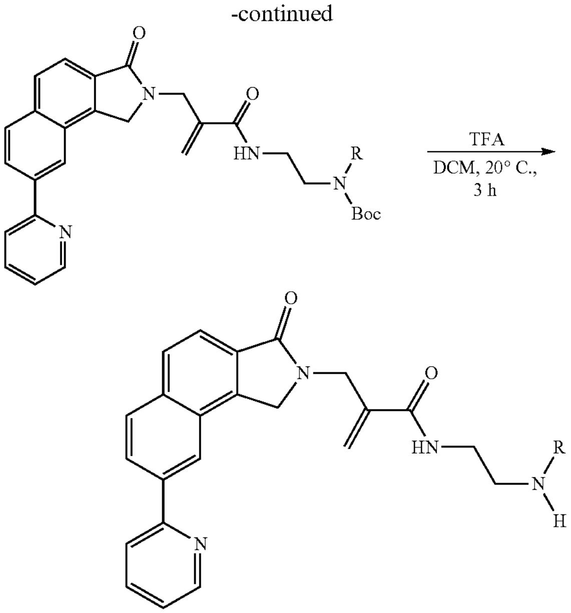

R = H
R = Me

General Procedure for tert-butyl N-methyl-N-[2-[2-[[3-oxo-8-(2-pyridyl)-1H-benzo[e]isoindol-2-yl]methyl]prop-2-enoylamino]ethyl]carbamate

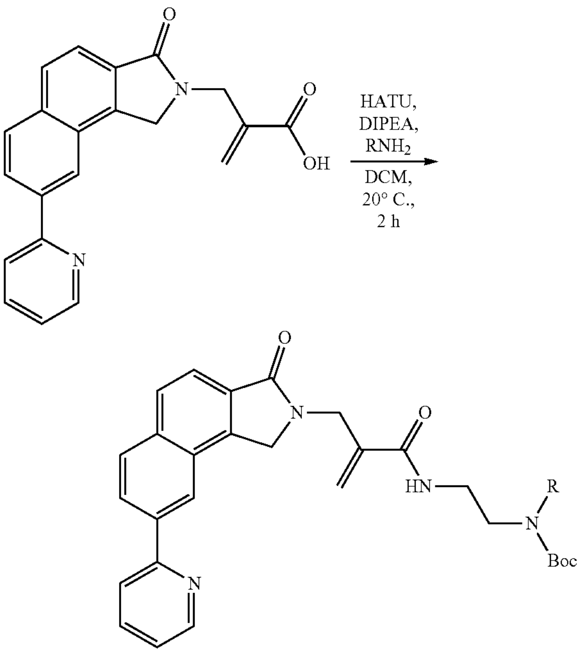

To a mixture of 2-[[3-oxo-8-(2-pyridyl)-1H-benzo[e]isoindol-2-yl]methyl]prop-2-enoic acid (100 mg, 290.39 μmol, 1 eq.) and tert-butyl N-(2-aminoethyl)carbamate (279.15 mg, 1.74 mmol, 273.67 μL, 6 eq.) in DCM (3 mL) were added DIPEA (112.59 mg, 871.17 μmol, 151.74 μL, 3 eq.) and HATU (165.62 mg, 435.59 μmol, 1.5 eq.). The mixture was stirred at 25° C. for 2 h. TLC showed that the reaction was complete. The residue was poured into ice-water (20 mL). The aqueous phase was extracted with EtOAc (10 mL×3). The combined organic phase was washed with brine (10 mL×3), dried over anhydrous sodium sulfate, filtered, and concentrated in vacuo. The crude was purified by prep-TLC (silica gel; DCM:Methanol=10:1) to afford the title compound (60 mg, 119.86 μmol, 41.28% yield) as a brown solid.

General Procedure for N-(2-aminoethyl)-2-[[3-oxo-8-(2-pyridyl)-1H-benzo[e]isoindol-2-yl]methyl]prop-2-enamide (Compound 727)

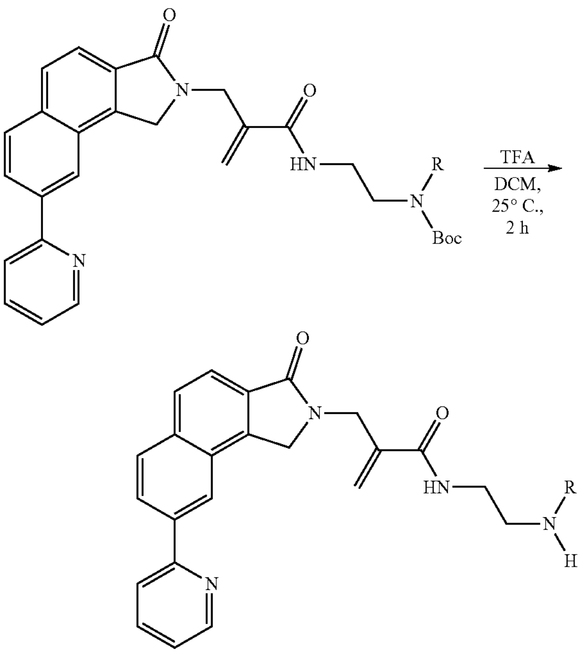

R = H
R = Me

To a mixture of tert-butyl N-[2-[2-[[3-oxo-8-(2-pyridyl)-1H-benzo[e]isoindol-2-yl]methyl]prop-2-enoylamino]ethyl]carbamate (40 mg, 82.21 μmol, 1 eq.) in DCM (1 mL) was added trifluoroacetic acid (9.37 mg, 82.21 μmol, 6.09 μL, 1 eq.). The mixture was stirred at 25° C. for 2 h. LCMS and TLC showed that the reaction was complete. The residue was poured into ice-water (10 mL), and the pH was adjusted to 7~8 using sat. $Na_2CO_3$. The aqueous phase was extracted with EtOAc (10 mL×3). The combined organic phase was washed with brine (10 mL×3), dried over anhydrous sodium sulfate, filtered, and concentrated in vacuo. The crude was purified by prep-HPLC to afford the title compound (5.1 mg, 12.74 μmol, 15.49% yield, 96.5% purity) as a white solid. LC-MS: $[M+H]^+$ 401.1.

Route 8:

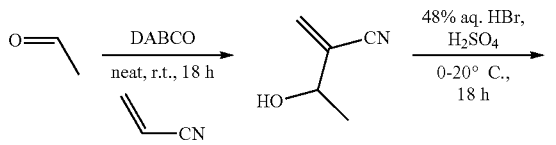

-continued

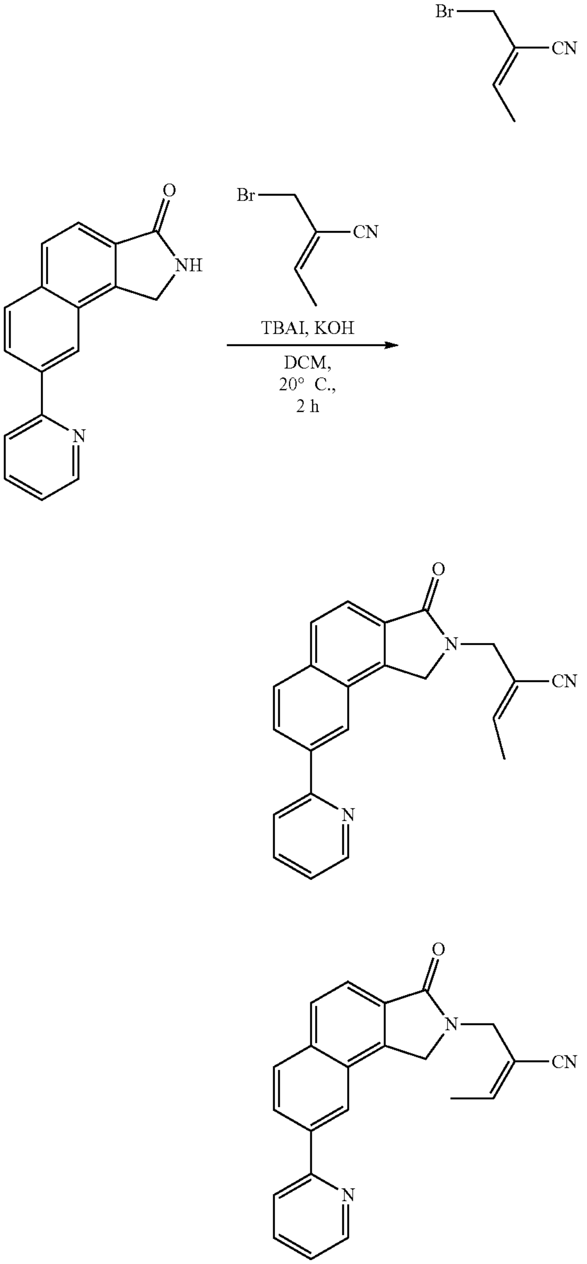

General Procedure for 8-(2-pyridyl)-1,2-dihydrobenzo[e]isoindol-3-one

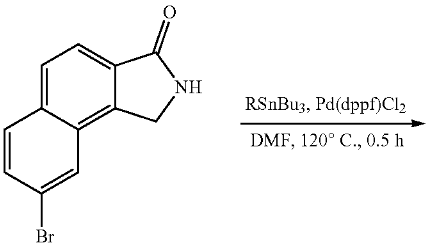

-continued

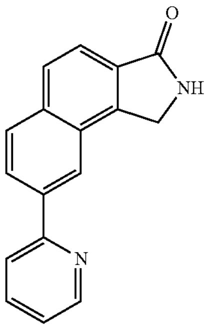

To a mixture of 8-bromo-1,2-dihydrobenzo[e]isoindol-3-one (300 mg, 686.76 μmol, 1 eq.) and tributyl(2-pyridyl) stannane (505.65 mg, 1.37 mmol, 2 eq.) in DMF (10 mL) was added Pd(dppf)$Cl_2$ (25.13 mg, 34.34 μmol, 0.05 eq.) in a sealed tube, and the mixture was stirred for 0.5 h at 120° C. TLC showed that the reaction was complete. The reaction was poured into saturated EDTA (30 mL) and stirred for 2 h. The aqueous phase was extracted with EtOAc (3×30 mL). The combined organic phase was washed with brine (3×30 mL), dried over anhydrous sodium sulfate, filtered, and concentrated in vacuo. The residue was purified by silica gel chromatography (PE:EtOAc=0:1) to afford the title compound (160 mg, 614.70 μmol, 89.51% yield) as a brown solid.

Preparation of (Z)-2-[(8-bromo-3-oxo-1H-benzo[e]isoindol-2-yl)methyl]but-2-enenitrile and (E)-2-[(8-bromo-3-oxo-1H-benzo[e]isoindol-2-yl)methyl]but-2-enenitrile (Compound 709 and 710)

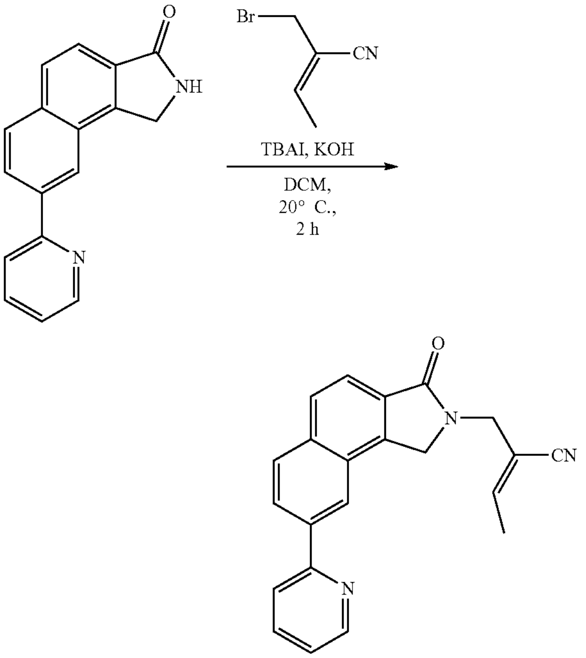

A

-continued

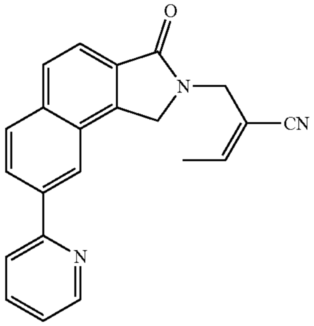

B

To a mixture of 8-(2-pyridyl)-1,2-dihydrobenzo[e]isoindol-3-one (140 mg, 537.86 μmol, 1 eq.) in DCM (8 mL) were added KOH (60.36 mg, 1.08 mmol, 2 eq.) and TBAI (39.73 mg, 107.57 μmol, 0.2 eq.), then (E)-2-(bromomethyl) but-2-enenitrile (154 mg, 673.70 μmol, 1.25 eq.) (70% purity) was added to the mixture. The mixture was stirred at 25° C. for 2 h. TLC showed that the reaction was complete. Cold sat. $NH_4Cl$ (5 mL) was added to the mixture, and the aqueous phase was extracted with DCM (20 mL×3). The combined organic phase was washed with water (20 mL×3) and brine (20 mL×3), dried over anhydrous sodium sulfate, filtered, and concentrated in vacuo. the product was purified by prep-TLC (silica gel; PE:EtOAc=0:1) then further purified by prep-HPLC and SFC to afford the desired product as a white solid. Example 709 (17.3 mg, 49.95 μmol, 9.29% yield). LC-MS: $[M+H]^+$ 340.1 Example 710 (10.5 mg, 30.94 μmol, 5.75% yield) LC-MS: $[M+H]^+$ 340.1.

Route 9

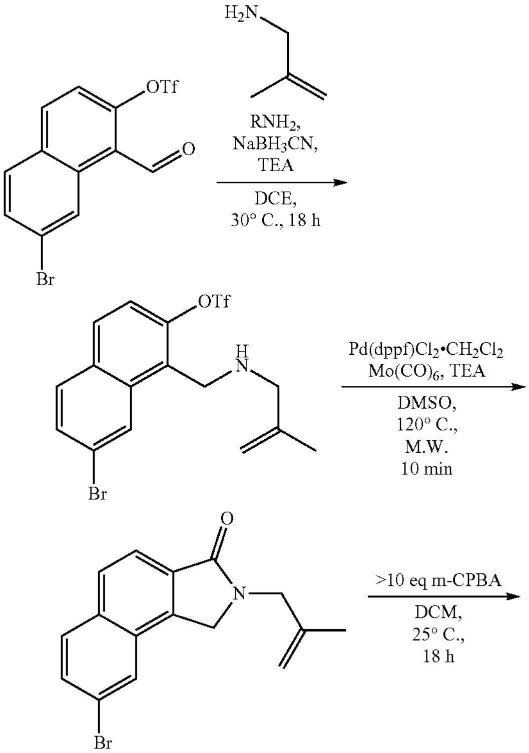

-continued

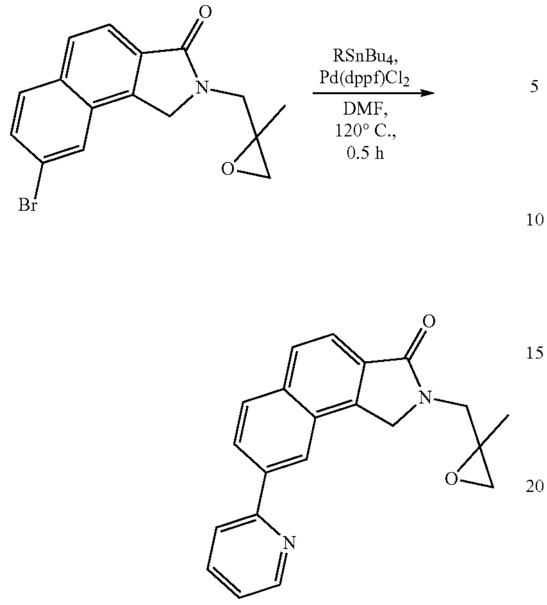

General Procedure for [7-bromo-1-[(2-methylallylamino)methyl]-2-naphthyl]trifluoromethanesulfonate

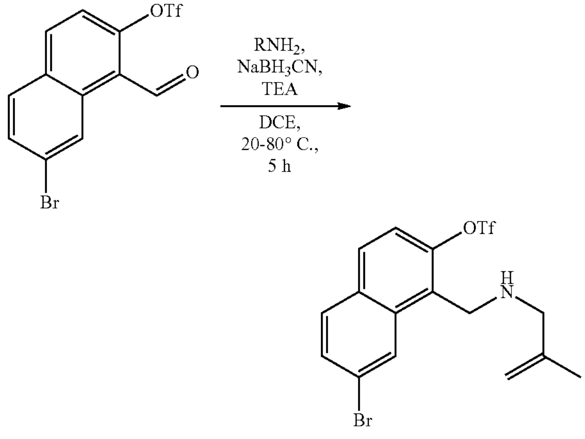

To a mixture of (7-bromo-1-formyl-2-naphthyl)trifluoromethanesulfonate (2 g, 4.70 mmol, 1 eq.) and 2-methylprop-2-en-1-amine (501.19 mg, 7.05 mmol, 4.33 mL, 1.5 eq.) in DME (20 mL) was added TEA (475.40 mg, 4.70 mmol, 653.91 μL, 1 eq.). The mixture was stirred 2 h at 20° C., then $NaBH_3CN$ (1.48 g, 23.49 mmol, 5 eq.) was added to the mixture and stirred for 3 h at 80° C. TLC showed that the reaction was complete. The reaction was quenched with ice water (50 mL) slowly and extracted with EtOAc (3×100 mL). The combined organic phase was washed with brine (3×100 mL), dried over anhydrous sodium sulfate, filtered, and concentrated in vacuo. The residue was purified by silica gel chromatography (PE:EtOAc=40:1) to afford the title compound (1.6 g, 3.29 mmol, 69.94% yield, 90% purity) as a yellow solid.

General Procedure for 8-bromo-2-(2-methylallyl)-1H-benzo[e]isoindol-3-one

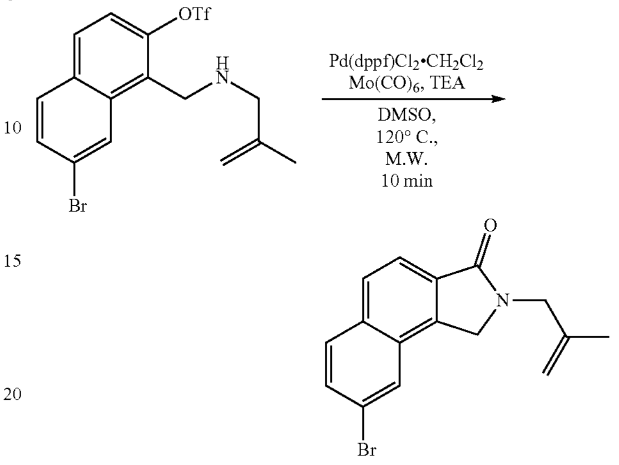

[7-bromo-1-[(2-methylallylamino)methyl]-2-naphthyl] trifluoromethanesulfonate (1.11 g, 2.28 mmol, 1 eq.), TEA (484.87 mg, 4.79 mmol, 666.95 μL, 2.1 eq.), $Pd(dppf)Cl_2$ (83.48 mg, 114.09 μmol, 0.05 eq.), and $Mo(CO)_6$ (120.48 mg, 456.35 μmol, 61.47 μL, 0.2 eq.) were added to a microwave tube in DMSO (10 mL). The sealed tube was heated to 120° C. for 10 min under microwave. TLC showed that the reaction was complete. The reaction was quenched with ice water (30 mL) slowly and extracted with DCM (3×30 mL). The combined organic phase was washed with brine (3×30 mL), dried over anhydrous sodium sulfate, filtered, and concentrated in vacuo at 40° C. The residue was purified by silica gel chromatography (PE:EtOAc=3:1) to afford the title compound (600 mg, 1.71 mmol, 74.85% yield, 90% purity) as a brown solid.

General Procedure for 8-bromo-2-[(2-methyloxiran-2-yl)methyl]-1H-benzo[e]isoindol-3-one

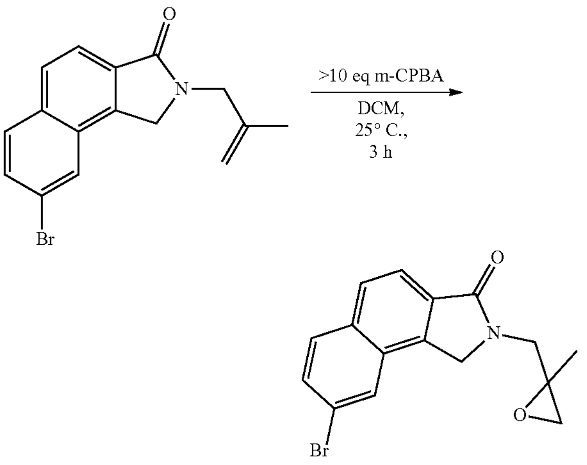

To a mixture of 8-bromo-2-(2-methylallyl)-1H-benzo[e]isoindol-3-one (500 mg, 1.42 mmol, 1 eq.) (90% purity) in DCM (10 mL) was added m-CPBA (3.68 g, 17.08 mmol, 80% purity, 12 eq.). The mixture was stirred at 25° C. for 3 h. TLC and LCMS showed that the reaction was complete. The reaction was quenched with ice water (20 mL) slowly then saturated $Na_2SO_3$ was added and stirred for 1 h and extracted with DCM (3×20 mL). The combined organic phase was washed with brine (3×20 mL) and saturated $NaHCO_3$ (3×20 mL), dried over anhydrous sodium sulfate, filtered, and concentrated in vacuo. The crude was purified by silica gel chromatography (PE:EtOAc=1:1) to afford the title compound (450 mg, 1.22 mmol, 85.67% yield, 90% purity) as a brown solid.

General Procedure for 2-[(2-methyloxiran-2-yl)methyl]-8-(2-pyridyl)-1H-benzo[e]isoindol-3-one (Compound 770)

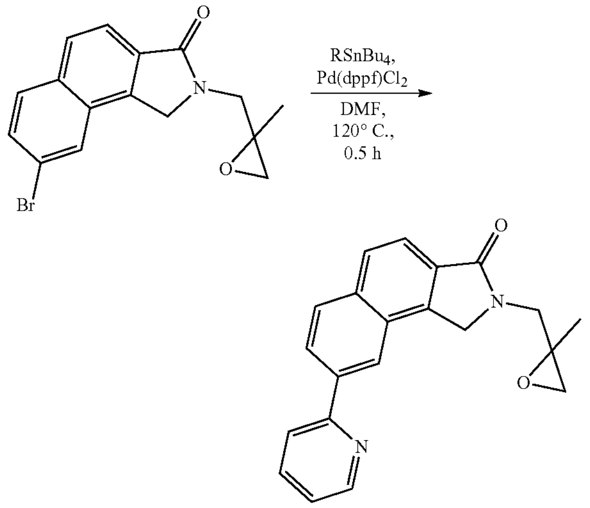

To a mixture of 8-bromo-2-[(2-methyloxiran-2-yl)methyl]-1H-benzo[e]isoindol-3-one (100 mg, 270.93 μmol, 1 eq.) (90% purity)) and tributyl(2-pyridyl)stannane (398.96 mg, 1.08 mmol, 4 eq.) in DMF (5 mL) was added Pd(dppf)$Cl_2$ (9.91 mg, 13.55 μmol, 0.05 eq.) in a sealed tube, then the mixture was stirred for 0.5 h at 120° C. TLC showed that the reaction was complete. The reaction was poured into saturated EDTA (50 mL) and stirred for 2 h. The aqueous phase was extracted with EtOAc (3×20 mL). The combined organic phase was washed with brine (20 mL×3), dried over anhydrous sodium sulfate, filtered, and concentrated in vacuo. the crude was purified by prep-TLC (silica gel; PE:EtOAc=0:1), purified a second time by prep-TLC (DCM:MeOH=20:1), then further purified by prep-HPLC to afford the title compound (6.2 mg, 18.73 μmol, 6.91% yield, 99.8% purity) as a white solid.

LC-MS: $[M+H]^+$ 331.1.

Route 10

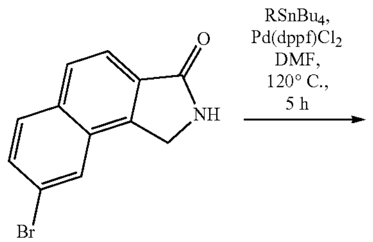

-continued

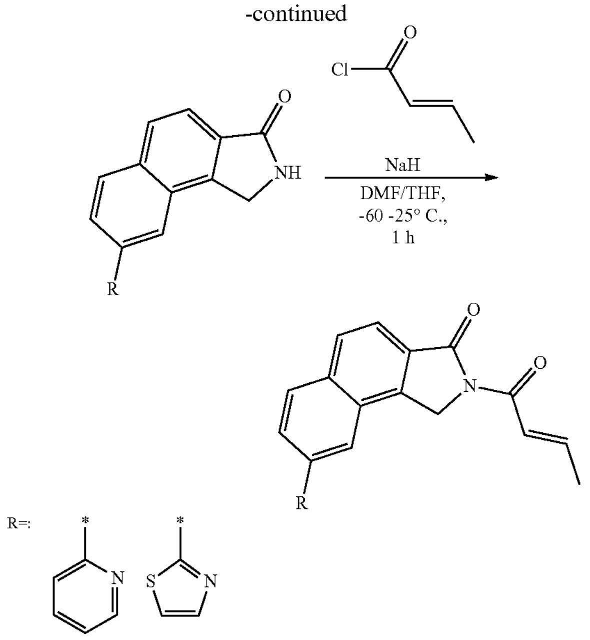

General Procedure for 8-bromo-1,2-dihydrobenzo[e]isoindol-3-one

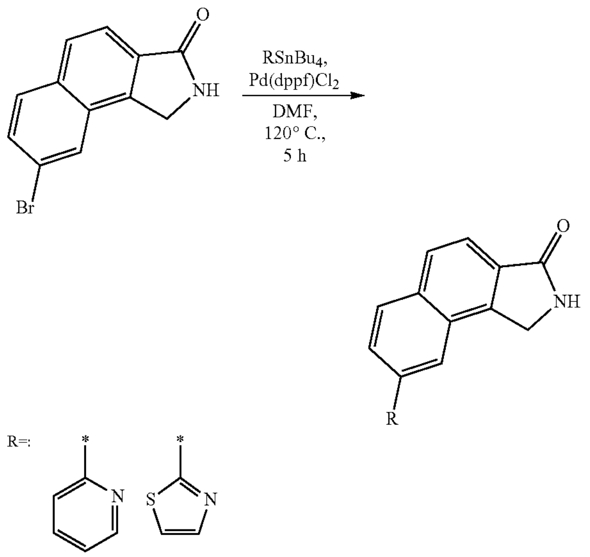

To a mixture of 8-bromo-1,2-dihydrobenzo[e]isoindol-3-one (500 mg, 1.14 mmol, 1 eq.) (60% purity) and tributyl(2-pyridyl)stannane (1.26 g, 3.43 mmol, 3 eq.) in DMF (10 mL) was added Pd(dppf)Cl2 (41.88 mg, 57.23 μmol, 0.05 eq.). The mixture was stirred for 5 h at 120° C. TLC showed that the reaction was complete. The saturated EDTA (50 mL) was added and stirred for 2 h. The aqueous phase was extracted with EtOAc (3×30 mL). The combined organic phase was washed with brine (3×30 mL), dried over anhydrous sodium sulfate, filtered, and concentrated in vacuo. The reaction was purified by prep-TLC (silica gel; EtOAc) to afford the title compound (240 mg, 922.05 μmol, 80.56% yield) as a brown solid General Procedure for 2-[(E)-but-2-enoyl]-8-(2-pyridyl)-1H-benzo[e]isoindol-3-one (Compound 764)

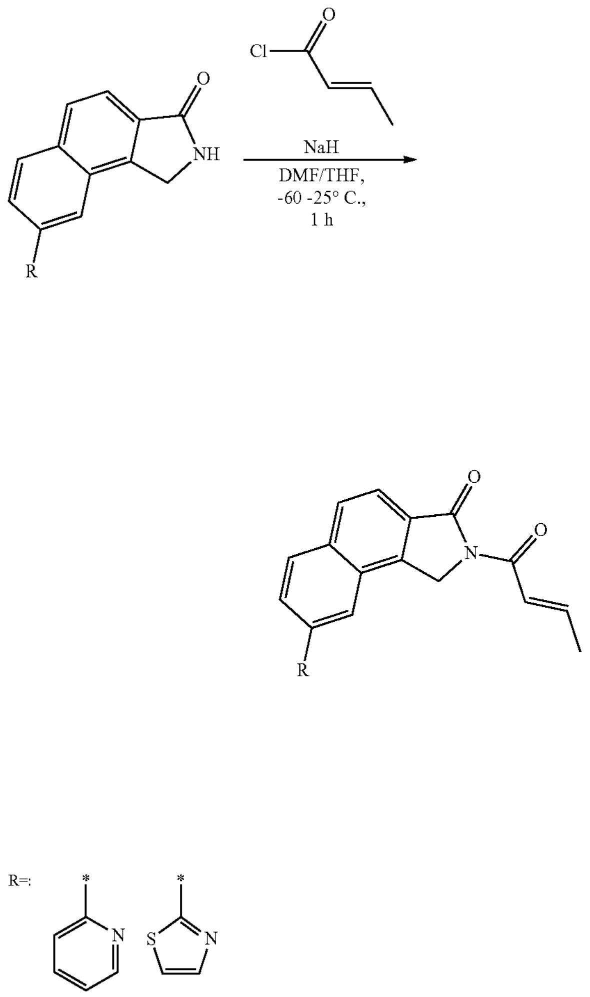

To a mixture of 8-(2-pyridyl)-1,2-dihydrobenzo[e]isoindol-3-one (50 mg, 192.09 μmol, 1 eq.) in DMF (1 mL) and THF (1 mL) was added NaH (46.10 mg, 576.28 μmol, 30% purity, 3 eq.). The mixture was stirred for 0.5 h at 25° C., then cooled to −60° C. (E)-but-2-enoyl chloride (109 mg, 1.04 mmol, 0.1 mL, 5.43 eq.) was added, and the mixture was stirred at −60° C. for 0.5 h. TLC and LCMS showed that the reaction was complete. Cold $NH_4Cl$ (20 mL) was added to the mixture. The aqueous phase was extracted with EtOAc (3×10 mL). The combined organic phase was washed with water (3×5 mL) and brine (3×5 mL), dried over anhydrous sodium sulfate, filtered, and concentrated in vacuo. The product was purified by prep-TLC (PE: EtOAc=2) and prep-HPLC to afford the title compound (5.1 mg, 14.75 μmol, 7.68% yield, 95% purity) as a white solid. LC-MS: $[M+H]^+$ 329.1.

General Procedure for 2-(2-methylprop-2-enoyl)-8-(2-pyridyl)-1H-benzo[e]isoindol-3-one (Compound 633)

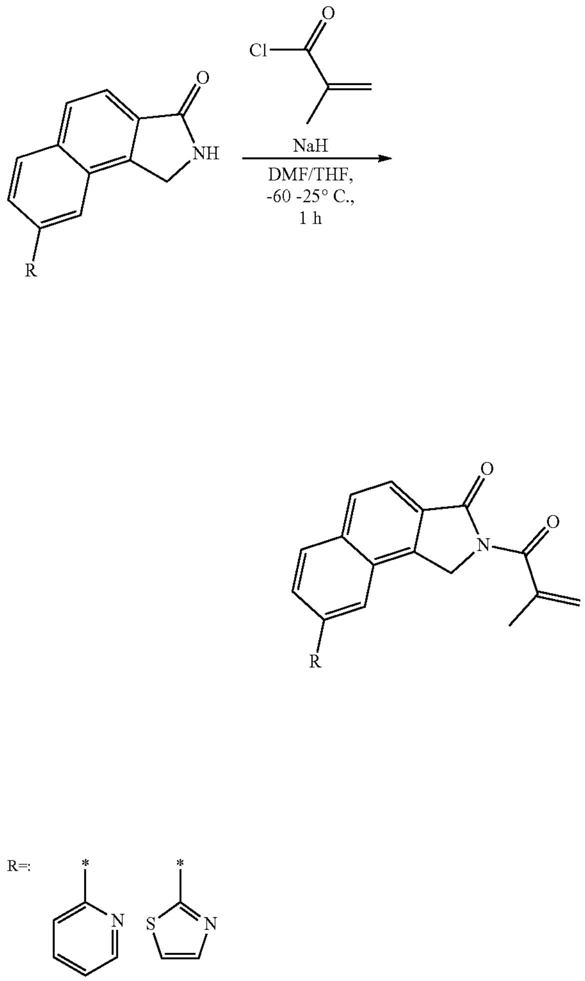

To a mixture of 8-(2-pyridyl)-1,2-dihydrobenzo[e]isoindol-3-one (50 mg, 192.09 μmol, 1 eq.) in DMF (1 mL) and THF (1 mL) was added NaH (46.10 mg, 576.27 μmol, 30% purity, 3 eq.). The mixture was stirred at 25° C. for 0.5 h, then cooled to −60° C., and 2-methylprop-2-enoyl chloride (107 mg, 1.02 mmol, 0.1 mL, 5.33 eq.) was added to the mixture. The mixture was stirred at −60° C. for 0.5 h. TLC showed that the reaction was not completed. Cold Sat. $NH_4Cl$ (5 mL) was added to the mixture, and the aqueous phase was extracted with EtOAc (3×10 mL). The combined organic phase was washed with water (3×5 mL) and brine (3×5 mL), dried over anhydrous sodium sulfate, filtered, and concentrated in vacuo. The product was purified by prep-HPLC to afford the title compound (5.5 mg, 16.48 μmol, 8.58% yield, 98.4% purity) as a white solid. LC-MS: $[M+H]^+$ 329.1

TABLE 14 shows compounds synthesized using the methods described in EXAMPLE 16.

TABLE 14
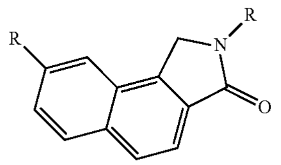
| Cpd. No. | Structure | IUPAC | LC-MS (ES+, m/z) |
|---|---|---|---|
| 570. | 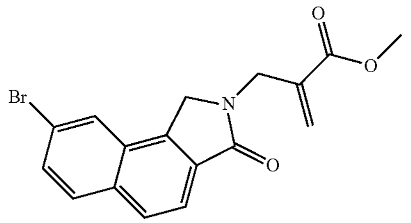 [SMILES: C=C(CN1Cc2c(ccc3ccc(Br)cc23)C1=O)C(=O)OC] | methyl 2-({8-bromo-3-oxo-1H,2H,3H-benzo[e]isoindol-2-yl}methyl)prop-2-enoate | 360 |
| 571. | 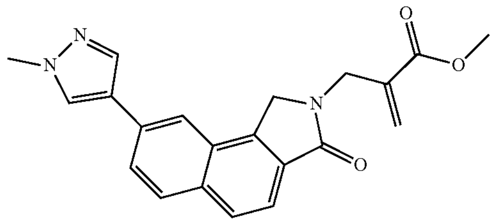 | methyl 2-{[8-(1-methyl-1H-pyrazol-4-yl)-3-oxo-1H,2H,3H-benzo[e]isoindol-2-yl]methyl}prop-2-enoate | 362.2 |
| 572. | 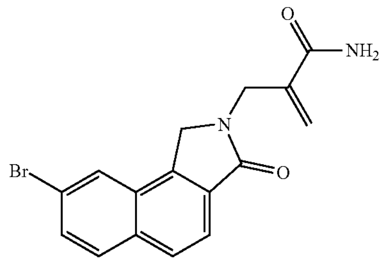 [SMILES: C=C(CN1Cc2c(ccc3ccc(Br)cc23)C1=O)C(N)=O] | 2-({8-bromo-3-oxo-1H,2H,3H-benzo[e]isoindol-2-yl}methyl)prop-2-enamide | 345.1 |
| 573. | 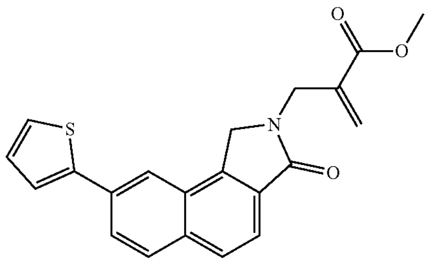 [SMILES: C=C(CN1Cc2c(ccc3ccc(-c4cccs4)cc23)C1=O)C(=O)OC] | methyl 2-{[3-oxo-8-(thiophen-2-yl)-1H,2H,3H-benzo[e]isoindol-2-yl]methyl}prop-2-enoate | 364.1 |
| 574. | 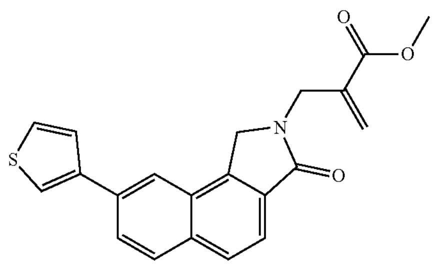 [SMILES: C=C(CN1Cc2c(ccc3ccc(-c4ccsc4)cc23)C1=O)C(=O)OC] | methyl 2-{[3-oxo-8-(thiophen-3-yl)-1H,2H,3H-benzo[e]isoindol-2-yl]methyl}prop-2-enoate | 364.1 |

TABLE 14-continued

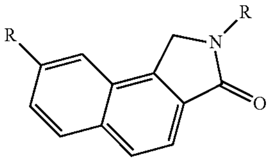

| Cpd. No. | Structure | IUPAC | LC-MS (ES+, m/z) |
|---|---|---|---|
| 575. | 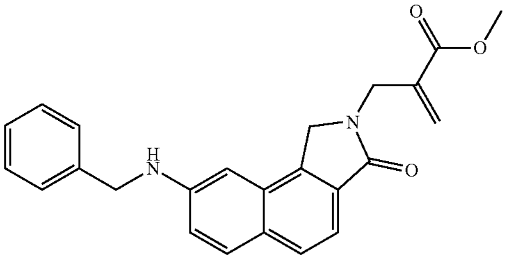 [SMILES: C=C(CN1Cc2c(ccc3ccc(NCc4ccccc4)cc23)C1=O)C(=O)OC] | methyl 2-{[8-(benzylamino)-3-oxo-1H,2H,3H-benzo[e]isoindol-2-yl]methyl}prop-2-enoate | 387.2 |
| 576. | 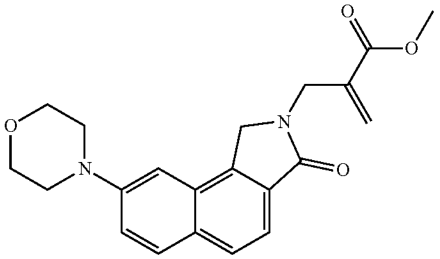 [SMILES: C=C(CN1Cc2c(ccc3ccc(N4CCOCC4)cc23)C1=O)C(=O)OC] | methyl 2-{[8-(morpholin-4-yl)-3-oxo-1H,2H,3H-benzo[e]isoindol-2-yl]methyl}prop-2-enoate | 367.2 |
| 577. | 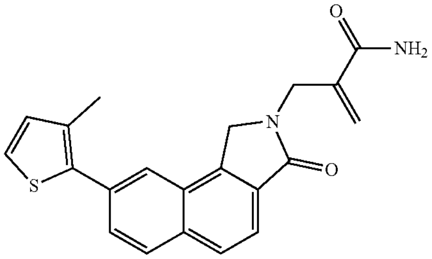 [SMILES: C=C(CN1Cc2c(ccc3ccc(-c4sccc4C)cc23)C1=O)C(N)=O] | 2-{[8-(3-methylthiophen-2-yl)-3-oxo-1H,2H,3H-benzo[e]isoindol-2-yl]methyl}prop-2-enamide | 363.1 |
| 578. | 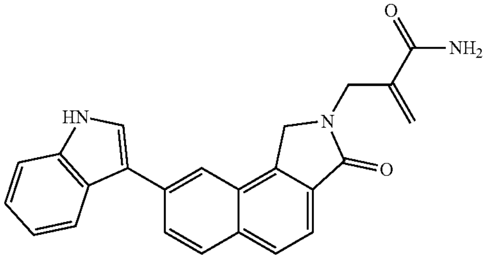 | 2-{[8-(1H-indol-3-yl)-3-oxo-1H,2H,3H-benzo[e]isoindol-2-yl]methyl}prop-2-enamide | 382.2 |
| 579. | 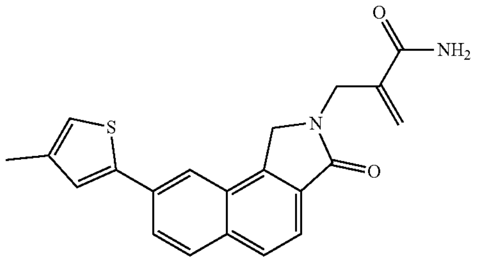 [SMILES: C=C(CN1Cc2c(ccc3ccc(-c4cc(C)cs4)cc23)C1=O)C(N)=O] | 2-{[8-(4-methylthiophen-2-yl)-3-oxo-1H,2H,3H-benzo[e]isoindol-2-yl]methyl}prop-2-enamide | 363.1 |

TABLE 14-continued
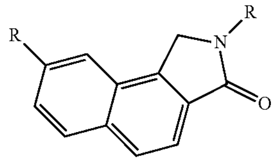
| Cpd. No. | Structure | IUPAC | LC-MS (ES+, m/z) |
|---|---|---|---|
| 580. | 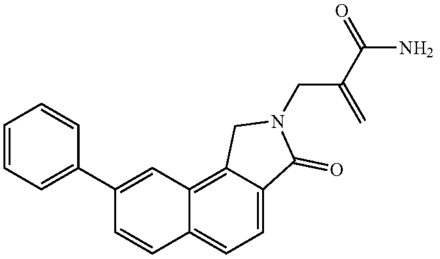 [SMILES: C=C(CN1Cc2c(ccc3ccc(-c4ccccc4)cc23)C1=O)C(N)=O] | 2-({3-oxo-8-phenyl-1H,2H,3H-benzo[e]isoindol-2-yl}methyl)prop-2-enamide | 343.1 |
| 581. | 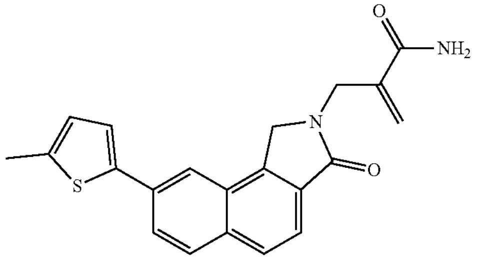 [SMILES: C=C(CN1Cc2c(ccc3ccc(-c4ccc(C)s4)cc23)C1=O)C(N)=O] | 2-{[8-(5-methylthiophen-2-yl)-3-oxo-1H,2H,3H-benzo[e]isoindol-2-yl]methyl}prop-2-enamide | 363.1 |
| 582. | 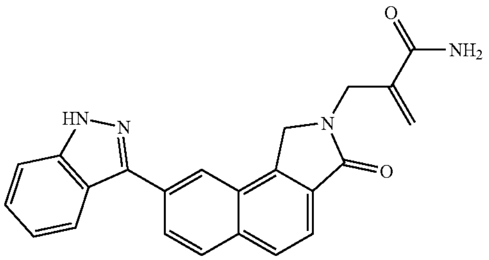 [SMILES: C=C(CN1Cc2c(ccc3ccc(-c4n[nH]c5ccccc45)cc23)C1=O)C(N)=O] | 2-{[8-(1H-indazol-3-yl)-3-oxo-1H,2H,3H-benzo[e]isoindol-2-yl]methyl}prop-2-enamide | 383.1 |
| 583. | 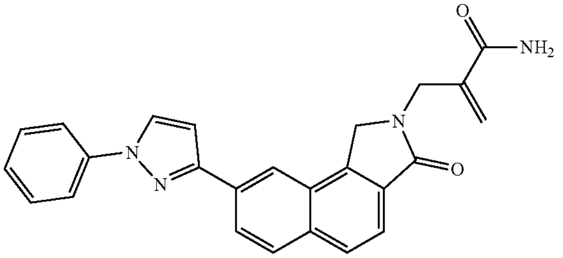 [SMILES: C=C(CN1Cc2c(ccc3ccc(-c4ccn(-c5ccccc5)n4)cc23)C1=O)C(N)=O] | 2-{[3-oxo-8-(1-phenyl-1H-pyrazol-3-yl)-1H,2H,3H-benzo[e]isoindol-2-yl]methyl}prop-2-enamide | 409.1 |
| 584. | 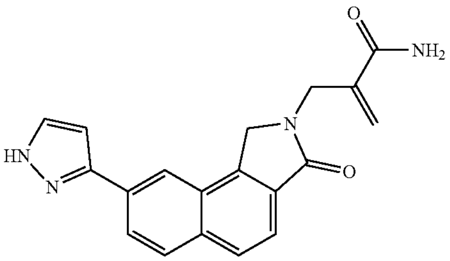 [SMILES: C=C(CN1Cc2c(ccc3ccc(-c4cc[nH]n4)cc23)C1=O)C(N)=O] | 2-{[3-oxo-8-(1H-pyrazol-3-yl)-1H,2H,3H-benzo[e]isoindol-2-yl]methyl}prop-2-enamide | 333.1 |

TABLE 14-continued
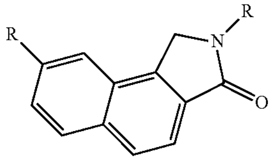
| Cpd. No. | Structure | IUPAC | LC-MS (ES+, m/z) |
|---|---|---|---|
| 585. | 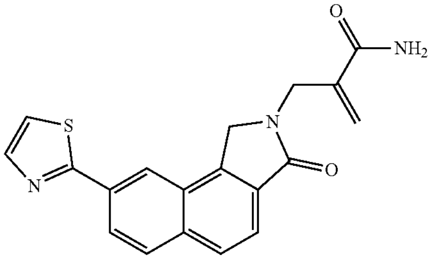 [SMILES: C=C(CN1Cc2c(ccc3ccc(-c4nccs4)cc23)C1=O)C(N)=O] | 2-{[3-oxo-8-(1,3-thiazol-2-yl)-1H,2H,3H-benzo[e]isoindol-2-yl]methyl}prop-2-enamide | 350 |
| 586. | 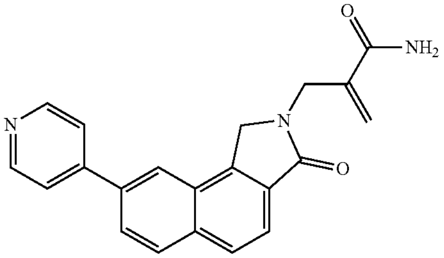 [SMILES: C=C(CN1Cc2c(ccc3ccc(-c4ccncc4)cc23)C1=O)C(N)=O] | 2-{[3-oxo-8-(pyridin-4-yl)-1H,2H,3H-benzo[e]isoindol-2-yl]methyl}prop-2-enamide | 344.1 |
| 587. | 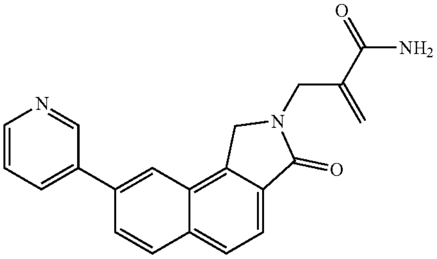 [SMILES: C=C(CN1Cc2c(ccc3ccc(-c4cccnc4)cc23)C1=O)C(N)=O] | 2-{[3-oxo-8-(pyridin-3-yl)-1H,2H,3H-benzo[e]isoindol-2-yl]methyl}prop-2-enamide | 344.1 |
| 588. | 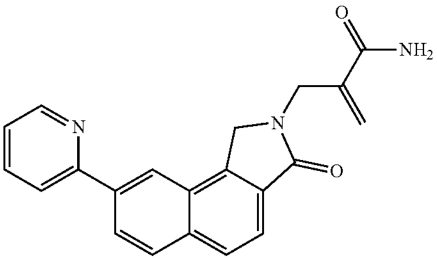 [SMILES: C=C(CN1Cc2c(ccc3ccc(-c4ccccn4)cc23)C1=O)C(N)=O] | 2-{[3-oxo-8-(pyridin-2-yl)-1H,2H,3H-benzo[e]isoindol-2-yl]methyl}prop-2-enamide | 344.1 |
| 589. | 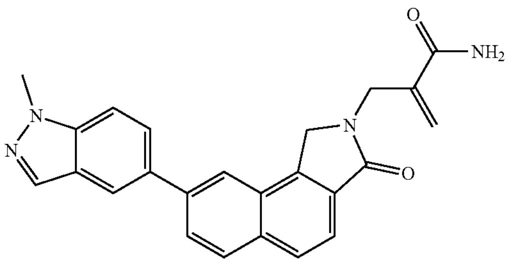 [SMILES: C=C(CN1Cc2c(ccc3ccc(-c4ccc5c(cnn5C)c4)cc23)C1=O)C(N)=O] | 2-{[8-(1-methyl-1H-indazol-5-yl)-3-oxo-1H,2H,3H-benzo[e]isoindol-2-yl]methyl}prop-2-enamide | 397.2 |

TABLE 14-continued

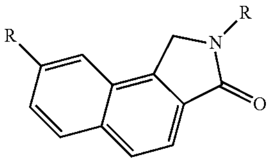

| Cpd. No. | Structure | IUPAC | LC-MS (ES+, m/z) |
|---|---|---|---|
| 590. | 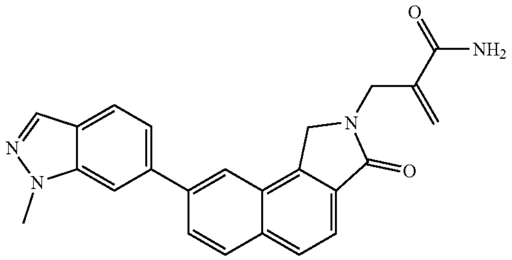 [SMILES: C=C(CN1Cc2c(ccc3ccc(-c4ccc5cnn(C)c5c4)cc23)C1=O)C(N)=O] | 2-{[8-(1-methyl-1H-indazol-6-yl)-3-oxo-1H,2H,3H-benzo[e]isoindol-2-yl]methyl}prop-2-enamide | 397.2 |
| 591. | 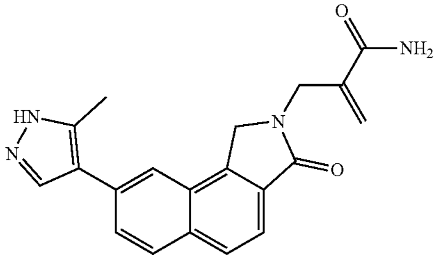 [SMILES: C=C(CN1Cc2c(ccc3ccc(-c4cn[nH]c4C)cc23)C1=O)C(N)=O] | 2-{[8-(5-methyl-1H-pyrazol-4-yl)-3-oxo-1H,2H,3H-benzo[e]isoindol-2-y]methyl}prop-2-enamide | 347.1 |
| 592. | 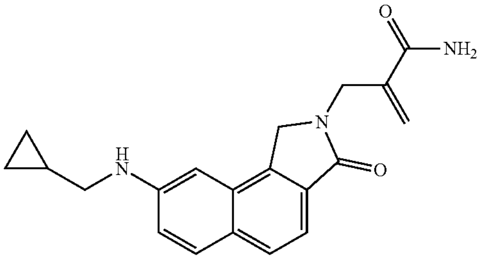 [SMILES: C=C(CN1Cc2c(ccc3ccc(NCC4CC4)cc23)C1=O)C(N)=O] | 2-({8-[(cyclopropylmethyl)amino]-3-oxo-1H,2H,3H-benzo[e]isoindol-2-yl]methyl}prop-2-enamide | 336.1 |
| 593. | 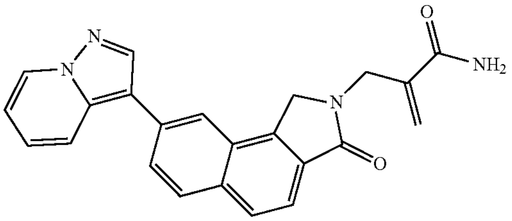 [SMILES: C=C(CN1Cc2c(ccc3ccc(-c4cnn5ccccc45)cc23)C1=O)C(N)=O] | 3-[2-(2-carbamoyl-2-methylideneethyl)-3-oxo-1H,2H,3H-benzo[e]isoindol-8-yl]-8H-8λ$^4$-pyrazolo[1,5-a]pyridin-8-yl | 383.2 |
| 594. | 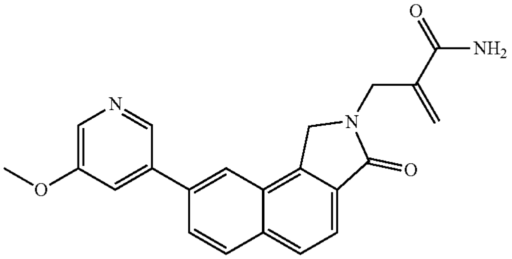 [SMILES: C=C(CN1Cc2c(ccc3ccc(-c4cncc(OC)c4)cc23)C1=O)C(N)=O] | 2-{[8-(5-methoxypyridin-3-yl)-3-oxo-1H,2H,3H-benzo[e]isoindol-2-yl]methyl}prop-2-enamide | 374.1 |

TABLE 14-continued

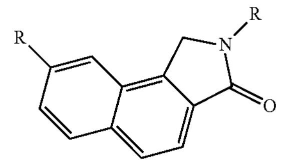

| Cpd. No. | Structure | IUPAC | LC-MS (ES+, m/z) |
|---|---|---|---|
| 595. | 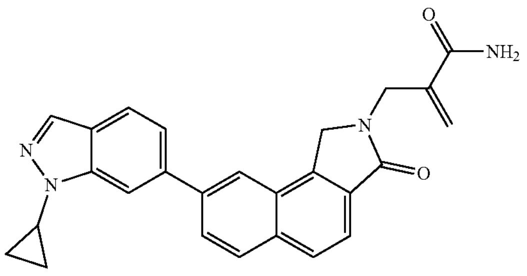 [SMILES: C=C(CN1Cc2c(ccc3ccc(-c4ccc5cnn(C6CC6)c5c4)cc23)C1=O)C(N)=O] | 2-{[8-(1-cyclopropyl-1H-indazol-6-yl)-3-oxo-1H,2H,3H-benzo[e]isoindol-2-yl]methyl}prop-2-enamide | 423.2 |
| 596. | 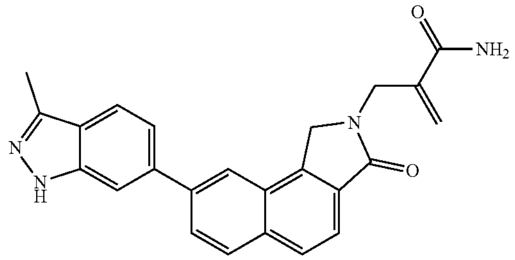 [SMILES: C=C(CN1Cc2c(ccc3ccc(-c4ccc5c(C)n[nH]c5c4)cc23)C1=O)C(N)=O] | 2-{[8-(3-methyl-1H-indazol-6-yl)-3-oxo-1H,2H,3H-benzo[e]isoindol-2-yl]methyl}prop-2-enamide | 397 |
| 597. | 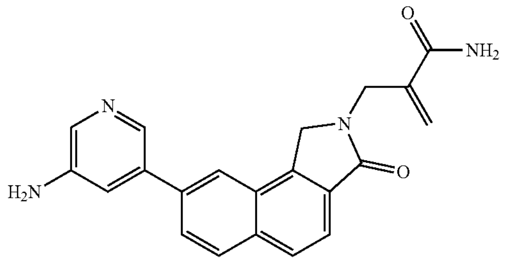 [SMILES: C=C(CN1Cc2c(ccc3ccc(-c4cncc(N)c4)cc23)C1=O)C(N)=O] | 2-{[5-(5-aminopyridin-3-yl)-3-oxo-1H,2H,3H-benzo[e]isoindol-2-yl]methyl}prop-2-enamide | 359.1 |
| 598. | 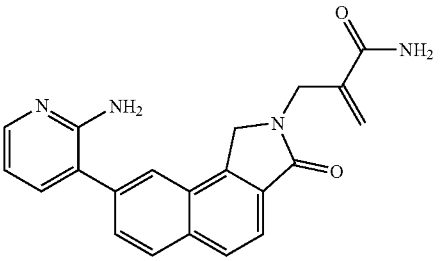 [SMILES: C=C(CN1Cc2c(ccc3ccc(-c4cccnc4N)cc23)C1=O)C(N)=O] | 2-{[8-(2-aminopyridin-3-yl)-3-oxo-1H,2H,3H-benzo[e]isoindol-2-yl]methyl}prop-2-enamide | 359.1 |
| 599. | 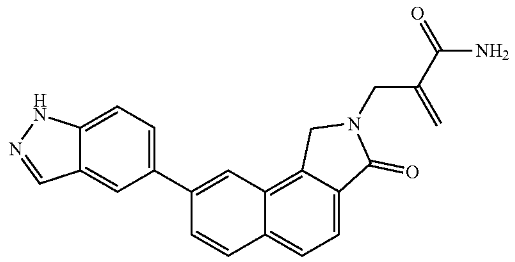 [SMILES: C=C(CN1Cc2c(ccc3ccc(-c4ccc5[nH]ncc5c4)cc23)C1=O)C(N)=O] | 2-{[8-(1H-indazol-5-yl)-3-oxo-1H,2H,3H-benzo[e]isoindol-2-yl]methyl}prop-2-enamide | 383.1 |

TABLE 14-continued

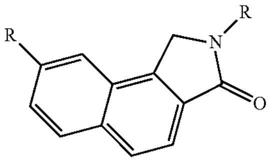

| Cpd. No. | Structure | IUPAC | LC-MS (ES+, m/z) |
|---|---|---|---|
| 600. | 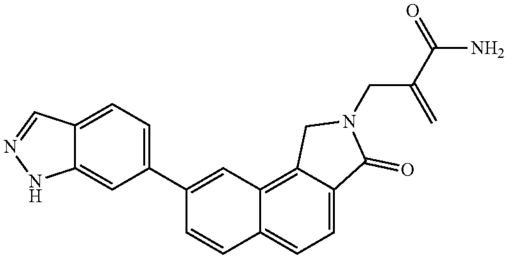 [SMILES: C=C(CN1Cc2c(ccc3ccc(-c4ccc5cn[nH]c5c4)cc23)C1=O)C(N)=O] | 2-{[8-(1H-indazol-6-yl)-3-oxo-1H,2H,3H-benzo[e]isoindol-2-yl]methyl}prop-2-enamide | 383.1 |
| 601. | 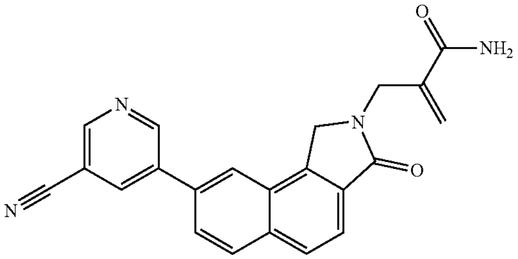 [SMILES: C=C(CN1Cc2c(ccc3ccc(-c4cncc(C#N)c4)cc23)C1=O)C(N)=O] | 2-{[8-(5-cyanopyridin-3-yl)-3-oxo-1H,2H,3H-benzo[e]isoindol-2-yl]methyl}prop-2-enamide | 369.2 |
| 602. | 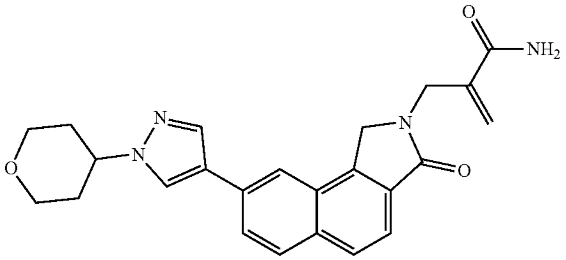 [SMILES: C=C(CN1Cc2c(ccc3ccc(-c4cnn(C5CCOCC5)c4)cc23)C1=O)C(N)=O] | 2-({8-[1-(oxan-4-yl)-1H-pyrazol-4-yl]-3-oxo-1H,2H,3H-benzo[e]isoindol-2-yl}methyl)prop-2-enamide | 417.2 |
| 603. | 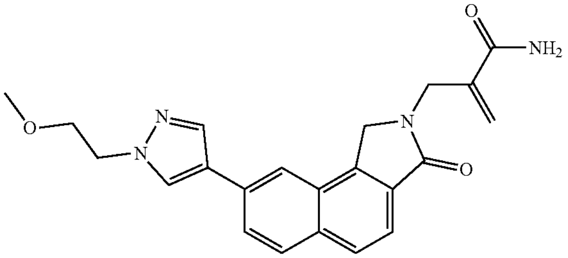 [SMILES: C=C(CN1Cc2c(ccc3ccc(-c4cnn(CCOC)c4)cc23)C1=O)C(N)=O] | 2-({8-[1-(2-methoxyethyl)-1H-pyrazol-4-yl]-3-oxo-1H,2H,3H-benzo[e]isoindol-2-yl}methyl)prop-2-enamide | 391.2 |
| 604. | 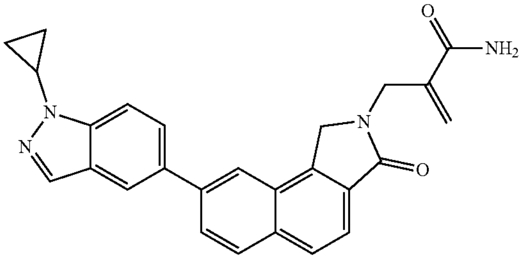 [SMILES: C=C(CN1Cc2c(ccc3ccc(-c4ccc5c(cnn5C5CC5)c4)cc23)C1=O)C(N)=O] | 2-{[8-(1-cyclopropyl-1H-indazol-5-yl)-3-oxo-1H,2H,3H-benzo[e]isoindol-2-yl]methyl}prop-2-enamide | 423.1 |

TABLE 14-continued

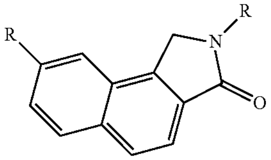

| Cpd. No. | Structure | IUPAC | LC-MS (ES+, m/z) |
|---|---|---|---|
| 605. | 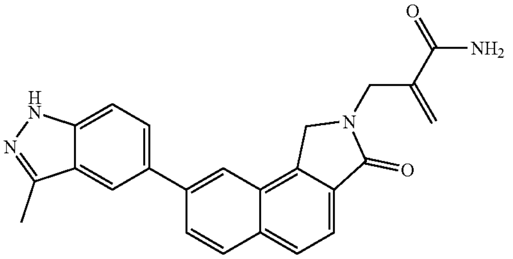 [SMILES: C=C(CN1Cc2c(ccc3ccc(-c4ccc5[nH]nc(C)c5c4)cc23)C1=O)C(N)=O] | 2-{[8-(3-methyl-1H-indazol-5-yl)-3-oxo-1H,2H,3H-benzo[e]isoindol-2-yl]methyl}prop-2-enamide | 397.1 |
| 606. | 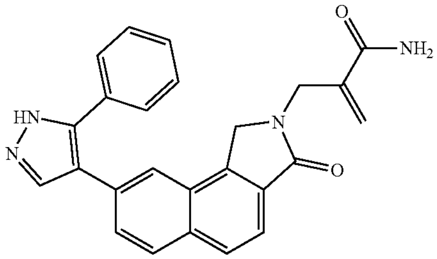 [SMILES: C=C(CN1Cc2c(ccc3ccc(-c4cn[nH]c4-c4ccccc4)cc23)C1=O)C(N)=O] | 2-{[3-oxo-8-(5-phenyl-1H-pyrazol-4-yl)-1H,2H,3H-benzo[e]isoindol-2-yl]methyl}prop-2-enamide | 409.1 |
| 607. | 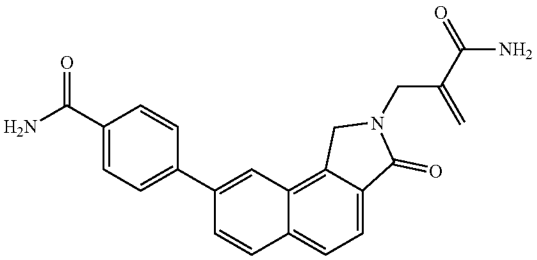 [SMILES: C=C(CN1Cc2c(ccc3ccc(-c4ccc(C(N)=O)cc4)cc23)C1=O)C(N)=O] | 4-[2-(2-carbamoyl-2-methylideneethyl)-3-oxo-1H,2H,3H-benzo[e]isoindol-8-yl]benzamide | 386 |
| 608. | 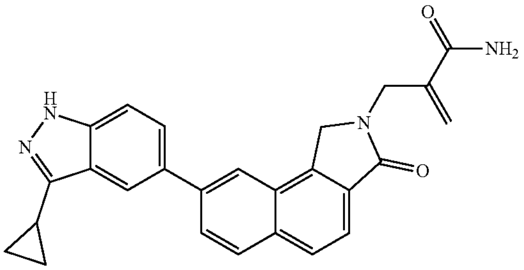 [SMILES: C=C(CN1Cc2c(ccc3ccc(-c4ccc5[nH]nc(C6CC6)c5c4)cc23)C1=O)C(N)=O] | 2-{[8-(3-cyclopropyl-1H-indazol-5-yl)-3-oxo-1H,2H,3H-benzo[e]isoindol-2-yl]methyl}prop-2-enamide | 423.1 |
| 609. | 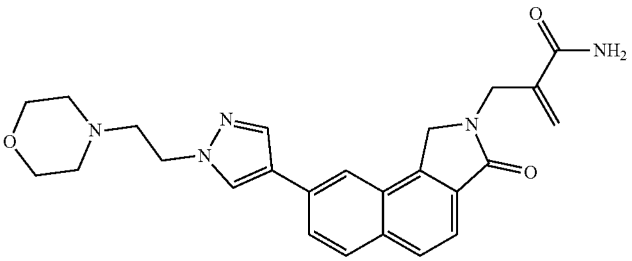 [SMILES: C=C(CN1Cc2c(ccc3ccc(-c4cnn(CCN5CCOCC5)c4)cc23)C1=O)C(N)=O] | 2-[(8-{1-[2-(morpholin-4-yl)ethyl]-1H-pyrazol-4-yl}-3-oxo-1H,2H,3H-benzo[e]isoindol-2-yl)methyl]prop-2-enamide | 446.2 |

TABLE 14-continued

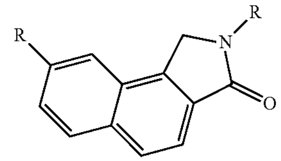

| Cpd. No. | Structure | IUPAC | LC-MS (ES+, m/z) |
|---|---|---|---|
| 610. | 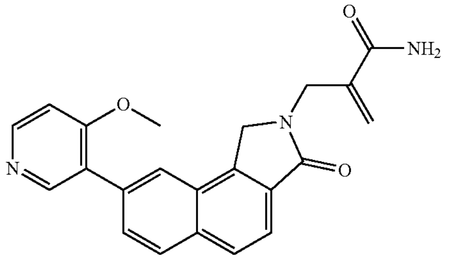 [SMILES: C=C(CN1Cc2c(ccc3ccc(-c4cnccc4OC)cc23)C1=O)C(N)=O] | 2-{[8-(4-methoxypyridin-3-yl)-3-oxo-1H,2H,3H-benzo[e]isoindol-2-yl]methyl}prop-2-enamide | 374.1 |
| 611. | 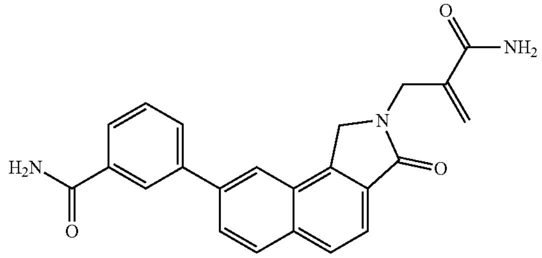 [SMILES: C=C(CN1Cc2c(ccc3ccc(-c4cccc(C(N)=O)c4)cc23)C1=O)C(N)=O] | 3-[2-(2-carbamoyl-2-methylideneethyl)-3-oxo-1H,2H,3H-benzo[e]isoindol-8-yl]benzamide | 386.1 |
| 612. | 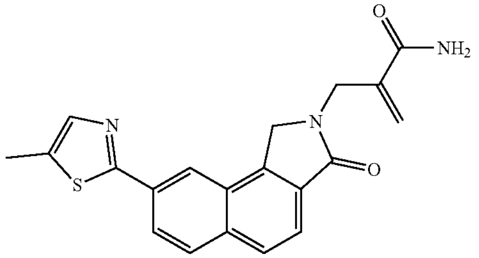 [SMILES: C=C(CN1Cc2c(ccc3ccc(-c4ncc(C)s4)cc23)C1=O)C(N)=O] | 2-{[8-(5-methyl-1,3-thiazol-2-yl)-3-oxo-1H,2H,3H-benzo[e]isoindol-2-yl]methyl}prop-2-enamide | 364.1 |
| 613. | 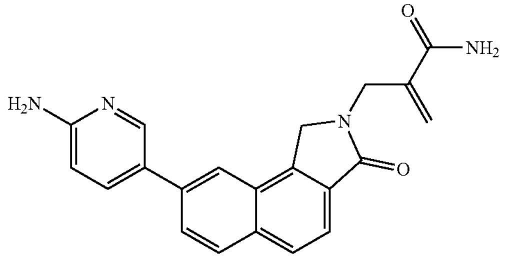 [SMILES: C=C(CN1Cc2c(ccc3ccc(-c4ccc(N)nc4)cc23)C1=O)C(N)=O] | 2-{[8-(6-aminopyridin-3-yl)-3-oxo-1H,2H,3H-benzo[e]isoindol-2-yl]methyl}prop-2-enamide | 359.1 |
| 614. | 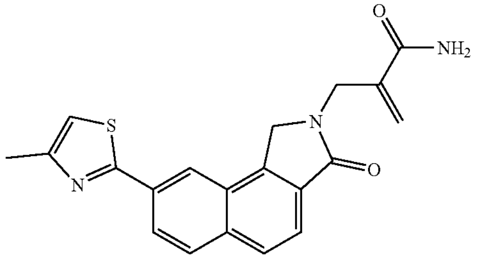 [SMILES: C=C(CN1Cc2c(ccc3ccc(-c4nc(C)cs4)cc23)C1=O)C(N)=O] | 2-{[8-(4-methyl-1,3-thiazol-2-yl)-3-oxo-1H,2H,3H-benzo[e]isoindol-2-yl]methyl}prop-2-enamide | 364.1 |

TABLE 14-continued

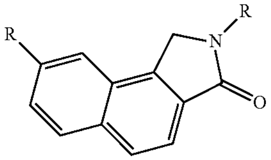

| Cpd. No. | Structure | IUPAC | LC-MS (ES+, m/z) |
|---|---|---|---|
| 615. | 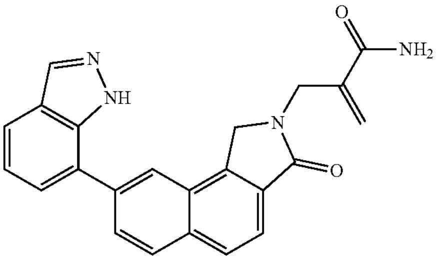 [SMILES: C=C(CN1Cc2c(ccc3ccc(-c4cccc5cn[nH]c45)cc23)C1=O)C(N)=O] | 2-{[8-(1H-indazol-7-yl)-3-oxo-1H,2H,3H-benzo[e]isoindol-2-yl]methyl}prop-2-enamide | 383.2 |
| 616. | 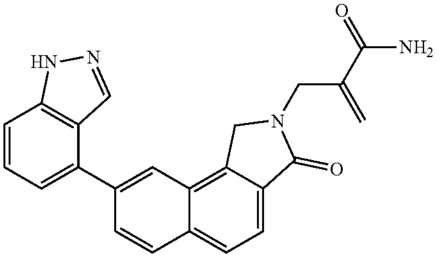 [SMILES: C=C(CN1Cc2c(ccc3ccc(-c4cccc5[nH]ncc45)cc23)C1=O)C(N)=O] | 2-{[8-(1H-indazol-4-yl)-3-oxo-1H,2H,3H-benzo[e]isoindol-2-yl]methyl}prop-2-enamide | 383.2 |
| 617. | 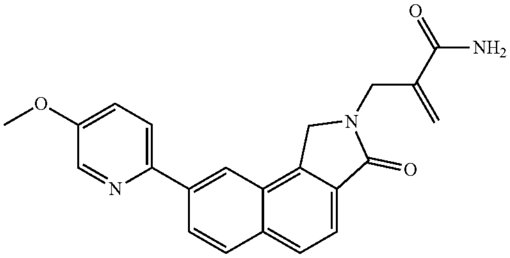 [SMILES: C=C(CN1Cc2c(ccc3ccc(-c4ccc(OC)cn4)cc23)C1=O)C(N)=O] | 2-{[8-(5-methoxypyridin-2-yl)-3-oxo-1H,2H,3H-benzo[e]isoindol-2-yl]methyl}prop-2-enamide | 374.1 |
| 618. | 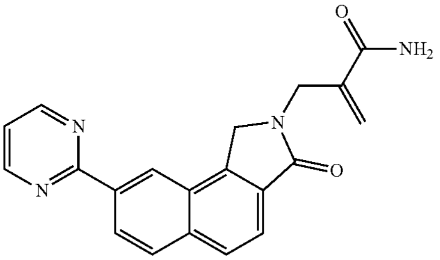 [SMILES: C=C(CN1Cc2c(ccc3ccc(-c4ncccn4)cc23)C1=O)C(N)=O] | 2-{[3-oxo-8-(pyrimidin-2-yl)-1H,2H,3H-benzo[e]isoindol-2-yl]methyl}prop-2-enamide | 345.1 |
| 619. | 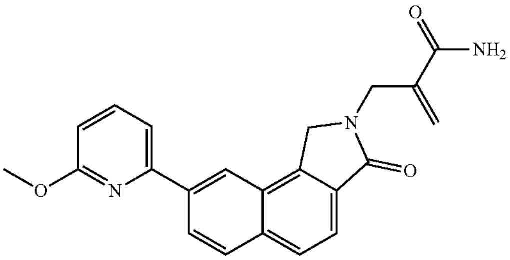 [SMILES: C=C(CN1Cc2c(ccc3ccc(-c4cccc(OC)n4)cc23)C1=O)C(N)=O] | 2-{[8-(6-methoxypyridin-2-yl)-3-oxo-1H,2H,3H-benzo[e]isoindol-2-yl]methyl}prop-2-enamide | 374.1 |

TABLE 14-continued

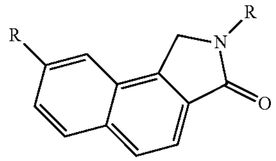

| Cpd. No. | Structure | IUPAC | LC-MS (ES+, m/z) |
|---|---|---|---|
| 620. | 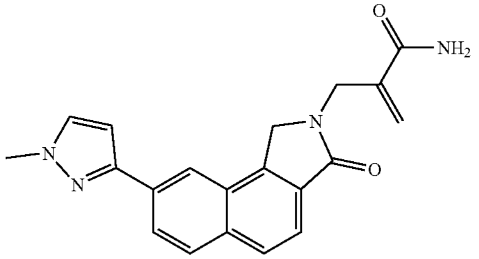 [SMILES: C=C(CN1Cc2c(ccc3ccc(-c4ccn(C)n4)cc23)C1=O)C(N)=O] | 2-{[8-(1-methyl-1H-pyrazol-3-yl)-3-oxo-1H,2H,3H-benzo[e]isoindol-2-yl]methyl}prop-2-enamide | 347.1 |
| 621. | 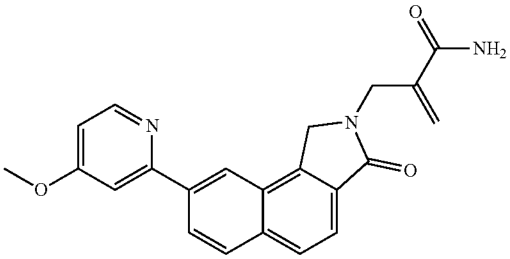 [SMILES: C=C(CN1Cc2c(ccc3ccc(-c4cc(OC)ccn4)cc23)C1=O)C(N)=O] | 2-{[8-(4-methoxypyridin-2-yl)-3-oxo-1H,2H,3H-benzo[e]isoindol-2-yl]methyl}prop-2-enamide | 374.1 |
| 622. | 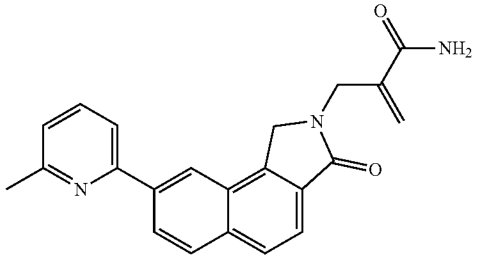 [SMILES: C=C(CN1Cc2c(ccc3ccc(-c4cccc(C)n4)cc23)C1=O)C(N)=O] | 2-{[8-(6-methylpyridin-2-yl)-3-oxo-1H,2H,3H-benzo[e]isoindol-2-yl]methyl}prop-2-enamide | 358.1 |
| 623. | 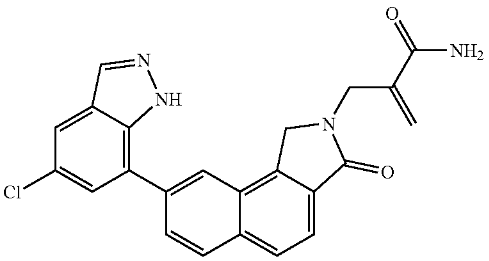 [SMILES: C=C(CN1Cc2c(ccc3ccc(-c4cc(Cl)cc5cn[nH]c45)cc23)C1=O)C(N)=O] | 2-{[8-(5-chloro-1H-indazol-7-yl)-3-oxo-1H,2H,3H-benzo[e]isoindol-2-yl]methyl}prop-2-enamide | 417 |
| 624. | 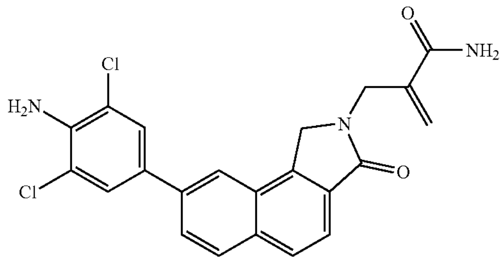 [SMILES: C=C(CN1Cc2c(ccc3ccc(-c4cc(Cl)c(N)c(Cl)c4)cc23)C1=O)C(N)=O] | 2-{[8-(4-amino-3,5-dichlorophenyl)-3-oxo-1H,2H,3H-benzo[e]isoindol-2-yl]methyl}prop-2-enamide | 426 |

TABLE 14-continued

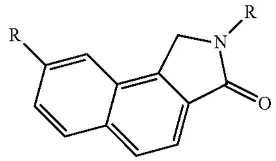

| Cpd. No. | Structure | IUPAC | LC-MS (ES+, m/z) |
|---|---|---|---|
| 625. | 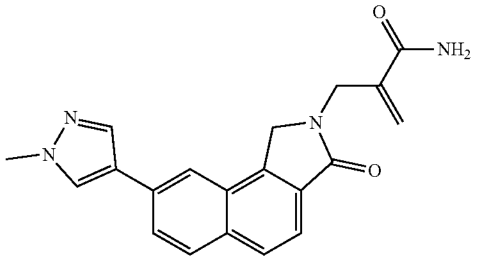 [SMILES: C=C(CN1Cc2c(ccc3ccc(-c4cnn(C)c4)cc23)C1=O)C(N)=O] | 2-{[8-(1-methyl-1H-pyrazol-4-yl)-3-oxo-1H,2H,3H-benzo[e]isoindol-2-yl]methyl}prop-2-enamide | 347 |
| 626. | 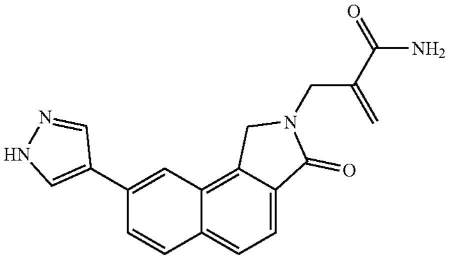 [SMILES: C=C(CN1Cc2c(ccc3ccc(-c4cn[nH]c4)cc23)C1=O)C(N)=O] | 2-{[3-oxo-8-(1H-pyrazol-4-yl)-1H,2H,3H-benzo[e]isoindol-2-yl]methyl}prop-2-enamide | 333 |
| 627. | 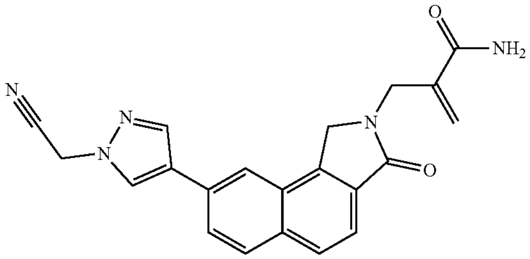 [SMILES: C=C(CN1Cc2c(ccc3ccc(-c4cnn(CC#N)c4)cc23)C1=O)C(N)=O] | 2-({8-[1-(cyanomethyl)-1H-pyrazol-4-yl]-3-oxo-1H,2H,3H-benzo[e]isoindol-2-yl}methyl)prop-2-enamide | 371.9 |
| 628. | 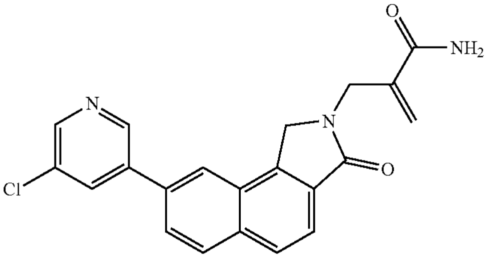 [SMILES: C=C(CN1Cc2c(ccc3ccc(-c4cncc(Cl)c4)cc23)C1=O)C(N)=O] | 2-{[8-(5-chloropyridin-3-yl)-3-oxo-1H,2H,3H-benzo[e]isoindol-2-yl]methyl}prop-2-enamide | 377.9 |
| 629. | 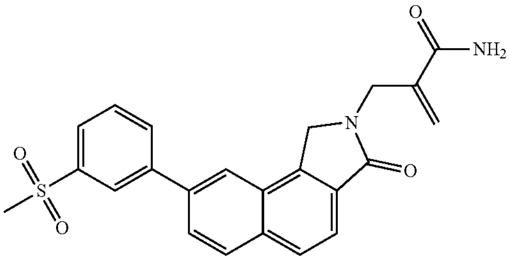 [SMILES: C=C(CN1Cc2c(ccc3ccc(-c4cccc(S(C)(=O)=O)c4)cc23)C1=O)C(N)=O] | 2-{[8-(3-methanesulfonylphenyl)-3-oxo-1H,2H,3H-benzo[e]isoindol-2-yl]methyl}prop-2-enamide | 420.9 |

TABLE 14-continued
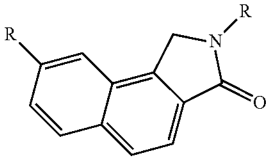
| Cpd. No. | Structure | IUPAC | LC-MS (ES+, m/z) |
|---|---|---|---|
| 630. | 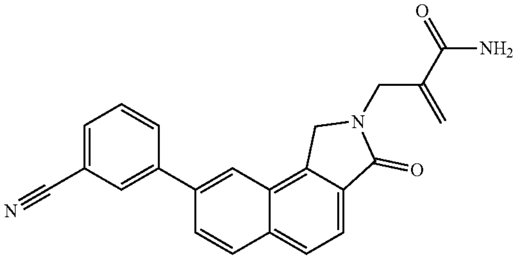 [SMILES: C=C(CN1Cc2c(ccc3ccc(-c4cccc(C#N)c4)cc23)C1=O)C(N)=O] | 2-{[8-(3-cyanophenyl)-3-oxo-1H,2H,3H-benzo[e]isoindol-2-yl]methyl}prop-2-enamide | 367.9 |
| 631. | 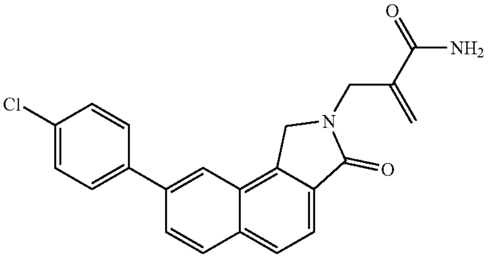 [SMILES: C=C(CN1Cc2c(ccc3ccc(-c4ccc(Cl)cc4)cc23)C1=O)C(N)=O] | 2-{[8-(4-chlorophenyl)-3-oxo-1H,2H,3H-benzo[e]isoindol-2-yl]methyl}prop-2-enamide | 376.9 |
| 632. | 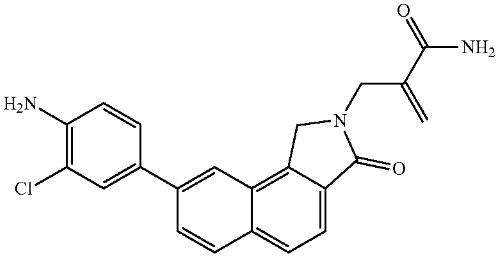 [SMILES: C=C(CN1Cc2c(ccc3ccc(-c4ccc(N)c(Cl)c4)cc23)C1=O)C(N)=O] | 2-{[8-(4-amino-3-chlorophenyl)-3-oxo-1H,2H,3H-benzo[e]isoindol-2-yl]methyl}prop-2-enamide | 392 |
| 633. | 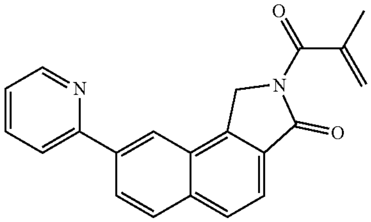 [SMILES: C=C(C)C(=O)N1Cc2c(ccc3ccc(-c4ccccn4)cc23)C1=O] | 2-(2-methylprop-2-enoyl)-8-(pyridin-2-yl)-1H,2H,3H-benzo[e]isoindol-3-one | 329.1 |
| 634. | 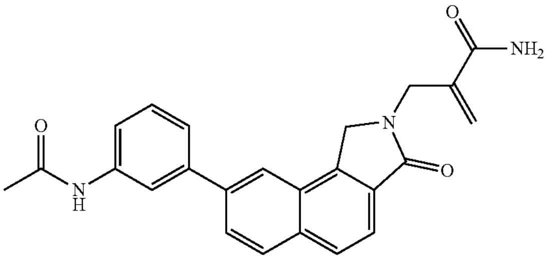 [SMILES: C=C(CN1Cc2c(ccc3ccc(-c4cccc(NC(C)=O)c4)cc23)C1=O)C(N)=O] | 2-{[8-(3-acetamidophenyl)-3-oxo-1H,2H,3H-benzo[e]isoindol-2-yl]methyl}prop-2-enamide | 400.1 |

TABLE 14-continued

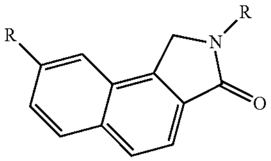

| Cpd. No. | Structure | IUPAC | LC-MS (ES+, m/z) |
|---|---|---|---|
| 635. | 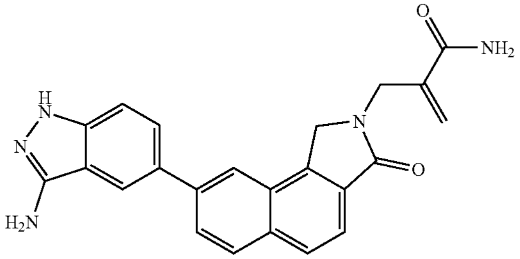 [SMILES: C=C(CN1Cc2c(ccc3ccc(-c4ccc5[nH]nc(N)c5c4)cc23)C1=O)C(N)=O] | 2-{[8-(3-amino-1H-indazol-5-yl)-3-oxo-1H,2H,3H-benzo[e]isoindol-2-yl]methyl}prop-2-enamide | 398.1 |
| 636. | 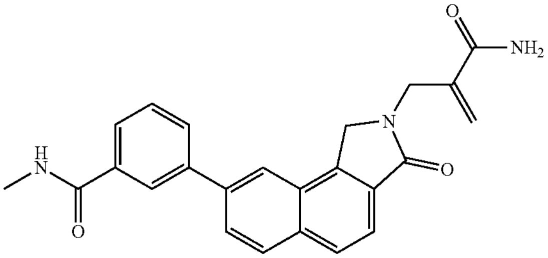 [SMILES: C=C(CN1Cc2c(ccc3ccc(-c4cccc(C(=O)NC)c4)cc23)C1=O)C(N)=O] | 3-[2-(2-carbamoyl-2-methylideneethyl)-3-oxo-1H,2H,3H-benzo[e]isoindol-8-yl]-N-methylbenzamide | 400.1 |
| 637. | 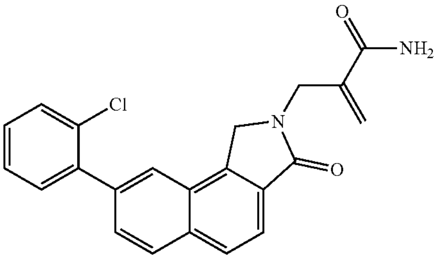 | 2-{[8-(2-chlorophenyl)-3-oxo-1H,2H,3H-benzo[e]isoindol-2-yl]methyl}prop-2-enamide | 376.9 |
| 638. | 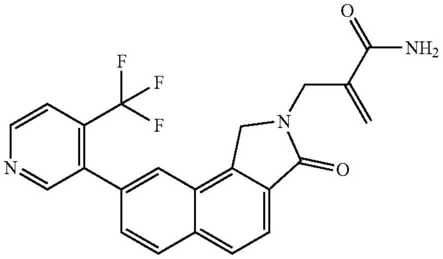 [SMILES: C=C(CN1Cc2c(ccc3ccc(-c4cnccc4C(F)(F)F)cc23)C1=O)C(N)=O] | 2-({3-oxo-8-[4-(trifluoromethyl)pyridin-3-yl]-1H,2H,3H-benzo[e]isoindol-2-yl}methyl)prop-2-enamide | 411.9 |
| 639. | 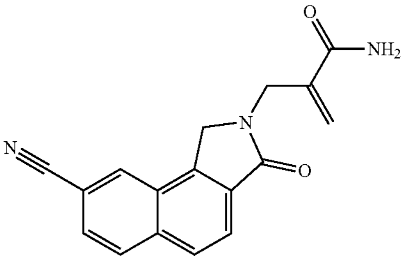 [SMILES: C=C(CN1Cc2c(ccc3ccc(C#N)cc23)C1=O)C(N)=O] | 2-({8-cyano-3-oxo-1H,2H,3H-benzo[e]isoindol-2-yl}methyl)prop-2-enamide | 291.9 |

TABLE 14-continued

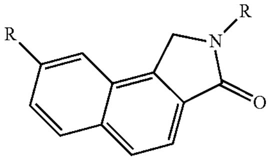

| Cpd. No. | Structure | IUPAC | LC-MS (ES+, m/z) |
|---|---|---|---|
| 640. | 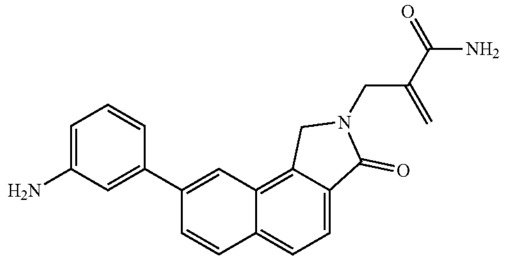 | 2-{[8-(3-aminophenyl)-3-oxo-1H,2H,3H-benzo[e]isoindol-2-yl]methyl}prop-2-enamide | 358 |
| 641. | 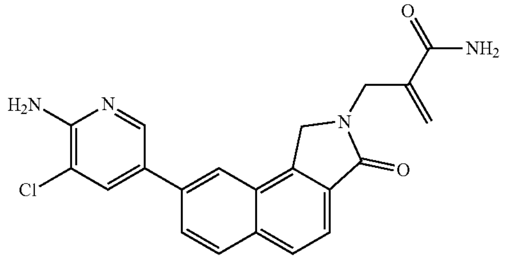 [SMILES: C=C(CN1Cc2c(ccc3ccc(-c4cnc(N)c(Cl)c4)cc23)C1=O)C(N)=O] | 2-{[8-(6-amino-5-chloropyridin-3-yl)-3-oxo-1H,2H,3H-benzo[e]isoindol-2-yl]methyl}prop-2-enamide | 392.9 |
| 642. | 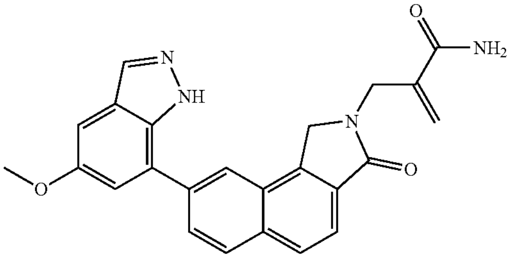 [SMILES: C=C(CN1Cc2c(ccc3ccc(-c4cc(OC)cc5cn[nH]c45)cc23)C1=O)C(N)=O] | 2-{[8-(5-methoxy-1H-indazol-7-yl)-3-oxo-1H,2H,3H-benzo[e]isoindol-2-yl]methyl}prop-2-enamide | 413.2 |
| 643. | 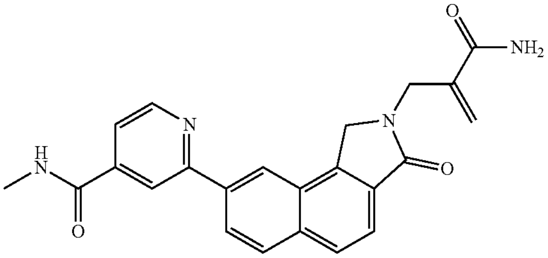 [SMILES: C=C(CN1Cc2c(ccc3ccc(-c4cc(C(=O)NC)ccn4)cc23)C1=O)C(N)=O] | 2-[2-(2-carbamoyl-2-methylideneethyl)-3-oxo-1H,2H,3H-benzo[e]isoindol-8-yl]-N-methylpyridine-4-carboxamide | 401.2 |
| 644. | 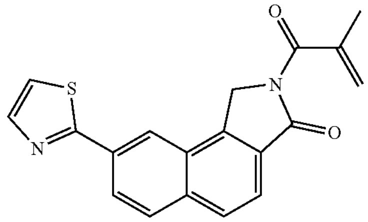 [SMILES: C=C(C)C(=O)N1Cc2c(ccc3ccc(-c4nccs4)cc23)C1=O] | 2-(2-methylprop-2-enoyl)-8-(1,3-thiazol-2-yl)-1H,2H,3H-benzo[e]isoindol-3-one | 335 |

TABLE 14-continued

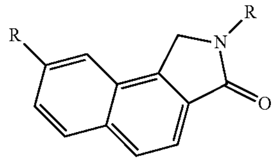

| Cpd. No. | Structure | IUPAC | LC-MS (ES+, m/z) |
|---|---|---|---|
| 645. | 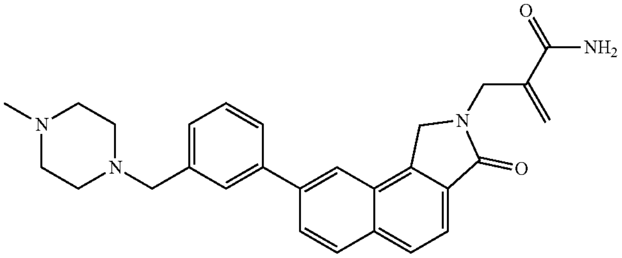 [SMILES: C=C(CN1Cc2c(ccc3ccc(-c4cccc(CN5CCN(C)CC5)c4)cc23)C1=O)C(N)=O] | 2-[(8-{3-[(4-methylpiperazin-1-yl)methyl]phenyl}-3-oxo-1H,2H,3H-benzo[e]isoindol-2-yl)methyl]prop-2-enamide | 455.3 |
| 646. | 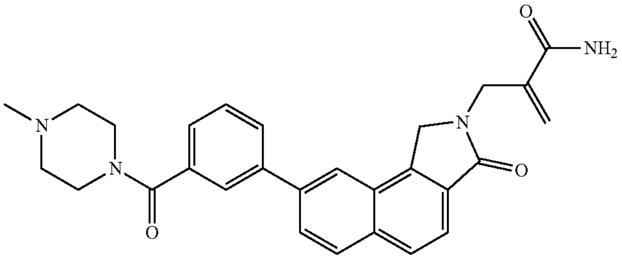 [SMILES: C=C(CN1Cc2c(ccc3ccc(-c4cccc(C(=O)N5CCN(C)CC5)c4)cc23)C1=O)C(N)=O] | 2-({8-[3-(4-methylpiperazine-1-carbonyl)phenyl]-3-oxo-1H,2H,3H-benzo[e]isoindol-2-yl}methyl)prop-2-enamide | 469.3 |
| 647. | 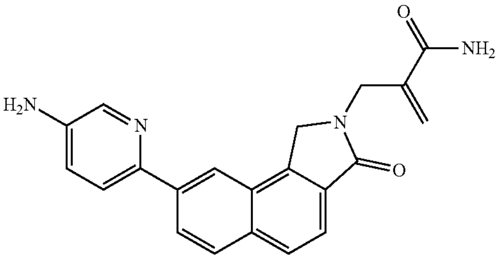 [SMILES: C=C(CN1Cc2c(ccc3ccc(-c4ccc(N)cn4)cc23)C1=O)C(N)=O] | 2-{[8-(5-aminopyridin-2-yl)-3-oxo-1H,2H,3H-benzo[e]isoindol-2-yl]methyl}prop-2-enamide | 359.1 |
| 648. | 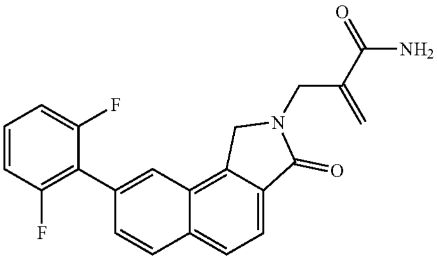 | 2-{[8-(2,6-difluorophenyl)-3-oxo-1H,2H,3H-benzo[e]isoindol-2-yl]methyl}prop-2-enamide | 379.1 |
| 649. | 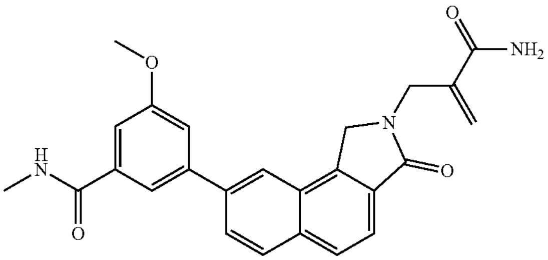 [SMILES: C=C(CN1Cc2c(ccc3ccc(-c4cc(OC)cc(C(=O)NC)c4)cc23)C1=O)C(N)=O] | 3-[2-(2-carbamoyl-2-methylideneethyl)-3-oxo-1H,2H,3H-benzo[e]isoindol-8-yl]-5-methoxy-N-methylbenzamide | 430.2 |

TABLE 14-continued

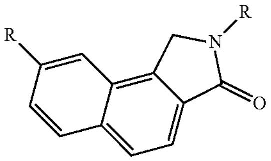

| Cpd. No. | Structure | IUPAC | LC-MS (ES+, m/z) |
|---|---|---|---|
| 650. | 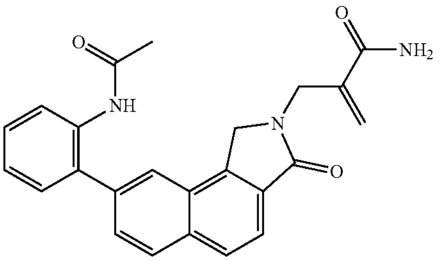 [SMILES: C=C(CN1Cc2c(ccc3ccc(-c4ccccc4NC(C)=O)cc23)C1=O)C(N)=O] | 2-{[8-(2-acetamidophenyl)-3-oxo-1H,2H,3H-benzo[e]isoindol-2-yl]methyl}prop-2-enamide | 400.1 |
| 651. | 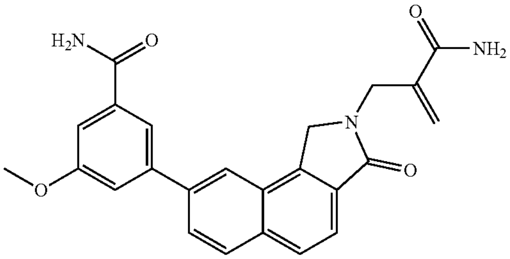 [SMILES: C=C(CN1Cc2c(ccc3ccc(-c4cc(OC)cc(C(N)=O)c4)cc23)C1=O)C(N)=O] | 3-[2-(2-carbamoyl-2-methylideneethyl)-3-oxo-1H,2H,3H-benzo[e]isoindol-8-yl]-5-methoxybenzamide | 416 |
| 652. | 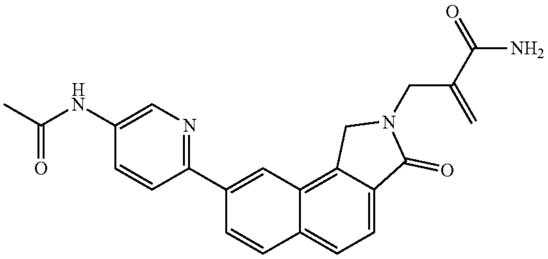 [SMILES: C=C(CN1Cc2c(ccc3ccc(-c4ccc(NC(C)=O)cn4)cc23)C1=O)C(N)=O] | 2-{[8-(5-acetamidopyridin-2-yl)-3-oxo-1H,2H,3H-benzo[e]isoindol-2-yl]methyl}prop-2-enamide | 401.1 |
| 653. | 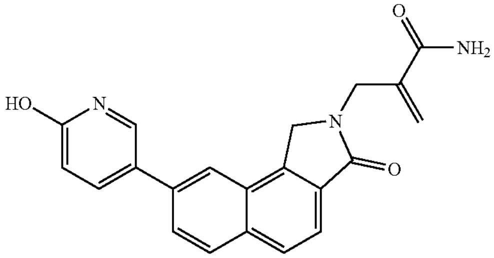 [SMILES: C=C(CN1Cc2c(ccc3ccc(-c4ccc(O)nc4)cc23)C1=O)C(N)=O] | 2-{[8-(6-hydroxypyridin-3-yl)-3-oxo-1H,2H,3H-benzo[e]isoindol-2-yl]methyl}prop-2-enamide | 359.9 |
| 654. | 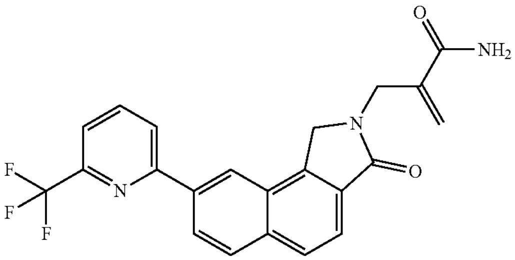 [SMILES: C=C(CN1Cc2c(ccc3ccc(-c4cccc(C(F)(F)F)n4)cc23)C1=O)C(N)=O] | 2-({3-oxo-8-[6-(trifluoromethyl)pyridin-2-yl]-1H,2H,3H-benzo[e]isoindol-2-yl}methyl)prop-2-enamide | 411.9 |

TABLE 14-continued

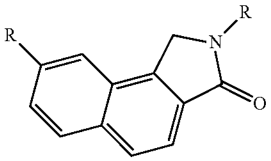

| Cpd. No. | Structure | IUPAC | LC-MS (ES+, m/z) |
|---|---|---|---|
| 655. | 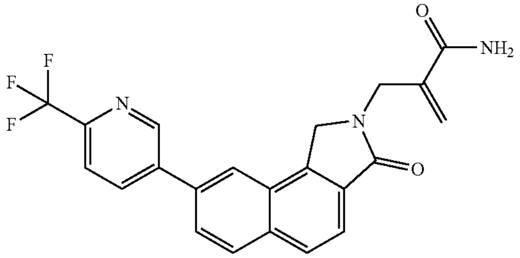 [SMILES: C=C(CN1Cc2c(ccc3ccc(-c4ccc(C(F)(F)F)nc4)cc23)C1=O)C(N)=O] | 2-({3-oxo-8-[6-(trifluoromethyl)pyridin-3-yl]-1H,2H,3H-benzo[e]isoindol-2-yl}methyl)prop-2-enamide | 411.9 |
| 656. | 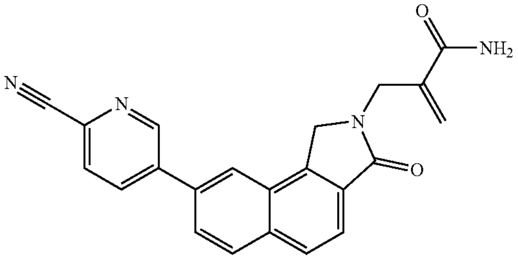 [SMILES: C=C(CN1Cc2c(ccc3ccc(-c4ccc(C#N)nc4)cc23)C1=O)C(N)=O] | 2-{[8-(6-cyanopyridin-3-yl)-3-oxo-1H,2H,3H-benzo[e]isoindol-2-yl]methyl}prop-2-enamide | 368.9 |
| 657. | 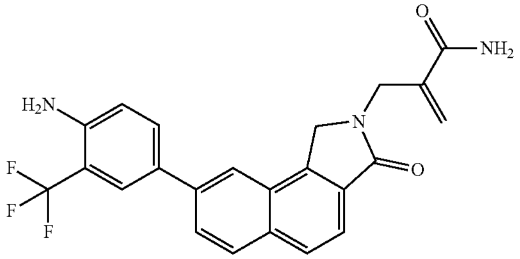 [SMILES: C=C(CN1Cc2c(ccc3ccc(-c4ccc(N)c(C(F)(F)F)c4)cc23)C1=O)C(N)=O] | 2-({8-[4-amino-3-(trifluoromethyl)phenyl]-3-oxo-1H,2H,3H-benzo[e]isoindol-2-yl}methyl)prop-2-enamide | 425.9 |
| 658. | 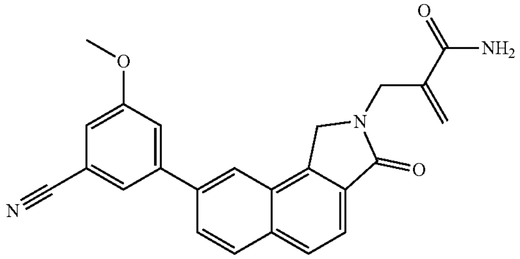 [SMILES: C=C(CN1Cc2c(ccc3ccc(-c4cc(C#N)cc(OC)c4)cc23)C1=O)C(N)=O] | 2-{[8-(3-cyano-5-methoxyphenyl)-3-oxo-1H,2H,3H-benzo[e]isoindol-2-yl]methyl}prop-2-enamide | 397.9 |
| 659. | 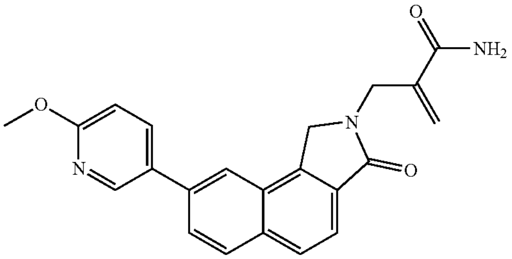 [SMILES: C=C(CN1Cc2c(ccc3ccc(-c4ccc(OC)nc4)cc23)C1=O)C(N)=O] | 2-{[8-(6-methoxypyridin-3-yl)-3-oxo-1H,2H,3H-benzo[e]isoindol-2-yl]methyl}prop-2-enamide | 373.9 |

TABLE 14-continued

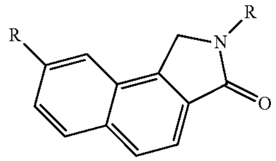

| Cpd. No. | Structure | IUPAC | LC-MS (ES+, m/z) |
|---|---|---|---|
| 660. | 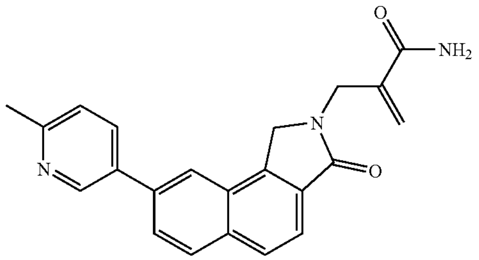 [SMILES: C=C(CN1Cc2c(ccc3ccc(-c4ccc(C)nc4)cc23)C1=O)C(N)=O] | 2-{[8-(6-methylpyridin-3-yl)-3-oxo-1H,2H,3H-benzo[e]isoindol-2-yl]methyl}prop-2-enamide | 357.9 |
| 661. | 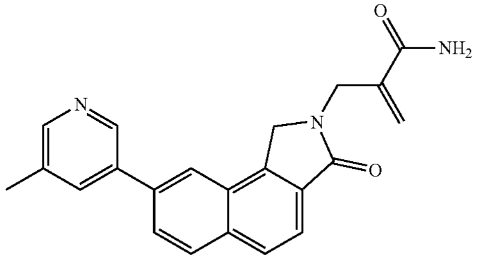 [SMILES: C=C(CN1Cc2c(ccc3ccc(-c4cncc(C)c4)cc23)C1=O)C(N)=O] | 2-{[8-(5-methylpyridin-3-yl)-3-oxo-1H,2H,3H-benzo[e]isoindol-2-yl]methyl}prop-2-enamide | 358 |
| 662. | 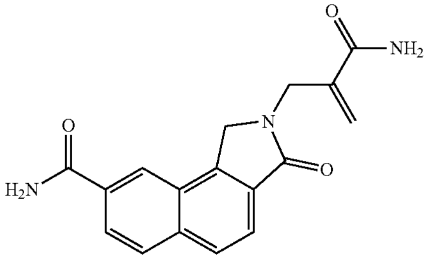 [SMILES: C=C(CN1Cc2c(ccc3ccc(C(N)=O)cc23)C1=O)C(N)=O] | 2-(2-carbamoyl-2-methylideneethyl)-3-oxo-1H,2H,3H-benzo[e]isoindole-8-carboxamide | 310 |
| 663. | 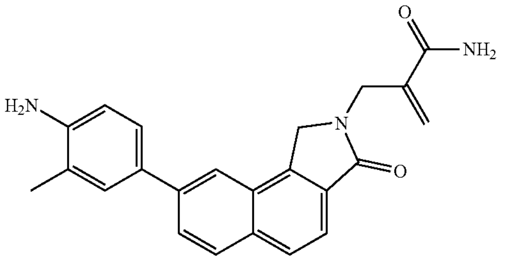 [SMILES: C=C(CN1Cc2c(ccc3ccc(-c4ccc(N)c(C)c4)cc23)C1=O)C(N)=O] | 2-{[8-(4-amino-3-methylphenyl)-3-oxo-1H,2H,3H-benzo[e]isoindol-2-yl]methyl}prop-2-enamide | 371.9 |
| 664. | 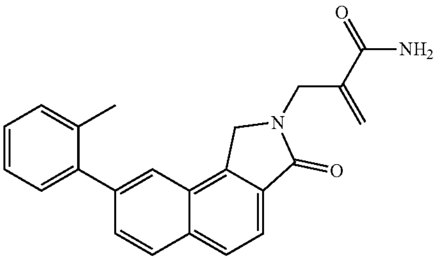 [SMILES: C=C(CN1Cc2c(ccc3ccc(-c4ccccc4C)cc23)C1=O)C(N)=O] | 2-{[8-(2-methylphenyl)-3-oxo-1H,2H,3H-benzo[e]isoindol-2-yl]methyl}prop-2-enamide | 357 |

TABLE 14-continued

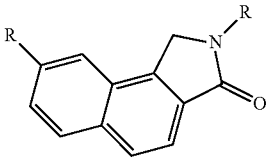

| Cpd. No. | Structure | IUPAC | LC-MS (ES+, m/z) |
|---|---|---|---|
| 665. | 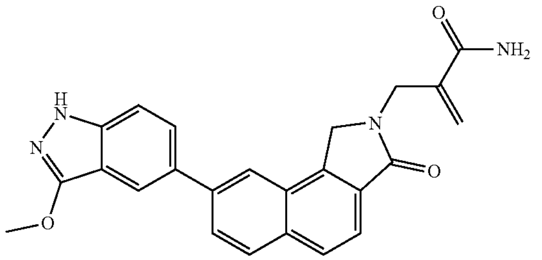 [SMILES: C=C(CN1Cc2c(ccc3ccc(-c4ccc5[nH]nc(OC)c5c4)cc23)C1=O)C(N)=O] | 2-{[8-(3-methoxy-1H-indazol-5-yl)-3-oxo-1H,2H,3H-benzo[e]isoindol-2-yl]methyl}prop-2-enamide | 413.2 |
| 666. | 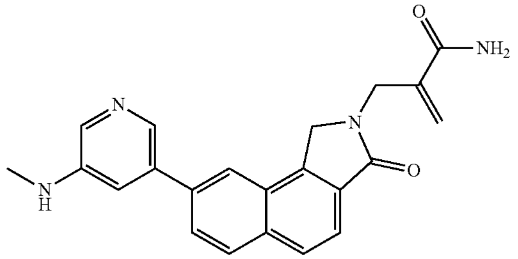 [SMILES: C=C(CN1Cc2c(ccc3ccc(-c4cncc(NC)c4)cc23)C1=O)C(N)=O] | 2-({8-[5-(methylamino)pyridin-3-yl]-3-oxo-1H,2H,3H-benzo[e]isoindol-2-yl}methyl)prop-2-enamide | 373.2 |
| 667. | 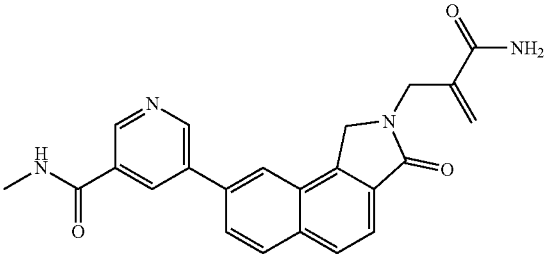 [SMILES: C=C(CN1Cc2c(ccc3ccc(-c4cncc(C(=O)NC)c4)cc23)C1=O)C(N)=O] | 5-[2-(2-carbamoyl-2-methylideneethyl)-3-oxo-1H,2H,3H-benzo[e]isoindol-8-yl]-N-methylpyridine-3-carboxamide | 401.1 |
| 668. | 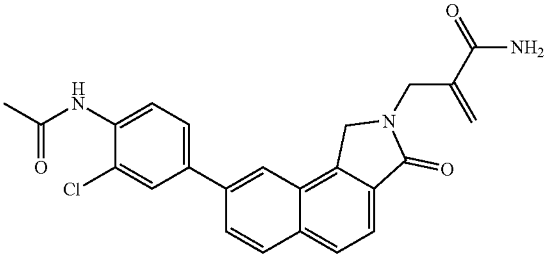 [SMILES: C=C(CN1Cc2c(ccc3ccc(-c4ccc(NC(C)=O)c(Cl)c4)cc23)C1=O)C(N)=O] | 2-{[8-(3-chloro-4-acetamidophenyl)-3-oxo-1H,2H,3H-benzo[e]isoindol-2-yl]methyl}prop-2-enamide | 434.1 |
| 669. | 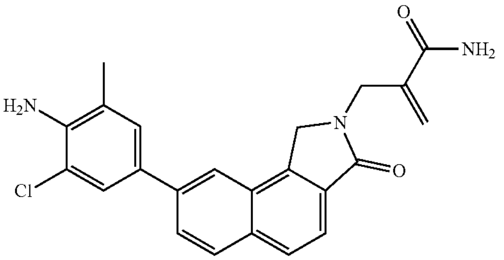 [SMILES: C=C(CN1Cc2c(ccc3ccc(-c4cc(C)c(N)c(Cl)c4)cc23)C1=O)C(N)=O] | 2-{[8-(4-amino-3-chloro-5-methylphenyl)-3-oxo-1H,2H,3H-benzo[e]isoindol-2-yl]methyl}prop-2-enamide | 406.1 |

TABLE 14-continued

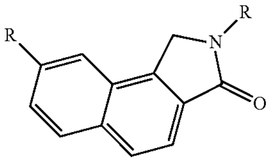

| Cpd. No. | Structure | IUPAC | LC-MS (ES+, m/z) |
|---|---|---|---|
| 670. | 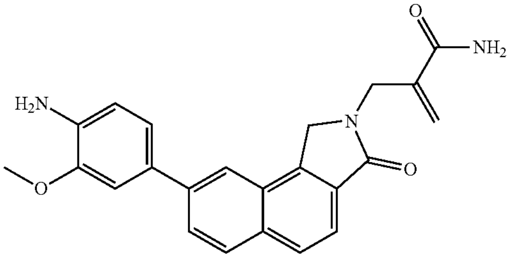 [SMILES: C=C(CN1Cc2c(ccc3ccc(-c4ccc(N)c(OC)c4)cc23)C1=O)C(N)=O] | 2-{[8-(4-amino-3-methoxyphenyl)-3-oxo-1H,2H,3H-benzo[e]isoindol-2-yl]methyl}prop-2-enamide | 387.9 |
| 671. | 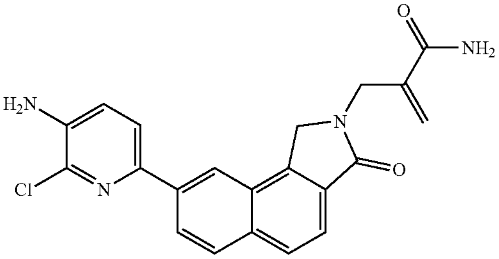 [SMILES: C=C(CN1Cc2c(ccc3ccc(-c4ccc(N)c(Cl)n4)cc23)C1=O)C(N)=O] | 2-{[8-(5-amino-6-chloropyridin-2-yl)-3-oxo-1H,2H,3H-benzo[e]isoindol-2-yl]methyl}prop-2-enamide | 392.9 |
| 672. | 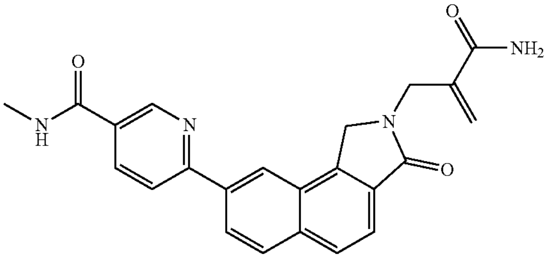 [SMILES: C=C(CN1Cc2c(ccc3ccc(-c4ccc(C(=O)NC)cn4)cc23)C1=O)C(N)=O] | 6-[2-(2-carbamoyl-2-methylideneethyl)-3-oxo-1H,2H,3H-benzo[e]isoindol-8-yl]-N-methylpyridine-3-carboxamide | 401.2 |
| 673. | 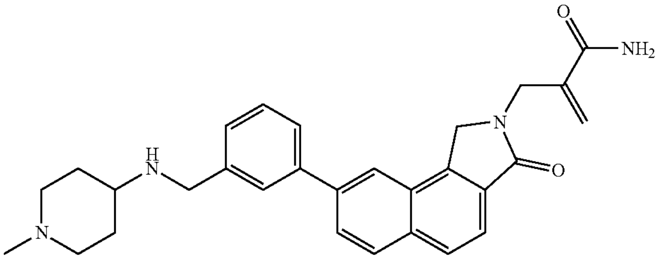 [SMILES: C=C(CN1Cc2c(ccc3ccc(-c4cccc(CNC5CCN(C)CC5)c4)cc23)C1=O)C(N)=O] | 2-{[8-(3-{[(1-methylpiperidin-4-yl)amino]methyl}phenyl)-3-oxo-1H,2H,3H-benzo[e]isoindol-2-yl]methyl}prop-2-enamide | 469.3 |
| 674. | 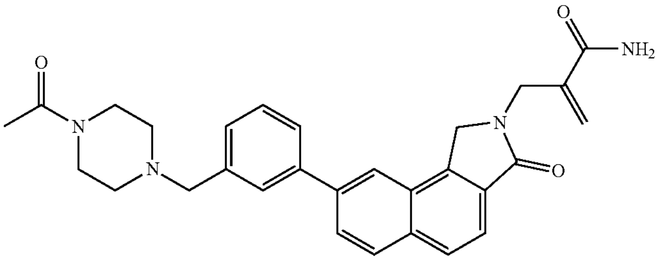 [SMILES: C=C(CN1Cc2c(ccc3ccc(-c4cccc(CN5CCN(C(C)=O)CC5)c4)cc23)C1=O)C(N)=O] | 2-[(8-{3-[(4-acetylpiperazin-1-yl)methyl]phenyl}-3-oxo-1H,2H,3H-benzo[e]isoindol-2-yl]methyl}prop-2-enamide | 483.3 |

TABLE 14-continued

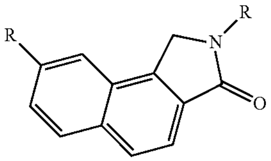

| Cpd. No. | Structure | IUPAC | LC-MS (ES+, m/z) |
|---|---|---|---|
| 675. | 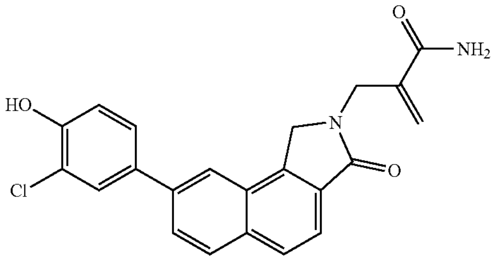 [SMILES: C=C(CN1Cc2c(ccc3ccc(-c4ccc(O)c(Cl)c4)cc23)C1=O)C(N)=O] | 2-{[8-(3-chloro-4-hydroxyphenyl)-3-oxo-1H,2H,3H-benzo[e]isoindol-2-yl]methyl}prop-2-enamide | 393.1 |
| 676. | 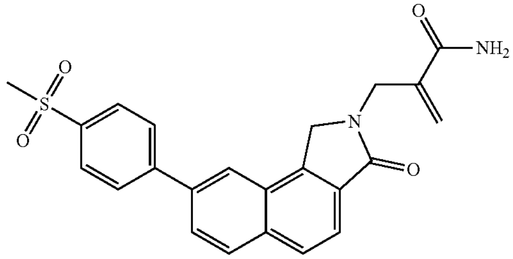 [SMILES: C=C(CN1Cc2c(ccc3ccc(-c4ccc(S(C)(=O)=O)cc4)cc23)C1=O)C(N)=O] | 2-{[8-(4-methanesulfonylphenyl)-3-oxo-1H,2H,3H-benzo[e]isoindol-2-yl]methyl}prop-2-enamide | 421.2 |
| 677. | 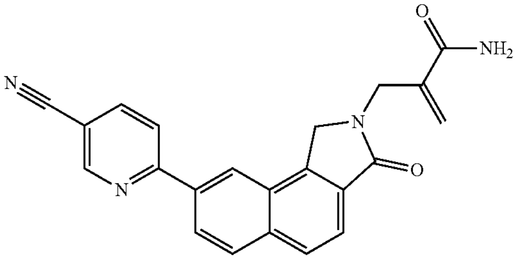 [SMILES: C=C(CN1Cc2c(ccc3ccc(-c4ccc(C#N)cn4)cc23)C1=O)C(N)=O] | 2-{[8-(5-cyanopyridin-2-yl)-3-oxo-1H,2H,3H-benzo[e]isoindol-2-yl]methyl}prop-2-enamide | 369.1 |
| 678. | 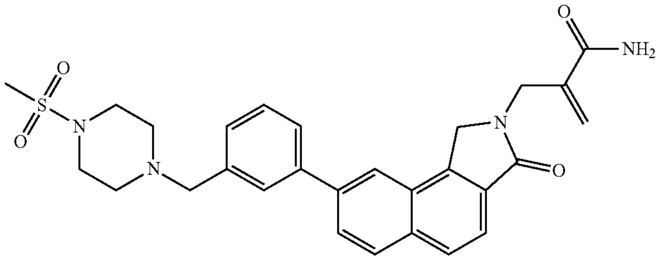 [SMILES: C=C(CN1Cc2c(ccc3ccc(-c4cccc(CN5CCN(S(C)(=O)=O)CC5)c4)cc23)C1=O)C(N)=O] | 2-[(8-{3-[(4-methanesulfonylpiperazin-1-yl)methyl]phenyl}-3-oxo-1H,2H,3H-benzo[e]isoindol-2-yl)methyl]prop-2-enamide | 519.3 |
| 679. | 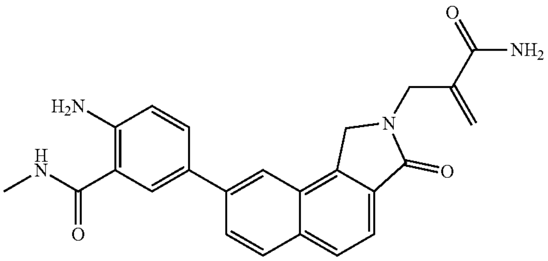 [SMILES: C=C(CN1Cc2c(ccc3ccc(-c4ccc(N)c(C(=O)NC)c4)cc23)C1=O)C(N)=O] | 2-amino-5-[2-(2-carbamoyl-2-methylideneethyl)-3-oxo-1H,2H,3H-benzo[e]isoindol-8-yl]-N-methylbenzamide | 415.2 |

TABLE 14-continued

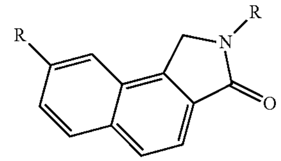

| Cpd. No. | Structure | IUPAC | LC-MS (ES+, m/z) |
|---|---|---|---|
| 680. | 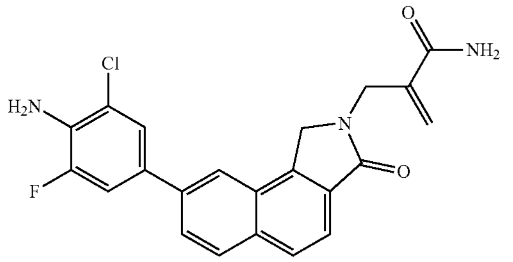 | 2-{[8-(4-amino-3-chloro-5-fluorophenyl)-3-oxo-1H,2H,3H-benzo[e]isoindol-2-yl]methyl}prop-2-enamide | 410.1 |
| 681. | 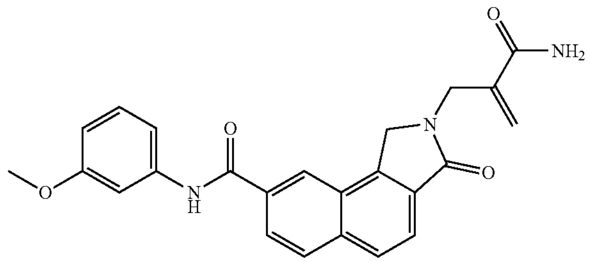 [SMILES: C=C(CN1Cc2c(ccc3ccc(C(=O)Nc4cccc(OC)c4)cc23)C1=O)C(N)=O] | 2-(2-carbamoyl-2-methylideneethyl)-N-(3-methoxyphenyl)-3-oxo-1H,2H,3H-benzo[e]isoindole-8-carboxamide | 416.1 |
| 682. | 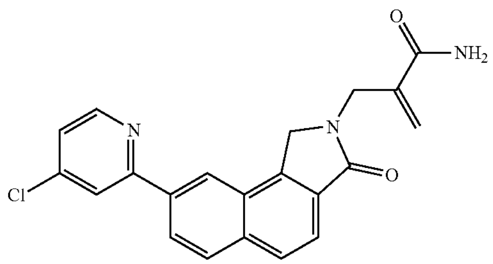 [SMILES: C=C(CN1Cc2c(ccc3ccc(-c4cc(Cl)ccn4)cc23)C1=O)C(N)=O] | 2-{[8-(4-chloropyridin-2-yl)-3-oxo-1H,2H,3H-benzo[e]isoindol-2-yl]methyl}prop-2-enamide | 378 |
| 683. | 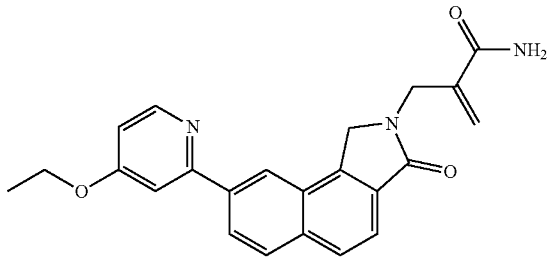 [SMILES: C=C(CN1Cc2c(ccc3ccc(-c4cc(OCC)ccn4)cc23)C1=O)C(N)=O] | 2-{[8-(4-ethoxypyridin-2-yl)-3-oxo-1H,2H,3H-benzo[e]isoindol-2-yl]methyl}prop-2-enamide | 388.1 |
| 684. | 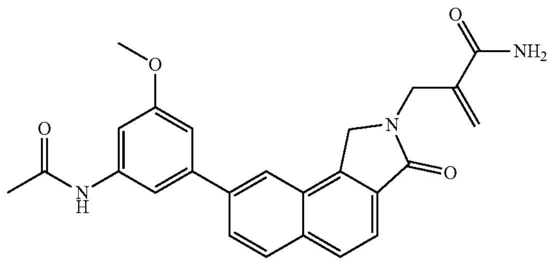 [SMILES: C=C(CN1Cc2c(ccc3ccc(-c4cc(NC(C)=O)cc(OC)c4)cc23)C1=O)C(N)=O] | 2-{[8-(3-acetamido-5-methoxyphenyl)-3-oxo-1H,2H,3H-benzo[e]isoindol-2-yl]methyl}prop-2-enamide | 430.2 |

TABLE 14-continued

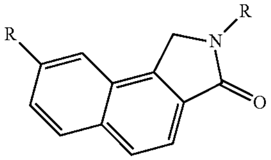

| Cpd. No. | Structure | IUPAC | LC-MS (ES+, m/z) |
|---|---|---|---|
| 685. | 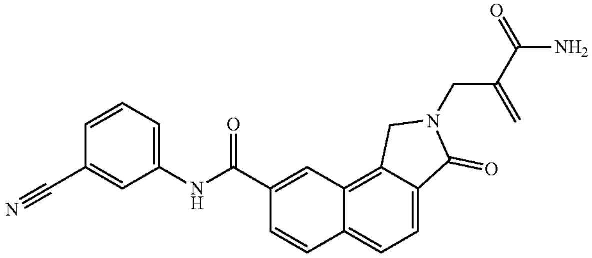 [SMILES: C=C(CN1Cc2c(ccc3ccc(C(=O)Nc4cccc(C#N)c4)cc23)C1=O)C(N)=O] | 2-(2-carbamoyl-2-methylideneethyl)-N-(3-cyanophenyl)-3-oxo-1H,2H,3H-benzo[e]isoindole-8-carboxamide | 411 |
| 686. | 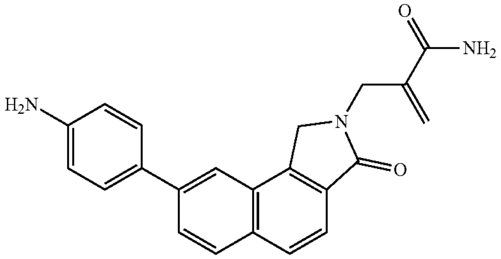 [SMILES: C=C(CN1Cc2c(ccc3ccc(-c4ccc(N)cc4)cc23)C1=O)C(N)=O] | 2-{[8-(4-aminophenyl)-3-oxo-1H,2H,3H-benzo[e]isoindol-2-yl]methyl}prop-2-enamide | 357.9 |
| 687. | 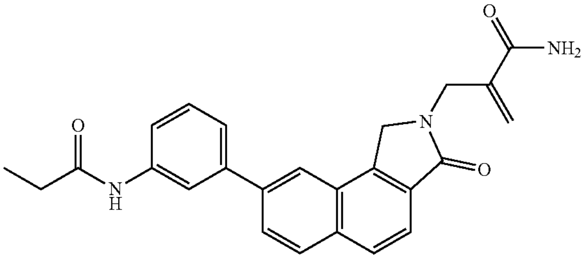 [SMILES: C=C(CN1Cc2c(ccc3ccc(-c4cccc(NC(=O)CC)c4)cc23)C1=O)C(N)=O] | 2-{[3-oxo-8-(3-propanamidophenyl)-1H,2H,3H-benzo[e]isoindol-2-yl]methyl}prop-2-enamide | 413.9 |
| 688. | 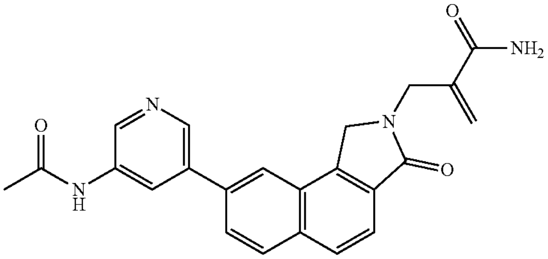 [SMILES: C=C(CN1Cc2c(ccc3ccc(-c4cncc(NC(C)=O)c4)cc23)C1=O)C(N)=O] | 2-{[8-(5-acetamidopyridin-3-yl)-3-oxo-1H,2H,3H-benzo[e]isoindol-2-yl]methyl}prop-2-enamide | 400.9 |
| 689. | 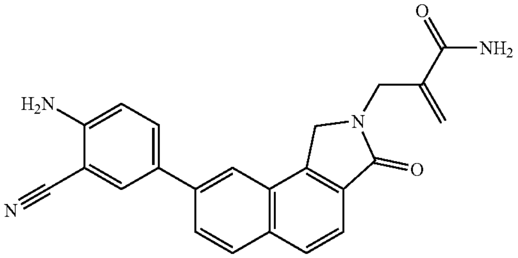 [SMILES: C=C(CN1Cc2c(ccc3ccc(-c4ccc(N)c(C#N)c4)cc23)C1=O)C(N)=O] | 2-{[8-(4-amino-3-cyanophenyl)-3-oxo-1H,2H,3H-benzo[e]isoindol-2-yl]methyl}prop-2-enamide | 382.9 |

TABLE 14-continued

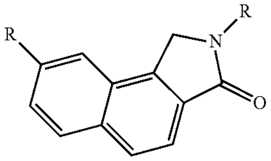

| Cpd. No. | Structure | IUPAC | LC-MS (ES+, m/z) |
|---|---|---|---|
| 690. | 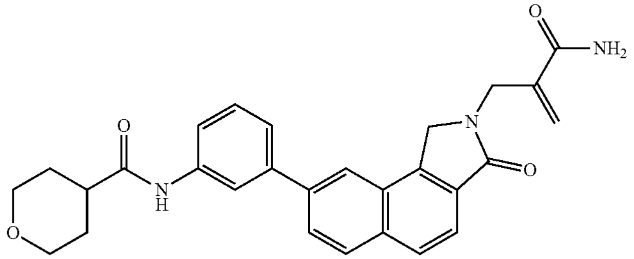 [SMILES: C=C(CN1Cc2c(ccc3ccc(-c4cccc(NC(=O)C5CCOCC5)c4)cc23)C1=O)C(N)=O] | N-{3-[2-(2-carbamoyl-2-methylideneethyl)-3-oxo-1H,2H,3H-benzo[e]isoindol-8-yl]phenyl}oxane-4-carboxamide | 469.9 |
| 691. | 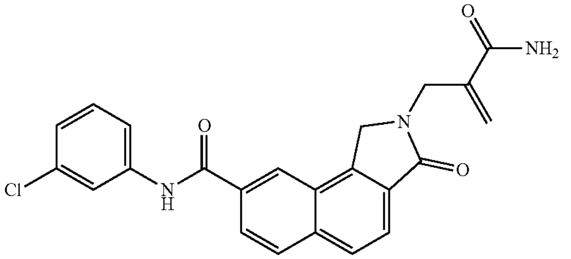 [SMILES: C=C(CN1Cc2c(ccc3ccc(C(=O)Nc4cccc(Cl)c4)cc23)C1=O)C(N)=O] | 2-(2-carbamoyl-2-methylideneethyl)-N-(3-chlorophenyl)-3-oxo-1H,2H,3H-benzo[e]isoindole-8-carboxamide | 420 |
| 692. | 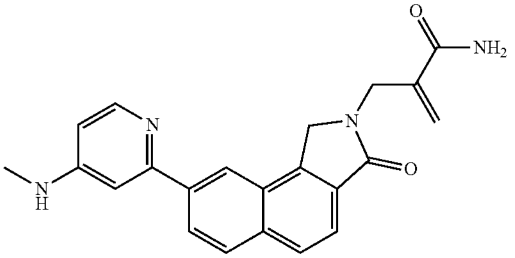 [SMILES: C=C(CN1Cc2c(ccc3ccc(-c4cc(NC)ccn4)cc23)C1=O)C(N)=O] | 2-({8-[4-(methylamino)pyridin-2-yl]-3-oxo-1H,2H,3H-benzo[e]isoindol-2-yl}methyl)prop-2-enamide | 373.1 |
| 693. | 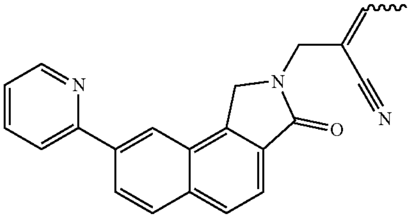 | 2-{[3-oxo-8-(pyridin-2-yl)-1H,2H,3H-benzo[e]isoindol-2-yl]methyl}but-2-enenitrile | 340.1 |
| 694. | 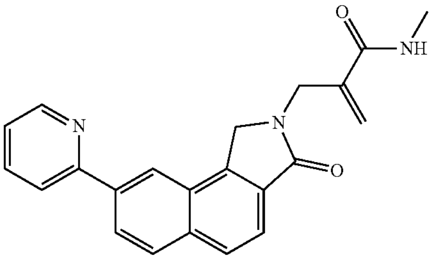 [SMILES: C=C(CN1Cc2c(ccc3ccc(-c4ccccn4)cc23)C1=O)C(=O)NC] | N-methyl-2-{[3-oxo-8-(pyridin-2-yl)-1H,2H,3H-benzo[e]isoindol-2-yl]methyl}prop-2-enamide | 358.1 |

TABLE 14-continued

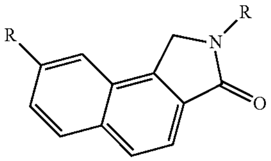

| Cpd. No. | Structure | IUPAC | LC-MS (ES+, m/z) |
|---|---|---|---|
| 695. | 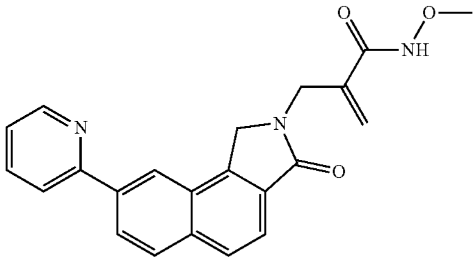 [SMILES: C=C(CN1Cc2c(ccc3ccc(-c4ccccn4)cc23)C1=O)C(=O)NOC] | N-methoxy-2-{[3-oxo-8-(pyridin-2-yl)-1H,2H,3H-benzo[e]isoindol-2-yl]methyl}prop-2-enamide | 374.1 |
| 696. | 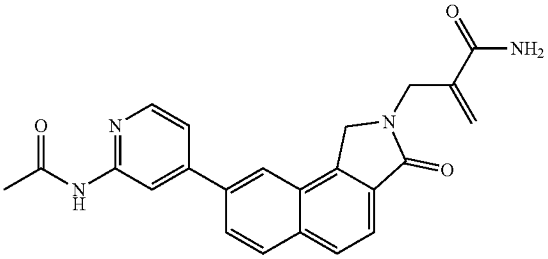 | 2-{[8-(2-acetamidopyridin-4-yl)-3-oxo-1H,2H,3H-benzo[e]isoindol-2-yl]methyl}prop-2-enamide | 401.1 |
| 697. | 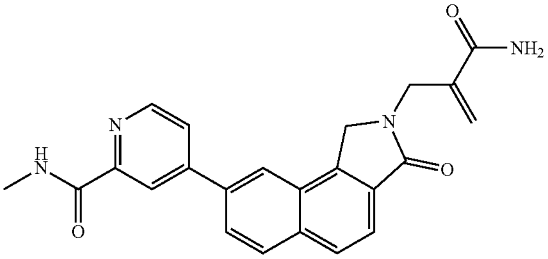 [SMILES: C=C(CN1Cc2c(ccc3ccc(-c4ccnc(C(=O)NC)c4)cc23)C1=O)C(N)=O] | 4-[2-(2-carbamoyl-2-methylideneethyl)-3-oxo-1H,2H,3H-benzo[e]isoindol-8-yl]-N-methylpyridine-2-carboxamide | 401.2 |
| 698. | 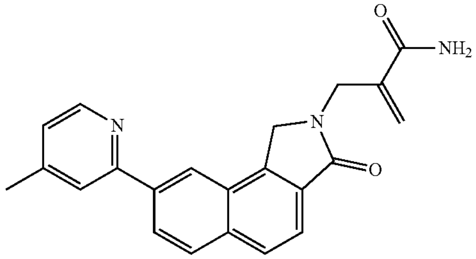 [SMILES: C=C(CN1Cc2c(ccc3ccc(-c4cc(C)ccn4)cc23)C1=O)C(N)=O] | 2-{[8-(4-methylpyridin-2-yl)-3-oxo-1H,2H,3H-benzo[e]isoindol-2-yl]methyl}prop-2-enamide | 358.1 |
| 699. | 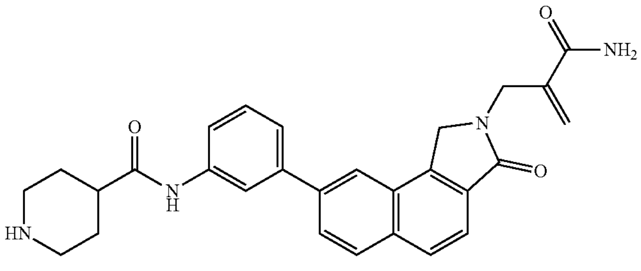 [SMILES: C=C(CN1Cc2c(ccc3ccc(-c4cccc(NC(=O)C5CCNCC5)c4)cc23)C1=O)C(N)=O] | N-{3-[2-(2-carbamoyl-2-methylideneethyl)-3-oxo-1H,2H,3H-benzo[e]isoindol-8-yl]phenyl}piperidine-4-carboxamide | 468.9 |

TABLE 14-continued

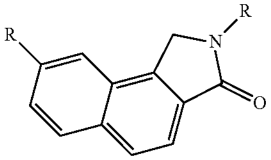

| Cpd. No. | Structure | IUPAC | LC-MS (ES+, m/z) |
|---|---|---|---|
| 700. | 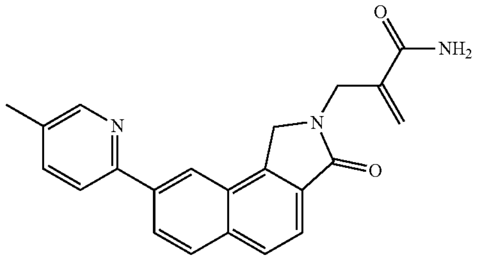 [SMILES: C=C(CN1Cc2c(ccc3ccc(-c4ccc(C)cn4)cc23)C1=O)C(N)=O] | 2-{[8-(5-methylpyridin-2-yl)-3-oxo-1H,2H,3H-benzo[e]isoindol-2-yl]methyl}prop-2-enamide | 358.1 |
| 701. | 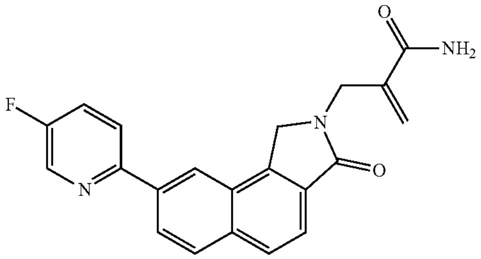 [SMILES: C=C(CN1Cc2c(ccc3ccc(-c4ccc(F)cn4)cc23)C1=O)C(N)=O] | 2-{[8-(5-fluoropyridin-2-yl)-3-oxo-1H,2H,3H-benzo[e]isoindol-2-yl]methyl}prop-2-enamide | 362.1 |
| 702. | 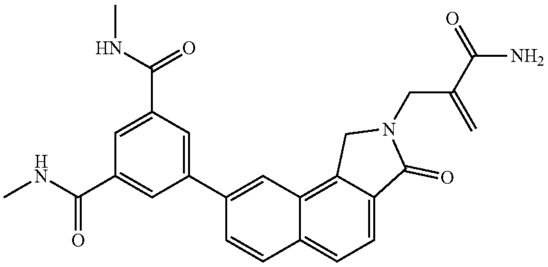 [SMILES: C=C(CN1Cc2c(ccc3ccc(-c4cc(C(=O)NC)cc(C(=O)NC)c4)cc23)C1=O)C(N)=O] | 5-[2-(2-carbamoyl-2-methylideneethyl)-3-oxo-1H,2H,3H-benzo[e]isoindol-8-yl]-N1,N3-dimethylbenzene-1,3-dicarboxamide | 457.1 |
| 703. | 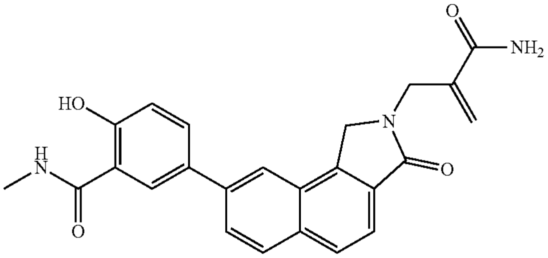 [SMILES: C=C(CN1Cc2c(ccc3ccc(-c4ccc(O)c(C(=O)NC)c4)cc23)C1=O)C(N)=O] | 5-[2-(2-carbamoyl-2-methylideneethyl)-3-oxo-1H,2H,3H-benzo[e]isoindol-8-yl] 2-hydroxy-N-methylbenzamide | 416.2 |
| 704. | 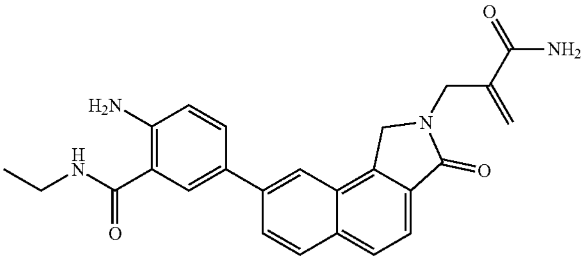 [SMILES: C=C(CN1Cc2c(ccc3ccc(-c4ccc(N)c(C(=O)NCC)c4)cc23)C1=O)C(N)=O] | 2-amino-5-[2-(2-carbamoyl-2-methylideneethyl)-3-oxo-1H,2H,3H-benzo[e]isoindol-8-yl]-N-ethylbenzamide | 429.2 |

TABLE 14-continued

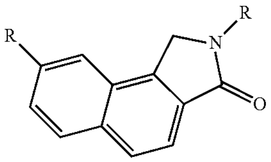

| Cpd. No. | Structure | IUPAC | LC-MS (ES+, m/z) |
|---|---|---|---|
| 705. | 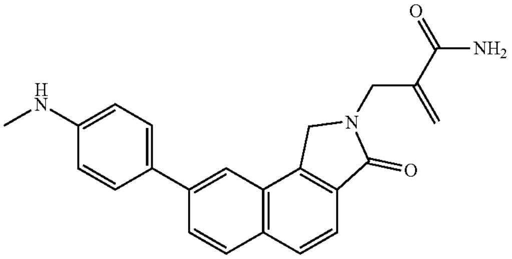 [SMILES: C=C(CN1Cc2c(ccc3ccc(-c4ccc(NC)cc4)cc23)C1=O)C(N)=O] | 2-({8-[4-(methylamino)phenyl]-3-oxo-1H,2H,3H-benzo[e]isoindol-2-yl}methyl)prop-2-enamide | 372 |
| 706. | 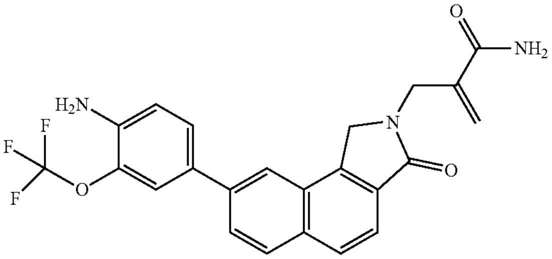 [SMILES: C=C(CN1Cc2c(ccc3ccc(-c4ccc(N)c(OC(F)(F)F)c4)cc23)C1=O)C(N)=O] | 2-({8-[4-amino-3-(trifluoromethoxy)phenyl]-3-oxo-1H,2H,3H-benzo[e]isoindol-2-yl}methyl)prop-2-enamide | 441.9 |
| 707. | 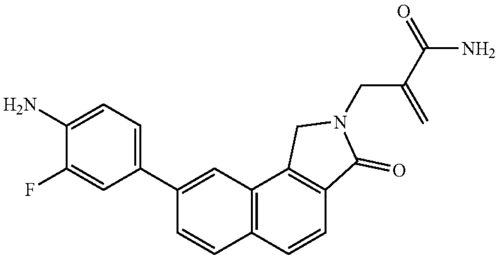 [SMILES: C=C(CN1Cc2c(ccc3ccc(-c4ccc(N)c(F)c4)cc23)C1=O)C(N)=O] | 2-{[8-(4-amino-3-fluorophenyl)-3-oxo-1H,2H,3H-benzo[e]isoindol-2-yl]methyl}prop-2-enamide | 375.9 |
| 708. | 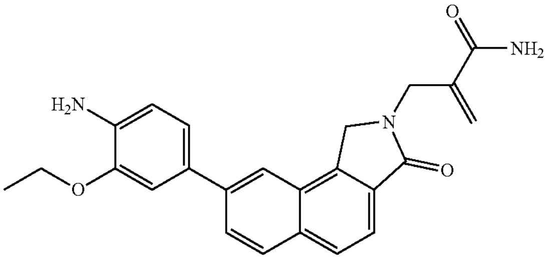 [SMILES: C=C(CN1Cc2c(ccc3ccc(-c4ccc(N)c(OCC)c4)cc23)C1=O)C(N)=O] | 2-{[8-(4-amino-3-ethoxyphenyl)-3-oxo-1H,2H,3H-benzo[e]isoindol-2-yl]methyl}prop-2-enamide | 402.1 |
| 709. | 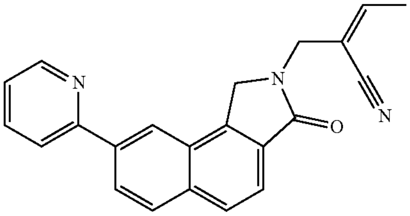 [SMILES: C/C=C(\C#N)CN1Cc2c(ccc3ccc(-c4ccccn4)cc23)C1=O] | (2Z)-2-{[3-oxo-8-(pyridin-2-yl)-1H,2H,3H-benzo[e]isoindol-2-yl]methyl}but-2-enenitrile | 340.1 |

TABLE 14-continued
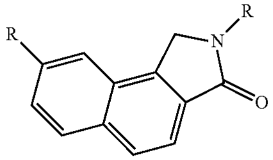
| Cpd. No. | Structure | IUPAC | LC-MS (ES+, m/z) |
|---|---|---|---|
| 710. | 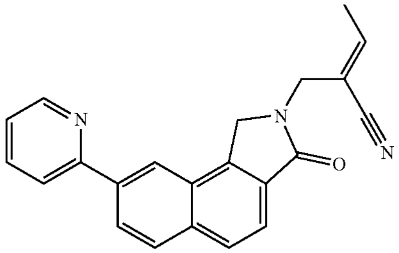 [SMILES: C/C=C(/C#N)CN1Cc2c(ccc3ccc(-c4ccccn4)cc23)C1=O] | (2E)-2-{[3-oxo-8-(pyridin-2-yl)-1H,2H,3H-benzo[e]isoindol-2-yl]methyl}but-2-enenitrile | 340.1 |
| 711. | 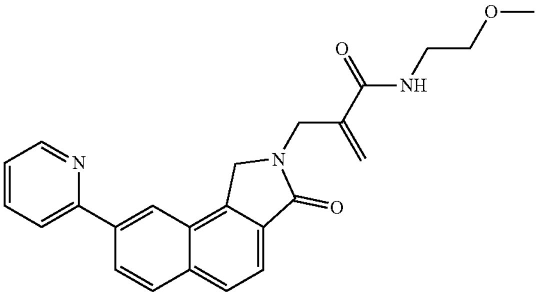 [SMILES: C=C(CN1Cc2c(ccc3ccc(-c4ccccn4)cc23)C1=O)C(=O)NCCOC] | N-(2-methoxyethyl)-2-{[3-oxo-8-(pyridin-2-yl)-1H,2H,3H-benzo[e]isoindol-2-yl]methyl}prop-2-enamide | 402.1 |
| 712. | 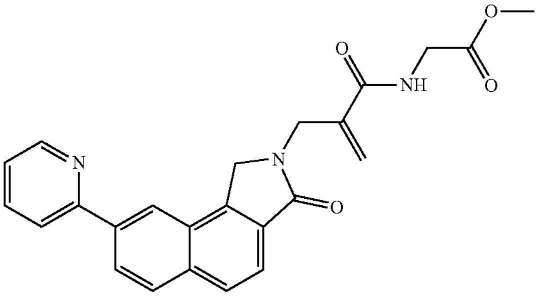 [SMILES: C=C(CN1Cc2c(ccc3ccc(-c4ccccn4)cc23)C1=O)C(=O)NCC(=O)OC] | methyl 2-(2-{[3-oxo-8-(pyridin-2-yl)-1H,2H,3H-benzo[e]isoindol-2-yl]methyl}prop-2-enamido)acetate | 416.1 |
| 713. | 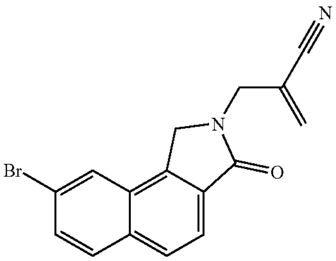 [SMILES: C=C(C#N)CN1Cc2c(ccc3ccc(Br)cc23)C1=O] | 2-({8-bromo-3-oxo-1H,2H,3H-benzo[e]isoindol-2-yl}methyl)prop-2-enenitrile | 328.9 |

TABLE 14-continued
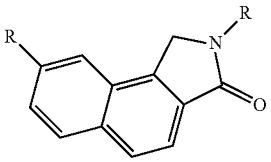
| Cpd. No. | Structure | IUPAC | LC-MS (ES+, m/z) |
|---|---|---|---|
| 714. | 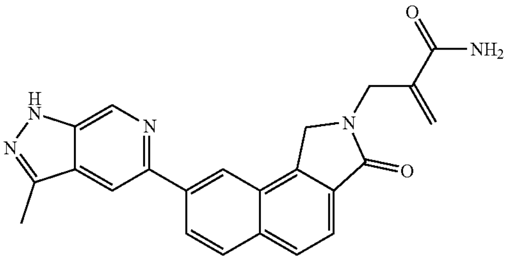 [SMILES: C=C(CN1Cc2c(ccc3ccc(-c4cc5c(C)n[nH]c5cn4)cc23)C1=O)C(N)=O] | 2-[(8-{3-methyl-1H-pyrazolo[3,4-c]pyridin-5-yl}-3-oxo-1H,2H,3H-benzo[e]isoindol-2-yl)methyl]prop-2-enamide | 398 |
| 715. | 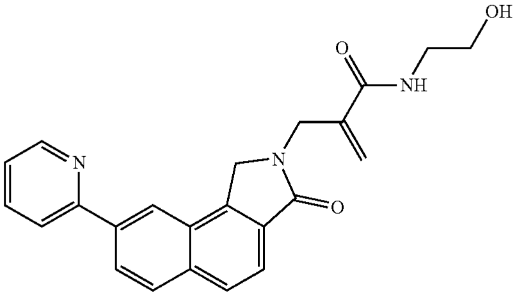 [SMILES: C=C(CN1Cc2c(ccc3ccc(-c4ccccn4)cc23)C1=O)C(=O)NCCO] | N-(2-hydroxyethyl)-2-{[3-oxo-8-(pyridin-2-yl)-1H,2H,3H-benzo[e]isoindol-2-yl]methyl}prop-2-enamide | 388.1 |
| 716. | 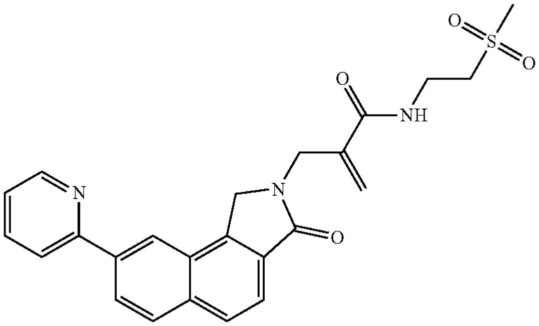 [SMILES: C=C(CN1Cc2c(ccc3ccc(-c4ccccn4)cc23)C1=O)C(=O)NCCS(C)(=O)=O] | N-(2-methanesulfonylethyl)-2-{[3-oxo-8-(pyridin-2-yl)-1H,2H,3H-benzo[e]isoindol-2-yl]methyl}prop-2-enamide | 450.1 |
| 717. | 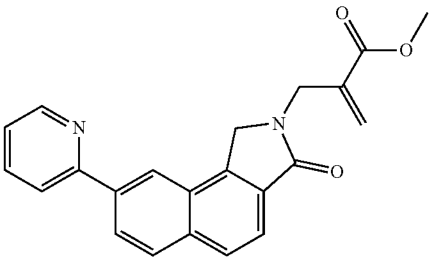 [SMILES: C=C(CN1Cc2c(ccc3ccc(-c4ccccn4)cc23)C1=O)C(=O)OC] | methyl 2-{[3-oxo-8-(pyridin-2-yl)-1H,2H,3H-benzo[e]isoindol-2-yl]methyl}prop-2-enamide | 359.1 |

TABLE 14-continued

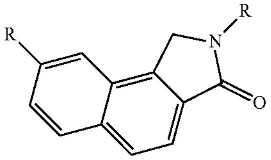

| Cpd. No. | Structure | IUPAC | LC-MS (ES+, m/z) |
|---|---|---|---|
| 718. | 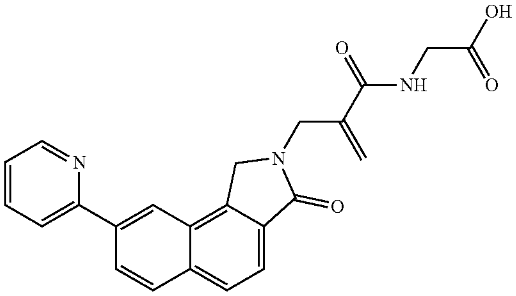 [SMILES: C=C(CN1Cc2c(ccc3ccc(-c4ccccn4)cc23)C1=O)C(=O)NCC(=O)O] | 2-(2-{[3-oxo-8-(pyridin-2-yl)-1H,2H,3H-benzo[e]isoindol-2-yl]methyl}prop-2-enamido)acetic acid | 402.1 |
| 719. | 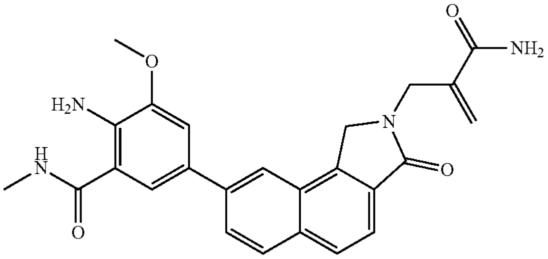 [SMILES: C=C(CN1Cc2c(ccc3ccc(-c4cc(OC)c(N)c(C(=O)NC)c4)cc23)C1=O)C(N)=O] | 2-amino-5-[2-(2-carbamoyl-2-methylideneethyl)-3-oxo-1H,2H,3H-benzo[e]isoindol-8-yl]-3-methoxy-N-methylbenzamide | 445.3 |
| 720. | 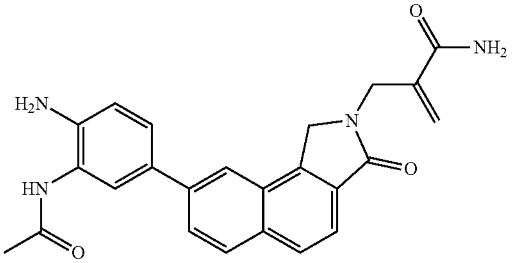 [SMILES: C=C(CN1Cc2c(ccc3ccc(-c4ccc(N)c(NC(C)=O)c4)cc23)C1=O)C(N)=O] | 2-{[8-(4-amino-3-acetamidophenyl)-3-oxo-1H,2H,3H-benzo[e]isoindol-2-yl]methyl}prop-2-enamide | 415.2 |
| 721. | 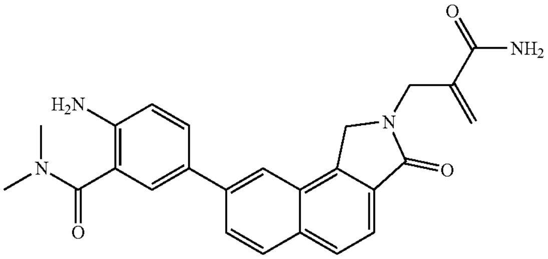 [SMILES: C=C(CN1Cc2c(ccc3ccc(-c4ccc(N)c(C(=O)N(C)C)c4)cc23)C1=O)C(N)=O] | 2-amino-5-[2-(2-carbamoyl-2-methylideneethyl)-3-oxo-1H,2H,3H-benzo[e]isoindol-8-yl]-N,N-dimethylbenzamide | 429.1 |
| 722. | 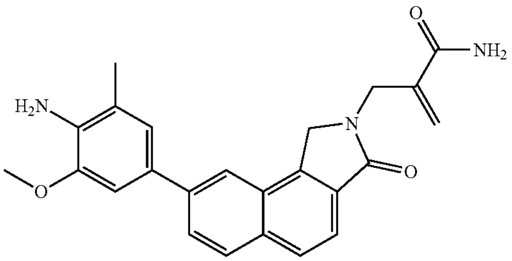 [SMILES: C=C(CN1Cc2c(ccc3ccc(-c4cc(C)c(N)c(OC)c4)cc23)C1=O)C(N)=O] | 2-{[8-(4-amino-3-methoxy-5-methylphenyl)-3-oxo-1H,2H,3H-benzo[e]isoindol-2-yl]methyl}prop-2-enamide | 402.2 |

TABLE 14-continued
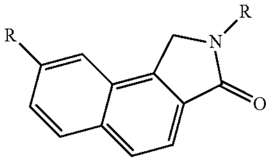
| Cpd. No. | Structure | IUPAC | LC-MS (ES+, m/z) |
|---|---|---|---|
| 723. | 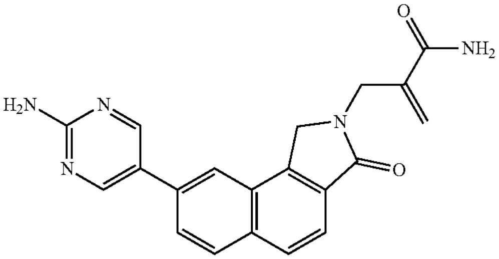 [SMILES: C=C(CN1Cc2c(ccc3ccc(-c4cnc(N)nc4)cc23)C1=O)C(N)=O] | 2-{[8-(2-aminopyrimidin-5-yl)-3-oxo-1H,2H,3H-benzo[e]isoindol-2-yl]methyl}prop-2-enamide | 360 |
| 724. | 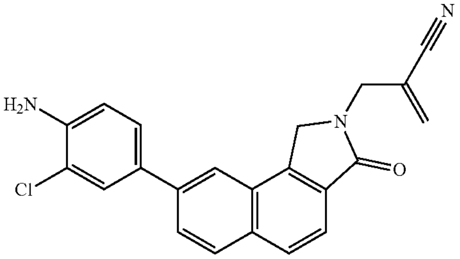 [SMILES: C=C(C#N)CN1Cc2c(ccc3ccc(-c4ccc(N)c(Cl)c4)cc23)C1=O] | 2-{[8-(4-amino-3-chlorophenyl)-3-oxo-1H,2H,3H-benzo[e]isoindol-2-yl]methyl}prop-2-enenitrile | 373.9 |
| 725. | 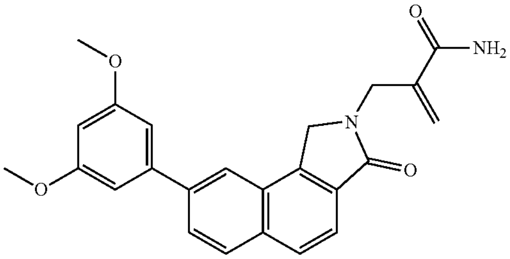 [SMILES: C=C(CN1Cc2c(ccc3ccc(-c4cc(OC)cc(OC)c4)cc23)C1=O)C(N)=O] | 2-{[8-(3,5-dimethoxyphenyl)-3-oxo-1H,2H,3H-benzo[e]isoindol-2-yl]methyl}prop-2-enamide | 402.9 |
| 726. | 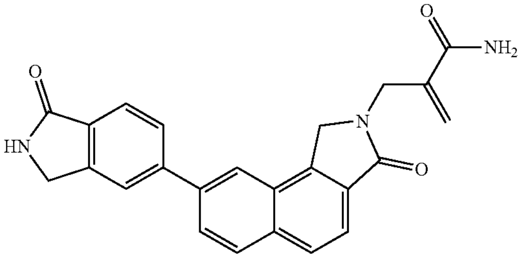 [SMILES: C=C(CN1Cc2c(ccc3ccc(-c4ccc5c(c4)CNC5=O)cc23)C1=O)C(N)=O] | 2-{[3-oxo-8-(1-oxo-2,3-dihydro-1H-isoindol-5-yl)-1H,2H,3H-benzo[e]isoindol-2-yl]methyl}prop-2-enamide | 398.1 |

TABLE 14-continued
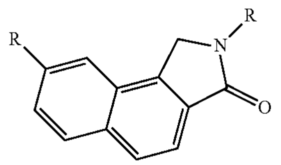
| Cpd. No. | Structure | IUPAC | LC-MS (ES+, m/z) |
|---|---|---|---|
| 727. | 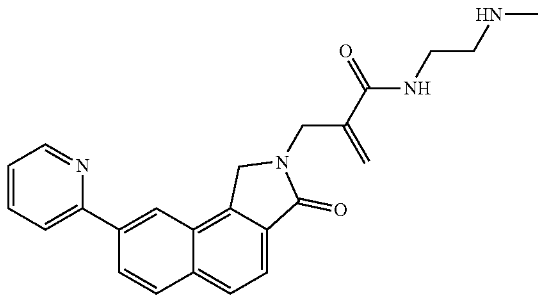 [SMILES: C=C(CN1Cc2c(ccc3ccc(-c4ccccn4)cc23)C1=O)C(=O)NCCNC] | N-[2-(methylamino)ethyl]-2-{[3-oxo-8-(pyridin-2-yl)-1H,2H,3H-benzo[e]isoindol-2-yl]methyl}prop-2-enamide | 401.1 |
| 728. | 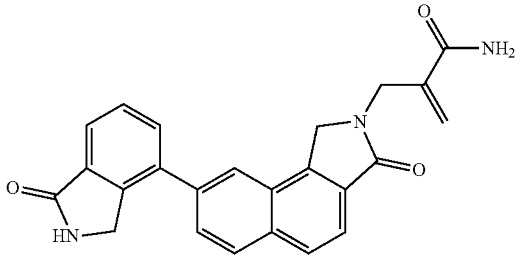 [SMILES: C=C(CN1Cc2c(ccc3ccc(-c4cccc5c4CNC5=O)cc23)C1=O)C(N)=O] | 2-{[3-oxo-8-(1-oxo-2,3-dihydro-1H-isoindol-4-yl)-1H,2H,3H-benzo[e]isoindol-2-yl]methyl}prop-2-enamide | 398.1 |
| 729. | 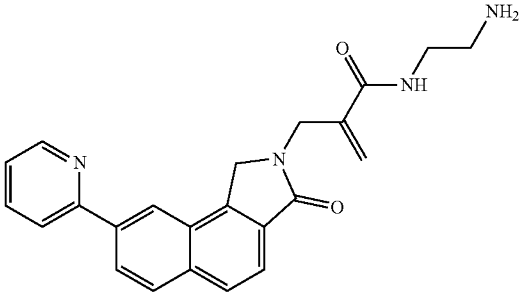 [SMILES: C=C(CN1Cc2c(ccc3ccc(-c4ccccn4)cc23)C1=O)C(=O)NCCN] | N-(2-aminoethyl)-2-{[3-oxo-8-(pyridin-2-yl)-1H,2H,3H-benzo[e]isoindol-2-yl]methyl}prop-2-enamide | 387.1 |
| 730. | 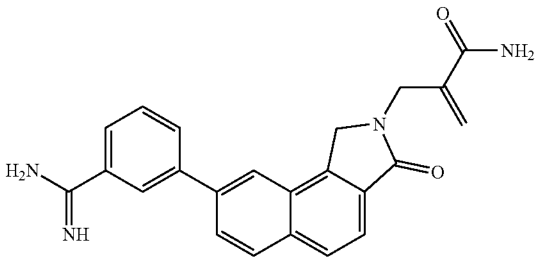 [SMILES: C=C(CN1Cc2c(ccc3ccc(-c4cccc(C(=N)N)c4)cc23)C1=O)C(N)=O] | 2-{[8-(3-carbamimidoylphenyl)-3-oxo-1H,2H,3H-benzo[e]isoindol-2-yl]methyl}prop-2-enamide | 385.1 |

TABLE 14-continued

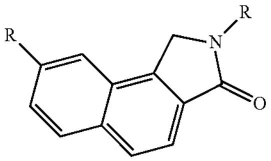

| Cpd. No. | Structure | IUPAC | LC-MS (ES+, m/z) |
|---|---|---|---|
| 731. | 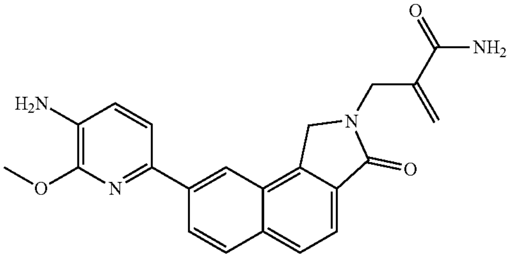 [SMILES: C=C(CN1Cc2c(ccc3ccc(-c4ccc(N)c(OC)n4)cc23)C1=O)C(N)=O] | 2-{[8-(5-amino-6-methoxypyridin-2-yl)-3-oxo-1H,2H,3H-benzo[e]isoindol-2-yl]methyl}prop-2-enamide | 389.1 |
| 732. | 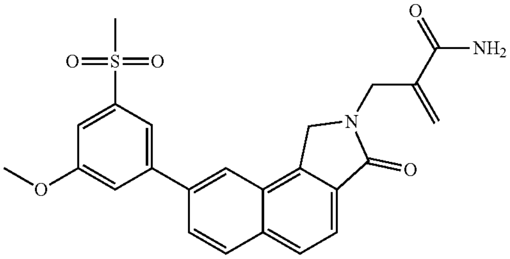 [SMILES: C=C(CN1Cc2c(ccc3ccc(-c4cc(OC)cc(S(C)(=O)=O)c4)cc23)C1=O)C(N)=O] | 2-{[8-(3-methanesulfonyl-5-methoxyphenyl)-3-oxo-1H,2H,3H-benzo[e]isoindol-2-yl]methyl}prop-2-enamide | 451 |
| 733. | 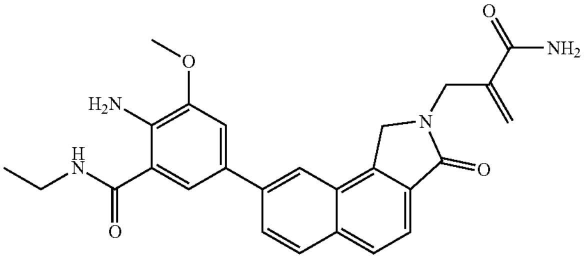 [SMILES: C=C(CN1Cc2c(ccc3ccc(-c4cc(OC)c(N)c(C(=O)NCC)c4)cc23)C1=O)C(N)=O] | 2-amino-5-[2-(2-carbamoyl-2-methylideneethyl)-3-oxo-1H,2H,3H-benzo[e]isoindol-8-yl]-N-ethyl-3-methoxybenzamide | 459.2 |
| 734. | 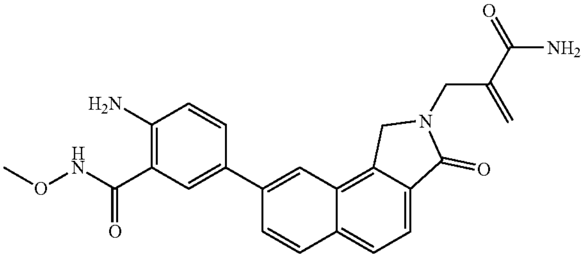 | 2-amino-5-[2-(2-carbamoyl-2-methylideneethyl)-3-oxo-1H,2H,3H-benzo[e]isoindol-8-yl]-N-methoxybenzamide | 431.1 |
| 735. | 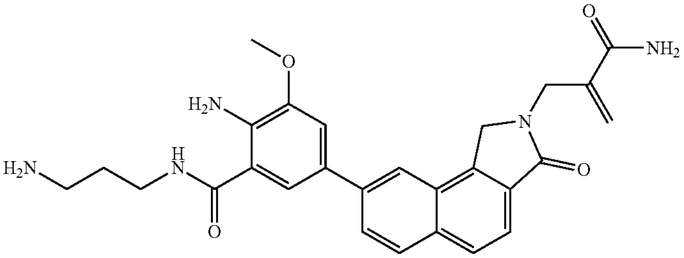 [SMILES: C=C(CN1Cc2c(ccc3ccc(-c4cc(OC)c(N)c(C(=O)NCCCN)c4)cc23)C1=O)C(N)=O] | 2-amino-N-(3-aminopropyl)-5-[2-(2-carbamoyl-2-methylideneethyl)-3-oxo-1H,2H,3H-benzo[e]isoindol-8-yl]-3-methoxybenzamide | 488.2 |

TABLE 14-continued

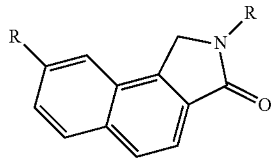

| Cpd. No. | Structure | IUPAC | LC-MS (ES+, m/z) |
|---|---|---|---|
| 736. | 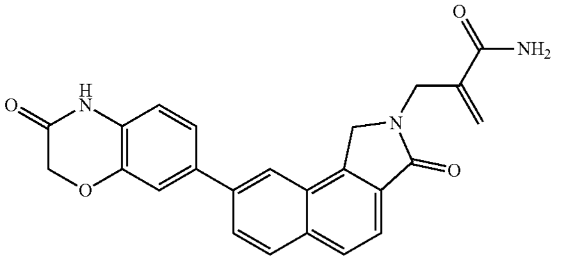 [SMILES: C=C(CN1Cc2c(ccc3ccc(-c4ccc5c(c4)OCC(=O)N5)cc23)C1=O)C(N)=O] | 2-{[3-oxo-8-(3-oxo-3,4-dihydro-2H-1,4-benzoxazin-7-yl)-1H,2H,3H-benzo[e]isoindol-2-yl]methyl}prop-2-enamide | 414.1 |
| 737. | 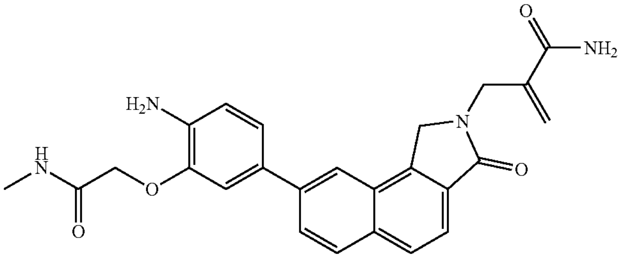 [SMILES: C=C(CN1Cc2c(ccc3ccc(-c4ccc(N)c(OCC(=O)NC)c4)cc23)C1=O)C(N)=O] | 2-[(8-{4-amino-3-[(methylcarbamoyl)methoxy]phenyl}-3-oxo-1H,2H,3H-benzo[e]isoindol-2-yl)methyl]prop-2-enamide | 445.2 |
| 738. | 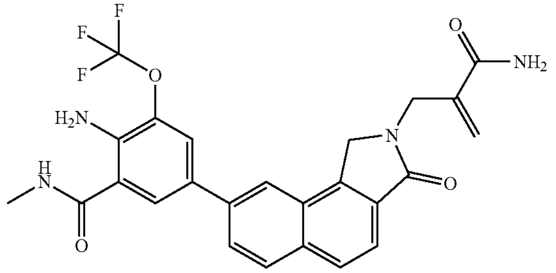 [SMILES: C=C(CN1Cc2c(ccc3ccc(-c4cc(OC(F)(F)F)c(N)c(C(=O)NC)c4)cc23)C1=O)C(N)=O] | 2-amino-5-[2-(2-carbamoyl-2-methylideneethyl)-3-oxo-1H,2H,3H-benzo[e]isoindol-8-yl]-N-methyl-3-(trifluoromethoxy)benzamide | 499.1 |
| 739. | 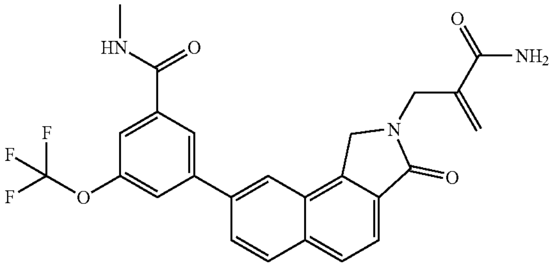 [SMILES: C=C(CN1Cc2c(ccc3ccc(-c4cc(OC(F)(F)F)cc(C(=O)NC)c4)cc23)C1=O)C(N)=O] | 3-[2-(2-carbamoyl-2-methylideneethyl)-3-oxo-1H,2H,3H-benzo[e]isoindol-8-yl]-N-methyl-5-(trifluoromethoxy)benzamide | 483.9 |

TABLE 14-continued

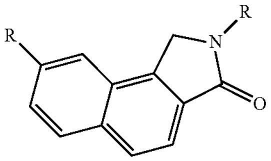

| Cpd. No. | Structure | IUPAC | LC-MS (ES+, m/z) |
|---|---|---|---|
| 740. | 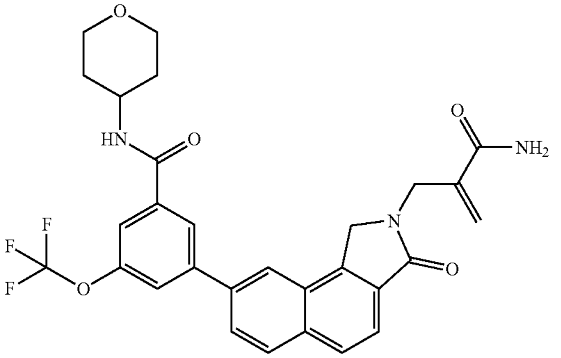 [SMILES: C=C(CN1Cc2c(ccc3ccc(-c4cc(OC(F)(F)F)cc(C(=O)NC5CCOCC5)c4)cc23)C1=O)C(N)=O] | 3-[2-(2-carbamoyl-2-methylideneethyl)-3-oxo-1H,2H,3H-benzo[e]isoindol-8-yl]-N-(oxan-4-yl)-5-(trifluoromethoxy)benzamide | 553.9 |
| 741. | 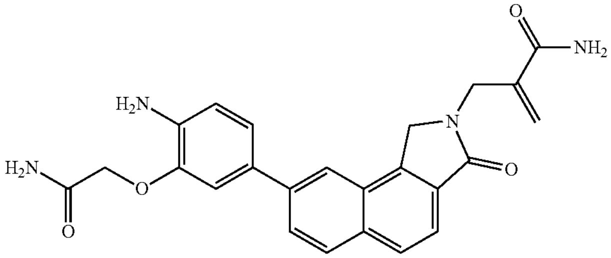 [SMILES: C=C(CN1Cc2c(ccc3ccc(-c4ccc(N)c(OCC(N)=O)c4)cc23)C1=O)C(N)=O] | 2-({8-[4-amino-3-(carbamoylmethoxy)phenyl]-3-oxo-1H,2H,3H-benzo[e]isoindol-2-yl}methyl)prop-2-enamide | 431.1 |
| 742. | 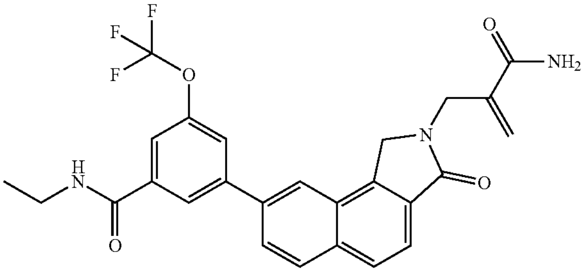 [SMILES: C=C(CN1Cc2c(ccc3ccc(-c4cc(OC(F)(F)F)cc(C(=O)NCC)c4)cc23)C1=O)C(N)=O] | 3-[2-(2-carbamoyl-2-methylideneethyl)-3-oxo-1H,2H,3H-benzo[e]isoindol-8-yl]-N-ethyl-5-(trifluoromethoxy) benzamide | 497.9 |
| 743. | 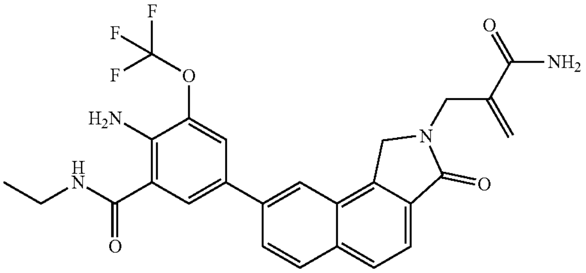 [SMILES: C=C(CN1Cc2c(ccc3ccc(-c4cc(OC(F)(F)F)c(N)c(C(=O)NCC)c4)cc23)C1=O)C(N)=O] | 2-amino-5-[2-(2-carbamoyl-2-methylideneethyl)-3-oxo-1H,2H,3H-benzo[e]isoindol-8-yl]-N-ethyl-3-(trifluoromethoxy) benzamide | 512.9 |

TABLE 14-continued

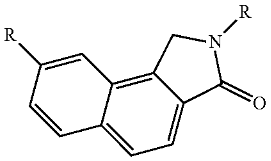

| Cpd. No. | Structure | IUPAC | LC-MS (ES+, m/z) |
|---|---|---|---|
| 744. | 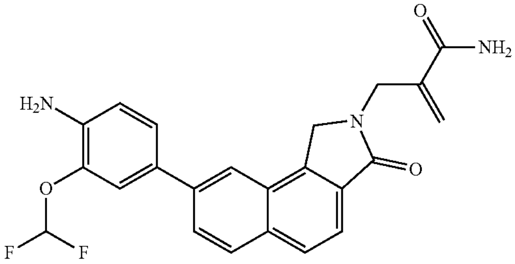 [SMILES: C=C(CN1Cc2c(ccc3ccc(-c4ccc(N)c(OC(F)F)c4)cc23)C1=O)C(N)=O] | 2-({8-[4-amino-3-(difluoromethoxy)phenyl]-3-oxo-1H,2H,3H-benzo[e]isoindol-2-yl}methyl)prop-2-enamide | 424.2 |
| 745. | 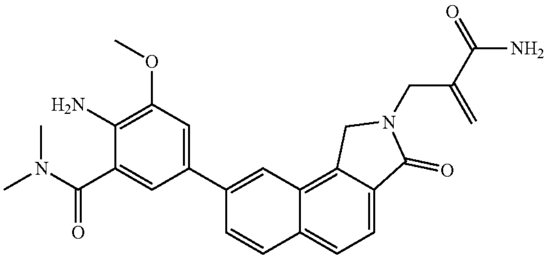 [SMILES: C=C(CN1Cc2c(ccc3ccc(-c4cc(OC)c(N)c(C(=O)N(C)C)c4)cc23)C1=O)C(N)=O] | 2-amino-5-[2-(2-carbamoyl-2-methylideneethyl)-3-oxo-1H,2H,3H-benzo[e]isoindol-8-yl]-3-methoxy-N,N-dimethylbenzamide | 459.2 |
| 746. | 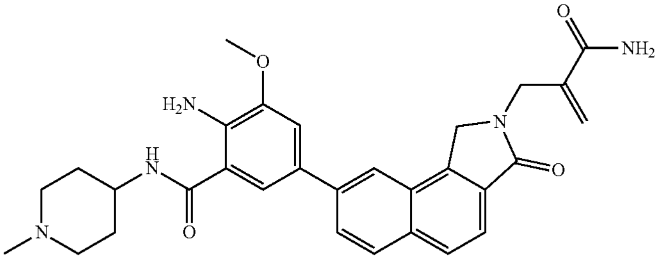 [SMILES: C=C(CN1Cc2c(ccc3ccc(-c4cc(OC)c(N)c(C(=O)NC5CCN(C)CC5)c4)cc23)C1=O)C(N)=O] | 2-amino-5-[2-(2-carbamoyl-2-methylideneethyl)-3-oxo-1H,2H,3H-benzo[e]isoindol-8-yl]-3-methoxy-N-(1-methylpiperidin-4-yl)benzamide | 528.3 |
| 747. | 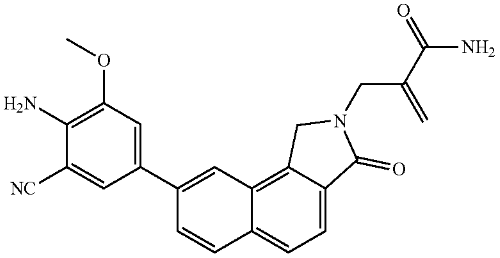 [SMILES: C=C(CN1Cc2c(ccc3ccc(-c4cc(C#N)c(N)c(OC)c4)cc23)C1=O)C(N)=O] | 4-[2-(2-carbamoyl-2-methylideneethyl)-3-oxo-1H,2H,3H-benzo[e]isoindol-8-yl]-2-cyano-6-methoxyaniline | 413.2 |
| 748. | 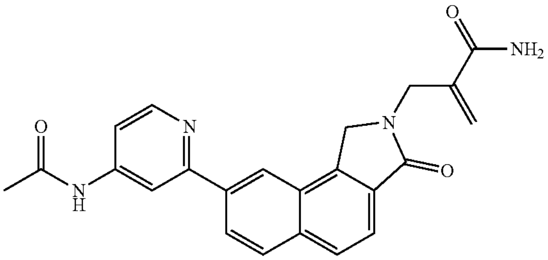 [SMILES: C=C(CN1Cc2c(ccc3ccc(-c4cc(NC(C)=O)ccn4)cc23)C1=O)C(N)=O] | 2-{[8-(4-acetamidopyridin-2-yl)-3-oxo-1H,2H,3H-benzo[e]isoindol-2-yl]methyl}prop-2-enamide | 401.2 |

TABLE 14-continued

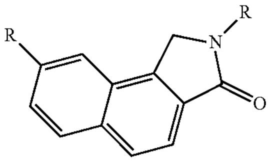

| Cpd. No. | Structure | IUPAC | LC-MS (ES+, m/z) |
|---|---|---|---|
| 749. | 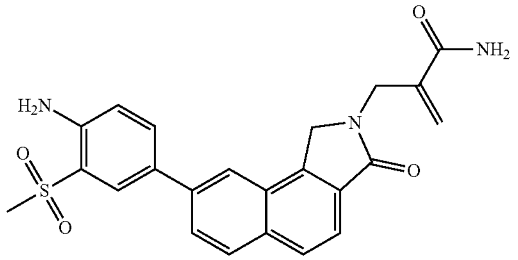 [SMILES: C=C(CN1Cc2c(ccc3ccc(-c4ccc(N)c(S(C)(=O)=O)c4)cc23)C1=O)C(N)=O] | 2-{[8-(4-amino-3-methanesulfonylphenyl)-3-oxo-1H,2H,3H-benzo[e]isoindol-2-yl]methyl}prop-2-enamide | 436.1 |
| 750. | 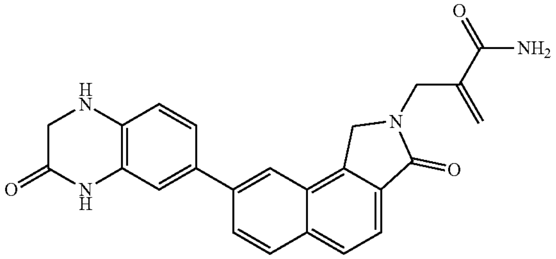 [SMILES: C=C(CN1Cc2c(ccc3ccc(-c4ccc5c(c4)NC(=O)CN5)cc23)C1=O)C(N)=O] | 2-{[3-oxo-8-(3-oxo-1,2,3,4-tetrahydroquinoxalin-6-yl)-1H,2H,3H-benzo[e]isoindol-2-yl] methyl}prop-2-enamide | 410.9 |
| 751. | 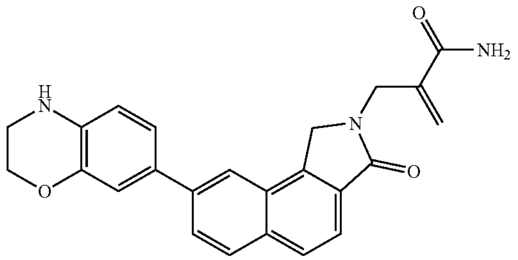 [SMILES: C=C(CN1Cc2c(ccc3ccc(-c4ccc5c(c4)OCCN5)cc23)C1=O)C(N)=O] | 2-{[8-(3,4-dihydro-2H-1,4-benzoxazin-7-yl)-3-oxo-1H,2H,3H-benzo[e]isoindol-2-yl]methyl}prop-2-enamide | 400.1 |
| 752. | 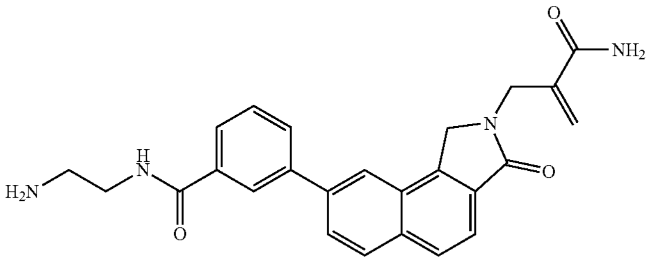 [SMILES: C=C(CN1Cc2c(ccc3ccc(-c4cccc(C(=O)NCCN)c4)cc23)C1=O)C(N)=O] | N-(2-aminoethyl)-3-[2-(2-carbamoyl-2-methyleneethyl)-3-oxo-1H,2H,3H-benzo[e]isoindol-8-yl]-benzamide | 429.1 |
| 753. | 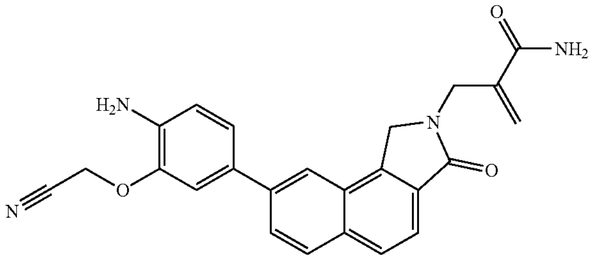 [SMILES: C=C(CN1Cc2c(ccc3ccc(-c4ccc(N)c(OCC#N)c4)cc23)C1=O)C(N)=O] | 2-({8-[4-amino-3-(cyanomethoxy)phenyl]-3-oxo-1H,2H,3H-benzo[e]isoindol-2-yl}methyl)prop-2-enamide | 413.2 |

TABLE 14-continued

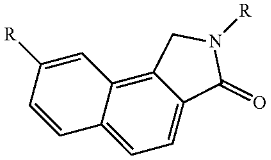

| Cpd. No. | Structure | IUPAC | LC-MS (ES+, m/z) |
|---|---|---|---|
| 754. | 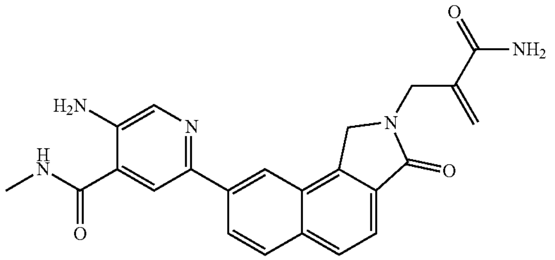 [SMILES: C=C(CN1Cc2c(ccc3ccc(-c4cc(C(=O)NC)c(N)cn4)cc23)C1=O)C(N)=O] | 5-amino-2-[2-(2-carbamoyl-2-methylideneethyl)-3-oxo-1H,2H,3H-benzo[e]isoindol-8-yl]-N-methylpyridine-4-carboxamide | 416 |
| 755. | 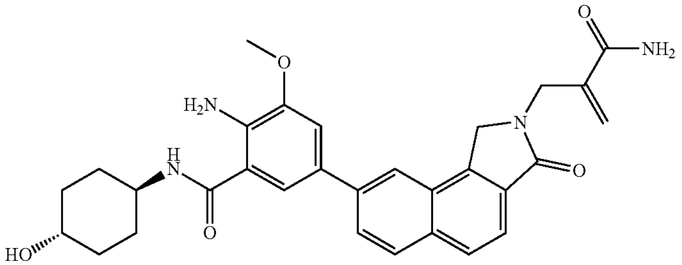 [SMILES: C=C(CN1Cc2c(ccc3ccc(-c4cc(OC)c(N)c(C(=O)N[C@H]5CC[C@H](O)CC5)c4)cc23)C1=O)C(N)=O] | 2-amino-5-[2-(2-carbamoyl-2-methylideneethyl)-3-oxo-1H,2H,3H-benzo[e]isoindol-8-yl]-3-methoxy-N-[(1r,4r)-4-hydroxycyclohexyl]benzamide | 529.3 |
| 756. | 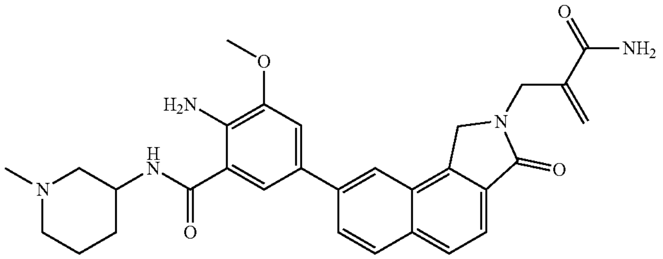 [SMILES: C=C(CN1Cc2c(ccc3ccc(-c4cc(OC)c(N)c(C(=O)NC5CCCN(C)C5)c4)cc23)C1=O)C(N)=O] | 2-amino-5-[2-(2-carbamoyl-2-methylideneethyl)-3-oxo-1H,2H,3H-benzo[e]isoindol-8-yl]-3-methoxy-N-(1-methylpiperidin-3-yl)benzamide | 528.3 |
| 757. | 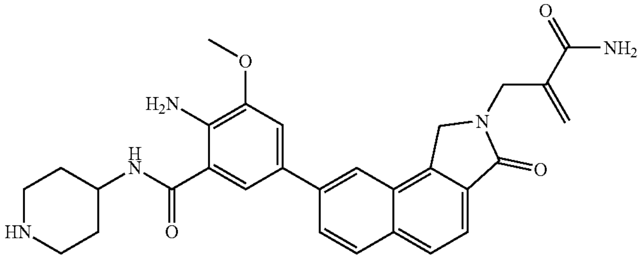 [SMILES: C=C(CN1Cc2c(ccc3ccc(-c4cc(OC)c(N)c(C(=O)NC5CCNCC5)c4)cc23)C1=O)C(N)=O] | 2-amino-5-[2-(2-carbamoyl-2-methylideneethyl)-3-oxo-1H,2H,3H-benzo[e]isoindol-8-yl]-3-methoxy-N-(piperidin-4-yl) benzamide | 514.3 |
| 758. | 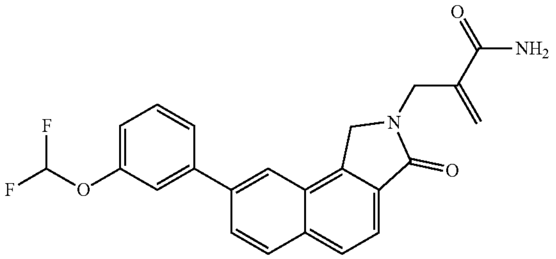 [SMILES: C=C(CN1Cc2c(ccc3ccc(-c4cccc(OC(F)F)c4)cc23)C1=O)C(N)=O] | 2-({8-[3-(difluoromethoxy)phenyl]-3-oxo-1H,2H,3H-benzo[e]isoindol-2-yl}methyl)prop-2-enamide | 409.1 |

TABLE 14-continued

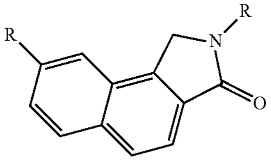

| Cpd. No. | Structure | IUPAC | LC-MS (ES+, m/z) |
|---|---|---|---|
| 759. | 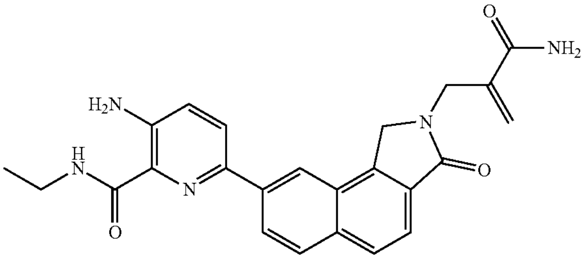 [SMILES: C=C(CN1Cc2c(ccc3ccc(-c4ccc(N)c(C(=O)NCC)n4)cc23)C1=O)C(N)=O] | 3-amino-6-[2-(2-carbamoyl-2-methylideneethyl)-3-oxo-1H,2H,3H-benzo[e]isoindol-8-yl]-N-ethylpyridine-2-carboxamide | 430.2 |
| 760. | 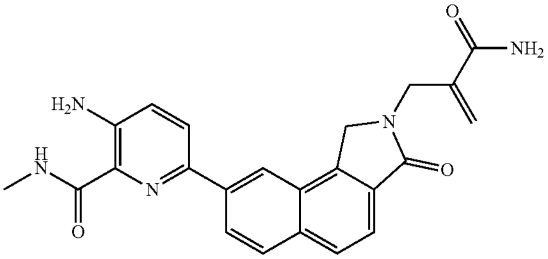 [SMILES: C=C(CN1Cc2c(ccc3ccc(-c4ccc(N)c(C(=O)NC)n4)cc23)C1=O)C(N)=O] | 3-amino-6-[2-(2-carbamoyl-2-methylideneethyl)-3-oxo-1H,2H,3H-benzo[e]isoindol-8-yl]-N-methylpyridine-2-carboxamide | 416 |
| 761. | 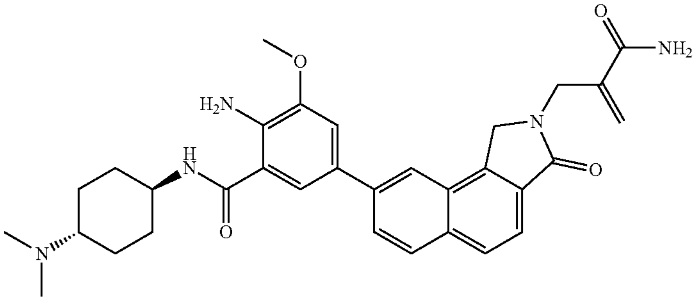 [SMILES: C=C(CN1Cc2c(ccc3ccc(-c4cc(OC)c(N)c(C(=O)N[C@H]5CC[C@H](N(C)C)CC5)c4)cc23)C1=O)C(N)=O] | 2-amino-5-[2-(2-carbamoyl-2-methylideneethyl)-3-oxo-1H,2H,3H-benzo[e]isoindol-8-yl]-3-methoxy-N-[(1r,4r)-4-(dimethylamino)cyclohexyl]benzamide | 555.2 |
| 762. | 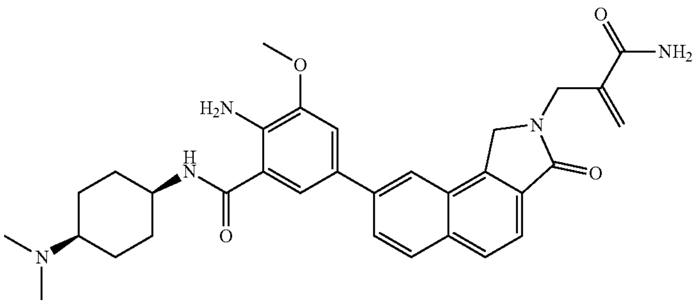 [SMILES: C=C(CN1Cc2c(ccc3ccc(-c4cc(OC)c(N)c(C(=O)N[C@H]5CC[C@@H](N(C)C)CC5)c4)cc23)C1=O)C(N)=O] | 2-amino-5-[2-(2-carbamoyl-2-methylideneethyl)-3-oxo-1H,2H,3H-benzo[e]isoindol-8-yl]-3-methoxy-N-[(1s,4s)-4-(dimethylamino)cyclohexyl] benzamide | 556.2 |

TABLE 14-continued
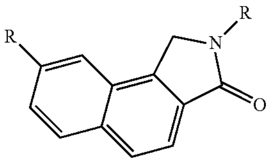
| Cpd. No. | Structure | IUPAC | LC-MS (ES+, m/z) |
|---|---|---|---|
| 763. | 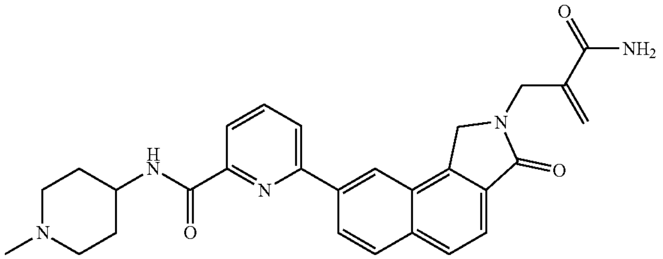 [SMILES: C=C(CN1Cc2c(ccc3ccc(-c4cccc(C(=O)NC5CCN(C)CC5)n4)cc23)C1=O)C(N)=O] | 6-[2-(2-carbamoyl-2-methylideneethyl)-3-oxo-1H,2H,3H-benzo[e]isoindol-8-yl]-N-(1-methylpiperidin-4-yl)pyridine-2-carboxamide | 484.2 |
| 764. | 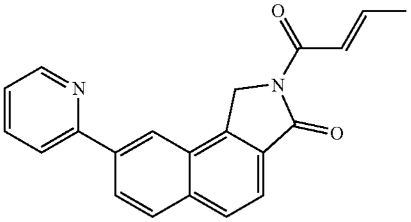 [SMILES: C/C=C/C(=O)N1Cc2c(ccc3ccc(-c4ccccn4)cc23)C1=O] | 2-[(2E)-but-2-enoyl]-8-(pyridin-2-yl)-1H,2H,3H-benzo[e]isoindol-3-one | 329.1 |
| 765. | 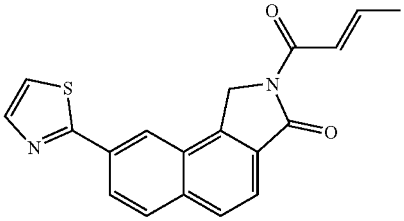 [SMILES: C/C=C/C(=O)N1Cc2c(ccc3ccc(-c4nccs4)cc23)C1=O] | 2-[(2E)-but-2-enoyl]-8-(1,3-thiazol-2-yl)-1H,2H,3H-benzo[e]isoindol-3-one | 335.1 |
| 766. | 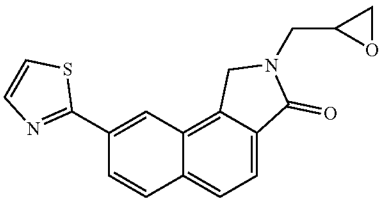 [SMILES: O=C1c2ccc3ccc(-c4nccs4)cc3c2CN1CC1CO1] | 2-[(oxiran-2-yl)methyl]-8-(1,3-thiazol-2-yl)-1H,2H,3H-benzo[e]isoindol-3-one | 323 |
| 767. | 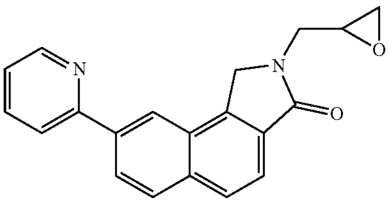 [SMILES: O=C1c2ccc3ccc(-c4ccccn4)cc3c2CN1CC1CO1] | 2-[(oxiran-2-yl)methyl]-8-(pyridin-2-yl)-1H,2H,3H-benzo[e]isoindol-3-one | 317.1 |

TABLE 14-continued
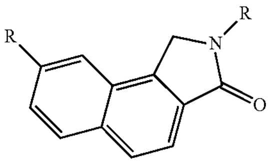
| Cpd. No. | Structure | IUPAC | LC-MS (ES+, m/z) |
|---|---|---|---|
| 768. | 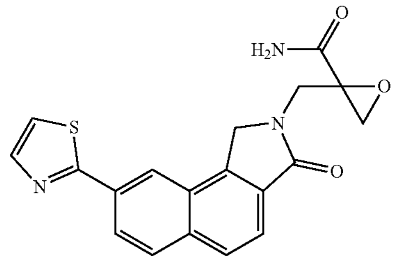 [SMILES: NC(=O)C1(CN2Cc3c(ccc4ccc(-c5nccs5)cc34)C2=O)CO1] | 2-{[3-oxo-8-(1,3-thiazol-2-yl)-1H,2H,3H-benzo[e]isoindol-2-yl]methyl}oxirane-2-carboxamide | 366 |
| 769. | 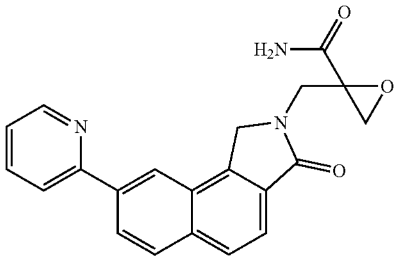 [SMILES: NC(=O)C1(CN2Cc3c(ccc4ccc(-c5ccccn5)cc34)C2=O)CO1] | 2-{[3-oxo-8-(pyridin-2-yl)-1H,2H,3H-benzo[e]isoindol-2-yl]methyl}oxirane-2-carboxamide | 360.1 |
| 770. | 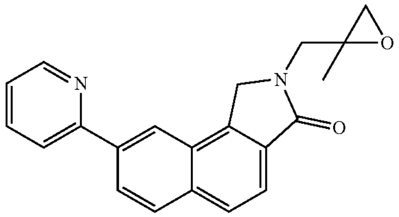 [SMILES: CC1(CN2Cc3c(ccc4ccc(-c5ccccn5)cc34)C2=O)CO1] | 2-[(2-methyloxiran-2-yl)methyl]-8-(pyridin-2-yl)-1H,2H,3H-benzo[e]isoindol-3-one | 331.1 |

Example 17: Additional Compounds of the Disclosure

TABLE 15 shows additional compounds synthesized using the methods described above.

TABLE 15

| Cpd. No. | Structure | IUPAC | MW (g/mol) |
|---|---|---|---|
| 771. | 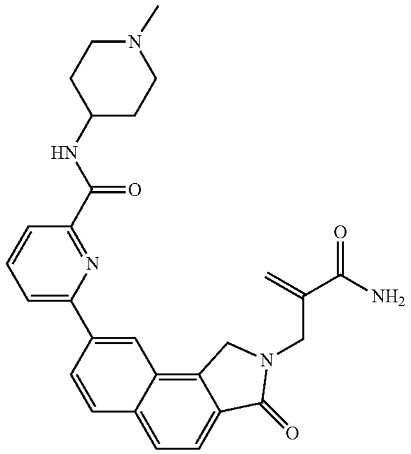 [SMILES: C=C(CN1Cc2c(ccc3ccc(-c4cccc(C(=O)NC5CCN(C)CC5)n4)cc23)C1=O)C(N)=O] | 6-[2-(2-carbamoyl-2-methylideneethyl)-3-oxo-1H,2H,3H-benzo[e]isoindol-8-yl]-N-(1-methylpiperidin-4-yl)pyridine-2-carboxamide | 483.6 |
| 772. | 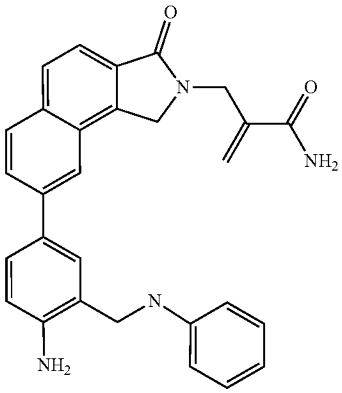 | 2-[(8-{4-amino-3-[(phenylamino)methyl]phenyl}-3-oxo-1H,2H,3H-benzo[e]isoindol-2-yl)methyl]prop-2-enamide | 462.6 |
| 773. | 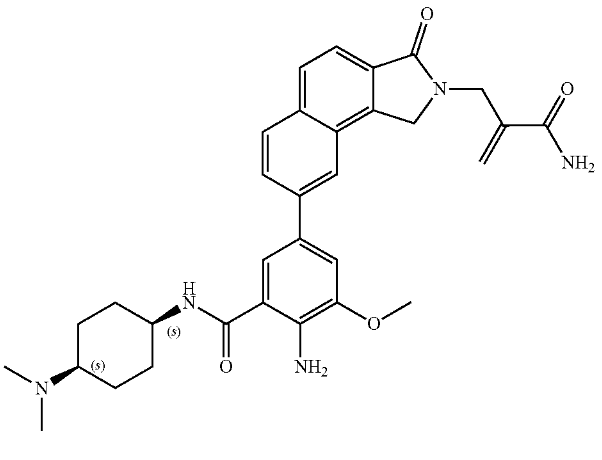 | 2-amino-5-[2-(2-carbamoyl-2-methylideneethyl)-3-oxo-1H,2H,3H-benzo[e]isoindol-8-yl]-3-methoxy-N-[(1s,4s)-4-(dimethylamino)cyclohexyl]benzamide | 555.7 |

TABLE 15-continued

| Cpd. No. | Structure | IUPAC | MW (g/mol) |
|---|---|---|---|
| 774. | 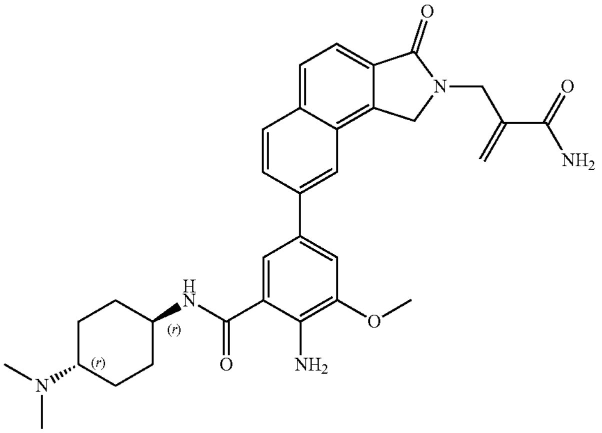 | 2-amino-5-[2-(2-carbamoyl-2-methylideneethyl)-3-oxo-1H,2H,3H-benzo[e]isoindol-8-yl]-3-methoxy-N-[(1r,4r)-4-(dimethylamino)cyclohexyl]benzamide | 555.7 |
| 775. | 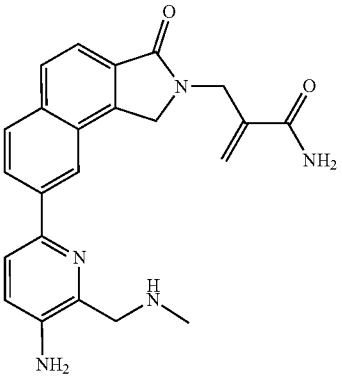 [SMILES: C=C(CN1Cc2c(ccc3ccc(-c4ccc(N)c(CNC)n4)cc23)C1=O)C(N)=O] | 3-amino-6-[2-(2-carbamoyl-2-methylideneethyl)-3-oxo-1H,2H,3H-benzo[e]isoindol-8-yl]-N-methylpyridine-2-carboxamide | 415.5 |
| 776. | 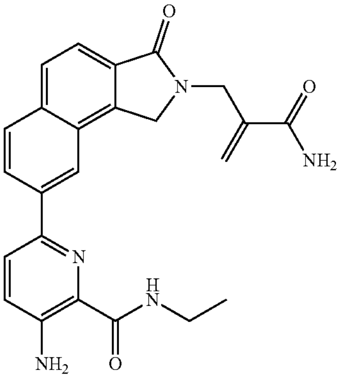 [SMILES: C=C(CN1Cc2c(ccc3ccc(-c4ccc(N)c(C(=O)NCC)n4)cc23)C1=O)C(N)=O] | 3-amino-6-[2-(2-carbamoyl-2-methylideneethyl)-3-oxo-1H,2H,3H-benzo[e]isoindol-8-yl]-N-ethylpyridine-2-carboxamide | 429.5 |
| 777. | 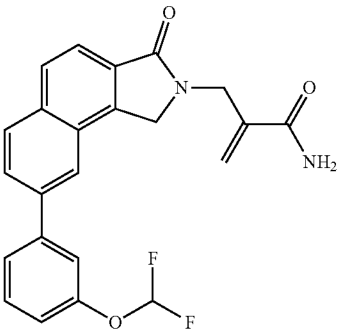 [SMILES: C=C(CN1Cc2c(ccc3ccc(-c4cccc(OC(F)F)c4)cc23)C1=O)C(N)=O] | 2-({8-[3-(difluoromethoxy)phenyl]-3-oxo-1H,2H,3H-benzo[e]isoindol-2-yl}methyl)prop-2-enamide | 408.4 |

TABLE 15-continued

| Cpd. No. | Structure | IUPAC | MW (g/mol) |
|---|---|---|---|
| 778. | 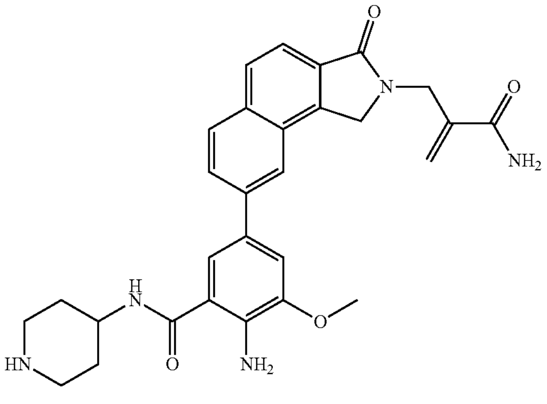 [SMILES: C=C(CN1Cc2c(ccc3ccc(-c4cc(OC)c(N)c(C(=O)NC5CCNCC5)c4)cc23)C1=O)C(N)=O] | 2-amino-5-[2-(2-carbamoyl-2-methylideneethyl)-3-oxo-1H,2H,3H-benzo[e]isoindol-8-yl]-3-methoxy-N-(piperidin-4-yl)benzamide | 513.6 |
| 779. | 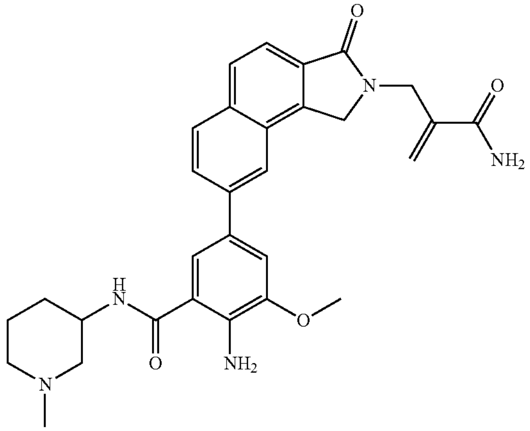 [SMILES: C=C(CN1Cc2c(ccc3ccc(-c4cc(OC)c(N)c(C(=O)NC5CCCN(C)C5)c4)cc23)C1=O)C(N)=O] | 2-amino-5-[2-(2-carbamoyl-2-methylideneethyl)-3-oxo-1H,2H,3H-benzo[e]isoindol-8-yl]-3-methoxy-N-(1-methylpiperidin-3-yl)benzamide | 527.6 |
| 780. | 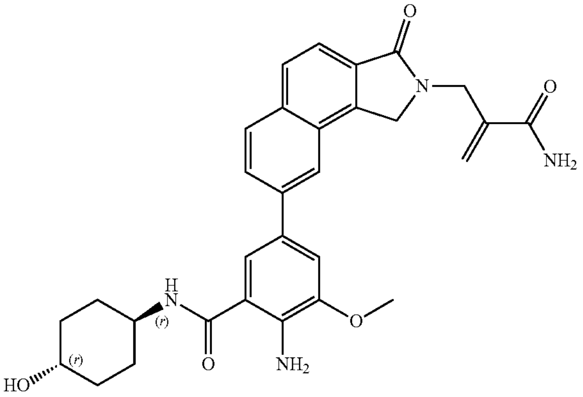 [SMILES: C=C(CN1Cc2c(ccc3ccc(-c4cc(OC)c(N)c(C(=O)N[C@H]5CC[C@H](O)CC5)c4)cc23)C1=O)C(N)=O] | 2-amino-5-[2-(2-carbamoyl-2-methylideneethyl)-3-oxo-1H,2H,3H-benzo[e]isoindol-8-yl]-3-methoxy-N-[(1r,4r)-4-hydroxycyclohexyl]benzamide | 528.6 |
| 781. | 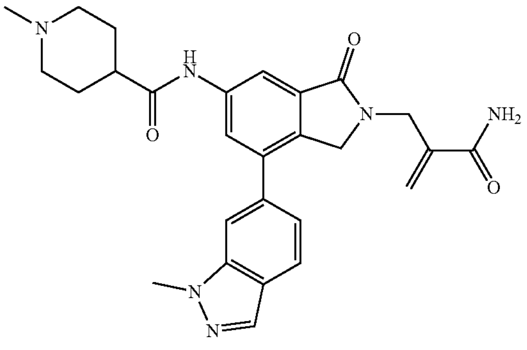 [SMILES: C=C(CN1Cc2c(cc(NC(=O)C3CCN(C)CC3)cc2-c2ccc3cnn(C)c3c2)C1=O)C(N)=O] | N-[2-(2-carbamoyl-2-methylideneethyl)-7-(1-methyl-1H-indazol-6-yl)-3-oxo-2,3-dihydro-1H-isoindol-5-yl]-1-methylpiperidine-4-carboxamide | 486.6 |

TABLE 15-continued

| Cpd. No. | Structure | IUPAC | MW (g/mol) |
|---|---|---|---|
| 782. | 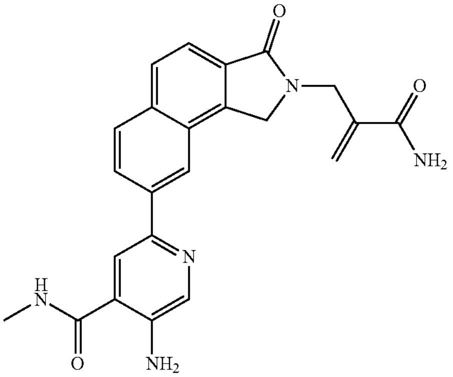 [SMILES: C=C(CN1Cc2c(ccc3ccc(-c4cc(C(=O)NC)c(N)cn4)cc23)C1=O)C(N)=O] | 5-amino-2-[2-(2-carbamoyl-2-methylideneethyl)-3-oxo-1H,2H,3H-benzo[e]isoindol-8-yl]-N-methylpyridine-4-carboxamide | 415.5 |
| 783. | 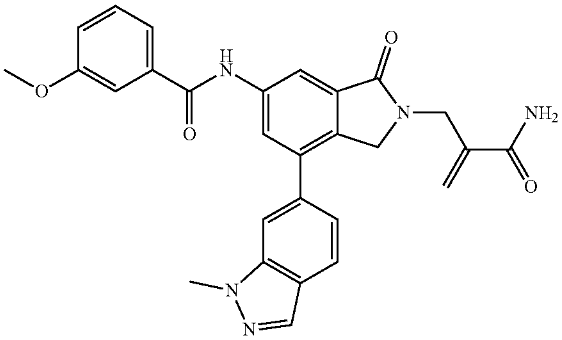 [SMILES: C=C(CN1Cc2c(cc(NC(=O)c3cccc(OC)c3)cc2-c2ccc3cnn(C)c3c2)C1=O)C(N)=O] | N-[2-(2-carbamoyl-2-methylideneethyl)-7-(1-methyl-1H-indazol-6-yl)-3-oxo-2,3-dihydro-1H-isoindol-5-yl]-3-methoxybenzamide | 495.5 |
| 784. | 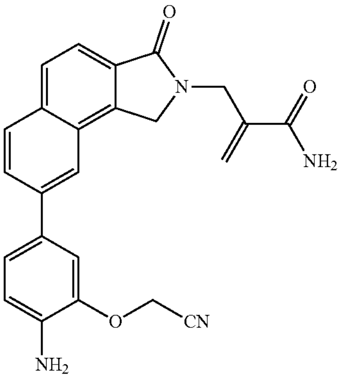 [SMILES: C=C(CN1Cc2c(ccc3ccc(-c4ccc(N)c(OCC#N)c4)cc23)C1=O)C(N)=O] | 2-({8-[4-amino-3-(cyanomethoxy)phenyl]-3-oxo-1H,2H,3H-benzo[e]isoindol-2-yl}methyl)prop-2-enamide | 412.4 |
| 785. | 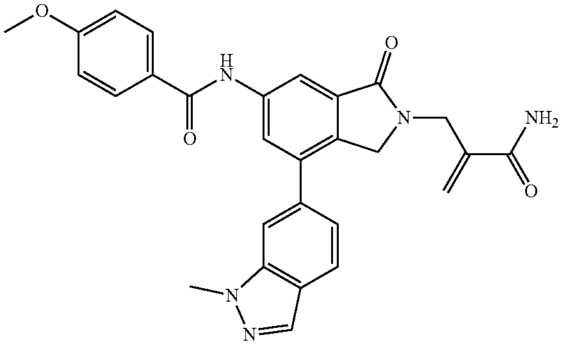 [SMILES: C=C(CN1Cc2c(cc(NC(=O)c3ccc(OC)cc3)cc2-c2ccc3cnn(C)c3c2)C1=O)C(N)=O] | N-[2-(2-carbamoyl-2-methylideneethyl)-7-(1-methyl-1H-indazol-6-yl)-3-oxo-2,3-dihydro-1H-isoindol-5-yl]-4-methoxybenzamide | 495.5 |

TABLE 15-continued

| Cpd. No. | Structure | IUPAC | MW (g/mol) |
|---|---|---|---|
| 786. | 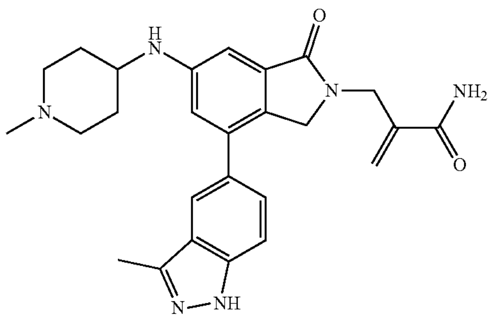 [SMILES: C=C(CN1Cc2c(cc(NC3CCN(C)CC3)cc2-c2ccc3[nH]nc(C)c3c2)C1=O)C(N)=O] | 2-{[4-(3-methyl-1H-indazol-5-yl)-6-[(1-methylpiperidin-4-yl)amino]-1-oxo-2,3-dihydro-1H-isoindol-2-yl]methyl}prop-2-enamide | 458.6 |
| 787. | 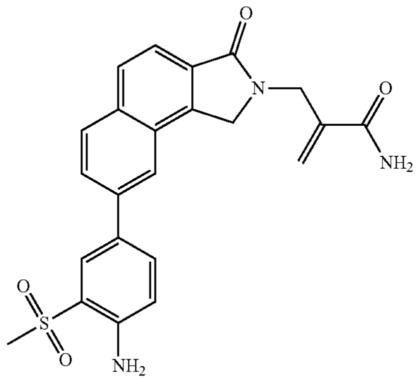 [SMILES: C=C(CN1Cc2c(ccc3ccc(-c4ccc(N)c(S(C)(=O)=O)c4)cc23)C1=O)C(N)=O] | 2-{[8-(4-amino-3-methanesulfonylphenyl)-3-oxo-1H,2H,3H-benzo[e]isoindol-2-yl]methyl}prop-2-enamide | 435.5 |
| 788. | 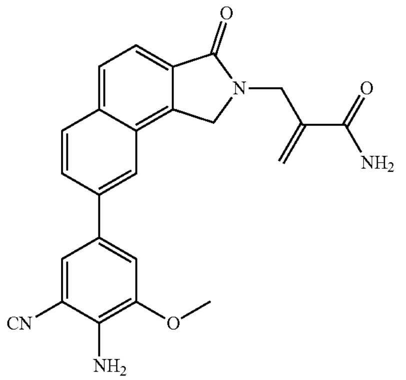 | 4-[2-(2-carbamoyl-2-methylideneethyl)-3-oxo-1H,2H,3H-benzo[e]isoindol-8-yl]-2-isocyano-6-methoxyaniline | 412.4 |
| 789. | 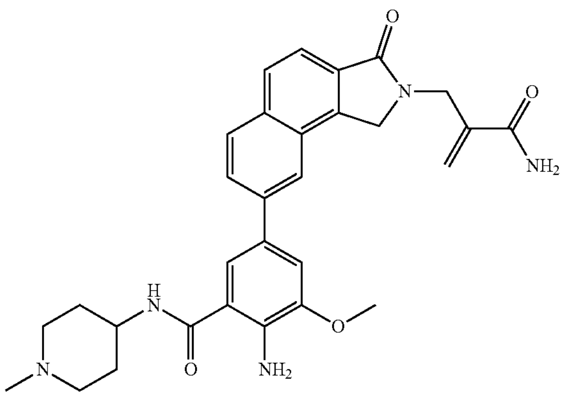 [SMILES: C=C(CN1Cc2c(ccc3ccc(-c4cc(OC)c(N)c(C(=O)NC5CCN(C)CC5)c4)cc23)C1=O)C(N)=O] | 2-amino-5-[2-(2-carbamoyl-2-methylideneethyl)-3-oxo-1H,2H,3H-benzo[e]isoindol-8-yl]-3-methoxy-N-(1-methylpiperidin-4-yl)benzamide | 527.6 |

TABLE 15-continued
| Cpd. No. | Structure | IUPAC | MW (g/mol) |
|---|---|---|---|
| 790. | 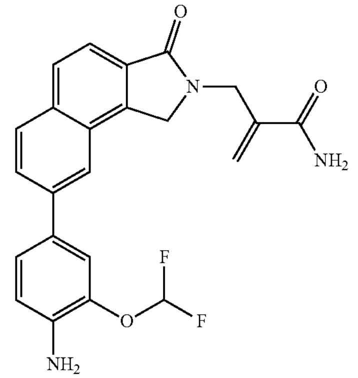 [SMILES: C=C(CN1Cc2c(ccc3ccc(-c4ccc(N)c(OC(F)F)c4)cc23)C1=O)C(N)=O] | 2-({8-[4-amino-3-(difluoromethoxy)phenyl]-3-oxo-1H,2H,3H-benzo[e]isoindol-2-yl}methyl)prop-2-enamide | 423.4 |
| 791. | 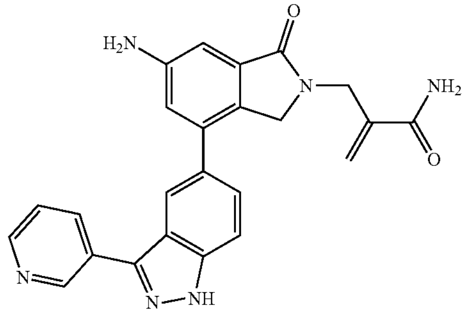 [SMILES: C=C(CN1Cc2c(cc(N)cc2-c2ccc3[nH]nc(-c4cccnc4)c3c2)C1=O)C(N)=O] | 2-({6-amino-1-oxo-4-[3-(pyridin-3-yl)-1H-indazol-5-yl]-2,3-dihydro-1H-isoindol-2-yl}methyl)prop-2-enamide | 424.5 |
| 792. | 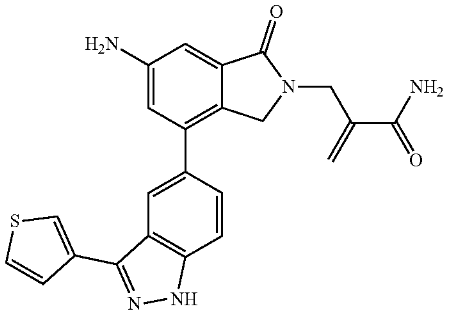 [SMILES: C=C(CN1Cc2c(cc(N)cc2-c2ccc3[nH]nc(-c4ccsc4)c3c2)C1=O)C(N)=O] | 2-({6-amino-1-oxo-4-[3-(thiophen-3-yl)-1H-indazol-5-yl]-2,3-dihydro-1H-isoindol-2-yl}methyl)prop-2-enamide | 429.5 |
| 793. | 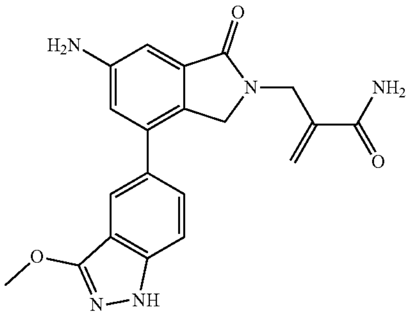 [SMILES: C=C(CN1Cc2c(cc(N)cc2-c2ccc3[nH]nc(OC)c3c2)C1=O)C(N)=O] | 2-{[6-amino-4-(3-methoxy-1H-indazol-5-yl)-1-oxo-2,3-dihydro-1H-isoindol-2-yl]methyl}prop-2-enamide | 377.4 |

TABLE 15-continued

| Cpd. No. | Structure | IUPAC | MW (g/mol) |
|---|---|---|---|
| 794. | 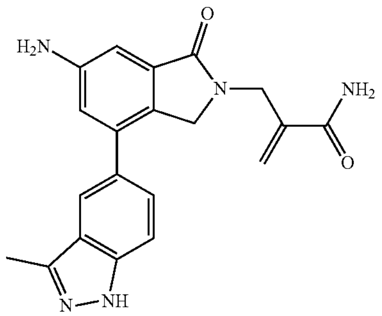 [SMILES: C=C(CN1Cc2c(cc(N)cc2-c2ccc3[nH]nc(C)c3c2)C1=O)C(N)=O] | 2-{[6-amino-4-(3-methyl-1H-indazol-5-yl)-1-oxo-2,3-dihydro-1H-isoindol-2-yl]methyl}prop-2-enamide | 361.4 |
| 795. | 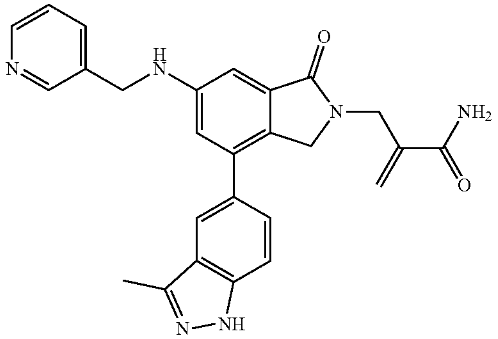 [SMILES: C=C(CN1Cc2c(cc(NCc3cccnc3)cc2-c2ccc3[nH]nc(C)c3c2)C1=O)C(N)=O] | 2-{[4-(3-methyl-1H-indazol-5-yl)-1-oxo-6-{[(pyridin-3-yl)methyl]amino}-2,3-dihydro-1H-isoindol-2-yl]methyl}prop-2-enamide | 452.5 |
| 796. | 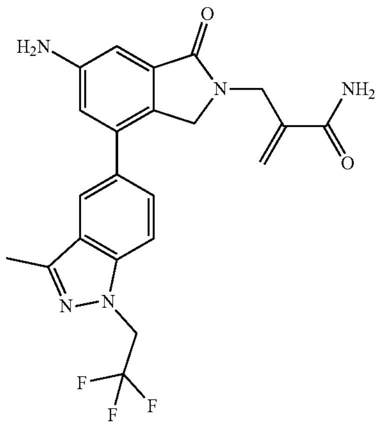 [SMILES: C=C(CN1Cc2c(cc(N)cc2-c2ccc3c(c2)c(C)nn3CC(F)(F)F)C1=O)C(N)=O] | 2-({6-amino-4-[3-methyl-1-(2,2,2-trifluoroethyl)-1H-indazol-5-yl]-1-oxo-2,3-dihydro-1H-isoindol-2-yl}methyl)prop-2-enamide | 443.4 |
| 797. | 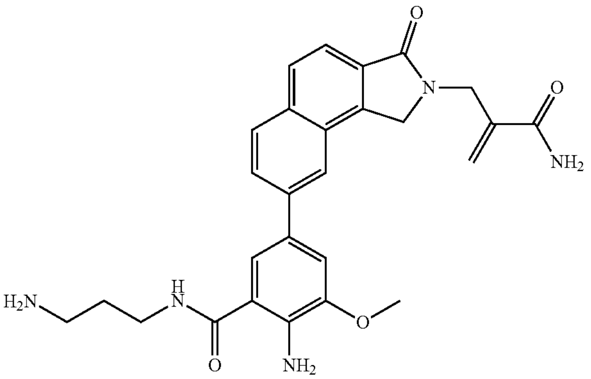 [SMILES: C=C(CN1Cc2c(ccc3ccc(-c4cc(OC)c(N)c(C(=O)NCCCN)c4)cc23)C1=O)C(N)=O] | 2-amino-N-(3-aminopropyl)-5-[2-(2-carbamoyl-2-methylideneethyl)-3-oxo-1H,2H,3H-benzo[e]isoindol-8-yl]-3-methoxybenzamide | 487.6 |

TABLE 15-continued

| Cpd. No. | Structure | IUPAC | MW (g/mol) |
|---|---|---|---|
| 798. | 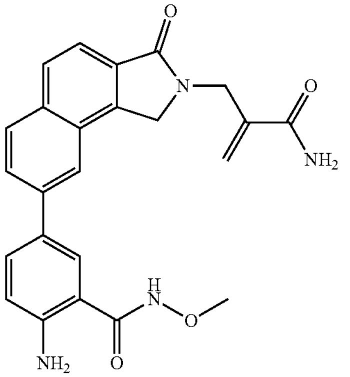 [SMILES: C=C(CN1Cc2c(ccc3ccc(-c4ccc(N)c(C(=O)NOC)c4)cc23)C1=O)C(N)=O] | 2-amino-5-[2-(2-carbamoyl-2-methylideneethyl)-3-oxo-1H,2H,3H-benzo[e]isoindol-8-yl]-N-methoxybenzamide | 430.5 |
| 799. | 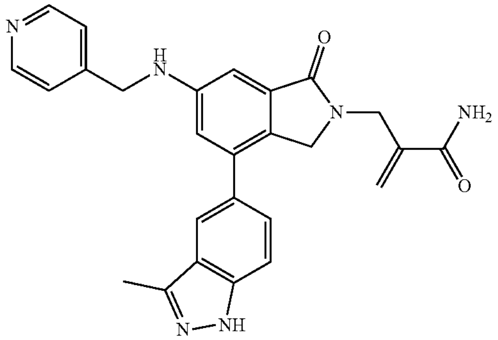 [SMILES: C=C(CN1Cc2c(cc(NCc3ccncc3)cc2-c2ccc3[nH]nc(C)c3c2)C1=O)C(N)=O] | 2-{[4-(3-methyl-1H-indaozl-5-yl)-1-oxo-6-{[(pyridin-4-yl)methyl]amino}-2,3-dihydro-1H-isoindol-2-yl]methyl}prop-2-enamide | 452.5 |
| 800. | 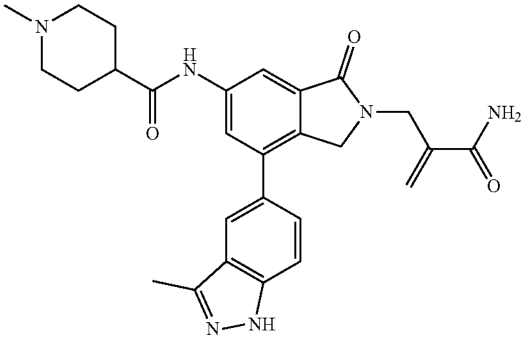 [SMILES: C=C(CN1Cc2c(cc(NC(=O)C3CCN(C)CC3)cc2-c2ccc3[nH]nc(C)c3c2)C1=O)C(N)=O] | N-[2-(2-carbamoyl-2-methylideneethyl)-7-(3-methyl-1H-indazol-5-yl)-3-oxo-2,3-dihydro-1H-isoindol-5-yl]-1-methylpiperidine-4-carboxamide | 486.6 |
| 801. | 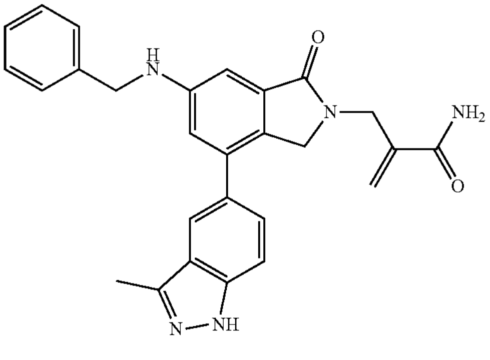 [SMILES: C=C(CN1Cc2c(cc(NCc3ccccc3)cc2-c2ccc3[nH]nc(C)c3c2)C1=O)C(N)=O] | 2-{[6-(benzylamino)-4-(3-methyl-1H-indazol-5-yl)-1-oxo-2,3-dihydro-1H-isoindol-2-yl]methyl}prop-2-enamide | 451.5 |

TABLE 15-continued

| Cpd. No. | Structure | IUPAC | MW (g/mol) |
|---|---|---|---|
| 802. | 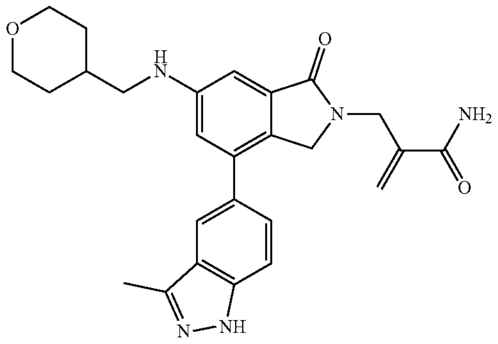 [SMILES: C=C(CN1Cc2c(cc(NCC3CCOCC3)cc2-c2ccc3[nH]nc(C)c3c2)C1=O)C(N)=O] | 2-{[4-(3-methyl-1H-indazol-5-yl)-6-{[(oxan-4-yl)methyl]amino}-1-oxo-2,3-dihydro-1H-isoindol-2-yl]methyl}prop-2-enamide | 459.6 |
| 803. | 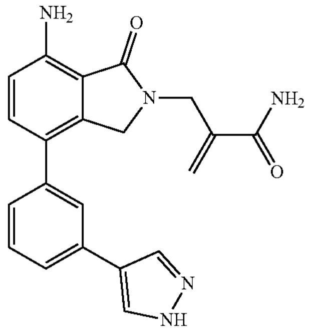 [SMILES: C=C(CN1Cc2c(-c3cccc(-c4cn[nH]c4)c3)ccc(N)c2C1=O)C(N)=O] | 2-({7-amino-1-oxo-4-[3-(1H-pyrazol-4-yl)phenyl]-2,3-dihydro-1H-isoindol-2-yl}methyl)prop-2-enamide | 373.4 |
| 804. | 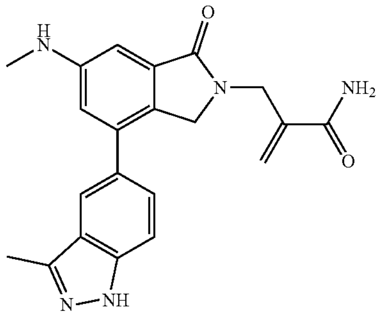 [SMILES: C=C(CN1Cc2c(cc(NC)cc2-c2ccc3[nH]nc(C)c3c2)C1=O)C(N)=O] | 2-{[4-(3-methyl-1H-indazol-5-yl)-6-(methylamino)-1-oxo-2,3-dihydro-1H-isoindol-2-yl]methyl}prop-2-enamide | 375.4 |
| 805. | 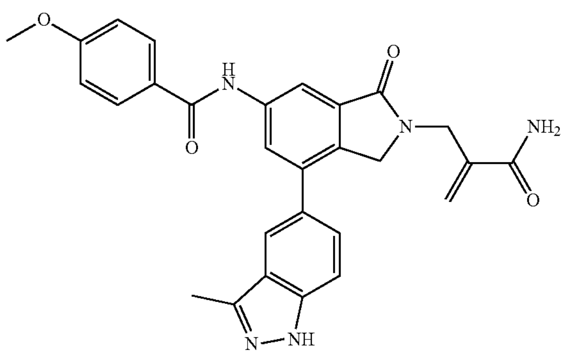 [SMILES: C=C(CN1Cc2c(cc(NC(=O)c3ccc(OC)cc3)cc2-c2ccc3[nH]nc(C)c3c2)C1=O)C(N)=O] | N-[2-(2-carbamoyl-2-methylideneethyl)-7-(3-methyl-1H-indazol-5-yl)-3-oxo-2,3-dihydro-1H-isoindol-5-yl]-4-methoxybenzamide | 495.5 |

TABLE 15-continued

| Cpd. No. | Structure | IUPAC | MW (g/mol) |
|---|---|---|---|
| 806. | 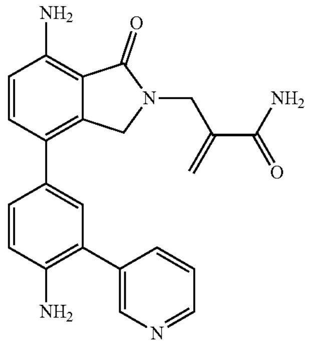 [SMILES: C=C(CN1Cc2c(-c3ccc(N)c(-c4cccnc4)c3)ccc(N)c2C1=O)C(N)=O] | 2-({7-amino-4-[4-amino-3-(pyridin-3-yl)phenyl]-1-oxo-2,3-dihydro-1H-isoindol-2-yl}methyl)prop-2-enamide | 399.5 |
| 807. | 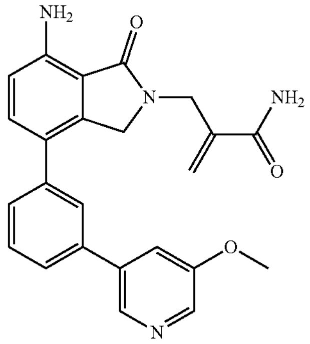 [SMILES: C=C(CN1Cc2c(-c3cccc(-c4cncc(OC)c4)c3)ccc(N)c2C1=O)C(N)=O] | 2-({7-amino-4-[3-(5-methoxypyridin-3-yl)phenyl]-1-oxo-2,3-dihydro-1H-isoindol-2-yl}methyl)prop-2-enamide | 414.5 |
| 808. | 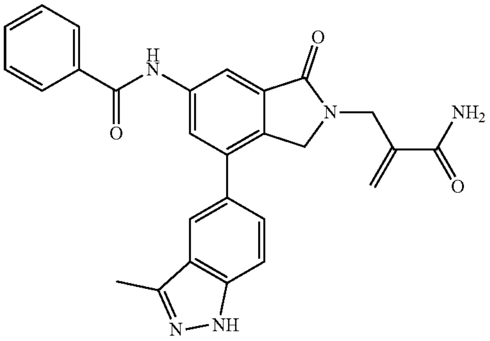 [SMILES: C=C(CN1Cc2c(cc(NC(=O)c3ccccc3)cc2-c2ccc3[nH]nc(C)c3c2)C1=O)C(N)=O] | N-[2-(2-carbamoyl-2-methylideneethyl)-7-(3-methyl-1H-indazol-5-yl)-3-oxo-2,3-dihydro-1H-isoindol-5-yl]benzamide | 465.5 |
| 809. | 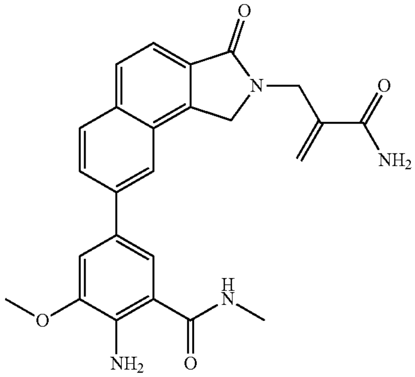 [SMILES: C=C(CN1Cc2c(ccc3ccc(-c4cc(OC)c(N)c(C(=O)NC)c4)cc23)C1=O)C(N)=O] | 2-amino-5-[2-(2-carbamoyl-2-methylideneethyl)-3-oxo-1H,2H,3H-benzo[e]isoindol-8-yl]-3-methoxy-N-methylbenzamide | 444.5 |

TABLE 15-continued

| Cpd. No. | Structure | IUPAC | MW (g/mol) |
|---|---|---|---|
| 810. | 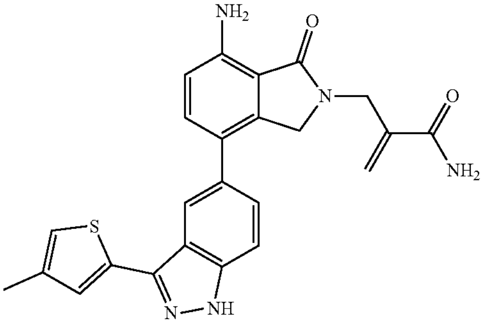 [SMILES: C=C(CN1Cc2c(-c3ccc4[nH]nc(-c5cc(C)cs5)c4c3)ccc(N)c2C1=O)C(N)=O] | 2-({7-amino-4-[3-(4-methylthiophen-2-yl)-1H-indazol-5-yl]-1-oxo-2,3-dihydro-1H-isoindol-3-yl}methyl)prop-2-enamide | 443.5 |
| 811. | 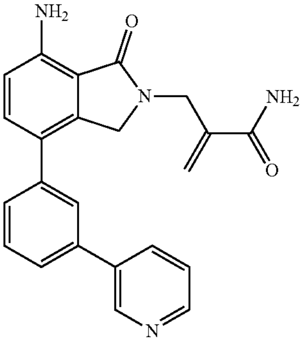 [SMILES: C=C(CN1Cc2c(-c3cccc(-c4cccnc4)c3)ccc(N)c2C1=O)C(N)=O] | 2-({7-amino-1-oxo-4-[3-(pyridin-3-yl)phenyl]-2,3-dihydro-1H-isoindol-2-yl}methyl)prop-2-enamide | 384.4 |
| 812. | 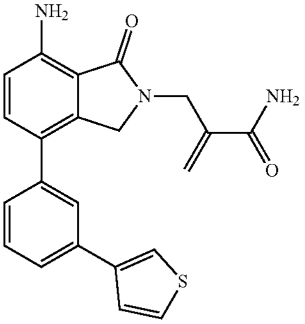 [SMILES: C=C(CN1Cc2c(-c3cccc(-c4ccsc4)c3)ccc(N)c2C1=O)C(N)=O] | 2-({7-amino-1-oxo-4-[3-(thiophen-3-yl)phenyl]-2,3-dihydro-1H-isoindol-2-yl}methyl)prop-2-enamide | 389.5 |
| 813. | 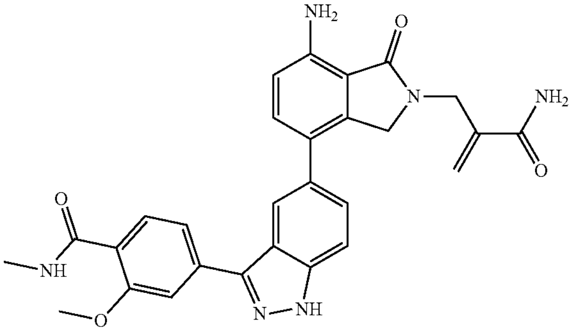 [SMILES: C=C(CN1Cc2c(-c3ccc4[nH]nc(-c5ccc(C(=O)NC)c(OC)c5)c4c3)ccc(N)c2C1=O)C(N)=O] | 4-{5-[7-amino-2-(2-carbamoyl-2-methylideneethyl)-1-oxo-2,3-dihydro-1H-isoindol-4-yl]-1H-indazol-3-yl}-2-methoxy-N-methylbenzamide | 510.6 |

TABLE 15-continued

| Cpd. No. | Structure | IUPAC | MW (g/mol) |
|---|---|---|---|
| 814. | 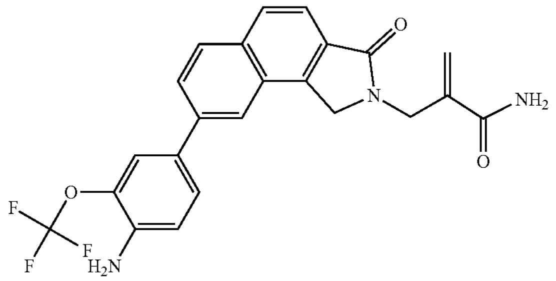 [SMILES: C=C(CN1Cc2c(ccc3ccc(-c4ccc(N)c(OC(F)(F)F)c4)cc23)C1=O)C(N)=O] | 2-({8-[4-amino-3-(trifluoromethoxy)phenyl]-3-oxo-1H,2H,3H-benzo[e]isoindol-2-yl}methyl)prop-2-enamide | 441.4 |
| 815. | 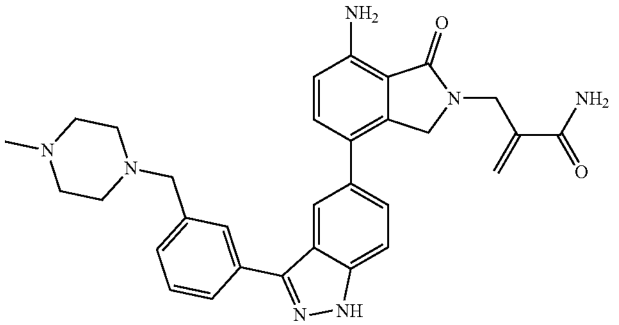 [SMILES: C=C(CN1Cc2c(-c3ccc4[nH]nc(-c5cccc(CN6CCN(C)CC6)c5)c4c3)ccc(N)c2C1=O)C(N)=O] | 2-{[7-amino-4-(3-{3-[(4-methylpiperazin-1-yl)methyl]phenyl}-1H-indazol-5-yl)-1-oxo-2,3-dihydro-1H-isoindol-2-yl]methyl}prop-2-enamide | 535.7 |
| 816. | 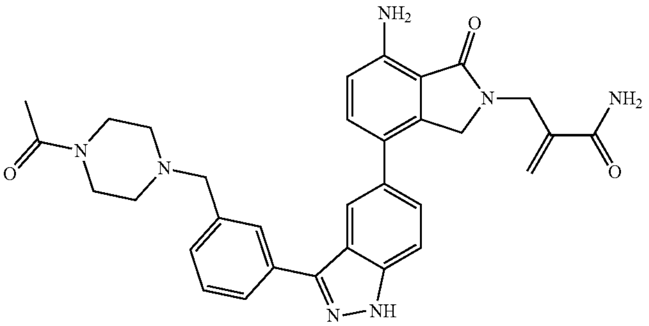 [SMILES: C=C(CN1Cc2c(-c3ccc4[nH]nc(-c5cccc(CN6CCN(C(C)=O)CC6)c5)c4c3)ccc(N)c2C1=O)C(N)=O] | 2-{[4-(3-{3-[(4-acetylpiperazin-1-yl)methyl]phenyl}-1H-indazol-5-yl)-7-amino-1-oxo-2,3-dihydro-1H-isoindol-2-yl]methyl}prop-2-enamide | 563.7 |
| 817. | 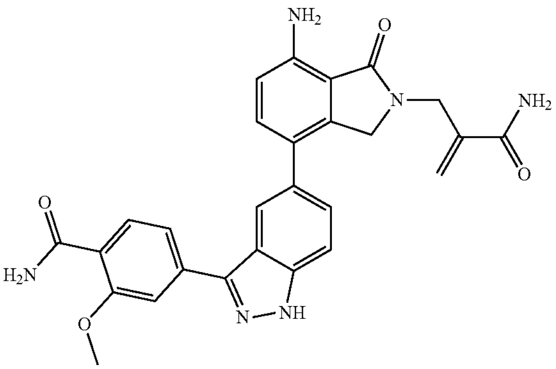 [SMILES: C=C(CN1Cc2c(-c3ccc4[nH]nc(-c5ccc(C(N)=O)c(OC)c5)c4c3)ccc(N)c2C1=O)C(N)=O] | 4-{5-[7-amino-2-(2-carbamoyl-2-methylideneethyl)-1-oxo-2,3-dihydro-1H-isoindol-4-yl]-1H-indazol-3-yl}-2-methoxybenzamide | 496.5 |

TABLE 15-continued
| Cpd. No. | Structure | IUPAC | MW (g/mol) |
|---|---|---|---|
| 818. | 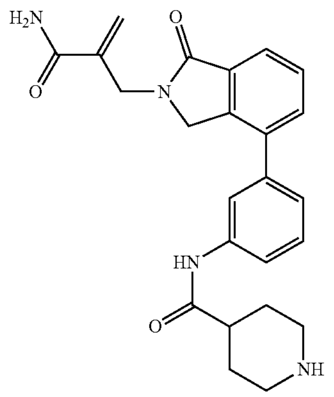 [SMILES: C=C(CN1Cc2c(cccc2-c2cccc(NC(=O)C3CCNCC3)c2)C1=O)C(N)=O] | N-{3-[2-(2-carbamoyl-2-methylideneethyl)-1-oxo-2,3-dihydro-1H-isoindol-4-yl]phenyl}piperidine-4-carboxamide | 418.5 |
| 819. | 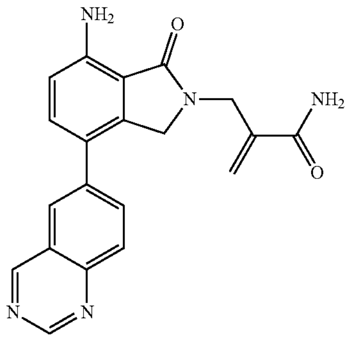 [SMILES: C=C(CN1Cc2c(-c3ccc4ncncc4c3)ccc(N)c2C1=O)C(N)=O] | 2-{[7-amino-1-oxo-4-(quinazolin-6-yl)-2,3-dihydro-1H-isoindol-2-yl]methyl}prop-2-enamide | 359.4 |
| 820. | 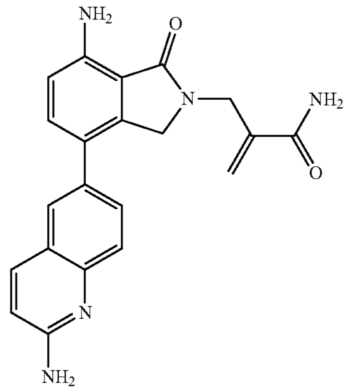 [SMILES: C=C(CN1Cc2c(-c3ccc4nc(N)ccc4c3)ccc(N)c2C1=O)C(N)=O] | 2-{[7-amino-4-(6-aminonaphthalen-2-yl)-1-oxo-2,3-dihydro-1H-isoindol-2-yl]methyl}prop-2-enamide | 372.4 |
| 821. | 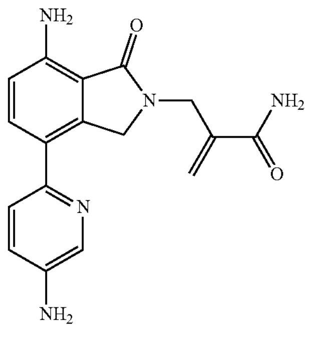 [SMILES: C=C(CN1Cc2c(-c3ccc(N)cn3)ccc(N)c2C1=O)C(N)=O] | 2-{[7-amino-4-(5-aminopyridin-2-yl)-1-oxo-2,3-dihydro-1H-isoindol-2-yl]methyl}prop-2-enamide | 323.4 |

TABLE 15-continued
| Cpd. No. | Structure | IUPAC | MW (g/mol) |
| --- | --- | --- | --- |
| 822. | 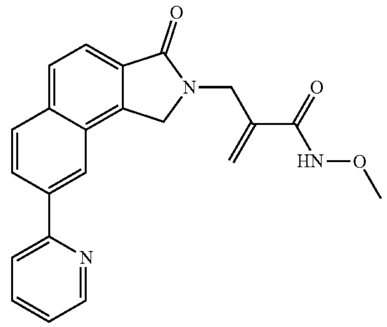 [SMILES: C=C(CN1Cc2c(ccc3ccc(-c4ccccn4)cc23)C1=O)C(=O)NOC] | N-methoxy-2-{[3-oxo-8-(pyridin-2-yl)-1H,2H,3H-benzo[e]isoindol-2-yl]methyl}prop-2-enamide | 373.4 |
| 823. | 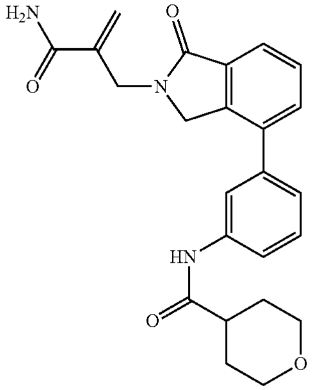 [SMILES: C=C(CN1Cc2c(cccc2-c2cccc(NC(=O)C3CCOCC3)c2)C1=O)C(N)=O] | N-{3-[2-(2-carbamoyl-2-methylideneethyl)-1-oxo-2,3-dihydro-1H-isoindol-4-yl]phenyl}oxane-4-carboxamide | 419.5 |
| 824. | 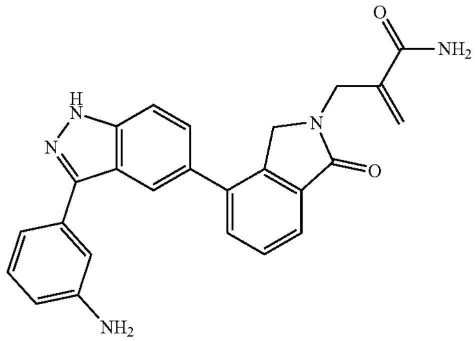 [SMILES: C=C(CN1Cc2c(cccc2-c2ccc3[nH]nc(-c4cccc(N)c4)c3c2)C1=O)C(N)=O] | 2-({4-[3-(3-aminophenyl)-1H-indazol-5-yl]-1-oxo-2,3-dihydro-1H-isoindol-2-yl}methyl)prop-2-enamide | 423.5 |
| 825. | 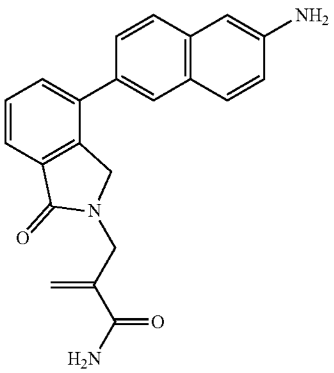 [SMILES: C=C(CN1Cc2c(cccc2-c2ccc3cc(N)ccc3c2)C1=O)C(N)=O] | 2-{[4-(6-aminonaphthalen-2-yl)-1-oxo-2,3-dihydro-1H-isoindol-2-yl]methyl}prop-2-enamide | 357.4 |

TABLE 15-continued

| Cpd. No. | Structure | IUPAC | MW (g/mol) |
|---|---|---|---|
| 826. | 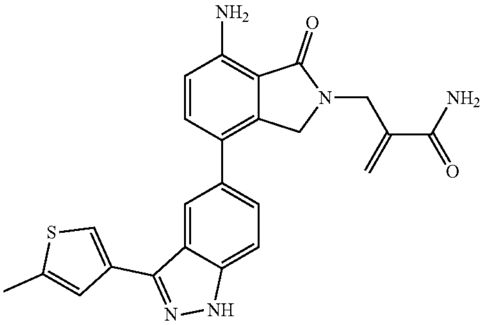 [SMILES: C=C(CN1Cc2c(-c3ccc4[nH]nc(-c5csc(C)c5)c4c3)ccc(N)c2C1=O)C(N)=O] | 2-({7-amino-4-[3-(5-methylthiophen-3-yl)-1H-indazol-5-yl]-1-oxo-2,3-dihydro-1H-isoindol-2-yl}methyl)prop-2-enamide | 443.5 |
| 827. | 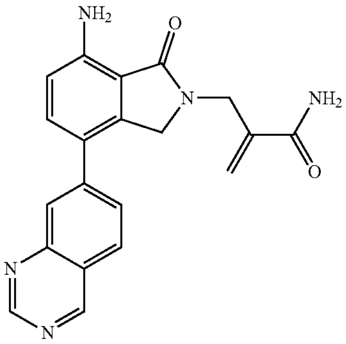 [SMILES: C=C(CN1Cc2c(-c3ccc4cncnc4c3)ccc(N)c2C1=O)C(N)=O] | 2-{[7-amino-1-oxo-4-(quinazolin-7-yl)-2,3-dihydro-1H-isoindol-2-yl]methyl}prop-2-enamide | 359.4 |
| 828. | 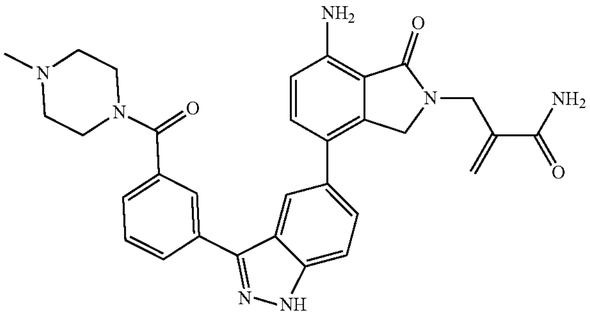 [SMILES: C=C(CN1Cc2c(-c3ccc4[nH]nc(-c5cccc(C(=O)N6CCN(C)CC6)c5)c4c3)ccc(N)c2C1=O)C(N)=O] | 2-[(7-amino-4-{3-[3-(4-methylpiperazin-1-carbonyl)phenyl]-1H-indazol-5-yl}-1-oxo-2,3-dihydro-1H-isoindol-2-yl)methyl]prop-2-enamide | 549.6 |
| 829. | 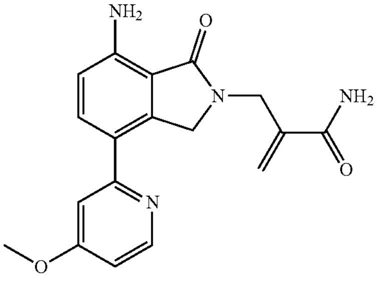 [SMILES: C=C(CN1Cc2c(-c3cc(OC)ccn3)ccc(N)c2C1=O)C(N)=O] | 2-{[7-amino-4-(4-methoxypyridin-2-yl)-1-oxo-2,3-dihydro-1H-isoindol-2-yl]methyl}prop-2-enamide | 338.4 |

TABLE 15-continued

| Cpd. No. | Structure | IUPAC | MW (g/mol) |
|---|---|---|---|
| 830. | 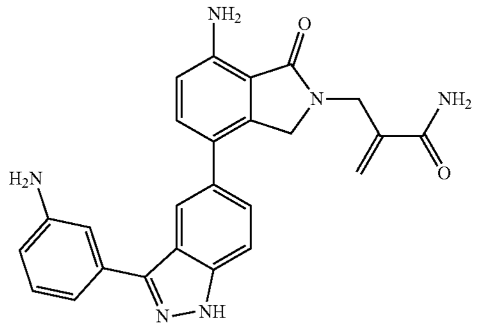 [SMILES: C=C(CN1Cc2c(-c3ccc4[nH]nc(-c5cccc(N)c5)c4c3)ccc(N)c2C1=O)C(N)=O] | 2-({7-amino-4-[3-(3-aminophenyl)-1H-indazol-5-yl]-1-oxo-2,3-dihydro-1H-isoindol-2-yl}methyl)prop-2-enamide | 438.5 |
| 831. | 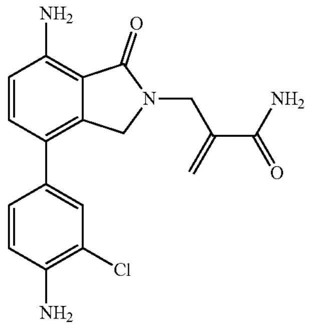 [SMILES: C=C(CN1Cc2c(-c3ccc(N)c(Cl)c3)ccc(N)c2C1=O)C(N)=O] | 2-{[7-amino-4-(4-amino-3-chlorophenyl)-1-oxo-2,3-dihydro-1H-isoindol-2-yl]methyl}prop-2-enamide | 356.8 |
| 832. | 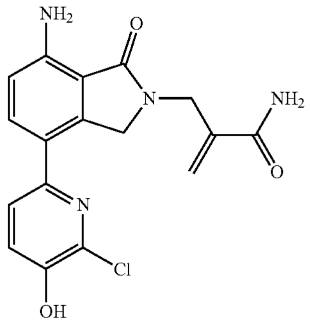 [SMILES: C=C(CN1Cc2c(-c3ccc(O)c(Cl)n3)ccc(N)c2C1=O)C(N)=O] | 2-{[7-amino-4-(3-chloro-4-hydroxyphenyl)-1-oxo-2,3-dihydro-1H-isoindol-2-yl]methyl}prop-2-enamide | 357.8 |
| 833. | 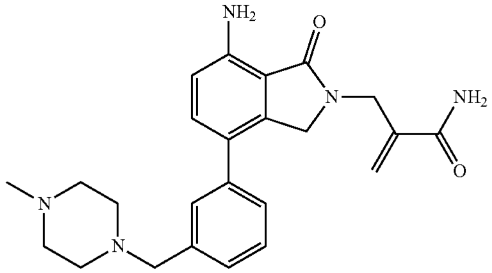 [SMILES: C=C(CN1Cc2c(-c3cccc(CN4CCN(C)CC4)c3)ccc(N)c2C1=O)C(N)=O] | 2-[(7-amino-4-{3-[(4-methylpiperazin-1-yl)methyl]phenyl}-1-oxo-2,3-dihydro-1H-isoindol-2-yl)methyl]prop-2-enamide | 419.5 |
| 834. | 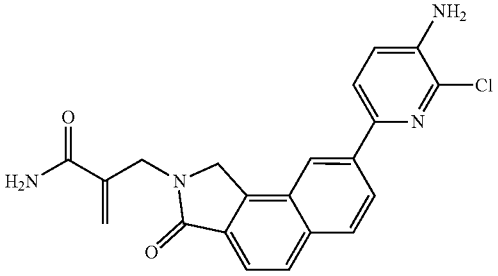 [SMILES: C=C(CN1Cc2c(ccc3ccc(-c4ccc(N)c(Cl)n4)cc23)C1=O)C(N)=O] | 2-{[8-(5-amino-6-chloropyridin-2-yl)-3-oxo-1H,2H,3H-benzo[e]isoindol-2-yl]methyl}prop-2-enamide | 392.8 |

TABLE 15-continued
| Cpd. No. | Structure | IUPAC | MW (g/mol) |
|---|---|---|---|
| 835. | 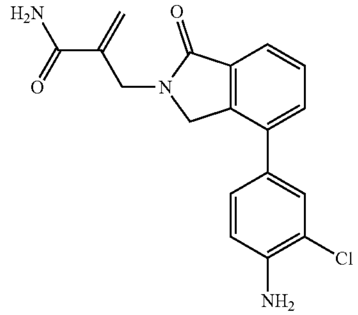 [SMILES: C=C(CN1Cc2c(cccc2-c2cnc(N)c(Cl)c2)C1=O)C(N)=O] | 2-{[4-(4-amino-3-chlorophenyl)-1-oxo-2,3-dihydro-1H-isoindol-2-yl]methyl}prop-2-enamide | 341.8 |
| 836. | 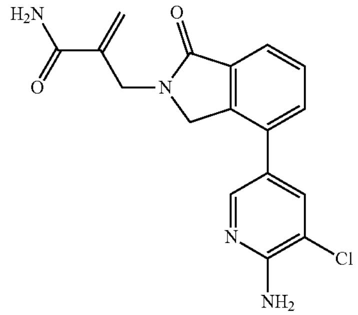 | 2-{[4-(6-amino-5-chloropyridin-3-yl)-1-oxo-2,3-dihydro-1H-isoindol-2-yl]methyl}prop-2-enamide | 342.8 |
| 837. | 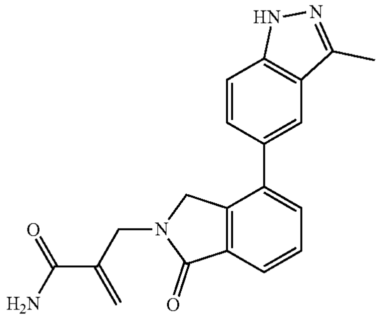 [SMILES: C=C(CN1Cc2c(cccc2-c2ccc3[nH]nc(C)c3c2)C1=O)C(N)=O] | 2-{[4-(3-methyl-1H-indazol-5-yl)-1-oxo-2,3-dihydro-1H-isoindol-2-yl]methyl}prop-2-enamide | 346.4 |
| 838. | 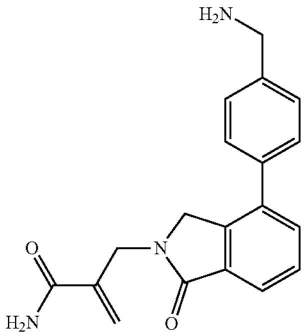 [SMILES: C=C(CN1Cc2c(cccc2-c2ccc(CN)cc2)C1=O)C(N)=O] | 2-({4-[4-(aminomethyl)phenyl]-1-oxo-2,3-dihydro-1H-isoindol-2-yl}methyl)prop-2-enamide | 321.4 |

TABLE 15-continued

| Cpd. No. | Structure | IUPAC | MW (g/mol) |
|---|---|---|---|
| 839. | 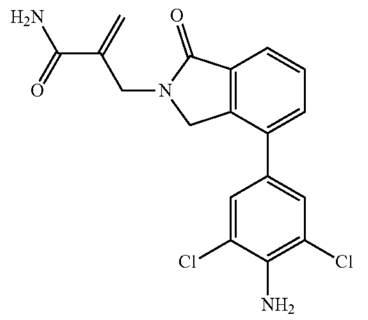 [SMILES: C=C(CN1Cc2c(cccc2-c2cc(Cl)c(N)c(Cl)c2)C1=O)C(N)=O] | 2-{[4-(4-amino-3,5-dichlorophenyl)-1-oxo-2,3-dihydro-1H-isoindol-2-yl]methyl}prop-2-enamide | 376.2 |
| 840. | 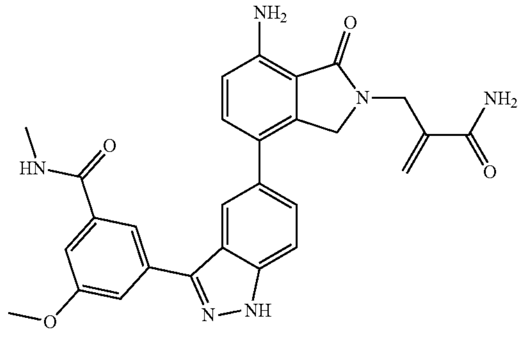 [SMILES: C=C(CN1Cc2c(-c3ccc4[nH]nc(-c5cc(OC)cc(C(=O)NC)c5)c4c3)ccc(N)c2C1=O)C(N)=O] | 3-{5-[7-amino-2-(2-carbamoyl-2-methylideneethyl)-1-oxo-2,3-dihydro-1H-isoindol-4-yl]-1H-indazol-3-yl}-5-methoxy-N-methylbenzamide | 510.6 |
| 841. | 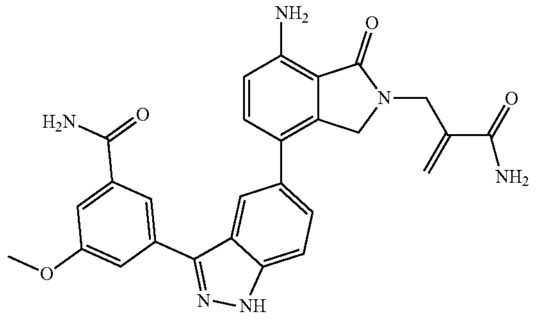 [SMILES: C=C(CN1Cc2c(-c3ccc4[nH]nc(-c5cc(OC)cc(C(N)=O)c5)c4c3)ccc(N)c2C1=O)C(N)=O] | 3-{5-[7-amino-2-(2-carbamoyl-2-methylideneethyl)-1-oxo-2,3-dihydro-1H-isoindol-4-yl]-1H-indazol-3-yl}-5-methoxybenzamide | 496.5 |
| 842. | 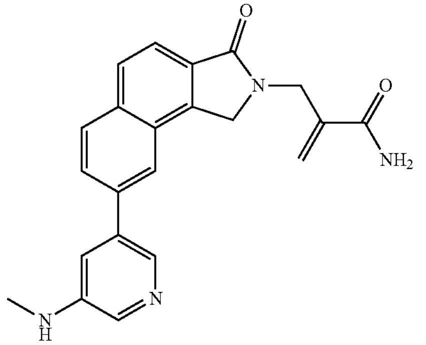 [SMILES: C=C(CN1Cc2c(ccc3ccc(-c4cncc(NC)c4)cc23)C1=O)C(N)=O] | 2-({8-[5-(methylamino)pyridin-3-yl]-3-oxo-1H,2H,3H-benzo[e]isoindol-2-yl}methyl)prop-2-enamide | 372.4 |

TABLE 15-continued
| Cpd. No. | Structure | IUPAC | MW (g/mol) |
|---|---|---|---|
| 843. | 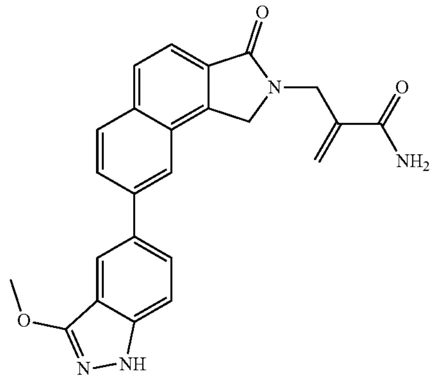 [SMILES: C=C(CN1Cc2c(ccc3ccc(-c4ccc5[nH]nc(OC)c5c4)cc23)C1=O)C(N)=O] | 2-{[8-(3-methoxy-1H-indaozl-5-yl)-3-oxo-1H,2H,3H-benzo[e]isoindol-2-yl]methyl}prop-2-enamide | 412.4 |
| 844. | 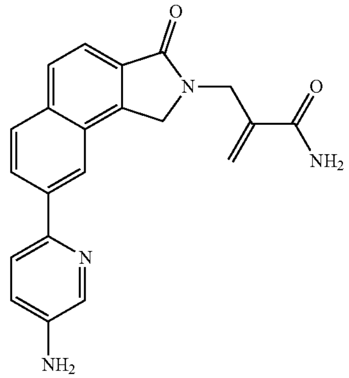 [SMILES: C=C(CN1Cc2c(ccc3ccc(-c4ccc(N)cn4)cc23)C1=O)C(N)=O] | 2-{[8-(5-aminopyridin-2-yl)-3-oxo-1H,2H,3H-benzo[e]isoindol-2-yl]methyl}prop-2-enamide | 358.4 |
| 845. | 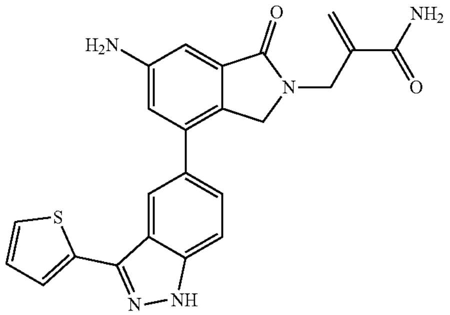 [SMILES: C=C(CN1Cc2c(cc(N)cc2-c2ccc3[nH]nc(-c4cccs4)c3c2)C1=O)C(N)=O] | 2-({6-amino-1-oxo-4-[3-(thiophen-2-yl)-1H-indazol-5-yl]-2,3-dihydro-1H-isoindol-2-yl}methyl)prop-2-enamide | 429.5 |
| 846. | 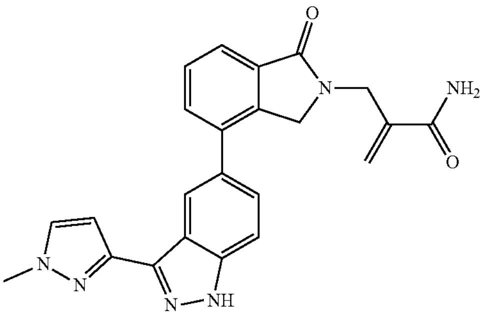 [SMILES: C=C(CN1Cc2c(cccc2-c2ccc3[nH]nc(-c4ccn(C)n4)c3c2)C1=O)C(N)=O] | 2-({4-[3-(1-methyl-1H-pyrazol-3-yl)-1H-indazol-5-yl]-1-oxo-2,3-dihydro-1H-isoindol-2-yl}methyl)prop-2-enamide | 412.5 |

TABLE 15-continued

| Cpd. No. | Structure | IUPAC | MW (g/mol) |
|---|---|---|---|
| 847. | 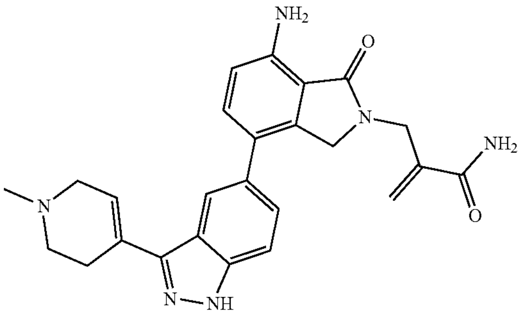 [SMILES: C=C(CN1Cc2c(-c3ccc4[nH]nc(C5=CCN(C)CC5)c4c3)ccc(N)c2C1=O)C(N)=O] | 2-({7-amino-4-[3-(1-methyl-1,2,3,6-tetrahydropyridin-4-yl)-1H-indazol-5-yl]-1-oxo-2,3-dihydro-1H-isoindol-2-yl}methyl)prop-2-enamide | 442.5 |
| 848. | 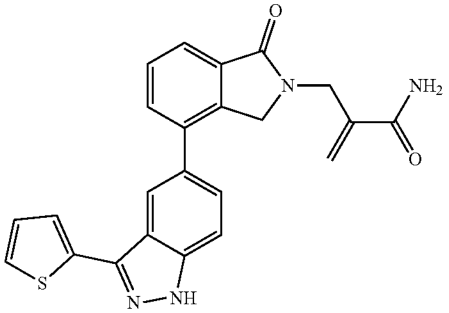 [SMILES: C=C(CN1Cc2c(cccc2-c2ccc3[nH]nc(-c4cccs4)c3c2)C1=O)C(N)=O] | 2-({1-oxo-4-[3-(thiophen-2-yl)-1H-indazol-5-yl]-2,3-dihydro-1H-isoindol-2-yl}methyl)prop-2-enamide | 414.5 |
| 849. | 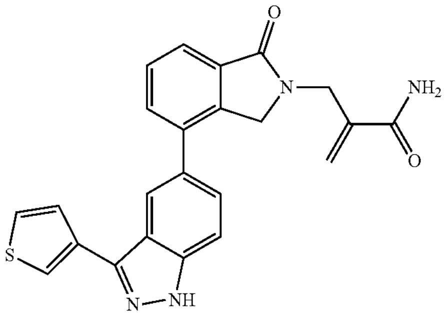 [SMILES: C=C(CN1Cc2c(cccc2-c2ccc3[nH]nc(-c4ccsc4)c3c2)C1=O)C(N)=O] | 2-({1-oxo-4-[3-(thiophen-3-yl)-1H-indazol-5-yl]-2,3-dihydro-1H-isoindol-2-yl}methyl)prop-2-enamide | 414.5 |
| 850. | 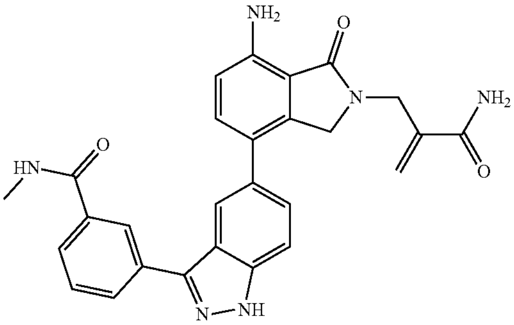 [SMILES: C=C(CN1Cc2c(-c3ccc4[nH]nc(-c5cccc(C(=O)NC)c5)c4c3)ccc(N)c2C1=O)C(N)=O] | 3-{5-[7-amino-2-(2-carbamoyl-2-methylideneethyl)-1-oxo-2,3-dihydro-1H-isoindol-4-yl]-1H-indazol-3-yl}-N-methylbenzamide | 480.5 |

TABLE 15-continued

| Cpd. No. | Structure | IUPAC | MW (g/mol) |
| --- | --- | --- | --- |
| 851. | 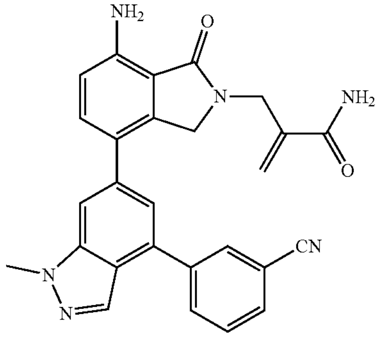 [SMILES: C=C(CN1Cc2c(-c3cc(-c4cccc(C#N)c4)c4cnn(C)c4c3)ccc(N)c2C1=O)C(N)=O] | 2-({7-amino-4-[4-(3-cyanophenyl)-1-methyl-1H-indazol-6-yl]-1-oxo-2,3-dihydro-1H-isoindol-2-yl}methyl)prop-2-enamide | 462.5 |
| 852. | 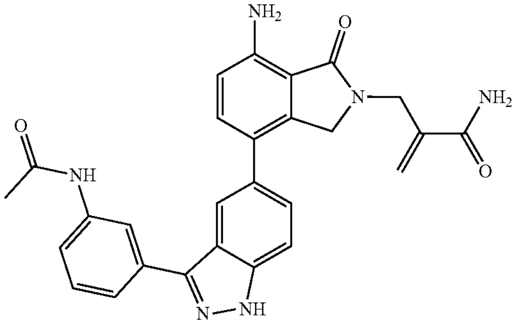 [SMILES: C=C(CN1Cc2c(-c3ccc4[nH]nc(-c5cccc(NC(C)=O)c5)c4c3)ccc(N)c2C1=O)C(N)=O] | 2-({7-amino-4-[3-(3-acetamidophenyl)-1H-indazol-5-yl]-1-oxo-2,3-dihydro-1H-isoindol-2-yl}methyl)prop-2-enamide | 480.5 |
| 853. | 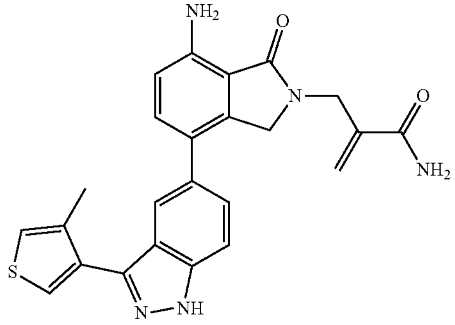 [SMILES: C=C(CN1Cc2c(-c3ccc4[nH]nc(-c5cscc5C)c4c3)ccc(N)c2C1=O)C(N)=O] | 2-({7-amino-4-[3-(4-methylthiophen-3-yl)-1H-indazol-5-yl]-1-oxo-2,3-dihydro-1H-isoindol-2-yl}methyl)prop-2-enamide | 443.5 |
| 854. | 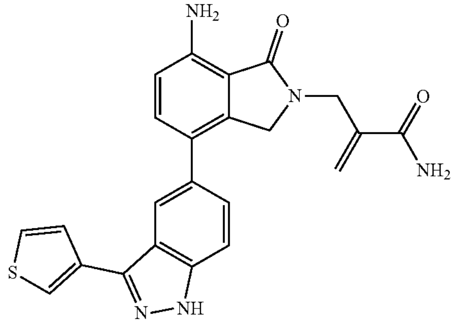 [SMILES: C=C(CN1Cc2c(-c3ccc4[nH]nc(-c5ccsc5)c4c3)ccc(N)c2C1=O)C(N)=O] | 2-({7-amino-1-oxo-4-[3-(thiophen-3-yl)-1H-indazol-5-yl]-2,3-dihydro-1H-isoindol-2-yl}methyl)prop-2-enamide | 429.5 |

TABLE 15-continued

| Cpd. No. | Structure | IUPAC | MW (g/mol) |
|---|---|---|---|
| 855. | 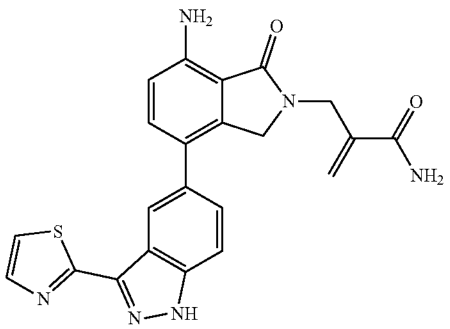 [SMILES: C=C(CN1Cc2c(-c3ccc4[nH]nc(-c5nccs5)c4c3)ccc(N)c2C1=O)C(N)=O] | 2-({7-amino-1-oxo-4-[3-(1,3-thiazol-2-yl)-1H-indazol-5-yl]-2,3-dihydro-1H-isoindol-2-yl}methyl)prop-2-enamide | 430.5 |
| 856. | 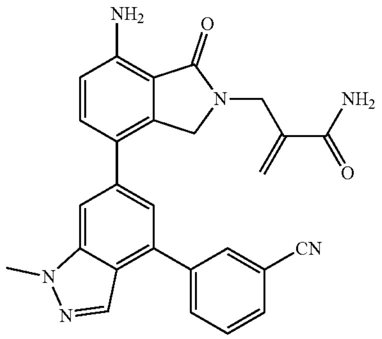 [SMILES: C=C(CN1Cc2c(-c3cc(-c4cccc(C#N)c4)c4cnn(C)c4c3)ccc(N)c2C1=O)C(N)=O] | 2-({7-amino-4-[4-(3-chlorophenyl)-1-methyl-1H-indazol-6-yl]-1-oxo-2,3-dihydro-1H-isoindol-2-yl}methyl)prop-2-enamide | 472.0 |
| 857. | 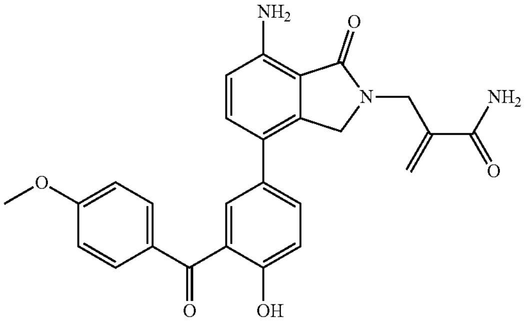 [SMILES: C=C(CN1Cc2c(-c3ccc(O)c(C(=O)c4ccc(OC)cc4)c3)ccc(N)c2C1=O)C(N)=O] | 2-({7-amino-4-[4-hydroxy-3-(4-methoxybenzoyl)phenyl]-1-oxo-2,3-dihydro-1H-isoindol-2-yl}methyl)prop-2-enamide | 457.5 |
| 858. | 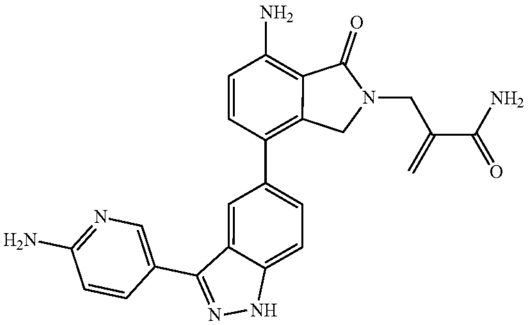 [SMILES: C=C(CN1Cc2c(-c3ccc4[nH]nc(-c5ccc(N)nc5)c4c3)ccc(N)c2C1=O)C(N)=O] | 2-({7-amino-4-[3-(6-aminopyridin-3-yl)-1H-indazol-5-yl]-1-oxo-2,3-dihydro-1H-isoindol-2-yl}methyl)prop-2-enamide | 439.5 |

TABLE 15-continued

| Cpd. No. | Structure | IUPAC | MW (g/mol) |
|---|---|---|---|
| 859. | 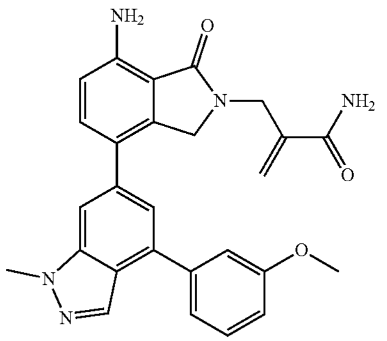 [SMILES: C=C(CN1Cc2c(-c3cc(-c4cccc(OC)c4)c4cnn(C)c4c3)ccc(N)c2C1=O)C(N)=O] | 2-({7-amino-4-[4-(3-methoxyphenyl)-1-methyl-1H-indazol-6-yl]-1-oxo-2,3-dihydro-1H-isoindol-2-yl}methyl)prop-2-enamide | 467.5 |
| 860. | 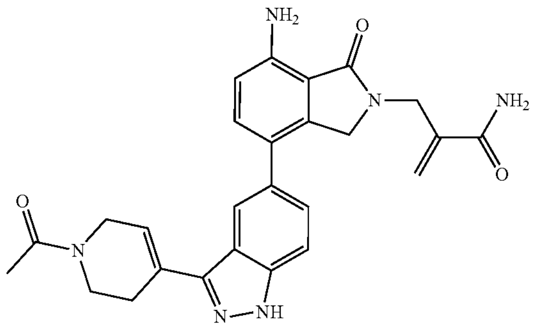 [SMILES: C=C(CN1Cc2c(-c3ccc4[nH]nc(C5=CCN(C(C)=O)CC5)c4c3)ccc(N)c2C1=O)C(N)=O] | 2-({4-[3-(1-acetyl-1,2,3,6-tetrahydropyridin-4-yl)-1H-indazol-5-yl]-7-amino-1-oxo-2,3-dihydro-1H-isoindol-2-yl}methyl)prop-2-enamide | 470.5 |
| 861. | 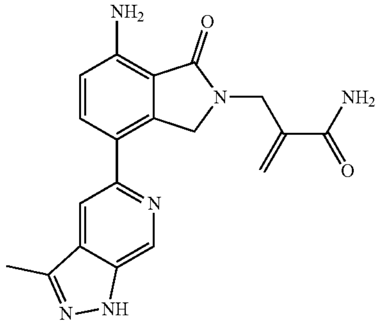 [SMILES: C=C(CN1Cc2c(-c3cc4c(C)n[nH]c4cn3)ccc(N)c2C1=O)C(N)=O] | 2-[(7-amino-4-{3-methyl-1H-pyrazolo[3,4-c]pyridin-5-yl}-1-oxo-2,3-dihydro-1H-isoindol-2-yl)methyl]prop-2-enamide | 362.4 |
| 862. | 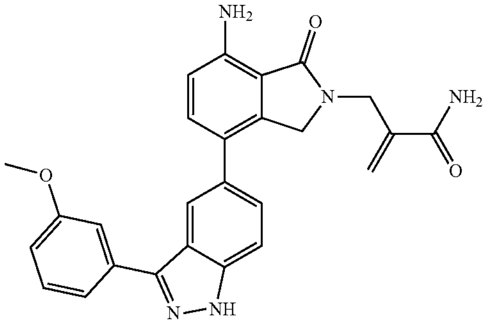 [SMILES: C=C(CN1Cc2c(-c3ccc4[nH]nc(-c5cccc(OC)c5)c4c3)ccc(N)c2C1=O)C(N)=O] | 2-({7-amino-4-[3-(3-methoxyphenyl)-1H-indazol-5-yl]-1-oxo-2,3-dihydro-1H-isoindol-2-yl}methyl)prop-2-enamide | 453.5 |

TABLE 15-continued

| Cpd. No. | Structure | IUPAC | MW (g/mol) |
| --- | --- | --- | --- |
| 863. | 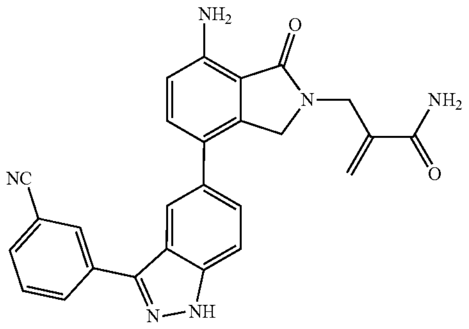 [SMILES: C=C(CN1Cc2c(-c3ccc4[nH]nc(-c5cccc(C#N)c5)c4c3)ccc(N)c2C1=O)C(N)=O] | 2-({7-amino-4-[3-(3-cyanophenyl)-1H-indazol-5-yl]-1-oxo-2,3-dihydro-1H-isoindol-2-yl}methyl)prop-2-enamide | 448.5 |
| 864. | 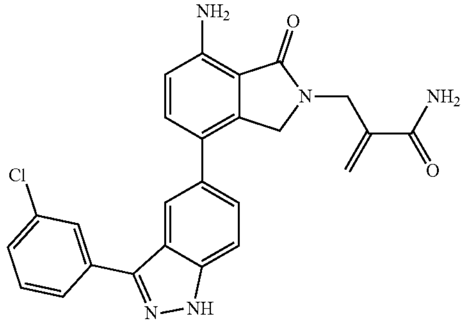 [SMILES: C=C(CN1Cc2c(-c3ccc4[nH]nc(-c5cccc(Cl)c5)c4c3)ccc(N)c2C1=O)C(N)=O] | 2-({7-amino-4-[3-(3-chlorophenyl)-1H-indazol-5-yl]-1-oxo-2,3-dihydro-1H-isoindol-2-yl}methyl)prop-2-enamide | 457.9 |
| 865. | 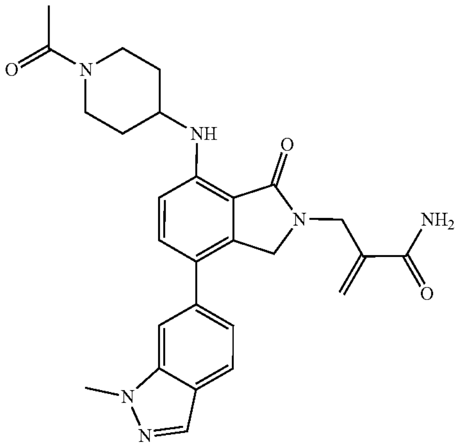 [SMILES: C=C(CN1Cc2c(-c3ccc4cnn(C)c4c3)ccc(NC3CCN(C(C)=O)CC3)c2C1=O)C(N)=O] | 2-({7-[(1-acetylpiperidin-4-yl)amino]-4-(1-methyl-1H-indazol-6-yl)-1-oxo-2,3-dihydro-1H-isoindol-2-yl}methyl)prop-2-enamide | 486.6 |
| 866. | 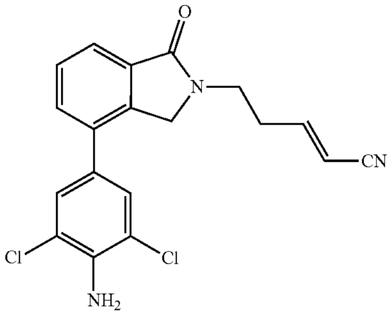 [SMILES: N#C/C=C/CCN1Cc2c(cccc2-c2cc(Cl)c(N)c(Cl)c2)C1=O] | (2E)-5-[4-(4-amino-3,6-dichlorophenyl)-1-oxo-2,3-dihydro-1H-isoindol-2-yl]pent-2-enenitrile | 372.3 |

TABLE 15-continued
| Cpd. No. | Structure | IUPAC | MW (g/mol) |
|---|---|---|---|
| 867. | 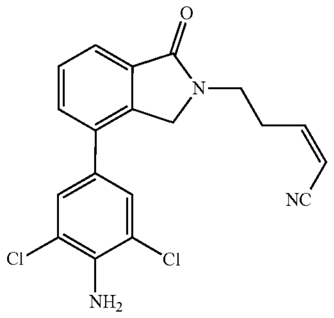 [SMILES: N#C/C=C\CCN1Cc2c(cccc2-c2cc(Cl)c(N)c(Cl)c2)C1=O] | (2Z)-5-[4-(4-amino-3,5-dichlorophenyl)-1-oxo-2,3-dihydro-1H-isoindol-2-yl]pent-2-enenitrile | 372.3 |
| 868. | 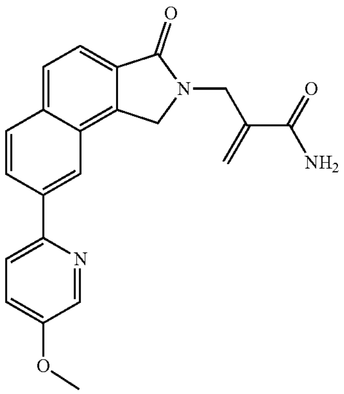 [SMILES: C=C(CN1Cc2c(ccc3ccc(-c4ccc(OC)cn4)cc23)C1=O)C(N)=O] | 2-{[8-(5-methoxypyridin-2-yl)-3-oxo-1H,2H,3H-benzo[e]isoindol-2-yl]methyl}prop-2-enamide | 373.4 |
| 869. | 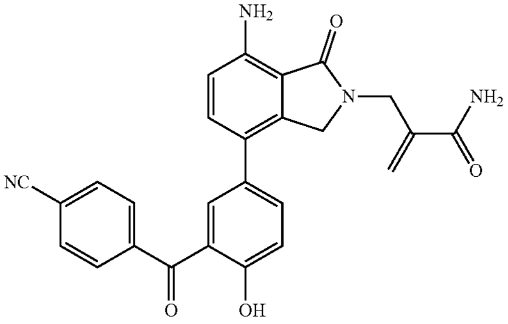 [SMILES: C=C(CN1Cc2c(-c3ccc(O)c(C(=O)c4ccc(C#N)cc4)c3)ccc(N)c2C1=O)C(N)=O] | 2-({7-amino-4-[3-(4-cyanobenzyl)-4-hydroxyphenyl]-1-oxo-2,3-dihydro-1H-isoindol-2-yl}methyl)prop-2-enamide | 452.5 |
| 870. | 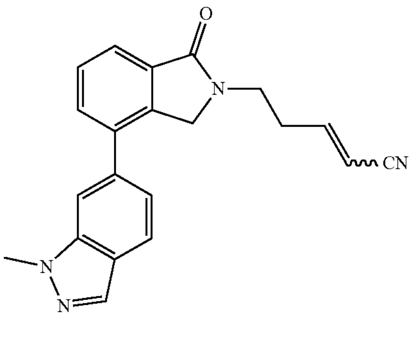 [SMILES: Cn1ncc2ccc(-c3cccc4c3CN(CCC=CC#N)C4=O)cc21] | 5-[4-(1-methyl-1H-indazol-6-yl)-1-oxo-2,3-dihydro-1H-isoindol-2-yl]pent-2-enenitrile | 342.4 |

TABLE 15-continued

| Cpd. No. | Structure | IUPAC | MW (g/mol) |
|---|---|---|---|
| 871. | 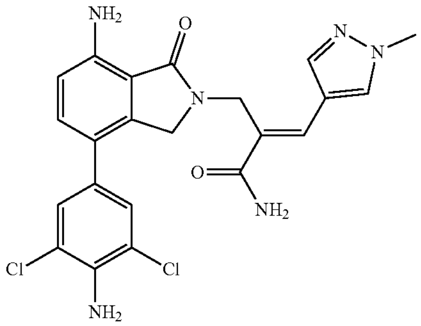 [SMILES: Cn1cc(/C=C(\CN2Cc3c(-c4cc(Cl)c(N)c(Cl)c4)ccc(N)c3C2=O)C(N)=O)cn1] | (2E)-2-{[7-amino-4-(4-amino-3,5-dichlorophenyl)-1-oxo-2,3-dihydro-1H-isoindol-2-yl]methyl}-3-(1-methyl-1H-pyrazol-4-yl)prop-2-enamide | 471.3 |
| 872. | 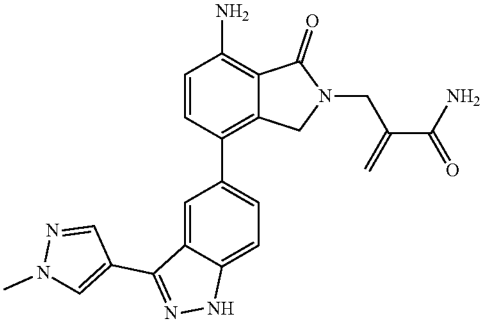 [SMILES: C=C(CN1Cc2c(-c3ccc4[nH]nc(-c5cnn(C)c5)c4c3)ccc(N)c2C1=O)C(N)=O] | 2-({7-amino-4-[3-(1-methyl-1H-pyrazol-4-yl)-1H-indazol-5-yl]-1-oxo-2,3-dihydro-1H-isoindol-2-yl}methyl)prop-2-enamide | 472.5 |
| 873. | 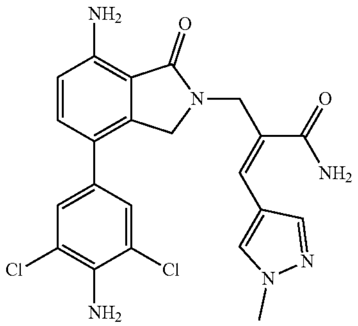 [SMILES: Cn1cc(/C=C(/CN2Cc3c(-c4cc(Cl)c(N)c(Cl)c4)ccc(N)c3C2=O)C(N)=O)cn1] | (2Z)-2-{[7-amino-4-(4-amino-3,5-dichlorophenyl)-1-oxo-2,3-dihydro-1H-isoindol-2-yl]methyl}-3-(1-methyl-1H-pyrazol-4-yl)prop-2-enamide | 471.3 |
| 874. | 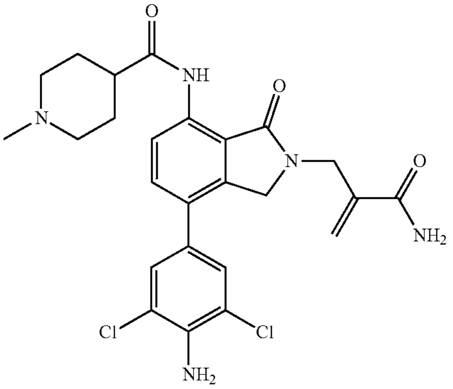 [SMILES: C=C(CN1Cc2c(-c3cc(Cl)c(N)c(Cl)c3)ccc(NC(=O)C3CCN(C)CC3)c2C1=O)C(N)=O] | N-[7-(4-amino-3,5-dichlorophenyl)-2-(2-carbamoyl-2-methylideneethyl)-3-oxo-2,3-dihydro-1H-isoindol-4-yl]-1-methylpiperidine-4-carboxamide | 516.4 |

TABLE 15-continued

| Cpd. No. | Structure | IUPAC | MW (g/mol) |
|---|---|---|---|
| 875. | 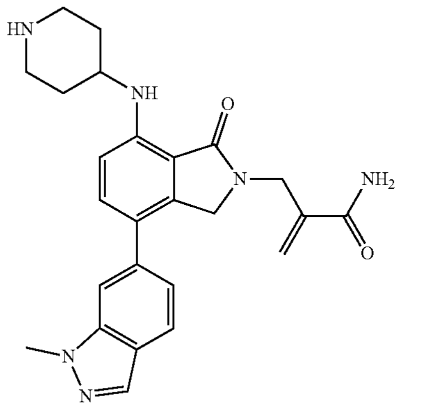 [SMILES: C=C(CN1Cc2c(-c3ccc4cnn(C)c4c3)ccc(NC3CCNCC3)c2C1=O)C(N)=O] | 2-{[4-(1-methyl-1H-indazol-6-yl)-1-oxo-7-[(piperidin-4-yl)amino]-2,3-dihydro-1H-isoindol-2-yl]methyl}prop-2-enamide | 444.5 |
| 876. | 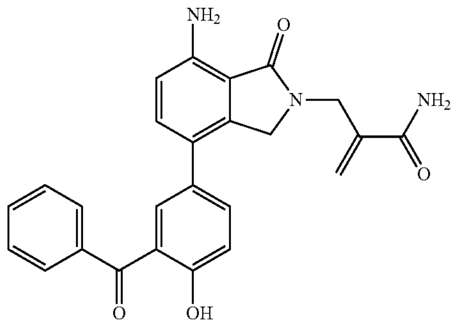 [SMILES: C=C(CN1Cc2c(-c3ccc(O)c(C(=O)c4ccccc4)c3)ccc(N)c2C1=O)C(N)=O] | 2-{[7-amino-4-(3-benzoyl-4-hydroxyphenyl)-1-oxo-2,3-dihydro-1H-isoindol-2-yl]methyl}prop-2-enamide | 427.5 |
| 877. | 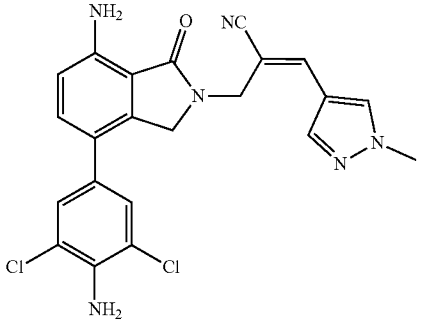 [SMILES: Cn1cc(/C=C(/C#N)CN2Cc3c(-c4cc(Cl)c(N)c(Cl)c4)ccc(N)c3C2=O)cn1] | (2E)-2-{[7-amino-4-(4-amino-3,5-dichlorophenyl)-1-oxo-2,3-dihydro-1H-isoindol-2-yl]methyl}-3-(1-methyl-1H-pyrazol-4-yl)prop-2-enenitrile | 453.3 |
| 878. | 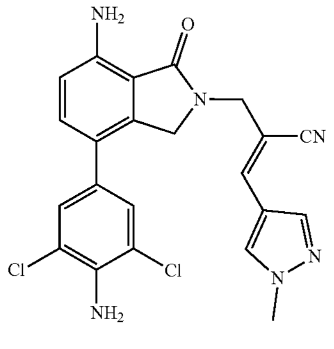 [SMILES: Cn1cc(/C=C(\C#N)CN2Cc3c(-c4cc(Cl)c(N)c(Cl)c4)ccc(N)c3C2=O)cn1] | (2Z)-2-{[7-amino-4-(4-amino-3,5-dichlorophenyl)-1-oxo-2,3-dihydro-1H-isoindol-2-yl]methyl}-3-(1-methyl-1H-pyrazol-4-yl)prop-2-enenitrile | 453.3 |

TABLE 15-continued
| Cpd. No. | Structure | IUPAC | MW (g/mol) |
|---|---|---|---|
| 879. | 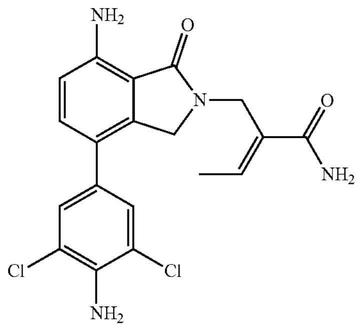 [SMILES: C/C=C(\CN1Cc2c(-c3cc(Cl)c(N)c(Cl)c3)ccc(N)c2C1=O)C(N)=O] | (2E)-2-{[7-amino-4-(4-amino-3,5-dichlorophenyl)-1-oxo-2,3-dihydro-1H-isoindol-2-yl]methyl}but-2-enamide | 405.3 |
| 880. | 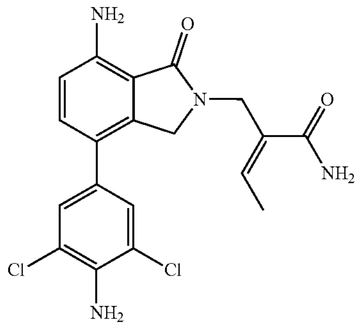 [SMILES: C/C=C(/CN1Cc2c(-c3cc(Cl)c(N)c(Cl)c3)ccc(N)c2C1=O)C(N)=O] | (2Z)-2-{[7-amino-4-(4-amino-3,5-dichlorophenyl)-1-oxo-2,3-dihydro-1H-isoindol-2-yl]methyl}but-2-enamide | 405.3 |
| 881. | 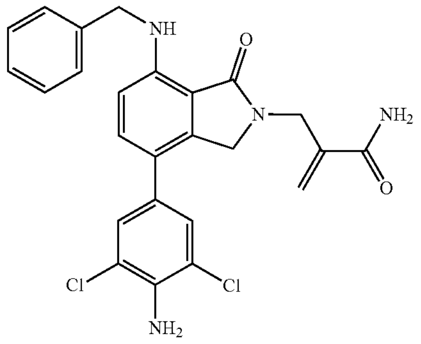 [SMILES: C=C(CN1Cc2c(-c3cc(Cl)c(N)c(Cl)c3)ccc(NCc3ccccc3)c2C1=O)C(N)=O] | 2-{[4-(4-amino-3,5-dichlorophenyl)-7-(benzylamino)-1-oxo-2,3-dihydro-1H-isoindol-2-yl]methyl}prop-2-enamide | 481.4 |
| 882. | 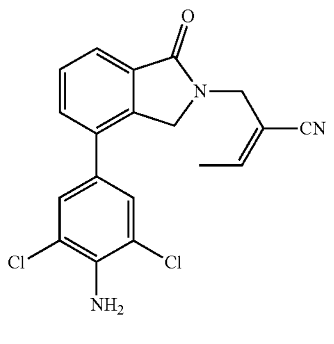 [SMILES: C/C=C(/C#N)CN1Cc2c(cccc2-c2cc(Cl)c(N)c(Cl)c2)C1=O] | (2E)-2-{[4-(4-amino-3,5-dichlorophenyl)-1-oxo-2,3-dihydro-1H-isoindol-2-yl]methyl}but-2-enenitrile | 372.3 |

TABLE 15-continued

| Cpd. No. | Structure | IUPAC | MW (g/mol) |
| --- | --- | --- | --- |
| 883. | 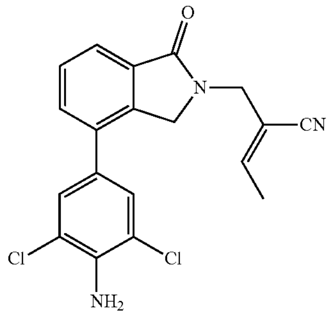 [SMILES: C/C=C(\C#N)CN1Cc2c(cccc2-c2cc(Cl)c(N)c(Cl)c2)C1=O] | (2Z)-2-{[4-(4-amino-3,5-dichlorophenyl)-1-oxo-2,3-dihydro-1H-isoindol-2-yl]methyl}but-2-enenitrile | 372.3 |
| 884. | 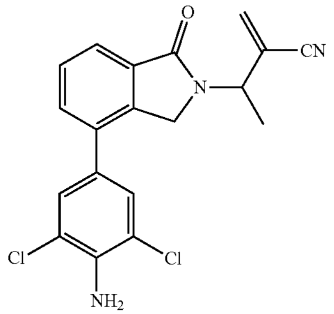 [SMILES: C=C(C#N)C(C)N1Cc2c(cccc2-c2cc(Cl)c(N)c(Cl)c2)C1=O] | 3-[4-(4-amino-3,5-dichlorophenyl)-1-oxo-2,3-dihydro-1H-isoindol-2-yl]-2-methylidenebutanenitrile | 372.3 |
| 885. | 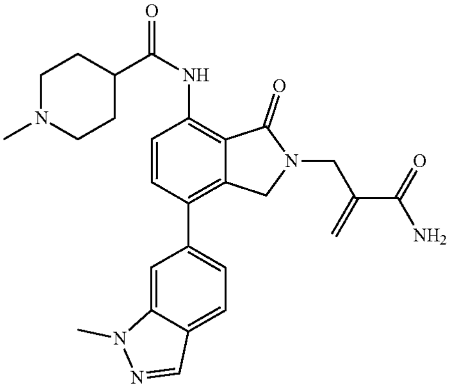 [SMILES: C=C(CN1Cc2c(-c3ccc4cnn(C)c4c3)ccc(NC(=O)C3CCN(C)CC3)c2C1=O)C(N)=O] | N-[2-(2-carbamoyl-2-methylideneethyl)-7-(1-methyl-1H-indazol-6-yl)-3-oxo-2,3-dihydro-1H-isoindol-4-yl]-1-methylpiperidine-4-carboxamide | 486.6 |
| 886. | 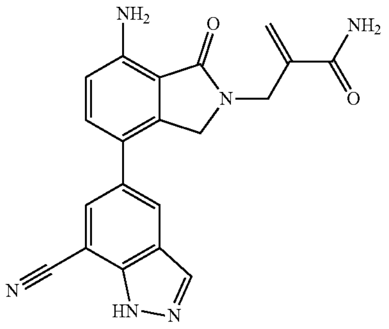 [SMILES: C=C(CN1Cc2c(-c3cc(C#N)c4[nH]ncc4c3)ccc(N)c2C1=O)C(N)=O] | 2-{[7-amino-4-(7-cyano-1H-indazol-5-yl)-1-oxo-2,3-dihydro-1H-isoindol-2-yl]methyl}prop-2-enamide | 372.4 |

TABLE 15-continued
| Cpd. No. | Structure | IUPAC | MW (g/mol) |
| --- | --- | --- | --- |
| 887. | 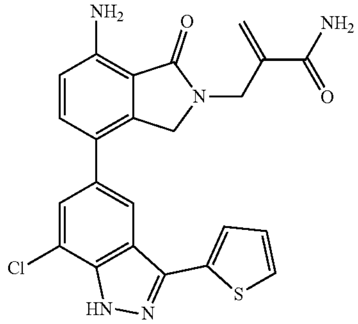 [SMILES: C=C(CN1Cc2c(-c3cc(Cl)c4[nH]nc(-c5cccs5)c4c3)ccc(N)c2C1=O)C(N)=O] | 2-({7-amino-4-[7-chloro-3-(thiophen-2-yl)-1H-indazol-5-yl]-1-oxo-2,3-dihydro-1H-isoindol-2-yl}methyl)prop-2-enamide | 463.9 |
| 888. | 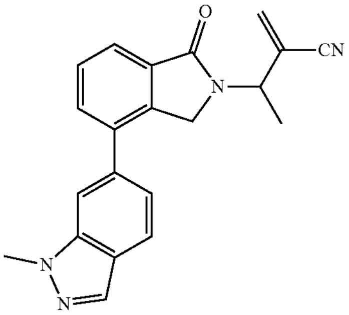 [SMILES: C=C(C#N)C(C)N1Cc2c(cccc2-c2ccc3cnn(C)c3c2)C1=O] | 3-[4-(1-methyl-1H-indazol-6-yl)-1-oxo-2,3-dihydro-1H-isoindol-2-yl]-2-methylidenebutanenitrile | 342.4 |
| 889. | 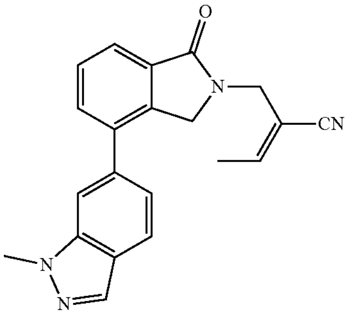 [SMILES: C/C=C(/C#N)CN1Cc2c(cccc2-c2ccc3cnn(C)c3c2)C1=O] | (2E)-2-{[4-(1-methyl-1H-indazol-6-yl)-1-oxo-2,3-dihydro-1H-isoindol-2-yl]methyl}but-2-enenitrile | 342.4 |
| 890. | 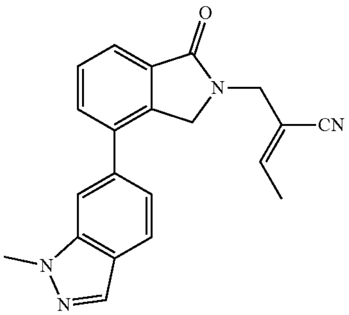 [SMILES: C/C=C(\C#N)CN1Cc2c(cccc2-c2ccc3cnn(C)c3c2)C1=O] | (2Z)-2-{[4-(1-methyl-1H-indazol-6-yl)-1-oxo-2,3-dihydro-1H-isoindol-2-yl]methyl}but-2-enenitrile | 342.4 |

TABLE 15-continued
| Cpd. No. | Structure | IUPAC | MW (g/mol) |
|---|---|---|---|
| 891. | 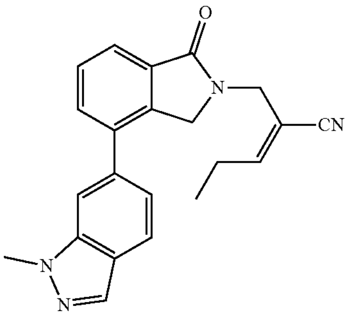 [SMILES: CC/C=C(/C#N)CN1Cc2c(cccc2-c2ccc3cnn(C)c3c2)C1=O] | (2E)-2-{[4-(1-methyl-1H-indazol-6-yl)-1-oxo-2,3-dihydro-1H-isoindol-2-yl]methyl}pent-2-enenitrile | 356.4 |
| 892. | 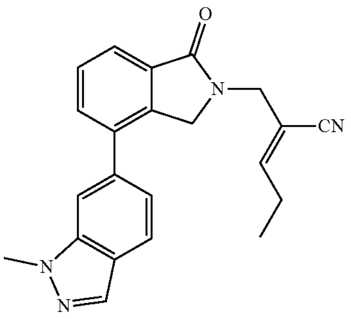 [SMILES: CC/C=C(\C#N)CN1Cc2c(cccc2-c2ccc3cnn(C)c3c2)C1=O] | (2Z)-2-{[4-(1-methyl-1H-indazol-6-yl)-1-oxo-2,3-dihydro-1H-isoindol-2-yl]methyl}pent-2-enenitrile | 356.4 |
| 893. | 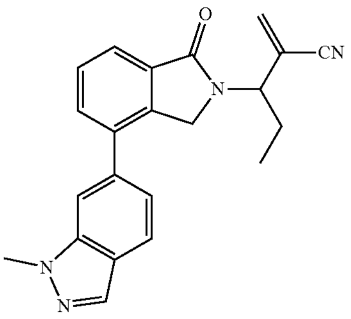 [SMILES: C=C(C#N)C(CC)N1Cc2c(cccc2-c2ccc3cnn(C)c3c2)C1=O] | 3-[4-(1-methyl-1H-indazol-6-yl)-1-oxo-2,3-dihydro-1H-isoindol-2-yl]-2-methylidenepentanenitrile | 356.4 |
| 894. | 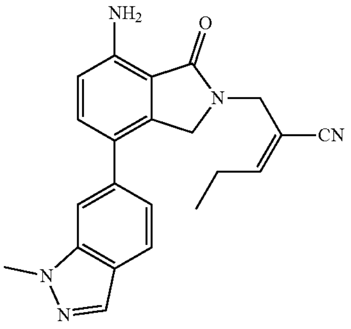 [SMILES: CC/C=C(/C#N)CN1Cc2c(-c3ccc4cnn(C)c4c3)ccc(N)c2C1=O] | (2E)-2-{[7-amino-4-(1-methyl-1H-indazol-6-yl)-1-oxo-2,3-dihydro-1H-isoindol-2-yl]methyl}pent-2-enenitrile | 371.4 |

TABLE 15-continued

| Cpd. No. | Structure | IUPAC | MW (g/mol) |
|---|---|---|---|
| 895. | 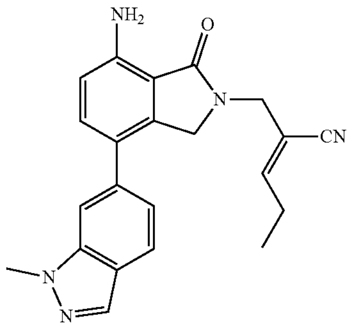 [SMILES: CC/C=C(\C#N)CN1Cc2c(-c3ccc4cnn(C)c4c3)ccc(N)c2C1=O] | (2Z)-2-{[7-amino-4-(1-methyl-1H-indazol-6-yl)-1-oxo-2,3-dihydro-1H-isoindol-2-yl]methyl}pent-2-enenitrile | 371.4 |
| 896. | 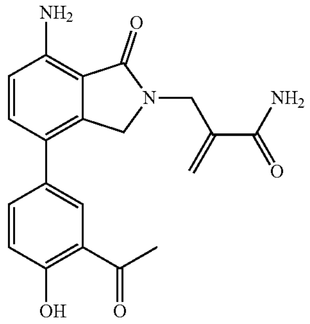 [SMILES: C=C(CN1Cc2c(-c3ccc(O)c(C(C)=O)c3)ccc(N)c2C1=O)C(N)=O] | 2-{[4-(3-acetyl-4-hydroxyphenyl)-7-amino-1-oxo-2,3-dihydro-1H-isoindol-2-yl]methyl}prop-2-enamide | 365.4 |
| 897. | 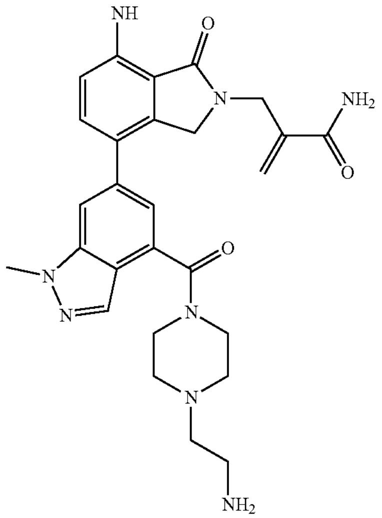 [SMILES: C=C(CN1Cc2c(-c3cc(C(=O)N4CCN(CCN)CC4)c4cnn(C)c4c3)ccc(N)c2C1=O)C(N)=O] | 2-[(7-amino-4-{4-[4-(2-aminoethyl)piperazine-1-carbonyl]-1-methyl-1H-indazol-6-yl}-1-oxo-2,3-dihydro-1H-isoindol-2-yl)methyl]prop-2-enamide | 516.6 |
| 898. | 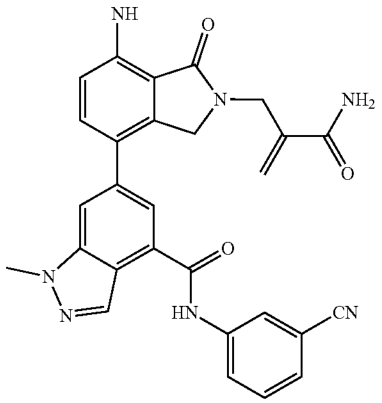 [SMILES: C=C(CN1Cc2c(-c3cc(C(=O)Nc4cccc(C#N)c4)c4cnn(C)c4c3)ccc(N)c2C1=O)C(N)=O] | 6-[7-amino-2-(2-carbamoyl-2-methylideneethyl)-1-oxo-2,3-dihydro-1H-isoindol-4-yl]-N-(3-cyanophenyl)-1-methyl-1H-indazole-4-carboxamide | 505.5 |

TABLE 15-continued

| Cpd. No. | Structure | IUPAC | MW (g/mol) |
|---|---|---|---|
| 899. | 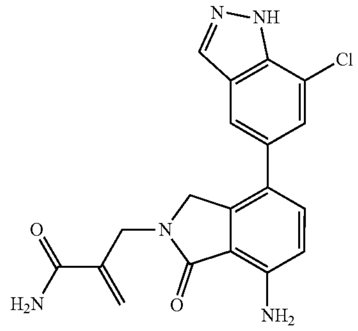 [SMILES: C=C(CN1Cc2c(-c3cc(Cl)c4[nH]ncc4c3)ccc(N)c2C1=O)C(N)=O] | 2-{[7-amino-4-(7-chloro-1H-indazol-5-yl)-1-oxo-2,3-dihydro-1H-isoindol-2-yl]methyl}prop-2-enamide | 381.8 |
| 900. | 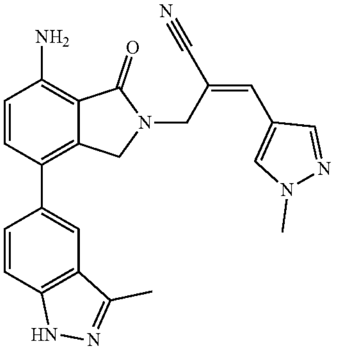 [SMILES: Cc1n[nH]c2ccc(-c3ccc(N)c4c3CN(C/C(C#N)=C\c3cnn(C)c3)C4=O)cc12] | (2E)-2-{[7-amino-4-(3-methyl-1H-indazol-5-yl)-1-oxo-2,3-dihydro-1H-isoindol-2-yl]methyl}-3-(1-methyl-1H-pyrazol-4-yl)prop-2-enenitrile | 423.5 |
| 901. | 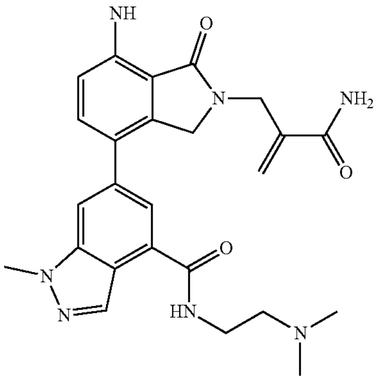 [SMILES: C=C(CN1Cc2c(-c3cc(C(=O)NCCN(C)C)c4cnn(C)c4c3)ccc(N)c2C1=O)C(N)=O] | 6-[7-amino-2-(2-carbamoyl-2-methylideneethyl)-1-oxo-2,3-dihydro-1H-isoindol-4-yl]-N-[2-(dimethylamino)ethyl]-1-methyl-1H-indazol-4-carboxamide | 475.6 |
| 902. | 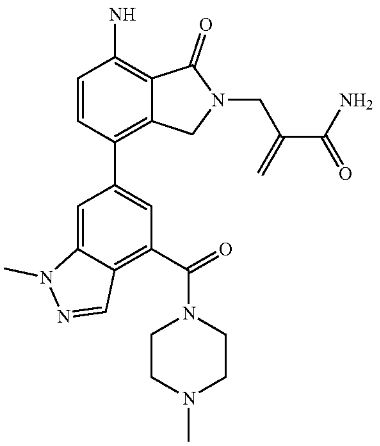 [SMILES: C=C(CN1Cc2c(-c3cc(C(=O)N4CCN(C)CC4)c4cnn(C)c4c3)ccc(N)c2C1=O)C(N)=O] | 2-({7-amino-4-[1-methyl-4-(4-methylpiperazine-1-carbonyl)-1H-indazol-6-yl]-1-oxo-2,3-dihydro-1H-isoindol-2-yl}methyl)prop-2-enamide | 487.6 |

TABLE 15-continued

| Cpd. No. | Structure | IUPAC | MW (g/mol) |
|---|---|---|---|
| 903. | 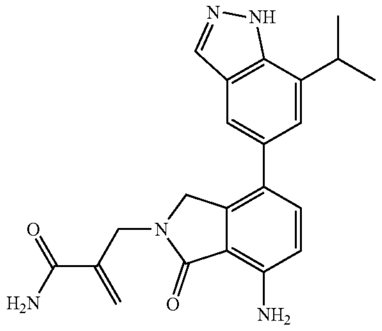 [SMILES: C=C(CN1Cc2c(-c3cc(C(C)C)c4[nH]ncc4c3)ccc(N)c2C1=O)C(N)=O] | 2-({7-amino-1-oxo-4-[7-(propan-2-yl)-1H-indazol-5-yl]-2,3-dihydro-1H-isoindol-2-yl}methyl)prop-2-enamide | 389.5 |
| 904. | 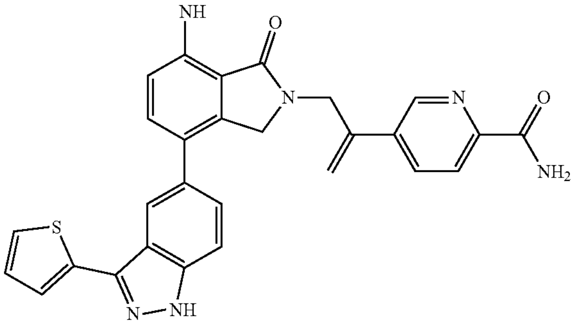 [SMILES: C=C(CN1Cc2c(-c3ccc4[nH]nc(-c5cccs5)c4c3)ccc(N)c2C1=O)c1ccc(C(N)=O)nc1] | 5-(3-{7-amino-1-oxo-4-[3-(thiophen-2-yl)-1H-indazol-5-yl]-2,3-dihydro-1H-isoindol-2-yl}prop-1-en-2-yl)pyridine-2-carboxamide | 506.6 |
| 905. | 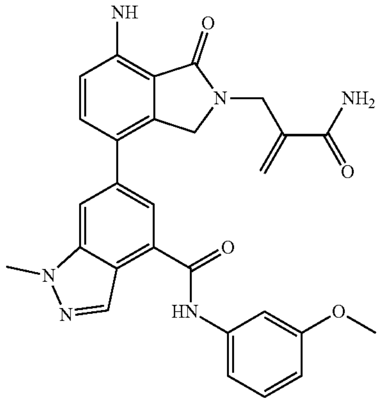 | 6-[7-amino-2-(2-carbamoyl-2-methylideneethyl)-1-oxo-2,3-dihydro-1H-isoindol-4-yl]-N-(3-methoxyphenyl)-1-methyl-1H-indazole-4-carboxamide | 510.6 |
| 906. | 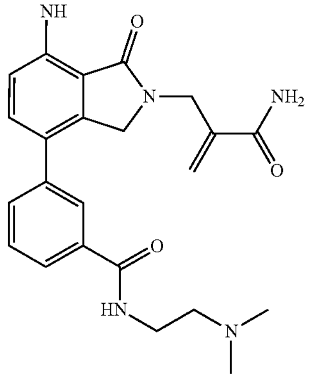 [SMILES: C=C(CN1Cc2c(-c3cccc(C(=O)NCCN(C)C)c3)ccc(N)c2C1=O)C(N)=O] | 3-[7-amino-2-(2-carbamoyl-2-methylideneethyl)-1-oxo-2,3-dihydro-1H-isoindol-4-yl]-N-[2-(dimethylamino)ethyl]benzamide | 421.5 |

TABLE 15-continued

| Cpd. No. | Structure | IUPAC | MW (g/mol) |
|---|---|---|---|
| 907. | 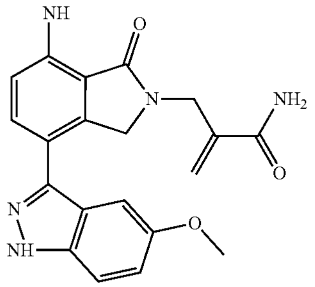 [SMILES: C=C(CN1Cc2c(-c3n[nH]c4ccc(OC)cc34)ccc(N)c2C1=O)C(N)=O] | 2-{[7-amino-4-(5-methoxy-1H-indazol-3-yl)-1-oxo-2,3-dihydro-1H-isoindol-2-yl]methyl}prop-2-enamide | 377.4 |
| 908. | 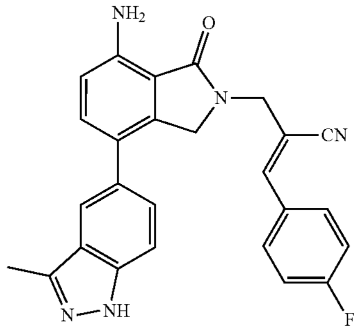 [SMILES: Cc1n[nH]c2ccc(-c3ccc(N)c4c3CN(C/C(C#N)=C/c3ccc(F)cc3)C4=O)cc12] | (2Z)-2-{[7-amino-4-(3-methyl-1H-indazol-5-yl)-1-oxo-2,3-dihydro-1H-isoindol-2-yl]methyl}-3-(4-fluorophenyl)prop-2-enenitrile | 437.5 |
| 909. | 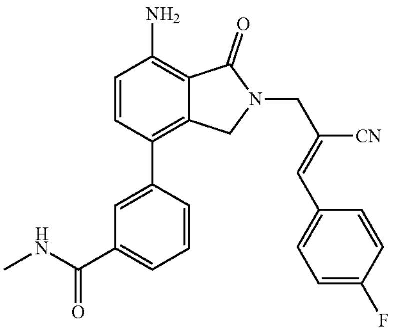 [SMILES: CNC(=O)c1cccc(-c2ccc(N)c3c2CN(C/C(C#N)=C/c2ccc(F)cc2)C3=O)c1] | 3-{7-amino-2-[(2Z)-2-cyano-2-[(4-fluorophenyl)methylidene]ethyl]-1-oxo-2,3-dihydro-1H-isoindol-4-yl}-N-methylbenzamide | 440.5 |
| 910. | 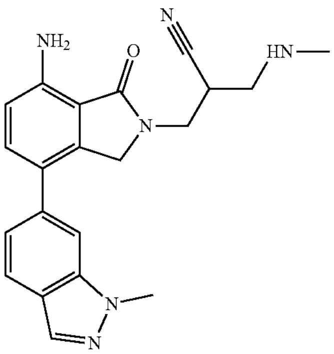 [SMILES: CNCC(C#N)CN1Cc2c(-c3ccc4cnn(C)c4c3)ccc(N)c2C1=O] | 2-{[7-amino-4-(1-methyl-1H-indazol-6-yl)-1-oxo-2,3-dihydro-1H-isoindol-2-yl]methyl}-3-(methylamino)propanenitrile | 374.4 |

TABLE 15-continued

| Cpd. No. | Structure | IUPAC | MW (g/mol) |
|---|---|---|---|
| 911. | 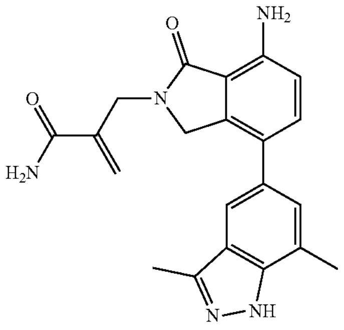 [SMILES: C=C(CN1Cc2c(-c3cc(C)c4[nH]nc(C)c4c3)ccc(N)c2C1=O)C(N)=O] | 2-{[7-amino-4-(3,7-dimethyl-1H-indazol-5-yl)-1-oxo-2,3-dihydro-1H-isoindol-2-yl]methyl}prop-2-enamide | 375.4 |
| 912. | 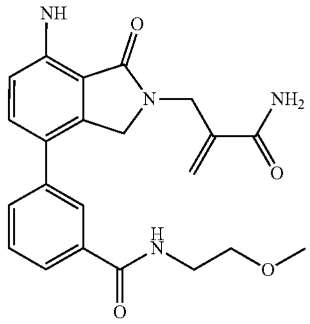 [SMILES: C=C(CN1Cc2c(-c3cccc(C(=O)NCCOC)c3)ccc(N)c2C1=O)C(N)=O] | 3-[7-amino-2-(2-carbamoyl-2-methylideneethyl)-1-oxo-2,3-dihydro-1H-isoindol-4-yl]-N-(2-methoxyethyl)benzamide | 408.5 |
| 913. | 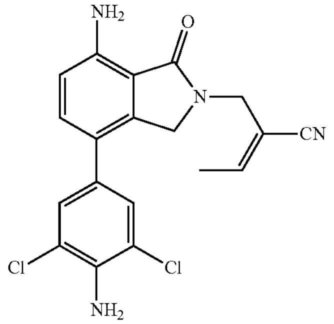 [SMILES: C/C=C(/C#N)CN1Cc2c(-c3cc(Cl)c(N)c(Cl)c3)ccc(N)c2C1=O] | (2E)-2-{[7-amino-4-(4-amino-3,5-dichlorophenyl)-1-oxo-2,3-dihydro-1H-isoindol-2-yl]methyl}but-2-enenitrile | 387.3 |
| 914. | 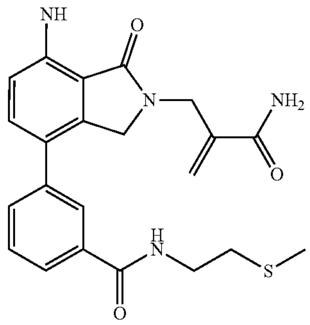 [SMILES: C=C(CN1Cc2c(-c3cccc(C(=O)NCCSC)c3)ccc(N)c2C1=O)C(N)=O] | 3-[7-amino-2-(2-carbamoyl-2-methylideneethyl)-1-oxo-2,3-dihydro-1H-isoindol-4-yl]-N-[2-(methylsulfanyl)ethyl]benzamide | 424.5 |

TABLE 15-continued

| Cpd. No. | Structure | IUPAC | MW (g/mol) |
|---|---|---|---|
| 915. | 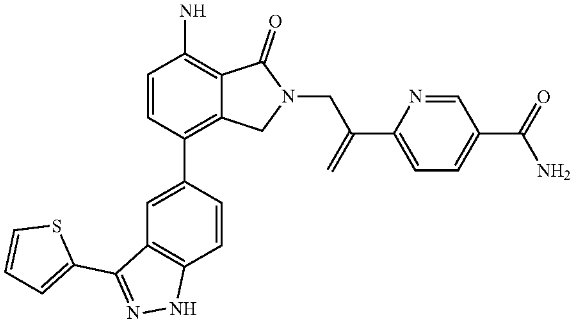 [SMILES: C=C(CN1Cc2c(-c3ccc4[nH]nc(-c5cccs5)c4c3)ccc(N)c2C1=O)c1ccc(C(N)=O)cn1] | 6-(3-{7-amino-1-oxo-4-[3-(thiophen-2-yl)-1H-indazol-5-yl]-2,3-dihydro-1H-isoindol-2-yl}prop-1-en-2-yl)pyridine-3-carboxamide | 506.6 |
| 916. | 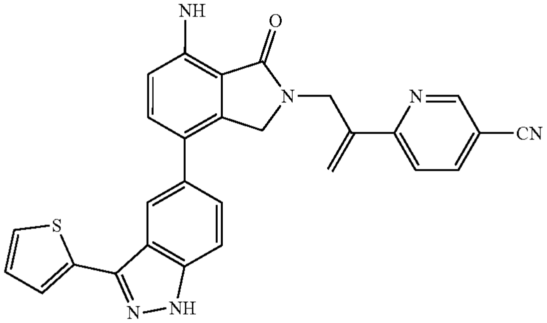 [SMILES: C=C(CN1Cc2c(-c3ccc4[nH]nc(-c5cccs5)c4c3)ccc(N)c2C1=O)c1ccc(C#N)cn1] | 6-(3-{7-amino-1-oxo-4-[3-(thiophen-2-yl)-1H-indazol-5-yl]-2,3-dihydro-1H-isoindol-2-yl}prop-1-en-2-yl)pyridine-3-carbonitrile | 488.6 |
| 917. | 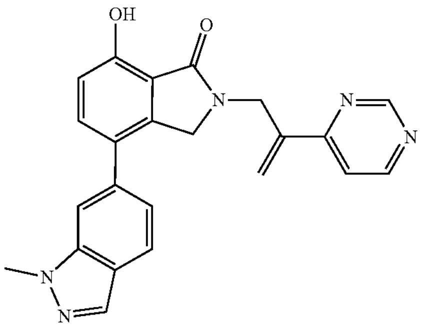 [SMILES: C=C(CN1Cc2c(-c3ccc4cnn(C)c4c3)ccc(O)c2C1=O)c1ccncn1] | 7-hydroxy-4-(1-methyl-1H-indazol-6-yl)-2-[2-(pyrimidin-4-yl)prop-2-en-1-yl]-2,3-dihydro-1H-isoindol-1-one | 397.4 |
| 918. | 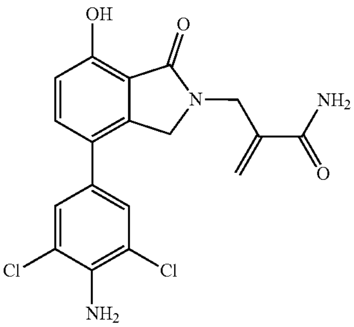 [SMILES: C=C(CN1Cc2c(-c3cc(Cl)c(N)c(Cl)c3)ccc(O)c2C1=O)C(N)=O] | 2-{[4-(4-amino-3,5-dichlorophenyl)-7-hydroxy-1-oxo-2,3-dihydro-1H-isoindol-2-yl]methyl}prop-2-enamide | 392.2 |

TABLE 15-continued
| Cpd. No. | Structure | IUPAC | MW (g/mol) |
|---|---|---|---|
| 919. | 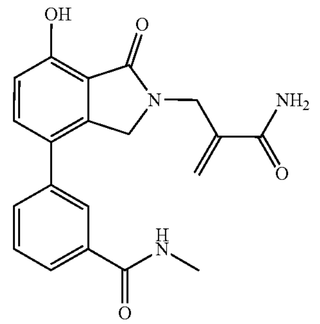 [SMILES: C=C(CN1Cc2c(-c3cccc(C(=O)NC)c3)ccc(O)c2C1=O)C(N)=O] | 3-[2-(2-carbamoyl-2-methylideneethyl)-7-hydroxy-1-oxo-2,3-dihydro-1H-isoindol-4-yl]-N-methylbenzamide | 365.4 |
| 920. | 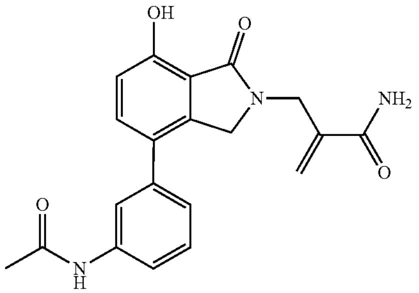 [SMILES: C=C(CN1Cc2c(-c3cccc(NC(C)=O)c3)ccc(O)c2C1=O)C(N)=O] | 2-{[4-(3-acetamidophenyl)-7-hydroxy-1-oxo-2,3-dihydro-1H-isoindol-4-yl]methyl}prop-2-enamide | 365.4 |
| 921. | 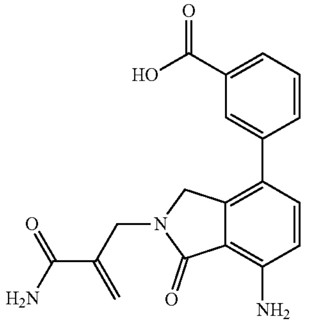 [SMILES: C=C(CN1Cc2c(-c3cccc(C(=O)O)c3)ccc(N)c2C1=O)C(N)=O] | 3-[7-amino-2-(2-carbamoyl-2-methylideneethyl)-1-oxo-2,3-dihydro-1H-isoindol-4-yl]benzoic acid | 351.4 |
| 922. | 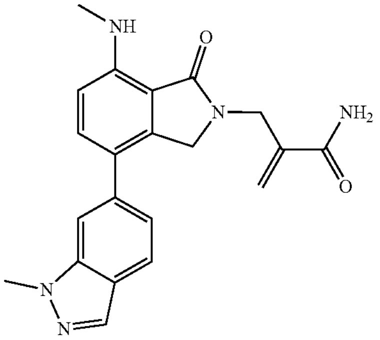 [SMILES: C=C(CN1Cc2c(-c3ccc4cnn(C)c4c3)ccc(NC)c2C1=O)C(N)=O] | 2-{[4-(1-methyl-1H-indazol-6-yl)-7-(methylamino)-1-oxo-2,3-dihydro-1H-isoindol-2-yl]methyl}prop-2-enamide | 375.4 |

TABLE 15-continued

| Cpd. No. | Structure | IUPAC | MW (g/mol) |
|---|---|---|---|
| 923. | 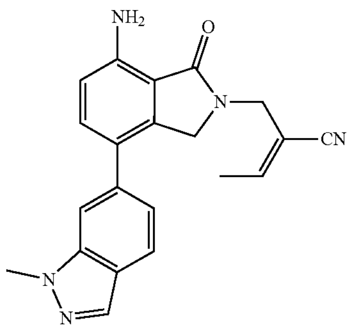 [SMILES: C/C=C(/C#N)CN1Cc2c(-c3ccc4cnn(C)c4c3)ccc(N)c2C1=O] | (2E)-2-{[7-amino-4-(1-methyl-1H-indazol-6-yl)-1-oxo-2,3-dihydro-1H-isoindol-2-yl]methyl}but-2-enenitrile | 357.4 |
| 924. | 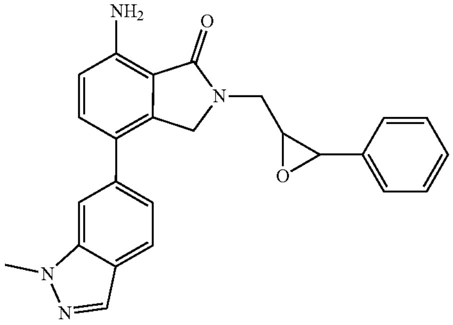 [SMILES: Cn1ncc2ccc(-c3ccc(N)c4c3CN(CC3OC3c3ccccc3)C4=O)cc21] | 7-amino-4-(1-methyl-1H-indazol-6-yl)-2-[(3-phenyloxiran-2-yl)methyl]-2,3-dihydro-1H-isoindol-1-one | 410.5 |
| 925. | 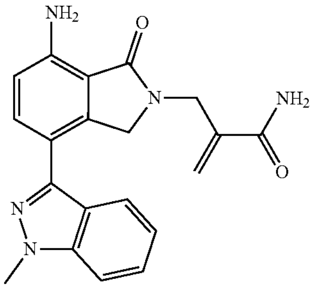 [SMILES: C=C(CN1Cc2c(-c3nn(C)c4ccccc34)ccc(N)c2C1=O)C(N)=O] | 2-{[7-amino-4-(1-methyl-1H-indazol-3-yl)-1-oxo-2,3-dihydro-1H-isoindol-2-yl]methyl}prop-2-enamide | 361.4 |
| 926. | 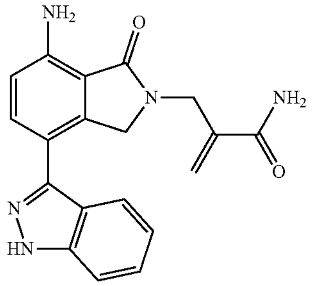 [SMILES: C=C(CN1Cc2c(-c3n[nH]c4ccccc34)ccc(N)c2C1=O)C(N)=O] | 2-{[7-amino-4-(1H-indazol-3-yl)-1-oxo-2,3-dihydro-1H-isoindol-2-yl]methyl}prop-2-enamide | 347.4 |
| 927. | 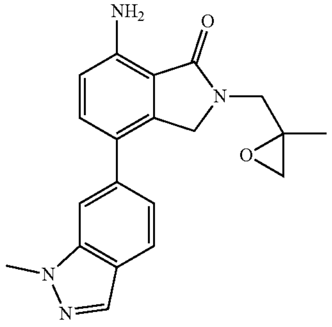 | 7-amino-4-(1-methyl-1H-indazol-6-yl)-2-[(2-methyloxiran-2-yl)methyl]-2,3-dihydro-1H-isoindol-1-one | 348.4 |

TABLE 15-continued

| Cpd. No. | Structure | IUPAC | MW (g/mol) |
|---|---|---|---|
| 928. | 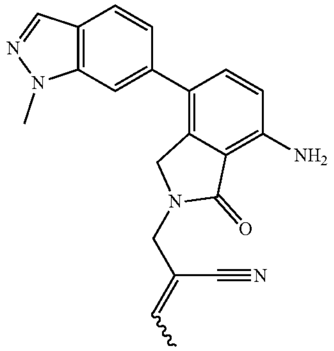 | 2-{[7-amino-4-(1-methyl-1H-indazol-6-yl)-1-oxo-2,3-dihydro-1H-isoindol-2-yl]methyl}but-2-enenitrile | 357.4 |
| 929. | 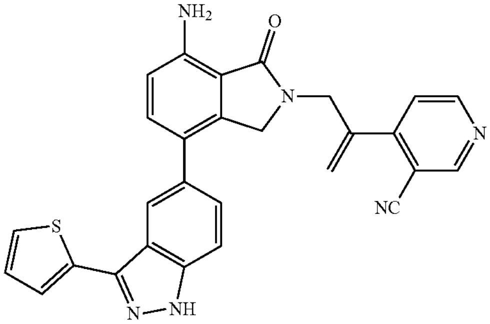 [SMILES: C=C(CN1Cc2c(-c3ccc4[nH]nc(-c5cccs5)c4c3)ccc(N)c2C1=O)c1ccncc1C#N] | 4-(3-{7-amino-1-oxo-4-[3-(thiophen-2-yl)-1H-indazol-5-yl]-2,3-dihydro-1H-isoindol-2-yl}prop-1-en-2-yl)pyridine-3-carbonitrile | 488.6 |
| 930. | 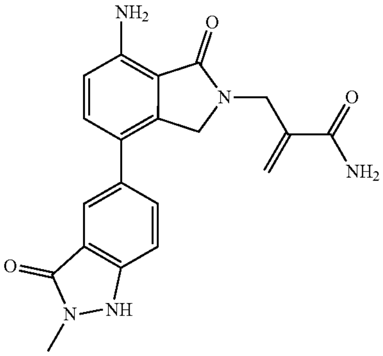 [SMILES: C=C(CN1Cc2c(-c3ccc4[nH]n(C)c(=O)c4c3)ccc(N)c2C1=O)C(N)=O] | 2-{[7-amino-4-(2-methyl-3-oxo-2,3-dihydro-1H-indazol-5-yl)-1-oxo-2,3-dihydro-1H-isoindol-2-yl]methyl}prop-2-enamide | 377.4 |
| 931. | 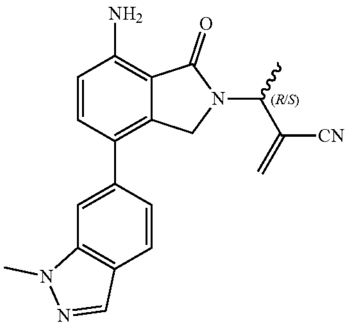 [SMILES: C=C(C#N)C(C)N1Cc2c(-c3ccc4cnn(C)c4c3)ccc(N)c2C1=O] | 3-[7-amino-4-(1-methyl-1H-indazol-6-yl)-1-oxo-2,3-dihydro-1H-isoindol-2-yl]-2-methylidenebutanenitrile | 357.4 |

TABLE 15-continued

| Cpd. No. | Structure | IUPAC | MW (g/mol) |
|---|---|---|---|
| 932. | 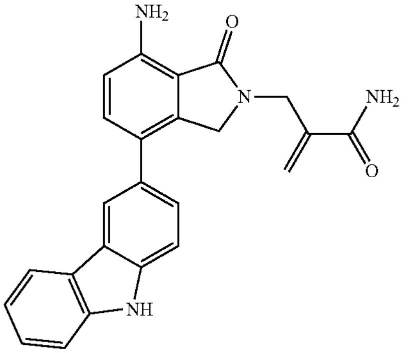 [SMILES: C=C(CN1Cc2c(-c3ccc4[nH]c5ccccc5c4c3)ccc(N)c2C1=O)C(N)=O] | 2-{[7-amino-4-(9H-carbazol-3-yl)-1-oxo-2,3-dihydro-1H-isoindol-2-yl]methyl}prop-2-enamide | 396.5 |
| 933. | 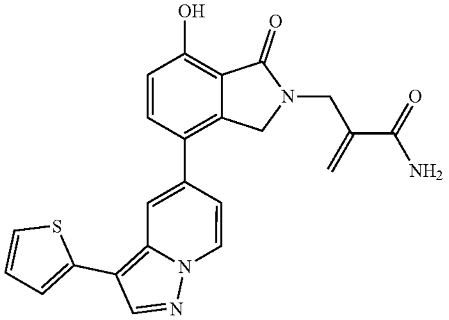 [SMILES: C=C(CN1Cc2c(-c3ccn4ncc(-c5cccs5)c4c3)ccc(O)c2C1=O)C(N)=O] | 2-({7-hydroxy-1-oxo-4-[3-(thiophen-2-yl)pyrazolo[1,5-a]pyridin-5-yl]-2,3-dihydro-1H-isoindol-2-yl}methyl)prop-2-enamide | 430.5 |
| 934. | 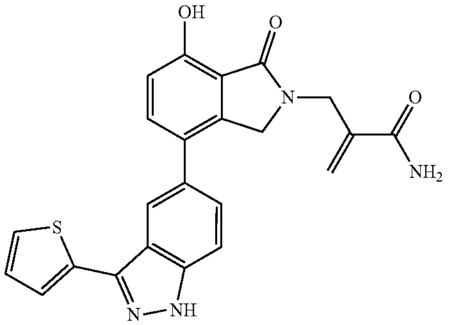 [SMILES: C=C(CN1Cc2c(-c3ccc4[nH]nc(-c5cccs5)c4c3)ccc(O)c2C1=O)C(N)=O] | 2-({7-hydroxy-1-oxo-4-[3-(thiophen-2-yl)-1H-indazol-5-yl]-2,3-dihydro-1H-isoindol-2-yl}methyl)prop-2-enamide | 430.5 |
| 935. | 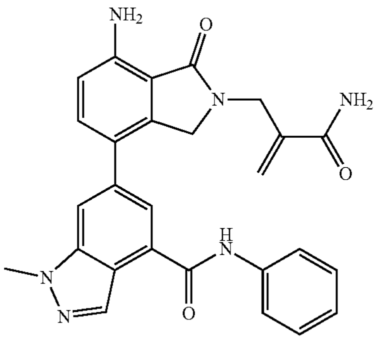 [SMILES: C=C(CN1Cc2c(-c3cc(C(=O)Nc4ccccc4)c4cnn(C)c4c3)ccc(N)c2C1=O)C(N)=O] | 6-[7-amino-2-(2-carbamoyl-2-methylideneethyl)-1-oxo-2,3-dihydro-1H-isoindol-4-yl]-1-methyl-N-phenyl-1H-indazole-4-carboxamide | 480.5 |

TABLE 15-continued
| Cpd. No. | Structure | IUPAC | MW (g/mol) |
|---|---|---|---|
| 936. | 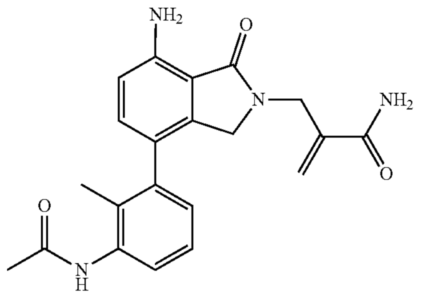 [SMILES: C=C(CN1Cc2c(-c3cccc(NC(C)=O)c3C)ccc(N)c2C1=O)C(N)=O] | 2-{[7-amino-4-(3-acetamido-2-methylphenyl)-1-oxo-2,3-dihydro-1H-isoindol-2-yl]methyl}prop-2-enamide | 378.4 |
| 937. | 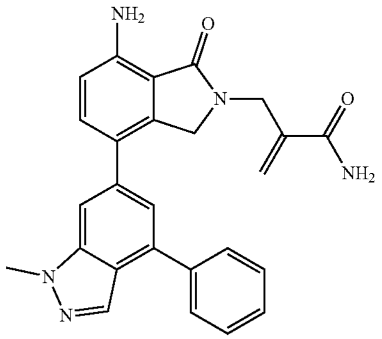 [SMILES: C=C(CN1Cc2c(-c3cc(-c4ccccc4)c4cnn(C)c4c3)ccc(N)c2C1=O)C(N)=O] | 2-{[7-amino-4-(1-methyl-4-phenyl-1H-indazol-6-yl)-1-oxo-2,3-dihydro-1H-isoindol-2-yl]methyl}prop-2-enamide | 437.5 |
| 938. | 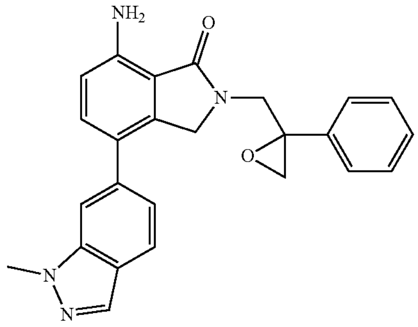 [SMILES: Cn1ncc2ccc(-c3ccc(N)c4c3CN(CC3(c5ccccc5)CO3)C4=O)cc21] | 7-amino-4-(1-methyl-1H-indazol-6-yl)-2-[(2-phenyloxiran-2-yl)methyl]-2,3-dihydro-1H-isoindol-1-one | 410.5 |
| 939. | 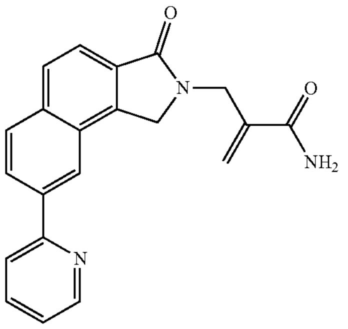 [SMILES: C=C(CN1Cc2c(ccc3ccc(-c4ccccn4)cc23)C1=O)C(N)=O] | 2-{[3-oxo-8-(pyridin-2-yl)-1H,2H,3H-benzo[e]isoindol-2-yl]methyl}prop-2-enamide | 343.4 |

TABLE 15-continued

| Cpd. No. | Structure | IUPAC | MW (g/mol) |
|---|---|---|---|
| 940. | 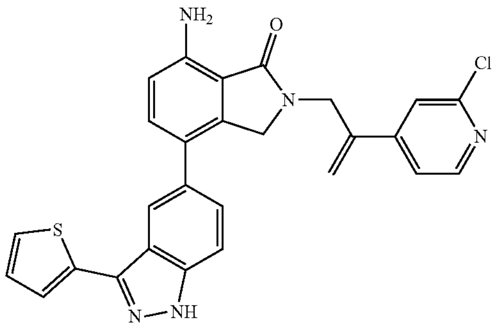 [SMILES: C=C(CN1Cc2c(-c3ccc4[nH]nc(-c5cccs5)c4c3)ccc(N)c2C1=O)c1ccnc(Cl)c1] | 7-amino-2-[2-(2-chloropyridin-4-yl)prop-2-en-1-yl]-4-[3-(thiophen-2-yl)-1H-indazol-5-yl]-2,3-dihydro-1H-isoindol-1-one | 498.0 |
| 941. | 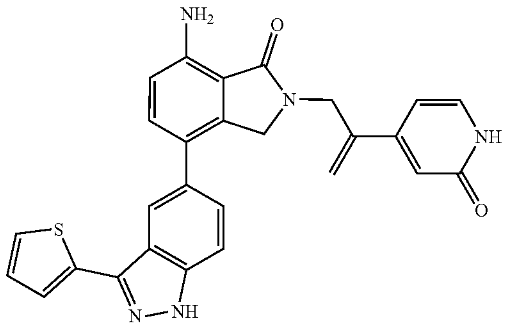 [SMILES: C=C(CN1Cc2c(-c3ccc4[nH]nc(-c5cccs5)c4c3)ccc(N)c2C1=O)c1cc[nH]c(=O)c1] | 7-amino-2-[2-(2-oxo-1,2-dihydropyridin-4-yl)prop-2-en-1-yl]-4-[3-(thiophen-2-yl)-1H-indazol-5-yl]-2,3-dihydro-1H-isoindol-1-one | 479.6 |
| 942. | 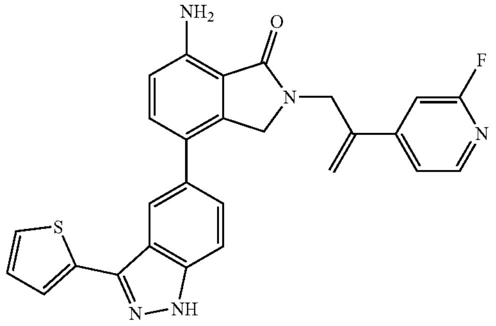 [SMILES: C=C(CN1Cc2c(-c3ccc4[nH]nc(-c5cccs5)c4c3)ccc(N)c2C1=O)c1ccnc(F)c1] | 7-amino-2-[2-(2-fluoropyridin-4-yl)prop-2-en-1-yl]-4-[3-(thiophen-2-yl)-1H-indazol-5-yl]-2,3-dihydro-1H-isoindol-1-one | 481.6 |
| 943. | 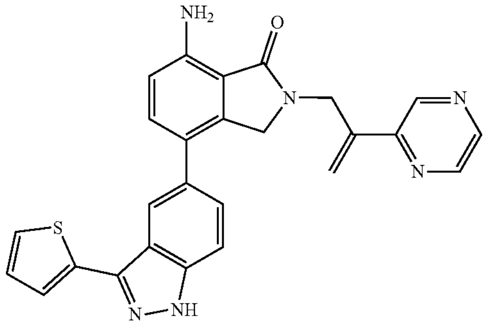 [SMILES: C=C(CN1Cc2c(-c3ccc4[nH]nc(-c5cccs5)c4c3)ccc(N)c2C1=O)c1cnccn1] | 7-amino-2-[2-(pyrazin-2-yl)prop-2-en-1-yl]-4-[3-(thiophen-2-yl)-1H-indazol-5-yl]-2,3-dihydro-1H-isoindol-1-one | 464.6 |

TABLE 15-continued

| Cpd. No. | Structure | IUPAC | MW (g/mol) |
|---|---|---|---|
| 944. | 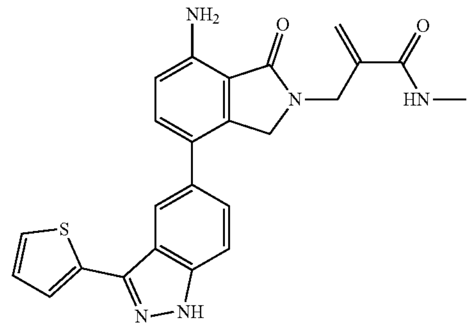 [SMILES: C=C(CN1Cc2c(-c3ccc4[nH]nc(-c5cccs5)c4c3)ccc(N)c2C1=O)C(=O)NC] | 2-({7-amino-1-oxo-4-[3-(thiophen-2-yl)-1H-indazol-5-yl]-2,3-dihydro-1H-isoindol-2-yl}methyl)-N-methylprop-2-enamide | 443.5 |
| 945. | 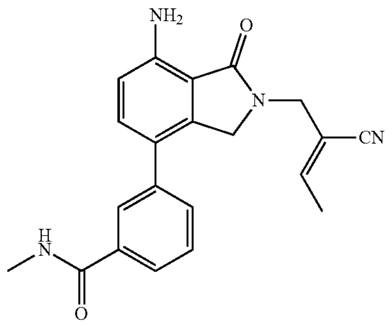 [SMILES: C/C=C(\C#N)CN1Cc2c(-c3cccc(C(=O)NC)c3)ccc(N)c2C1=O] | 3-{7-amino-2-[(2Z)-2-cyano-2-ethylideneethyl]-1-oxo-2,3-dihydro-1H-isoindol-4-yl}-N-methylbenzamide | 360.4 |
| 946. | 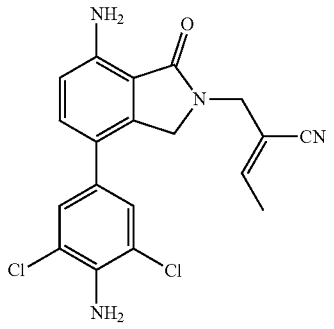 [SMILES: C/C=C(\C#N)CN1Cc2c(-c3cc(Cl)c(N)c(Cl)c3)ccc(N)c2C1=O] | (2Z)-2-{[7-amino-4-(4-amino-3,5-dichlorophenyl)-1-oxo-2,3-dihydro-1H-isoindol-2-yl]methyl}but-2-enenitrile | 387.3 |
| 947. | 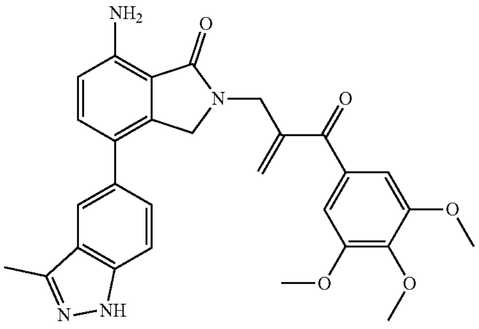 | 7-amino-4-(3-methyl-1H-indazol-5-yl)-2-[2-methylidene-3-oxo-3-(3,4,5-trimethoxyphenyl)propyl]-2,3-dihydro-1H-isoindol-1-one | 512.6 |

TABLE 15-continued
| Cpd. No. | Structure | IUPAC | MW (g/mol) |
| --- | --- | --- | --- |
| 948. | 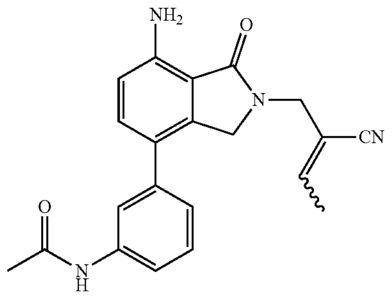 | N-{3-[7-amino-2-(2-cyano-2-ethylideneethyl)-1-oxo-2,3-dihydro-1H-isoindol-4-yl]phenyl}acetamide | 360.4 |
| 949. | 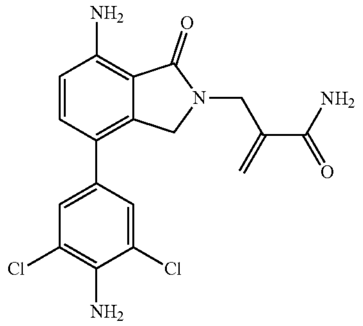 [SMILES: C=C(CN1Cc2c(-c3cc(Cl)c(N)c(Cl)c3)ccc(N)c2C1=O)C(N)=O] | 2-{[7-amino-4-(4-amino-3,5-dichlorophenyl)-1-oxo-2,3-dihydro-1H-isoindol-2-yl]methyl}prop-2-enamide | 391.3 |
| 950. | 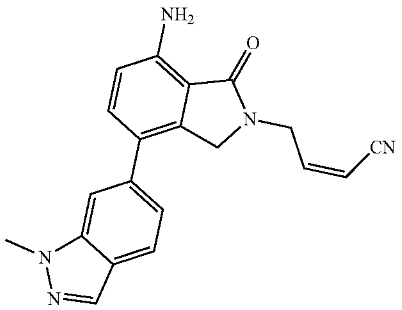 [SMILES: Cn1ncc2ccc(-c3ccc(N)c4c3CN(C/C=C\C#N)C4=O)cc21] | (2Z)-4-[7-amino-4-(1-methyl-1H-indazol-6-yl)-1-oxo-2,3-dihydro-1H-isoindol-2-yl]but-2-enenitrile | 343.4 |
| 951. | 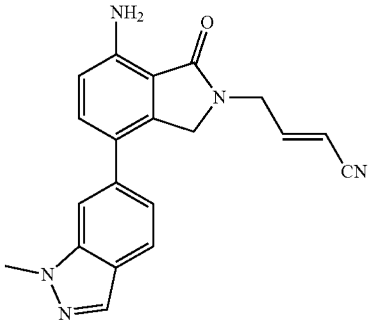 [SMILES: Cn1ncc2ccc(-c3ccc(N)c4c3CN(C/C=C/C#N)C4=O)cc21] | (2E)-4-[7-amino-4-(1-methyl-1H-indazol-6-yl)-1-oxo-2,3-dihydro-1H-isoindol-2-yl]but-2-enenitrile | 343.4 |

TABLE 15-continued
| Cpd. No. | Structure | IUPAC | MW (g/mol) |
|---|---|---|---|
| 952. | 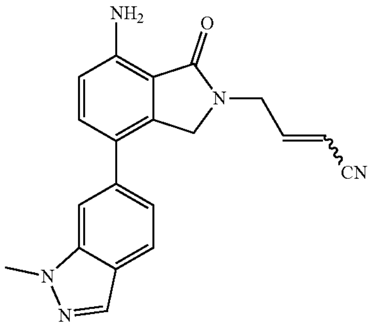 | 4-[7-amino-4-(1-methyl-1H-indazol-6-yl)-1-oxo-2,3-dihydro-1H-isoindol-2-yl]but-2-enenitrile | 343.4 |
| 953. | 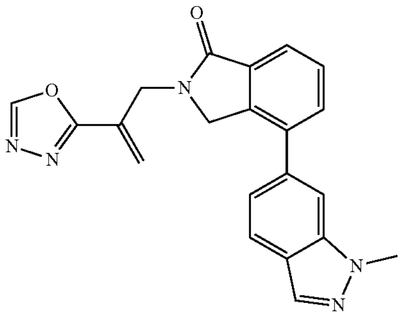 [SMILES: C=C(CN1Cc2c(cccc2-c2ccc3cnn(C)c3c2)C1=O)c1nnco1] | 4-(1-methyl-1H-indazol-6-yl)-2-[2-(1,3,4-oxadiazol-2-yl)prop-2-en-1-yl]-2,3-dihydro-1H-isoindol-1-one | 371.4 |
| 954. | 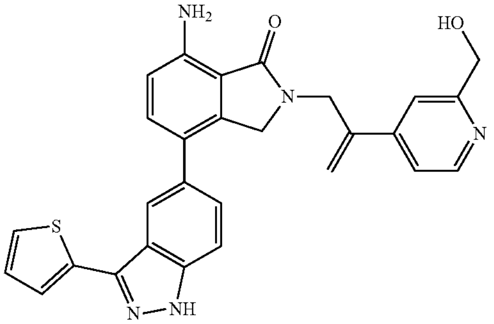 [SMILES: C=C(CN1Cc2c(-c3ccc4[nH]nc(-c5cccs5)c4c3)ccc(N)c2C1=O)c1ccnc(CO)c1] | 7-amino-2-{2-[2-(hydroxymethyl)pyridin-4-yl]prop-2-en-1-yl}-4-[3-(thiophen-2-yl)-1H-indazol-5-yl]-2,3-dihydro-1H-isoindol-1-one | 493.6 |
| 955. | 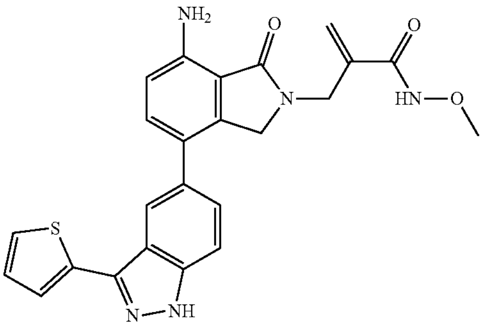 [SMILES: C=C(CN1Cc2c(-c3ccc4[nH]nc(-c5cccs5)c4c3)ccc(N)c2C1=O)C(=O)NOC] | 2-({7-amino-1-oxo-4-[3-(thiophen-2-yl)-1H-indazol-5-yl]-2,3-dihydro-1H-isoindol-2-yl}methyl)-N-methoxyprop-2-enamide | 459.5 |

TABLE 15-continued

| Cpd. No. | Structure | IUPAC | MW (g/mol) |
|---|---|---|---|
| 956. | 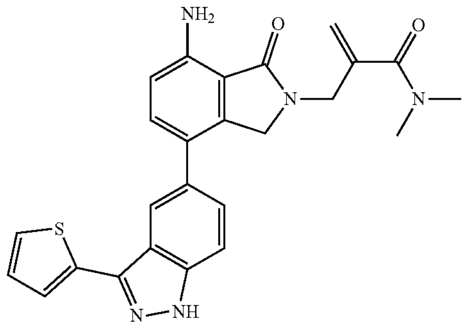 [SMILES: C=C(CN1Cc2c(-c3ccc4[nH]nc(-c5cccs5)c4c3)ccc(N)c2C1=O)C(=O)N(C)C] | 2-({7-amino-1-oxo-4-[3-(thiophen-2-yl)-1H-indazol-5-yl]-2,3-dihydro-1H-isoindol-2-yl}methyl)-N,N-dimethylprop-2-enamide | 457.6 |
| 957. | 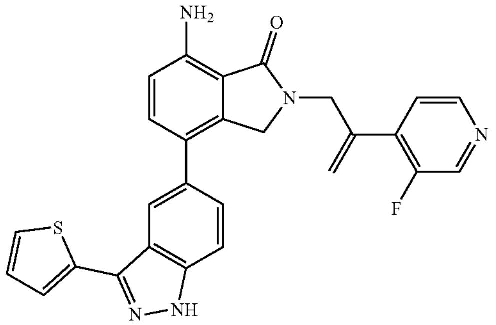 [SMILES: C=C(CN1Cc2c(-c3ccc4[nH]nc(-c5cccs5)c4c3)ccc(N)c2C1=O)c1ccncc1F] | 7-amino-2-[2-(3-fluoropyridin-4-yl)prop-2-en-1-yl]-4-[3-(thiophen-2-yl)-1H-indazol-5-yl]-2,3-dihydro-1H-isoindol-1-one | 481.6 |
| 958. | 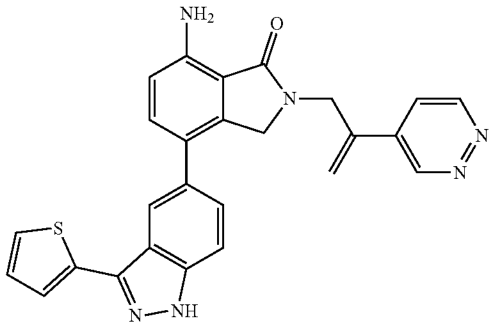 | 7-amino-2-[2-(pyridazin-4-yl)prop-2-en-1-yl]-4-[3-(thiophen-2-yl)-1H-indazol-5-yl]-2,3-dihydro-1H-isoindol-1-one | 464.6 |
| 959. | 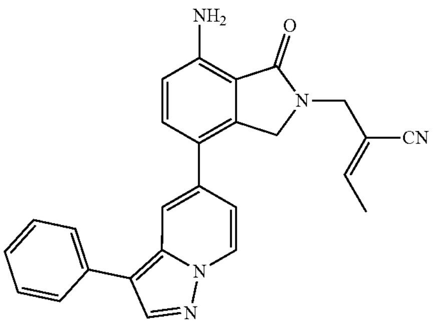 [SMILES: C/C=C(\C#N)CN1Cc2c(-c3ccn4ncc(-c5ccccc5)c4c3)ccc(N)c2C1=O] | (2Z)-2-[(7-amino-1-oxo-4-{3-phenylpyrazolo[1,5-a]pyridin-5-yl}-2,3-dihydro-1H-isoindol-2-yl)methyl]but-2-enenitrile | 419.5 |

TABLE 15-continued

| Cpd. No. | Structure | IUPAC | MW (g/mol) |
|---|---|---|---|
| 960. | 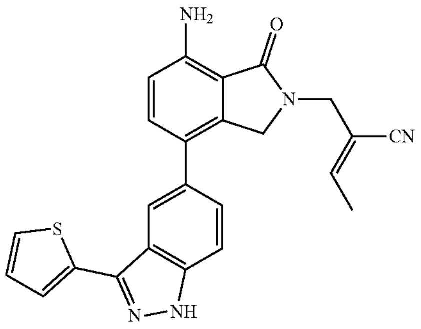 [SMILES: C/C=C(\C#N)CN1Cc2c(-c3ccc4[nH]nc(-c5cccs5)c4c3)ccc(N)c2C1=O] | (2Z)-2-({7-amino-1-oxo-4-[3-(thiophen-2-yl)-1H-indazol-5-yl]-2,3-dihydro-1H-isoindol-2-yl}methyl)but-2-enenitrile | 425.5 |
| 961. | 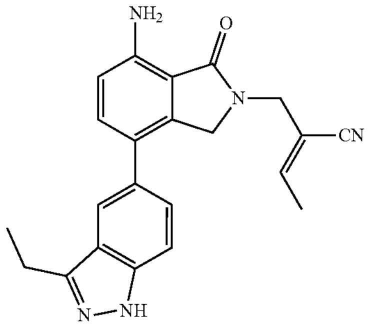 [SMILES: C/C=C(\C#N)CN1Cc2c(-c3ccc4[nH]nc(CC)c4c3)ccc(N)c2C1=O] | (2Z)-2-{[7-amino-4-(3-ethyl-1H-indazol-5-yl)-1-oxo-2,3-dihydro-1H-isoindol-2-yl]methyl}but-2-enenitrile | 371.4 |
| 962. | 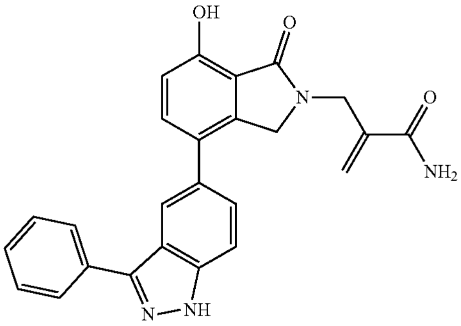 [SMILES: C=C(CN1Cc2c(-c3ccc4[nH]nc(-c5ccccc5)c4c3)ccc(O)c2C1=O)C(N)=O] | 2-{[7-hydroxy-1-oxo-4-(3-phenyl-1H-indazol-5-yl)-2,3-dihydro-1H-isoindol-2-yl]methyl}prop-2-enamide | 424.5 |
| 963. | 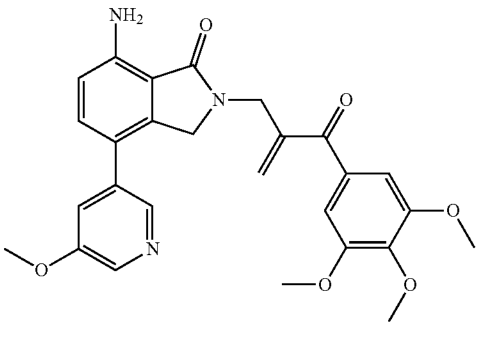 | 7-amino-4-(5-methoxypyridin-3-yl)-2-[2-methylidene-3-oxo-3-(3,4,5-trimethoxyphenyl)propyl]-2,3-dihydro-1H-isoindol-1-one | 489.5 |

TABLE 15-continued

| Cpd. No. | Structure | IUPAC | MW (g/mol) |
|---|---|---|---|
| 964. | 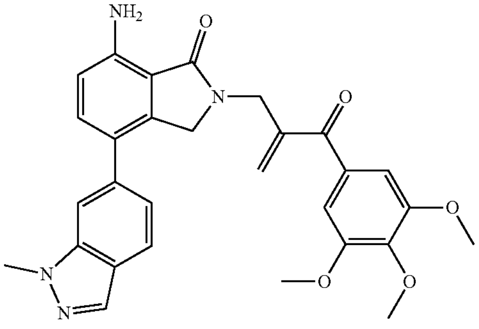 | 7-amino-4-(1-methyl-1H-indazol-6-yl)-2-[2-methylidene-3-oxo-3-(3,4,5-trimethoxyphenyl)propyl]-2,3-dihydro-1H-isoindol-1-one | 512.6 |
| 965. | 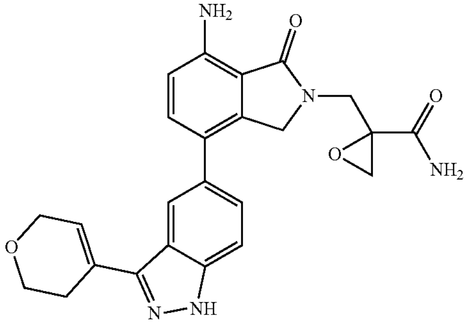 [SMILES: NC(=O)C1(CN2Cc3c(-c4ccc5[nH]nc(C6=CCOCC6)c5c4)ccc(N)c3C2=O)CO1] | 2-({7-amino-4-[3-(3,6-dihydro-2H-pyran-4-yl)-1H-indazol-5-yl]-1-oxo-2,3-dihydro-1H-isoindol-2-yl}methyl)oxirane-2-carboxamide | 445.5 |
| 966. | 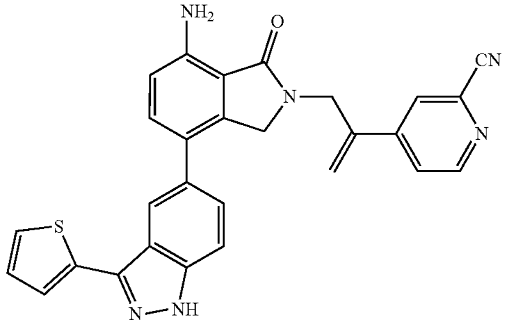 [SMILES: C=C(CN1Cc2c(-c3ccc4[nH]nc(-c5cccs5)c4c3)ccc(N)c2C1=O)c1ccnc(C#N)c1] | 4-(3-{7-amino-1-oxo-4-[3-(thiophen-2-yl)-1H-indazol-5-yl]-2,3-dihydro-1H-isoindol-2-yl}prop-1-en-2-yl)pyridine-2-carbonitrile | 488.6 |
| 967. | 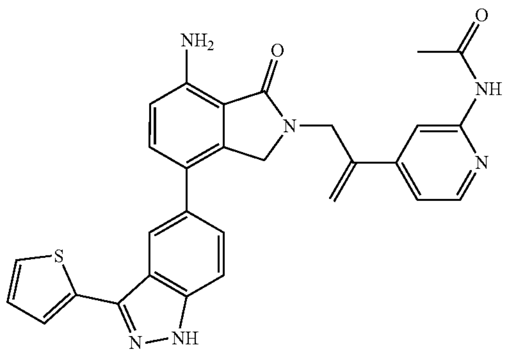 [SMILES: C=C(CN1Cc2c(-c3ccc4[nH]nc(-c5cccs5)c4c3)ccc(N)c2C1=O)c1ccnc(NC(C)=O)c1] | N-[4-(3-{7-amino-1-oxo-4-[3-(thiophen-2-yl)-1H-indazol-5-yl]-2,3-dihydro-1H-isoindol-2-yl}prop-1-en-2-yl)pyridin-2-yl]acetamide | 520.6 |

TABLE 15-continued

| Cpd. No. | Structure | IUPAC | MW (g/mol) |
|---|---|---|---|
| 968. | 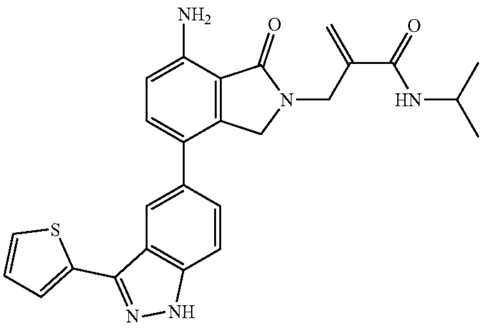 [SMILES: C=C(CN1Cc2c(-c3ccc4[nH]nc(-c5cccs5)c4c3)ccc(N)c2C1=O)C(=O)NC(C)C] | 2-({7-amino-1-oxo-4-[3-(thiophen-2-yl)-1H-indazol-5-yl]-2,3-dihydro-1H-isoindol-2-yl}methyl)-N-(propan-2-yl)prop-2-enamide | 471.6 |
| 969. | 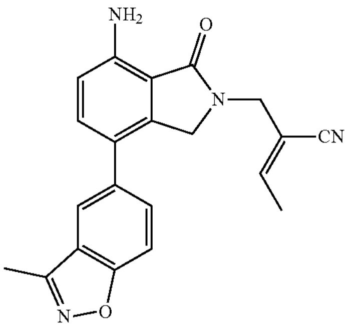 [SMILES: C/C=C(\C#N)CN1Cc2c(-c3ccc4onc(C)c4c3)ccc(N)c2C1=O] | (2Z)-2-{[7-amino-4-(3-methyl-1,2-benzoxazol-5-yl)-1-oxo-2,3-dihydro-1H-isoindol-2-yl]methyl}but-2-enenitrile | 358.4 |
| 970. | 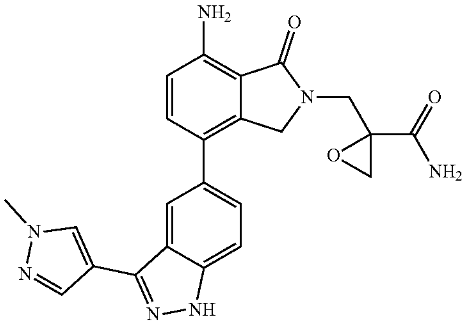 [SMILES: Cn1cc(-c2n[nH]c3ccc(-c4ccc(N)c5c4CN(CC4(C(N)=O)CO4)C5=O)cc23)cn1] | 2-({7-amino-4-[3-(1-methyl-1H-pyrazol-4-yl)-1H-indazol-5-yl]-1-oxo-2,3-dihydro-1H-isoindol-2-yl}methyl)oxirane-2-carboxamide | 443.5 |
| 971. | 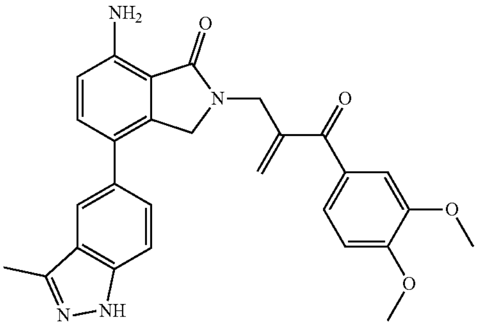 | 7-amino-2-[3-(3,4-dimethoxyphenyl)-2-methylidene-3-oxopropyl]-4-(3-methyl-1H-indazol-5-yl)-2,3-dihydro-1H-isoindol-1-one | 482.5 |

TABLE 15-continued

| Cpd. No. | Structure | IUPAC | MW (g/mol) |
|---|---|---|---|
| 972. | 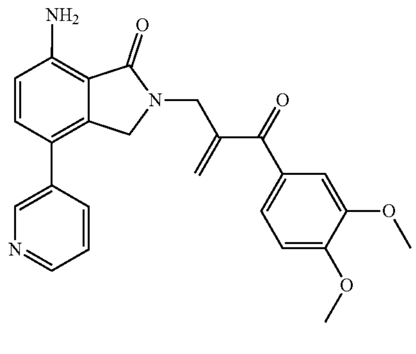 [SMILES: C=C(CN1Cc2c(-c3cccnc3)ccc(N)c2C1=O)C(=O)c1ccc(OC)c(OC)c1] | 7-amino-2-[3-(3,4-dimethoxyphenyl)-2-methylidene-3-oxopropyl]-4-(pyridin-3-yl)-2,3-dihydro-1H-isoindol-1-one | 429.5 |
| 973. | 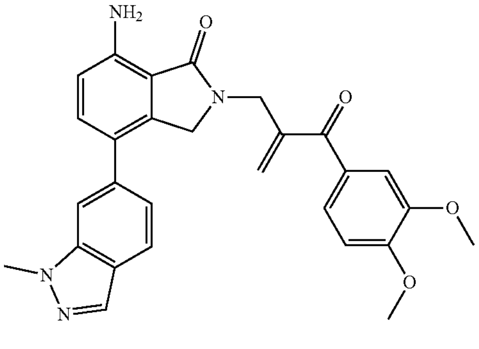 | 7-amino-2-[3-(3,4-dimethoxyphenyl)-2-methylidene-3-oxopropyl]-4-(1-methyl-1H-indazol-6-yl)-2,3-dihydro-1H-isoindol-1-one | 482.5 |
| 974. | 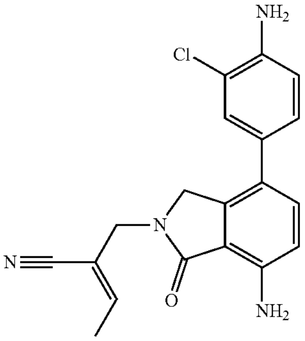 [SMILES: C/C=C(\C#N)CN1Cc2c(-c3ccc(N)c(Cl)c3)ccc(N)c2C1=O] | (2Z)-2-{[7-amino-4-(4-amino-3-chlorophenyl)-1-oxo-2,3-dihydro-1H-isoindol-2-yl]methyl}but-2-enenitrile | 352.8 |
| 975. | 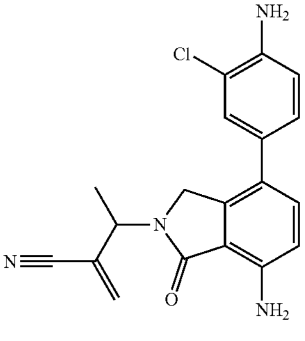 [SMILES: C=C(C#N)C(C)N1Cc2c(-c3ccc(N)c(Cl)c3)ccc(N)c2C1=O] | 3-[7-amino-4-(4-amino-3-chlorophenyl)-1-oxo-2,3-dihydro-1H-isoindol-2-yl]-2-methylidenebutanenitrile | 352.8 |

TABLE 15-continued
| Cpd. No. | Structure | IUPAC | MW (g/mol) |
|---|---|---|---|
| 976. | 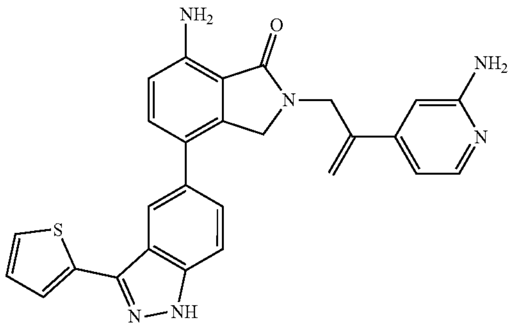 [SMILES: C=C(CN1Cc2c(-c3ccc4[nH]nc(-c5cccs5)c4c3)ccc(N)c2C1=O)c1ccnc(N)c1] | 7-amino-2-[2-(2-aminopyridin-4-yl)prop-2-en-1-yl]-4-[3-(thiophen-2-yl)-1H-indazol-5-yl]-2,3-dihydro-1H-isoindol-1-one | 478.6 |
| 977. | 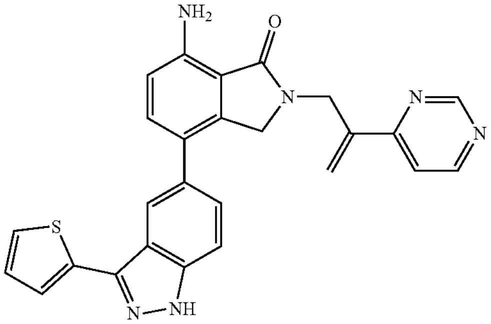 | 7-amino-2-[2-(pyrimidin-4-yl)prop-2-en-1-yl]-4-[3-(thiophen-2-yl)-1H-indazol-5-yl]-2,3-dihydro-1H-isoindol-1-one | 464.6 |
| 978. | 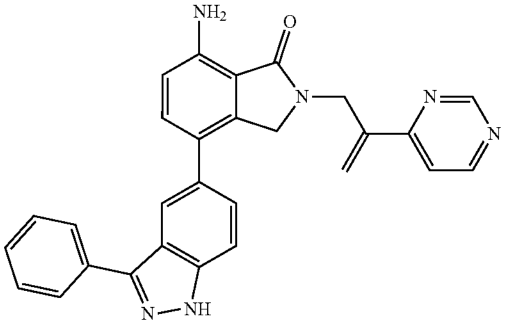 [SMILES: C=C(CN1Cc2c(-c3ccc4[nH]nc(-c5ccccc5)c4c3)ccc(N)c2C1=O)c1ccncn1] | 7-amino-4-(3-phenyl-1H-indazol-5-yl)-2-[2-(pyrimidin-4-yl)prop-2-en-1-yl]-2,3-dihydro-1H-isoindol-1-one | 458.5 |
| 979. | 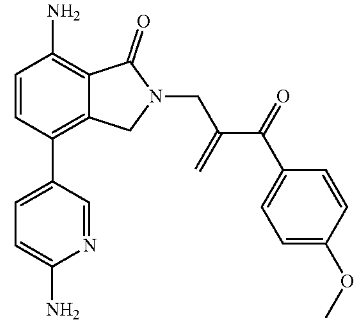 [SMILES: C=C(CN1Cc2c(-c3ccc(N)nc3)ccc(N)c2C1=O)C(=O)c1ccc(OC)cc1] | 7-amino-4-(6-aminopyridin-3-yl)-2-[3-(4-methoxyphenyl)-2-methylidene-3-oxopropyl]-2,3-dihydro-1H-isoindol-1-one | 414.5 |

TABLE 15-continued

| Cpd. No. | Structure | IUPAC | MW (g/mol) |
|---|---|---|---|
| 980. | 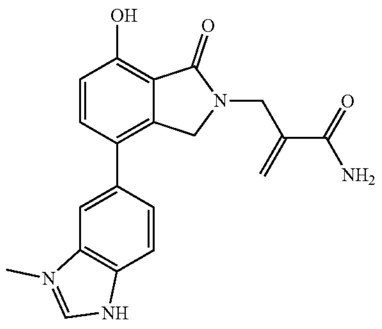 | 2-{[7-hydroxy-4-(3-methyl-1H-indazol-5-yl)-1-oxo-2,3-dihydro-1H-isoindol-2-yl]methyl}prop-2-enamide | 362.4 |
| 981. | 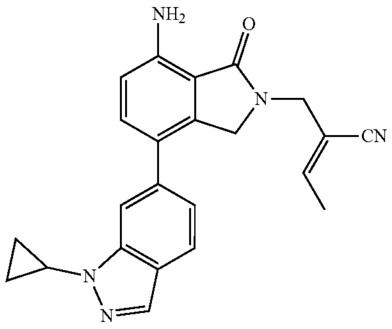 [SMILES: C/C=C(\C#N)CN1Cc2c(-c3ccc4cnn(C5CC5)c4c3)ccc(N)c2C1=O] | (2Z)-2-{[7-amino-4-(1-cyclopropyl-1H-indazol-6-yl)-1-oxo-2,3-dihydro-1H-isoindol-2-yl]methyl}but-2-enenitrile | 383.5 |
| 982. | 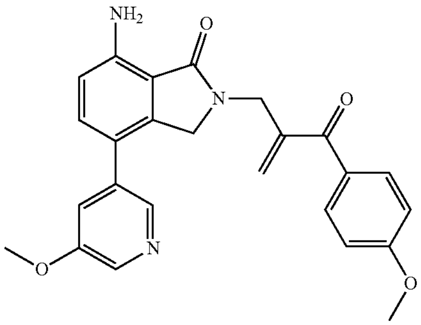 [SMILES: C=C(CN1Cc2c(-c3cncc(OC)c3)ccc(N)c2C1=O)C(=O)c1ccc(OC)cc1] | 7-amino-2-[3-(4-methoxyphenyl)-2-methylidene-3-oxopropyl]-4-(5-methoxypyridin-3-yl)-2,3-dihydro-1H-isoindol-1-one | 429.5 |
| 983. | 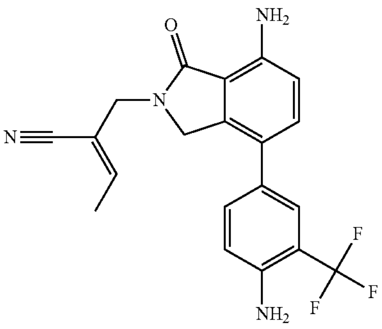 [SMILES: C/C=C(\C#N)CN1Cc2c(-c3ccc(N)c(C(F)(F)F)c3)ccc(N)c2C1=O] | (2Z)-2-({7-amino-4-[4-amino-3-(trifluoromethyl)phenyl]-1-oxo-2,3-dihydro-1H-isoindol-2-yl}methyl)but-2-enenitrile | 386.4 |

TABLE 15-continued

| Cpd. No. | Structure | IUPAC | MW (g/mol) |
| --- | --- | --- | --- |
| 984. | 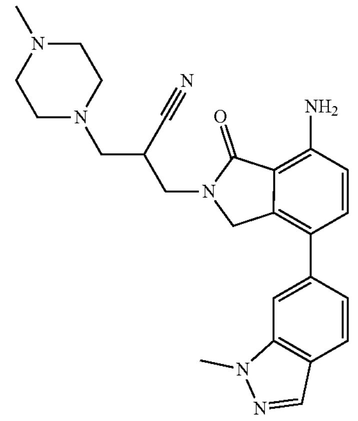 [SMILES: CN1CCN(CC(C#N)CN2Cc3c(-c4ccc5cnn(C)c5c4)ccc(N)c3C2=O)CC1] | 2-{[7-amino-4-(1-methyl-1H-indazol-6-yl)-1-oxo-2,3-dihydro-1H-isoindol-2-yl]methyl}-3-(4-methylpiperazin-1-yl)propanenitrile | 443.6 |
| 985. | 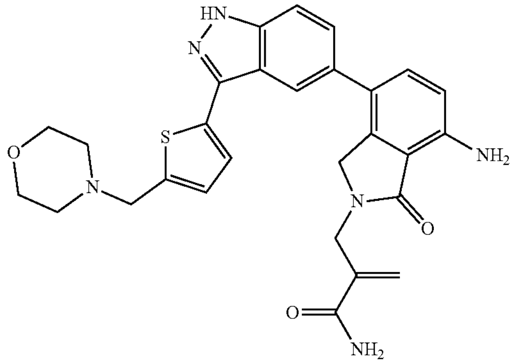 [SMILES: C=C(CN1Cc2c(-c3ccc4[nH]nc(-c5ccc(CN6CCOCC6)s5)c4c3)ccc(N)c2C1=O)C(N)=O] | 2-{[7-amino-4-(3-{5-[(morpholin-4-yl)methyl]thiophen-2-yl}-1H-indazol-5-yl)-1-oxo-2,3-dihydro-1H-isoindol-2-yl]methyl}prop-2-enamide | 528.6 |
| 986. | 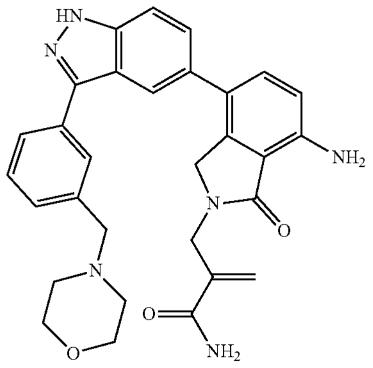 [SMILES: C=C(CN1Cc2c(-c3ccc4[nH]nc(-c5cccc(CN6CCOCC6)c5)c4c3)ccc(N)c2C1=O)C(N)=O] | 2-{[7-amino-4-(3-{3-[(morpholin-4-yl)methyl]phenyl}-1H-indazol-5-yl)-1-oxo-2,3-dihydro-1H-isoindol-2-yl]methyl}prop-2-enamide | 522.6 |
| 987. | 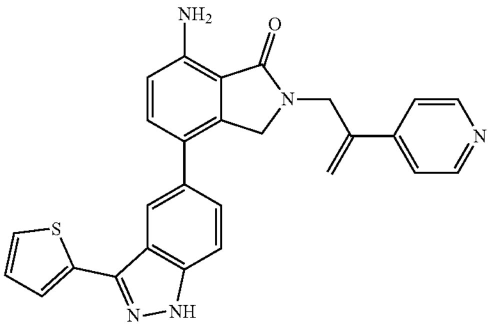 [SMILES: C=C(CN1Cc2c(-c3ccc4[nH]nc(-c5cccs5)c4c3)ccc(N)c2C1=O)c1ccncc1] | 7-amino-2-[2-(pyridin-4-yl)prop-2-en-1-yl]-4-[3-(thiophen-2-yl)-1H-indazol-5-yl]-2,3-dihydro-1H-isoindol-1-one | 463.6 |

TABLE 15-continued
| Cpd. No. | Structure | IUPAC | MW (g/mol) |
| --- | --- | --- | --- |
| 988. | 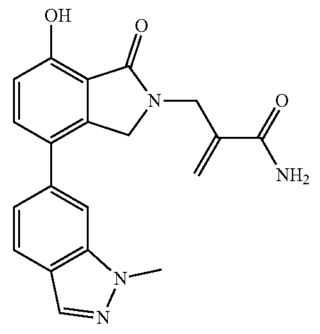 [SMILES: C=C(CN1Cc2c(-c3ccc4cnn(C)c4c3)ccc(O)c2C1=O)C(N)=O] | 2-{[7-hydroxy-4-(1-methyl-1H-indazol-6-yl)-1-oxo-2,3-dihydro-1H-isoindol-2-yl]methyl}prop-2-enamide | 362.4 |
| 989. | 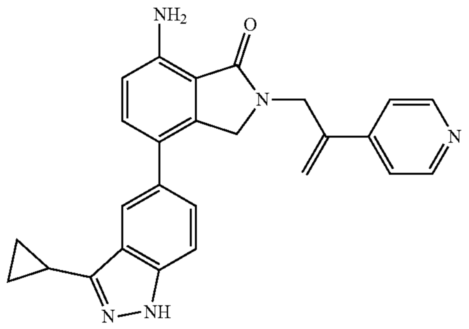 [SMILES: C=C(CN1Cc2c(-c3ccc4[nH]nc(C5CC5)c4c3)ccc(N)c2C1=O)c1ccncc1] | 7-amino-4-(3-cyclopropyl-1H-indazol-5-yl)-2-[2-(pyridin-4-yl)prop-2-en-1-yl]-2,3-dihydro-1H-isoindol-1-one | 421.5 |
| 990. | 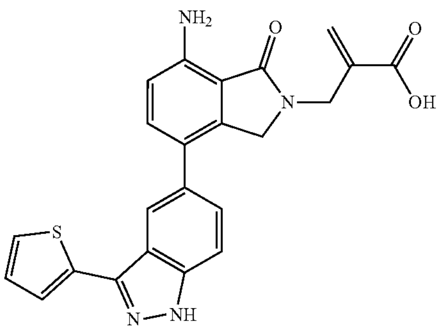 [SMILES: C=C(CN1Cc2c(-c3ccc4[nH]nc(-c5cccs5)c4c3)ccc(N)c2C1=O)C(=O)O] | 2-({7-amino-1-oxo-4-[3-(thiophen-2-yl)-1H-indazol-5-yl]-2,3-dihydro-1H-isoindol-2-yl}methyl)propyl-2-enoic acid | 430.5 |
| 991. | 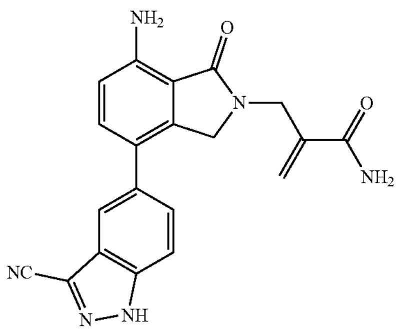 [SMILES: C=C(CN1Cc2c(-c3ccc4[nH]nc(C#N)c4c3)ccc(N)c2C1=O)C(N)=O] | 2-{[7-amino-4-(3-cyano-1H-indazol-5-yl)-1-oxo-2,3-dihydro-1H-isoindol-2-yl]methyl}prop-2-enamide | 372.4 |

TABLE 15-continued
| Cpd. No. | Structure | IUPAC | MW (g/mol) |
|---|---|---|---|
| 992. | 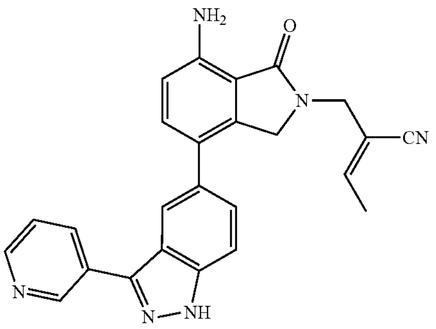 [SMILES: C/C=C(\C#N)CN1Cc2c(-c3ccc4[nH]nc(-c5cccnc5)c4c3)ccc(N)c2C1=O] | (2Z)-2-({7-amino-1-oxo-4-[3-(pyridin-3-yl)-1H-indazol-5-yl]-2,3-dihydro-1H-isoindol-2-yl}methyl)but-2-enenitrile | 420.5 |
| 993. | 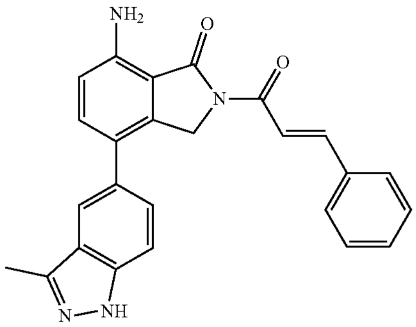 [SMILES: Cc1n[nH]c2ccc(-c3ccc(N)c4c3CN(C(=O)/C=C/c3ccccc3)C4=O)cc12] | 7-amino-4-(1-methyl-1H-indazol-6-yl)-2-[(2E)-3-phenylprop-2-enoyl]-2,3-dihydro-1H-isoindol-1-one | 408.5 |
| 994. | 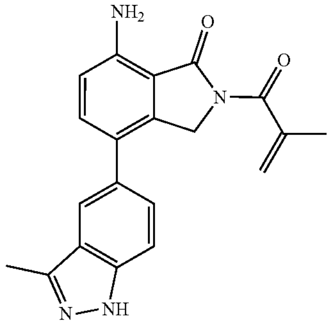 [SMILES: C=C(C)C(=O)N1Cc2c(-c3ccc4[nH]nc(C)c4c3)ccc(N)c2C1=O] | 7-amino-4-(1-methyl-1H-indazol-6-yl)-2-(2-methylprop-2-enoyl)-2,3-dihydro-1H-isoindol-1-one | 346.4 |
| 995. | 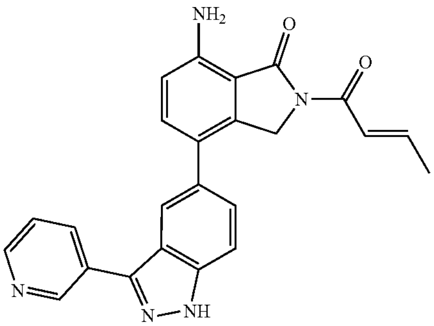 | 7-amino-2-[(2E)-but-2-enoyl]-4-[3-(pyridin-3-yl)-1H-indazol-5-yl]-2,3-dihydro-1H-isoindol-1-one | 409.4 |

TABLE 15-continued
| Cpd. No. | Structure | IUPAC | MW (g/mol) |
|---|---|---|---|
| 996. | 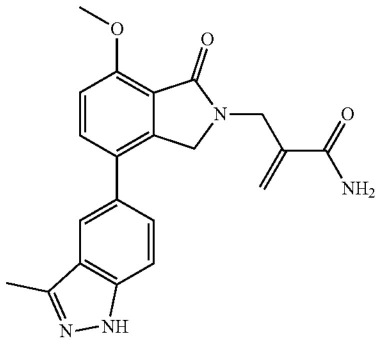 [SMILES: C=C(CN1Cc2c(-c3ccc4[nH]nc(C)c4c3)ccc(OC)c2C1=O)C(N)=O] | 2-{[7-methoxy-4-(3-methyl-1H-indazol-5-yl)-1-oxo-2,3-dihydro-1H-isoindol-2-yl]methyl}prop-2-enamide | 376.4 |
| 997. | 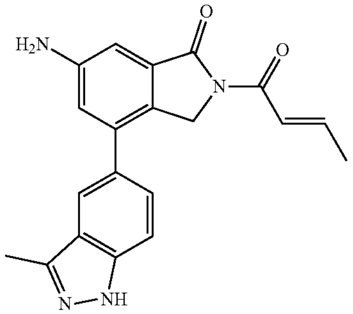 [SMILES: C/C=C/C(=O)N1Cc2c(cc(N)cc2-c2ccc3[nH]nc(C)c3c2)C1=O] | 6-amino-2-[(2E)-but-2-enoyl]-4-(3-methyl-1H-indazol-5-yl)-2,3-dihydro-1H-isoindol-1-one | 346.4 |
| 998. | 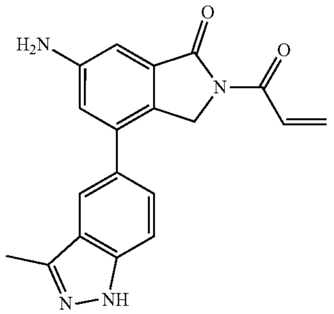 [SMILES: C=CC(=O)N1Cc2c(cc(N)cc2-c2ccc3[nH]nc(C)c3c2)C1=O] | 6-amino-4-(3-methyl-1H-indazol-5-yl)-2-(prop-2-enoyl)-2,3-dihydro-1H-isoindol-1-one | 332.4 |
| 999. | 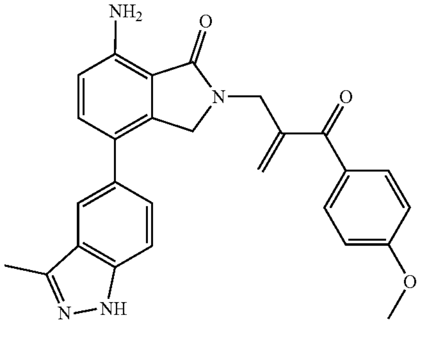 [SMILES: C=C(CN1Cc2c(-c3ccc4[nH]nc(C)c4c3)ccc(N)c2C1=O)C(=O)c1ccc(OC)cc1] | 7-amino-2-[3-(4-methoxyphenyl)-2-methylidene-3-oxopropyl]-4-(3-methyl-1H-indazol-5-yl)-2,3-dihydro-1H-isoindol-1-one | 452.5 |

TABLE 15-continued
| Cpd. No. | Structure | IUPAC | MW (g/mol) |
|---|---|---|---|
| 1000. | 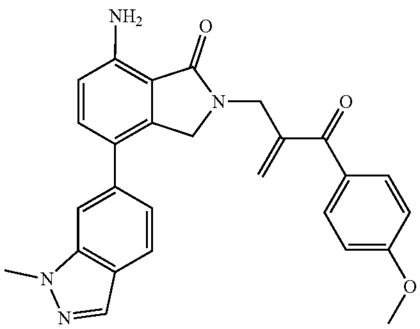 [SMILES: C=C(CN1Cc2c(-c3ccc4cnn(C)c4c3)ccc(N)c2C1=O)C(=O)c1ccc(OC)cc1] | 7-amino-2-[3-(4-methoxyphenyl)-2-methylidene-3-oxopropyl]-4-(1-methyl-1H-indazol-6-yl)-2,3-dihydro-1H-isoindol-1-one | 452.5 |
| 1001. | 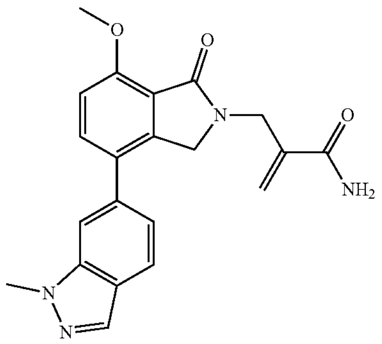 [SMILES: C=C(CN1Cc2c(-c3ccc4cnn(C)c4c3)ccc(OC)c2C1=O)C(N)=O] | 2-{[7-methoxy-4-(1-methyl-1H-indazol-6-yl)-1-oxo-2,3-dihydro-1H-isoindol-2-yl]methyl}prop-2-enamide | 376.4 |
| 1002. | 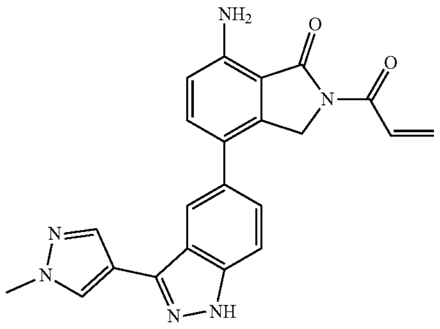 [SMILES: C=CC(=O)N1Cc2c(-c3ccc4[nH]nc(-c5cnn(C)c5)c4c3)ccc(N)c2C1=O] | 7-amino-4-[3-(1-methyl-1H-pyrazol-4-yl)-1H-indazol-5-yl]-2-(prop-2-enoyl)-2,3-dihydro-1H-isoindol-1-one | 398.4 |
| 1003. | 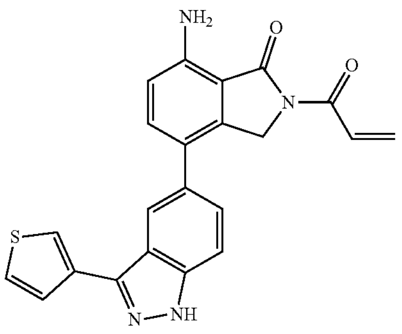 [SMILES: C=CC(=O)N1Cc2c(-c3ccc4[nH]nc(-c5ccsc5)c4c3)ccc(N)c2C1=O] | 7-amino-2-(prop-2-enoyl)-4-[3-(thiophen-3-yl)-1H-indazol-5-yl]-2,3-dihydro-1H-isoindol-1-one | 400.5 |

TABLE 15-continued

| Cpd. No. | Structure | IUPAC | MW (g/mol) |
|---|---|---|---|
| 1004. | 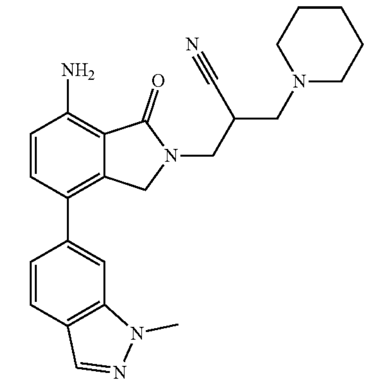 [SMILES: Cn1ncc2ccc(-c3ccc(N)c4c3CN(CC(C#N)CN3CCCCC3)C4=O)cc21] | 2-{[7-amino-4-(1-methyl-1H-indazol-6-yl)-1-oxo-2,3-dihydro-1H-isoindol-2-yl]methyl}-3-(piperidin-1-yl)propanenitrile | 428.5 |
| 1005. | 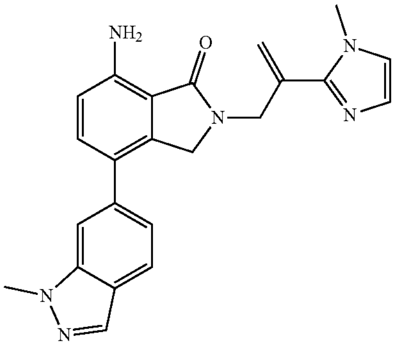 [SMILES: C=C(CN1Cc2c(-c3ccc4cnn(C)c4c3)ccc(N)c2C1=O)c1nccn1C] | 7-amino-2-[2-(1-methyl-1H-imidazol-2-yl)prop-2-en-1-yl]-4-(1-methyl-1H-indazol-6-yl)-2,3-dihydro-1H-isoindol-1-one | 398.5 |
| 1006. | 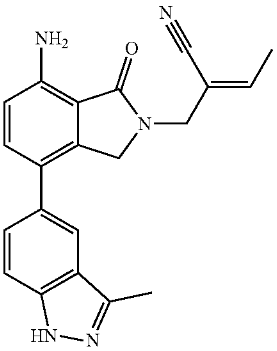 [SMILES: C/C=C(\C#N)CN1Cc2c(-c3ccc4[nH]nc(C)c4c3)ccc(N)c2C1=O] | (2Z)-2-{[7-amino-4-(3-methyl-1H-indazol-5-yl)-1-oxo-2,3-dihydro-1H-isoindol-2-yl]methyl}but-2-enenitrile | 357.4 |
| 1007. | 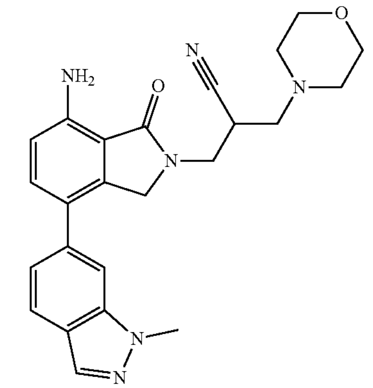 [SMILES: Cn1ncc2ccc(-c3ccc(N)c4c3CN(CC(C#N)CN3CCOCC3)C4=O)cc21] | 2-{[7-amino-4-(1-methyl-1H-indazol-6-yl)-1-oxo-2,3-dihydro-1H-isoindol-2-yl]methyl}-3-(morpholin-4-yl)propanenitrile | 430.5 |

TABLE 15-continued
| Cpd. No. | Structure | IUPAC | MW (g/mol) |
|---|---|---|---|
| 1008. | 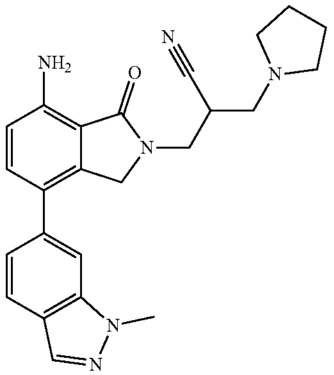 [SMILES: Cn1ncc2ccc(-c3ccc(N)c4c3CN(CC(C#N)CN3CCCC3)C4=O)cc21] | 2-{[7-amino-4-(1-methyl-1H-indazol-6-yl)-1-oxo-2,3-dihydro-1H-isoindol-2-yl]methyl}-3-(pyrrolidin-1-yl)propanenitrile | 414.5 |
| 1009. | 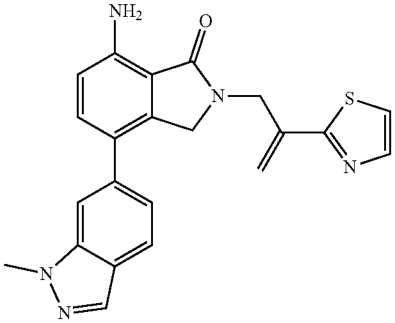 | 7-amino-4-(1-methyl-1H-indazol-6-yl)-2-[2-(1,3-thiazol-2-yl)prop-2-en-1-yl]-2,3-dihydro-1H-isoindol-1-one | 401.5 |
| 1010. | 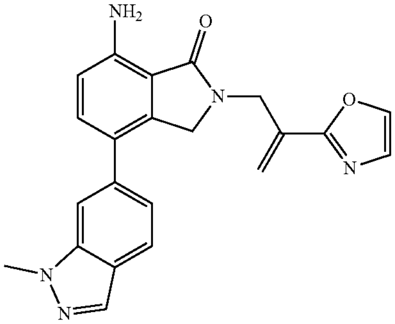 [SMILES: C=C(CN1Cc2c(-c3ccc4cnn(C)c4c3)ccc(N)c2C1=O)c1ncco1] | 7-amino-4-(1-methyl-1H-indazol-6-yl)-2-[2-(1,3-oxazol-2-yl)prop-2-en-1-yl]-2,3-dihydro-1H-isoindol-1-one | 385.4 |
| 1011. | 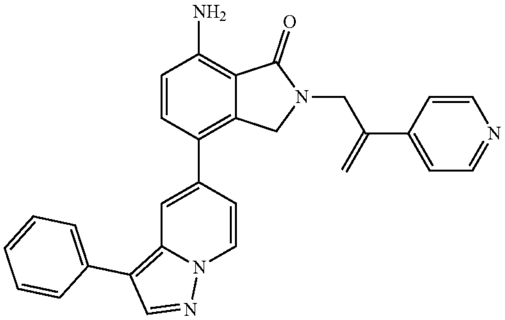 [SMILES: C=C(CN1Cc2c(-c3ccn4ncc(-c5ccccc5)c4c3)ccc(N)c2C1=O)c1ccncc1] | 7-amino-4-{3-phenylpyrazolo[1,5-a]pyridin-5-yl}-2-[2-(pyridin-4-yl)prop-2-en-1-yl]-2,3-dihydro-1H-isoindol-1-one | 457.5 |

TABLE 15-continued
| Cpd. No. | Structure | IUPAC | MW (g/mol) |
|---|---|---|---|
| 1012. | 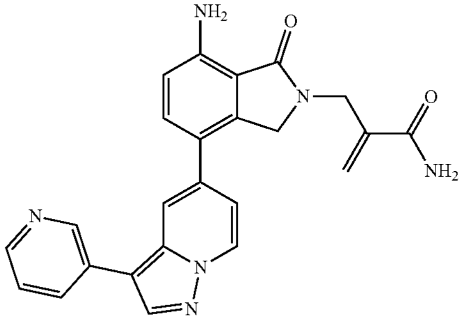 [SMILES: C=C(CN1Cc2c(-c3ccn4ncc(-c5cccnc5)c4c3)ccc(N)c2C1=O)C(N)=O] | 2-({7-amino-1-oxo-4-[3-(pyridin-3-yl)pyrazolo[1,5-a]pyridin-5-yl]-2,3-dihydro-1H-isoindol-2-yl}methyl)prop-2-enamide | 424.5 |
| 1013. | 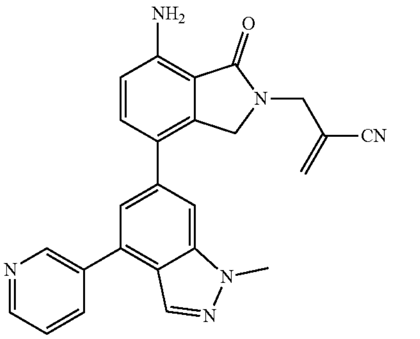 [SMILES: C=C(C#N)CN1Cc2c(-c3cc(-c4cccnc4)c4cnn(C)c4c3)ccc(N)c2C1=O] | 2-({7-amino-4-[1-methyl-4-(pyridin-3-yl)-1H-indazol-6-yl]-1-oxo-2,3-dihydro-1H-isoindol-2-yl}methyl)prop-2-enenitrile | 420.5 |
| 1014. | 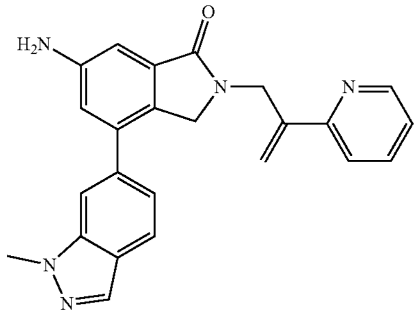 [SMILES: C=C(CN1Cc2c(cc(N)cc2-c2ccc3cnn(C)c3c2)C1=O)c1ccccn1] | 6-amino-4-(1-methyl-1H-indazol-6-yl)-2-[2-(pyridin-2-yl)prop-2-en-1-yl]-2,3-dihydro-1H-isoindol-1-one | 395.5 |
| 1015. | 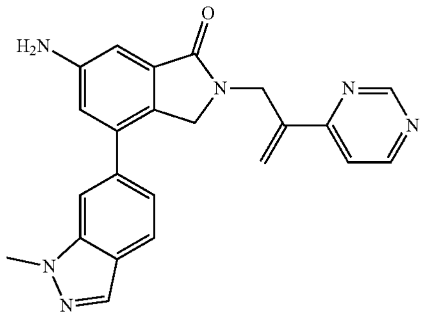 [SMILES: C=C(CN1Cc2c(cc(N)cc2-c2ccc3cnn(C)c3c2)C1=O)c1ccncn1] | 6-amino-4-(1-methyl-1H-indazol-6-yl)-2-[2-(pyrimidin-4-yl)prop-2-en-1-yl]-2,3-dihydro-1H-isoindol-1-one | 396.5 |

TABLE 15-continued
| Cpd. No. | Structure | IUPAC | MW (g/mol) |
|---|---|---|---|
| 1016. | 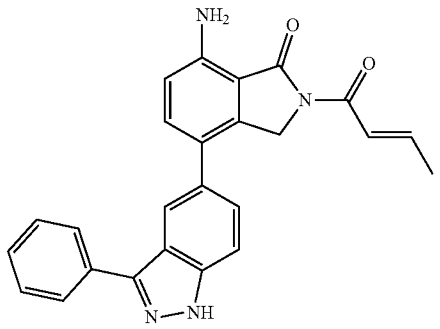 [SMILES: C/C=C/C(=O)N1Cc2c(-c3ccc4[nH]nc(-c5ccccc5)c4c3)ccc(N)c2C1=O] | 7-amino-2-[(2E)-but-2-enoyl]-4-(3-phenyl-1H-indazol-5-yl)-2,3-dihydro-1H-isoindol-1-one | 408.5 |
| 1017. | 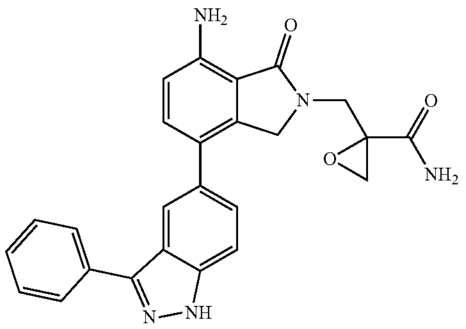 [SMILES: NC(=O)C1(CN2Cc3c(-c4ccc5[nH]nc(-c6ccccc6)c5c4)ccc(N)c3C2=O)CO1] | 2-{[7-amino-1-oxo-4-(3-phenyl-1H-indazol-5-yl)-2,3-dihydro-1H-isoindol-2-yl]methyl}oxirane-2-carboxamide | 439.5 |
| 1018. | 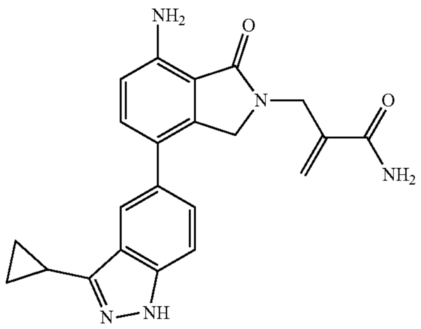 [SMILES: C=C(CN1Cc2c(-c3ccc4[nH]nc(C5CC5)c4c3)ccc(N)c2C1=O)C(N)=O] | 2-{[7-amino-4-(3-cyclopropyl-1H-indazol-5-yl)-1-oxo-2,3-dihydro-1H-isoindol-2-yl]methyl}prop-2-enamide | 387.4 |
| 1019. | 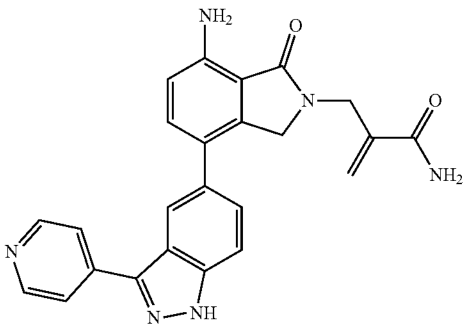 [SMILES: C=C(CN1Cc2c(-c3ccc4[nH]nc(-c5ccncc5)c4c3)ccc(N)c2C1=O)C(N)=O] | 2-({7-amino-1-oxo-4-[3-(pyridin-4-yl)-1H-indazol-5-yl]-2,3-dihydro-1H-isoindol-2-yl}methyl)prop-2-enamide | 424.5 |

TABLE 15-continued

| Cpd. No. | Structure | IUPAC | MW (g/mol) |
|---|---|---|---|
| 1020. | 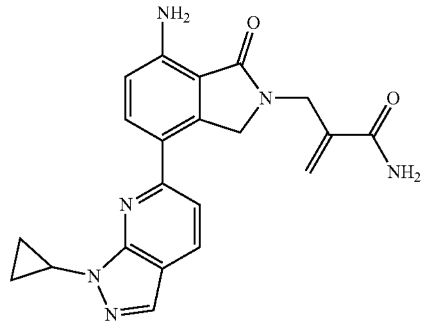 [SMILES: C=C(CN1Cc2c(-c3ccc4cnn(C5CC5)c4n3)ccc(N)c2C1=O)C(N)=O] | 2-[(7-amino-4-{1-cyclopropyl-1H-pyrazolo[3,4-b]pyridin-6-yl}-1-oxo-2,3-dihydro-1H-isoindol-2-yl)methyl]prop-2-enamide | 388.4 |
| 1021. | 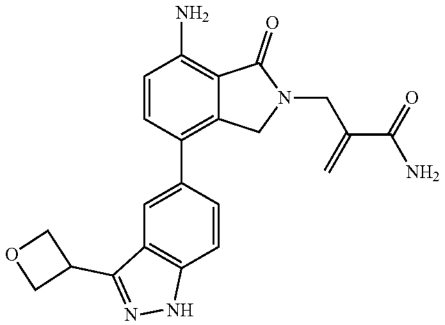 [SMILES: C=C(CN1Cc2c(-c3ccc4[nH]nc(C5COC5)c4c3)ccc(N)c2C1=O)C(N)=O] | 2-({7-amino-4-[3-(oxetan-3-yl)-1H-indazol-5-yl]-1-oxo-2,3-dihydro-1H-isoindol-2-yl}methyl)prop-2-enamide | 403.4 |
| 1022. | 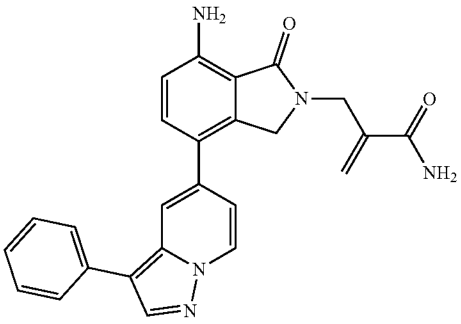 | 2-[(7-amino-1-oxo-4-{3-phenylpyrazolo[1,5-a]pyridin-5-yl}-2,3-dihydro-1H-isoindol-2-yl)methyl]prop-2-enamide | 423.5 |
| 1023. | 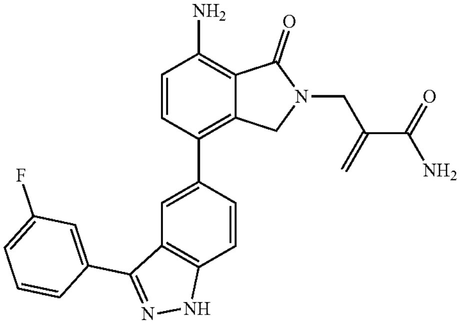 [SMILES: C=C(CN1Cc2c(-c3ccc4[nH]nc(-c5cccc(F)c5)c4c3)ccc(N)c2C1=O)C(N)=O] | 2-({7-amino-4-[3-(3-fluorophenyl)-1H-indazol-5-yl]-1-oxo-2,3-dihydro-1H-isoindol-2-yl}methyl)prop-2-enamide | 441.5 |

TABLE 15-continued

| Cpd. No. | Structure | IUPAC | MW (g/mol) |
|---|---|---|---|
| 1024. | 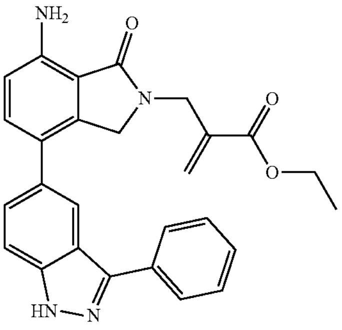 [SMILES: C=C(CN1Cc2c(-c3ccc4[nH]nc(-c5ccccc5)c4c3)ccc(N)c2C1=O)C(=O)OCC] | ethyl 2-{[7-amino-1-oxo-4-(3-phenyl-1H-indazol-5-yl)-2,3-dihydro-1H-isoindol-2-yl]methyl}prop-2-enoate | 452.5 |
| 1025. | 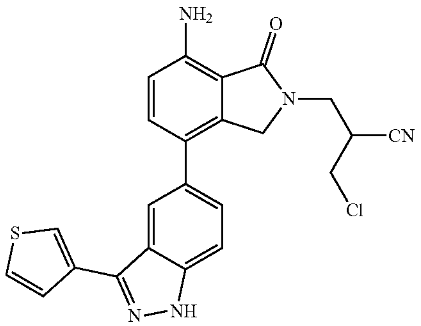 [SMILES: N#CC(CCl)CN1Cc2c(-c3ccc4[nH]nc(-c5ccsc5)c4c3)ccc(N)c2C1=O] | 2-({7-amino-1-oxo-4-[3-(thiophen-3-yl)-1H-indazol-5-yl]-2,3-dihydro-1H-isoindol-2-yl}methyl)-3-chloropropanenitrile | 447.9 |
| 1026. | 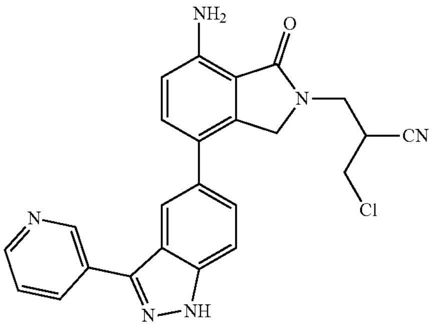 [SMILES: N#CC(CCl)CN1Cc2c(-c3ccc4[nH]nc(-c5cccnc5)c4c3)ccc(N)c2C1=O] | 2-({7-amino-1-oxo-4-[3-(pyridin-3-yl)-1H-indazol-5-yl]-2,3-dihydro-1H-isoindol-2-yl}methyl)-3-chloropropanenitrile | 442.9 |
| 1027. | 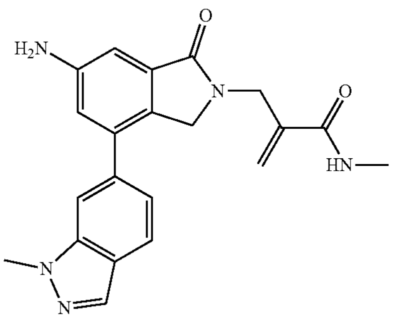 | 2-{[6-amino-4-(1-methyl-1H-indazol-6-yl)-1-oxo-2,3-dihydro-1H-isoindol-2-yl]methyl}-N-methylprop-2-enamide | 375.4 |

TABLE 15-continued
| Cpd. No. | Structure | IUPAC | MW (g/mol) |
|---|---|---|---|
| 1028. | 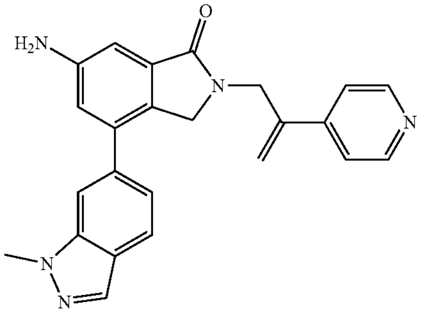 [SMILES: C=C(CN1Cc2c(cc(N)cc2-c2ccc3cnn(C)c3c2)C1=O)c1ccncc1] | 6-amino-4-(1-methyl-1H-indazol-6-yl)-2-[2-(pyridin-4-yl)prop-2-en-1-yl]-2,3-dihydro-1H-isoindol-1-one | 395.5 |
| 1029. | 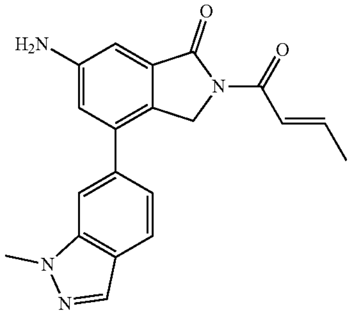 [SMILES: C/C=C/C(=O)N1Cc2c(cc(N)cc2-c2ccc3cnn(C)c3c2)C1=O] | 6-amino-2-[(2E)-but-2-enoyl]-4-(1-methyl-1H-indazol-6-yl)-2,3-dihydro-1H-isoindol-1-one | 346.4 |
| 1030. | 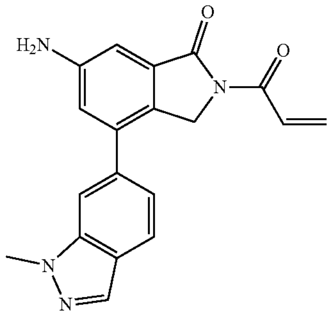 [SMILES: C=CC(=O)N1Cc2c(cc(N)cc2-c2ccc3cnn(C)c3c2)C1=O] | 6-amino-4-(1-methyl-1H-indazol-6-yl)-2-(prop-2-enoyl)-2,3-dihydro-1H-isoindol-1-one | 332.4 |
| 1031. | 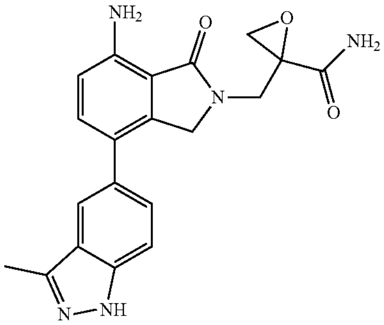 [SMILES: Cc1n[nH]c2ccc(-c3ccc(N)c4c3CN(CC3(C(N)=O)CO3)C4=O)cc12] | 2-{[7-amino-4-(3-methyl-1H-indazol-5-yl)-1-oxo-2,3-dihydro-1H-isoindol-2-yl]methyl}oxirane-2-carboxamide | 377.4 |

TABLE 15-continued

| Cpd. No. | Structure | IUPAC | MW (g/mol) |
|---|---|---|---|
| 1032. | 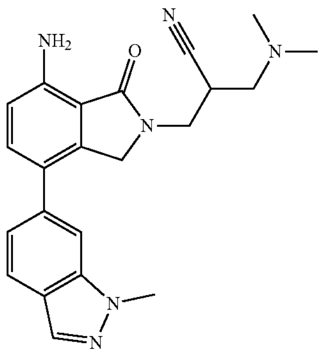 [SMILES: CN(C)CC(C#N)CN1Cc2c(-c3ccc4cnn(C)c4c3)ccc(N)c2C1=O] | 2-{[7-amino-4-(1-methyl-1H-indazol-6-yl)-1-oxo-2,3-dihydro-1H-isoindol-2-yl]methyl}-3-(dimethylamino)propanenitrile | 388.5 |
| 1033. | 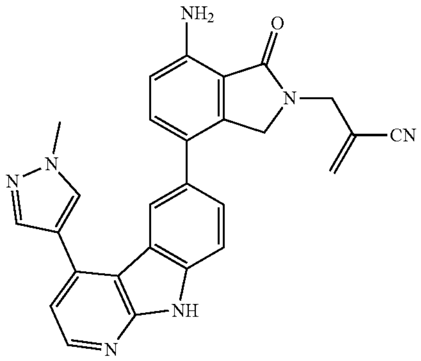 [SMILES: C=C(C#N)CN1Cc2c(-c3ccc4[nH]c5nccc(-c6cnn(C)c6)c5c4c3)ccc(N)c2C1=O] | 2-({7-amino-4-[4-(1-methyl-1H-pyrazol-4-yl)-9H-pyrido[2,3-b]indol-6-yl]-1-oxo-2,3-dihydro-1H-isoindol-2-yl}methyl)prop-2-enenitrile | 459.5 |
| 1034. | 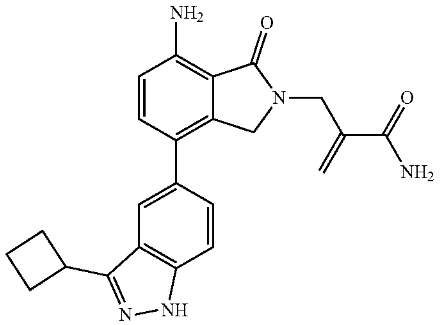 [SMILES: C=C(CN1Cc2c(-c3ccc4[nH]nc(C5CCC5)c4c3)ccc(N)c2C1=O)C(N)=O] | 2-{[7-amino-4-(3-cyclobutyl-1H-indazol-5-yl)-1-oxo-2,3-dihydro-1H-isoindol-2-yl]methyl}prop-2-enamide | 401.5 |
| 1035. | 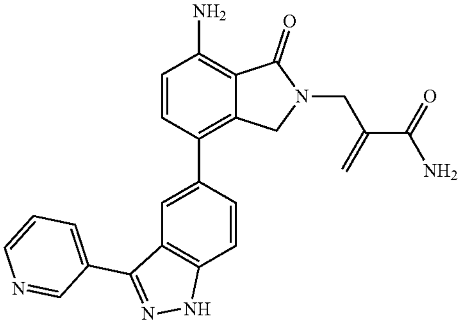 [SMILES: C=C(CN1Cc2c(-c3ccc4[nH]nc(-c5cccnc5)c4c3)ccc(N)c2C1=O)C(N)=O] | 2-({7-amino-1-oxo-4-[3-(pyridin-3-yl)-1H-indazol-5-yl]-2,3-dihydro-1H-isoindol-2-yl}methyl)prop-2-enamide | 424.5 |

TABLE 15-continued

| Cpd. No. | Structure | IUPAC | MW (g/mol) |
|---|---|---|---|
| 1036. | 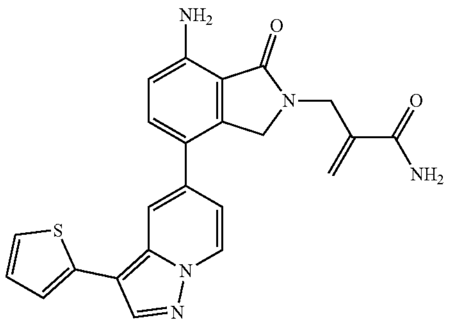 [SMILES: C=C(CN1Cc2c(-c3ccn4ncc(-c5cccs5)c4c3)ccc(N)c2C1=O)C(N)=O] | 2-({7-amino-1-oxo-4-[3-(thiophen-2-yl)pyrazolo[1,5-a]pyridin-5-yl]-2,3-dihydro-1H-isoindol-2-yl}methyl)prop-2-enamide | 429.5 |
| 1037. | 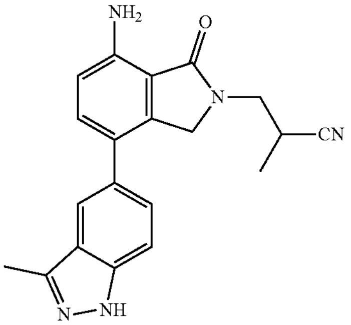 [SMILES: Cc1n[nH]c2ccc(-c3ccc(N)c4c3CN(CC(C)C#N)C4=O)cc12] | 3-[7-amino-4-(3-methyl-1H-indazol-5-yl)-1-oxo-2,3-dihydro-1H-isoindol-2-yl]-2-methylpropanenitrile | 345.4 |
| 1038. | 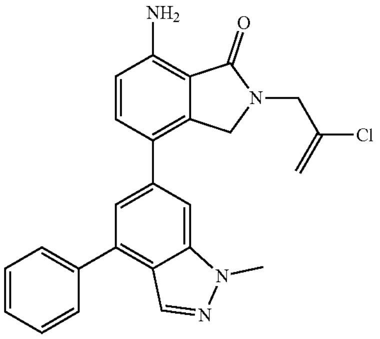 [SMILES: C=C(Cl)CN1Cc2c(-c3cc(-c4ccccc4)c4cnn(C)c4c3)ccc(N)c2C1=O] | 2-{[7-amino-4-(1-methyl-4-phenyl-1H-indazol-6-yl)-1-oxo-2,3-dihydro-1H-isoindol-2-yl]methyl}prop-2-enenitrile | 419.5 |
| 1039. | 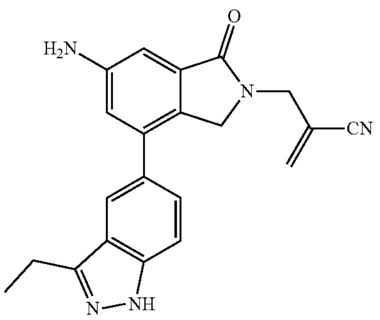 [SMILES: C=C(C#N)CN1Cc2c(cc(N)cc2-c2ccc3[nH]nc(CC)c3c2)C1=O] | 2-{[6-amino-4-(3-ethyl-1H-indazol-5-yl)-1-oxo-2,3-dihydro-1H-isoindol-2-yl]methyl}prop-2-enenitrile | 357.4 |

TABLE 15-continued
| Cpd. No. | Structure | IUPAC | MW (g/mol) |
|---|---|---|---|
| 1040. | 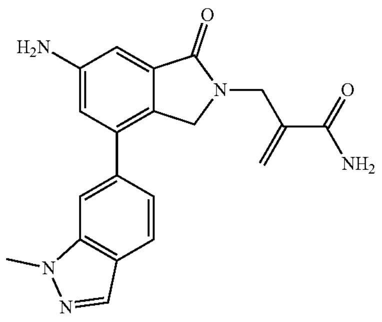 [SMILES: C=C(CN1Cc2c(cc(N)cc2-c2ccc3cnn(C)c3c2)C1=O)C(N)=O] | 2-{[6-amino-4-(1-methyl-1H-indazol-6-yl)-1-oxo-2,3-dihydro-1H-isoindol-2-yl]methyl}prop-2-enamide | 361.4 |
| 1041. | 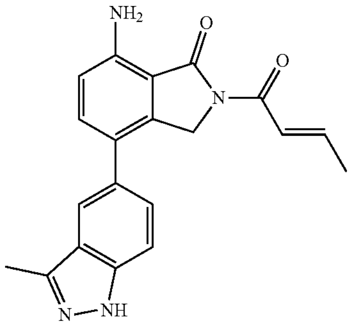 [SMILES: C/C=C/C(=O)N1Cc2c(-c3ccc4[nH]nc(C)c4c3)ccc(N)c2C1=O] | 7-amino-2-[(2E)-but-2-enoyl]-4-(3-methyl-1H-indazol-5-yl)-2,3-dihydro-1H-isoindol-1-one | 346.4 |
| 1042. | 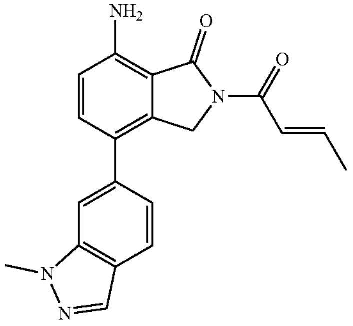 [SMILES: C/C=C/C(=O)N1Cc2c(-c3ccc4cnn(C)c4c3)ccc(N)c2C1=O] | 7-amino-2-[(2E)-but-2-enoyl]-4-(1-methyl-1H-indazol-6-yl)-2,3-dihydro-1H-isoindol-1-one | 346.4 |
| 1043. | 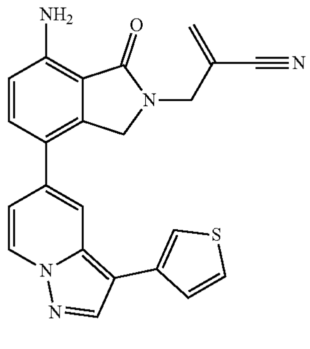 [SMILES: C=C(C#N)CN1Cc2c(-c3ccn4ncc(-c5ccsc5)c4c3)ccc(N)c2C1=O] | 2-({7-amino-1-oxo-4-[3-(thiophen-3-yl)pyrazolo[1,5-a]pyridin-5-yl]-2,3-dihydro-1H-isoindol-2-yl}methyl)prop-2-enenitrile | 411.5 |

TABLE 15-continued

| Cpd. No. | Structure | IUPAC | MW (g/mol) |
|---|---|---|---|
| 1044. | 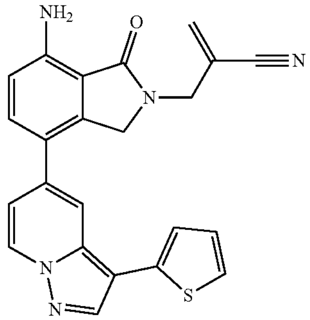 [SMILES: C=C(C#N)CN1Cc2c(-c3ccn4ncc(-c5cccs5)c4c3)ccc(N)c2C1=O] | 2-({7-amino-1-oxo-4-[3-(thiophen-2-yl)pyrazolo[1,5-a]pyridin-5-yl]-2,3-dihydro-1H-isoindol-2-yl}methyl)prop-2-enenitrile | 411.5 |
| 1045. | 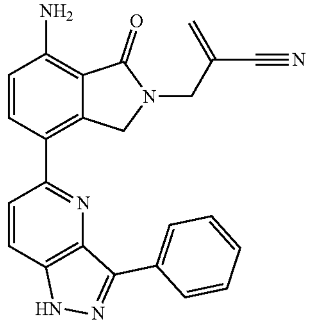 [SMILES: C=C(C#N)CN1Cc2c(-c3ccc4[nH]nc(-c5ccccc5)c4n3)ccc(N)c2C1=O] | 2-[(7-amino-1-oxo-4-{3-phenyl-1H-pyrazolo[4,3-b]pyridin-5-yl}-2,3-dihydro-1H-isoindol-2-yl)methyl]prop-2-enenitrile | 406.4 |
| 1046. | 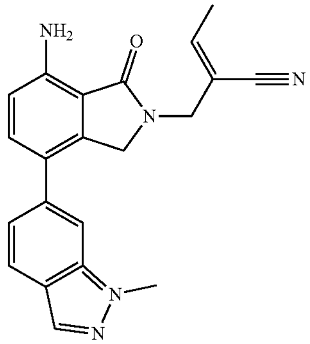 | (2Z)-2-{[7-amino-4-(1-methyl-1H-indazol-6-yl)-1-oxo-2,3-dihydro-1H-isoindol-2-yl]methyl}but-2-enenitrile | 357.4 |
| 1047. | 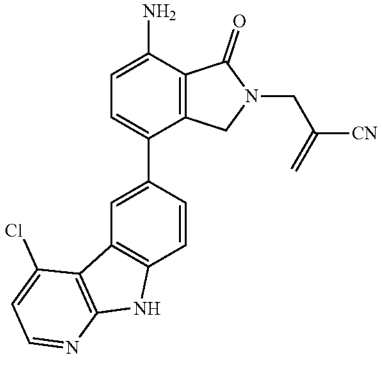 [SMILES: C=C(C#N)CN1Cc2c(-c3ccc4[nH]c5nccc(Cl)c5c4c3)ccc(N)c2C1=O] | 2-[(7-amino-4-{4-chloro-9H-pyrido[2,3-b]indol-6-yl}-1-oxo-2,3-dihydro-1H-isoindol-2-yl)methyl]prop-2-enenitrile | 413.9 |

TABLE 15-continued

| Cpd. No. | Structure | IUPAC | MW (g/mol) |
|---|---|---|---|
| 1048. | 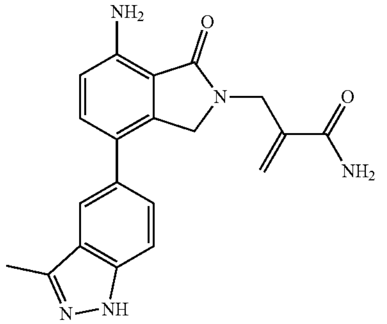 [SMILES: C=C(CN1Cc2c(-c3ccc4[nH]nc(C)c4c3)ccc(N)c2C1=O)C(N)=O] | 2-{[7-amino-4-(3-methyl-1H-indazol-5-yl)-1-oxo-2,3-dihydro-1H-isoindol-2-yl]methyl}prop-2-enamide | 361.4 |
| 1049. | 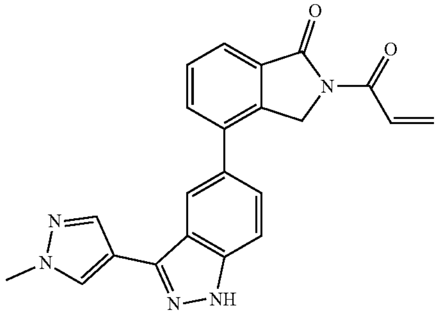 [SMILES: C=CC(=O)N1Cc2c(cccc2-c2ccc3[nH]nc(-c4cnn(C)c4)c3c2)C1=O] | 4-[3-(1-methyl-1H-pyrazol-4-yl)-1H-indazol-5-yl]-2-(prop-2-enoyl)-2,3-dihydro-1H-isoindol-1-one | 383.4 |
| 1050. | 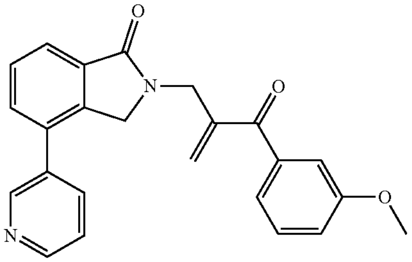 [SMILES: C=C(CN1Cc2c(cccc2-c2cccnc2)C1=O)C(=O)c1cccc(OC)c1] | 2-[3-(3-methoxyphenyl)-2-methylidene-3-oxopropyl]-4-(pyridin-3-yl)-2,3-dihydro-1H-isoindol-1-one | 384.4 |
| 1051. | 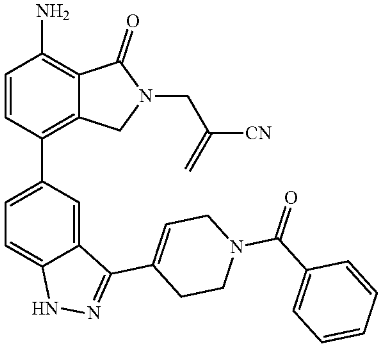 [SMILES: C=C(C#N)CN1Cc2c(-c3ccc4[nH]nc(C5=CCN(C(=O)c6ccccc6)CC5)c4c3)ccc(N)c2C1=O] | 2-({7-amino-4-[3-(1-benzoyl-1,2,3,6-tetrahydropyridin-4-yl)-1H-indazol-5-yl]-1-oxo-2,3-dihydro-1H-isoindol-2-yl}methyl)prop-2-enenitrile | 514.6 |
| 1052. | 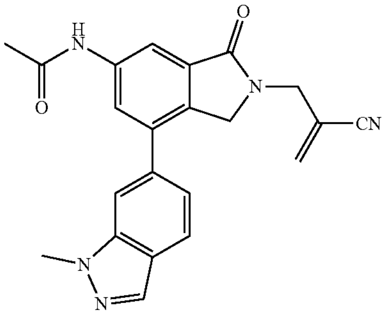 [SMILES: C=C(C#N)CN1Cc2c(cc(NC(C)=O)cc2-c2ccc3cnn(C)c3c2)C1=O] | N-[2-(2-cyano-2-methylideneethyl)-7-(1-methyl-1H-indazol-6-yl)-3-oxo-2,3-dihydro-1H-isoindol-5-yl]acetamide | 385.4 |

TABLE 15-continued
| Cpd. No. | Structure | IUPAC | MW (g/mol) |
|---|---|---|---|
| 1053. | 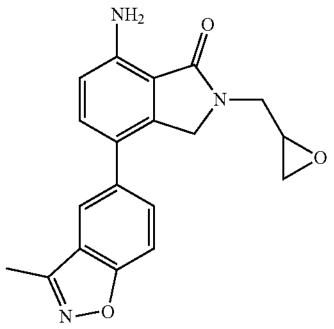 [SMILES: Cc1noc2ccc(-c3ccc(N)c4c3CN(CC3CO3)C4=O)cc12] | 7-amino-4-(3-methyl-1,2-benzoxazol-5-yl)-2-[(oxiran-2-yl)methyl]-2,3-dihydro-1H-isoindol-1-one | 335.4 |
| 1054. | 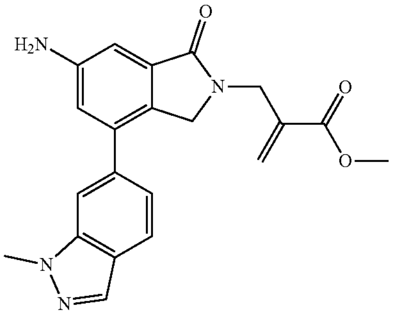 | methyl 2-{[6-amino-4-(1-methyl-1H-indazol-6-yl)-1-oxo-2,3-dihydro-1H-isoindol-2-yl]methyl}prop-2-enoate | 376.4 |
| 1055. | 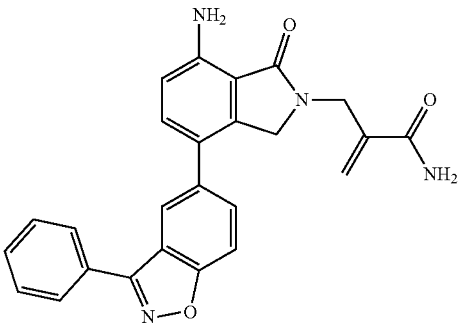 [SMILES: C=C(CN1Cc2c(-c3ccc4onc(-c5ccccc5)c4c3)ccc(N)c2C1=O)C(N)=O] | 2-{[7-amino-1-oxo-4-(3-phenyl-1,2-benzoxazol-5-yl)-2,3-dihydro-1H-isoindol-2-yl]methyl}prop-2-enamide | 424.5 |
| 1056. | 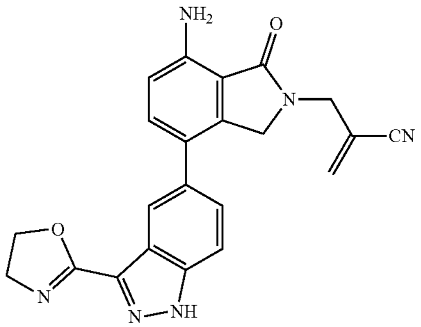 [SMILES: C=C(C#N)CN1Cc2c(-c3ccc4[nH]nc(C5=NCCO5)c4c3)ccc(N)c2C1=O] | 2-({7-amino-4-[3-(4,5-dihydro-1,3-oxazol-2-yl)-1H-indazol-5-yl]-1-oxo-2,3-dihydro-1H-isoindol-2-yl}methyl)prop-2-enenitrile | 398.4 |

TABLE 15-continued

| Cpd. No. | Structure | IUPAC | MW (g/mol) |
|---|---|---|---|
| 1057. | 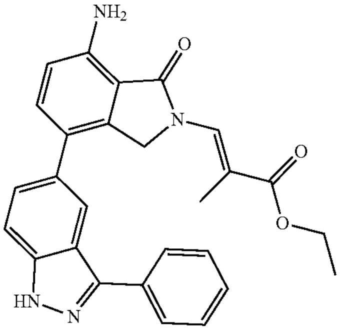 [SMILES: CCOC(=O)/C(C)=C/N1Cc2c(-c3ccc4[nH]nc(-c5ccccc5)c4c3)ccc(N)c2C1=O] | ethyl (2E)-3-[7-amino-1-oxo-4-(3-phenyl-1H-indazol-5-yl)-2,3-dihydro-1H-isoindol-2-yl]-2-methylprop-2-enoate | 452.5 |
| 1058. | 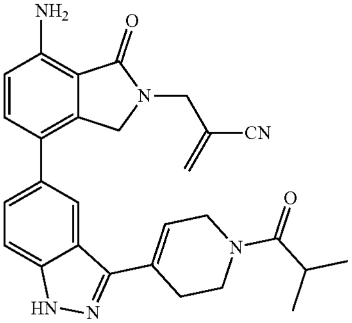 [SMILES: C=C(C#N)CN1Cc2c(-c3ccc4[nH]nc(C5=CCN(C(=O)C(C)C)CC5)c4c3)ccc(N)c2C1=O] | 2-[(7-amino-4-{3-[1-(2-methylpropanoyl)-1,2,3,6-tetrahydropyridin-4-yl]-1H-indazol-5-yl}-1-oxo-2,3-dihydro-1H-isoindol-2-yl)methyl]prop-2-enenitrile | 480.6 |
| 1059. | 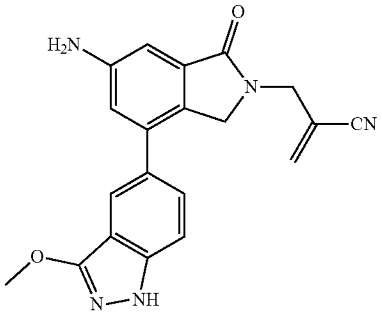 [SMILES: C=C(C#N)CN1Cc2c(cc(N)cc2-c2ccc3[nH]nc(OC)c3c2)C1=O] | 2-{[6-amino-4-(3-methoxy-1H-indazol-5-yl)-1-oxo-2,3-dihydro-1H-isoindol-2-yl]methyl}prop-2-enenitrile | 359.4 |
| 1060. | 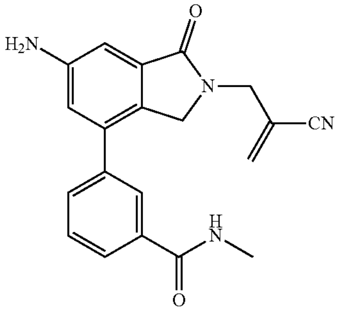 [SMILES: C=C(C#N)CN1Cc2c(cc(N)cc2-c2cccc(C(=O)NC)c2)C1=O] | 3-[6-amino-2-(2-cyano-2-methylideneethyl)-1-oxo-2,3-dihydro-1H-isoindol-4-yl]-N-methylbenzamide | 346.4 |

TABLE 15-continued

| Cpd. No. | Structure | IUPAC | MW (g/mol) |
|---|---|---|---|
| 1061. | 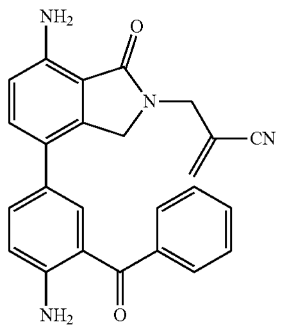 [SMILES: C=C(C#N)CN1Cc2c(-c3ccc(N)c(C(=O)c4ccccc4)c3)ccc(N)c2C1=O] | 2-{[7-amino-4-(4-amino-3-benzoylphenyl)-1-oxo-2,3-dihydro-1H-isoindol-2-yl]methyl}prop-2-enenitrile | 408.5 |
| 1062. | 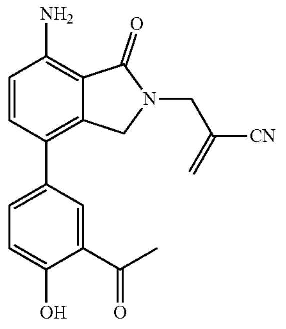 [SMILES: C=C(C#N)CN1Cc2c(-c3ccc(O)c(C(C)=O)c3)ccc(N)c2C1=O] | 2-{[4-(3-acetyl-4-hydroxyphenyl)-7-amino-1-oxo-2,3-dihydro-1H-isoindol-2-yl]methyl}prop-2-enenitrile | 347.4 |
| 1063. | 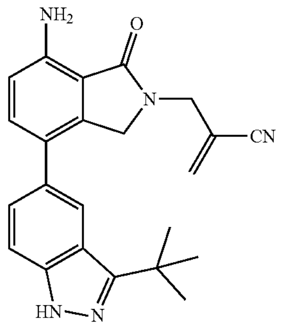 [SMILES: C=C(C#N)CN1Cc2c(-c3ccc4[nH]nc(C(C)(C)C)c4c3)ccc(N)c2C1=O] | 2-{[7-amino-4-(3-tert-butyl-1H-indazol-5-yl)-1-oxo-2,3-dihydro-1H-isoindol-2-yl]methyl}prop-2-enenitrile | 385.5 |
| 1064. | 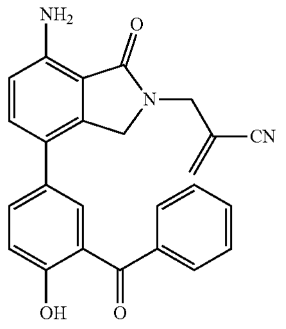 [SMILES: C=C(C#N)CN1Cc2c(-c3ccc(O)c(C(=O)c4ccccc4)c3)ccc(N)c2C1=O] | 2-{[7-amino-4-(3-benzoyl-4-hydroxyphenyl)-1-oxo-2,3-dihydro-1H-isoindol-2-yl]methyl}prop-2-enenitrile | 409.4 |

TABLE 15-continued
| Cpd. No. | Structure | IUPAC | MW (g/mol) |
|---|---|---|---|
| 1065. | 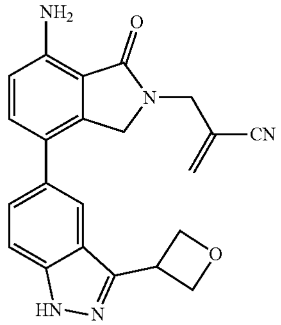 [SMILES: C=C(C#N)CN1Cc2c(-c3ccc4[nH]nc(C5COC5)c4c3)ccc(N)c2C1=O] | 2-({7-amino-4-[3-(oxetan-3-yl)-1H-indazol-5-yl]-1-oxo-2,3-dihydro-1H-isoindol-2-yl}methyl)prop-2-enenitrile | 385.4 |
| 1066. | 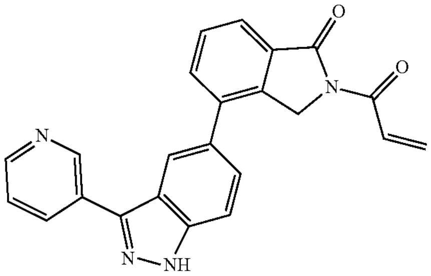 [SMILES: C=CC(=O)N1Cc2c(cccc2-c2ccc3[nH]nc(-c4cccnc4)c3c2)C1=O] | 2-(prop-2-enoyl)-4-[3-(pyridin-3-yl)-1H-indazol-5-yl]-2,3-dihydro-1H-isoindol-1-one | 380.4 |
| 1067. | 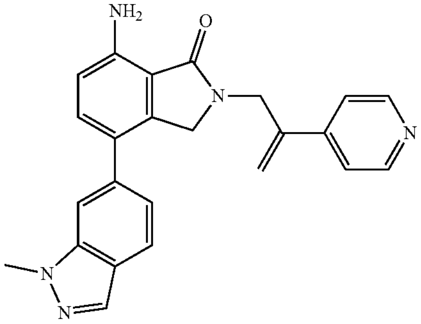 [SMILES: C=C(CN1Cc2c(-c3ccc4cnn(C)c4c3)ccc(N)c2C1=O)c1ccncc1] | 7-amino-4-(1-methyl-1H-indazol-6-yl)-2-[2-(pyridin-4-yl)prop-2-en-1-yl]-2,3-dihydro-1H-isoindol-1-one | 395.5 |
| 1068. | 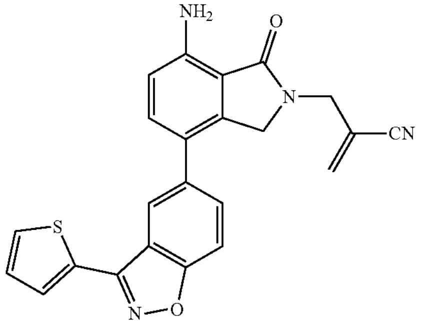 [SMILES: C=C(C#N)CN1Cc2c(-c3ccc4onc(-c5cccs5)c4c3)ccc(N)c2C1=O] | 2-({7-amino-1-oxo-4-[3-(thiophen-2-yl)-1,2-benzoxazol-5-yl]-2,3-dihydro-1H-isoindol-2-yl}methyl)prop-2-enenitrile | 412.5 |

TABLE 15-continued
| Cpd. No. | Structure | IUPAC | MW (g/mol) |
| --- | --- | --- | --- |
| 1069. | 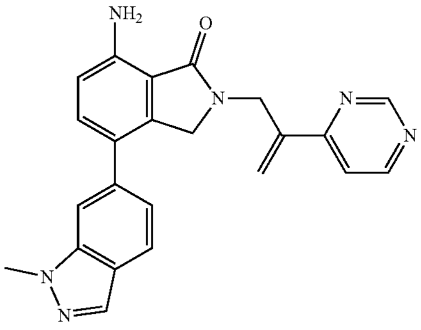 [SMILES: C=C(CN1Cc2c(-c3ccc4cnn(C)c4c3)ccc(N)c2C1=O)c1ccncn1] | 7-amino-4-(1-methyl-1H-indazol-6-yl)-2-[2-(pyrimidin-4-yl)prop-2-en-1-yl]-2,3-dihydro-1H-isoindol-1-one | 396.5 |
| 1070. | 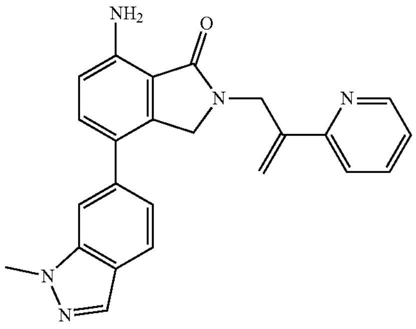 [SMILES: C=C(CN1Cc2c(-c3ccc4cnn(C)c4c3)ccc(N)c2C1=O)c1ccccn1] | 7-amino-4-(1-methyl-1H-indazol-6-yl)-2-[2-(pyridin-2-yl)prop-2-en-1-yl]-2,3-dihydro-1H-isoindol-1-one | 395.5 |
| 1071. | 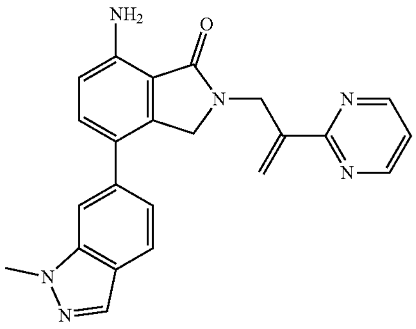 [SMILES: C=C(CN1Cc2c(-c3ccc4cnn(C)c4c3)ccc(N)c2C1=O)c1ncccn1] | 7-amino-4-(1-methyl-1H-indazol-6-yl)-2-[2-(pyrimidin-2-yl)prop-2-en-1-yl]-2,3-dihydro-1H-isoindol-1-one | 396.5 |
| 1072. | 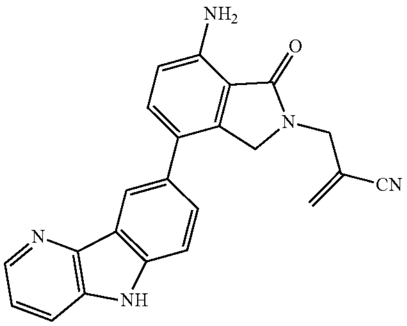 [SMILES: C=C(C#N)CN1Cc2c(-c3ccc4[nH]c5cccnc5c4c3)ccc(N)c2C1=O] | 2-[(7-amino-1-oxo-4-{5H-pyrido[3,2-b]indol-8-yl}-2,3-dihydro-1H-isoindol-2-yl)methyl]prop-2-enenitrile | 379.4 |

TABLE 15-continued

| Cpd. No. | Structure | IUPAC | MW (g/mol) |
|---|---|---|---|
| 1073. | 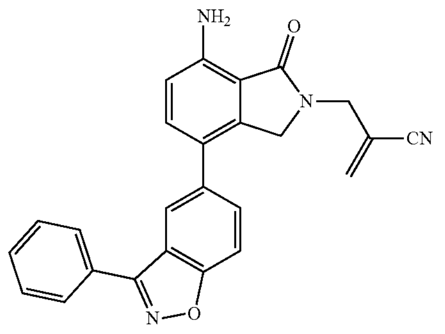 [SMILES: C=C(C#N)CN1Cc2c(-c3ccc4onc(-c5ccccc5)c4c3)ccc(N)c2C1=O] | 2-{[7-amino-1-oxo-4-(3-phenyl-1,2-benzoxazol-5-yl)-2,3-dihydro-1H-isoindol-2-yl]methyl}prop-2-enenitrile | 406.4 |
| 1074. | 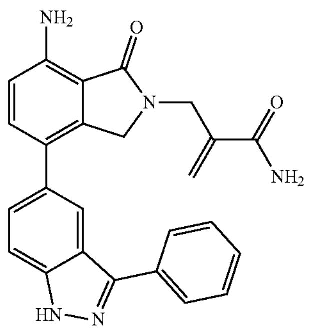 [SMILES: C=C(CN1Cc2c(-c3ccc4[nH]nc(-c5ccccc5)c4c3)ccc(N)c2C1=O)C(N)=O] | 2-{[7-amino-1-oxo-4-(3-phenyl-1H-indazol-5-yl)-2,3-dihydro-1H-isoindol-2-yl]methyl}prop-2-enamide | 423.5 |
| 1075. | 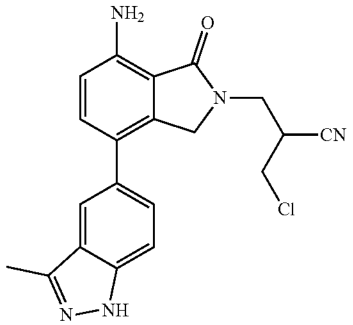 [SMILES: Cc1n[nH]c2ccc(-c3ccc(N)c4c3CN(CC(C#N)CCl)C4=O)cc12] | 2-{[7-amino-4-(3-methyl-1H-indazol-5-yl)-1-oxo-2,3-dihydro-1H-isoindol-2-yl]methyl}-3-chloropropanenitrile | 379.9 |
| 1076. | 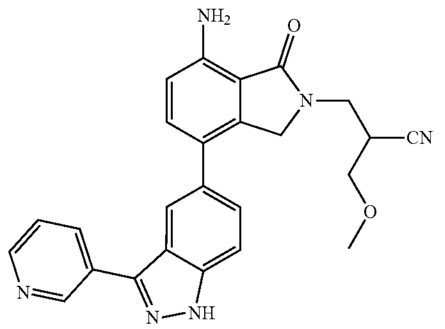 [SMILES: COCC(C#N)CN1Cc2c(-c3ccc4[nH]nc(-c5cccnc5)c4c3)ccc(N)c2C1=O] | 2-({7-amino-1-oxo-4-[3-(pyridin-3-yl)-1H-indazol-5-yl]-2,3-dihydro-1H-isoindol-2-yl}methyl)-3-methoxypropanenitrile | 438.5 |

TABLE 15-continued

| Cpd. No. | Structure | IUPAC | MW (g/mol) |
|---|---|---|---|
| 1077. | 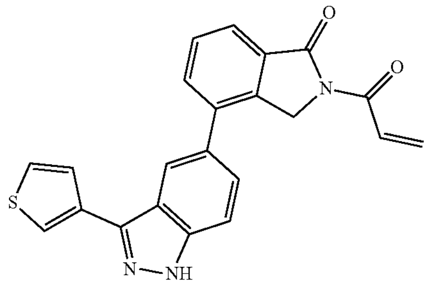 [SMILES: C=CC(=O)N1Cc2c(cccc2-c2ccc3[nH]nc(-c4ccsc4)c3c2)C1=O] | 2-(prop-2-enoyl)-4-[3-(thiophen-3-yl)-1H-indazol-5-yl]-2,3-dihydro-1H-isoindol-1-one | 385.4 |
| 1078. | 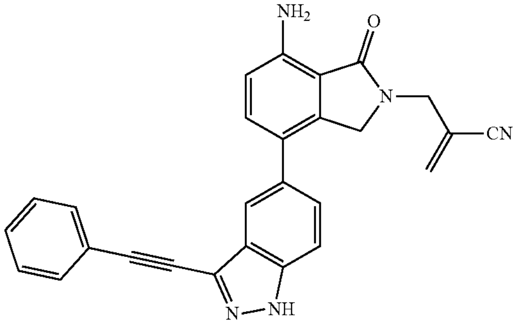 [SMILES: C=C(C#N)CN1Cc2c(-c3ccc4[nH]nc(C#Cc5ccccc5)c4c3)ccc(N)c2C1=O] | 2-({7-amino-1-oxo-4-[3-(2-phenylethynyl)-1H-indazol-5-yl]-2,3-dihydro-1H-isoindol-1-yl}methyl)prop-2-enenitrile | 429.5 |
| 1079. | 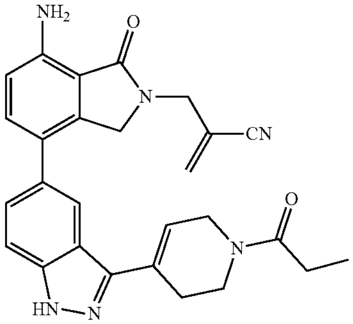 [SMILES: C=C(C#N)CN1Cc2c(-c3ccc4[nH]nc(C5=CCN(C(=O)CC)CC5)c4c3)ccc(N)c2C1=O] | 2-({7-amino-1-oxo-4-[3-(1-propanoyl-1,2,3,6-tetrahydropyridin-4-yl)-1H-indazol-5-yl]-2,3-dihydro-1H-isoindol-2-yl}methyl)prop-2-enenitrile | 466.5 |
| 1080. | 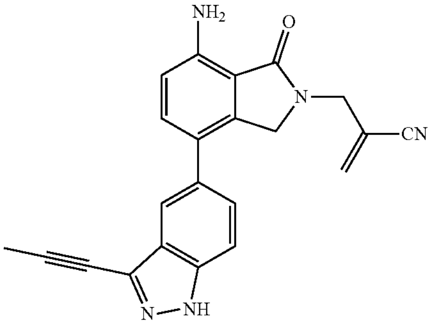 [SMILES: C=C(C#N)CN1Cc2c(-c3ccc4[nH]nc(C#CC)c4c3)ccc(N)c2C1=O] | 2-({7-amino-1-oxo-4-[3-(prop-1-yn-1-yl)-1H-indazol-5-yl]-2,3-dihydro-1H-isoindol-2-yl}methyl)prop-2-enenitrile | 367.4 |

TABLE 15-continued
| Cpd. No. | Structure | IUPAC | MW (g/mol) |
|---|---|---|---|
| 1081. | 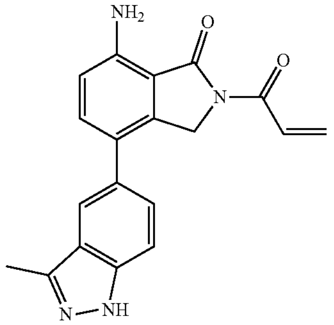 [SMILES: C=CC(=O)N1Cc2c(-c3ccc4[nH]nc(C)c4c3)ccc(N)c2C1=O] | 7-amino-4-(3-methyl-1H-indazol-5-yl)-2-(prop-2-enoyl)-2,3-dihydro-1H-isoindol-1-one | 332.4 |
| 1082. | 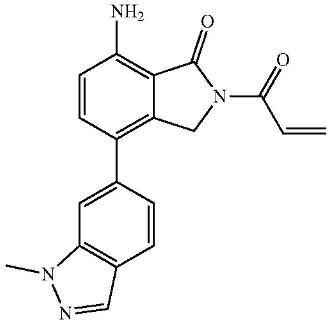 [SMILES: C=CC(=O)N1Cc2c(-c3ccc4cnn(C)c4c3)ccc(N)c2C1=O] | 7-amino-4-(1-methyl-1H-indazol-6-yl)-2-(prop-2-enoyl)-2,3-dihydro-1H-isoindol-1-one | 332.4 |
| 1083. | 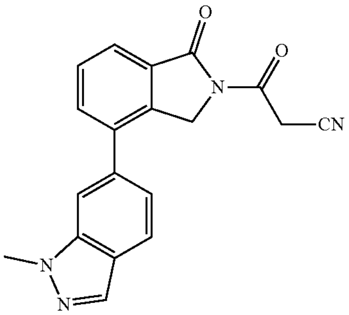 [SMILES: Cn1ncc2ccc(-c3cccc4c3CN(C(=O)CC#N)C4=O)cc21] | 3-[4-(1-methyl-1H-indazol-6-yl)-1-oxo-2,3-dihydro-1H-isoindol-2-yl]-3-oxopropanenitrile | 330.3 |
| 1084. | 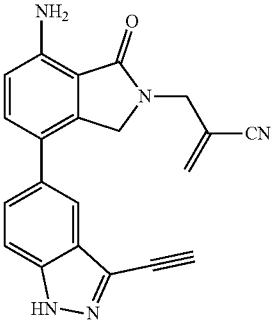 [SMILES: C#Cc1n[nH]c2ccc(-c3ccc(N)c4c3CN(CC(=C)C#N)C4=O)cc12] | 2-{[7-amino-4-(3-ethynyl-1H-indazol-5-yl)-1-oxo-2,3-dihydro-1H-isoindol-2-yl]methyl}prop-2-enenitrile | 353.4 |

TABLE 15-continued
| Cpd. No. | Structure | IUPAC | MW (g/mol) |
|---|---|---|---|
| 1085. | 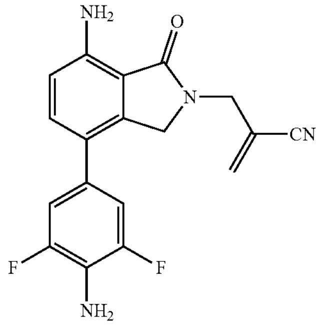 [SMILES: C=C(C#N)CN1Cc2c(-c3cc(F)c(N)c(F)c3)ccc(N)c2C1=O] | 2-{[7-amino-4-(4-amino-3,5-difluorophenyl)-1-oxo-2,3-dihydro-1H-isoindol-2-yl]methyl}prop-2-enenitrile | 340.3 |
| 1086. | 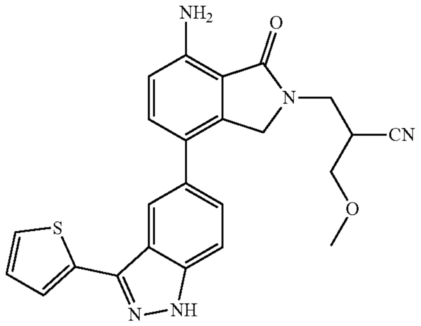 [SMILES: COCC(C#N)CN1Cc2c(-c3ccc4[nH]nc(-c5cccs5)c4c3)ccc(N)c2C1=O] | 2-({7-amino-1-oxo-4-[3-(thiophen-2-yl)-1H-indazol-5-yl]-2,3-dihydro-1H-isoindol-2-yl}methyl)-3-methoxypropanenitrile | 443.5 |
| 1087. | 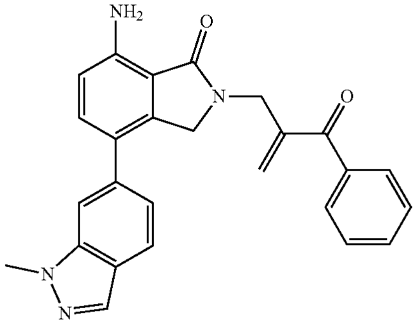 [SMILES: C=C(CN1Cc2c(-c3ccc4cnn(C)c4c3)ccc(N)c2C1=O)C(=O)c1ccccc1] | 7-amino-4-(1-methyl-1H-indazol-6-yl)-2-(2-methylidene-3-oxo-3-phenylpropyl)-2,3-dihydro-1H-isoindol-1-one | 422.5 |
| 1088. | 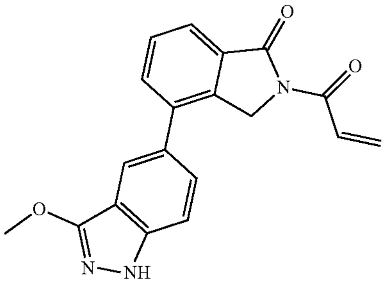 [SMILES: C=CC(=O)N1Cc2c(cccc2-c2ccc3[nH]nc(OC)c3c2)C1=O] | 4-(3-methoxy-1H-indazol-5-yl)-2-(prop-2-enoyl)-2,3-dihydro-1H-isoindol-1-one | 333.3 |

TABLE 15-continued
| Cpd. No. | Structure | IUPAC | MW (g/mol) |
|---|---|---|---|
| 1089. | 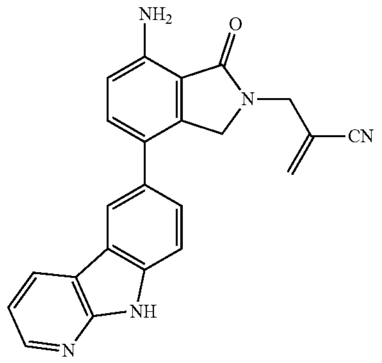 [SMILES: C=C(C#N)CN1Cc2c(-c3ccc4[nH]c5ncccc5c4c3)ccc(N)c2C1=O] | 2-[7-amino-1-oxo-4-{9H-pyrido[2,3-b]indol-6-yl}-2,3-dihydro-1H-isoindol-2-yl)methyl)prop-2-enenitrile | 379.4 |
| 1090. | 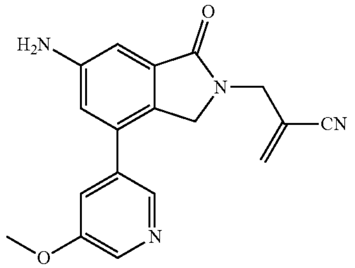 [SMILES: C=C(C#N)CN1Cc2c(cc(N)cc2-c2cncc(OC)c2)C1=O] | 2-{[6-amino-4-(5-methoxypyridin-3-yl)-1-oxo-2,3-dihydro-1H-isoindol-2-yl]methyl}prop-2-enenitrile | 320.4 |
| 1091. | 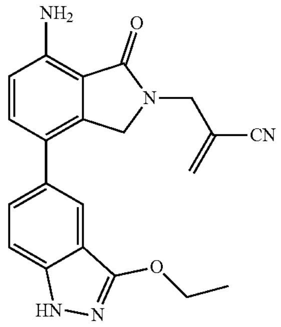 [SMILES: C=C(C#N)CN1Cc2c(-c3ccc4[nH]nc(OCC)c4c3)ccc(N)c2C1=O] | 2-{[7-amino-4-(3-ethoxy-1H-indazol-5-yl)-1-oxo-2,3-dihydro-1H-isoindol-2-yl]methyl}prop-2-enenitrile | 373.4 |
| 1092. | 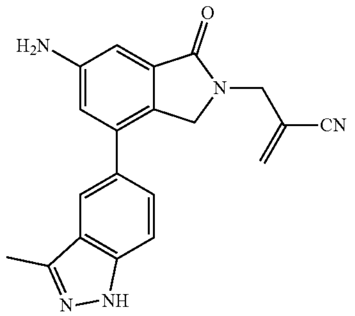 [SMILES: C=C(C#N)CN1Cc2c(cc(N)cc2-c2ccc3[nH]nc(C)c3c2)C1=O] | 2-{[6-amino-4-(3-methyl-1H-indazol-5-yl)-1-oxo-2,3-dihydro-1H-isoindol-2-yl]methyl}prop-2-enenitrile | 343.4 |

TABLE 15-continued

| Cpd. No. | Structure | IUPAC | MW (g/mol) |
|---|---|---|---|
| 1093. | 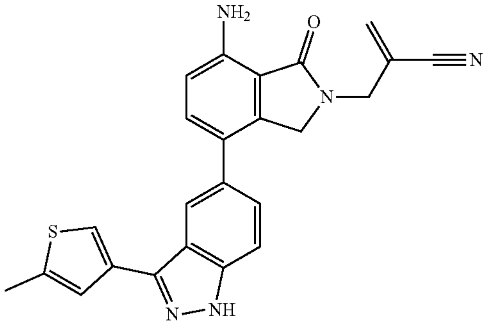 [SMILES: C=C(C#N)CN1Cc2c(-c3ccc4[nH]nc(-c5csc(C)c5)c4c3)ccc(N)c2C1=O] | 2-({7-amino-4-[3-(5-methylthiophen-3-yl)-1H-indazol-5-yl]-1-oxo-2,3-dihydro-1H-isoindol-2-yl}methyl)prop-2-enenitrile | 425.5 |
| 1094. | 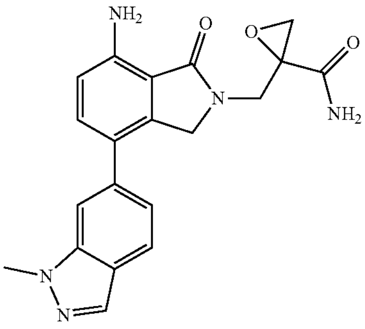 [SMILES: Cn1ncc2ccc(-c3ccc(N)c4c3CN(CC3(C(N)=O)CO3)C4=O)cc21] | 2-{[7-amino-4-(1-methyl-1H-indazol-6-yl)-1-oxo-2,3-dihydro-1H-isoindol-2-yl]methyl}oxirane-2-carboxamide | 377.4 |
| 1095. | 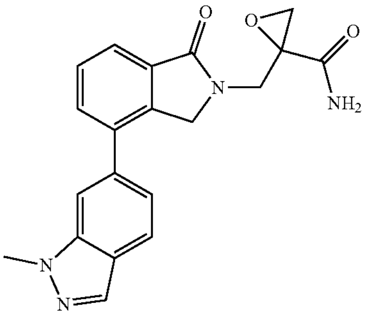 [SMILES: Cn1ncc2ccc(-c3cccc4c3CN(CC3(C(N)=O)CO3)C4=O)cc21] | 2-{[4-(1-methyl-1H-indazol-6-yl)-1-oxo-2,3-dihydro-1H-isoindol-2-yl]methyl}oxirane-2-carboxamide | 362.4 |
| 1096. | 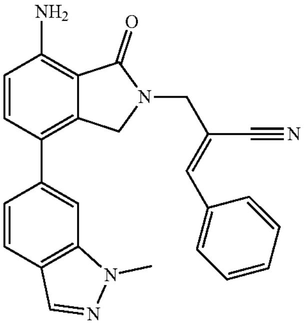 [SMILES: Cn1ncc2ccc(-c3ccc(N)c4c3CN(C/C(C#N)=C/c3ccccc3)C4=O)cc21] | (2Z)-2-{[7-amino-4-(1-methyl-1H-indazol-6-yl)-1-oxo-2,3-dihydro-1H-isoindol-2-yl]methyl}-3-phenylprop-2-enenitrile | 419.5 |

TABLE 15-continued
| Cpd. No. | Structure | IUPAC | MW (g/mol) |
|---|---|---|---|
| 1097. | 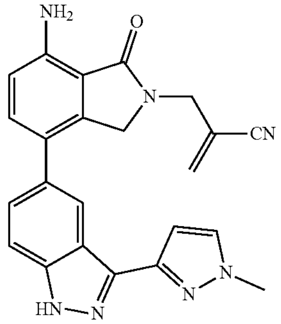 [SMILES: C=C(C#N)CN1Cc2c(-c3ccc4[nH]nc(-c5ccn(C)n5)c4c3)ccc(N)c2C1=O] | 2-({7-amino-4-[3-(1-methyl-1H-pyrazol-3-yl)-1H-indazol-5-yl]-1-oxo-2,3-dihydro-1H-isoindol-2-yl}methyl)prop-2-enenitrile | 409.5 |
| 1098. | 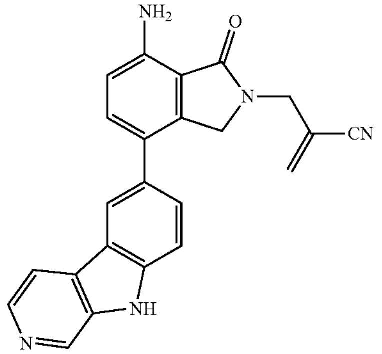 [SMILES: C=C(C#N)CN1Cc2c(-c3ccc4[nH]c5cnccc5c4c3)ccc(N)c2C1=O] | 2-[(7-amino-1-oxo-4-{9H-pyrido[3,4-b]indol-6-yl}-2,3-dihydro-1H-isoindol-2-yl)methyl]prop-2-enenitrile | 379.4 |
| 1099. | 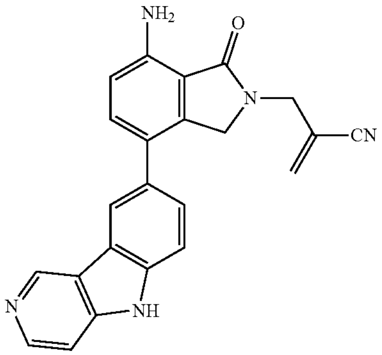 [SMILES: C=C(C#N)CN1Cc2c(-c3ccc4[nH]c5ccncc5c4c3)ccc(N)c2C1=O] | 2-[(7-amino-1-oxo-4-{5H-pyrido[4,3-b]indol-8-yl}-2,3-dihydro-1H-isoindol-2-yl)methyl]prop-2-enenitrile | 379.4 |
| 1100. | 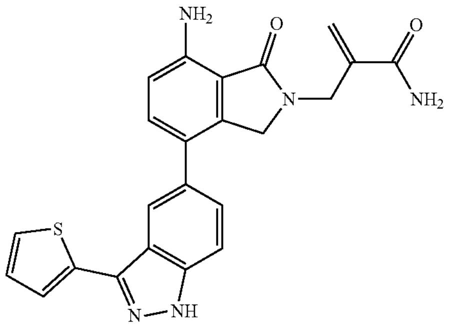 [SMILES: C=C(CN1Cc2c(-c3ccc4[nH]nc(-c5cccs5)c4c3)ccc(N)c2C1=O)C(N)=O] | 2-({7-amino-1-oxo-4-[3-(thiophen-2-yl)-1H-indazol-5-yl]-2,3-dihydro-1H-isoindol-2-yl}methyl)prop-2-enamide | 429.5 |

TABLE 15-continued

| Cpd. No. | Structure | IUPAC | MW (g/mol) |
|---|---|---|---|
| 1101. | 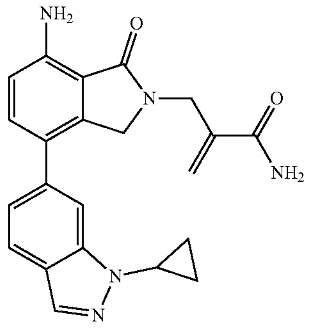 [SMILES: C=C(CN1Cc2c(-c3ccc4cnn(C5CC5)c4c3)ccc(N)c2C1=O)C(N)=O] | 2-{[7-amino-4-(1-cyclopropyl-1H-indazol-6-yl)-1-oxo-2,3-dihydro-1H-isoindol-2-yl]methy}prop-2-enamide | 387.4 |
| 1102. | 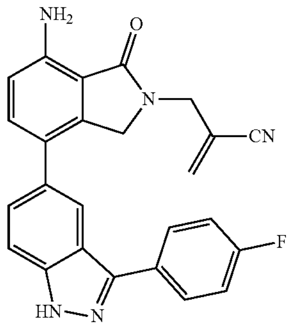 [SMILES: C=C(C#N)CN1Cc2c(-c3ccc4[nH]nc(-c5ccc(F)cc5)c4c3)ccc(N)c2C1=O] | 2-({7-amino-4-[3-(4-fluorophenyl)-1H-indazol-5-yl]-1-oxo-2,3-dihydro-1H-isoindol-2-yl}methyl)prop-2-enenitrile | 423.5 |
| 1103. | 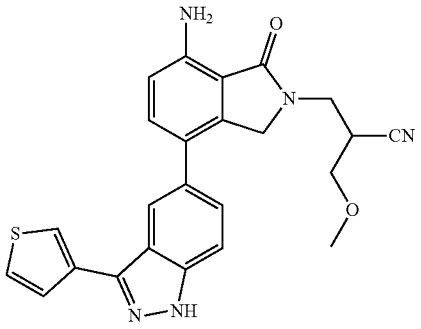 [SMILES: COCC(C#N)CN1Cc2c(-c3ccc4[nH]nc(-c5ccsc5)c4c3)ccc(N)c2C1=O] | 2-({7-amino-1-oxo-4-[3-(thiophen-3-yl)-1H-indazol-5-yl]-2,3-dihydro-1H-isoindol-2-yl}methyl)-3-methoxypropanenitrile | 443.5 |
| 1104. | 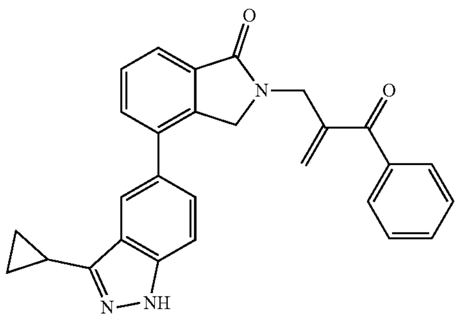 [SMILES: C=C(CN1Cc2c(cccc2-c2ccc3[nH]nc(C4CC4)c3c2)C1=O)C(=O)c1ccccc1] | 4-(3-cyclopropyl-1H-indazol-5-yl)-2-(2-methylidene-3-oxo-3-phenylpropyl)-2,3-dihydro-1H-isoindol-1-one | 433.5 |

TABLE 15-continued

| Cpd. No. | Structure | IUPAC | MW (g/mol) |
|---|---|---|---|
| 1105. | 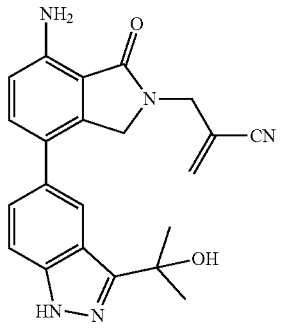 [SMILES: C=C(C#N)CN1Cc2c(-c3ccc4[nH]nc(C(C)(C)O)c4c3)ccc(N)c2C1=O] | 2-({7-amino-4-[3-(2-hydroxypropan-2-yl)-1H-indazol-5-yl]-1-oxo-2,3-dihydro-1H-isoindol-2-yl}methyl)prop-2-enenitrile | 387.4 |
| 1106. | 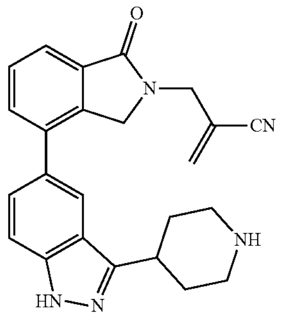 [SMILES: C=C(C#N)CN1Cc2c(cccc2-c2ccc3[nH]nc(C4CCNCC4)c3c2)C1=O] | 2-({1-oxo-4-[3-(piperidin-4-yl)-1H-indazol-5-yl]-2,3-dihydro-1H-isoindol-2-yl}methyl)prop-2-enenitrile | 397.5 |
| 1107. | 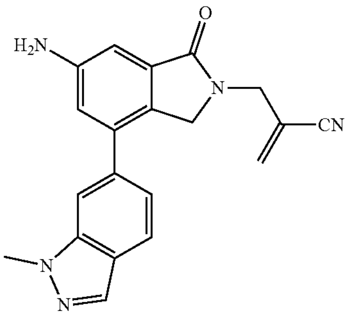 [SMILES: C=C(C#N)CN1Cc2c(cc(N)cc2-c2ccc3cnn(C)c3c2)C1=O] | 2-{[6-amino-4-(1-methyl-1H-indazol-6-yl)-1-oxo-2,3-dihydro-1H-isoindol-2-yl]methyl}prop-2-enenitrile | 343.4 |
| 1108. | 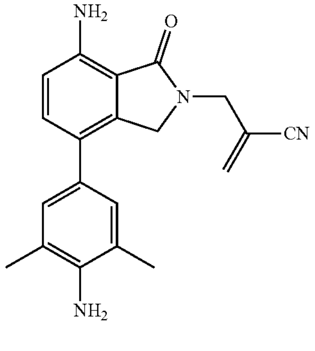 [SMILES: C=C(C#N)CN1Cc2c(-c3cc(C)c(N)c(C)c3)ccc(N)c2C1=O] | 2-{[7-amino-4-(4-amino-3,5-dimethylphenyl)-1-oxo-2,3-dihydro-1H-isoindol-2-yl]methyl}prop-2-enenitrile | 332.4 |

TABLE 15-continued

| Cpd. No. | Structure | IUPAC | MW (g/mol) |
|---|---|---|---|
| 1109. | 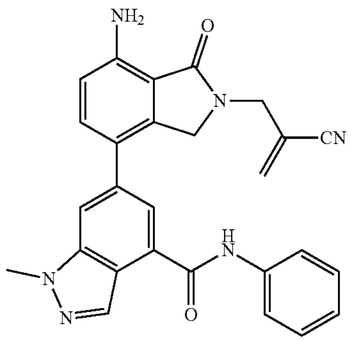 [SMILES: C=C(C#N)CN1Cc2c(-c3cc(C(=O)Nc4ccccc4)c4cnn(C)c4c3)ccc(N)c2C1=O] | 6-[7-amino-2-(2-cyano-2-methylideneethyl)-1-oxo-2,3-dihydro-1H-isoindol-4-yl]-1-methyl-N-phenyl-1H-indazole-4-carboxamide | 462.5 |
| 1110. | 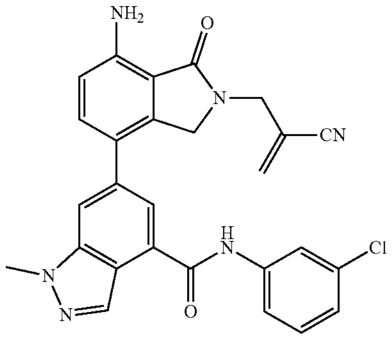 [SMILES: C=C(C#N)CN1Cc2c(-c3cc(C(=O)Nc4cccc(Cl)c4)c4cnn(C)c4c3)ccc(N)c2C1=O] | 6-[7-amino-2-(2-cyano-2-methylideneethyl)-1-oxo-2,3-dihydro-1H-isoindol-4-yl]-N-(3-chlorophenyl)-1-methyl-1H-indazole-4-carboxamide | 497.0 |
| 1111. | 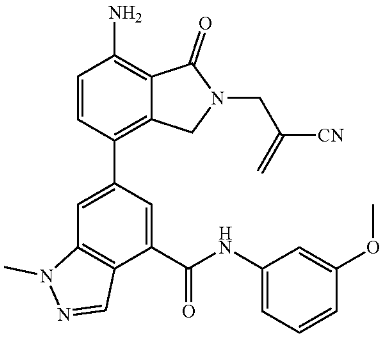 | 6-[7-amino-2-(2-cyano-2-methylideneethyl)-1-oxo-2,3-dihydro-1H-isoindol-4-yl]-N-(3-methoxyphenyl)-1-methyl-1H-indazole-4-carboxamide | 492.5 |
| 1112. | 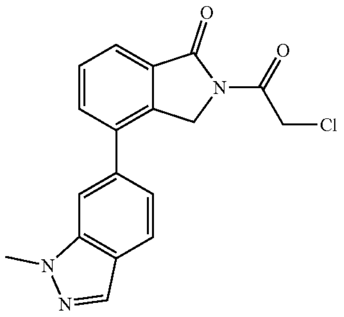 [SMILES: Cn1ncc2ccc(-c3cccc4c3CN(C(=O)CCl)C4=O)cc21] | 2-(2-chloroacetyl)-4-(1-methyl-1H-indazol-6-yl)-2,3-dihydro-1H-isoindol-1-one | 339.8 |

TABLE 15-continued

| Cpd. No. | Structure | IUPAC | MW (g/mol) |
|---|---|---|---|
| 1113. | 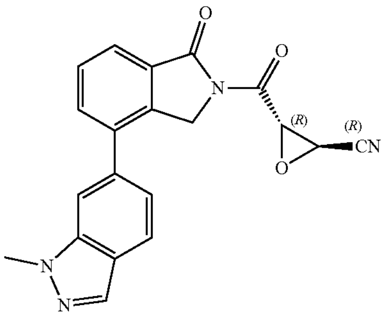 | (2R,3R)-3-{[4-(1-methyl-1H-indazol-6-yl)-1-oxo-2,3-dihydro-1H-isoindol-2-yl]methyl}oxirane-2-carbonitrile | 344.4 |
| 1114. | 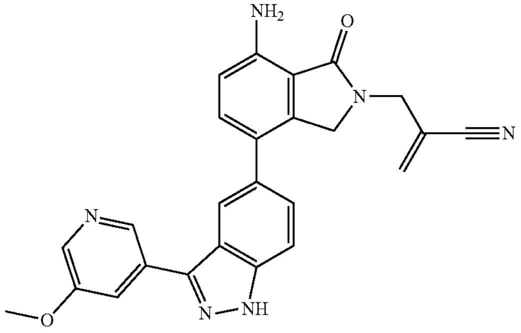 [SMILES: C=C(C#N)CN1Cc2c(-c3ccc4[nH]nc(-c5cncc(OC)c5)c4c3)ccc(N)c2C1=O] | 2-({7-amino-4-[3-(5-methoxypyridin-3-yl)-1H-indazol-5-yl]-1-oxo-2,3-dihydro-1H-isoindol-2-yl}methyl)prop-2-enenitrile | 436.5 |
| 1115. | 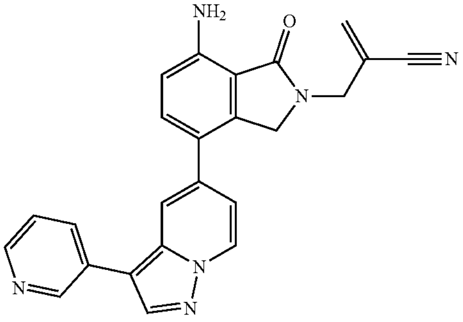 | 2-({7-amino-1-oxo-4-[3-(pyridin-3-yl)pyrazolo[1,5-a]pyridin-5-yl]-2,3-dihydro-1H-isoindol-2-yl}methyl)prop-2-enenitrile | 406.4 |
| 1116. | 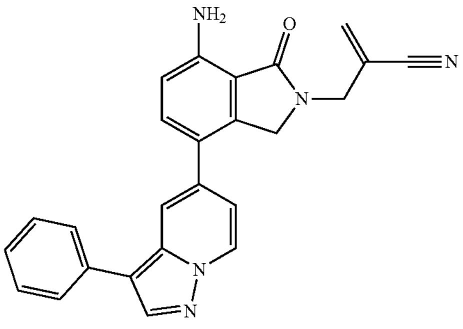 [SMILES: C=C(C#N)CN1Cc2c(-c3ccn4ncc(-c5ccccc5)c4c3)ccc(N)c2C1=O] | 2-[(7-amino-1-oxo-4-{3-phenylpyrazolo[1,5-a]pyridin-5-yl}-2,3-dihydro-1H-isoindol-2-yl)methyl]prop-2-enenitrile | 405.5 |

TABLE 15-continued

| Cpd. No. | Structure | IUPAC | MW (g/mol) |
|---|---|---|---|
| 1117. | 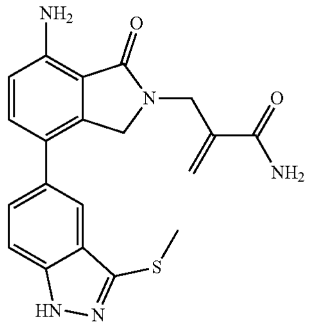 [SMILES: C=C(CN1Cc2c(-c3ccc4[nH]nc(SC)c4c3)ccc(N)c2C1=O)C(N)=O] | 2-({4-[3-(methylsulfanyl)-1H-indazol-5-yl]-1-oxo-2,3-dihydro-1H-isoindol-2-yl}methyl)prop-2-enamide | 378.5 |
| 1118. | 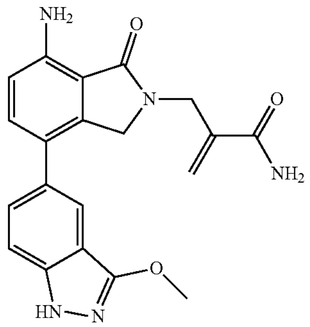 [SMILES: C=C(CN1Cc2c(-c3ccc4[nH]nc(OC)c4c3)ccc(N)c2C1=O)C(N)=O] | 2-{[7-amino-4-(3-methoxy-1H-indazol-5-yl)-1-oxo-2,3-dihydro-1H-isoindol-2-yl]methyl}prop-2-enamide | 377.4 |
| 1119. | 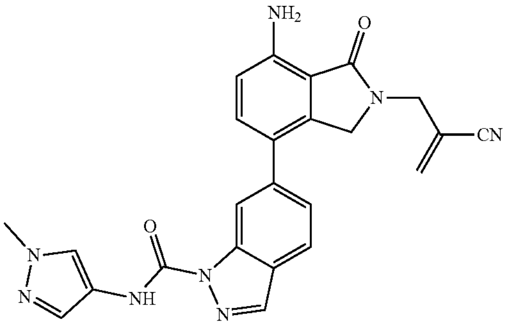 [SMILES: C=C(C#N)CN1Cc2c(-c3ccc4cnn(C(=O)Nc5cnn(C)c5)c4c3)ccc(N)c2C1=O] | 5-[7-amino-2-(2-cyano-2-methylideneethyl)-1-oxo-2,3-dihydro-1H-isoindol-4-yl]-N-(1-methyl-1H-pyrazol-4-yl)-1H-indazole-3-carboxamide | 452.5 |
| 1120. | 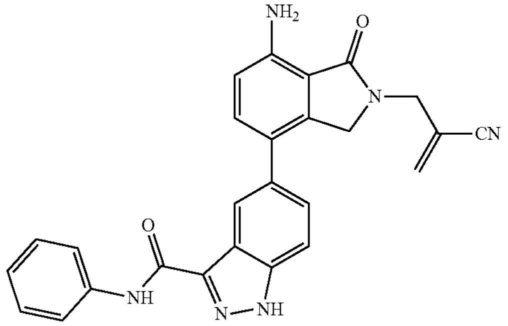 [SMILES: C=C(C#N)CN1Cc2c(-c3ccc4[nH]nc(C(=O)Nc5ccccc5)c4c3)ccc(N)c2C1=O] | 5-[7-amino-2-(2-cyano-2-methylideneethyl)-1-oxo-2,3-dihydro-1H-isoindol-4-yl]-N-phenyl-1H-indazole-3-carboxamide | 448.5 |

TABLE 15-continued

| Cpd. No. | Structure | IUPAC | MW (g/mol) |
|---|---|---|---|
| 1121. | 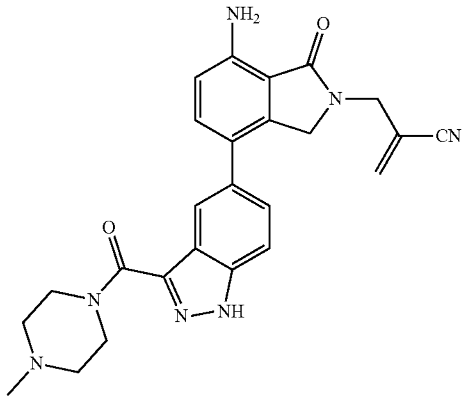 [SMILES: C=C(C#N)CN1Cc2c(-c3ccc4[nH]nc(C(=O)N5CCN(C)CC5)c4c3)ccc(N)c2C1=O] | 2-({7-amino-4-[3-(4-methylpiperazine-1-carbonyl)-1H-indazol-5-yl]-1-oxo-2,3-dihydro-1H-isoindol-2-yl}methyl)prop-2-enenitrile | 455.5 |
| 1122. | 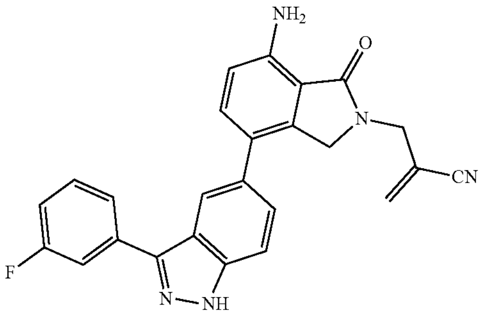 [SMILES: C=C(C#N)CN1Cc2c(-c3ccc4[nH]nc(-c5cccc(F)c5)c4c3)ccc(N)c2C1=O] | 2-({7-amino-4-[3-(3-fluorophenyl)-1H-indazol-5-yl]-1-oxo-2,3-dihydro-1H-isoindol-2-yl}methyl)prop-2-enenitrile | 423.5 |
| 1123. | 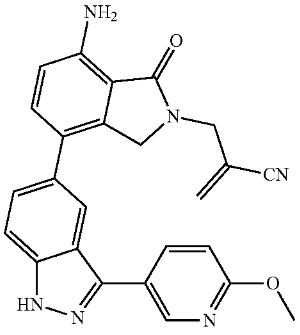 [SMILES: C=C(C#N)CN1Cc2c(-c3ccc4[nH]nc(-c5ccc(OC)nc5)c4c3)ccc(N)c2C1=O] | 2-({7-amino-4-[3-(6-methoxypyridin-3-yl)-1H-indazol-5-yl]-1-oxo-2,3-dihydro-1H-isoindol-2-yl}methyl)prop-2-enenitrile | 436.5 |
| 1124. | 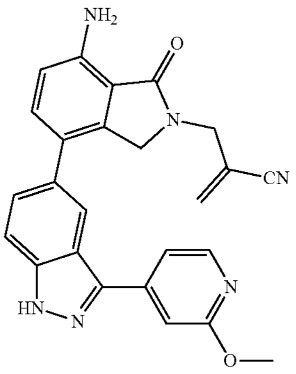 [SMILES: C=C(C#N)CN1Cc2c(-c3ccc4[nH]nc(-c5ccnc(OC)c5)c4c3)ccc(N)c2C1=O] | 2-({7-amino-4-[3-(2-methoxypyridin-4-yl)-1H-indazol-5-yl]-1-oxo-2,3-dihydro-1H-isoindol-2-yl}methyl)prop-2-enenitrile | 436.5 |

TABLE 15-continued
| Cpd. No. | Structure | IUPAC | MW (g/mol) |
|---|---|---|---|
| 1125. | 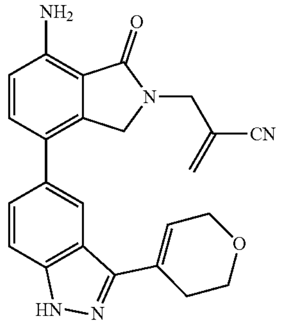 [SMILES: C=C(C#N)CN1Cc2c(-c3ccc4[nH]nc(C5=CCOCC5)c4c3)ccc(N)c2C1=O] | 2-({7-amino-4-[3-(3,6-dihydro-2H-pyran-4-yl)-1H-indazol-5-yl]-1-oxo-2,3-dihydro-1H-isoindol-2-yl}methyl)prop-2-enenitrile | 411.5 |
| 1126. | 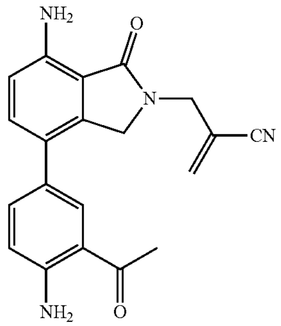 [SMILES: C=C(C#N)CN1Cc2c(-c3ccc(N)c(C(C)=O)c3)ccc(N)c2C1=O] | 2-{[4-(3-acetyl-4-aminophenyl)-7-amino-1-oxo-2,3-dihydro-1H-isoindol-2-yl]methyl}prop-2-enenitrile | 346.4 |
| 1127. | 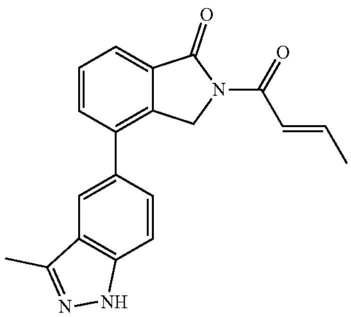 [SMILES: C/C=C/C(=O)N1Cc2c(cccc2-c2ccc3[nH]nc(C)c3c2)C1=O] | 2-[(2E)-but-2-enoyl]-4-(3-methyl-1H-indazol-5-yl)-2,3-dihydro-1H-isoindol-1-one | 331.4 |
| 1128. | 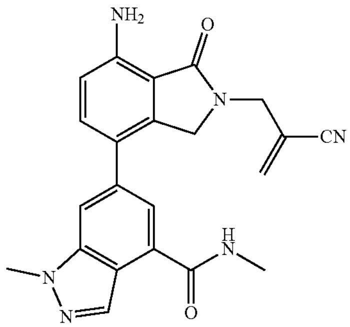 [SMILES: C=C(C#N)CN1Cc2c(-c3cc(C(=O)NC)c4cnn(C)c4c3)ccc(N)c2C1=O] | 6-[7-amino-2-(2-cyano-2-methylideneethyl)-1-oxo-2,3-dihydro-1H-isoindol-4-yl]-N,1-dimethyl-1H-indazole-4-carboxamide | 400.4 |

TABLE 15-continued
| Cpd. No. | Structure | IUPAC | MW (g/mol) |
|---|---|---|---|
| 1129. | 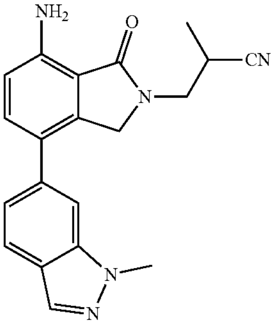 [SMILES: CC(C#N)CN1Cc2c(-c3ccc4cnn(C)c4c3)ccc(N)c2C1=O] | 3-[7-amino-4-(1-methyl-1H-indazol-6-yl)-1-oxo-2,3-dihydro-1H-isoindol-2-yl]-2-methylpropanenitrile | 345.4 |
| 1130. | 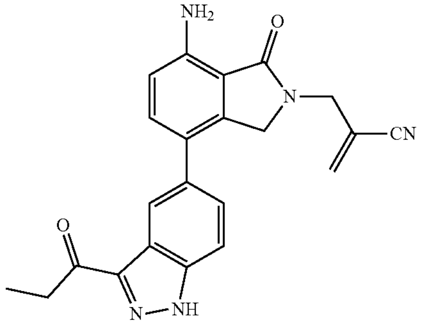 [SMILES: C=C(C#N)CN1Cc2c(-c3ccc4[nH]nc(C(=O)CC)c4c3)ccc(N)c2C1=O] | 2-{[7-amino-1-oxo-4-(3-propanoyl-1H-indazol-5-yl)-2,3-dihydro-1H-isoindol-2-yl]methyl}prop-2-enenitrile | 385.4 |
| 1131. | 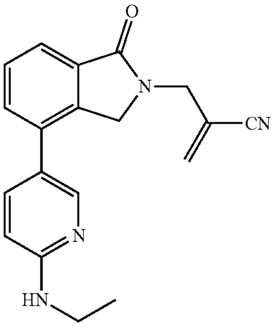 [SMILES: C=C(C#N)CN1Cc2c(cccc2-c2ccc(NCC)nc2)C1=O] | 2-({4-[6-(ethylamino)pyridin-3-yl]-1-oxo-2,3-dihydro-1H-isoindol-2-yl}methyl)prop-2-enenitrile | 318.4 |
| 1132. | 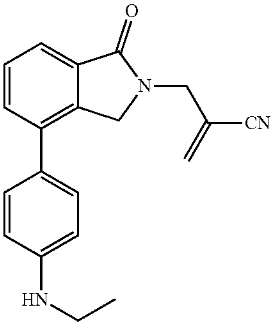 [SMILES: C=C(C#N)CN1Cc2c(cccc2-c2ccc(NCC)cc2)C1=O] | 2-({4-[4-(ethylamino)phenyl]-1-oxo-2,3-dihydro-1H-isoindol-2-yl}methyl)prop-2-enenitrile | 317.4 |

TABLE 15-continued

| Cpd. No. | Structure | IUPAC | MW (g/mol) |
|---|---|---|---|
| 1133. | 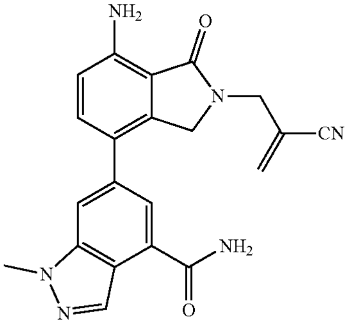 [SMILES: C=C(C#N)CN1Cc2c(-c3cc(C(N)=O)c4cnn(C)c4c3)ccc(N)c2C1=O] | 6-[7-amino-2-(2-cyano-2-methylideneethyl)-1-oxo-2,3-dihydro-1H-isoindol-4-yl]-1-methyl-1H-indazole-4-carboxamide | 386.4 |
| 1134. | 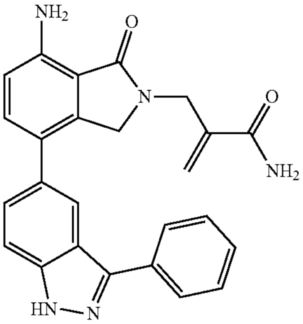 [SMILES: C=C(CN1Cc2c(-c3ccc4[nH]nc(-c5ccccc5)c4c3)ccc(N)c2C1=O)C(N)=O] | 2-{[1-oxo-4-(3-phenyl-1H-indazol-5-yl)-2,3-dihydro-1H-isoindol-2-yl]methyl}prop-2-enamide | 408.5 |
| 1135. | 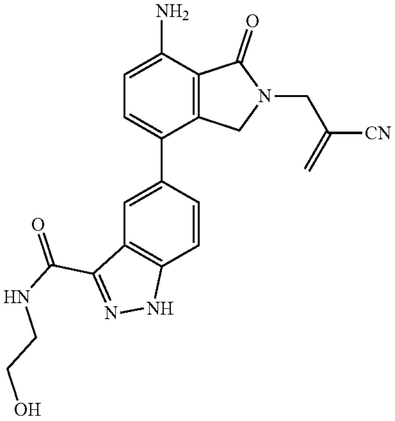 [SMILES: C=C(C#N)CN1Cc2c(-c3ccc4[nH]nc(C(=O)NCCO)c4c3)ccc(N)c2C1=O] | 5-[7-amino-2-(2-cyano-2-methylideneethyl)-1-oxo-2,3-dihydro-1H-isoindol-4-yl]-N-(2-hydroxyethyl)-1H-indazole-3-carboxamide | 416.4 |
| 1136. | 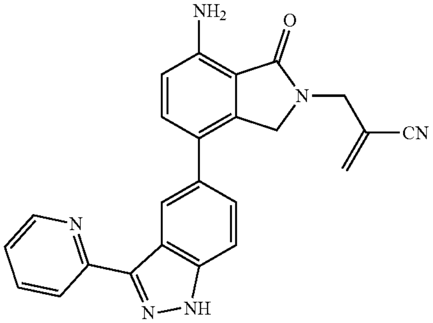 [SMILES: C=C(C#N)CN1Cc2c(-c3ccc4[nH]nc(-c5ccccn5)c4c3)ccc(N)c2C1=O] | 2-({7-amino-1-oxo-4-[3-(pyridin-2-yl)-1H-indazol-5-yl]-2,3-dihydro-1H-isoindol-2-yl}methyl)prop-2-enenitrile | 406.4 |

TABLE 15-continued
| Cpd. No. | Structure | IUPAC | MW (g/mol) |
|---|---|---|---|
| 1137. | 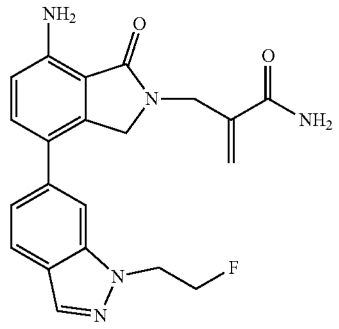 [SMILES: C=C(CN1Cc2c(-c3ccc4cnn(CCF)c4c3)ccc(N)c2C1=O)C(N)=O] | 2-({7-amino-4-[1-(2-fluoroethyl)-1H-indazol-6-yl]-1-oxo-2,3-dihydro-1H-isoindol-2-yl}methyl)prop-2-enamide | 393.4 |
| 1138. | 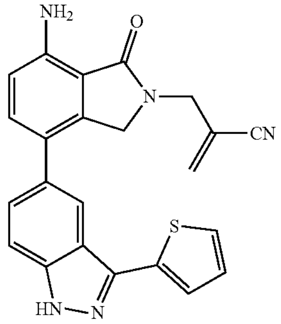 [SMILES: C=C(C#N)CN1Cc2c(-c3ccc4[nH]nc(-c5cccs5)c4c3)ccc(N)c2C1=O] | 2-({7-amino-1-oxo-4-[3-(thiophen-2-yl)-1H-indazol-5-yl]-2,3-dihydro-1H-isoindol-2-yl}methyl)prop-2-enenitrile | 411.5 |
| 1139. | 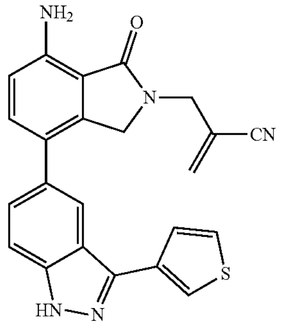 [SMILES: C=C(C#N)CN1Cc2c(-c3ccc4[nH]nc(-c5ccsc5)c4c3)ccc(N)c2C1=O] | 2-({7-amino-1-oxo-4-[3-(thiophen-3-yl)-1H-indazol-5-yl]-2,3-dihydro-1H-isoindol-2-yl}methyl)prop-2-enenitrile | 411.5 |
| 1140. | 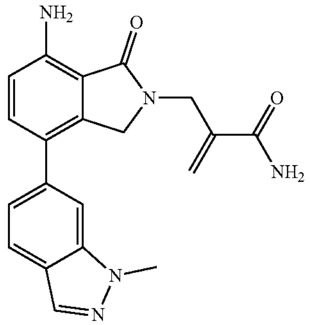 [SMILES: C=C(CN1Cc2c(-c3ccc4cnn(C)c4c3)ccc(N)c2C1=O)C(N)=O] | 2-{[7-amino-4-(1-methyl-1H-indazol-6-yl)-1-oxo-2,3-dihydro-1H-isoindol-2-yl]methyl}prop-2-enamide | 361.4 |

TABLE 15-continued
| Cpd. No. | Structure | IUPAC | MW (g/mol) |
|---|---|---|---|
| 1141. | 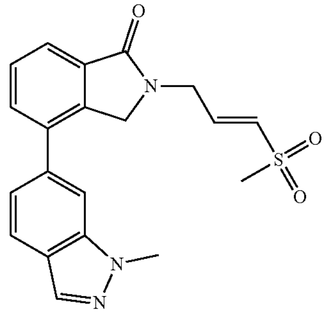 [SMILES: Cn1ncc2ccc(-c3cccc4c3CN(C/C=C/S(C)(=O)=O)C4=O)cc21] | 2-[(2E)-3-methanesulfonylprop-2-en-1-yl]-4-(1-methyl-1H-indazol-6-yl)-2,3-dihydro-1H-isoindol-1-one | 381.5 |
| 1142. | 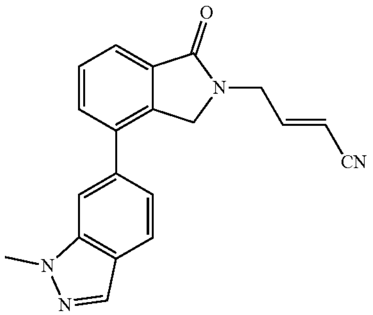 [SMILES: Cn1ncc2ccc(-c3cccc4c3CN(C/C=C/C#N)C4=O)cc21] | (2E)-4-[4-(1-methyl-1H-indazol-6-yl)-1-oxo-2,3-dihydro-1H-isoindol-2-yl]but-2-enenitrile | 328.4 |
| 1143. | 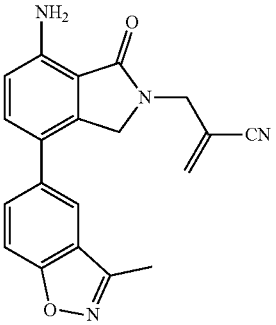 [SMILES: C=C(C#N)CN1Cc2c(-c3ccc4onc(C)c4c3)ccc(N)c2C1=O] | 2-{[7-amino-4-(3-methyl-1,2-benzoxazol-5-yl)-1-oxo-2,3-dihydro-1H-isoindol-2-yl]methyl}prop-2-enenitrile | 344.4 |
| 1144. | 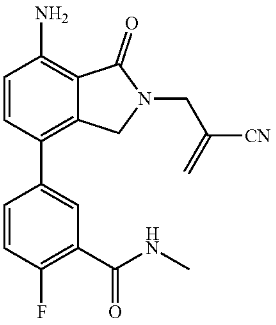 [SMILES: C=C(C#N)CN1Cc2c(-c3ccc(F)c(C(=O)NC)c3)ccc(N)c2C1=O] | 5-[7-amino-2-(2-cyano-2-methylideneethyl)-1-oxo-2,3-dihydro-1H-isoindol-4-yl]-2-fluoro-N-methylbenzamide | 364.4 |

TABLE 15-continued

| Cpd. No. | Structure | IUPAC | MW (g/mol) |
|---|---|---|---|
| 1145. | 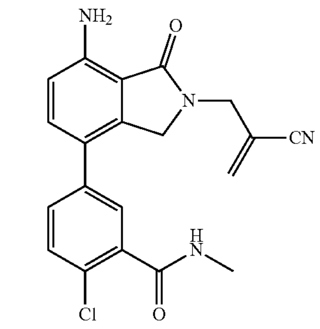 [SMILES: C=C(C#N)CN1Cc2c(-c3ccc(Cl)c(C(=O)NC)c3)ccc(N)c2C1=O] | 5-[7-amino-2-(2-cyano-2-methylideneethyl)-1-oxo-2,3-dihydro-1H-isoindol-4-yl]-2-chloro-N-methylbenzamide | 380.8 |
| 1146. | 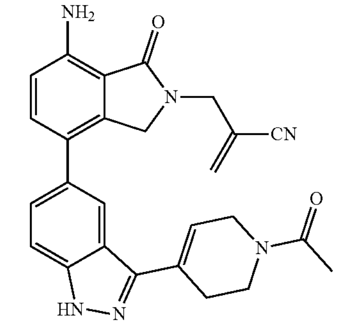 [SMILES: C=C(C#N)CN1Cc2c(-c3ccc4[nH]nc(C5=CCN(C(C)=O)CC5)c4c3)ccc(N)c2C1=O] | 2-({4-[3-(1-acetyl-1,2,3,6-tetrahydropyridin-4-yl)-1H-indazol-5-yl]-7-amino-1-oxo-2,3-dihydro-1H-isoindol-2-yl}methyl)prop-2-enenitrile | 452.5 |
| 1147. | 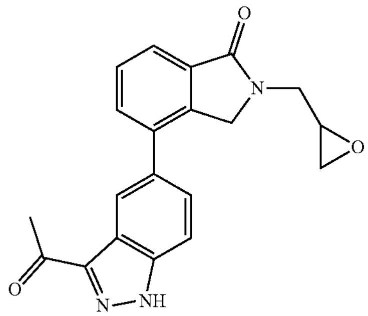 [SMILES: CC(=O)c1n[nH]c2ccc(-c3cccc4c3CN(CC3CO3)C4=O)cc12] | 4-(3-acetyl-1H-indazol-5-yl)-2-[(oxiran-2-yl)methyl]-2,3-dihydro-1H-isoindol-1-one | 347.4 |
| 1148. | 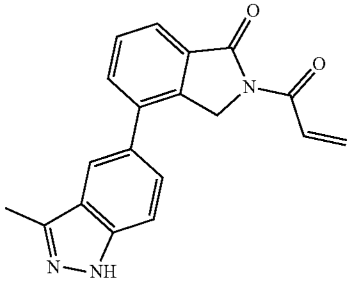 [SMILES: C=CC(=O)N1Cc2c(cccc2-c2ccc3[nH]nc(C)c3c2)C1=O] | 4-(3-methyl-1H-indazol-5-yl)-2-(prop-2-enoyl)-2,3-dihydro-1H-isoindol-1-one | 317.3 |
| 1149. | 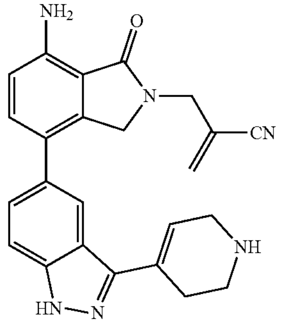 [SMILES: C=C(C#N)CN1Cc2c(-c3ccc4[nH]nc(C5=CCNCC5)c4c3)ccc(N)c2C1=O] | 2-({7-amino-1-oxo-4-[3-(1,2,3,6-tetrahydropyridin-4-yl)-1H-indazol-5-yl]-2,3-dihydro-1H-isoindol-2-yl}methyl)prop-2-enenitrile | 410.5 |

TABLE 15-continued

| Cpd. No. | Structure | IUPAC | MW (g/mol) |
|---|---|---|---|
| 1150. | 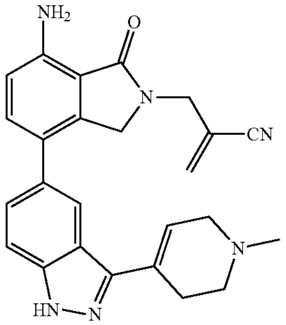 [SMILES: C=C(C#N)CN1Cc2c(-c3ccc4[nH]nc(C5=CCN(C)CC5)c4c3)ccc(N)c2C1=O] | 2-({7-amino-4-[3-(1-methyl-1,2,3,6-tetrahydropyridin-4-yl)-1H-indazol-5-yl]-1-oxo-2,3-dihydro-1H-isoindol-2-yl}methyl)prop-2-enenitrile | 424.5 |
| 1151. | 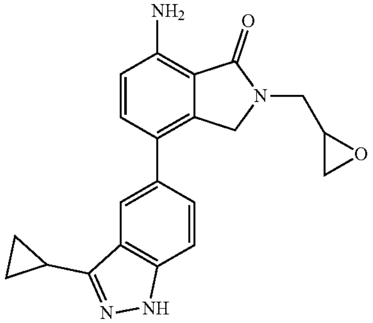 [SMILES: Nc1ccc(-c2ccc3[nH]nc(C4CC4)c3c2)c2c1C(=O)N(CC1CO1)C2] | 7-amino-4-(3-cyclopropyl-1H-indazol-5-yl)-2-[(oxiran-2-yl)methyl]-2,3-dihydro-1H-isoindol-1-one | 360.4 |
| 1152. | 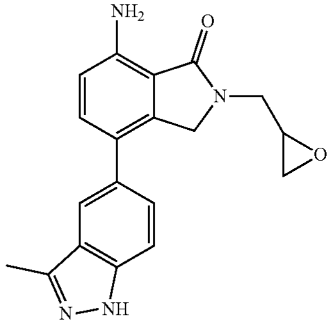 [SMILES: Cc1n[nH]c2ccc(-c3ccc(N)c4c3CN(CC3CO3)C4=O)cc12] | 7-amino-4-(3-methyl-1H-indazol-5-yl)-2-[(oxiran-2-yl)methyl]-2,3-dihydro-1H-isoindol-1-one | 334.4 |
| 1153. | 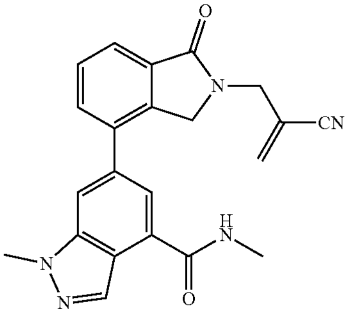 [SMILES: C=C(C#N)CN1Cc2c(cccc2-c2cc(C(=O)NC)c3cnn(C)c3c2)C1=O] | 6-[2-(2-cyano-2-methylideneethyl)-1-oxo-2,3-dihydro-1H-isoindol-4-yl]-N,1-dimethyl-1H-indazole-4-carboxamide | 385.4 |

TABLE 15-continued

| Cpd. No. | Structure | IUPAC | MW (g/mol) |
|---|---|---|---|
| 1154. | 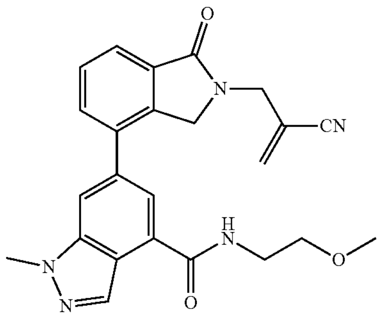 | 6-[2-(2-cyano-2-methylideneethyl)-1-oxo-2,3-dihydro-1H-isoindol-4-yl]-N-(2-methoxyethyl)-1-methyl-1H-indazole-4-carboxamide | 429.5 |
| 1155. | 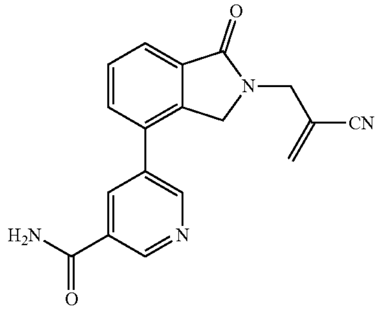 [SMILES: C=C(C#N)CN1Cc2c(cccc2-c2cncc(C(N)=O)c2)C1=O] | 5-[2-(2-cyano-2-methylideneethyl)-1-oxo-2,3-dihydro-1H-isoindol-4-yl]pyridine-3-carboxamide | 318.3 |
| 1156. | 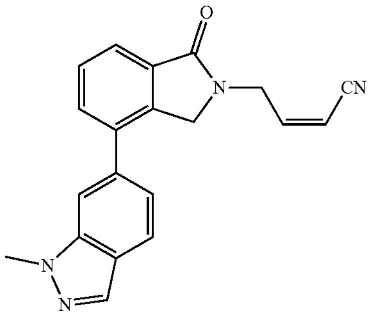 [SMILES: Cn1ncc2ccc(-c3cccc4c3CN(C/C=C\C#N)C4=O)cc21] | (2Z)-4-[4-(1-methyl-1H-indazol-6-yl)-1-oxo-2,3-dihydro-1H-isoindol-2-yl]but-2-enenitrile | 328.4 |
| 1157. | 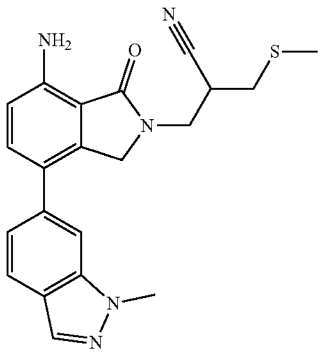 [SMILES: CSCC(C#N)CN1Cc2c(-c3ccc4cnn(C)c4c3)ccc(N)c2C1=O] | 2-{[7-amino-4-(1-methyl-1H-indazol-6-yl)-1-oxo-2,3-dihydro-1H-isoindol-2-yl]methyl}-3-(methylsulfanyl)propanenitrile | 391.5 |

TABLE 15-continued
| Cpd. No. | Structure | IUPAC | MW (g/mol) |
|---|---|---|---|
| 1158. | 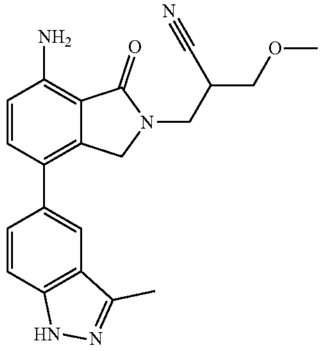 [SMILES: COCC(C#N)CN1Cc2c(-c3ccc4[nH]nc(C)c4c3)ccc(N)c2C1=O] | 2-{[7-amino-4-(3-methyl-1H-indazol-5-yl)-1-oxo-2,3-dihydro-1H-isoindol-2-yl]methyl}-3-methoxypropanenitrile | 375.4 |
| 1159. | 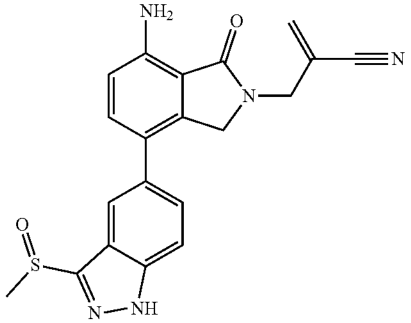 [SMILES: C=C(C#N)CN1Cc2c(-c3ccc4[nH]nc(S(C)=O)c4c3)ccc(N)c2C1=O] | 2-{[7-amino-4-(3-methanesulfinyl-1H-indazol-5-yl)-1-oxo-2,3-dihydro-1H-isoindol-2-yl]methyl}prop-2-enenitrile | 391.5 |
| 1160. | 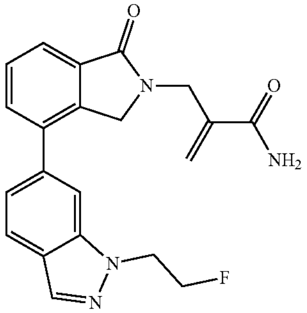 [SMILES: C=C(CN1Cc2c(cccc2-c2ccc3cnn(CCF)c3c2)C1=O)C(N)=O] | 2-({4-[1-(2-fluoroethyl)-1H-indazol-6-yl]-1-oxo-2,3-dihydro-1H-isoindol-2-yl}methyl)prop-2-enamide | 378.4 |
| 1161. | 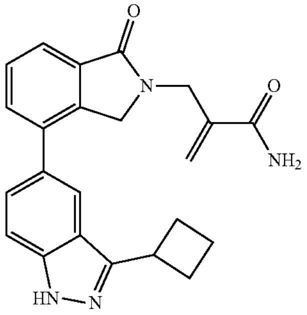 [SMILES: C=C(CN1Cc2c(cccc2-c2ccc3[nH]nc(C4CCC4)c3c2)C1=O)C(N)=O] | 2-{[4-(3-cyclobutyl-1H-indazol-5-yl)-1-oxo-2,3-dihydro-1H-isoindol-2-yl]methyl}prop-2-enamide | 386.5 |

TABLE 15-continued

| Cpd. No. | Structure | IUPAC | MW (g/mol) |
|---|---|---|---|
| 1162. | 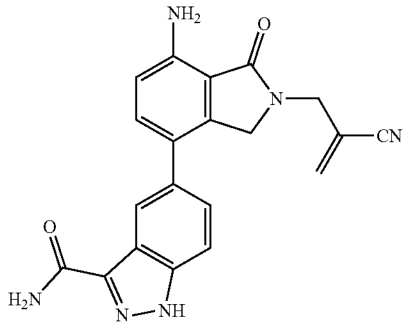 [SMILES: C=C(C#N)CN1Cc2c(-c3ccc4[nH]nc(C(N)=O)c4c3)ccc(N)c2C1=O] | 5-[7-amino-2-(2-cyano-2-methylideneethyl)-1-oxo-2,3-dihydro-1H-isoindol-4-yl]-1H-indazole-3-carboxamide | 372.4 |
| 1163. | 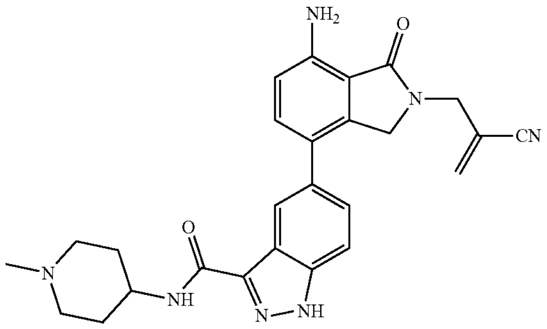 [SMILES: C=C(C#N)CN1Cc2c(-c3ccc4[nH]nc(C(=O)NC5CCN(C)CC5)c4c3)ccc(N)c2C1=O] | 5-[7-amino-2-(2-cyano-2-methylideneethyl)-1-oxo-2,3-dihydro-1H-isoindol-4-yl]-N-(1-methylpiperidin-4-yl)-1H-indazole-3-carboxamide | 469.5 |
| 1164. | 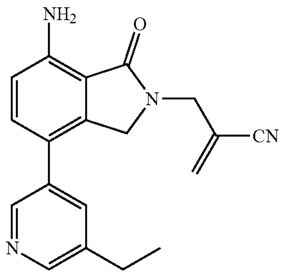 [SMILES: C=C(C#N)CN1Cc2c(-c3cncc(CC)c3)ccc(N)c2C1=O] | 2-{[7-amino-4-(5-ethylpyridin-3-yl)-1-oxo-2,3-dihydro-1H-isoindol-2-yl]methyl}prop-2-enenitrile | 318.4 |
| 1165. | 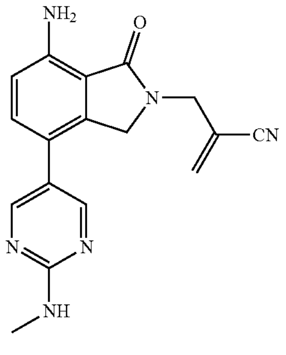 [SMILES: C=C(C#N)CN1Cc2c(-c3cnc(NC)nc3)ccc(N)c2C1=O] | 2-({7-amino-4-[2-(methylamino)pyrimidin-5-yl]-1-oxo-2,3-dihydro-1H-isoindol-2-yl}methyl)prop-2-enenitrile | 320.4 |

TABLE 15-continued

| Cpd. No. | Structure | IUPAC | MW (g/mol) |
|---|---|---|---|
| 1166. | 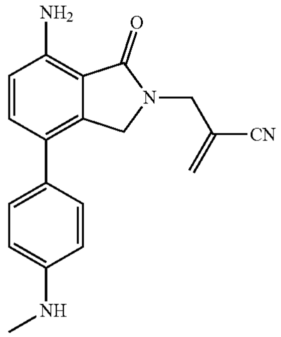 [SMILES: C=C(C#N)CN1Cc2c(-c3ccc(NC)cc3)ccc(N)c2C1=O] | 2-({7-amino-4-[4-(methylamino)phenyl]-1-oxo-2,3-dihydro-1H-isoindol-2-yl}methyl)prop-2-enenitrile | 318.4 |
| 1167. | 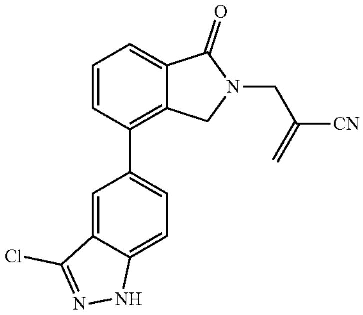 [SMILES: C=C(C#N)CN1Cc2c(cccc2-c2ccc3[nH]nc(Cl)c3c2)C1=O] | 2-{[4-(3-chloro-1H-indazol-5-yl)-1-oxo-2,3-dihydro-1H-isoindol-2-yl]methyl}prop-2-enenitrile | 348.8 |
| 1168. | 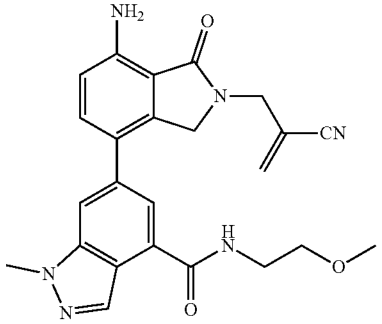 | 6-[7-amino-2-(2-cyano-2-methylideneethyl)-1-oxo-2,3-dihydro-1H-isoindol-4-yl]-N-(2-methoxyethyl)-1-methyl-1H-indazole-4-carboxamide | 444.5 |
| 1169. | 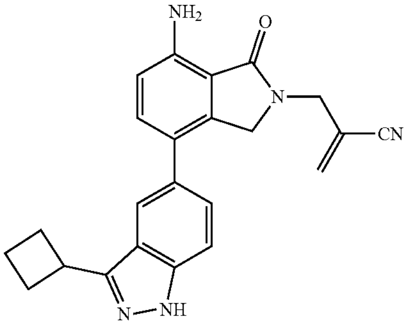 [SMILES: C=C(C#N)CN1Cc2c(-c3ccc4[nH]nc(C5CCC5)c4c3)ccc(N)c2C1=O] | 2-{[7-amino-4-(3-cyclobutyl-1H-indazol-5-yl)-1-oxo-2,3-dihydro-1H-isoindol-2-yl]methyl}prop-2-enenitrile | 383.5 |

TABLE 15-continued
| Cpd. No. | Structure | IUPAC | MW (g/mol) |
|---|---|---|---|
| 1170. | 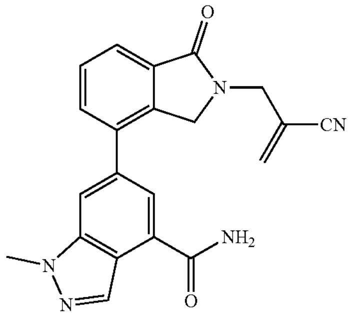 [SMILES: C=C(C#N)CN1Cc2c(cccc2-c2cc(C(N)=O)c3cnn(C)c3c2)C1=O] | 6-[2-(2-cyano-2-methylideneethyl)-1-oxo-2,3-dihydro-1H-isoindol-4-yl]-1-methyl-1H-indazole-4-carboxamide | 371.4 |
| 1171. | 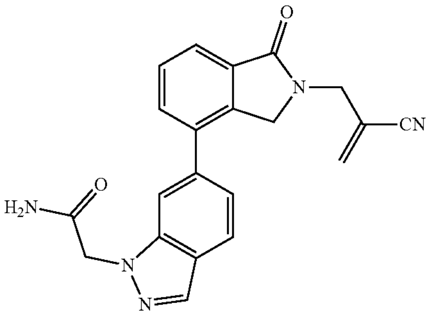 [SMILES: C=C(C#N)CN1Cc2c(cccc2-c2ccc3cnn(CC(N)=O)c3c2)C1=O] | 2-{6-[2-(2-cyano-2-methylideneethyl)-1-oxo-2,3-dihydro-1H-isoindol-4-yl]-1H-indazol-1-yl}acetamide | 371.4 |
| 1172. | 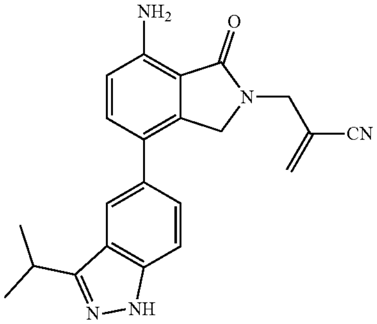 [SMILES: C=C(C#N)CN1Cc2c(-c3ccc4[nH]nc(C(C)C)c4c3)ccc(N)c2C1=O] | 2-({7-amino-1-oxo-4-[3-(propan-2-yl)-1H-indazol-5-yl]-2,3-dihydro-1H-isoindol-2-yl}methyl)prop-2-enenitrile | 371.4 |
| 1173. | 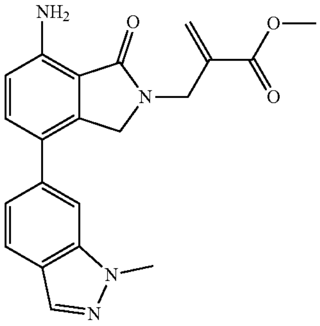 [SMILES: C=C(CN1Cc2c(-c3ccc4cnn(C)c4c3)ccc(N)c2C1=O)C(=O)OC] | methyl 2-{[7-amino-4-(1-methyl-1H-indazol-6-yl)-1-oxo-2,3-dihydro-1H-isoindol-2-yl]methyl}prop-2-enoate | 376.4 |

TABLE 15-continued
| Cpd. No. | Structure | IUPAC | MW (g/mol) |
|---|---|---|---|
| 1174. | 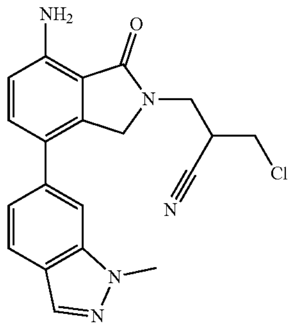 [SMILES: Cn1ncc2ccc(-c3ccc(N)c4c3CN(CC(C#N)CCl)C4=O)cc21] | 2-{[7-amino-4-(1-methyl-1H-indazol-6-yl)-1-oxo-2,3-dihydro-1H-isoindol-2-yl]methyl}-3-chloropropanenitrile | 379.9 |
| 1175. | 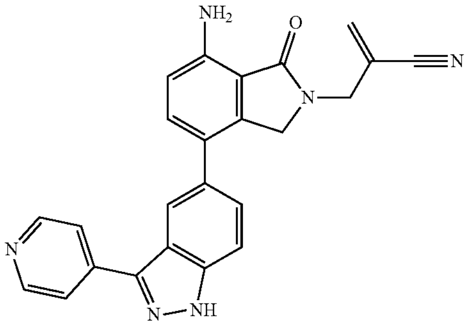 [SMILES: C=C(C#N)CN1Cc2c(-c3ccc4[nH]nc(-c5ccncc5)c4c3)ccc(N)c2C1=O] | 2-({7-amino-1-oxo-4-[3-(pyridin-4-yl)-1H-indazol-5-yl]-2,3-dihydro-1H-isoindol-2-yl}methyl)prop-2-enenitrile | 406.4 |
| 1176. | 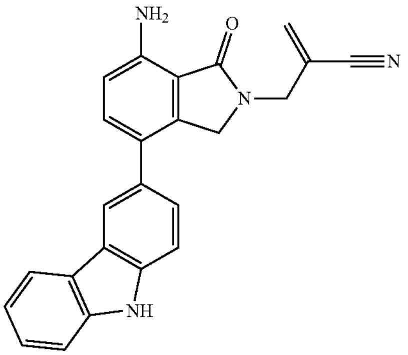 [SMILES: C=C(C#N)CN1Cc2c(-c3ccc4[nH]c5ccccc5c4c3)ccc(N)c2C1=O] | 2-{[7-amino-4-(9H-carbazol-3-yl)-1-oxo-2,3-dihydro-1H-isoindol-2-yl]methyl}prop-2-enenitrile | 378.4 |
| 1177. | 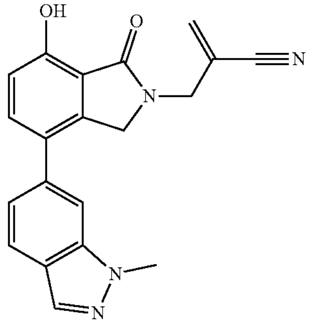 [SMILES: C=C(C#N)CN1Cc2c(-c3ccc4cnn(C)c4c3)ccc(O)c2C1=O] | 2-{[7-hydroxy-4-(1-methyl-1H-indazol-6-yl)-1-oxo-2,3-dihydro-1H-isoindol-2-yl]methyl}prop-2-enenitrile | 344.4 |

TABLE 15-continued

| Cpd. No. | Structure | IUPAC | MW (g/mol) |
|---|---|---|---|
| 1178. | 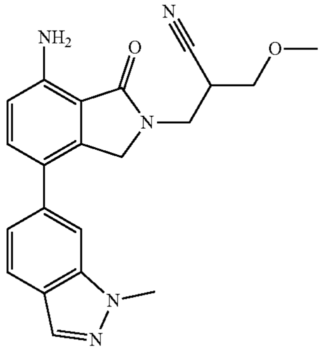 [SMILES: COCC(C#N)CN1Cc2c(-c3ccc4cnn(C)c4c3)ccc(N)c2C1=O] | 2-{[7-amino-4-(1-methyl-1H-indazol-6-yl)-1-oxo-2,3-dihydro-1H-isoindol-2-yl]methyl}-3-methoxypropanenitrile | 375.4 |
| 1179. | 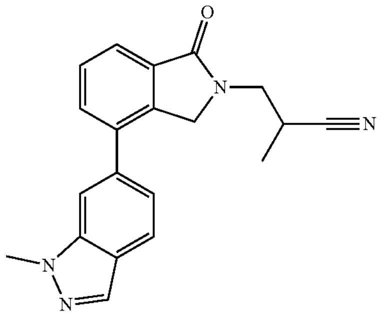 [SMILES: CC(C#N)CN1Cc2c(cccc2-c2ccc3cnn(C)c3c2)C1=O] | 2-methyl-3-[4-(1-methyl-1H-indazol-6-yl)-1-oxo-2,3-dihydro-1H-isoindol-2-yl]propanenitrile | 330.4 |
| 1180. | 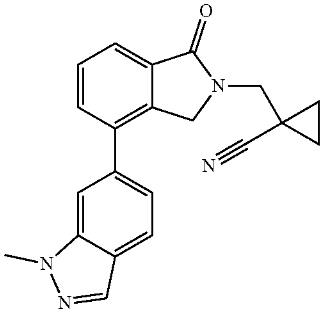 [SMILES: Cn1ncc2ccc(-c3cccc4c3CN(CC3(C#N)CC3)C4=O)cc21] | 1-{[4-(1-methyl-1H-indazol-6-yl)-1-oxo-2,3-dihydro-1H-isoindol-2-yl]methyl}cyclopropane-1-carbonitrile | 342.4 |
| 1181. | 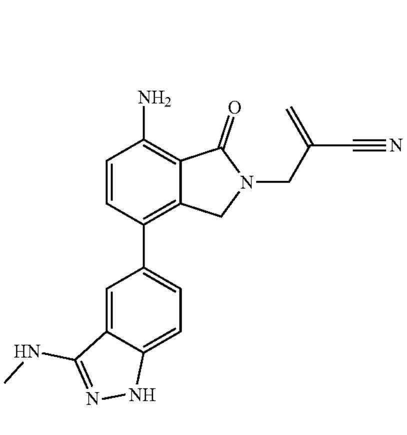 [SMILES: C=C(C#N)CN1Cc2c(-c3ccc4[nH]nc(NC)c4c3)ccc(N)c2C1=O] | 2-({7-amino-4-[3-(methylamino)-1H-indazol-5-yl]-1-oxo-2,3-dihydro-1H-isoindol-2-yl}methyl)prop-2-enenitrile | 358.4 |

TABLE 15-continued

| Cpd. No. | Structure | IUPAC | MW (g/mol) |
| --- | --- | --- | --- |
| 1182. | 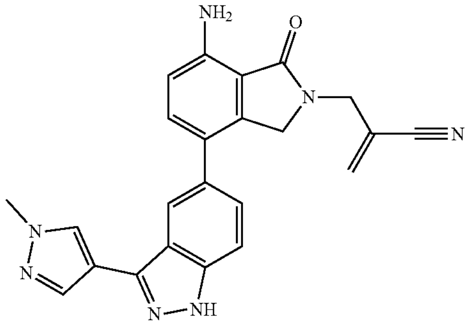 [SMILES: C=C(C#N)CN1Cc2c(-c3ccc4[nH]nc(-c5cnn(C)c5)c4c3)ccc(N)c2C1=O] | 2-({7-amino-4-[3-(1-methyl-1-pyrazol-4-yl)-1H-indazol-5-yl]-1-oxo-2,3-dihydro-1H-isoindol-2-yl}methyl)prop-2-enenitrile | 409.5 |
| 1183. | 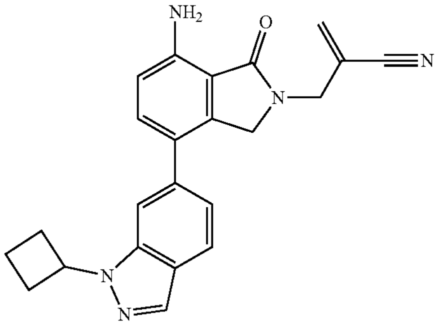 [SMILES: C=C(C#N)CN1Cc2c(-c3ccc4cnn(C5CCC5)c4c3)ccc(N)c2C1=O] | 2-{[7-amino-4-(1-cyclobutyl-1H-indazol-6-yl)-1-oxo-2,3-dihydro-1H-isoindol-2-yl]methyl}prop-2-enenitrile | 383.5 |
| 1184. | 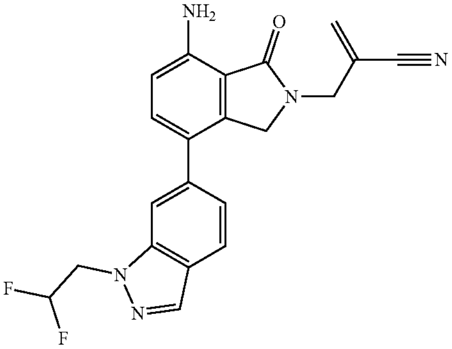 [SMILES: C=C(C#N)CN1Cc2c(-c3ccc4cnn(CC(F)F)c4c3)ccc(N)c2C1=O] | 2-({7-amino-4-[1-(2,2-difluoroethyl)-1H-indazol-6-yl]-1-oxo-2,3-dihydro-1H-isoindol-2-yl}methyl)prop-2-enenitrile | 393.4 |
| 1185. | 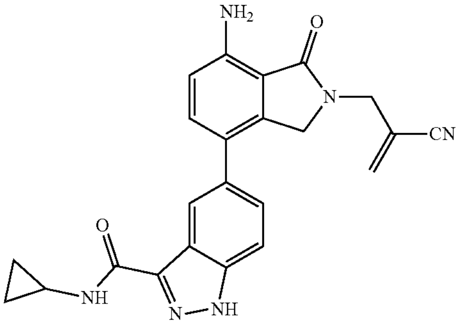 [SMILES: C=C(C#N)CN1Cc2c(-c3ccc4[nH]nc(C(=O)NC5CC5)c4c3)ccc(N)c2C1=O] | 5-[7-amino-2-(2-cyano-2-methylideneethyl)-1-oxo-2,3-dihydro-1H-isoindol-4-yl]-N-cyclopropyl-1H-indazole-3-carboxamide | 412.5 |

TABLE 15-continued

| Cpd. No. | Structure | IUPAC | MW (g/mol) |
|---|---|---|---|
| 1186. | 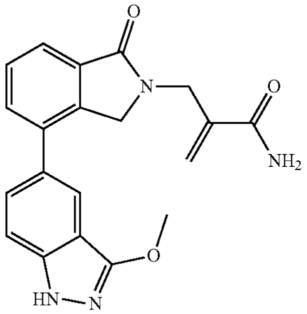 [SMILES: C=C(CN1Cc2c(cccc2-c2ccc3[nH]nc(OC)c3c2)C1=O)C(N)=O] | 2-{[4-(3-methoxy-1H-indazol-5-yl)-1-oxo-2,3-dihydro-1H-isoindol-2-yl]methyl}prop-2-enamide | 362.4 |
| 1187. | 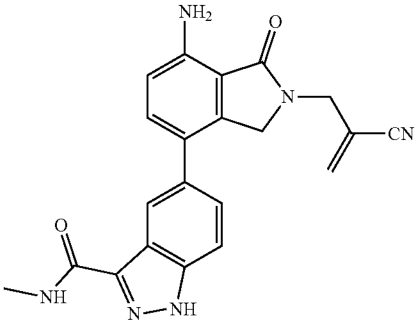 [SMILES: C=C(C#N)CN1Cc2c(-c3ccc4[nH]nc(C(=O)NC)c4c3)ccc(N)c2C1=O] | 5-[7-amino-2-(2-cyano-2-methylideneethyl)-1-oxo-2,3-dihydro-1H-isoindol-4-yl]-N-methyl-1H-indazole-3-carboxamide | 386.4 |
| 1188. | 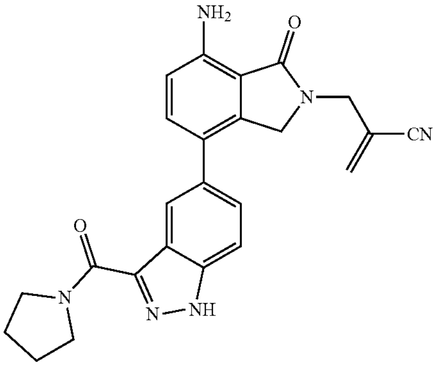 [SMILES: C=C(C#N)CN1Cc2c(-c3ccc4[nH]nc(C(=O)N5CCCC5)c4c3)ccc(N)c2C1=O] | 2-({7-amino-1-oxo-4-[3-(pyrrolidine-1-carbonyl)-1H-indazol-5-yl]-2,3-dihydro-1H-isoindol-2-yl}methyl)prop-2-enenitrile | 426.5 |
| 1189. | 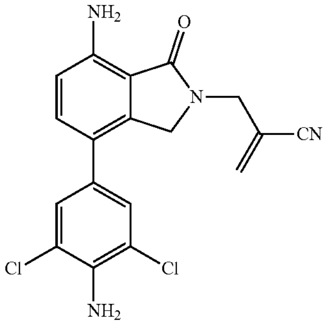 [SMILES: C=C(C#N)CN1Cc2c(-c3cc(Cl)c(N)c(Cl)c3)ccc(N)c2C1=O] | 2-{[7-amino-4-(4-amino-3,5-dichlorophenyl)-1-oxo-2,3-dihydro-1H-isoindol-2-yl]methyl}prop-2-enenitrile | 373.2 |

TABLE 15-continued
| Cpd. No. | Structure | IUPAC | MW (g/mol) |
|---|---|---|---|
| 1190. | 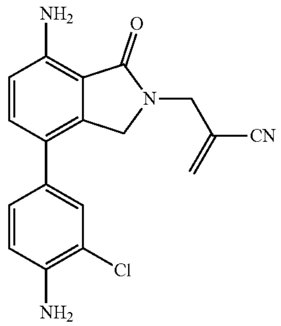 [SMILES: C=C(C#N)CN1Cc2c(-c3ccc(N)c(Cl)c3)ccc(N)c2C1=O] | 2-{[7-amino-4-(4-amino-3-chlorophenyl)-1-oxo-2,3-dihydro-1H-isoindol-2-yl]methyl}prop-2-enenitrile | 338.8 |
| 1191. | 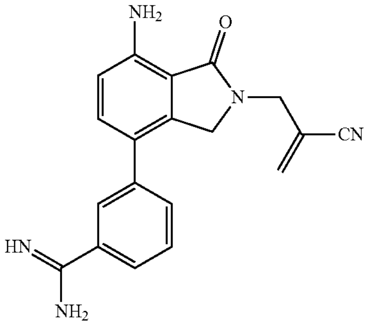 [SMILES: C=C(C#N)CN1Cc2c(-c3cccc(C(=N)N)c3)ccc(N)c2C1=O] | 3-[7-amino-2-(2-cyano-2-methylideneethyl)-1-oxo-2,3-dihydro-1H-isoindol-4-yl]benzene-1-carboximidamide | 331.4 |
| 1192. | 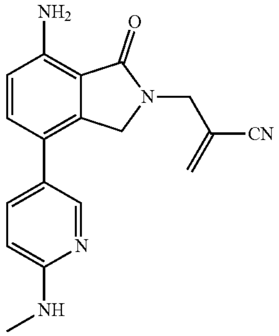 [SMILES: C=C(C#N)CN1Cc2c(-c3ccc(NC)nc3)ccc(N)c2C1=O] | 2-({7-amino-4-[6-(methylamino)pyridin-3-yl]-1-oxo-2,3-dihydro-1H-isoindol-2-yl}methyl)prop-2-enenitrile | 319.4 |
| 1193. | 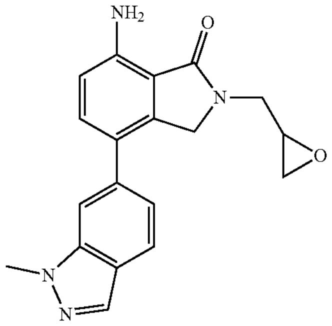 [SMILES: Cn1ncc2ccc(-c3ccc(N)c4c3CN(CC3CO3)C4=O)cc21] | 7-amino-4-(1-methyl-1H-indazol-6-yl)-2-[(oxiran-2-yl)methyl]-2,3-dihydro-1H-isoindol-1-one | 334.4 |

TABLE 15-continued

| Cpd. No. | Structure | IUPAC | MW (g/mol) |
|---|---|---|---|
| 1194. | 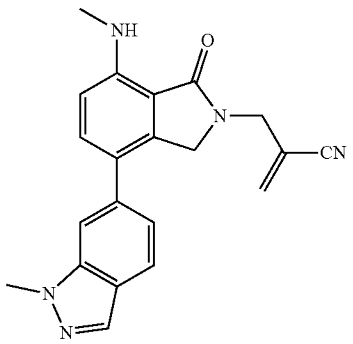 [SMILES: C=C(C#N)CN1Cc2c(-c3ccc4cnn(C)c4c3)ccc(NC)c2C1=O] | 2-{[4-(1-methyl-1H-indazol-6-yl)-7-(methylamino)-1-oxo-2,3-dihydro-1H-isoindol-2-yl]methyl}prop-2-enenitrile | 357.4 |
| 1195. | 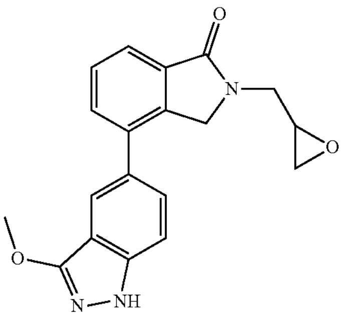 [SMILES: COc1n[nH]c2ccc(-c3cccc4c3CN(CC3CO3)C4=O)cc12] | 4-(3-methoxy-1H-indazol-5-yl)-2-[(oxiran-2-yl)methyl]-2,3-dihydro-1H-isoindol-1-one | 335.4 |
| 1196. | 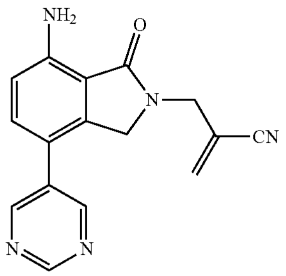 [SMILES: C=C(C#N)CN1Cc2c(-c3cncnc3)ccc(N)c2C1=O] | 2-{[7-amino-1-oxo-4-(pyrimidin-5-yl)-2,3-dihydro-1H-isoindol-2-yl]methyl}prop-2-enenitrile | 291.3 |
| 1197. | 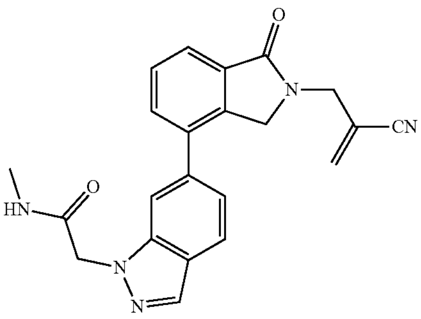 [SMILES: C=C(C#N)CN1Cc2c(cccc2-c2ccc3cnn(CC(=O)NC)c3c2)C1=O] | 2-{6-[2-(2-cyano-2-methylideneethyl)-1-oxo-2,3-dihydro-1H-isoindol-4-yl]-1H-indazol-1-yl}-N-methylacetamide | 385.4 |
| 1198. | 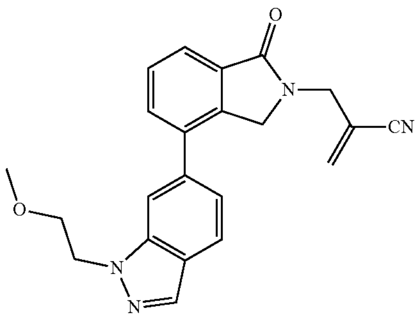 [SMILES: C=C(C#N)CN1Cc2c(cccc2-c2ccc3cnn(CCOC)c3c2)C1=O] | 2-({4-[1-(2-methoxyethyl)-1H-indazol-6-yl]-1-oxo-2,3-dihydro-1H-isoindol-2-yl}methyl)prop-2-enenitrile | 372.4 |

TABLE 15-continued
| Cpd. No. | Structure | IUPAC | MW (g/mol) |
|---|---|---|---|
| 1199. | 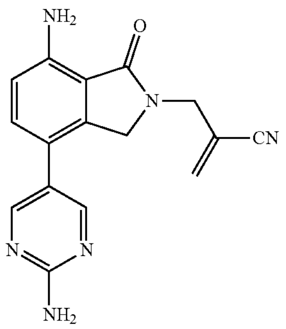 [SMILES: C=C(C#N)CN1Cc2c(-c3cnc(N)nc3)ccc(N)c2C1=O] | 2-{[7-amino-4-(2-aminopyrimidin-5-yl)-1-oxo-2,3-dihydro-1H-isoindol-2-yl]methyl}prop-2-enenitrile | 306.3 |
| 1200. | 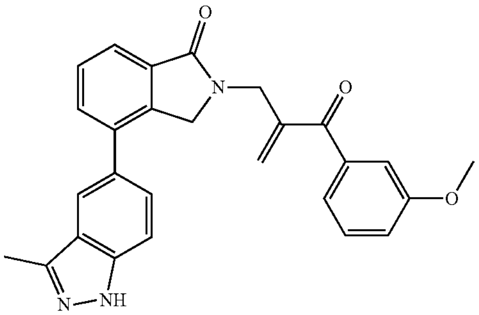 | 2-[3-(3-methoxyphenyl)-2-methylidene-3-oxopropyl]-4-(3-methyl-1H-indazol-5-yl)-2,3-dihydro-1H-isoindol-1-one | 437.5 |
| 1201. | 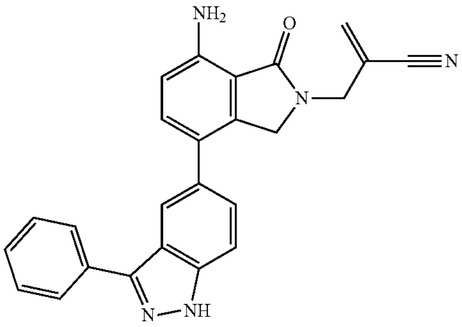 [SMILES: C=C(C#N)CN1Cc2c(-c3ccc4[nH]nc(-c5ccccc5)c4c3)ccc(N)c2C1=O] | 2-{[7-amino-1-oxo-4-(3-phenyl-1H-indazol-5-yl)-2,3-dihydro-1H-isoindol-2-yl]methyl}prop-2-enenitrile | 405.5 |
| 1202. | 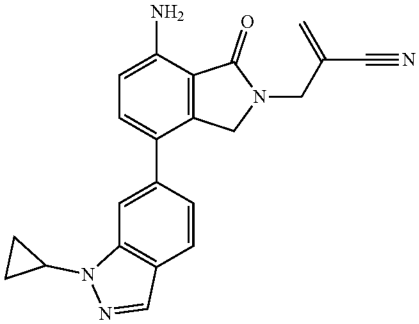 [SMILES: C=C(C#N)CN1Cc2c(-c3ccc4cnn(C5CC5)c4c3)ccc(N)c2C1=O] | 2-{[7-amino-4-(1-cyclopropyl-1H-indazol-6-yl)-1-oxo-2,3-dihydro-1H-isoindol-2-yl]methyl}prop-2-enenitrile | 369.4 |

TABLE 15-continued

| Cpd. No. | Structure | IUPAC | MW (g/mol) |
| --- | --- | --- | --- |
| 1203. | 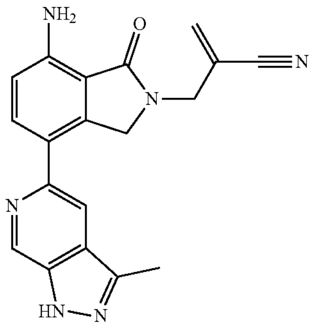 [SMILES: C=C(C#N)CN1Cc2c(-c3cc4c(C)n[nH]c4cn3)ccc(N)c2C1=O] | 2-[(7-amino-4-{3-methyl-1H-pyrazolo[3,4-c]pyridin-5-yl}-1-oxo-2,3-dihydro-1H-isoindol-2-yl)methyl]prop-2-enenitrile | 344.4 |
| 1204. | 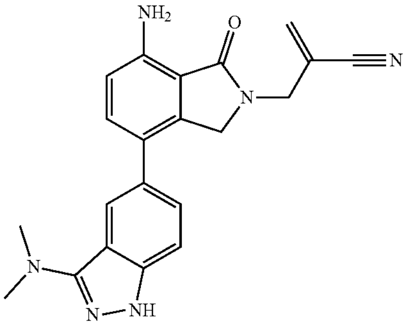 [SMILES: C=C(C#N)CN1Cc2c(-c3ccc4[nH]nc(N(C)C)c4c3)ccc(N)c2C1=O] | 2-({7-amino-4-[3-(dimethylamino)-1H-indazol-5-yl]-1-oxo-2,3-dihydro-1H-isoindol-2-yl}methyl)prop-2-enenitrile | 372.4 |
| 1205. | 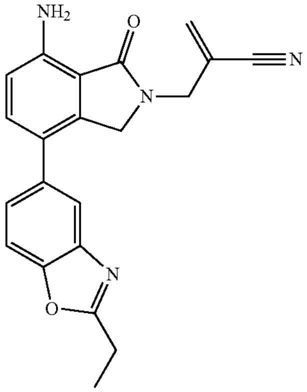 [SMILES: C=C(C#N)CN1Cc2c(-c3ccc4oc(CC)nc4c3)ccc(N)c2C1=O] | 2-{[7-amino-4-(2-ethyl-1,3-benzoxazol-5-yl)-1-oxo-2,3-dihydro-1H-isoindol-2-yl]methyl}prop-2-enenitrile | 358.4 |
| 1206. | 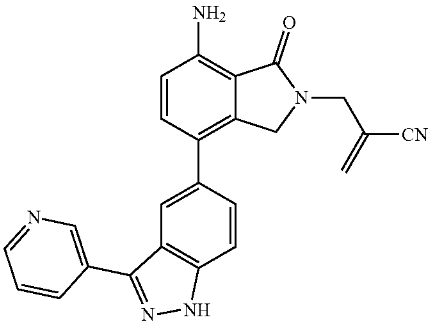 [SMILES: C=C(C#N)CN1Cc2c(-c3ccc4[nH]nc(-c5cccnc5)c4c3)ccc(N)c2C1=O] | 2-({7-amino-1-oxo-4-[3-(pyridin-3-yl)-1H-indazol-5-yl]-2,3-dihydro-1H-isoindol-2-yl}methyl)prop-2-enenitrile | 406.4 |

TABLE 15-continued

| Cpd. No. | Structure | IUPAC | MW (g/mol) |
|---|---|---|---|
| 1207. | 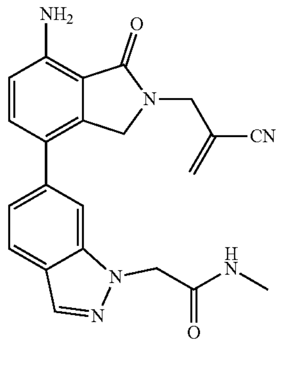 [SMILES: C=C(C#N)CN1Cc2c(-c3ccc4cnn(CC(=O)NC)c4c3)ccc(N)c2C1=O] | 2-{6-[7-amino-2-(2-cyano-2-methylideneethyl)-1-oxo-2,3-dihydro-1H-isoindol-4-yl]-1H-indazol-1-yl}-N-methylacetamide | 400.4 |
| 1208. | 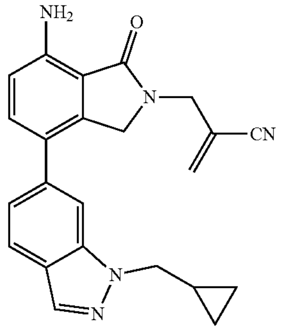 [SMILES: C=C(C#N)CN1Cc2c(-c3ccc4cnn(CC5CC5)c4c3)ccc(N)c2C1=O] | 2-({7-amino-4-[1-(cyclopropylmethyl)-1H-indazol-6-yl]-1-oxo-2,3-dihydro-1H-isoindol-2-yl}methyl)prop-2-enenitrile | 383.5 |
| 1209. | 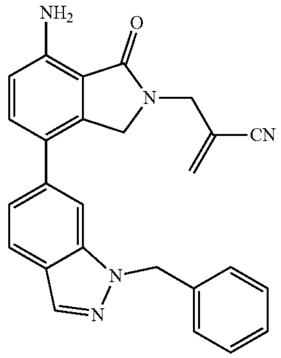 [SMILES: C=C(C#N)CN1Cc2c(-c3ccc4cnn(Cc5ccccc5)c4c3)ccc(N)c2C1=O] | 2-{[7-amino-4-(1-benzyl-1H-indazol-6-yl)-1-oxo-2,3-dihydro-1H-isoindol-2-yl]methyl}prop-2-enenitrile | 419.5 |
| 1210. | 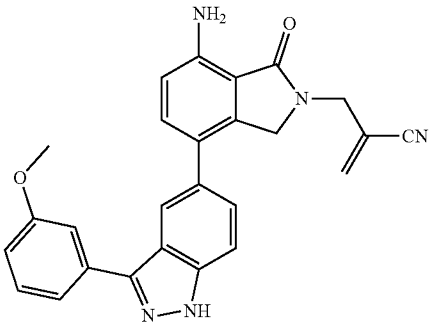 [SMILES: C=C(C#N)CN1Cc2c(-c3ccc4[nH]nc(-c5cccc(OC)c5)c4c3)ccc(N)c2C1=O] | 2-({7-amino-4-[3-(3-methoxyphenyl)-1H-indazol-5-yl]-1-oxo-2,3-dihydro-1H-isoindol-2-yl}methyl)prop-2-enenitrile | 435.5 |

TABLE 15-continued
| Cpd. No. | Structure | IUPAC | MW (g/mol) |
|---|---|---|---|
| 1211. | 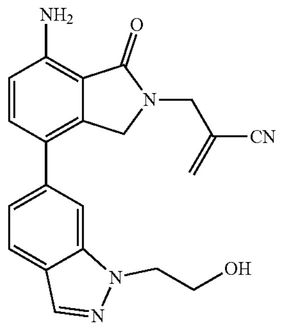 [SMILES: C=C(C#N)CN1Cc2c(-c3ccc4cnn(CCO)c4c3)ccc(N)c2C1=O] | 2-({7-amino-4-[1-(2-hydroxyethyl)-1H-indazol-6-yl]-1-oxo-2,3-dihydro-1H-isoindol-2-yl}methyl)prop-2-enenitrile | 373.4 |
| 1212. | 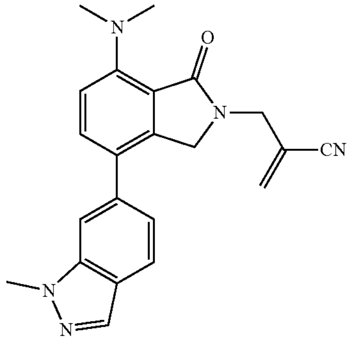 [SMILES: C=C(C#N)CN1Cc2c(-c3ccc4cnn(C)c4c3)ccc(N(C)C)c2C1=O] | 2-{[7-(dimethylamino)-4-(1-methyl-1H-indazol-6-yl)-1-oxo-2,3-dihydro-1H-isoindol-2-yl]methyl}prop-2-enenitrile | 371.4 |
| 1213. | 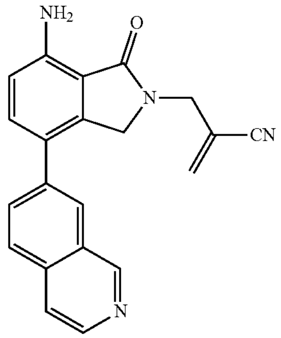 [SMILES: C=C(C#N)CN1Cc2c(-c3ccc4ccncc4c3)ccc(N)c2C1=O] | 2-{[7-amino-4-(isoquinolin-7-yl)-1-oxo-2,3-dihydro-1H-isoindol-2-yl]methyl}prop-2-enenitrile | 340.4 |
| 1214. | 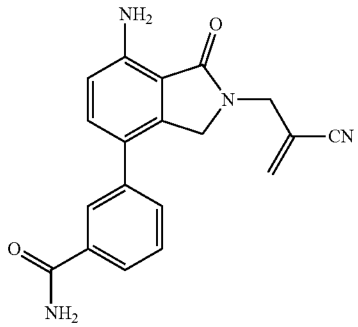 [SMILES: C=C(C#N)CN1Cc2c(-c3cccc(C(N)=O)c3)ccc(N)c2C1=O] | 3-[7-amino-2-(2-cyano-2-methylideneethyl)-1-oxo-2,3-dihydro-1H-isoindol-4-yl]benzamide | 332.4 |

TABLE 15-continued

| Cpd. No. | Structure | IUPAC | MW (g/mol) |
|---|---|---|---|
| 1215. | 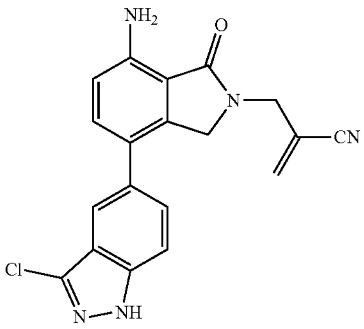 [SMILES: C=C(C#N)CN1Cc2c(-c3ccc4[nH]nc(Cl)c4c3)ccc(N)c2C1=O] | 2-{[7-amino-4-(3-chloro-1H-indazol-5-yl)-1-oxo-2,3-dihydro-1H-isoindol-2-yl]methyl}prop-2-enenitrile | 363.8 |
| 1216. | 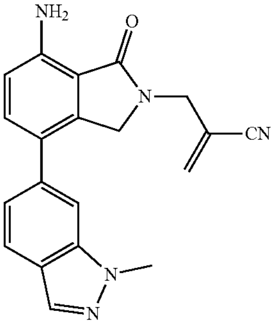 [SMILES: C=C(C#N)CN1Cc2c(-c3ccc4cnn(C)c4c3)ccc(N)c2C1=O] | 2-{[7-amino-4-(1-methyl-1H-1,2,3-benzotriazol-6-yl)-1-oxo-2,3-dihydro-1H-isoindol-2-yl]methyl}prop-2-enenitrile | 344.4 |
| 1217. | 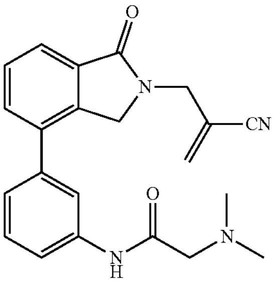 [SMILES: C=C(C#N)CN1Cc2c(cccc2-c2cccc(NC(=O)CN(C)C)c2)C1=O] | N-{3-[2-(2-cyano-2-methylideneethyl)-1-oxo-2,3-dihydro-1H-isoindol-4-yl]phenyl}-2-(dimethylamino)acetamide | 374.4 |
| 1218. | 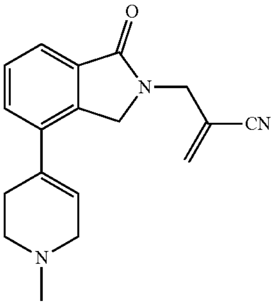 [SMILES: C=C(C#N)CN1Cc2c(cccc2C2=CCN(C)CC2)C1=O] | 2-{[4-(1-methyl-1,2,3,6-tetrahydropyridin-4-yl)-1-oxo-2,3-dihydro-1H-isoindol-2-yl]methyl}prop-2-enenitrile | 293.4 |
| 1219. | 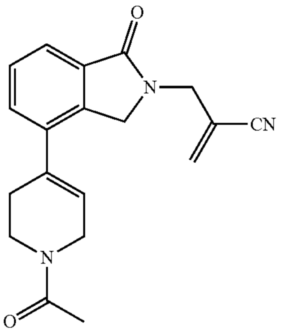 [SMILES: C=C(C#N)CN1Cc2c(cccc2C2=CCN(C(C)=O)CC2)C1=O] | 2-{[4-(1-acetyl-1,2,3,6-tetrahydropyridin-4-yl)-1-oxo-2,3-dihydro-1H-isoindol-2-yl]methyl}prop-2-enenitrile | 321.4 |

TABLE 15-continued
| Cpd. No. | Structure | IUPAC | MW (g/mol) |
|---|---|---|---|
| 1220. | 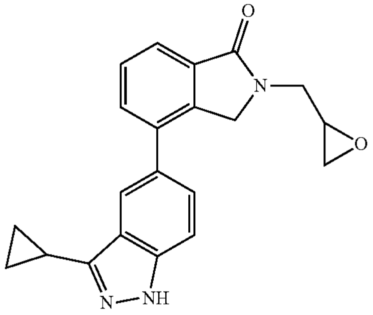 [SMILES: O=C1c2cccc(-c3ccc4[nH]nc(C5CC5)c4c3)c2CN1CC1CO1] | 4-(3-cyclopropyl-1H-indazol-5-yl)-2-[(oxiran-2-yl)methyl]-2,3-dihydro-1H-isoindol-1-one | 345.4 |
| 1221. | 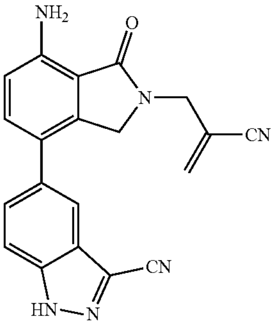 [SMILES: C=C(C#N)CN1Cc2c(-c3ccc4[nH]nc(C#N)c4c3)ccc(N)c2C1=O] | 5-[7-amino-2-(2-cyano-2-methylideneethyl)-1-oxo-2,3-dihydro-1H-isoindol-4-yl]-1H-indazole-3-carbonitrile | 354.4 |
| 1222. | 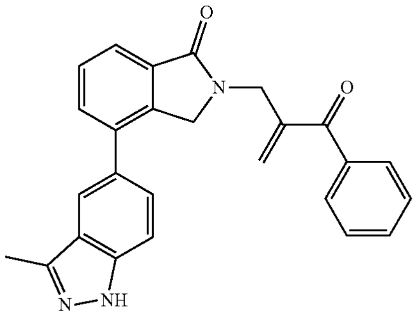 [SMILES: C=C(CN1Cc2c(cccc2-c2ccc3[nH]nc(C)c3c2)C1=O)C(=O)c1ccccc1] | 4-(3-methyl-1H-indazol-5-yl)-2-(2-methylidene-3-oxo-3-phenylpropyl)-2,3-dihydro-1H-isoindol-1-one | 407.5 |
| 1223. | 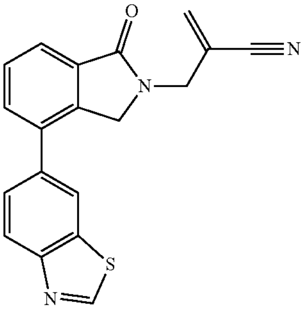 [SMILES: C=C(C#N)CN1Cc2c(cccc2-c2ccc3ncsc3c2)C1=O] | 2-{[4-(1,3-benzothiazol-6-yl)-1-oxo-2,3-dihydro-1H-isoindol-2-yl]methyl}prop-2-enenitrile | 331.4 |

TABLE 15-continued
| Cpd. No. | Structure | IUPAC | MW (g/mol) |
|---|---|---|---|
| 1224. | 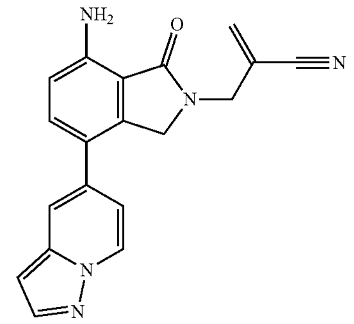 [SMILES: C=C(C#N)CN1Cc2c(-c3ccn4nccc4c3)ccc(N)c2C1=O] | 2-[(7-amino-1-oxo-4-{pyrazolo[1,5-a]pyridin-5-yl}-2,3-dihydro-1H-isoindol-2-yl)methyl]prop-2-enenitrile | 329.4 |
| 1225. | 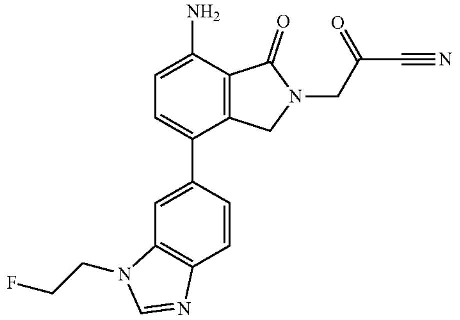 [SMILES: N#CC(=O)CN1Cc2c(-c3ccc4ncn(CCF)c4c3)ccc(N)c2C1=O] | 2-({7-amino-4-[1-(2-fluoroethyl)-1H-indazol-6-yl]-1-oxo-2,3-dihydro-1H-isoindol-2-yl}methyl)prop-2-enenitrile | 375.4 |
| 1226. | 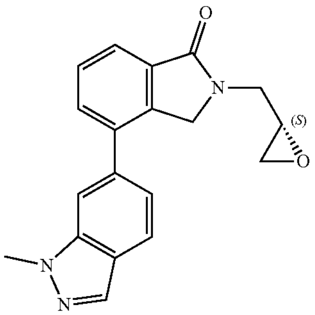 | 4-(1-methyl-1H-indazol-6-yl)-2-{[(2S)-oxiran-2-yl]methyl}-2,3-dihydro-1H-isoindol-1-one | 319.4 |
| 1227. | 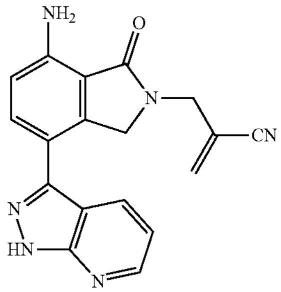 [SMILES: C=C(C#N)CN1Cc2c(-c3n[nH]c4ncccc34)ccc(N)c2C1=O] | 2-[(7-amino-1-oxo-4-{1H-pyrazolo[3,4-b]pyridin-3-yl}-2,3-dihydro-1H-isoindol-2-yl)methyl]prop-2-enenitrile | 330.4 |

TABLE 15-continued

| Cpd. No. | Structure | IUPAC | MW (g/mol) |
|---|---|---|---|
| 1228. | 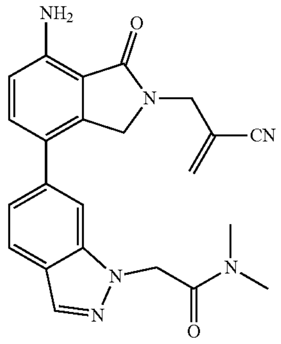 [SMILES: C=C(C#N)CN1Cc2c(-c3ccc4cnn(CC(=O)N(C)C)c4c3)ccc(N)c2C1=O] | 2-{6-[7-amino-2-(2-cyano-2-methylideneethyl)-1-oxo-2,3-dihydro-1H-isoindol-4-yl]-1H-indazol-1-yl}-N,N-dimethylacetamide | 414.5 |
| 1229. | 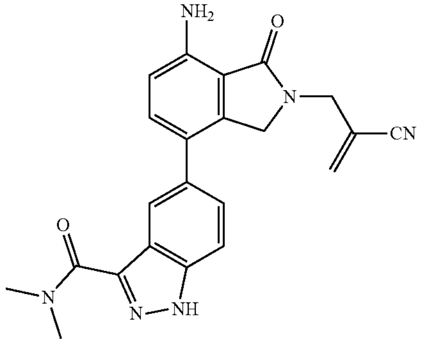 [SMILES: C=C(C#N)CN1Cc2c(-c3ccc4[nH]nc(C(=O)N(C)C)c4c3)ccc(N)c2C1=O] | 5-[7-amino-2-(2-cyano-2-methylideneethyl)-1-oxo-2,3-dihydro-1H-isoindol-4-yl]-N,N-dimethyl-1H-indazole-3-carboxamide | 400.4 |
| 1230. | 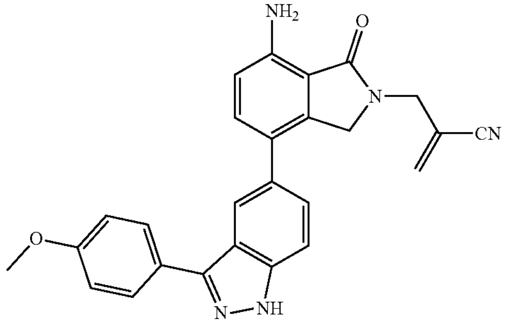 [SMILES: C=C(C#N)CN1Cc2c(-c3ccc4[nH]nc(-c5ccc(OC)cc5)c4c3)ccc(N)c2C1=O] | 2-({7-amino-4-[3-(3-methoxyphenyl)-1H-indazol-5-yl]-1-oxo-2,3-dihydro-1H-isoindol-2-yl}methyl)prop-2-enenitrile | 435.5 |
| 1231. | 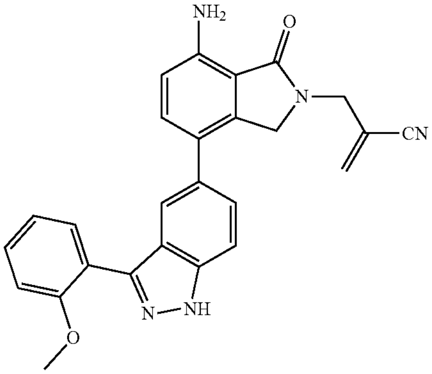 [SMILES: C=C(C#N)CN1Cc2c(-c3ccc4[nH]nc(-c5ccccc5OC)c4c3)ccc(N)c2C1=O] | 2-({7-amino-4-[3-(2-methoxyphenyl)-1H-indazol-5-yl]-1-oxo-2,3-dihydro-1H-isoindol-2-yl}methyl)prop-2-enenitrile | 435.5 |

TABLE 15-continued

| Cpd. No. | Structure | IUPAC | MW (g/mol) |
|---|---|---|---|
| 1232. | 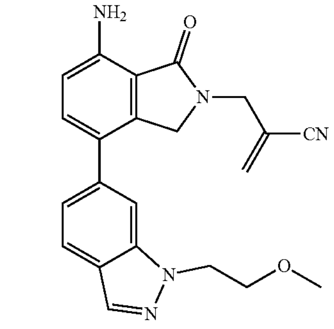 [SMILES: C=C(C#N)CN1Cc2c(-c3ccc4cnn(CCOC)c4c3)ccc(N)c2C1=O] | 2-({7-amino-4-[1-(2-methoxyethyl)-1H-indazol-6-yl]-1-oxo-2,3-dihydro-1H-isoindol-2-yl}methyl)prop-2-enenitrile | 387.4 |
| 1233. | 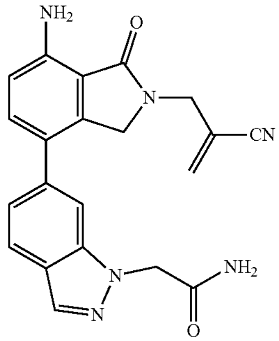 [SMILES: C=C(C#N)CN1Cc2c(-c3ccc4cnn(CC(N)=O)c4c3)ccc(N)c2C1=O] | 2-{6-[7-amino-2-(2-cyano-2-methylideneethyl)-1-oxo-2,3-dihydro-1H-isoindol-4-yl]-1H-indazol-1-yl}acetamide | 386.4 |
| 1234. | 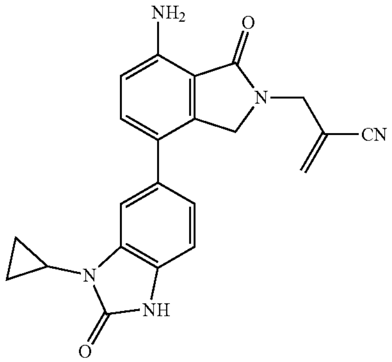 [SMILES: C=C(C#N)CN1Cc2c(-c3ccc4[nH]c(=O)n(C5CC5)c4c3)ccc(N)c2C1=O] | 2-{[7-amino-4-(3-cyclopropyl-2-oxo-2,3-dihydro-1H-1,3-benzodiazol-5-yl)-1-oxo-2,3-dihydro-1H-isoindol-2-yl]methyl}prop-2-enenitrile | 385.4 |
| 1235. | 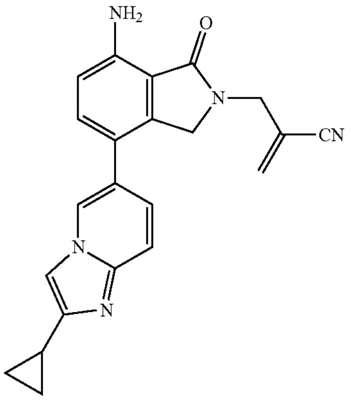 [SMILES: C=C(C#N)CN1Cc2c(-c3ccc4nc(C5CC5)cn4c3)ccc(N)c2C1=O] | 2-[(7-amino-4-{2-cyclopropylimidazo[1,2-a]pyridin-6-yl}-1-oxo-2,3-dihydro-1H-isoindol-2-yl)methyl]prop-2-enenitrile | 369.4 |

TABLE 15-continued

| Cpd. No. | Structure | IUPAC | MW (g/mol) |
|---|---|---|---|
| 1236. | 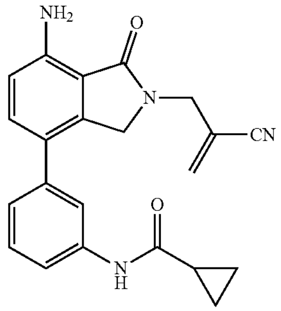 [SMILES: C=C(C#N)CN1Cc2c(-c3cccc(NC(=O)C4CC4)c3)ccc(N)c2C1=O] | N-{3-[7-amino-2-(2-cyano-2-methylideneethyl)-1-oxo-2,3-dihydro-1H-isoindol-4-yl]phenyl}cyclopropanecarboxamide | 372.4 |
| 1237. | 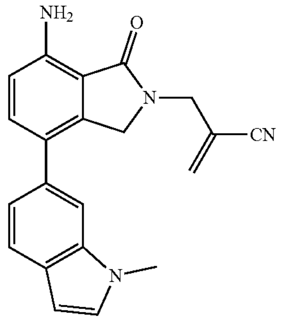 [SMILES: C=C(C#N)CN1Cc2c(-c3ccc4ccn(C)c4c3)ccc(N)c2C1=O] | 2-{[7-amino-4-(1-methyl-1H-indol-6-yl)-1-oxo-2,3-dihydro-1H-isoindol-2-yl]methyl}prop-2-enenitrile | 342.4 |
| 1238. | 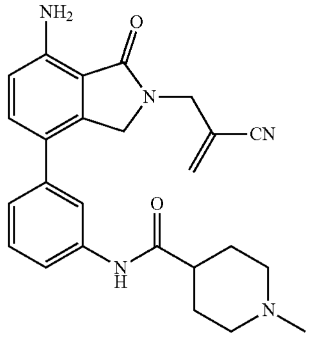 [SMILES: C=C(C#N)CN1Cc2c(-c3cccc(NC(=O)C4CCN(C)CC4)c3)ccc(N)c2C1=O] | N-{3-[2-(2-cyano-2-methylideneethyl)-1-oxo-2,3-dihydro-1H-isoindol-4-yl]phenyl}-1-methylpiperidine-4-carboxamide | 414.5 |
| 1239. | 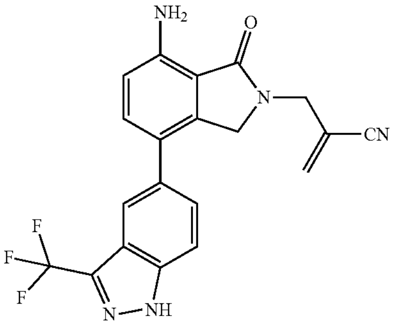 [SMILES: C=C(C#N)CN1Cc2c(-c3ccc4[nH]nc(C(F)(F)F)c4c3)ccc(N)c2C1=O] | 2-({7-amino-1-oxo-4-[3-(trifluoromethyl)-1H-indazol-5-yl]-2,3-dihydro-1H-isoindol-2-yl}methyl)prop-2-enenitrile | 397.4 |

TABLE 15-continued
| Cpd. No. | Structure | IUPAC | MW (g/mol) |
|---|---|---|---|
| 1240. | 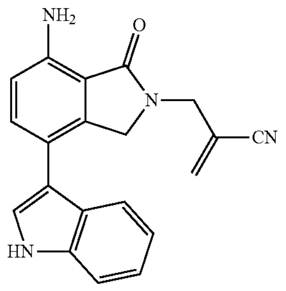 [SMILES: C=C(C#N)CN1Cc2c(-c3c[nH]c4ccccc34)ccc(N)c2C1=O] | 2-{[7-amino-4-(1H-indol-3-yl)-1-oxo-2,3-dihydro-1H-isoindol-2-yl]methyl}prop-2-enenitrile | 328.4 |
| 1241. | 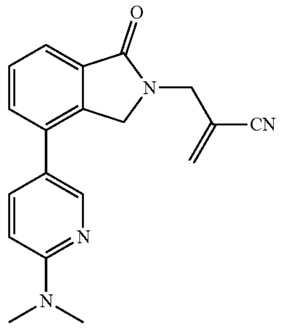 [SMILES: C=C(C#N)CN1Cc2c(cccc2-c2ccc(N(C)C)nc2)C1=O] | 2-({4-[6-(dimethylamino)pyridin-3-yl]-1-oxo-2,3-dihydro-1H-isoindol-2-yl}methyl)prop-2-enenitrile | 318.4 |
| 1242. | 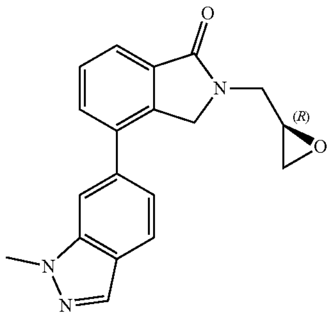 | 4-(1-methyl-1H-indazol-6-yl)-2-{[(2R)-oxiran-2-yl]methyl}-2,3-dihydro-1H-isoindol-1-one | 319.4 |
| 1243. | 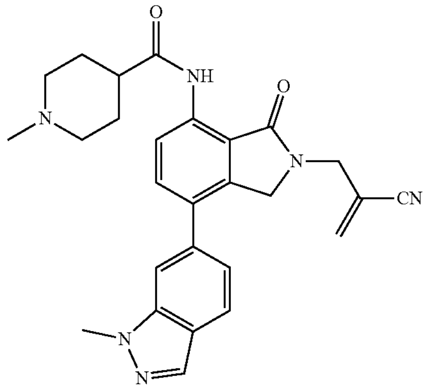 [SMILES: C=C(C#N)CN1Cc2c(-c3ccc4cnn(C)c4c3)ccc(NC(=O)C3CCN(C)CC3)c2C1=O] | N-[2-(2-cyano-2-methylideneethyl)-7-(1-methyl-1H-indazol-6-yl)-3-oxo-2,3-dihydro-1H-isoindol-4-yl]-1-methylpiperidine-4-carboxamide | 468.6 |

TABLE 15-continued
| Cpd. No. | Structure | IUPAC | MW (g/mol) |
|---|---|---|---|
| 1244. | 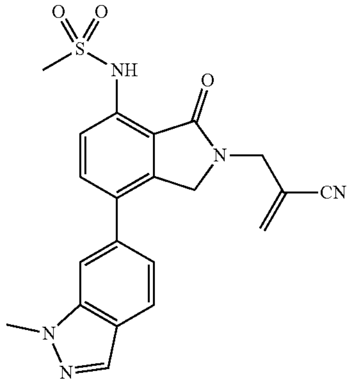 [SMILES: C=C(C#N)CN1Cc2c(-c3ccc4cnn(C)c4c3)ccc(NS(C)(=O)=O)c2C1=O] | N-[2-(2-cyano-2-methylideneethyl)-7-(1-methyl-1H-indazol-6-yl)-3-oxo-2,3-dihydro-1H-isoindol-4-yl]methanesulfonamide | 421.5 |
| 1245. | 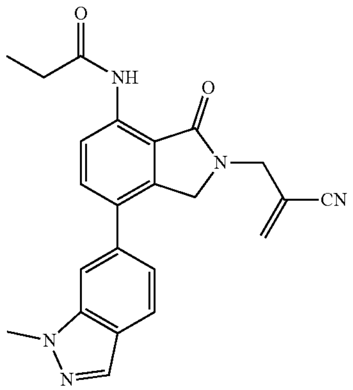 [SMILES: C=C(C#N)CN1Cc2c(-c3ccc4cnn(C)c4c3)ccc(NC(=O)CC)c2C1=O] | N-[2-(2-cyano-2-methylideneethyl)-7-(1-methyl-1H-indazol-6-yl)-3-oxo-2,3-dihydro-1H-isoindol-4-yl]propanamide | 399.5 |
| 1246. | 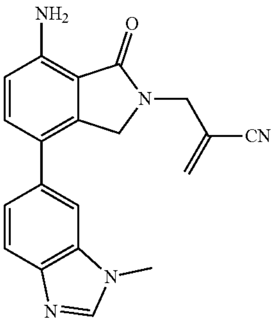 [SMILES: C=C(C#N)CN1Cc2c(-c3ccc4ncn(C)c4c3)ccc(N)c2C1=O] | 2-{[7-amino-4-(1-methyl-1H-1,3-benzodiazol-6-yl)-1-oxo-2,3-dihydro-1H-isoindol-2-yl]methyl}prop-2-enenitrile | 343.4 |
| 1247. | 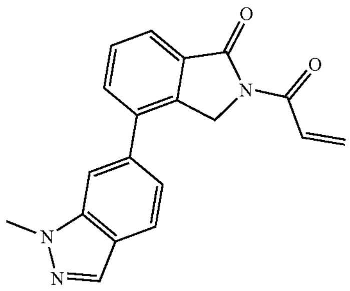 [SMILES: C=CC(=O)N1Cc2c(cccc2-c2ccc3cnn(C)c3c2)C1=O] | 4-(1-methyl-1H-indazol-6-yl)-2-(prop-2-enoyl)-2,3-dihydro-1H-isoindol-1-one | 317.3 |

TABLE 15-continued
| Cpd. No. | Structure | IUPAC | MW (g/mol) |
|---|---|---|---|
| 1248. | 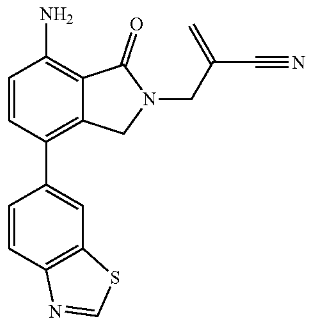 [SMILES: C=C(C#N)CN1Cc2c(-c3ccc4ncsc4c3)ccc(N)c2C1=O] | 2-{[7-amino-4-(1,3-benzothiazol-6-yl)-1-oxo-2,3-dihydro-1H-isoindol-2-yl]methyl}prop-2-enenitrile | 346.4 |
| 1249. | 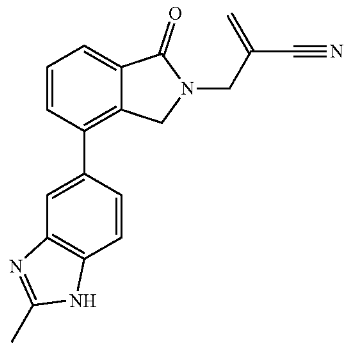 [SMILES: C=C(C#N)CN1Cc2c(cccc2-c2ccc3[nH]c(C)nc3c2)C1=O] | 2-{[4-(2-methyl-1H-1,3-benzodiazol-5-yl)-1-oxo-2,3-dihydro-1H-isoindol-2-yl]methyl}prop-2-enenitrile | 328.4 |
| 1250. | 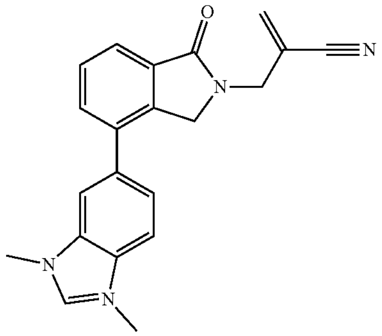 | 2-{[4-(1,3-dimethyl-1H-indazol-6-yl)-1-oxo-2,3-dihydro-1H-isoindol-2-yl]methyl}prop-2-enenitrile | 342.4 |
| 1251. | 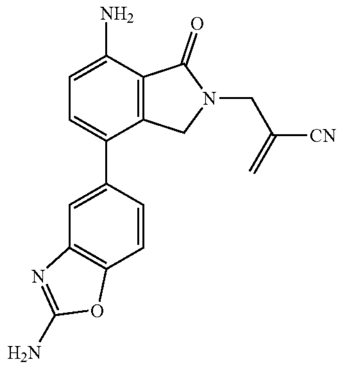 [SMILES: C=C(C#N)CN1Cc2c(-c3ccc4oc(N)nc4c3)ccc(N)c2C1=O] | 2-{[7-amino-4-(2-amino-1,3-benzoxazol-5-yl)-1-oxo-2,3-dihydro-1H-isoindol-2-yl]methyl}prop-2-enenitrile | 345.4 |

TABLE 15-continued
| Cpd. No. | Structure | IUPAC | MW (g/mol) |
|---|---|---|---|
| 1252. | 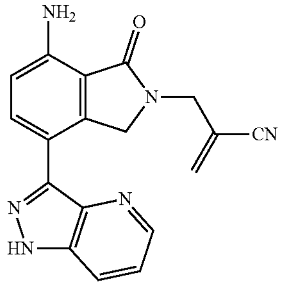 [SMILES: C=C(C#N)CN1Cc2c(-c3n[nH]c4cccnc34)ccc(N)c2C1=O] | 2-[(7-amino-1-oxo-4-{1H-pyrazolo[4,3-b]pyridin-3-yl}-2,3-dihydro-1H-isoindol-2-yl)methyl]prop-2-enenitrile | 330.4 |
| 1253. | 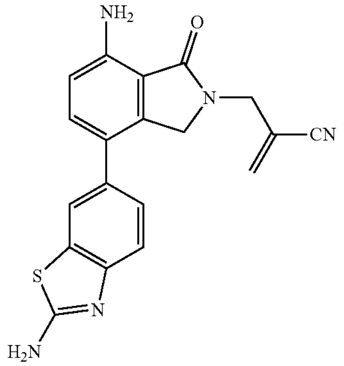 [SMILES: C=C(C#N)CN1Cc2c(-c3ccc4nc(N)sc4c3)ccc(N)c2C1=O] | 2-{[7-amino-4-(2-amino-1,3-benzothiazol-6-yl)-1-oxo-2,3-dihydro-1H-isoindol-2-yl]methyl}prop-2-enenitrile | 361.4 |
| 1254. | 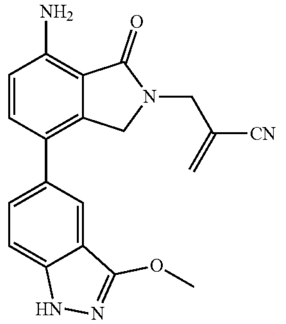 [SMILES: C=C(C#N)CN1Cc2c(-c3ccc4[nH]nc(OC)c4c3)ccc(N)c2C1=O] | 2-{[7-amino-4-(3-methoxy-1H-indazol-5-yl)-1-oxo-2,3-dihydro-1H-isoindol-2-yl]methyl}prop-2-enenitrile | 359.4 |
| 1255. | 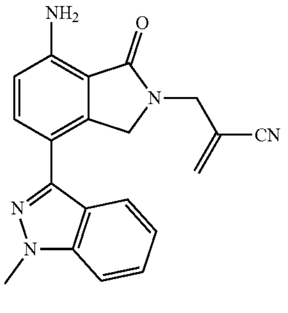 [SMILES: C=C(C#N)CN1Cc2c(-c3nn(C)c4ccccc34)ccc(N)c2C1=O] | 2-{[7-amino-4-(1-methyl-1H-indazol-3-yl)-1-oxo-2,3-dihydro-1H-isoindol-2-yl]methyl}prop-2-enenitrile | 343.4 |

TABLE 15-continued

| Cpd. No. | Structure | IUPAC | MW (g/mol) |
|---|---|---|---|
| 1256. | 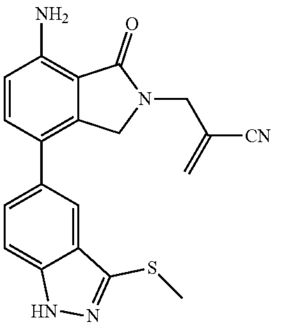 [SMILES: C=C(C#N)CN1Cc2c(-c3ccc4[nH]nc(SC)c4c3)ccc(N)c2C1=O] | 2-({7-amino-4-[3-(methylsulfanyl)-1H-indazol-5-yl]-1-oxo-2,3-dihydro-1H-isoindol-2-yl}methyl)prop-2-enenitrile | 375.5 |
| 1257. | 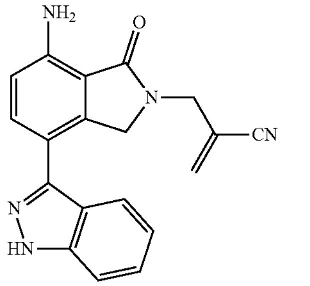 [SMILES: C=C(C#N)CN1Cc2c(-c3n[nH]c4ccccc34)ccc(N)c2C1=O] | 2-{[7-amino-4-(1H-indazol-3-yl)-1-oxo-2,3-dihydro-1H-isoindol-2-yl]methyl}prop-2-enenitrile | 329.4 |
| 1258. | 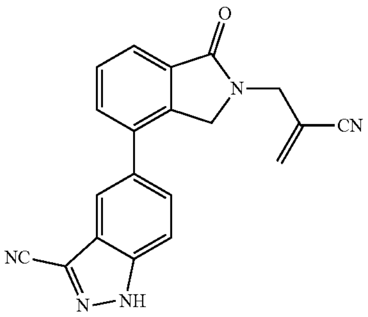 [SMILES: C=C(C#N)CN1Cc2c(cccc2-c2ccc3[nH]nc(C#N)c3c2)C1=O] | 5-[2-(2-cyano-2-methylideneethyl)-1-oxo-2,3-dihydro-1H-isoindol-4-yl]-1H-indazole-3-carbonitrile | 339.4 |
| 1259. | 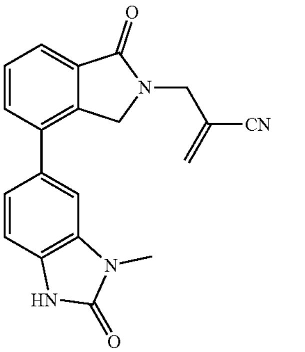 [SMILES: C=C(C#N)CN1Cc2c(cccc2-c2ccc3[nH]c(=O)n(C)c3c2)C1=O] | 2-{[4-(3-methyl-2-oxo-2,3-dihydro-1H-1,3-benzodiazol-5-yl)-1-oxo-2,3-dihydro-1H-isoindol-2-yl]methyl}prop-2-enenitrile | 344.4 |

TABLE 15-continued

| Cpd. No. | Structure | IUPAC | MW (g/mol) |
|---|---|---|---|
| 1260. | 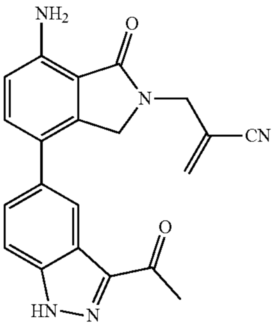 [SMILES: C=C(C#N)CN1Cc2c(-c3ccc4[nH]nc(C(C)=O)c4c3)ccc(N)c2C1=O] | 2-{[4-(3-acetyl-1H-indazol-5-yl)-7-amino-1-oxo-2,3-dihydro-1H-isoindol-2-yl]methyl}prop-2-enenitrile | 371.4 |
| 1261. | 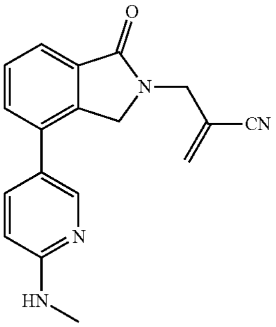 [SMILES: C=C(C#N)CN1Cc2c(cccc2-c2ccc(NC)nc2)C1=O] | 2-({4-[6-(methylamino)pyridin-3-yl]-1-oxo-2,3-dihydro-1H-isoindol-2-yl}methyl)prop-2-enenitrile | 304.4 |
| 1262. | 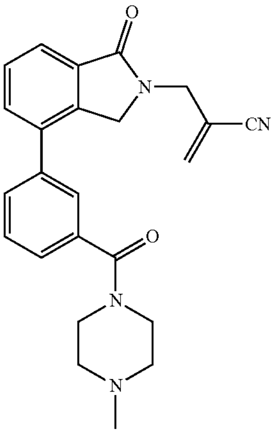 [SMILES: C=C(C#N)CN1Cc2c(cccc2-c2cccc(C(=O)N3CCN(C)CC3)c2)C1=O] | 2-({4-[3-(4-methylpiperazine-1-carbonyl)phenyl]-1-oxo-2,3-dihydro-1H-isoindol-2-yl}methyl)prop-2-enenitrile | 400.5 |
| 1263. | 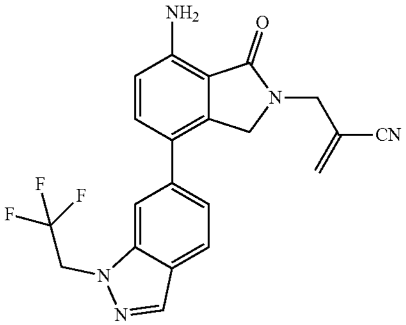 [SMILES: C=C(C#N)CN1Cc2c(-c3ccc4cnn(CC(F)(F)F)c4c3)ccc(N)c2C1=O] | 2-({7-amino-1-oxo-4-[1-(2,2,2-trifluoroethyl)-1H-indazol-6-yl]-2,3-dihydro-1H-isoindol-2-yl}methyl)prop-2-enenitrile | 411.4 |

TABLE 15-continued
| Cpd. No. | Structure | IUPAC | MW (g/mol) |
|---|---|---|---|
| 1264. | 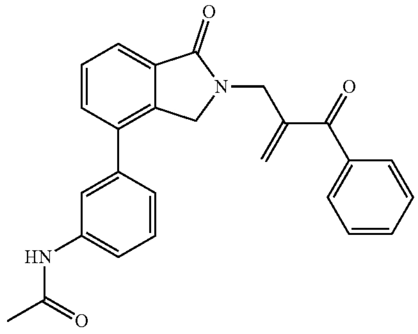 [SMILES: C=C(CN1Cc2c(cccc2-c2cccc(NC(C)=O)c2)C1=O)C(=O)c1ccccc1] | N-{3-[2-(2-methylidene-3-oxo-3-phenylpropyl)-1-oxo-2,3-dihydro-1H-isoindol-4-yl]phenyl}acetamide | 410.5 |
| 1265. | 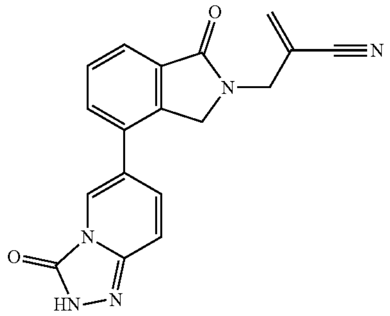 [SMILES: C=C(C#N)CN1Cc2c(cccc2-c2ccc3n[nH]c(=O)n3c2)C1=O] | 2-[(1-oxo-4-{3-oxo-2H,3H-[1,2,4]triazolo[4,3-a]pyridin-6-yl}-2,3-dihydro-1H-isoindol-2-yl)methyl]prop-2-enenitrile | 331.3 |
| 1266. | 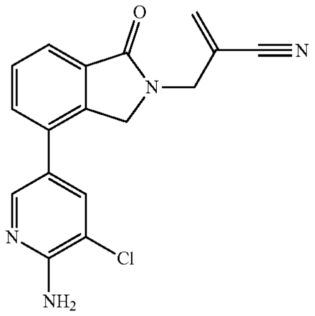 [SMILES: C=C(C#N)CN1Cc2c(cccc2-c2cnc(N)c(Cl)c2)C1=O] | 2-{[4-(6-amino-5-chloropyridin-3-yl)-1-oxo-2,3-dihydro-1H-isoindol-2-yl]methyl}prop-2-enenitrile | 324.8 |
| 1267. | 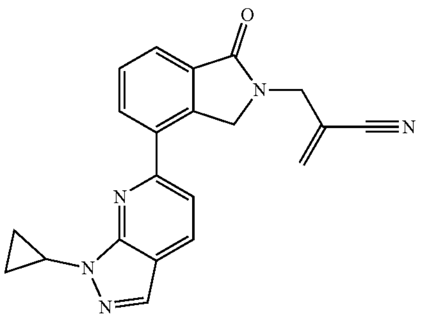 [SMILES: C=C(C#N)CN1Cc2c(cccc2-c2ccc3cnn(C4CC4)c3n2)C1=O] | 2-[(4-{1-cyclopropyl-1H-pyrazolo[3,4-b]pyridin-6-yl}-1-oxo-2,3-dihydro-1H-isoindol-2-yl)methyl]prop-2-enenitrile | 355.4 |

TABLE 15-continued
| Cpd. No. | Structure | IUPAC | MW (g/mol) |
|---|---|---|---|
| 1268. | 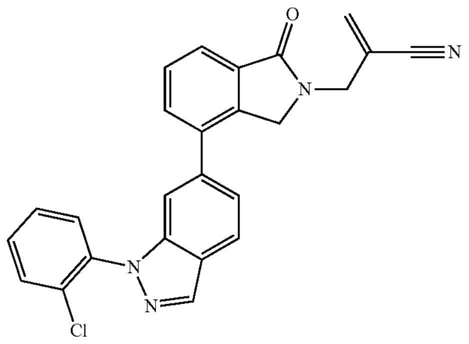 [SMILES: C=C(C#N)CN1Cc2c(cccc2-c2ccc3cnn(-c4ccccc4Cl)c3c2)C1=O] | 2-({4-[1-(2-chlorophenyl)-1H-indazol-6-yl]-1-oxo-2,3-dihydro-1H-isoindol-2-yl}methyl)prop-2-enenitrile | 424.9 |
| 1269. | 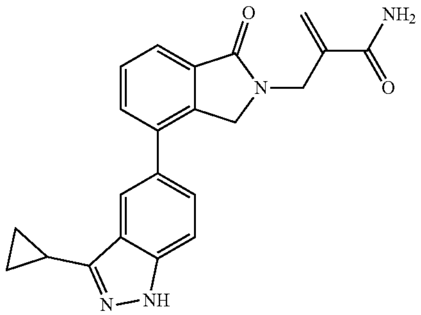 [SMILES: C=C(CN1Cc2c(cccc2-c2ccc3[nH]nc(C4CC4)c3c2)C1=O)C(N)=O] | 2-{[4-(3-cyclopropyl-1H-indazol-5-yl)-1-oxo-2,3-dihydro-1H-isoindol-2-yl]methyl}prop-2-enamide | 372.4 |
| 1270. | 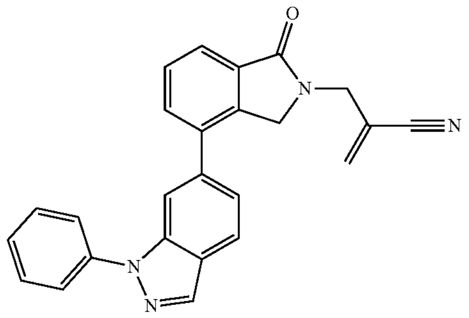 [SMILES: C=C(C#N)CN1Cc2c(cccc2-c2ccc3cnn(-c4ccccc4)c3c2)C1=O] | 2-{[1-oxo-4-(1-phenyl-1H-indazol-6-yl)-2,3-dihydro-1H-isoindol-2-yl]methyl}prop-2-enenitrile | 390.4 |
| 1271. | 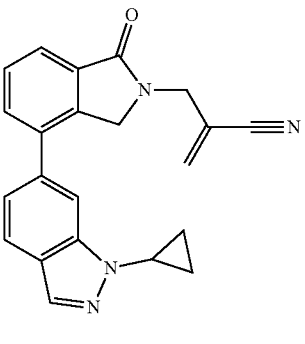 [SMILES: C=C(C#N)CN1Cc2c(cccc2-c2ccc3cnn(C4CC4)c3c2)C1=O] | 2-{[4-(1-cyclopropyl-1H-indazol-6-yl)-1-oxo-2,3-dihydro-1H-isoindol-2-yl]methyl}prop-2-enenitrile | 354.4 |

TABLE 15-continued
| Cpd. No. | Structure | IUPAC | MW (g/mol) |
|---|---|---|---|
| 1272. | 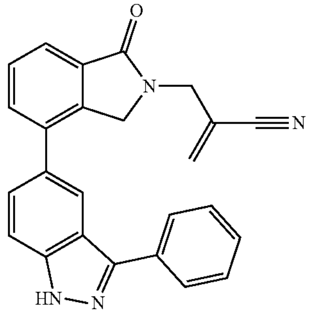 [SMILES: C=C(C#N)CN1Cc2c(cccc2-c2ccc3[nH]nc(-c4ccccc4)c3c2)C1=O] | 2-{[1-oxo-4-(3-phenyl-1H-indazol-5-yl)-2,3-dihydro-1H-isoindol-2-yl]methyl}prop-2-enenitrile | 390.4 |
| 1273. | 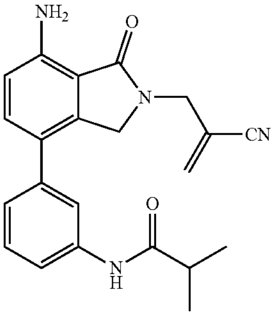 [SMILES: C=C(C#N)CN1Cc2c(-c3cccc(NC(=O)C(C)C)c3)ccc(N)c2C1=O] | N-{3-[7-amino-2-(2-cyano-2-methylideneethyl)-1-oxo-2,3-dihydro-1H-isoindol-4-yl]phenyl}-2-methylpropanamide | 374.4 |
| 1274. | 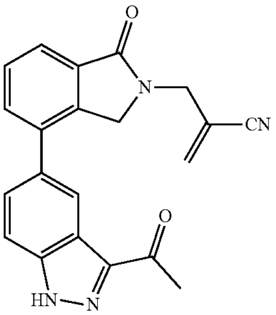 [SMILES: C=C(C#N)CN1Cc2c(cccc2-c2ccc3[nH]nc(C(C)=O)c3c2)C1=O] | 2-{[4-(3-acetyl-1H-indazol-5-yl)-1-oxo-2,3-dihydro-1H-isoindol-2-yl]methyl}prop-2-enenitrile | 356.4 |
| 1275. | 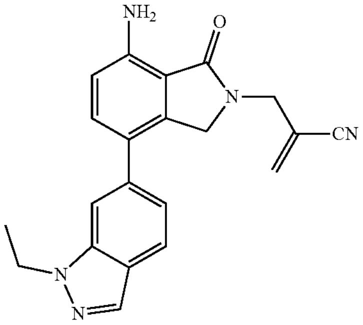 [SMILES: C=C(C#N)CN1Cc2c(-c3ccc4cnn(CC)c4c3)ccc(N)c2C1=O] | 2-{[7-amino-4-(1-ethyl-1H-indazol-6-yl)-1-oxo-2,3-dihydro-1H-isoindol-2-yl]methyl}prop-2-enenitrile | 357.4 |

TABLE 15-continued
| Cpd. No. | Structure | IUPAC | MW (g/mol) |
|---|---|---|---|
| 1276. | 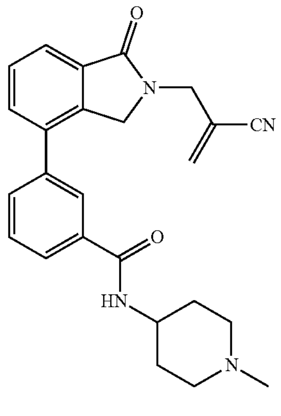 [SMILES: C=C(C#N)CN1Cc2c(cccc2-c2cccc(C(=O)NC3CCN(C)CC3)c2)C1=O] | 3-[2-(2-cyano-2-methylideneethyl)-1-oxo-2,3-dihydro-1H-isoindol-4-yl]-N-(1-methylpiperidin-4-yl)benzamide | 414.5 |
| 1277. | 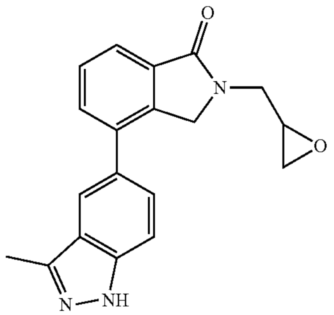 [SMILES: Cc1n[nH]c2ccc(-c3cccc4c3CN(CC3CO3)C4=O)cc12] | 4-(3-methyl-1H-indazol-5-yl)-2-[(oxiran-2-yl)methyl]-2,3-dihydro-1H-isoindol-1-one | 319.4 |
| 1278. | 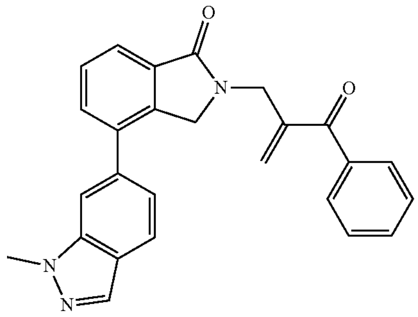 [SMILES: C=C(CN1Cc2c(cccc2-c2ccc3cnn(C)c3c2)C1=O)C(=O)c1ccccc1] | 4-(1-methyl-1H-indazol-6-yl)-2-(2-methylidene-3-oxo-3-phenylpropyl)-2,3-dihydro-1H-isoindol-1-one | 407.5 |
| 1279. | 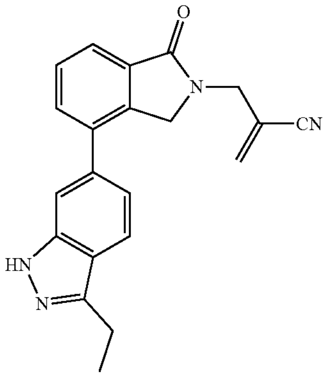 [SMILES: C=C(C#N)CN1Cc2c(cccc2-c2ccc3c(CC)n[nH]c3c2)C1=O] | 2-{[4-(3-ethyl-1H-indazol-6-yl)-1-oxo-2,3-dihydro-1H-isoindol-2-yl]methyl}prop-2-enenitrile | 342.4 |

TABLE 15-continued
| Cpd. No. | Structure | IUPAC | MW (g/mol) |
|---|---|---|---|
| 1280. | 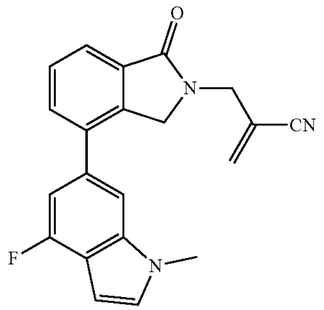 [SMILES: C=C(C#N)CN1Cc2c(cccc2-c2cc(F)c3ccn(C)c3c2)C1=O] | 2-{[4-(4-fluoro-1-methyl-1H-indol-6-yl)-1-oxo-2,3-dihydro-1H-isoindol-2-yl]methyl}prop-2-enenitrile | 345.4 |
| 1281. | 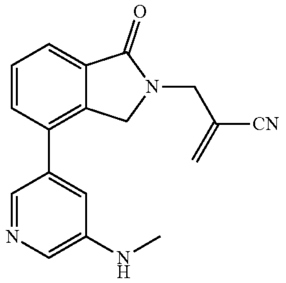 [SMILES: C=C(C#N)CN1Cc2c(cccc2-c2cncc(NC)c2)C1=O] | 2-({4-[5-(methylamino)pyridin-3-yl]-1-oxo-2,3-dihydro-1H-isoindol-2-yl}methyl)prop-2-enenitrile | 304.4 |
| 1282. | 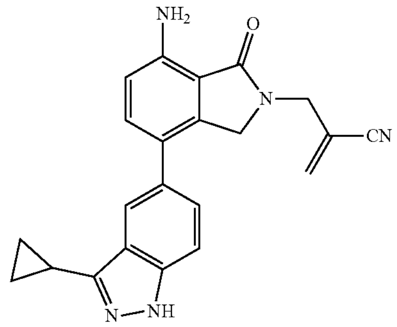 [SMILES: C=C(C#N)CN1Cc2c(-c3ccc4[nH]nc(C5CC5)c4c3)ccc(N)c2C1=O] | 2-{[7-amino-4-(3-cyclopropyl-1H-indazol-5-yl)-1-oxo-2,3-dihydro-1H-isoindol-2-yl]methyl}prop-2-enenitrile | 369.4 |
| 1283. | 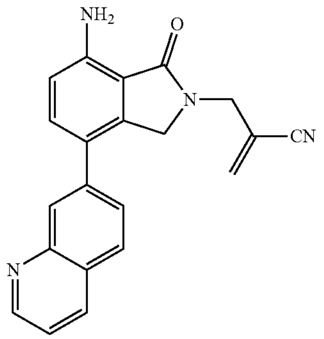 [SMILES: C=C(C#N)CN1Cc2c(-c3ccc4cccnc4c3)ccc(N)c2C1=O] | 2-{[7-amino-1-oxo-4-(quinolin-7-yl)-2,3-dihydro-1H-isoindol-2-yl]methyl}prop-2-enenitrile | 340.4 |

TABLE 15-continued

| Cpd. No. | Structure | IUPAC | MW (g/mol) |
|---|---|---|---|
| 1284. | 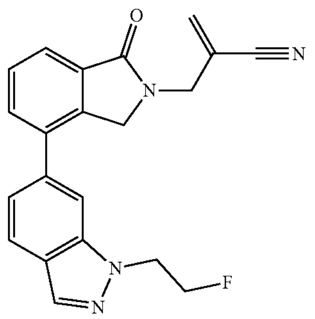 [SMILES: C=C(C#N)CN1Cc2c(cccc2-c2ccc3cnn(CCF)c3c2)C1=O] | 2-({4-[1-(2-fluoroethyl)-1H-indazol-6-yl-1-oxo-2,3-dihydro-1H-isoindol-2-yl}methyl)prop-2-enenitrile | 360.4 |
| 1285. | 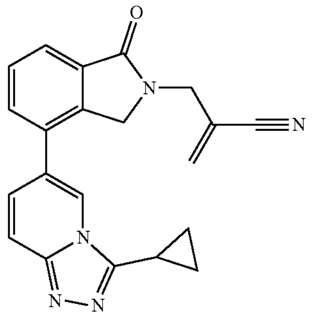 [SMILES: C=C(C#N)CN1Cc2c(cccc2-c2ccc3nnc(C4CC4)n3c2)C1=O] | 2-[(4-{3-cyclopropyl-[1,2,4]triazolo[4,3-a]pyridin-6-yl}-1-oxo-2,3-dihydro-1H-isoindol-2-yl)methyl]prop-2-enenitrile | 355.4 |
| 1286. | 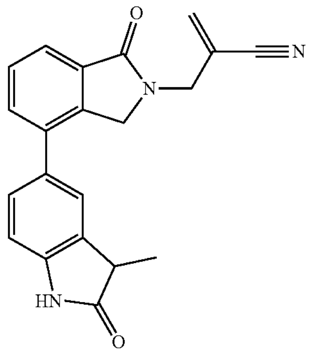 [SMILES: C=C(C#N)CN1Cc2c(cccc2-c2ccc3c(c2)C(C)C(=O)N3)C1=O] | 2-{[4-(3-methyl-2-oxo-2,3-dihydro-1H-indol-5-yl)-1-oxo-2,3-dihydro-1H-isoindol-2-yl]methyl}prop-2-enenitrile | 343.4 |
| 1287. | 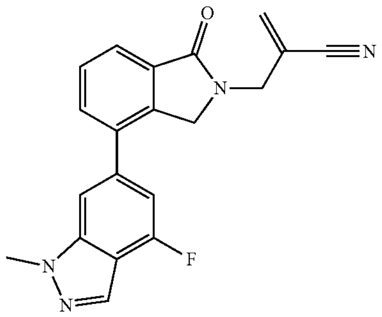 [SMILES: C=C(C#N)CN1Cc2c(cccc2-c2cc(F)c3cnn(C)c3c2)C1=O] | 2-{[4-(4-fluoro-1-methyl-1H-indazol-6-yl)-1-oxo-2,3-dihydro-1H-isoindol-2-yl]methyl}prop-2-enenitrile | 346.4 |

TABLE 15-continued
| Cpd. No. | Structure | IUPAC | MW (g/mol) |
|---|---|---|---|
| 1288. | 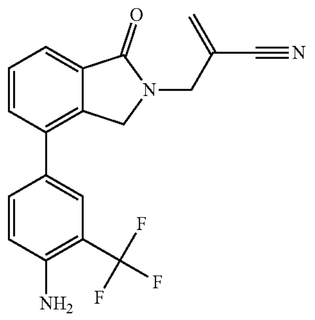 [SMILES: C=C(C#N)CN1Cc2c(cccc2-c2ccc(N)c(C(F)(F)F)c2)C1=O] | 2-({4-[4-amino-3-(trifluoromethyl)phenyl]-1-oxo-2,3-dihydro-1H-isoindol-2-yl}methyl)prop-2-enenitrile | 357.3 |
| 1289. | 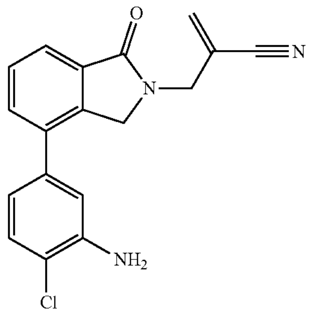 [SMILES: C=C(C#N)CN1Cc2c(cccc2-c2ccc(Cl)c(N)c2)C1=O] | 2-{[4-(3-amino-4-chlorophenyl)-1-oxo-2,3-dihydro-1H-isoindol-2-yl]methyl}prop-2-enenitrile | 323.8 |
| 1290. | 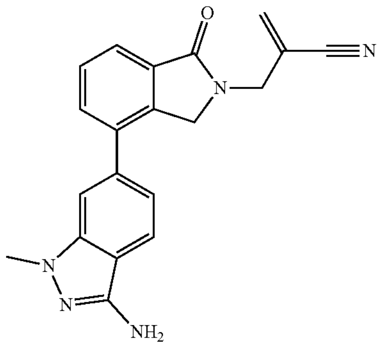 [SMILES: C=C(C#N)CN1Cc2c(cccc2-c2ccc3c(N)nn(C)c3c2)C1=O] | 2-{[4-(3-amino-1-methyl-1H-indazol-6-yl)-1-oxo-2,3-dihydro-1H-isoindol-2-yl]methyl}prop-2-enenitrile | 343.4 |
| 1291. | 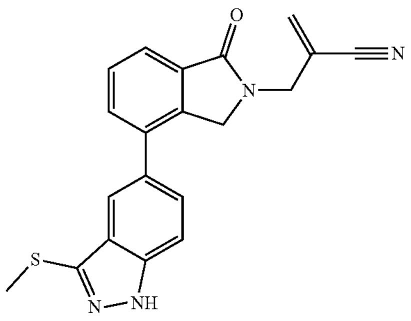 [SMILES: C=C(C#N)CN1Cc2c(cccc2-c2ccc3[nH]nc(SC)c3c2)C1=O] | 2-({4-[3-(methylsulfanyl)-1H-indazol-5-yl]-1-oxo-2,3-dihydro-1H-isoindol-2-yl}methyl)prop-2-enenitrile | 360.4 |

TABLE 15-continued
| Cpd. No. | Structure | IUPAC | MW (g/mol) |
|---|---|---|---|
| 1292. | 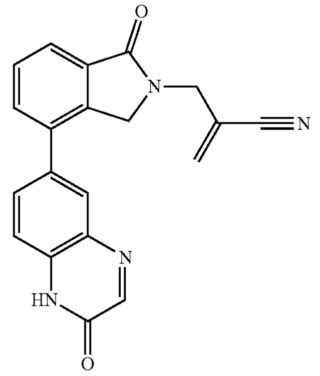 [SMILES: C=C(C#N)CN1Cc2c(cccc2-c2ccc3[nH]c(=O)cnc3c2)C1=O] | 2-{[1-oxo-4-(2-oxo-1,2-dihydroquinoxalin-6-yl)-2,3-dihydro-1H-isoindol-2-yl]methyl}prop-2-enenitrile | 342.4 |
| 1293. | 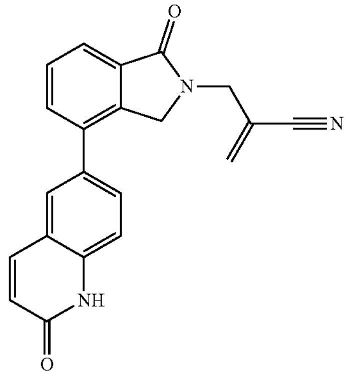 [SMILES: C=C(C#N)CN1Cc2c(cccc2-c2ccc3[nH]c(=O)ccc3c2)C1=O] | 2-{[1-oxo-4-(2-oxo-1,2-dihydroquinolin-6-yl)-2,3-dihydro-1H-isoindol-2-yl]methyl}prop-2-enenitrile | 341.4 |
| 1294. | 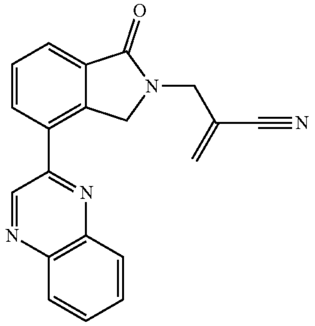 [SMILES: C=C(C#N)CN1Cc2c(cccc2-c2cnc3ccccc3n2)C1=O] | 2-{[1-oxo-4-(quinoxalin-2-yl)-2,3-dihydro-1H-isoindol-2-yl]methyl}prop-2-enenitrile | 326.4 |
| 1295. | 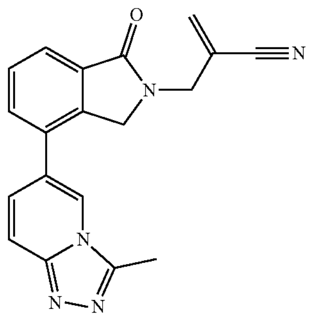 [SMILES: C=C(C#N)CN1Cc2c(cccc2-c2ccc3nnc(C)n3c2)C1=O] | 2-[(4-{3-methyl-[1,2,4]triazolo[4,3-a]pyridin-6-yl}-1-oxo-2,3-dihydro-1H-isoindol-2-yl)methyl]prop-2-enenitrile | 329.4 |

TABLE 15-continued

| Cpd. No. | Structure | IUPAC | MW (g/mol) |
|---|---|---|---|
| 1296. | 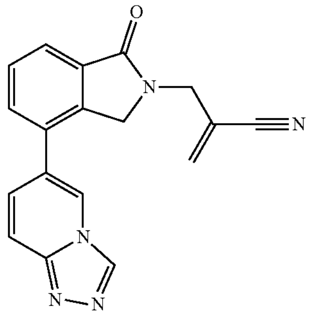 [SMILES: C=C(C#N)CN1Cc2c(cccc2-c2ccc3nncn3c2)C1=O] | 2-[(1-oxo-4-{[1,2,4]triazolo[4,3-a]pyridin-6-yl}-2,3-dihydro-1H-isoindol-2-yl)methyl]prop-2-enenitrile | 315.3 |
| 1297. | 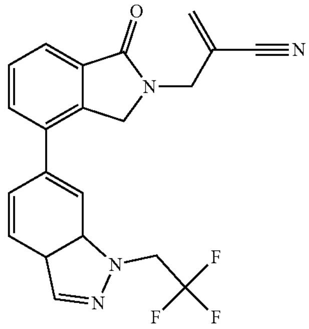 [SMILES: C=C(C#N)CN1Cc2c(cccc2C2=CC3C(C=C2)C=NN3CC(F)(F)F)C1=O] | 2-({1-oxo-4-[1-(2,2,2-trifluoroethyl)-1H-indazol-6-yl]-2,3-dihydro-1H-isoindol-2-yl}methyl)prop-2-enenitrile | 396.4 |
| 1298. | 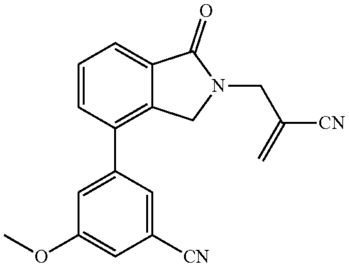 [SMILES: C=C(C#N)CN1Cc2c(cccc2-c2cc(C#N)cc(OC)c2)C1=O] | 3-[2-(2-cyano-2-methylideneethyl)-1-oxo-2,3-dihydro-1H-isoindol-4-yl]-5-methoxybenzonitrile | 329.4 |
| 1299. | 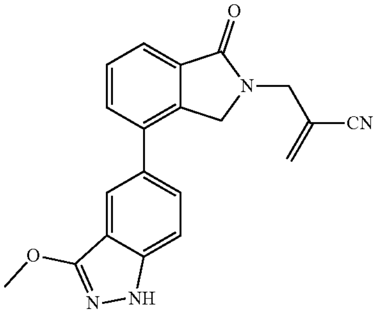 [SMILES: C=C(C#N)CN1Cc2c(cccc2-c2ccc3[nH]nc(OC)c3c2)C1=O] | 2-{[4-(3-methoxy-1H-indazol-5-yl)-1-oxo-2,3-dihydro-1H-isoindol-2-yl]methyl}prop-2-enenitrile | 344.4 |
| 1300. | 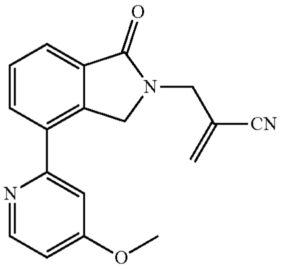 [SMILES: C=C(C#N)CN1Cc2c(cccc2-c2cc(OC)ccn2)C1=O] | 2-{[4-(4-methoxypyridin-2-yl)-1-oxo-2,3-dihydro-1H-isoindol-2-yl]methyl}prop-2-enenitrile | 305.3 |

TABLE 15-continued

| Cpd. No. | Structure | IUPAC | MW (g/mol) |
|---|---|---|---|
| 1301. | 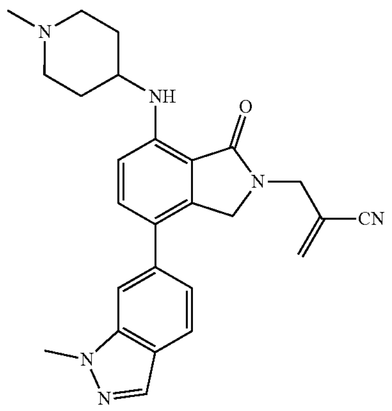 [SMILES: C=C(C#N)CN1Cc2c(-c3ccc4cnn(C)c4c3)ccc(NC3CCN(C)CC3)c2C1=O] | 2-{[4-(1-methyl-1H-indazol-6-yl)-7-[(1-methylpiperidin-4-yl)amino]-1-oxo-2,3-dihydro-1H-isoindol-2-yl]methyl}prop-2-enenitrile | 440.6 |
| 1302. | 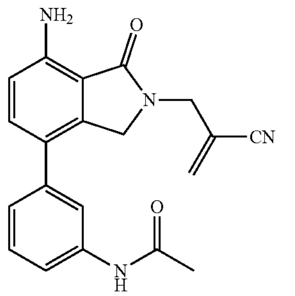 [SMILES: C=C(C#N)CN1Cc2c(-c3cccc(NC(C)=O)c3)ccc(N)c2C1=O] | N-{3-[7-amino-2-(2-cyano-2-methylideneethyl)-1-oxo-2,3-dihydro-1H-isoindol-4-yl]phenyl}acetamide | 346.4 |
| 1303. | 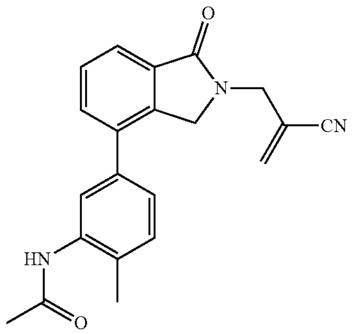 [SMILES: C=C(C#N)CN1Cc2c(cccc2-c2ccc(C)c(NC(C)=O)c2)C1=O] | N-{5-[2-(2-cyano-2-methylideneethyl)-1-oxo-2,3-dihydro-1H-isoindol-4-yl]-2-methylphenyl}acetamide | 345.4 |
| 1304. | 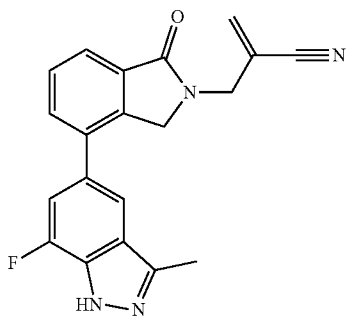 [SMILES: C=C(C#N)CN1Cc2c(cccc2-c2cc(F)c3[nH]nc(C)c3c2)C1=O] | 2-{[4-(7-fluoro-3-methyl-1H-indazol-5-yl)-1-oxo-2,3-dihydro-1H-isoindol-2-yl]methyl}prop-2-enenitrile | 346.4 |

TABLE 15-continued
| Cpd. No. | Structure | IUPAC | MW (g/mol) |
|---|---|---|---|
| 1305. | 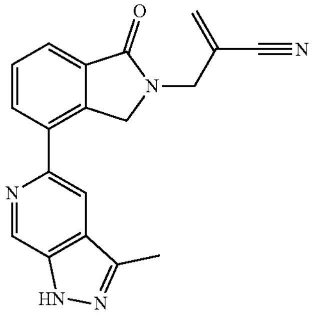 [SMILES: C=C(C#N)CN1Cc2c(cccc2-c2cc3c(C)n[nH]c3cn2)C1=O] | 2-[(4-{3-methyl-1H-pyrazolo[3,4-c]pyridin-5-yl}-1-oxo-2,3-dihydro-1H-isoindol-2-yl)methyl]prop-2-enenitrile | 329.4 |
| 1306. | 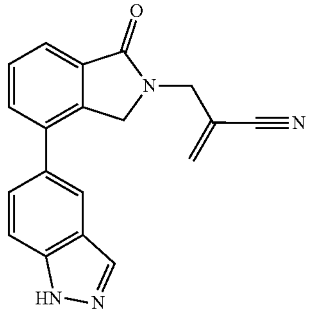 [SMILES: C=C(C#N)CN1Cc2c(cccc2-c2ccc3[nH]ncc3c2)C1=O] | 2-{[4-(1H-indazol-5-yl)-1-oxo-2,3-dihydro-1H-isoindol-2-yl]methyl}prop-2-enenitrile | 314.3 |
| 1307. | 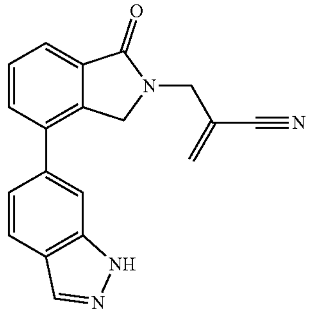 [SMILES: C=C(C#N)CN1Cc2c(cccc2-c2ccc3cn[nH]c3c2)C1=O] | 2-{[4-(1H-indazol-6-yl)-1-oxo-2,3-dihydro-1H-isoindol-2-yl]methyl}prop-2-enenitrile | 314.3 |
| 1308. | 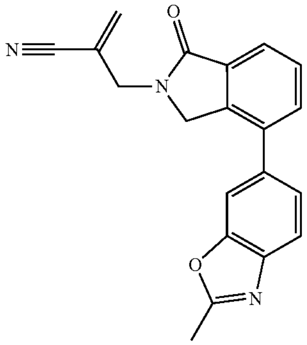 [SMILES: C=C(C#N)CN1Cc2c(cccc2-c2ccc3nc(C)oc3c2)C1=O] | 2-{[4-(2-methyl-1,3-benzoxazol-6-yl)-1-oxo-2,3-dihydro-1H-isoindol-2-yl]methyl}prop-2-enenitrile | 329.4 |

TABLE 15-continued
| Cpd. No. | Structure | IUPAC | MW (g/mol) |
|---|---|---|---|
| 1309. | 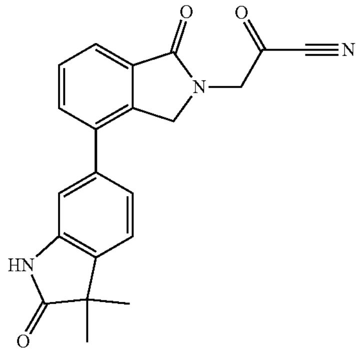 [SMILES: CC1(C)C(=O)Nc2cc(-c3cccc4c3CN(CC(=O)C#N)C4=O)ccc21] | 2-{[4-(3,3-dimethyl-2-oxo-2,3-dihydro-1H-indol-6-yl)-1-oxo-2,3-dihydro-1H-isoindol-2-yl]methyl}prop-2-enenitrile | 357.4 |
| 1310. | 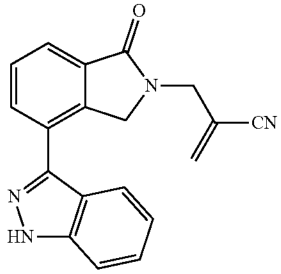 [SMILES: C=C(C#N)CN1Cc2c(cccc2-c2n[nH]c3ccccc23)C1=O] | 2-{[4-(1H-indazol-3-yl)-1-oxo-2,3-dihydro-1H-isoindol-2-yl]methyl}prop-2-enenitrile | 314.3 |
| 1311. | 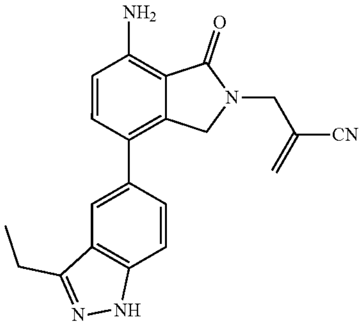 [SMILES: C=C(C#N)CN1Cc2c(-c3ccc4[nH]nc(CC)c4c3)ccc(N)c2C1=O] | 2-{[7-amino-4-(3-ethyl-1H-indazol-5-yl)-1-oxo-2,3-dihydro-1H-isoindol-2-yl]methyl}prop-2-enenitrile | 357.4 |
| 1312. | 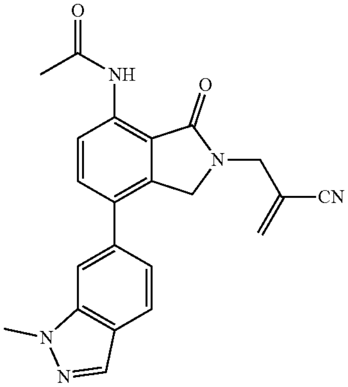 [SMILES: C=C(C#N)CN1Cc2c(-c3ccc4cnn(C)c4c3)ccc(NC(C)=O)c2C1=O] | N-[2-(2-cyano-2-methylideneethyl)-7-(1-methyl-1H-indazol-6-yl)-3-oxo-2,3-dihydro-1H-isoindol-4-yl]acetamide | 385.4 |

TABLE 15-continued

| Cpd. No. | Structure | IUPAC | MW (g/mol) |
|---|---|---|---|
| 1313. | 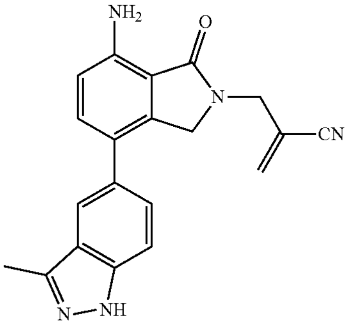 [SMILES: C=C(C#N)CN1Cc2c(-c3ccc4[nH]nc(C)c4c3)ccc(N)c2C1=O] | 2-{[7-amino-4-(3-methyl-1H-indazol-5-yl)-1-oxo-2,3-dihydro-1H-isoindol-2-yl]methyl}prop-2-enenitrile | 343.4 |
| 1314. | 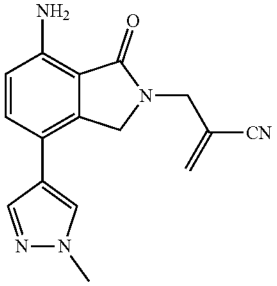 [SMILES: C=C(C#N)CN1Cc2c(-c3cnn(C)c3)ccc(N)c2C1=O] | 2-{[7-amino-4-(1-methyl-1H-pyrazol-4-yl)-1-oxo-2,3-dihydro-1H-isoindol-2-yl]methyl}prop-2-enenitrile | 293.3 |
| 1315. | 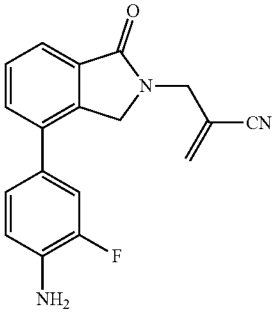 | 2-{[4-(4-amino-3-fluorophenyl)-1-oxo-2,3-dihydro-1H-isoindol-2-yl]methyl}prop-2-enenitrile | 307.3 |
| 1316. | 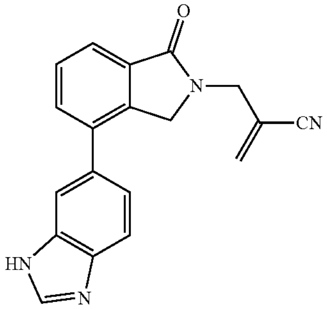 [SMILES: C=C(C#N)CN1Cc2c(cccc2-c2ccc3nc[nH]c3c2)C1=O] | 2-{[4-(1H-1,3-benzothiazol-6-yl)-1-oxo-2,3-dihydro-1H-isoindol-2-yl]methyl}prop-2-enenitrile | 314.3 |
| 1317. | 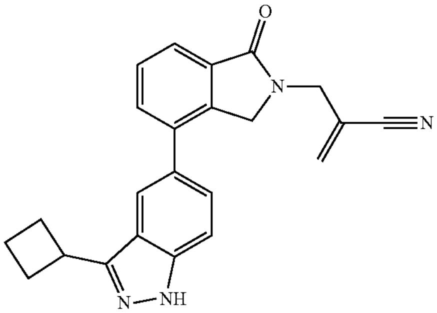 [SMILES: C=C(C#N)CN1Cc2c(cccc2-c2ccc3[nH]nc(C4CCC4)c3c2)C1=O] | 2-{[4-(3-cyclobutyl-1H-indazol-5-yl)-1-oxo-2,3-dihydro-1H-isoindol-2-yl]methyl}prop-2-enenitrile | 368.4 |

TABLE 15-continued
| Cpd. No. | Structure | IUPAC | MW (g/mol) |
|---|---|---|---|
| 1318. | 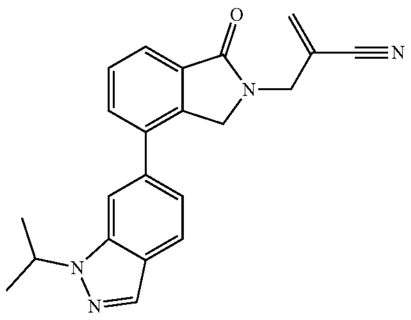 [SMILES: C=C(C#N)CN1Cc2c(cccc2-c2ccc3cnn(C(C)C)c3c2)C1=O] | 2-({1-oxo-4-[1-(propan-2-yl)-1H-indazol-6-yl]-2,3-dihydro-1H-isoindol-2-yl}methyl)prop-2-enenitrile | 356.4 |
| 1319. | 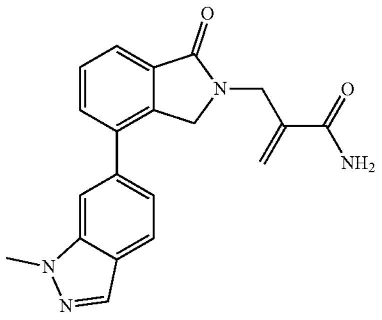 [SMILES: C=C(CN1Cc2c(cccc2-c2ccc3cnn(C)c3c2)C1=O)C(N)=O] | 2-{[4-(1-methyl-1H-indazol-6-yl)-1-oxo-2,3-dihydro-1H-isoindol-2-yl]methyl}prop-2-enenitrile | 346.4 |
| 1320. | 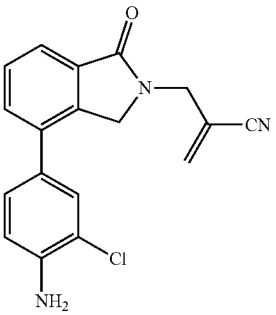 [SMILES: C=C(C#N)CN1Cc2c(cccc2-c2ccc(N)c(Cl)c2)C1=O] | 2-{[4-(4-amino-3-chlorophenyl)-1-oxo-2,3-dihydro-1H-isoindol-2-yl]methyl}prop-2-enenitrile | 323.8 |
| 1321. | 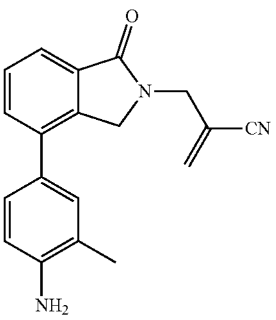 [SMILES: C=C(C#N)CN1Cc2c(cccc2-c2ccc(N)c(C)c2)C1=O] | 2-{[4-(4-amino-3-methylphenyl)-1-oxo-2,3-dihydro-1H-isoindol-2-yl]methyl}prop-2-enenitrile | 303.4 |

TABLE 15-continued
| Cpd. No. | Structure | IUPAC | MW (g/mol) |
| --- | --- | --- | --- |
| 1322. | 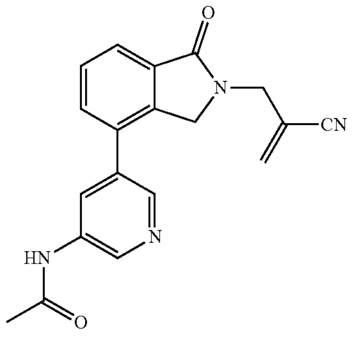 [SMILES: C=C(C#N)CN1Cc2c(cccc2-c2cncc(NC(C)=O)c2)C1=O] | N-{5-[2-(2-cyano-2-methylideneethyl)-1-oxo-2,3-dihydro-1H-isoindol-4-yl]pyridin-3-yl}acetamide | 332.4 |
| 1323. | 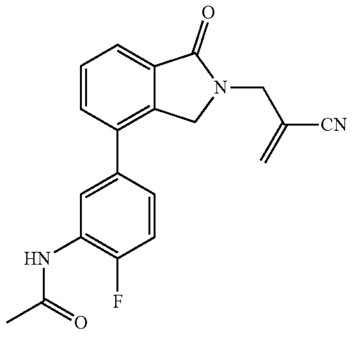 | N-{5-[2-(2-cyano-2-methylideneethyl)-1-oxo-2,3-dihydro-1H-isoindol-4-yl]-2-fluorophenyl}acetamide | 349.4 |
| 1324. | 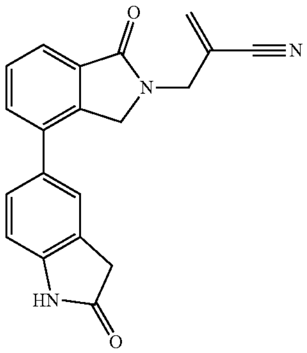 [SMILES: C=C(C#N)CN1Cc2c(cccc2-c2ccc3c(c2)CC(=O)N3)C1=O] | 2-{[1-oxo-4-(2-oxo-2,3-dihydro-1H-indol-5-yl)-2,3-dihydro-1H-isoindol-2-yl]methyl}prop-2-enenitrile | 329.4 |
| 1325. | 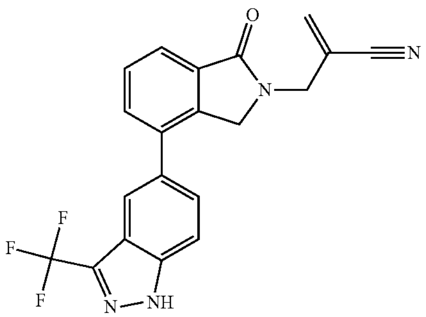 [SMILES: C=C(C#N)CN1Cc2c(cccc2-c2ccc3[nH]nc(C(F)(F)F)c3c2)C1=O] | 2-({1-oxo-4-[3-(trifluoromethyl)-1H-indazol-5-yl]-2,3-dihydro-1H-isoindol-2-yl}methyl)prop-2-enenitrile | 382.3 |

TABLE 15-continued

| Cpd. No. | Structure | IUPAC | MW (g/mol) |
|---|---|---|---|
| 1326. | 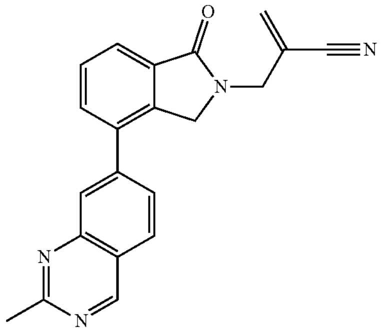 [SMILES: C=C(C#N)CN1Cc2c(cccc2-c2ccc3cnc(C)nc3c2)C1=O] | 2-{[4-(2-methylquinazolin-7-yl)-1-oxo-2,3-dihydro-1H-isoindol-2-yl]methyl}prop-2-enenitrile | 340.4 |
| 1327. | 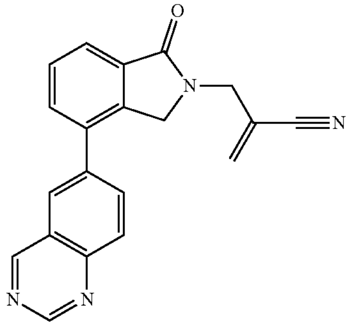 [SMILES: C=C(C#N)CN1Cc2c(cccc2-c2ccc3ncncc3c2)C1=O] | 2-{[1-oxo-4-(quinazolin-6-yl)-2,3-dihydro-1H-isoindol-2-yl]methyl}prop-2-enenitrile | 326.4 |
| 1328. | 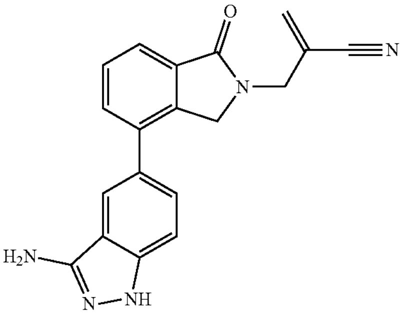 [SMILES: C=C(C#N)CN1Cc2c(cccc2-c2ccc3[nH]nc(N)c3c2)C1=O] | 2-{[4-(3-amino-1H-indazol-5-yl)-1-oxo-2,3-dihydro-1H-isoindol-2-yl]methyl}prop-2-enenitrile | 329.4 |
| 1329. | 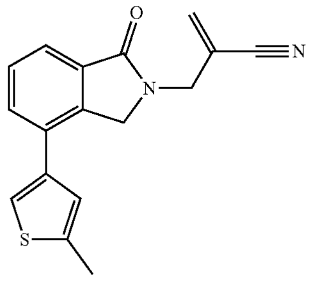 [SMILES: C=C(C#N)CN1Cc2c(cccc2-c2csc(C)c2)C1=O] | 2-{[4-(5-methylthiophen-3-yl)-1-oxo-2,3-dihydro-1H-isoindol-2-yl]methyl}prop-2-enenitrile | 294.4 |
| 1330. | 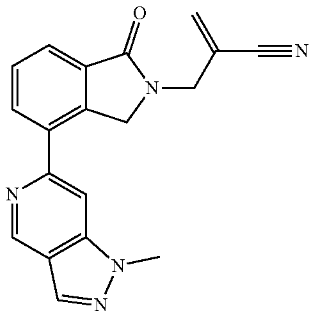 [SMILES: C=C(C#N)CN1Cc2c(cccc2-c2cc3c(cn2)cnn3C)C1=O] | 2-[(4-{1-methyl-1H-pyrazolo[4,3-c]pyridin-6-yl}-1-oxo-2,3-dihydro-1H-isoindol-2-yl)methyl]prop-2-enenitrile | 329.4 |

TABLE 15-continued
| Cpd. No. | Structure | IUPAC | MW (g/mol) |
|---|---|---|---|
| 1331. | 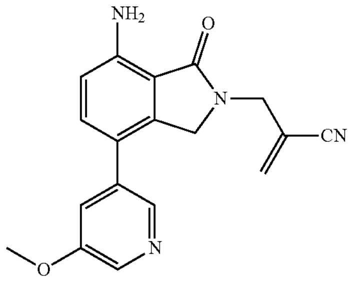 [SMILES: C=C(C#N)CN1Cc2c(-c3cncc(OC)c3)ccc(N)c2C1=O] | 2-{[7-amino-4-(5-methoxypyridin-3-yl)-1-oxo-2,3-dihydro-1H-isoindol-2-yl]methyl}prop-2-enenitrile | 320.4 |
| 1332. | 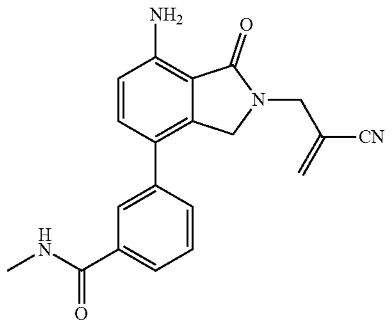 [SMILES: C=C(C#N)CN1Cc2c(-c3cccc(C(=O)NC)c3)ccc(N)c2C1=O] | 3-[7-amino-2-(2-cyano-2-methylideneethyl)-1-oxo-2,3-dihydro-1H-isoindol-4-yl]-N-methylbenzamide | 346.4 |
| 1333. | 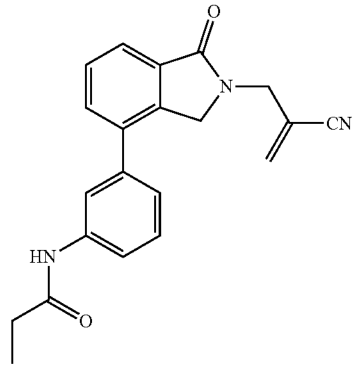 [SMILES: C=C(C#N)CN1Cc2c(cccc2-c2cccc(NC(=O)CC)c2)C1=O] | N-{3-[2-(2-cyano-2-methylideneethyl)-1-oxo-2,3-dihydro-1H-isoindol-4-yl]phenyl}propanamide | 345.4 |
| 1334. | 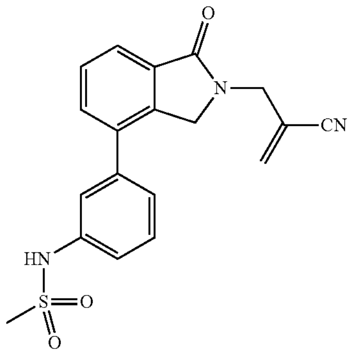 [SMILES: C=C(C#N)CN1Cc2c(cccc2-c2cccc(NS(C)(=O)=O)c2)C1=O] | N-{3-[2-(2-cyano-2-methylideneethyl)-1-oxo-2,3-dihydro-1H-isoindol-4-yl]phenyl}methanesulfonamide | 367.4 |

TABLE 15-continued
| Cpd. No. | Structure | IUPAC | MW (g/mol) |
|---|---|---|---|
| 1335. | 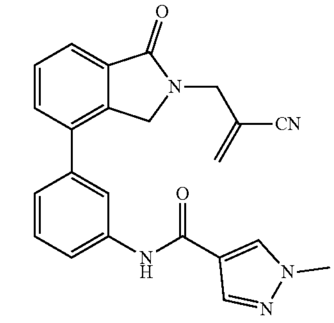 [SMILES: C=C(C#N)CN1Cc2c(cccc2-c2cccc(NC(=O)c3cnn(C)c3)c2)C1=O] | N-{3-[2-(2-cyano-2-methylideneethyl)-1-oxo-2,3-dihydro-1H-isoindol-4-yl]phenyl}-1-methyl-1H-pyrazole-4-carboxamide | 397.4 |
| 1336. | 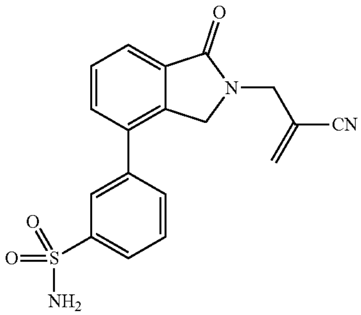 [SMILES: C=C(C#N)CN1Cc2c(cccc2-c2cccc(S(N)(=O)=O)c2)C1=O] | 3-[2-(2-cyano-2-methylideneethyl)-1-oxo-2,3-dihydro-1H-isoindol-4-yl]benzene-1-sulfonamide | 353.4 |
| 1337. | 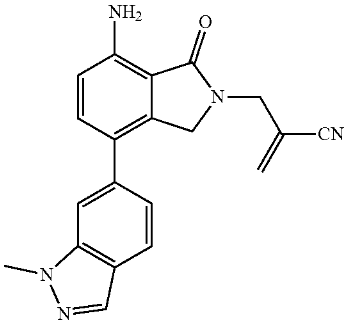 [SMILES: C=C(C#N)CN1Cc2c(-c3ccc4cnn(C)c4c3)ccc(N)c2C1=O] | 2-{[7-amino-4-(1-methyl-1H-indazol-6-yl)-1-oxo-2,3-dihydro-1H-isoindol-2-yl]methyl}prop-2-enenitrile | 343.4 |
| 1338. | 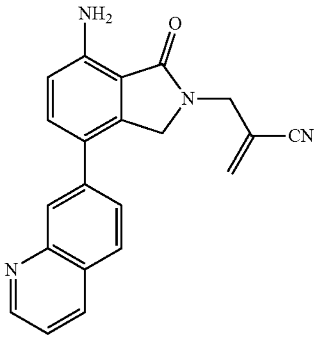 [SMILES: C=C(C#N)CN1Cc2c(-c3ccc4cccnc4c3)ccc(N)c2C1=O] | 2-{[1-oxo-4-(quinolin-7-yl)-2,3-dihydro-1H-isoindol-2-yl]methyl}prop-2-enenitrile | 325.4 |

TABLE 15-continued

| Cpd. No. | Structure | IUPAC | MW (g/mol) |
|---|---|---|---|
| 1339. | 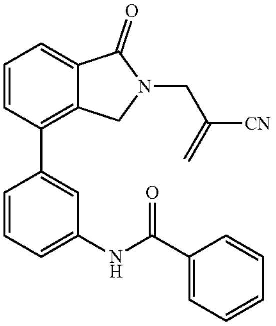 [SMILES: C=C(C#N)CN1Cc2c(cccc2-c2cccc(NC(=O)c3ccccc3)c2)C1=O] | N-{3-[2-(2-cyano-2-methylideneethyl)-1-oxo-2,3-dihydro-1H-isoindol-4-yl]phenyl}benzamide | 393.4 |
| 1340. | 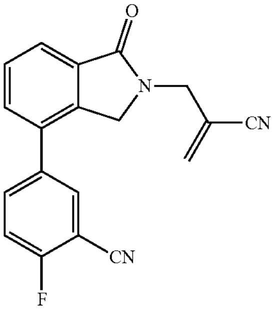 [SMILES: C=C(C#N)CN1Cc2c(cccc2-c2ccc(F)c(C#N)c2)C1=O] | 5-[2-(2-cyano-2-methylideneethyl)-1-oxo-2,3-dihydro-1H-isoindol-4-yl]-4-fluorobenzonitrile | 317.3 |
| 1341. | 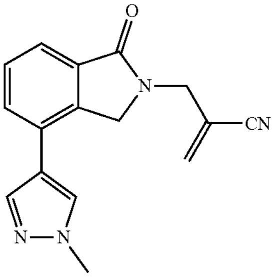 [SMILES: C=C(C#N)CN1Cc2c(cccc2-c2cnn(C)c2)C1=O] | 2-{[4-(1-methyl-1H-pyrazol-4-yl)-1-oxo-2,3-dihydro-1H-isoindol-2-yl]methyl}prop-2-enenitrile | 278.3 |
| 1342. | 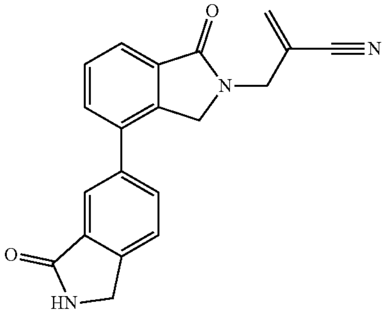 [SMILES: C=C(C#N)CN1Cc2c(cccc2-c2ccc3c(c2)C(=O)NC3)C1=O] | 2-({1,3'-dioxo-1H,1'H,2H,2'H,3H,3'H-[4,5'-biisoindol]-2-yl}methyl)prop-2-enenitrile | 329.4 |
| 1343. | 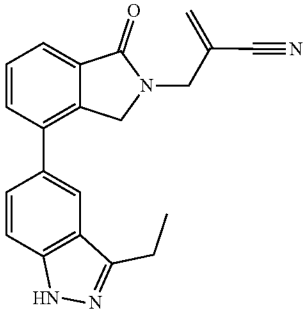 [SMILES: C=C(C#N)CN1Cc2c(cccc2-c2ccc3[nH]nc(CC)c3c2)C1=O] | 2-{[4-(3-ethyl-1H-indazol-5-yl)-1-oxo-2,3-dihydro-1H-isoindol-2-yl]methyl}prop-2-enenitrile | 342.4 |

TABLE 15-continued
| Cpd. No. | Structure | IUPAC | MW (g/mol) |
|---|---|---|---|
| 1344. | 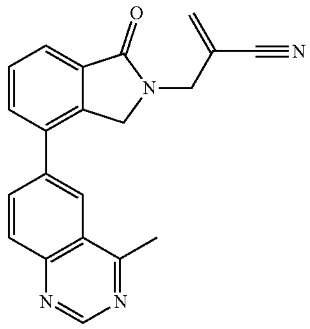 [SMILES: C=C(C#N)CN1Cc2c(cccc2-c2ccc3ncnc(C)c3c2)C1=O] | 2-{[4-(4-methylquinazolin-6-yl)-1-oxo-2,3-dihydro-1H-isoindol-2-yl]methyl}prop-2-enenitrile | 340.4 |
| 1345. | 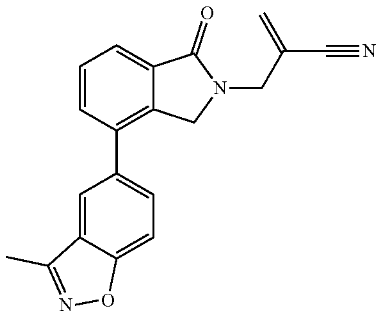 [SMILES: C=C(C#N)CN1Cc2c(cccc2-c2ccc3onc(C)c3c2)C1=O] | 2-{[4-(3-methyl-1,2-benzoxazol-5-yl)-1-oxo-2,3-dihydro-1H-isoindol-2-yl]methyl}prop-2-enenitrile | 329.4 |
| 1346. | 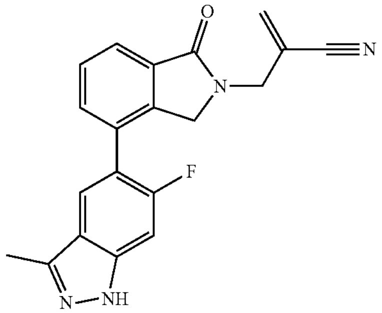 [SMILES: C=C(C#N)CN1Cc2c(cccc2-c2cc3c(C)n[nH]c3cc2F)C1=O] | 2-{[4-(6-fluoro-3-methyl-1H-indazol-5-yl)-1-oxo-2,3-dihydro-1H-isoindol-2-yl]methyl}prop-2-enenitrile | 346.4 |
| 1347. | 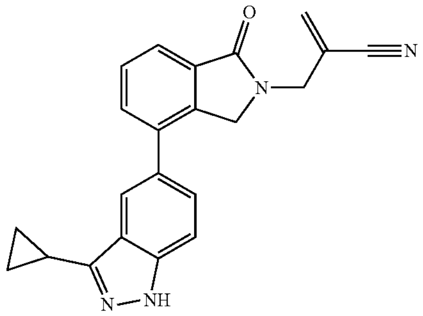 [SMILES: C=C(C#N)CN1Cc2c(cccc2-c2ccc3[nH]nc(C4CC4)c3c2)C1=O] | 2-{[4-(3-cyclopropyl-1H-indazol-5-yl)-1-oxo-2,3-dihydro-1H-isoindol-2-yl]methyl}prop-2-enenitrile | 354.4 |

TABLE 15-continued
| Cpd. No. | Structure | IUPAC | MW (g/mol) |
|---|---|---|---|
| 1348. | 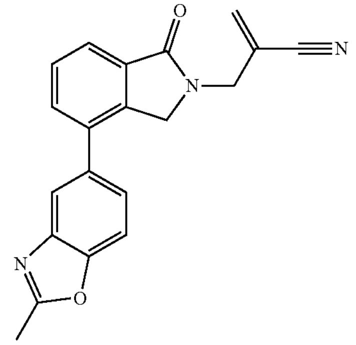 [SMILES: C=C(C#N)CN1Cc2c(cccc2-c2ccc3oc(C)nc3c2)C1=O] | 2-{[4-(2-methyl-1,3-benzoxazol-5-yl)-1-oxo-2,3-dihydro-1H-isoindol-2-yl]methyl}prop-2-enenitrile | 329.4 |
| 1349. | 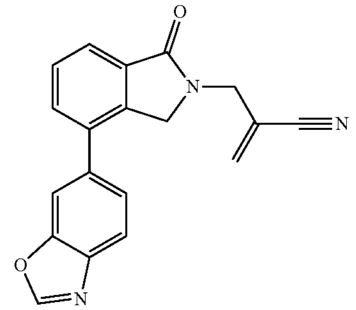 [SMILES: C=C(C#N)CN1Cc2c(cccc2-c2ccc3ncoc3c2)C1=O] | 2-{[4-(1,3-benzoxazol-6-yl)-1-oxo-2,3-dihydro-1H-isoindol-2-yl]methyl}prop-2-enenitrile | 315.3 |
| 1350. | 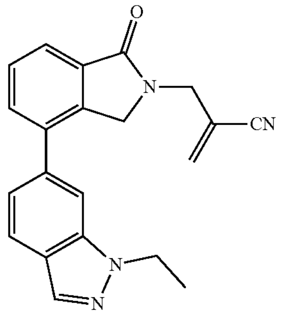 [SMILES: C=C(C#N)CN1Cc2c(cccc2-c2ccc3cnn(CC)c3c2)C1=O] | 2-{[4-(1-ethyl-1H-indazol-6-yl)-1-oxo-2,3-dihydro-1H-isoindol-2-yl]methyl}prop-2-enenitrile | 342.4 |
| 1351. | 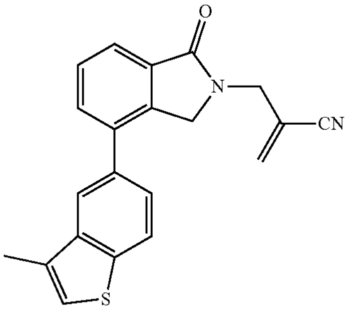 [SMILES: C=C(C#N)CN1Cc2c(cccc2-c2ccc3scc(C)c3c2)C1=O] | 2-{[4-(3-methyl-1-benzothiophen-5-yl)-1-oxo-2,3-dihydro-1H-isoindol-2-yl]methyl}prop-2-enenitrile | 344.4 |

TABLE 15-continued
| Cpd. No. | Structure | IUPAC | MW (g/mol) |
|---|---|---|---|
| 1352. | 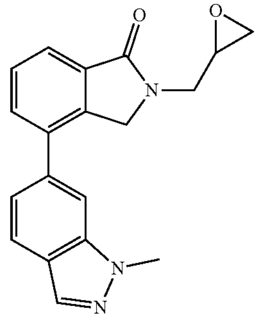 [SMILES: Cn1ncc2ccc(-c3cccc4c3CN(CC3CO3)C4=O)cc21] | 4-(1-methyl-1H-indazol-6-yl)-2-[(oxiran-2-yl)methyl]-2,3-dihydro-1H-isoindol-1-one | 319.4 |
| 1353. | 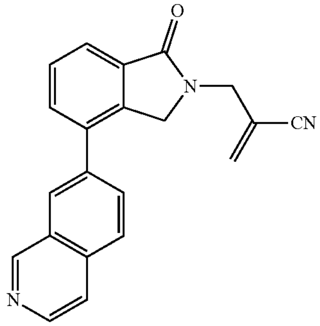 [SMILES: C=C(C#N)CN1Cc2c(cccc2-c2ccc3ccncc3c2)C1=O] | 2-{[4-(isoquinolin-7-yl)-1-oxo-2,3-dihydro-1H-isoindol-2-yl]methyl}prop-2-enenitrile | 325.4 |
| 1354. | 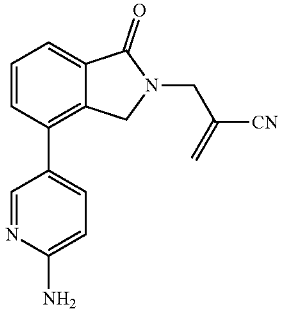 [SMILES: C=C(C#N)CN1Cc2c(cccc2-c2ccc(N)nc2)C1=O] | 2-{[4-(6-aminopyridin-3-yl)-1-oxo-2,3-dihydro-1H-isoindol-2-yl]methyl}prop-2-enenitrile | 290.3 |
| 1355. | 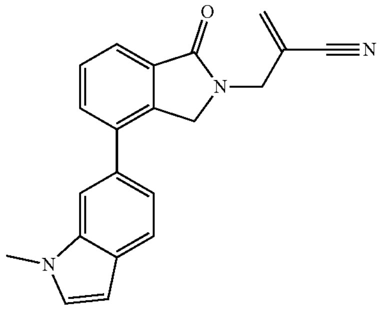 [SMILES: C=C(C#N)CN1Cc2c(cccc2-c2ccc3ccn(C)c3c2)C1=O] | 2-{[4-(1-metjhyl-1H-indol-6-yl)-1-oxo-2,3-dihydro-1H-isoindol-2-yl]methyl}prop-2-enenitrile | 327.4 |

TABLE 15-continued

| Cpd. No. | Structure | IUPAC | MW (g/mol) |
|---|---|---|---|
| 1356. | 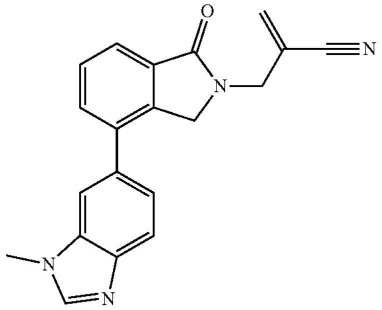 [SMILES: C=C(C#N)CN1Cc2c(cccc2-c2ccc3ncn(C)c3c2)C1=O] | 2-{[4-(1-methyl-1H-1,3-benzodiazol-6-yl)-1-oxo-2,3-dihydro-1H-isoindol-2-yl]methyl}prop-2-enenitrile | 328.4 |
| 1357. | 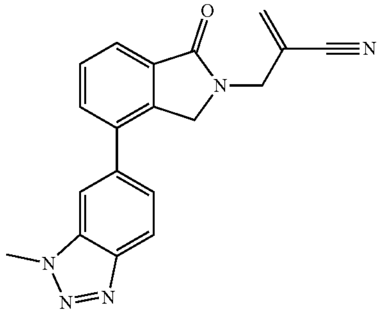 [SMILES: C=C(C#N)CN1Cc2c(cccc2-c2ccc3nnn(C)c3c2)C1=O] | 2-{[4-(1-methyl-1H-1,2,3-benzotriazol-6-yl)-1-oxo-2,3-dihydro-1H-isoindol-2-yl]methyl}prop-2-enenitrile | 329.4 |
| 1358. | 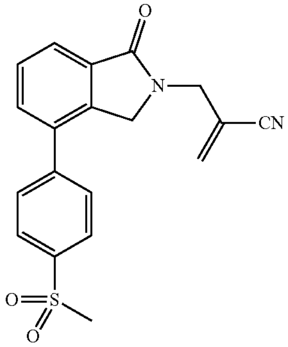 [SMILES: C=C(C#N)CN1Cc2c(cccc2-c2ccc(S(C)(=O)=O)cc2)C1=O] | 2-{[4-(4-methanesulfonylphenyl)-1-oxo-2,3-dihydro-1H-isoindol-2-yl]methyl}prop-2-enenitrile | 352.4 |
| 1359. | 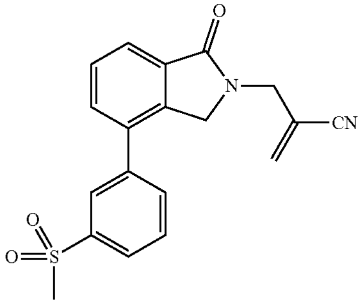 [SMILES: C=C(C#N)CN1Cc2c(cccc2-c2cccc(S(C)(=O)=O)c2)C1=O] | 2-{[4-(3-methanesulfonylphenyl)-1-oxo-2,3-dihydro-1H-isoindol-2-yl]methyl}prop-2-enenitrile | 352.4 |
| 1360. | 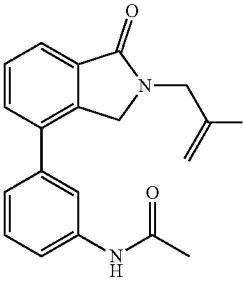 | N-{3-[2-(2-cyano-2-methylideneethyl)-1-oxo-2,3-dihydro-1H-isoindol-4-yl]phenyl}acetamide | 331.4 |

TABLE 15-continued
| Cpd. No. | Structure | IUPAC | MW (g/mol) |
|---|---|---|---|
| 1361. | 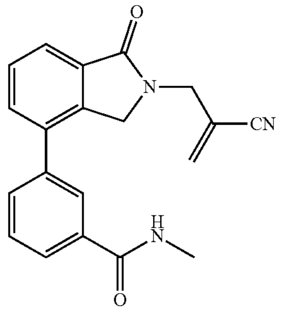 [SMILES: C=C(C#N)CN1Cc2c(cccc2-c2cccc(C(=O)NC)c2)C1=O] | 3-[2-(2-cyano-2-methylideneethyl)-1-oxo-2,3-dihydro-1H-isoindol-4-yl]-N-methylbenzamide | 331.4 |
| 1362. | 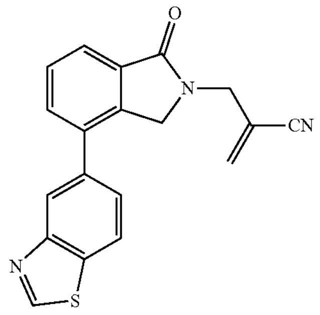 [SMILES: C=C(C#N)CN1Cc2c(cccc2-c2ccc3scnc3c2)C1=O] | 2-{[4-(1,3-benzothiazol-5-yl)-1-oxo-2,3-dihydro-1H-isoindol-2-yl]methyl}prop-2-enenitrile | 331.4 |
| 1363. | 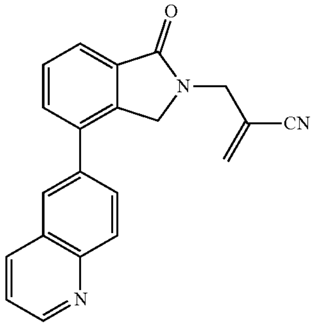 [SMILES: C=C(C#N)CN1Cc2c(cccc2-c2ccc3ncccc3c2)C1=O] | 2-{[1-oxo-4-(quinolin-6-yl)-2,3-dihydro-1H-isoindol-2-yl]methyl}prop-2-enenitrile | 325.4 |
| 1364. | 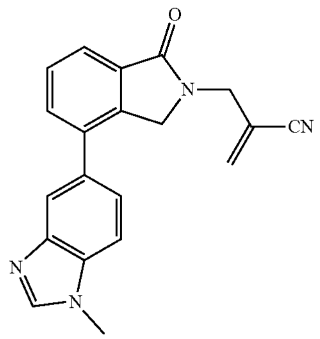 [SMILES: C=C(C#N)CN1Cc2c(cccc2-c2ccc3c(c2)ncn3C)C1=O] | 2-{[4-(1-methyl-1H-1,3-benzodiazol-5-yl)-1-oxo-2,3-dihydro-1H-isoindol-2-yl]methyl}prop-2-enenitrile | 328.4 |

TABLE 15-continued

| Cpd. No. | Structure | IUPAC | MW (g/mol) |
|---|---|---|---|
| 1365. | 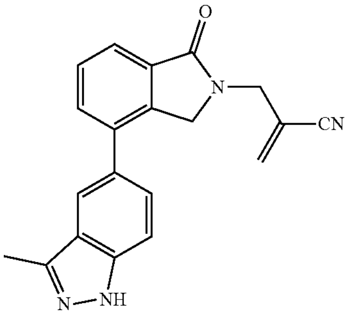 [SMILES: C=C(C#N)CN1Cc2c(cccc2-c2ccc3[nH]nc(C)c3c2)C1=O] | 2-{[4-(3-methyl-1H-indazol-5-yl)-1-oxo-2,3-dihydro-1H-isoindol-2-yl]methyl}prop-2-enenitrile | 328.4 |
| 1366. | 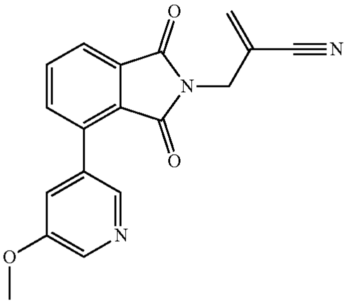 [SMILES: C=C(C#N)CN1C(=O)c2cccc(-c3cncc(OC)c3)c2C1=O] | 2-{[4-(5-methoxypyridin-3-yl)-1,3-dioxo-2,3-dihydro-1H-isoindol-2-yl]methyl}prop-2-enenitrile | 319.3 |
| 1367. | 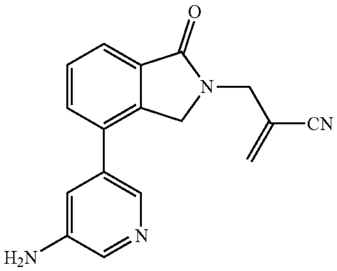 [SMILES: C=C(C#N)CN1Cc2c(cccc2-c2cncc(N)c2)C1=O] | 2-{[4-(5-aminopyridin-3-yl)-1-oxo-2,3-dihydro-1H-isoindol-2-yl]methyl}prop-2-enenitrile | 290.3 |
| 1368. | 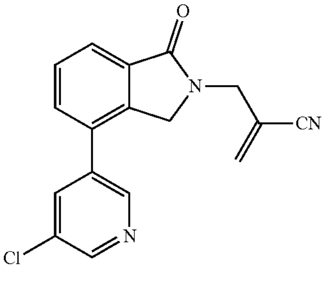 [SMILES: C=C(C#N)CN1Cc2c(cccc2-c2cncc(Cl)c2)C1=O] | 2-{[4-(5-chloropyridin-3-yl)-1-oxo-2,3-dihydro-1H-isoindol-2-yl]methyl}prop-2-enenitrile | 309.8 |
| 1369. | 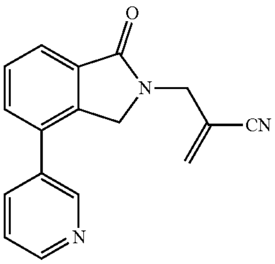 [SMILES: C=C(C#N)CN1Cc2c(cccc2-c2cccnc2)C1=O] | 2-{[1-oxo-4-(pyridin-3-yl)-2,3-dihydro-1H-isoindol-2-yl]methyl}prop-2-enenitrile | 275.3 |

TABLE 15-continued

| Cpd. No. | Structure | IUPAC | MW (g/mol) |
| --- | --- | --- | --- |
| 1370. | 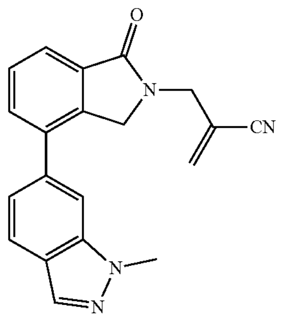 [SMILES: C=C(C#N)CN1Cc2c(cccc2-c2ccc3cnn(C)c3c2)C1=O] | 2-{[4-(1-methyl-1H-indazol-6-yl)-1-oxo-2,3-dihydro-1H-isoindol-2-yl]methyl}prop-2-enenitrile | 328.4 |
| 1371. | 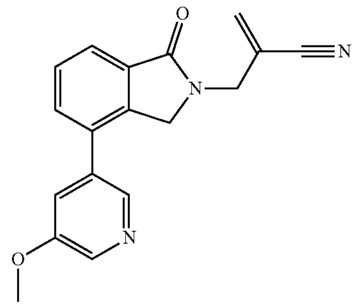 [SMILES: C=C(C#N)CN1Cc2c(cccc2-c2cncc(OC)c2)C1=O] | 2-{[4-(5-methoxypyridin-3-yl)-1-oxo-2,3-dihydro-1H-isoindol-2-yl]methyl}prop-2-enenitrile | 305.3 |
| 1372. | 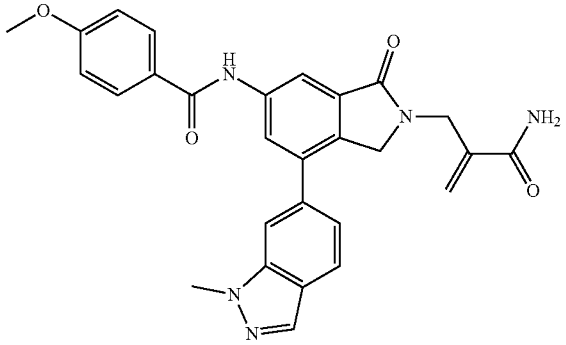 [SMILES: C=C(CN1Cc2c(cc(NC(=O)c3ccc(OC)cc3)cc2-c2ccc3cnn(C)c3c2)C1=O)C(N)=O] | N-[2-(2-carbamoyl-2-methylideneethyl)-7-(1-methyl-1H-indazol-6-yl)-3-oxo-2,3-dihydro-1H-isoindol-5-yl]-4-methoxybenzamide | 495.5 |
| 1373. | 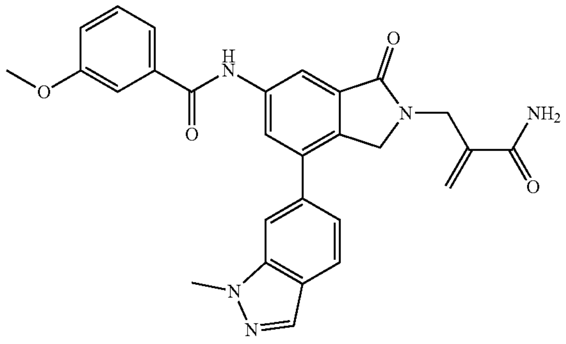 [SMILES: C=C(CN1Cc2c(cc(NC(=O)c3cccc(OC)c3)cc2-c2ccc3cnn(C)c3c2)C1=O)C(N)=O] | N-[2-(2-carbamoyl-2-methylideneethyl)-7-(1-methyl-1H-indazol-6-yl)-3-oxo-2,3-dihydro-1H-isoindol-5-yl]-3-methoxybenzamide | 495.5 |

TABLE 15-continued

| Cpd. No. | Structure | IUPAC | MW (g/mol) |
|---|---|---|---|
| 1374. | 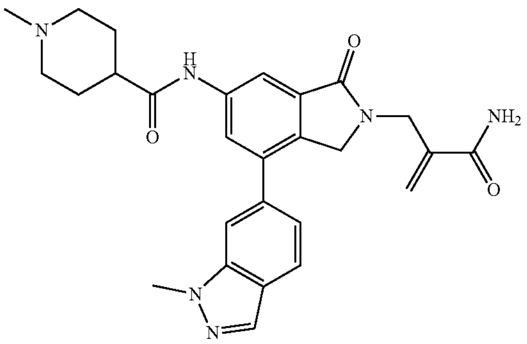 [SMILES: C=C(CN1Cc2c(cc(NC(=O)C3CCN(C)CC3)cc2-c2ccc3cnn(C)c3c2)C1=O)C(N)=O] | N-[2-(2-carbamoyl-2-methylideneethyl)-7-(1-methyl-1H-indazol-6-yl)-3-oxo-2,3-dihydro-1H-isoindol-5-yl]-1-methylpiperidine-4-carboxamide | 486.6 |
| 1375. | 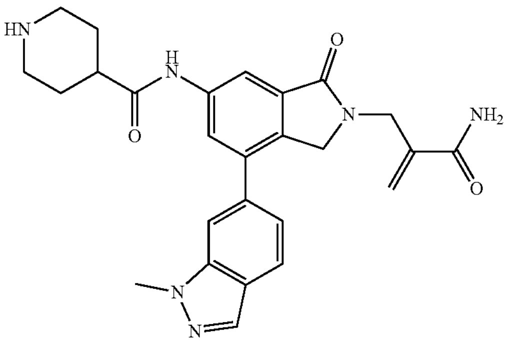 [SMILES: C=C(CN1Cc2c(cc(NC(=O)C3CCNCC3)cc2-c2ccc3cnn(C)c3c2)C1=O)C(N)=O] | N-[2-(2-carbamoyl-2-methylideneethyl)-7-(1-methyl-1H-indazol-6-yl)-3-oxo-2,3-dihydro-1H-isoindol-5-yl]piperidine-4-carboxamide | 472.5 |

EMBODIMENTS

The following non-limiting embodiments provide illustrative examples of the invention, but do not limit the scope of the disclosure.

Embodiment 1

A compound of the formula:

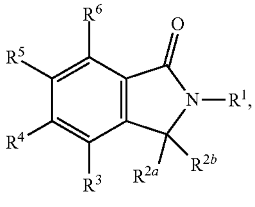

wherein:

$R^{3a}$ is

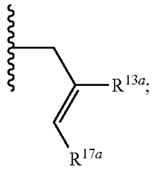

$R^{13a}$ is —C(O)$NH_2$ or —CN;

$R^{17a}$ is —CN, alkyl, aryl, heteroaryl, —$NR^7R^8$, —S$(O)_2R^7$, —$SR^7$, or $OR^7$, each which is unsubstituted or substituted, or hydrogen or halogen;

each $R^{2a}$, $R^{2b}$, $R^3$, $R^4$, $R^5$, and $R^6$ is independently alkyl, cycloalkyl, alkenyl, alkynyl, aryl, heteroaryl, heterocyclyl, —CN, —C(O)$R^9$, —C(O)$OR^9$, —C(O)$NR^9R^{10}$, —C(═N)$NR^9R^{10}$, —$OR^9$, —$SR^9$, —$NR^9R^{10}$, —$NR^9$C(O)$R^{10}$, —$NR^9$C(O)$OR^{10}$, —OC(O)$R^9$, —OC(O)$NR^9R^{10}$, —S$(O)_2R^9$, —NHS$(O)_2R^9$, —OS$(O)_2R^9$, each which is independently substituted or unsubstituted, or hydrogen or halogen; or $R^{2a}$ and $R^{2b}$ together with the carbon atom to which $R^{2a}$ and $R^{2b}$ are bound is C═O or C═S; and $R^3$, $R^4$, $R^5$, and $R^6$ is independently alkyl, cycloalkyl, alkenyl, alkynyl, aryl, heteroaryl, heterocyclyl, —CN, —C(O)$R^9$, —C(O)$OR^9$, —C(O)$NR^9R^{10}$, —C(═N)$NR^9R^{10}$, —$OR^9$, —$SR^9$, —$NR^9R^{10}$, —$NR^9$C(O)$R^{10}$, —$NR^9$C(O)$OR^{10}$, —OC(O)$R^9$, —OC(O)$NR^9R^{10}$, —S$(O)_2R^9$, —NHS$(O)_2R^9$, —OS$(O)_2R^9$, each which is independently substituted or unsubstituted, or hydrogen or halogen; or $R^3$ and $R^4$ together with the carbon atom to which $R^3$ and $R^4$ are bound form a ring, wherein the ring is unsubstituted or substituted; and each $R^{2a}$, $R^{2b}$, $R^5$ and $R^6$ is independently alkyl, cycloalkyl, alkenyl, alkynyl, aryl, heteroaryl, heterocyclyl, —CN, —C(O)$R^9$, —C(O)$OR^9$, —C(O)$NR^9R^{10}$, —C(═N)$NR^9R^{10}$, —$OR^9$, —$SR^9$, —$NR^9R^{10}$, —$NR^9$C(O)$R^{10}$, —$NR^9$C(O)$OR^{10}$, —OC(O)$R^9$, —OC(O)$NR^9R^{10}$, —S$(O)_2R^9$, —NHS$(O)_2R^9$, —OS$(O)_2R^9$, each which is independently substituted or unsubstituted, or hydrogen or halogen; or $R^4$ and $R^5$ together with the carbon atom to which $R^4$ and $R^5$ are bound form a ring, wherein the ring is unsubstituted or substituted; and each $R^{2a}$, $R^{2b}$, $R^3$, and $R^6$ is independently alkyl, cycloalkyl, alkenyl, alkynyl, aryl, heteroaryl, heterocyclyl, —CN, —C(O)$R^9$, —C(O)O$R^9$, —C(O)N$R^9R^{10}$, —C(═N)N$R^9R^{10}$, —O$R^9$, —S$R^9$, —N$R^9R^{10}$, —N$R^9$C(O)$R^{10}$, —N$R^9$C(O)O$R^{10}$, —OC(O)$R^9$, —OC(O)N$R^9R^{10}$, —S(O)$_2R^9$, —NHS(O)$_2R^9$, —OS(O)$_2R^9$, each which is independently substituted or unsubstituted, or hydrogen or halogen; or $R^5$ and $R^6$ together with the carbon atom to which $R^5$ and $R^6$ are bound form a ring, wherein the ring is unsubstituted or substituted; and each $R^{2a}$, $R^{2b}$, $R^3$, and $R^4$ is independently alkyl, cycloalkyl, alkenyl, alkynyl, aryl, heteroaryl, heterocyclyl, —CN, —C(O)$R^9$, —C(O)O$R^9$, —C(O)N$R^9R^{10}$, —C(═N)N$R^9R^{10}$, —O$R^9$, —S$R^9$, —N$R^9R^{10}$, —N$R^9$C(O)$R^{10}$, —N$R^9$C(O)O$R^{10}$, —OC(O)$R^9$, —OC(O)N$R^9R^{10}$, —S(O)$_2R^9$, —NHS(O)$_2R^9$, —OS(O)$_2R^9$, each which is independently substituted or unsubstituted, or hydrogen or halogen; and each $R^7$, $R^8$, $R^9$, and $R^{10}$ is independently alkyl, cycloalkyl, alkenyl, alkynyl, aryl, heteroaryl, or heterocyclyl, each which is independently substituted or unsubstituted, or hydrogen or halogen, or a pharmaceutically-acceptable salt thereof.

Embodiment 2

The compound of embodiment 1, wherein $R^1$ is

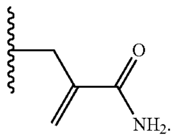

Embodiment 3

The compound of embodiment 1, wherein $R^1$ is

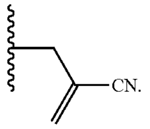

Embodiment 4

The compound of any one of embodiments 1-3, wherein $R^{2a}$ and $R^{2b}$ are each hydrogen.

Embodiment 5

The compound of any one of embodiments 1-4, wherein $R^4$ is H.

Embodiment 6

The compound of any one of embodiments 1-5, wherein $R^5$ is H.

Embodiment 7

The compound of any one of embodiments 1-5, wherein $R^5$ is —NHC(O)$R^8$.

Embodiment 8

The compound of any one of embodiments 1-7, wherein $R^8$ is phenyl or heterocyclyl, each which is unsubstituted or substituted.

Embodiment 9

The compound of any one of embodiments 1-5, wherein $R^5$ is —N$R^7R^8$.

Embodiment 10

The compound of any one of embodiments 1-5 or 9, wherein $R^5$ is NH$R^8$ wherein $R^8$ is alkyl or heterocyclyl, each which is unsubstituted or substituted, or hydrogen.

Embodiment 11

Embodiment 1. The compound of embodiment 9, wherein $R^5$ is $NH_2$.

Embodiment 12

The compound of any one of embodiments 1-11, wherein $R^6$ is H.

Embodiment 13

The compound of any one of embodiments 1-11, wherein $R^6$ is $NH_2$.

Embodiment 14

The compound of embodiment 1, wherein the compound has the formula:

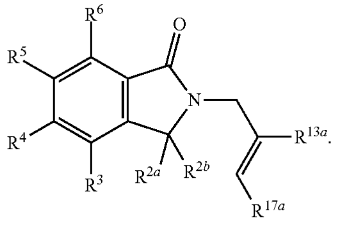

Embodiment 15

The compound of embodiment 1, wherein the compound has the formula:

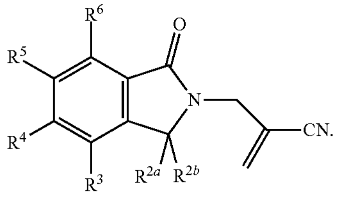

Embodiment 16

The compound of embodiment 1, wherein the compound has the formula:

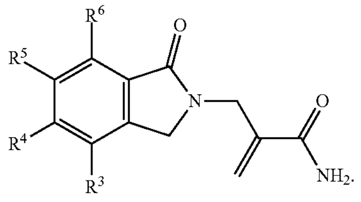

Embodiment 17

The compound of embodiment 1, wherein the compound has the formula:

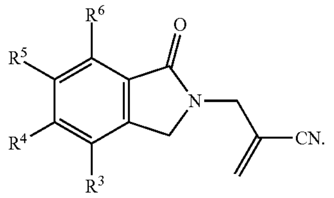

Embodiment 18

The compound of embodiment 1, wherein the compound has the formula:

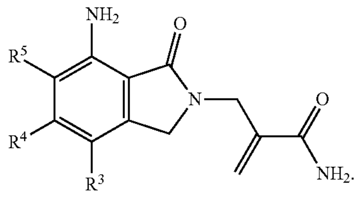

Embodiment 19

The compound of embodiment 1, wherein the compound has the formula:

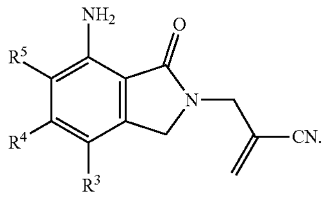

Embodiment 20

The compound of any one of embodiments 1-19, wherein $R^3$ is aryl, heterocyclyl, or heteroaryl, each which is unsubstituted or substituted.

Embodiment 21

The compound of any one of embodiments 1-20, wherein $R^3$ is phenyl, naphthalenyl, pyridinyl, dihydropyridinyl, tetrahydropyridinyl, pyrazolopyridinyl, imidazopyridinyl, triazolopyridinyl, pyrimidinyl, indolyl, dihydroindolyl, pyridoindolyl, isoindolyl, indazolyl, imidazolyl, benzimidazolyl, benzodiazolyl, carbazolyl, pyrazolyl, oxazolyl, benzoxazolyl, thiazolyl, benzothiazolyl, thiophenyl, benzothiapenyl, quinolinyl, dihydroquinolinyl, isoquinolinyl, dihydroisoquinolinyl, quinoxalinyl, or dihydroquinoxalinyl, each which is unsubstituted or substituted.

Embodiment 22

The compound of any one of embodiments 1-21, wherein the compound has the formula:

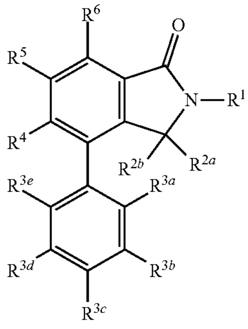

wherein each $R^{3a}$, $R^{3b}$, $R^{3c}$, $R^{3d}$ and $R^{3e}$ is independently alkyl, cycloalkyl, alkenyl, alkynyl, aryl, heteroaryl, heterocyclyl, —CN, —C(O)$R^7$, —C(O)O$R^7$, —C(O)N$R^7R^8$, —C(=N)N$R^7R^8$, —O$R^7$, —S$R^7$, —N$R^7R^8$, —N$R^7$C(O)$R^8$, —N$R^7$C(O)O$R^8$, —OC(O)$R^7$, —OC(O)N$R^7R^8$, —$S(O)_2R^7$, —$NHS(O)_2R^7$, —$OS(O)_2R^7$, each which is independently substituted or unsubstituted, or hydrogen or halogen, or $R^{3a}$ and $R^{3b}$ together with the carbon atom to which $R^{3a}$ and $R^{3b}$ are bound form a ring, wherein the ring is unsubstituted or substituted; or $R^{3b}$ and $R^{3c}$ together with the carbon atoms to which $R^{3b}$ and $R^{3c}$ are bound form a ring, wherein the ring is unsubstituted or substituted; or $R^{3c}$ and $R^{3d}$ together with the carbon atoms to which $R^{3c}$ and $R^{3d}$ are bound form a ring, wherein the ring is unsubstituted or substituted; or $R^{3d}$ and $R^{3e}$ together with the carbon atoms to which $R^{3d}$ and $R^{3e}$ are bound form a ring, wherein the ring is unsubstituted or substituted.

Embodiment 23

The compound of embodiment 22, wherein $R^{2a}$ and $R^{2b}$ are each hydrogen.

Embodiment 24

The compound of embodiment 22 or 23, wherein $R^6$ is $NH_2$.

Embodiment 25

The compound of any one of embodiments 22-24, wherein $R^4$ and $R^5$ are each hydrogen.

Embodiment 26

The compound of any one of embodiments 22-25, wherein each $R^{3a}$, $R^{3b}$, $R^{3e}$, $R^{3d}$ and $R^{3e}$ is independently $C(O)R^7$, $—C(O)OR^7$, $—C(O)NR^7R^8$, $—OR^7$, $—NR^7R^8$, $—NR^7C(O)R^8$, alkyl, aryl, heterocyclyl or heteroaryl, each which is independently substituted or unsubstituted, or hydrogen or halogen.

Embodiment 27

The compound of any one of embodiments 22-26, wherein $R^{3b}$ and $R^{3d}$ are halogen.

Embodiment 28

The compound of any one of embodiments 22-27, wherein $R^{3c}$ is $NH_2$.

Embodiment 29

The compound of any one of embodiments 22-28, wherein $R^{3a}$ and $R^{3e}$ are hydrogen.

Embodiment 30

The compound of any one of embodiments 22-29, wherein the compound has the formula:

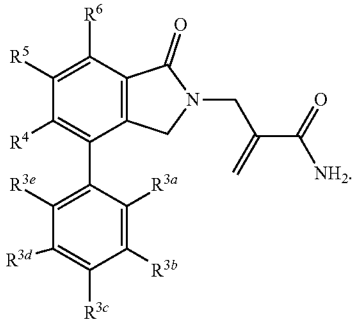

Embodiment 31

The compound of any one of embodiments 22-29, wherein the compound has the formula:

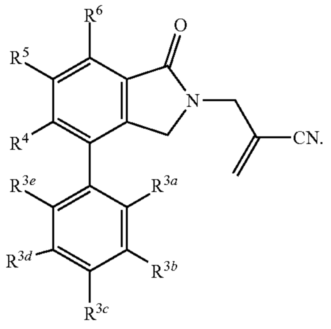

Embodiment 32

The compound of any one of embodiments 22-25, 30 or 31, wherein $R^{3c}$ and $R^{3d}$ together with the carbon atoms to which $R^{3c}$ and $R^{3d}$ are bound form a ring, wherein the ring is unsubstituted or substituted.

Embodiment 33

The compound of embodiment 1, wherein the compound has the formula:

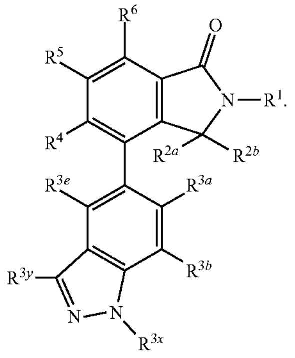

Embodiment 34

The compound of embodiment 1, wherein the compound has the formula:

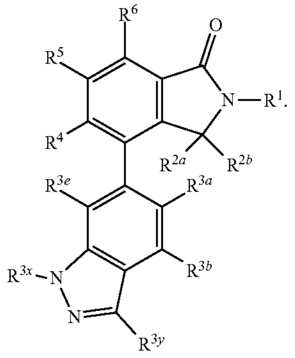

Embodiment 35

The compound of embodiment 33 or 34, wherein $R^{2a}$ and $R^{2b}$ are each hydrogen.

Embodiment 36

The compound of any one of embodiments 33-35, wherein $R^6$ is $NH_2$.

Embodiment 37

The compound of any one of embodiments 33-36, wherein $R^{3x}$ is hydrogen.

Embodiment 38

The compound of any one of embodiments 33-36, wherein $R^{3x}$ is methyl.

Embodiment 39

The compound of any one of embodiments 33-38, wherein $R^{3y}$ is phenyl which is unsubstituted or substituted.

Embodiment 40

The compound of any one of embodiments 33-38, wherein $R^{3y}$ is heteroaryl which is unsubstituted or substituted.

Embodiment 41

The compound of any one of embodiments 33-38, wherein $R^{3y}$ is heterocyclyl which is unsubstituted or substituted.

Embodiment 42

The compound of any one of embodiments 33-38, wherein $R^{3y}$ is thiophenyl.

Embodiment 43

The compound of any one of embodiments 33-38, wherein $R^{3y}$ is alkyl or alkoxy, each which is substituted or unsubstituted.

Embodiment 44

The compound of any one of embodiments 33-38 or 43, wherein $R^{3y}$ is methyl.

Embodiment 45

The compound of embodiment 33, wherein the compound has the formula:

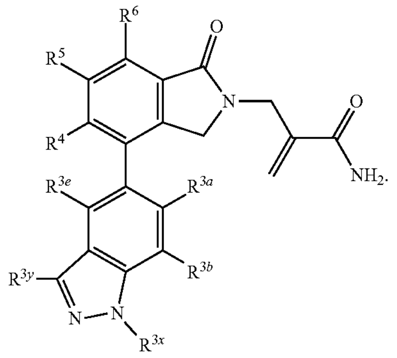

Embodiment 46

The compound of embodiment 34, wherein the compound has the formula:

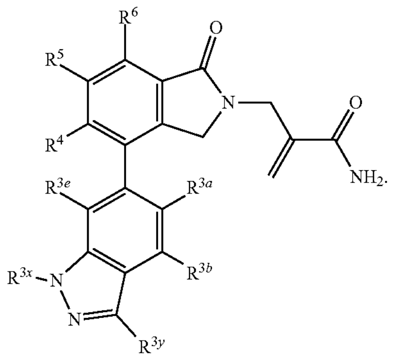

Embodiment 47

The compound of embodiment 45 or 46, wherein $R^6$ is $NH_2$.

Embodiment 48

The compound of 33, wherein the compound has the formula:

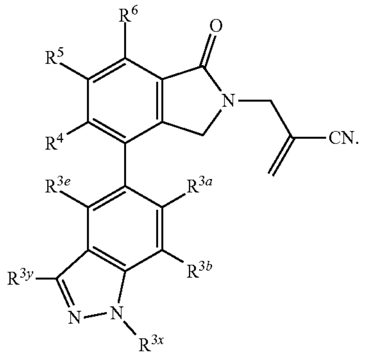

Embodiment 49

The compound of 34, wherein the compound has the formula:

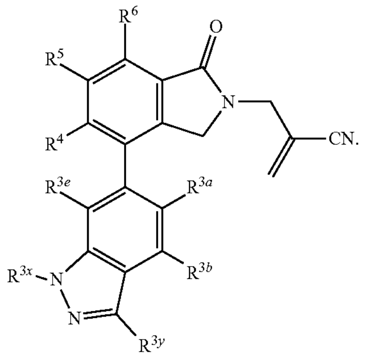

Embodiment 50

The compound of embodiment 48 or 49, wherein $R^6$ is $NH_2$.

Embodiment 51

The compound of embodiment 1, wherein $R^3$ and $R^4$ together with the carbon atom to which $R^3$ and $R^4$ are bound form a ring.

Embodiment 52

The compound of embodiment 51, wherein the ring is aryl which is unsubstituted or substituted.

Embodiment 53

The compound of embodiment 51 or 52, wherein the ring is phenyl which is unsubstituted or substituted.

Embodiment 54

The compound of any one of embodiments 51-53, wherein the compound has the formula.

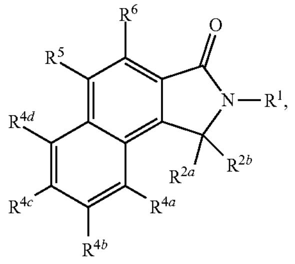

wherein each $R^{4a}$, $R^{4b}$, $R^{4c}$, and $R^{4d}$ is independently alkyl, cycloalkyl, alkenyl, alkynyl, aryl, heteroaryl, heterocyclyl, —CN, —C(O)$R^7$, —C(O)O$R^7$, —C(O)N$R^7R^8$, —C(=N)N$R^7R^8$, —O$R^7$, —S$R^7$, —N$R^7R^8$, —N$R^7$C(O)$R^8$, —N$R^7$C(O)O$R^8$, —OC(O)$R^7$, —OC(O)N$R^7R^8$, —S(O)$_2R^7$, —NHS(O)$_2R^7$, —OS(O)$_2R^7$, each which is independently substituted or unsubstituted, or hydrogen or halogen.

Embodiment 55

The compound of any one of embodiments 51-54, wherein $R^2$ and $R^{2a}$ are each hydrogen.

Embodiment 56

The compound of any one of embodiments 51-55, wherein $R^1$ is —C(O)$NH_2$.

Embodiment 57

The compound of any one of embodiments 51-56, wherein $R^6$ is $NH_2$.

Embodiment 58

The compound of embodiment 54, wherein the compound has the formula

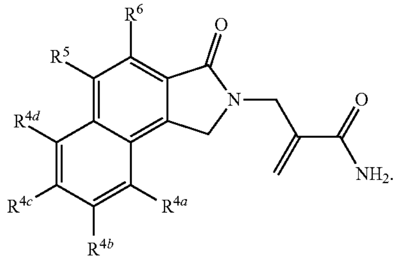

Embodiment 59

The compound of any one of embodiments 54-58, wherein $R^{4a}$, $R^{4c}$ and $R^{4d}$ are each hydrogen.

Embodiment 60

The compound of any one of embodiments 54-59, wherein $R^{4b}$ is aryl or heteroaryl, each which is unsubstituted or substituted.

Embodiment 61

The compound of any one of embodiments 54-60, wherein the compound has the formula:

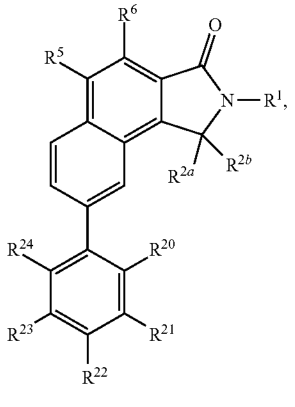

wherein each $R^{20}$, $R^{21}$, $R^{22}$, $R^{23}$ and $R^{24}$ is alkyl, cycloalkyl, alkenyl, alkynyl, aryl, heteroaryl, heterocyclyl, —CN, —C(O)$R^7$, —C(O)O$R^7$, —C(O)N$R^7R^8$, —C(=N)N$R^7R^8$, —O$R^7$, —S$R^7$, —N$R^7R^8$, —N$R^7$C(O)$R^8$, —N$R^7$C(O)O$R^8$, —OC(O)$R^7$, —OC(O)N$R^7R^8$, —S(O)$_2R^7$, —NHS(O)$_2R^7$, —OS(O)$_2R^7$, each which is independently substituted or unsubstituted, or hydrogen or halogen.

Embodiment 62

The compound of embodiment 60, wherein the compound has the formula:

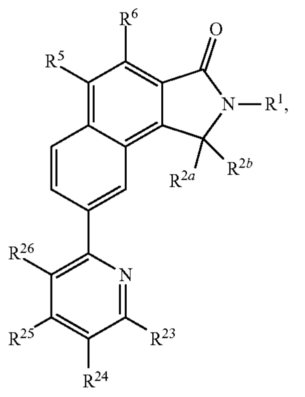

wherein each $R^{20}$, $R^{21}$, $R^{22}$, $R^{23}$ and $R^{24}$ is alkyl, cycloalkyl, alkenyl, alkynyl, aryl, heteroaryl, heterocyclyl, —CN, —C(O)$R^7$, —C(O)O$R^7$, —C(O)N$R^7R^8$, —C(=N)N$R^7R^8$, —O$R^7$, —S$R^7$, —N$R^7R^8$, —N$R^7$C(O)$R^8$, —N$R^7$C(O)O$R^8$, —OC(O)$R^7$, —OC(O)N$R^7R^8$, —S$(O)_2R^7$, —NHS$(O)_2R^7$, —OS$(O)_2R^7$, each which is independently substituted or unsubstituted, or hydrogen or halogen.

Embodiment 63

The compound of embodiment 61, wherein the compound has the formula:

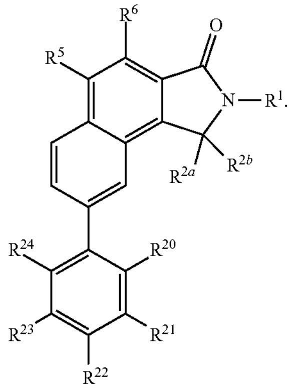

Embodiment 64

The compound of embodiment 63, wherein each $R^{20}$, $R^{21}$, $R^{22}$, $R^{23}$ and $R^{24}$ is alkyl, heteroaryl, —CN, —C(O)$R^7$, —N$R^7$C(O)N$R^8$, —C(O)N$R^7R^8$, —C(=N)N$R^7R^8$, —O$R^7$, —N$R^7R^8$, —S$(O)_2R^7$, —NHS$(O)_2R^7$, —S$(O)_2R^7$, or each which is unsubstituted or substituted, or hydrogen or halogen.

Embodiment 65

The compound of embodiment 61, wherein the compound has the formula:

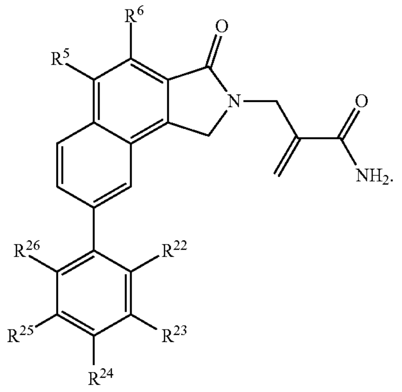

Embodiment 66

The compound of embodiment 65, wherein $R^6$ is $NH_2$.

Embodiment 67

The compound of embodiment 1, wherein the compound has the formula:

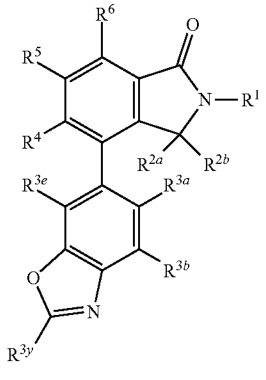

wherein each $R^{3a}$, $R^{3b}$, $R^{3e}$ and $R^{3y}$ is independently alkyl, cycloalkyl, alkenyl, alkynyl, aryl, heteroaryl, heterocyclyl, —CN, —C(O)$R^7$, —C(O)O$R^7$, —C(O)N$R^7R^8$, —C(=N)N$R^7R^8$, —O$R^7$, —S$R^7$, —N$R^7R^8$, —N$R^7$C(O)$R^8$, —N$R^7$C(O)O$R^8$, —OC(O)$R^7$, —OC(O)N$R^7R^8$, —S$(O)_2R^7$, —NHS$(O)_2R^7$, —OS$(O)_2R^7$, each which is independently substituted or unsubstituted, or hydrogen or halogen.

Embodiment 68

The compound of embodiment 1, wherein the compound has the formula:

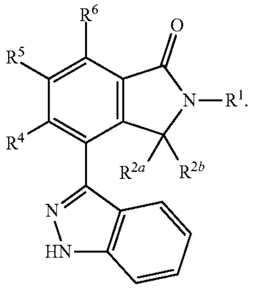

Embodiment 69

The compound of embodiment 1, wherein the compound has the formula:

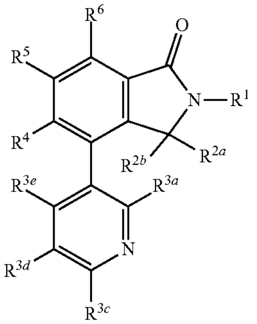

wherein each $R^{3a}$, $R^{3c}$, $R^{3d}$ and $R^{3e}$ is independently alkyl, cycloalkyl, alkenyl, alkynyl, aryl, heteroaryl, heterocyclyl, —CN, —C(O)$R^7$, —C(O)O$R^7$, —C(O)N$R^7R^8$, —C(=N)N$R^7R^8$, —O$R^7$, —S$R^7$, —N$R^7R^8$, —N$R^7$C(O)$R^8$, —N$R^7$C(O)O$R^8$, —OC(O)$R^7$, —OC(O)N$R^7R^8$, —S(O)$_2R^7$, —NHS(O)$_2R^7$, —OS(O)$_2R^7$, each which is independently substituted or unsubstituted, or hydrogen or halogen, or $R^{3c}$ and $R^{3d}$ together with the carbon atoms to which $R^{3c}$ and $R^{3d}$ are bound form a ring, wherein the ring is unsubstituted or substituted; or $R^{3d}$ and $R^{3e}$ together with the carbon atoms to which $R^{3d}$ and $R^{3e}$ are bound form a ring, wherein the ring is unsubstituted or substituted.

Embodiment 70

The compound of embodiment 69, wherein the compound has the formula:

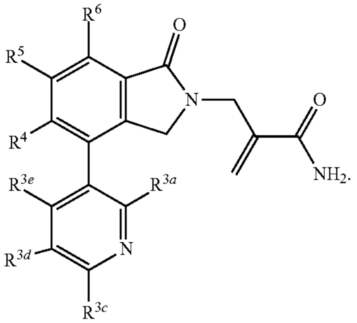

Embodiment 71

The compound of embodiment 69, wherein the compound has the formula:

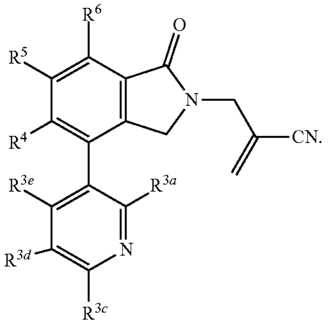

Embodiment 72

A compound of the formula:

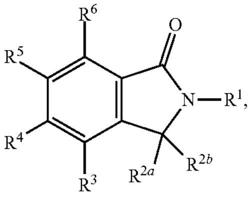

wherein:

$R^1$ is alkyl, cycloalkyl, alkenyl, alkynyl, aryl, heteroaryl, heterocyclyl, —CN, —C(O)$R^7$, —C(O)O$R^7$, —C(O)N$R^7R^8$, —C(=N)N$R^7R^8$, —O$R^7$, —S$R^7$, —N$R^7R^8$, —N$R^7$C(O)$R^8$, —N$R^7$C(O)O$R^8$, —OC(O)$R^7$, —OC(O)N$R^7R^8$, —S(O)$_2R^7$, —NHS(O)$_2R^7$, —OS(O)$_2R^7$, each which is independently substituted or unsubstituted, or hydrogen or halogen;

each $R^{2a}$, $R^{2b}$, $R^4$, $R^5$, and $R^6$ is independently alkyl, cycloalkyl, alkenyl, alkynyl, aryl, heteroaryl, heterocyclyl, —CN, —C(O)$R^9$, —C(O)O$R^9$, —C(O)N$R^9R^{10}$, —C(=N)N$R^9R^{10}$, —O$R^9$, —S$R^9$, —N$R^9R^{10}$, —$NR^9C(O)R^{10}$, —$NR^9C(O)OR^{10}$, —$OC(O)R^9$, —$OC(O)NR^9R^{10}$, —$S(O)_2R^9$, —$NHS(O)_2R^9$, —$OS(O)_2R^9$, each which is independently substituted or unsubstituted, or hydrogen or halogen; or $R^{2a}$ and $R^{2b}$ together with the carbon atom to which $R^{2a}$ and $R^{2b}$ are bound is C═O or C═S; and $R^4$, $R^5$, and $R^6$ is independently alkyl, cycloalkyl, alkenyl, alkynyl, aryl, heteroaryl, heterocyclyl, —CN, —$C(O)R^9$, —$C(O)OR^9$, —$C(O)NR^9R^{10}$, —$C(═N)NR^9R^{10}$, —$OR^9$, —$SR^9$, —$NR^9R^{10}$, —$NR^9C(O)R^{10}$, —$NR^9C(O)OR^{10}$, —$OC(O)R^9$, —$OC(O)NR^9R^{10}$, —$S(O)_2R^9$, —$NHS(O)_2R^9$, —$OS(O)_2R^9$, each which is independently substituted or unsubstituted, or hydrogen or halogen; or $R^4$ and $R^5$ together with the carbon atom to which $R^4$ and $R^5$ are bound form a ring, wherein the ring is unsubstituted or substituted; and each $R^{2a}$, $R^{2b}$, and $R^6$ is independently alkyl, cycloalkyl, alkenyl, alkynyl, aryl, heteroaryl, heterocyclyl, —CN, —$C(O)R^9$, —$C(O)OR^9$, —$C(O)NR^9R^{10}$, —$C(═N)NR^9R^{10}$, —$OR^9$, —$SR^9$, —$NR^9R^{10}$, —$NR^9C(O)R^{10}$, —$NR^9C(O)OR^{10}$, —$OC(O)R^9$, —$OC(O)NR^9R^{10}$, —$S(O)_2R^9$, —$NHS(O)_2R^9$, —$OS(O)_2R^9$, each which is independently substituted or unsubstituted, or hydrogen or halogen; or $R^5$ and $R^6$ together with the carbon atom to which $R^5$ and $R^6$ are bound form a ring, wherein the ring is unsubstituted or substituted; and each $R^{2a}$, $R^{2b}$, and $R^4$ is independently alkyl, cycloalkyl, alkenyl, alkynyl, aryl, heteroaryl, heterocyclyl, —CN, —$C(O)R^9$, —$C(O)OR^9$, —$C(O)NR^9R^{10}$, —$C(═N)NR^9R^{10}$, —$OR^9$, —$SR^9$, —$NR^9R^{10}$, —$NR^9C(O)R^{10}$, —$NR^9C(O)OR^{10}$, —$OC(O)R^9$, —$OC(O)NR^9R^{10}$, —$S(O)_2R^9$, —$NHS(O)_2R^9$, —$OS(O)_2R^9$, each which is independently substituted or unsubstituted, or hydrogen or halogen;

$R^3$ is

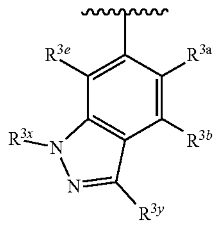

or

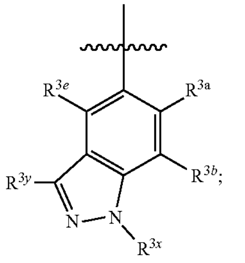

each $R^{3a}$, $R^{3b}$, $R^{3e}$, $R^{3x}$, and $R^{3y}$ is independently alkyl, cycloalkyl, alkenyl, alkynyl, aryl, heteroaryl, heterocyclyl, —CN, —$C(O)R^7$, —$C(O)OR^7$, —$C(O)NR^7R^8$, —$C(═N)NR^7R^8$, —$OR^7$, —$SR^7$, —$NR^7R^8$, —$NR^7C(O)R^8$, —$NR^7C(O)OR^8$, —$OC(O)R^7$, —$OC(O)NR^7R^8$, —$S(O)_2R^7$, —$NHS(O)_2R^7$, —$OS(O)_2R^7$, each which is independently substituted or unsubstituted, or hydrogen or halogen; and each $R^7$, $R^8$, $R^9$, and $R^{10}$ is independently alkyl, cycloalkyl, alkenyl, alkynyl, aryl, heteroaryl, or heterocyclyl, each which is independently substituted or unsubstituted, or hydrogen or halogen, or a pharmaceutically-acceptable salt thereof.

Embodiment 73

The compound of embodiment 72, wherein $R^1$ is —$C(O)R^7$.

Embodiment 74

The compound of embodiment 72 or 73, wherein $R^1$ is

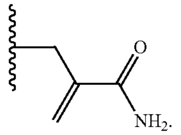 [SMILES: *CC(=C)C(N)=O]

Embodiment 75

The compound of embodiment 72 or 73, wherein $R^1$ is

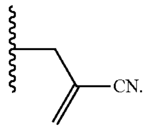 [SMILES: *CC(=C)C#N]

Embodiment 76

The compound of any one of embodiments 72-75, wherein $R^1$ is an unsubstituted or substituted alkyl or alkenyl.

Embodiment 77

The compound of embodiment 76, wherein the compound has the formula:

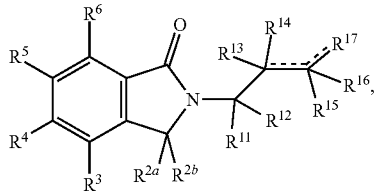

each ═══ is independently a single bond or a double bond, epoxide or cyclopropyl; wherein at least one of ═══ is a single bond;

each $R^{11}$ and $R^{12}$ is independently alkyl, cycloalkyl, alkenyl, alkynyl, aryl, heteroaryl, or heterocyclyl, each which is independently substituted or unsubstituted, or hydrogen; or $R^{11}$ and $R^{12}$ together with the carbon atom to which $R^{11}$ and $R^{12}$ are bound is —C═O or —C═S;

each $R^{13}$, $R^{14}$, $R^{15}$ and $R^{16}$ is independently absent, alkyl, cycloalkyl, alkenyl, alkynyl, aryl, heteroaryl, heterocyclyl, —CN, —$C(O)R^7$, —$C(O)OR^7$, —$C(O)NR^7R^8$, —$C(═N)NR^7R^8$, —$OR^7$, —$SR^7$, —$NR^7R^8$, —$NR^7C(O)R^8$, —$NR^7C(O)OR^8$, —$OC(O)R^7$, —$OC(O)NR^7R^8$, —$S(O)_2R^7$, —$NHS(O)_2R^7$, —$OS(O)_2R^7$, each which is independently substituted or unsubstituted, or hydrogen or halogen;

$R^{17}$ is alkyl, cycloalkyl, alkenyl, alkynyl, aryl, heteroaryl, heterocyclyl, —CN, —$C(O)R^7$, —$C(O)OR^7$, —$C(O)NR^7R^8$, —$C(═N)NR^7R^8$, —$OR^7$, —$SR^7$, —$NR^7R^8$, —$NR^7C(O)R^8$, —$NR^7C(O)OR^8$, —$OC(O)R^7$, —OC (O)$NR^7R^8$, —$S(O)_2R^7$, —$NHS(O)_2R^7$, —$OS(O)_2R^7$, —$CR^{18}R^{19}$, alkyl, cycloalkyl, aryl, heteroaryl, heterocyclyl, each which is independent substituted or unsubstituted, or hydrogen or halogen; and each $R^{18}$ and $R^{19}$ is independently —CN, alkyl, cycloalkyl, alkenyl, alkynyl, aryl, heteroaryl, or heterocyclyl, each which is independently substituted or unsubstituted, or hydrogen.

Embodiment 78

The compound of embodiment 77, wherein $R^{11}$ and $R^{12}$ are each hydrogen.

Embodiment 79

The compound of embodiment 77, wherein $R^{11}$ and $R^{12}$ together with the carbon atom to which $R^{11}$ and $R^{12}$ are bound is —C═O.

Embodiment 80

The compound of embodiment 77, wherein one ═══ is epoxide.

Embodiment 81

The compound of embodiment 77, wherein the compound has the formula:

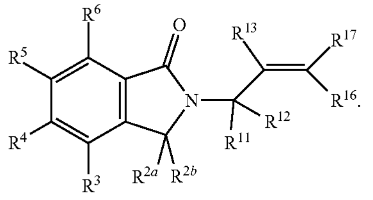

Embodiment 82

The compound of embodiment 81, wherein $R^{16}$ and $R^{17}$ are each hydrogen.

Embodiment 83

The compound of embodiment 81, wherein one of $R^{16}$ and $R^{17}$ is hydrogen and the other is —CN.

Embodiment 84

The compound of embodiment 81, wherein $R^{13}$ is —CN, —C(O)$NR^7R^8$, —C(O)$R^7$, C(O)$OR^7$, heteroaryl, or —$OR^7$, each which is unsubstituted or substituted.

Embodiment 85

The compound of embodiment 81, wherein the compound has the formula:

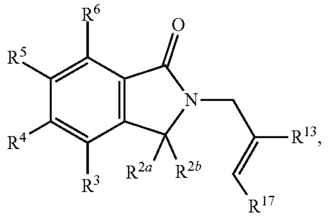

wherein $R^{17}$ is —CN, alkyl, aryl, heteroaryl, —$NR^7R^8$, —$S(O)_2R^7$, —$SR^7$, or $OR^7$, each which is unsubstituted or substituted, or hydrogen or halogen.

Embodiment 86

The compound of embodiment 85, wherein $R^{13}$ is CN.

Embodiment 87

The compound of embodiment 85, wherein $R^{13}$ is —C(O)$NH_2$.

Embodiment 88

The compound of embodiment 85, wherein $R^{13}$ is heteroaryl which is unsubstituted or substituted.

Embodiment 89

The compound of embodiment 85, wherein $R^{13}$ is aryl which is unsubstituted or substituted.

Embodiment 90

The compound of any one of embodiments 85-89, wherein $R^{17}$ is hydrogen.

Embodiment 91

The compound of any one of embodiments 85-89, wherein $R^{17}$ is methyl.

Embodiment 92

The compound of any one of embodiments 85-89, wherein $R^{17}$ is heteroaryl which is unsubstituted or substituted.

Embodiment 93

The compound of any one of embodiments 85-89, wherein $R^{17}$ is aryl which is unsubstituted or substituted.

Embodiment 94

The compound of any one of embodiments 72-93, wherein $R^{2a}$ and $R^{2b}$ are each hydrogen.

Embodiment 95

The compound of any one of embodiments 72-94, wherein $R^4$ is H.

Embodiment 96

The compound of any one of embodiments 72-95, wherein $R^5$ is H.

Embodiment 97

The compound of any one of embodiments 72-95, wherein $R^5$ is —NHC(O)$R^8$.

Embodiment 98

The compound of any one of embodiments 72-97, wherein $R^8$ is phenyl or heterocyclyl, each which is unsubstituted or substituted.

Embodiment 99

The compound of any one of embodiments 72-95, wherein $R^5$ is —$NR^7R^8$.

Embodiment 100

The compound of embodiment 99, wherein $R^5$ is $NHR^8$ wherein $R^8$ is alkyl or heterocyclyl, each which is unsubstituted or substituted, or hydrogen.

Embodiment 101

The compound of embodiment 99, wherein $R^5$ is $NH_2$.

Embodiment 102

The compound of any one of embodiments 72-101, wherein $R^6$ is H.

Embodiment 103

The compound of any one of embodiments 72-101, wherein $R^6$ is $NH_2$.

Embodiment 104

The compound of embodiment 72, wherein the compound has the formula:

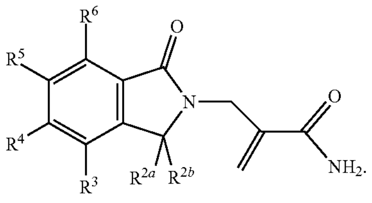

Embodiment 105

The compound of embodiment 72, wherein the compound has the formula:

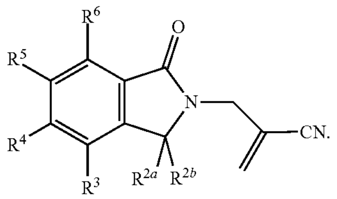

Embodiment 106

The compound of embodiment 72, wherein the compound has the formula:

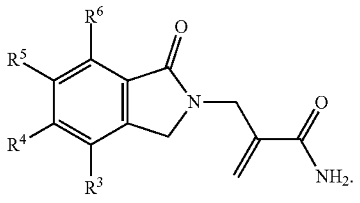

Embodiment 107

The compound of embodiment 72, wherein the compound has the formula:

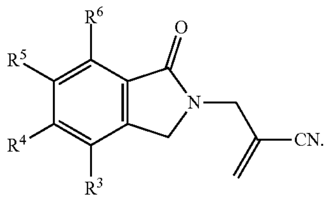

Embodiment 108

The compound of embodiment 72 wherein the compound has the formula:

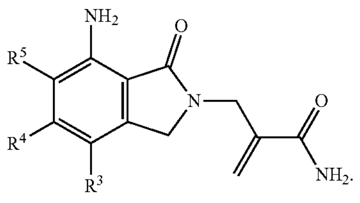

Embodiment 109

The compound of embodiment 72, wherein the compound has the formula:

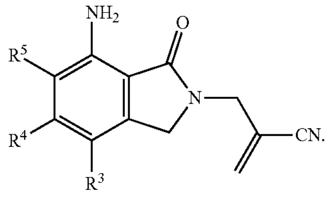

Embodiment 110

The compound of any one of embodiments 72-109, wherein $R^{2a}$ and $R^{2b}$ are each hydrogen.

Embodiment 111

The compound of any one of embodiments 72-110, wherein $R^6$ is $NH_2$.

Embodiment 112

The compound of any one of embodiments 72-111, wherein $R^{3x}$ is hydrogen.

Embodiment 113

The compound of any one of embodiments 72-111, wherein $R^{3x}$ is methyl.

Embodiment 114

The compound of any one of embodiments 72-113, wherein $R^{3y}$ is phenyl which is unsubstituted or substituted.

Embodiment 115

The compound of any one of embodiments 72-113, wherein $R^{3y}$ is heteroaryl which is unsubstituted or substituted.

Embodiment 116

The compound of any one of embodiments 72-113, wherein $R^{3y}$ is heterocyclyl which is unsubstituted or substituted.

Embodiment 117

The compound of any one of embodiments 72-113, wherein $R^{3y}$ is thiophenyl.

Embodiment 118

The compound of any one of embodiments 72-111, wherein $R^{3y}$ is alkyl or alkoxy, each which is substituted or unsubstituted.

Embodiment 119

The compound of any one of embodiments 72-111 or 118, wherein $R^{3y}$ is methyl.

Embodiment 120

The compound of embodiment 72, wherein the compound has the formula:

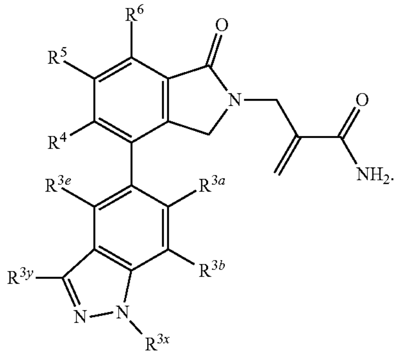

Embodiment 121

The compound of embodiment 72 wherein the compound has the formula:

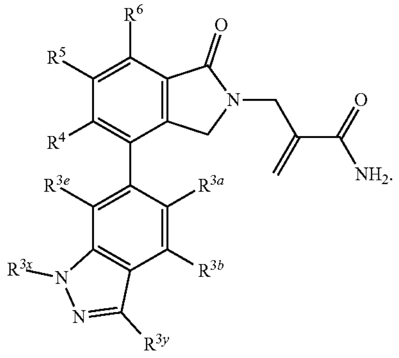

Embodiment 122

The compound of embodiment 120 or 121, wherein $R^6$ is $NH_2$.

Embodiment 123

The compound of 120, wherein the compound has the formula:

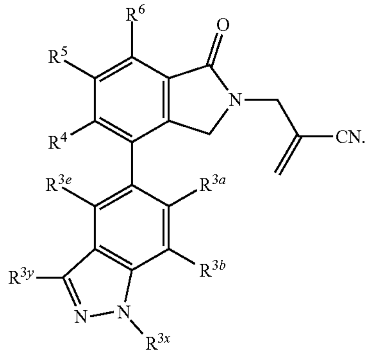

Embodiment 124

The compound of embodiment 121, wherein the compound has the formula:

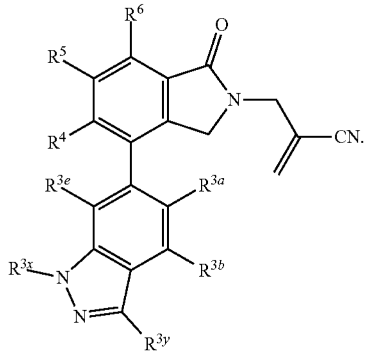

Embodiment 125

The compound of embodiment 123 or 124, wherein $R^6$ is $NH_2$.

Embodiment 126

A compound of the formula:

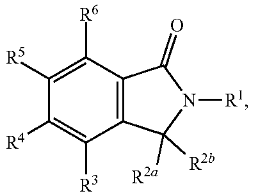

wherein:

$R^1$ is

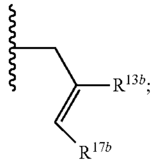

$R^{13b}$ is alkyl, cycloalkyl, alkenyl, alkynyl, aryl, heteroaryl, heterocyclyl, —CN, —C(O)$R^7$, —C(O)O$R^7$, —C(O)N$R^7R^8$, —C(═N)N$R^7R^8$, —O$R^7$, —S$R^7$, —N$R^7R^8$, —N$R^7$C(O)$R^8$, —N$R^7$C(O)O$R^8$, —OC(O)$R^7$, —OC(O)N$R^7R^8$, —S$(O)_2R^7$, —NHS$(O)_2R^7$, —OS$(O)_2R^7$, each which is independently substituted or unsubstituted, or hydrogen or halogen;

$R^{17b}$ is —CN, alkyl, aryl, heteroaryl, —N$R^7R^8$, —S$(O)_2R^7$, —S$R^7$, or O$R^7$, each which is unsubstituted or substituted, or hydrogen or halogen;

each $R^{2a}$, $R^{2b}$, $R^3$, $R^4$, and $R^5$ is independently alkyl, cycloalkyl, alkenyl, alkynyl, aryl, heteroaryl, heterocyclyl, —CN, —C(O)$R^9$, —C(O)O$R^9$, —C(O)N$R^9R^{10}$, —C(═N)N$R^9R^{10}$, —O$R^9$, —S$R^9$, —N$R^9R^{10}$, —N$R^9$C(O)$R^{10}$, —N$R^9$C(O)O$R^{10}$, —OC(O)$R^9$, —OC(O)N$R^9R^{10}$, —S$(O)_2R^9$, —NHS$(O)_2R^9$, —OS$(O)_2R^9$, each which is independently substituted or unsubstituted, or hydrogen or halogen; or $R^{2a}$ and $R^{2b}$ together with the carbon atom to which $R^{2a}$ and $R^{2b}$ are bound is C═O or C═S; and $R^3$, $R^4$, and $R^5$ is independently alkyl, cycloalkyl, alkenyl, alkynyl, aryl, heteroaryl, heterocyclyl, —CN, —C(O)$R^9$, —C(O)O$R^9$, —C(O)N$R^9R^{10}$, —C(═N)N$R^9R^{10}$, —O$R^9$, —S$R^9$, —N$R^9R^{10}$, —N$R^9$C(O)$R^{10}$, —N$R^9$C(O)O$R^{10}$, —OC(O)$R^9$, —OC(O)N$R^9R^{10}$, —S$(O)_2R^9$, —NHS$(O)_2R^9$, —OS$(O)_2R^9$, each which is independently substituted or unsubstituted, or hydrogen or halogen; or $R^3$ and $R^4$ together with the carbon atom to which $R^3$ and $R^4$ are bound form a ring, wherein the ring is unsubstituted or substituted; and each $R^{2a}$, $R^{2b}$, and $R^5$ is independently alkyl, cycloalkyl, alkenyl, alkynyl, aryl, heteroaryl, heterocyclyl, —CN, —C(O)$R^9$, —C(O)O$R^9$, —C(O)N$R^9R^{10}$, —C(═N)N$R^9R^{10}$, —O$R^9$, —S$R^9$, —N$R^9R^{10}$, —N$R^9$C(O)$R^{10}$, —N$R^9$C(O)O$R^{10}$, —OC(O)$R^9$, —OC(O)N$R^9R^{10}$, —S$(O)_2R^9$, —NHS$(O)_2R^9$, —OS$(O)_2R^9$, each which is independently substituted or unsubstituted, or hydrogen or halogen; or $R^4$ and $R^5$ together with the carbon atom to which $R^4$ and $R^5$ are bound form a ring, wherein the ring is unsubstituted or substituted; and each $R^{2a}$, $R^{2b}$, and $R^3$ is independently alkyl, cycloalkyl, alkenyl, alkynyl, aryl, heteroaryl, heterocyclyl, —CN, —C(O)$R^9$, —C(O)O$R^9$, —C(O)N$R^9R^{10}$, —C(═N)N$R^9R^{10}$, —O$R^9$, —S$R^9$, —N$R^9R^{10}$, —N$R^9$C(O)$R^{10}$, —N$R^9$C(O)O$R^{10}$, —OC(O)$R^9$, —OC(O)N$R^9R^{10}$, —S$(O)_2R^9$, —NHS$(O)_2R^9$, —OS$(O)_2R^9$, each which is independently substituted or unsubstituted, or hydrogen or halogen; or $R^6$ is $NH_2$; and each $R^7$, $R^8$, $R^9$, and $R^{10}$ is independently alkyl, cycloalkyl, alkenyl, alkynyl, aryl, heteroaryl, or heterocyclyl, each which is independently substituted or unsubstituted, or hydrogen or halogen, or a pharmaceutically-acceptable salt thereof.

Embodiment 127

The compound of embodiment 126, wherein $R^1$ is

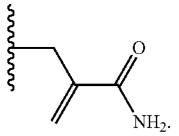

Embodiment 128

The compound of embodiment 126, wherein $R^1$ is

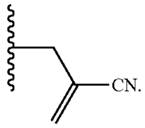

Embodiment 129

The compound of any one of embodiments 126-128, wherein $R^{2a}$ and $R^{2b}$ are each hydrogen.

Embodiment 130

The compound of any one of embodiments 126-129, wherein $R^4$ is H.

Embodiment 131

The compound of any one of embodiments 126-130, wherein $R^5$ is H.

Embodiment 132

The compound of any one of embodiments 126-130, wherein $R^5$ is —NHC(O)$R^8$.

Embodiment 133

The compound of any one of embodiments 126-132, wherein $R^8$ is phenyl or heterocyclyl, each which is unsubstituted or substituted.

Embodiment 134

The compound of any one of embodiments 126-133, wherein $R^5$ is —$NR^7R^8$.

Embodiment 135

The compound of any one of embodiments 126-134, wherein $R^5$ is $NHR^8$ wherein $R^8$ is alkyl or heterocyclyl, each which is unsubstituted or substituted, or hydrogen.

Embodiment 136

The compound of any one of embodiments 126-134, wherein $R^5$ is $NH_2$.

Embodiment 137

The compound of any one of embodiments 126-136, wherein $R^6$ is H.

Embodiment 138

The compound of any one of embodiments 126-136, wherein $R^6$ is $NH_2$.

Embodiment 139

The compound of embodiment 126, wherein the compound has the formula:

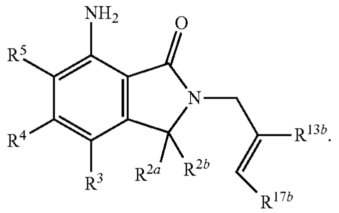

Embodiment 140

The compound of embodiment 126, wherein the compound has the formula:

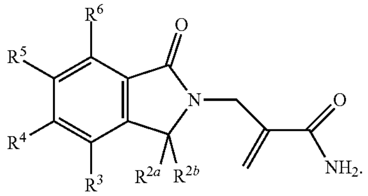

Embodiment 141

The compound of embodiment 126, wherein the compound has the formula:

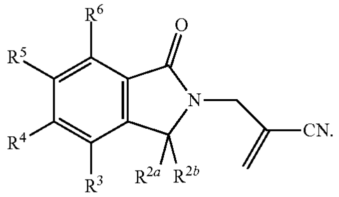

Embodiment 1424

The compound of embodiment 126, wherein the compound has the formula:

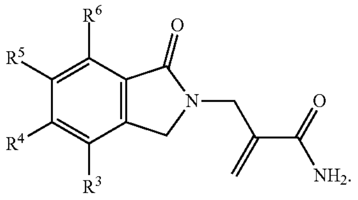

Embodiment 143

The compound of embodiment 126, wherein the compound has the formula:

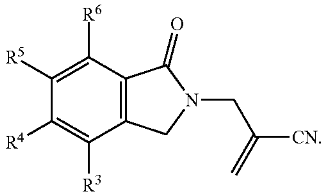

Embodiment 144

The compound of embodiment 126, wherein the compound has the formula:

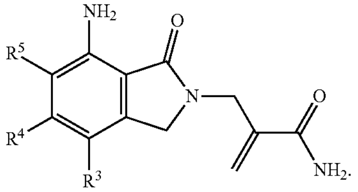

Embodiment 145

The compound of embodiment 126, wherein the compound has the formula:

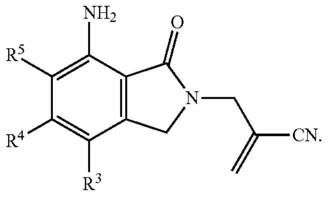

Embodiment 146

The compound of any one of embodiments 126-145, wherein $R^3$ is aryl, heterocyclyl, or heteroaryl, each which is unsubstituted or substituted.

Embodiment 147

The compound of any one of embodiments 126-146, wherein $R^3$ is phenyl, naphthalenyl, pyridinyl, dihydropyridinyl, tetrahydropyridinyl, pyrazolopyridinyl, imidazopyridinyl, triazolopyridinyl, pyrimidinyl, indolyl, dihydroindolyl, pyridoindolyl, isoindolyl, indazolyl, imidazolyl, benzimidazolyl, benzodiazolyl, carbazolyl, pyrazolyl, oxazolyl, benzoxazolyl, thiazolyl, benzothiazolyl, thiophenyl, benzothiapenyl, quinolinyl, dihydroquinolinyl, isoquinolinyl, dihydroisoquinolinyl, quinoxalinyl, or dihydroquinoxalinyl, each which is unsubstituted or substituted.

Embodiment 148

The compound of any one of embodiments 126-147, wherein the compound has the formula:

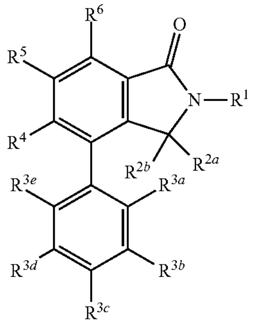

wherein each $R^{3a}$, $R^{3b}$, $R^{3c}$, $R^{3d}$ and $R^{3e}$ is independently alkyl, cycloalkyl, alkenyl, alkynyl, aryl, heteroaryl, heterocyclyl, —CN, —C(O)$R^7$, —C(O)O$R^7$, —C(O)N$R^7R^8$, —C(=N)N$R^7R^8$, —O$R^7$, —S$R^7$, —N$R^7R^8$, —N$R^7$C(O)$R^8$, —N$R^7$C(O)O$R^8$, —OC(O)$R^7$, —OC(O)N$R^7R^8$, —$S(O)_2R^7$, —NHS$(O)_2R^7$, —OS$(O)_2R^7$, each which is independently substituted or unsubstituted, or hydrogen or halogen, or $R^{3a}$ and $R^{3b}$ together with the carbon atom to which $R^{3a}$ and $R^{3b}$ are bound form a ring, wherein the ring is unsubstituted or substituted; or $R^{3b}$ and $R^{3c}$ together with the carbon atoms to which $R^{3b}$ and $R^{3c}$ are bound form a ring, wherein the ring is unsubstituted or substituted; or $R^{3c}$ and $R^{3d}$ together with the carbon atoms to which $R^{3c}$ and $R^{3d}$ are bound form a ring, wherein the ring is unsubstituted or substituted; or $R^{3d}$ and $R^{3e}$ together with the carbon atoms to which $R^{3d}$ and $R^{3e}$ are bound form a ring, wherein the ring is unsubstituted or substituted.

Embodiment 149

The compound of embodiment 148, wherein $R^{2a}$ and $R^{2b}$ are each hydrogen.

Embodiment 150

The compound of embodiment 148 or 149, wherein $R^6$ is $NH_2$.

Embodiment 151

The compound of any one of embodiments 148-150, wherein $R^4$ and $R^5$ are each hydrogen.

Embodiment 152

The compound of any one of embodiments 148-151, wherein each $R^{3a}$, $R^{3b}$, $R^{3c}$, $R^{3d}$ and $R^{3e}$ is independently C(O)$R^7$, —C(O)O$R^7$, —C(O)N$R^7R^8$, —O$R^7$, —N$R^7R^8$, —N$R^7$C(O)$R^8$, alkyl, aryl, heterocyclyl or heteroaryl, each which is independently substituted or unsubstituted, or hydrogen or halogen.

Embodiment 153

The compound of any one of embodiments 148-152, wherein $R^{3b}$ and $R^{3d}$ are halogen.

Embodiment 154

The compound of any one of embodiments 148-153, wherein $R^{3c}$ is $NH_2$.

Embodiment 155

The compound of any one of embodiments 148-154, wherein $R^{3a}$ and $R^{3e}$ are hydrogen.

Embodiment 156

The compound of embodiment 148, wherein the compound has the formula:

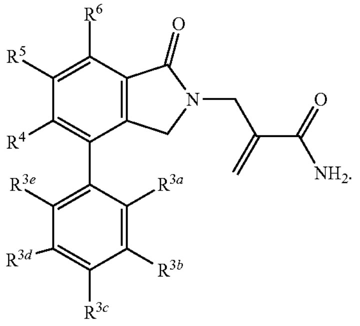

Embodiment 157

The compound of embodiment 148, wherein the compound has the formula:

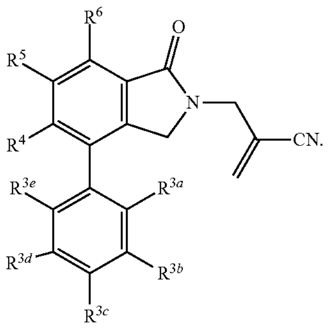

Embodiment 158

The compound of embodiment 148, wherein $R^{3c}$ and $R^{3d}$ together with the carbon atoms to which $R^{3c}$ and $R^{3d}$ are bound form a ring, wherein the ring is unsubstituted or substituted.

Embodiment 159

The compound of embodiment 126, wherein the compound has the formula:

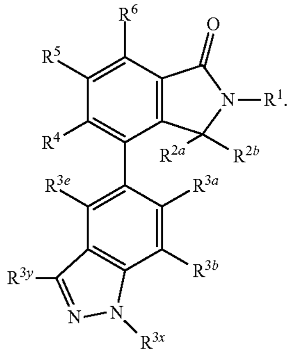

Embodiment 160

The compound of embodiment 126, wherein the compound has the formula:

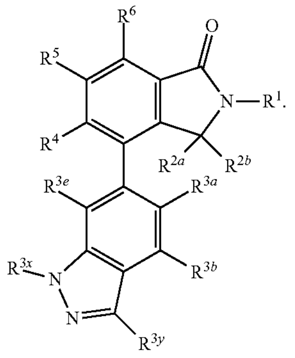

Embodiment 161

The compound of embodiment 159 or 160, wherein $R^{2a}$ and $R^{2b}$ are each hydrogen.

Embodiment 162

The compound of any one of embodiments 159-161, wherein $R^6$ is $NH_2$.

Embodiment 163

The compound of any one of embodiments 159-162, wherein $R^{3x}$ is hydrogen.

Embodiment 164

The compound of any one of embodiments 159-162, wherein $R^{3x}$ is methyl.

Embodiment 165

The compound of any one of embodiments 159-164, wherein $R^{3y}$ is phenyl which is unsubstituted or substituted.

Embodiment 166

The compound of any one of embodiments 159-164, wherein $R^{3y}$ is heteroaryl which is unsubstituted or substituted.

Embodiment 167

The compound of any one of embodiments 159-164, wherein $R^{3y}$ is heterocyclyl which is unsubstituted or substituted.

Embodiment 168

The compound of any one of embodiments 159-164, wherein $R^{3y}$ is thiophenyl.

Embodiment 169

The compound of any one of embodiments 159-164, wherein $R^{3y}$ is alkyl or alkoxy, each which is substituted or unsubstituted.

Embodiment 170

The compound of any one of embodiments 159-164, wherein $R^{3y}$ is methyl.

Embodiment 171

The compound of embodiment 159, wherein the compound has the formula:

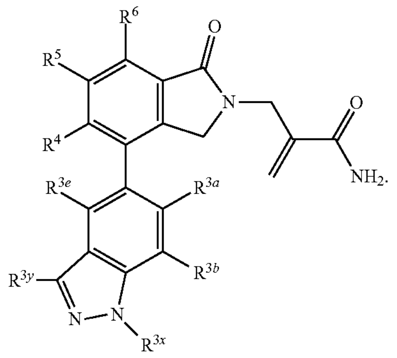

Embodiment 172

The compound of embodiment 159, wherein the compound has the formula:

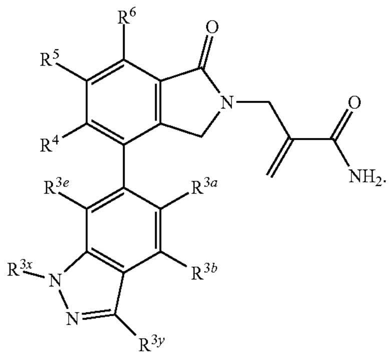

Embodiment 173

The compound of embodiment 171 or 172, wherein $R^6$ is $NH_2$.

Embodiment 174

The compound of 126, wherein the compound has the formula:

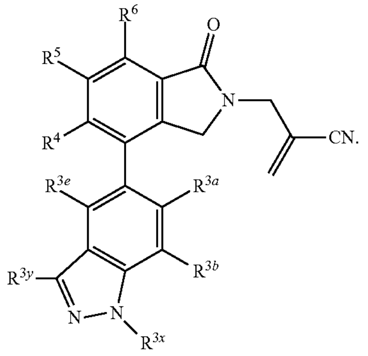

Embodiment 175

The compound of 126, wherein the compound has the formula:

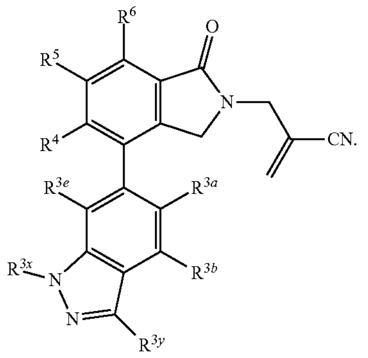

Embodiment 176

The compound of embodiment 175 or 176, wherein $R^6$ is $NH_2$.

Embodiment 177

The compound of embodiment 126, wherein $R^3$ and $R^4$ together with the carbon atom to which $R^3$ and $R^4$ are bound form a ring.

Embodiment 178

The compound of embodiment 177, wherein the ring is aryl which is unsubstituted or substituted.

Embodiment 179

The compound of embodiment 177, wherein the ring is phenyl which is unsubstituted or substituted.

Embodiment 180

The compound of embodiment 177, wherein the compound has the formula.

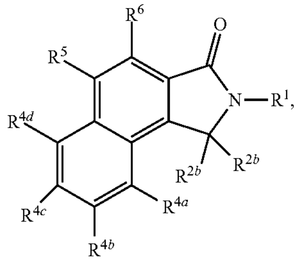

wherein each $R^{4a}$, $R^{4b}$, $R^{4c}$, and $R^{4d}$ is independently alkyl, cycloalkyl, alkenyl, alkynyl, aryl, heteroaryl, heterocyclyl, —CN, —C(O)$R^7$, —C(O)O$R^7$, —C(O)N$R^7R^8$, —C(═N)N$R^7R^8$, —O$R^7$, —S$R^7$, —N$R^7R^8$, —N$R^7$C(O)$R^8$, —N$R^7$C(O)O$R^8$, —OC(O)$R^7$, —OC(O)N$R^7R^8$, —S(O)$_2R^7$, —NHS(O)$_2R^7$, —OS(O)$_2R^7$, each which is independently substituted or unsubstituted, or hydrogen or halogen.

Embodiment 181

The compound of embodiment 180, wherein $R^{2a}$ and $R^{2b}$ are each hydrogen.

Embodiment 182

The compound of embodiment 180 or 181, wherein $R^1$ is —C(O)$NH_2$.

Embodiment 183

The compound of any one of embodiments 180-182, wherein $R^6$ is $NH_2$.

Embodiment 184

The compound of embodiment 180, wherein the compound has the formula

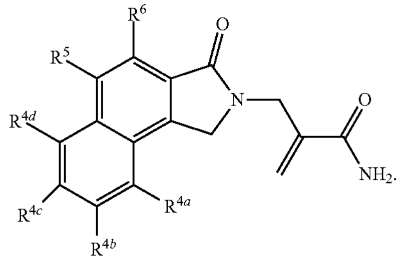

Embodiment 185

The compound of any one of embodiments 180-184, wherein $R^{4a}$, $R^{4c}$ and $R^{4d}$ are each hydrogen.

Embodiment 186

The compound of any one of embodiments 180-185, wherein $R^{4b}$ is aryl or heteroaryl, each which is unsubstituted or substituted.

Embodiment 187

The compound of embodiment 186, wherein the compound has the formula:

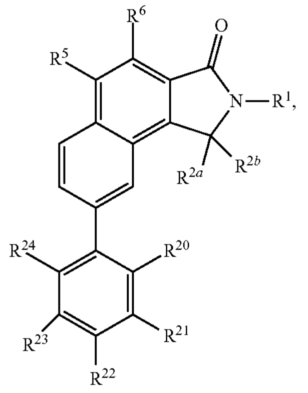

wherein each $R^{20}$, $R^{21}$, $R^{22}$, $R^{23}$ and $R^{24}$ is alkyl, cycloalkyl, alkenyl, alkynyl, aryl, heteroaryl, heterocyclyl, —CN, —C(O)$R^7$, —C(O)O$R^7$, —C(O)N$R^7R^8$, —C(═N)N$R^7R^8$, —O$R^7$, —S$R^7$, —N$R^7R^8$, —N$R^7$C(O)$R^8$, —N$R^7$C(O)O$R^8$, —OC(O)$R^7$, —OC(O)N$R^7R^8$, —S(O)$_2R^7$, —NHS(O)$_2R^7$, —OS(O)$_2R^7$, each which is independently substituted or unsubstituted, or hydrogen or halogen.

Embodiment 188

The compound of embodiment 186, wherein the compound has the formula:

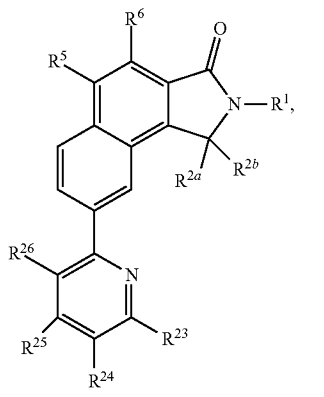

wherein each $R^{20}$, $R^{21}$, $R^{22}$, $R^{23}$ and $R^{24}$ is alkyl, cycloalkyl, alkenyl, alkynyl, aryl, heteroaryl, heterocyclyl, —CN, —C(O)$R^7$, —C(O)O$R^7$, —C(O)N$R^7R^8$, —C(=N)N$R^7R^8$, —O$R^7$, —S$R^7$, —N$R^7R^8$, —N$R^7$C(O)$R^8$, —N$R^7$C(O)O$R^8$, —OC(O)$R^7$, —OC(O)N$R^7R^8$, —S$(O)_2R^7$, —NHS$(O)_2R^7$, —OS$(O)_2R^7$, each which is independently substituted or unsubstituted, or hydrogen or halogen Embodiment 189

The compound of embodiment 187, wherein the compound has the formula:

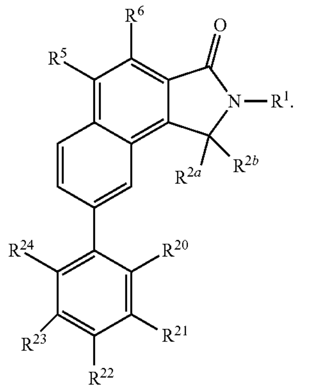

Embodiment 190

The compound of embodiment 188, wherein each $R^{20}$, $R^{21}$, $R^{22}$, $R^{23}$ and $R^{24}$ is alkyl, heteroaryl, —CN, —C(O)$R^7$, —N$R^7$C(O)N$R^8$, —C(O)N$R^7R^8$, —C(=N)N$R^7R^8$, —O$R^7$, —N$R^7R^8$, —S$(O)_2R^7$, —NHS$(O)_2R^7$, —S$(O)_2R^7$, or each which is unsubstituted or substituted, or hydrogen or halogen.

Embodiment 191

The compound of embodiment 190, wherein the compound has the formula:

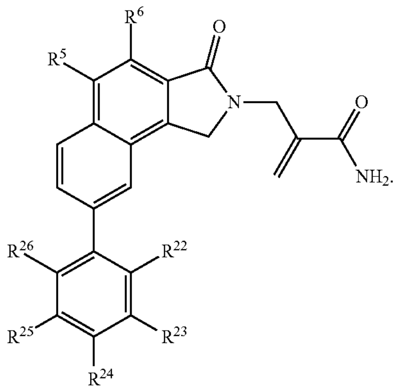

Embodiment 192

The compound of embodiment 191, wherein $R^6$ is $NH_2$.

Embodiment 193

The compound of embodiment 126, wherein the compound has the formula:

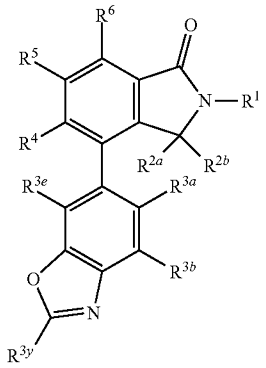

wherein each $R^{3a}$, $R^{3b}$, $R^{3e}$ and $R^{3y}$ is independently alkyl, cycloalkyl, alkenyl, alkynyl, aryl, heteroaryl, heterocyclyl, —CN, —C(O)$R^7$, —C(O)O$R^7$, —C(O)N$R^7R^8$, —C(=N)N$R^7R^8$, —O$R^7$, —S$R^7$, —N$R^7R^8$, —N$R^7$C(O)$R^8$, —N$R^7$C(O)O$R^8$, —OC(O)$R^7$, —OC(O)N$R^7R^8$, —S$(O)_2R^7$, —NHS$(O)_2R^7$, —OS$(O)_2R^7$, each which is independently substituted or unsubstituted, or hydrogen or halogen.

Embodiment 194

The compound of embodiment 126, wherein the compound has the formula:

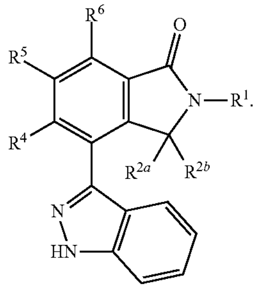

Embodiment 195

The compound of embodiment 126, wherein the compound has the formula:

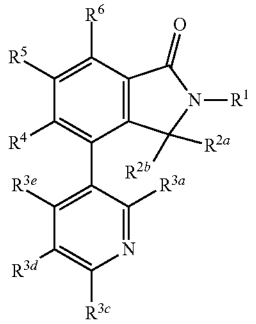

wherein each $R^{3a}$, $R^{3c}$, $R^{3d}$ and $R^{3e}$ is independently alkyl, cycloalkyl, alkenyl, alkynyl, aryl, heteroaryl, heterocyclyl, —CN, —C(O)$R^7$, —C(O)O$R^7$, —C(O)N$R^7R^8$, —C(=N)N$R^7R^8$, —O$R^7$, —S$R^7$, —N$R^7R^8$, —N$R^7$C(O)$R^8$, —N$R^7$C(O)O$R^8$, —OC(O)$R^7$, —OC(O)N$R^7R^8$, —S(O)$_2R^7$, —NHS(O)$_2R^7$, —OS(O)$_2R^7$, each which is independently substituted or unsubstituted, or hydrogen or halogen, or $R^{3c}$ and $R^{3d}$ together with the carbon atoms to which $R^{3c}$ and $R^{3d}$ are bound form a ring, wherein the ring is unsubstituted or substituted; or $R^{3d}$ and $R^{3e}$ together with the carbon atoms to which $R^{3d}$ and $R^{3e}$ are bound form a ring, wherein the ring is unsubstituted or substituted.

Embodiment 196

The compound of embodiment 195, wherein the compound has the formula:

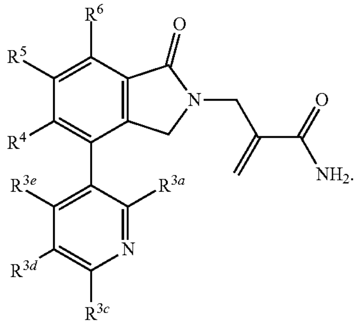

Embodiment 197

The compound of embodiment 195, wherein the compound has the formula:

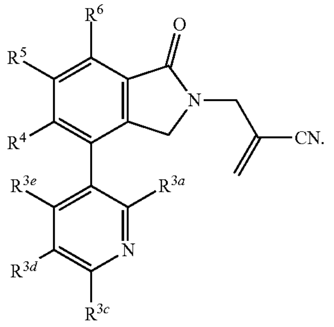

Embodiment 198

A pharmaceutical composition in unit dosage form comprising a pharmaceutically-acceptable excipient, and a compound of any one of embodiments 1-197.

Embodiment 199

A method of inducing apoptosis in a cell, the method comprising contacting the cell with a therapeutically-effective amount of a compound of any one of embodiments 1-197 that binds a p53 mutant.

Embodiment 200

The method of embodiment 199, wherein the compound increases an ability of a mutant p53 protein to bind DNA.

Embodiment 201

The method of embodiment 199 or 200, wherein the cell expresses a mutant p53 protein.

Embodiment 202

The method of any one of embodiments 199-201, wherein the mutant p53 protein has a mutation at amino acid R248.

Embodiment 203

The method of any one of embodiments 199-202, wherein the mutant p53 protein is p53 R248Q.

Embodiment 204

The method of any one of embodiments 199-202, wherein the mutant p53 protein is p53 R248W.

Embodiment 205

The method of any one of embodiments 199-201, wherein the mutant p53 protein has a mutation at amino acid R273.

Embodiment 206

The method of any one of embodiments 199-201 or 205, wherein the mutant p53 protein is p53 R273C.

Embodiment 207

The method of any one of embodiments 199-201, 205, or 206, wherein the mutant p53 protein is p53 R273H.

Embodiment 208

The method of any one of embodiments 199-207, wherein the compound selectively binds the mutant p53 protein as compared to a wild type p53 protein.

Embodiment 209

The method of any one of embodiments 199-208, wherein the therapeutically-effective amount is from about 50 mg to about 3,000 mg.

Embodiment 210

The method of any one of embodiments 199-209, wherein the therapeutically-effective amount is about 600 mg.

Embodiment 211

The method of any one of embodiments 199-209, wherein the therapeutically-effective amount is about 1,200 mg.

Embodiment 212

A method of treating a condition, the method comprising administering to a subject in need thereof a therapeutically-effective amount of a compound of any one of embodiments 1-188.

Embodiment 213

The method of embodiment 212, wherein the condition is a cancer.

Embodiment 214

The method of embodiment 212 or 213, wherein the cancer is ovarian cancer.

Embodiment 215

The method of embodiment 212 or 213, wherein the cancer is breast cancer.

Embodiment 216

The method of embodiment 212 or 213, wherein the cancer is lung cancer.

Embodiment 217

The method of embodiment 212 or 213, wherein the cancer is pancreatic cancer.

Embodiment 218

The method of any one of embodiments 212-217, wherein the administering is oral.

Embodiment 219

The method of any one of embodiments 212-217, wherein the administering is intravenous.

Embodiment 220

The method of any one of embodiments 212-217, wherein the administering is subcutaneous.

Embodiment 221

The method of any one of embodiments 212-217, wherein the administering is topical.

Embodiment 222

The method of any one of embodiments 212-221, wherein the subject is human.

Embodiment 223

The method of any one of embodiments 212-222, wherein the therapeutically-effective amount is from about 50 mg to about 3,000 mg.

Embodiment 224

The method of any one of embodiments 212-223, wherein the therapeutically-effective amount is about 600 mg.

Embodiment 225

The method of any one of embodiments 212-223, wherein the therapeutically-effective amount is about 1,200 mg.

Embodiment 226

The method of any one of embodiments 212-225, wherein the compound increases a stability of a biologically-active conformation of a p53 mutant relative to a stability of the biologically-active conformation of the p53 mutant in an absence of the compound.

Embodiment 227

The method of any one of embodiments 212-226, wherein the compound selectively binds a mutant p53 protein as compared to a wild type p53 protein.

Embodiment 228

The method of any one of embodiments 212-227, wherein the compound increases an ability of a mutant p53 protein to bind DNA.

Embodiment 229

The method of any one of embodiments 212-228, wherein the mutant p53 protein has a mutation at amino acid R248.

Embodiment 230

The method of any one of embodiments 212-229, wherein the mutant p53 protein is p53 R248Q.

Embodiment 231

The method of any one of embodiments 212-229, wherein the mutant p53 protein is p53 R248W.

Embodiment 232

The method of any one of embodiments 212-228, wherein the mutant p53 protein has a mutation at amino acid R273.

Embodiment 233

The method of any one of embodiments 212-228 or 232, wherein the mutant p53 protein is p53 R273C.

Embodiment 234

The method of any one of embodiments 212-228 or 232, wherein the mutant p53 protein is p53 R273H.

What is claimed is:

1. A compound of the formula:

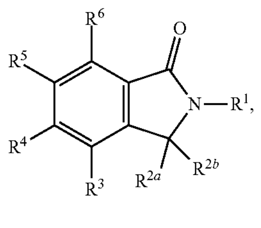

wherein:

$R^1$ is

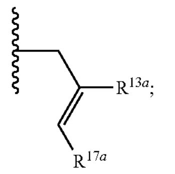

$R^{13a}$ is —C(O)$NH_2$ or —CN;

$R^{17a}$ is alkyl, aryl, or heteroaryl, each of which is unsubstituted or substituted, or —CN, —$NR^7R^8$, —$S(O)_2R^7$, —$SR^7$, $OR^7$, hydrogen, or halogen; and each $R^3$, $R^4$, $R^5$, and $R^6$ is independently alkyl, cycloalkyl, alkenyl, alkynyl, aryl, heteroaryl, or heterocyclyl, each of which is independently substituted or unsubstituted, or —CN, —C(O)$R^9$, —C(O)$OR^9$, —C(O)$NR^9R^{10}$, —C(=N)$NR^9R^{10}$, —$OR^9$, —$SR^9$, —$NR^9R^{10}$, —$NR^9C(O)R^{10}$, —$NR^9C(O)OR^{10}$, —OC(O)$R^9$, —OC(O)$NR^9R^{10}$, —$S(O)_2R^9$, —NHS$(O)_2R^9$, —$OS(O)_2R^9$, hydrogen, or halogen; or $R^3$ and $R^4$ together with the carbon atoms to which $R^3$ and $R^4$ are bound form a ring, wherein the ring is unsubstituted or substituted; and each $R^5$ and $R^6$ is independently alkyl, cycloalkyl, alkenyl, alkynyl, aryl, heteroaryl, or heterocyclyl, each of which is independently substituted or unsubstituted, or —CN, —C(O)$R^9$, —C(O)$OR^9$, —C(O)$NR^9R^{10}$, —C(=N)$NR^9R^{10}$, —$OR^9$, —$SR^9$, —$NR^9R^{10}$, —$NR^9C(O)R^{10}$, —$NR^9C(O)OR^{10}$, —OC(O)$R^9$, —OC(O)$NR^9R^{10}$, —$S(O)_2R^9$, —NHS$(O)_2R^9$, —$OS(O)_2R^9$, hydrogen, or halogen; or $R^4$ and $R^5$ together with the carbon atoms to which $R^4$ and $R^5$ are bound form a ring, wherein the ring is unsubstituted or substituted; and each $R^3$ and $R^6$ is independently alkyl, cycloalkyl, alkenyl, alkynyl, aryl, heteroaryl, or heterocyclyl, each of which is independently substituted or unsubstituted, or —CN, —C(O)$R^9$, —C(O)$OR^9$, —C(O)$NR^9R^{10}$, —C(=N)$NR^9R^{10}$, —$OR^9$, —$SR^9$, —$NR^9R^{10}$, —$NR^9C(O)R^{10}$, —$NR^9C(O)OR^{10}$, —OC(O)$R^9$, —OC(O)$NR^9R^{10}$, —$S(O)_2R^9$, —NHS$(O)_2R^9$, —$OS(O)_2R^9$, hydrogen, or halogen; or $R^5$ and $R^6$ together with the carbon atoms to which $R^5$ and $R^6$ are bound form a ring, wherein the ring is unsubstituted or substituted; and each $R^3$ and $R^4$ is independently alkyl, cycloalkyl, alkenyl, alkynyl, aryl, heteroaryl, or heterocyclyl, each of which is independently substituted or unsubstituted, or —CN, —C(O)$R^9$, —C(O)$OR^9$, —C(O)$NR^9R^{10}$, —C(=N)$NR^9R^{10}$, —$OR^9$, —$SR^9$, —$NR^9R^{10}$, —$NR^9C(O)R^{10}$, —$NR^9C(O)OR^{10}$, —OC(O)$R^9$, —OC(O)$NR^9R^{10}$, —$S(O)_2R^9$, —NHS$(O)_2R^9$, —$OS(O)_2R^9$, hydrogen, or halogen;

each $R^{2a}$ and $R^{2b}$ is hydrogen; and each $R^7$, $R^8$, $R^9$, and $R^{10}$ is independently alkyl, cycloalkyl, alkenyl, alkynyl, aryl, heteroaryl, or heterocyclyl, each of which is independently substituted or unsubstituted, or hydrogen or halogen, or a pharmaceutically-acceptable salt thereof.

2. The compound of claim 1, wherein $R^1$ is

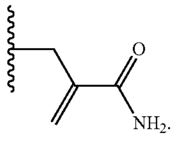

3. The compound of claim 1, wherein $R^1$ is

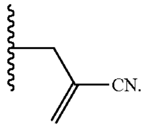 [SMILES: *CC(=C)C#N]

4. The compound of claim 1, wherein $R^4$ is H.

5. The compound of claim 1, wherein $R^5$ is H.

6. The compound of claim 1, wherein $R^5$ is —NHC(O)$R^{10}$.

7. The compound of claim 6, wherein $R^8$ is phenyl or heterocyclyl, each of which is unsubstituted or substituted.

8. The compound of claim 1, wherein $R^5$ is —$NR^9R^{10}$.

9. The compound of claim 8, wherein $R^5$ is —$NHR^{10}$, wherein $R^{10}$ is alkyl or heterocyclyl, each of which is unsubstituted or substituted, or hydrogen.

10. The compound of claim 8, wherein $R^5$ is $NH_2$.

11. The compound of claim 1, wherein $R^6$ is H.

12. The compound of claim 1, wherein $R^6$ is $NH_2$.

13. The compound of claim 1, wherein $R^3$ is aryl, heterocyclyl, or heteroaryl, each of which is unsubstituted or substituted.

14. The compound of claim 13, wherein $R^3$ is phenyl, naphthalenyl, pyridinyl, dihydropyridinyl, tetrahydropyridinyl, pyrazolopyridinyl, imidazopyridinyl, triazolopyridinyl, pyrimidinyl, indolyl, dihydroindolyl, pyridoindolyl, isoindolyl, indazolyl, imidazolyl, benzimidazolyl, benzodiazolyl, carbazolyl, pyrazolyl, oxazolyl, benzoxazolyl, thiazolyl, benzothiazolyl, thiophenyl, benzothiapenyl, quinolinyl, dihydroquinolinyl, isoquinolinyl, dihydroisoquinolinyl, quinoxalinyl, or dihydroquinoxalinyl, each of which is unsubstituted or substituted.

15. The compound of claim 1, wherein the compound has the formula:

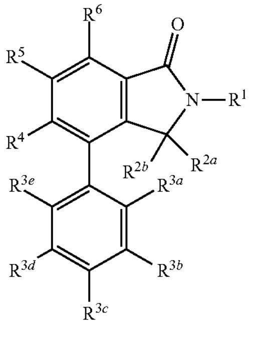

wherein each $R^{3a}$, $R^{3b}$, $R^{3c}$, $R^{3d}$ and $R^{3e}$ is independently alkyl, cycloalkyl, alkenyl, alkynyl, aryl, heteroaryl, or heterocyclyl, each of which is independently substituted or unsubstituted, or —CN, —C(O)$R^7$, —C(O)O$R^7$, —C(O)$NR^7R^8$, —C(=N)$NR^7R^8$, —$SR^7$, —$NR^7R^8$, —$NR^7$C(O)$R^8$, —$NR^7$C(O)O$R^8$, —OC(O)$R^7$, —OC(O)$NR^7R^8$, —$S(O)_2R^7$, —$NHS(O)_2R^7$, —$OS(O)_2R^7$, hydrogen, or halogen, or $R^{3a}$ and $R^{3b}$ together with the carbon atoms to which $R^{3a}$ and $R^{3b}$ are bound form a ring, wherein the ring is unsubstituted or substituted; and each $R^{3c}$, $R^{3d}$ and $R^{3e}$ is independently alkyl, cycloalkyl, alkenyl, alkynyl, aryl, heteroaryl, or heterocyclyl, each of which is independently substituted or unsubstituted, or —CN, —C(O)$R^7$, —C(O)O$R^7$, —C(O)$NR^7R^8$, —C(=N)$NR^7R^8$, —$SR^7$, —$NR^7R^8$, —$NR^7$C(O)$R^8$, —$NR^7$C(O)O$R^8$, —OC(O)$R^7$, —OC(O)$NR^7R^8$, —$S(O)_2R^7$, —$NHS(O)_2R^7$, —$OS(O)_2R^7$, hydrogen, or halogen; or $R^{3b}$ and $R^{3c}$ together with the carbon atoms to which $R^{3b}$ and $R^{3e}$ are bound form a ring, wherein the ring is unsubstituted or substituted; and each $R^{3a}$, $R^{3d}$ and $R^{3e}$ is independently alkyl, cycloalkyl, alkenyl, alkynyl, aryl, heteroaryl, or heterocyclyl, each of which is independently substituted or unsubstituted, or —CN, —C(O)$R^7$, —C(O)O$R^7$, —C(O)$NR^7R^8$, —C(=N)$NR^7R^8$, —$SR^7$, —$NR^7R^8$, —$NR^7$C(O)$R^8$, —$NR^7$C(O)O$R^8$, —OC(O)$R^7$, —OC(O)$NR^7R^8$, —$S(O)_2R^7$, —$NHS(O)_2R^7$, —$OS(O)_2R^7$, hydrogen, or halogen; or $R^{3c}$ and $R^{3d}$ together with the carbon atoms to which $R^{3c}$ and $R^{3d}$ are bound form a ring, wherein the ring is unsubstituted or substituted; and each $R^{3a}$, $R^{3b}$, and $R^{3e}$ is independently alkyl, cycloalkyl, alkenyl, alkynyl, aryl, heteroaryl, or heterocyclyl, each of which is independently substituted or unsubstituted, or —CN, —C(O)$R^7$, —C(O)O$R^7$, —C(O)$NR^7R^8$, —C(=N)$NR^7R^8$, —$SR^7$, —$NR^7R^8$, —$NR^7$C(O)$R^8$, —$NR^7$C(O)O$R^8$, —OC(O)$R^7$, —OC(O)$NR^7R^8$, —$S(O)_2R^7$, —$NHS(O)_2R^7$, —$OS(O)_2R^7$, hydrogen, or halogen; or $R^{3d}$ and $R^{3e}$ together with the carbon atoms to which $R^{3d}$ and $R^{3e}$ are bound form a ring, wherein the ring is unsubstituted or substituted; and each $R^{3a}$, $R^{3b}$, and $R^{3c}$ is independently alkyl, cycloalkyl, alkenyl, alkynyl, aryl, heteroaryl, or heterocyclyl, each of which is independently substituted or unsubstituted, or —CN, —C(O)$R^7$, —C(O)O$R^7$, —C(O)$NR^7R^8$, —C(=N)$NR^7R^8$, —$SR^7$, —$NR^7R^8$, —$NR^7$C(O)$R^8$, —$NR^7$C(O)O$R^8$, —OC(O)$R^7$, —OC(O)$NR^7R^8$, —$S(O)_2R^7$, —$NHS(O)_2R^7$, —$OS(O)_2R^7$, hydrogen, or halogen.

16. The compound of claim 15, wherein each $R^{3a}$, $R^{3b}$, $R^{3c}$, $R^{3d}$ and $R^{3e}$ is independently alkyl, aryl, heterocyclyl, or heteroaryl, each of which is independently substituted or unsubstituted, or C(O)$R^7$, —C(O)O$R^7$, —C(O)$NR^7R^8$, —$NR^7R^8$, —$NR^7$C(O)$R^8$, hydrogen, or halogen.

17. The compound of claim 16, wherein $R^{3b}$ and $R^{3d}$ are halogen.

18. The compound of claim 16, wherein $R^{3c}$ is $NH_2$.

19. The compound of claim 16, wherein $R^{3a}$ and $R^{3e}$ are hydrogen.

20. The compound of claim 15, wherein $R^{3c}$ and $R^{3d}$ together with the carbon atoms to which $R^{3c}$ and $R^{3d}$ are bound form a ring, wherein the ring is unsubstituted or substituted.

21. The compound of claim 1, wherein $R^3$ and $R^4$ together with the carbon atoms to which $R^3$ and $R^4$ are bound form a ring that is substituted or unsubstituted.

22. The compound of claim 21, wherein the compound has the formula:

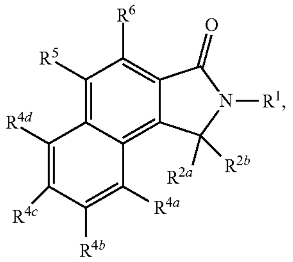

wherein each $R^{4a}$, $R^{4b}$, $R^{4c}$, and $R^{4d}$ is independently alkyl, cycloalkyl, alkenyl, alkynyl, aryl, heteroaryl, or heterocyclyl, each of which is independently substituted or unsubstituted, or —CN, —C(O)$R^7$, —C(O)O$R^7$, —C(O)N$R^7R^8$, —C(=N)N$R^7R^8$, —S$R^7$, —N$R^7R^8$, —N$R^7$C(O)$R^8$, —N$R^7$C(O)O$R^8$, —OC(O)$R^7$, —OC(O)N$R^7R^8$, —S$(O)_2R^7$, —NHS$(O)_2R^7$, —OS$(O)_2R^7$, hydrogen, or halogen.

* * * * *